US012497460B2

(12) United States Patent
Gromada et al.

(10) Patent No.: US 12,497,460 B2
(45) Date of Patent: Dec. 16, 2025

(54) ANTI-MSR1 ANTIBODIES AND METHODS OF USE THEREOF

(71) Applicant: REGENERON PHARMACEUTICALS, INC., Tarrytown, NY (US)

(72) Inventors: Jesper Gromada, Concord, MA (US); Viktoria Gusarova, Pleasantville, NY (US); Amy Han, Hockessin, DE (US); Sokol Haxhinasto, Brookfield, CT (US); Christos Kyratsous, Irvington, NY (US); Andrew J. Murphy, Croton-on Hudson, NY (US); Thomas Nittoli, Pearl River, NY (US); William Olson, Yorktown Heights, NY (US); Matthew Sleeman, White Plains, NY (US); Anna Zumsteg, Elmsford, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 393 days.

(21) Appl. No.: 17/727,432

(22) Filed: Apr. 22, 2022

(65) Prior Publication Data

US 2023/0079407 A1 Mar. 16, 2023

Related U.S. Application Data

(63) Continuation of application No. 16/407,099, filed on May 8, 2019, now Pat. No. 11,377,502.

(60) Provisional application No. 62/821,362, filed on Mar. 20, 2019, provisional application No. 62/789,987, filed on Jan. 8, 2019, provisional application No. 62/769,946, filed on Nov. 20, 2018, provisional application No. 62/678,200, filed on May 30, 2018, provisional application No. 62/669,276, filed on May 9, 2018.

(51) Int. Cl.

| | |
|---|---|
| ***C07K 16/28*** | (2006.01) |
| ***A61K 31/165*** | (2006.01) |
| ***A61K 31/167*** | (2006.01) |
| ***A61K 31/417*** | (2006.01) |
| ***A61K 31/4985*** | (2006.01) |
| ***A61K 31/5383*** | (2006.01) |
| ***A61K 31/58*** | (2006.01) |
| ***A61K 38/14*** | (2006.01) |
| ***A61K 39/00*** | (2006.01) |
| ***A61K 39/395*** | (2006.01) |
| ***A61K 47/60*** | (2017.01) |
| ***A61K 47/61*** | (2017.01) |
| ***A61K 47/68*** | (2017.01) |
| ***A61P 3/06*** | (2006.01) |
| ***A61P 9/10*** | (2006.01) |
| ***A61P 19/02*** | (2006.01) |
| ***A61P 31/04*** | (2006.01) |
| ***A61P 37/06*** | (2006.01) |

(52) U.S. Cl.

CPC ........ *C07K 16/2896* (2013.01); *A61K 31/165* (2013.01); *A61K 31/167* (2013.01); *A61K 31/417* (2013.01); *A61K 31/4985* (2013.01); *A61K 31/5383* (2013.01); *A61K 31/58* (2013.01); *A61K 38/14* (2013.01); *A61K 39/3955* (2013.01); *A61K 47/60* (2017.08); *A61K 47/61* (2017.08); *A61K 47/6803* (2017.08); *A61K 47/6849* (2017.08); *A61K 47/6889* (2017.08); *A61P 3/06* (2018.01); *A61P 9/10* (2018.01); *A61P 19/02* (2018.01); *A61P 31/04* (2018.01); *A61P 37/06* (2018.01); *A61K 2039/505* (2013.01); *C07K 2317/565* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 2,920,999 A | 1/1960 | Agnello et al. | |
| 3,007,923 A | 11/1961 | Muller et al. | |
| 3,020,275 A | 2/1962 | Marx et al. | |
| 3,033,873 A | 5/1962 | Pinson et al. | |
| 3,033,874 A | 5/1962 | Pinson et al. | |

(Continued)

FOREIGN PATENT DOCUMENTS

| | | |
|---|---|---|
| CN | 1414008 A | 4/2003 |
| CN | 101397328 A | 4/2009 |

(Continued)

OTHER PUBLICATIONS

International Search Report and Written Opinion for PCT Application No. PCT/US2019/031383 dated Oct. 17, 2019, 30 pages.

(Continued)

*Primary Examiner* — Ruixiang Li

(74) *Attorney, Agent, or Firm* — Biospark Intellectual Property Law

(57) ABSTRACT

Provided herein are antibodies and antigen-binding fragments that bind MSR1 and methods of use thereof. According to certain embodiments, the antibodies bind human MSR1 with high affinity. In certain embodiments, the antibodies bind MSR1 without blocking, or blocking less than 90%, of modified LDL binding to MSR1. In some embodiments, the antibodies bind cell surface expressed-MSR1 and are internalized. The antibodies of the invention may be fully human antibodies. The invention includes anti-MSR1 antibodies, or antigen-binding fragments thereof, conjugated to drugs or therapeutic compounds.

30 Claims, 35 Drawing Sheets

Specification includes a Sequence Listing.

(56) References Cited

U.S. PATENT DOCUMENTS

| | | | |
|---|---|---|---|
| 3,047,468 | A | 7/1962 | Origoni et al. |
| 3,197,469 | A | 7/1965 | Fried |
| 3,232,839 | A | 2/1966 | Kieslich et al. |
| 3,383,394 | A | 5/1968 | Weber et al. |
| 3,723,484 | A | 3/1973 | Laurant et al. |
| 3,798,216 | A | 3/1974 | Boissier et al. |
| 3,886,145 | A | 5/1975 | Diamanti |
| 3,928,326 | A | 12/1975 | Brattsand et al. |
| 3,929,768 | A | 12/1975 | Brattsand et al. |
| 4,076,737 | A | 2/1978 | Anner et al. |
| 4,925,933 | A | 5/1990 | Jakupovic et al. |
| 5,116,829 | A | 5/1992 | Hori et al. |
| 5,183,815 | A | 2/1993 | Saari et al. |
| 5,208,020 | A | 5/1993 | Chari et al. |
| 5,500,362 | A | 3/1996 | Robinson et al. |
| 5,714,586 | A | 2/1998 | Kunstmann et al. |
| 5,821,337 | A | 10/1998 | Carter et al. |
| 5,837,698 | A | 11/1998 | Tjoeng et al. |
| 5,908,833 | A | 6/1999 | Brattsand et al. |
| 6,596,541 | B2 | 7/2003 | Murphy et al. |
| 6,908,934 | B2 | 6/2005 | Adams et al. |
| 7,750,116 | B1 | 7/2010 | Doronina et al. |
| 8,524,697 | B2 | 9/2013 | Anthes et al. |
| 8,703,714 | B2 | 4/2014 | Doronina et al. |
| 9,375,473 | B2 | 6/2016 | Latov et al. |
| 10,711,032 | B2 | 7/2020 | Han et al. |
| 11,491,237 | B2 | 11/2022 | Han et al. |
| 11,760,775 | B2 | 9/2023 | Han et al. |
| 2003/0125357 | A1 | 7/2003 | Adams et al. |
| 2003/0199529 | A1 | 10/2003 | Garvey et al. |
| 2004/0077595 | A1 | 4/2004 | Cheng et al. |
| 2004/0157810 | A1 | 8/2004 | Teicher et al. |
| 2004/0192778 | A1 | 9/2004 | Jardien et al. |
| 2005/0009798 | A1 | 1/2005 | Currie et al. |
| 2005/0192257 | A1 | 9/2005 | Peyman |
| 2005/0287155 | A1 | 12/2005 | Santi et al. |
| 2006/0046967 | A1 | 3/2006 | Satyam |
| 2006/0074008 | A1 | 4/2006 | Senter et al. |
| 2007/0258987 | A1 | 11/2007 | Francisco et al. |
| 2008/0171040 | A1 | 7/2008 | Ebens et al. |
| 2008/0305044 | A1 | 12/2008 | McDonagh et al. |
| 2008/0305497 | A1 | 12/2008 | Kosmeder et al. |
| 2009/0221543 | A1 | 9/2009 | Soldato et al. |
| 2009/0318396 | A1 | 12/2009 | Baker et al. |
| 2010/0041633 | A1 | 2/2010 | Benedini et al. |
| 2010/0093685 | A1 | 4/2010 | Benedini et al. |
| 2010/0129314 | A1 | 5/2010 | Singh et al. |
| 2010/0209508 | A1 | 8/2010 | Baker et al. |
| 2010/0226987 | A1 | 9/2010 | Gnaim et al. |
| 2010/0323973 | A1 | 12/2010 | Leamon et al. |
| 2011/0178287 | A1 | 7/2011 | Glucksmann et al. |
| 2011/0182828 | A1 | 7/2011 | Anthes et al. |
| 2011/0262368 | A1 | 10/2011 | Anthes et al. |
| 2012/0058892 | A1 | 3/2012 | Braun et al. |
| 2012/0059158 | A1 | 3/2012 | Ishii |
| 2012/0096572 | A1 | 4/2012 | Macdonald et al. |
| 2012/0258107 | A1 | 10/2012 | Graversen et al. |
| 2012/0276193 | A1 | 11/2012 | Graversen et al. |
| 2012/0302505 | A1 | 11/2012 | Fetzer et al. |
| 2013/0101546 | A1 | 4/2013 | Yurkovetskiy et al. |
| 2014/0227294 | A1 | 8/2014 | Anderson et al. |
| 2015/0152187 | A1 | 6/2015 | Sun et al. |
| 2015/0165064 | A1 | 6/2015 | Bregeon et al. |
| 2015/0258203 | A1 | 9/2015 | Vlahov et al. |
| 2015/0290337 | A1 | 10/2015 | Vetter et al. |
| 2015/0291563 | A1 | 10/2015 | Park et al. |
| 2016/0082119 | A1 | 3/2016 | Gonzalez et al. |
| 2016/0158369 | A1 | 6/2016 | Sato et al. |
| 2016/0279054 | A1 | 9/2016 | Rangaramanujam et al. |
| 2016/0310612 | A1 | 10/2016 | Lyon et al. |
| 2016/0340445 | A1 | 11/2016 | Bouckaert et al. |
| 2017/0007715 | A1 | 1/2017 | Andreev et al. |
| 2017/0182181 | A1 | 6/2017 | Garbaccio et al. |
| 2018/0002372 | A1 | 1/2018 | Tripathi et al. |
| 2018/0126000 | A1 | 5/2018 | Mcpherson et al. |
| 2018/0155389 | A1 | 6/2018 | Han et al. |
| 2018/0333504 | A1 | 11/2018 | Han et al. |
| 2018/0334426 | A1 | 11/2018 | Han et al. |
| 2018/0360979 | A1 | 12/2018 | Mejia Oneto et al. |
| 2019/0030171 | A1 | 1/2019 | Garbaccio et al. |
| 2019/0134220 | A1 | 5/2019 | Godwin |
| 2019/0209702 | A1 | 7/2019 | Han |
| 2019/0309061 | A1 | 10/2019 | Papadopoulos et al. |
| 2020/0115326 | A1 | 4/2020 | Tsuchikama et al. |
| 2021/0040144 | A1 | 2/2021 | Han et al. |
| 2022/0080052 | A1 | 3/2022 | Gromada et al. |
| 2023/0079407 | A1 | 3/2023 | Gromada et al. |
| 2023/0119539 | A1 | 4/2023 | Han |

FOREIGN PATENT DOCUMENTS

| | | | |
|---|---|---|---|
| CN | 103694375 | A | 4/2014 |
| CN | 104302664 | A | 1/2015 |
| CN | 107849131 | A | 3/2018 |
| CN | 108 853 514 | A | 11/2018 |
| CN | 109 106 951 | A | 1/2019 |
| DE | 1165595 | B | 3/1964 |
| EP | 1625854 | A1 | 2/2006 |
| ES | 544825 | A1 | 7/1985 |
| GB | 889766 | A | 2/1962 |
| GB | 898295 | A | 6/1962 |
| GB | 1428416 | | 3/1976 |
| IL | 73337 | A | 9/1988 |
| WO | WO 94/22898 | A1 | 10/1994 |
| WO | WO 2000/049993 | A2 | 8/2000 |
| WO | WO 2002/080931 | A1 | 10/2002 |
| WO | WO 2004/017904 | A2 | 3/2004 |
| WO | WO 2004/022099 | A2 | 3/2004 |
| WO | WO 2005/063777 | A1 | 7/2005 |
| WO | WO 2005/079523 | A2 | 9/2005 |
| WO | WO 2005/089808 | | 9/2005 |
| WO | WO 2005/119266 | A1 | 12/2005 |
| WO | WO 2006/135371 | A1 | 12/2006 |
| WO | WO 2008/122039 | | 10/2008 |
| WO | WO 2008/127347 | A1 | 10/2008 |
| WO | WO 2009/085879 | A2 | 7/2009 |
| WO | WO 2009/085880 | A2 | 7/2009 |
| WO | WO 2010/010119 | A1 | 1/2010 |
| WO | WO 2010/010324 | | 1/2010 |
| WO | WO 2010/126953 | A1 | 11/2010 |
| WO | WO 2010/132743 | A1 | 11/2010 |
| WO | WO 2011/018611 | A1 | 2/2011 |
| WO | WO 2011/020107 | A2 | 2/2011 |
| WO | WO 2011/039511 | A2 | 4/2011 |
| WO | WO 2011/081937 | A1 | 7/2011 |
| WO | WO 2011/103389 | A1 | 8/2011 |
| WO | WO 2011/130598 | | 10/2011 |
| WO | WO 2012/011591 | A1 | 1/2012 |
| WO | WO 2012/058592 | | 5/2012 |
| WO | WO 2012/166559 | | 12/2012 |
| WO | WO 2013/053872 | | 4/2013 |
| WO | WO 2013/053873 | | 4/2013 |
| WO | WO 2013/055990 | | 4/2013 |
| WO | WO 2013/055993 | | 4/2013 |
| WO | WO 2013/068874 | | 5/2013 |
| WO | WO 2013/085925 | | 6/2013 |
| WO | WO 2013/093465 | A2 | 6/2013 |
| WO | WO 2014/065661 | | 5/2014 |
| WO | WO 2014/165119 | | 10/2014 |
| WO | WO 2014/197854 | | 12/2014 |
| WO | WO 2015/026907 | | 2/2015 |
| WO | WO 2015/153401 | A1 | 10/2015 |
| WO | WO 2015/155998 | A1 | 10/2015 |
| WO | WO 2015/189478 | | 12/2015 |
| WO | WO 2016/090038 | A1 | 6/2016 |
| WO | WO 2016/090040 | A1 | 6/2016 |
| WO | WO 2016/094509 | A1 | 6/2016 |
| WO | WO 2016/094517 | A1 | 6/2016 |
| WO | WO 2016127081 | A1 | 8/2016 |
| WO | WO 2017006279 | A1 | 1/2017 |
| WO | WO 2017/062271 | A1 | 4/2017 |
| WO | WO 2017/132103 | A2 | 8/2017 |
| WO | WO 2017/147542 | | 8/2017 |
| WO | WO 2017/165851 | A1 | 9/2017 |

(56) References Cited

FOREIGN PATENT DOCUMENTS

| | | | |
|---|---|---|---|
| WO | WO 2017/199046 | A1 | 11/2017 |
| WO | WO 2017/210471 | A1 | 12/2017 |
| WO | WO 2017/214458 | A2 | 12/2017 |
| WO | WO 2018/058001 | | 3/2018 |
| WO | WO 2018/089373 | A2 | 5/2018 |
| WO | WO 2018/160539 | A1 | 9/2018 |
| WO | WO 2018/213077 | A1 | 11/2018 |
| WO | WO 2018/213082 | A1 | 11/2018 |
| WO | WO 2019/094395 | A2 | 5/2019 |
| WO | WO 2019/136487 | A2 | 7/2019 |
| WO | WO 2019/195665 | A1 | 10/2019 |
| WO | WO 2020/132483 | A1 | 6/2020 |
| WO | WO 2020/146541 | A2 | 7/2020 |

OTHER PUBLICATIONS

Agard et al., "A Strain-Promoted [3+2] Azide-Alkyne Cycloaddition for Covalent Modification of Biomolecules in Living Systems", J. Am. Chem. Soc., Nov. 24, 2004, vol. 126, No. 46, pp. 15046-15047.

Agarwal et al., "A Pictet-Spengler ligation for protein chemical modification", PNAS, Jan. 2, 2013, vol. 110, No. 1, pp. 46-51.

Agarwal et al., "Site-Specific Antibody-Drug Conjugates: the Nexus of Bioorthogonal Chemistry, Protein Engineering, and Drug Development", Bioconjugate Chem., 2015, 26, pp. 176-192.

Aherne et al., "A sensitive radioimmunoassay for budesonide in plasma", Journal of Steroid Biochemistry, vol. 17, No. 5, Nov. 1982, pp. 559-565.

Angal et al., "A Single Amino Acid Substitution Abolishes the Heterogeneity of Chimeric Mouse/Human (IgG4) Antibody", Molecular Immunology, Jan. 1993, vol. 30, No. 1, pp. 105-108.

Bajaj et al., "Topochemical model for prediction of anti-HIV activity of HEPT analogs", Bioorganic & Medicinal Chemistry Letters, vol. 15, No. 2, Jan. 17, 2005, pp. 467-469.

Baskin et al., "Copper-free click chemistry for dynamic in vivo imaging", PNAS, Oct. 23, 2007, vol. 104, No. 43, pp. 16793-16797.

Beck et al., "Strategies and challenges for the next generation of antibody-drug conjugates", Nature Reviews, Drug Discovery, vol. 16, No. 5, Mar. 17, 2017, pp. 315-337.

Berge et al., "Pharmaceutical Salts", Review Article, Jan. 1977, vol. 66, No. 1, pp. 1-19.

Berlin M., "Recent advances in the development of novel glucocorticoid receptor modulators", Review, Expert Opinion on Therapeutic Patents (2010) 20(7), pp. 855-873; DOI: 10.1517/13543776.2010.493876.

Biju et al., "Synthesis of novel anti-inflammatory steroidal macrocycles using ring closing metathesis reaction", Tetrahedron Letters, Jan. 2015, vol. 56, issue 4, pp. 636-638.

Boersma et al., "DARPins and other repeat protein scaffolds: advances in engineering and applications", 2011, Current Opinion in Biotechnology, 2011, vol. 22, pp. 849-857.

Bogan et al., "Liver X Receptor Modulation of Gene Expression Leading to Proluteolytic Effects in Primate Luteal Cells", Biology of Reproduction, (2012) 86(3):89, 1-9.

Cannon et al., "The liver X receptor agonist AZ876 protects against pathological cardiac hypertrophy and fibrosis without lipogenic side effects", European Journal of Heart Failure, 2015, vol. 17, pp. 273-282.

Carrico et al., "Introducing genetically enclosed aldehydes into proteins", Nature Chemical Biology, Jun. 2007, vol. 3, No. 6, pp. 321-322.

CAS Registry Compounds, accessed Jul. 16, 2019; 355 pages.

CAS Registry No. 803648-23-9; STN Entry Date Dec. 29, 2004; 21-(Diethylamino)-11,17-dihydroxy- (11β)-(9Cl)pregna-1,4-diene-3,20-dione [2] Category: X Claims: 1, 2, 4, 14; SciFinder™®.

Cas RN 2341-08-4, 1984 (entered into STN Nov. 16, 1984).

Cas RN 3859-14-1, 1984 (entered into STN Nov. 16, 1984).

Cas RN 57-86-3, 1984 (entered into STN Nov. 16, 1984).

Casati et al., "Unraveling Unidirectional Threading of α-Cyclodextrin in a [2]Rotaxane through Spin Labeling Approach", Journal of the American Chemical Society, Oct. 29, 2012, vol. 134, pp. 19108-19117.

Cho et al., "Regioselective Synthesis of Heterocycles Containing Nitrogen Neighboring an Aromatic Ring by Reductive Ring Expansion Using Diisobutylaluminum Hydride and Studies on the Reaction Mechanism", J. Org. Chem., 2010, vol. 75, pp. 627-636; published online Dec. 29, 2009.

Cho et al., "The first preparation of alpha-functionalized benzylamine", Tetrahedron Letters, vol. 40, No. 47, Nov. 19, 1999, p. 8215.

Chuu, "Modulation of liver X receptor signaling as a prevention and therapy for colon cancer", Medical Hypotheses, 2011, vol. 76, pp. 697-699.

Clynes et al., "Fc receptors are required in passive and active immunity to melanoma", Proc. Natl. Acad. Sci. USA, Jan. 1998, vol. 95, pp. 652-656.

Compounds from CAS Registry database, accessed May 20, 2019; 16 pages.

Compounds retrieved on Nov. 18, 2017 from SciFinder, Set 1; 4 pages.

Compounds retrieved on Nov. 18, 2017 from SciFinder, Set 2; 1 page.

Compounds retrieved on Nov. 18, 2017 from SciFinder, Set 3; 3 pages.

Czerkies et al., "An interplay between scavenger receptor A and CD14 during activation of J774 cells by high concentrations of LPS", Immunobiology, Apr. 12, 2013, vol. 218, pp. 1217-1226.

Dai et al., "Regulation of MSR-1 and CD36 in macrophages by LOX-1 mediated through PPAR-γ", Biochemical and Biophysical Research Communications, 431, pp. 496-500, Publication Date: Jan. 16, 2013.

Database Registry [Online] Chemical Abstracts Service Retrieved from STN on Aug. 11, 2020; Compounds with CAS Registry No. of 23640-98-4 (Entered STN: Nov. 16, 1984); 23640-97-3 (Entered STN: Nov. 16, 1984); 6477-56-1 (Entered STN: Nov. 16, 1984); 5514-61-4 (Entered STN: Nov. 16, 1984); 2353-16-4 (Entered STN: Nov. 16, 1984).

Database Registry: Compounds with CAS Registry No. of 23640-98-4; 23640-97-3; 6477-56-1; 5514-61-4; 2353-16-4.

Dennler et al., "Antibody Conjugates: From Heterogeneous Populations to Defined Reagents", Antibodies 2015, 4, pp. 197-224; doi:10.3390/antib4030197.

Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.

Diamantis et al., "Antibody-drug conjugates an emerging class of cancer treatment", British Journal of Cancer, 2016, vol. 114, pp. 362-367; D01:10.1038/bjc.2015.435.

Doi et al., "The Histidine Interruption of an α-Helical Coiled Coil Allosterically Mediates A pH-Dependent Ligand Dissociation From Macrophage Scavenger Receptors", The Journal of Biological Chemistry, vol. 269, No. 41, Oct. 14, 1994, pp. 25598-25604.

Doronina et al., "Novel Peptide Linkers for Highly Potent Antibody-Auristatin Conjugate", Bioconjugate Chem., 2008, vol. 19, No. 10, pp. 1960-1963.

Doronina et al., "Development of potent monoclonal antibody auristatin conjugates for cancer therapy", Nature Biotechnology, Jul. 2003, vol. 21, No. 7, pp. 778-941.

Dubois-Camacho et al., "Glucocorticosteroid therapy in inflammatory bowel diseases: From clinical practice to molecular biology", World J Gastroenterol, Sep. 28, 2017, vol. 23(36), pp. 6628-6638; DOI: 10.3748/wjg.v23.i36.6628.

Effenberger et al., "Trifluormethansulfonate von [alpha]-Hydroxycarbonsaureestern—Edukte zur racemisierungsfreien Synthese N-substituierter [alpha]-Aminosauren", Angewandte Chemie, vol. 95, No. 1, Jan. 1, 1983, p. 50.

Fellier et al., "Bindung von Cortisol, Fluocortolon und Difluocortolon a Humanplasmaproteine", J. Clin. Chem. Clin. Biochem., 1977, vol. 15, pp. 545-548.

Ferraboschi et al., "Estimation and characterisation of budesonide tablets impurities", Journal of Pharmaceutical and Biomedical Analysis, 2008, 47(3), pp. 636-640.

(56) References Cited

OTHER PUBLICATIONS

Friedman et al., "The Smart Targeting of Nanoparticles", Current Pharmaceutical Design, 2013, vol. 19, pp. 6315-6329.
Gidwani et al., "A Comprehensive Review on Cyclodextrin-Based Carriers for Delivery of Chemotherapeutic Cytotoxic Anticancer Drugs", Hindawi Publishing Corporation, BioMed Research International, vol. 2015, article ID 198268, 15 pages.
Graversen et al., "Targeting the Hemoglobin Scavenger receptor CD163 in Macrophages Highly Increases the Anti-inflammatory Potency of Dexamethasone", Molecular Therapy, vol. 20, No. 8, Aug. 2012, pp. 1550-1558.
Hamasaki et al., "Fluorescent sensors of molecular recognition. Modified cyclodextrins capable of exhibiting guest-responsive twisted intramolecular charge transfer fluorescence", J. Am. Chem. Soc., Jun. 1993, vol. 115, No. 12, pp. 5035-5040.
Hein et al., "The Synthesis of a Multiblock Osteotropic Polyrotaxane by Copper(I)-Catalyzed Huisgen 1,3-Dipolar Cycloaddition", Macromolecular Bioscience, Dec. 8, 2010, vol. 10, No. 12, pp. 1544-1556.
Hofer et al., "An engineered selenocysteine defines a unique class of antibody derivatives", PNAS, Aug. 26, 2008, vol. 105, No. 34, p. 12451-12456.
Hollander et al., "Selection of Reaction Additives Used in the Preparetion of Monomeric Antibody-Calicheamicin Conjugates", Bioconjugate Chem., 2008, vol. 19, pp. 358-361; published online Nov. 10, 2007.
Huisgen, "1,3-Dipolar Cycloadditions", Proceedings of the Chemical Society, Oct. 1961, pp. 357-369.
Jain et al., "Current ADC Linker Chemistry", Pharm Res, 2015, vol. 32, pp. 3526-3540; DOI 10.1007/s11095-015-1657-7.
Jain R. A., "The manufacturing techniques of various drug loaded biodegradable poly(lactide-co-glycolide) (PLGA) devices", Biomaterials 21(23), 2000, pp. 2475-2490.
Jeger, "Site-specific conjugation of tumour-targeting, antibodies using transglutaminase", Ph.D. thesis, 2009, XP055208841, ETH Zurich, CH; 140 pages. DOI: 10.3929/ethz-a-005963273; pp. 41-46.
Kapp et al., "Studies on the Pharmacology of 6alpha,9-difluoro-11 beta-hydroxy-16alpha-methyl-21-valeryloxy-1,4-pregnadiene-3,20-dione", Arzneimittel-Forschung Drug Reserch. 1976;26(7b):1463-1475; with an English abstract.
Kern et al., "Discovery of Pyrophosphate Diesters as Tunable, Soluble, and Bioorthogonal Linkers for Site-Specific Antibody-Drug Conjugates", J. Am. Chem. Soc. (JACS), Jan. 25, 2016, vol. 138, No. 4, pp. 1430-1445.
Kern et al., "Novel Phosphate Modified Cathepsin B Linkers: Improving Aqueous Solubility and Enhancing Payload Scope of ADCs", Bioconjugate Chem. Bioconjugate Chem., Jul. 28, 2016, vol. 27, No. 9, pp. 2081-2088.
Kovtun et al., "Antibody-Maytansinoid Conjugates Designed to Bypass Multidrug Resistance", Cancer Research, vol. 70, No. 6, Mar. 15, 2010, pp. 2528-2537.
Krajcsi et al., "Novel Synthesis of 21-Aminopregnanes", J. Chem. Research (S), Nov. 1987, issue 11, pp. 382-383.
Kronkvist et al., "Determination of Drugs in Biosamples at Picomolar Concentrations Using Competitive Elisa With Electrochemical Detection: Application to Steroids", Journal of Pharmaceutical and Biomedical Analysis, vol. 11, No. 6, 1993, pp. 459-463.
Lehar et al., "Novel antibody-antibiotic conjugate eliminates intracellular *S. aureus*", Nature, Nov. 19, 2015, vol. 527, No. 7578, pp. 323-328.
Lemke et al., Foye's Principles of Medicinal Chemistry, Chapter 44, p. 1253, Publication Year: 2008.
Lhospice et al. "Site-Specific Conjugation of Monomethyl Auristatin E to Anti-CD30 Antibodies Improves Their Pharmacokinetics and Therapeutic Index in Rodent Models", Mol. Pharmaceutics, 2015, vol. 12, pp. 1863-1871.
Lichtenecker R. J., "Synthesis of aromatic $^{13}C/^{2}H$-α-ketoacid precursors to be used in selective phenylalanine and tyrosine protein labelling", Organic & Biomolecular Chemistry, Jul. 31, 2014, vol. 12, pp. 7551-7560.
Lim et al., "Targeted Delivery of LXR Agonist Using a Site-Specific Antibody-Drug Conjugate", Bioconjugate Chemistry, 2015, vol. 26, No. 11, pp. 2216-2222.
Lu et al., "Linkers Having a Crucial Role in Antibody-Drug Conjugates", Int. J. Mol. Sci., Apr. 14, 2016, vol. 17, No. 561, 22 pages.
Lyon et al., "Reducing hydrophobicity of homogeneous antibody-drug conjugates improves pharmacokinetics and therapeutic index", Nature Biotechnology, Jul. 2015, vol. 33, No. 7, pp. 733-735.
McCombs et al., "Antibody Drug Conjugates: Design and Selection of Linker, Payload and Conjugation Chemistry", The AAPS Journal, Mar. 2015, vol. 17, No. 2, pp. 339-351.
Milles-Larsson et al., "Reversible Fatty Acid Conjugation of Budesonide—Novel Mechanism for Prolonged Retention of Topically Applied Steroid in Airway Tissue", Drug Metab. Dispos. 1998, vol. 26, pp. 623-630.
Mori et al., "Endocytic Pathway of Scavenger Receptors via Trans-Golgi System in Bovine Alveolar Macrophages", Laboratory Investigation, vol. 71, No. 3, 1994, pp. 409-417.
Muck et al., "High pressure liquid chromatography of some triamcinolone derivatives", Bollettino chimico farmaceutica, Italy, Apr. 1981, 120(4), pp. 240-247; with an English abstract.
Papachristos et al., "Antibody-drug conjugates: a mini-review. The synopsis of two approved medicines", Drug Delivery, 2016, vol. 23, No. 5, pp. 1662-1666; published online Jan. 27, 2015.
Park T. G., "Degradation of poly(lactic-co-glycolic acid) microspheres: effect of copolymer composition", Biomaterials 16(15), 1995, pp. 1123-1130.
Paul-Clark et al., "Glucocorticoid Receptor Nitration Leads to Enhanced Anti-Inflammatory Effects of Novel Steroid Ligands", The Journal of Immunology, 2003, vol. 171, pp. 3245-3252; doi: 10.4049/jimmunol.171.6.3245.
Peng, J., et al. "Chemoselective reduction of 21-azidocorticosteroids to primary 21-primary aminocorticoster-oids." Chemical Research In Chinese Universities (2004), 25(5), pp. 866-869.
Pufall "Glucocorticoids and Cancer", Adv Exp Med Biol., 2015, vol. 872, pp. 315-333.
Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.
Reggelin et al., "Asymmetric Synthesis of Highly Substituted Azapolycyclic Compounds via 2-Alkenyl Sulfoximines: Potential Scaffolds for Peptide Mimetics", J. American Chemical Society, Mar. 8, 2006, vol. 128, pp. 4023-4034.
Romero-Hernandez et al., "Diosgenin-based thio (seleno) ureas and triazolyl glycoconjugates as hybrid drugs. Antioxidant and antiproliferative profile", European Journal of Medicinal Chemistry, Editions Scientifique Elsevier, Paris, FR, May 14, 2015, vol. 99, pp. 67-82; XP029222662.
Ryan et al., "Polyclonal Antibody Production Against Chito-Oligosaccharides", Food and Agricultural Immunology, 2001, vol. 13, pp. 127-130.
Sagar S. et al., Bifidobacterium breve and Lactobacillus rhamnosus treatment is as effective as budesonide at reducing inflammation in a murine model for chronic asthma. Respiratory Research, Apr. 16, 2014, vol. 15, No. 1, article No. 46; Abstract.
Samal et al., "The First Synthesis of Water-Soluble Cyclodextrinazafullerenes", Synthetic Communications, 2002, vol. 32, No. 21, pp. 3367-3372.
Samant et al., "Synthesis of 3-hydroxypyrid-2-ones from furfural for treatment against iron overload and iron deficiency", European Journal of Medicinal Chemistry, vol. 43, No. 9,Sep. 1, 2008, pp. 1978-1982.
Sehgal et al., "Desoxymethasone: a new topical corticosteroid", International Journal of Dermatology, Dec. 1976, vol. 15, pp. 770-773; with an English abstract.
Shaunak et al., "Site-specific PEGylation of native disulfide bonds in therapeutic proteins", Nature Chemical Biology, Jun. 2006, vol. 2, No. 6, pp. 312-313.
Simons S S Jr et al., "Alpha Keto Mesylate 1,2,4, 14 a Reactive Thiol Specific Functional Group", Journal of Organic Chemistry, American Chemical Society, Washington, vol. 45, No. 15, Jan. 1, 1980, pp. 3084-3088.

(56) References Cited

OTHER PUBLICATIONS

Singh et al., "Polymer Drug Conjugates: Recent Advancements in Various Diseases", Current Pharmaceutical Design, May 10, 2016, vol. 22, No. 19, pp. 2821-2843, XP055490895.
Svendsen et al., "Antibody-Directed Glucocorticoid Targeting to CD163 M2-type Macrophages Attenuates Fructose-Induced Liver Inflammatory Changes", Molecular Therapy—Methods & Clinical Develop, vol. 4, Mar. 2017, pp. 50-61.
Tang et al., "One-pot N-glycosylation remodeling of igG with non-natural sialyiglycopeptides enables Glycosite-specific and dual-payload antibody—drug conjugates", Org Biomol Chem 14:9501-9518, Oct. 28, 2016.
Taylor et al., "A transgenic mouse that expresses a diversity of human sequence heavy and light chain immunoglobulins", Nucleic Acids Research, 1992, vol. 20, No. 23, pp. 6287-6295.
Thalen et al., "Epimers of budesonide and related corticosteroids. I. Preparative resolution by chromatography on Sephadex LH-20", Acta Pharmaceutica Suecica, 1982, 19(4), pp. 247-266.
Thalen et al., "Synthesis and pharmacological properties of some 16α, 17α-acetals of 16α hydroxyhydrocortisone, 16α-hydroxyprednisolone and fluorinated 16α-hydroxyprednisolones", Acta Pharmaceutica Suecica, 1984, 21(2), pp. 109-124.
Thalen, "Epimers of budesonide and related corticosteroids. II. Structure elucidation by mass spectrometry", Acta Pharmaceutica Suecica, 1982, 19(5), pp. 327-354.
Tian et al., "Inhibition of influenza virus infection by multivalent pentacyclic triterpene-functionalized per-0-methylated cyclodextrin conjugates", European Journal of Medicinal Chemistry, Editions Scientifique Elsevier, Paris, FR, Apr. 2, 2017, vol. 134, pp. 133-139, XP029995979.
Toth et al., "Amino-derivatives of 11,17,21-Trihydroxy-3,20-Dioxo-1,4-Pregnadiene", Nature, vol. 191, Aug. 5, 1961, p. 607.
Tumey et al., "ADME Considerations for the Development of Biopharmaceutical Conjugates Using Cleavable Linkers", Current Topics In Medicinal Chemistry, vol. 17, No. 32, 2017, pp. 3444-3462.
Tunek et al., "Reversible Formation of Fatty Acid Esters of Budesonide, an Antiasthma Glucgcorticoid, in Human Lung and Liver Microsomes", Drug Metab. Dispos. 1997, vol. 25, No. 11, pp. 1311-1317.
Uekama et al., "$6^A$-O-[(4-Biphenylyl)acetyl]-α-, -β-, and -γ-cyclodextrins and 6 $^A$-Deoxy-6 $^A$-[[(4-biphenylyl)acetyl]amino]- α-, -β-, and -γ-cyclodextrins: Potential Prodrugs for Colon-Specific Delivery", J. Med. Chem., 1997, vol. 40, pp. 2755-2761.
Uhrich et al., "Polymeric Systems for Controlled Drug Release", Chemical Reviews, 1999, vol. 11, pp. 3181-3198.
Vert et al., "Something new in the field of PLA/GA bioresorbable polymers?" Journal of Controlled Release 53, 1998, pp. 85-92.
Wang et al., "Bioconjugation by Copper(I)-Catalyzed Azide-Alkyne [3+2] Cycloaddition", J. Am. Chem. Soc. 2003, vol. 125, pp. 3192-3193.
Wikby et al., "Separation of epimers of budesonide and related corticosteroids by high-performance liquid chromatography. A comparison between straight- and reversed-phase systems", Journal of Chromatography, 1978, 157(1), pp. 65-74.
Wikby et al., "Separation of epimers of budesonide and related corticosteroids by reversed bonded-phase liquid chromatography", Journal of Chromatography, 1978, 157(1), pp. 51-64.
Williams et al., Foye's Principles of Medicinal Chemistry, 5th Ed, pp. 59-63, 2002.
Xiao et al., "Synthesis and biological evaluation of novel pentacyclic triterpene [alpha]—cyclodextrin conjugates as HCV entry inhibitors", European Journal of Medicinal Chemistry, Nov. 1, 2016, vol. 124, pp. 1-9, XP055490888.
Yano et al., "Preparation of prednisolone-appended [alpha]-, [beta]- and [gamma]-cyclodextrins: Substitution at secondary hydroxyl groups and in vitro hydrolysis behavior", Journal of Pharmaceutical Sciences, American Chemical Society and American Pharmaceutical Association, US, Apr. 1, 2001, vol. 90, No. 4, pp. 493-503.
Zoltan, T., et al., "Synthesis of biologically active amino and aza steroids and some of their new chemical reactions", Int. Conf. Chem. Biotechnol. Biol. Act. Nat. Prod., 1981, 2, pp. 135-149.
Patani et al., "Bioisosterism: a Rational Approach in Drug Design", Chem. Rev. 96, 1996, pp. 3147-3176.
Thalen et al., "6a-Fluoro- and 6a,9a-difluoro-11b,21-dihydroxy-16a, 17a-propylmethylenedioxypregn-4-ene-3,20-dione: Synthesis and evaluation of activity and kinetics of their C-22 epimers", Steroids 63:37-43, 1998.
Reyna et al., "Targeted Delivery of LXR Agonist Using a Site-Specific Antibody—Drug Conjugate", Bioconjugate Chem. 2015, 26, pp. 2216-2222; DOI: 10.1021/acs.bioconjchem.5b00203.
Makinen et al., "Silencing of either SR-A or CD36 reduces at herosclerosis in hyperlipidaemic mice and reveals reciprocal upregulation of these receptors", Cardiovascular Research, 2010, vol. 88, No. 3, pp. 530-538.
Ozment et al., "Blood Monocyte Scavenger Receptor A (Cd204) Expression Is Increased in Septic Patients", SHOCK, 2016, vol. 45, No. 6S, p. 129.
CAS RN 917480-21-8 (entered into STN on Jan. 16, 2007).
Mark Frigerio et al., "The Chemical Design and Synthesis of Linkers Used in Antibody Drug Conjugates", Current Topics in Medicinal Chemistry, 2017, 17(32), pp. 3393-3424.
Everts et al., "Selective Intracellular Delivery of Dexamethasone into Activated Endothelial Cells Using an E-Selectin-Directed Immunoconjugate", J Immunol (2002) 168 (2): 883-889; https://doi.org/10.4049/jimmunol.168.2.883.
Han et al., "Development of Novel Glucocorticoids for Use in Antibody-Drug Conjugates for the Treatment of Inflammatory Diseases", J. Med. Chem. 2021, 64, pp. 11958-11971.
Pang et al., "Synthesis of an enzyme-dependent prodrug and evaluation of its potential for colon targeting", World J Gastroenterol., Oct. 15, 2002; 8(5): 913-917; doi: 10.3748/wjg.v8.15.913.
Varshosaz et al. "Synthesis and evaluation of dextran-budesonide conjugates as colon specific prodrugs for treatment of ulcerative colitis", International Journal of Pharmaceutics, Jan. 5, 2009;365(1-2):69-76; doi:10.1016/j.ijpharm.2008.08.034.
Gonzales et al., "Minimizing the Immunogenicity of Antibodies for Clinical Application", Tumor Biol. 2005; vol. 26, pp. 31-43; doi: 10.1159/000084184.
Kunik, Vered et al: "Structural consensus among antibodies defines the antigen binding site", PLoS Comput Biol 8(2): e1002388. https://doi.org/10.1371/journal.pcbi.1002388; Published Feb. 23, 2012.
Kussie et al., "A Single Engineered Amino Acid Substitution Changes Antibody Fine Specificity", Journal of Immunology, 1994, pp. 146-152.
Opalinski et al., "High Affinity Promotes Internalization of Engineered Antibodies Targeting FGFR1", International Journal of Molecular Sciences, 2018, vol. 19, 1435; Published online May 1, 20180. doi: 10.3390/ijms19051435.
Panka et al., "Variable region framework differences result in decreased or increased affinity of variant anti-digoxin antibodies", Proc. Natl. Acad. Sci. USA, vol. 85, May 1988, pp. 3080-30844, Immunology; doi: 10.1073/pnas.85.9.3080.
Rudikoff, Stuart el al., "Single amino acid substitution altering antigen-binding specificity", Proc. Nat. Acad. Sci., USA, vol. 79, Mar. 1982, pp. 1979-1983; DOI: 10.1073/pnas.79.6.1979.
Sela-Culang et al., "The Structural Basis of Antibody-Antigen Recognition", Frontiers in Immunology, vol. 4, article 302, Oct. 2013; doi: 10.3389/fimmu.2013.00302.
Wark et al., "Latest technologies for the enhancement of antibody affinity", Advanced Drug Delivery Reviews, 2006, vol. 58, pp. 657-670; doi:10.1016/j.addr.2006.01.025.
Besret et al., "Thiocarbamate-Linked Polysulfonate-Peptide Conjugates as Selective Hepatocyte Growth Factor Receptor Binders", dx.doi.org/10.1021/bc500137j | Bioconjugate Chem. 2014, 25, pp. 1000-1010.

P3-1
Fluocinolone acetonide

P3-2

P3-3

P4

P4-4

P3

P3

LP3-2

LP3

P4

LP3-1

LP13-1

LP3-3

LP13

LP14-1

LP15-1

LP15-2

LP15-3

LP15

Statistical comparison by Welch's t-test, *p<0.05

Scheme 1. Synthesis of Spacer-Budesonide 1c-1e, 1g-1i, and 1j-1l (a) piperidine, DCM,10-20 °C, 16 hrs.

Where the Compound of Formula (III) comprises 1c, 1d, 1e, 1g, 1h, 1i, 1j, 1k, 1l

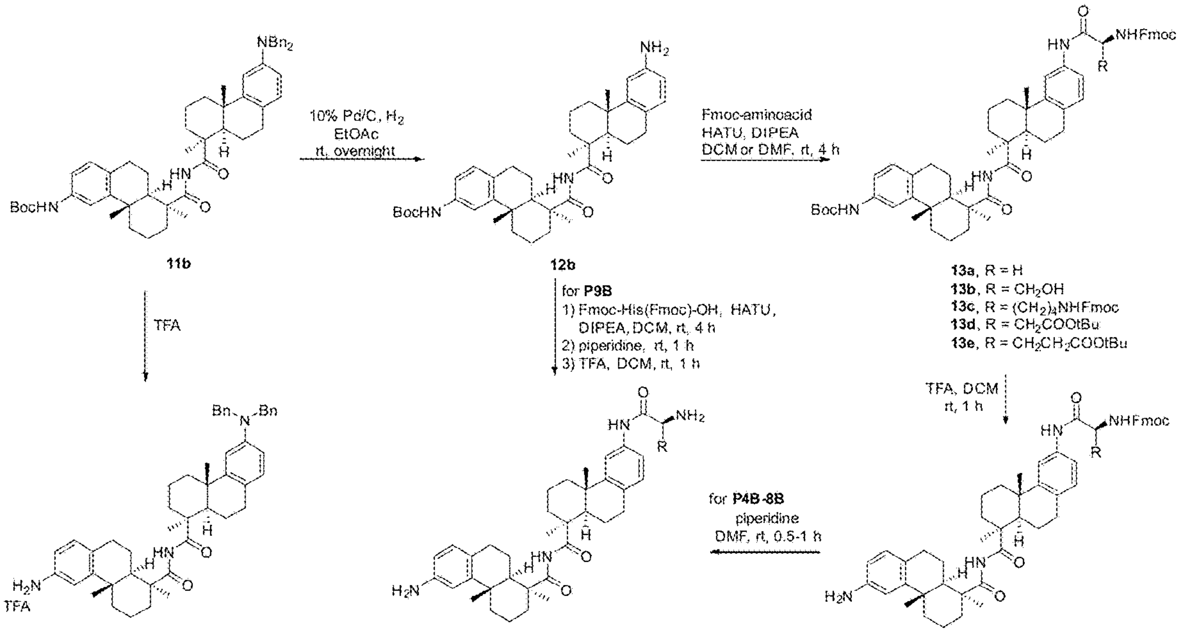
11b
12b
13a, R = H
13b, R = $CH_2OH$
13c, R = $(CH_2)_4NHFmoc$
13d, R = $CH_2COOtBu$
13e, R = $CH_2CH_2COOtBu$
P3B
P4B, R = H
P5B, R = $CH_2OH$
P6B, R = $(CH_2)_4NH_2$
P7B, R = $CH_2COOH$
P8B, R = $CH_2CH_2COOH$
P9B, R = $CH_2$-imidazole
14a, R = H
14b, R = $CH_2OH$
14c, R = $(CH_2)_4NHFmoc$
14d, R = $CH_2COOH$
14e, R = $CH_2CH_2COOH$
FIG. 23 Synthesis of Payloads P3B-P9B

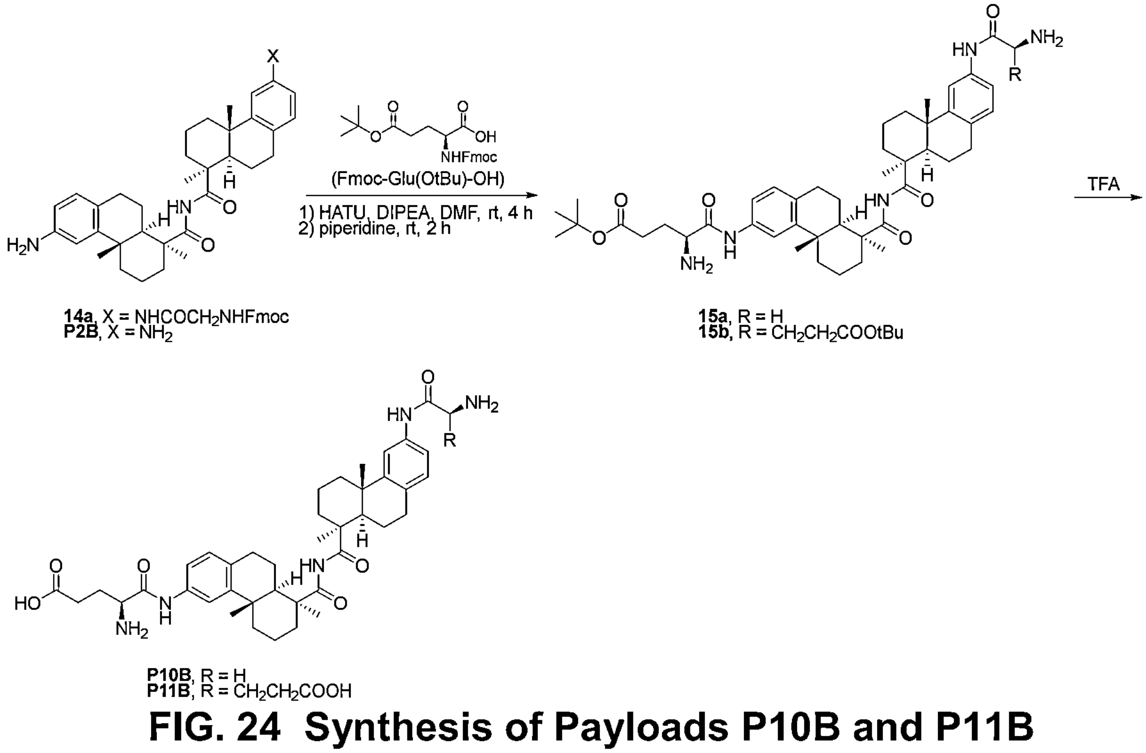
14a, X = $NHCOCH_2NHFmoc$
P2B, X = $NH_2$
15a, R = H
15b, R = $CH_2CH_2COOtBu$
P10B, R = H
P11B, R = $CH_2CH_2COOH$
FIG. 24 Synthesis of Payloads P10B and P11B

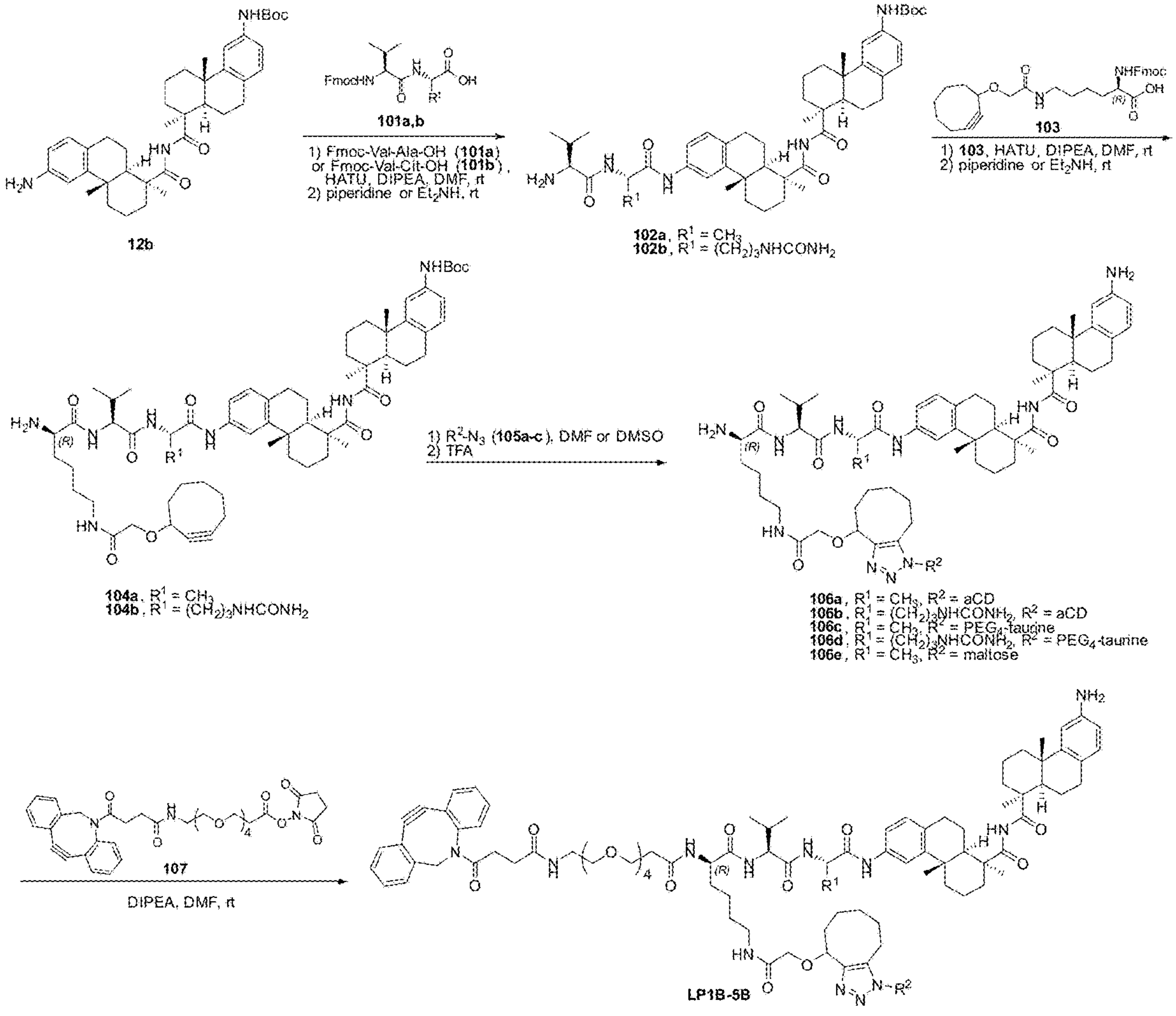
| Cpd# | $R^1$ | $R^2$ |
|---|---|---|
| LP1B | $CH_3$ | αCD |
| LP2B | $(CH_2)_3NHCONH_2$ | αCD |
| LP3B | $CH_3$ | $PEG_4$-taurine |
| LP4B | $(CH_2)_3NHCONH_2$ | $PEG_4$-taurine |
| LP5B | $CH_3$ | maltose |
FIG. 25 General Synthesis of Linker and LP1B-5B

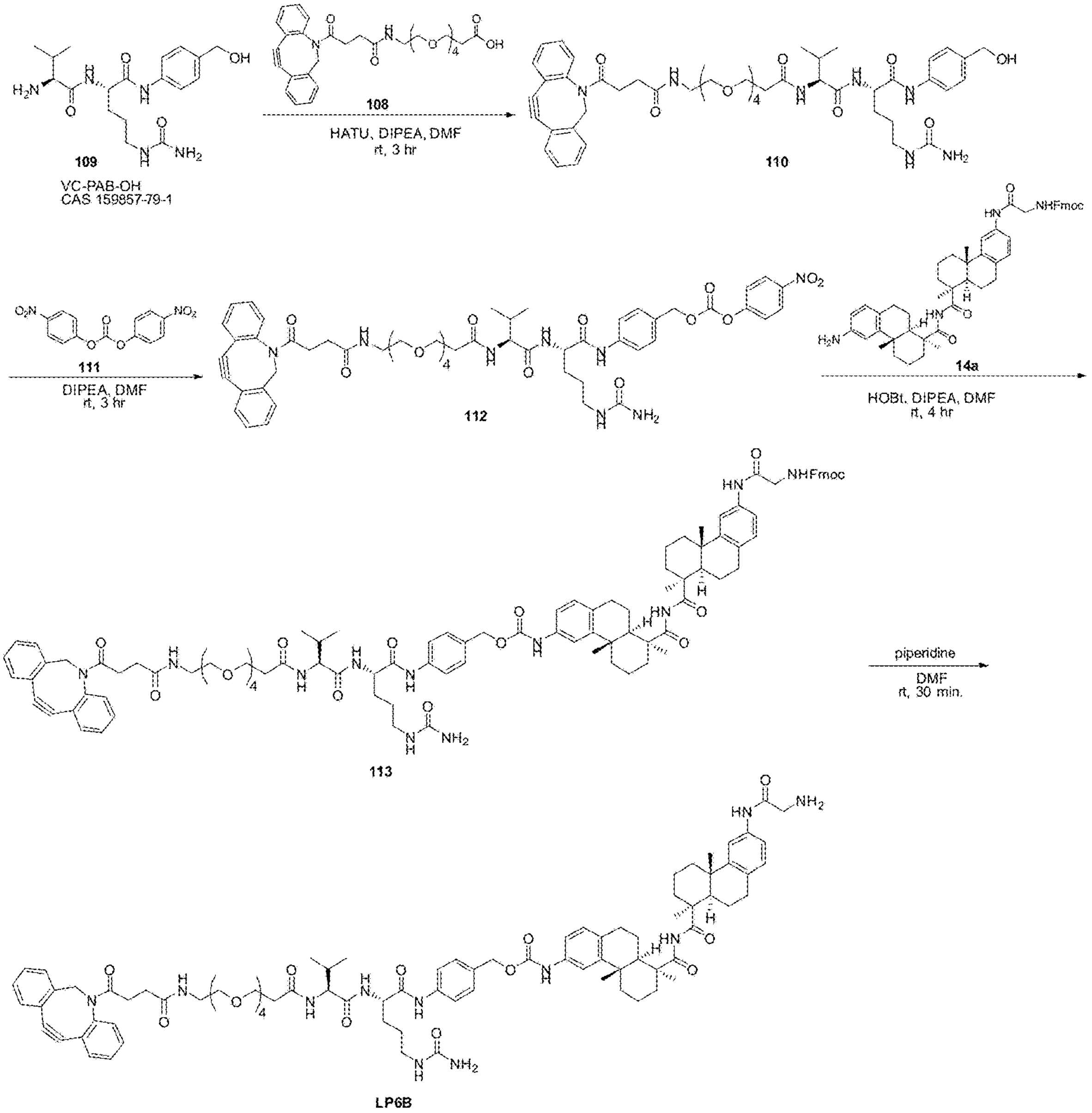
FIG. 26 Synthesis of LP6B

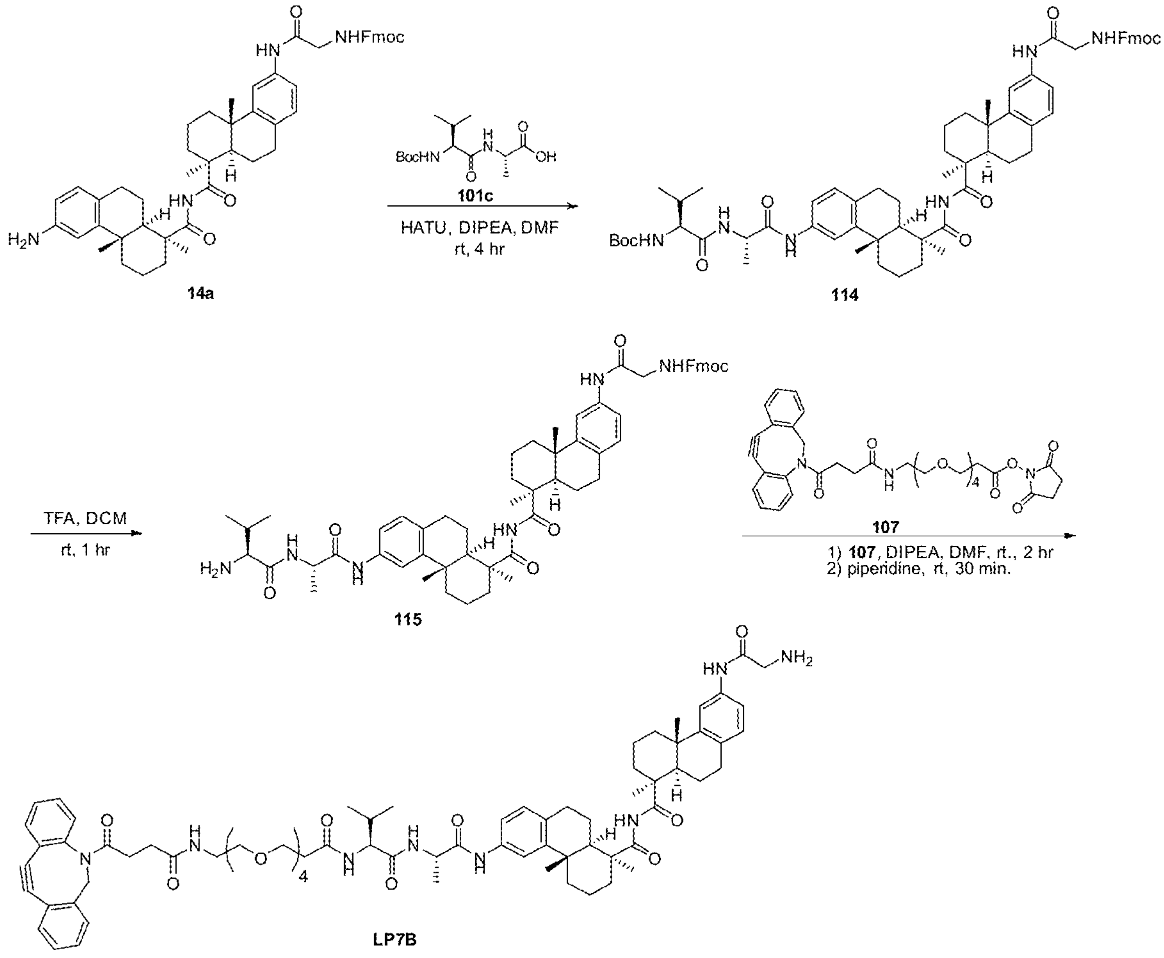
FIG. 27 Synthesis of LP7B

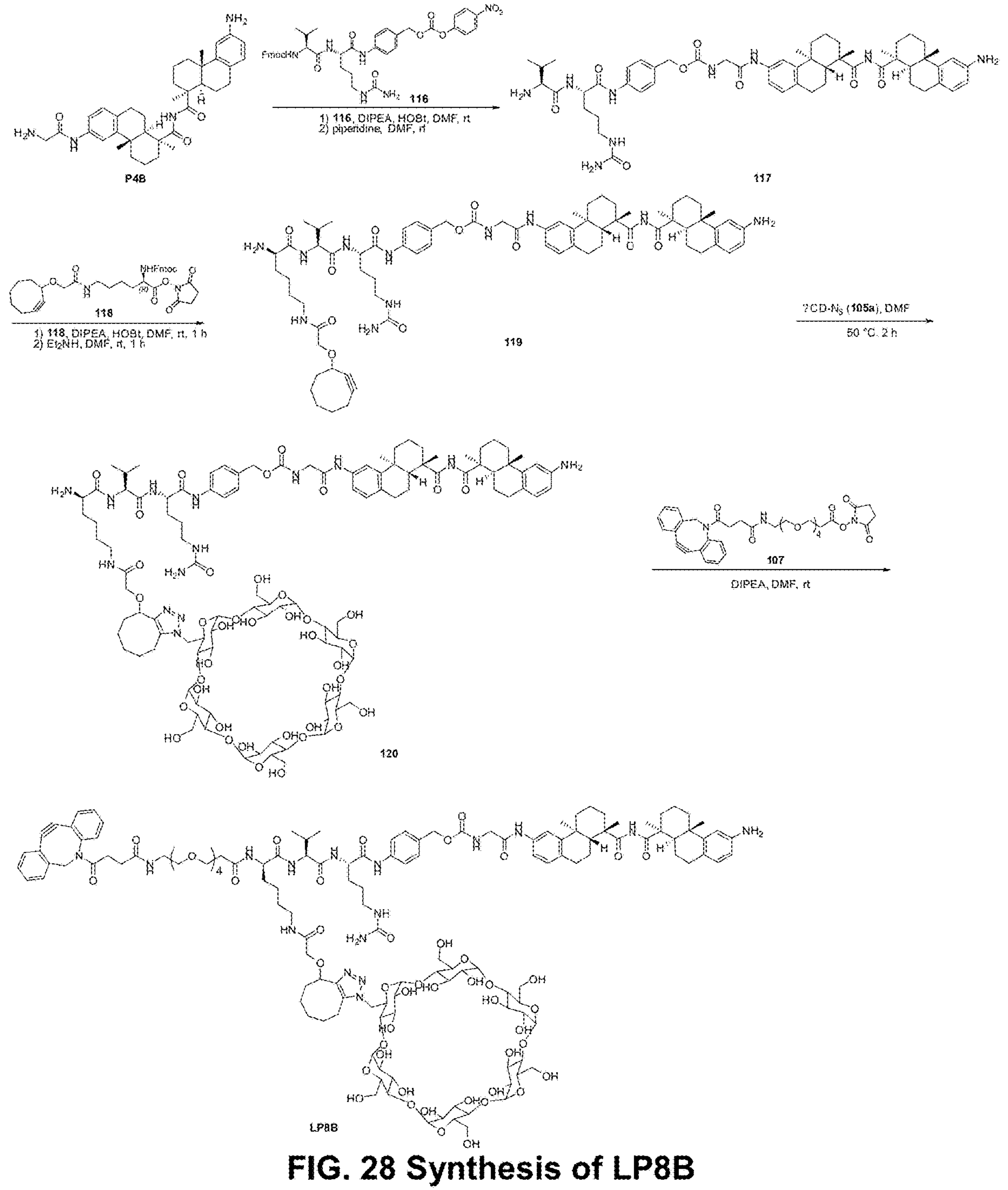
FIG. 28 Synthesis of LP8B

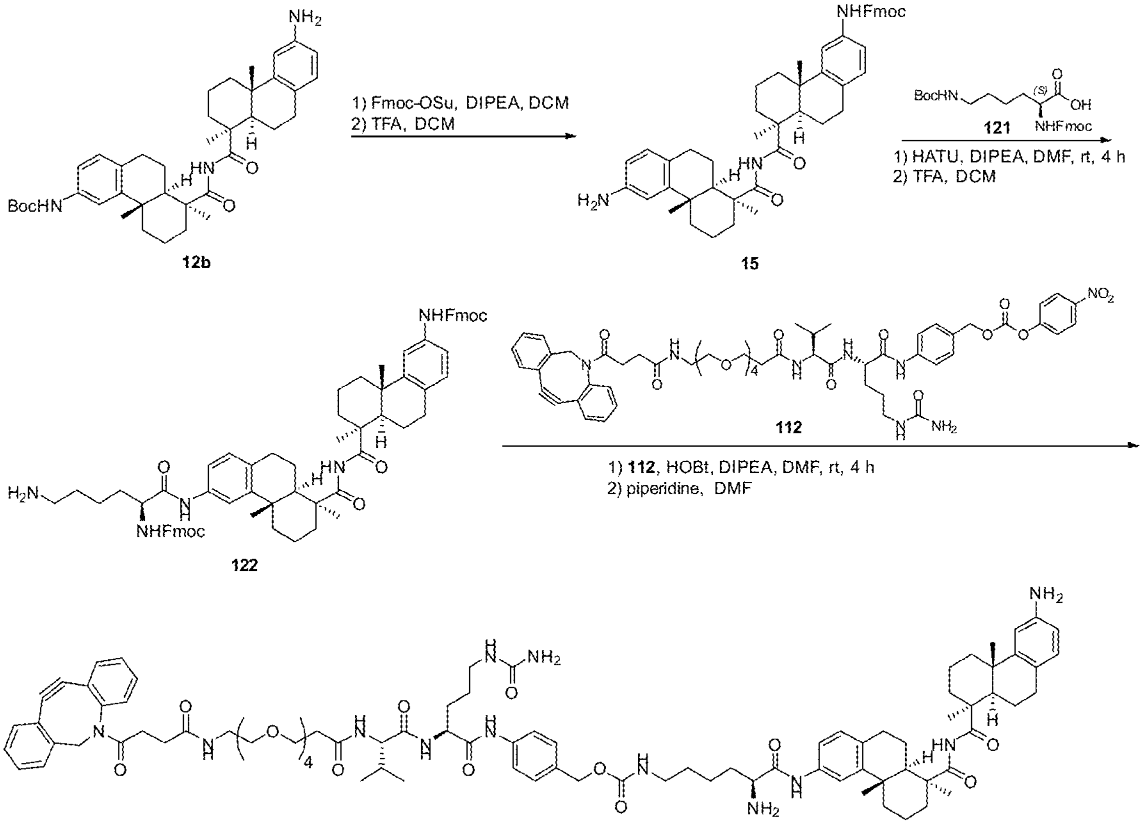
12b
15
121
122
112
LP9B
FIG. 29 Synthesis of LP9B

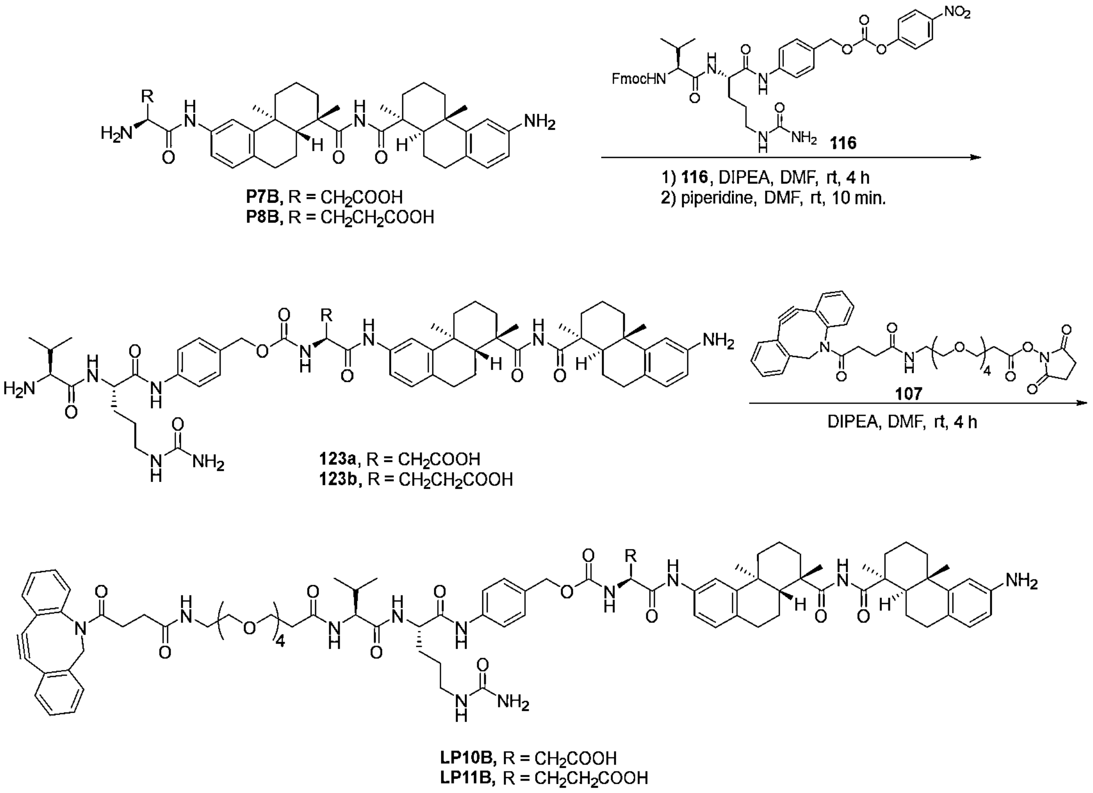
FIG. 30 Synthesis of LP10B and LP11B

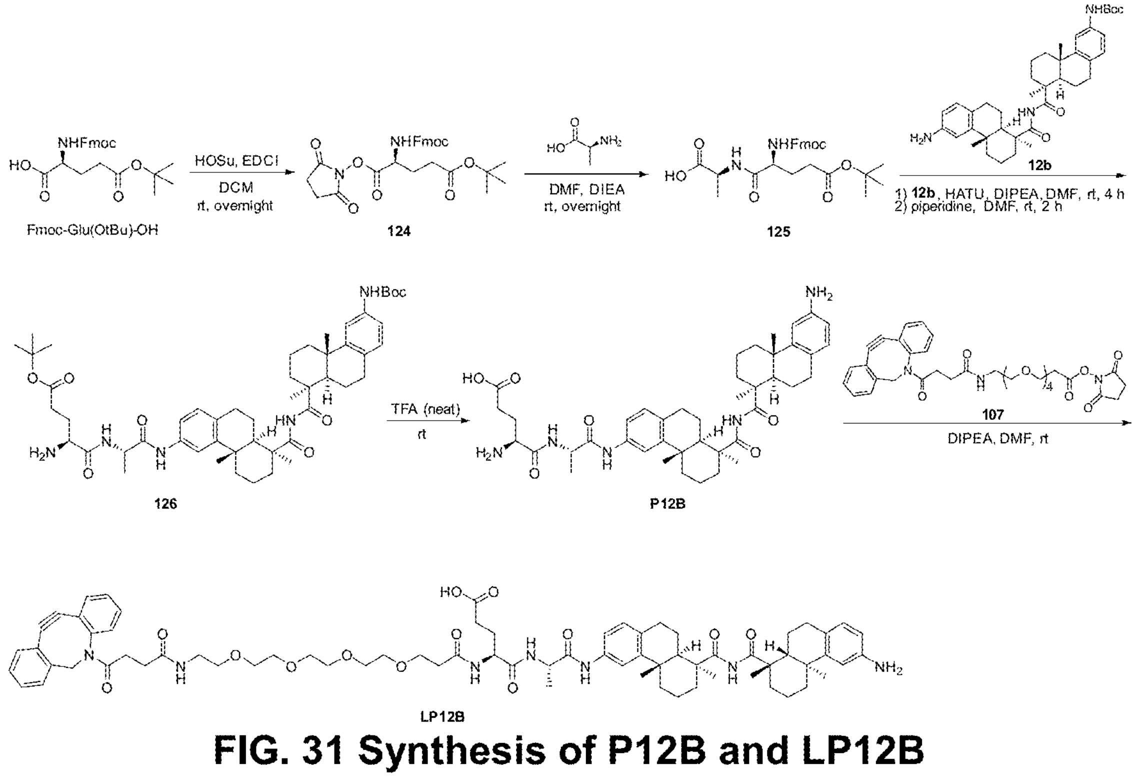
Fmoc-Glu(OtBu)-OH
124
125
12b
126
P12B
107
LP12B
FIG. 31 Synthesis of P12B and LP12B

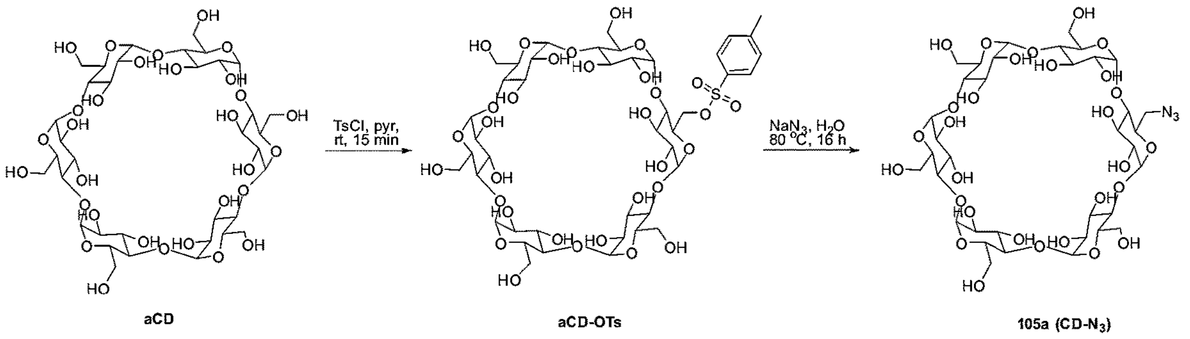
FIG. 32 Synthesis of Azide 105a
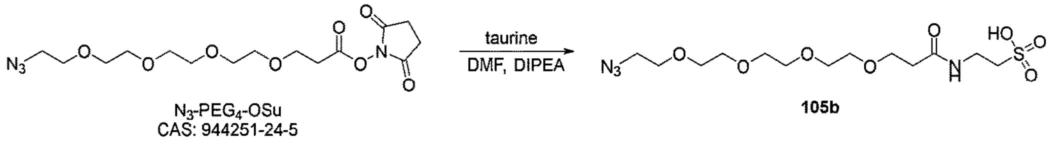
FIG. 33 Synthesis of Azide 105b
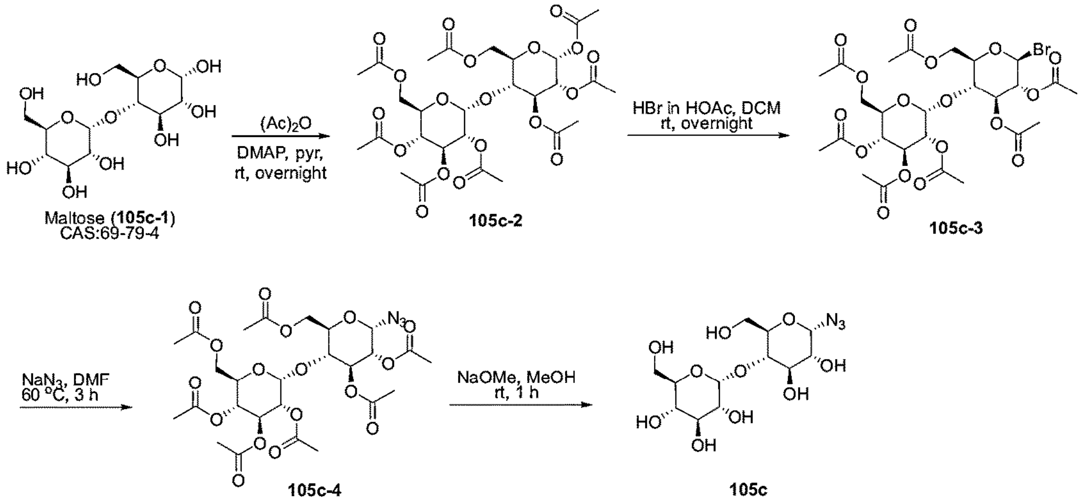
FIG. 34 Synthesis of intermediate 105c

ANTI-MSR1 ANTIBODIES AND METHODS OF USE THEREOF

This application is a Continuation application of U.S. patent application Ser. No. 16/407,099, filed on May 8, 2019, which claims the benefit of U.S. Provisional Application No. 62/669,276, filed May 9, 2018, U.S. Provisional Application No. 62/678,200, filed May 30, 2018, U.S. Provisional Application No. 62/769,946, filed Nov. 20, 2018, U.S. Provisional Application No. 62/789,987, filed Jan. 8, 2019, and U.S. Provisional Application No. 62/821,362, filed Mar. 20, 2019, which are incorporated herein by reference in their entireties for all purposes.

FIELD OF THE INVENTION

The present invention relates to antibodies, and antigen-binding fragments thereof, as well as antibody-drug conjugates of such antibodies, which specifically bind the trimeric membrane glycoprotein receptor (MSR1) and modulate MSR1 signal transduction, and methods of use thereof.

SEQUENCE LISTING

This application includes an electronically submitted sequence listing in .txt format. The .txt file contains a sequence listing entitled "114581_00514-SequenceListing.txt," created on Mar. 16, 2022, and is 169,122 bytes in size. The sequence listing contained in this .txt file is part of the specification and is incorporated herein by reference in its entirety. The sequence listing information submitted in the .txt file and recorded in computer readable format is identical to the written sequence listing.

BACKGROUND

Macrophage scavenger receptor 1 (MSR1) is a single-pass, trimeric type II transmembrane glycoprotein pattern recognition receptor that mediates uptake of a series of negatively charged/polyanionic ligands, including modified low density lipoproteins (LDL) (Krieger, M. 1994. *Annu. Rev. Biochem.* 63:601-637; Platt, N. and S. Gordon. 2001. *J Clin Invest.* 108(5):649-654) and advanced glycation end products of bovine serum albumin (AGE-BSA) (Smedsrød et al. 1997. *Biochem J.* 322 (Pt 2):567-573.) MSR1 receptors have been implicated in many macrophage-associated physiological and pathological processes including atherosclerosis, Alzheimer's disease, and host defense.

MSR1 expression was originally considered to be macrophage-specific. However, it has recently been demonstrated to be present on different classes of dendritic cells (Herber et al. 2010. *Nat. Med.* 16(8): 880-886). In addition, MSR1 appears to be expressed in endothelial cells and smooth muscle cells. It is internalized via coated pits at the cell surface and releases its ligand at acidic pH before being recycled back to the cell surface from the trans-Golgi apparatus (Doi et al. 1994. *Journal of Biological Chemistry*; Mori, T. 1994. *Lab Invest.*). It promotes conversion of monocyte-derived macrophages into foam cells, which is a critical step for atherosclerosis progression.

MSR1 isoforms type 1 and type 2 are functional receptors and are able to mediate endocytosis of modified low density lipoproteins (LDLs). MSR1 isoform type 3 can bind modified LDL (acetyl-LDL) but appears to be incapable of internalizing the bound complex. However, MSR1 also binds to a wide variety of ligands other than modified LDLs. These ligands include beta-amyloid protein, molecular chaperones, extracellular matrix protein, advanced glycation end products, apoptotic cells, and activated B-cells.

Liver X Receptor (LXR) includes LXRα and LXRβ which are ligand-dependent transcription factors that control the expression of genes involved in cholesterol, lipid and glucose homeostasis, inflammation, and innate immunity. LXRα is highly expressed in liver, intestine, adipose tissue, and differentiated macrophages; and LXRβ is ubiquitously expressed. LXRs have various biological functions including (i) stimulating the expression of cholesterol transporters, for example, ABCA1 and ABCG1, both of which mediate cellular cholesterol efflux; and (ii) negatively regulating macrophage inflammatory gene expression via repression of NF-kB activation. LXRs have also been implicated in atherosclerosis, proliferative disorders, neurodegenerative disorders, and inflammation. Proliferative disorders include melanomas, lung cancer, oral squamous carcinoma, and prostate cancer. (Pencheva et al. 2004; Wu et al. 2015; Kaneko et al. 2015; Chuu et al. 2006) Neurodegenerative disorders include Alzheimer's disease and myelin gene expression. (Terwel et al. 2011; Sandoval-Hernandez et al. 2016; Meffre et al. 2014) Inflammation includes inflammatory bowel disease, ulcerative colitis, Crohn's disease, and arthritis. (Anderson et al. 2011; Huang et al. 2015; Cui et al. 2012). Macrophage LXRs are known to include anti-atherogenic activity. LXR agonists are believed to be capable of (i) inhibiting the initiation and delay the progression of atherosclerosis; (ii) mitigating atherosclerosis and stabilizing established atherosclerotic lesions; and (iii) reducing lesion macrophage content by apoptosis.

The therapeutic potential of small molecule LXR modulators is limited by, for example, undesired modulation of LXR at non-target cells and/or low bioavailability. Modulation of LXR at non-target cells can lead to undesirable side effects, and low bioavailability may manifest for myriad reasons including, without limitation, low solubility that further exacerbates poor therapeutic windows for treatment. The development of ADCs comprising LXR modulators would allow for target-specific modulation of LXR, thereby avoiding side-effects caused by off-target modulation of LXR. Furthermore, such ADCs would provide improved modulation of biological targets, improved bioavailability, and improved therapeutic window. Therefore, there is a continuing need for effective treatments of, for example, metabolic diseases using antibody-drug conjugates of LXR modulators.

Glucocorticoids (GCs) are small molecule steroids that bind to glucocorticoid receptors (GRs) and are widely utilized in anti-inflammatory and immunosuppressive therapies. However, due to the ubiquitous expression of glucocorticoid receptors in many cell types, glucocorticoid treatments are compromised by toxicities to most organ systems. Thus, there is need for both novel glucocorticoids as well as novel therapies that minimize the side effects arising from glucocorticoid administration, particularly those arising from activating glucocorticoid receptors in non-target cells.

Rifamycins form a subclass of the ansamycin antibiotics family with an activity spectrum against gram-positive and gram-negative bacteria, and are commonly prescribed anti-mycobacterial drugs for the treatment of tuberculosis, leprosy and/or *Mycobacterium avium* complex (MAC). The rifamycin group of antibiotics includes the "classic" rifamycin drugs as well as rifamycin derivatives such as rifampicin (or rifampin), rifabutin, rifapentine, rifalazil and rifaximin. The increasing occurrence of antibiotic resistant strains of bacteria (e.g., methicillin resitant *S. aureus* (MRSA), vancomycin resistant *S. aureus* (VRSA)), multi-drug resistant *M. tuberculosis*), particularly in nosocomial settings, is an ongoing problem. There is a need for more effective analogs of rifamycins. Rifamycins are moderate to potent inducers of the cytochrome P450 enzyme system (notably CYP3A4), which can lead to reduced bioavailability and enhanced clearance of some coadministered drugs undergoing metabolism by the cytochrome P450 enzyme system (notably CYP3A4). Such interactions may be delayed in onset but persist beyond rifamycin coadministration. Rifampin may also induce P-glycoprotein (P-gp) multidrug efflux transporters. There is a need for novel therapies that minimize the side effects arising from administration of rifamycins, particularly those arising from activation of the cytochrome P450 enzyme system.

As disclosed in this application, MSR antibodies may provide a means for specific targeting of therapeutic molecules such as LXR agonists, steroids and rifamycins to minimize unwanted side effects arising from systemic administration of such compounds.

SUMMARY

Provided herein are antibodies, antigen-binding fragments of antibodies, and antibody-drug conjugates thereof that bind the membrane glycoprotein receptor known as MSR1. The antibodies are useful, inter alia, for targeting cells that express MSR1, such as macrophage cells. The anti-MSR1 antibodies, and antigen-binding portions thereof, can be used alone in unmodified form, or can be included as part of an antibody-drug conjugate.

The antibodies disclosed herein can be full-length (for example, an IgG1 or IgG4 antibody) or can comprise only an antigen-binding portion (for example, a Fab, $F(ab')_2$ or scFv fragment), and may be modified to affect functionality, e.g., to eliminate residual effector functions (Reddy et al., 2000, J. Immunol. 164:1925-1933).

Embodiments of anti-MSR1 antibodies disclosed herein are listed in Tables 4 and 5. Table 4 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MSR1 antibodies. Table 5 sets forth the nucleic acid sequence identifiers of the HCVRs, LCVRs, HCDR1, HCDR2 HCDR3, LCDR1, LCDR2 and LCDR3 of the exemplary anti-MSR1 antibodies.

Provided herein are antibodies or antigen-binding fragments thereof that specifically bind MSR1, comprising an HCVR comprising an amino acid sequence selected from any of the HCVR amino acid sequences listed in Table 4, or a substantially similar sequence thereof having at least 90%, at least 95%, at least 98% or at least 99% sequence identity thereto.

Also provided herein are antibodies or antigen-binding fragments thereof that specifically bind MSR1, comprising an LCVR comprising an amino acid sequence selected from any of the LCVR amino acid sequences listed in Table 4, or a substantially similar sequence thereof having at least 90%, at least 95%, at least 98% or at least 99% sequence identity thereto.

Also provided herein are antibodies or antigen-binding fragments thereof that specifically bind MSR1, comprising an HCVR and an LCVR amino acid sequence pair (HCVR/LCVR) comprising any of the HCVR amino acid sequences listed in Table 4 paired with any of the LCVR amino acid sequences listed in Table 4. Certain embodiments relate to antibodies, or antigen-binding fragments thereof, comprising an HCVR/LCVR amino acid sequence pair contained within any of the exemplary anti-MSR1 antibodies listed in Table 4. In some embodiments, the HCVR/LCVR amino acid sequence pair is selected from the group consisting of: 2/10, 34/42, 50/58; 98/106, and 290/298.

Provided herein are antibodies or antigen-binding fragments thereof that specifically bind MSR1, comprising a heavy chain CDR1 (HCDR1) comprising an amino acid sequence selected from any of the HCDR1 amino acid sequences listed in Table 4 or a substantially similar sequence thereof having at least 90%, at least 95%, at least 98% or at least 99% sequence identity.

Also provided herein are antibodies or antigen-binding fragments thereof that specifically bind MSR1, comprising a heavy chain CDR2 (HCDR2) comprising an amino acid sequence selected from any of the HCDR2 amino acid sequences listed in Table 4 or a substantially similar sequence thereof having at least 90%, at least 95%, at least 98% or at least 99% sequence identity.

Also provided herein are antibodies or antigen-binding fragments thereof that specifically bind MSR1, comprising a heavy chain CDR3 (HCDR3) comprising an amino acid sequence selected from any of the HCDR3 amino acid sequences listed in Table 4 or a substantially similar sequence thereof having at least 90%, at least 95%, at least 98% or at least 99% sequence identity.

Provided herein are antibodies or antigen-binding fragments thereof that specifically bind MSR1, comprising a light chain CDR1 (LCDR1) comprising an amino acid sequence selected from any of the LCDR1 amino acid sequences listed in Table 4 or a substantially similar sequence thereof having at least 90%, at least 95%, at least 98% or at least 99% sequence identity.

Also provided herein are antibodies or antigen-binding fragments thereof that specifically bind MSR1, comprising a light chain CDR2 (LCDR2) comprising an amino acid sequence selected from any of the LCDR2 amino acid sequences listed in Table 4 or a substantially similar sequence thereof having at least 90%, at least 95%, at least 98% or at least 99% sequence identity.

Also provided herein are antibodies or antigen-binding fragments thereof that specifically bind MSR1, comprising a light chain CDR3 (LCDR3) comprising an amino acid sequence selected from any of the LCDR3 amino acid sequences listed in Table 4 or a substantially similar sequence thereof having at least 90%, at least 95%, at least 98% or at least 99% sequence identity.

Also provided herein are antibodies or antigen-binding fragments thereof that specifically bind MSR1, comprising an HCDR3 and an LCDR3 amino acid sequence pair (HCDR3/LCDR3) comprising any of the HCDR3 amino acid sequences listed in Table 4 paired with any of the LCDR3 amino acid sequences listed in Table 4. Certain embodiments relate to antibodies, or antigen-binding fragments thereof, comprising an HCDR3/LCDR3 amino acid sequence pair contained within any of the exemplary anti-MSR1 antibodies listed in Table 4. In some embodiments, the HCDR3/LCDR3 amino acid sequence pair is selected from the group consisting of: 8/16, 40/48, 56/64; 96/104, and 288/296.

Provided herein are antibodies or antigen-binding fragments thereof that specifically bind MSR1, comprising a set of six CDRs (i.e., HCDR1-HCDR2-HCDR3-LCDR1-LCDR2-LCDR3) contained within any of the exemplary anti-MSR1 antibodies listed in Table 4. In certain embodiments, the HCDR1-HCDR2-HCDR3-LCDR1-LCDR2-

LCDR3 amino acid sequences set is selected from the group consisting of: 4-6-8-12-14-16; 36-38-40-44-46-48; 52-54-56-60-62-64; 100-102-104-108-110-112, and 292-294-296-300-302-304.

In a related embodiment, provided herein are antibodies, or antigen-binding fragments thereof that specifically bind MSR1, comprising a set of six CDRs (i.e., HCDR1-HCDR2-HCDR3-LCDR1-LCDR2-LCDR3) contained within an HCVR/LCVR amino acid sequence pair as defined by any of the exemplary anti-MSR1 antibodies listed in Table 4. For example, the present invention includes antibodies or antigen-binding fragments thereof that specifically bind MSR1, comprising the HCDR1-HCDR2-HCDR3-LCDR1-LCDR2-LCDR3 amino acid sequences set contained within an HCVR/LCVR amino acid sequence pair selected from the group consisting of: 2/10, 34/42, 50/58, 98/106, and 290/298. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are nucleic acid molecules encoding anti-MSR1 antibodies or portions thereof. For example, provided herein are nucleic acid molecules encoding any of the HCVR amino acid sequences listed in Table 4; in certain embodiments the nucleic acid molecule comprises a polynucleotide sequence selected from any of the HCVR nucleic acid sequences listed in Table 5, or a substantially similar sequence thereof having at least 90%, at least 95%, at least 98% or at least 99% sequence identity thereto.

Also provided herein are nucleic acid molecules encoding any of the LCVR amino acid sequences listed in Table 4; in certain embodiments the nucleic acid molecule comprises a polynucleotide sequence selected from any of the LCVR nucleic acid sequences listed in Table 5, or a substantially similar sequence thereof having at least 90%, at least 95%, at least 98% or at least 99% sequence identity thereto.

Also provided herein are nucleic acid molecules encoding any of the HCDR1 amino acid sequences listed in Table 4; in certain embodiments the nucleic acid molecule comprises a polynucleotide sequence selected from any of the HCDR1 nucleic acid sequences listed in Table 5, or a substantially similar sequence thereof having at least 90%, at least 95%, at least 98% or at least 99% sequence identity thereto.

Also provided herein are nucleic acid molecules encoding any of the HCDR2 amino acid sequences listed in Table 4; in certain embodiments the nucleic acid molecule comprises a polynucleotide sequence selected from any of the HCDR2 nucleic acid sequences listed in Table 5, or a substantially similar sequence thereof having at least 90%, at least 95%, at least 98% or at least 99% sequence identity thereto.

Also provided herein are nucleic acid molecules encoding any of the HCDR3 amino acid sequences listed in Table 4; in certain embodiments the nucleic acid molecule comprises a polynucleotide sequence selected from any of the HCDR3 nucleic acid sequences listed in Table 5, or a substantially similar sequence thereof having at least 90%, at least 95%, at least 98% or at least 99% sequence identity thereto.

Also provided herein are nucleic acid molecules encoding any of the LCDR1 amino acid sequences listed in Table 4; in certain embodiments the nucleic acid molecule comprises a polynucleotide sequence selected from any of the LCDR1 nucleic acid sequences listed in Table 5, or a substantially similar sequence thereof having at least 90%, at least 95%, at least 98% or at least 99% sequence identity thereto.

Also provided herein are nucleic acid molecules encoding any of the LCDR2 amino acid sequences listed in Table 4; in certain embodiments the nucleic acid molecule comprises a polynucleotide sequence selected from any of the LCDR2 nucleic acid sequences listed in Table 5, or a substantially similar sequence thereof having at least 90%, at least 95%, at least 98% or at least 99% sequence identity thereto.

Also provided herein are nucleic acid molecules encoding any of the LCDR3 amino acid sequences listed in Table 4; in certain embodiments the nucleic acid molecule comprises a polynucleotide sequence selected from any of the LCDR3 nucleic acid sequences listed in Table 5, or a substantially similar sequence thereof having at least 90%, at least 95%, at least 98% or at least 99% sequence identity thereto.

Also provided herein are nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-MSR1 antibodies listed in Table 4.

Also provided herein are nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-MSR1 antibodies listed in Table 4.

Also provided herein are nucleic acid molecules encoding both an HCVR and an LCVR, wherein the HCVR comprises an amino acid sequence of any of the HCVR amino acid sequences listed in Table 4, and wherein the LCVR comprises an amino acid sequence of any of the LCVR amino acid sequences listed in Table 4. In certain embodiments, the nucleic acid molecule comprises a polynucleotide sequence selected from any of the HCVR nucleic acid sequences listed in Table 5, or a substantially similar sequence thereof having at least 90%, at least 95%, at least 98% or at least 99% sequence identity thereto, and a polynucleotide sequence selected from any of the LCVR nucleic acid sequences listed in Table 5, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-MSR1 antibody listed in Table 4.

Also provided herein are recombinant expression vectors capable of expressing a polypeptide comprising a heavy or light chain variable region of an anti-MSR1 antibody. For example, embodiments include recombinant expression vectors comprising any of the nucleic acid molecules mentioned above, i.e., nucleic acid molecules encoding any of the HCVR, LCVR, and/or CDR sequences as set forth in Table 4. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

Provided herein are anti-MSR1 antibodies having a modified glycosylation pattern. In some embodiments, modification to remove undesirable glycosylation sites, may be useful for example, to increase antibody dependent cellular cytotoxicity (ADCC) function (see Shield et al. (2002) JBC 277:26733). In some embodiments, modification to provide an antibody lacking a fucose moiety present on the oligosaccharide chain, may be useful for example, to increase antibody dependent cellular cytotoxicity (ADCC) function. In other applications, modification of galactosylation can be made in order to modify complement dependent cytotoxicity (CDC).

In another aspect, provided herein is a pharmaceutical composition comprising a recombinant human antibody or fragment thereof which specifically binds MSR1 and a pharmaceutically acceptable carrier. In a related aspect, embodiments relate to a composition which is a combination of an anti-MSR1 antibody and a second therapeutic agent. In one embodiment, the second therapeutic agent is any agent that is advantageously combined with an anti-MSR1 antibody. Also provided herein are antibody-drug conjugates (ADCs) comprising an anti-MSR1 antibody conjugated to a drug or a therapeutic agent. Exemplary combination therapies, co-formulations, and ADCs involving the anti-MSR1 antibodies are disclosed elsewhere herein.

Also provided herein are antibody-drug conjugates (ADCs) comprising an anti-MSR1 antibody, or an MSR1 antigen-binding fragment thereof, conjugated to a drug or a therapeutic agent. Also provided herein are reactive linker-payloads useful for making the ADCs. Further provided herein are modified anti-MSR1 antibodies and modified MSR1 antigen-binding fragments useful for making the ADCs.

Also provided herein are therapeutic methods comprising administration of an anti-MSR1 antibody, an antigen-binding portion of an MSR1 antibody, or an ADC comprising an anti-MSR1 antibody of MSR1 antigen-binding fragment thereof, to a subject in need thereof. The therapeutic methods comprise administering a therapeutically effective amount of a pharmaceutical composition comprising an anti-MSR1 antibody, an antigen-binding portion of an MSR1 antibody, or an ADC comprising an anti-MSR1 antibody of MSR1 antigen-binding fragment thereof to the subject. The disorder treated is any disease or condition which is improved, ameliorated, inhibited or prevented by targeting MSR1. In some embodiments, the disease or condition is a proliferative disease, a metabolic disease, inflammation, a neurodegenerative disease, or disease, disorder, or condition associated with glucocorticoid receptor signaling. In some embodiments the disease or condition is atherosclerosis. In some embodiments, the disease, disorder, or condition associated with glucocorticoid receptor signaling is an inflammatory disease, disorder, or condition. In some of such embodiments, the side effects associated with administration of the unconjugated steroid payload of said compound are reduced. Also provided herein are therapeutic methods comprising administration an anti-MSR1 antibody, an antigen-binding portion of an MSR1 antibody, or an ADC comprising an anti-MSR1 antibody of MSR1 antigen-binding fragment thereof, for the treatment and/or prevention of bacterial infection in a subject.

Provided herein is the use of an anti-MSR1 antibody, an antigen-binding portion of an MSR1 antibody, or an ADC comprising an anti-MSR1 antibody of MSR1 antigen-binding fragment thereof, described herein, for the treatment of any disease disorder or condition described herein.

Also provided herein are therapeutic methods for treating, attenuating, or ameliorating atherosclerosis, comprising administration of an anti-MSR1 antibody, an antigen-binding portion of an MSR1 antibody, or an ADC comprising an anti-MSR1 antibody of MSR1 antigen-binding fragment thereof, to a subject in need thereof. The therapeutic methods comprise administering a therapeutically effective amount of a pharmaceutical composition comprising an anti-MSR1 antibody, an antigen-binding portion of an MSR1 antibody, or an ADC comprising an anti-MSR1 antibody of MSR1 antigen-binding fragment thereof to the subject.

Other embodiments will become apparent from a review of the ensuing detailed description.

BRIEF DESCRIPTION OF THE FIGURES

FIG. 23 provides a scheme for the synthesis of payloads, compounds, and bis-octahydrophenanthrene carboxamides P3B-P9B.

FIG. 24 provides a scheme for the synthesis of payloads, compounds, and bis-octahydrophenanthrene carboxamides P10B-P11B.

FIG. 25 provides a scheme for the synthesis of linkers and linker payloads LP1B-LP5B.

FIG. 26 provides a scheme for the synthesis of linkers and linker payload LP6B.

FIG. 27 provides a scheme for the synthesis of linkers and linker payload LP7B.

FIG. 28 provides a scheme for the synthesis of linkers and linker payload LP8B.

FIG. 29 provides a scheme for the synthesis of linkers and linker payload LP9B.

FIG. 30 provides a scheme for the synthesis of linkers and linker payloads LP10B, and LP11B.

FIG. 31 provides a scheme for the synthesis of payloads 12B, linkers and linker payload LP12B.

FIG. 32 provides a scheme for the synthesis of cyclodextrin-azide 105a.

FIG. 33 provides a scheme for the synthesis of azido-$PEG_4$-taurine 105b.

FIG. 34 provides a scheme for the synthesis of maltose-azide 105c.

DETAILED DESCRIPTION

Figure 1:
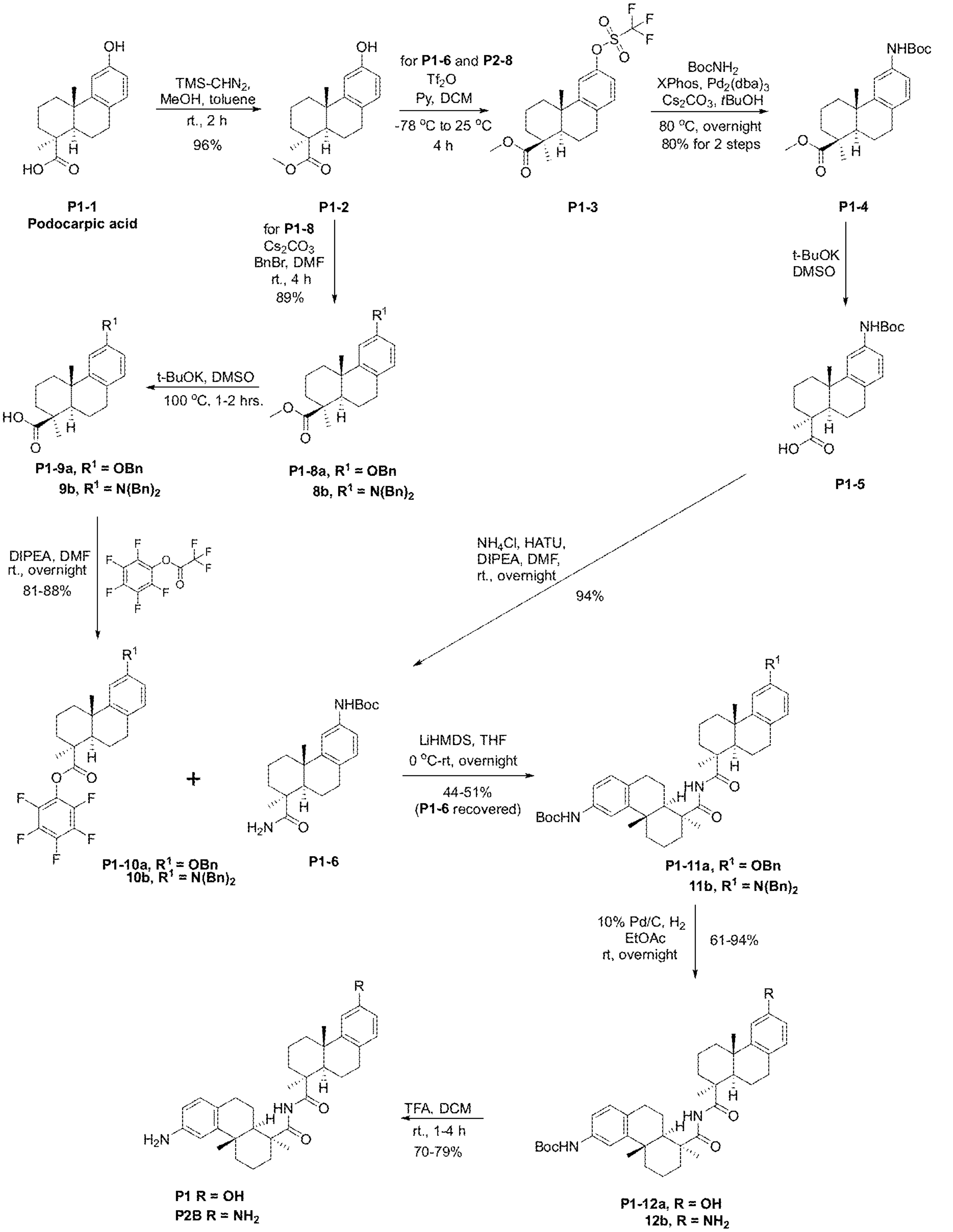
FIG. 1 provides a scheme for the synthesis of P1 and P2B.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "MSR1," "hMSR1" and the like, as used herein, refer to the human single-pass, trimeric type II transmembrane glycoprotein pattern recognition receptor comprising (i) the amino acid sequence as set forth in NCBI accession No. NP_002436.1, (ii) the amino acid sequence as set forth in NCBI accession No. NP_619729.1, and/or (iii) the amino acid sequence as set forth in NCBI accession No. NP_619730.1, which represent the various types and isoforms of class A macrophage scavenger receptors. The expression "MSR1" includes both monomeric and multimeric MSR1 molecules. As used herein, the expression "monomeric human MSR1" means a MSR1 protein or portion thereof that does not contain or possess any multimerizing domains and that exists under normal conditions as a single MSR1 molecule without a direct physical connection to another MSR1 molecule. An exemplary monomeric MSR1 molecule is the molecule referred to herein as "His-hMSR1" comprising the amino acid sequence of SEQ ID NO: 393 (see, e.g., Example 3, herein).

All references to proteins, polypeptides and protein fragments herein are intended to refer to the human version of the respective protein, polypeptide or protein fragment unless explicitly specified as being from a non-human species. Thus, the expression "MSR1" means human MSR1 unless specified as being from a non-human species, e.g., "mouse MSR1," "monkey MSR1," etc.

As used herein, the expression "cell surface-expressed MSR1" means one or more MSR1 protein(s), or the extracellular domain thereof, that is/are expressed on the surface of a cell in vitro or in vivo, such that at least a portion of a MSR1 protein is exposed to the extracellular side of the cell membrane and is accessible to an antigen-binding portion of an antibody. A "cell surface-expressed MSR1" can comprise or consist of a MSR1 protein expressed on the surface of a cell which normally expresses MSR1 protein. Alternatively, "cell surface-expressed MSR1" can comprise or consist of MSR1 protein expressed on the surface of a cell that normally does not express human MSR1 on its surface but has been artificially engineered to express MSR1 on its surface.

As used herein, the expression "anti-MSR1 antibody" includes monovalent antibodies with a single specificity, as well as bispecific antibodies comprising a first arm that binds MSR1 and a second arm that binds a second (target) antigen, wherein the anti-MSR1 arm comprises any of the HCVR/LCVR or CDR sequences as set forth in Table 4 herein. The expression "anti-MSR1 antibody" also includes antibody-drug conjugates (ADCs) comprising an anti-MSR1 antibody or antigen-binding portion thereof conjugated to a drug or a therapeutic agent. The expression "anti-MSR1 antibody" also includes antibody-radionuclide conjugates (ARCs) comprising an anti-MSR1 antibody or antigen-binding portion thereof conjugated to a radionuclide.

The term "antibody", as used herein, means any antigen-binding molecule or molecular complex comprising at least one complementarity determining region (CDR) that specifically binds to or interacts with a particular antigen (e.g., MSR1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-MSR1 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$—$C_H3$; (iv) $V_H$—$C_H1$-$C_H2$; (v) $V_H$—$C_H1$-$C_H^2$—$C_H^3$; (vi) $V_H$-$C_H^2$—$C_H^3$; (vii) $V_H$-$C_L$; (viii) $V_L$-$C_H1$; (ix) $V_L$-$C_H^2$; (x) $V_L$-$C_H3$; (xi) $V_L$-$C_H1$-$C_H2$; (xii) $V_L$-$C_H1$-$C_H^2$—$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the anti-MSR1 antibodies disclosed herein are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies disclosed herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. Embodiments disclosed herein encompass antibodies having one or more mutations in the hinge, $C_H2$ or $C_H3$ region which may be desirable, for example, in production, to improve the yield of the desired antibody form.

The antibodies disclosed herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-MSR1 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. Embodiments include antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within embodiments disclosed herein.

Embodiments also include anti-MSR1 antibodies comprising variants of any of the HCVR, LCVR, and/or CDR amino acid sequences disclosed herein having one or more conservative substitutions. For example, embodiments include anti-MSR1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 4 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term provided herein, these Definitions prevail unless stated otherwise.

The terms "a" or "an," as used in herein means one or more, unless context clearly dictates otherwise.

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those radicals having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. A pentyl moiety includes, but is not limited to, n-pentyl and i-pentyl. A hexyl moiety includes, but is not limited to, n-hexyl.

As used herein, "alkylene" refers to a divalent alkyl group. Unless specified otherwise, alkylene includes, but is not limited to, 1-20 carbon atoms. The alkylene group is optionally substituted as described herein for alkyl. In some embodiments, alkylene is unsubstituted. In some embodiments, alkylene is a divalent branched alkyl group.

The term "amino" means $—NH_2$.

The term "alkylamino," as used herein, and unless otherwise specified, refers to the group —NHR' where R' is $C_{1-10}$ alkyl, as defined herein. In some or any embodiments, the alkylamino is $C_{1-6}$alkylamino.

The term "dialkylamino," as used herein, and unless otherwise specified, refers to the group —NR'R' where each R' is independently $C_{1-10}$ alkyl, as defined herein. In some or any embodiments, the dialkylamino is di-$C_{1-6}$alkylamino.

The term "aminoalkyl," as used herein, and unless otherwise specified, refers to an alkyl group, as defined herein, which is substituted with one or more amino groups. In some or any embodiments, the aminoalkyl is an alkyl group substituted with one $—NH_2$ group (e.g., $—R'(NH_2)$ where R' is $—C_{1-10}$ alkyl, as defined herein). In some or any embodiments, the aminoalkyl is an alkyl group substituted with two $—NH_2$ groups. In some embodiments, "aminoalkyl" is amino$C_{1-6}$alkyl An "alkylaminoalkyl," as used herein, and unless otherwise specified, refers to an alkyl group, as defined herein, which is substituted with one or more alkylamino groups as defined herein. In some embodiments, an "alkylaminoalkyl" is $C_{1-6}$alkylamino$C_{1-6}$alkyl. In some embodiments, each alkyl in alkylaminoalkyl is independently selected.

A "dialkylaminoalkyl" as used herein, and unless otherwise specified, refers to an alkyl group, as defined herein, which is substituted with one or more dialkylamino groups as defined herein. In some embodiments, "dialkylaminoalkyl" is di-$C_{1-6}$alkylamino$C_{1-6}$alkyl. In some embodiments, each alkyl in dialkylaminoalkyl is independently selected.

As used herein, the term "O-amino acid" or "HO-amino acid" designates an amino acid wherein the native amino group at the N-terminus of an amino acid or an amino acid sequence has been replaced with an oxygen or hydroxyl group, respectively. For example, "O-AAAA" or "HO-AAAA" is intended to designate an amino acid sequence (AAAA) wherein the native amino group at the N-terminus has been replaced with an oxygen or hydroxyl group, respectively (e.g.,

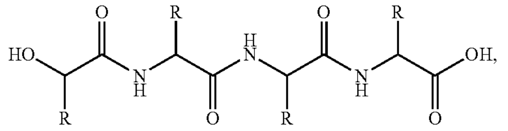

where each R is an amino acid side chain). Similarly, the terms "O-amino acid residue" or "HO-amino acid residue" refers to the chemical moiety within a compound that remains after a chemical reaction. For example, "O-amino acid residue" or "HO-amino acid residue" refers to the product of an amide coupling or peptide coupling of an O-amino acid or a HO-amino acid to a suitable coupling partner; wherein, for example, a water molecule is expelled after the amide or peptide coupling of the O-amino acid or a HO-amino acid, resulting in the product having the O-amino acid residue or a HO-amino acid residue incorporated therein.

Designation of an amino acid or amino acid residue without specifying its stereochemistry is intended to encompass the L form of the amino acid, the D form of the amino acid, or a racemic mixture thereof.

As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, $—CF_3$, $—CH_2CF_3$, $—CCl_2F$, and $—CCl_3$.

As used herein, "alkenyl" refers to a monovalent hydrocarbon radical moiety containing at least two carbon atoms and one or more non-aromatic carbon-carbon double bonds. Alkenyl is optionally substituted and can be linear, branched, or cyclic. Alkenyl includes, but is not limited to, those radicals having 2-20 carbon atoms, i.e., $C_{2-20}$ alkenyl; 2-12 carbon atoms, i.e., $C_{2-12}$ alkenyl; 2-8 carbon atoms, i.e., $C_{2-8}$ alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those radicals having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2—O—$ for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to, those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are not limited to, phenyl, naphthyl, fluorenyl, azulenyl, anthryl, phenanthryl, and pyrenyl.

As used herein, "arylalkyl" refers to a monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

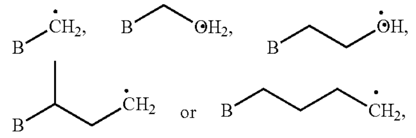

wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "alkylaryl" refers to a monovalent moiety that is a radical of an aryl compound, wherein the aryl compound is substituted with an alkyl substituent, i.e., the aryl compound includes a single bond to an alkyl group and wherein the radical is localized on the aryl group. An alkylaryl group bonds to the illustrated chemical structure via the aryl group. An alkylaryl can be represented by the structure, e.g.,

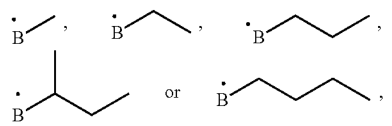

wherein B is an aromatic moiety, e.g., phenyl. Alkylaryl is optionally substituted, i.e., the aryl group and/or the alkyl group, can be substituted as disclosed herein. Examples of alkylaryl include, but are not limited to, toluyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.,

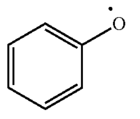

for phenoxy. Aryloxy substituents bond to the compound which they substitute through this oxygen atom. Aryloxy is optionally substituted. Aryloxy includes, but is not limited to, those radicals having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^b$N-aryloxy" refers to a monovalent moiety that is a radical of an aromatic compound wherein the ring atoms are carbon atoms and wherein the ring is substituted with at least one $R^aR^b$N-substituent and at least one oxygen radical, i.e., the aromatic compound includes a single bond to an $R^aR^b$N-substituent and a single bond to an oxygen atom and wherein the radical is localized on the oxygen atom, e.g.,

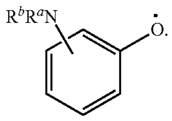

$R^aR^b$N-aryloxy substituents bond to the compound which they substitute through this oxygen atom. $R^aR^b$N-aryloxy is optionally substituted. $R^aR^b$N-aryloxy includes, but is not limited to, those having 6 to 20 ring carbon atoms, for example, $C_{6-20}$ ($R^aR^b$N)n-aryloxy, 6 to 15 ring carbon atoms, for example, $C_{6-15}$ ($R^aR^b$N)n-aryloxy, and 6 to 10 ring carbon atoms, for example, $C_{6-10}$ ($R^aR^b$N)n-aryloxy, wherein n represents the number of $R^aR^b$N-substituents. An example of an $R^aR^b$N-aryloxy moiety includes, but is not limited to 4-(dimethylamino)-phenoxy,

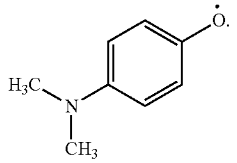

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, and sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, for example, optionally substituted alkyl, optionally substituted aryl, optionally substituted heteroaryl, optionally substituted arylene, and optionally substituted heteroarylene, means that such moiety is optionally bonded to one or more substituents. Examples of such substituents include, but are not limited to, halo, cyano, nitro, optionally substituted haloalkyl, azido, epoxy, optionally substituted heteroaryl, optionally substituted heterocycloalkyl,

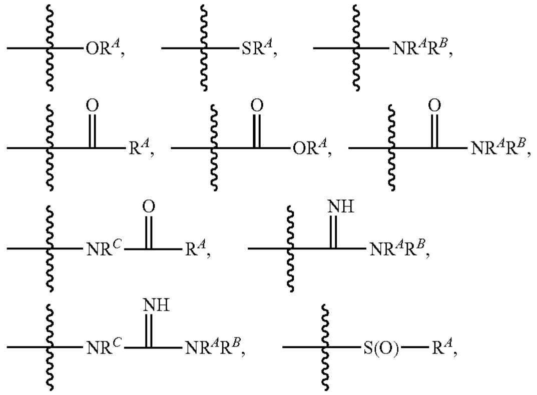

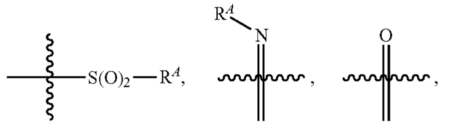

or

-continued

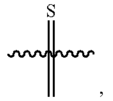

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic ring, wherein the ring is optionally substituted, and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "O-glucose" refers to a monovalent moiety attached via an exocyclic glucose oxygen atom. Suitable 0-glucose moieties include, without limitation,

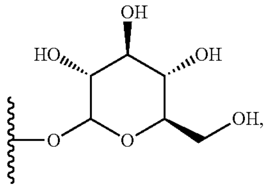 [SMILES: *OC1O[C@H](CO)[C@@H](O)[C@H](O)[C@H]1O]

and the like.

As used herein, "O-$PEG_n$" refers to a monovalent moiety attached via the terminal oxygen atom, where n is from 1 to 100. For example, when n is 1, then O-PEGn is $—O—CH_2CH_2OH$; when n is two, then O-PEGn is $—O—CH_2CH_2O—CH_2CH_2OH$; and when n is three, then O-PEGn is $—O—CH_2CH_2O—CH_2CH_2O—CH_2CH_2OH$.

As used herein, "binding agent" refers to any molecule, e.g., protein or antibody, capable of binding with specificity to a given binding partner, e.g., antigen.

As used herein, "linker" refers to a divalent, trivalent, or multivalent moiety that covalently links the binding agent to one or more compounds described herein, for instance payload compounds and/or a hydrophilic group, as described herein.

As used herein, a "connector group" or a "connector group residue" refers to any group which may facilitate a release of a payload. Suitable connector groups facilitate the release of divalent or multivalent appended payloads back to the original unconjugated forms with little or no derivatization. Examples of connector groups include and are not limited to

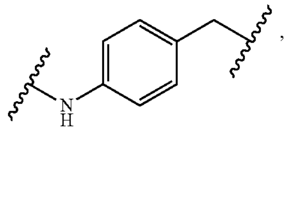

-continued

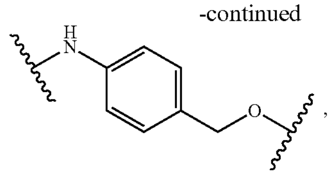

or derivatives thereof. In another example, a connector group is

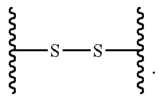 [SMILES: *SS*]

In further examples, a connector group is a self immolative group. A "self-immolative group" refers to any such group known to those of skill in the art. In particular embodiments, the self-immolative group is p-aminobenzyloxycarbonyl (PAB/PABC), i.e.

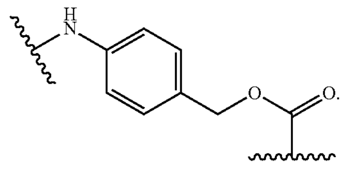 [SMILES: *Nc1ccc(COC(*)=O)cc1]

Those of skill will recognize that a self-immolative group is capable of carrying out a chemical reaction which releases the remaining atoms of a linker from a payload.

As used herein. "connecting linker" ($L^2$) or "connecting linkers" refers to divalent groups which are cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable connecting linkers include, but are not limited to, acid-labile linkers, hydrolysis-labile linkers, enzymatically cleavable linkers, reduction labile linkers, and non-cleavable linkers. Suitable linkers also include, but are not limited to, those that are or comprise glucuronides, succinimide-thioethers, polyethylene glycol (PEG) units, hydrazones, mal-caproyl units, disulfide units (e.g., —S—S—, $—S—C(R^{1b}R^{2b})—$, wherein $R^{1b}$ and $R^{2b}$ are independently hydrogen or hydrocarbyl), carbamate units, para-amino-benzyl units (PAB), phosphate units, e.g., mono-, bis-, or tris-phosphate units, and peptide units, e.g., peptide units containing two, three four, five, six, seven, eight, or more amino acid residues, including but not limited to valine-citrulline residue units. As used herein, "caproyl" means a $—(CH_2)_5—C(O)—$ group.

As used herein, the phrase "reactive group" ("RG"), refers to a functional group or moiety that reacts with a reactive portion of an antibody, modified antibody, or antigen binding fragment thereof. In certain embodiments, the "reactive group" is a functional group or moiety (e.g., maleimide or NHS ester) that reacts with a cysteine or lysine residue of an antibody or antigen-binding fragment thereof. In certain embodiments, the "reactive group" is a functional group or moiety that is capable of undergoing a click chemistry reaction. In some embodiments of said click chemistry reaction, the reactive group comprises an alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, DIBAC (where the —$C(O)CH_2CH_2C(O)$— portion of DIBAC moiety can be represented by L and/or $L^2$), DIBO (where the —O— portion of DIBO moiety can be represented by L and/or $L^2$), BARAC (where the

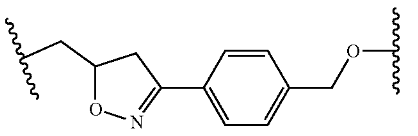 [SMILES: *CC1CC(c2ccc(CO*)cc2)=NO1]

portion of BARAC moiety can be represented by L and/or $L^2$), DIFO (where the —O— portion can be represented by L and/or $L^2$), substituted alkynes, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295 (EU numbering), with a compound according to the formula $H_2N$-LL-$N_3$, wherein LL is a divalent polyethylene glycol group, in the presence of the enzyme transglutaminase.

In some embodiments, the reactive group (RG) is an alkyne, e.g.,

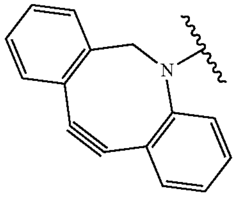

, which can react via click chemistry with an azide, e.g.,

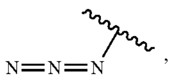

, to form a click chemistry product, e.g.,

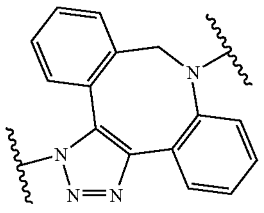

, its regioisomer, or mixture thereof. In some embodiments, the reactive group is an alkyne, e.g.,

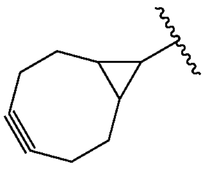

or

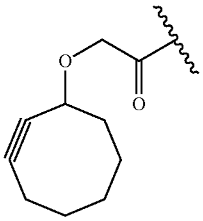

(where L and/or $L^2$ encompasses —OCH2C(O)—), which can react via click chemistry with an azide, e.g.,

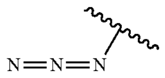

to form a click chemistry product, e.g.,

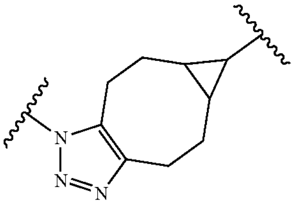

.

In some embodiments, the reactive group is an alkyne, e.g.,

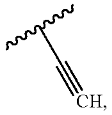 [SMILES: *C#C]

, which can react via click chemistry with an azide, e.g.,

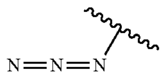

, to form a click chemistry product, e.g.,

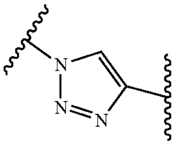

.

its regioisomer, or mixture thereof. In some embodiments, the reactive group is a functional group, e.g.,

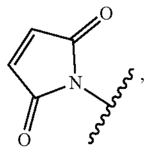 [SMILES: *N1C(=O)C=CC1=O]

which reacts with a cysteine residue on an antibody or antigen-binding fragment thereof, to form a bond thereto, e.g.,

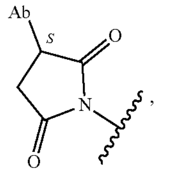

wherein Ab refers to an antibody or antigen-binding fragment thereof and S refers to the S atom on a cysteine residue through which the functional group bonds to the Ab. In some embodiments, the reactive group is a functional group, e.g.,

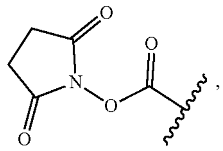 [SMILES: *C(=O)ON1C(=O)CCC1=O]

which reacts with a lysine residue on an antibody or antigen-binding fragment thereof, to form a bond thereto, e.g.,

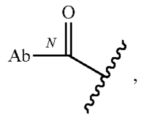

wherein Ab refers to an antibody or antigen-binding fragment thereof and N refers to the N atom on, e.g., a lysine or an amino terminus residue through which the functional group bonds to the Ab. In some instances, a reactive group is

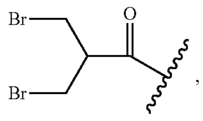

which reacts with two thiols (e.g., thiols on two different chains) of an antibody or antigen-binding fragment thereof, to form a bond thereto, e.g.,

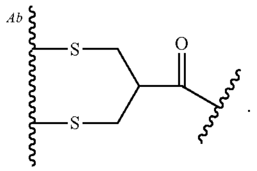

In some instances, a reactive group is

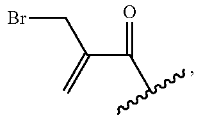 [SMILES: *C(=O)C(=C)CBr]

which reacts with two thiols (e.g., thiols on two different chains) of an antibody or antigen-binding fragment thereof, to form a bond thereto, e.g.,

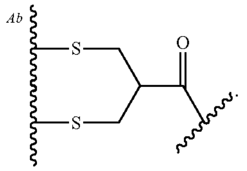 [SMILES: *SCC(CS*)C(*)=O]

As used herein, the phrase "reactive group residue" refers to a product of the reaction of a functional group in the linker moiety with the reactive portion of a binding agent (BA), including the product of click chemistry. The reactive group residue is formed by the reaction of a reactive group on an amino acid of the binding agent, and is attached to the binding agent (e.g. antibody) and to the linker. In some embodiments, the reactive group residue is a group which comprises 1,2,3-tetrazole, i.e. is formed by the reaction of an alkyne with an azide. In some embodiments, the reactive group residue is (a)

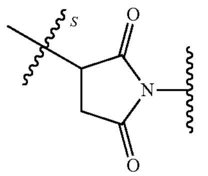

wherein S refers to the S atom on a cysteine residue through which (a) bonds to the Ab, and which is formed by the reaction of

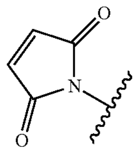 [SMILES: *N1C(=O)C=CC1=O]

with a cysteine residue on an antibody or antigen-binding fragment thereof. In some embodiments, the reactive group residue is

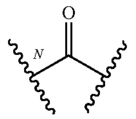

wherein N refers to the N atom on a lysine residue, and which is formed by the reaction of a functional group, e.g.,

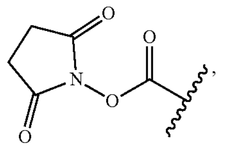 [SMILES: *C(=O)ON1C(=O)CCC1=O]

with a lysine residue on an antibody or antigen-binding fragment thereof. Those of skill in the art will recognize that portions of the reactive group residue may come from the reactive group, from the antibody, or both. In some instances the reactive group residue is

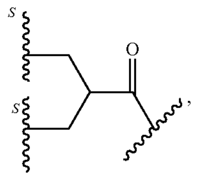

where S refers to the S atom on a cysteine residue, and which is formed by the reaction of a functional group

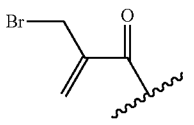

or

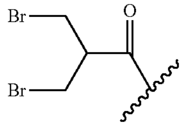

with a cysteine residue on an antibody or antigen-binding fragment thereof.

As used herein, "pharmaceutically acceptable salt" refers to any salt suitable for administration to a patient. Suitable salts include, but are not limited to, those disclosed in. Berge et al., "Pharmaceutical Salts", *J. Pharm. Sci.,* 1977, 66:1, incorporated herein by reference. Examples of salts include, but are not limited to, acid-derived, base-derived, organic, inorganic, amine, and alkali or alkaline earth metal salts, including but not limited to calcium salts, magnesium salts, potassium salts, sodium salts, salts of hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. In some examples, a payload described herein (e.g., a rifamycin analog described herein) comprises a tertiary amine, where the nitrogen atom in the tertiary amine is the atom through which the payload is bonded to a linker or a linker-spacer. In such instances, bonding to the tertiary amine of the payload yields a quarternary amine in the linker-payload molecule. The positive charge on the quarternary amine can be balanced by a counter ion (e.g., chloro, bromo, iodo, or any other suitably charged moiety such as those described above).

Certain groups, moieties, substituents, and atoms are depicted with a wavy line. The wavy line can intersect or cap a bond or bonds. The wavy line indicates the atom through which the groups, moieties, substituents, or atoms are bonded. For example, a phenyl group that is substituted with a propyl group depicted as:

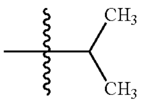

or

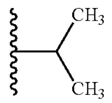

has the following structure:

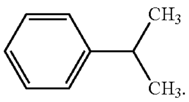

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy)tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b]pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

"Amino acid" or "amino acid residue" refers, in some embodiments, to naturally occurring amino acids. In other embodiments, an amino acid or amino acid residue may be a naturally occurring amino acid and/or an unnatural amino acid (e.g., β-amino acids ($\beta^3$ and $\beta^2$), homo-amino acids, proline and pyruvic acid derivatives, 3-substituted alanine derivatives, glycine derivatives, ring-substituted phenylalanine and tyrosine derivatives, linear core amino acids, and/or N-methyl amino acids, or any other commercially available unnatural amino acid (e.g., unnatural amino acids available from Sigma-Aldrich)). In other embodiments, an amino acid residue may be a residue having a side chain involved in a reaction mediated by a transglutaminase, e.g., a transglutaminase-mediated reaction of an amino acid side chain with a primary amine. For example, a reaction of an asparagine and/or glutamine side chain with a primary amine is used for preparation of certain ADCs described herein. In certain embodiments, such functionalized antibody is derived by reacting an antibody comprising at least one glutamine residue, e.g., heavy chain Q295 (EU numbering), with a compound according to the formula $H_2N$-LL-$N_3$, wherein LL is a divalent polyethylene glycol group, in the presence of the enzyme transglutaminase.

As used herein, "taurine" refers to the reagent

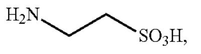

or the group

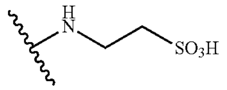 [SMILES: *NCCS(=O)(=O)O]

where

indicates the atom through which the taurine is bonded to the adjacent groups in the formula.

As used herein, "stereoisomeric form" or "stereoisomer" refers to the relative spatial orientation of different groups in a compound. Stereoisomeric forms include enantiomers, diasteromers, and/or mixtures thereof.

As used herein, "regioisomer," "regioisomers," or "mixture of regioisomers" refers to the product(s) of 1,3-cycloadditions or strain-promoted alkyne-azide cycloadditions (SPAACs)—otherwise known as click reactions—that derive from suitable azides (e.g., —$N_3$, or PEG-$N_3$ derivitized antibodies) treated with suitable alkynes. In certain embodiments, for example, regioisomers and mixtures of regioisomers are characterized by the click reaction products shown below:

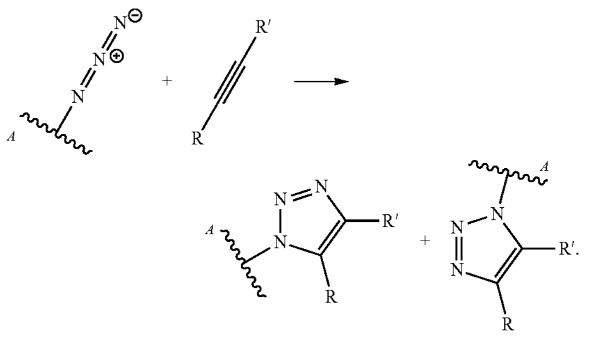

By way of example only, regioisomers of compound A1', i.e., compounds A2', A3', A4', are shown below, wherein each

is a bond to the binding agent; and each

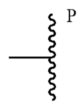

is a bond to the payload:

compound A1'

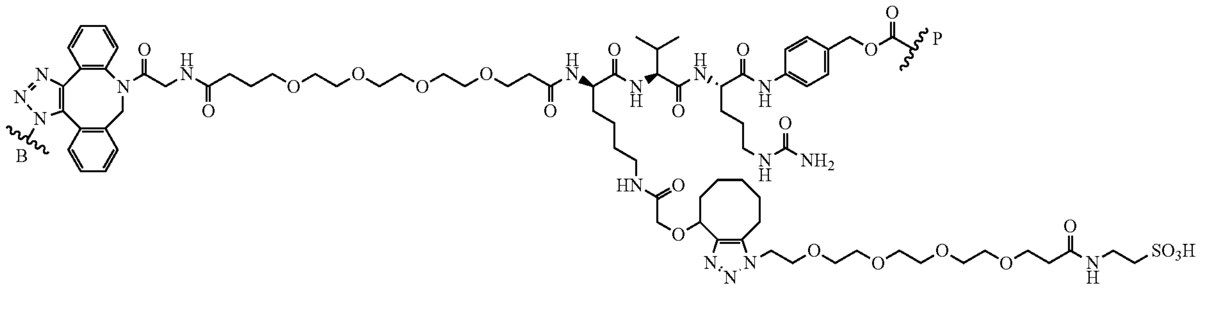

-continued compound A2′

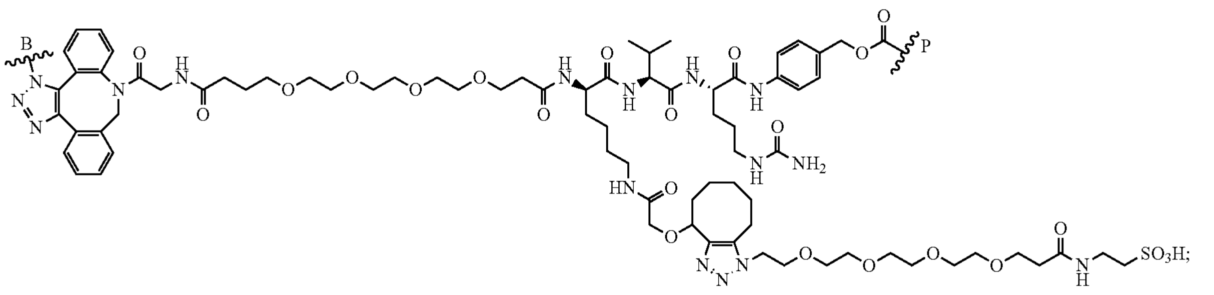

compound A3′

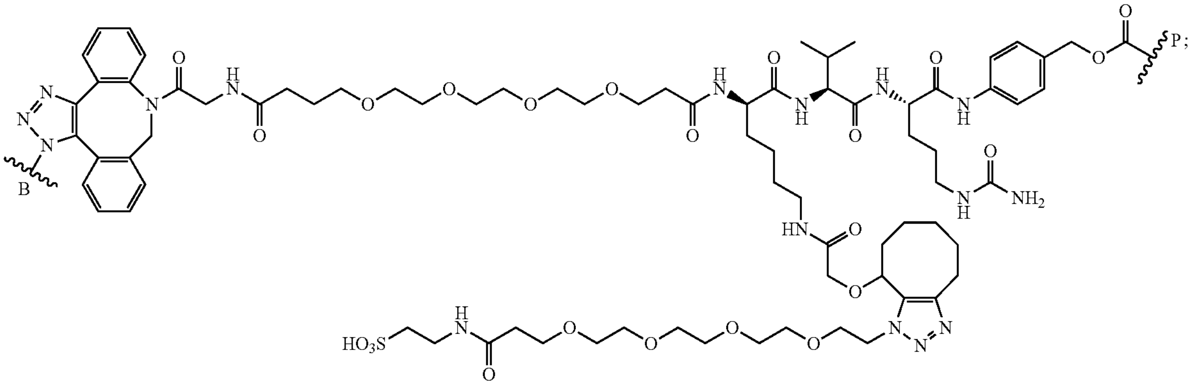

compound A4′

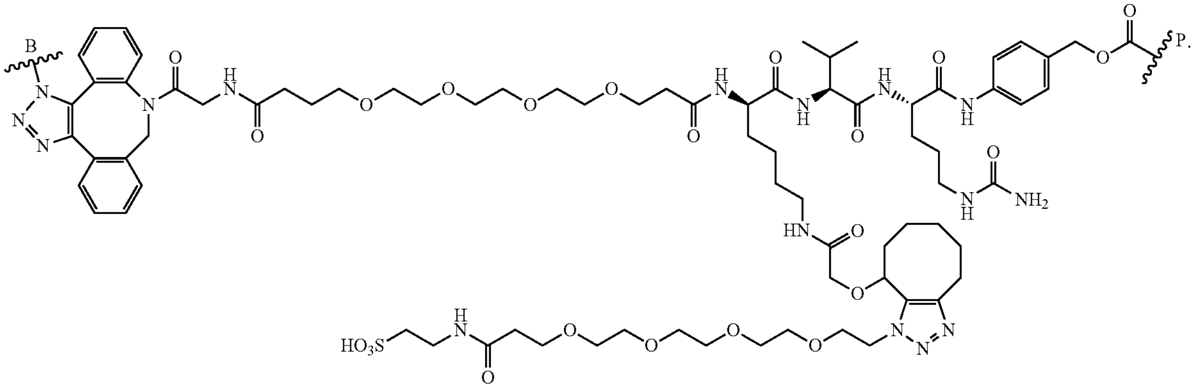

Anti-MSR1 Antibodies Comprising Fc Variants

According to certain embodiments, anti-MSR1 antibodies are provided comprising an Fc domain comprising one or more mutations which enhance or diminish antibody binding to the FcRn receptor, e.g., at acidic pH as compared to neutral pH. For example, provided herein are anti-MSR1 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, embodiments include anti-MSR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies

Embodiments include antibodies and antigen-binding fragments thereof that bind human MSR1 with high affinity. For example, the present invention includes anti-MSR1 antibodies that bind human MSR1 extracellular domain expressed with an N-terminal nonahistidine tag (e.g., His9-hMSR1) with a $K_D$ of less than about 10 nM as measured by surface plasmon resonance at 25° C. or 37° C., e.g., using an assay format as defined in Example 3 herein, or a substantially similar assay. According to certain embodiments, anti-MSR1 antibodies are provided that bind human MSR1 at 37° C. with a $K_D$ of less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 3 herein, or a substantially similar assay. In some embodiments, the anti-MSR1 antibodies disclosed herein bind human MSR1 at 25° C. with a $K_D$ of less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 3 herein, or a substantially similar assay.

Embodiments also include antibodies and antigen-binding fragments thereof that bind monkey MSR1 with high affinity. For example, disclosed herein are anti-MSR1 antibodies that bind monkey MSR1 extracellular domain expressed with an N-terminal myc-myc-hexahistidine tag (e.g., HMM-mfMSR1) with a $K_D$ of less than about 20 nM as measured by surface plasmon resonance at 25° C. or 37° C., e.g., using an assay format as defined in Example 3 herein, or a substantially similar assay. According to certain embodiments, anti-MSR1 antibodies are provided that bind monkey MSR1 at 37° C. with a $K_D$ of less than about 20 nM, less than about 18 pM, less than about 15 nM, less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 3 herein, or a substantially similar assay. In some embodiments, the anti-MSR1 antibodies disclosed herein bind monkey MSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 3 herein, or a substantially similar assay.

The present invention also includes antibodies and antigen-binding fragments thereof that bind human MSR1 extracellular domain expressed with an N-terminal nonahistidine tag (e.g., His9-hMSR1) with a dissociative half-life (t½) of greater than about 5 minutes as measured by surface plasmon resonance at 25° C. or 37° C., e.g., using an assay format as defined in Example 3 herein, or a substantially similar assay. According to certain embodiments, anti-MSR1 antibodies are provided that bind human MSR1 at 37° C. with a t % of greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, greater than about 240 minutes, or longer, as measured by surface plasmon resonance, e.g., using an assay format as defined in Example 3 herein, or a substantially similar assay.

Embodiments also include antibodies and antigen-binding fragments thereof that can bind monkey MSR1 extracellular domain expressed with an N-terminal myc-myc-hexahistidine tag (e.g. HMM-mfMSR1) with high affinity. For example, the present invention includes anti-MSR1 antibodies that bind HMM-mfMSR1 with a $K_D$ of less than about 20 nM as measured by surface plasmon resonance at 25° C. or 37° C., e.g., using an assay format as defined in Example 3 herein, or a substantially similar assay. According to certain embodiments, anti-MSR1 antibodies are provided that bind HMM-mfMSR1 at 37° C. with a $K_D$ of less than about 20 nM, less than about 15 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 3 herein, or a substantially similar assay. In some embodiments, the anti-MSR1 antibodies disclosed herein bind HMM-mfMSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 3 herein, or a substantially similar assay.

Embodiments also include antibodies and antigen-binding fragments thereof that bind monkey MSR1 extracellular domain expressed with an N-terminal myc-myc-hexahistidine tag (e.g. HMM-mfMSR1) with a dissociative half-life (t½) of greater than about 55 minutes as measured by surface plasmon resonance at 25° C. or 37° C., e.g., using an assay format as defined in Example 3 herein, or a substantially similar assay. According to certain embodiments, anti-MSR1 antibodies are provided that bind dimeric human MSR1 at 37° C. with a t½ of greater than about 1 minute, greater than about 2 minutes, greater than about 3 minutes, greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, or longer, as measured by surface plasmon resonance, e.g., using an assay format as defined in Example 3 herein, or a substantially similar assay.

Embodiments also include antibodies and antigen-binding fragments thereof that bind engineered cell-surface expressed hMSR1 with binding ratios of engineered hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 5 herein, or a substantially similar assay. In some embodiments, provided herein are antibodies that bind cells with endogenously-expressed hMSR1 with binding ratios of endogenous hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, or greater at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 5 herein, or a substantially similar assay. In some embodiments, an MSR1 antibody or antigen binding fragment disclosed herein bind engineered cell-surface expressed mouse MSR1 with binding ratios of engineered mouse MSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 5 herein, or a substantially similar assay.

Embodiments also include antibodies and antigen-binding fragments thereof that bind MSR1 and exhibit maximum inhibition of uptake of modified low-density lipoprotein (LDL) in cells expressing human MSR1 of less than about 95%. For example, embodiments include anti-MSR1 antibodies that exhibit maximum inhibition of uptake of modified LDL (e.g., oxidized or acetylated) in cells that express human MSR1 of less than about 95%, with an $IC_{50}$ of less than about 6.1 nM as measured using a ligand uptake assay, e.g., using an assay format as defined in Example 8 herein, or a substantially similar assay. According to certain embodiments, anti-MSR1 antibodies are provided that exhibit maximum inhibition of modified LDL uptake in cells expressing human MSR1 of less than about 95%, with an $IC_{50}$ of less than about 6.1 nM, less than about 5 nM, less than about 4 nM, less than about 3 nM, less than about 2 nM, less than about 1.5 nM, less than about 1.4 nM, less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a ligand uptake assay, e.g., using an assay format as defined in Example 8 herein, or a substantially similar assay.

In some embodiments, the anti-MSR1 antibodies exhibit maximum inhibition of modified LDL uptake in cells expressing human MSR1 of less than about 90%, with an $IC_{50}$ of less than about 6.1 nM, less than about 5 nM, less than about 4 nM, less than about 3 nM, less than about 2 nM, less than about 1.5 nM, less than about 1.4 nM, less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a ligand uptake assay, e.g., using an assay format as defined in Example 8 herein, or a substantially similar assay.

In some embodiments, the anti-MSR1 antibodies exhibit maximum inhibition of modified LDL uptake in cells expressing human MSR1 of less than about 75%, with an $IC_{50}$ of less than about 6.1 nM, less than about 5 nM, less than about 4 nM, less than about 3 nM, less than about 2 nM, less than about 1.5 nM, less than about 1.4 nM, less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a ligand uptake assay, e.g., using an assay format as defined in Example 8 herein, or a substantially similar assay.

In some embodiments, the anti-MSR1 antibodies exhibit maximum inhibition of modified LDL uptake in cells expressing human MSR1 of less than about 60%, with an $IC_{50}$ of less than about 6.1 nM, less than about 5 nM, less than about 4 nM, less than about 3 nM, less than about 2 nM, less than about 1.5 nM, less than about 1.4 nM, less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a ligand uptake assay, e.g., using an assay format as defined in Example 8 herein, or a substantially similar assay.

In some embodiments, the anti-MSR1 antibodies exhibit maximum inhibition of modified LDL uptake in cells expressing human MSR1 of less than about 50%, with an $IC_{50}$ of less than about 6.1 nM, less than about 5 nM, less than about 4 nM, less than about 3 nM, less than about 2 nM, less than about 1.5 nM, less than about 1.4 nM, less than about 1.3 nM, less than about 1.2 nM, less than about 1.0 nM, less than about 900 pM, less than about 800 pM, less than about 600 pM, less than about 400 pM, less than about 200 pM, less than about 100 pM, less than about 80 pM, less than about 60 pM, less than about 40 pM, less than about 20 pM as measured using a ligand uptake assay, e.g., using an assay format as defined in Example 8 herein, or a substantially similar assay.

Embodiments also include antibodies and antigen-binding fragments thereof that bind cell surface-expressed MSR1 and are internalized by the cells. For example, antibodies that bind to cell surface-expressed MSR1 on THP-1 cells and become internalized by the cells are provided herein. For example, the instant disclosure includes anti-MSR1 antibodies that bind to cell surface-expressed MSR1 on THP-1 cells and become internalized by the cells with a relative percentage of at least about 10%, as measured by chemiluminescence, e.g., using an assay format as defined in Example 9 herein, or a substantially similar assay. In certain embodiments, anti-MSR1 antibodies that bind to cell surface-expressed MSR1 on THP-1 cells and become internalized by the cells with a relative percentage of at least about 10%, 15%, 20%, 25%, 30%, 35%, 40%, 45%, or 50%, as measured by chemiluminescence, e.g., using an assay format as defined in Example 9 herein, or a substantially similar assay.

The antibodies disclosed herein may possess one or more of the aforementioned biological characteristics, or any combination thereof. The foregoing list of biological characteristics of the antibodies disclosed herein is not intended to be exhaustive. Other biological characteristics of the antibodies disclosed herein will be evident to a person of ordinary skill in the art from a review of the present disclosure including the working Examples herein.

Antibody-Drug Conjugates (ADCs)

Provided herein are antibody-drug conjugates (ADCs) comprising an anti-MSR1 antibody or antigen-binding fragment thereof conjugated to a drug or a therapeutic agent. In some embodiments, the therapeutic agent is a liver X receptor (LXR) agonist or a steroid. Also provided herein are reactive linker-payloads useful for making the ADCs. Further provided herein are modified anti-MSR1 antibodies and modified MSR1 antigen-binding fragments useful for making the ADCs.

The ADCs generally have the Formula (I): $BA-[(L)_{0-1}-PA]_n$. In the formula, BA is a binding agent, for instance, an anti-MSR1, antibody, or an MSR1 antigen-binding fragment thereof. L is a linker, described in detail below. PA is a payload. Suitable payloads include any small molecule that can provide a therapeutic benefit through its delivery to MSR1. In certain embodiments, a payload may be, for instance, a steroid, an LXR modulator, or a rifamycin analog. Useful payloads are described in detail below. In the formula, n is an integer from 1 to 30, for instance from 1 to 4, e.g., 2 or 4. Each L-PA is covalently bonded to a functional group of PA. In some particular embodiments, each L-PA is covalently bonded to a lysine side chain, a cysteine side chain, a glutamine side chain, or an amino terminus of BA.

Techniques and linkers for conjugating to residues of an antibody or antigen binding fragment are known in the art. Exemplary amino acid attachments that can be used in the context of this aspect, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci.*, USA, 2008, 105:12451-12456), formyl glycine (see, e.g., Carrico et al., *Nat. Chem. Biol.,* 2007, 3:321-322; Agarwal et al., *Proc. Natl. Acad. Sci.*, USA, 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36 (Suppl 1): 100). Site specific conjugation techniques, include, but are not limited to glutamine conjugation via transglutaminase (see e.g., Schibli, Angew Chemie Inter Ed. 2010, 49,9995).

Linkers can be conjugated to one or more glutamine residues via transglutaminase-based chemo-enzymatic conjugation (see, e.g., Dennler et al., *Bioconjugate Chem.* 2014, 25, 569-578, and WO 2017/147542). For example, in the presence of transglutaminase, one or more glutamine residues of an antibody can be coupled to a primary amine compound. Briefly, in some embodiments, an antibody having a glutamine residue (e.g., a Gln295 residue) is treated with a primary amine compound, described in more detail below, in the presence of the enzyme transglutaminase. Primary amine compounds include payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule comprises at least one glutamine residue in at least one polypeptide chain sequence. In certain embodiments, the antibody or a glutaminyl-modified antibody or antigen binding molecule comprises two heavy chain polypeptides, each with one Gln295 residue. In further embodiments, the antibody or a glutaminyl-modified antibody or antigen binding molecule comprises one or more glutamine residues at a site other than a heavy chain 295. In some embodiments, an antibody can be prepared by site-directed mutagenesis to insert a glutamine residue at a site without resulting in disabled antibody function or binding. For example, included herein are antibodies bearing Asn297Gln (N297Q) mutation(s) as described herein. In some embodiments, an antibody having a Gln295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the antibody conjugated via transglutaminase can have a higher than expected DAR value (e.g., a DAR higher than 4). Any such antibodies can be isolated from natural or artificial sources.

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula $H_2N—R$, where R can be any group compatible with the antibody and reaction conditions. In certain embodiments, R is alkyl, substituted alkyl, heteroalkyl, or substituted heteroalkyl.

In some embodiments, the primary amine compound comprises a reactive group or protected reactive group. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulfhydryl, cycloalkyne, aldehyde, and carboxyl.

In certain embodiments, the primary amine compound is according to the formula $H_2N$-LL-X, where LL is a divalent spacer and X is a reactive group or protected reactive group. In particular embodiments, LL is a divalent polyethylene glycol (PEG) group. In certain embodiments, X is selected from the group consisting of —SH, —$N_3$, alkyne, aldehyde, and tetrazole. In particular embodiments, X is —$N_3$.

In certain embodiments, the primary amine compound is according to one of the following formulas:

$H_2N—(CH_2)_n—X$;

$H_2N—(CH_2CH_2O)_n—(CH_2)_p—X$;

$H_2N—(CH_2)_n—N(H)C(O)—(CH_2)_m—X$;

$H_2N—(CH_2CH_2O)_n—N(H)C(O)—(CH_2CH_2O)_m—(CH_2)_p—X$;

$H_2N—(CH_2)_n—C(O)N(H)—(CH_2)_m—X$;

$H_2N—(CH_2CH_2O)_n—C(O)N(H)—(CH_2CH_2O)_m—(CH_2)_p—X$;

$H_2N—(CH_2)_n—N(H)C(O)—(CH_2CH_2O)_m—(CH_2)_p—X$;

$H_2N—(CH_2CH_2O)_n—N(H)C(O)—(CH_2)_m—X$;

$H_2N—(CH_2)_n—C(O)N(H)—(CH_2CH_2O)_m—(CH_2)_p—X$; and $H_2N—(CH_2CH_2O)_n—C(O)N(H)—(CH_2)_m—X$;

where n is an integer selected from 1 to 12;
m is an integer selected from 0 to 12;
p is an integer selected from 0 to 2;
and X is selected from the group consisting of —SH, —$N_3$, —C≡CH, —C(O)H, tetrazole, and any of

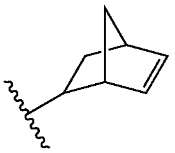

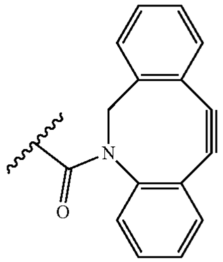

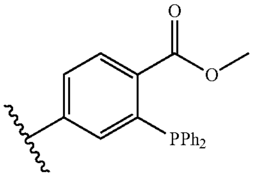

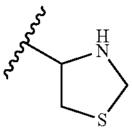

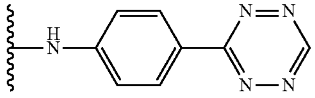

.

In the above, any of the alkyl or alkylene (i.e., —$CH_2$—) groups can optionally be substituted, for example with $C_{1-8}$alkyl, methylformyl, or —$SO_3H$. In certain embodiments, the alkyl groups are unsubstituted.

In certain embodiments, the primary amine compound is selected from the group consisting of:

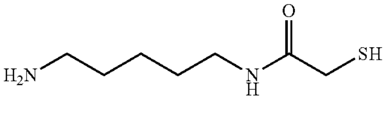

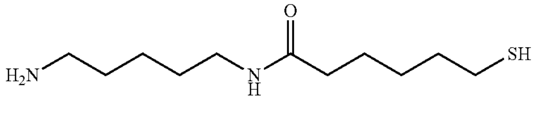

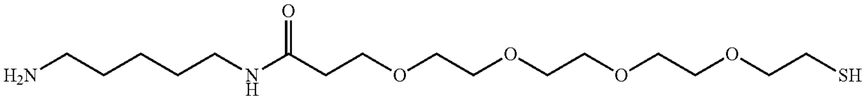

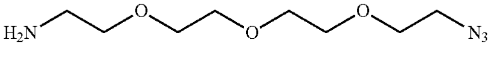

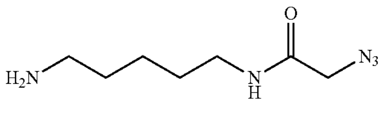

and

-continued

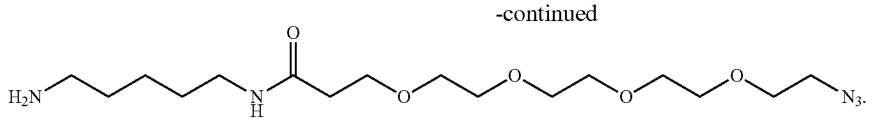

In particular embodiments, the primary amine compound is

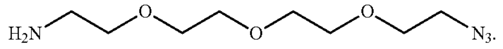

Exemplary conditions for the above reactions are provided in the Examples below:

Accordingly, provided herein are modified anti-MSR1 antibodies, and antigen-binding fragments thereof, linked to one or more primary amine compounds. In particular embodiments, provided herein are modified anti-MSR1 antibodies, and antigen-binding fragments thereof, according to the formula:

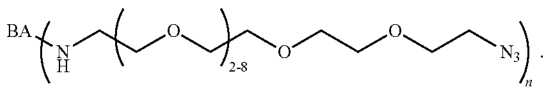

In the formula, BA is an anti-MSR1 antibody, or an antigen binding fragment thereof. The variable n is an integer from 1 to 30. In certain embodiments, n is from 1 to the number of glutamine residues in BA. In certain embodiments, n is from 1 to 4. In certain embodiments, n is 1, 2, 3, or 4. In some embodiments, n is 2. In some embodiments, n is 4. The modified anti-MSR1 antibodies, and antigen-binding fragments thereof, are useful, for example, for linking to one or more L-PA molecules to form an ADC.

In certain embodiments, BA comprises two or four glutamine residues. In certain embodiments, BA comprises a Q295 residue. In certain embodiments, BA comprises an N297Q mutation. In certain embodiments, BA comprises Q295 and N297Q. In such embodiments, because BA can be dimeric, BA has four glutamine residues for conjugation to L-PA moieties.

Compounds

In one aspect, provided herein is a compound and/or an antibody-drug conjugate comprising any antibody, or antigen-binding fragment thereof, described herein conjugated to a payload residue optionally through a linker or through a linker-spacer, In a group of embodiments, the compound and/or the antibody-drug conjugate has the structure of Formula (I):

Formula (I)

$$BA\left[(L)_{0\text{-}1}PA\right]_n$$

wherein:

BA is a binding agent;

L is a linker;

PA is a payload moiety selected from the group consisting of a steroid residue, a LXR modulator residue, or a rifamycin analog residue; and subscript n is an integer from 1 to 30.

In a group of embodiments, a compound and/or antibody-drug conjugate described above and herein has the structure of Formula (IA):

Formula (IA)

$$BA\left[RG^1—SP^1—AA^1—AA^2—(Q)_{0\text{-}1}—SP—PA\right]_n$$

wherein $SP^1$ is absent, or a spacer;

$RG^1$ is a reactive group residue;

$AA^1$ is absent, or a divalent or trivalent linker comprising an amino acid residue which is optionally bonded directly or indirectly to a group HG;

$AA^2$ is absent, or a dipeptide, tripeptide, or tetrapeptide residue;

Q, when present, is a connector group residue;

SP is absent, or a spacer; and

HG, when present, is a hydrophilic group.

In a group of embodiments, a compound and/or antibody-drug conjugate described above and herein has the structure of Formula (IB-1):

Formula (IB-1)

$$BA\left[RG^1—SP^1—(Q)_{0\text{-}1}—SP—PA\right]_n$$

wherein $SP^1$ is absent, or a spacer;

$RG^1$ is a reactive group residue;

Q, when present, is

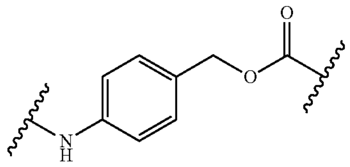,

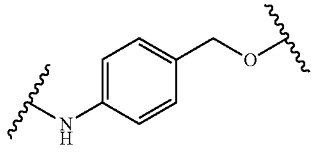, or

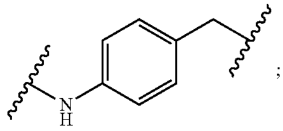; or 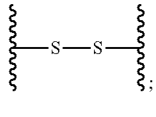;

and

SP is absent, or a spacer;

wherein the

indicates the atoms through which the referenced group is bonded to the adjacent groups in the formula.

In a group of embodiments, a compound and/or antibody-drug conjugate described above and herein has the structure of Formula (IB-2):

Formula (IB-2)

$$BA-\!\!\!+\!\!RG^1-SP^1-AA^1-AA^2-(Q)_{0\text{-}1}-SP-PA]_n$$

wherein $SP^1$ is absent, or a spacer;

$RG^1$ is a reactive group residue;

$AA^1$ is absent, or a divalent or trivalent linker comprising an amino acid residue which is optionally bonded directly or indirectly to a group HG;

$AA^2$ is absent, or a dipeptide, tripeptide, or tetrapeptide residue;

Q, when present, is

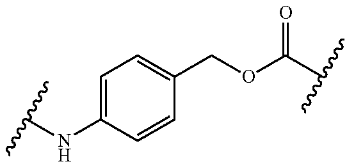

,

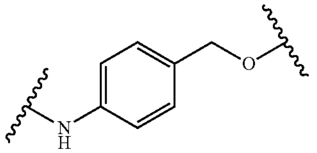

, or

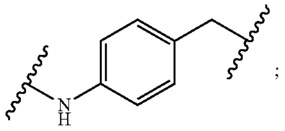

;

SP is absent, or a spacer; and

HG, when present, is

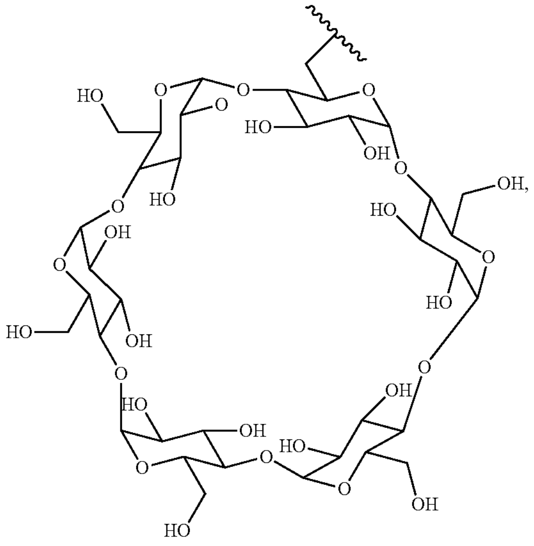

-continued

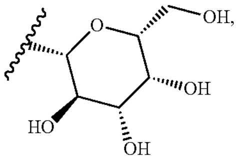

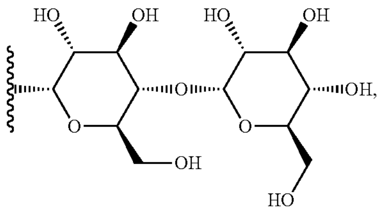

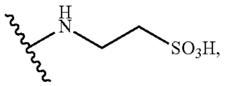

or

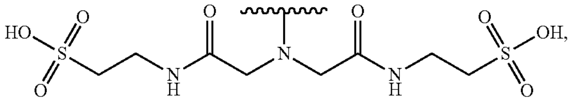

wherein the

indicates the atoms through which the referenced group is bonded to the adjacent groups in the formula.

In a group of embodiments, a compound and/or antibody-drug conjugate described above and herein has the structure of Formula (IC), Formula (ID), or Formula (IE):

Formula (IC)

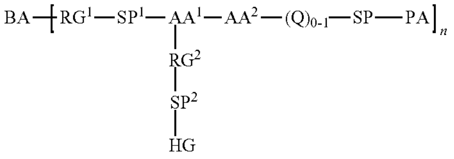

Formula (ID)

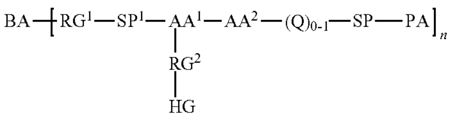

-continued

Formula (IE)

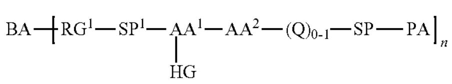

wherein $SP^1$ is absent, or a spacer;

$RG^1$ is a reactive group residue;

$SP^2$ is absent, or a spacer;

$RG^2$ is a reactive group residue;

$AA^1$ is a divalent or trivalent linker comprising an amino acid residue;

$AA^2$ is a dipeptide, tripeptide, or tetrapeptide residue;

Q, when present, is

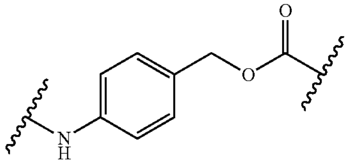

,

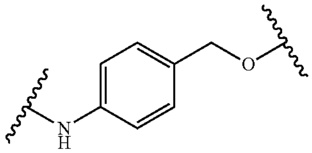

, or

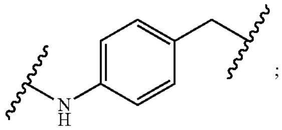

;

SP is absent, or a spacer; and

HG is

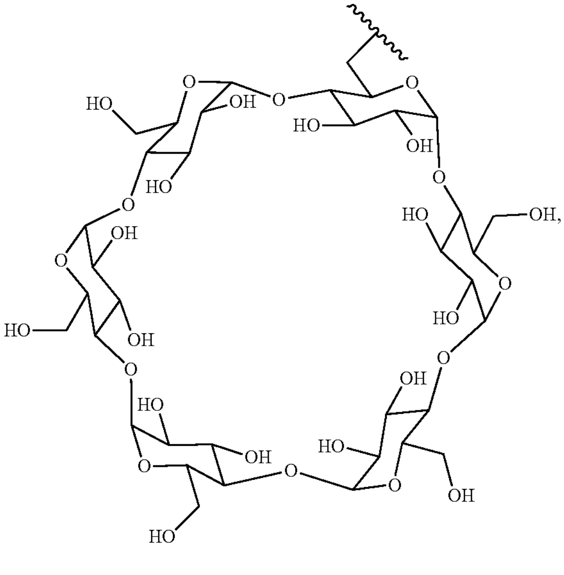

-continued

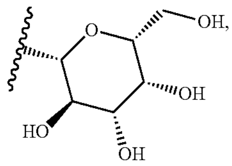

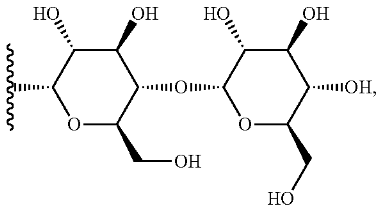

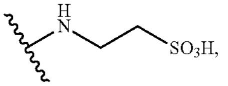

or

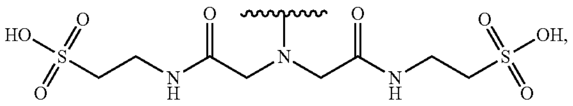

wherein the

indicates the atoms through which the referenced group is bonded to the adjacent groups in the formula. In some or any instances, for any compound and/or antibody-drug conjugate described above and herein, $AA^1$-$AA^2$ is according to Formula (LL1):

(LL1)

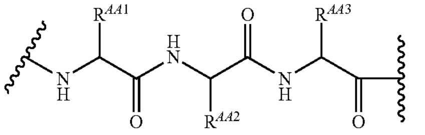

wherein $R^{AA1}$, $R^{AA2}$, and $R^{AA3}$ are each, independently, amino acid side chains, at least one of which is bonded to —$(RG^2)$-$SP^2$-HG, -$(RG^2)$-HG or HG; wherein the

indicates the atoms through which $AA^1$-$AA^2$ is bonded to the adjacent groups in the formula. In some of such embodiments, $R^{AA1}$ is a lysine, glutamine, glutamic acid or aspartic acid side chain bonded directly or indirectly to HG, and $R^{AA2}$ and $R^{AA3}$ are either valine and alanine or valine and citrulline sidechains respectively.

In some or any instances, for any compound and/or antibody-drug conjugate described above and herein, $AA^1$-$AA^2$ is

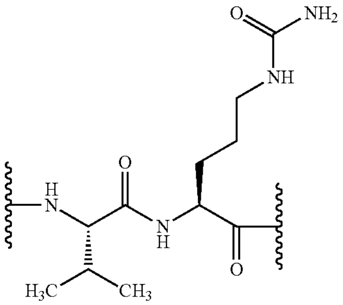
or
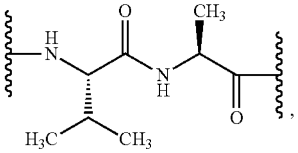
wherein the
indicates the atoms through which $AA^1$-$AA^2$ is bonded to the adjacent groups in the formula.
In some or any instances, for any compound and/or antibody-drug conjugate described above and herein, the $RG^1$ and $RG^2$ residues are independently, in each instance, selected from the group consisting of:
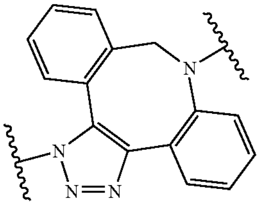
,
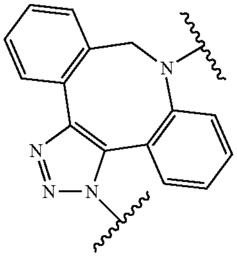
,
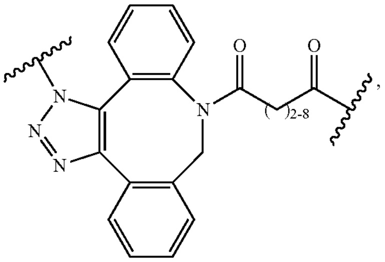
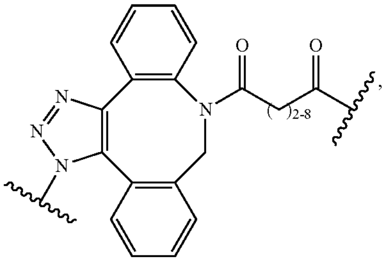
-continued
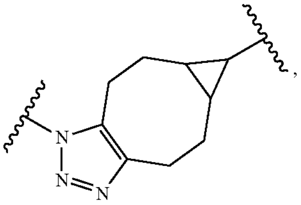
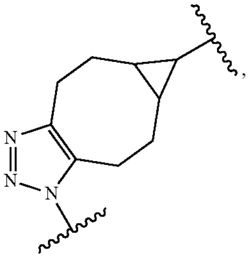
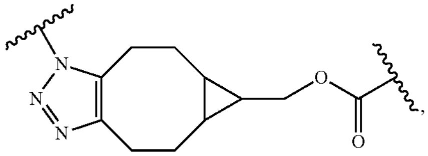
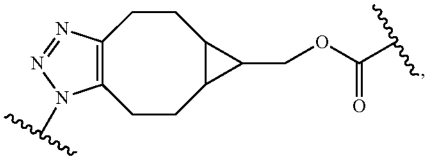
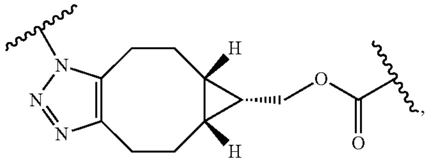
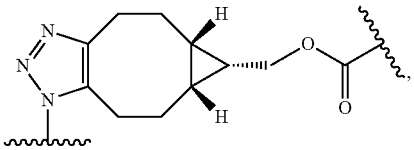
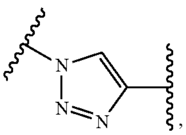
, or
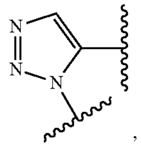
,
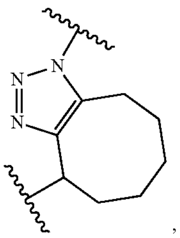
,
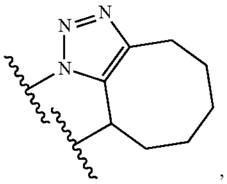
, -continued

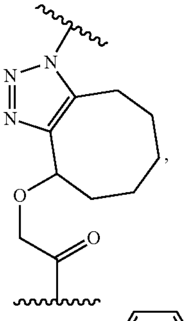,
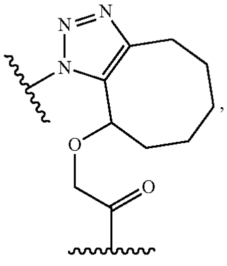,

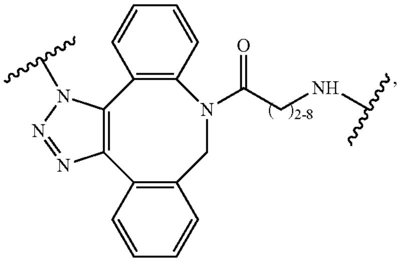,

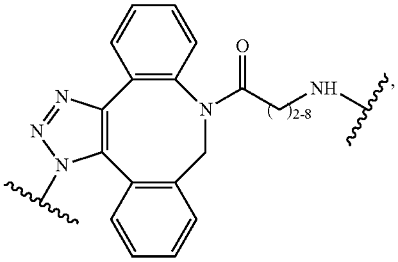,

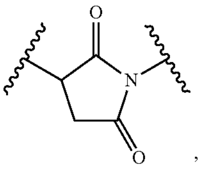, 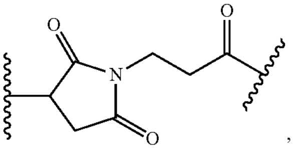,

-continued

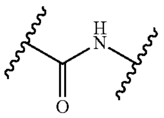; and 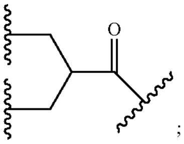;

wherein the

indicates the atom through which the $RG^1$ or $RG^2$ residue is bonded to the adjacent groups in the formula.

In some or any instances, for any compound and/or antibody-drug conjugate described above and herein, SP, $SP^1$ and $SP^2$ are independently, in each instance, absent, or selected from the group consisting of $C_{1-6}$ alkylene, —NH—, —S—, —O—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, $(glycine)_4$-serine, and combinations thereof, wherein subscript e is an integer from 0 to 4, subscript u is an integer from 1 to 8, and subscript v is an integer from 1 to 8.

In some or any instances, for any compound and/or antibody-drug conjugate described above and herein, n is an integer from 1 to 10, from 1 to 8, from 1 to 6, from 1 to 4, or n is 1, 2, 3, or 4.

In some or any instances, for any compound, linker-payload, and/or antibody-drug conjugate described above and herein,

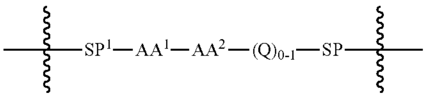 is

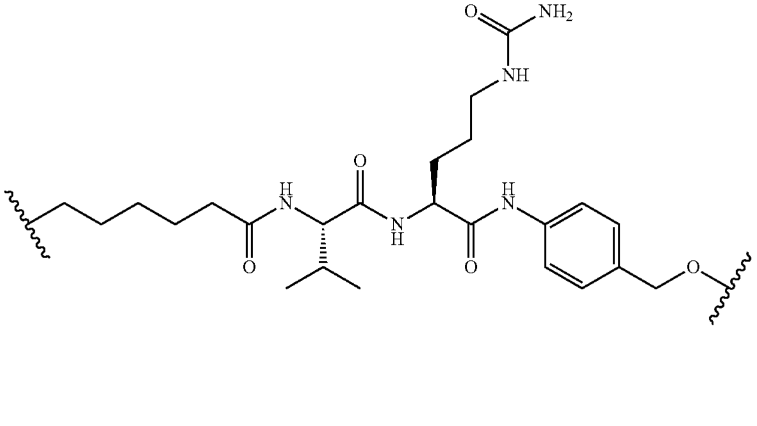

-continued
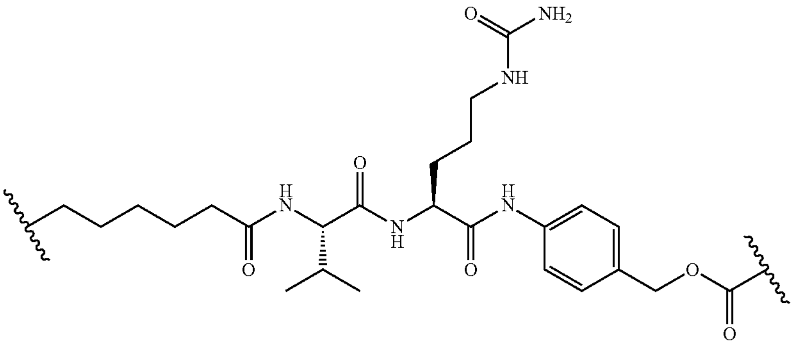
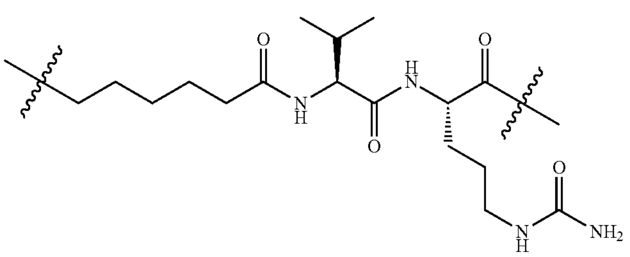
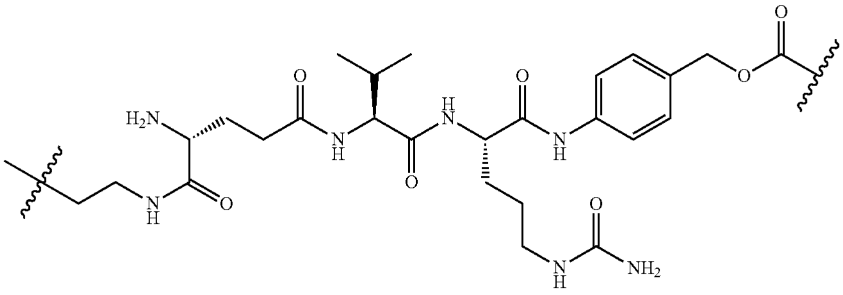

-continued
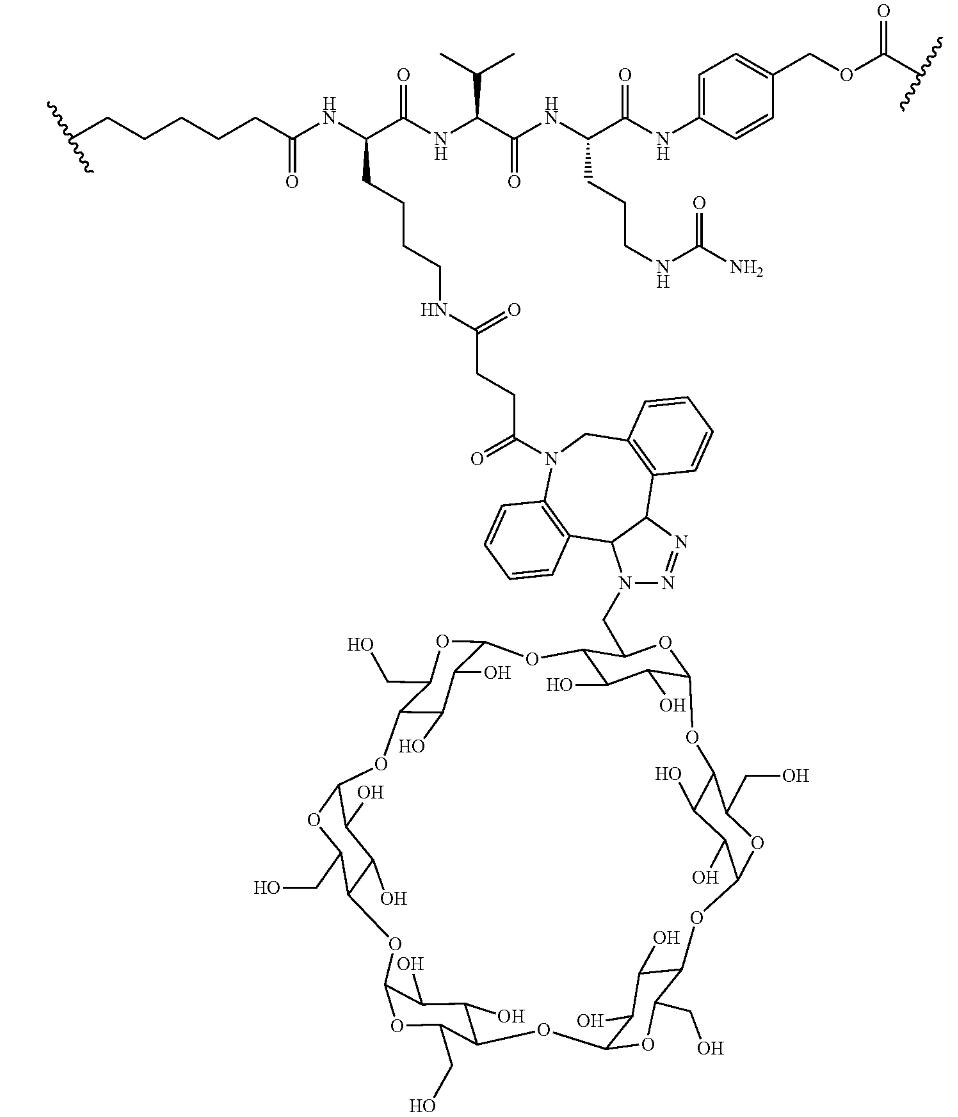
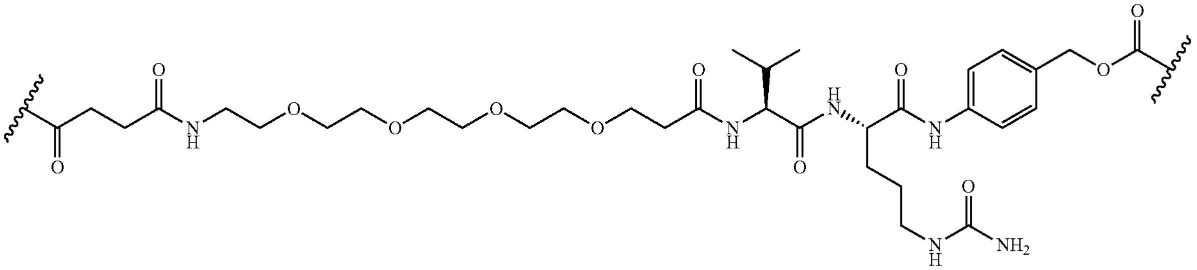
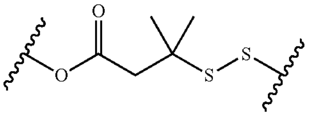
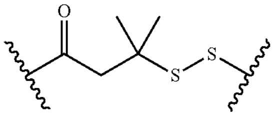
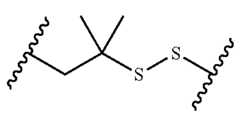
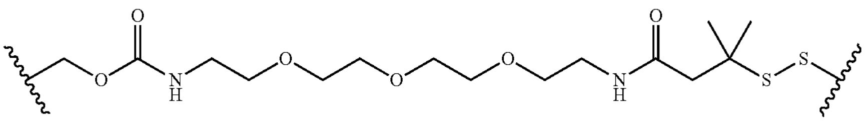

-continued
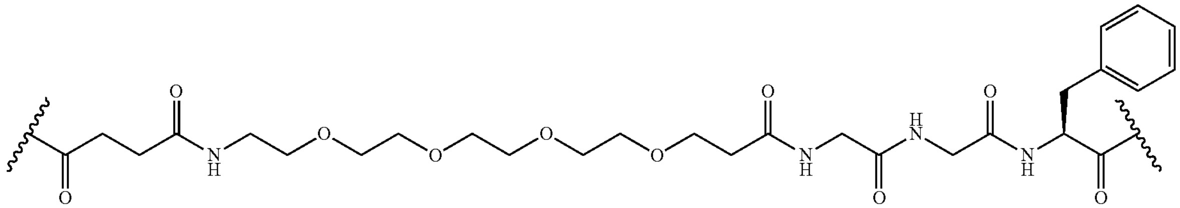
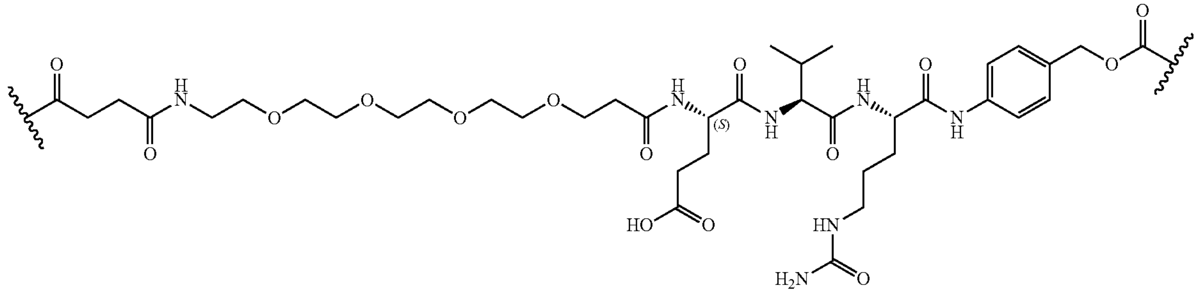
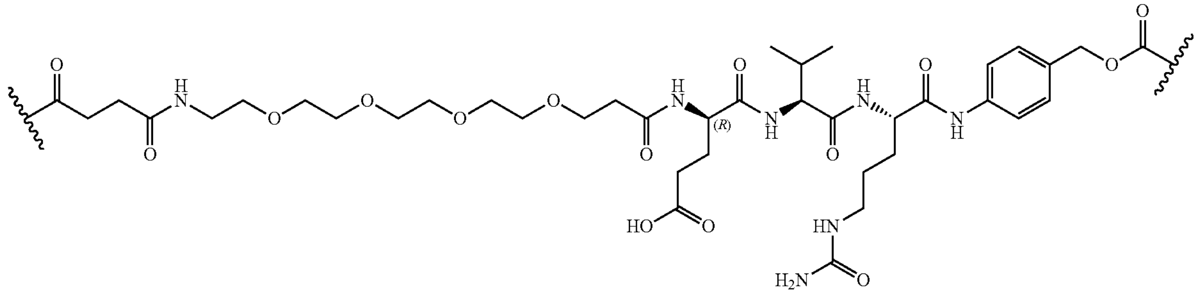
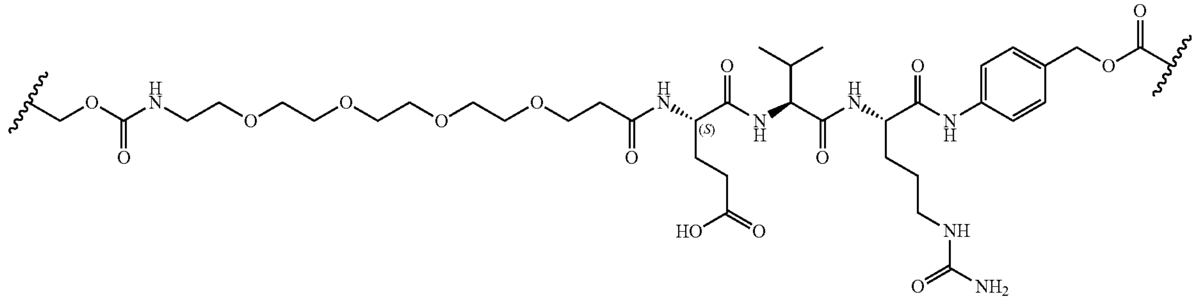
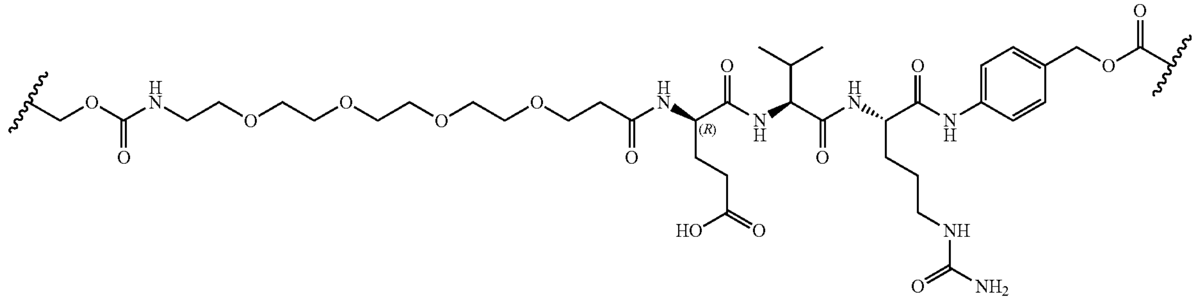
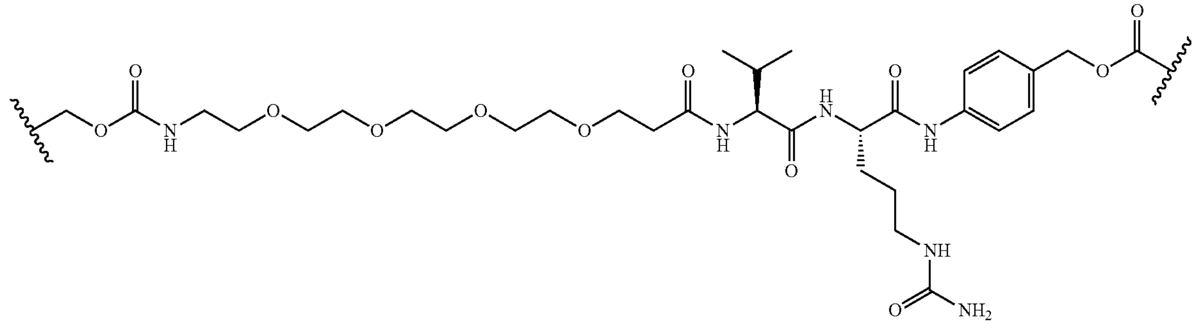

-continued
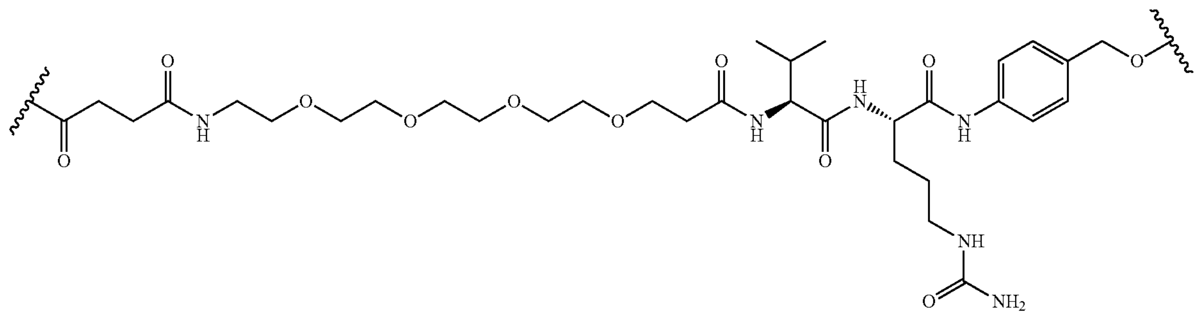
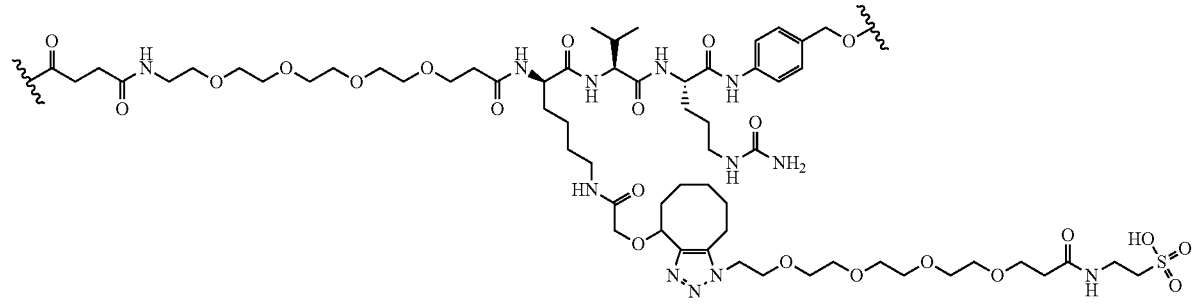
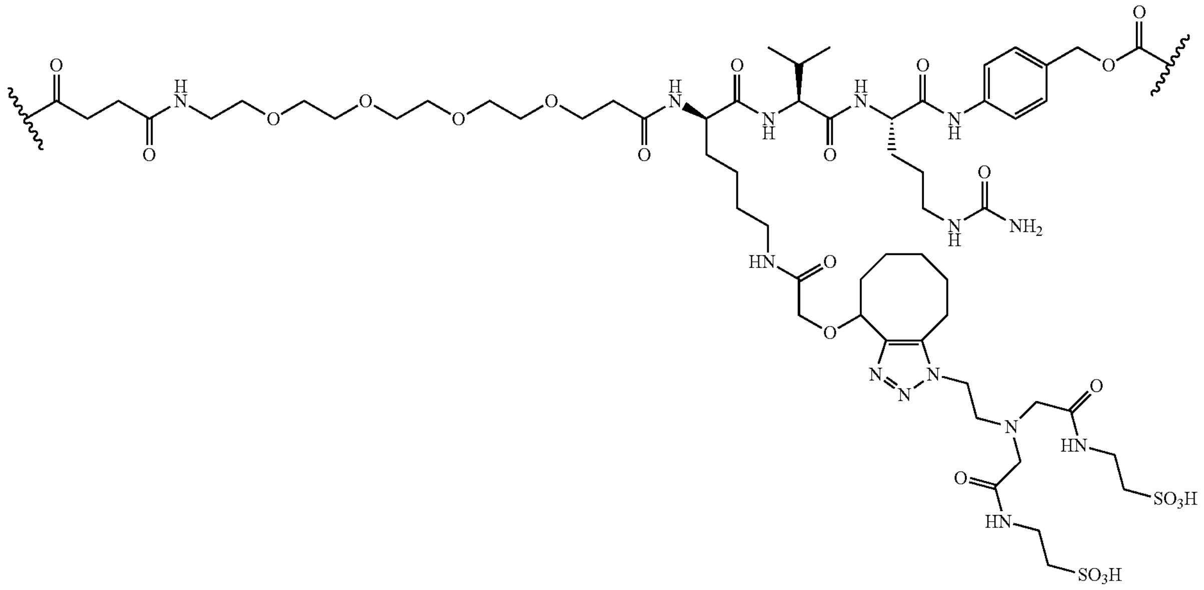
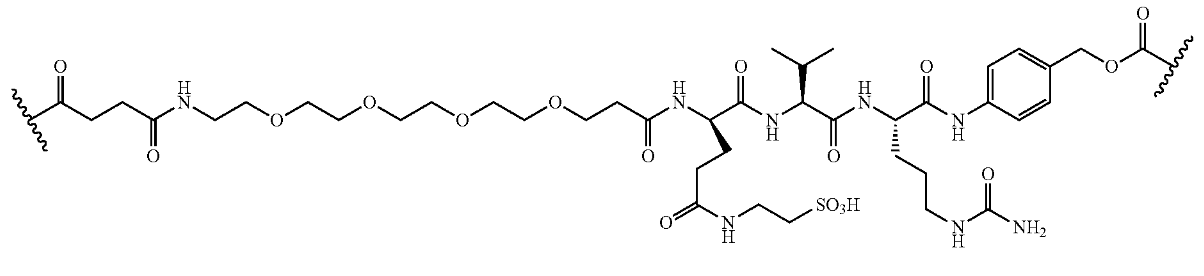

-continued
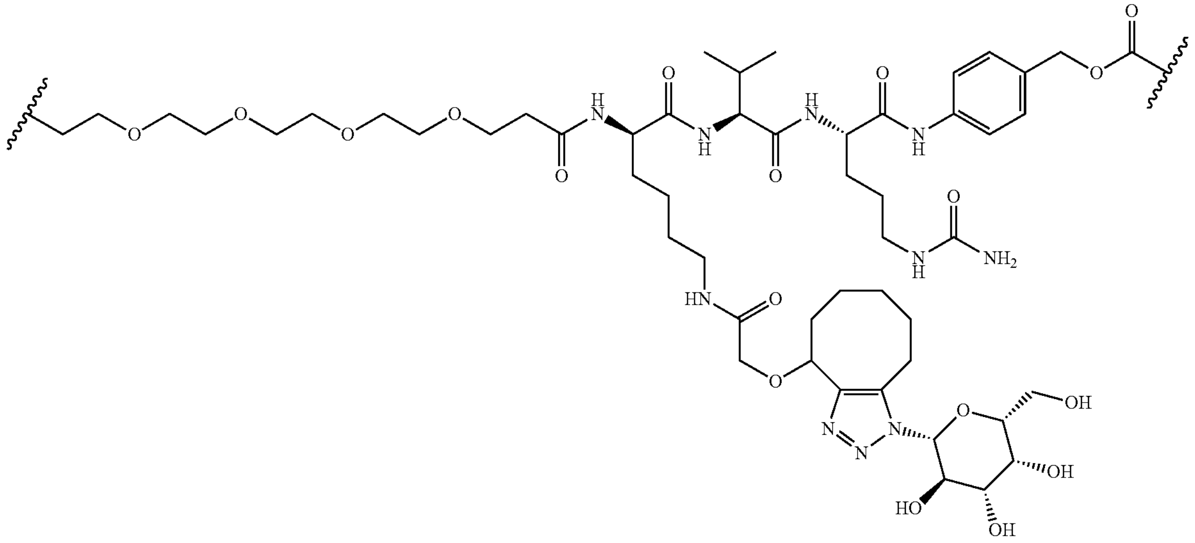
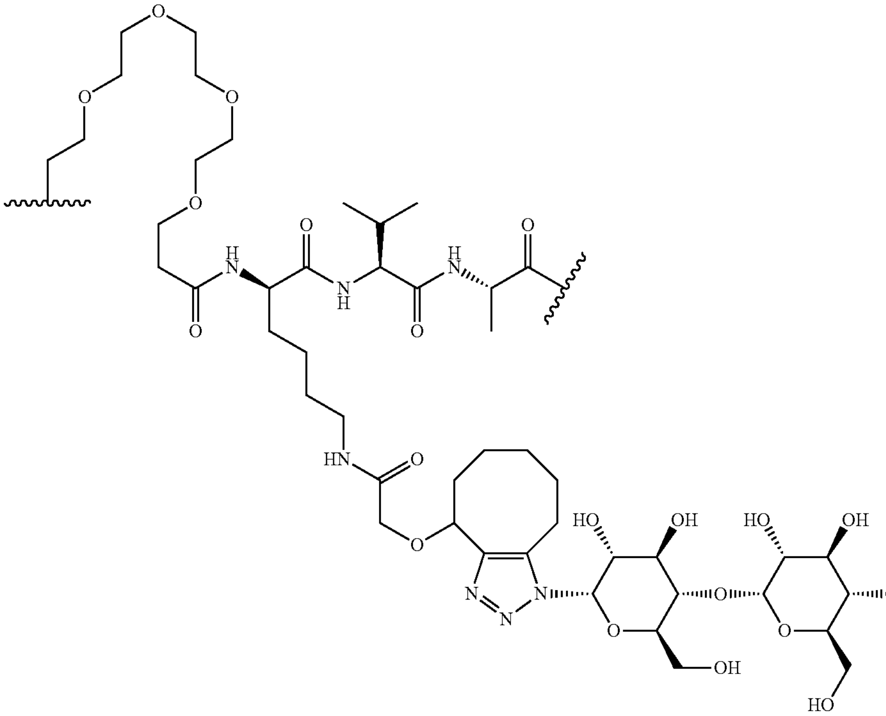
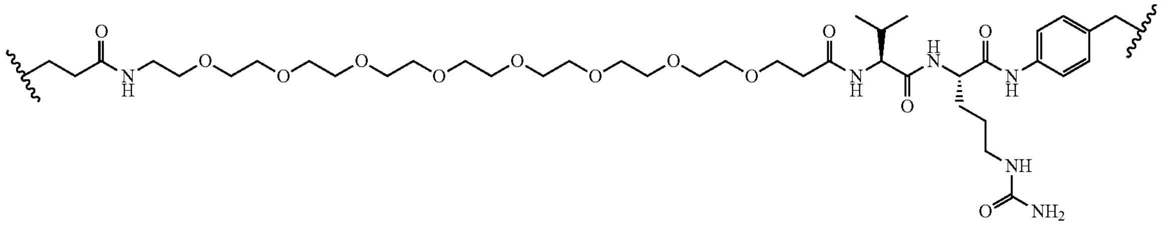
or

-continued

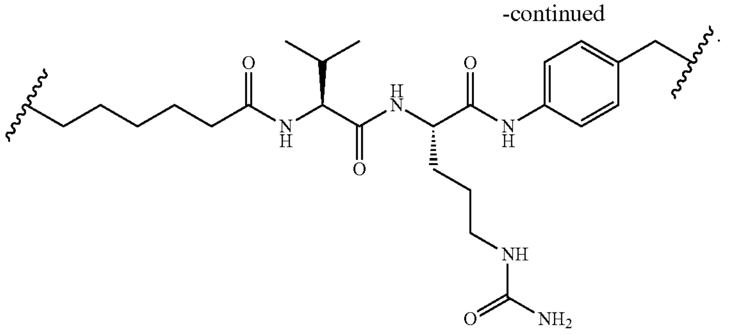

In some or any embodiments, for any compound and/or antibody-drug conjugate described above and herein, the antibody, or antigen-binding fragment thereof, is conjugated to a steroid payload through a linker or a linker-spacer.

In some or any embodiments, for any compound and/or antibody-drug conjugate described above and herein, the antibody, or antigen-binding fragment thereof, is conjugated to a LXR modulator payload through a linker.

In some or any embodiments, for any compound and/or antibody-drug conjugate described above and herein, the antibody, or antigen-binding fragment thereof, is conjugated to a rifamycin analog payload through a linker.

Payloads

In the Formula (I) BA-[L-PA]$_n$, PA can be any payload deemed useful. Such payloads include small molecules that provide a therapeutic benefit through their delivery via MSR1. In certain embodiments, PA is the residue of a molecule selected from the group consisting of a steroid, an LXR modulator, or a rifamycin analog. In some cases, PA is a steroid. In some cases, PA is an LXR modulator. In some cases, PA is an LXR agonist. In some embodiments, PA is an LXR antagonist. Exemplary LXR modulator payloads are described, e.g., in U.S. Application No. 62/508,327, filed May 18, 2017, entitled "BIS-OCTAHYDRO-PHENANTHRENE CARBOXAMIDES AND PROTEIN CONJUGATES THEREOF," published as US 2018/0334426, which is incorporated herein by reference in its entirety. In some instances PA is a rifamycin analog, including any rifamycin analog described herein. In some instances, PA is rifalogue, having the following structure:

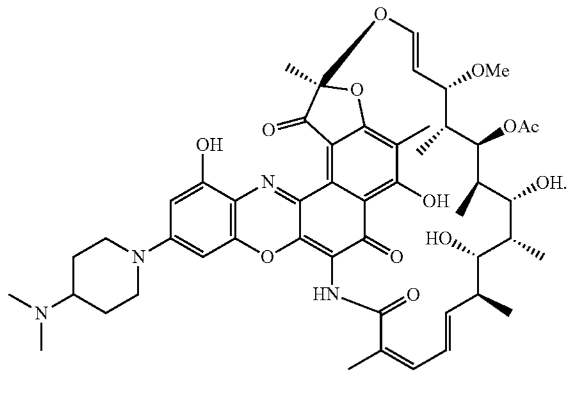

In certain embodiments, the payloads in compounds of Formula (I) are glucocorticoids according to Formula (A):

Formula (A)

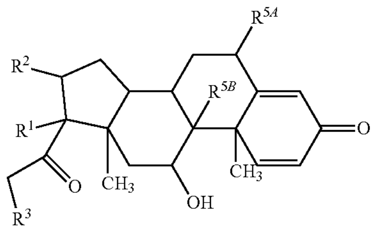

or a pharmaceutically acceptable salt, solvate, or stereoisomeric form thereof; wherein $R^1$ and $R^2$ are, independently, —H, alkyl, alkyl-C(O)—O—, —OH, or halo; or $R^1$ and $R^2$ together form

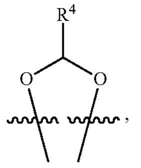

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^{Aa}R^{Ab}$;

$R^3$ is —OH, $R^Z$—C(O)—X—, heteroalkyl, piperidinyl, —$NR^{Aa}R^{Ab}$, -oxyaryl-$NR^{Aa}R^{Ab}$ or —Z-A'$(R^P)_t$;

$R^Z$ is alkyl;

X is O or $NR^{Aa}$;

Z is S, S(O), $S(O)_2$, $SO_2NR^{Aa}$, O, $C(O)NR^{Aa}$, C(O), or $NR^{Aa}$;

A' is aryl, arylalkyl, or heteroaryl;

$R^P$ is, independently in each instance, halo, optionally substituted alkyl, —OH, or —$N^{Aa}R^{Ab}$;

$R^{Aa}$ and $R^{Ab}$ are, independently in each instance, —H, optionally substituted alkyl, or optionally substituted aryl;

subscript a is an integer from 0-19; and t is an integer from 1-3;

with the proviso that:

(1) $R^3$ is not —OH (a) when $R^1$ is —OH or (b) when $R^1$ and $R^2$ together form

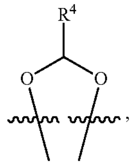

wherein $R^4$ is $C_{1-9}$alkyl or

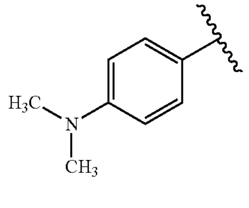

and (2) $R^3$ is not

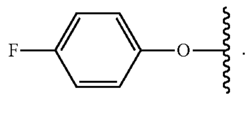

and $R^{5A}$ and $R^{5B}$ are each, independently, halo or a hydrogen atom;

wherein the group $R^3$ or $R^4$ is bonded to the linker.

In some of such embodiments, $R^3$ is $NH_2$. In some other of such embodiments, $R^3$ is

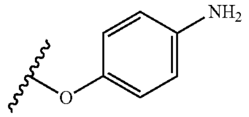 [SMILES: *Oc1ccc(N)cc1]

wherein

indicates the atom through which $R^3$ is attached to the adjacent groups in Formula (I).

In certain embodiments, PA is a steroid. Exemplary steroid payloads are described, e.g., in U.S. Application No. 62/614,905, filed Jan. 8, 2018, entitled "STEROIDS AND ANTIBODY CONJUGATES THEREOF," and U.S. application Ser. No. 15/806,197, filed Nov. 7, 2017, entitled "STEROIDS AND PROTEIN-CONJUGATES THEREOF," published as US 2018/0155389, each of which is incorporated herein by reference in its entirety. In certain embodiments, PA is selected from

1110

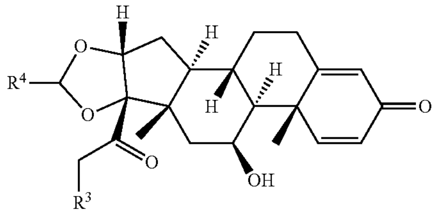

1120

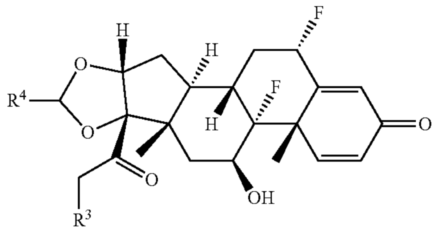

1130

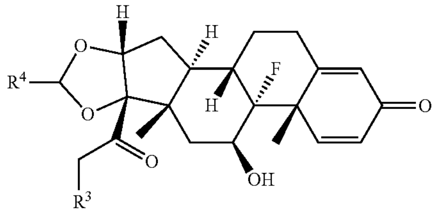

1140

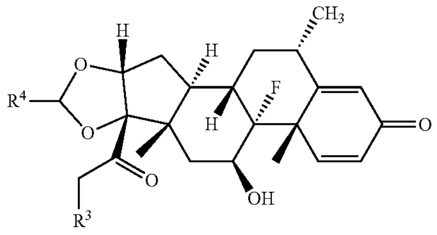

or a pharmaceutically acceptable salt, solvate, or stereoisomer thereof. In certain embodiments according to any of Formulas 1110-1140, $R^3$ is —O-aryl, —$NR^{4a}R^{4b}$, -alkylene-$NR^{4a}R^{4b}$, —X-arylene-Y—$NR^{4a}R^{4b}$, —X-heteroarylene-Y—$NR^{4a}R^{4b}$, or N-containing heterocycloalkyl; wherein X is absent, —N—, —$CH_2$—, or —O—; wherein Y is absent or —$CH_2$—; and $R^4$ is alkyl, aryl, alkylaryl, or arylalkyl. In certain embodiments, $R^3$ is —O-arylene-$NR^{4a}R^{4b}$, —O-heteroarylene-$NR^{4a}R^{4b}$; wherein aryl or heteroaryl is optionally substituted with halogen, deuterium, hydroxyl, or methoxyl. In certain embodiments, $R^3$ is —O-phenyl-$NR^{4a}R^{4b}$, —O-heteroarylene-$NR^{4a}R^{4b}$; wherein phenyl or heteroaryl is optionally substituted with halogen or deuterium. In certain embodiments, $R^4$ is n-propyl. In certain embodiments, $R^4$a and $R^{4b}$ are each independently hydrogen or alkyl. In particular embodiments, one of $R^{4a}$ and $R^{4b}$ is substituted with a bond to the linker (e.g., L or LL). In certain embodiments, PA is -continued
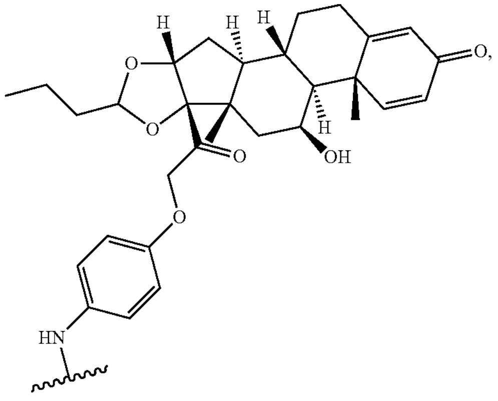
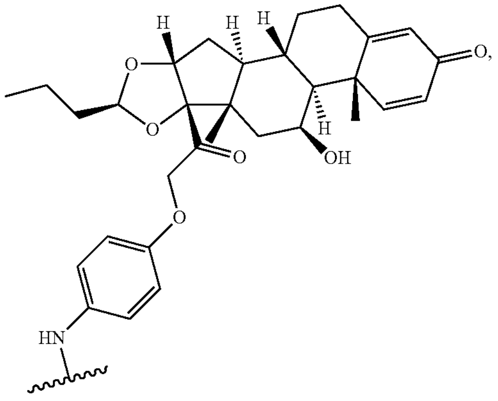
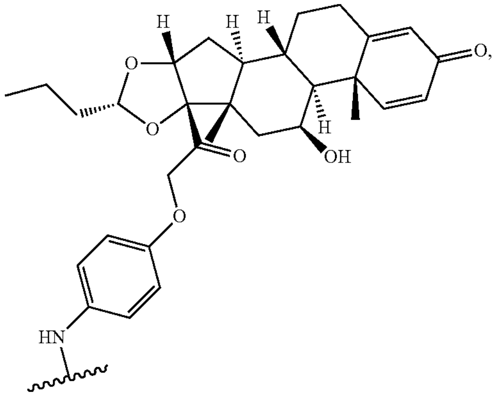
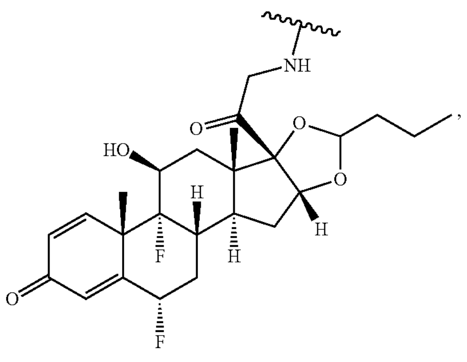
or
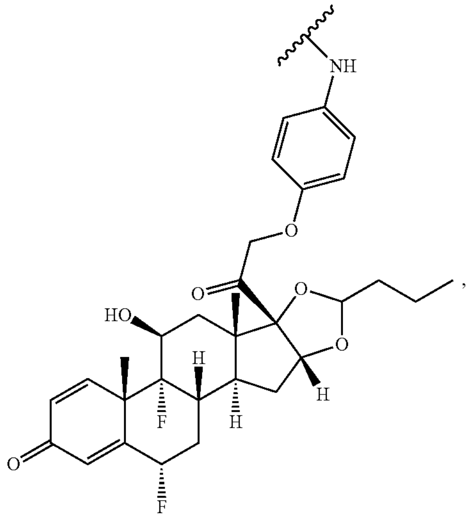
or a pharmaceutically acceptable salt, solvate, or stereoisomer thereof. In certain embodiments, PA is
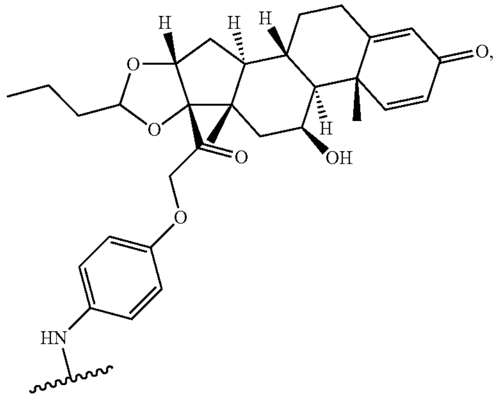 [SMILES: *Nc1ccc(OCC(=O)[C@@]23OC(CCC)O[C@@H]2C[C@H]2[C@@H]4CCC5=CC(=O)C=C[C@]5(C)[C@H]4[C@@H](O)C[C@@]23C)cc1]
or a pharmaceutically acceptable salt, solvate, or stereoisomer thereof In certain embodiments, PA is
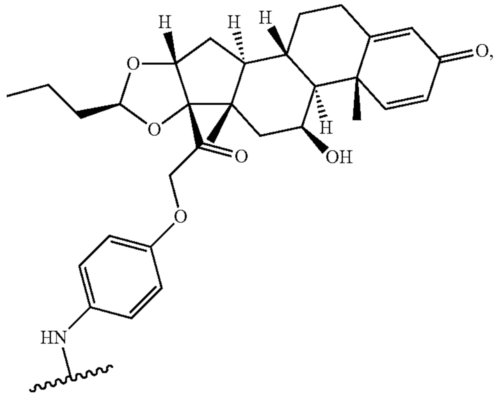 [SMILES: *Nc1ccc(OCC(=O)[C@@]23O[C@@H](CCC)O[C@@H]2C[C@H]2[C@@H]4CCC5=CC(=O)C=C[C@]5(C)[C@H]4[C@@H](O)C[C@@]23C)cc1]
or a pharmaceutically acceptable salt, solvate, or stereoisomer thereof In certain embodiments, PA is

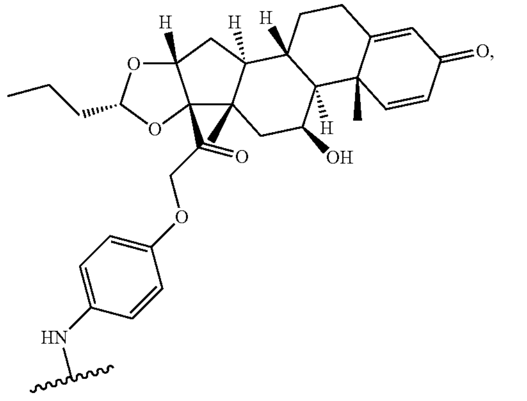 [SMILES: *Nc1ccc(OCC(=O)[C@@]23O[C@H](CCC)O[C@@H]2C[C@H]2[C@@H]4CCC5=CC(=O)C=C[C@]5(C)[C@H]4[C@@H](O)C[C@@]23C)cc1]

or a pharmaceutically acceptable salt, solvate, or stereoisomer thereof. In certain embodiments, PA is

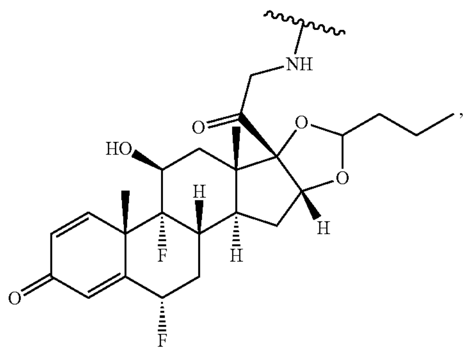

or a pharmaceutically acceptable salt, solvate, or stereoisomer thereof. In certain embodiments, PA is

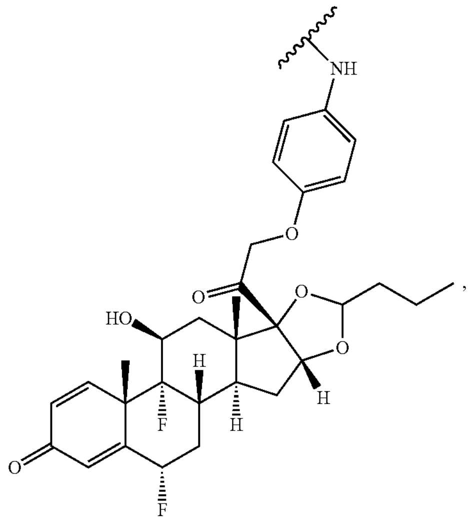

or a pharmaceutically acceptable salt, solvate, or stereoisomer thereof. In such embodiments, the wavy line indicates a bond to the linker (e.g., L or LL).

In certain embodiments, PA is selected from residues of the following:

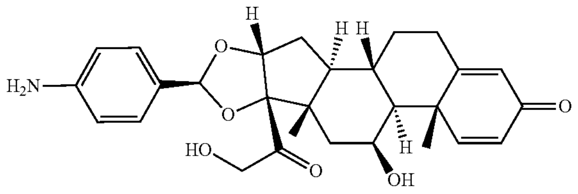

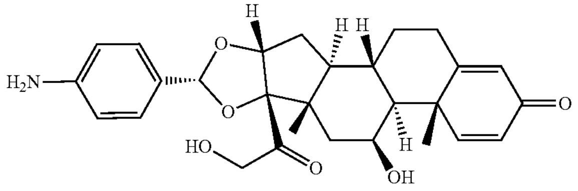

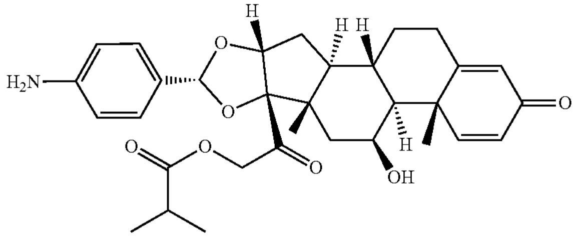

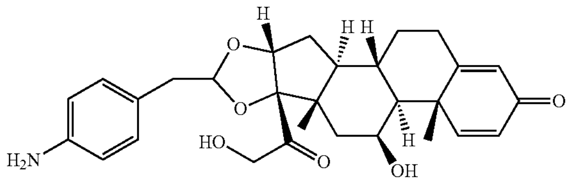

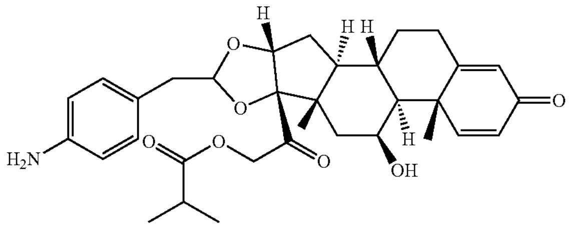

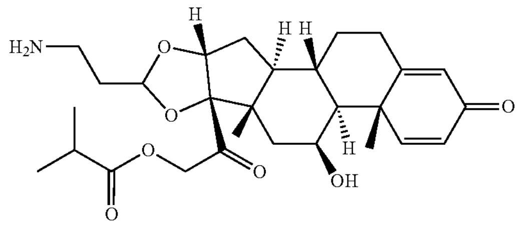

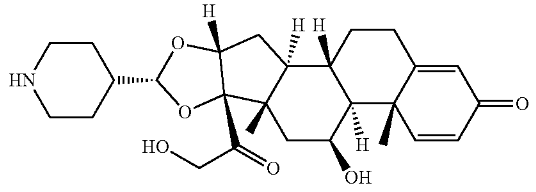

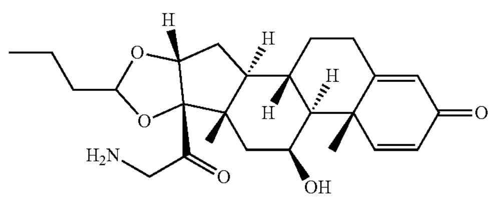

-continued
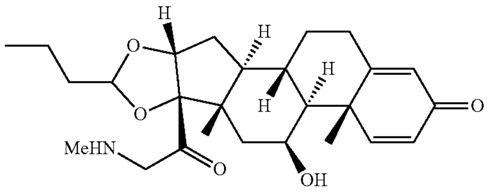
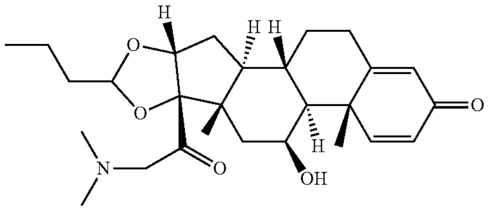
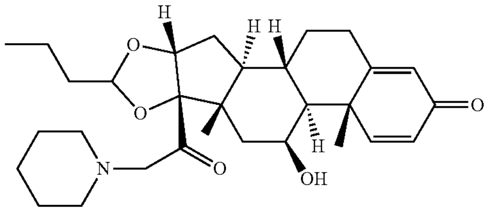
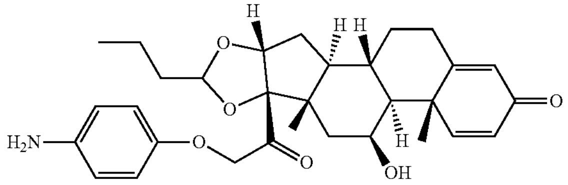
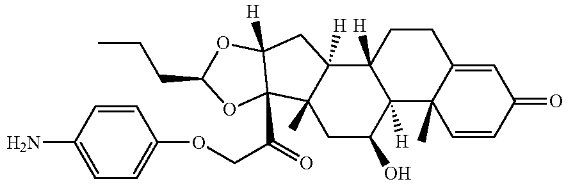
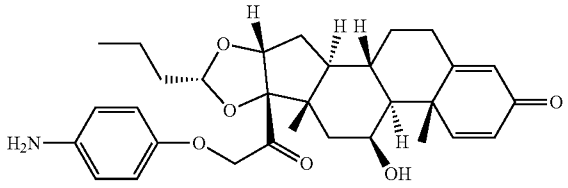
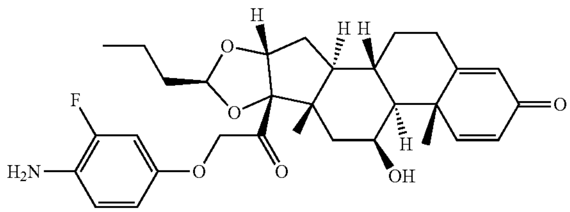
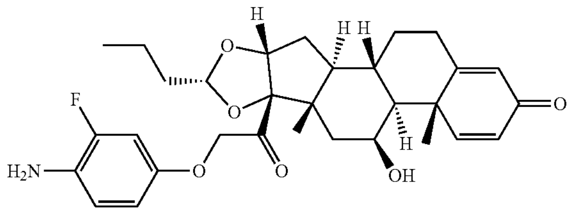
-continued
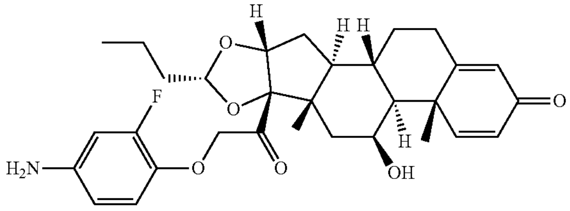
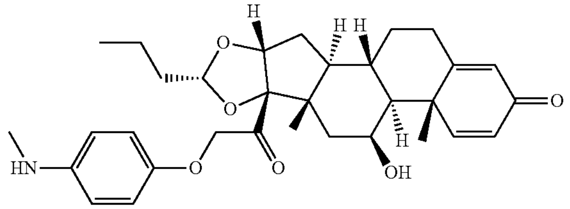
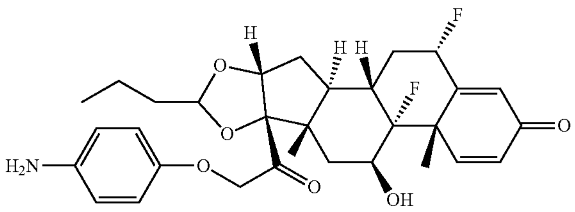
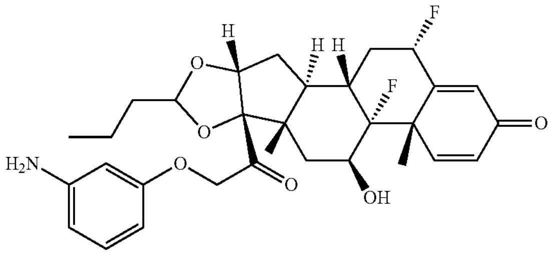
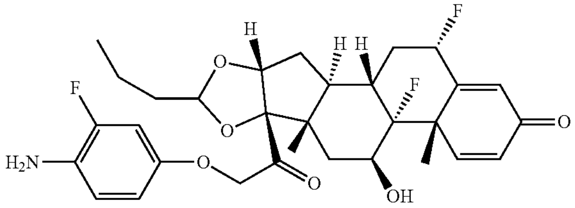
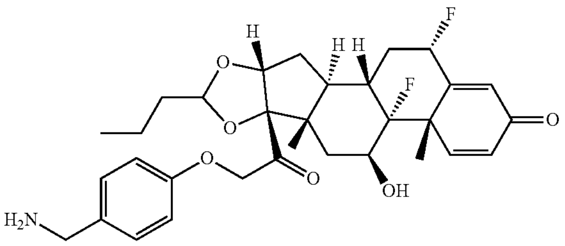
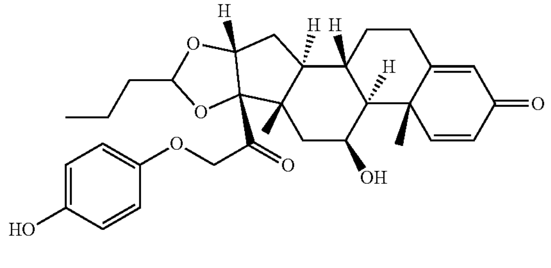

-continued
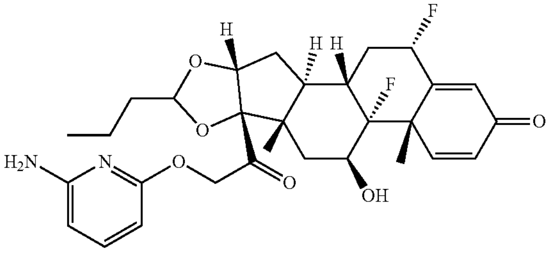
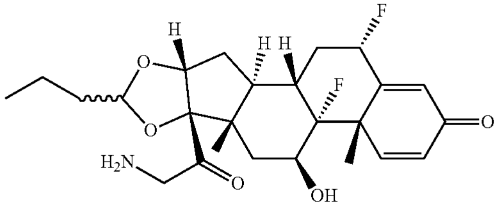
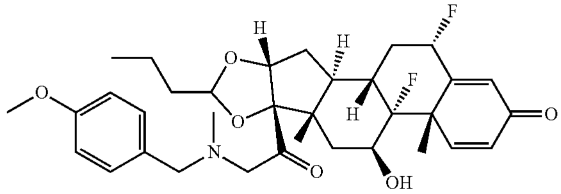
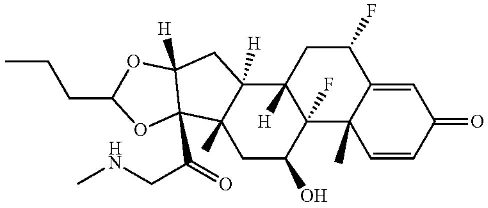
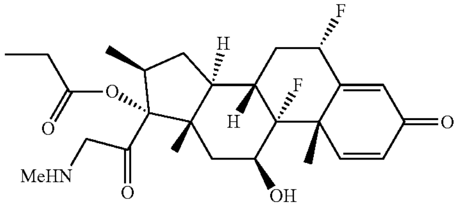
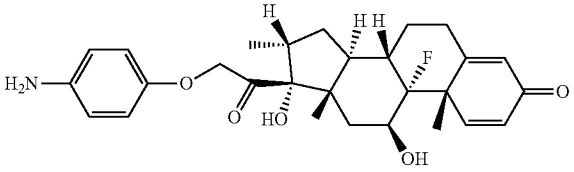
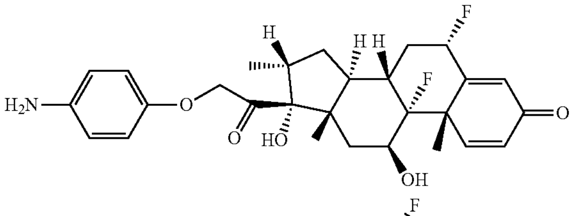
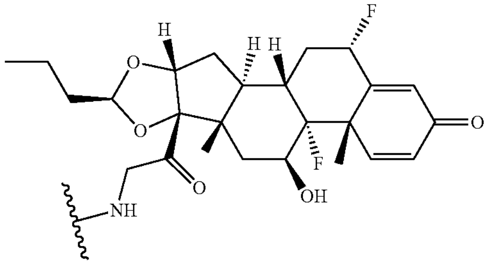
-continued
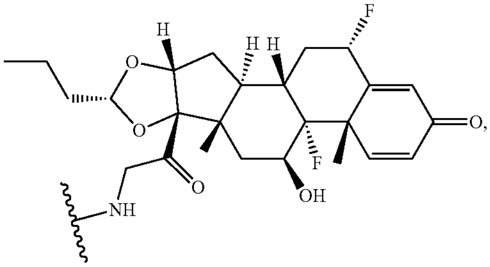
,
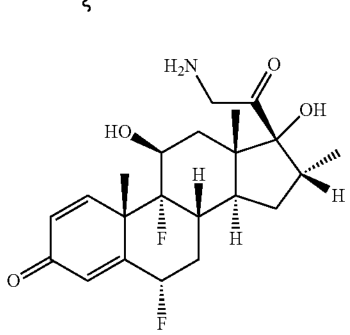
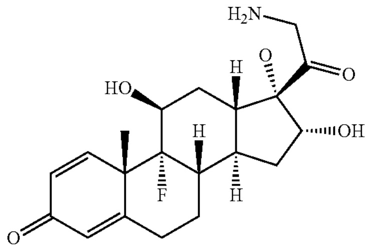
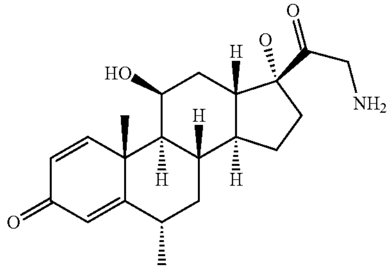
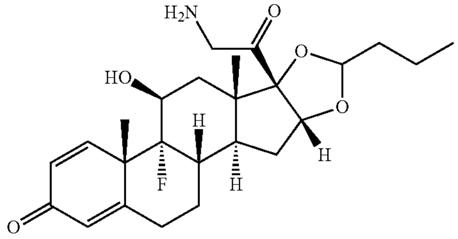
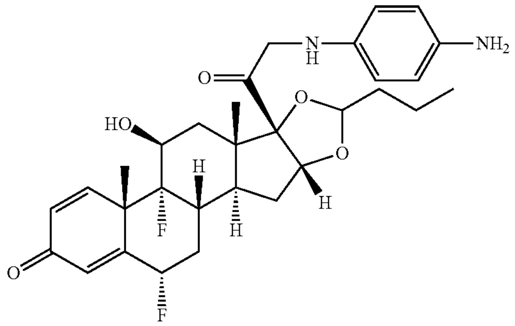

-continued

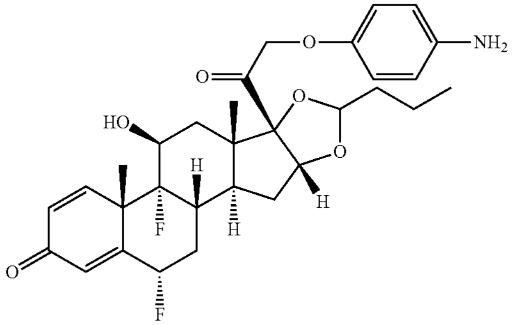

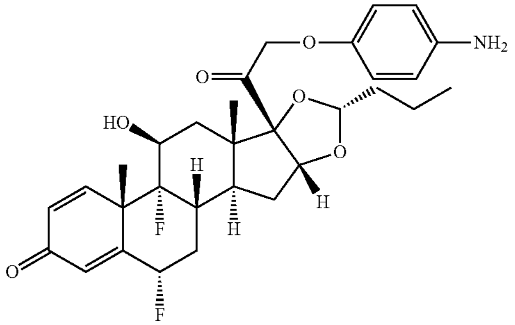

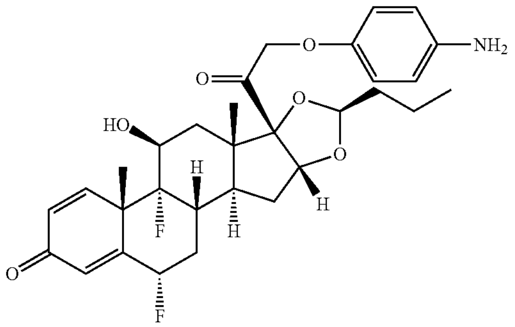

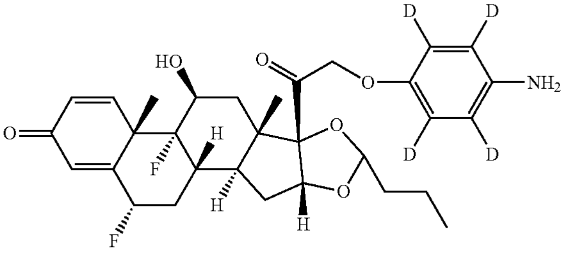

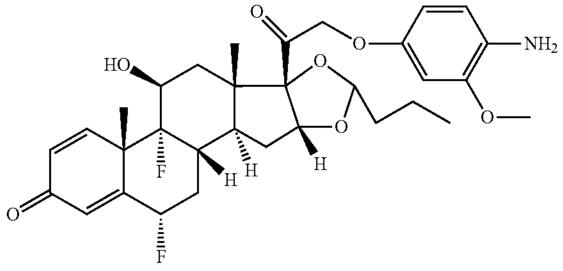

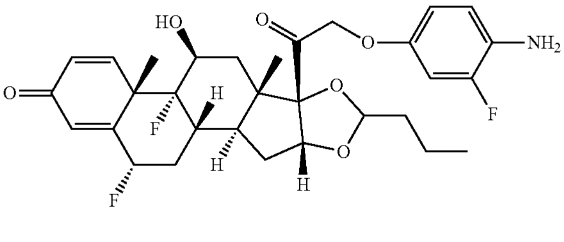

-continued

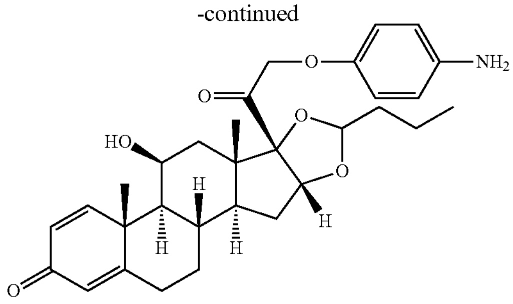

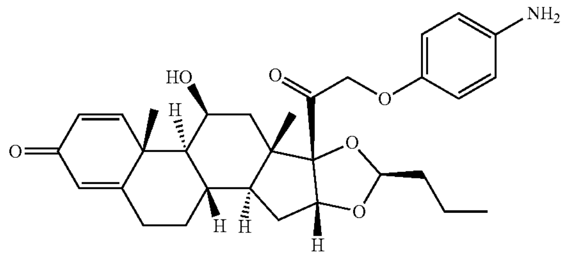

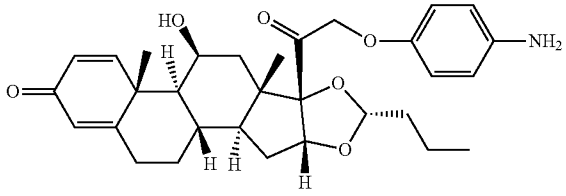

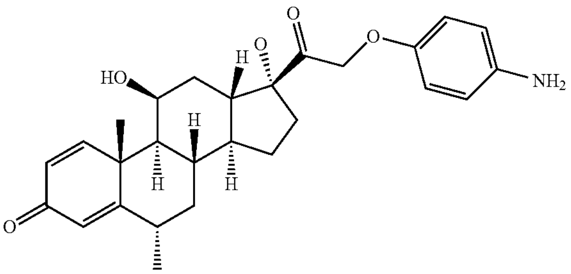

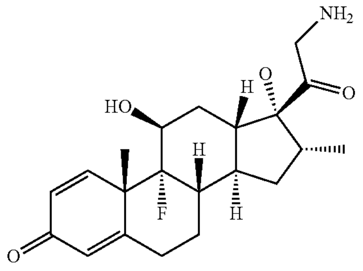

or a pharmaceutically acceptable salt or stereoisomer thereof. In particular embodiments, a primary or secondary amine is linked to a linker L to form a linker payload, which is linked to BA to form a conjugate. Those of skill will recognize that the above compounds can be linked to L with a bond to a primary or secondary amine group, substituting for an H.

In some embodiments, the anti-MSR1 antibodies described herein are conjugated to:

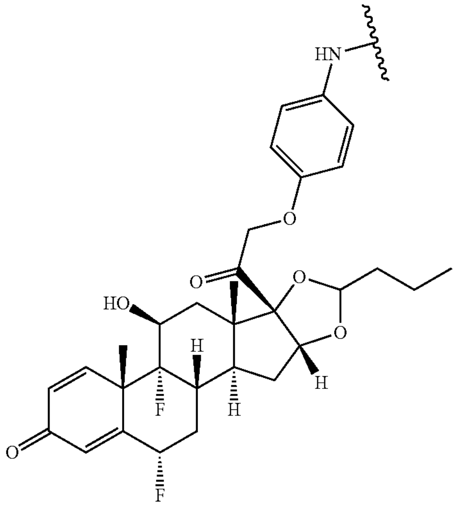

or

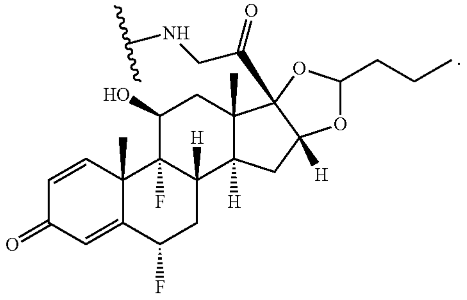

In some embodiments, the antibody-drug conjugates described herein comprise a steroid payload, wherein the steroid payload is selected from the group consisting of:

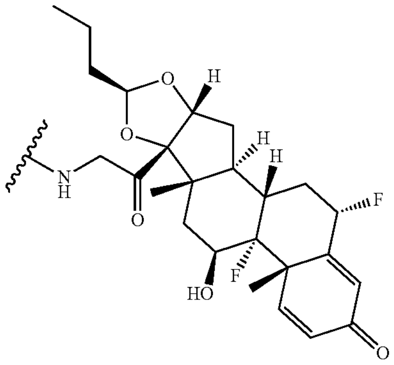

and

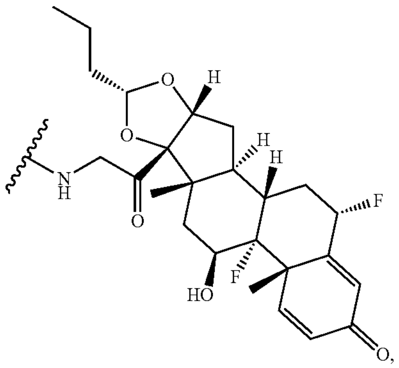

or mixtures thereof.

In certain embodiments, PA is:

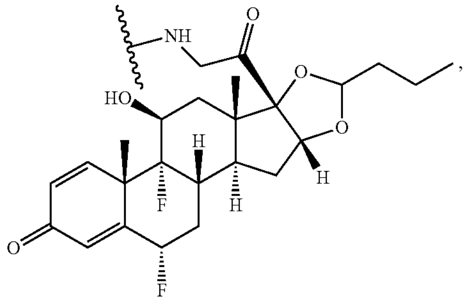

or a pharmaceutically acceptable salt or stereoisomer thereof. In certain embodiments, PA is:

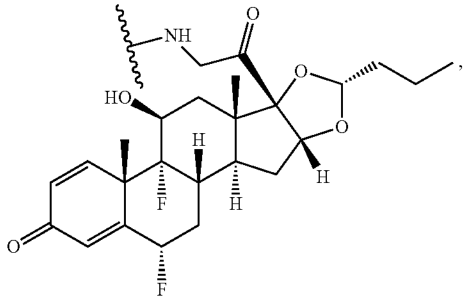

or a pharmaceutically acceptable salt or stereoisomer thereof. In certain embodiments, PA is:

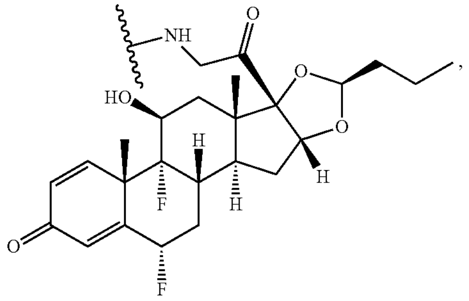

or a pharmaceutically acceptable salt or stereoisomer thereof.

In certain embodiments, PA is:

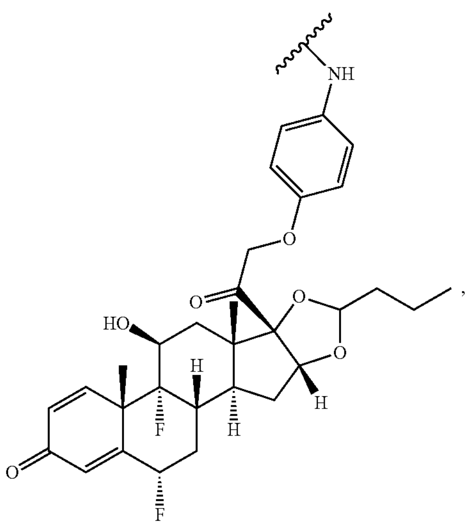

or a pharmaceutically acceptable salt or stereoisomer thereof. In certain embodiments, PA is:

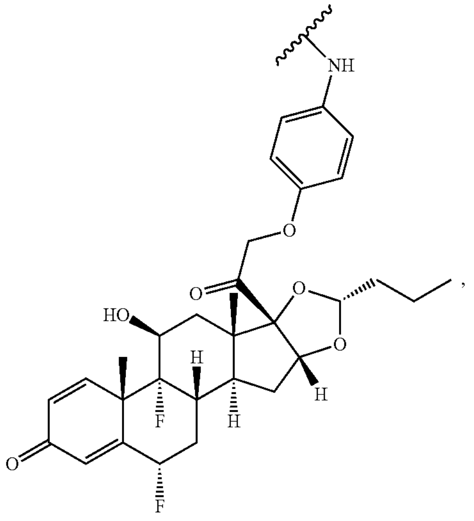

or a pharmaceutically acceptable salt or stereoisomer thereof. In certain embodiments, PA is:

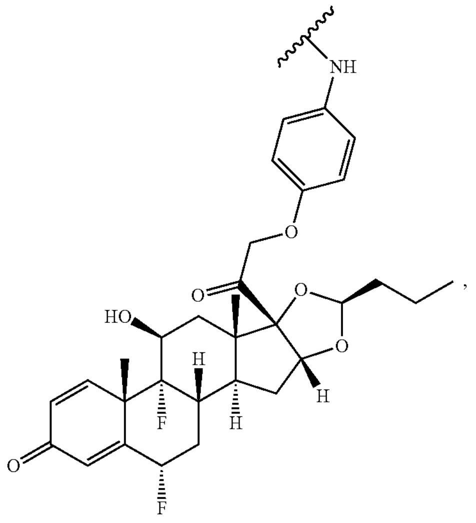

or a pharmaceutically acceptable salt or stereoisomer thereof.

In certain embodiments, PA is a liver X receptor (LXR) modulator. In certain embodiments, PA is according to Formula (B):

Formula (B)

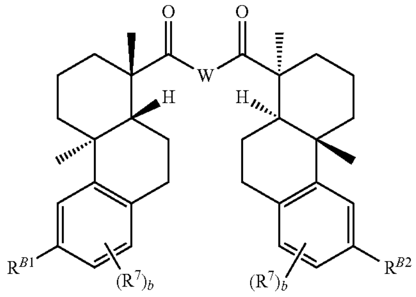

or a pharmaceutically acceptable salt, solvate, or stereoisomeric form thereof, wherein W is —$CH_2$—, —N(H)—, or —O—;

$R^{B1}$ is —H, —OH, —$NH_2$, alkyl, or —OP(O)($OR^6$)$_2$;

$R^{B2}$ is —H, —OH, —$CH_2NH_2$, $R^{B3}$, $R^{B4}$, $R^{B5}$, or —O—$R^{B5}$, wherein $R^{B1}$ and $R^{B2}$ are not simultaneously —H;

$R^{B3}$ is —N($R^6$)$_2$;

$R^{B4}$ is —X—Y—Z;

X is selected from the group consisting of —O— and —N(H)—;

Y is selected from the group consisting of alkylene, substituted alkylene (including, without limitation, oxo substitution, i.e., ═O)), heteroalkylene, and substituted heteroalkylene (including, without limitation, oxo substitution (i.e., ═O));

Z is selected from the group consisting of —OH and —$NH_2$;

$R^{B5}$ is alkyl, heterocycloalkyl, or substituted heterocycloalkyl, wherein each heterocycloalkyl or substituted heterocycloalkyl includes one, two, or three heteroatoms selected from nitrogen and oxygen, and includes at least one —OH and —$CH_2OH$ substituent, or at least one primary or secondary nitrogen, for instance, 0-glucose;

each $R^6$ is in each instance, —H, an amino acid residue, an N-alkyl amino acid residue, a peptide, or alkyl; and each $R^7$ is, independently, halo, $C_{1-6}$ alkyl, $C_{1-6}$ alkoxy, —CN, O-glucose, O-amino acid residue, and O-$PEG_b$, wherein each subscript b is an integer from 0-3;

wherein the group $R^{B1}$, $R^{B2}$ or $R^7$ is bonded to the linker.

In particular embodiments, $R^{B1}$ or $R^{B2}$ is substituted with a bond to the linker (e.g., L or LL).

In certain embodiments, PA is selected from:

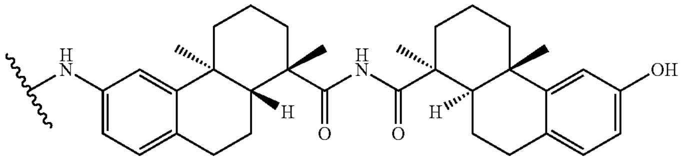

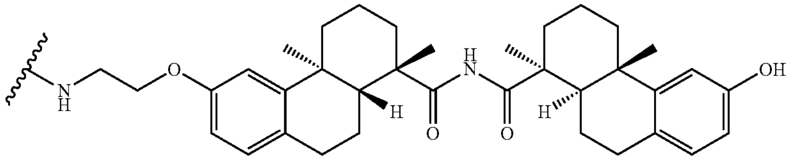

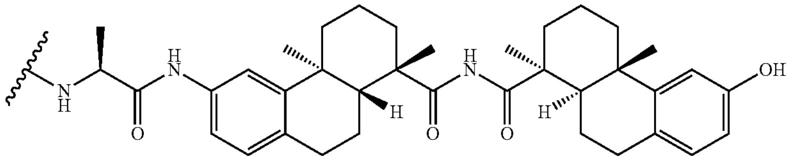

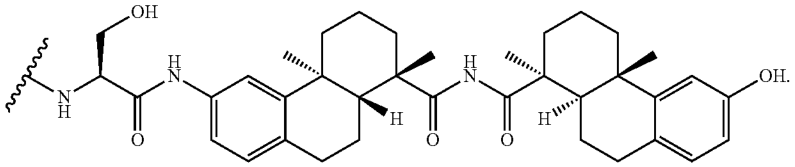

In particular embodiments, the wavy line in

indicates a bond to the linker (e.g., L or LL).

In certain embodiments, the payload of Formula (B) is selected from the group consisting of:

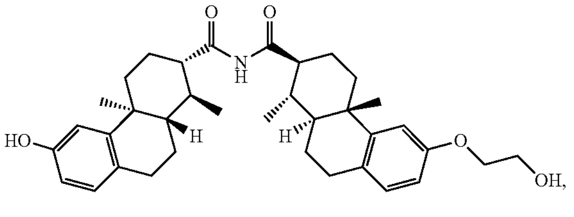

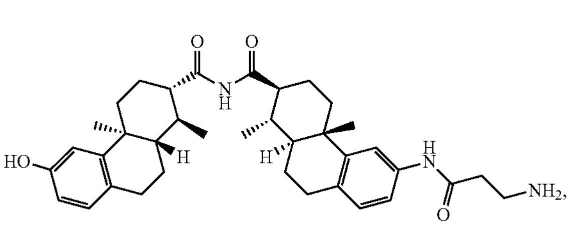

-continued

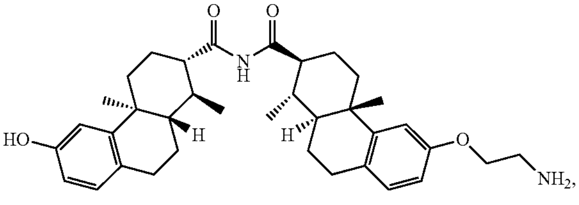

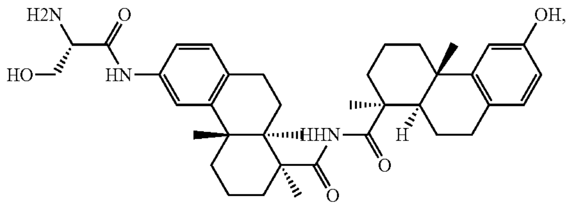

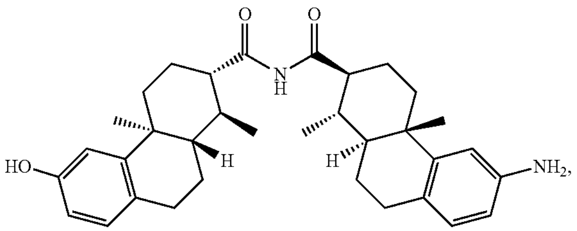

-continued
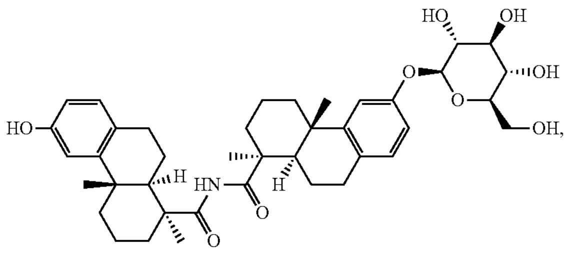
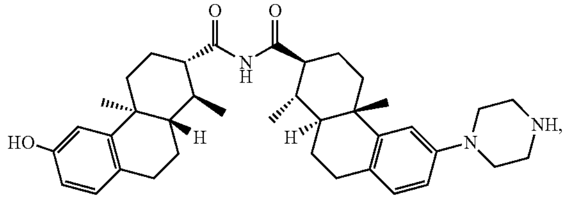
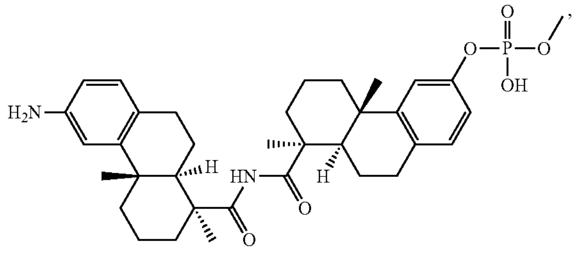
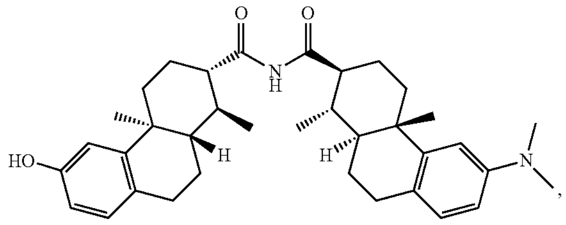
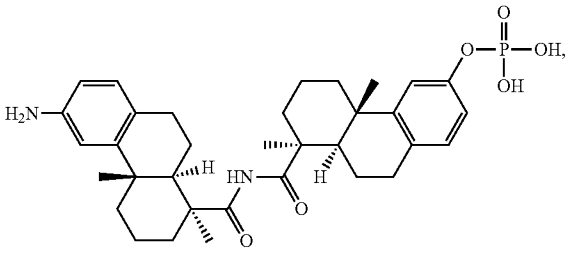
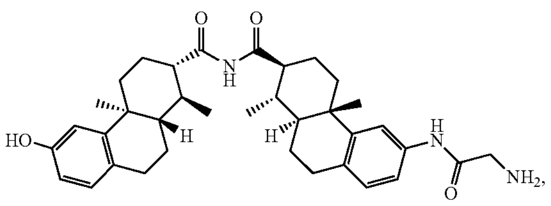
-continued
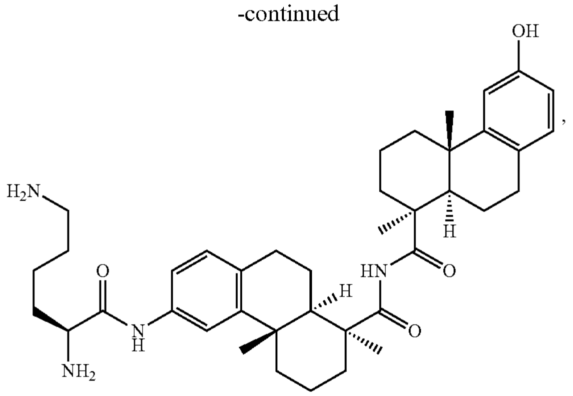
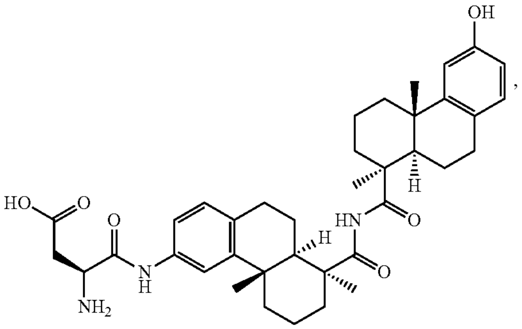
and
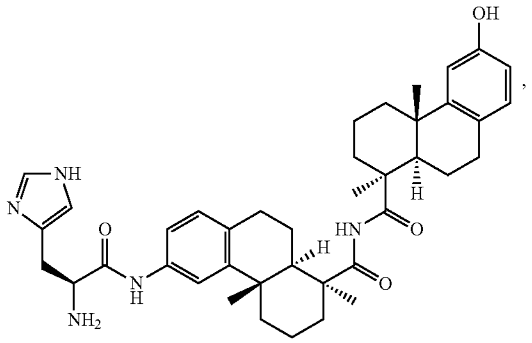
or a pharmaceutically acceptable stereoisomeric form thereof.
In certain embodiments, PA is:
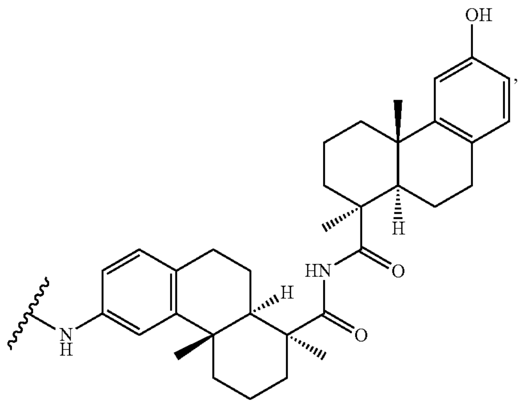 [SMILES: *Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]
or a pharmaceutically acceptable salt or stereoisomer thereof.

In certain embodiments, PA is:

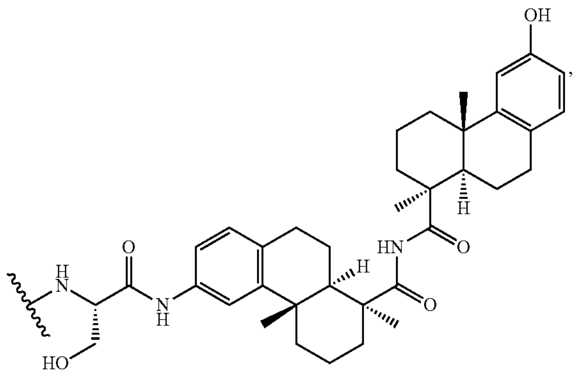 [SMILES: *N[C@@H](CO)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

or a pharmaceutically acceptable salt or stereoisomer thereof.

In certain embodiments, PA is:

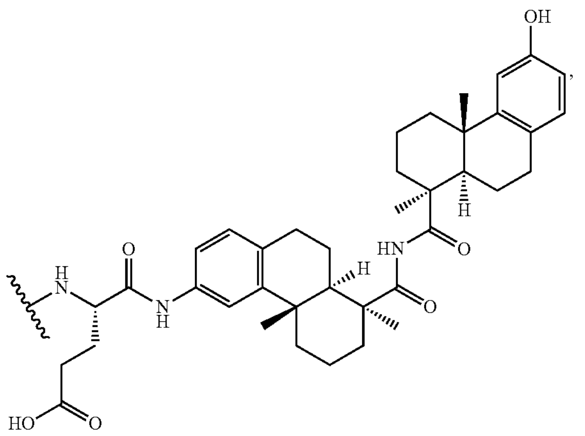 [SMILES: *N[C@@H](CCC(=O)O)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

or a pharmaceutically acceptable salt or stereoisomer thereof.

In some embodiments, the anti-MSR1 antibodies described herein are conjugated to:

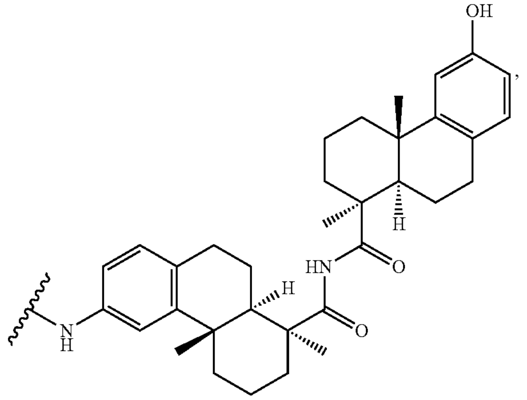

-continued

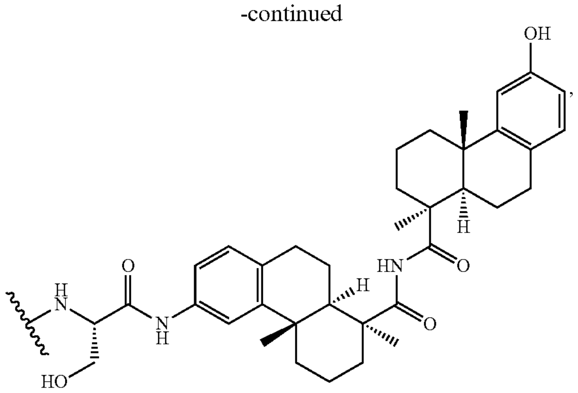

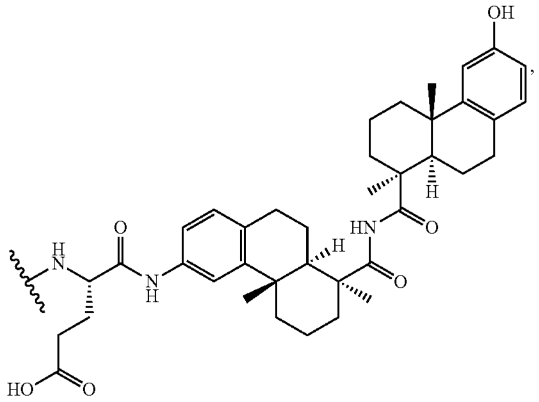

or

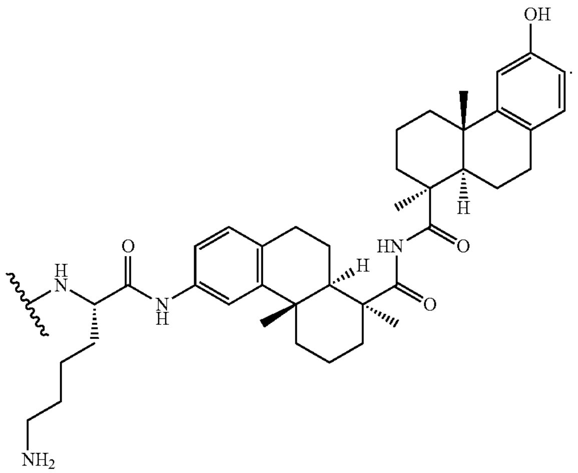

In some embodiments, PA is a liver X receptor (LXR) modulator according to Formula (B-1):

Formula (B-1)

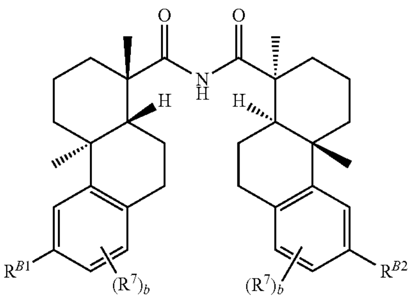

or a pharmaceutically acceptable salt, solvate, or stereoisomeric form thereof, wherein $R^{B1}$ is —N(H)$R^8$ or —N($R^9$)$_2$;

$R^{B2}$ is —N(H)$R^8$;

each $R^8$ is, independently in each instance, hydrogen, an amino acid residue, an N-alkyl amino acid residue, a peptide residue, a biodegradable moiety, or alkyl;

$R^9$ is alkyl, aryl, arylalkyl, heterocycloalkyl, or substituted heterocycloalkyl, wherein each heterocycloalkyl or substituted heterocycloalkyl comprises one, two, or three heteroatoms selected from nitrogen and oxygen, and when substituted includes at least one —OH and —$CH_2$OH, or at least one primary or secondary nitrogen;

each $R^7$ is independently halo, $C_{1-6}$ alkyl, $C_{1-6}$ alkoxy, —CN, O-glucose, O-amino acid residue, or O-PEG$_b$, wherein each subscript b is an integer from 0-3;

wherein the group $R^{B1}$, $R^{B2}$ or $R^7$ is bonded to the linker.

In some instances, a compound of Formula (B-1) is selected from the group consisting of:

P4B

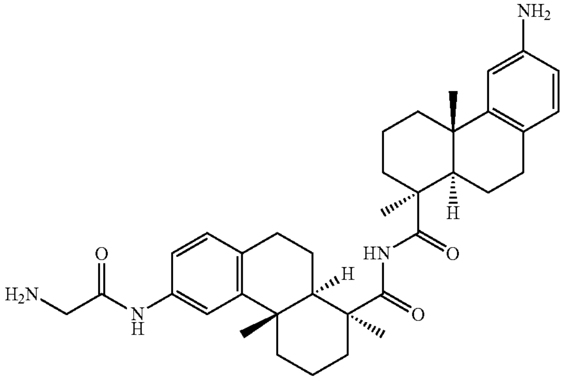

;

-continued

P5B

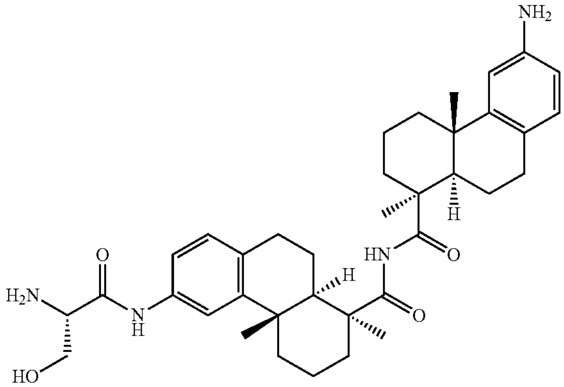

;

P6B

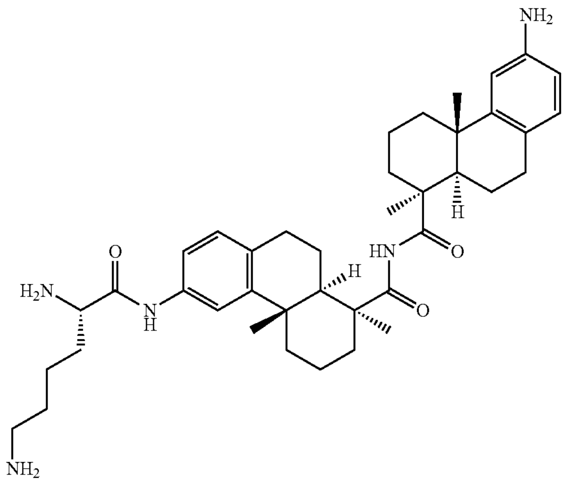

;

P7B

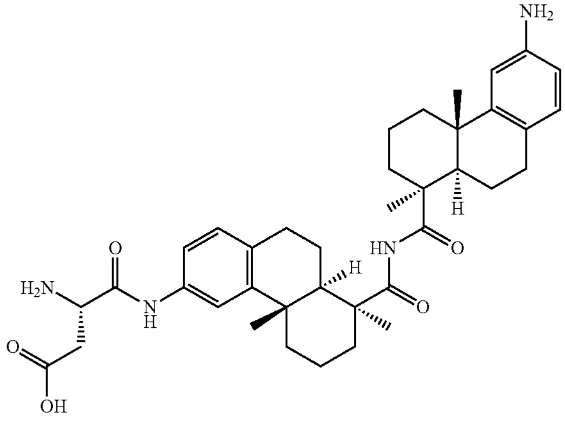

;

-continued
P8B
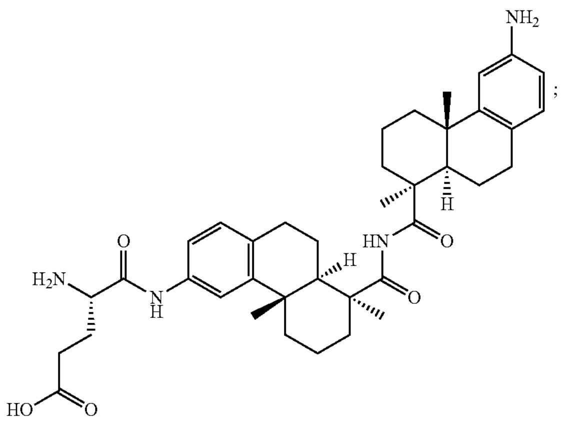
P9B
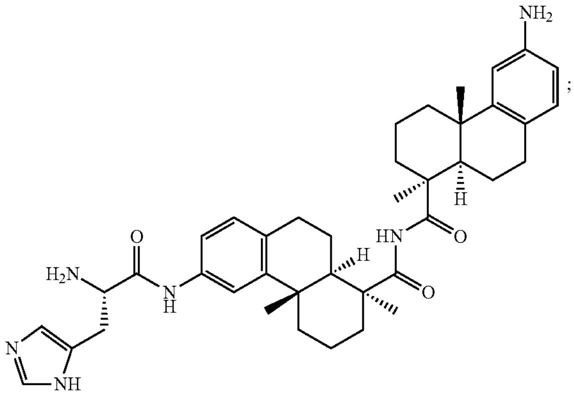
P12B
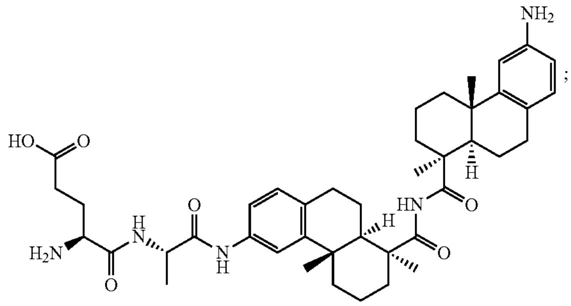
P2B
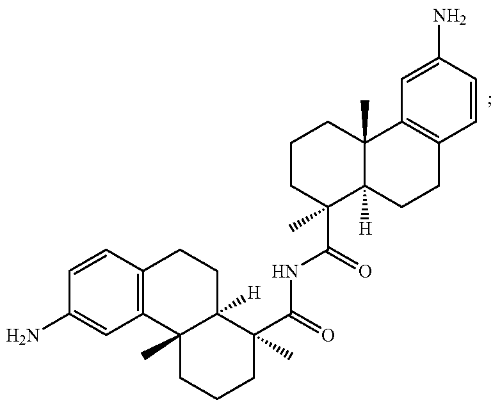
-continued
P10B
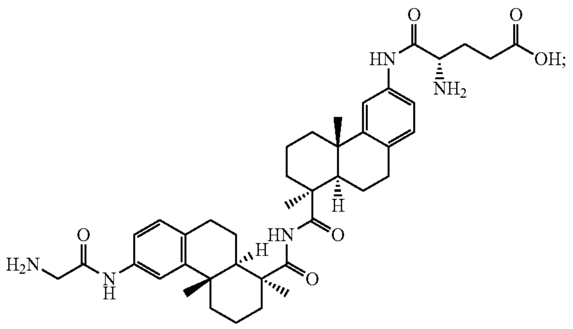
P11B
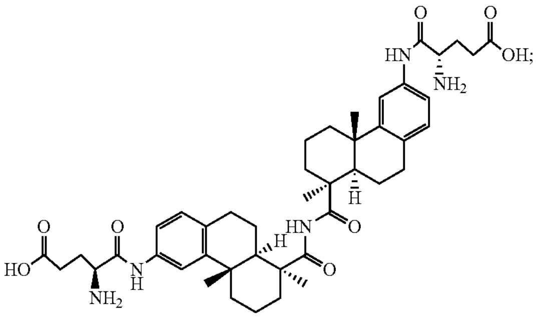
and
P3B
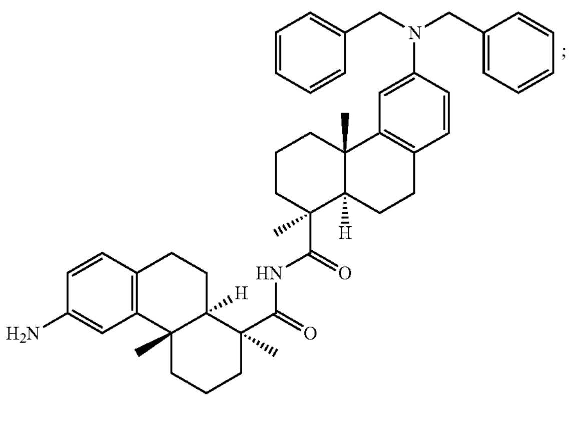
or a pharmaceutically acceptable salt or solvate thereof.
In particular embodiments, $R^{B1}$ or $R^{B2}$ is substituted with a bond to the linker (e.g., L or LL).

In certain embodiments, PA is

P4B

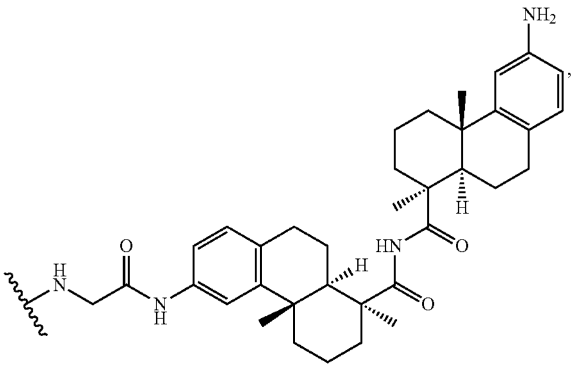

or a pharmaceutically acceptable salt or stereoisomer thereof. In certain embodiments, PA is:

P5B

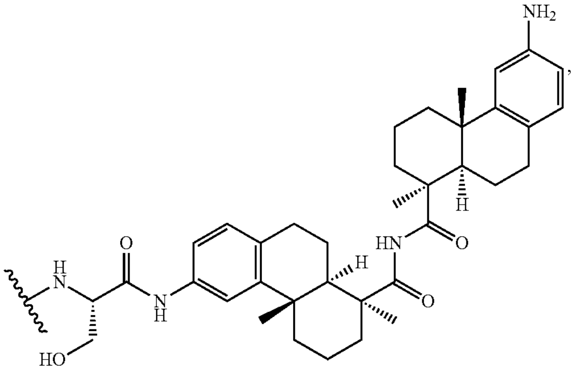

or a pharmaceutically acceptable salt or stereoisomer thereof. In certain embodiments, PA is:

P6B

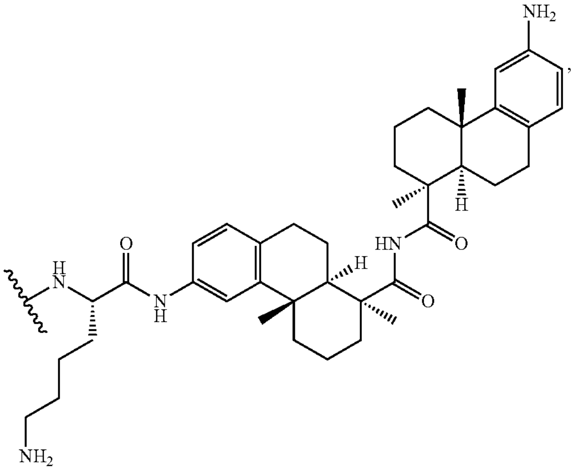

or a pharmaceutically acceptable salt or stereoisomer thereof. In certain embodiments, PA is:

P7B

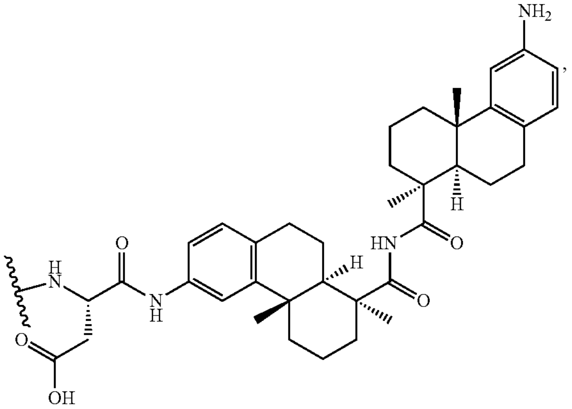

or a pharmaceutically acceptable salt or stereoisomer thereof. In certain embodiments, PA is

P8B

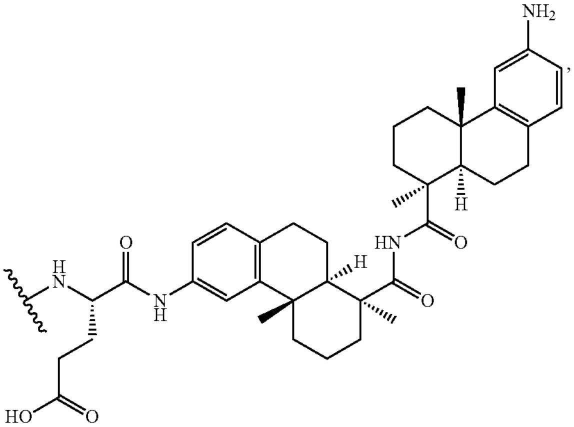

or a pharmaceutically acceptable salt or stereoisomer thereof. In certain embodiments, PA is

P9B

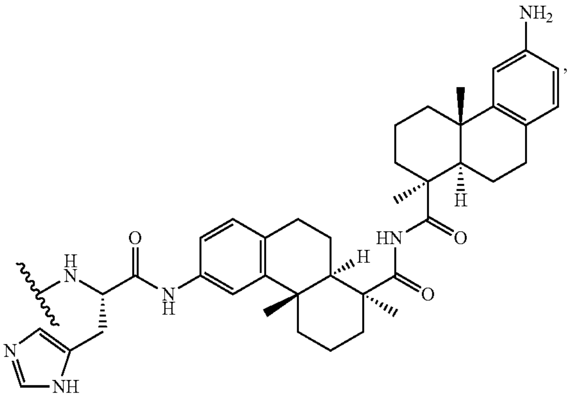

or a pharmaceutically acceptable salt or stereoisomer thereof. In certain embodiments, PA is P12B
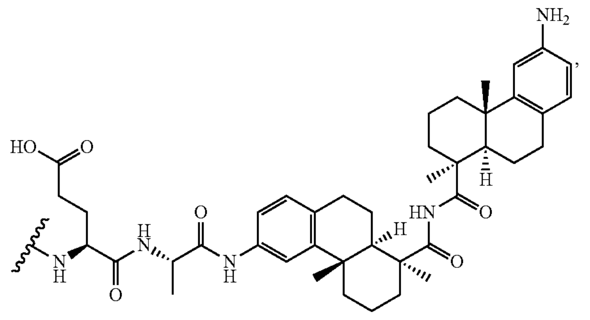
or a pharmaceutically acceptable salt or stereoisomer thereof. In certain embodiments, PA is
P2B
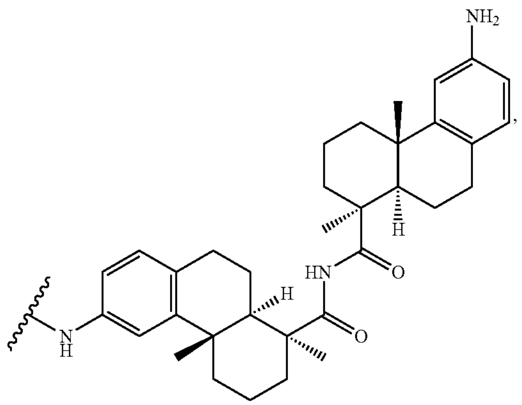
or a pharmaceutically acceptable salt or stereoisomer thereof. In certain embodiments, PA is
P10B
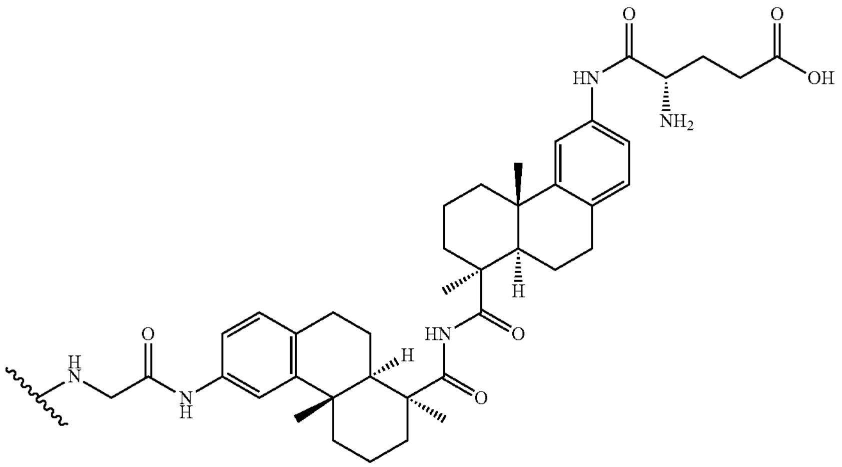
or
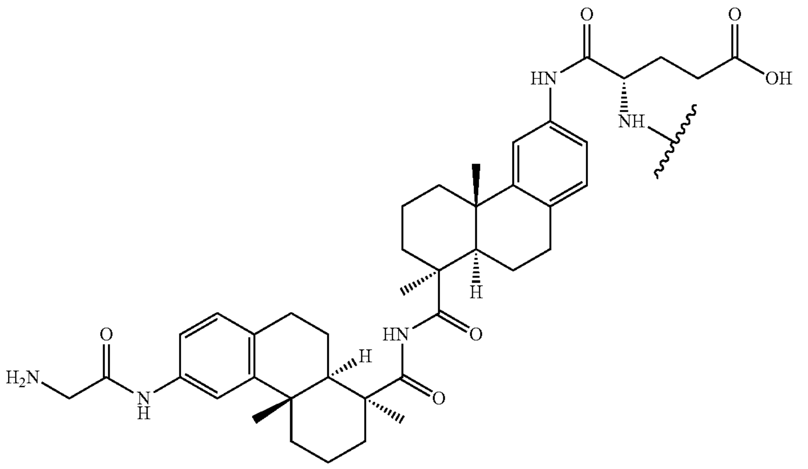
or -continued
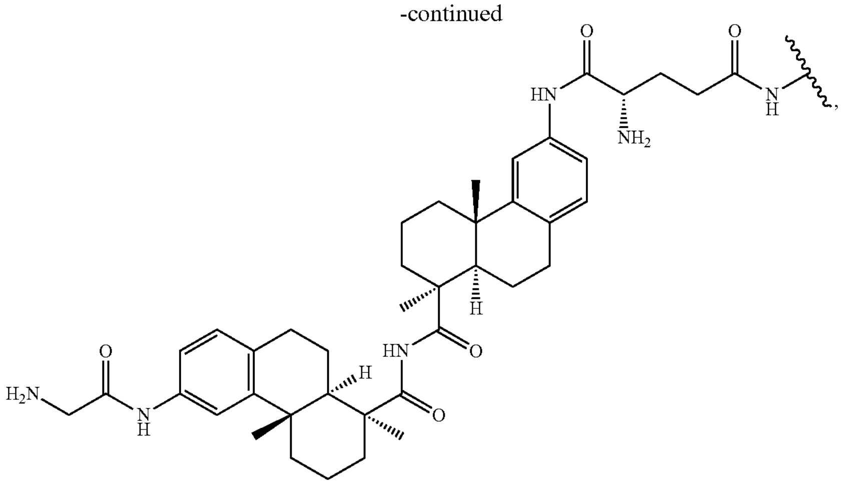
or a pharmaceutically acceptable salt or stereoisomer thereof. In some of such embodiments, the carboxylic acid group of P10B is bonded to the linker through an amide linkage as shown above. In certain embodiments, PA is
P11B
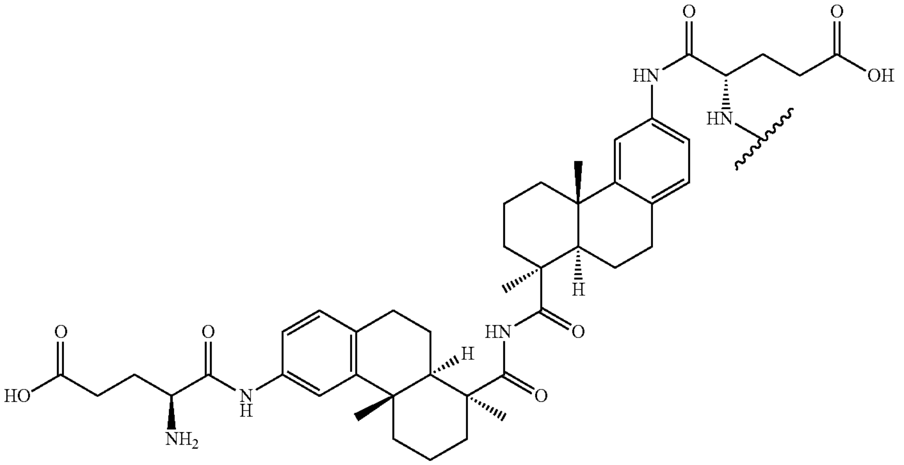
or
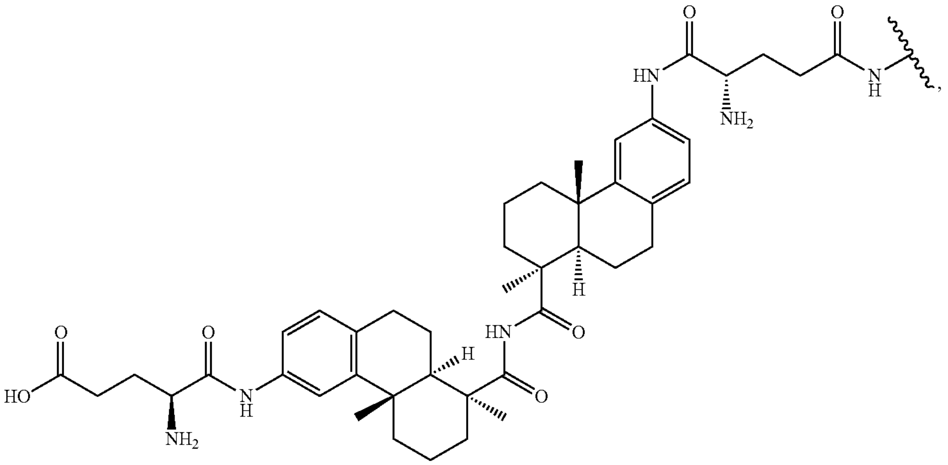

or a pharmaceutically acceptable salt or stereoisomer thereof. In some of such embodiments, the carboxylic acid group of P11B is bonded to the linker through an amide linkage as shown above. In certain embodiments, PA is

P3B

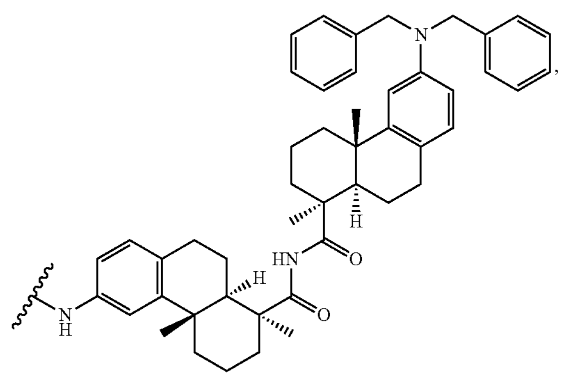

or a pharmaceutically acceptable salt or stereoisomer thereof.

For any embodiments described in this paragraph, the wavy line in

indicates a bond to the linker (e.g., L or LL) as described herein.

In a group of embodiments, provided herein are compounds of Formula (III):

Formula (III)

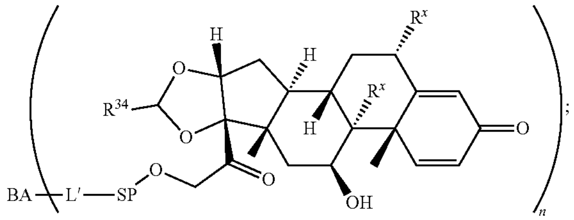

or a pharmaceutically acceptable salt, solvate, or stereoisomer thereof, wherein:

$R^{34}$ is alkyl, aryl, arylalkyl, or an N-containing heterocycloalkyl;

both $R^x$ are hydrogen; and SP is —C(O)—$C_1$-$C_{10}$-alkylene-C(O)—, —C(O)—N($C_{1-6}$alkyl)-$C_1$-$C_{10}$-alkylene-$X^1$— where $X^1$ is attached to L' in Formula (III), —C(O)—N(H)—($C_1$-$C_{10}$-alkylene)-S— where S is attached to L' in Formula (III), —C(O)—N($C_{1-6}$alkyl)-($C_1$-$C_{10}$-alkylene)-S— where S is attached to L' in Formula (III),

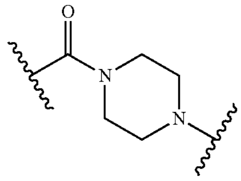 [SMILES: *C(=O)N1CCN(*)CC1]

where the point of attachment on the right hand side (i.e. at N) is to L' in Formula (III), —$CH_2$—NH— where the N is attached to L' in Formula (III),

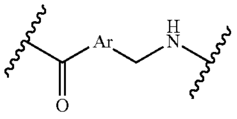

where the N is attached to L' in Formula (III) and where Ar is optionally substituted arylene or optionally substituted heteroarylene, —($C_1$-$C_{10}$-alkylene)-$NR^{5c}$ C(O)—($C_1$-$C_{10}$-alkylene)-$NR^{50a}$— where $NR^{50a}$ is attached to L' in Formula (III), —C(O)—($C_1$-$C_{10}$-alkylene)-$NR^{5c}$ C(O)—($C_1$-$C_{10}$-alkylene)-$NR^{50a}$— where $NR^{50a}$ is attached to L' in Formula (III) and where each $C_1$-$C_{10}$-alkylene is independently optionally substituted with one or more hydroxy, —C(O)—N($R^{35}$)—$C_1$-$C_{10}$-alkylene-C(O)NH—$X^2$— where $X^2$ is attached to L' in Formula (III), or

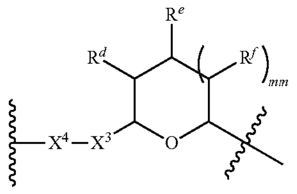

O where $X^4$ is attached to L' in Formula (III); or both $R^x$ are fluoro; and SP is —C(O)—$C_1$-$C_{10}$-alkylene-C(O)—, —C(O)—N($C_{1-6}$alkyl)-$C_1$-$C_{10}$-alkylene-$X^{1b}$— where $X^{1b}$ is attached to L in Formula (III), —C(O)—N(H)—($C_1$-$C_{10}$-alkylene)-$X^{1b}$— where $X^{1b}$ is attached to L' in Formula (III),

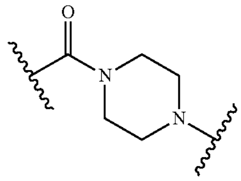 [SMILES: *C(=O)N1CCN(*)CC1]

where the point of attachment on the right hand side (i.e. at N) is to L' in Formula (III), —$CH_2$—NH— where the N is attached to L' in Formula (III),

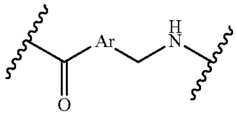

where the N is attached to L' in Formula (III) and where Ar is optionally substituted arylene or optionally substituted heteroarylene, —($C_1$-$C_{10}$-alkylene)-$NR^{5c}$ C(O)—($C_1$-$C_{10}$-alkylene)-$NR^{50a}$— where $NR^{50a}$ is attached to L' in Formula (III), —C(O)—($C_1$-$C_{10}$-alkylene)-$NR^{5c}$ C(O)—($C_1$-$C_{10}$-alkylene)-$NR^{50a}$— where $NR^{50a}$ is attached to L' in Formula (III) and where each $C_1$-$C_{10}$-alkylene is independently optionally substituted with one or more hydroxy, —C(O)—N($R^{35}$)—($C_1$-$C_{10}$-alkylene)-C(O)NH—$X^2$— where $X^2$ is attached to L' in Formula (III), or

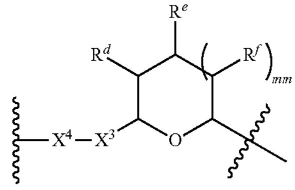

where $X^4$ is attached to L' in Formula (III); and $X^1$ is —N($C_{1-6}$alkyl)-;

$X^{1b}$ is —S—, —NH—, or —N($C_{1-6}$alkyl)-;

$X^2$ is —NH—;

$X^3$ is —$CH_2$—, $X^3$ is —$CH_2$—O—($C_1$-$C_{10}$-alkylene)-C(O)— where the C(O) is attached to $X^4$, or $X^3$ is —C(O)—;

$X^4$ is —O—;

$R^{35}$ is H, —OH, —$OCH_3$, or $C_{1-6}$alkyl;

$R^{5c}$ and $R^{51a}$ are independently hydrogen or $C_1$-$C_6$-alkyl;

$R^d$, $R^e$, and $R^f$ are independently —H, —OH, hydroxyalkyl, alkoxycarbonyl, —C(O)OH, or —$CH_2OR^g$, where each $R^g$ is independently —$CH_2C(O)OH$ or —$CH_2C(O)O$(alkyl); and mm is 0 or 1;

n is an integer selected from 1-30, inclusive;

L' is a linker; and

BA is a binding agent.

In some embodiments, in a compound of Formula (III), both $R^x$ are hydrogen, and SP, BA, L', $R^{34}$, and n are as described herein in some or any embodiments. In some embodiments, in a compound of Formula (III), both $R^x$ are fluoro, and SP, BA, L', $R^{34}$, and n are as described herein in some or any embodiments. In some embodiments, $R^{34}$ is in the R-configuration. In some embodiments, $R^{34}$ is in the S-configuration. In some embodiments, $R^{34}$ is a mixture of the R- and S-configurations. In some embodiments, $R^{34}$ is a mixture of the R- and S-configurations, wherein the R:S mixture is about 1:1, about 2:1, about 3:1, about 4:1, about 5:1, about 6:1, about 7:1, about 8:1, about 9:1, or about 10:1.

In some embodiments are compounds of Formula (III) where both $R^x$ are hydrogen; and SP is —C(O)—$C_1$-$C_{10}$-alkylene-C(O)—, —C(O)—N($C_{1-6}$alkyl)-$C_1$-$C_{10}$-alkylene-$X^1$— where $X^1$ is attached to L' in Formula (III), —C(O)—N(H)—($C_1$-$C_{10}$-alkylene)-S— where S is attached to L' in Formula (III), —C(O)—N($C_{1-6}$alkyl)-($C_1$-$C_{10}$-alkylene)-S— where S is attached to L' in Formula (III), —($C_1$-$C_{10}$-alkylene)-$NR^{50}$C(O)—($C_1$-$C_{10}$-alkylene)-$NR^{50a}$— where $NR^{50a}$ is attached to L' in Formula (III), —C(O)—($C_1$-$C_{10}$-alkylene)-$NR^{50}$C(O)—($C_1$-$C_{10}$-alkylene)-$NR^{50a}$— where $NR^{50a}$ is attached to L' in Formula (III) and where each $C_1$-$C_{10}$-alkylene is independently optionally substituted with one or more hydroxy, —C(O)—N($R^5$)—$C_1$-$C_{10}$-alkylene-C(O)NH—$X^2$— where $X^2$ is attached to L' in Formula (III), or

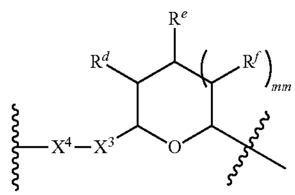

where $X^4$ is attached to L' in Formula (III); or both $R^x$ are fluoro; and SP is —C(O)—N($C_{1-6}$alkyl)-$C_1$-$C_{10}$-alkylene-$X^{1b}$— where $X^{1b}$ is attached to L' in Formula (III), —C(O)—N(H)—($C_1$-$C_{10}$-alkylene)-$X^{1b}$— where $X^{1b}$ is attached to L' in Formula (III),

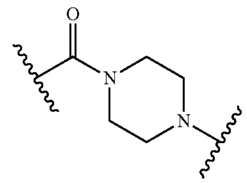 [SMILES: *C(=O)N1CCN(*)CC1]

where the point of attachment on the right hand side (i.e. at N) is to L' in Formula (III), —($C_1$-$C_{10}$-alkylene)-$NR^{50}$C(O)—($C_1$-$C_{10}$-alkylene)-$NR^{50a}$— where $NR^{50a}$ is attached to L' in Formula (III), —C(O)—($C_1$-$C_{10}$-alkylene)-$NR^{50}$C(O)—($C_1$-$C_{10}$-alkylene)-$NR^{50a}$— where $NR^{50a}$ is attached to L' in Formula (III) and where each $C_1$-$C_{10}$-alkylene is independently optionally substituted with one or more hydroxy, or —C(O)—N($R^5$)—($C_1$-$C_{10}$-alkylene)-C(O)NH—$X^2$— where $X^2$ is attached to L' in Formula (III).

In some embodiments, a compound of Formula (I) is a compound of Formula (3000):

$$BA\text{-}(L'\text{-}SP\text{-}D)_n \qquad \text{Formula (3000)}$$

or a pharmaceutically acceptable salt, solvate, or stereoisomer thereof, wherein D is selected from a)

Formula (a)

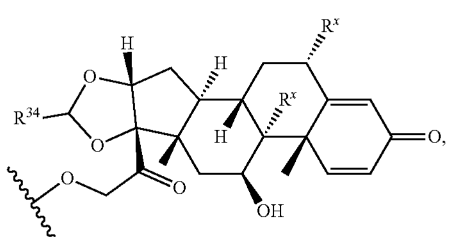

where both $R^x$ in Formula (a) are hydrogen; $R^{34}$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^1$— where $X^1$ is attached to L' in Formula (3000), —C(O)—N(H)—($C_1$-$C_{10}$-alkylene)-S— where S is attached to L' in Formula (3000), —C(O)—N($C_{1-6}$alkyl)-($C_1$-$C_{10}$-alkylene)-S— where S is attached to L' in Formula (3000),

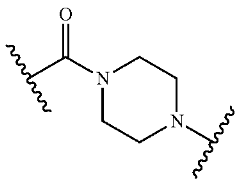 [SMILES: *C(=O)N1CCN(*)CC1]

where the point of attachment on the right hand side (i.e. at N) is to L in Formula (3000), —$CH_2$—NH— where the N is attached to L' in Formula (3000),

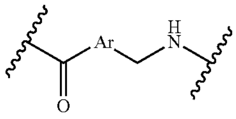

where the N is attached to L' in Formula (3000) and where Ar is optionally substituted arylene (in some embodiments

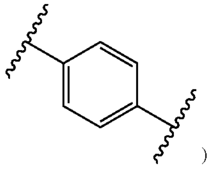 [SMILES: *c1ccc(*)cc1]

or optionally substituted heteroarylene, —($C_1$-$C_{10}$-alkylene)-$NR^{50}$C(O)—($C_1$-$C_{10}$-alkylene)-$NR^{50a}$— where $NR^{50a}$ is attached to L' in Formula (3000), —C(O)—($C_1$-$C_{10}$-alkylene)-$NR^{5c}$ C(O)—($C_1$-$C_{10}$-alkylene)-$NR^{50a}$— where $NR^{50a}$ is attached to L' in Formula (3000) and where each $C_1$-$C_{10}$-alkylene is independently optionally substituted with one or more hydroxy, —C(O)—N($R^{35}$)—$C_1$-$C_{10}$-alkylene-C(O)NH—$X^2$— where $X^2$ is attached to L' in Formula (3000), or

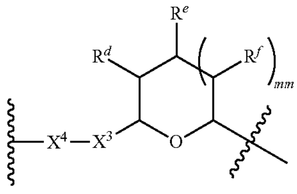

where $X^4$ is attached to L' in Formula (3000); or where both $R^x$ in Formula (a) are fluoro; $R^{34}$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^{1b}$— where $X^{1b}$ is attached to L' in Formula (3000), —C(O)—N(H)—($C_1$-$C_{10}$-alkylene)-$X^{1b}$— where $X^{1b}$ is attached to L' in Formula (3000),

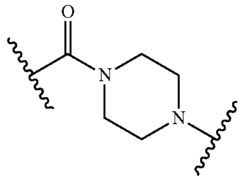 [SMILES: *C(=O)N1CCN(*)CC1]

where the point of attachment on the right hand side (i.e. at N) is to L' in Formula (3000), —$CH_2$—NH— where the N is attached to L' in Formula (3000),

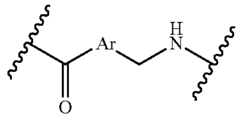

where the N is attached to L in Formula (3000) and where Ar is optionally substituted arylene (in some embodiments

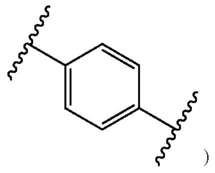 [SMILES: *c1ccc(*)cc1]

or optionally substituted heteroarylene, —($C_1$-$C_{10}$-alkylene)-$NR^{50}$C(O)—($C_1$-$C_{10}$-alkylene)-$NR^{50a}$— where $NR^{50a}$ is attached to L' in Formula (3000), —C(O)—($C_1$-$C_{10}$-alkylene)-$NR^{5c}$ C(O)—($C_1$-$C_{10}$-alkylene)-$NR^{50a}$— where $NR^{50a}$ is attached to L' in Formula (3000) and where each $C_1$-$C_{10}$-alkylene is independently optionally substituted with one or more hydroxy, —C(O)—N($R^{35}$)—($C_1$-$C_{10}$-alkylene)-C(O)NH—$X^2$— where $X^2$ is attached to L' in Formula (3000), or

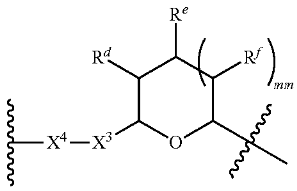

where $X^4$ is attached to L' in Formula (3000); and/or b) the compounds in Table A below, where the compounds in Table A are linked to BA of the Compound of Formula (III) through the hydroxy of the —C(O)$CH_2$OH group, i.e. by —C(O)$CH_2$—O—SP-L'—, or through the hydroxy of Mapracorat, i.e. by —O—SP-L'—;

$X^1$ is —N($C_{1-6}$alkyl)-;

$X^{1b}$ is —S—, —NH—, or —N($C_{1-6}$alkyl)-;

$X^2$ is —NH—;

$X^3$ is —$CH_2$—, $X^3$ is —$CH_2$—O—($C_1$-$C_{10}$-alkylene)-C(O)— where the C(O) is attached to $X^4$, or $X^3$ is —C(O)—;

$X^4$ is —O—;

$R^{35}$ is H, —OH, —$OCH_3$, or $C_{1-6}$alkyl;

$R^{5c}$ and $R^{50a}$ are independently hydrogen or $C_1$-$C_6$-alkyl;

$R^d$, $R^e$, and $R^f$ are independently —H, —OH, hydroxyalkyl, alkoxycarbonyl, —C(O)OH, or —$CH_2OR^g$, where each R9 is independently —$CH_2C(O)OH$ or —$CH_2C(O)O$(alkyl); and mm is 0 or 1;

n is an integer selected from 1-30, inclusive;

L' is a linker; and

BA is a binding agent.

In some instances of Formula (3000), D is budesonide or any other steroid shown in Table A. In some instances of Formula (3000), D is any budesonide analog described herein. The compounds in Table A are linked to BA of the Compound of Formula (III) through the hydroxy of the —C(O)$CH_2$OH group, i.e. by —C(O)$CH_2$—O—SP-L'—, or through the hydroxy of Mapracorat, i.e. by —O—SP-L'—. In some instances of Formula (3000), the moiety SP-D (or H-SP-D) is referred to herein as a "budesonide-spacer" and includes, e.g., budesonide-spacers shown in Table B, in the examples section and in Scheme 1 in FIG. 22.

TABLE A

| Trade name | Structure |
|---|---|
| Hydrocortisone butyrate<br>Locoid ® | 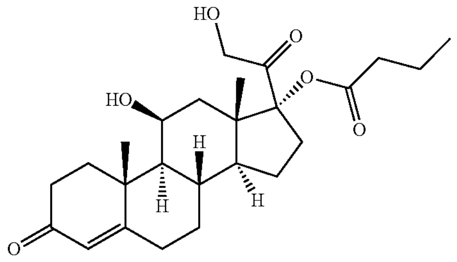 |
| Halometasone<br>Sicorten ®/<br>(C-48401-Ba) | 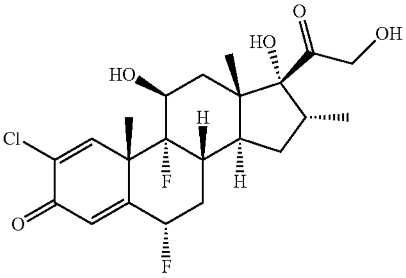 |
| Betamethasone<br>Celestone ®/Rinderson ®/Diprosone ®<br>(NSC-39470; Sch-4831) | 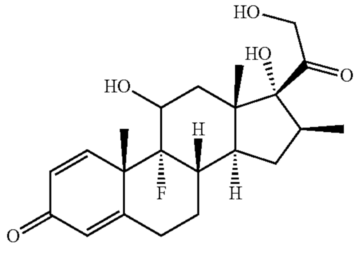 |
| Fluclorolone Acetonide<br>Cutanit ®/Topicon ®<br>(RS-2252) | 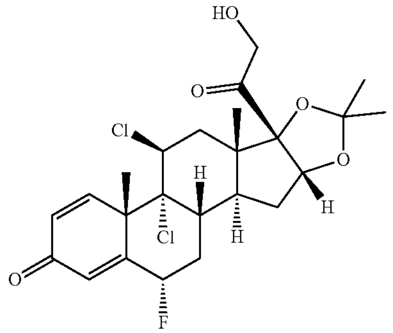 |

TABLE A-continued
| Trade name | Structure |
|---|---|
| Fluocinolone Acetonide<br>Flucort ®/Fluonid ®/Iluvien ®/Retisert ®/<br>Synalar ®/Synalar-HP ®/Synemol ®<br>(NSC-92339; DF-277) | 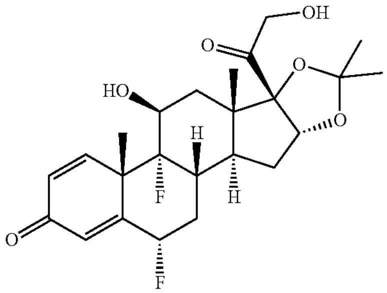 |
| Flunisolide<br>(RS-3999; RS-1320) | 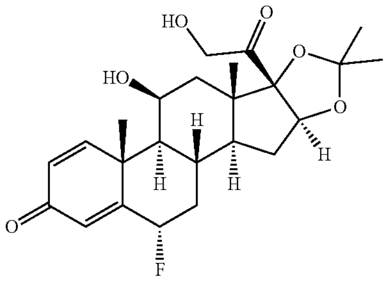 |
| Clopednol<br>(RS-4691) | 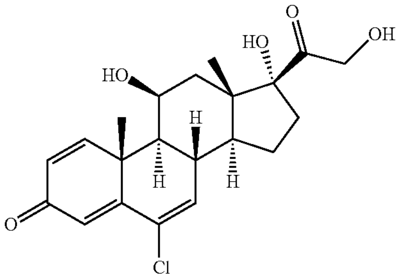 |
| Triamcinolone<br>Aristocort ®/Kenacort ® | 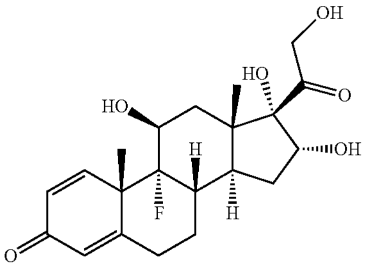 |
| Budesonide | 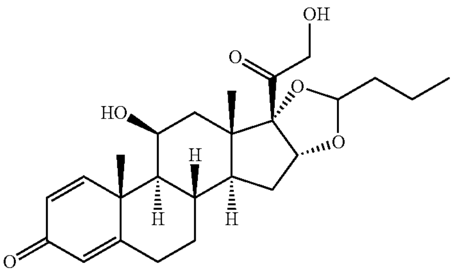 |

TABLE A-continued
| Trade name | Structure |
| --- | --- |
| Flurandrenolide<br>Cordran ® | 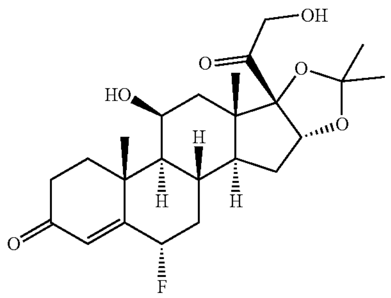 |
| Desoximetasone<br>Topicort ®<br>(DSXS) | 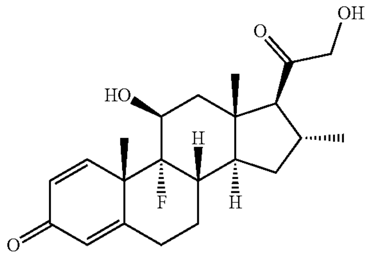 |
| Betamethasone benzoate<br>Uticort ®<br>(W-5975) | 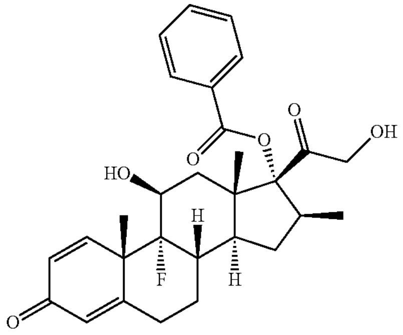 |
| Desonide<br>Desonate ®<br>(D-2083) | 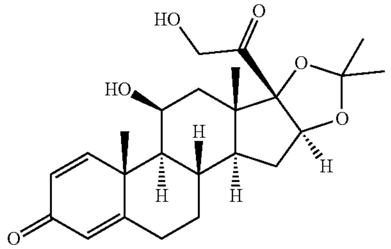 |
| Meprednisone<br>(NSC-527579; Sch-4358) | 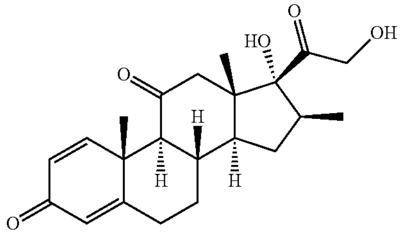 |

TABLE A-continued
| Trade name | Structure |
|---|---|
| Prednisolone<br>Delta-Cortef ®<br>(NCS-9120) | 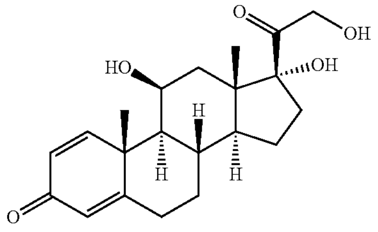 |
| Triamcinolone Acetonide | 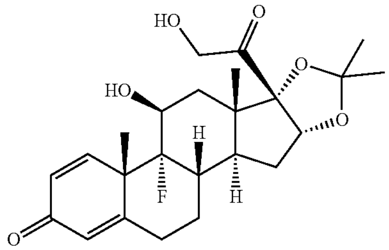 |
| Methylprednisolone<br>Depo-Medrol; Medrol; Urbason ®<br>(NSC-19987) | 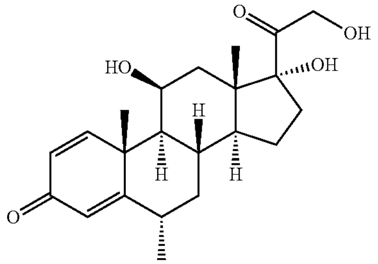 |
| Prednisone<br>Decortin ®/Deltasone ®/Lodotra ®/<br>Meticorten ®/Rayos ®<br>(NSC-10023) | 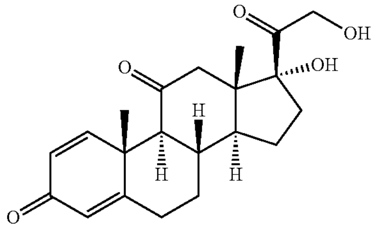 |
| Dexamethasone<br>Decadron ®<br>(FT-4145; ENV-1105; IBI-10090;<br>ISV-305; OTO-104) | 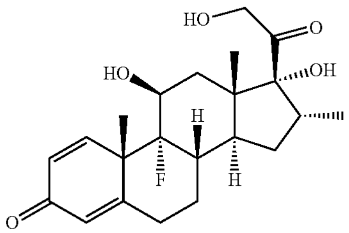 |
| Hydrocortisone valerate<br>Westcort ® | 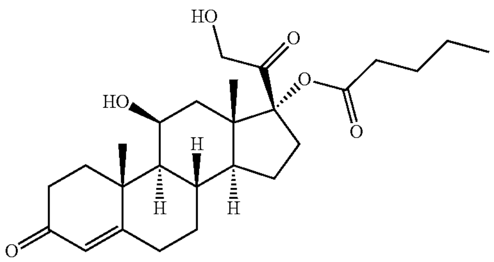 |

TABLE A-continued
| Trade name | Structure |
| --- | --- |
| Mapracorat (BOL-242X; BOL-303242-X; ZK-245186; BAY-865319; BOL-303242-X) | 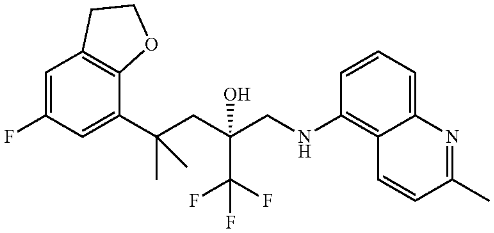 [SMILES: Cc1ccc2c(NC[C@](O)(CC(C)(C)c3cc(F)cc4c3OCC4)C(F)(F)F)cccc2n1] |
| Benzodrocortisone | 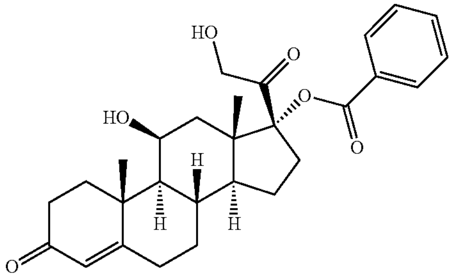 |
TABLE B
| Budesonide-spacer (Budesonide-SP) | |
| --- | --- |
| Compound No. | Structure |
| 1a (Budesonide) | 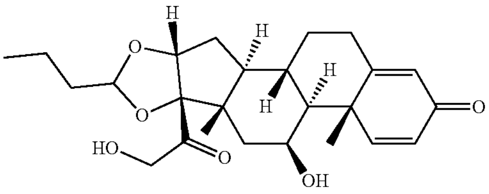 |
| 1c | 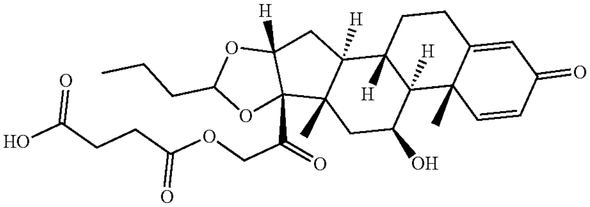 |
| 1d | 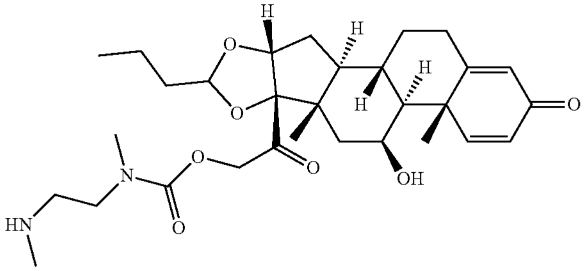 |

TABLE B-continued
| Budesonide-spacer (Budesonide-SP) | |
|---|---|
| Compound No. | Structure |
| 1e | 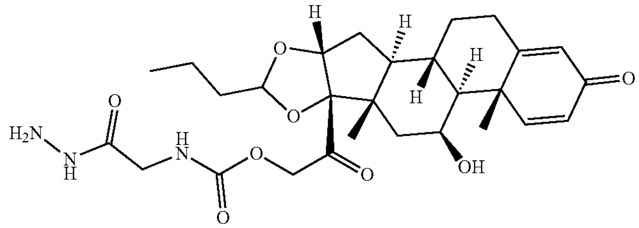 |
| 1g | 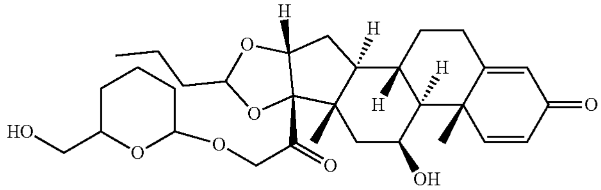 |
| 1h | 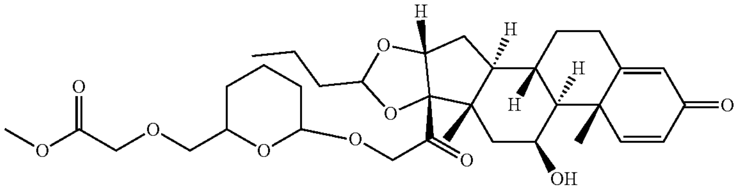 |
| 1i | 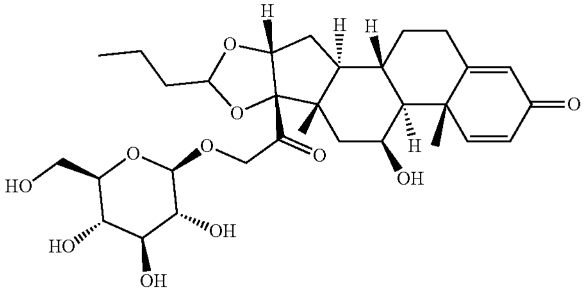 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1] |
| 1j | 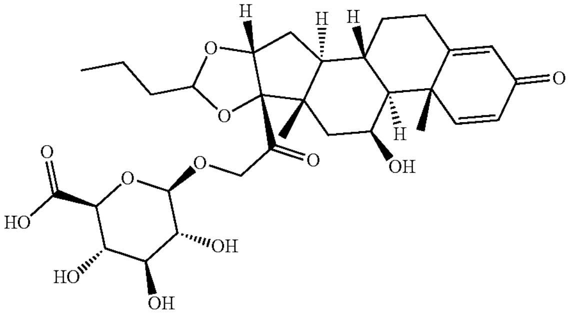 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](C(=O)O)[C@@H](O)[C@H](O)[C@H]2O)O1] |
| 1k | 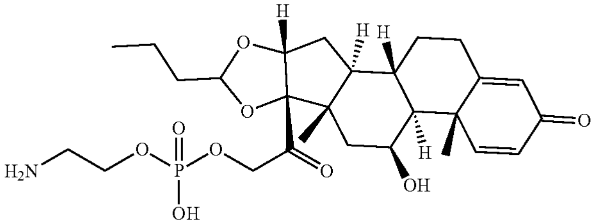 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCN)O1] |

TABLE B-continued
| Budesonide-spacer (Budesonide-SP) | |
|---|---|
| Compound No. | Structure |
| 1l | 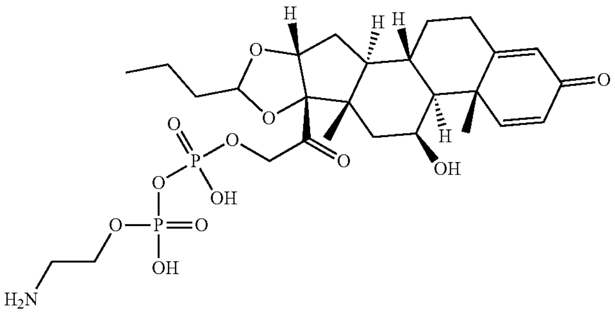 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OP(=O)(O)OCCN)O1] |
| 1m | 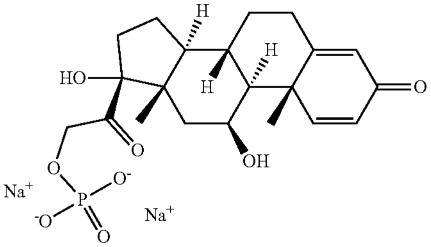 |
| 100 | 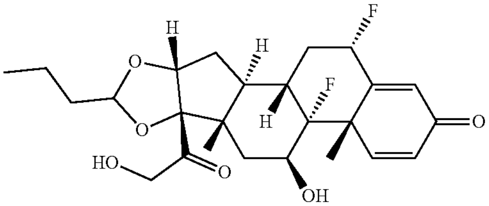 |
| 101a | 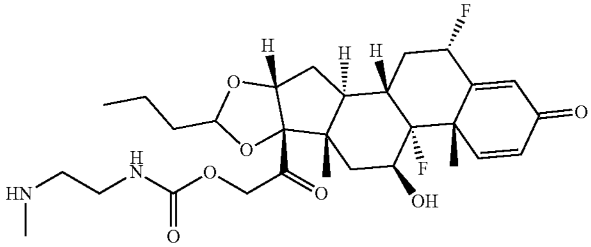 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1] |
| 101b | 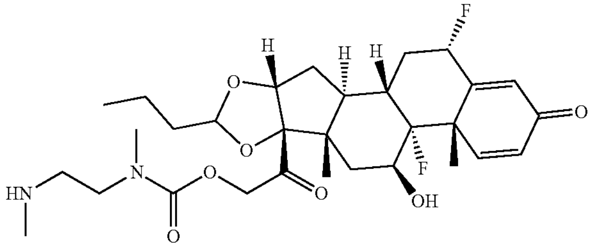 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1] |
| 101c | 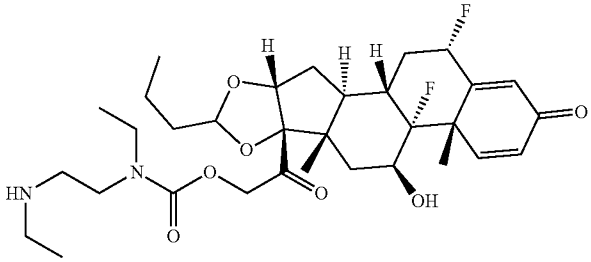 |

TABLE B-continued
| Budesonide-spacer (Budesonide-SP) | |
|---|---|
| Compound No. | Structure |
| 101d | 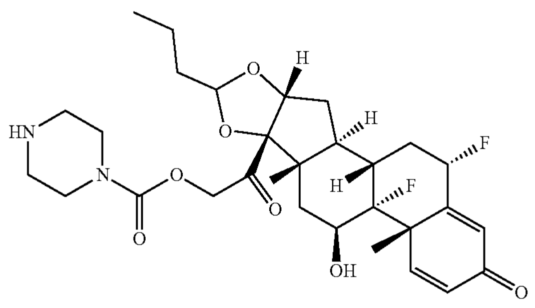 |
| 102c | 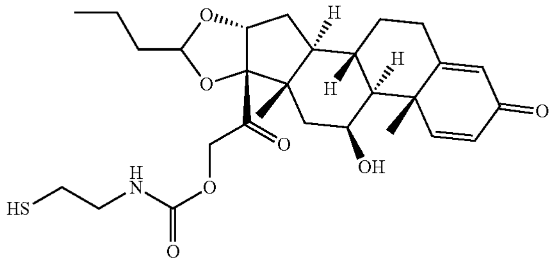 |
| 102d | 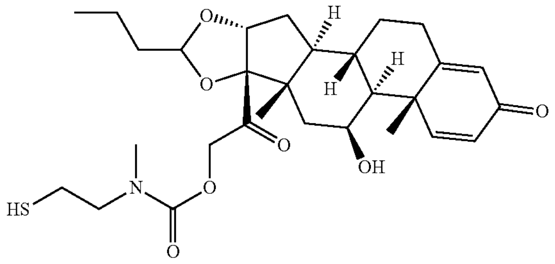 |
| 102e | 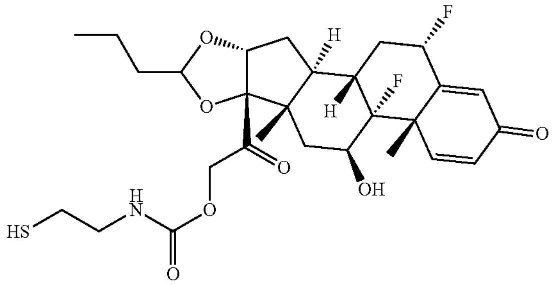 |
| 102f | 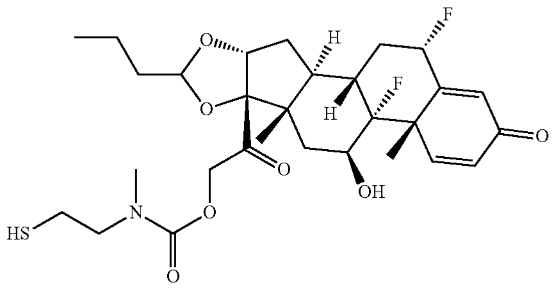 |

TABLE B-continued
| Budesonide-spacer (Budesonide-SP) | |
|---|---|
| Compound No. | Structure |
| 103a | 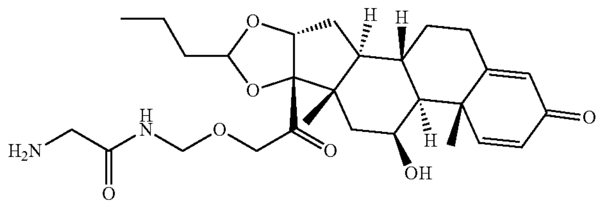 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COCNC(=O)CN)O1] |
| 103b | 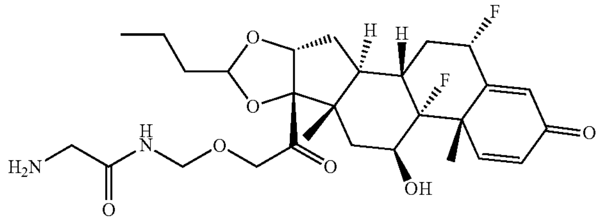 |
| 104a | 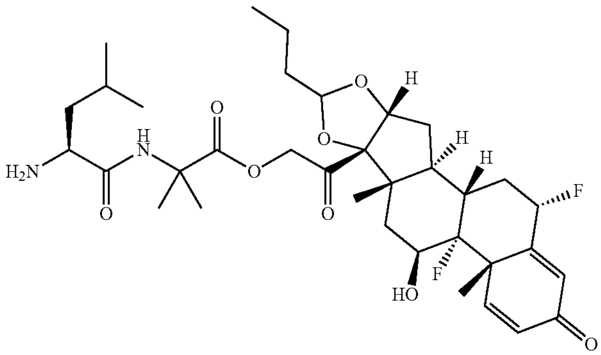 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@@H](N)CC(C)C)O1] |
| 104b | 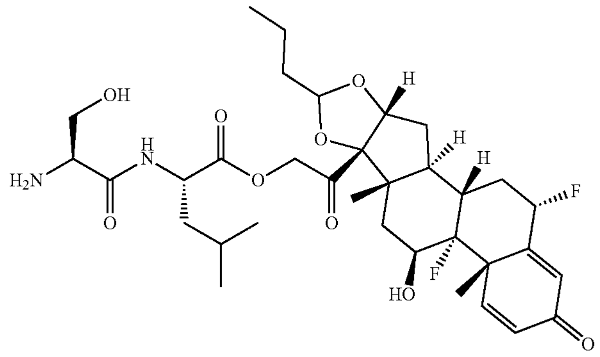 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@@H](N)CO)O1] |
| 105aa | 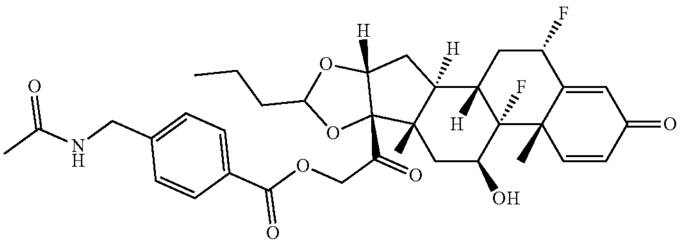 |

TABLE B-continued

Budesonide-spacer (Budesonide-SP)

| Compound No. | Structure |
|---|---|
| 106a | 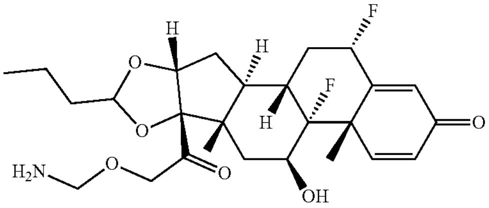 |
| 107a | 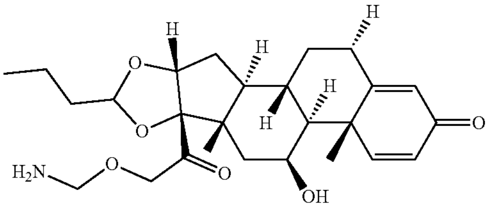 |

or a pharmaceutically acceptable salt, solvate, or stereoisomer thereof. In some instances, the n-propyl of

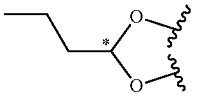 [SMILES: *OC(CCC)O*]

in each of the above structures is in the R-configuration, i.e. at the carbon indicated by the asterisk. In some instances, the n-propyl of

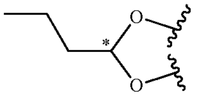 [SMILES: *OC(CCC)O*]

in each of the above structures is in the S-configuration, i.e. at the carbon indicated by the asterisk. In some instances, the n-propyl of

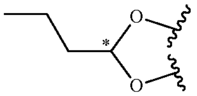

in each of the above structures is a mixture of the R- and S-configurations, i.e. at the carbon indicated by the asterisk. In some instances, the n-propyl of

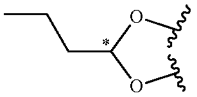

in each of the above structures is a mixture of the R- and S-configurations, i.e. at the carbon indicated by the asterisk, wherein the R:S mixture is about 1:1, about 2:1, about 3:1, about 4:1, about 5:1, about 6:1, about 7:1, about 8:1, about 9:1, or about 10:1.

In various embodiments, —SP-D of Ab-L'-SP-D or

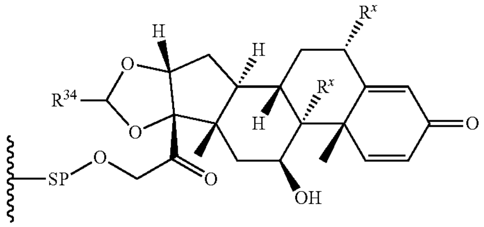

of Formula (3000) is selected from

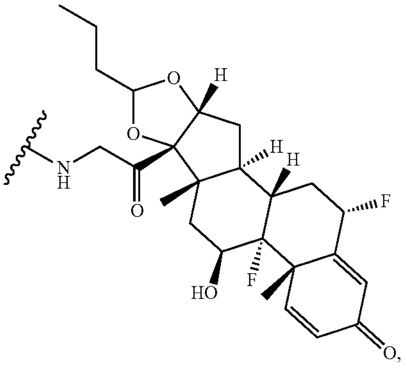

-continued
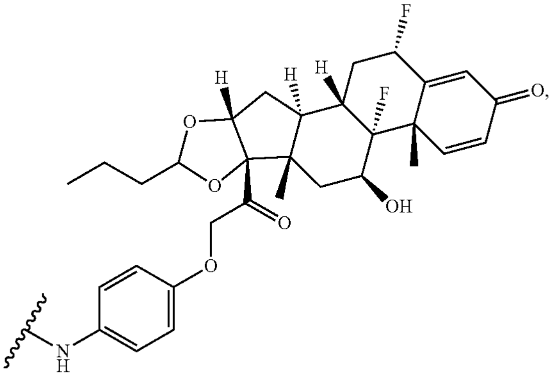
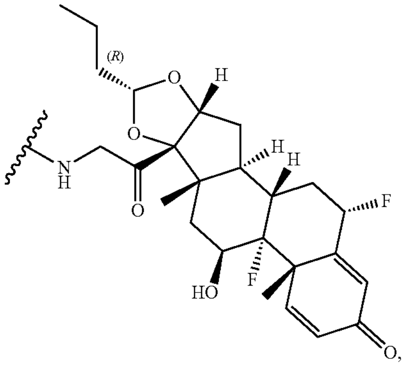
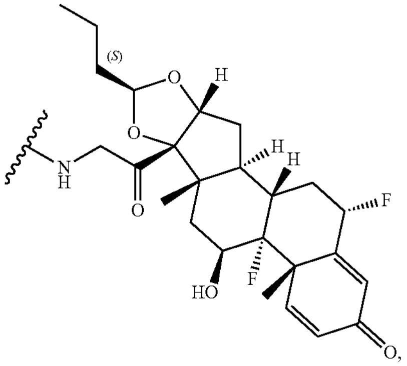
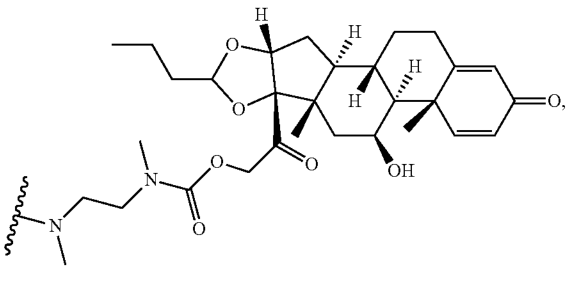
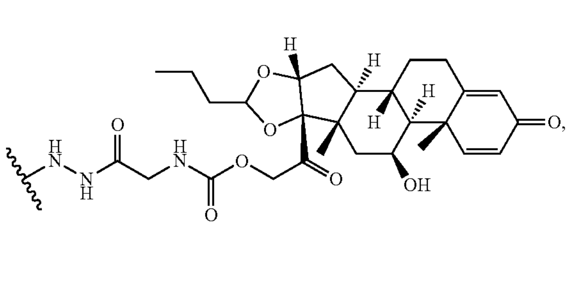
-continued
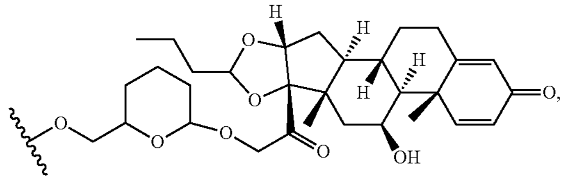
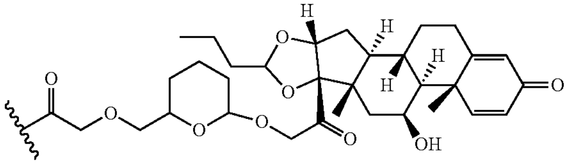
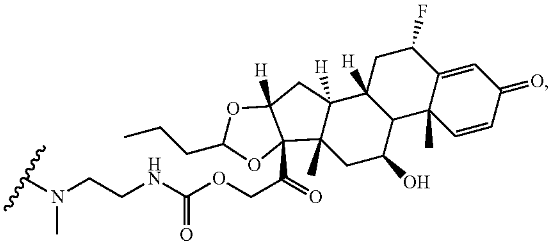
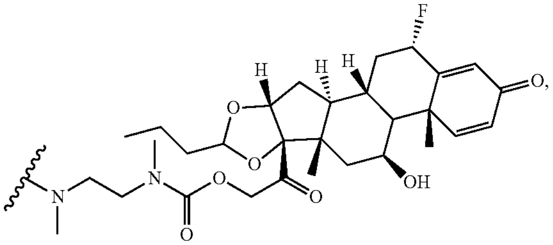
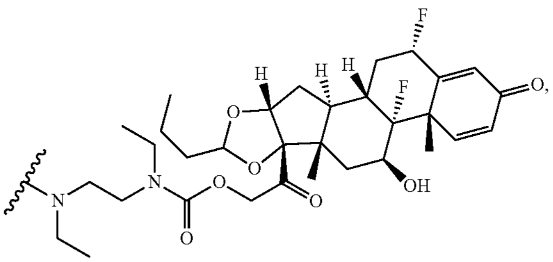
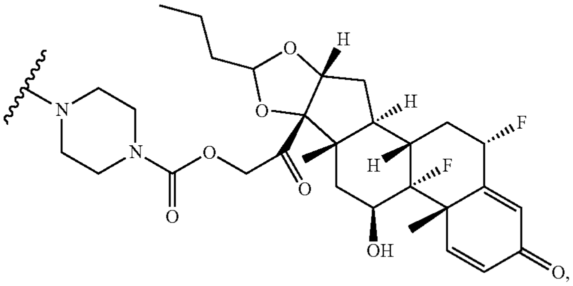
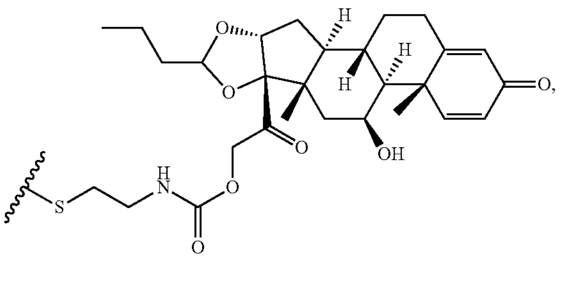

-continued
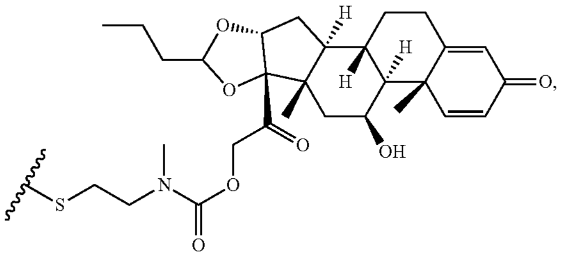
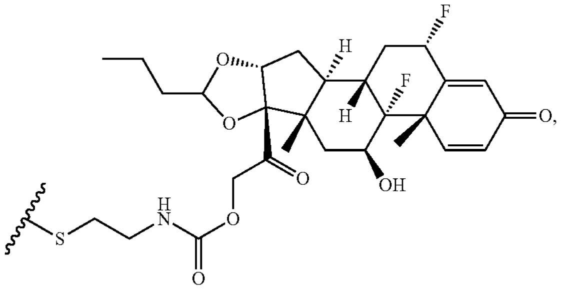
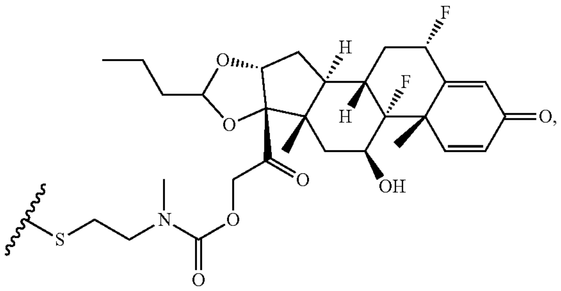
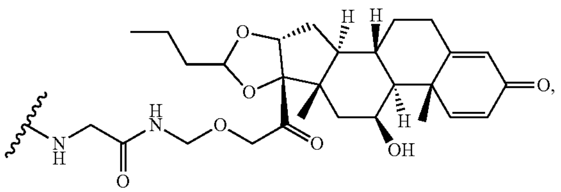
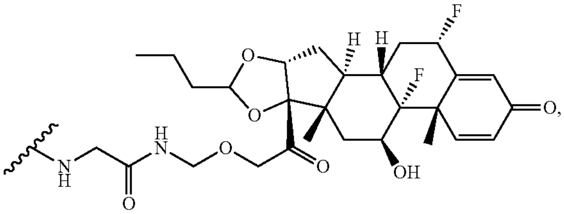
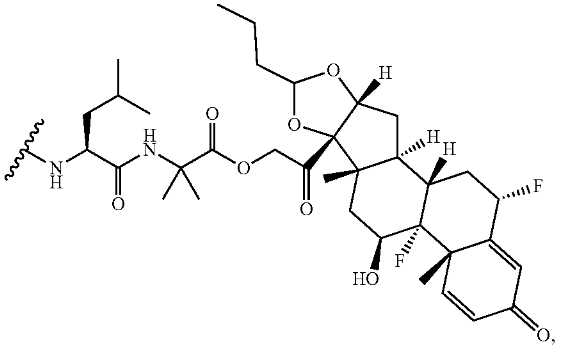
-continued
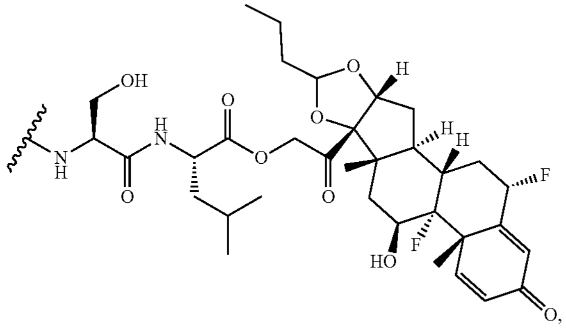
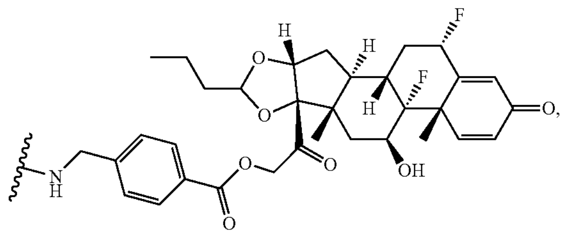
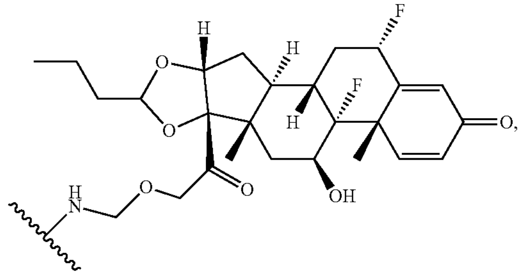
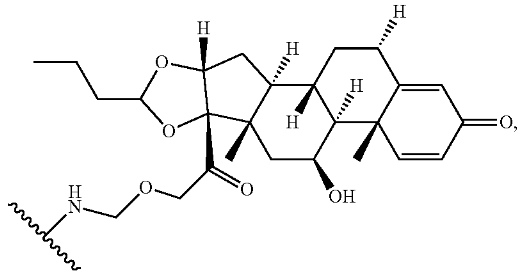
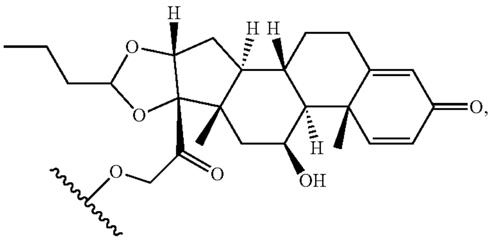
and
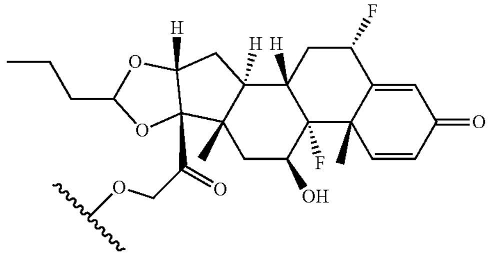 [SMILES: *OCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]

wherein the

is the bond to the linker.

In some instances, the n-propyl of

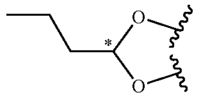 [SMILES: *OC(CCC)O*]

in each of the above structures is in the R-configuration, i.e. at the carbon indicated by the asterisk. In some instances, the n-propyl of

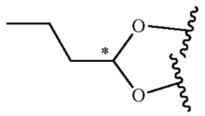 [SMILES: *OC(CCC)O*]

in each of the above structures is in the S-configuration, i.e. at the carbon indicated by the asterisk. In some instances, the n-propyl of

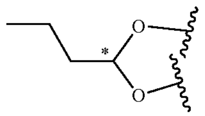 [SMILES: *OC(CCC)O*]

in each of the above structures is a mixture of the R- and S-configurations, i.e. at the carbon indicated by the asterisk. In some instances, the n-propyl of

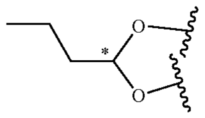

in each of the above structures is a mixture of the R- and S-configurations, i.e. at the carbon indicated by the asterisk, wherein the R:S mixture is about 1:1, about 2:1, about 3:1, about 4:1, about 5:1, about 6:1, about 7:1, about 8:1, about 9:1, or about 10:1.

In various embodiments,

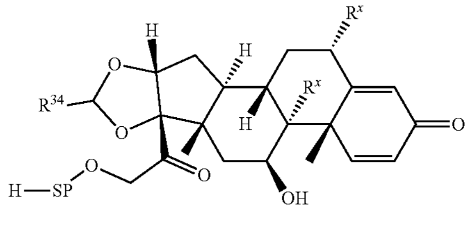

is selected from Table B, or is selected from

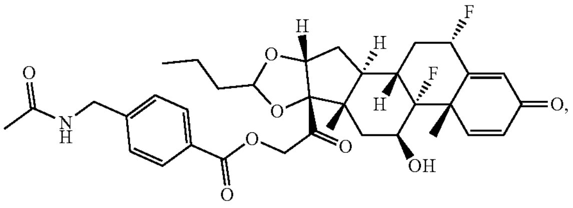

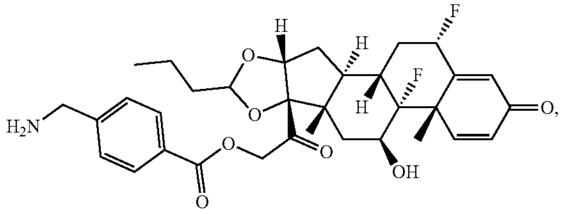

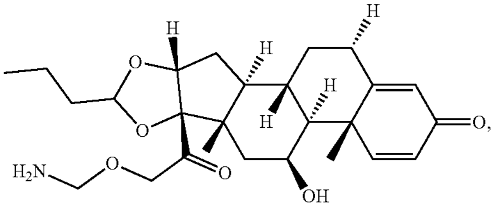

or

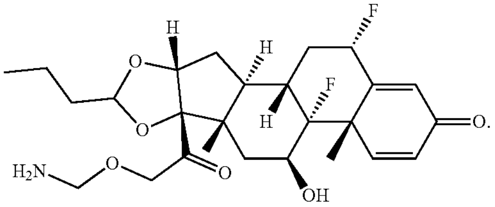

In some embodiments, the payload is a rifamycin analog having the structure of Formula (C):

Formula (C)

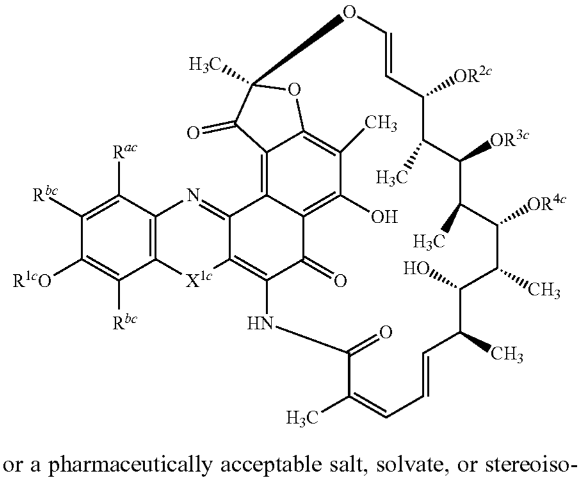

or a pharmaceutically acceptable salt, solvate, or stereoisomeric form thereof;

wherein:

$X^{1c}$ is selected from —O—, —S—, and —$NR^{5c}$;

$R^{1c}$ is hydrogen; amino-$C_{1-6}$alkyl; $C_{1-6}$alkylamino$C_{1-6}$alkyl; di-$C_{1-6}$alkylamino$C_{1-6}$alkyl; hydroxy-$C_{1-6}$alkyl; HS—$C_{1-6}$alkyl; $(R^{5c})_2$N—$C_{1-6}$alkylene-N($R^{5c}$)—$C_{1-6}$ alkyl; $(R^{5c})_2$N—$C_{1-6}$alkylene-O—$C_{1-6}$alkyl; $(R^{5c})_2$ N—$C_{1-6}$alkylene-S—$C_{1-6}$alkyl; heterocycloalkyl or heterocycloalkyl-$C_{1-6}$alkyl; wherein heterocycloalkyl includes one, two, or three heteroatoms selected from O, N, and S; and wherein heterocyloalkyl is optionally substituted with halo, $C_{1-6}$alkyl, —OH, =O, or —$N(R^{5c})_2$;

$R^{2c}$, $R^{3c}$, and $R^{4c}$ are independently selected from hydrogen, $C_{1-6}$alkyl, and —(C=O)—$R^{5c}$;

$R^{ac}$ is selected from —F; —Cl; —Br; —I; —OH; —$NH_2$; and $C_{1-6}$alkoxy;

$R^{bc}$ is hydrogen at each occurrence; and $R^{5c}$ is independently, at each occurrence, selected from hydrogen; and $C_{1-6}$alkyl;

with a proviso that $R^{1c}$ is not an n-butyl group; and a further proviso that when $X^{1c}$ is —O—, $R^{1c}$ is not hydrogen;

wherein the group $R^{1c}$ is bonded to the linker.

In some embodiments, the payload is a rifamycin analog having the structure of Formula (C-1):

Formula (C-1)

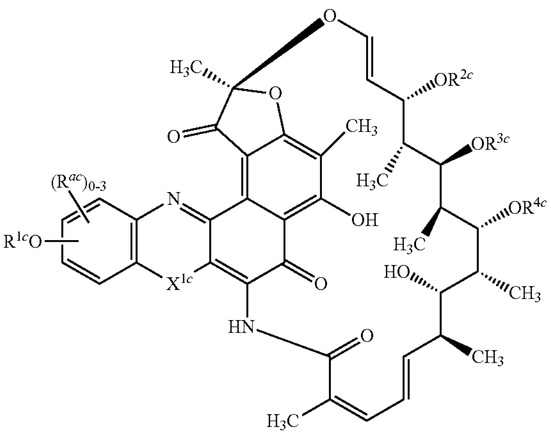

or a pharmaceutically acceptable salt, solvate, or stereoisomeric form thereof;

wherein:

$X^{1c}$ is selected from —S—; —O— and —$NR^{5c}$;

$R^{1c}$ is amino-$C_{1-6}$alkyl; $C_{1-6}$alkylamino$C_{1-6}$alkyl; di-$C_{1-6}$ alkylamino$C_{1-6}$alkyl; hydroxy-$C_{1-6}$alkyl; HS—$C_{1-6}$alkyl; $(R^{5c})_2N$—$C_{1-6}$alkylene-$N(R^{5c})$—$C_{1-6}$alkyl; $(R^{5c})_2$N—$C_{1-6}$alkylene-O—$C_{1-6}$alkyl; $(R^{5c})_2N$—$C_{1-6}$alkylene-S—$C_{1-6}$alkyl; heterocycloalkyl or heterocycloalkyl-$C_{1-6}$alkyl; wherein heterocycloalkyl includes one, two, or three heteroatoms selected from O, N, and S; and wherein heterocyloalkyl is optionally substituted with halo, $C_{1-6}$alkyl, —OH, =O, or —$N(R^{5c})_2$;

$R^{2c}$, $R^{3c}$, and $R^{4c}$ are independently selected from hydrogen, $C_{1-6}$alkyl, and —(C=O)—$R^{5c}$;

each $R^{ac}$, when present, is independently selected from —F; —Cl; —Br; —I; —OH; —$NH_2$; and $C_{1-6}$alkoxy; and $R^{5c}$ is independently, at each occurrence, selected from hydrogen; and $C_{1-6}$alkyl; wherein the group $R^{1c}$ is bonded to the linker.

In some embodiments, the payload is a rifamycin analog having the structure of Formula (C-2):

Formula (C-2)

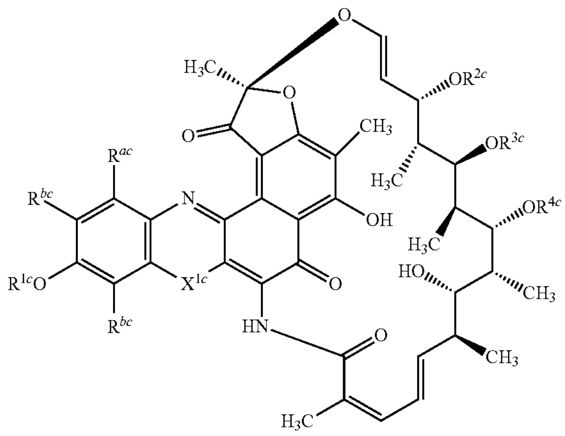

or a pharmaceutically acceptable salt, solvate, or stereoisomeric form thereof;

wherein:

$X^{1c}$ is selected from —S—; —O— and —$NR^{5c}$;

$R^{1c}$ is amino-$C_{1-6}$alkyl; $C_{1-6}$alkylamino$C_{1-6}$alkyl; di-$C_{1-6}$ alkylamino$C_{1-6}$alkyl; hydroxy-$C_{1-6}$alkyl; HS—$C_{1-6}$alkyl; $(R^{5c})_2N$—$C_{1-6}$alkylene-$N(R^{5c})$—$C_{1-6}$alkyl; $(R^{5c})_2$N—$C_{1-6}$alkylene-O—$C_{1-6}$alkyl; $(R^{5c})_2N$—$C_{1-6}$alkylene-S—$C_{1-6}$alkyl; heterocycloalkyl or heterocycloalkyl-$C_{1-6}$alkyl; wherein heterocycloalkyl includes one, two, or three heteroatoms selected from O, N, and S; and wherein heterocyloalkyl is optionally substituted with halo, $C_{1-6}$alkyl, —OH, =O, or —$N(R^{5c})_2$;

$R^{2c}$, $R^{3c}$, and $R^{4c}$ are independently selected from hydrogen, $C_{1-6}$alkyl, and —(C=O)—$R^{5c}$;

$R^{ac}$ and $R^{bc}$ are independently selected from —F; —Cl; —Br; —I; —OH; —$NH_2$; and $C_{1-6}$alkoxy; and $R^{5c}$ is independently, at each occurrence, selected from hydrogen; and $C_{1-6}$alkyl; wherein the group $R^{1c}$ is bonded to the linker.

In some embodiments, the payload is a rifamycin analog having the structure of Formula (C-3):

Formula (C-3)

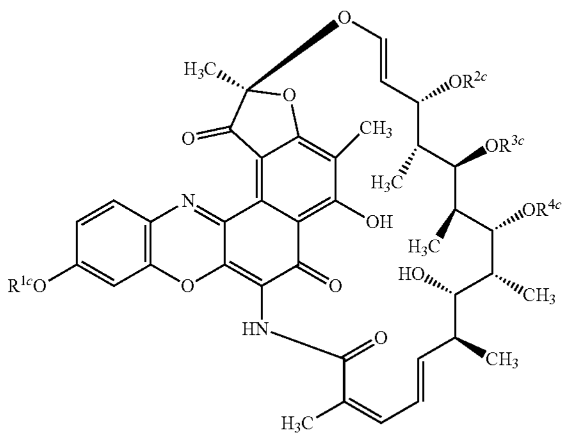

or a pharmaceutically acceptable salt, solvate, or stereoisomeric form thereof;

wherein:

$R^{1c}$ is di-$C_{1-6}$alkylamino$C_{1-6}$alkyl; $(R^{5c})_2N$—$C_{1-6}$alkylene-$N(R^{5c})$—$C_{1-6}$alkyl; heterocycloalkyl or heterocycloalkyl-$C_{1-6}$alkyl; wherein heterocycloalkyl includes one, two, or three heteroatoms selected from O, N, and S; and wherein heterocyloalkyl is optionally substituted with halo, $C_{1-6}$alkyl, —OH, ═O, or —$N(R^{5c})_2$; and $R^{2c}$, $R^{3c}$, and $R^{4c}$ are independently selected from hydrogen, $C_{1-6}$alkyl, and —(C═O)—$R^{5c}$; and $R^{5c}$ is selected from hydrogen and $C_{1-6}$alkyl;

wherein the group $R^{1c}$ is bonded to the linker.

In some embodiments, the payload is a rifamycin analog having the structure of Formula (C-4):

Formula (C-4)

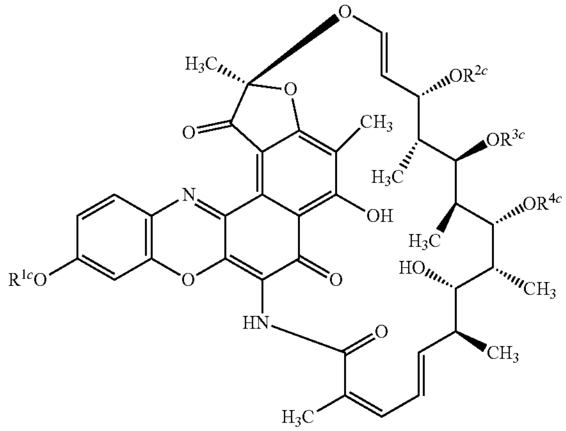

or a pharmaceutically acceptable salt, solvate, or stereoisomeric form thereof;

wherein:

$R^{1c}$ is

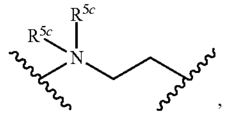
,
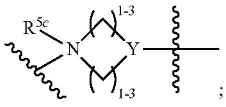
; or
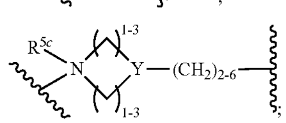
;

wherein Y is C or N;

$R^{2c}$, $R^{3c}$, and $R^{4c}$ are independently selected from hydrogen, $C_{1-6}$alkyl, and —(C═O)—$R^{5c}$;

and $R^{5c}$ is selected from hydrogen and $C_{1-6}$alkyl;

wherein the group $R^{1c}$ is bonded to the linker via the nitrogen atom as indicated by the wavy line

.

In some or any embodiments of Formula (C-1) and/or (C-2) an/or (C-3) and/or (C-4), $R^{bc}$ is hydrogen and/or $R^{ac}$ is hydrogen. In some or any embodiments of Formula (C-1) and/or (C-2) an/or (C-3) and/or (C-4), $R^{2c}$ is methyl, ethyl, propyl or isopropyl, preferably methyl. In some or any embodiments of Formula (C-1) and/or (C-2) an/or (C-3) and/or (C-4), $R^{3c}$ is $CH_3$—(C═O)— (acetyl) group, $CH_3CH_2$—(C═O)—. $CH_3CH_2CH_2$—(C═O)—, or $(CH_3)_2CH$—(C═O)—; preferably acetyl. In some or any embodiments of Formula (C-1) and/or (C-2) an/or (C-3) and/or (C-4), $R^4$, is hydrogen.

In some embodiments of Formula (C-1) and/or (C-2) an/or (C-3) and/or (C-4), —$OR^{1c}$ is one or more of

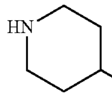
,
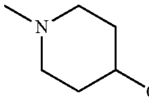
,
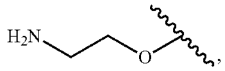
,
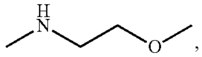
,
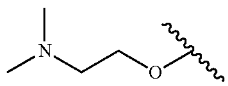
or
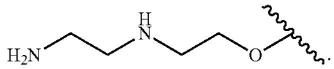
.

In some embodiments of Formula (C-1) and/or (C-2) an/or (C-3) and/or (C-4), —$OR^{1c}$ is

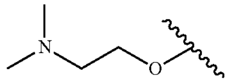
and/or.
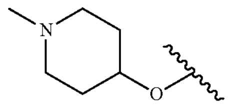

In some or any embodiments of Formula (C-1) and/or (C-2) an/or (C-3) and/or (C-4), $X^{1c}$ is O, and —$OR^{1c}$ comprises a tertiary amine, said tertiary amine, after bonding to a linker, 1 N changes to a quarternary amine. In some of such embodiments, —$OR^{1c}$ is

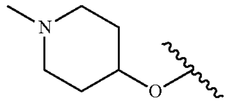
or
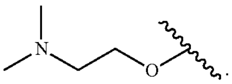
.

In such embodiments, where a quarternary amine is formed, a suitable counter ion is present, i.e., the rifamycin analog is present as a pharmaceutically acceptable salt comprising a quarternary amine bearing a positive charge, and, as a salt, for instance, a charge-balancing negatively charged counter ion (e.g., $I^-$, $Br^-$, $Cl^-$ or any other suitable counter ion).

In some embodiments. a compound of Formula (C-1) and/or (C-2) an/or (C-3) and/or (C-4) is selected from the group consisting of:

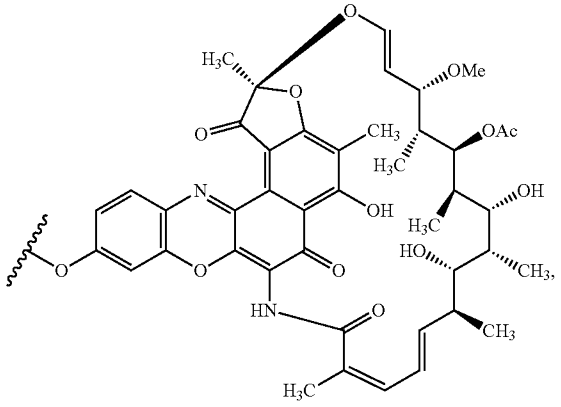
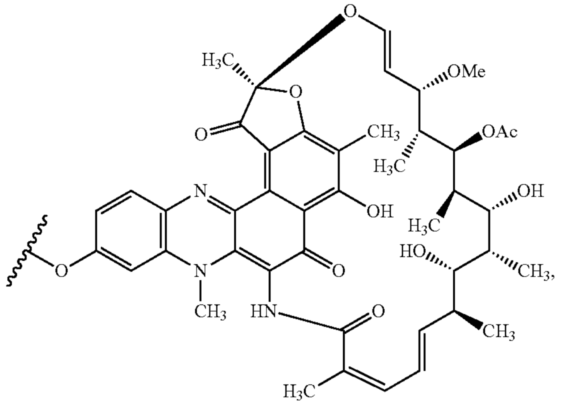
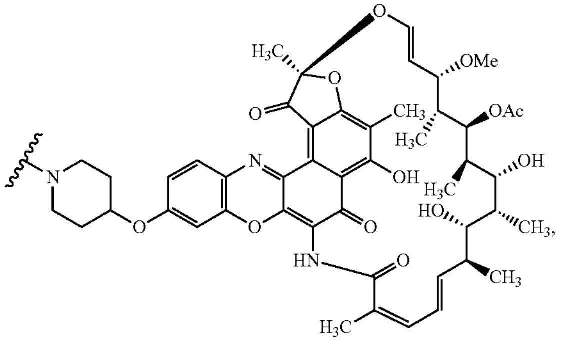
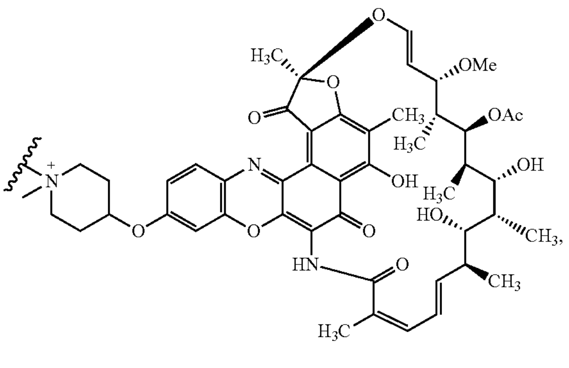
-continued
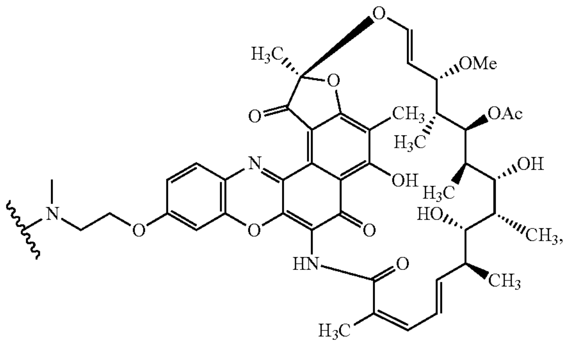
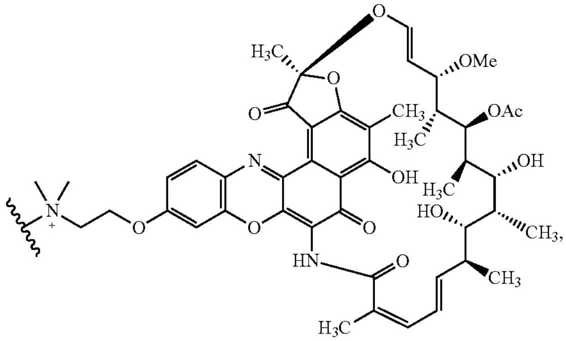
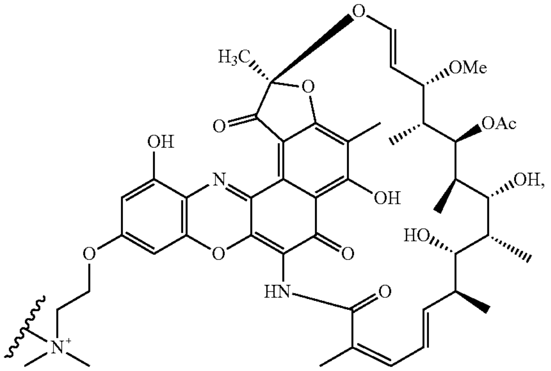
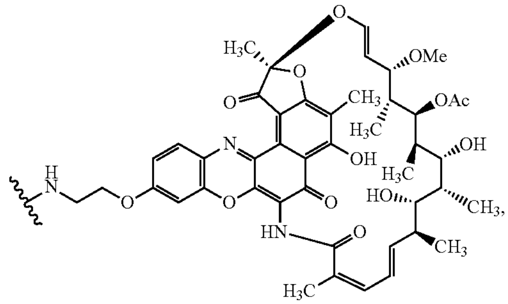
and
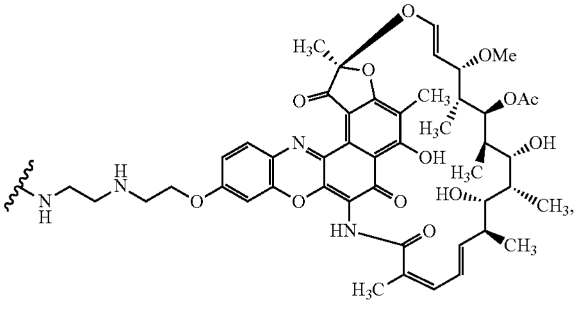

wherein the

is the bond to the linker.

Linkers

In some embodiments of Formula (I), (III), or (3000), L comprises -$L^1$-$L^2$-$(L^3)_{0-1}$- and $L^2$ comprises

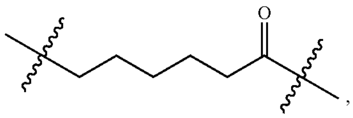,

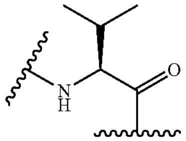, 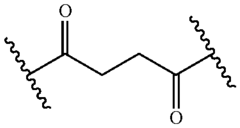,

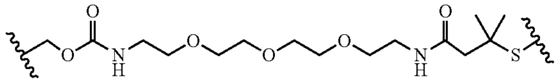,

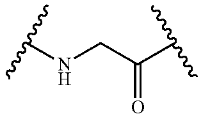, 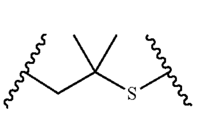,

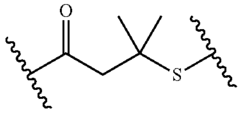, 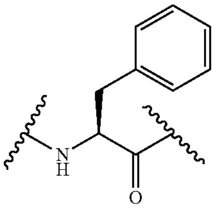,

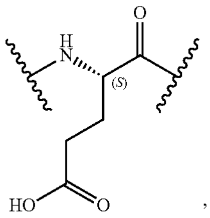, 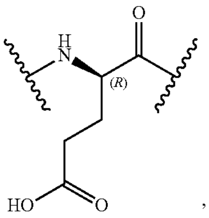,

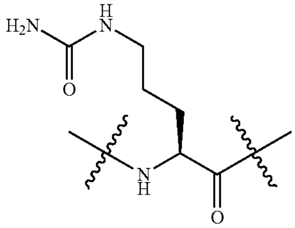,

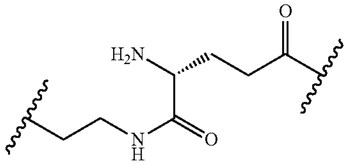,

—C(O)$CH_2CH_2$C(O)NH— ,

-continued

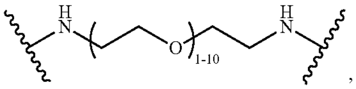,

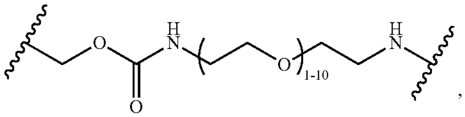,

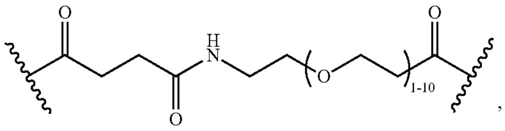,

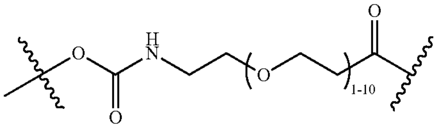

—$OCH_2$C(O)—, or cyclodextrin residue (CD); or combinations thereof. In some embodiments, L comprises -$L^1$-$L^2$-$(L^3)_{0-1}$- and $L^2$ comprises

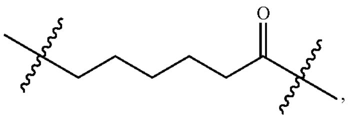,

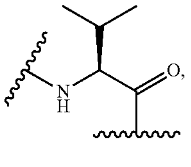 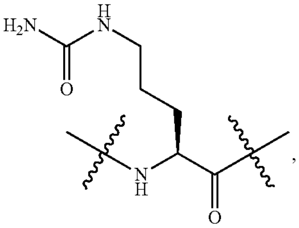,

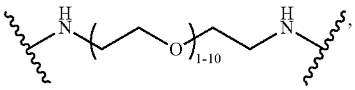

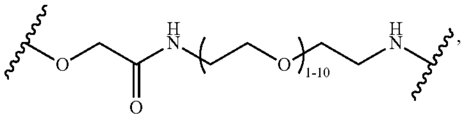

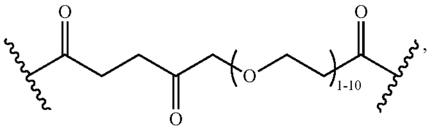

or CD, or combinations thereof. In some embodiments, L comprises -$L^1$-$L^2$-$(L^3)_{0-1}$- and $L^2$ comprises CD. In some embodiments, where L and/or $L^2$ comprises CD, CD is selected from the group consisting of -continued
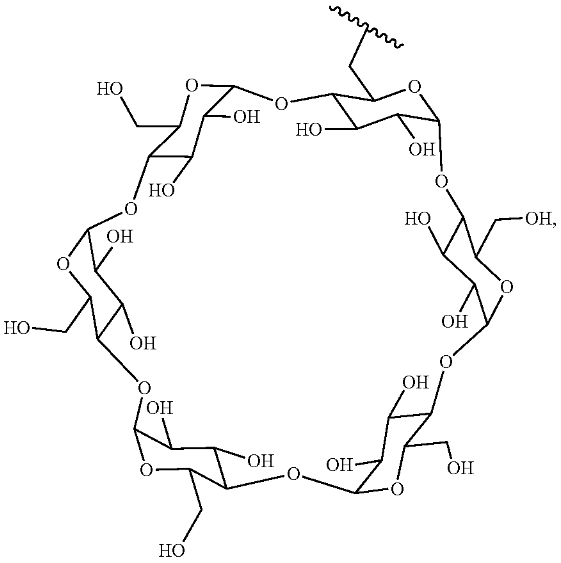
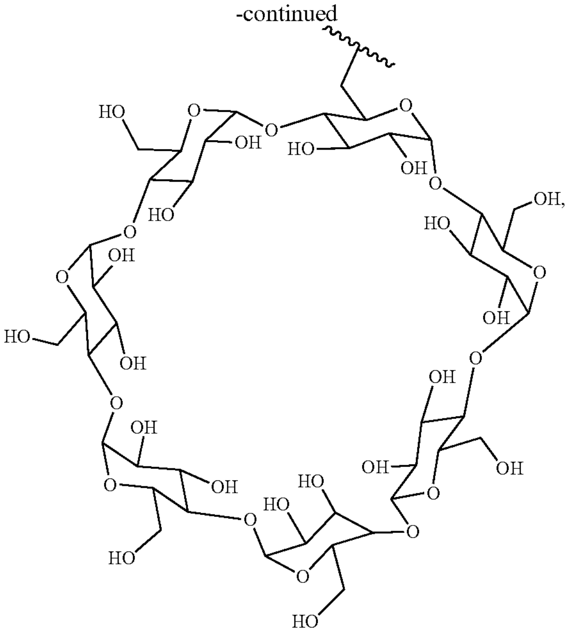
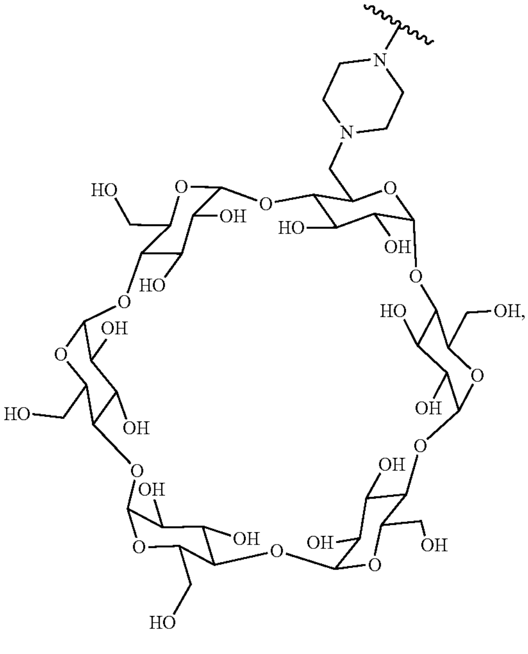
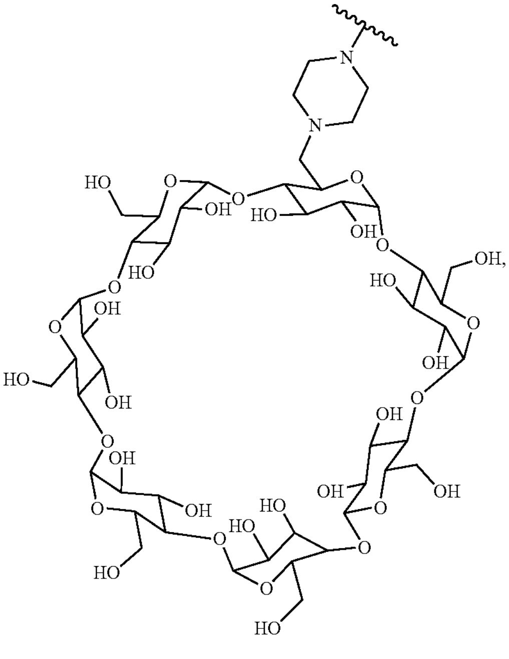

-continued

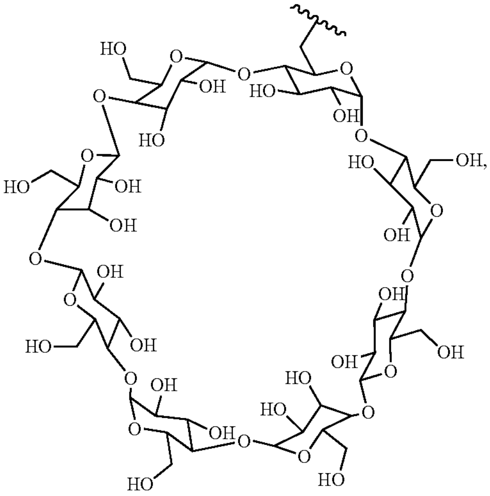

and

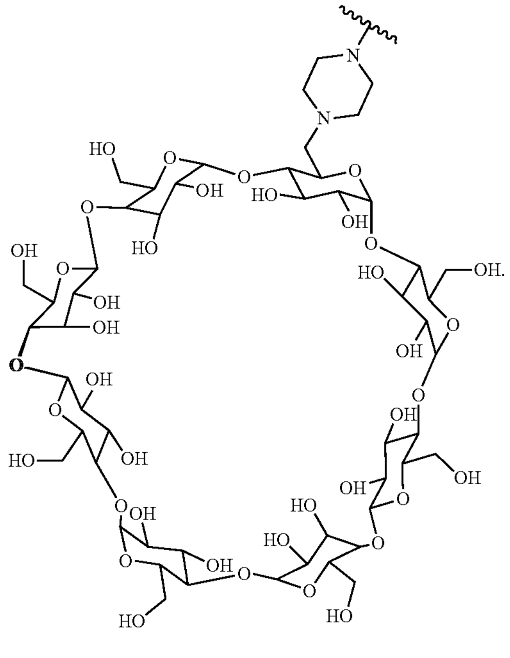

In some embodiments of Formula (I), (III), or (3000), L comprises $-L^1-L^2-(L^3)_{0-1}-$ and $L^2$ comprises HG as described herein. In some embodiments, L and/or $L^2$ comprises

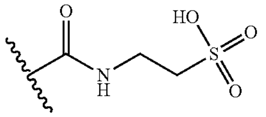

or

-continued

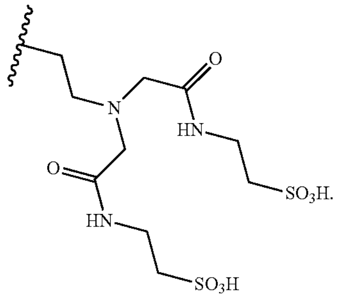

In some embodiments, L and/or $L^2$ comprises

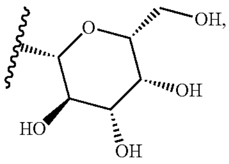

or

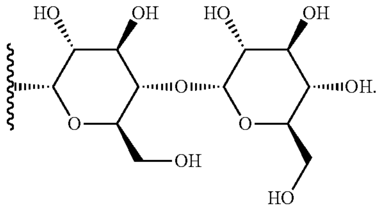

In some embodiments of Formula (I), (III), or (3000), L comprises $-L^1-L^2-(L^3)_{0-1}-$ and $L^1$ is selected from

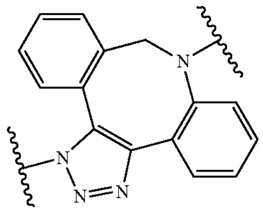 [SMILES: *N1Cc2ccccc2-c2c(nnn2*)-c2ccccc21]

or a regioisomer or mixture of isomers thereof;

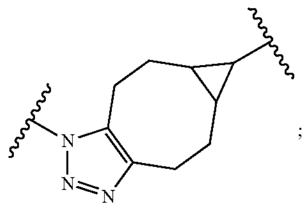

;

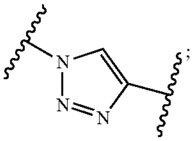

;

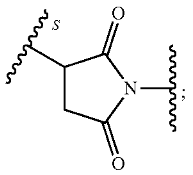

;

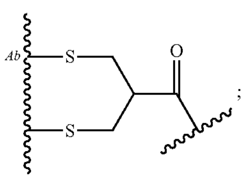

;

or a stereoisomer or mixture of stereoisomers thereof, where S refers to the S atom on a cysteine residue through which the reactive group residue is attached to BA; and

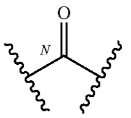
where N refers to the N atom on a lysine residue through which the reactive group residue is attached to BA.
In some embodiments, L comprises $-L^1-L^2-(L^3)_{0-1}-$ and $-L^2-(L^3)_{0-1}-$ as described herein. In some embodiments, L is $L^1$-SP as described herein for Formula (III) and Formula (3000). In some embodiments L comprises:
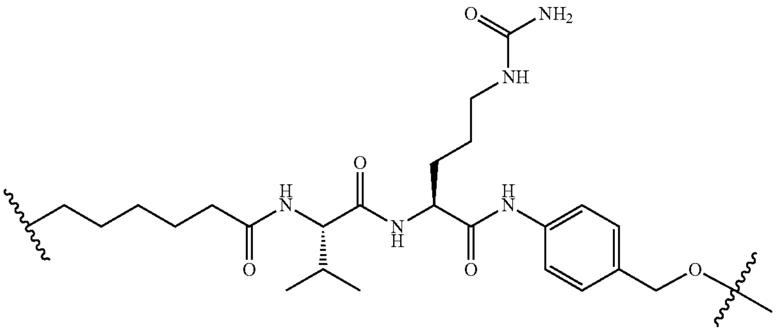
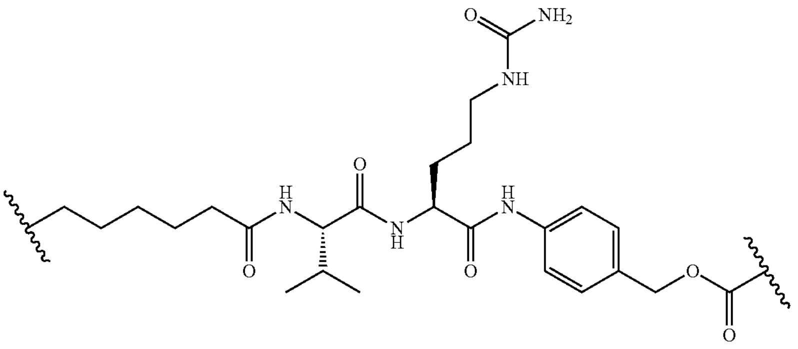
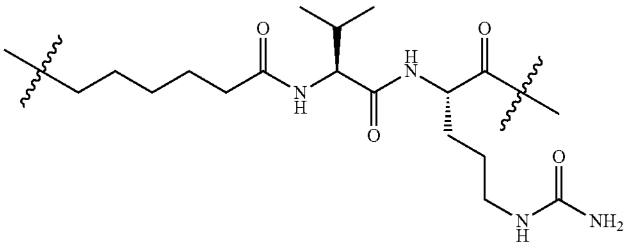

-continued
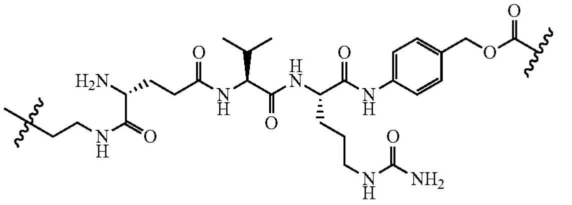
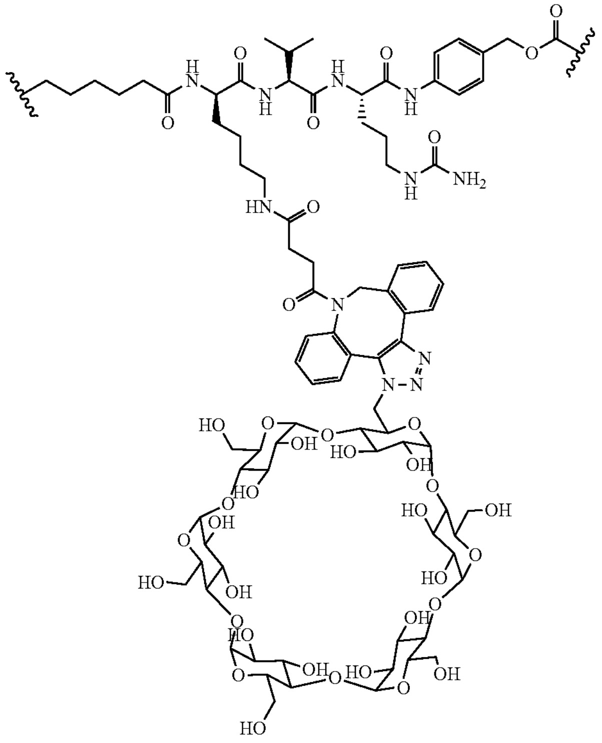
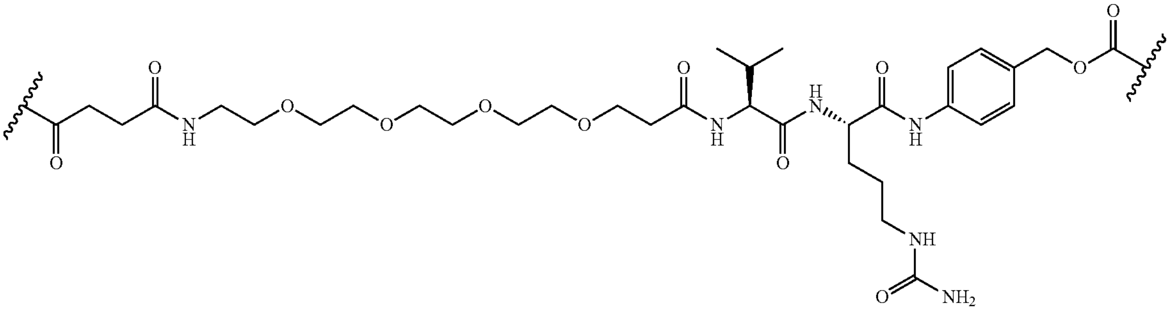
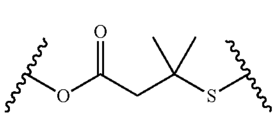 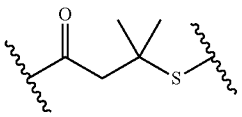 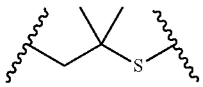
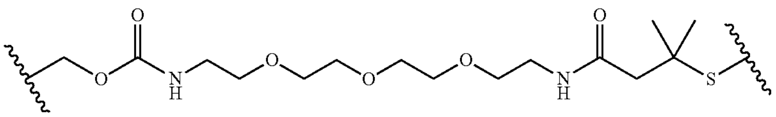
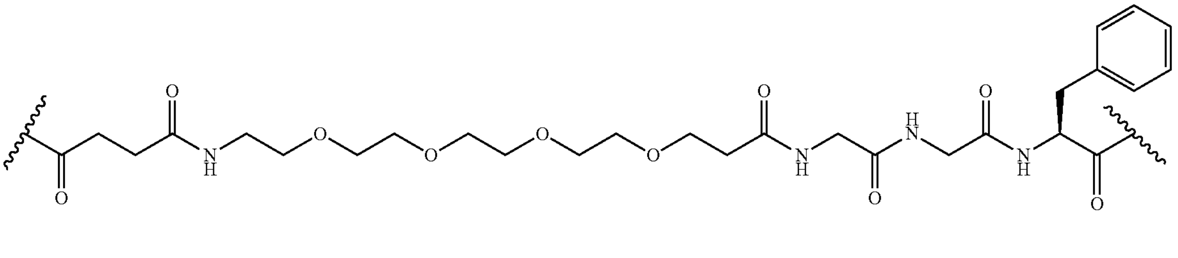

-continued
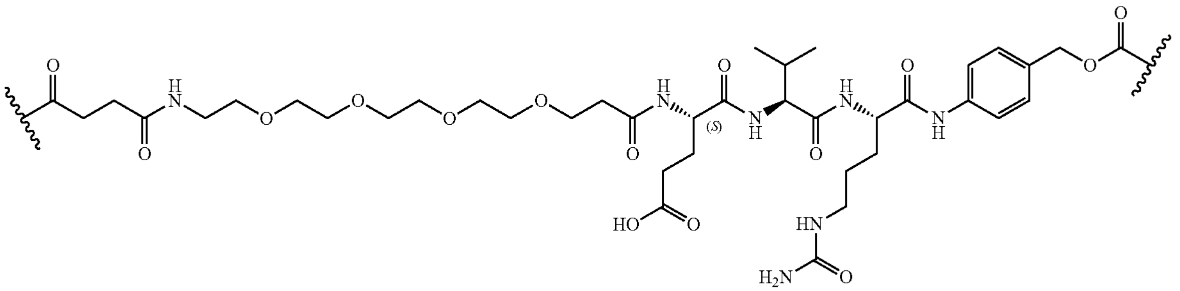
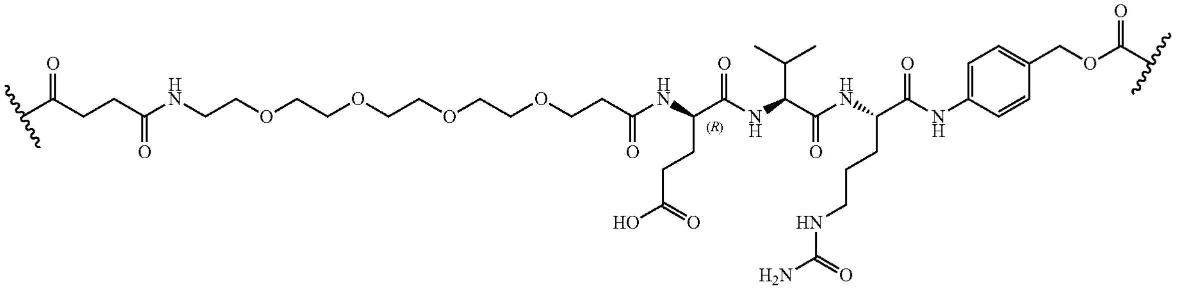
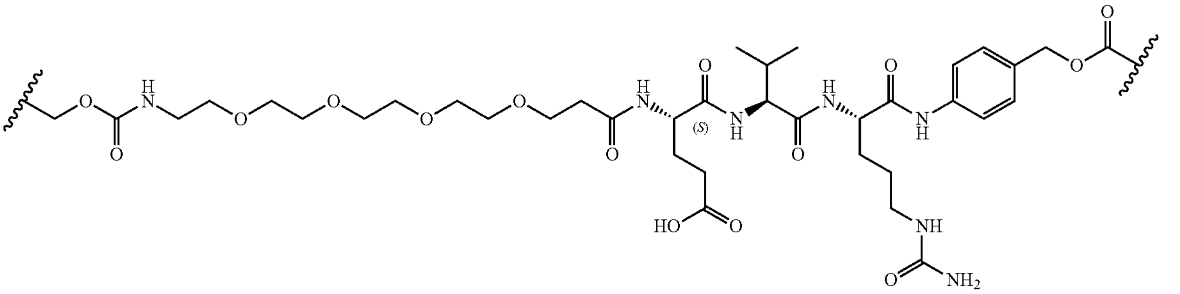
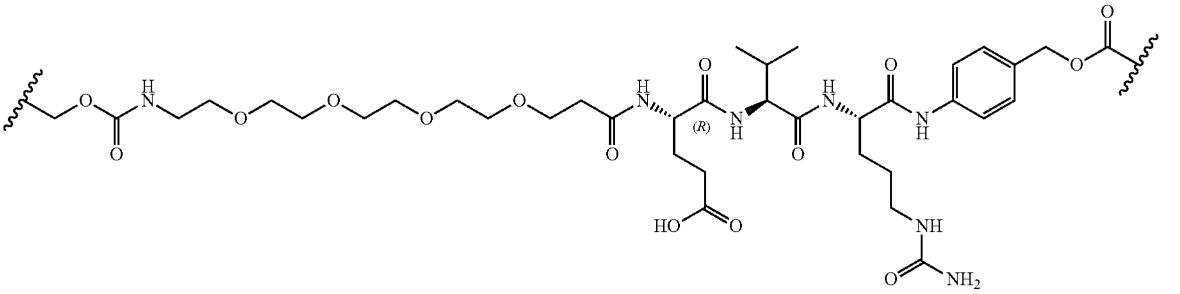
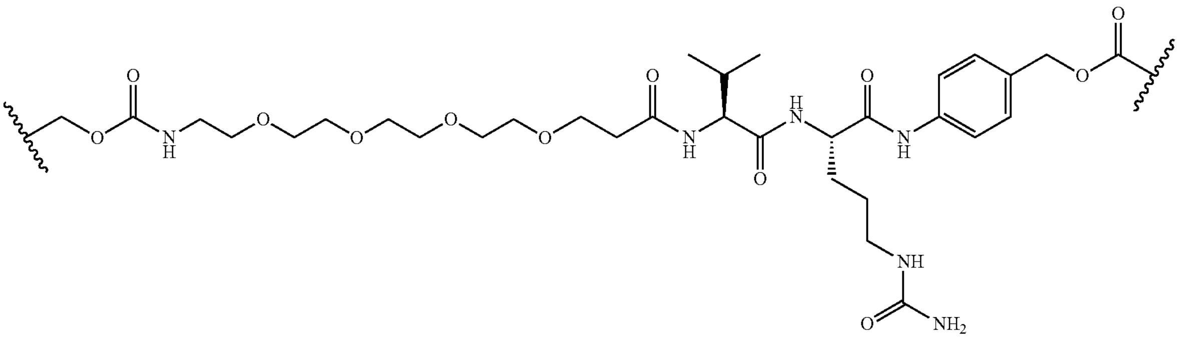

-continued
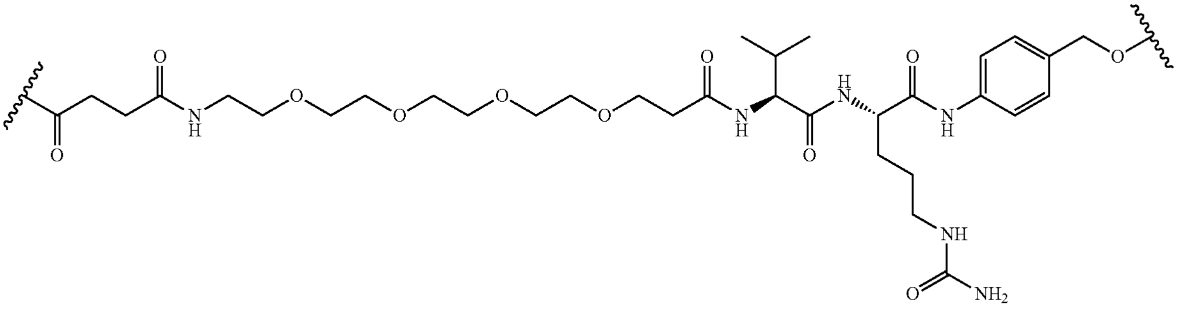
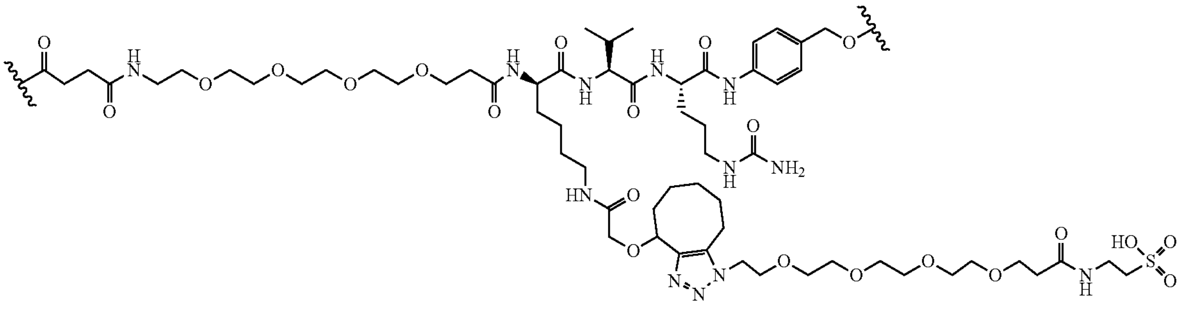
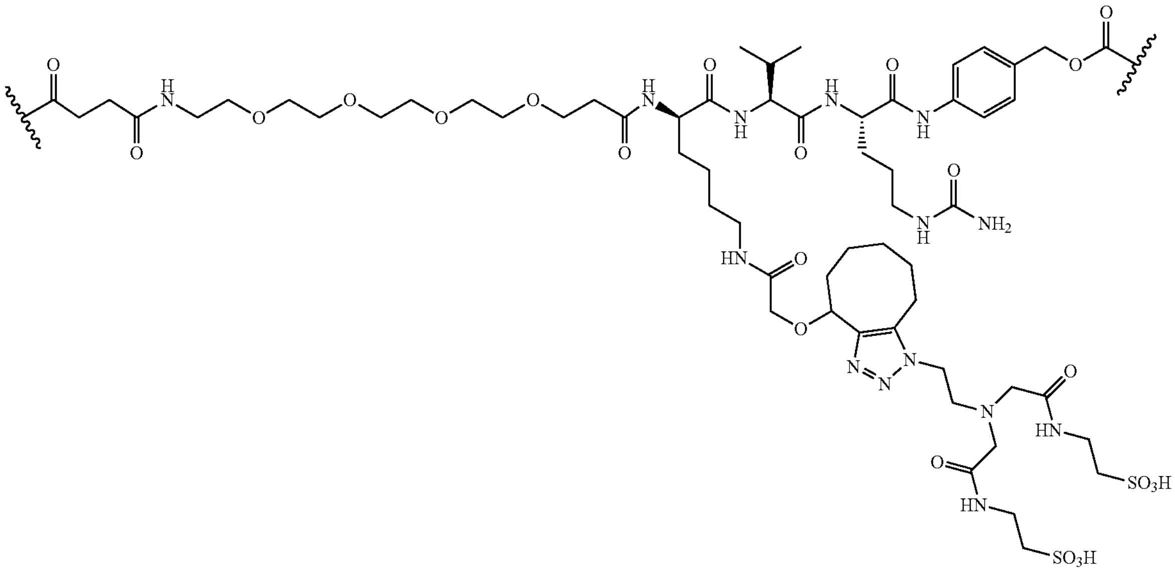
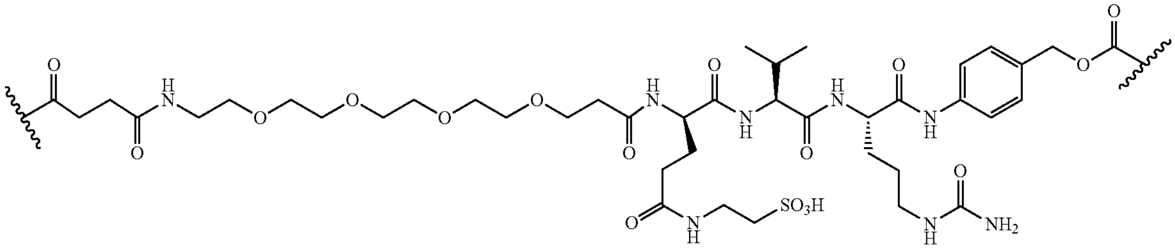

-continued
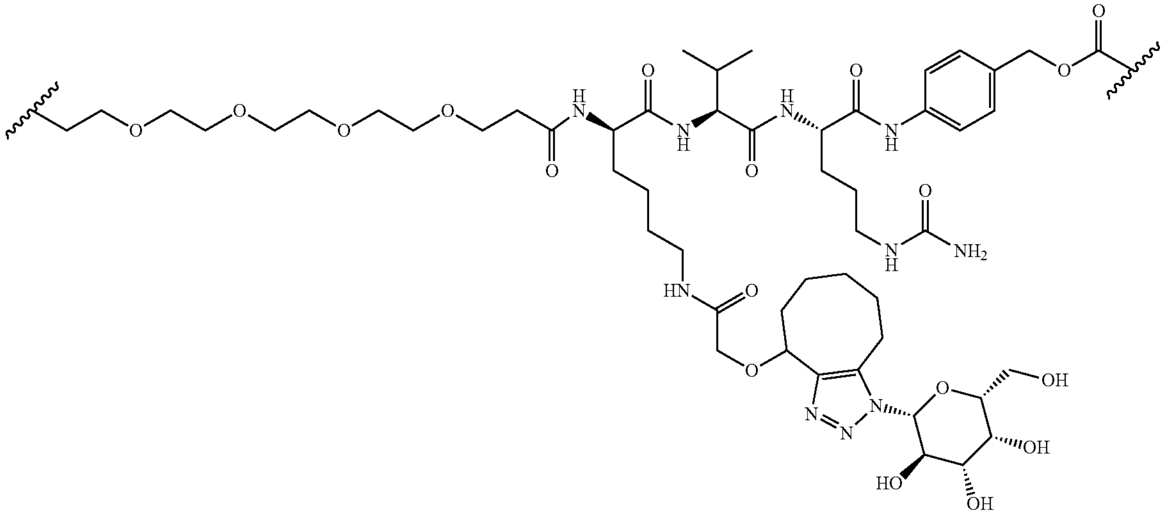
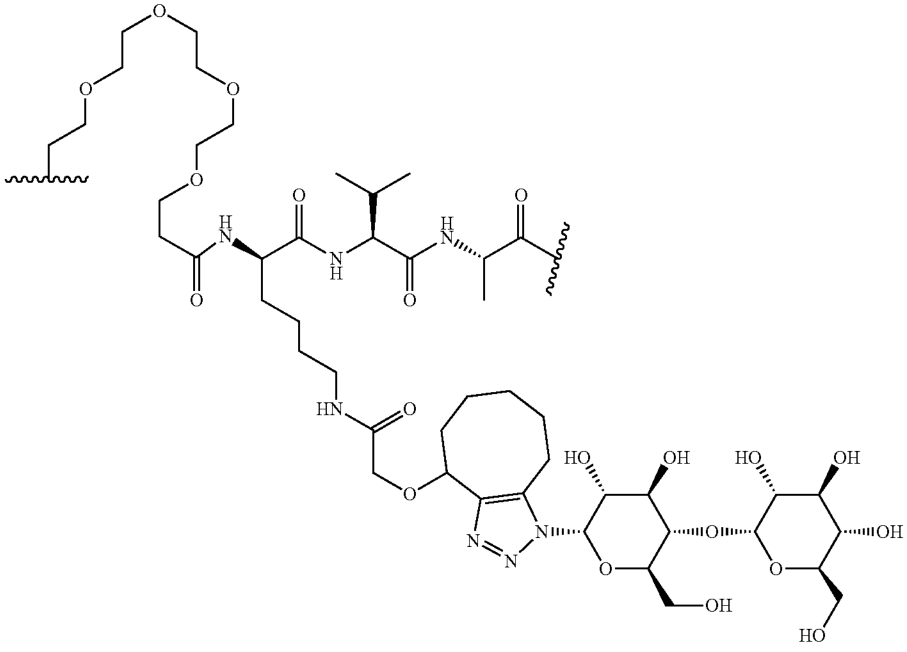
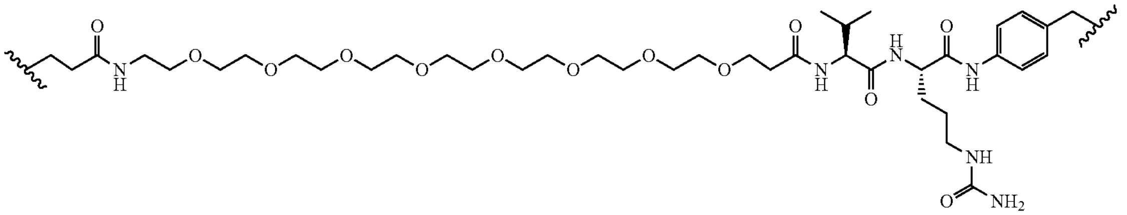
or
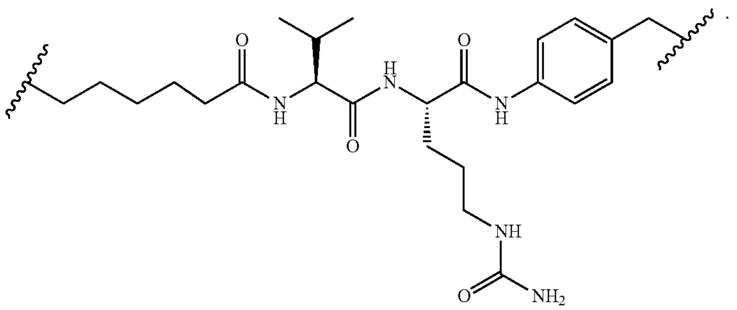

In some instances, a compound of Formula (I) or (III) or (3000), is selected from

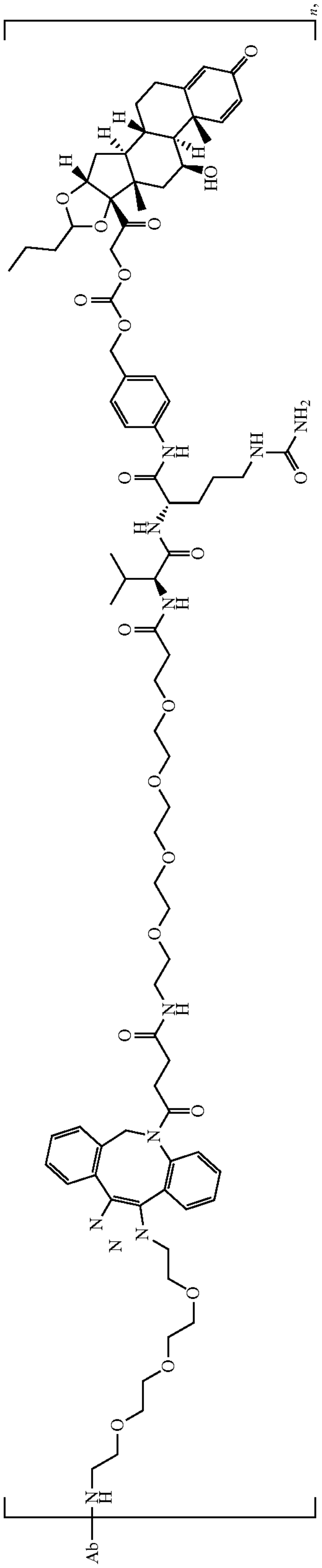
and
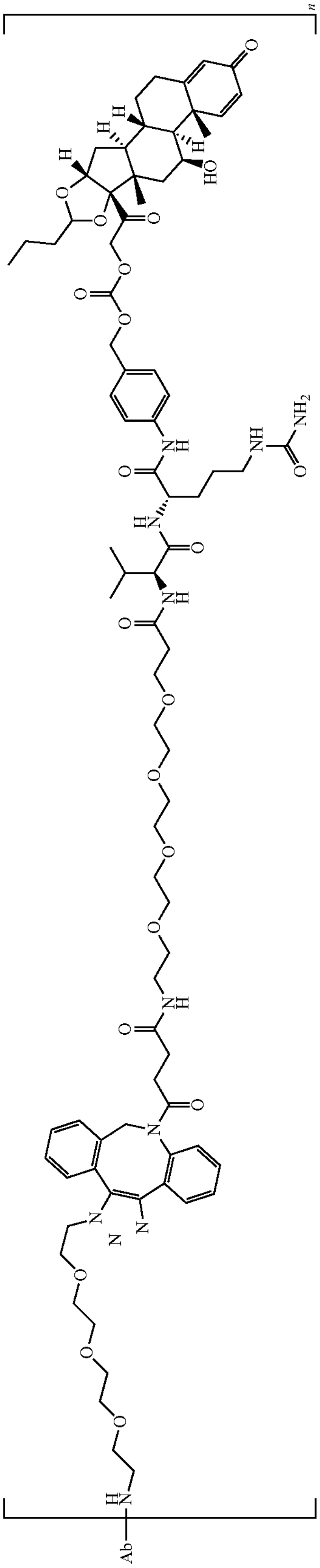
or a mixture thereof;

or a stereoisomeric form thereof, or a regioisomer thereof, or a mixture of regioisomers thereof, wherein
each Ab is an anti-MSR1 antibody, or an antigen binding fragment thereof; and
each n is an integer from 1 to 4.
In some instances, a compound of Formula (I) or (III) or (3000), is selected from
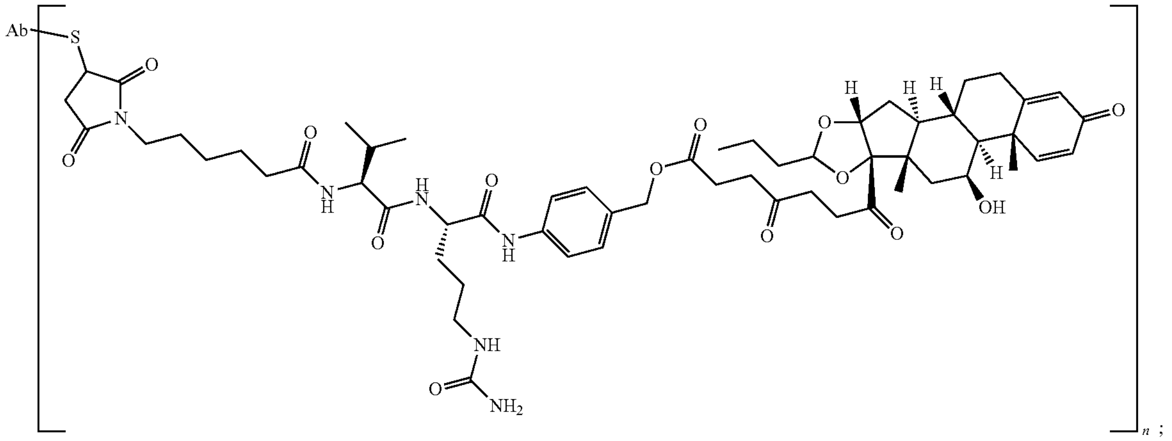
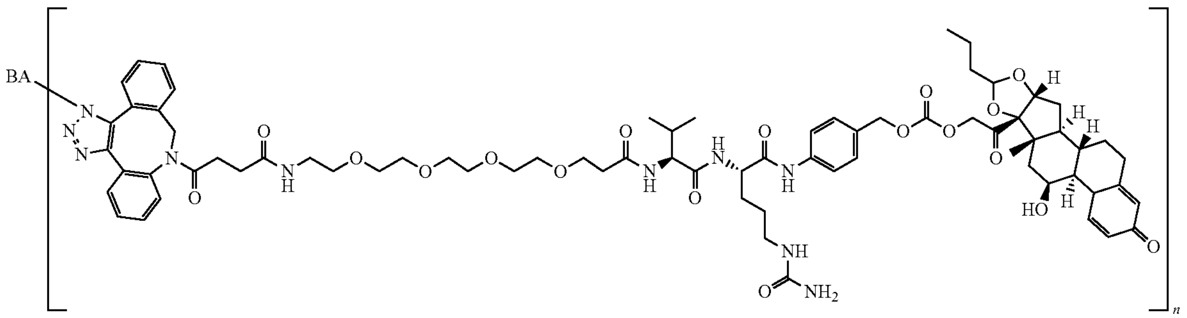
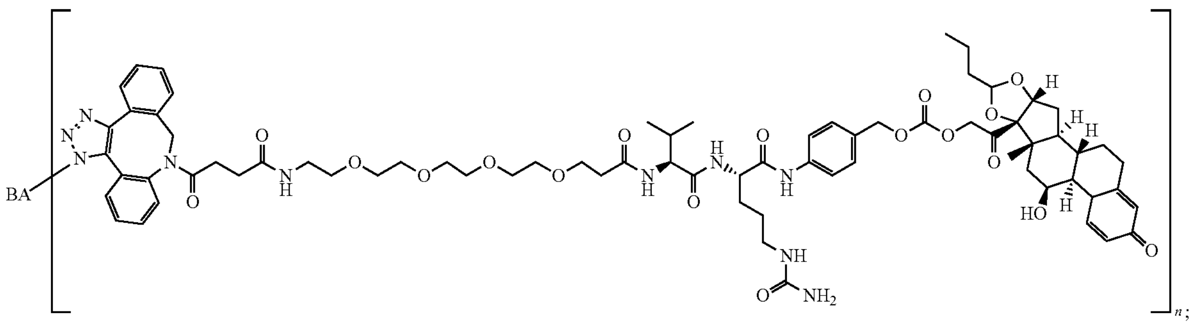
or a mixture thereof -continued
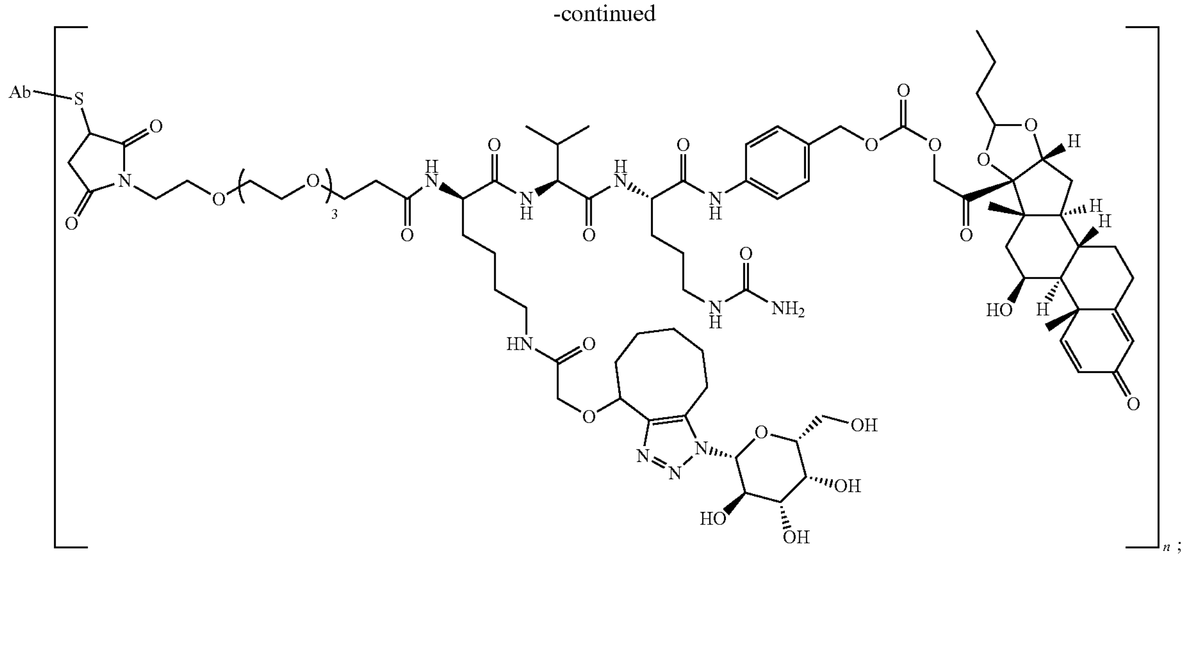
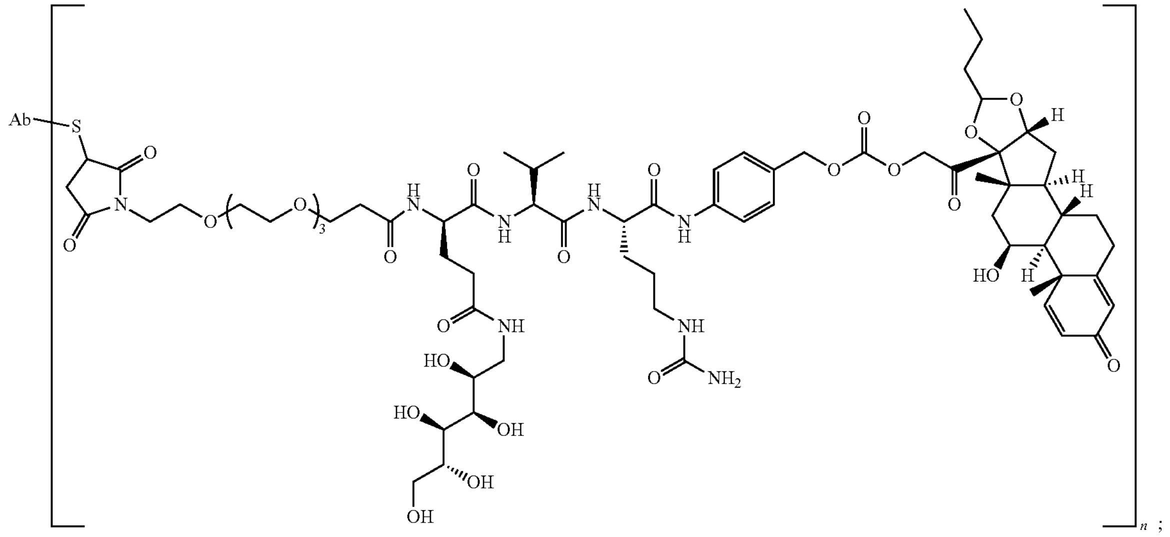
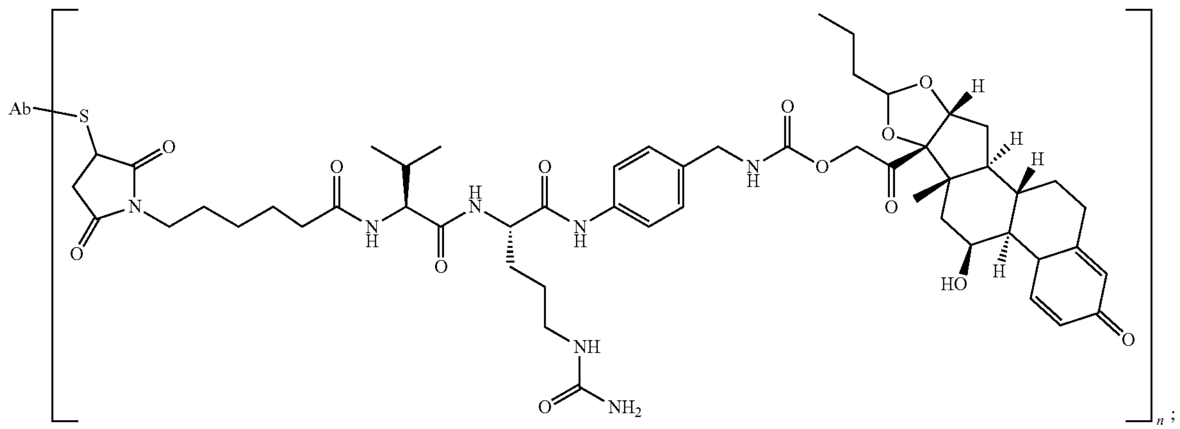

-continued
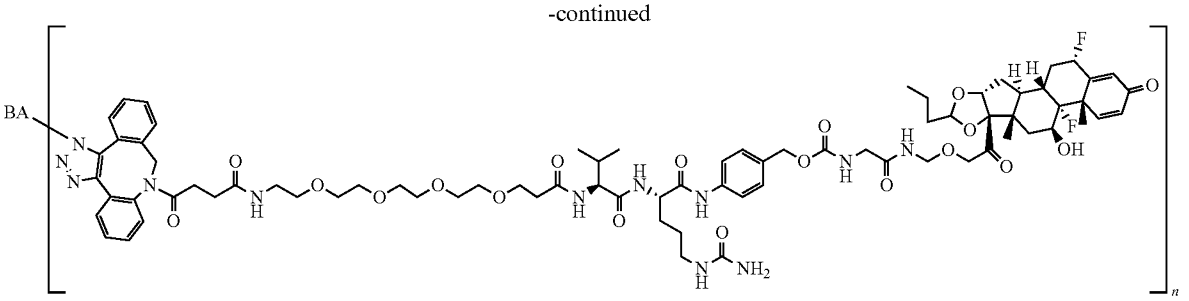
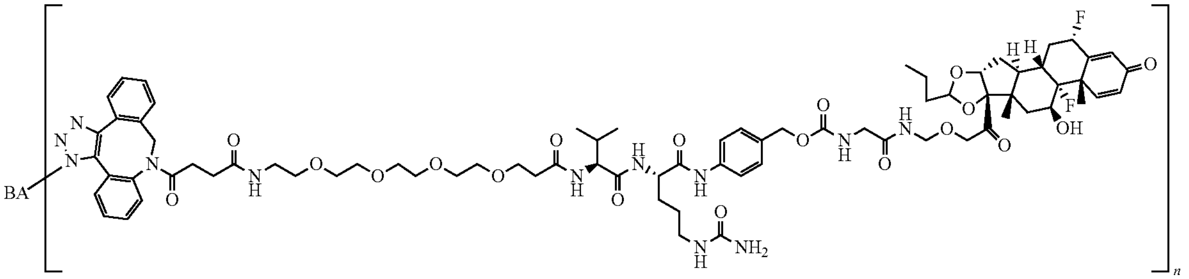
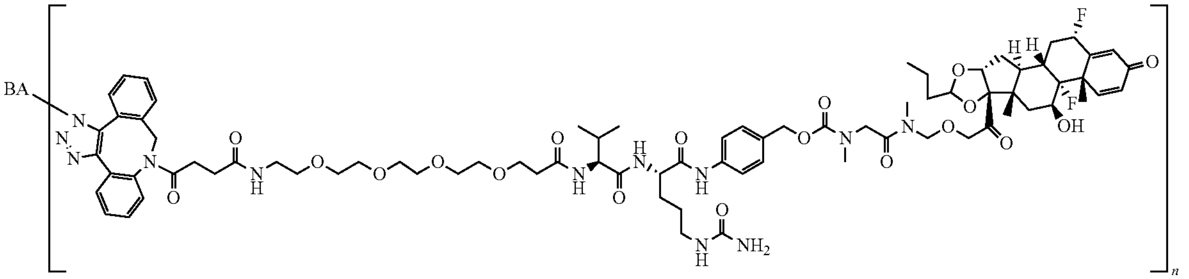
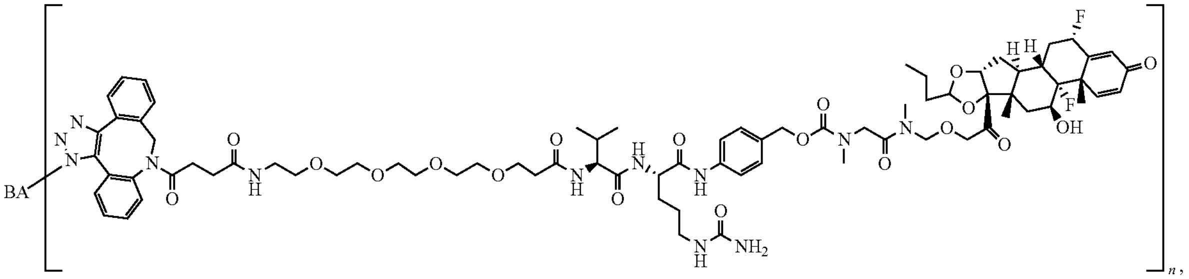
or a mixture thereof
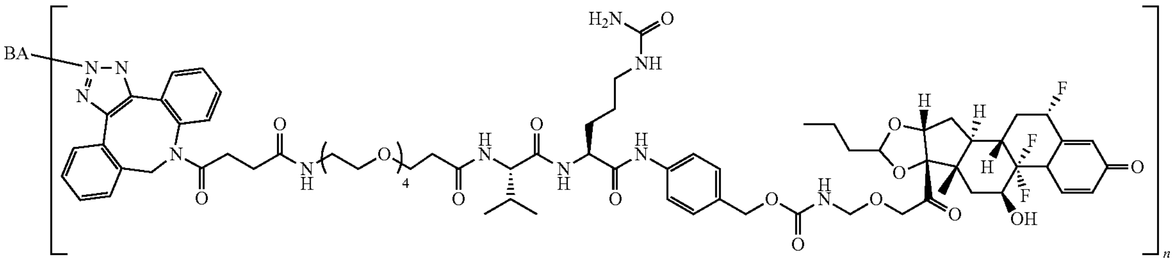
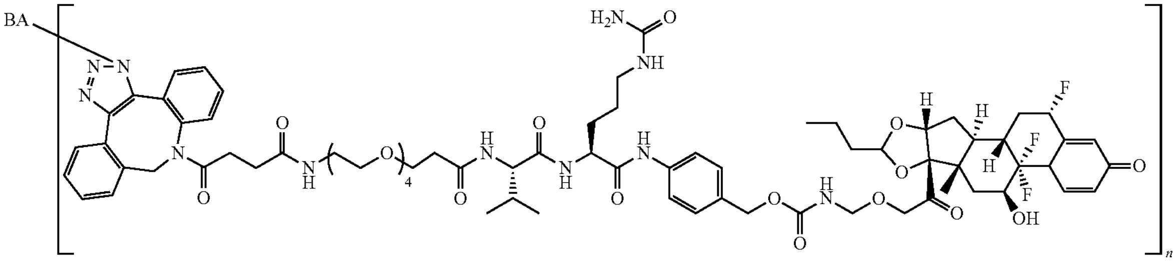
or a mixture thereof -continued
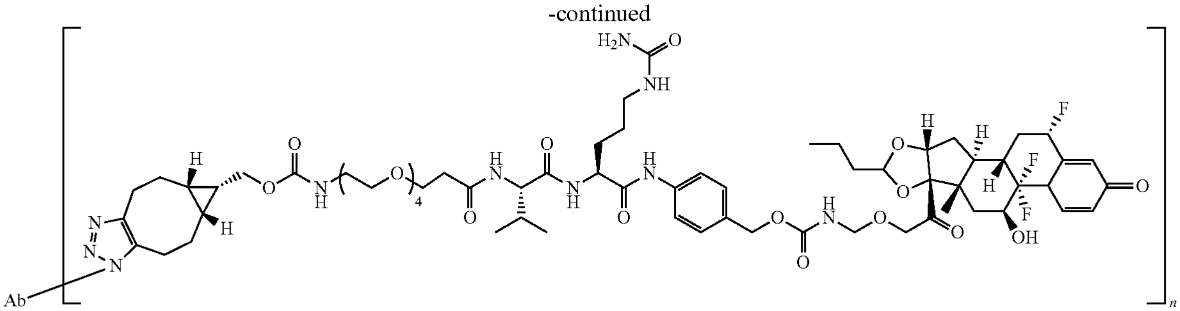
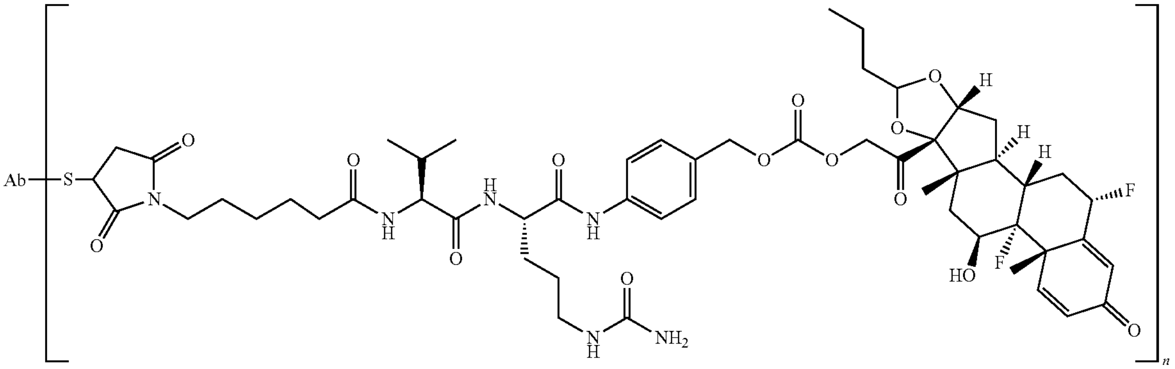
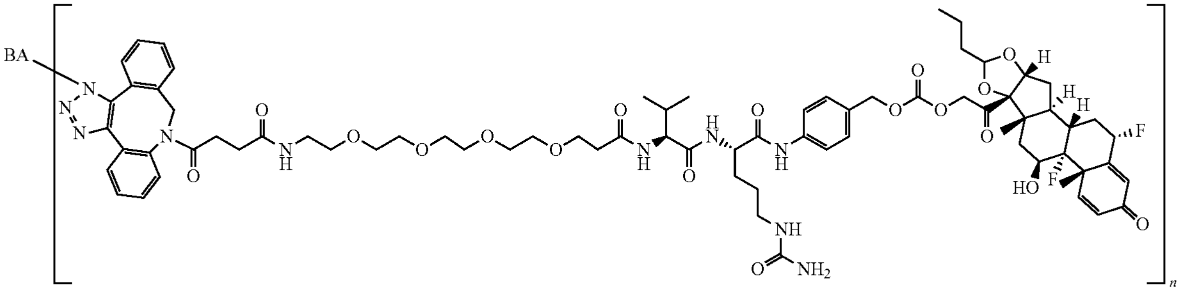
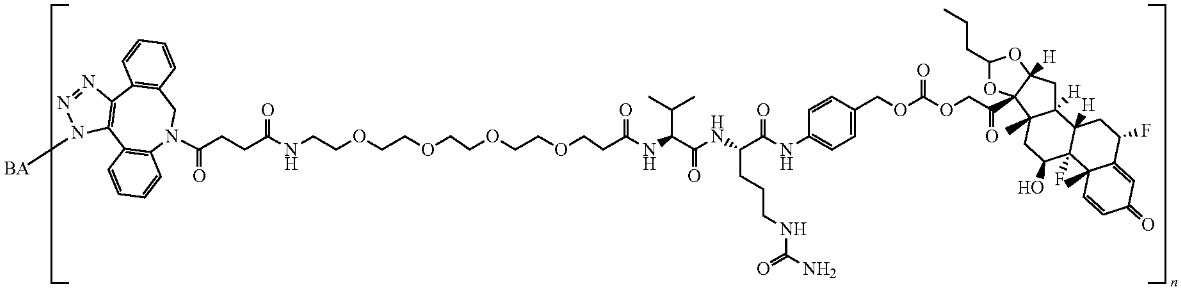
or a mixture thereof
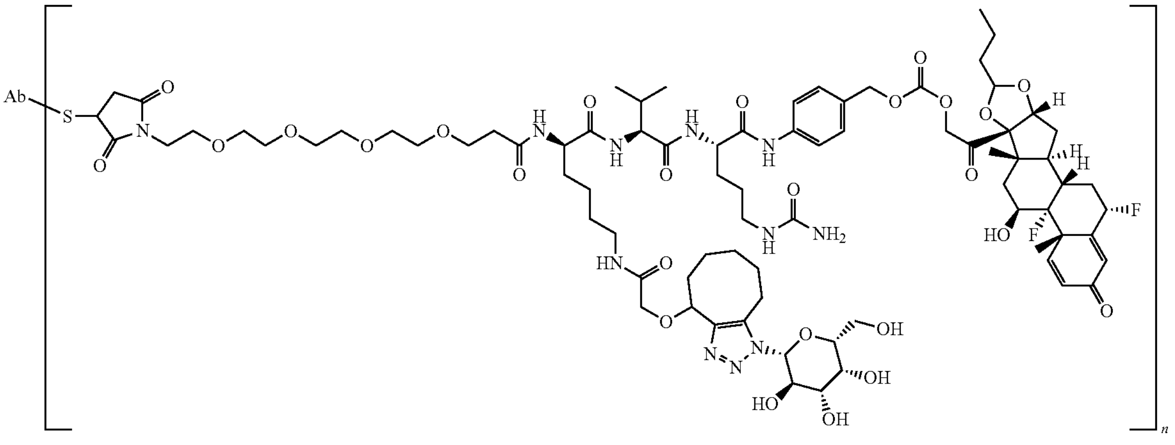

-continued
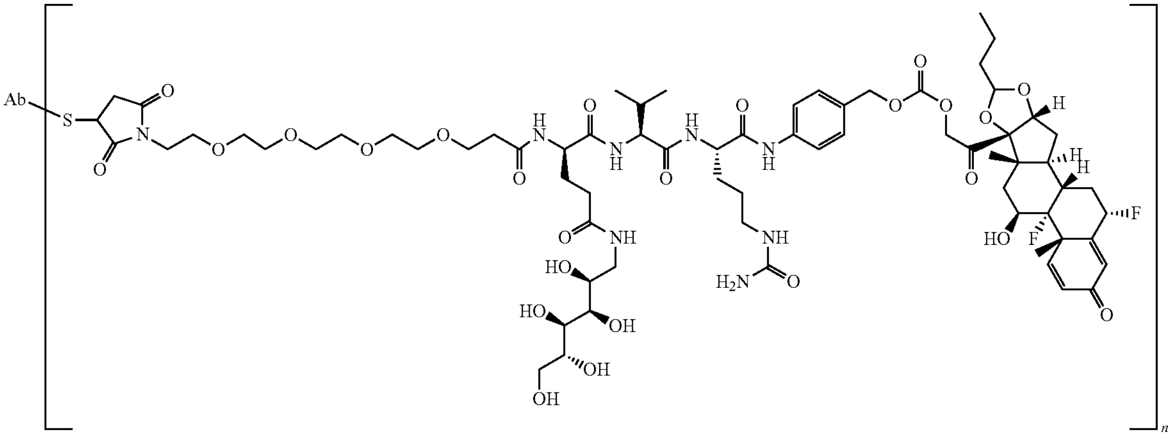
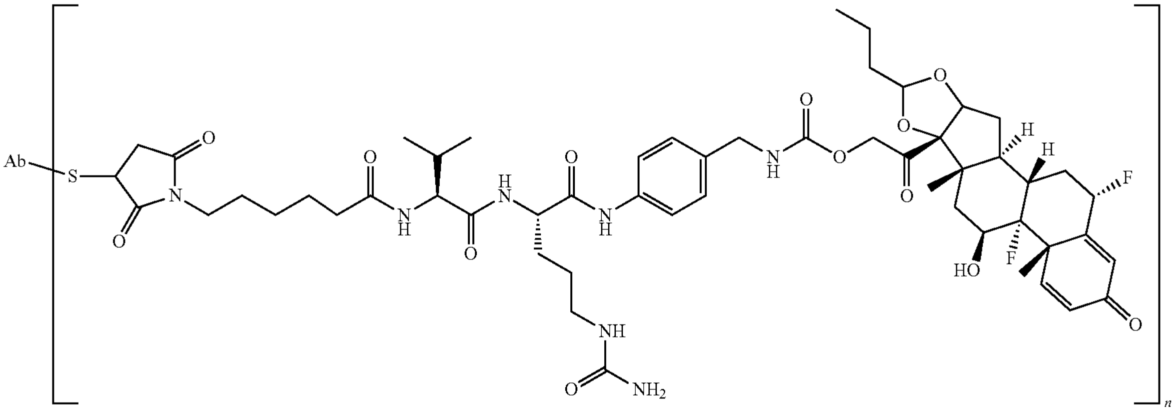
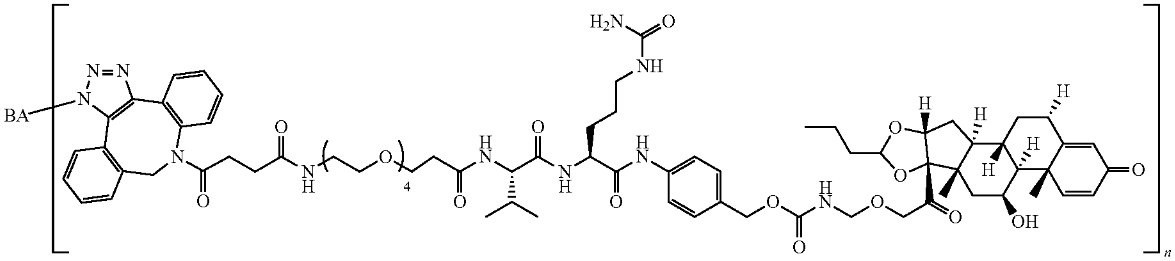
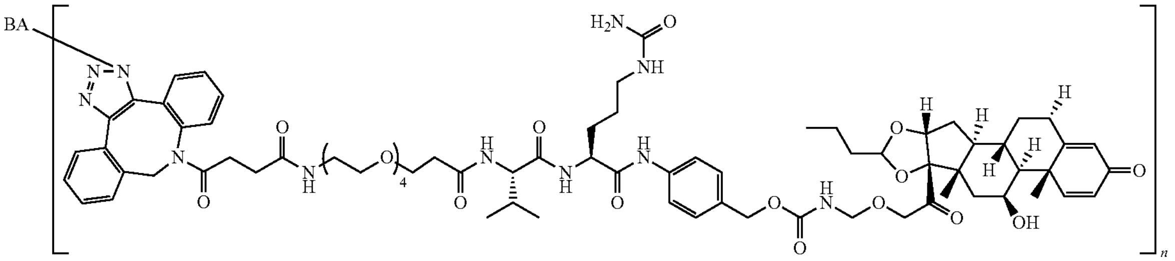
or a mixture thereof
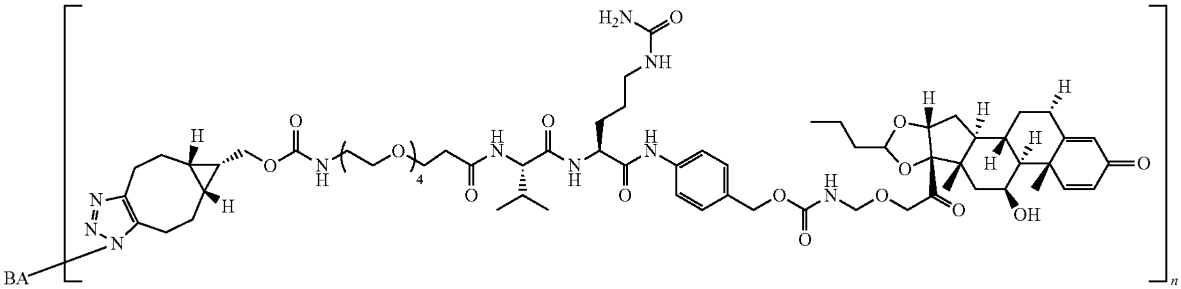

or a stereoisomeric form thereof, or a regioisomer thereof, or a mixture of regioisomers thereof, wherein each Ab is an anti-MSR1 antibody, or an antigen binding fragment thereof;

each BA is

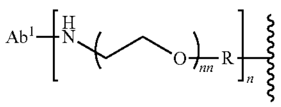

where $Ab^1$ is an anti-MSR1 antibody, or an antigen-binding fragment thereof; R is $C_{2-4}$-alkylene; and nn is an integer selected from 2 to 4, inclusive, and each n is an integer from 1 to 4.

In some additional embodiments, the ADCs described herein may comprise linkers described in U.S. Pat. No. 9,951,141 B2, filed Nov. 29, 2016, and issued on Apr. 24, 2018, which linkers are incorporated herein by reference. In some instances, the linker comprises:

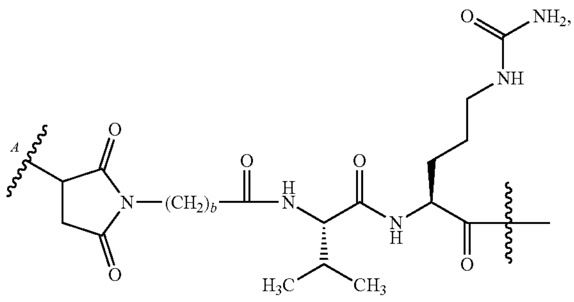

wherein b is an integer from 2 to 8 and

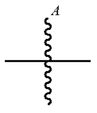

is a bond to the binding agent. In some embodiments, the linker comprises two reactive groups and can form bonds with, for example, thiols on two different chains of an antibody, or antigen binding fragment thereof:

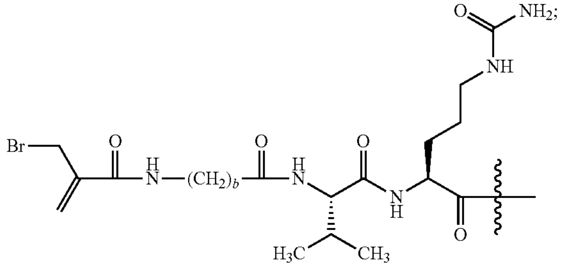

wherein b is an integer from 2 to 8. In further embodiments, the linker comprises two reactive groups and can form bonds with, for example, thiols on two different chains of an antibody, or antigen binding fragment thereof:

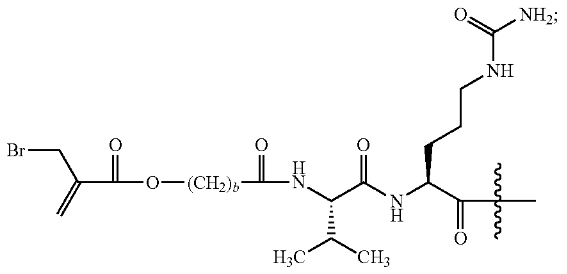

wherein b is an integer from 2 to 8. In some other embodiments, the linker comprises two reactive groups and can form bonds with, for example, thiols on two different chains of an antibody, or antigen binding fragment thereof:

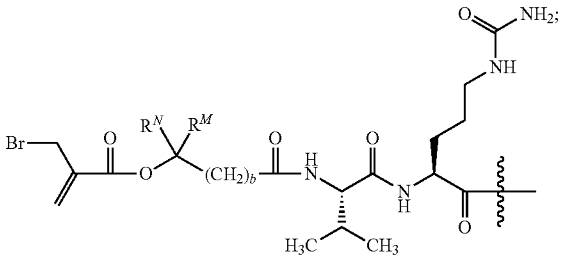

wherein b is an integer from 2 to 8, $R^N$ is a hydrogen atom or alkyl, and $R^M$ is alkyl. In additional embodiments, the linker comprises two reactive groups and can form bonds with, for example, thiols on two different chains of an antibody, or antigen binding fragment thereof:

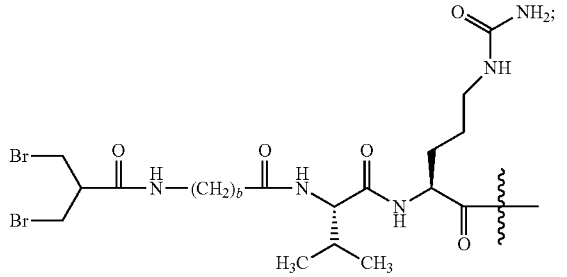

wherein b is an integer form 2 to 8. In certain embodiments, the linker comprises two reactive groups and can form bonds with, for example, thiols on two different chains of an antibody, or antigen binding fragment thereof:

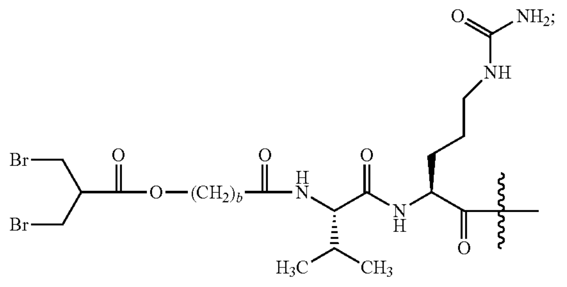

wherein b is an integer from 2 to 8. In some embodiments, the linker comprises two reactive groups and can form bonds with, for example, thiols on two different chains of an antibody, or antigen binding fragment thereof:

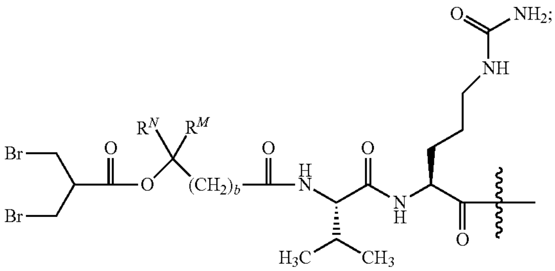

wherein b is an integer from 2 to 8; $R^N$ is a hydrogen atom or alkyl; and $R^M$ is alkyl.

In the Formulae (I), (IA), (IB), (IB-1), (IB-2), (IC), (ID), (IE), (III), (3000), (5001), (5002), (5003), (5004), (6001), (6002), (6003), (6004), (6005), (7001), (7002), (7003), (7004), and/or (7005) described herein, and/or in BA-$[(L)_{0\text{-}1}\text{-PA}]_n$, PA can be linked to BA with any linker L deemed suitable. Linkers are any group or moiety that links, connects, or bonds the antibody or antigen-binding proteins described herein with a therapeutic moiety, e.g. a steroid or an LXR modulator. Suitable linkers may be found, for example, in *Antibody-Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers/groups, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker comprises an enzyme-cleavable moiety. Illustrative enzyme-cleavable moieties include, but are not limited to, peptide bonds, ester linkages, hydrazones, and disulfide linkages. In some embodiments, the linker comprises a cathepsin-cleavable linker.

In some embodiments, the linker comprises a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker comprises one or more amino acids. Suitable amino acids include natural, non-natural, standard, non-standard, proteinogenic, non-proteinogenic, and L- or D-α-amino acids. In some embodiments, the linker comprises alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker comprises valine and citrulline. In some embodiments, the linker comprises lysine, valine, and citrulline. In some embodiments, the linker comprises lysine, valine, and alanine. In some embodiments, the linker comprises valine and alanine.

In some embodiments, the linker comprises a self-immolative group. The self-immolative group can be any such group known to those of skill. In particular embodiments, the self-immolative group is p-aminobenzyl (PAB), or a derivative thereof. In some embodiments, the self-immolative group is p-aminobenzyloxy. In some embodiments the self-immolative group comprises a cleavable di-sulfide group. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker is:

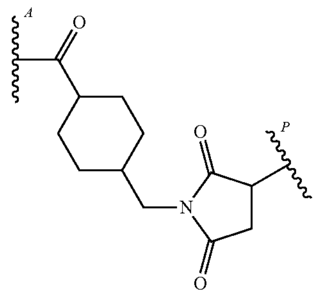

wherein

is a bond to the antibody or antigen-binding protein (e.g., via lysine residue) and

is a bond to the payload. In some embodiments, the linker is:

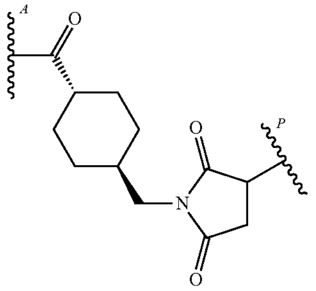

wherein

is a bond to the antibody or antigen-binding protein (e.g., via lysine residue) and

is a bond to the payload. In certain embodiments, the linker is:

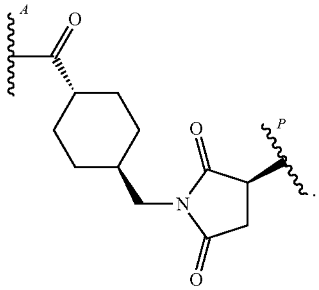

.

In certain embodiments, the linker is:

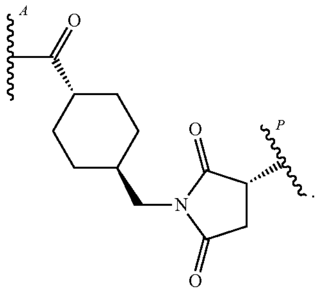

.

In some embodiments, the linker is derived from maleimidylmethyl-4-trans-cyclohexanecarboxysuccinate:

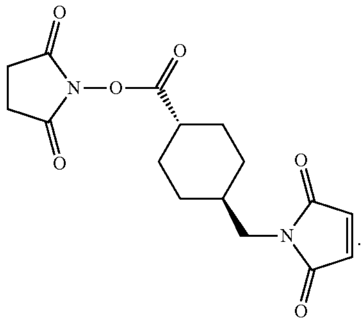 [SMILES: O=C1C=CC(=O)N1C[C@H]1CC[C@H](C(=O)ON2C(=O)CCC2=O)CC1]

.

In some embodiments, the linker is:

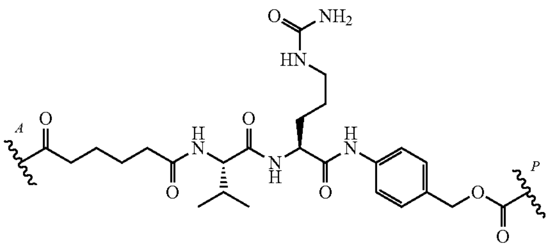

wherein

is a bond to the antibody or antigen-binding protein (e.g., via lysine residue) and

is a bond to the payload.

In some embodiments, L is a cleavable linker. In some embodiments, L is a non-cleavable linker. In some embodiments, L comprises a dipeptide. In some embodiments, L comprises a PAB moiety. In some embodiments, L comprises a disulfide moiety.

In some embodiments, L comprises a moiety having the following structure:

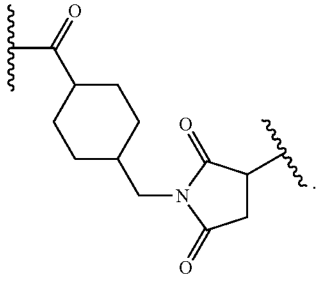 [SMILES: *C(=O)C1CCC(CN2C(=O)CC(*)C2=O)CC1]

In some embodiments, L comprises a moiety having the following structure:

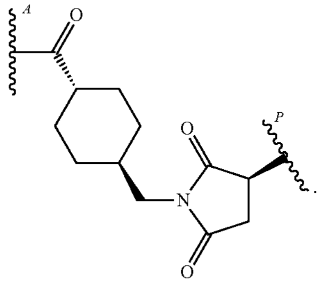

In some embodiments, L comprises a moiety having the following structure:

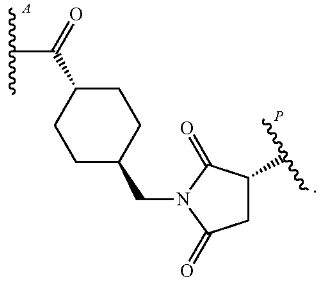

In some embodiments, L comprises a moiety having the following structure:

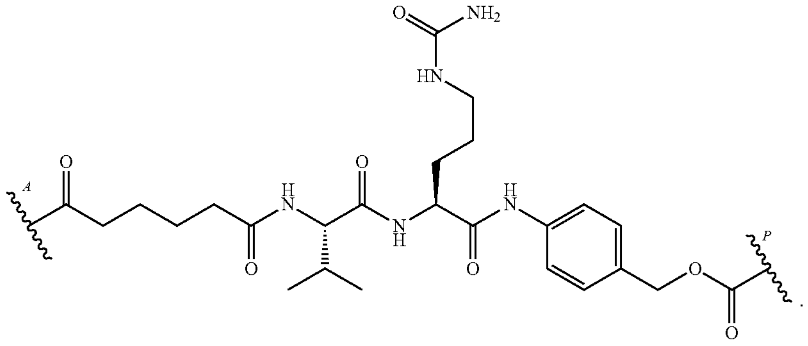

In certain embodiments, the linker comprises a cyclodextrin group. In certain embodiments, the linker provides an ADC according to Formula (Ia):

(Ia)

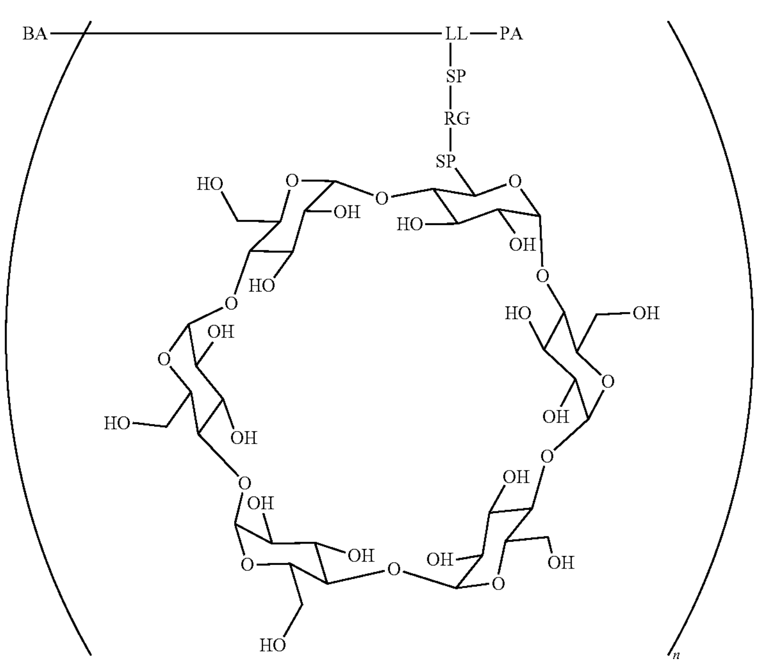

In Formula (Ia), BA is an anti-MSR1 antibody, or an antigen-binding fragment thereof, LL is a trivalent linker, RG is a reactive linker residue, SP is, independently in each instance, absent or a spacer group, subscript n is an integer from 1 to 30; and PA is a payload. In certain embodiments, n is from 1 to 4. In certain embodiments, n is 4. In certain embodiments, n is 2. In certain embodiments, n is 1. In certain embodiments, n is 3.

In certain embodiments, the linker comprises a cyclodextrin group. In certain embodiments, the linker provides an ADC according to Formula (Id):

(Id)

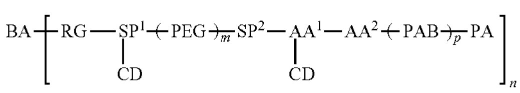

In Formula (Id), BA is an anti-MSR1 antibody, or an antigen-binding fragment thereof; RG is a reactive group residue; $SP^1$ and $SP^2$ are each, independently in each instance, absent or a spacer group residue, and wherein $SP^1$ comprises a trivalent linker; $AA^1$ is a trivalent linker comprising an amino acid residue; $AA^2$ is a di-peptide residue; PEG is a polyethylene glycol residue; PAB is

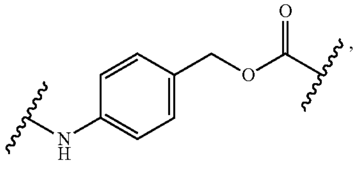 [SMILES: *Nc1ccc(COC(*)=O)cc1]

wherein the

indicates the atom through which the PAB is bonded to the adjacent groups in the formula, CD is, independently in each instance, absent or a cyclodextrin residue, wherein at least one CD is present, subscript n is an integer from 1 to 30; subscript m is an integer from 0 to 5; subscript p is 0 or 1; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, subscript p is 0. In some examples, subscript p is 1. In some examples, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is lysine. In certain embodiments, $AA^1$ is lysine or a derivative of lysine. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ glutamine-valine-citrulline. In some embodiments, the $AA^1$-$AA^2$ is glutamine-valine-citrulline. In some embodiments, the $AA^1$-$AA^2$ is lysine-valine-alanine. In some embodiments, the $AA^1$-$AA^2$ is lysine-valine-citrulline. In some embodiments, the $AA^1$-$AA^2$ is glutamine-valine-citrulline. In certain embodiments, the lysine is L-lysine. In certain embodiments, the lysine is D-lysine. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In certain embodiments, for Formulas (I), (IA), (IB), (IB-1), (IB-2), (IC), (ID), (IE), (III), (3000), (5001), (5002), (5003), (5004), (6001), (6002), (6003), (6004), (6005), (7001), (7002), (7003), (7004), and/or (7005), the linker is selected from:

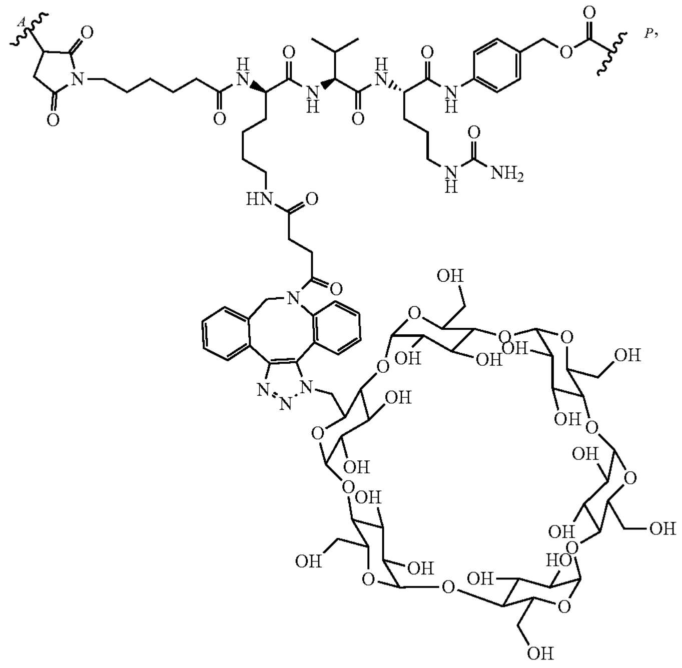

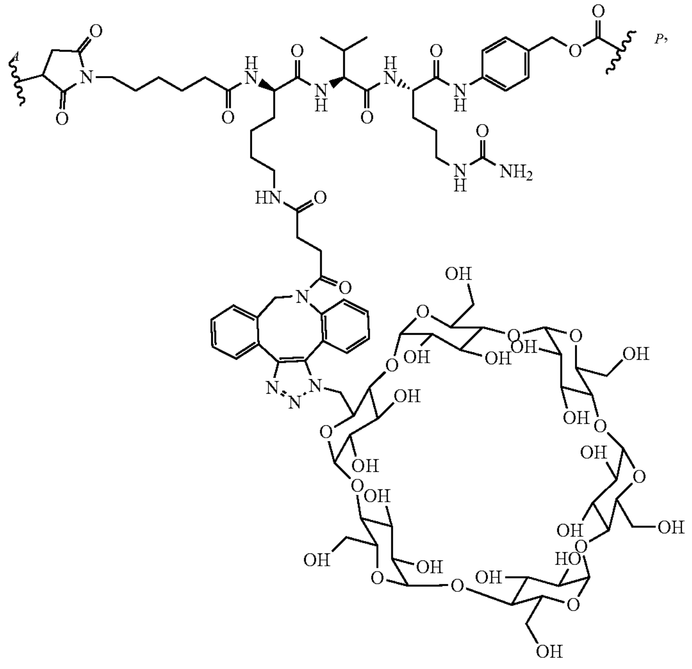

-continued
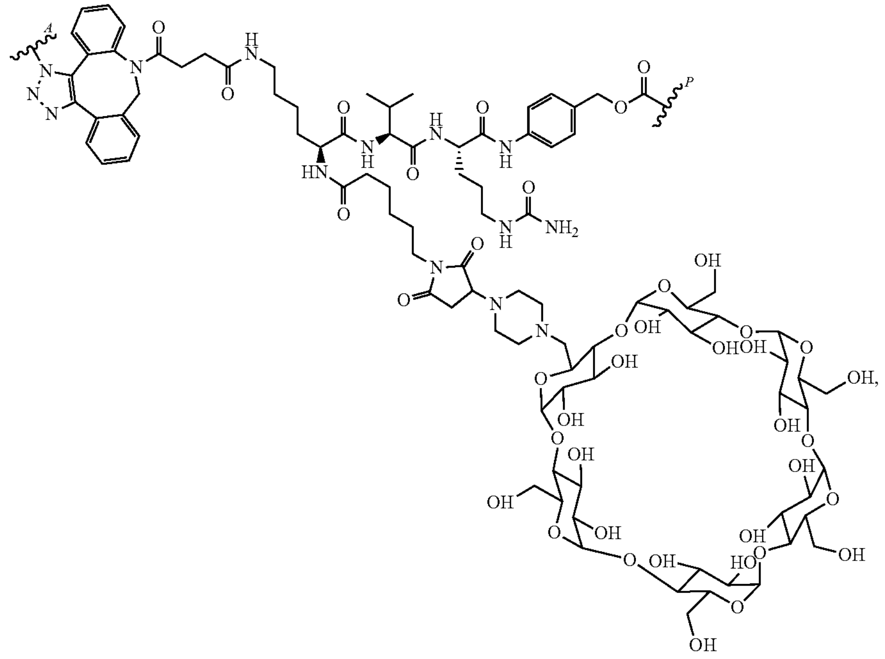
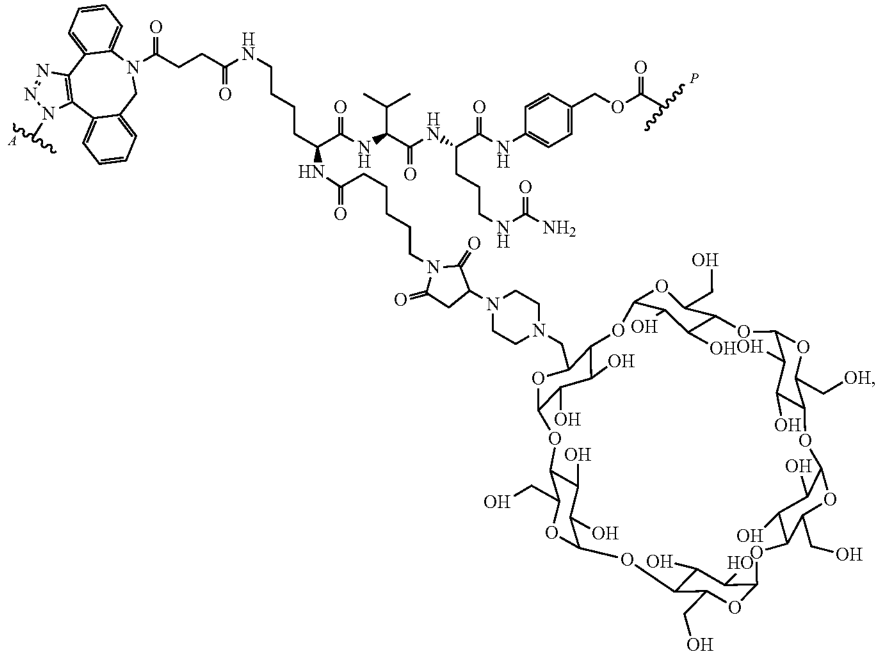

-continued
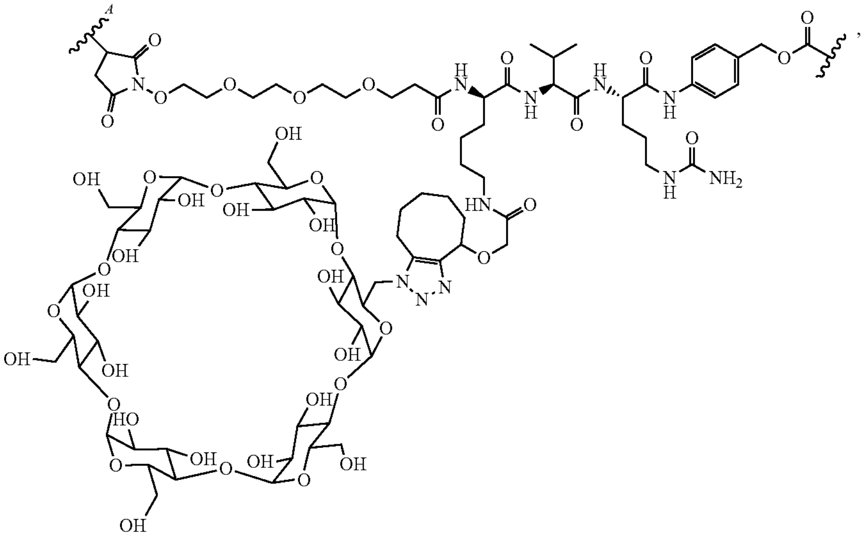
,
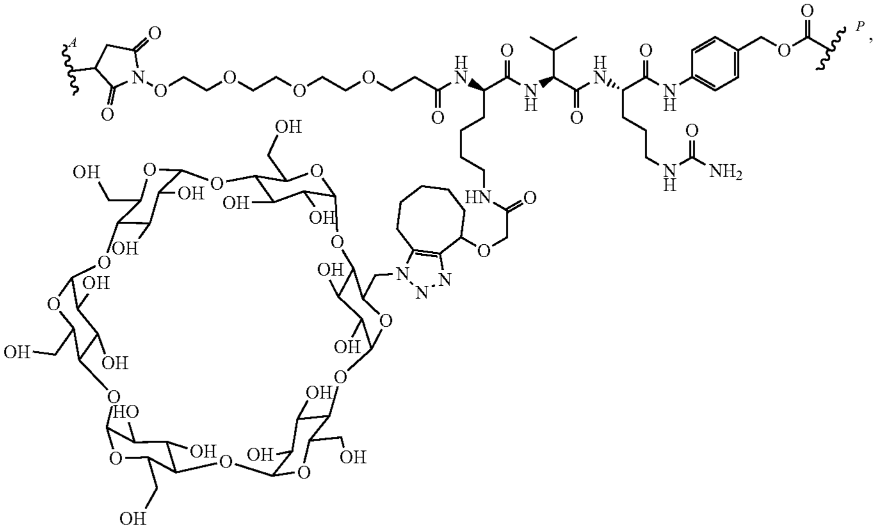
,
,

-continued
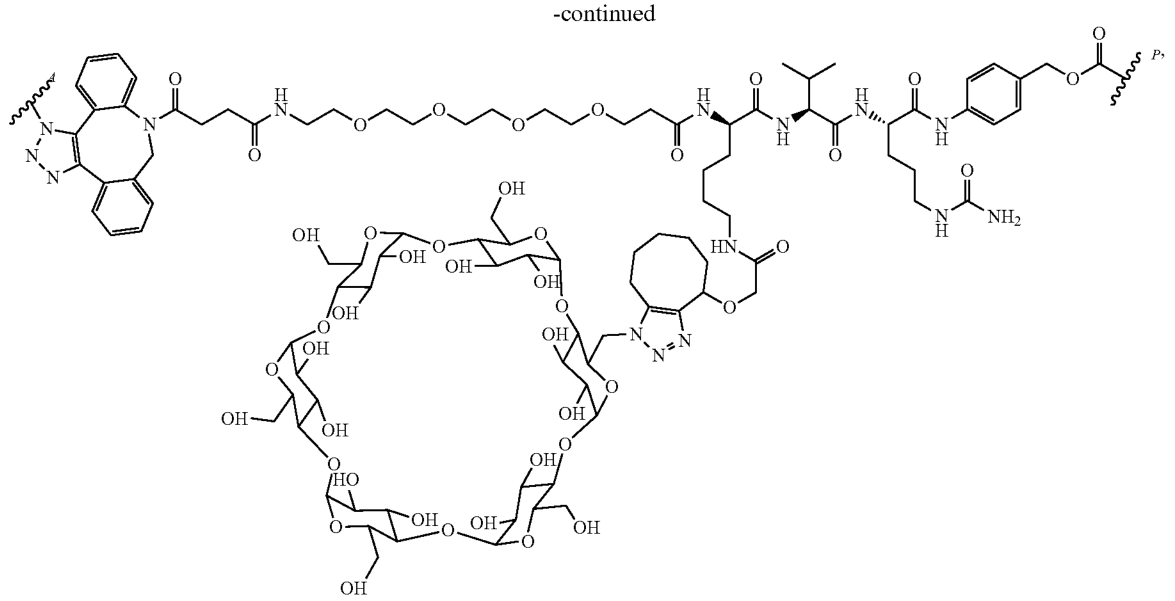
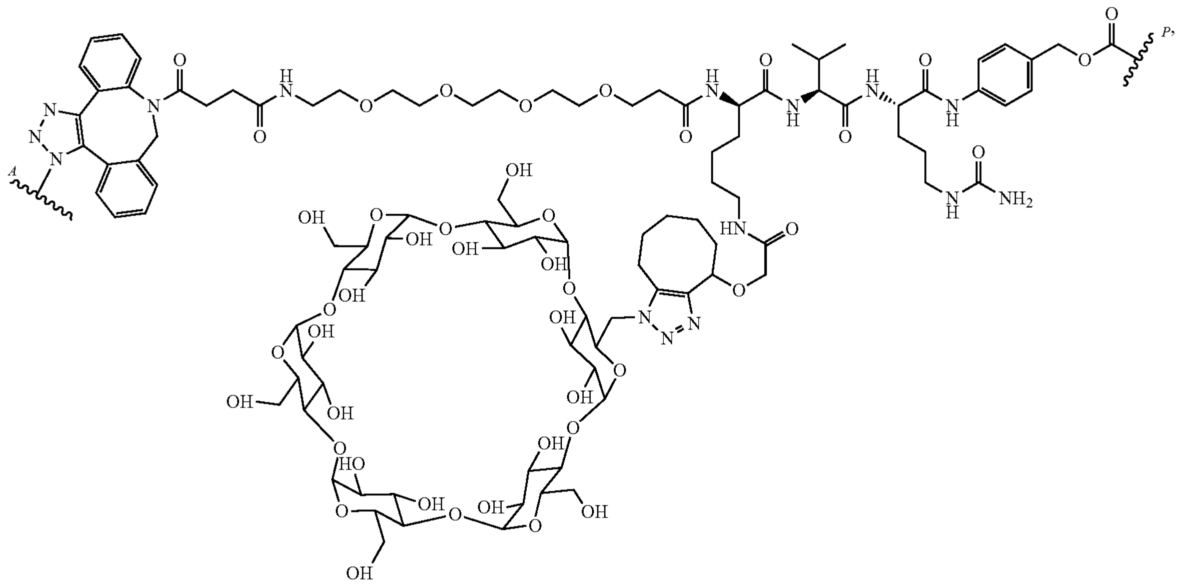

-continued
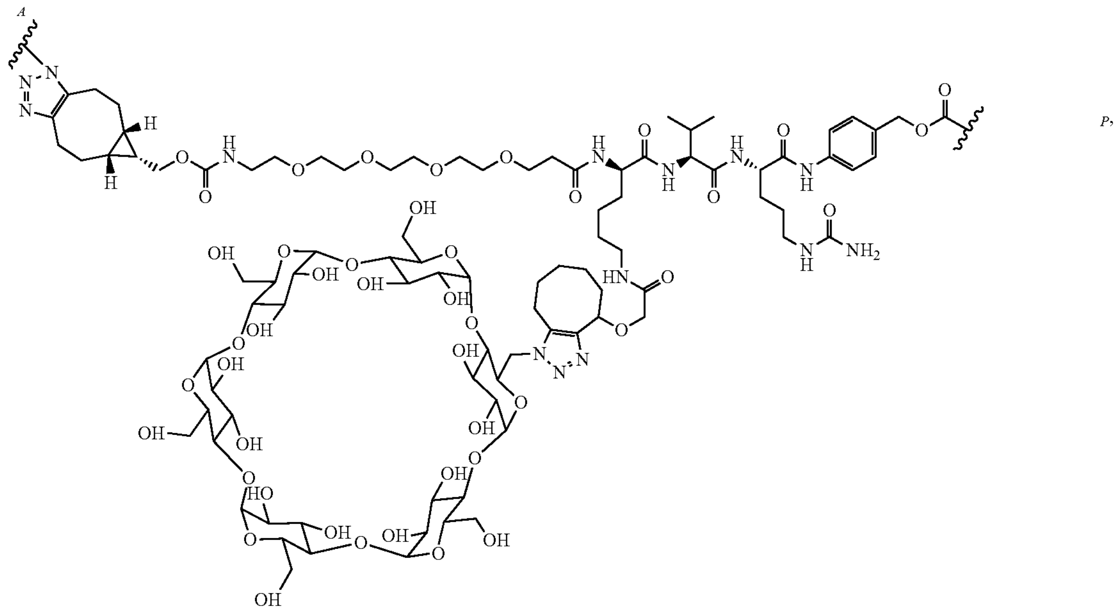
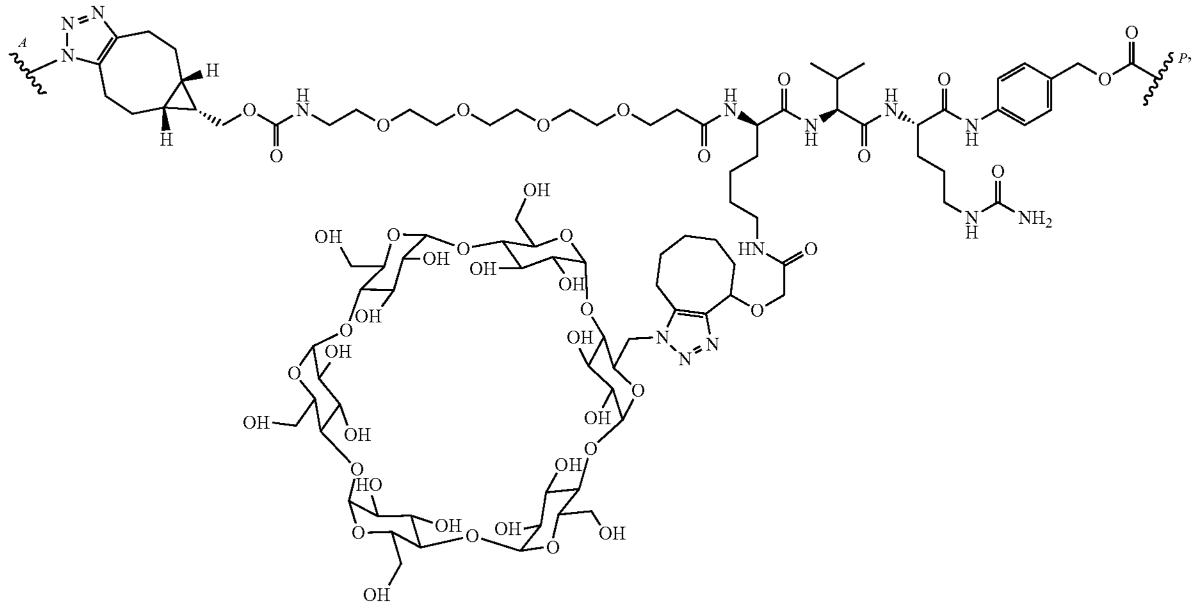
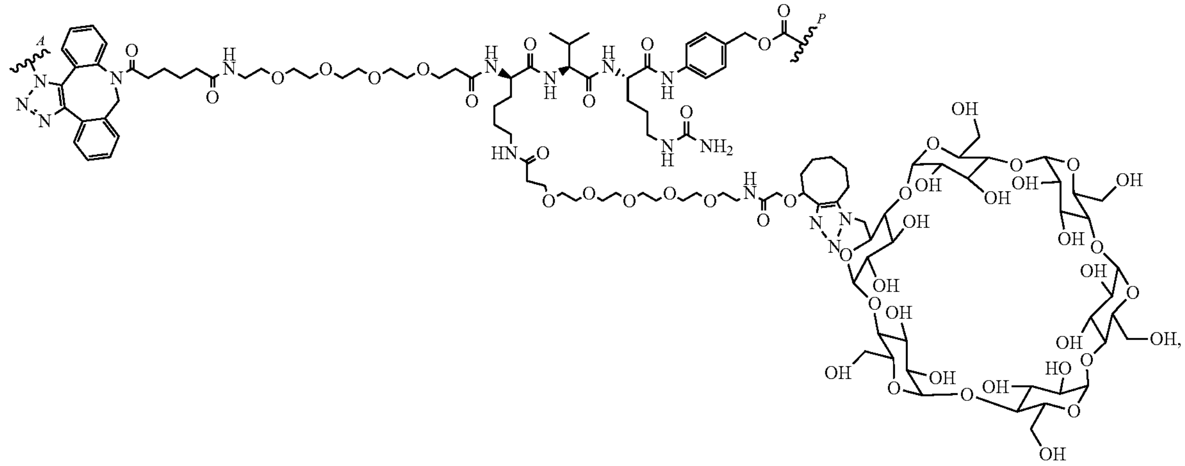

-continued
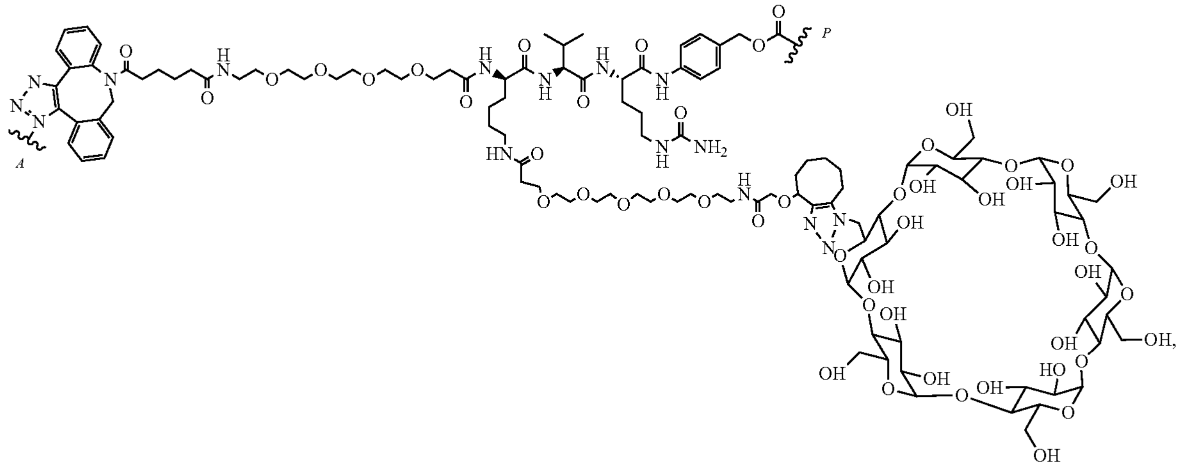
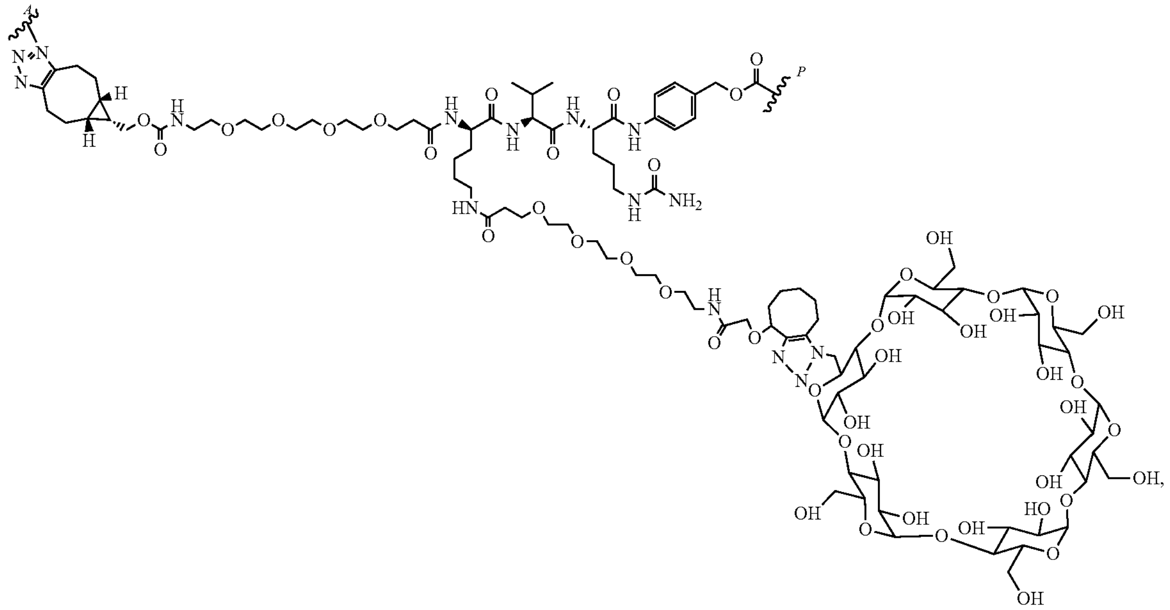
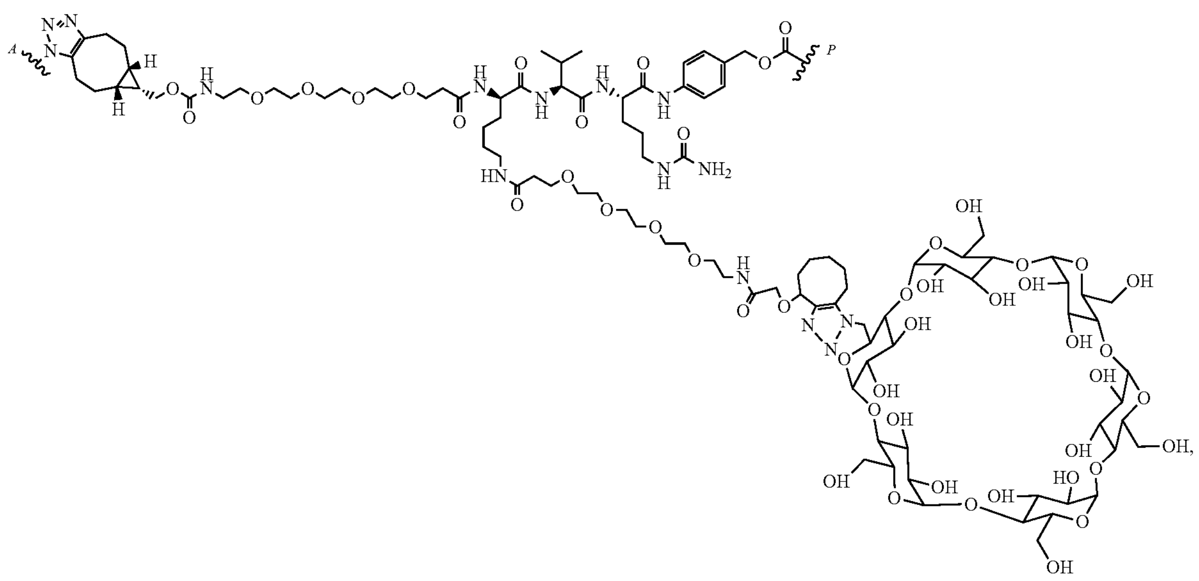

-continued
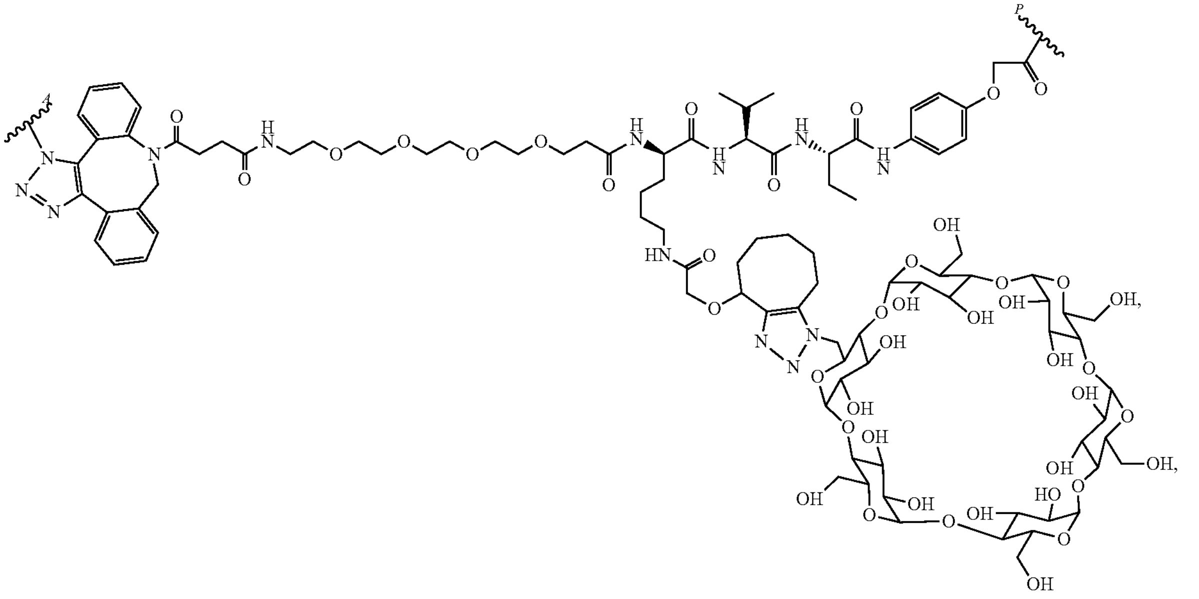
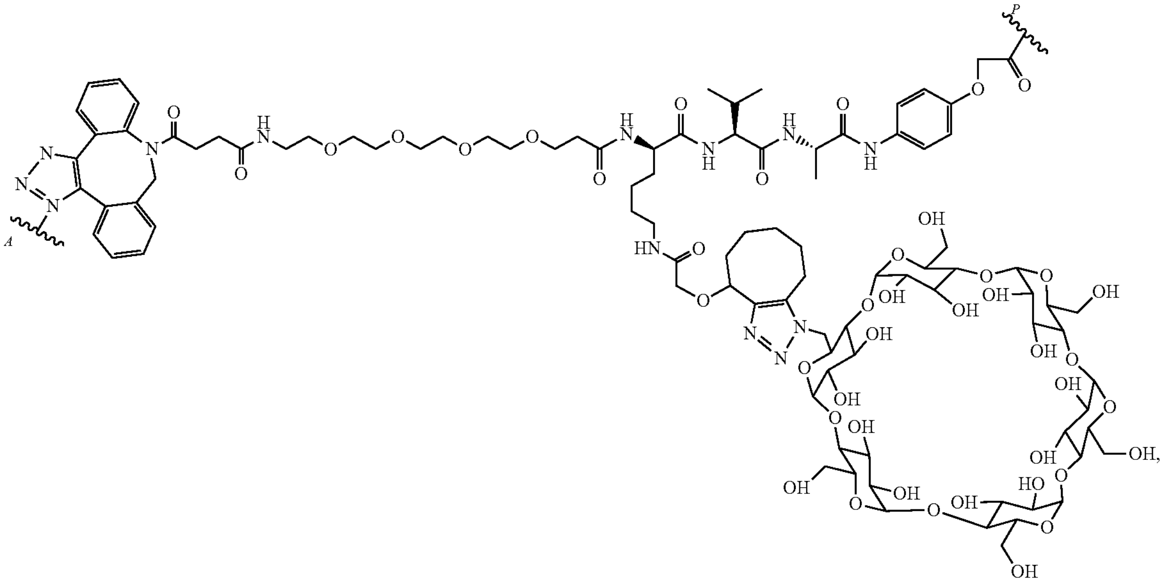
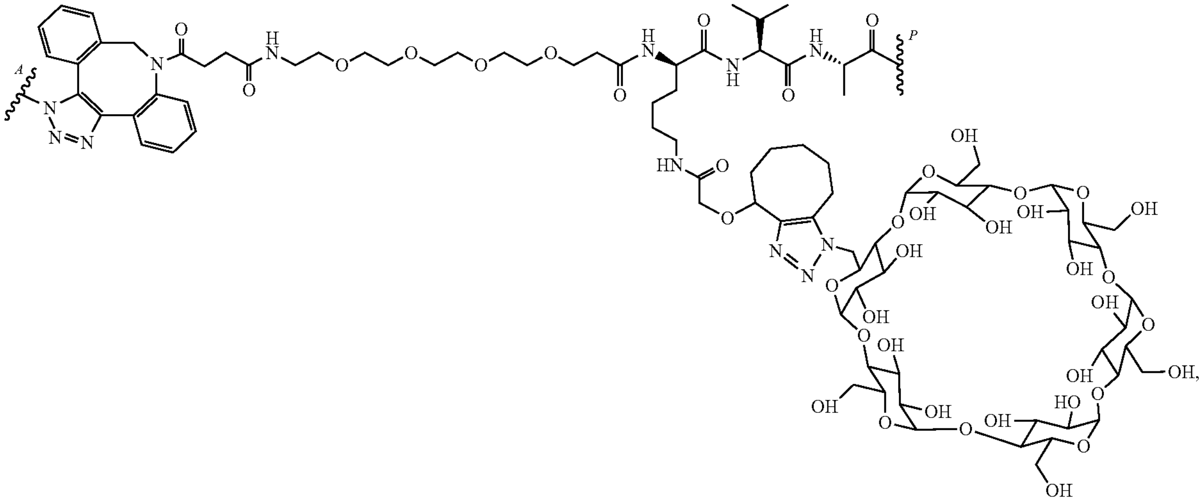

-continued
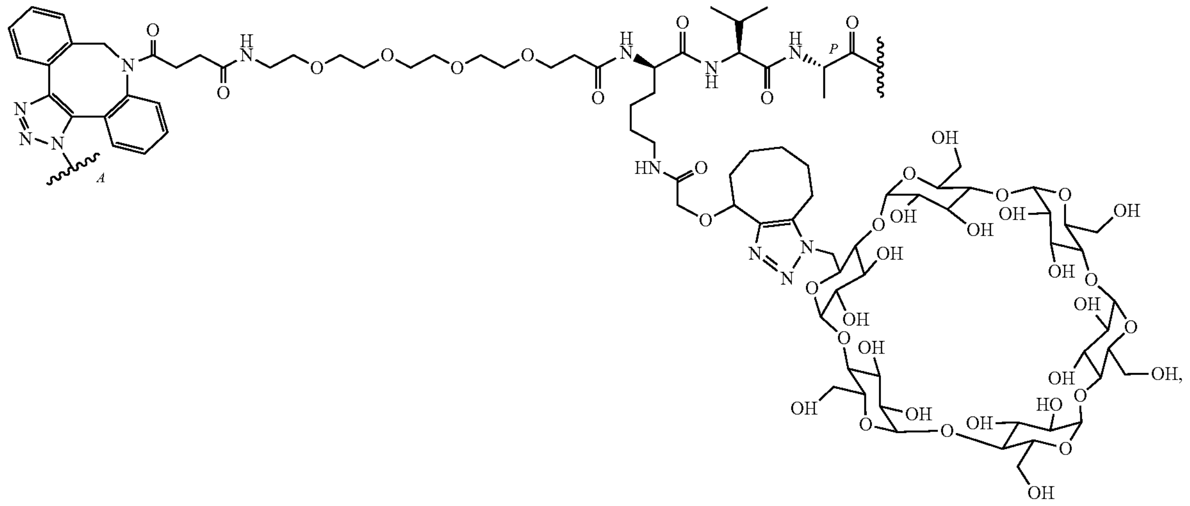
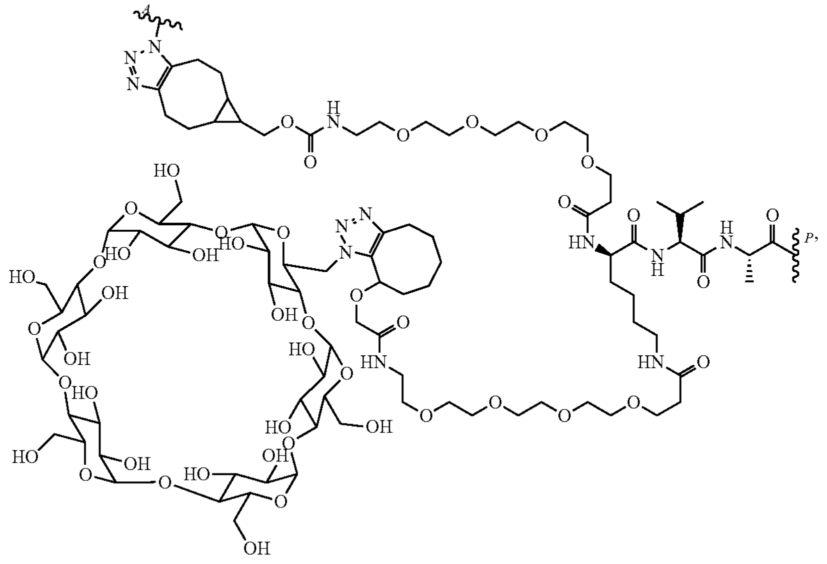
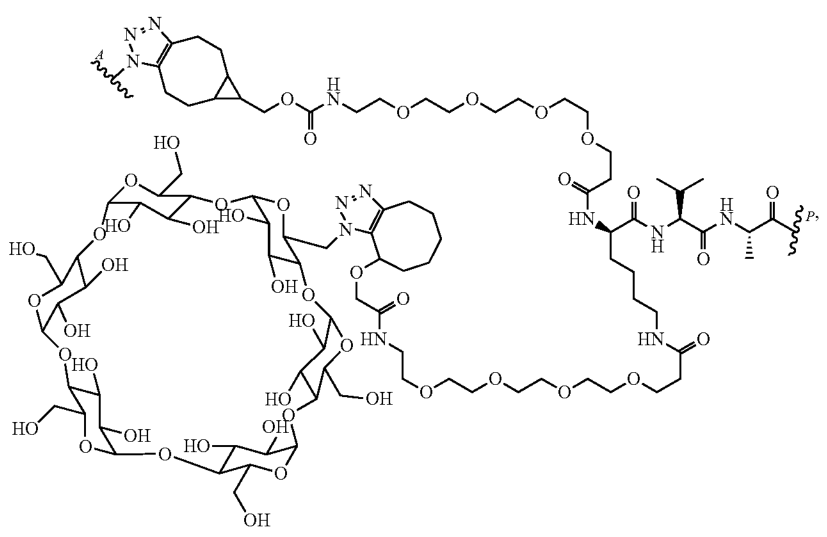

-continued
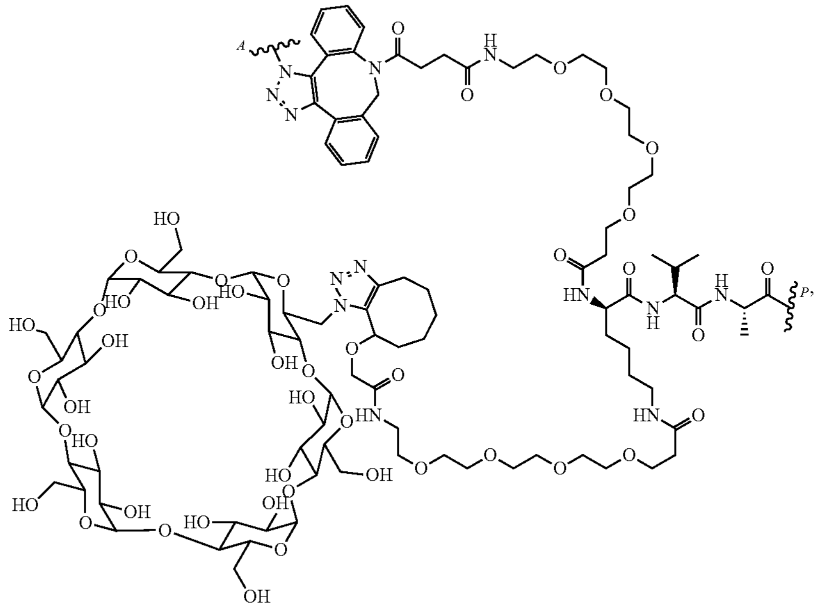
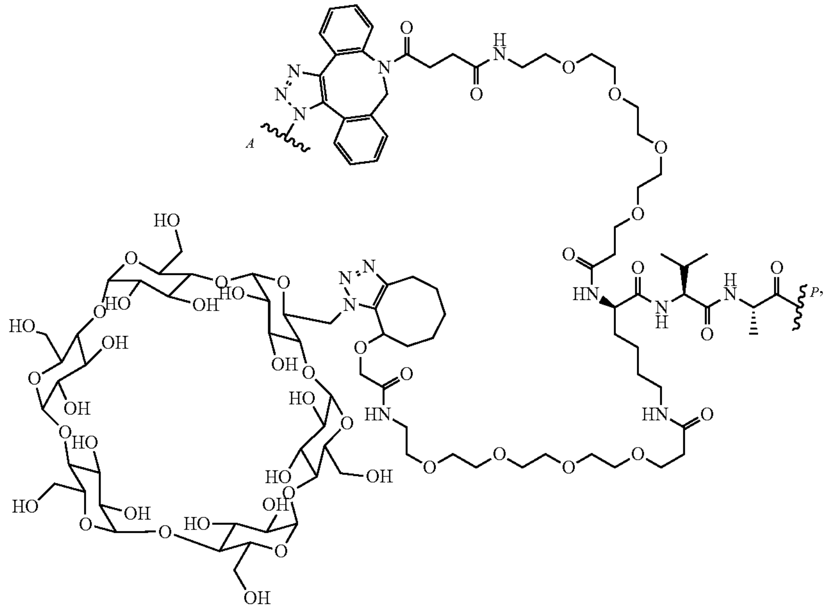

-continued
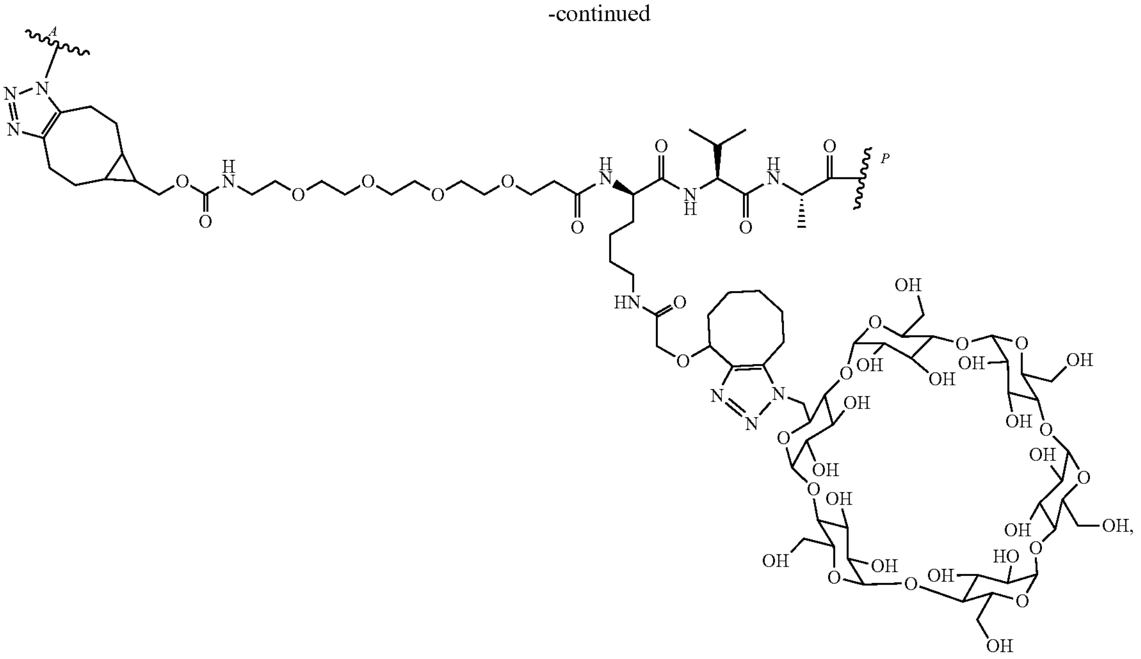
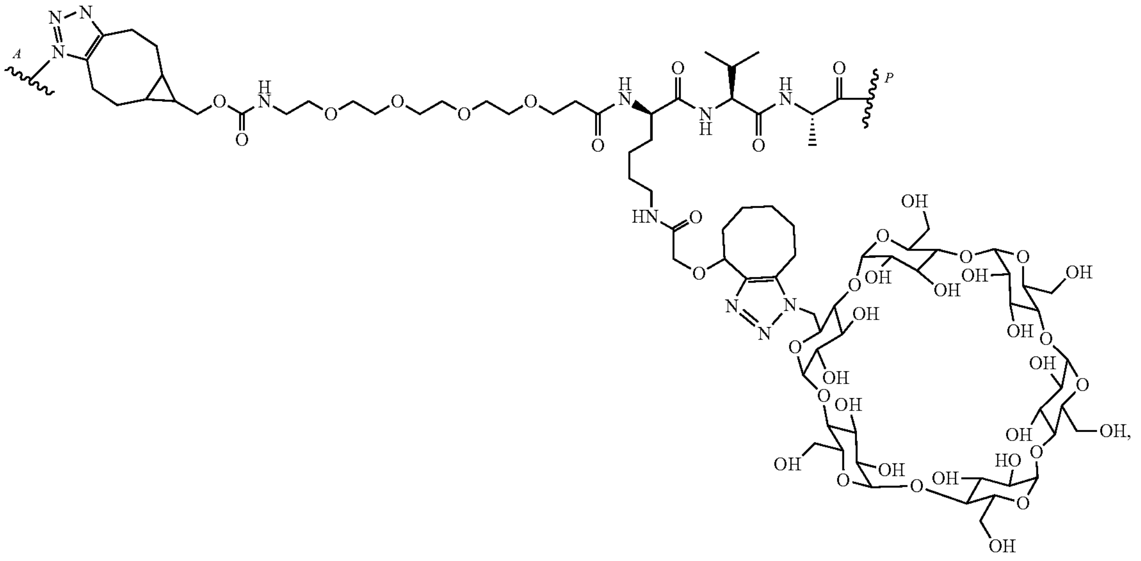

-continued
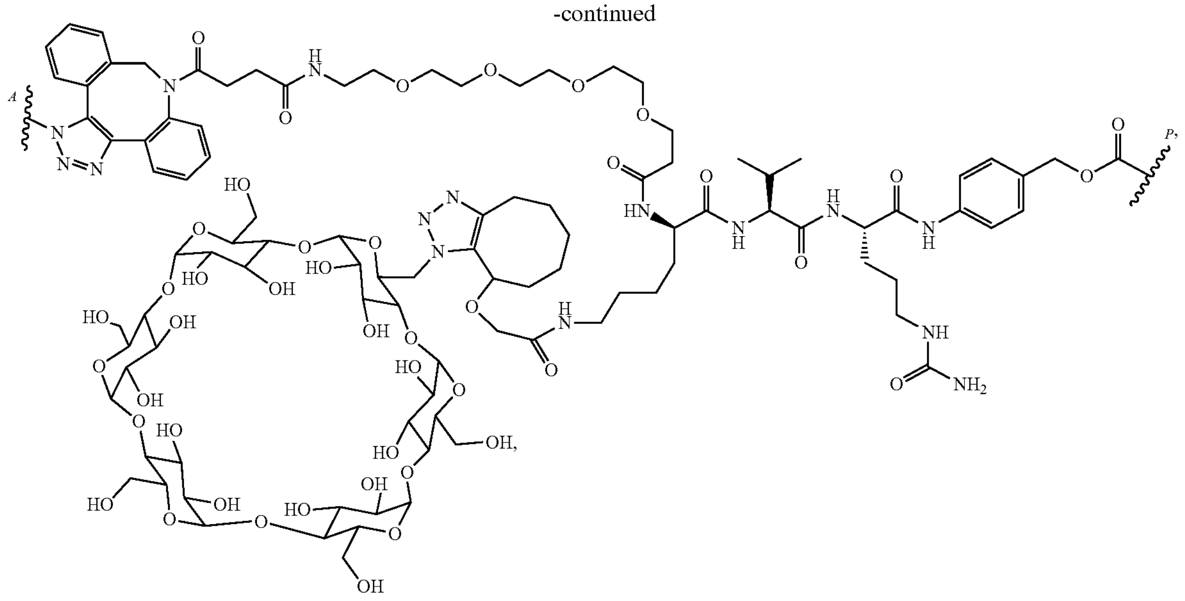
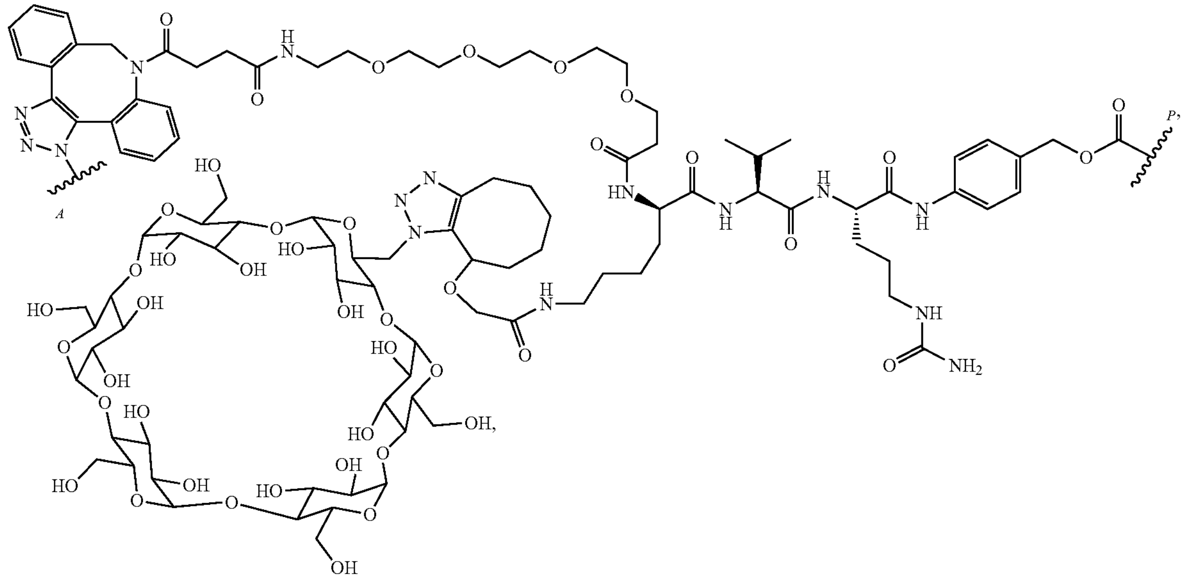

-continued

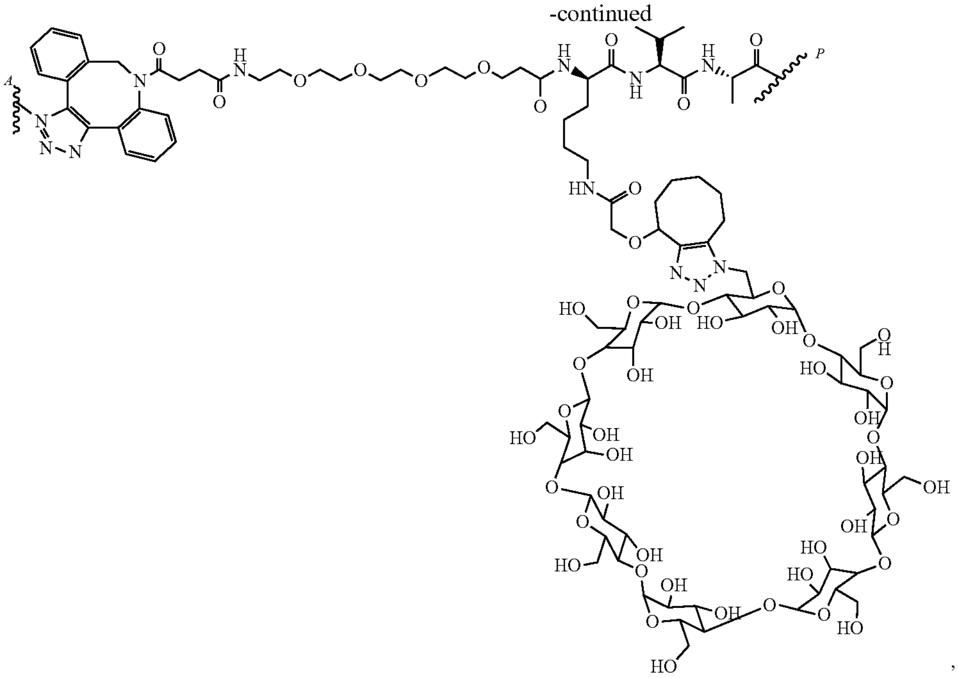

, and

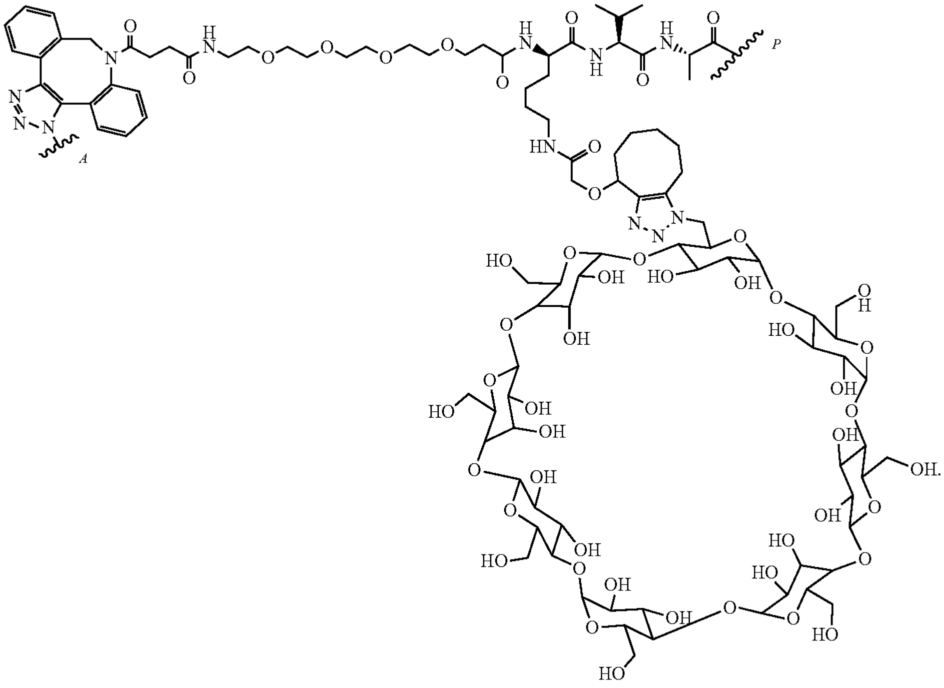

Also included in these examples, is a pharmaceutically acceptable salt, solvate, stereoisomeric form thereof, a regioisomer thereof, or mixture of regioisomers thereof, wherein each

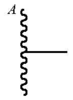

is a bond to the binding agent; and each

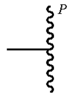

is a bond to the payload.

In certain embodiments, the linker comprises a terminal hydrophilic group (HG). In certain embodiments, the linker comprises a taurine group. In certain embodiments, the linker comprises a terminal sulfonic acid group. In certain embodiments, the linker provides an ADC according to Formula (II):

(II)

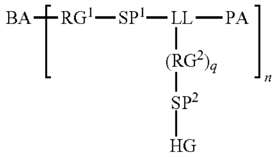

wherein, in Formula (II), BA is a binding agent; LL is a trivalent linker; $RG^1$ and $RG^2$ are reactive group residues; $SP^1$ and $SP^2$ are independently, in each instance, absent, or a spacer group residue; HG is a hydrophilic residue; PA is a payload residue; subscript n is an integer from 1 to 30; and subscript q is 0 or 1. In some instances more than one trivalent linker LL may be present. In some instances, n is an integer from 1 to 4. In some instances n is 1. In some instances n is 2. In some instances n is 3. In some instances n is 4. In some instances, HG is a terminal hydrophilic group. In some instances, HG comprises one terminal sulfonic acid group or a salt thereof. In other instances, HG comprises more than one terminal sulfonic acid groups or salts thereof. In some instances, HG comprises one terminal phosphonic acid group or a salt thereof. In other instances, HG comprises more than one terminal phosphonic acid groups or salts thereof. In some instances, HG comprises one terminal tertiary amine group or a salt thereof. In other instances, HG comprises more than one terminal tertiary amine groups or salts thereof. In some instances, HG comprises one terminal polyol (e.g., glucose, maltose) or a derivative thereof. In other instances, HG comprises more than one terminal polyol (e.g., glucose, maltose) or derivatives thereof.

In another example, the compound of Formula (II) is according to Formula (IV):

(IV)

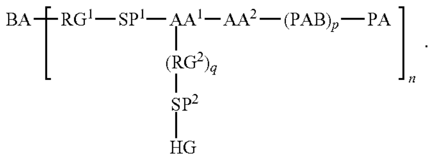

In Formula (IV), BA, $RG^1$, $SP^1$, $RG^2$, $SP^2$ and HG are as defined above, $AA^1$ is a trivalent linker comprising an amino acid residue; $AA^2$ is a dipeptide residue; and PAB is

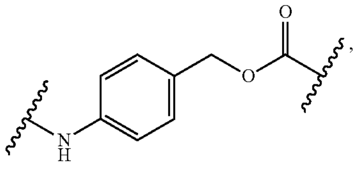 [SMILES: *Nc1ccc(COC(*)=O)cc1]

wherein the

indicates the atom through which the PAB is bonded to the adjacent groups in the formula; subscript p is 0 or 1; and subscript q is 0 or 1. In some instances, subscript p is 0 and subscript q is 0. In some instances, subscript p is 1; and subscript q is 0. In some instances, subscript p is 0; and subscript q is 1. In some instances, subscript p is 1; and subscript q is 1. In some instances $SP^1$ comprises from 0-5 polyethylene glycol (PEG) residues. In some instances $SP^2$ comprises from 0-5 PEG residues. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, any one of $AA^1$ or $AA^2$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^1$ is lysine. In certain embodiments, $AA^1$ is lysine or a derivative of lysine. In certain embodiments, $AA^1$ is glutamic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine. In certain embodiments, the lysine is L-lysine. In certain embodiments, the lysine is D-lysine.

In certain embodiments, for Formulas (I), (IA), (IB), (IB-1), (IB-2), (IC), (ID), (IE), (III), (3000), (5001), (5002), (5003), (5004), (6001), (6002), (6003), (6004), (6005), (7001), (7002), (7003), (7004), and/or (7005), the linker is selected from:

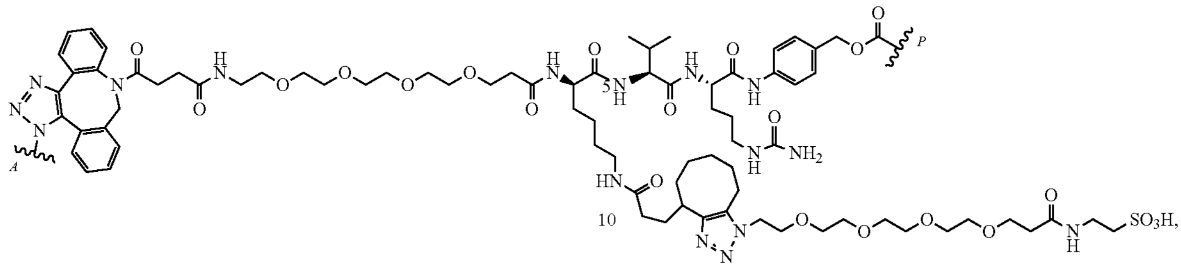
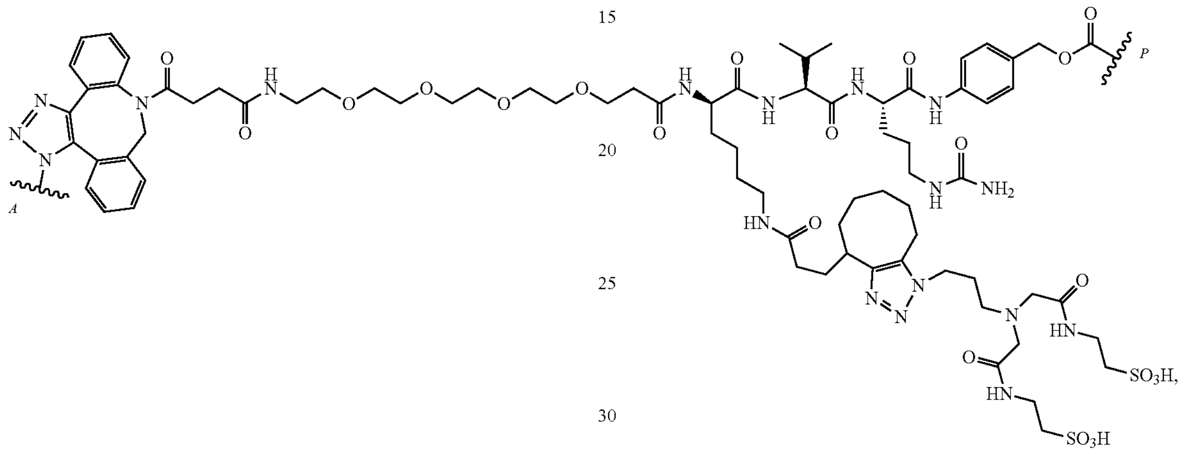
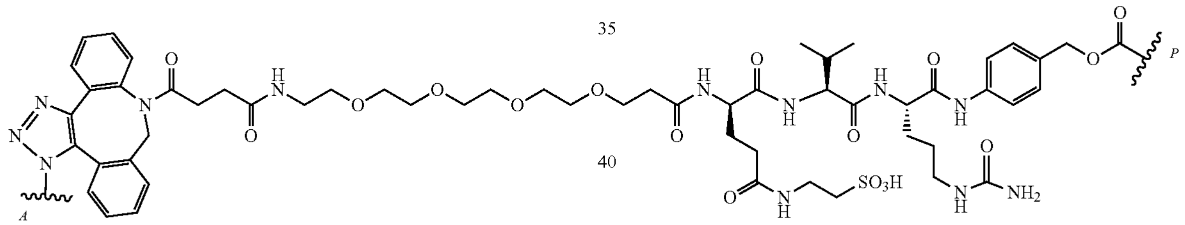
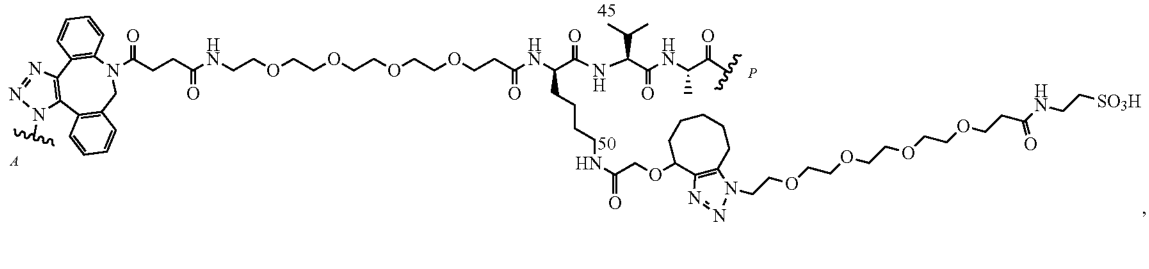
, and
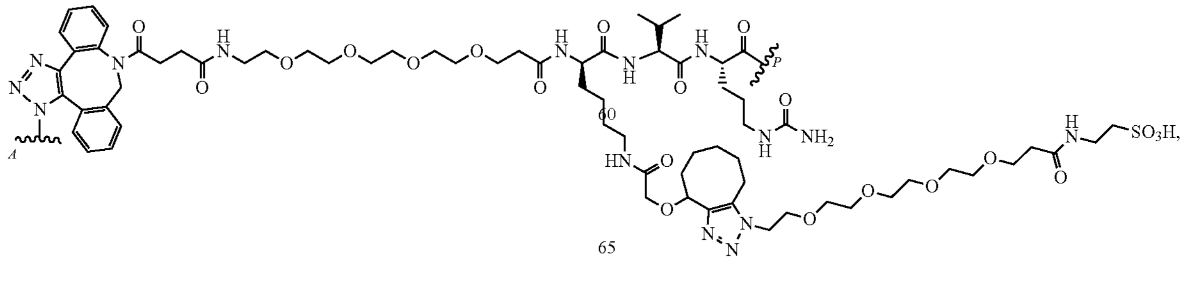

or a stereoisomeric form thereof, or a regioisomer thereof, or a mixture of regioisomers thereof, wherein each

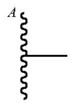

is a bond to the binding agent; and each

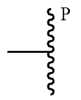

is a bond to the payload residue.

In some instances, the moiety L-PA is attached to a reactive group (RG) to form RG-L-PA (e.g., linker payloads shown in Table 3). In some instances, BA (or a modified from of BA, e.g., PEG-modified Ab, as shown in Table 2, or $Ab^1$) reacts with linker payloads to form the ADCs described in Table 1 and Table 2. Also contemplated within the scope of embodiments presented herein are ADCs prepared from any linker payloads described in Table 5A and Table 5B.

Linker Payloads

Provided herein are linker-steroids according to Formula (2000), $RG\text{-}L^2\text{-}(L^3)_{0\text{-}1}\text{-}SP\text{-}D$ or a pharmaceutically acceptable salt, solvate, or stereoisomer thereof; which are useful in the preparation of antibody-drug conjugates, wherein D is selected from a)

Formula (a)

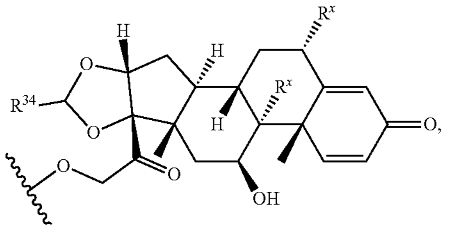

where both $R^x$ in formula (a) are hydrogen; $R^{34}$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^1$— where $X^1$ is attached to $(L^3)_{0\text{-}1}$ in Formula (2000), —C(O)—N(H)—($C_1$-$C_{10}$-alkylene)-S— where S is attached to $(L^3)_{0\text{-}1}$ in Formula (2000), —C(O)—N($C_{1-6}$alkyl)-($C_1$-$C_{10}$-alkylene)-S— where S is attached to $(L^3)_{0\text{-}1}$ in Formula (2000),

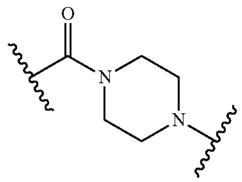 [SMILES: *C(=O)N1CCN(*)CC1]

where the point of attachment on the right hand side (i.e. at N) is to $(L^3)_{0\text{-}1}$ in Formula (2000), —$CH_2$—NH— where N is attached to $(L^3)_{0\text{-}1}$ in Formula (2000),

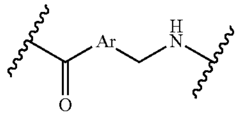

where the N is attached to $(L^3)_{0\text{-}1}$ in Formula (2000) and where Ar is optionally substituted arylene (in some embodiments,

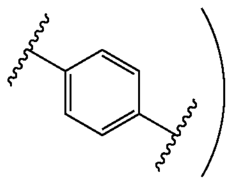

or optionally substituted heteroarylene, —($C_1$-$C_{10}$-alkylene)-$NR^{50}$C(O)—($C_1$-$C_{10}$-alkylene)-$NR^{50a}$— where $NR^{50a}$ is attached to $(L^3)_{0\text{-}1}$ in Formula (2000), —C(O)—($C_1$-$C_{10}$-alkylene)-$NR^{50}$C(O)—($C_1$-$C_{10}$-alkylene)-$NR^{50a}$— where $NR^{50a}$ is attached to $(L^3)_{0\text{-}1}$ in Formula (2000) and where each $C_1$-$C_{10}$-alkylene is independently optionally substituted with one or more hydroxy, —C(O)—N($R^5$)—$C_1$-$C_{10}$-alkylene-C(O)NH— $X^2$— where $X^2$ is attached to $(L^3)_{0\text{-}1}$ in Formula (2000), or

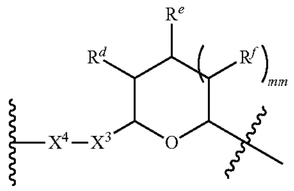

where $X^4$ is attached to $(L^3)_{0\text{-}1}$ in Formula (2000); or where both $R^x$ in formula (a) are fluoro; $R^{34}$ is alkyl, aryl, arylalkyl, or an N-containing heterocycloalkyl; and SP is —C(O)—$C_1$-$C_{10}$-alkylene-C(O)—, —C(O)—N($C_{1-6}$alkyl)-$C_1$-$C_{10}$-alkylene-$X^{1b}$— where $X^{1b}$ is attached to $(L^3)_{0\text{-}1}$ in Formula (2000), —C(O)—N(H)—($C_1$-$C_{10}$-alkylene)-$X^{1b}$— where $X^{1b}$ is attached to $(L^3)_{0\text{-}1}$ in Formula (2000),

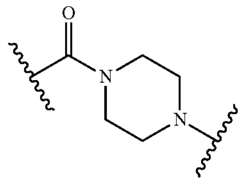 [SMILES: *C(=O)N1CCN(*)CC1]

where the point of attachment on the right hand side (i.e. at N) is to $(L^3)_{0-1}$ in Formula (2000), —$CH_2$—NH— where N is attached to $(L^3)_{0-1}$, in Formula (2000),

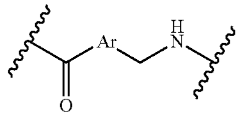

where the N is attached to $(L^3)_{0-1}$ in Formula (2000) and where Ar is optionally substituted arylene (in some embodiments,

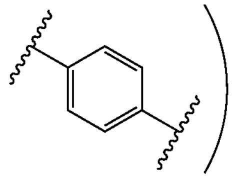

or optionally substituted heteroarylene, —($C_1$-$C_{10}$-alkylene)-$NR^{50}$C(O)—($C_1$-$C_{10}$-alkylene)-$NR^{50a}$— where $NR^{50a}$ is attached to $(L^3)_{0-1}$ in Formula (2000), —C(O)—($C_1$-$C_{10}$-alkylene)-$NR^{50}$C(O)—($C_1$-$C_{10}$-alkylene)-$NR^{50a}$— where $NR^{50a}$ is attached to $(L^3)_{0-1}$ in Formula (2000) and where each $C_1$-$C_{10}$-alkylene is independently optionally substituted with one or more hydroxy, —C(O)—N($R^5$)—($C_1$-$C_{10}$-alkylene)-C(O)NH—$X^2$— where $X^2$ is attached to $(L^3)_{0-1}$ in Formula (2000), or

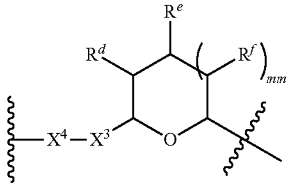

where $X^4$ is attached to $(L^3)_{0-1}$ in Formula (2000); and/or b) the compounds in Table A above, where the compounds in Table A are linked to RG of the Compound of Formula (2000) through the hydroxy of the —C(O)$CH_2$OH group, i.e. by —C(O)$CH_2$—O—SP-$(L^3)_{0-1}$-, or through the hydroxy of Mapracorat, i.e. by —O—SP-$(L^3)_{0-1}$-;

$X^1$ is —N($C_{1-6}$alkyl)-;

$X^{1b}$ is —S—, —NH—, or —N($C_{1-6}$alkyl)-;

$X^2$ is —NH—;

$X^3$ is —$CH_2$—, $X^3$ is —$CH_2$—O—($C_1$-$C_{10}$-alkylene)-C(O)— where the C(O) is attached to $X^4$, or $X^3$ is —C(O)—;

$X^{34}$ is —O—;

$R^{35}$ is H, —OH, —$OCH_3$, or $C_{1-6}$alkyl;

$R^{5c}$ and $R^{50a}$ are independently hydrogen or $C_1$-$C_6$-alkyl;

$R^d$, $R^e$, and $R^f$ are independently —H, —OH, hydroxyalkyl, alkoxycarbonyl, —C(O)OH, or —$CH_2OR^g$, where each R9 is independently —$CH_2$C(O)OH or —$CH_2$C(O)O(alkyl); and mm is 0 or 1;

RG is a reactive group residue;

$L^2$ is a connecting linker; and $L^3$, when present, is a self-immolative group.

Provided herein are linker-LXR-modulators according to Formula (4000),

RG-L-E  Formula (4000)

or a pharmaceutically acceptable salt, solvate, or stereoisomer thereof;

which are useful in the preparation of antibody-drug conjugates, wherein

E is selected from a) compounds of Formula (B) described above and herein; and/or b) compounds of Formula (B-1) described above and herein; and/or c) payloads described in Table C herein;

L is a linker described herein; and

RG is any reactive group residue described herein.

In some embodiments, the LXR payload is

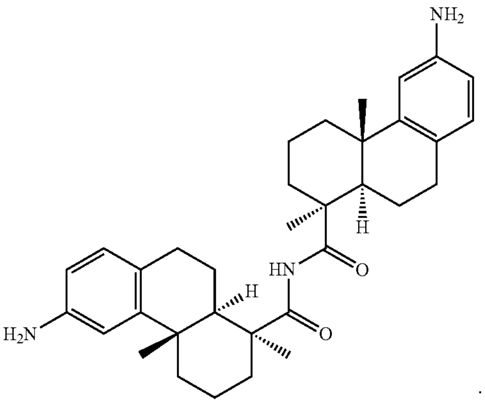 [SMILES: C[C@]1(C(=O)NC(=O)[C@@]2(C)CCC[C@]3(C)c4cc(N)ccc4CC[C@@H]23)CCC[C@]2(C)c3cc(N)ccc3CC[C@@H]12]

.

In some embodiments, the LXR payload is

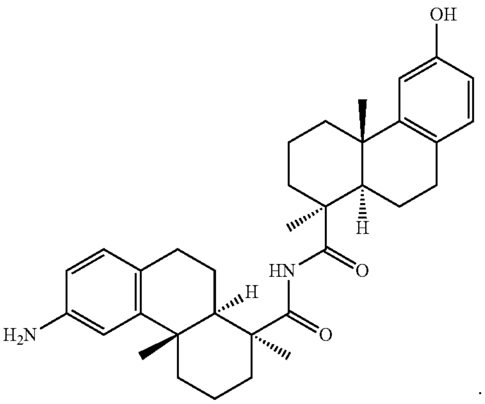 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12]

.

In some embodiments, linker-payloads of Formula (4000) have the structures of Formula (4001), (4002), (4003), or (4004):

Formula (4001)

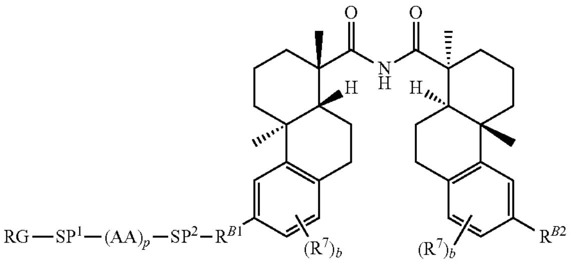

Formula (4002)

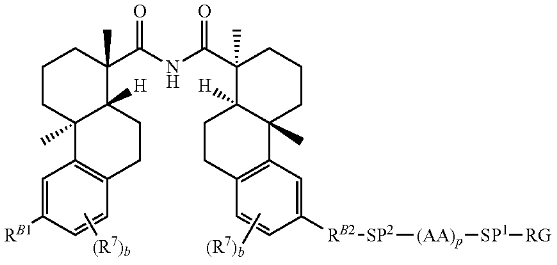

Formula (4003)

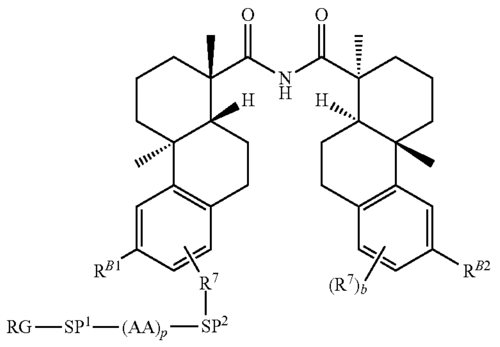

or

Formula (4004)

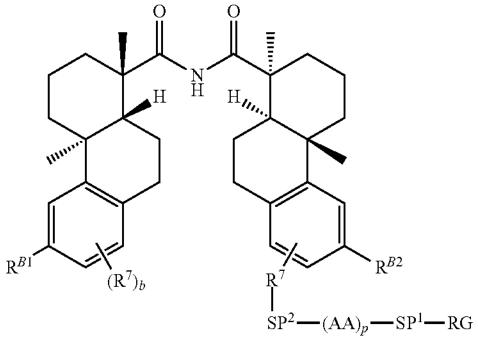

or a pharmaceutically acceptable salt, solvate, or stereoisomer thereof;

wherein $SP^1$ and $SP^2$, when present, are spacer groups as defined herein in some and any embodiments;

each AA is an amino acid residue;

p is an integer from 1 to 10;

RG is a reactive group residue; and $R^{B1}$, $R^{B2}$, $R^7$ and b are as defined herein in some or any embodiments.

In some embodiments, linker-payloads of Formula (4000), (4001), (4002), (4003), or (4004) are selected from linker-payloads in Table 3.

Provided herein are linker-rifamycin analogs according to Formula (7000),

RG-L-F Formula (7000)

or a pharmaceutically acceptable salt, solvate, or stereoisomer thereof;

wherein F is a rifamycin analog;

L is a linker described herein; and

RG is any reactive group residue described herein.

In some embodiments, F is a rifamycin analog described herein. In some embodiments, F is rifalogue:

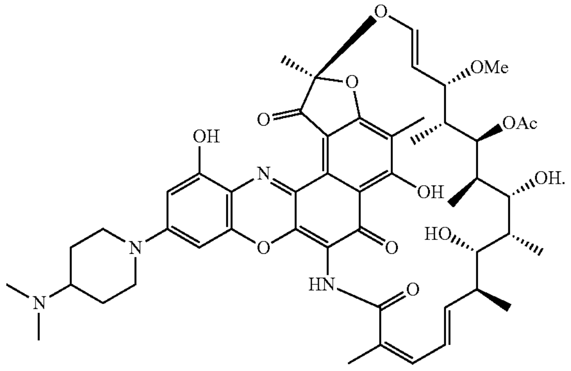 [SMILES: CO[C@H]1/C=C/O[C@@]2(C)Oc3c(C)c(O)c4c(=O)c(c5oc6cc(N7CCC(N(C)C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In some embodiments, F is rifampicin:

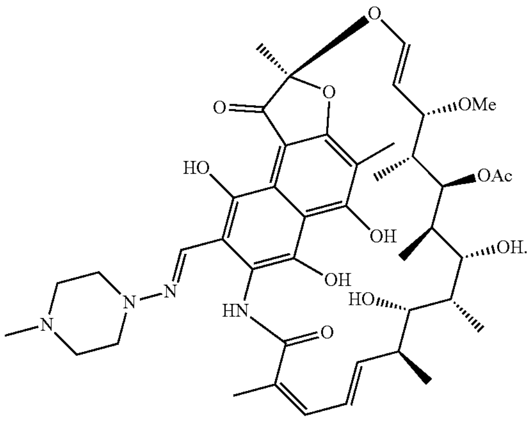 [SMILES: CO[C@H]1/C=C/O[C@@]2(C)Oc3c(C)c(O)c4c(O)c(c(/C=N/N5CCN(C)CC5)c(O)c4c3C2=O)NC(=O)/C(C)=C\C=C\[C@H](C)[C@H](O)[C@@H](C)[C@@H](O)[C@@H](C)[C@H](OC(C)=O)[C@@H]1C]

Also provided herein is a linker payload according to Formula (D):

Formula (D)

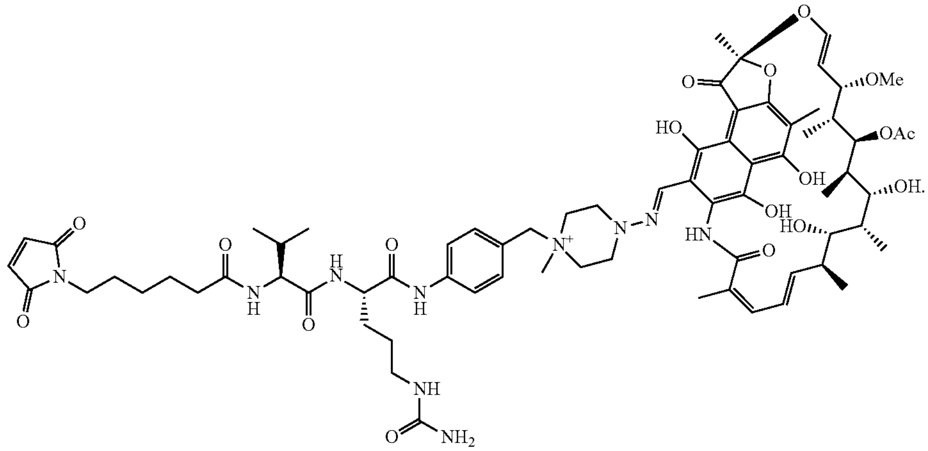

Provided herein are linker-steroids wherein the steroid conjugated to the antibody, or antigen-binding fragment thereof, through a linker or a linker-spacer is a compound of Formula (A-1)

Formula (A-1)

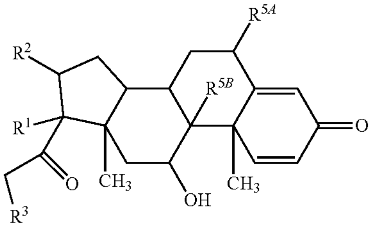

or a pharmaceutically acceptable salt, solvate, or stereoisomeric form thereof;

wherein $R^1$ and $R^2$ are, independently, —H, alkyl, alkyl-C(O)—O—, —OH, or halo; or $R^1$ and $R^2$ together form

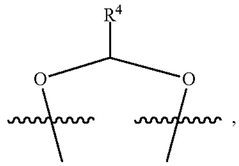

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with $—NR^{Aa}R^{Ab}$;

$R^3$ is —O, $R^Z$—C(O)—X—, -heteroalkyl, -piperidinyl, $—NR^{Aa}R^{Ab}$, -oxyaryl-$NR^{Aa}R^{Ab}$ or $—Z\text{-}A'(R^P)_t$;

$R^Z$ is alkyl;

X is O or $NR^{Aa}$;

Z is S, S(O), $S(O)_2$, $SO_2NR^{Aa}$, O, $C(O)NR^{Aa}$, C(O), or $NR^{Aa}$;

A' is aryl, arylalkyl, or heteroaryl;

$R^P$ is, independently in each instance, halo, optionally substituted alkyl, —OH, or $—NR^{Aa}R^{Ab}—$;

$R^{Aa}$ and $R^{Ab}$ are, independently in each instance, —H, optionally substituted alkyl, or optionally substituted aryl;

subscript a is an integer from 0-19; and t is an integer from 1-3;

and $R^{5A}$ and $R^{5B}$ are each, independently, halo or a hydrogen atom;

wherein the group $R^3$ or $R^4$ is bonded to the linker.

Provided herein are antibody-drug conjugates of formula Ab-L'-SP-D or BA-L'-SP-D, where D is a budesonide prodrug or a prodrug of a budesonide analog or derivative (including fluorinated analogs and derivatives), and where Ab, BA, L', and SP are as defined in any embodiment described herein. In some embodiments, SP is a moiety capable of releasing D or

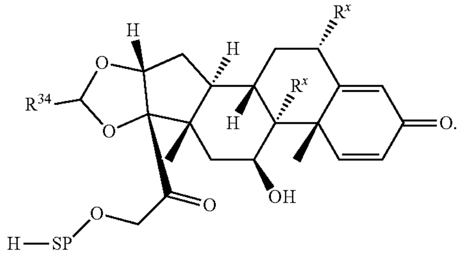

In some embodiments, under physiological conditions the bond between L and SP is cleaved to release a steroid prodrug, i.e. H-SP-D or

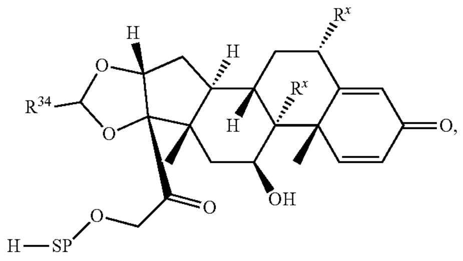

and the bond between SP and D, or between SP and

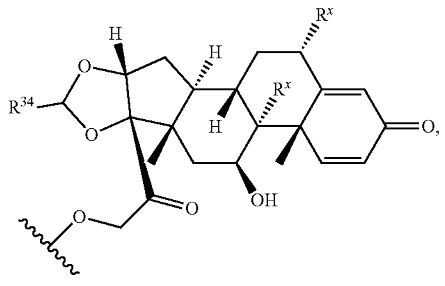

is subsequently cleaved to release a biologically active steroid.

In some instances, ADCs of Formula (I), (IA), (IB), (IB-1), (IB-2), (IC), (ID), (IE), (III), or (3000), are ADCs described in Table 1 and/or Table 2 and the Examples section. In some embodiments, the steroid payload in any antibody drug conjugate described herein is

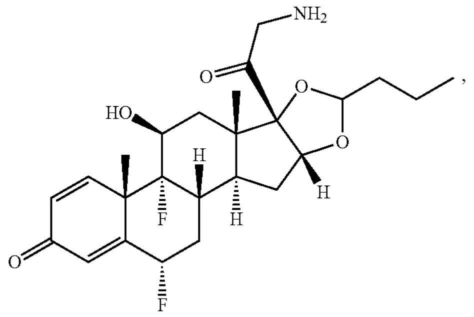

or

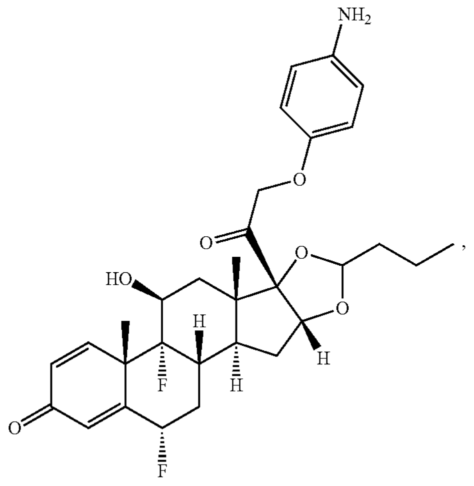

or a pharmaceutically acceptable salt, solvate, or stereoisomer thereof.

Provided herein are antibody-drug conjugates of any LXR-modulator compounds described herein of Formula (5001), (5002), (5003), or (5004):

Formula (5001)

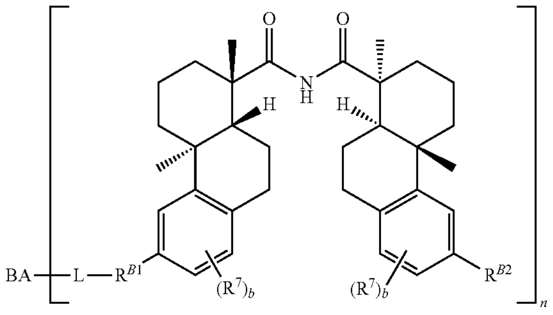

Formula (5002)

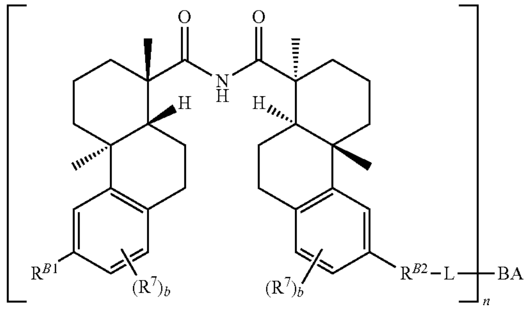

Formula (5003)

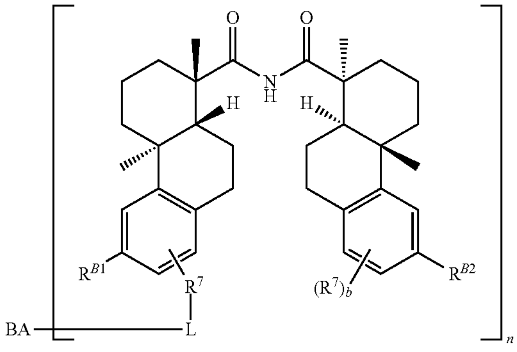

or

Formula (5004)

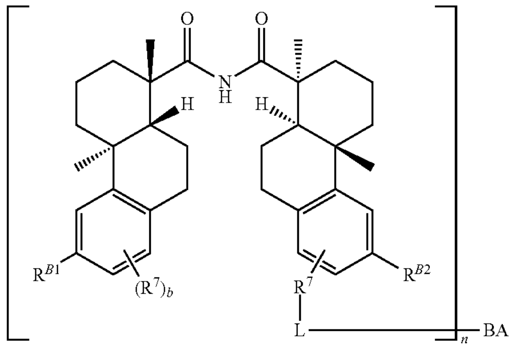

or a pharmaceutically acceptable salt, solvate, stereoisomeric form thereof, or regioisomer thereof, or mixtures thereof;

wherein L is any linker described herein in some or any embodiments;

n is an integer from 1 to 30;

BA is a binding agent or a PEG-modified binding agent; and $R^{B1}$, $R^{B}2$, $R^7$ and b are as defined herein in some or any embodiments.

Provided herein are antibody-drug conjugates of any LXR-modulator compounds described herein of Formula (6001), (6002), (6003), or (6004):

Formula (6001)

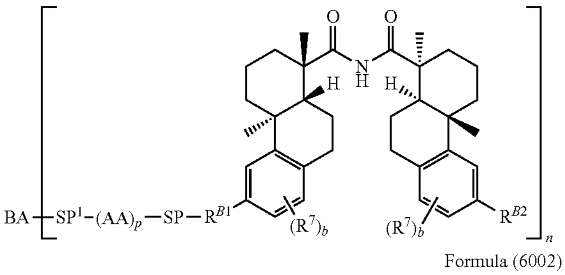

Formula (6002)

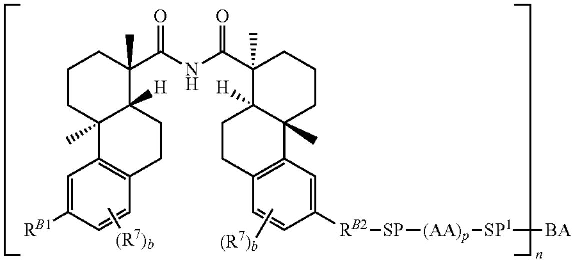

Formula (6003)

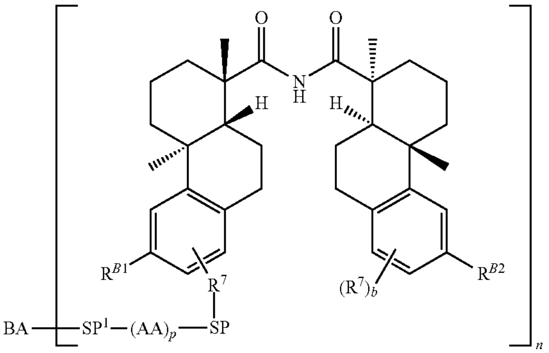

or

Formula (6004)

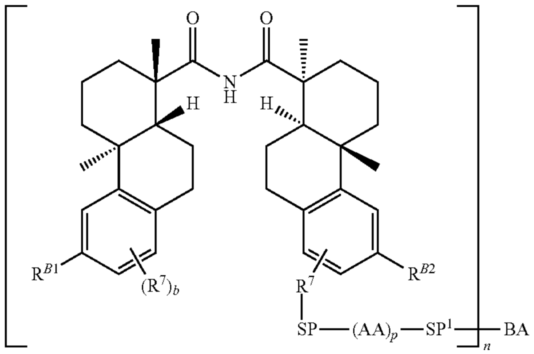

or a pharmaceutically acceptable salt, solvate, stereoisomeric form thereof, or regioisomer thereof, or mixtures thereof;

wherein $SP^1$ and SP, when present, are spacer groups as defined herein in some and any embodiments;

each AA is an amino acid residue;

p is an integer from 1 to 10;

n is an integer from 1 to 30;

BA is a binding agent or a PEG-modified binding agent; and $R^{B1}$, $R^{B2}$, $R^7$ and b are as defined herein in some or any embodiments.

Provided herein are antibody-drug conjugates of any LXR-modulator compounds described herein of Formula (6005):

Formula (6005)

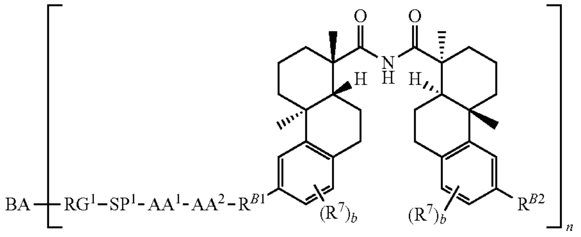

or a pharmaceutically acceptable salt, solvate, stereoisomeric form thereof, or regioisomer thereof, or mixtures thereof; wherein $R^{B1}$, $R^{B2}$, $R^7$, b, BA, $RG^1$, $SP^1$, $AA^1$ and $AA^2$ are as defined herein in some or any embodiments.

In some instances, ADCs of Formula (I), (IA), (IB), (IB-1), (IB-2), (IC), (ID), (IE), (5001), (5002), (5003), (5004), (6001), (6002), (6003), (6004), or (6005), are ADCs described in Table 1 and/or Table 2 and the Examples section. In some embodiments, the LXR modulator payload in any antibody drug conjugate described herein is

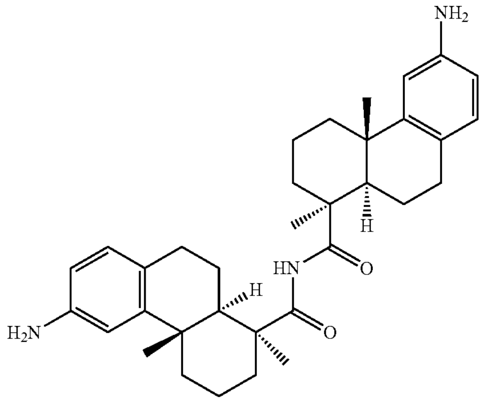

or

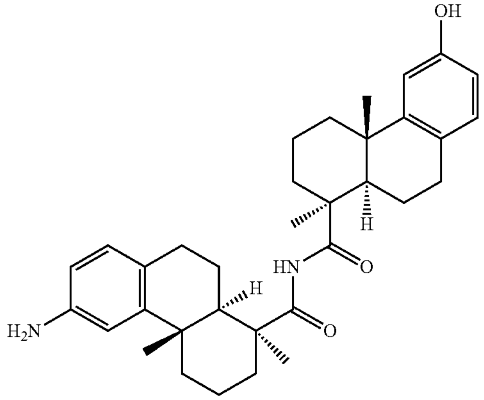

;

or a pharmaceutically acceptable salt or solvate thereof.

Provided herein are antibody-drug conjugates of any rifamycin analogs described herein and having the structure of Formula (7001)

Formula (7001)

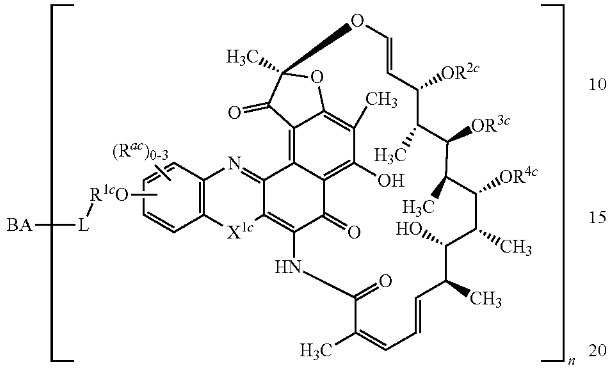

or a pharmaceutically acceptable salt, solvate, stereoisomeric form thereof, or regioisomer thereof, or mixtures thereof;

wherein:

$X^{1c}$ is selected from —S—; —O— and —$NR^{5c}$;

$R^{1c}$ is amino-$C_{1-6}$alkyl; $C_{1-6}$alkylamino$C_{1-6}$alkyl; di-$C_{1-6}$ alkylamino$C_{1-6}$alkyl; hydroxy-$C_{1-6}$alkyl; HS—$C_{1-6}$alkyl; $(R^{5c})_2$N—$C_{1-6}$alkylene-N($R^{5c}$)—$C_{1-6}$alkyl; $(R^{5c})_2$N—$C_{1-6}$alkylene-O—$C_{1-6}$alkyl; $(R^{5c})_2$N—$C_{1-6}$alkylene-S—$C_{1-6}$alkyl; heterocycloalkyl or heterocycloalkyl-$C_{1-6}$alkyl; wherein heterocycloalkyl includes one, two, or three heteroatoms selected from O, N, and S; and wherein heterocyloalkyl is optionally substituted with halo, $C_{1-6}$alkyl, —OH, or =O;

$R^{2c}$, $R^{3c}$, and $R^{4c}$ are independently selected from hydrogen, $C_{1-6}$alkyl, and —(C=O)—$R^{5c}$;

each $R^{ac}$, when present, is independently selected from —F; —Cl; —Br; —I; —OH; —$NH_2$; and $C_{1-6}$alkoxy; and $R^{5c}$ is independently, at each occurrence, selected from hydrogen; and $C_{1-6}$alkyl;

L is a linker;

BA is a binding agent; and subscript n is an integer from 1 to 30.

Provided herein are antibody-drug conjugates of any rifamycin analogs described herein and having the structure of Formula (7002):

Formula (7002)

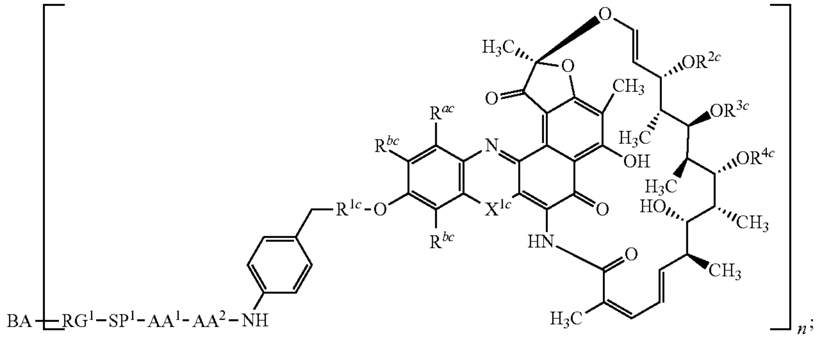

or a pharmaceutically acceptable salt, solvate, stereoisomeric form thereof, or regioisomer thereof, or mixtures thereof;

wherein BA, $RG^1$, $SP^1$, $AA^1$, $AA^2$, $R^{1c}$, $R^{bc}$, $R^{ac}$, $X^{1c}$, $R^{2c}$, $R^{ac}$, $R^{4c}$ and n are as defined herein in some or any embodiments.

Provided herein are antibody-rifamycin analog conjugates having the structure of Formula (7003):

Formula (7003)

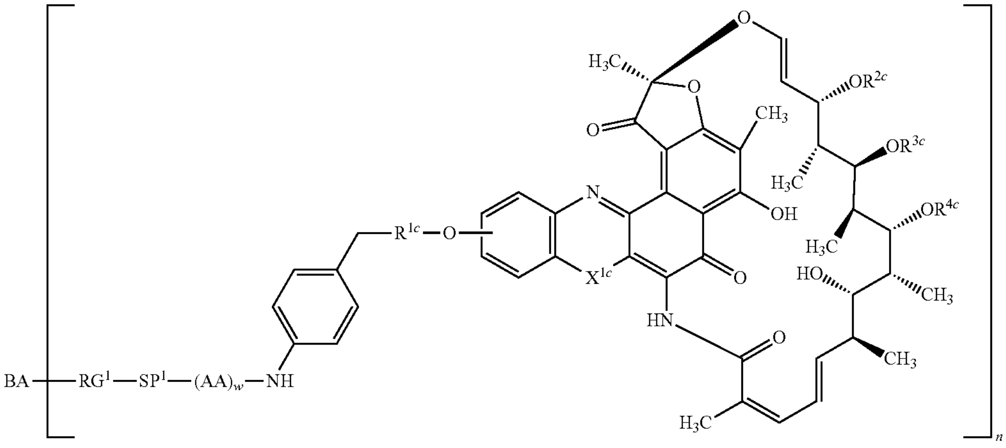

or a pharmaceutically acceptable salt, solvate, stereoisomeric form thereof, or regioisomer thereof, or mixtures thereof;

wherein:

$X^{1c}$ is selected from —S—; —O— and c;

$R^{1c}$ is

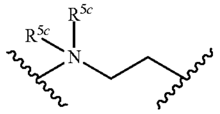

,

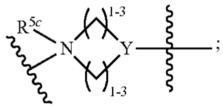

; or

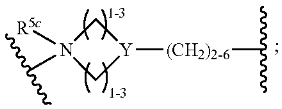

;

wherein Y is C or N;

$R^{2c}$, $R^{3c}$, and $R^{4c}$ are independently selected from hydrogen, $C_{1-6}$alkyl, and —(C═O)—$R^{5c}$;

$R^{5c}$ is independently, at each occurrence, absent, or selected from hydrogen; and $C_{1-6}$alkyl;

each AA is an independently selected amino acid;

$SP^1$ is absent, or a spacer;

$RG^1$ is a reactive group residue;

BA is an anti-MSR1 antibody or antigen binding fragment thereof;

subscript n is an integer from 1 to 30;

subscript w is 2, 3, or 4;

wherein $R^{1c}$ is bonded to the linker via a nitrogen atom as indicated by the wavy line

.

In various embodiments of Formula (7003), $SP^1$, $RG^1$ and AA are as defined herein in some and/or any particular embodiments.

In some embodiments of Formula (7003), $X^{1c}$ is O. In some embodiments of Formula (7003), $X^{1c}$ is S. In some embodiments of Formula (7003), $X^{1c}$ is C. In some embodiments of Formula (7003), $X^{1c}$ is $NR^5$.

In some embodiments of Formula (7003), BA is an anti-MSR1 antibody or antigen binding fragment thereof; comprising an N297Q mutation.

In some embodiments of Formula (7003), subscript w is 2.

In some embodiments of Formula (7003), $(AA)_2$ is valine-citrulline.

In some embodiments of Formula (7003), $SP^1$ comprises

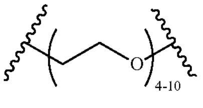

.

In some embodiments of Formula (7003), $SP^1$ comprises

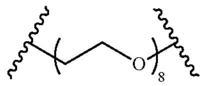

.

In some embodiments of Formula (7003), $RG^1$ comprises

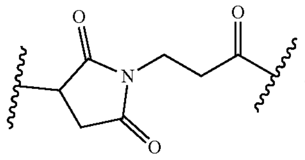

.

In some embodiments of Formula (7003), $X^{1c}$ is O;

$R^{1c}$ is

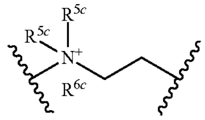

,

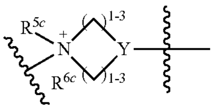

; or

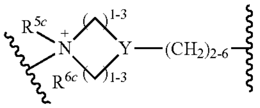

;

wherein Y is C or N; wherein $R^{1c}$ is bonded to the linker via the quaternary nitrogen atom of $R^{1c}$;

$R^{5c}$ is $C_{1-6}$alkyl; and $R^{6c}$ is a counter ion.

In some of such embodiments, $R^{1c}$ is

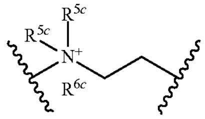

, or

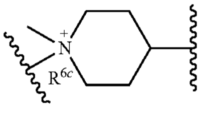

.

In some of such embodiments, $R^{1c}$ is

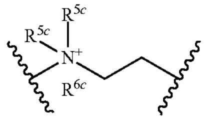

.

In some of such embodiments, $R^{1c}$ is

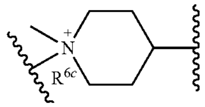

.

In some of such embodiments, $R^{6c}$ is $I^-$, $Cl^-$ or $Br^-$, and in some instances, $R^{6c}$ is $I^-$.

In some embodiments of Formula (7003), the rifamycin analog is:

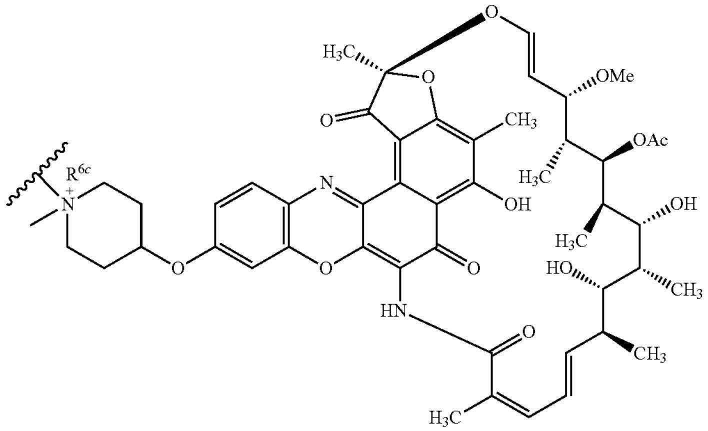
or
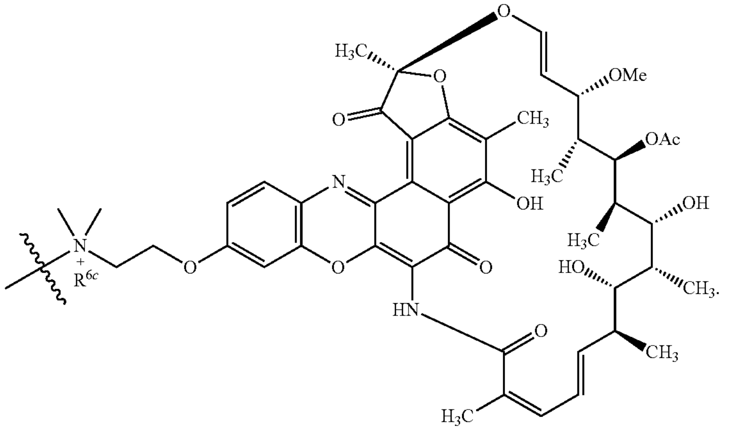
In some embodiments of Formula (7003), the rifamycin analog is:
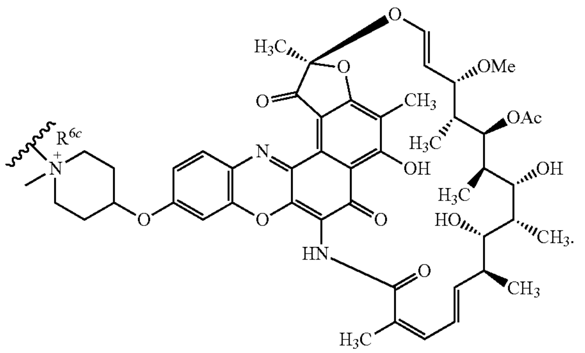
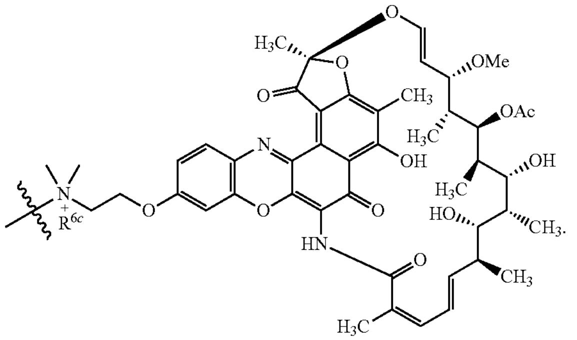
In some embodiments of Formula (7003), the rifamycin analog is:
Further provided herein is an antibody-drug conjugate comprising a rifamycin compound (e.g., rifampicin), according to Formula (7004):

Formula (7004)

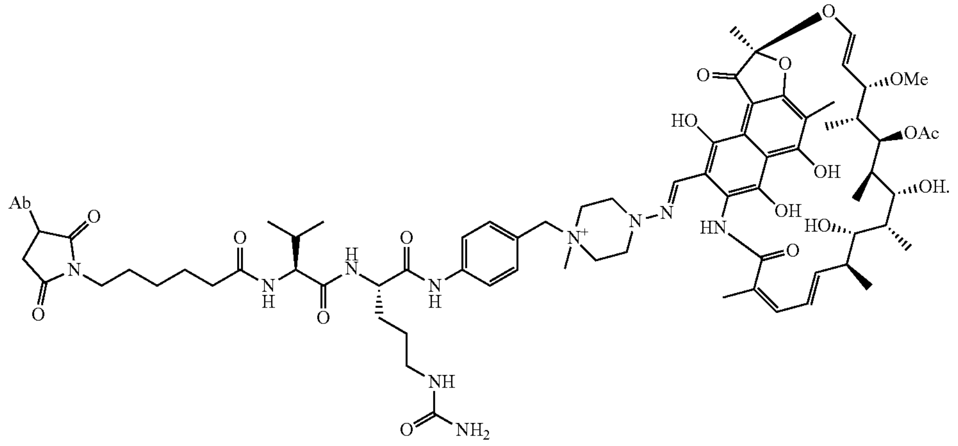

Further provided herein is an antibody-drug conjugate comprising a rifamycin compound (e.g., rifampicin), according to Formula (7005):

Formula (7005)

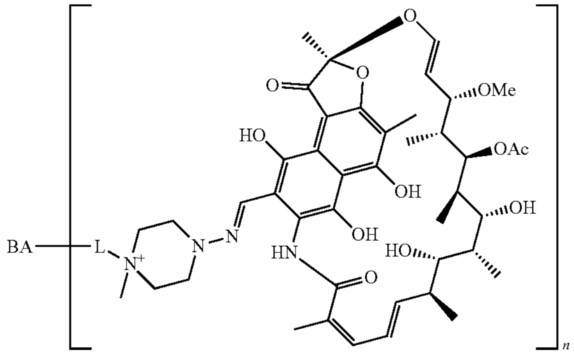

wherein L and BA are as defined herein in some or any embodiments.

In some instances, ADCs of Formula (I), (IA), (IB), (IB-1), (IB-2), (IC), (ID), (IE), (7001) (7002), (7003), (7004), and/or (7005) are ADCs described in Table 2 and/or the Examples section.

Also included in these examples of ADCs, is a pharmaceutically acceptable salt, solvate, stereoisomeric form thereof, a regioisomer thereof, or mixture of regioisomers thereof, wherein each

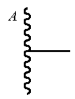

is a bond to the binding agent; and each

is a bond to the payload.

In certain embodiments, provided herein is an ADC comprising an anti-MSR1 antibody or an antigen binding fragment thereof, or a PEG-modified anti-MSR1 antibody or an antigen binding fragment thereof, disclosed herein and a linker-payload (LP) selected from the group consisting of the linker-payloads in Table 3, or a stereoisomeric form thereof, or a regioisomer thereof, or a mixture of regioisomers thereof.

Also provided herein are antibody-radionuclide conjugates (ARCs) comprising Anti-MSR1 antibodies conjugated to one or more radionuclides. Exemplary radionuclides that can be used in the context of this aspect of the disclosure include, but are not limited to, e.g., $^{225}Ac$, $^{212}Bi$, $^{213}Bi$, $^{131}I$, $^{186}Re$, $^{227}Th$, $^{222}Rn$, $^{223}Ra$, $^{224}Ra$, and $^{90}Y$.

TABLE 1
List of ADCs and their structures
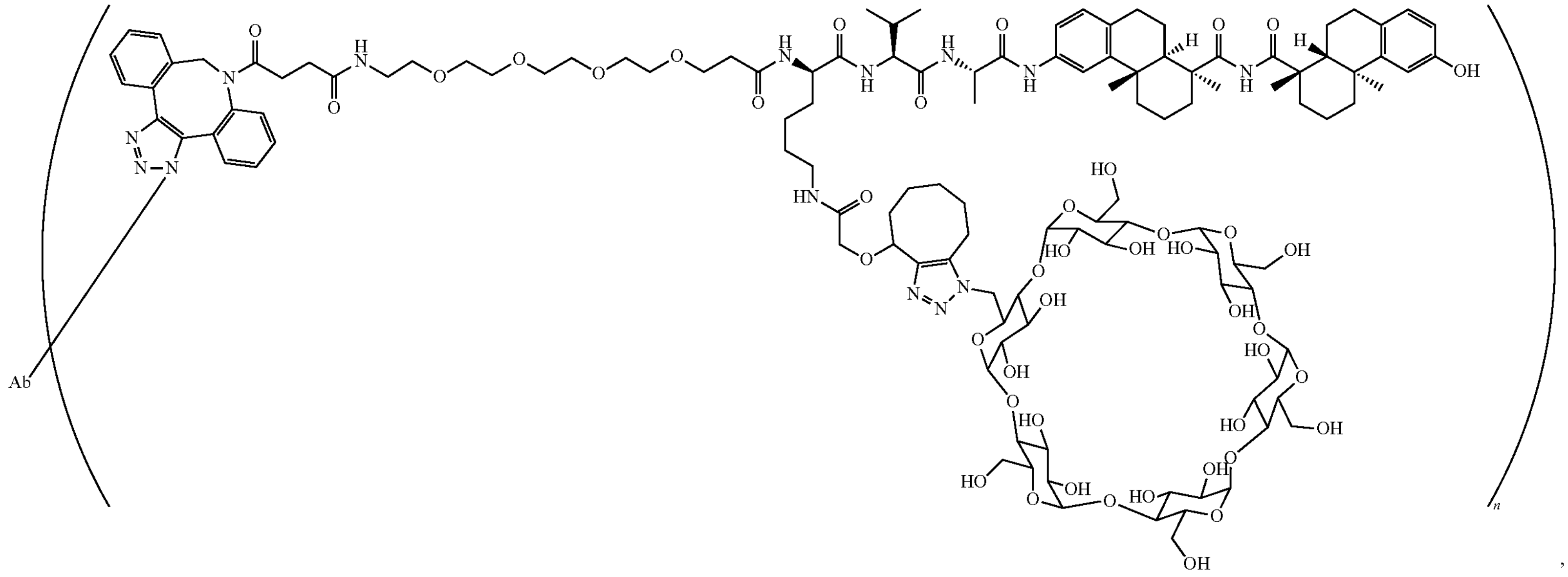

TABLE 1-continued
List of ADCs and their structures
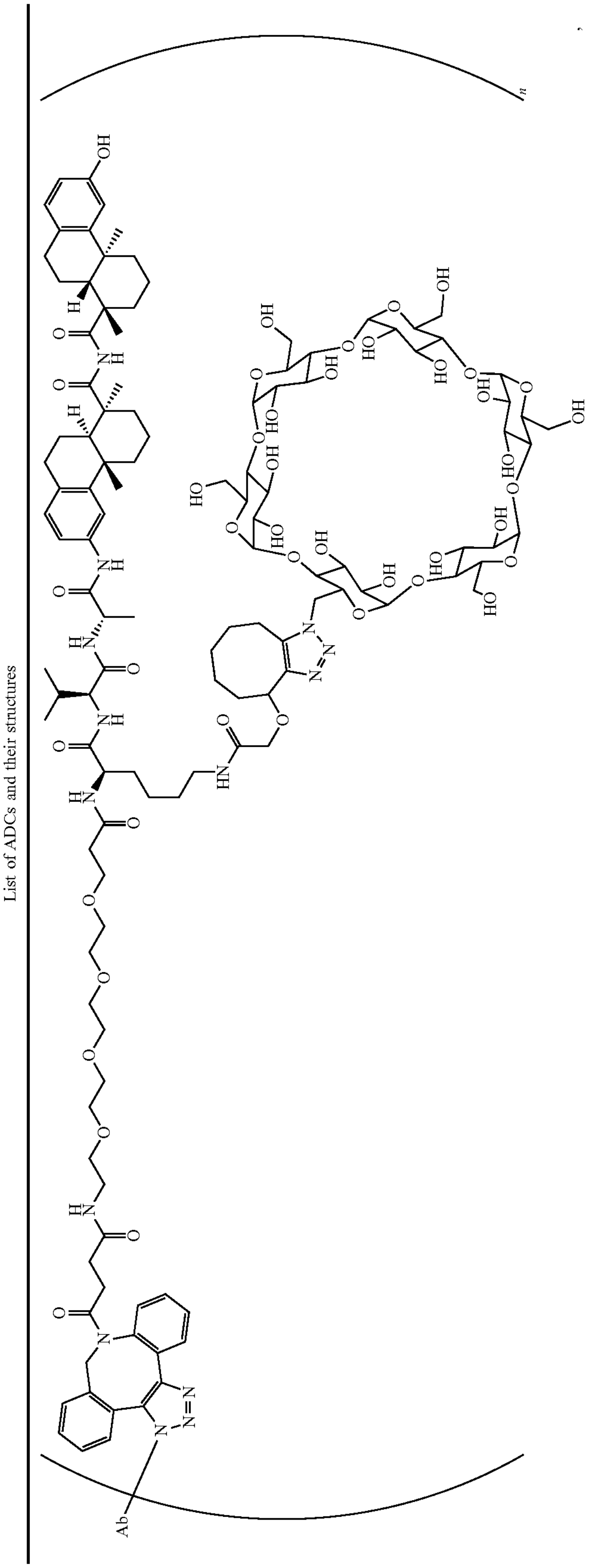

TABLE 1-continued
| List of ADCs and their structures |
| --- |
| 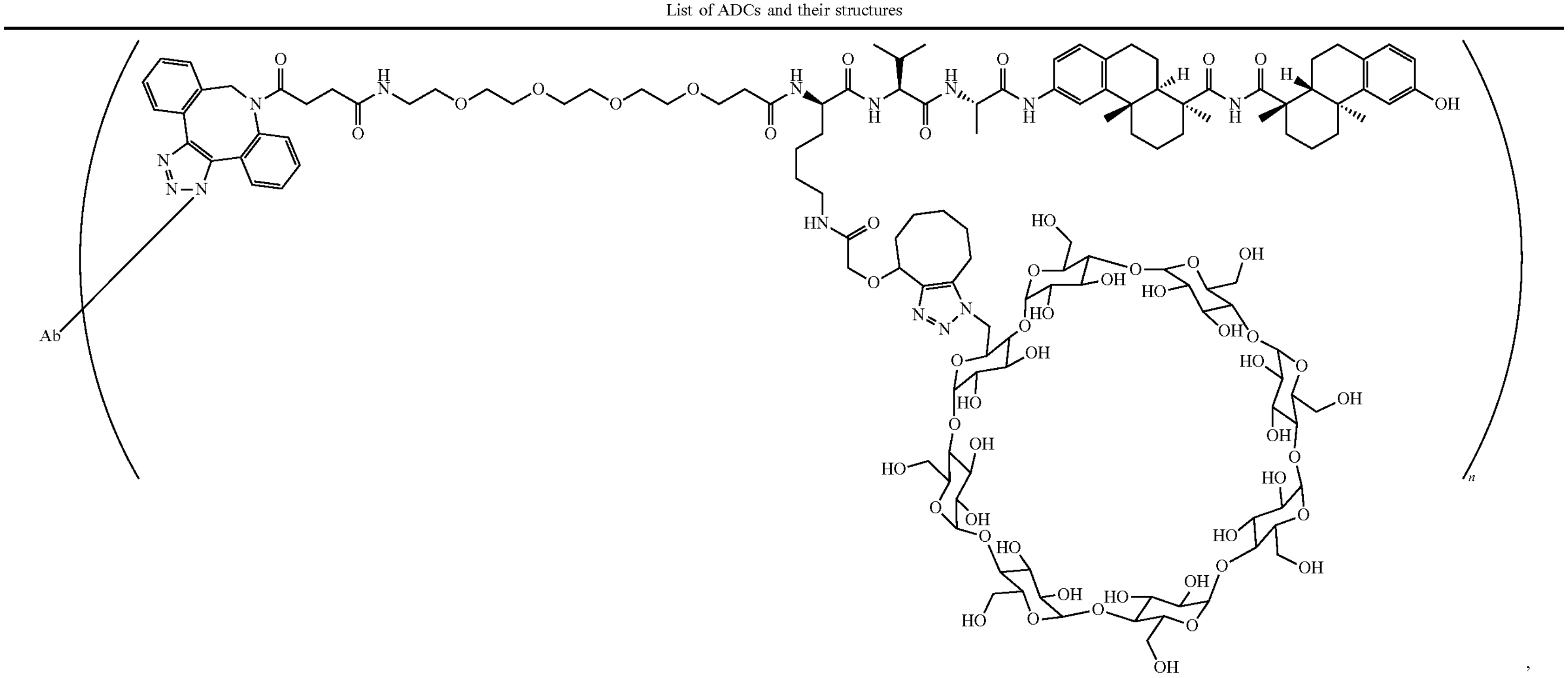 , |

TABLE 1-continued
| List of ADCs and their structures |
| --- |
| 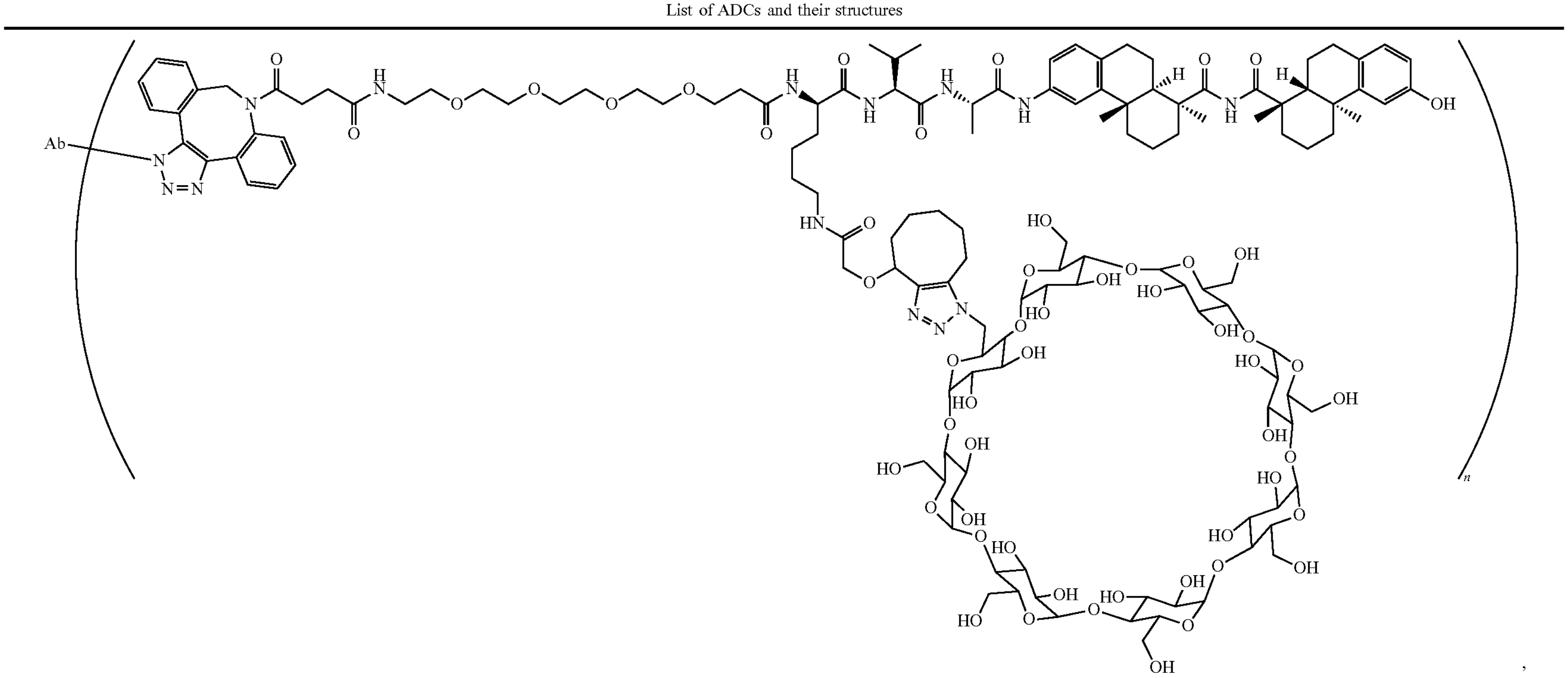 , |

TABLE 1-continued
| List of ADCs and their structures |
| --- |
| 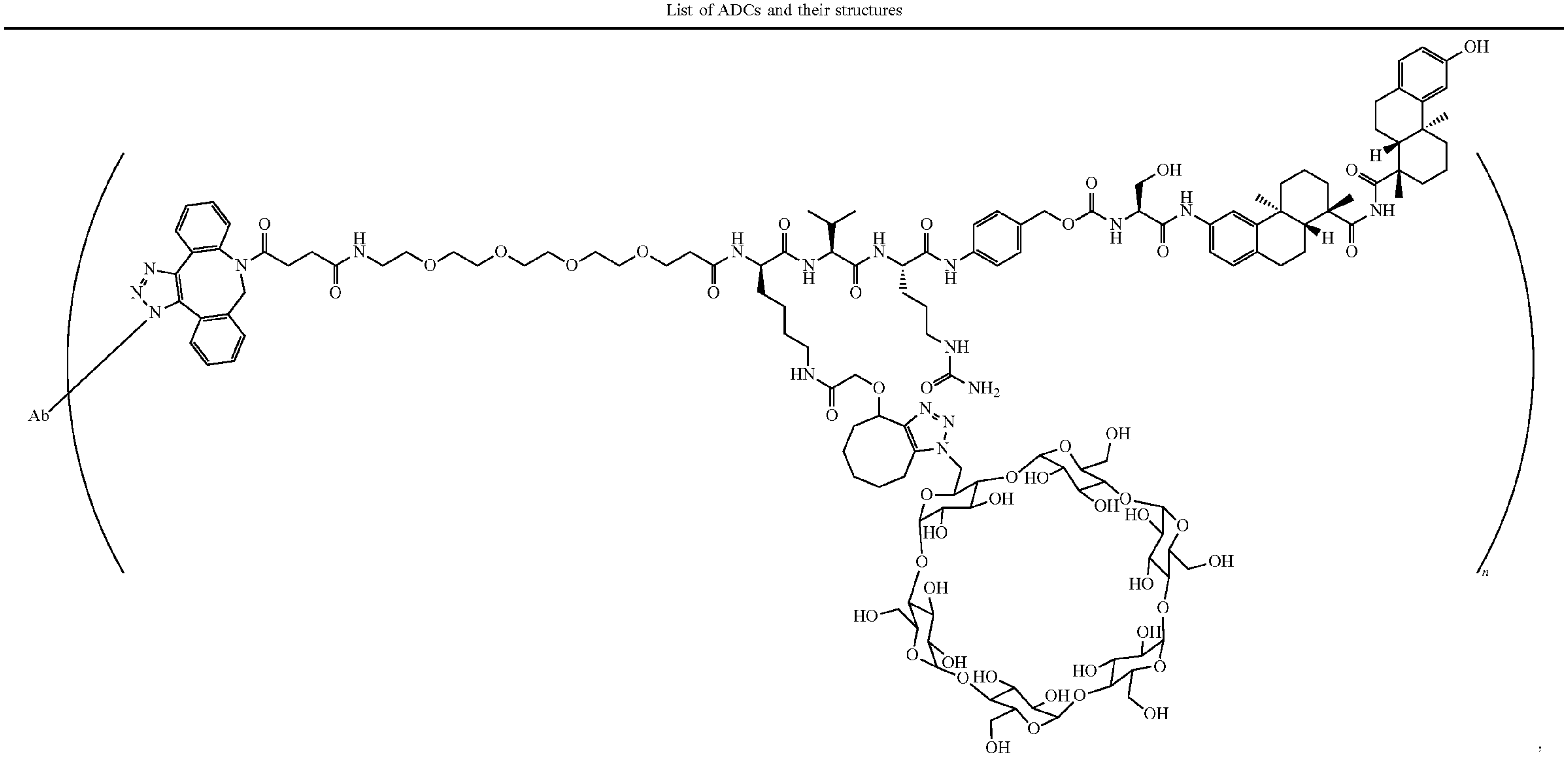 , |

TABLE 1-continued
List of ADCs and their structures
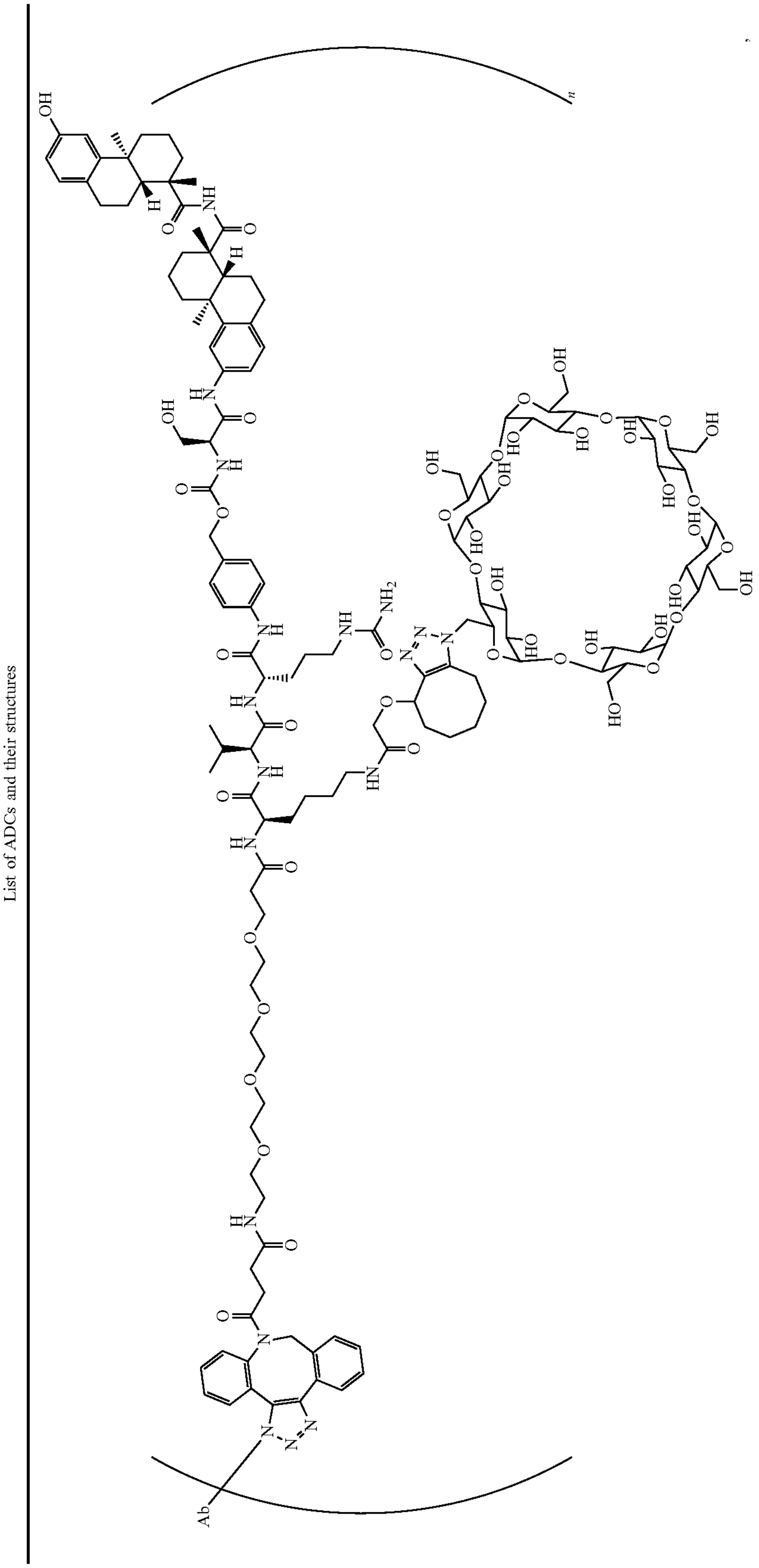

TABLE 1-continued
List of ADCs and their structures
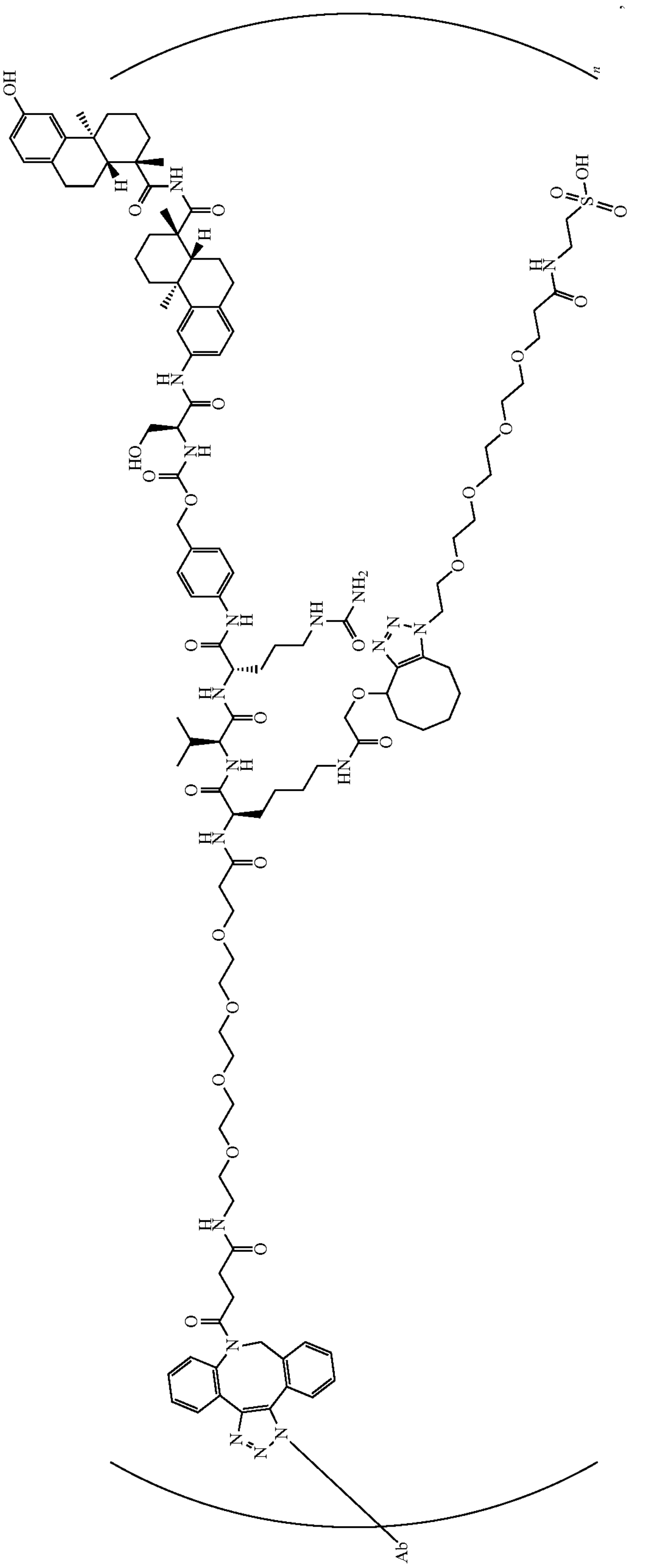

TABLE 1-continued
| List of ADCs and their structures |
| --- |
| 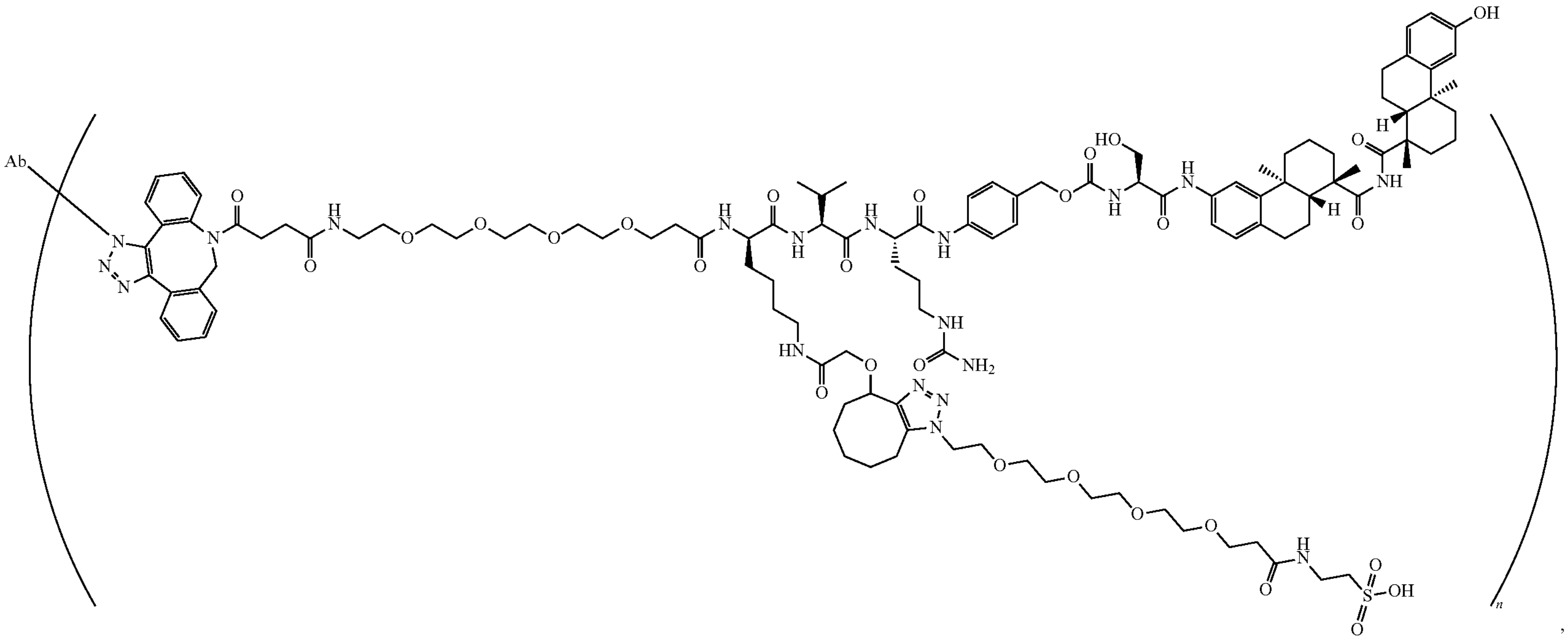 , |
| 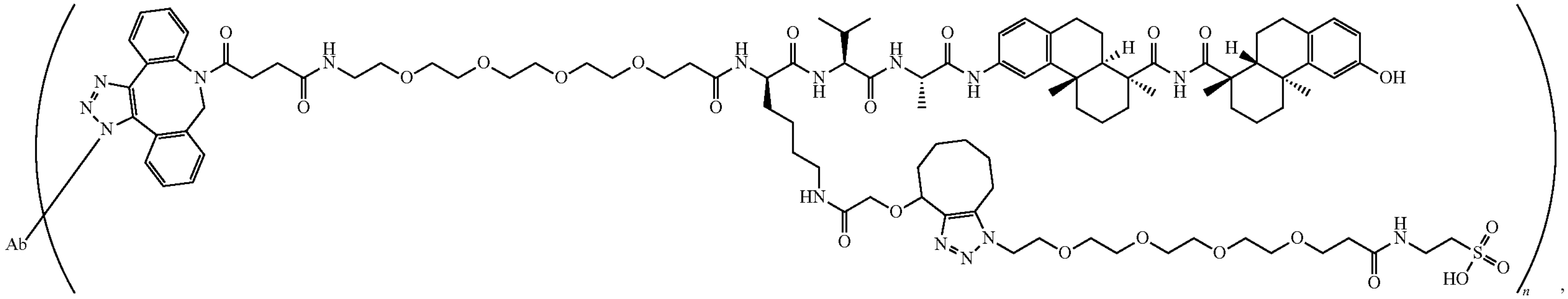 , |

TABLE 1-continued
List of ADCs and their structures
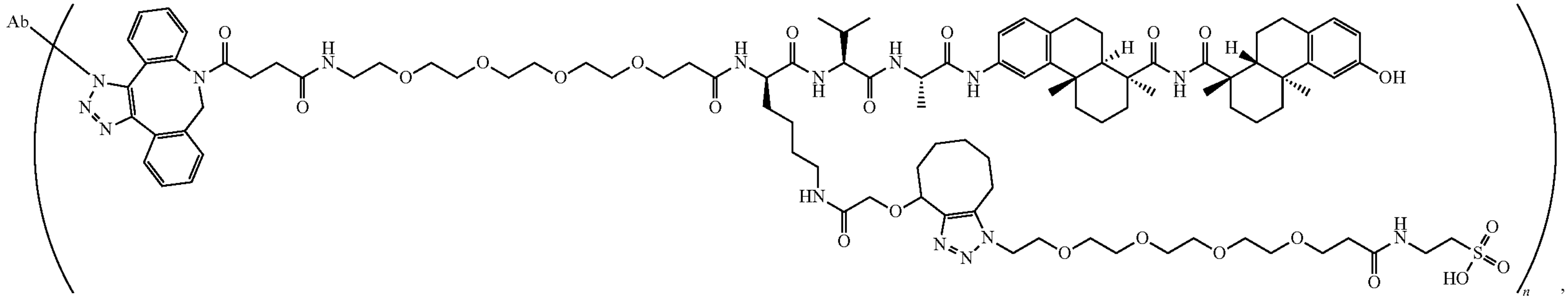
,
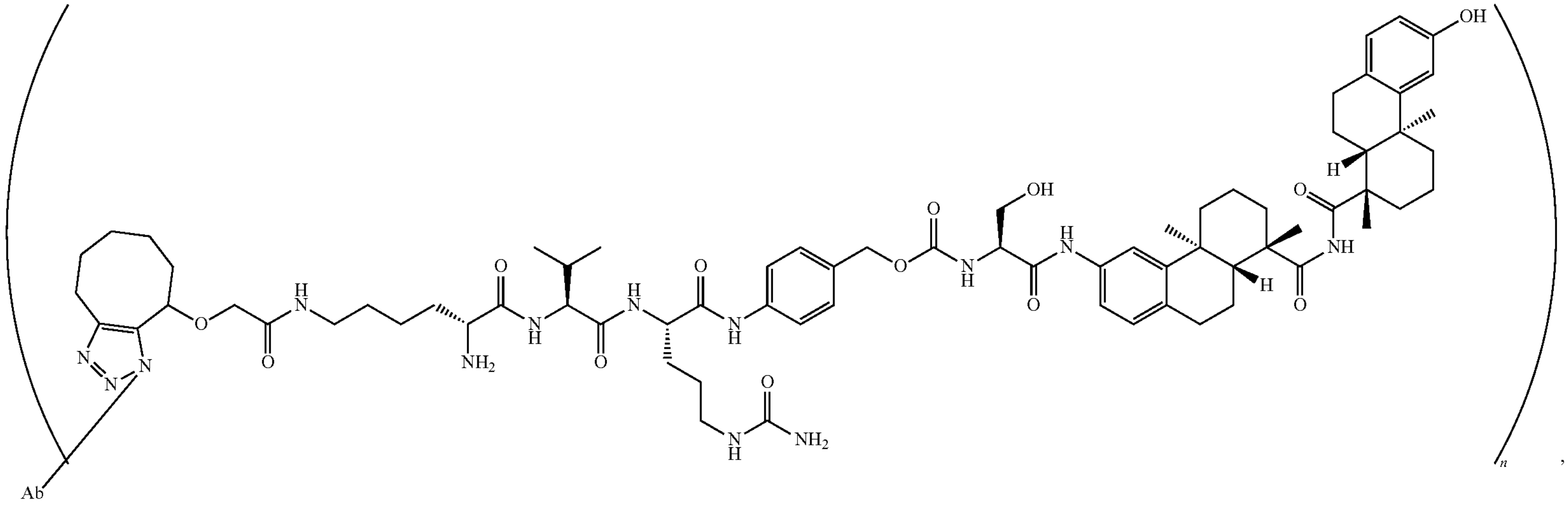
,

TABLE 1-continued
List of ADCs and their structures
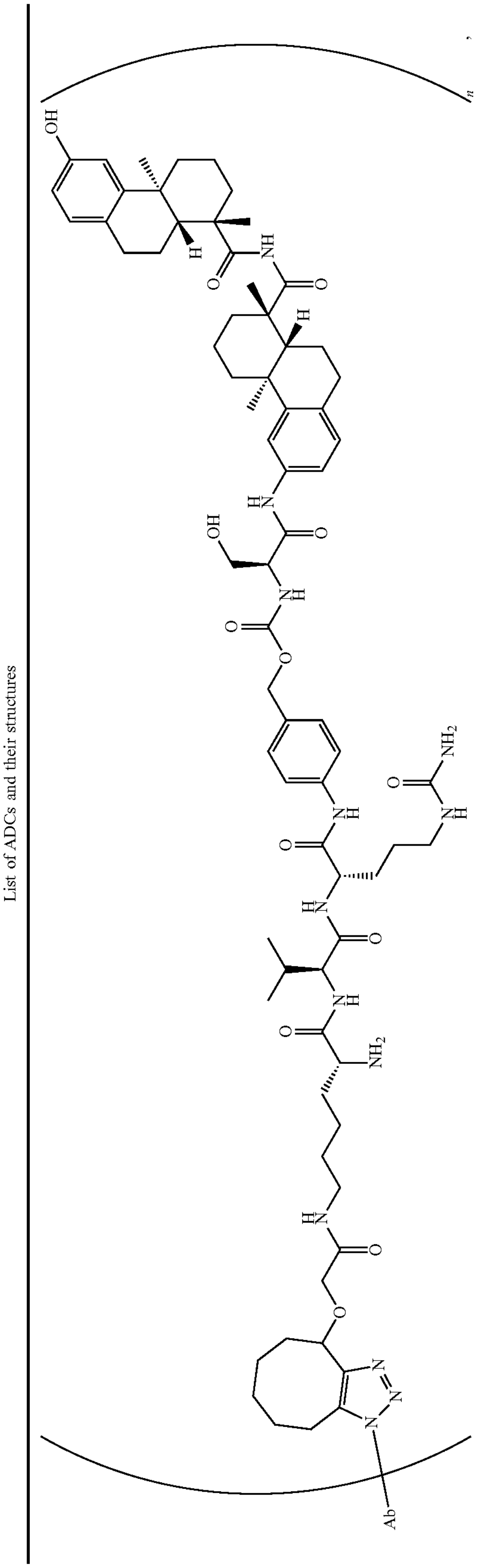
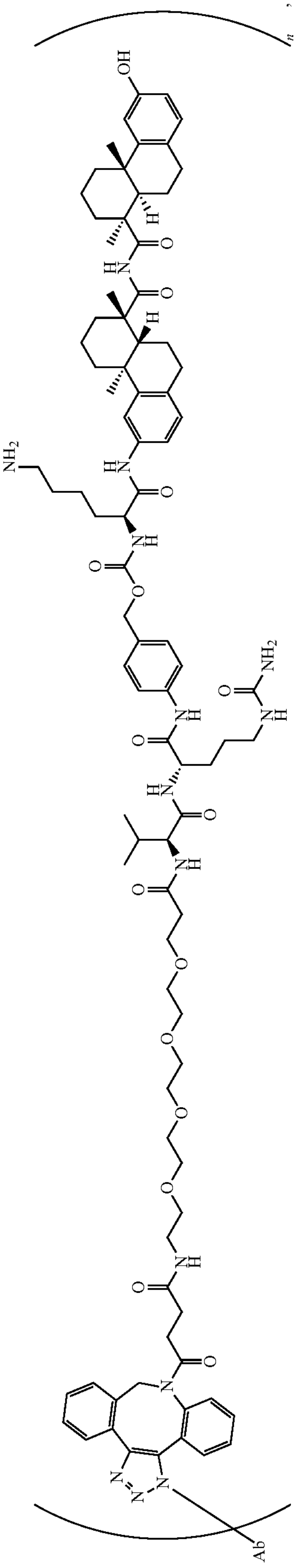

TABLE 1-continued
List of ADCs and their structures
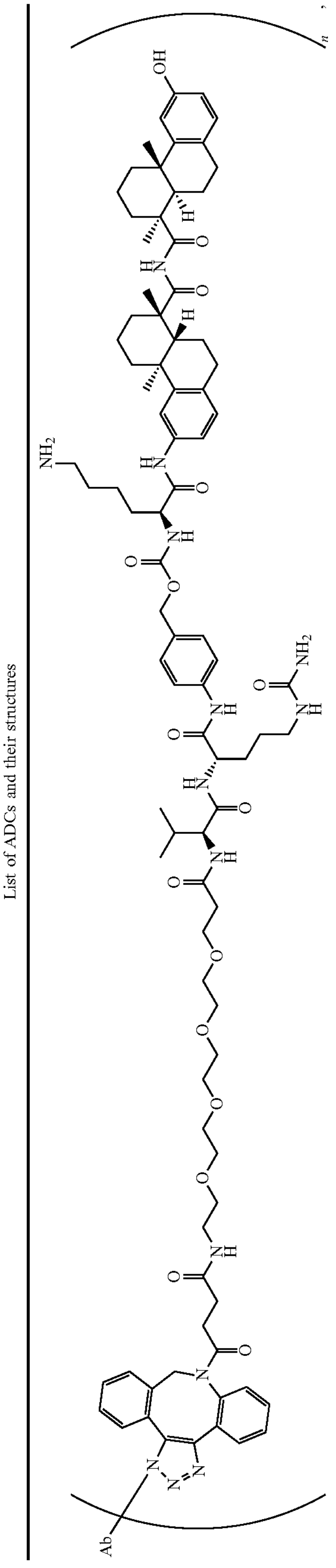
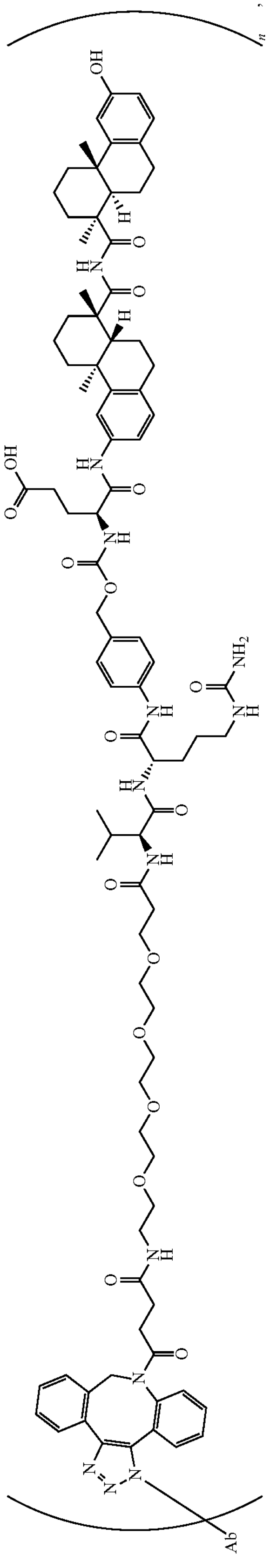
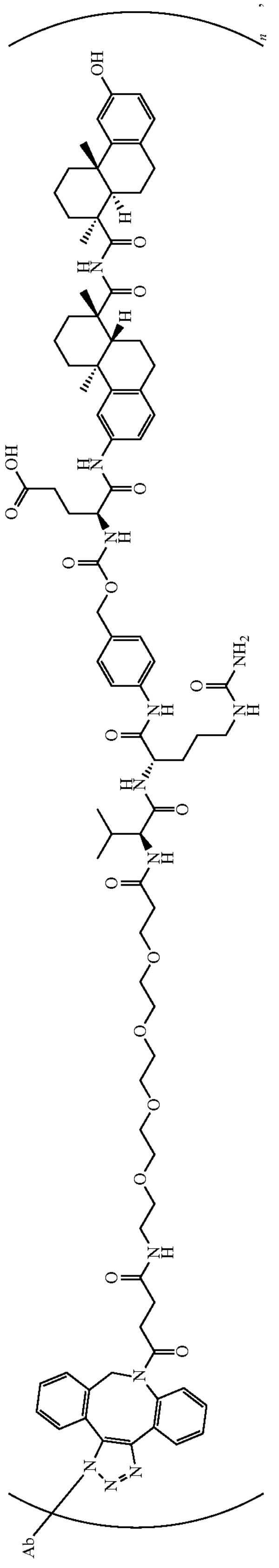

TABLE 1-continued
| List of ADCs and their structures |
| --- |
| 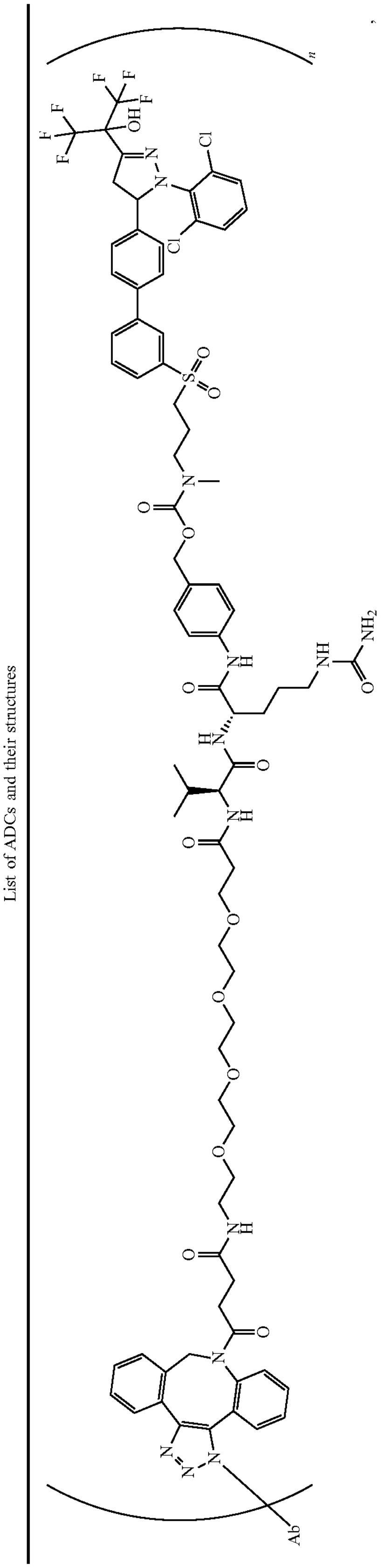 |
| 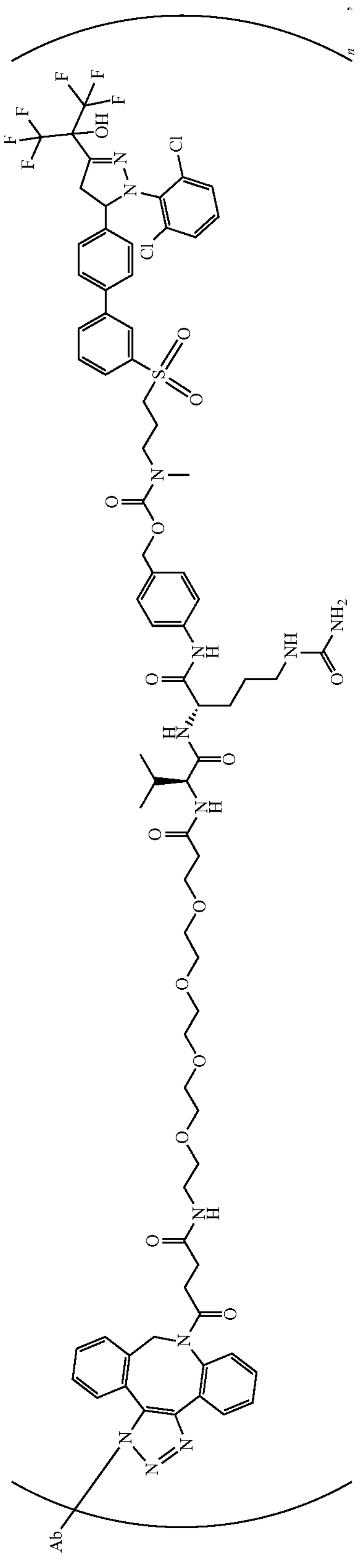 |

TABLE 1-continued
List of ADCs and their structures
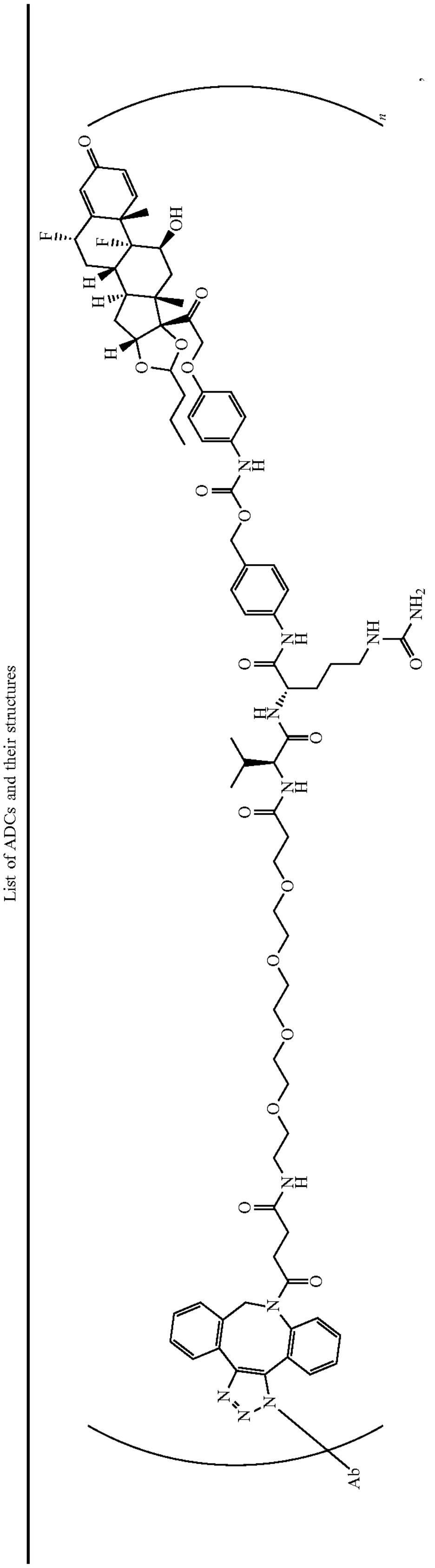
,
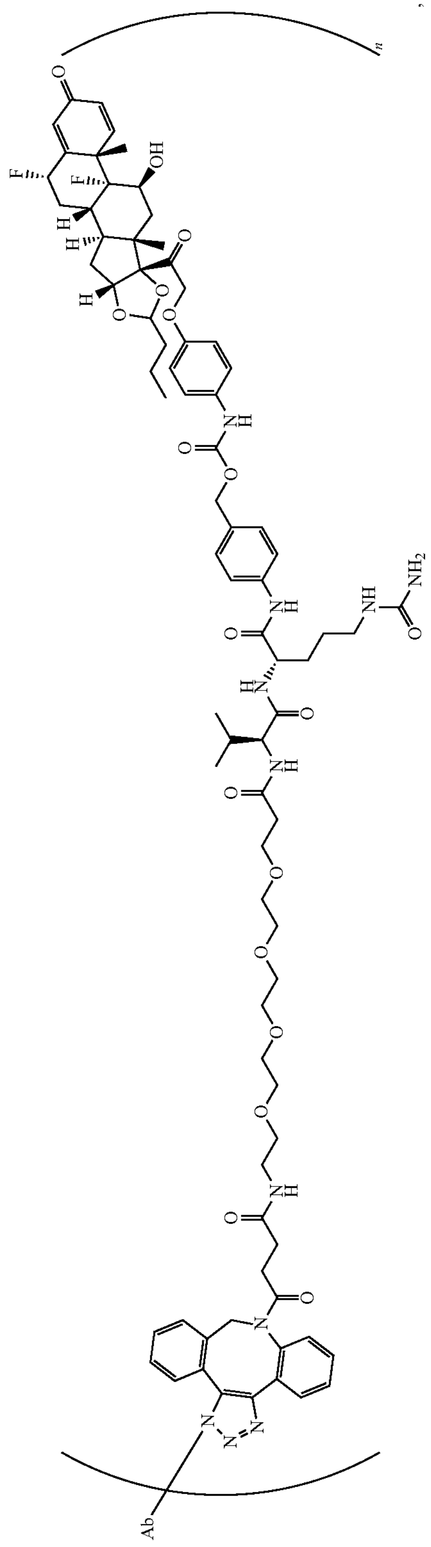
,

TABLE 1-continued
List of ADCs and their structures
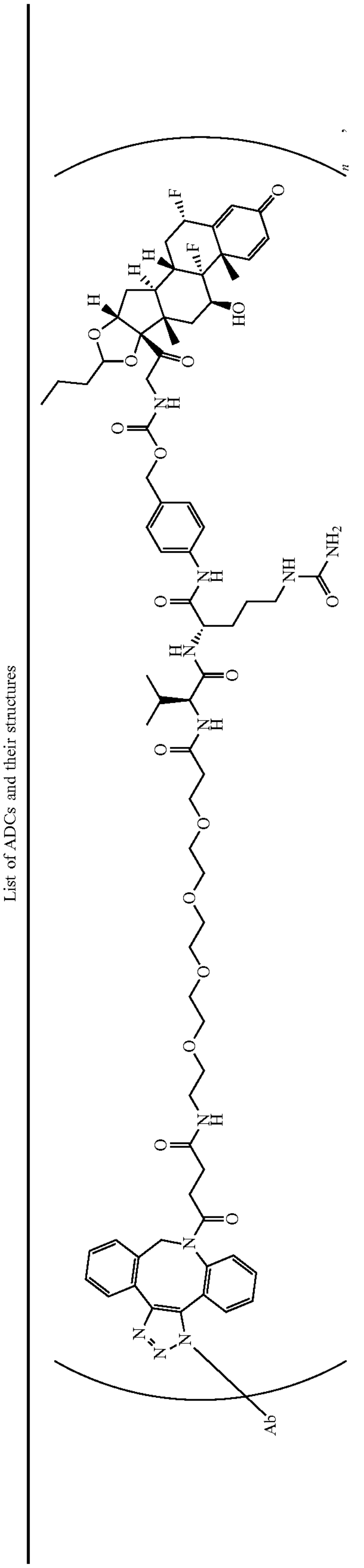
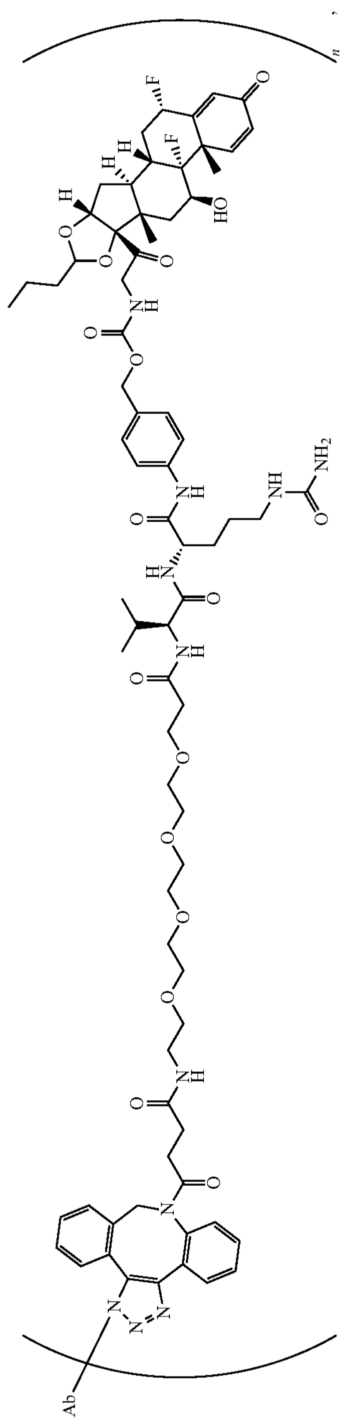
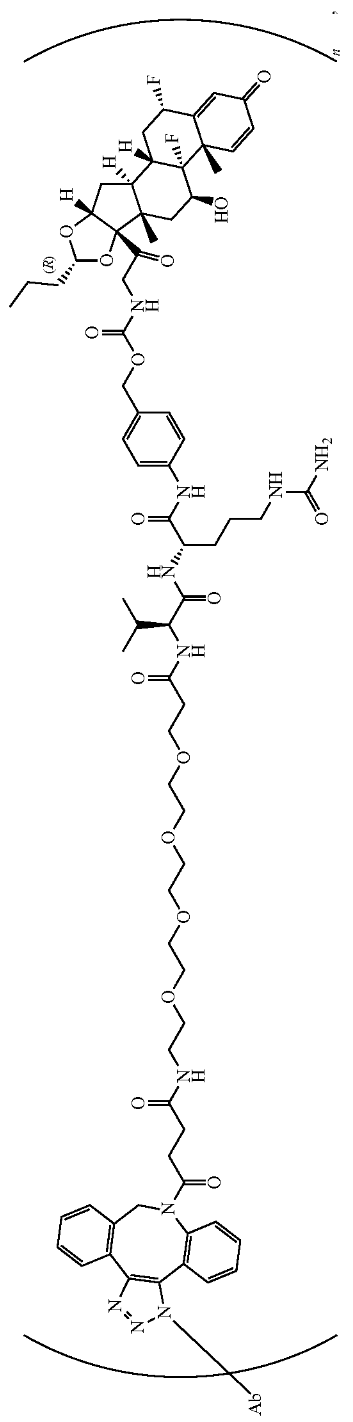

TABLE 1-continued
List of ADCs and their structures
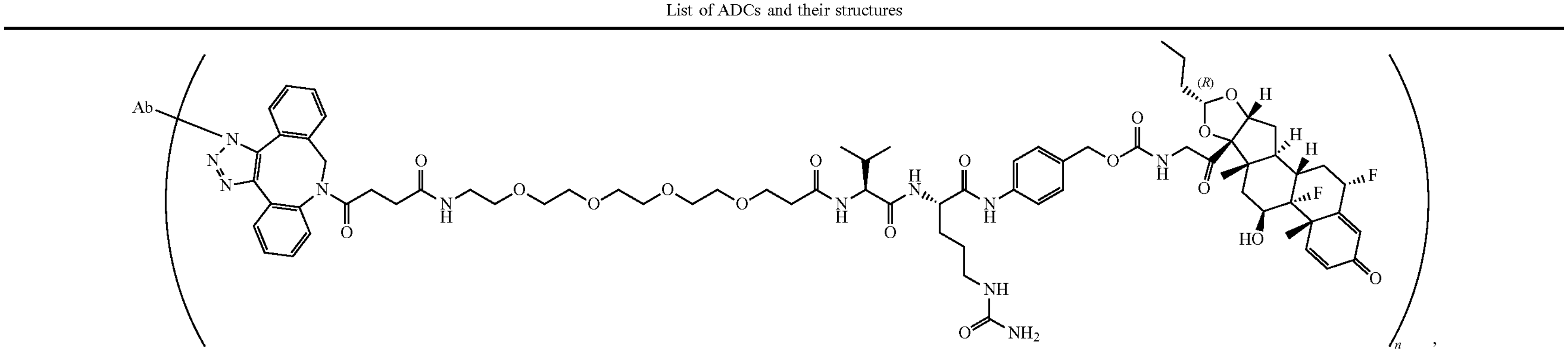
,
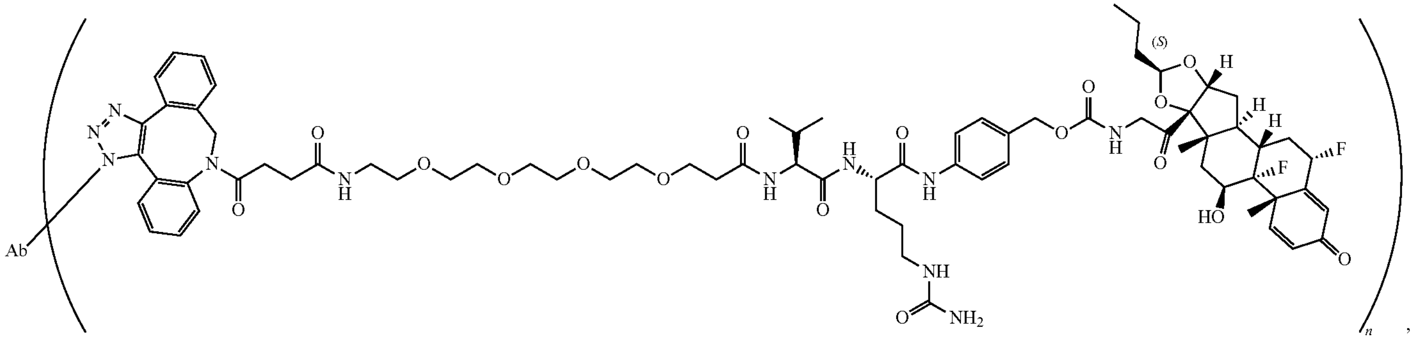
,
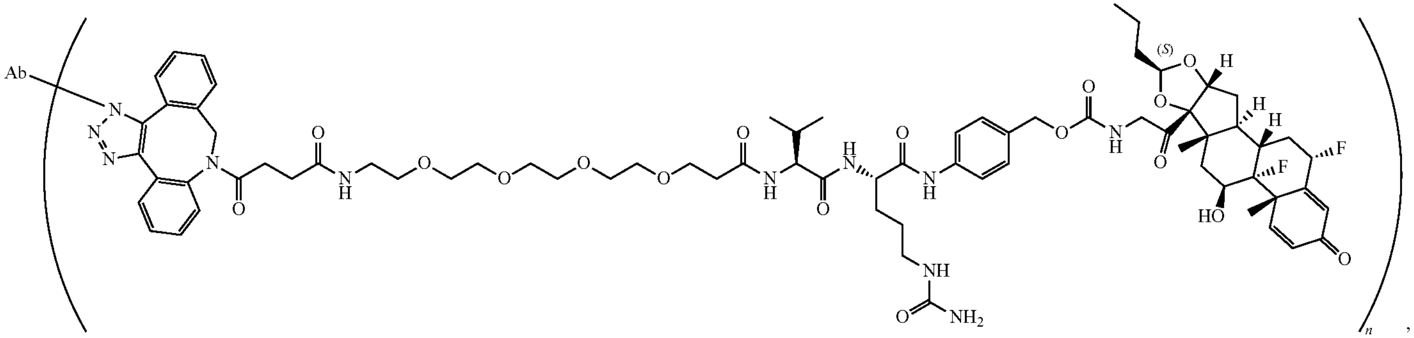
, TABLE 1-continued
| List of ADCs and their structures |
| --- |
| 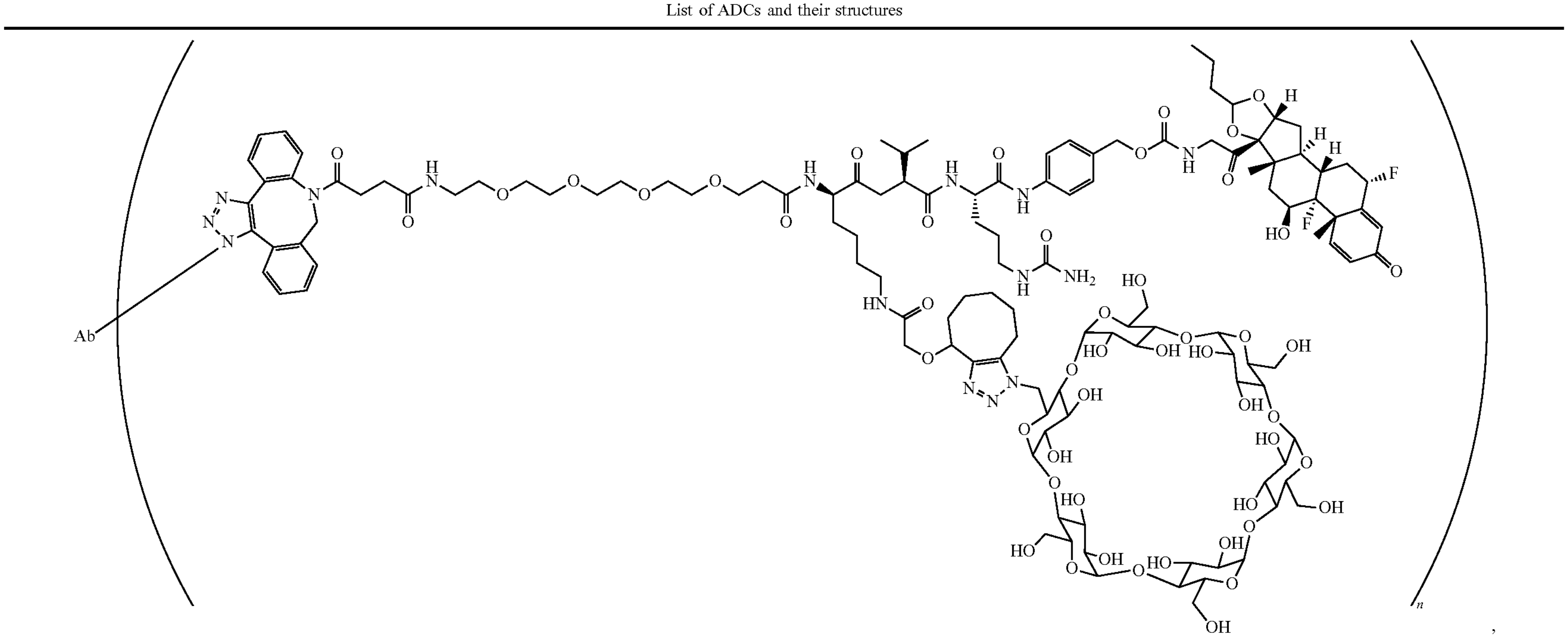 , |

TABLE 1-continued
List of ADCs and their structures
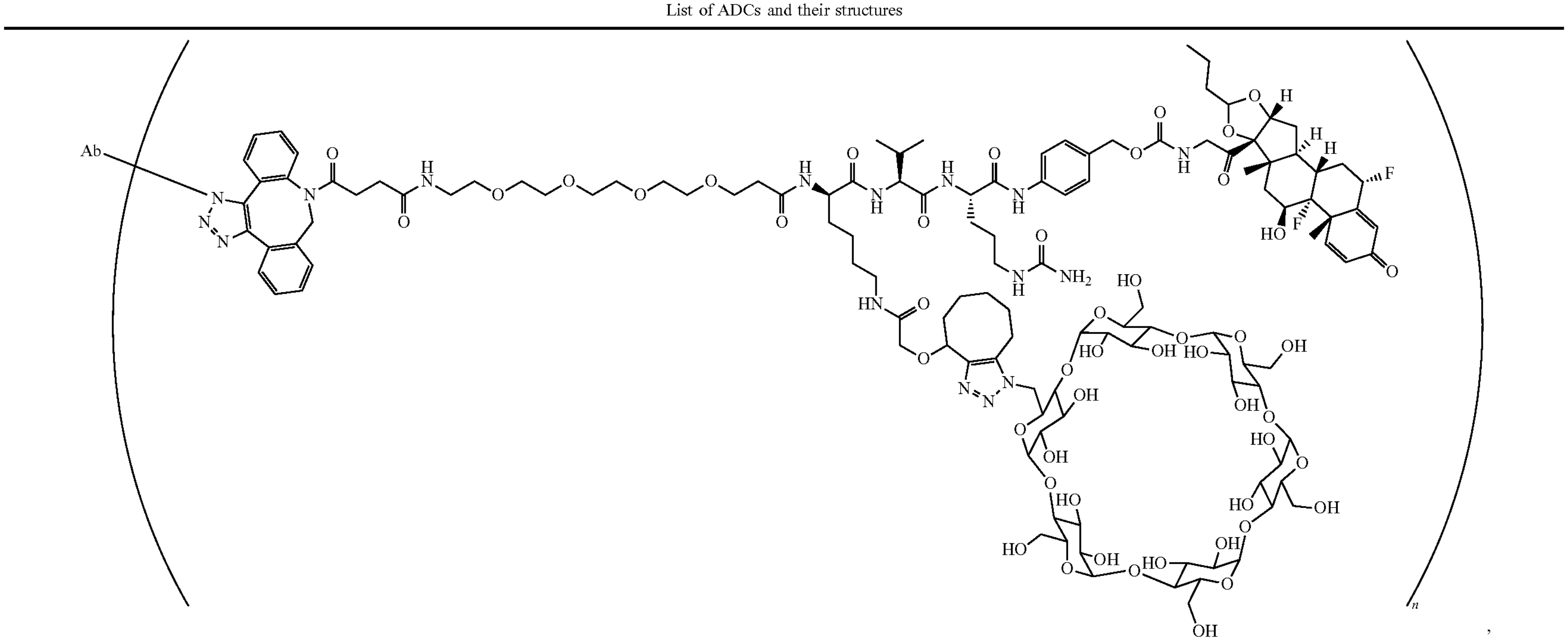
,
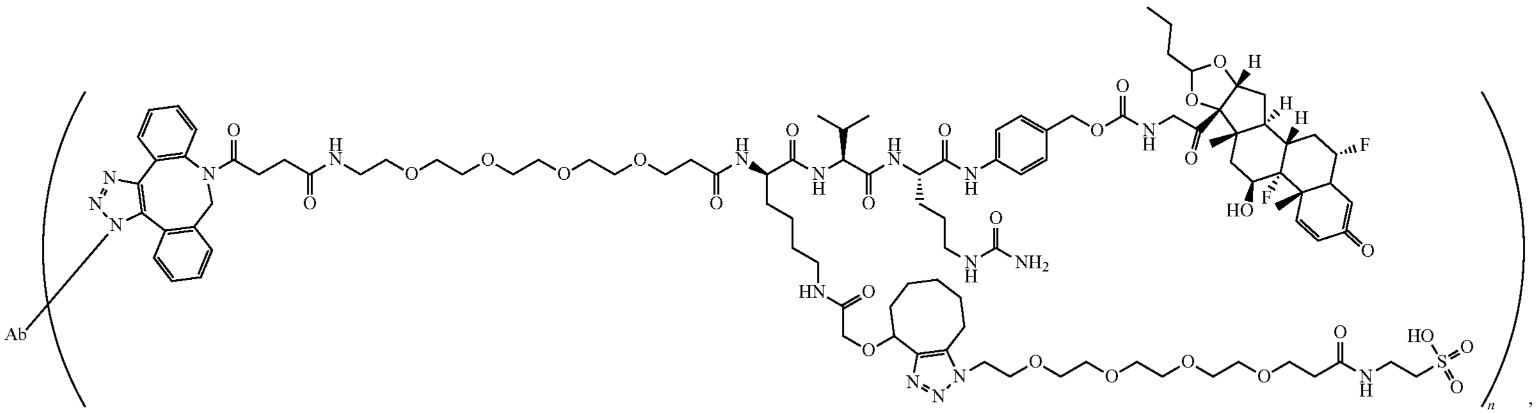
, and TABLE 1-continued
| List of ADCs and their structures |
| --- |
| 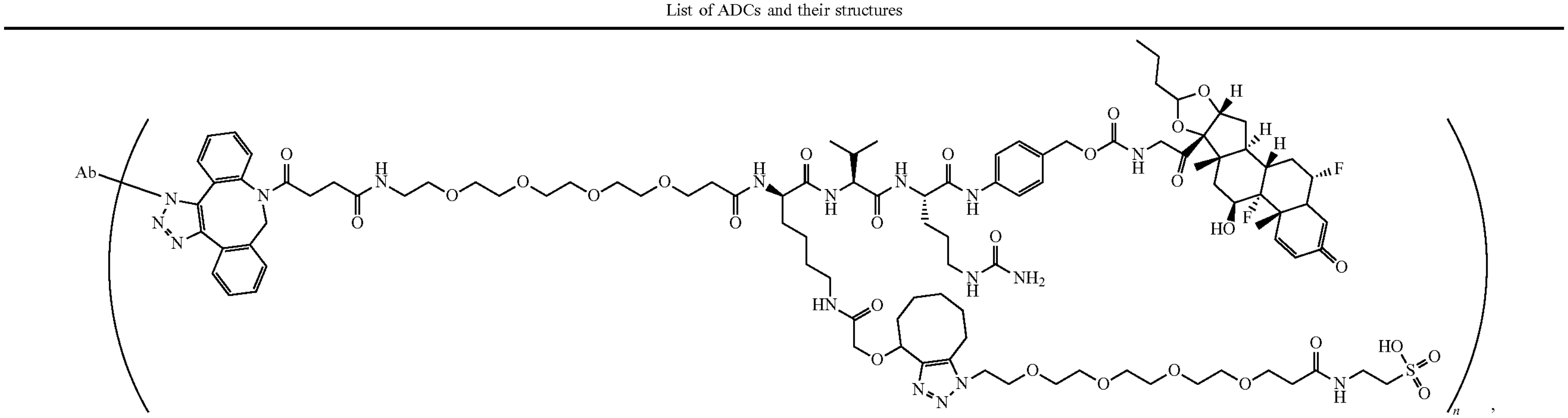 |

In the ADCs of Table 1, Ab is an anti-MSR1 antibody provided herein, or an antigen-binding fragment thereof. In particular embodiments, Ab is modified with a PEG group

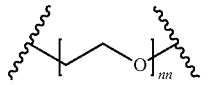

on a glutamine side chain described herein (referred to herein as a PEG-modified antibody). In certain embodiments, the PEG group terminates with an azido group, facilitating reaction with linker-payloads described here (e.g., linker payloads described in Table 3 and in the examples). In certain embodiments, the PEG group is linked to a linker-payload through a triazole or triazole derivative as described herein. In the ADCs, n is an integer from 1 to 10, for instance, 1, 2, 3, or 4. In the PEG group, nn is an integer from 1-10, for instance, 1, 2, 3, 4, or 5. In other embodiments, each BA in the ADCs in Table 1 is

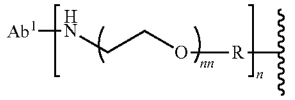

where $Ab^1$ is an anti-MSR1 antibody, or an antigen-binding fragment thereof; R is $C_{2-4}$-alkylene; and nn is an integer selected from 2 to 4, inclusive, and each n is an integer from 1 to 10, for instance, 1, 2, 3, or 4.

In certain embodiments, provided herein is an ADC comprising an antibody disclosed herein and a linker-payload (LP) selected from the group consisting of the linker-payloads in Table 2, or a stereoisomeric form thereof, or a regioisomer thereof, or a mixture of regioisomers thereof.

TABLE 2
List of ADCs and their structures
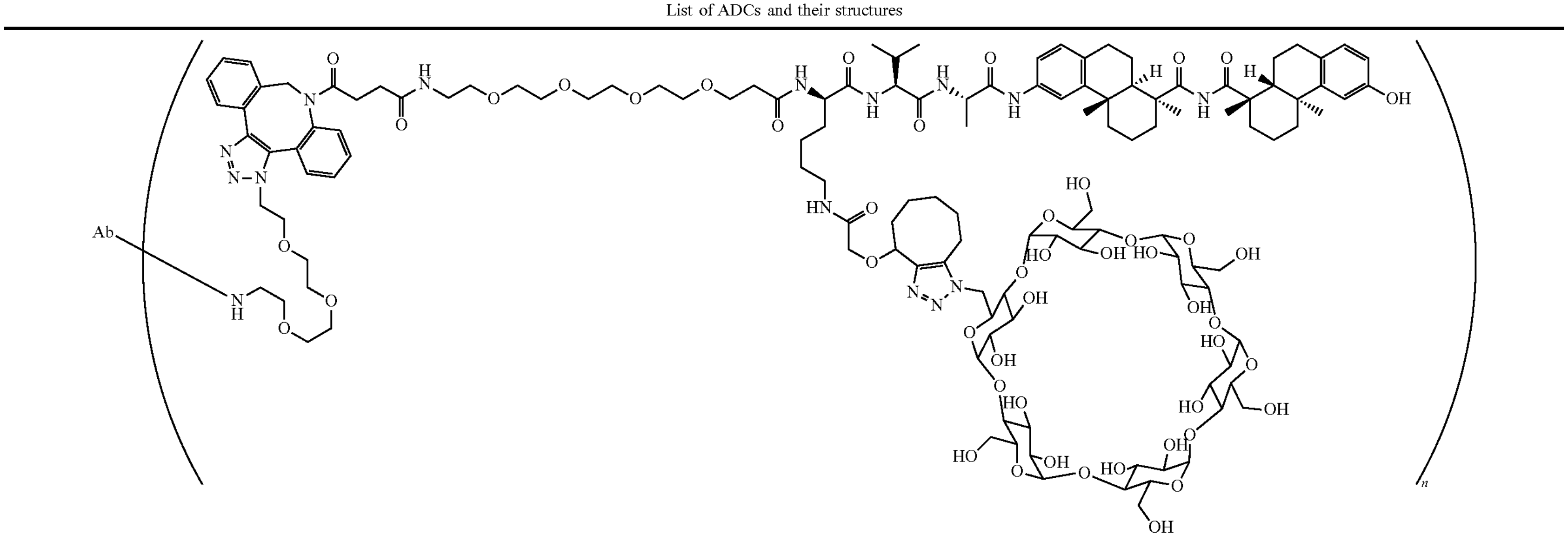

TABLE 2-continued
List of ADCs and their structures
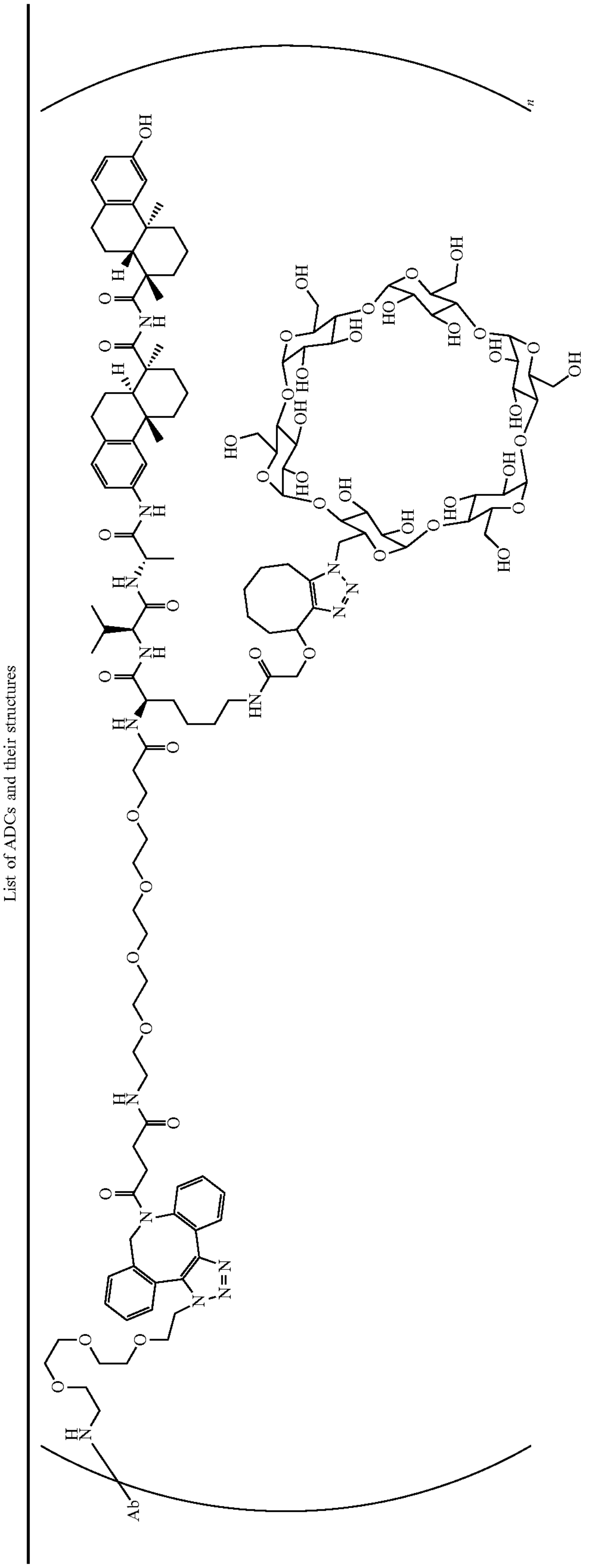

TABLE 2-continued
List of ADCs and their structures
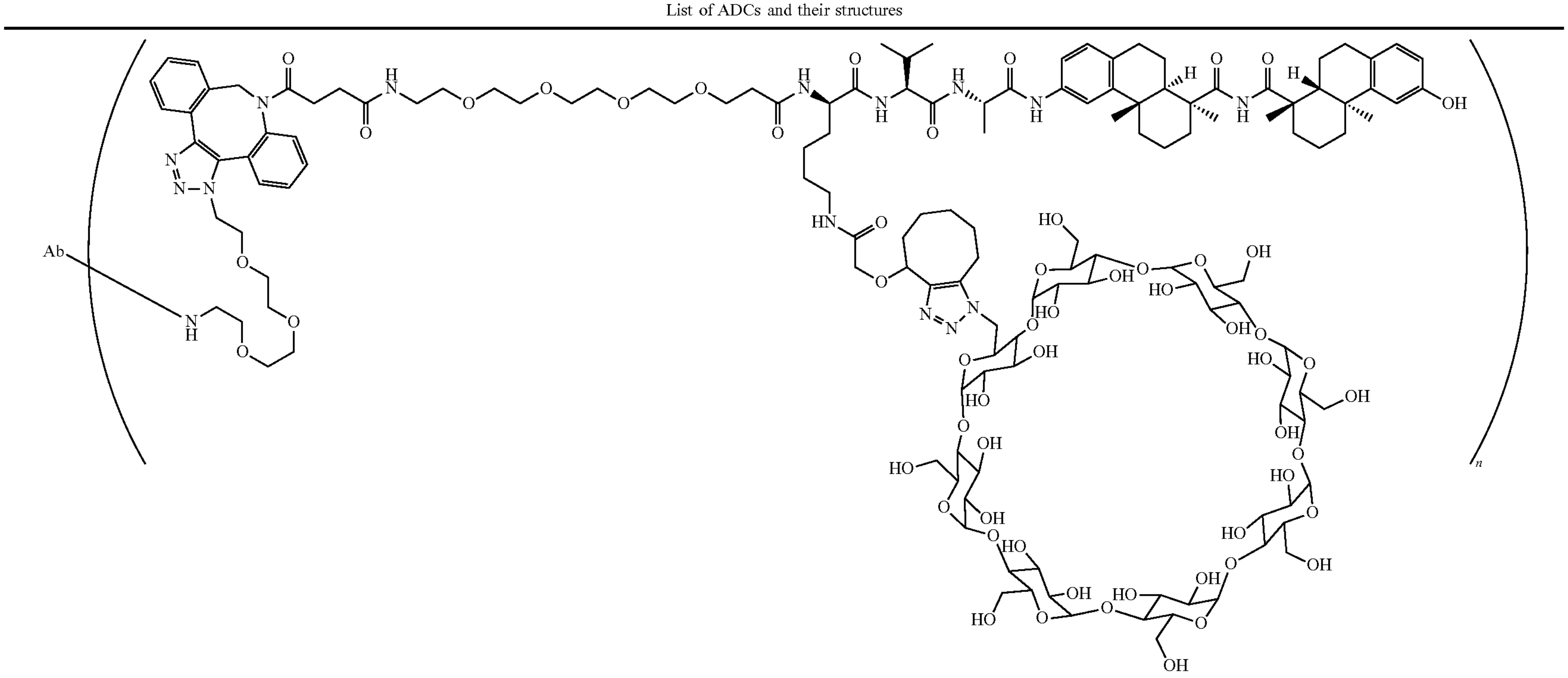

TABLE 2-continued
List of ADCs and their structures
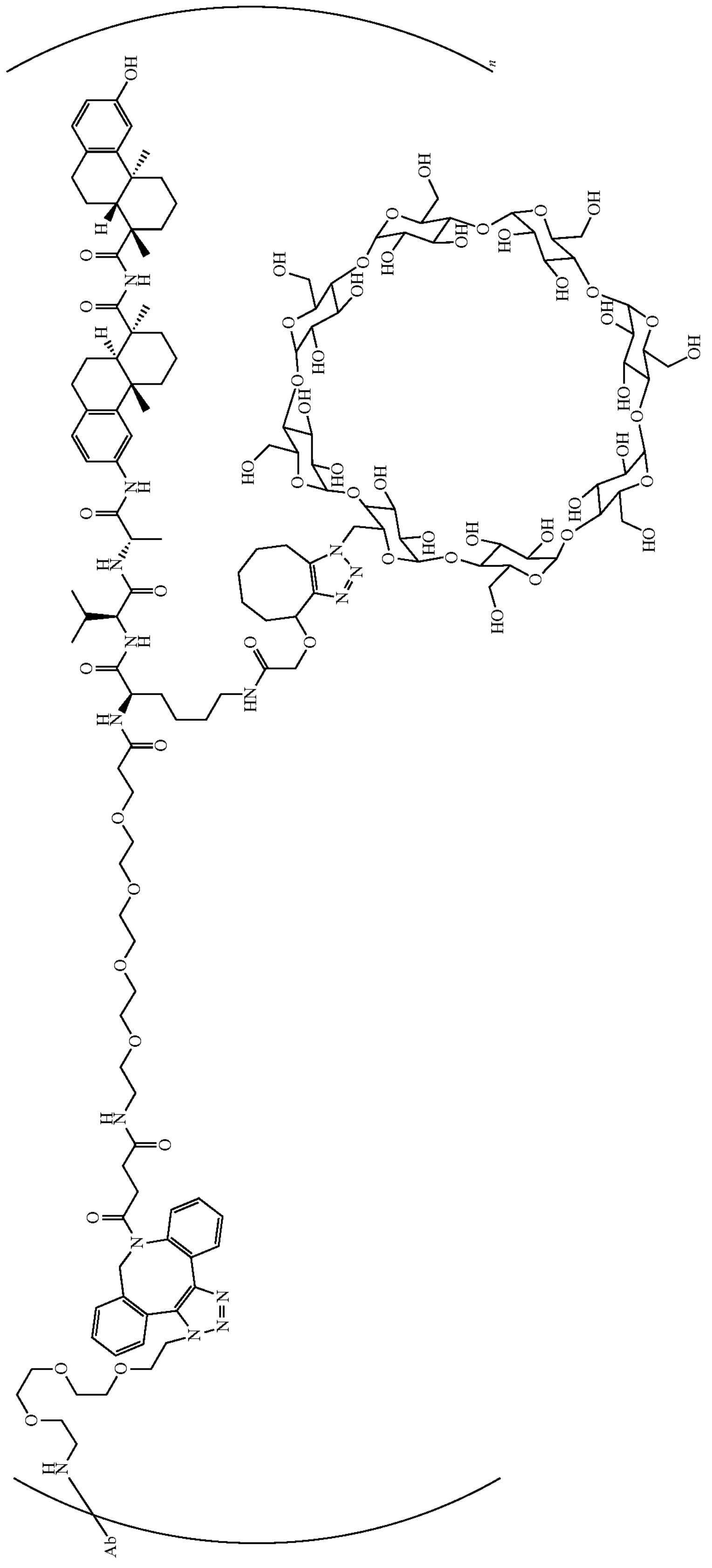

TABLE 2-continued
List of ADCs and their structures
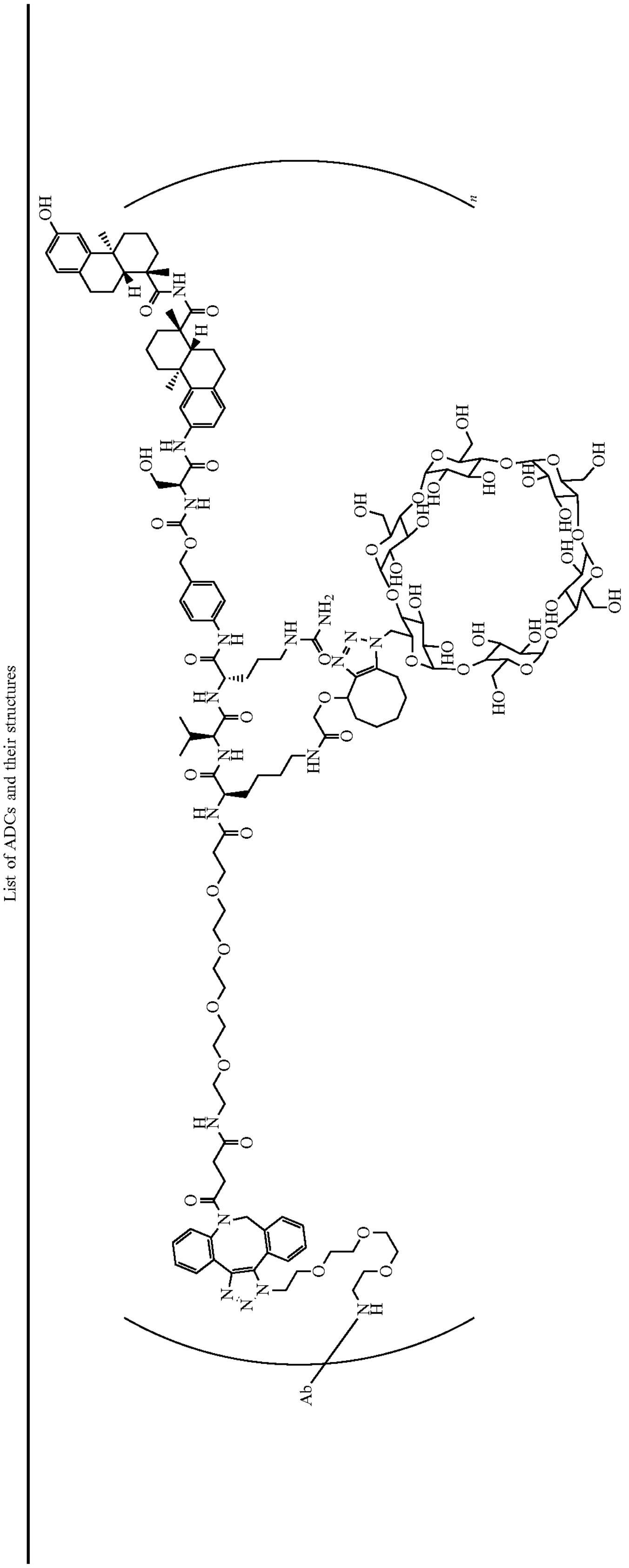

TABLE 2-continued
List of ADCs and their structures
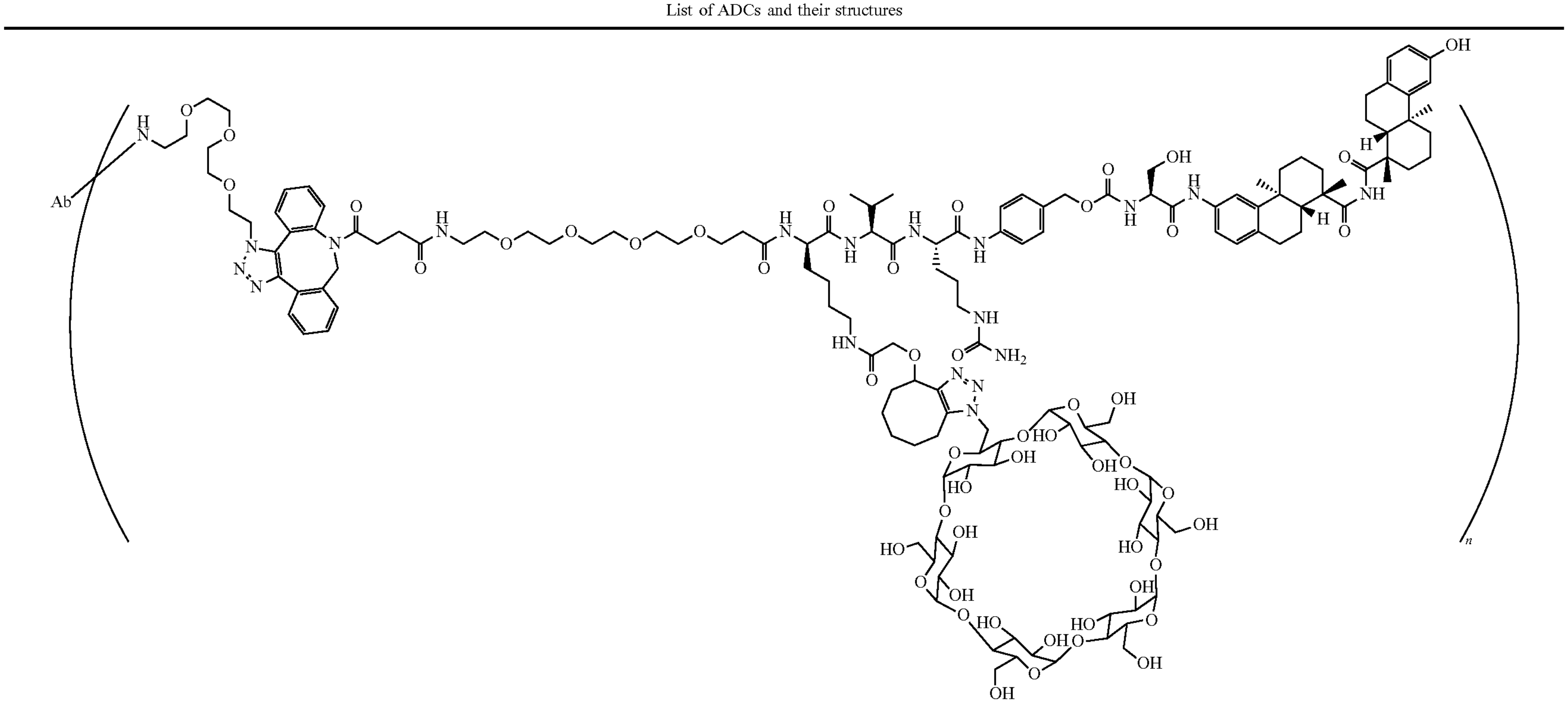

TABLE 2-continued
| List of ADCs and their structures |
| --- |
| 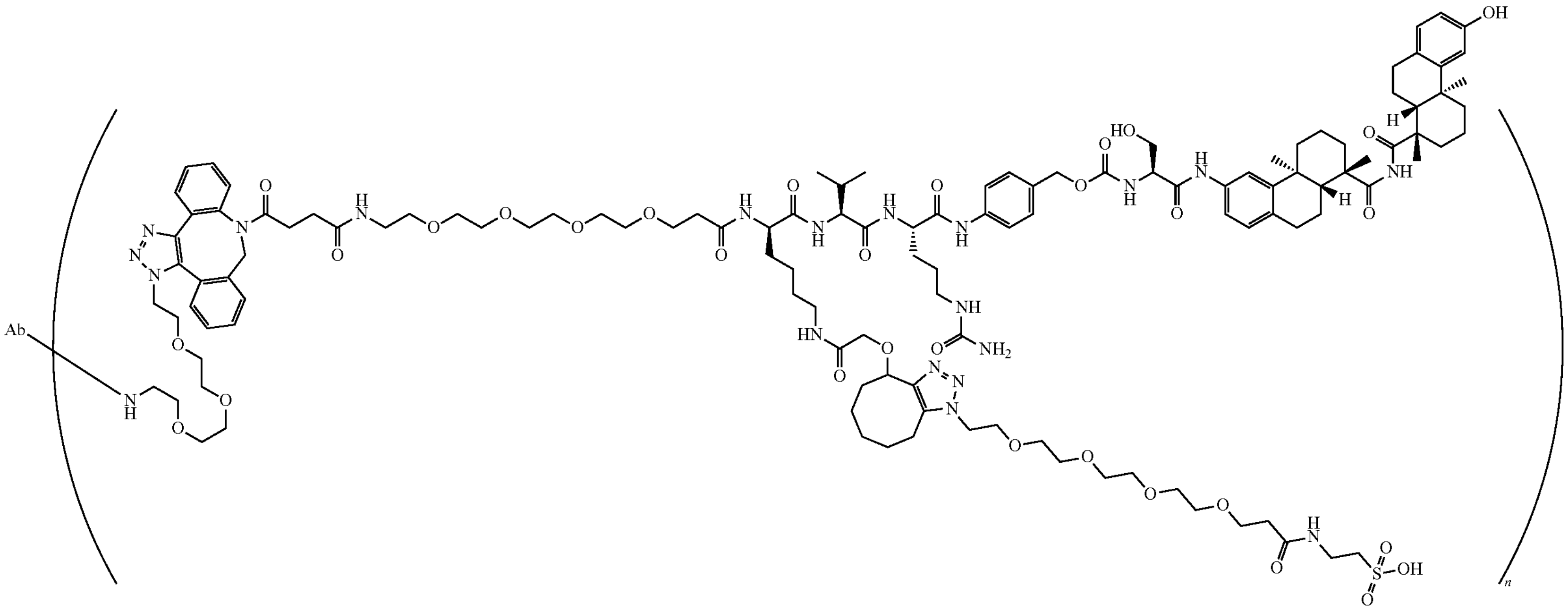 |

TABLE 2-continued
List of ADCs and their structures
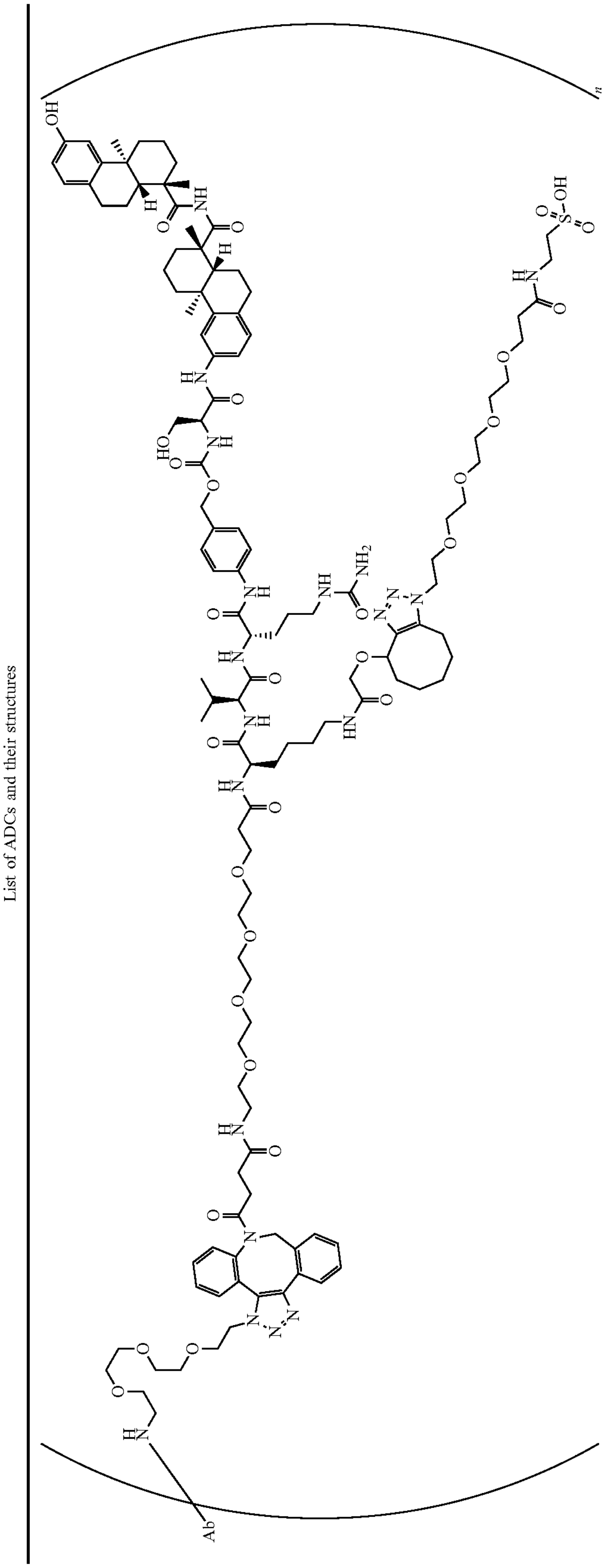
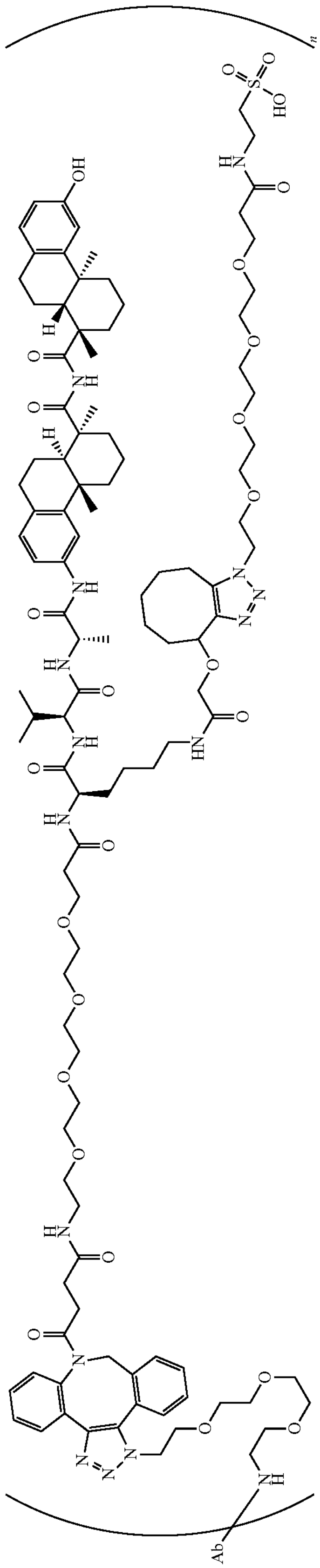

TABLE 2-continued
List of ADCs and their structures
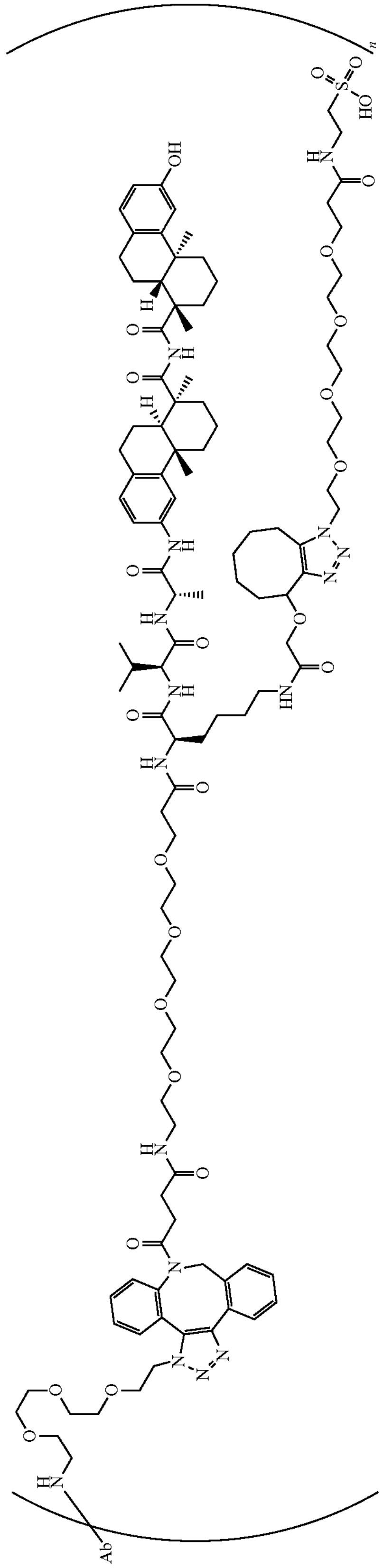
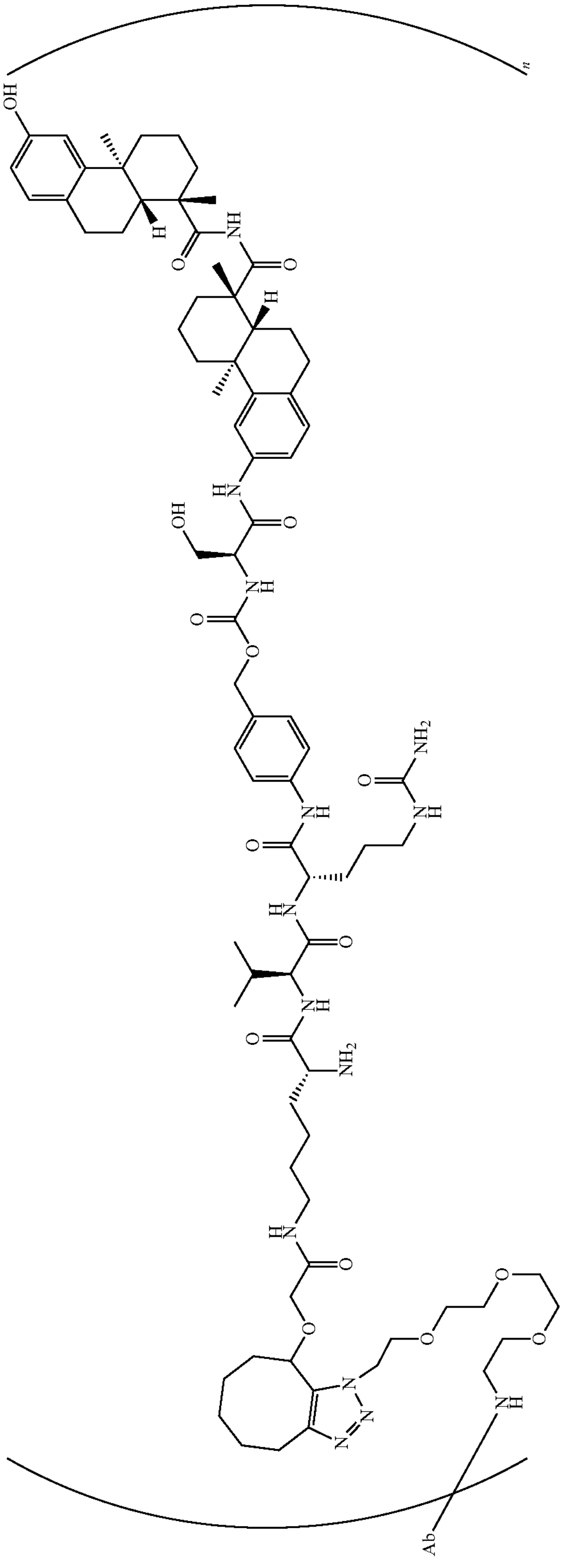

TABLE 2-continued
List of ADCs and their structures
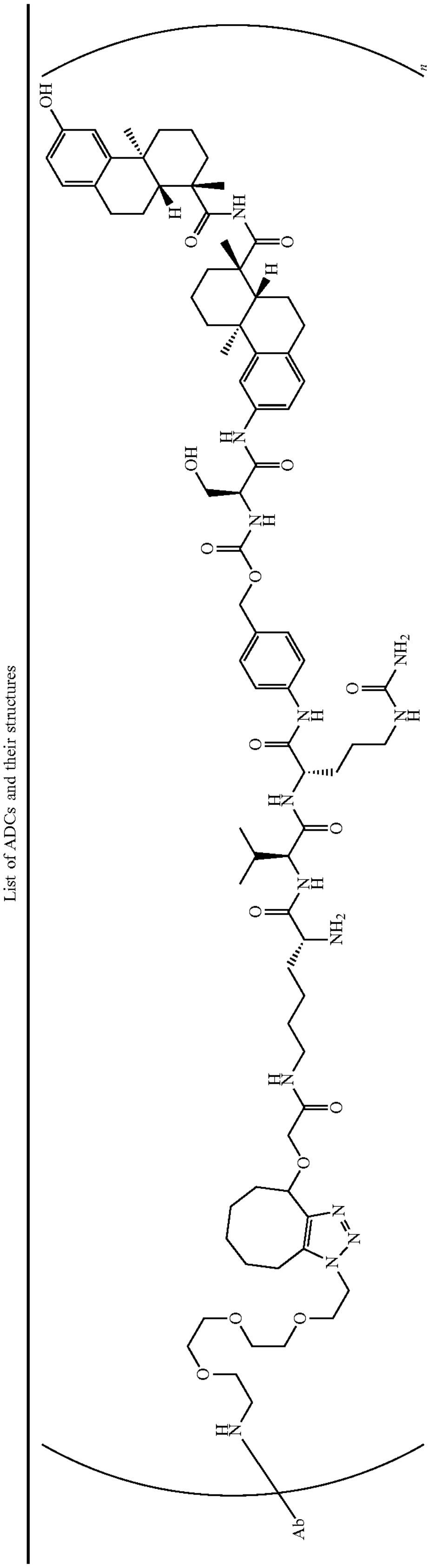
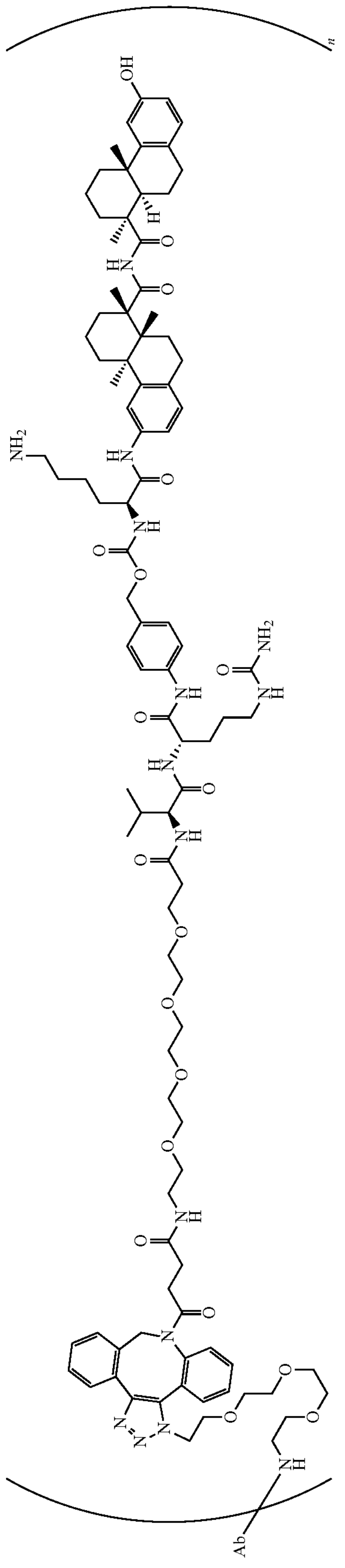

TABLE 2-continued
| List of ADCs and their structures |
|---|
| 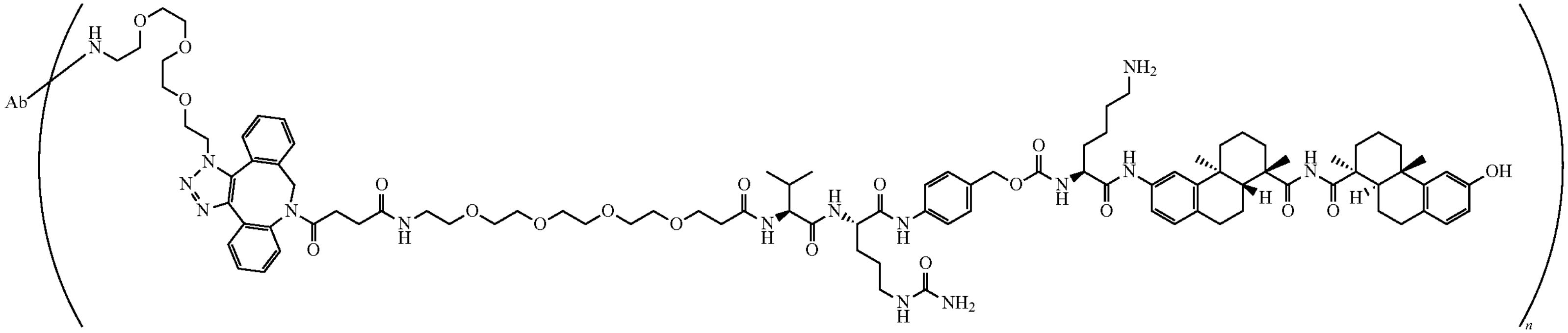 |
| 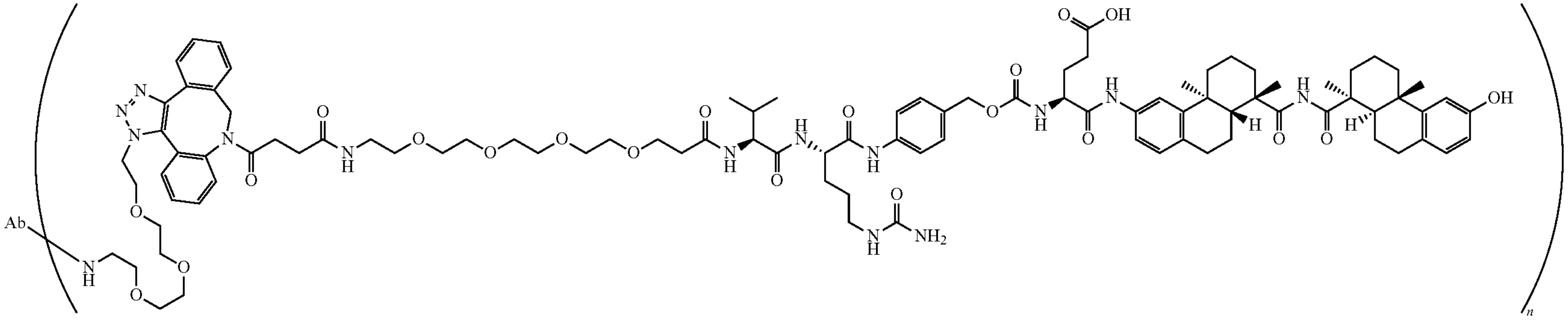 |
| 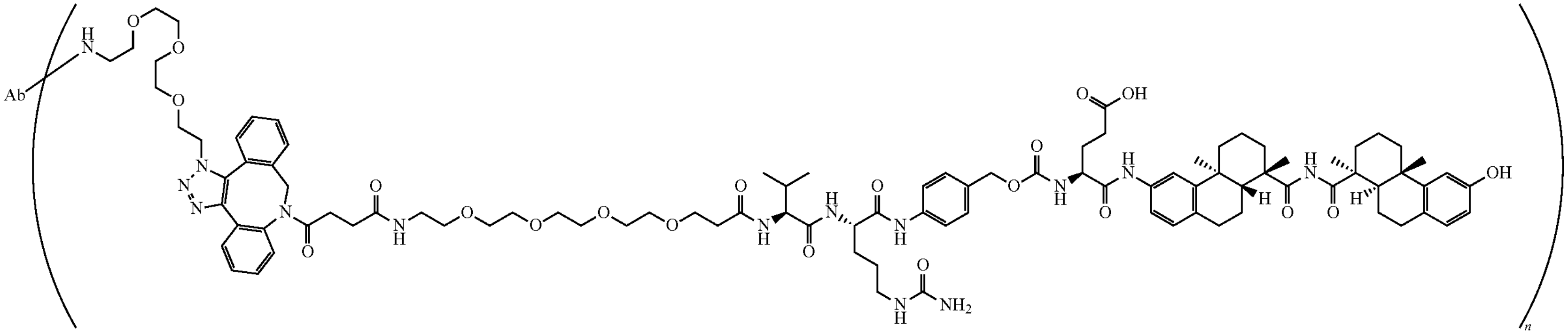 |

TABLE 2-continued
| List of ADCs and their structures |
| --- |
| 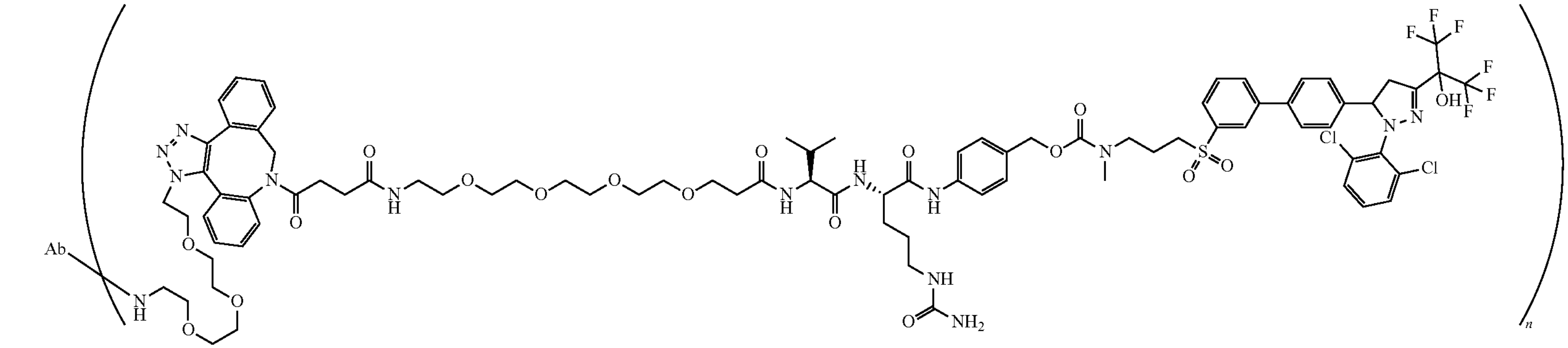 |
| 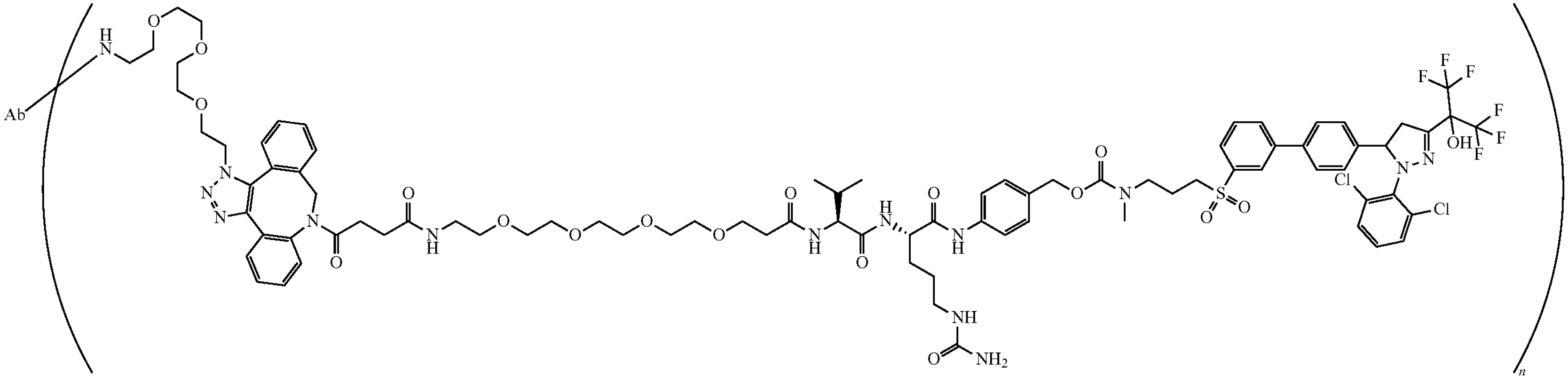 |

TABLE 2-continued
List of ADCs and their structures
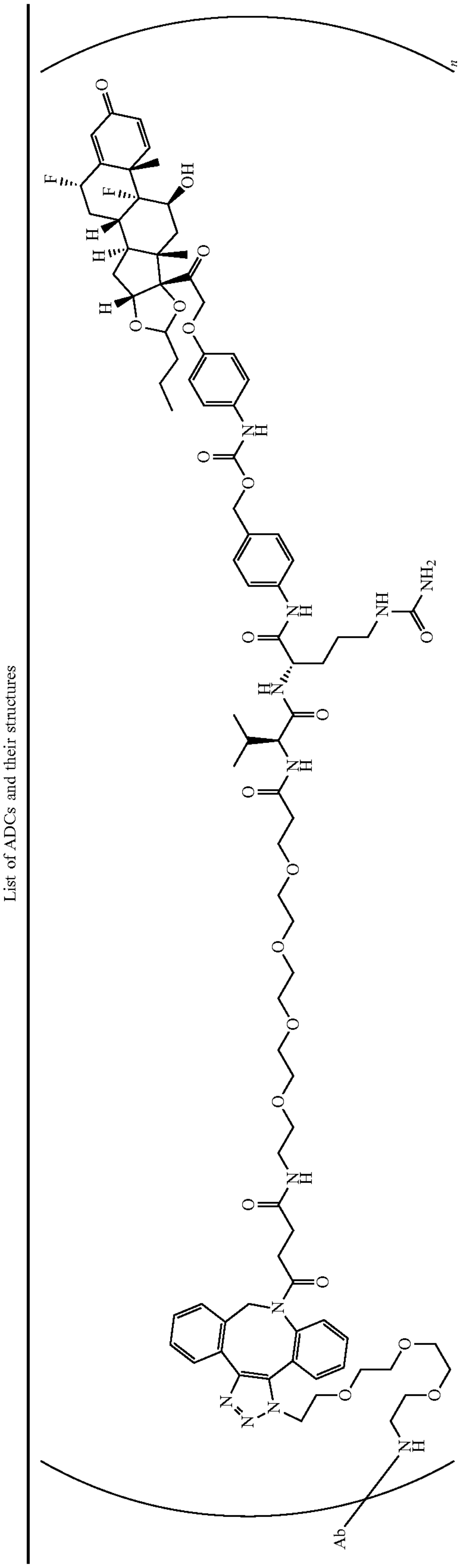
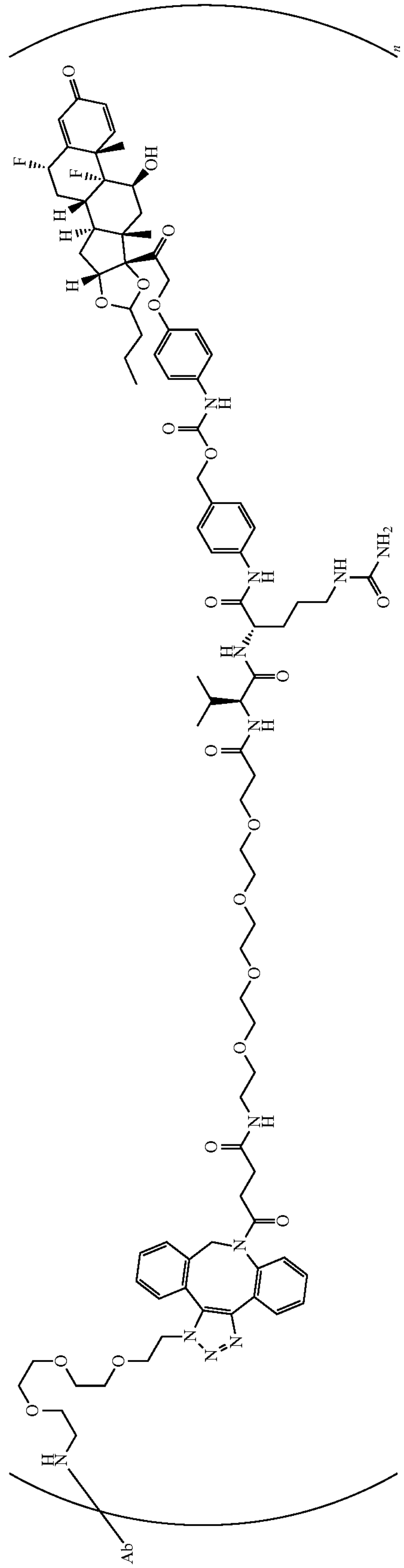

TABLE 2-continued
List of ADCs and their structures
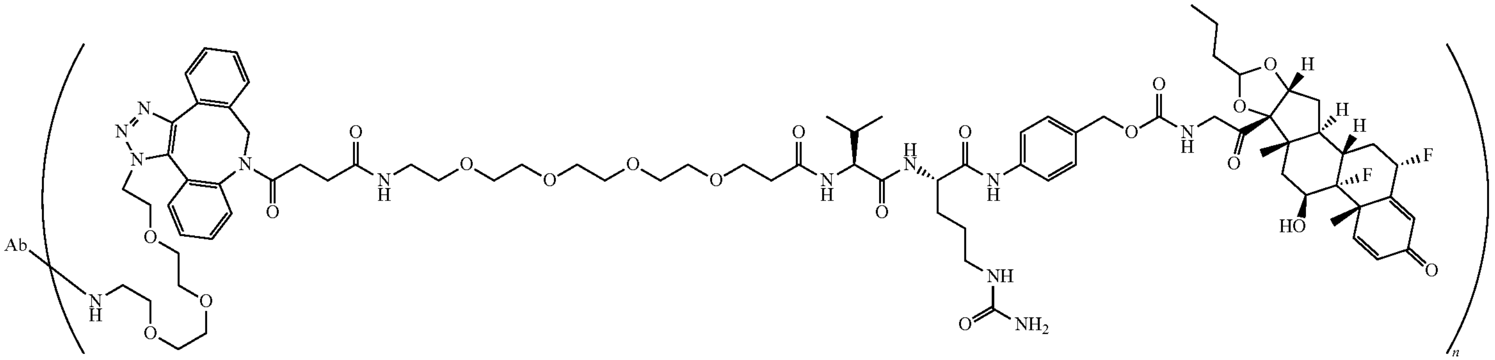
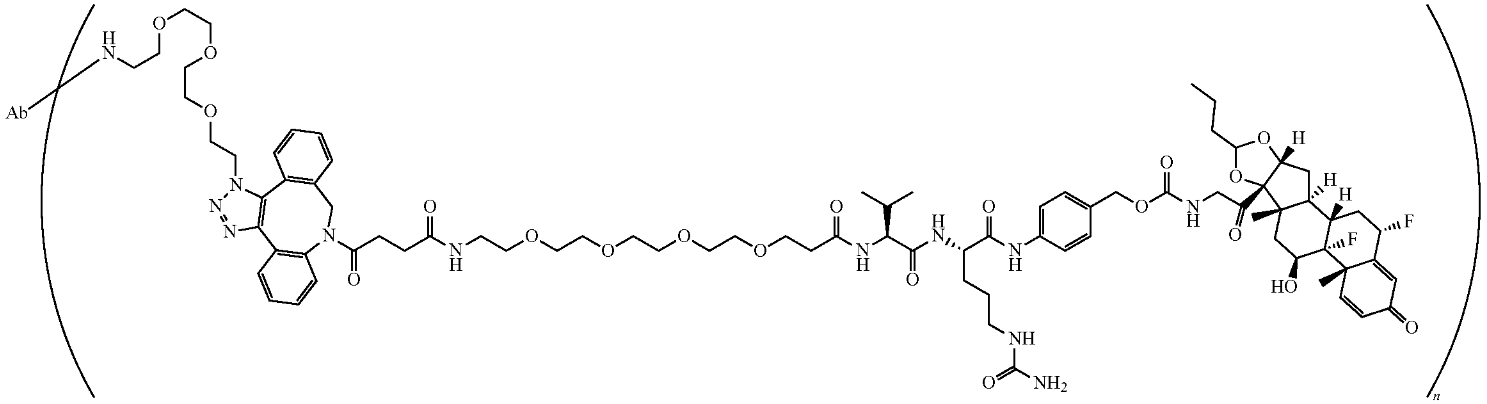

TABLE 2-continued
List of ADCs and their structures
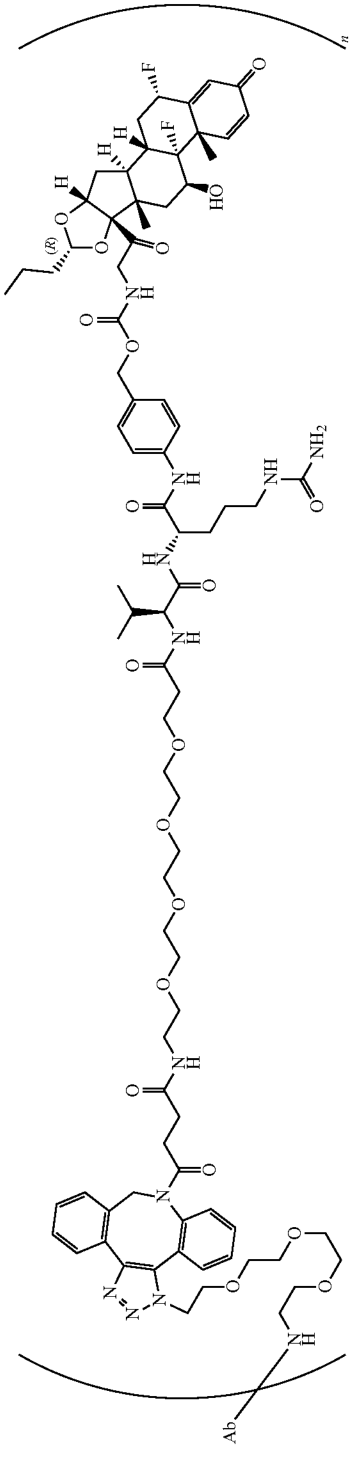
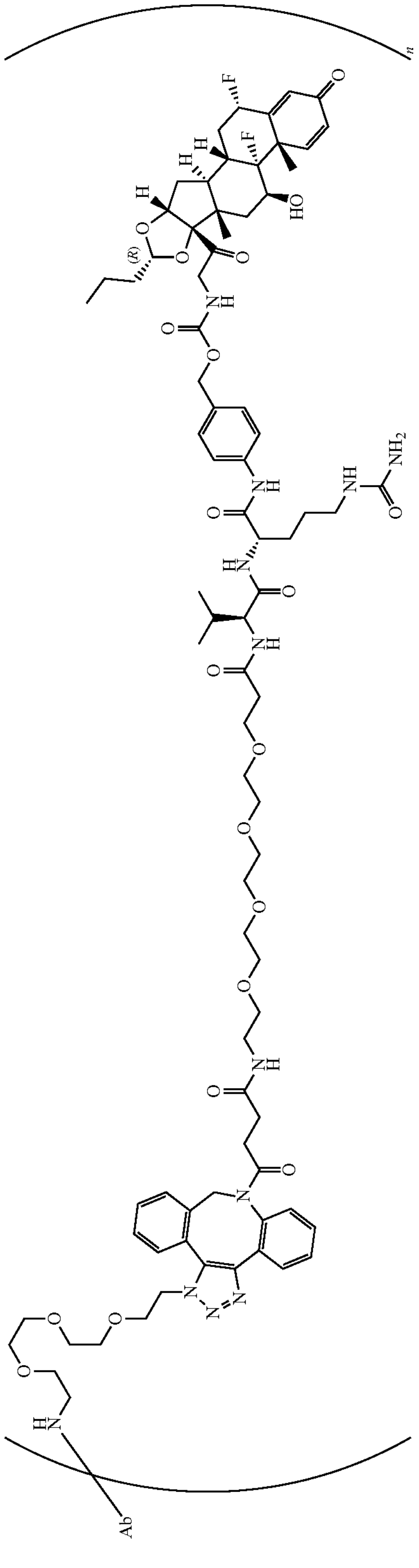

TABLE 2-continued
List of ADCs and their structures
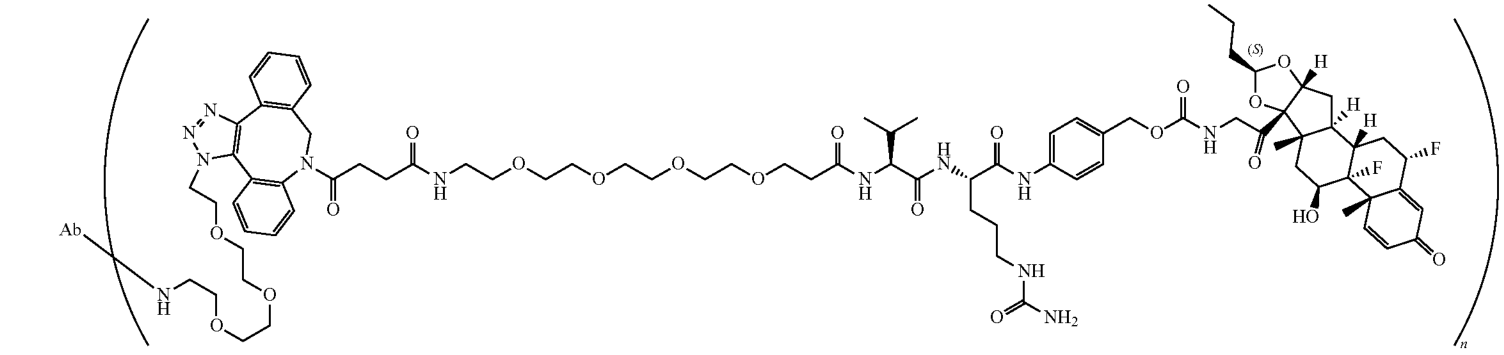
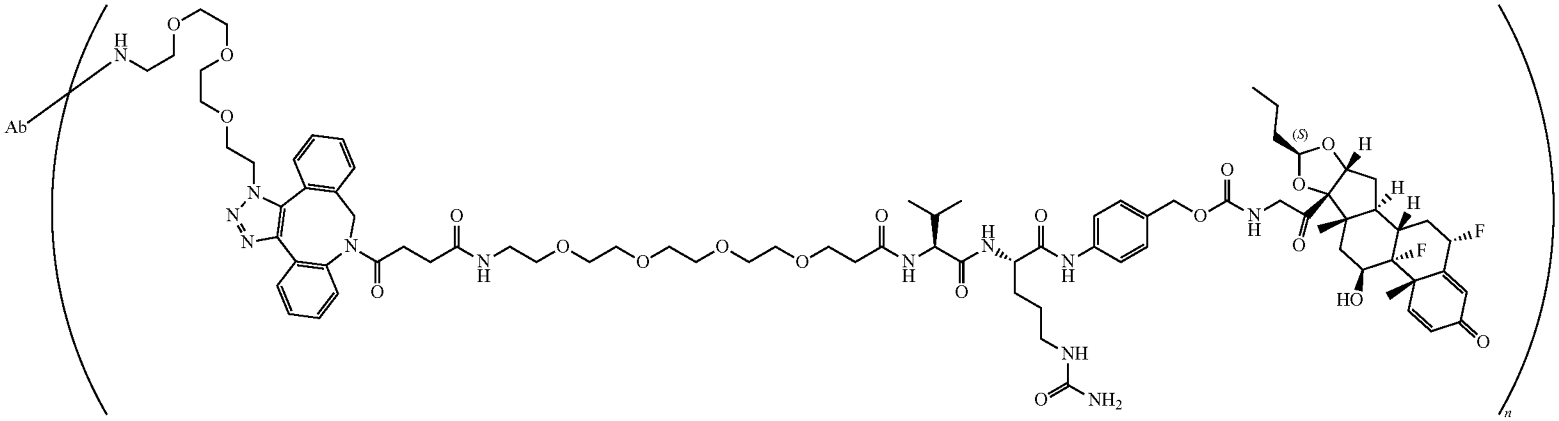

TABLE 2-continued
| List of ADCs and their structures |
| --- |
| 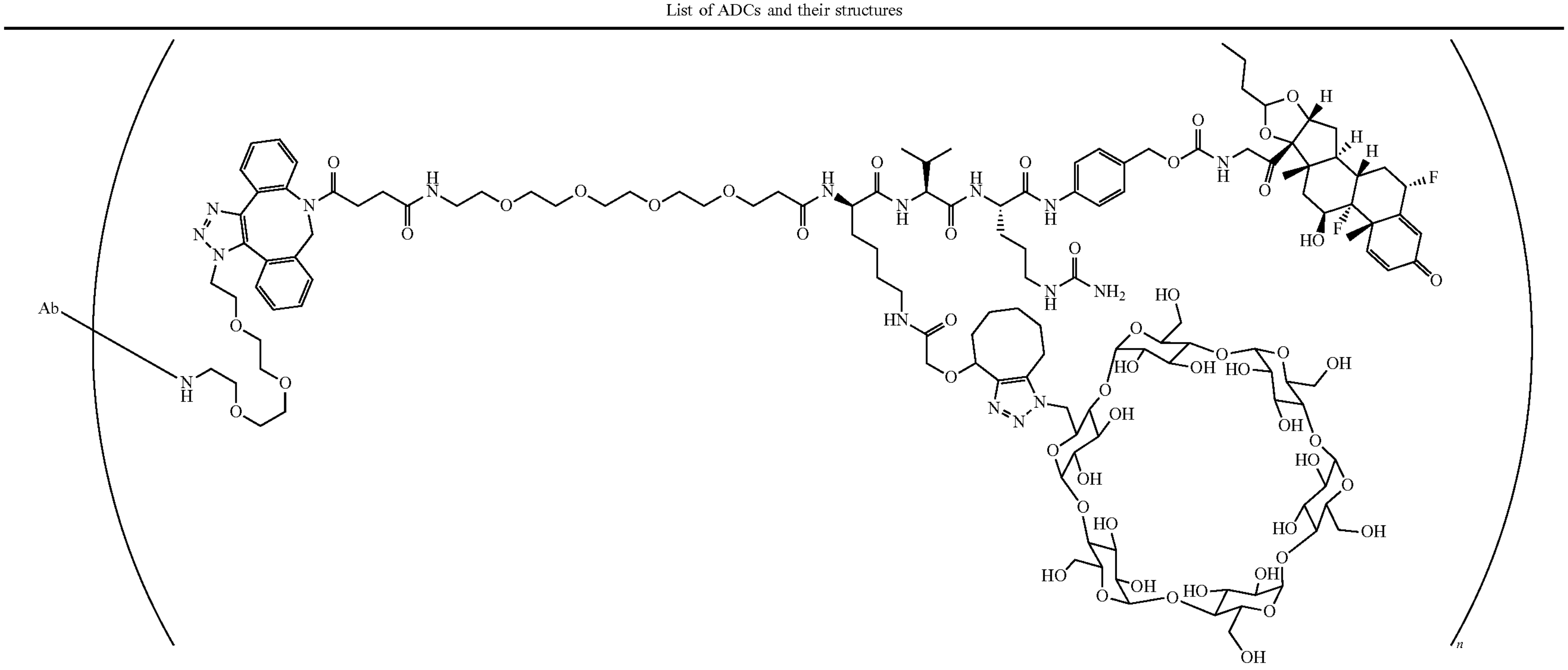 |

TABLE 2-continued
List of ADCs and their structures
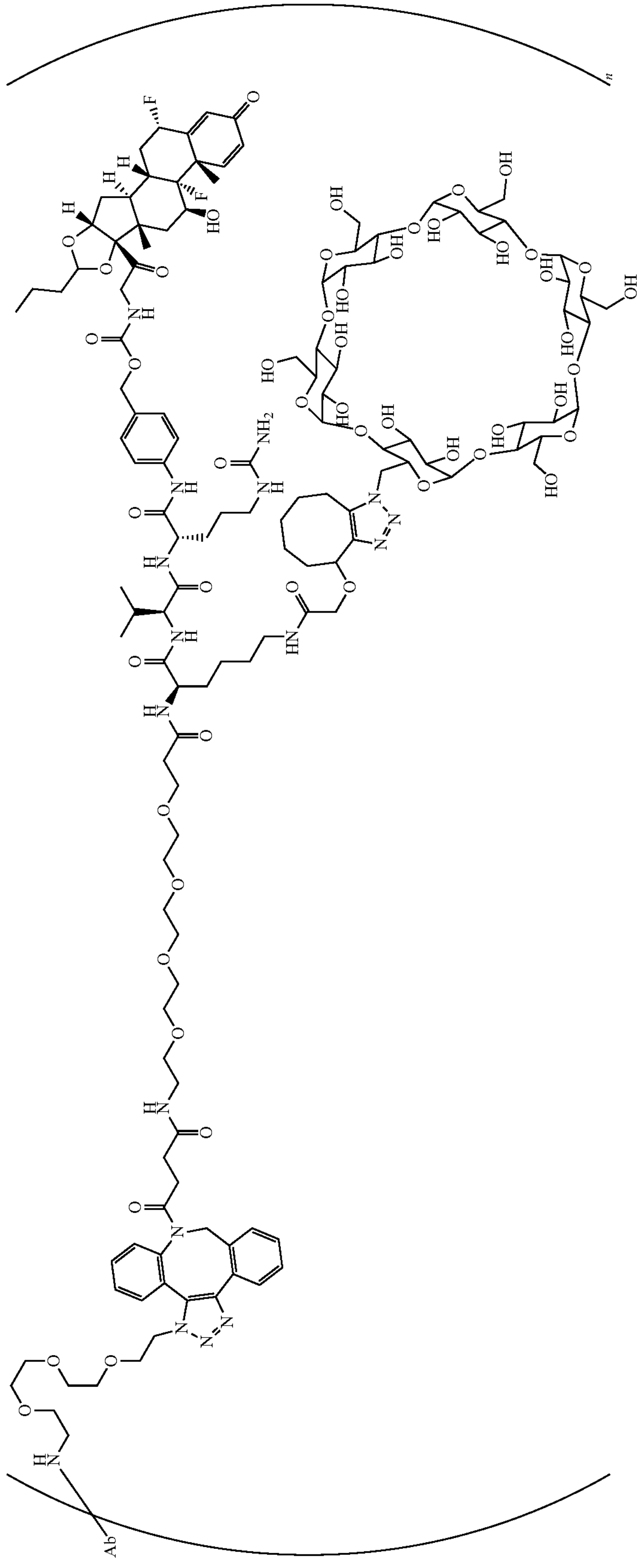

TABLE 2-continued
| List of ADCs and their structures |
| --- |
| 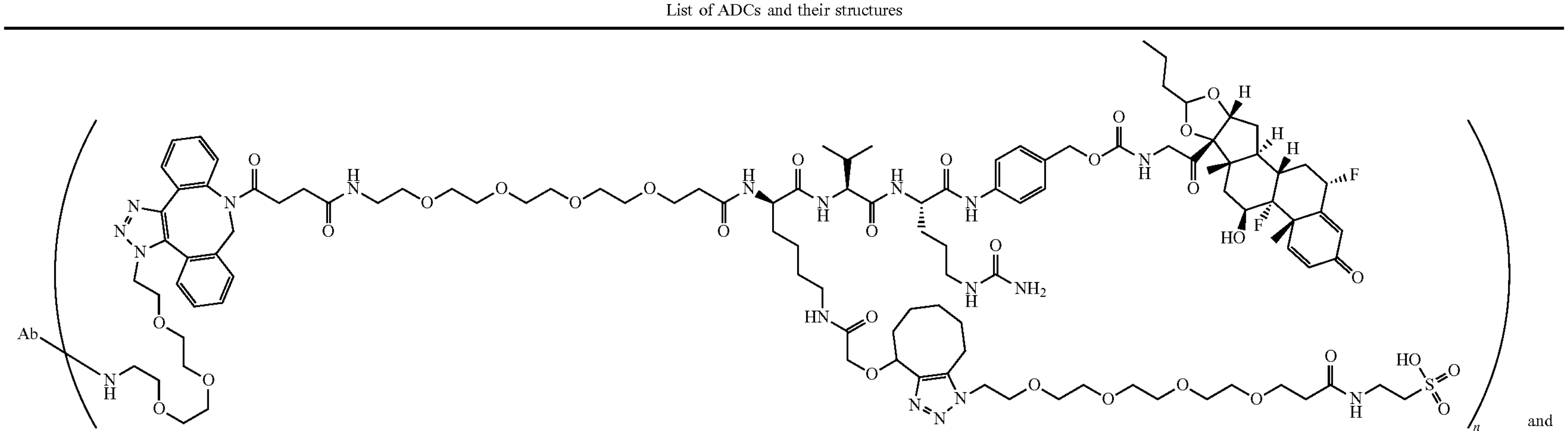 and 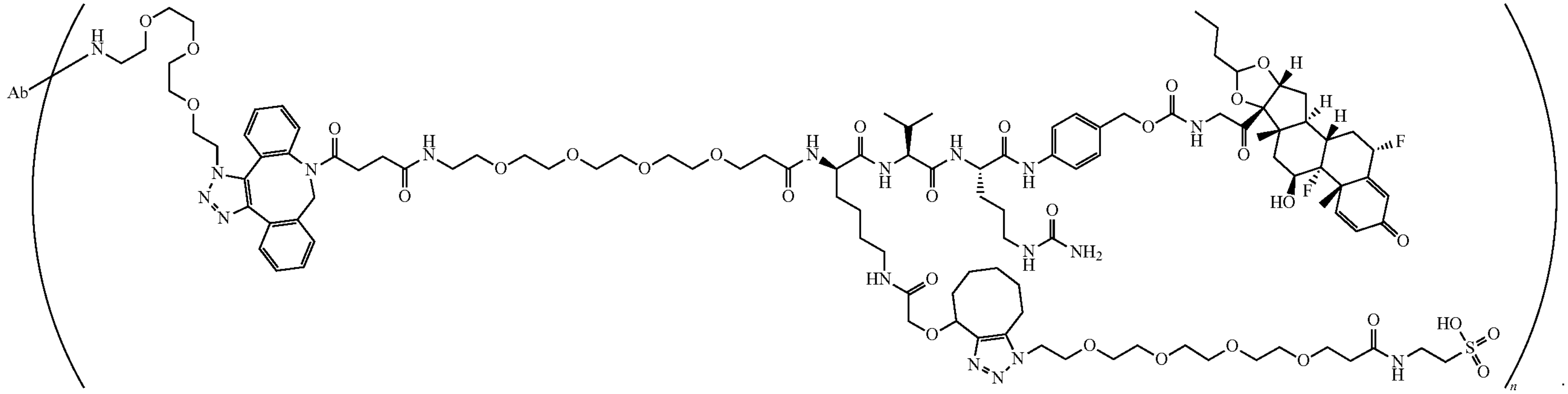 . |

TABLE 2-continued
List of ADCs and their structures
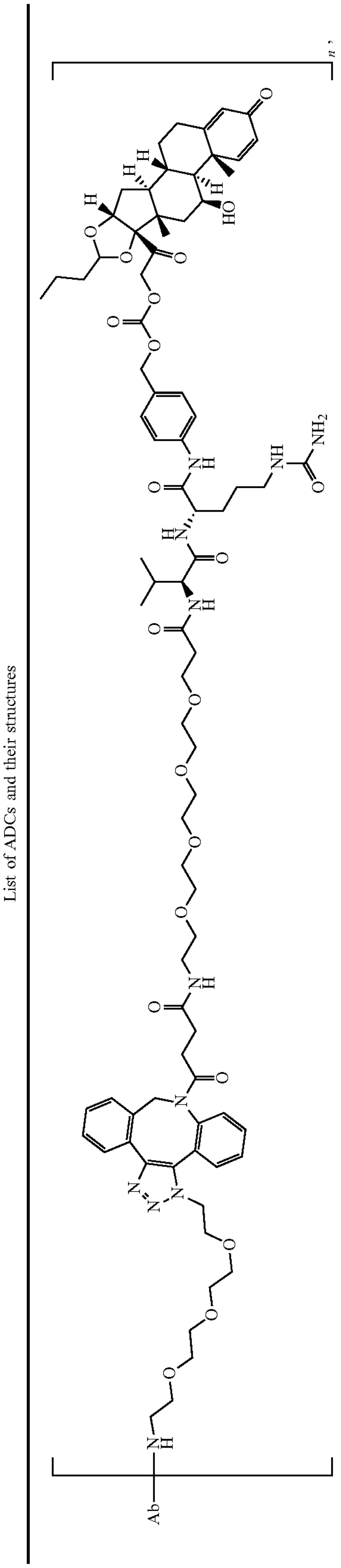
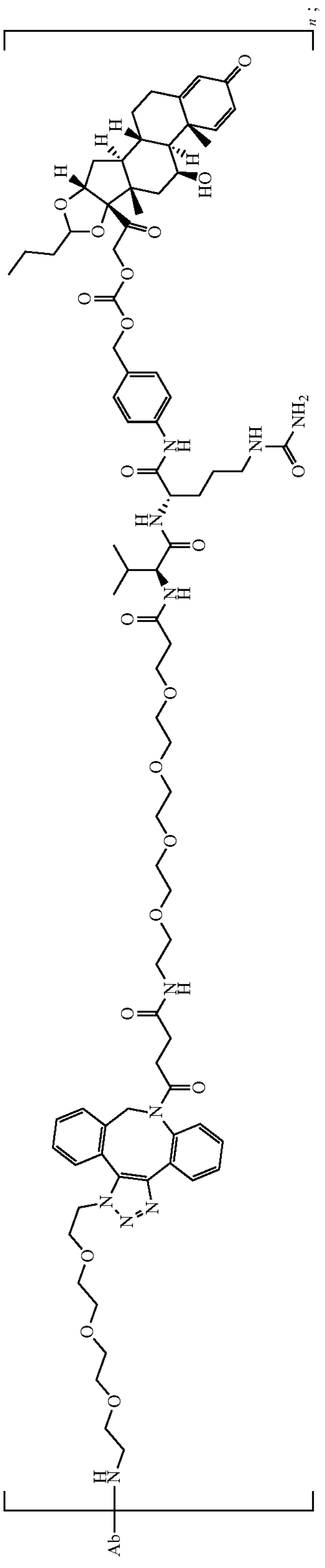
or a mixture thereof TABLE 2-continued
| List of ADCs and their structures |
| --- |
| 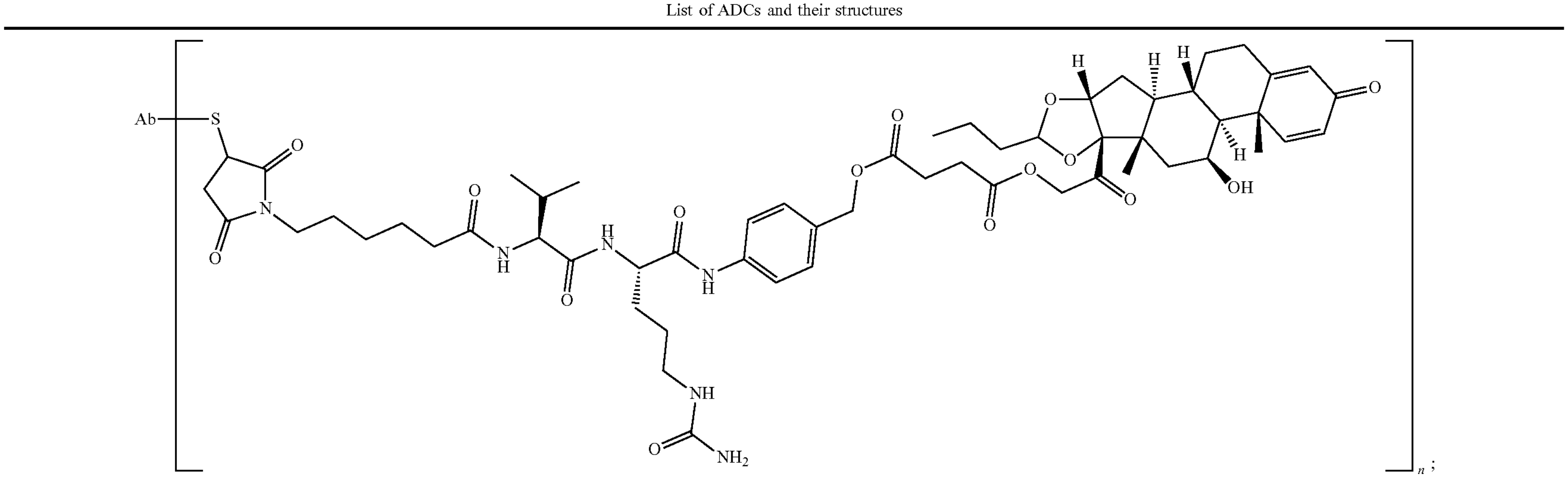 |
| or a stereoisomer or mixture of stereoisomers thereof |
| 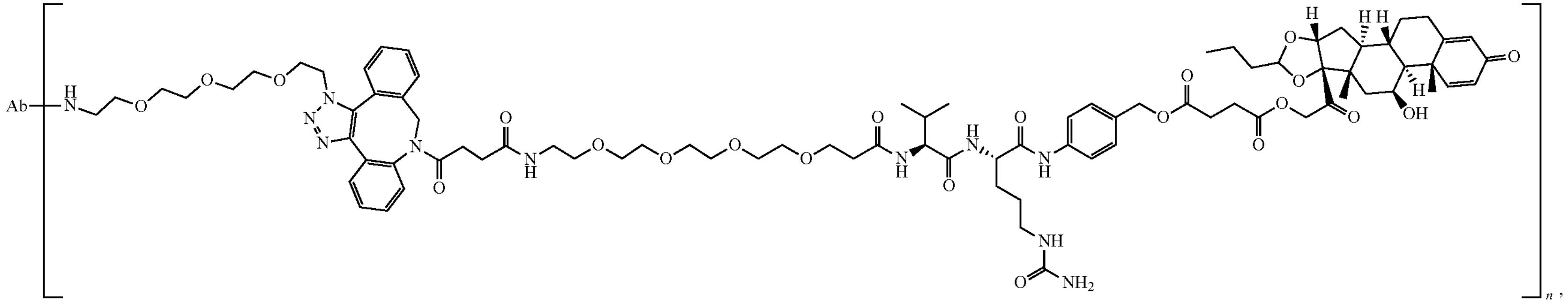 |

TABLE 2-continued
| List of ADCs and their structures |
| --- |
| 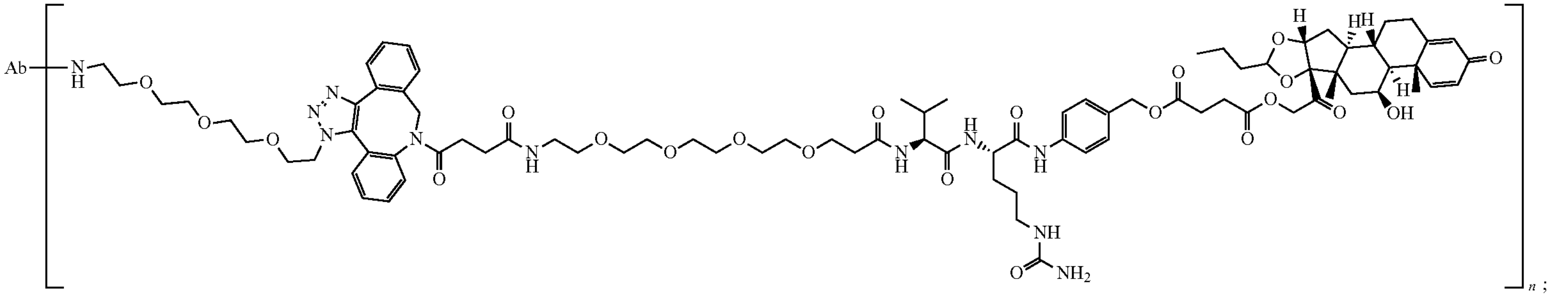 |
| or a mixture thereof |
| 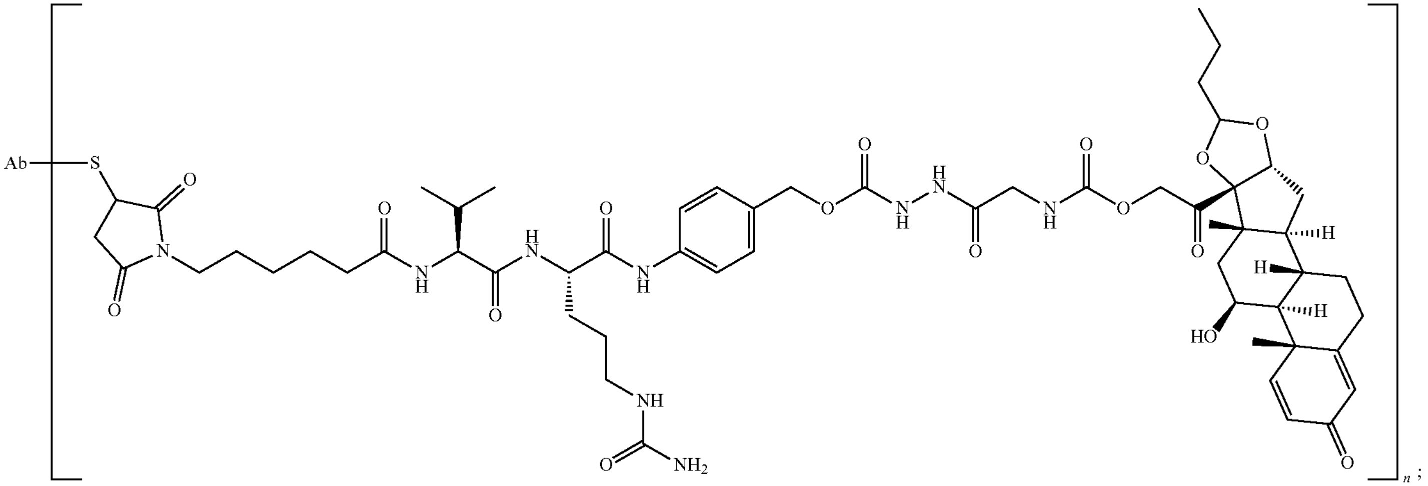 |
| or a stereoisomer or mixture of stereoisomers thereof |

TABLE 2-continued
List of ADCs and their structures
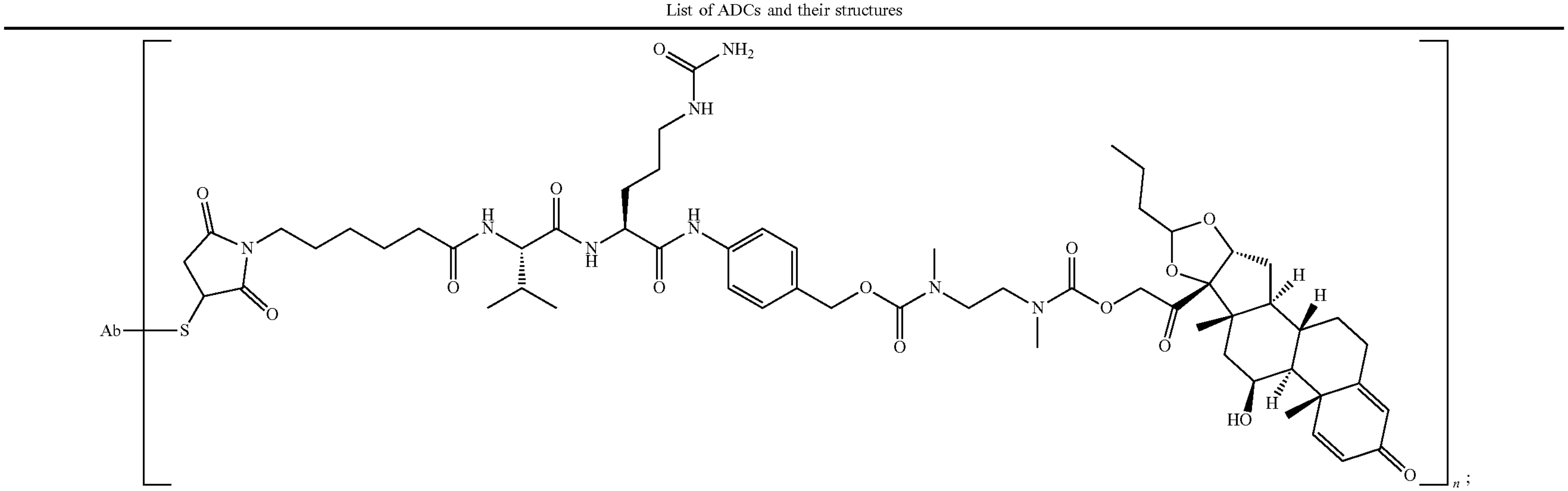
or a stereoisomer or mixture of stereoisomers thereof
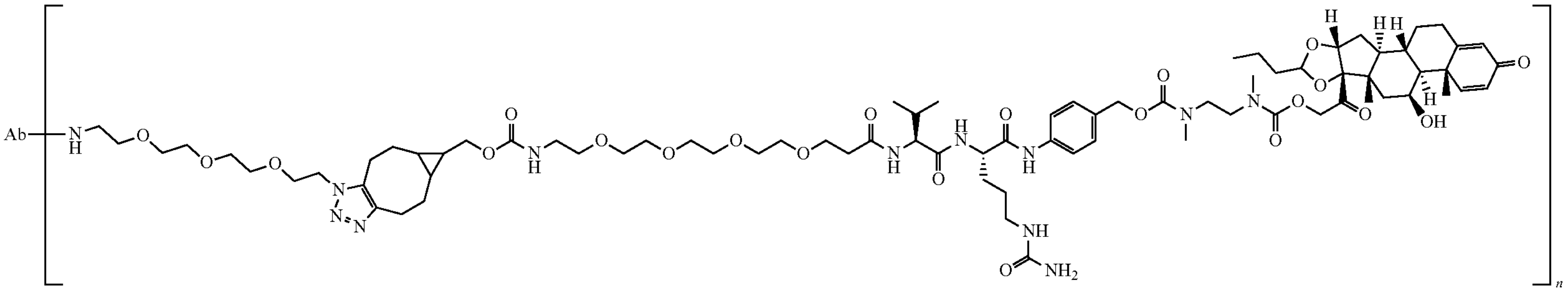

TABLE 2-continued
List of ADCs and their structures
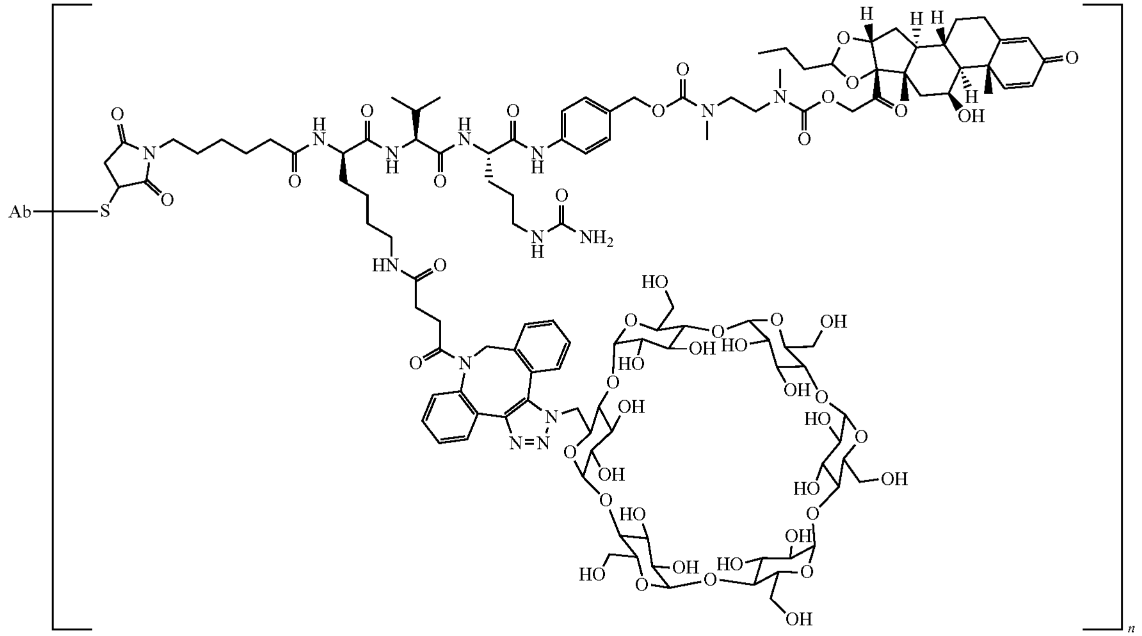

TABLE 2-continued
| List of ADCs and their structures |
| --- |
| 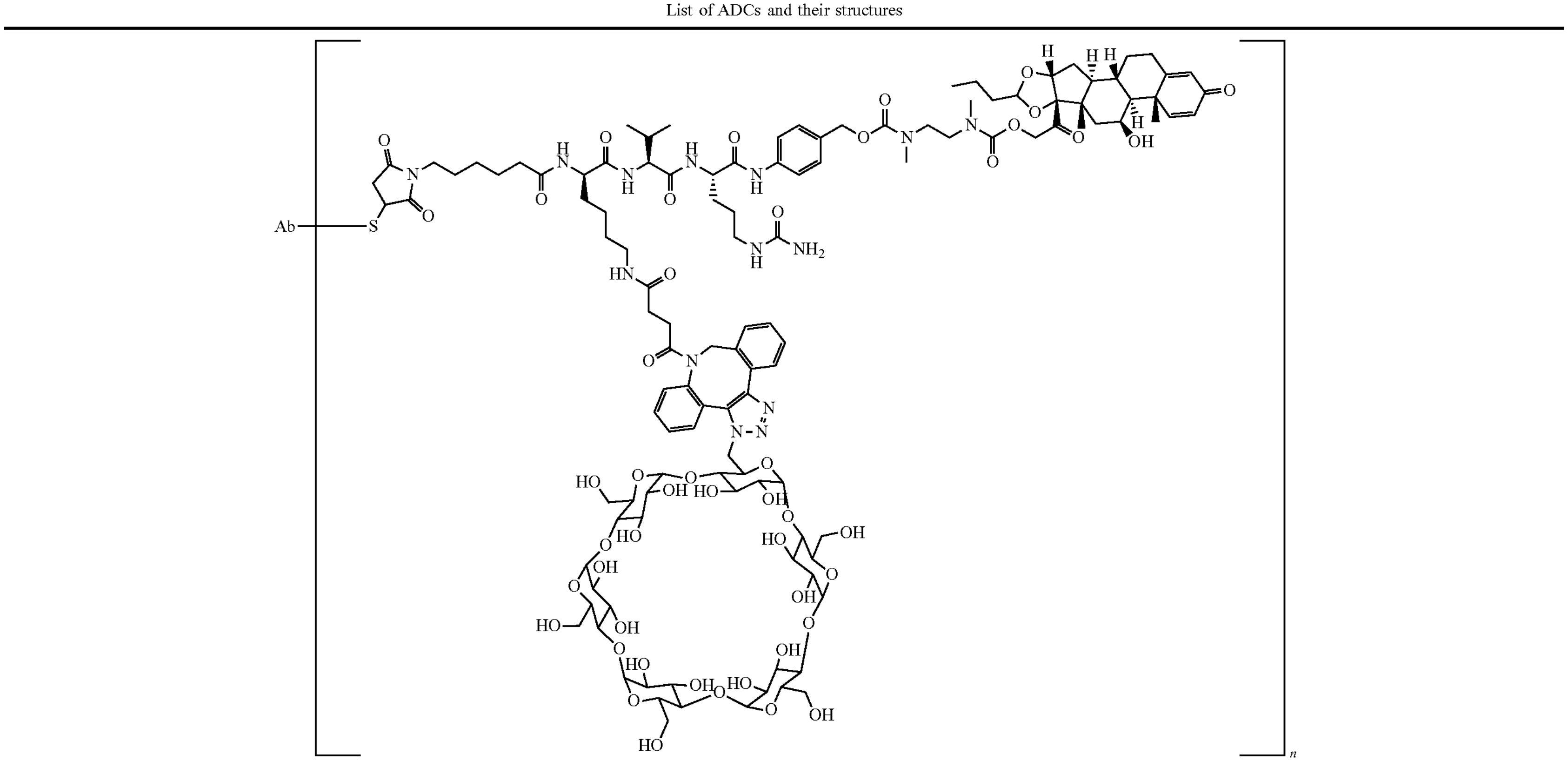 |
| or a mixture thereof |

TABLE 2-continued
List of ADCs and their structures
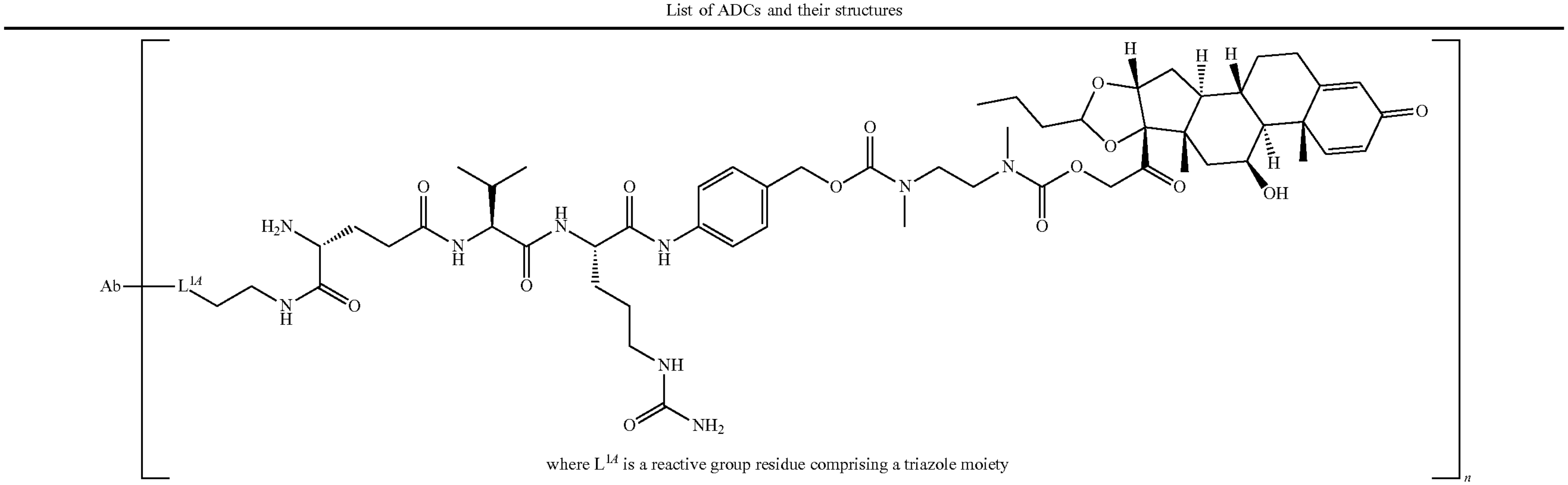
where $L^{1A}$ is a reactive group residue comprising a triazole moiety
or a mixture thereof
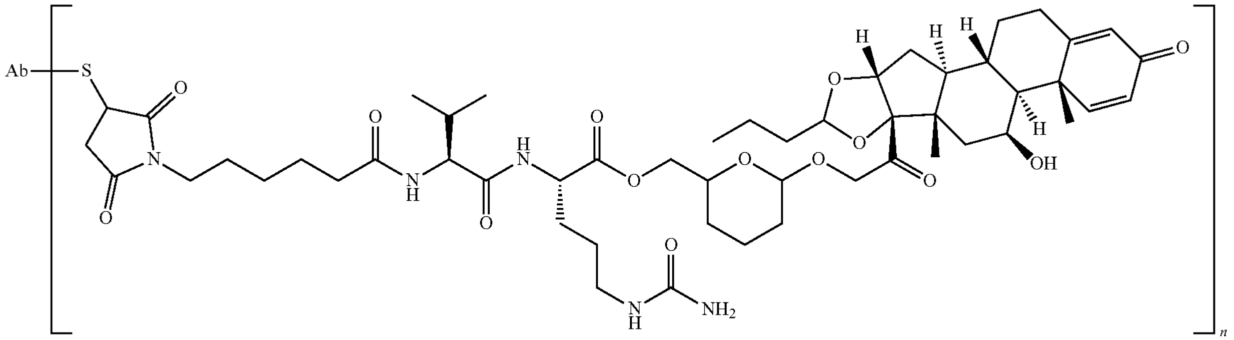
or a stereoisomer or mixture of stereoisomers thereof TABLE 2-continued
List of ADCs and their structures
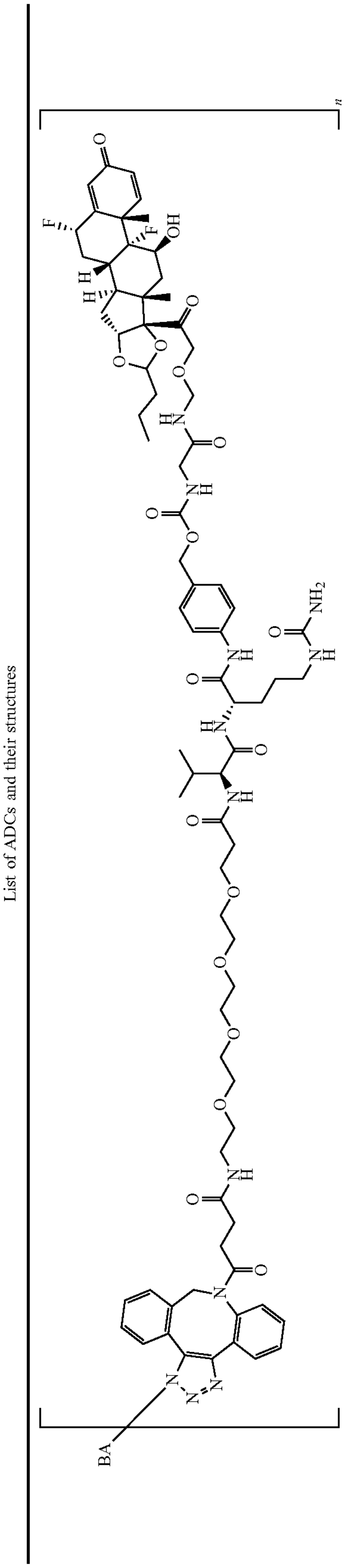
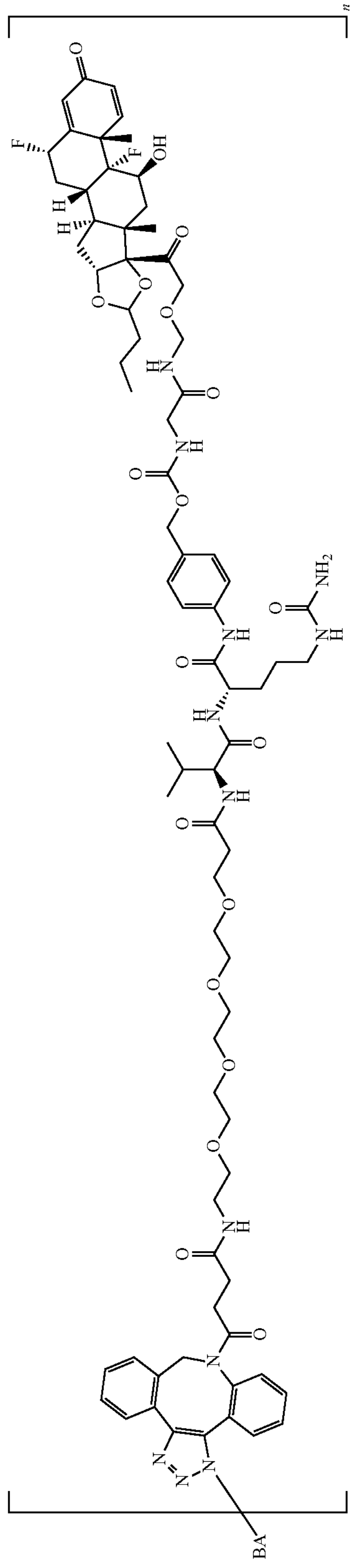
or a mixture thereof TABLE 2-continued
List of ADCs and their structures
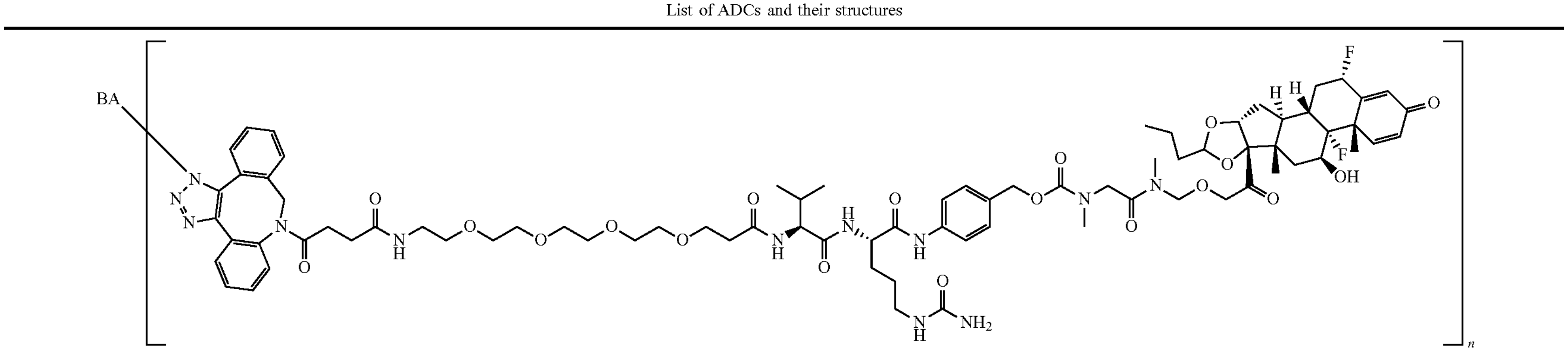
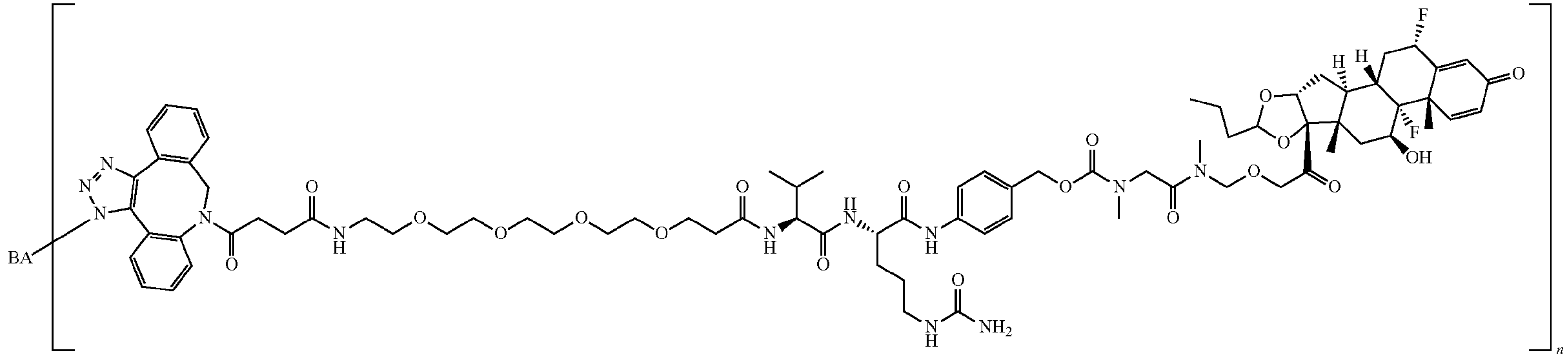
or a mixture thereof TABLE 2-continued
List of ADCs and their structures
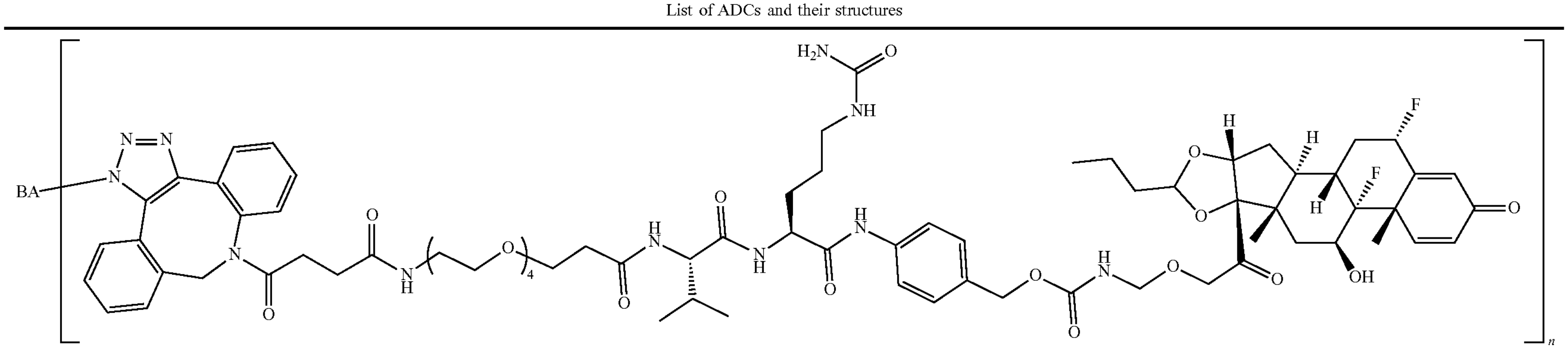
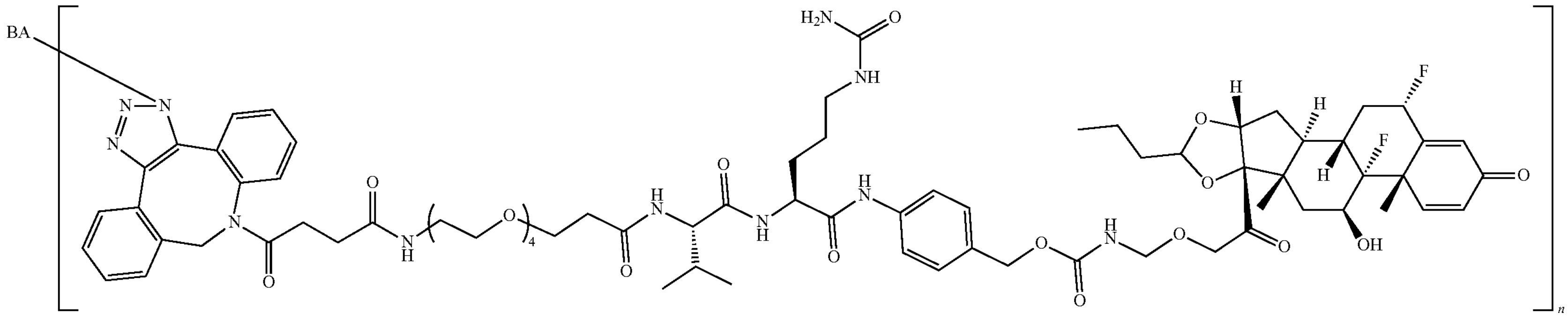
or a mixture thereof TABLE 2-continued
| List of ADCs and their structures |
| --- |
| 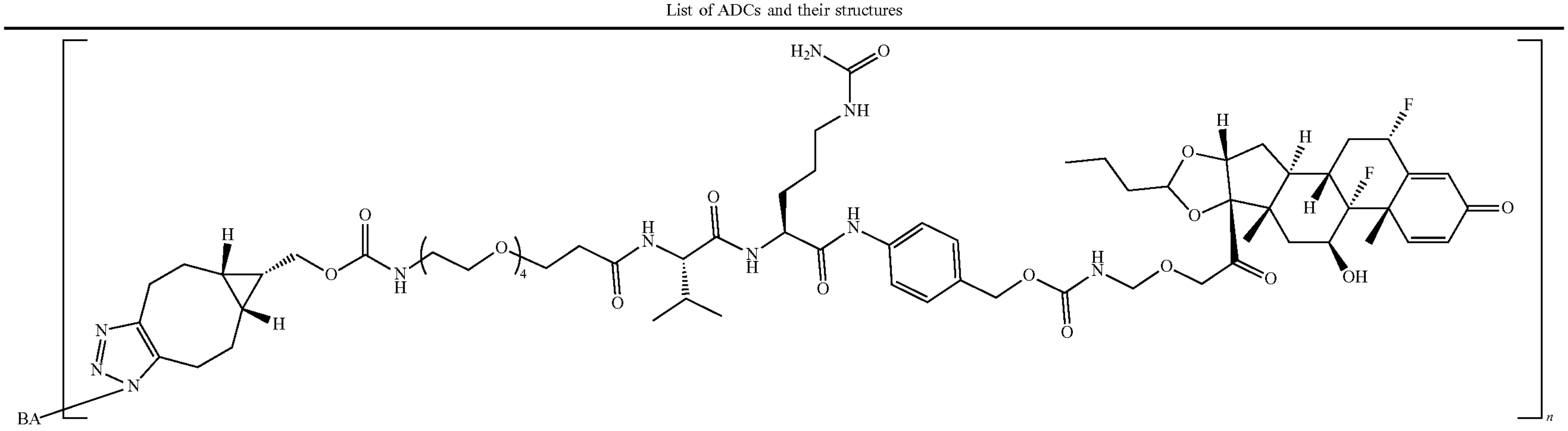 |
| 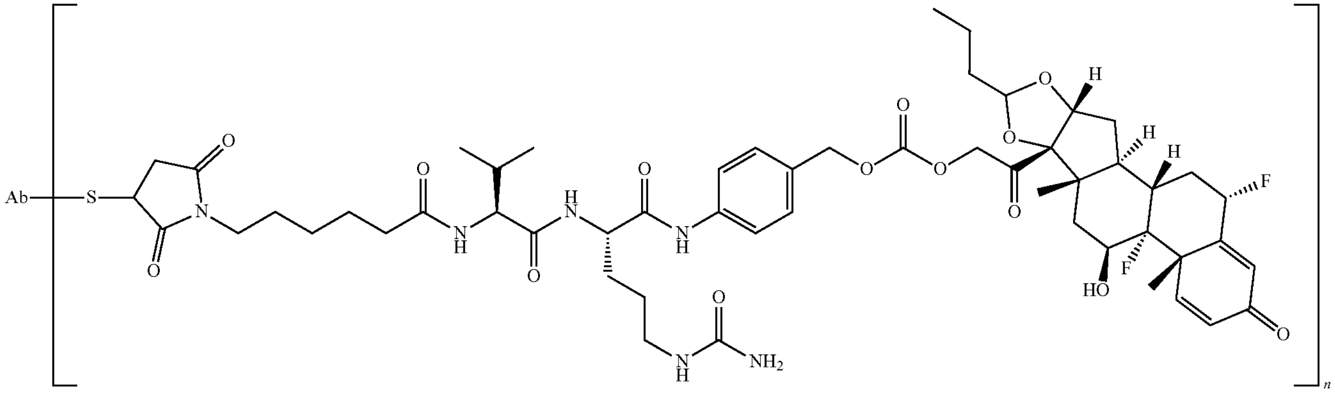 |

TABLE 2-continued
List of ADCs and their structures
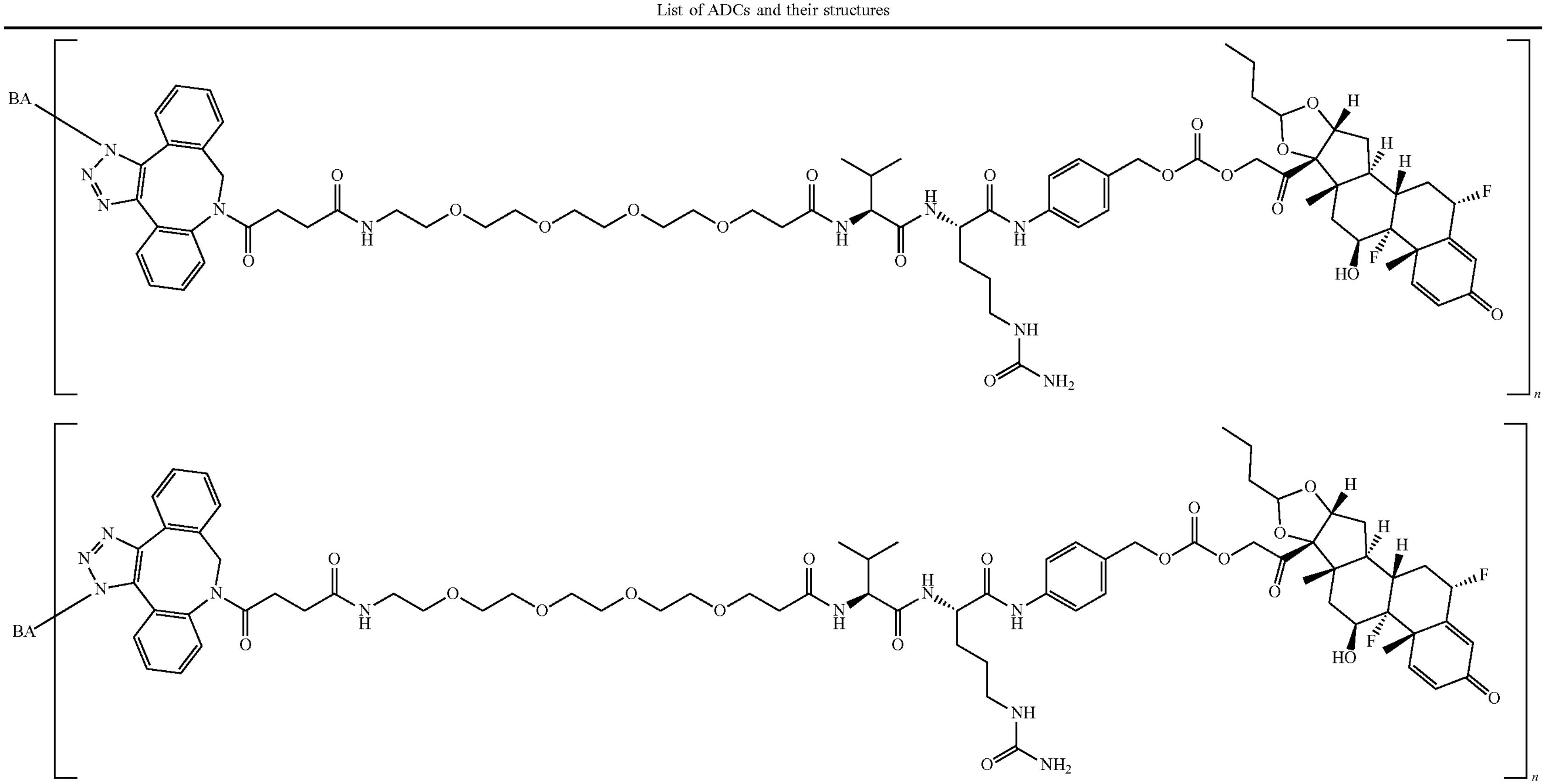
or a mixture thereof TABLE 2-continued
List of ADCs and their structures
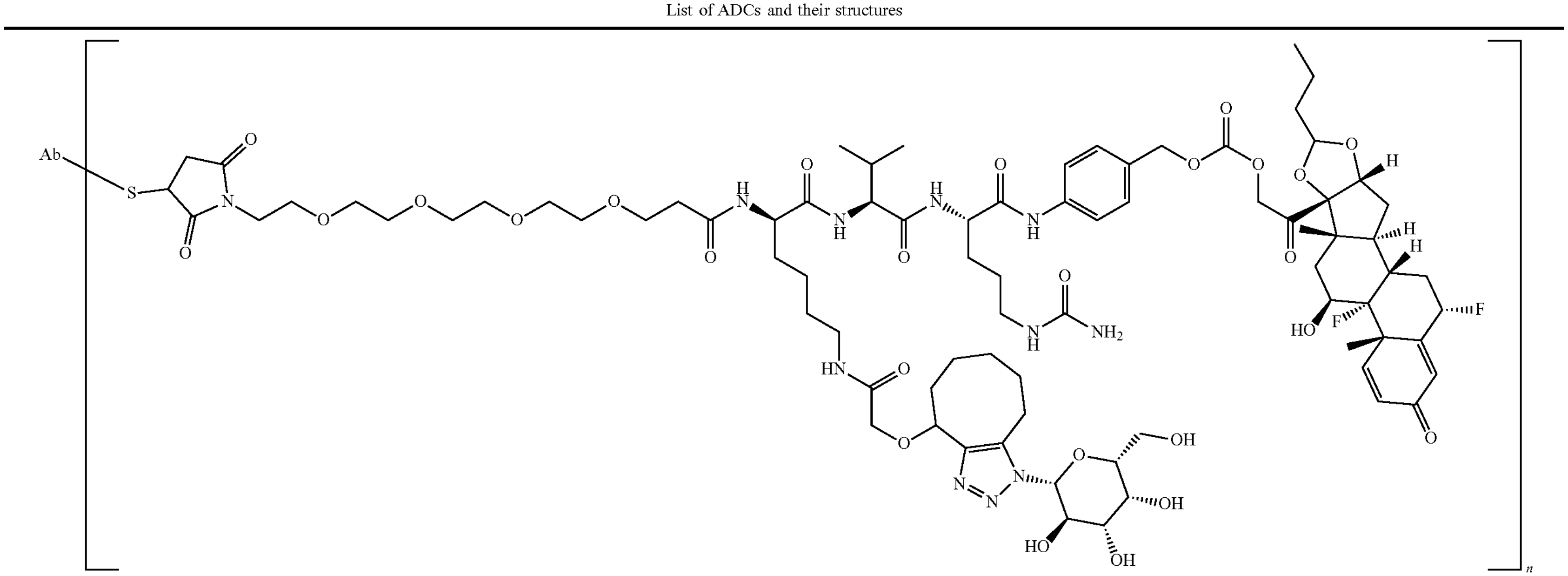

TABLE 2-continued
List of ADCs and their structures
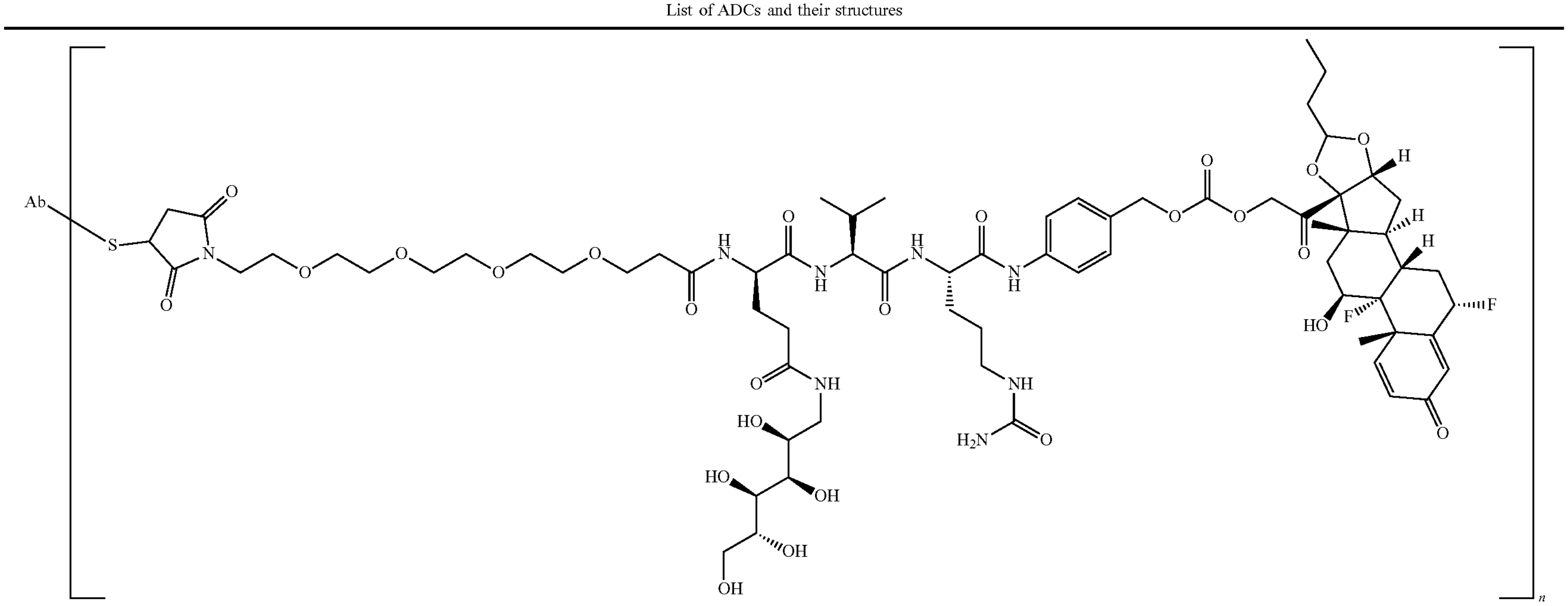
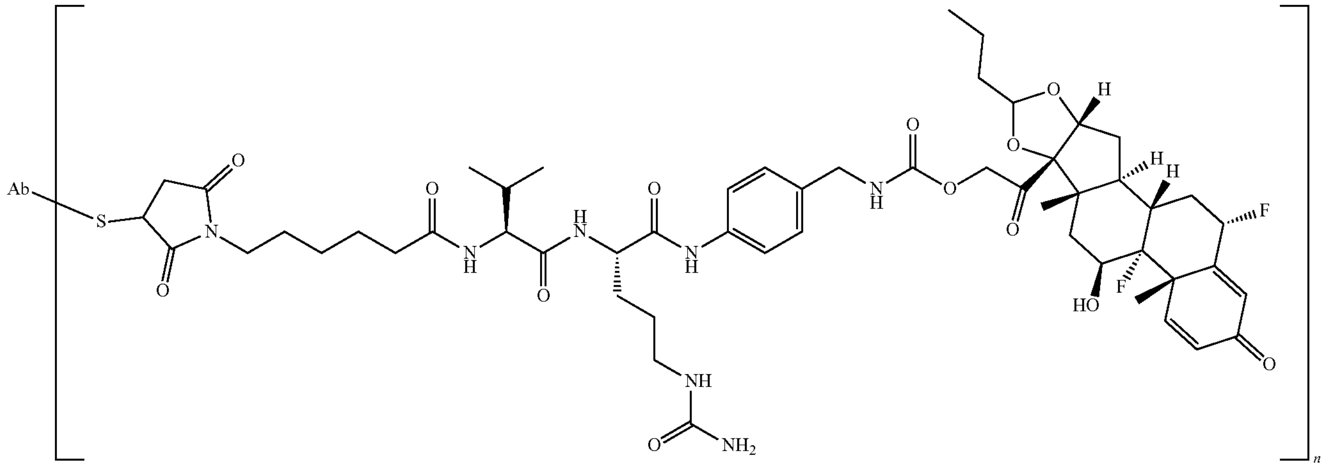

TABLE 2-continued
| List of ADCs and their structures |
| --- |
| 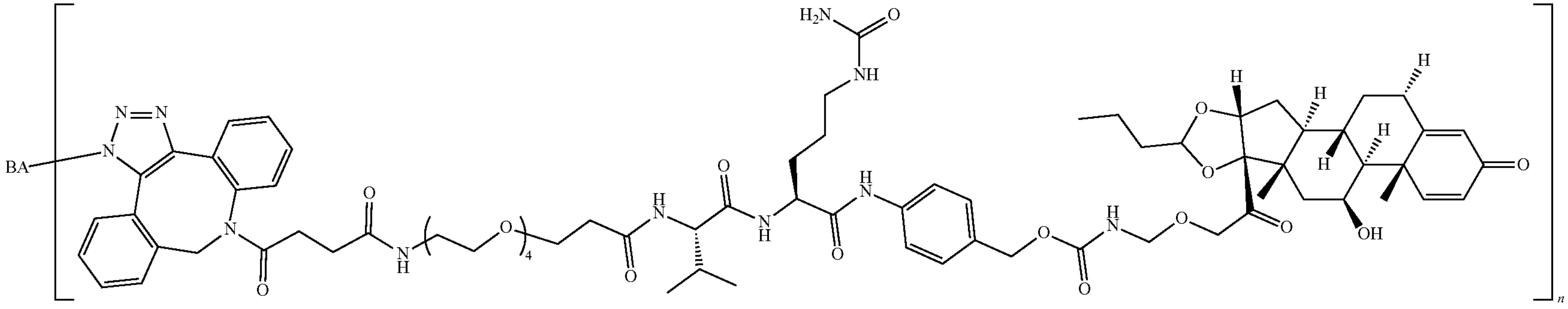 |
| 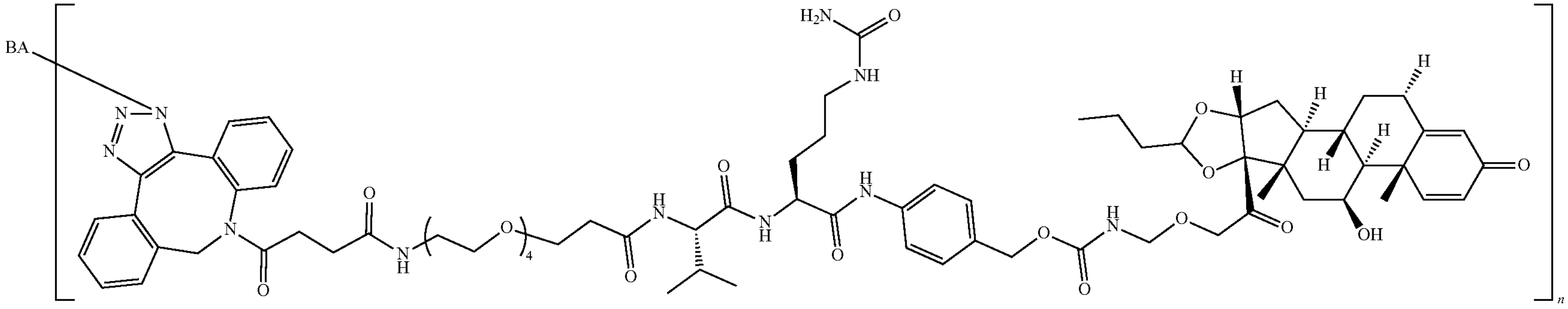 |
| or a mixture thereof |

TABLE 2-continued
List of ADCs and their structures
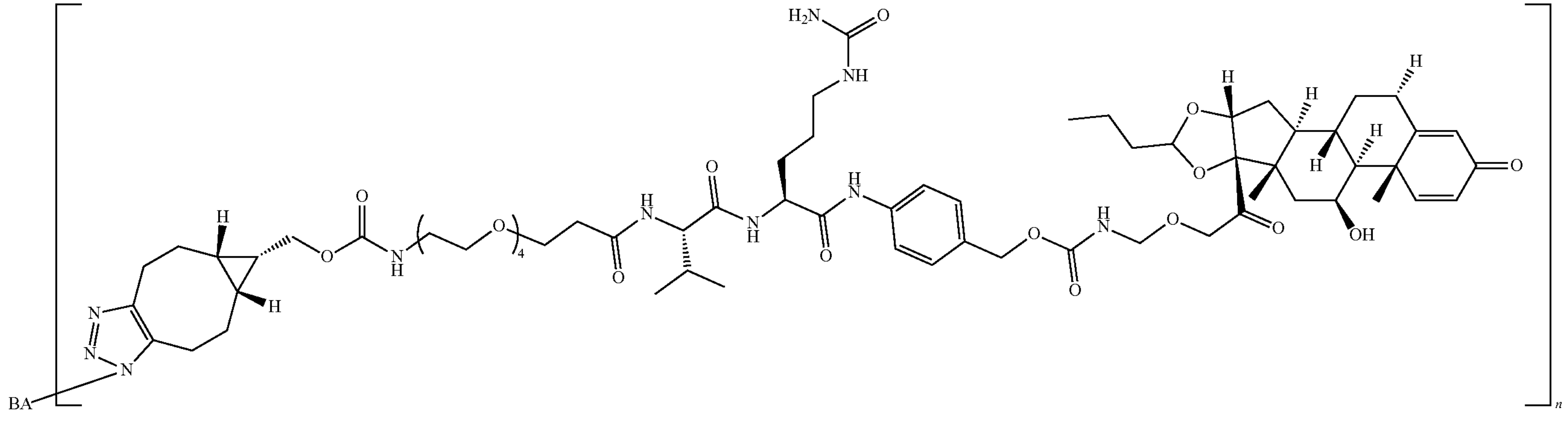
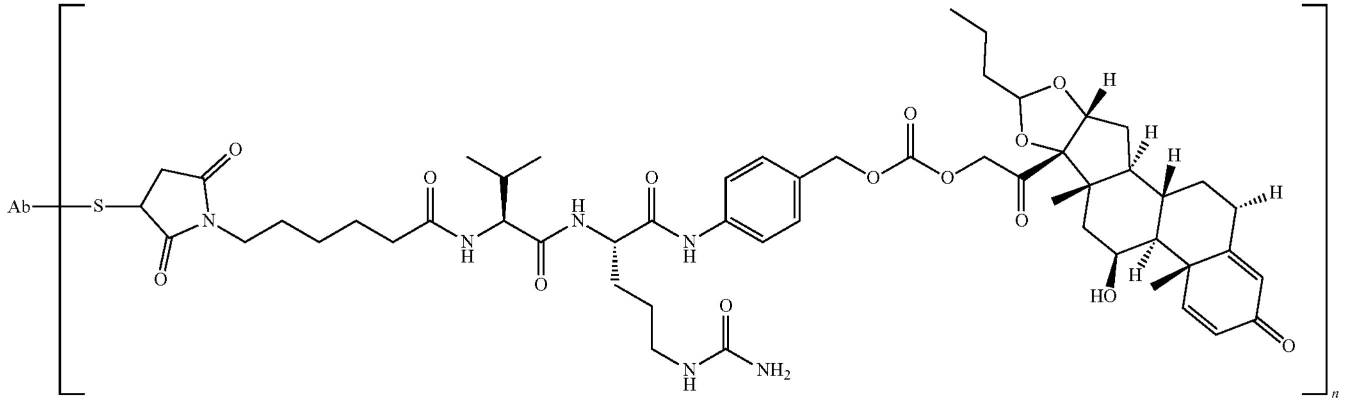

TABLE 2-continued
List of ADCs and their structures
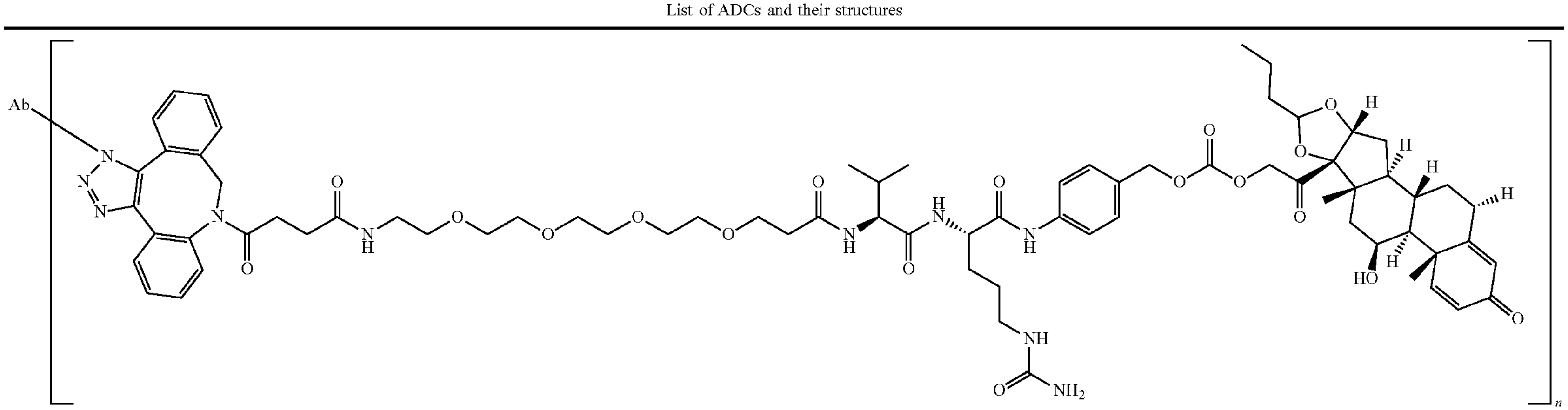
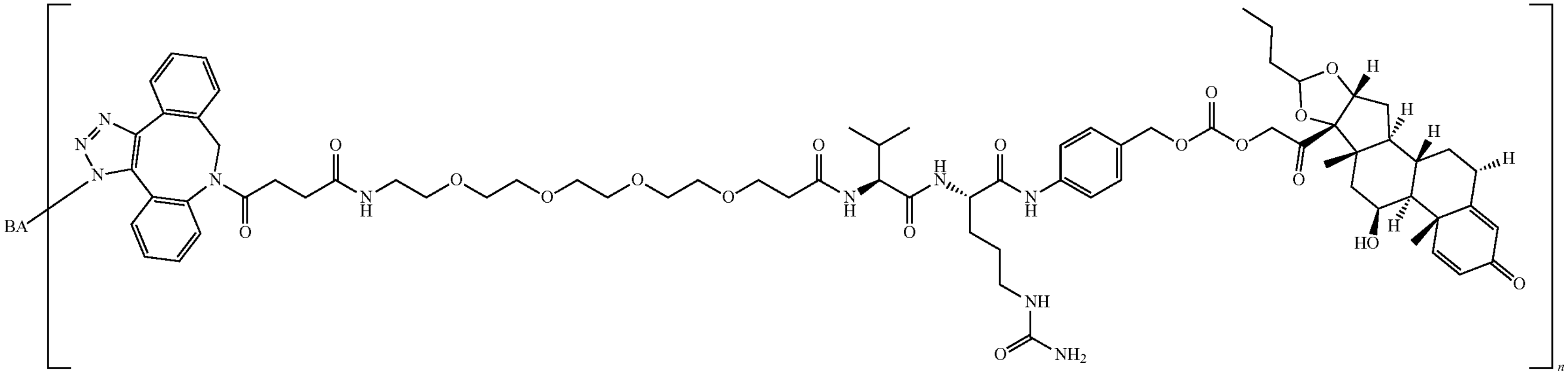
or a mixture thereof TABLE 2-continued
| List of ADCs and their structures |
|---|
| 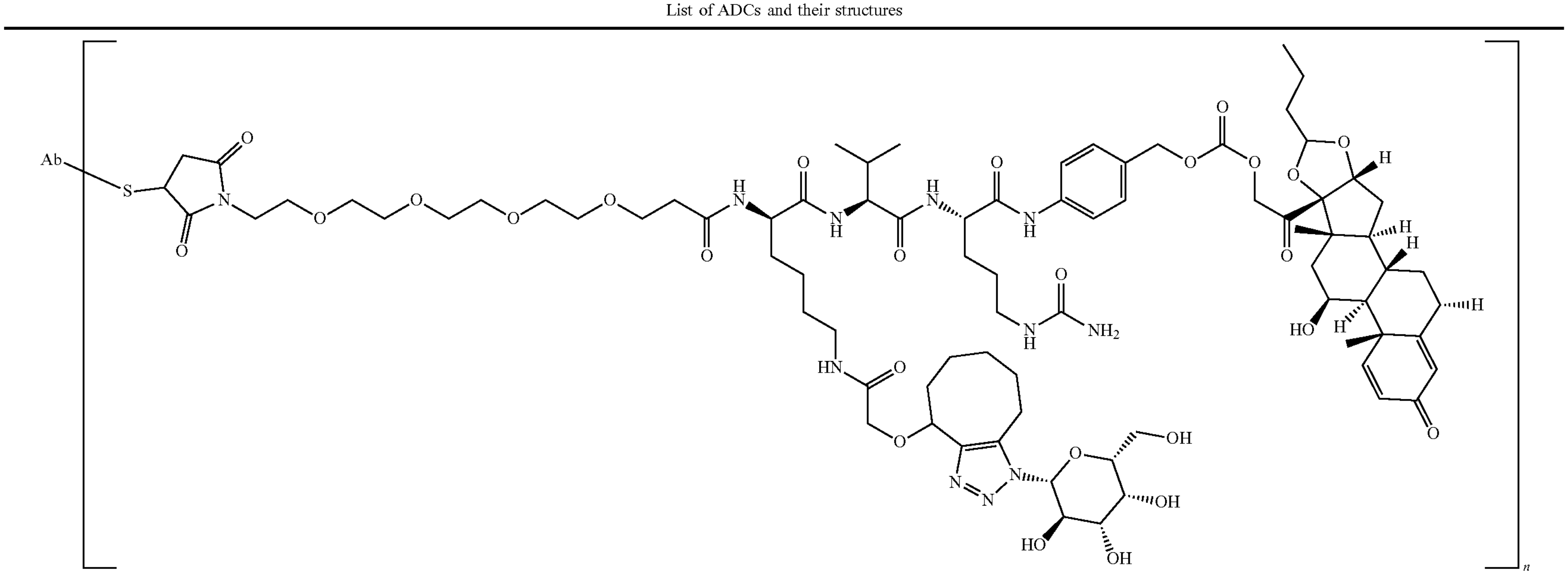 |

TABLE 2-continued
List of ADCs and their structures
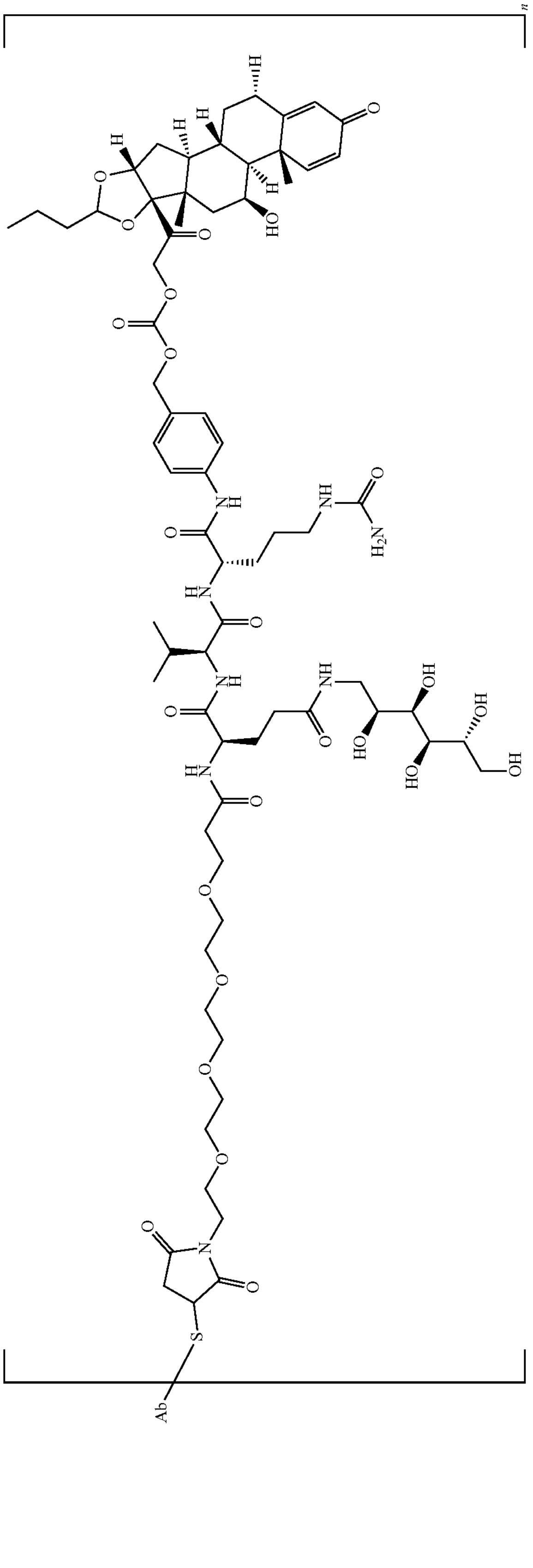
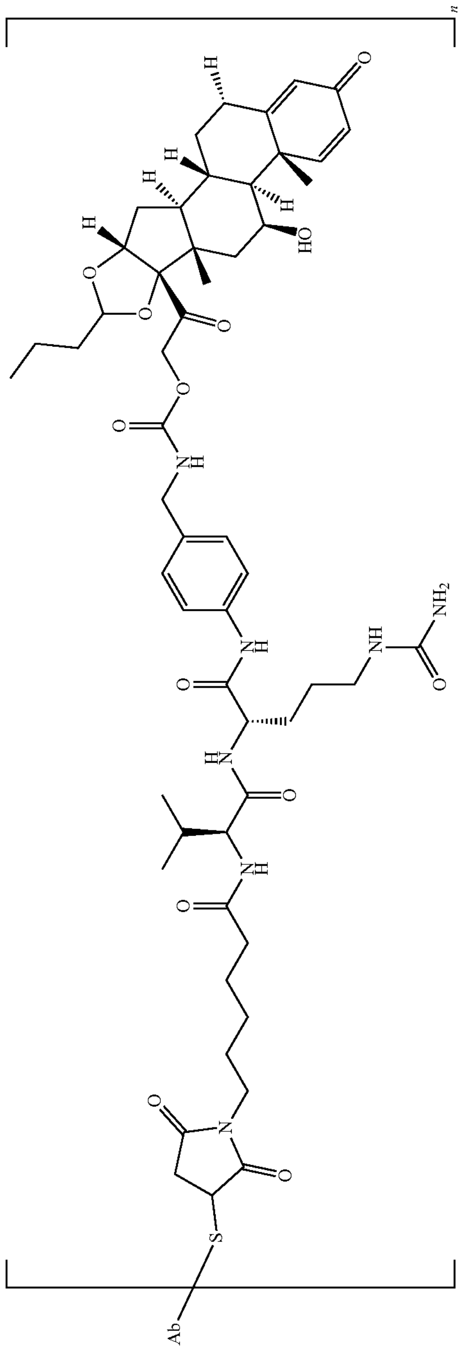

TABLE 2-continued
List of ADCs and their structures
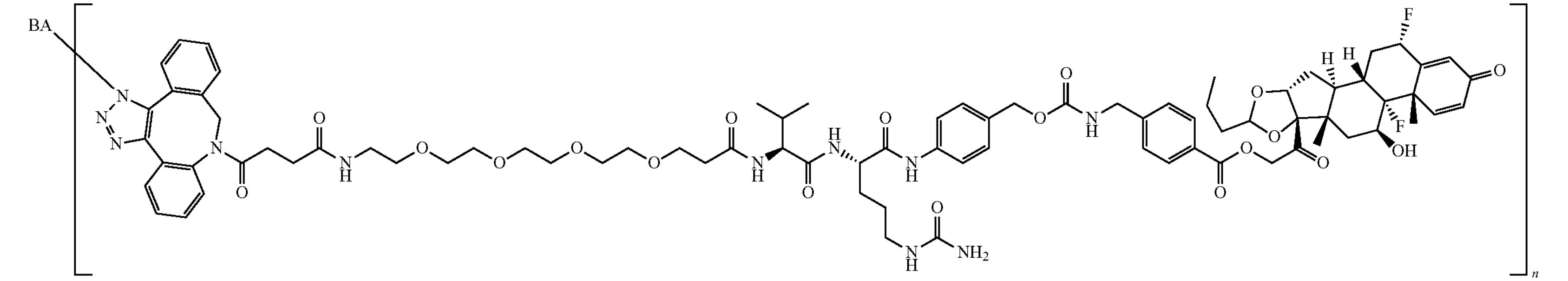
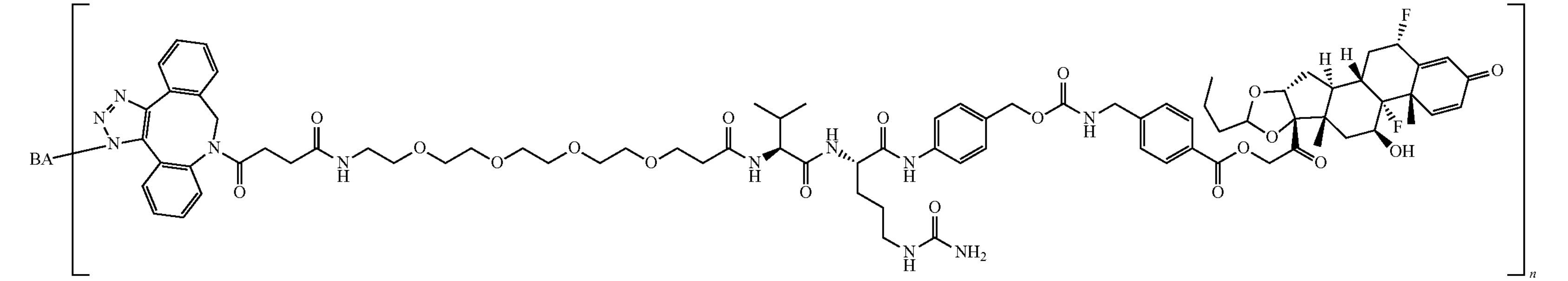
or a mixture thereof
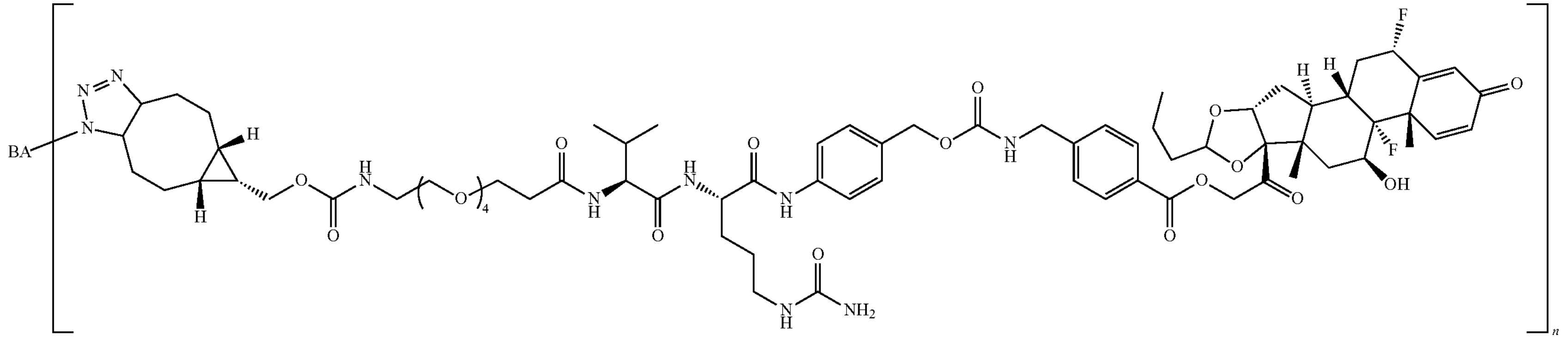

TABLE 2-continued
List of ADCs and their structures
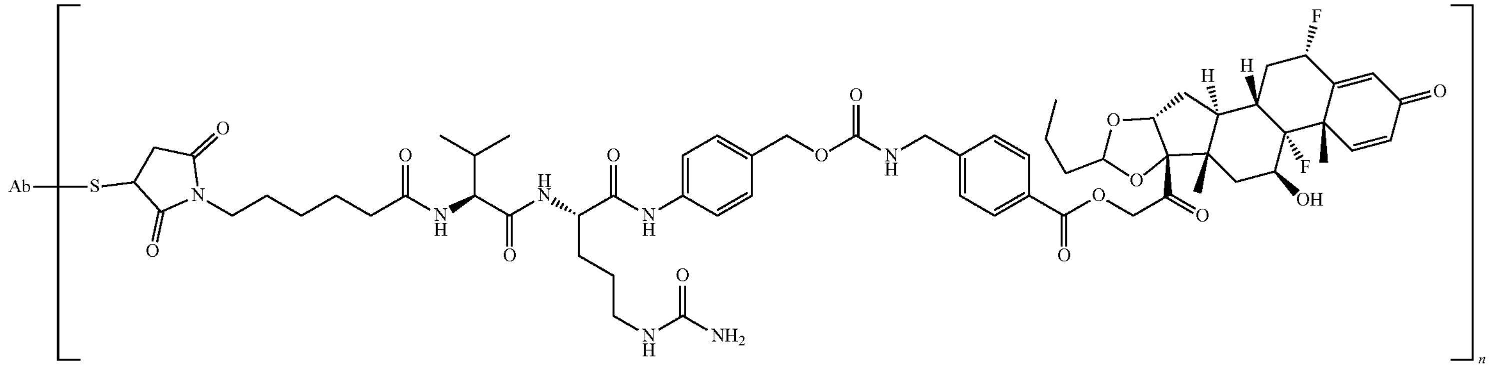
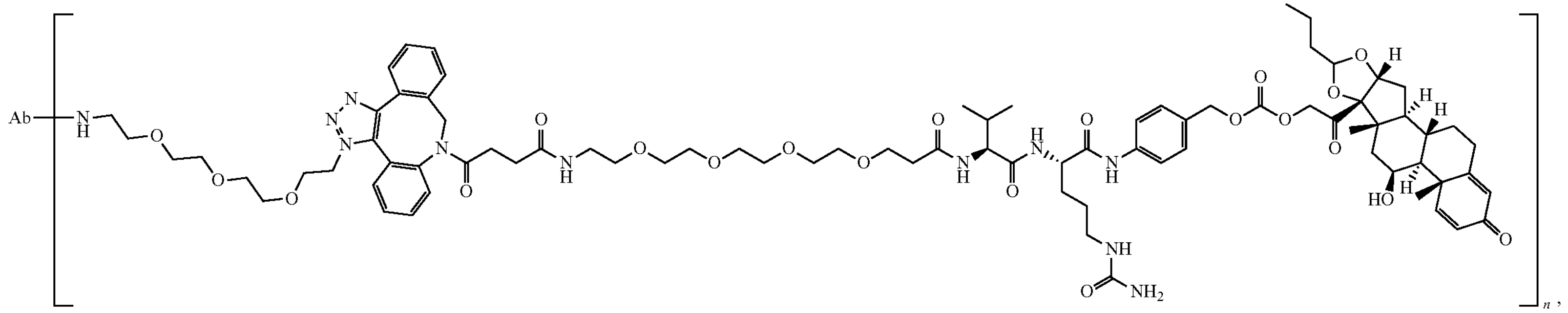
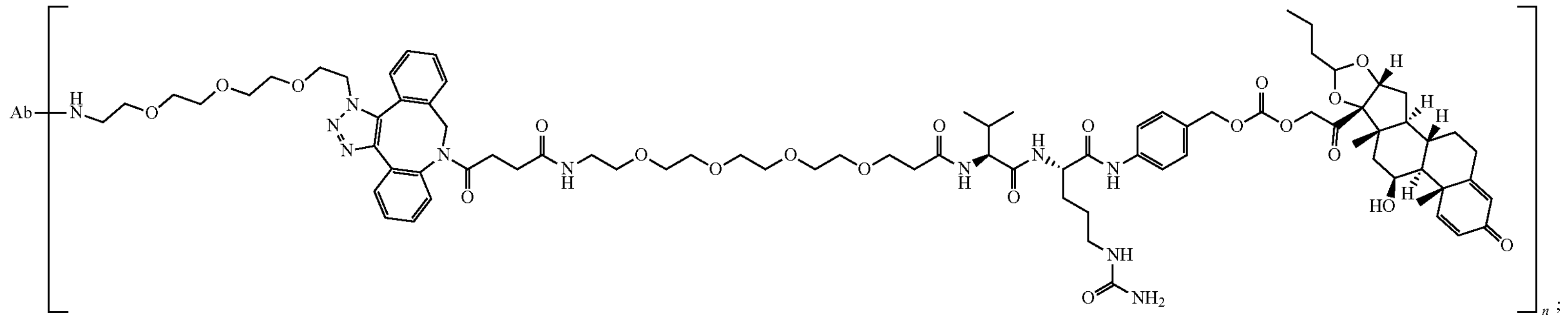
or a mixture thereof TABLE 2-continued
List of ADCs and their structures
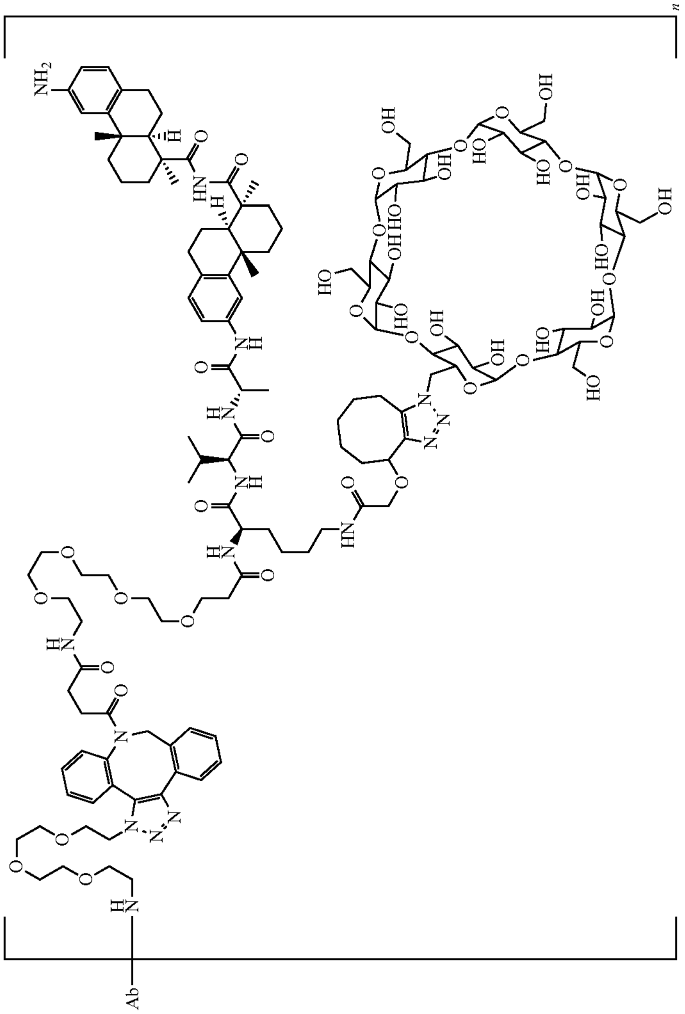

TABLE 2-continued
List of ADCs and their structures
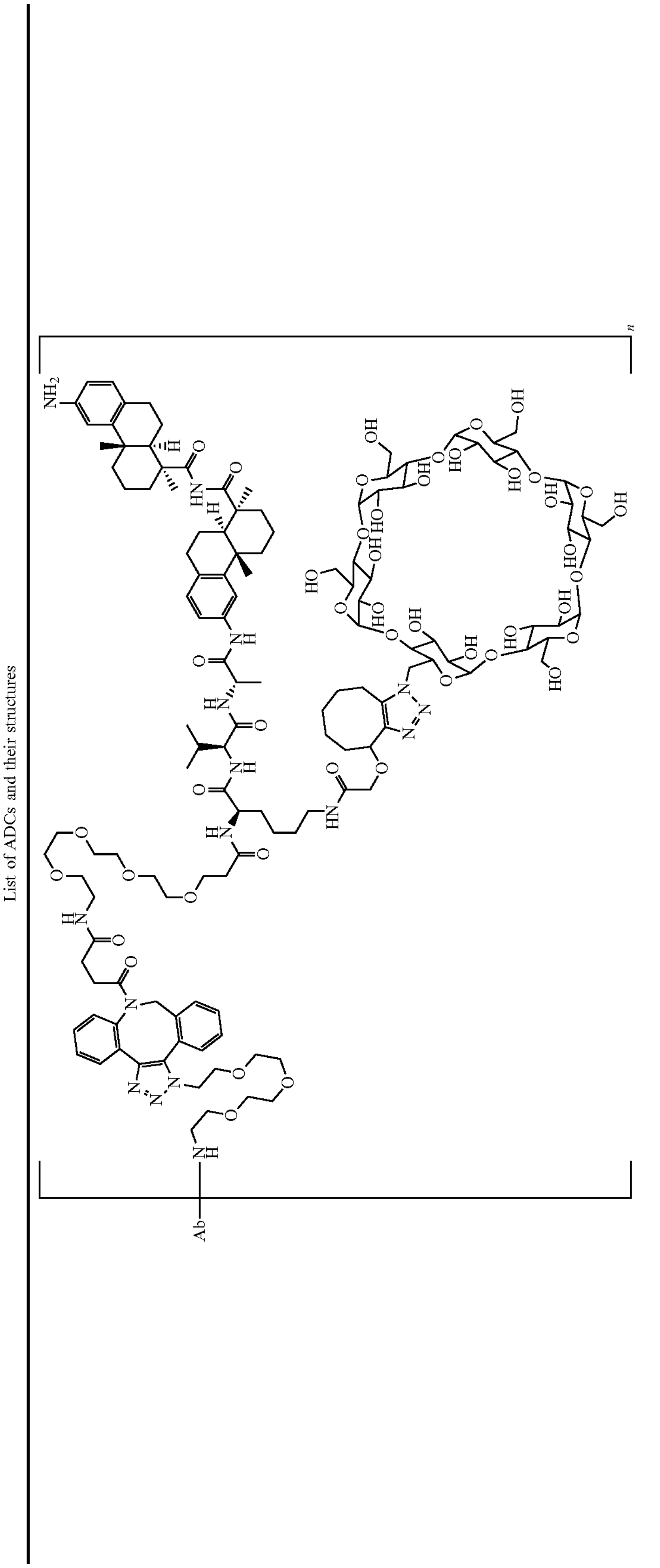

TABLE 2-continued
List of ADCs and their structures
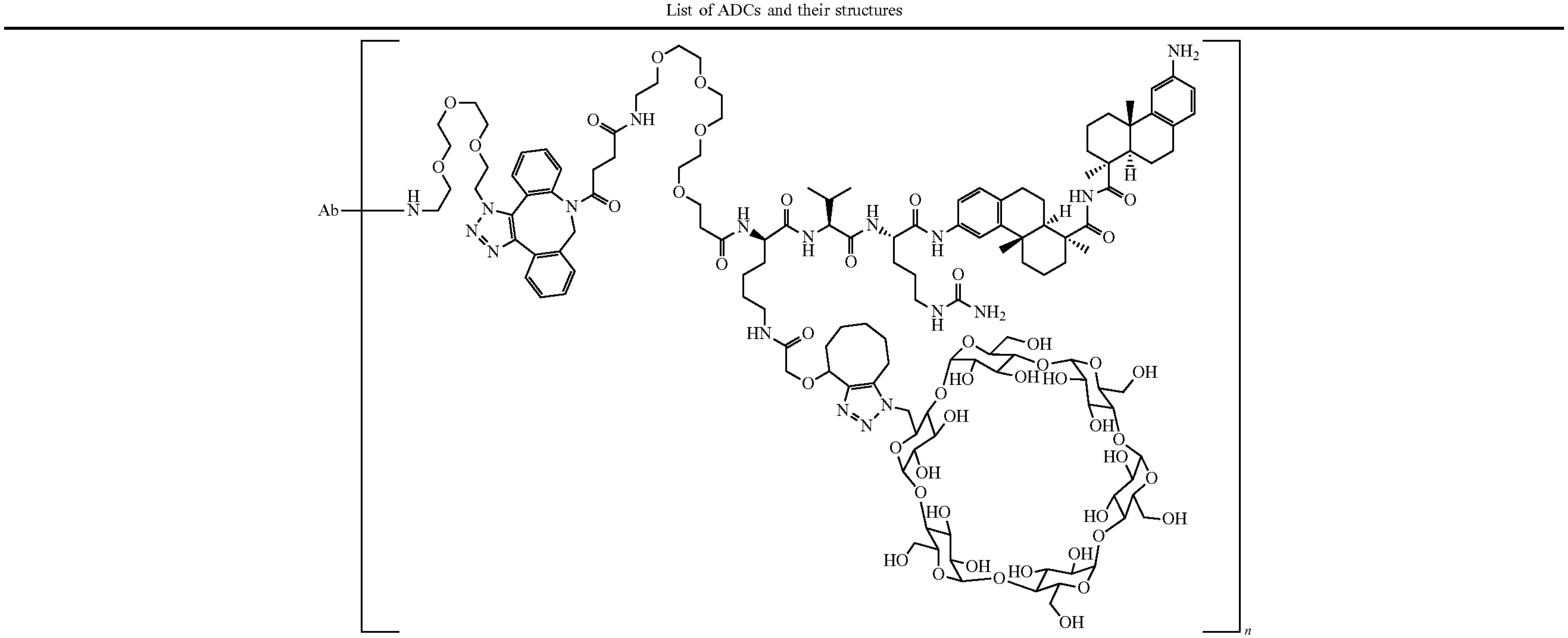

TABLE 2-continued
List of ADCs and their structures
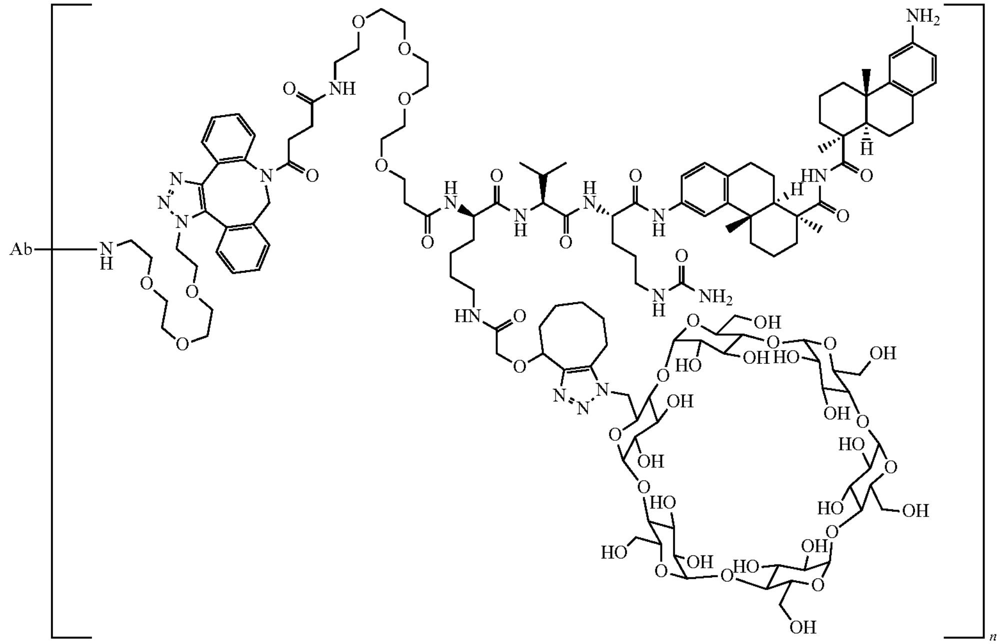

TABLE 2-continued
List of ADCs and their structures
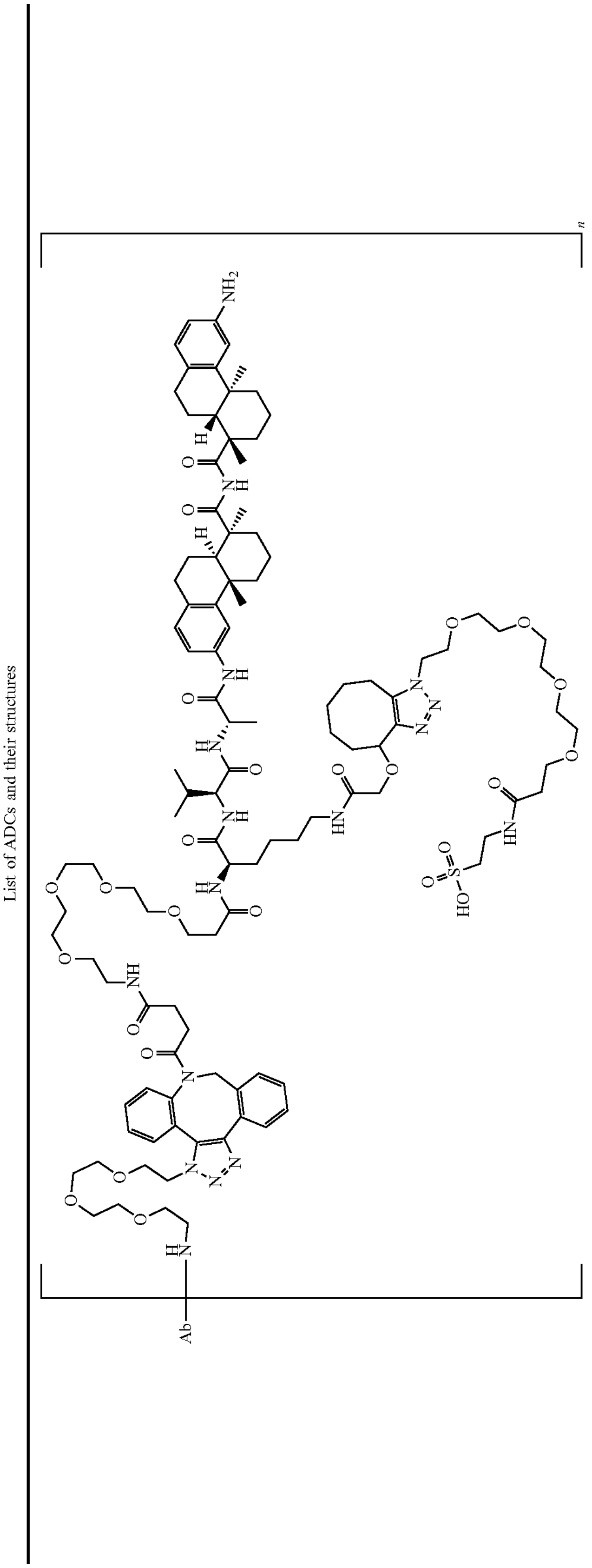

TABLE 2-continued
List of ADCs and their structures
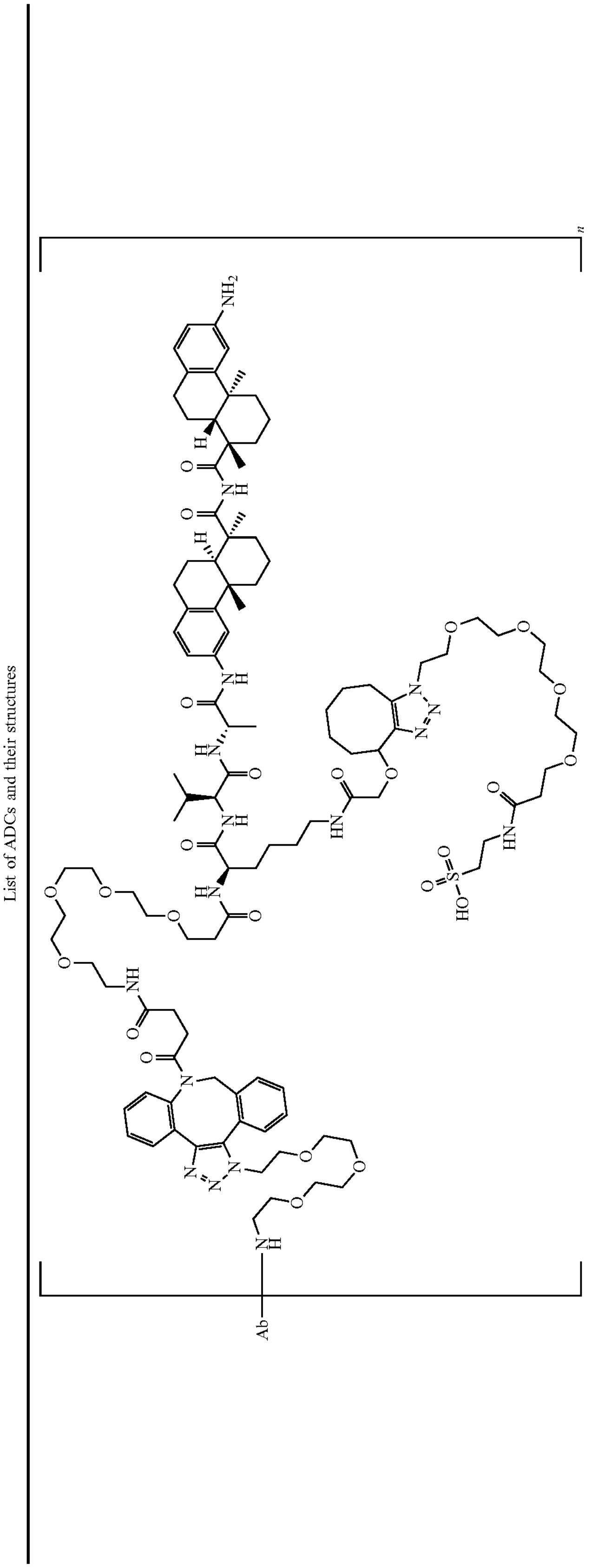

TABLE 2-continued
List of ADCs and their structures
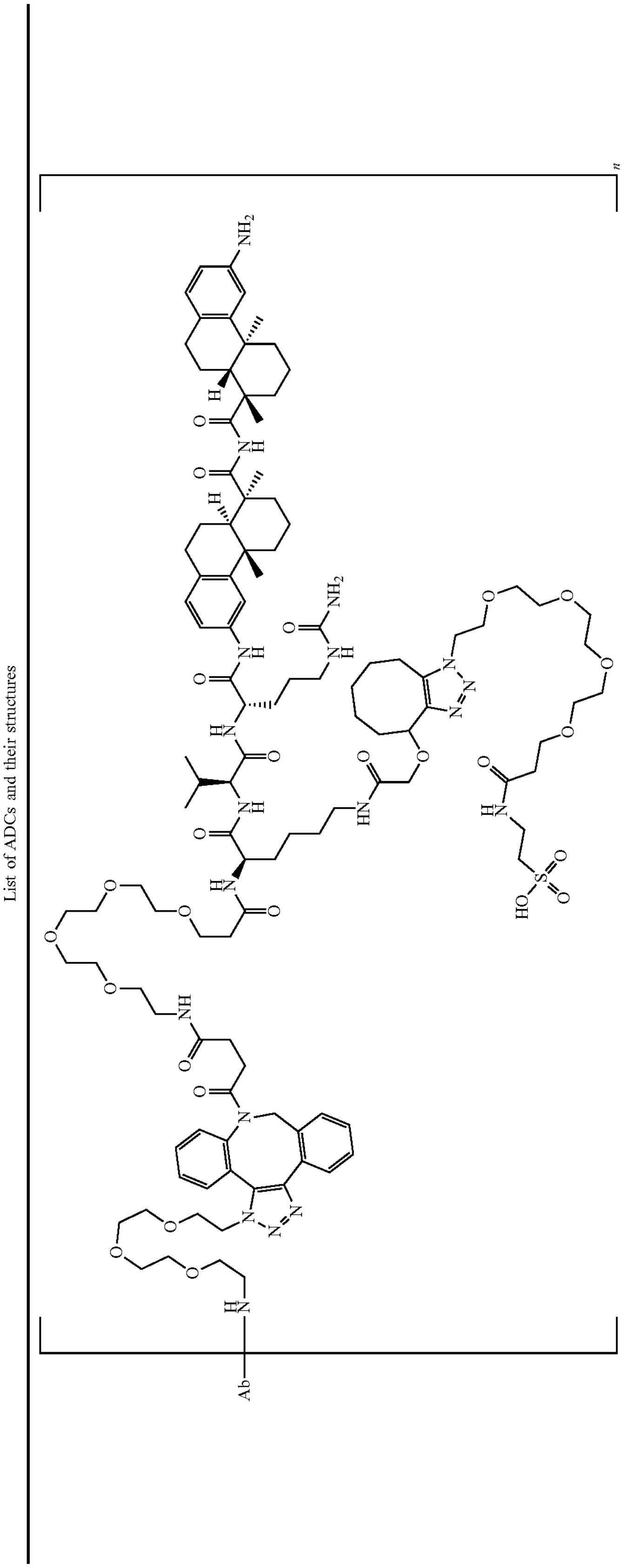

TABLE 2-continued
List of ADCs and their structures
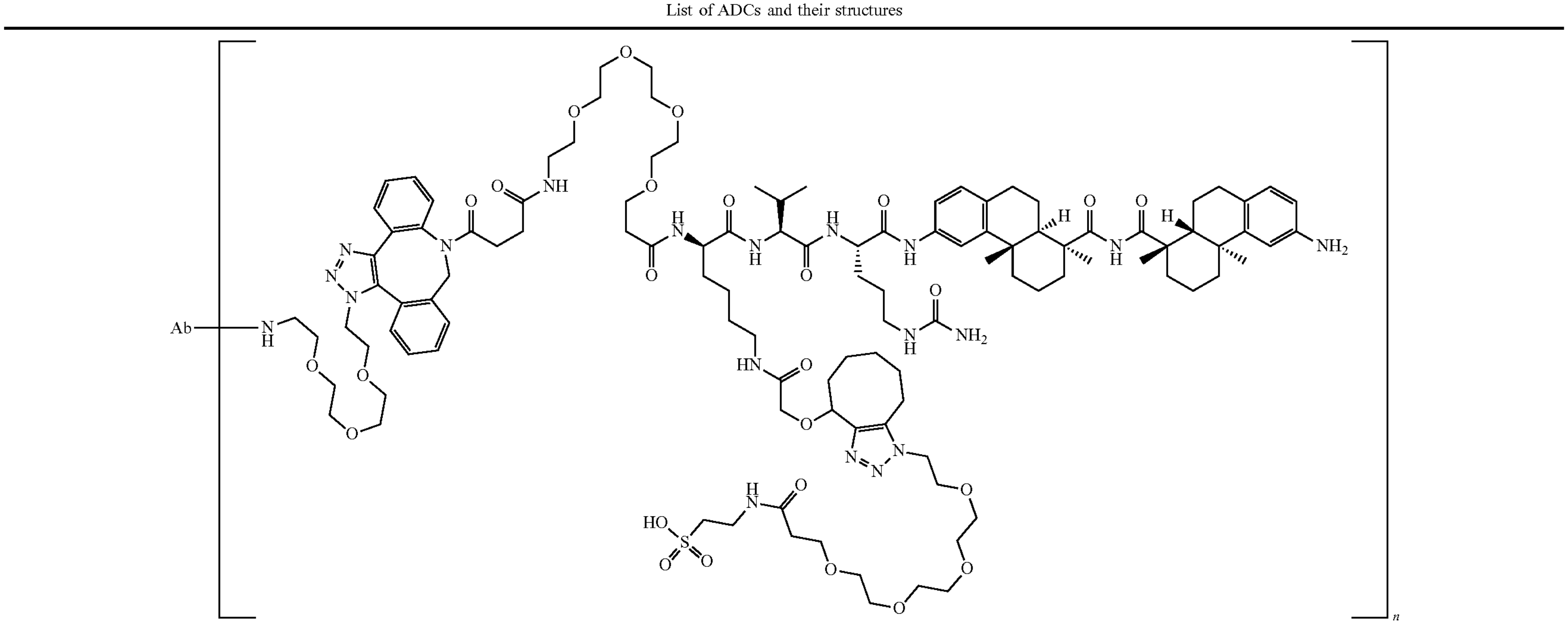

TABLE 2-continued
| List of ADCs and their structures |
| --- |
| 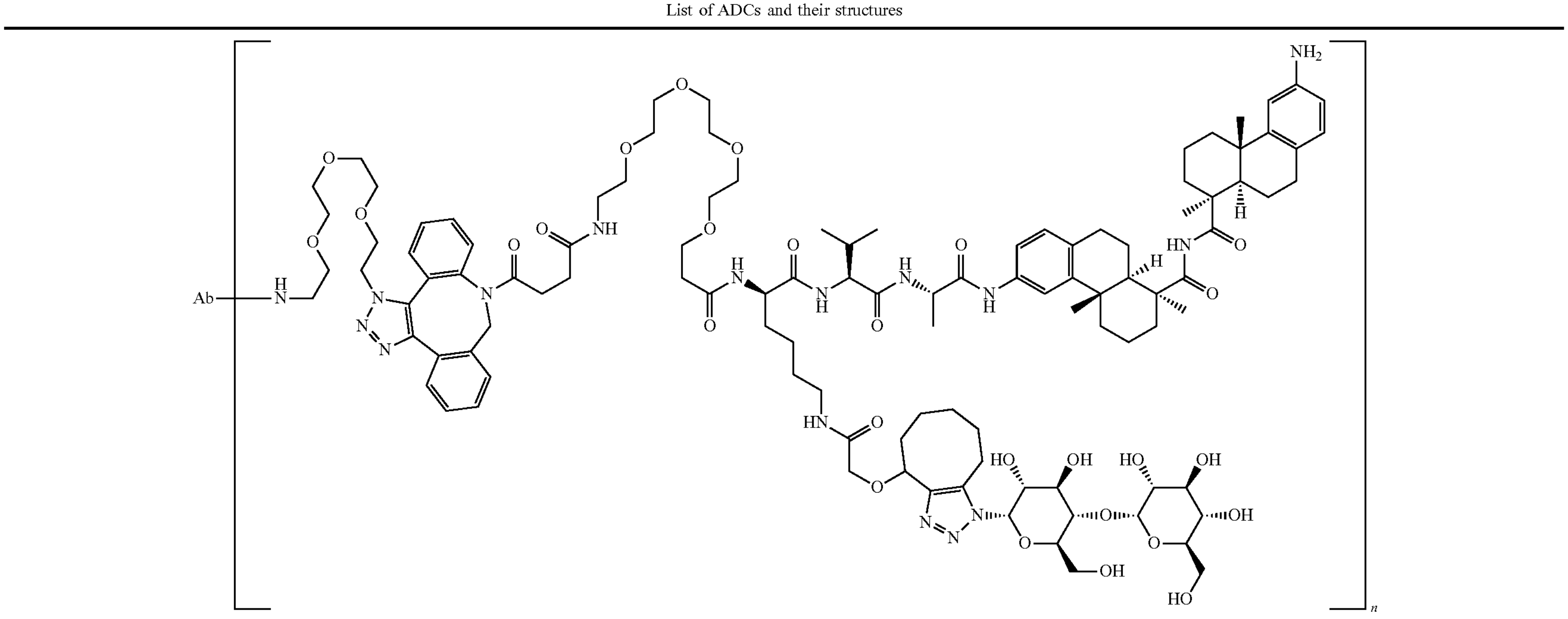 |

TABLE 2-continued
List of ADCs and their structures
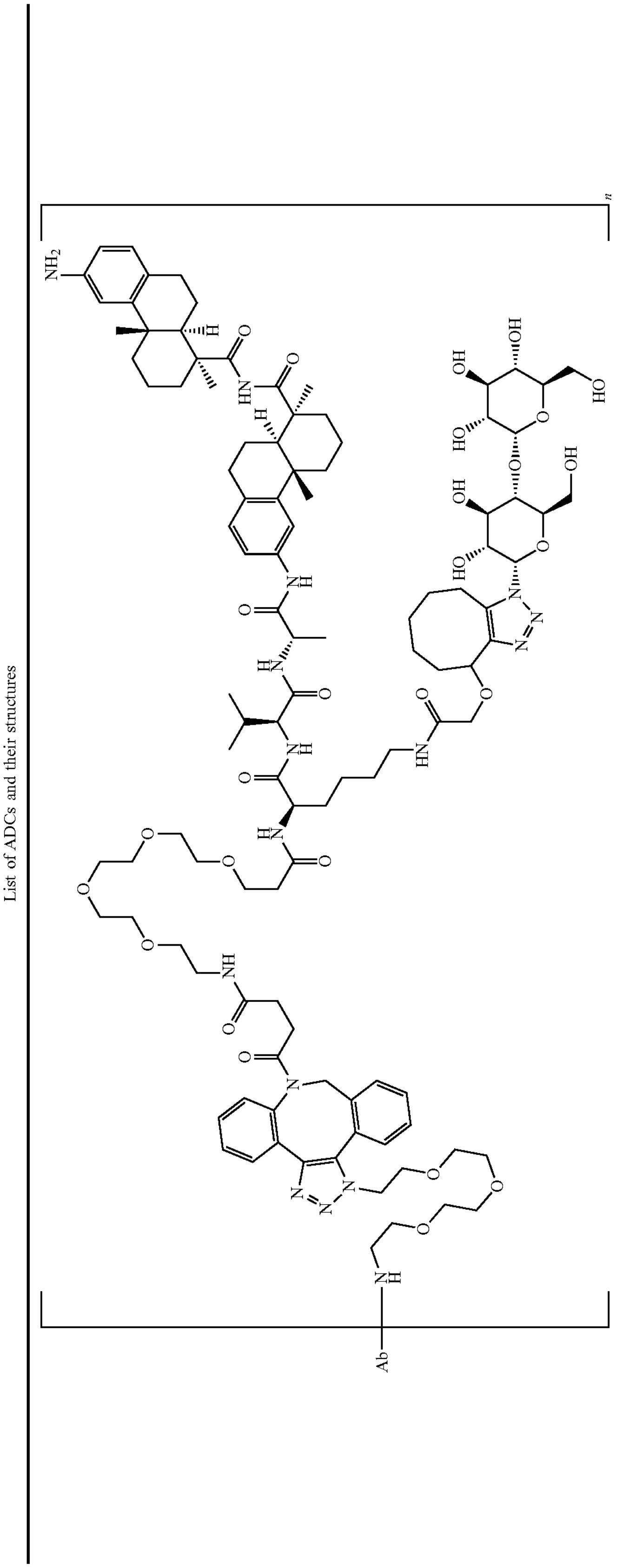

TABLE 2-continued
| List of ADCs and their structures |
| --- |
| 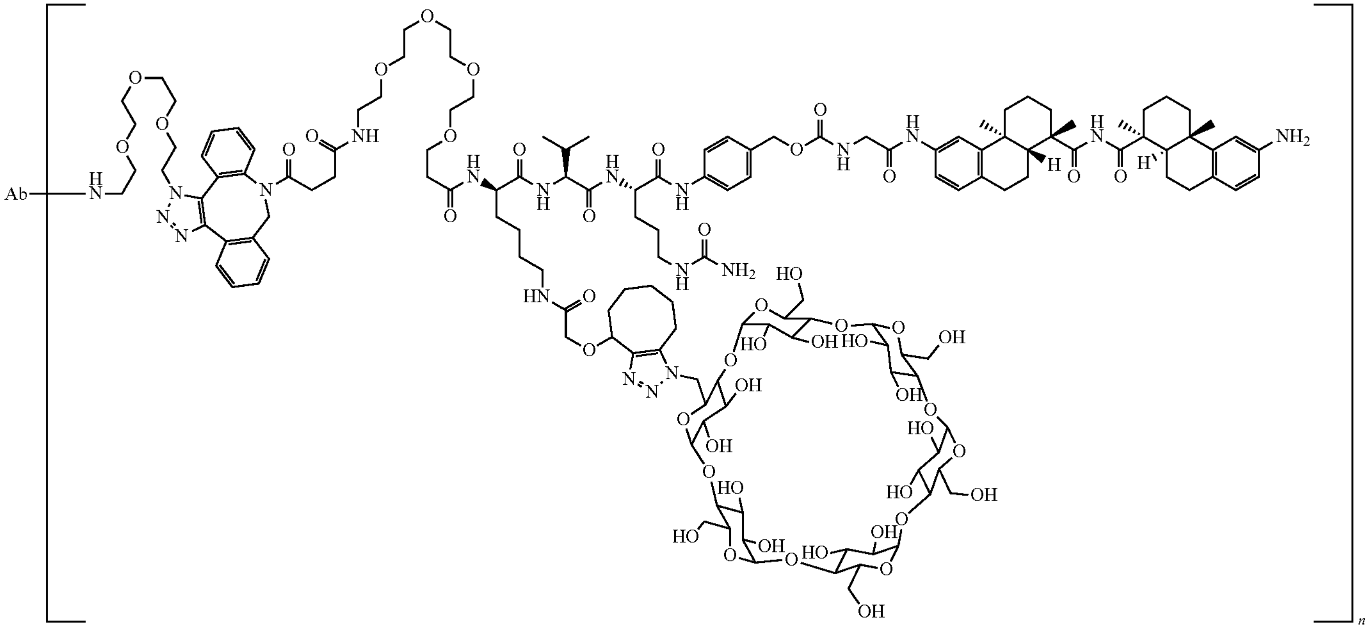 |

TABLE 2-continued
List of ADCs and their structures
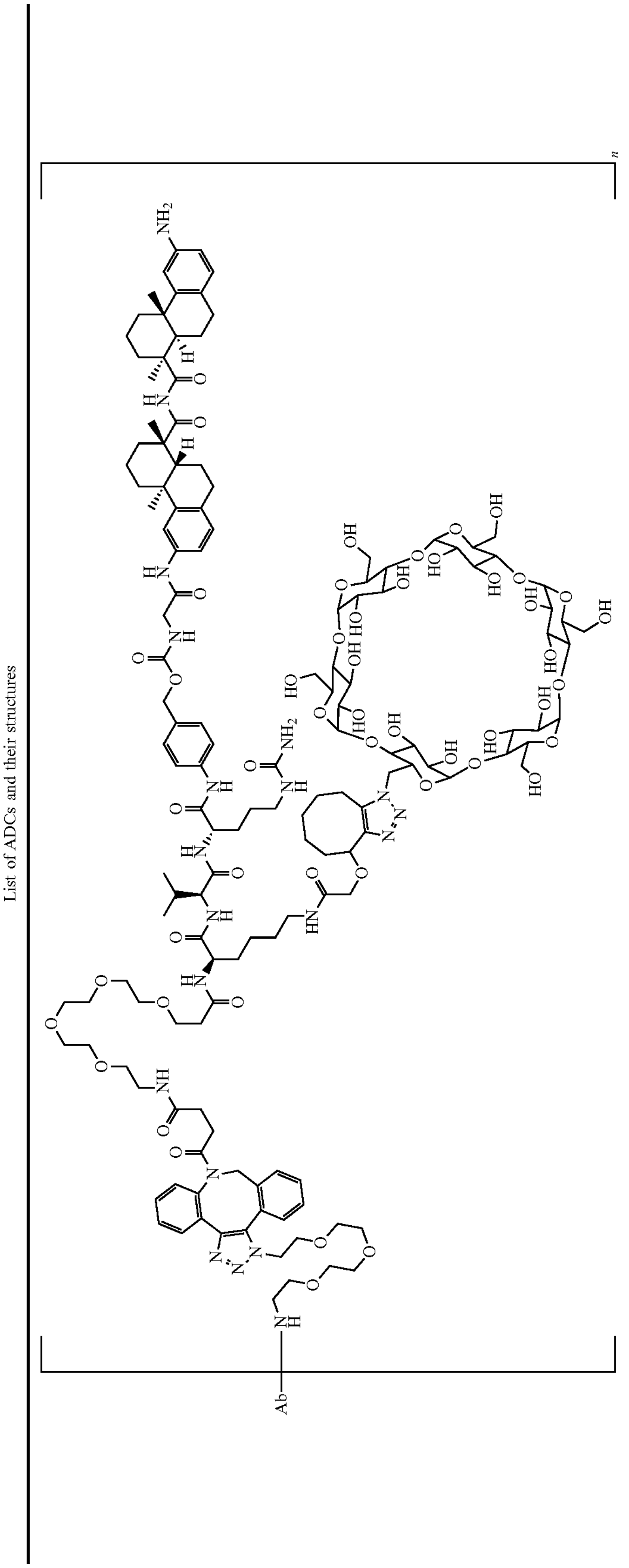

TABLE 2-continued
| List of ADCs and their structures |
|---|
| 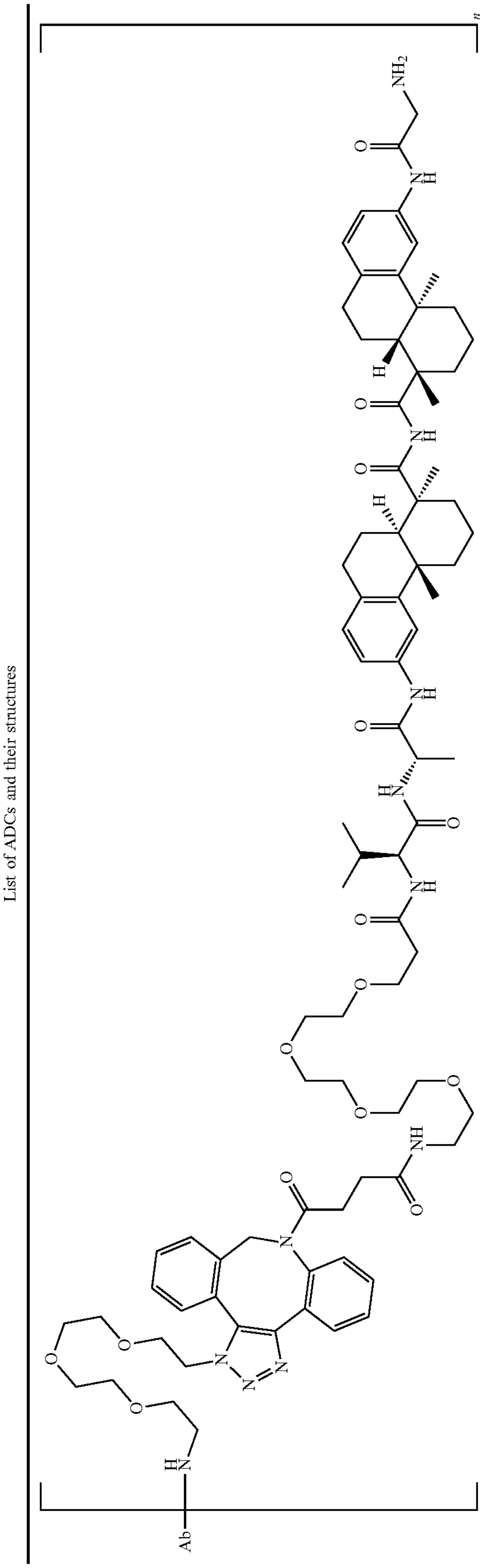 |
| 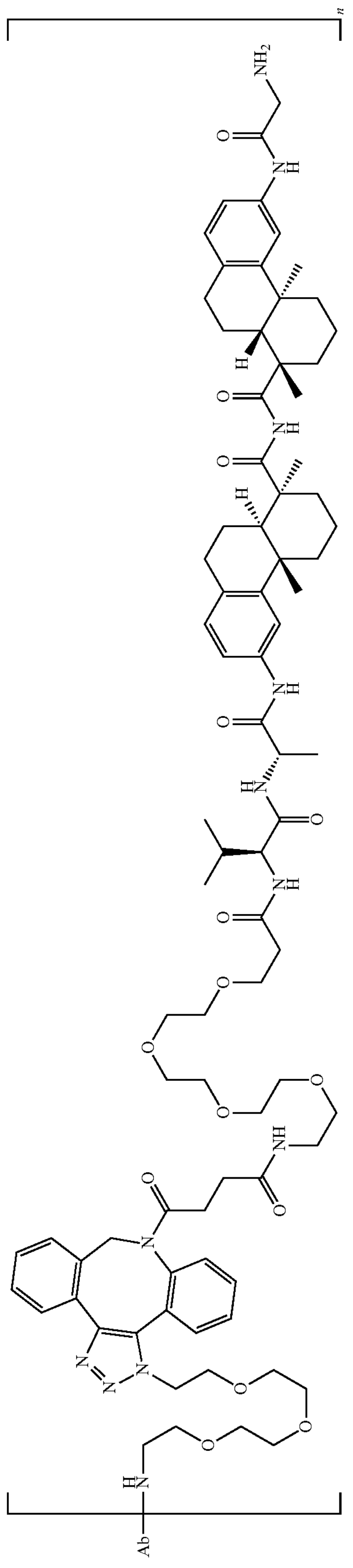 |

TABLE 2-continued
List of ADCs and their structures
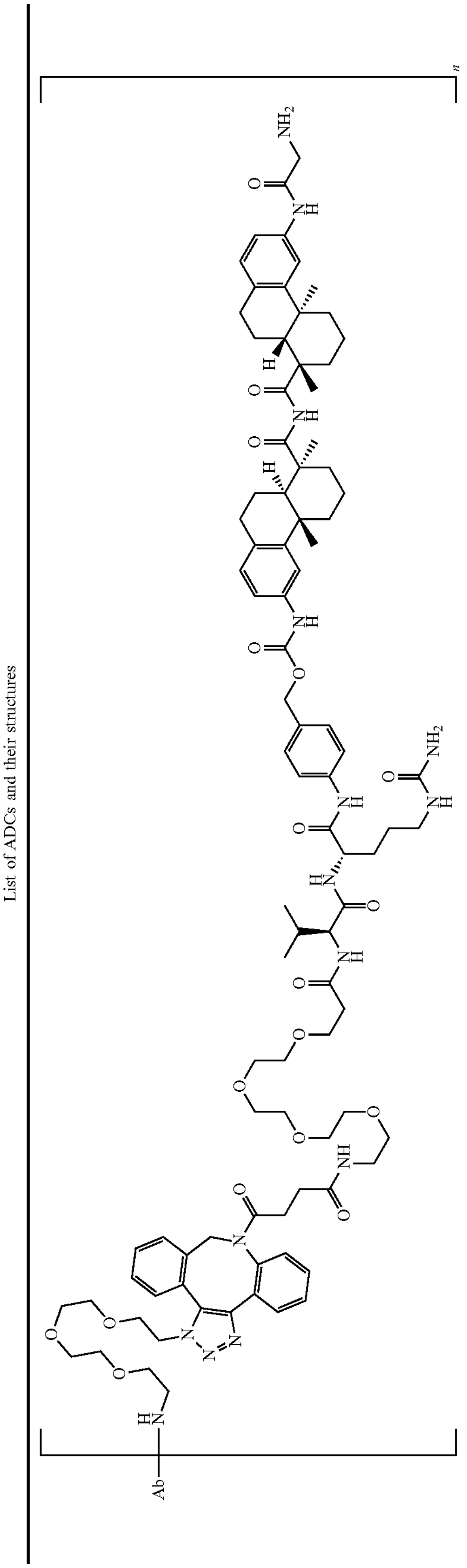
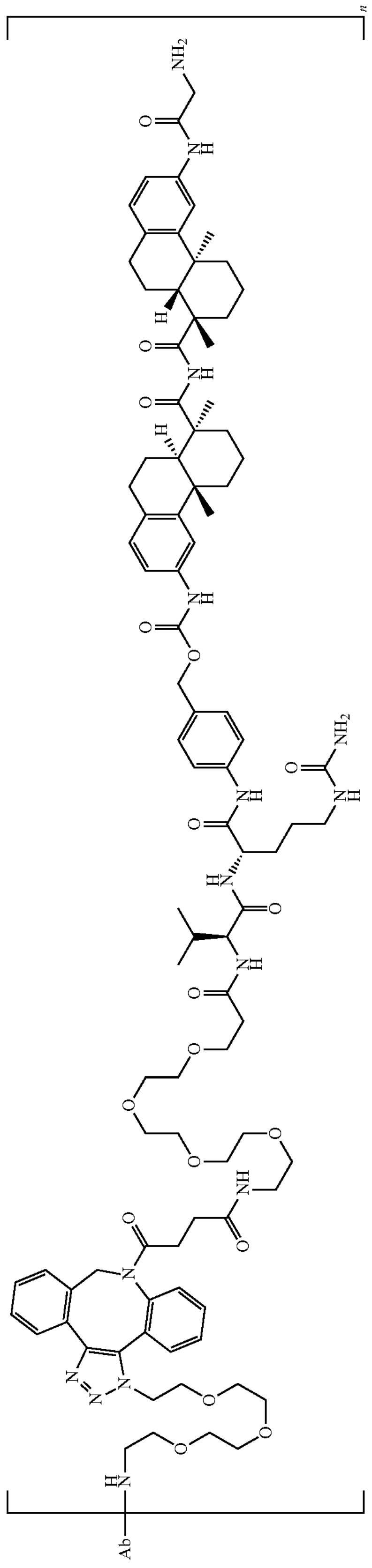

TABLE 2-continued
List of ADCs and their structures
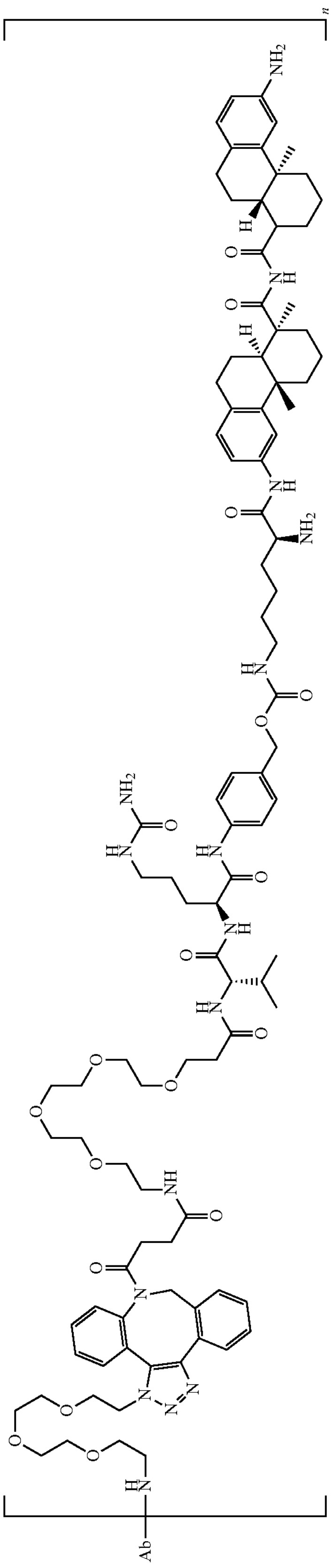
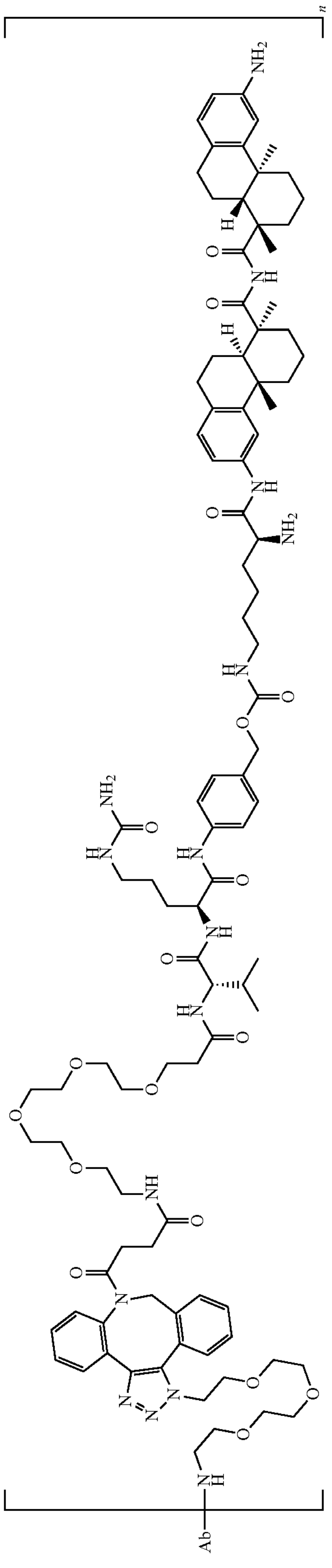

TABLE 2-continued
List of ADCs and their structures
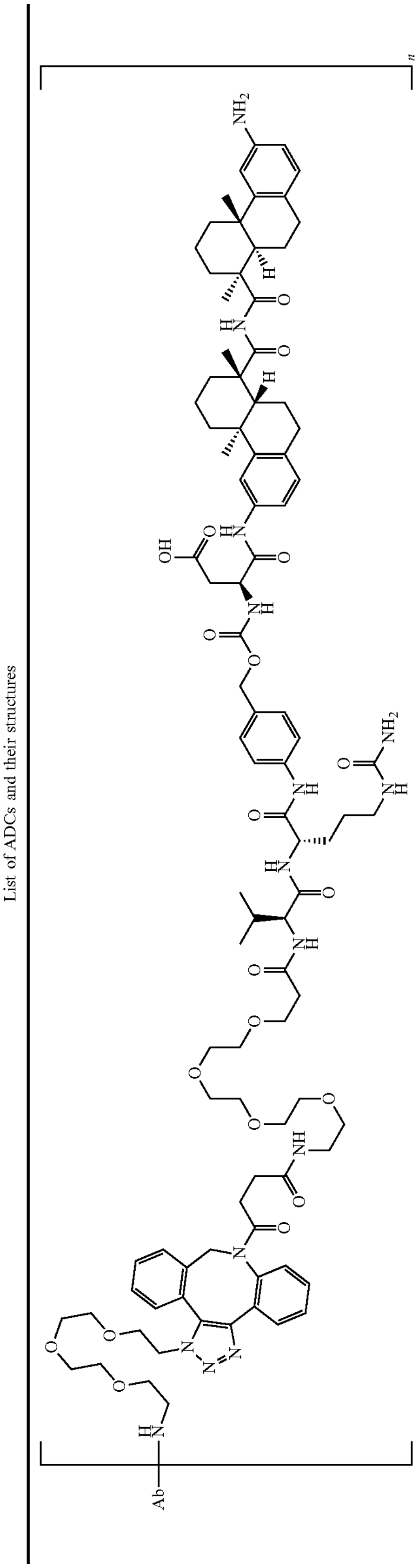
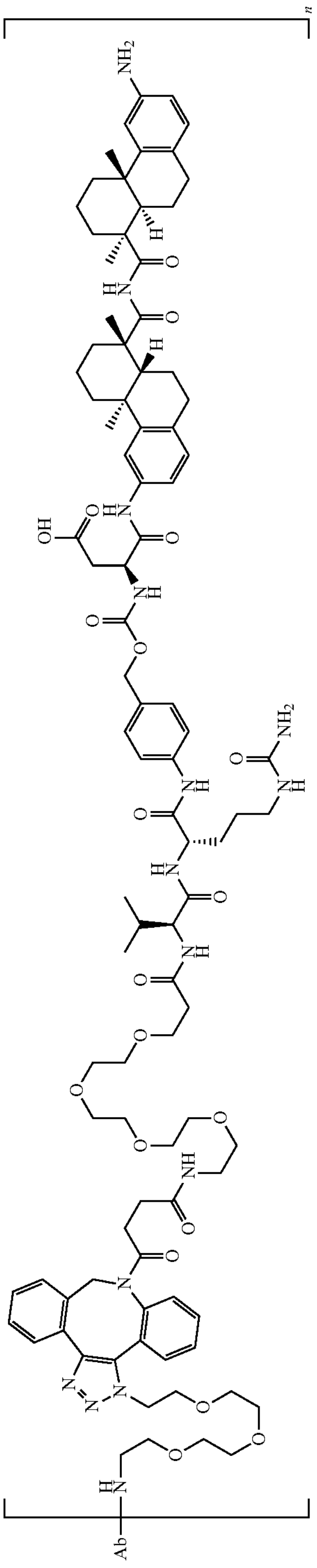

TABLE 2-continued
| List of ADCs and their structures |
| --- |
| 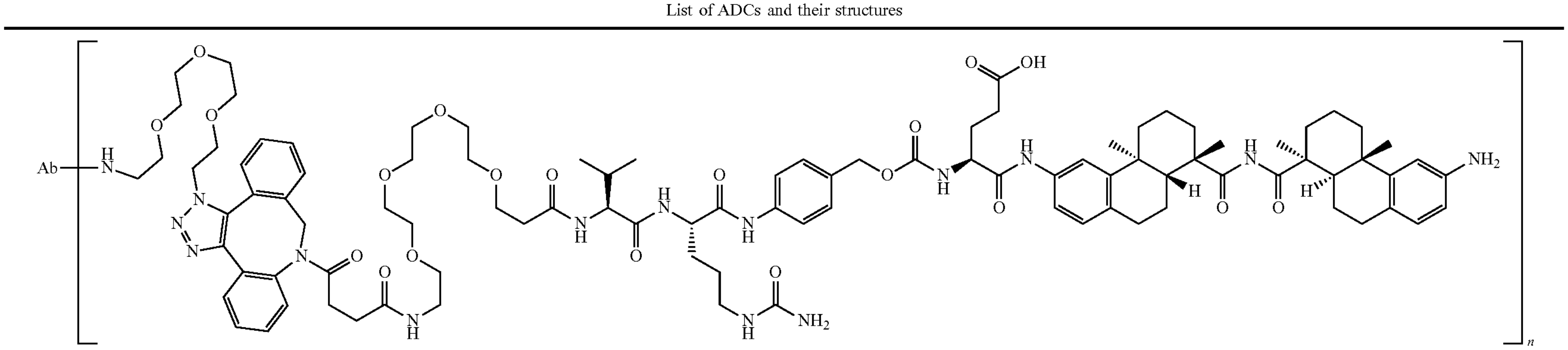 |
| 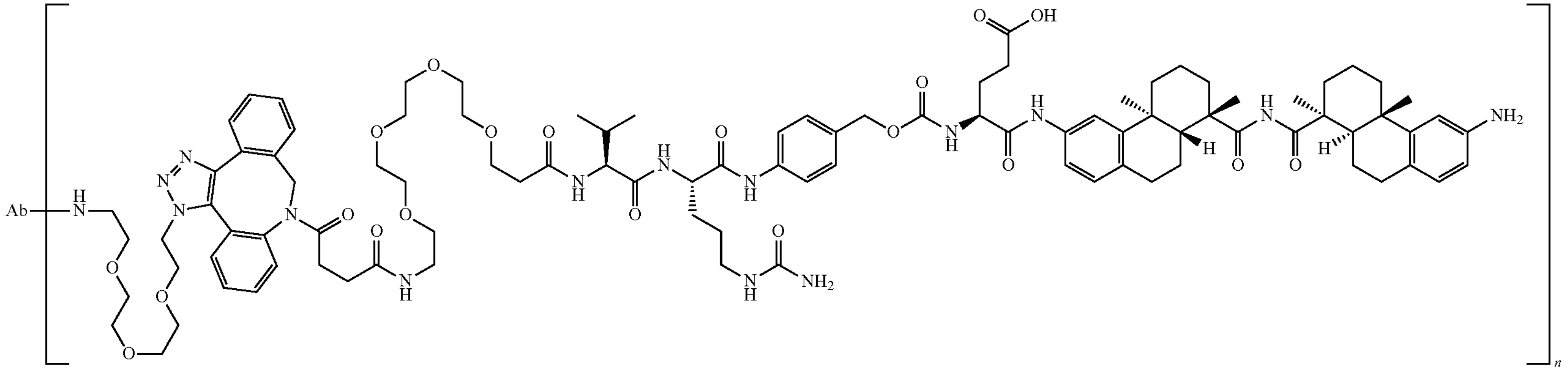 |

TABLE 2-continued
| List of ADCs and their structures |
| --- |
| 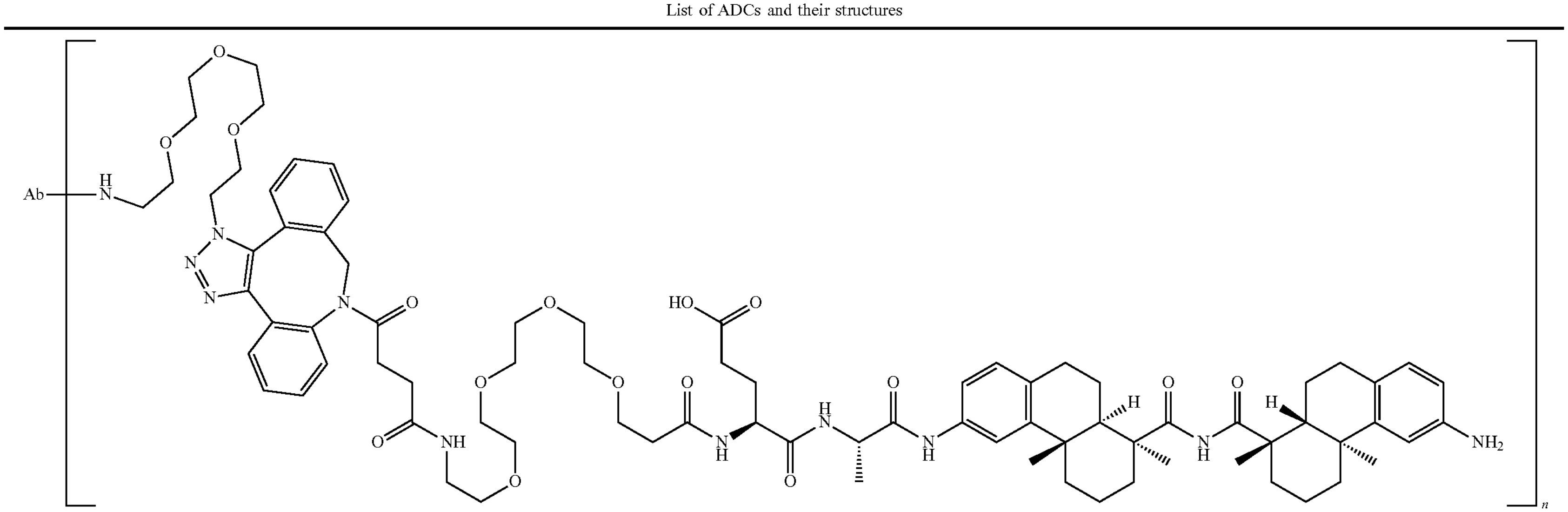 |
| 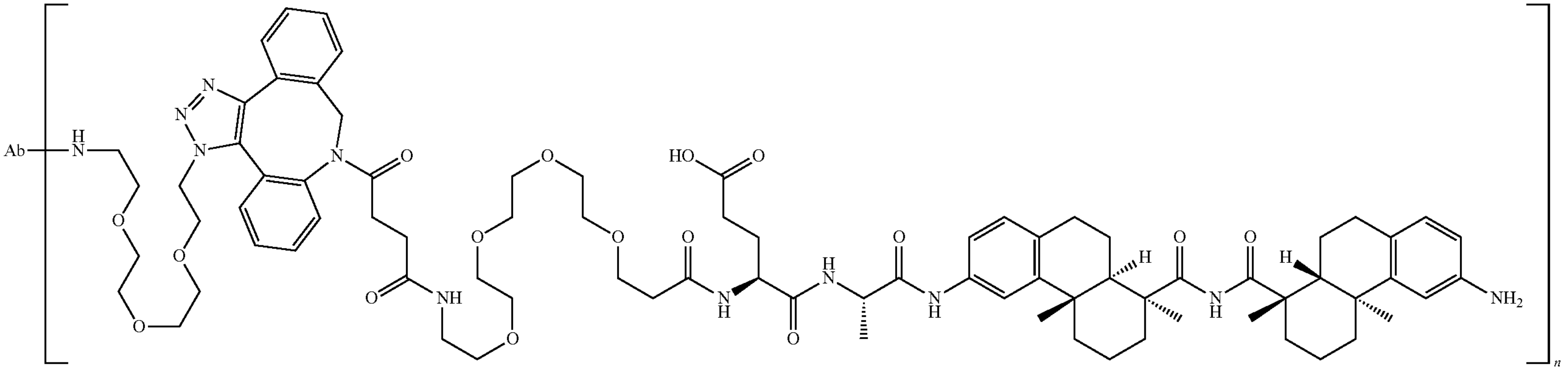 |

TABLE 2-continued
List of ADCs and their structures
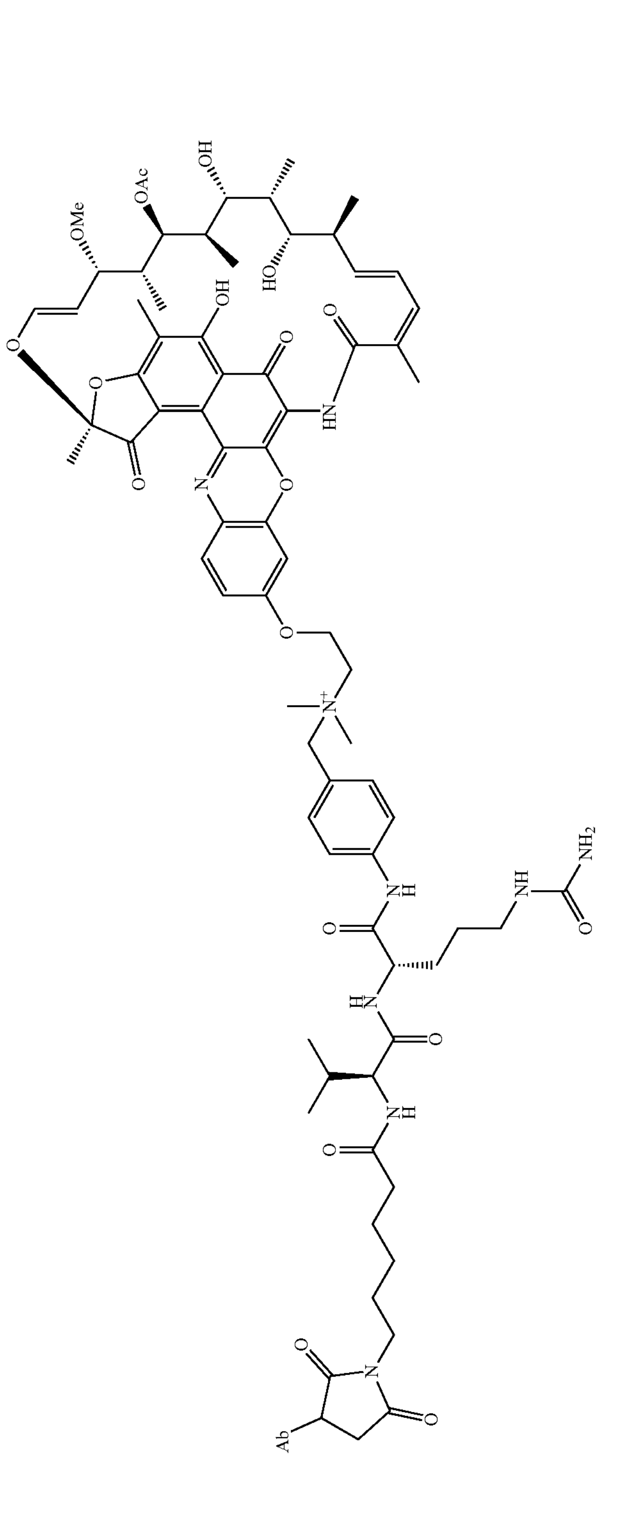
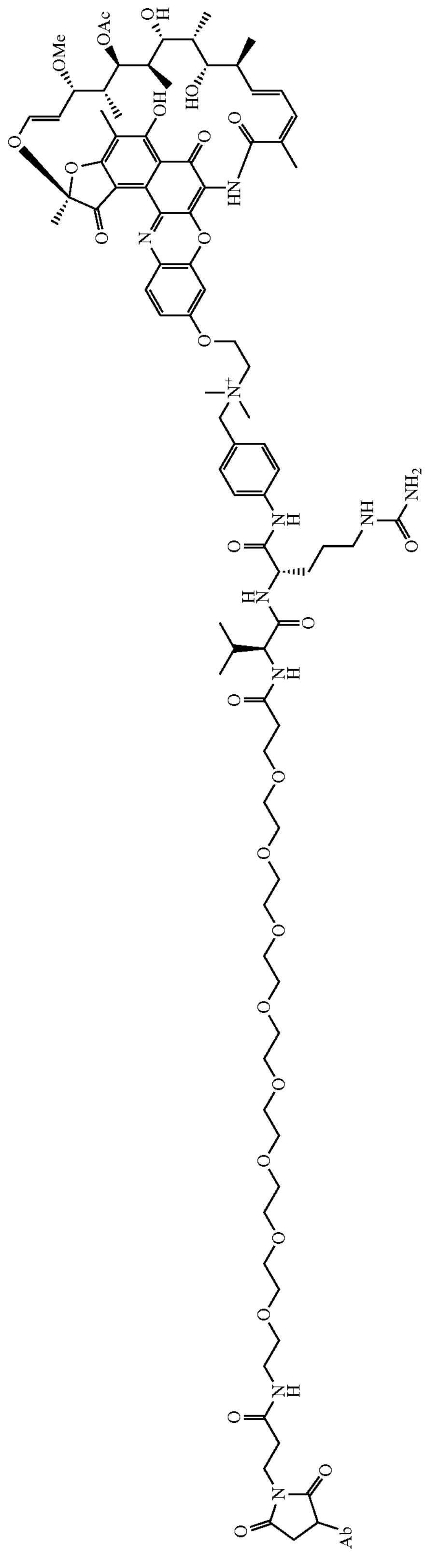

In the ADCs in Table 2, Ab is an anti-MSR1 antibody provided herein, or an antigen-binding fragment thereof. In particular embodiments, Ab is modified with a PEG group on a glutamine side chain as described herein. In the ADCs, n is an integer from 1 to 10, for instance, 1, 2, 3, or 4.

Provided herein is an anti-MSR1 antibody, or antigen binding fragment thereof, conjugated to the payload

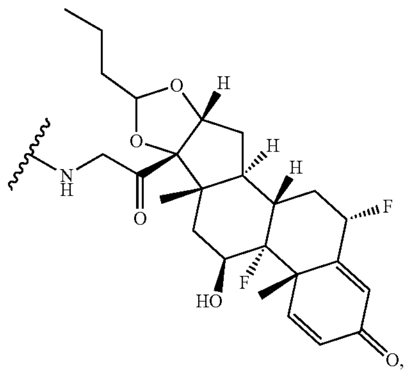 [SMILES: *NCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]

or pharmaceutically acceptable salt, solvate or stereoisomeric form thereof. In some embodiments, the anti-MSR1 antibody, or antigen binding fragment thereof, comprises an N297Q mutation.

Provided herein is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4 and conjugated to the payload

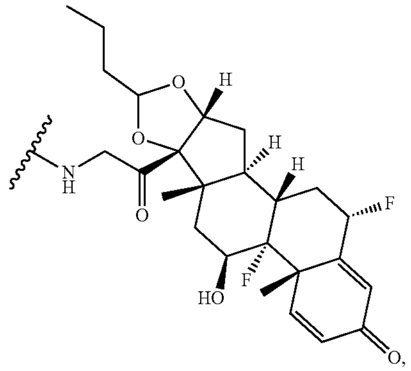 [SMILES: *NCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]

or pharmaceutically acceptable salt, solvate or stereoisomeric form thereof. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

Provided herein is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64 and conjugated to the payload

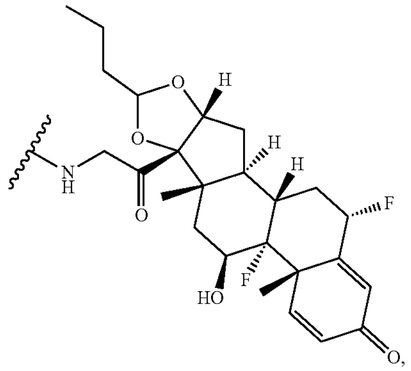 [SMILES: *NCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]

or pharmaceutically acceptable salt, solvate or stereoisomeric form thereof. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

Provided herein is an anti-MSR1 antibody, or antigen binding fragment thereof, comprising a set of variable regions heavy chain variable regions (HCVR) and a set of light chain variable regions (LCVR) from Table 4 and conjugated to the payload

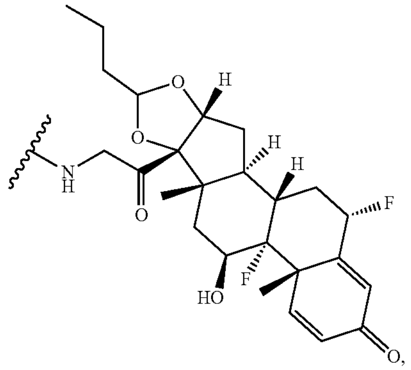 [SMILES: *NCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]

or pharmaceutically acceptable salt, solvate or stereoisomeric form thereof. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

Provided herein is an anti-MSR1 antibody, or antigen binding fragment thereof, comprising a heavy chain variable region (HCVR) comprising SEQ ID NO: 50 and a light chain variable region (LCVR) SEQ ID NO: 58 and conjugated to the payload

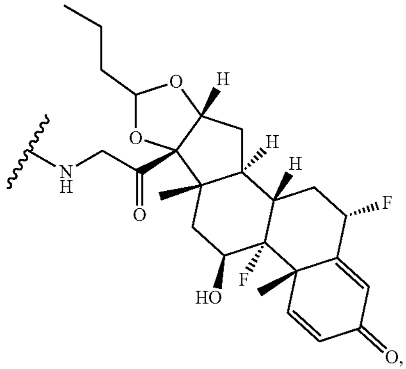 [SMILES: *NCC(=O)[C@@]12OC(CCC)O[C@@H]1C[C@H]1[C@@H]3C[C@H](F)C4=CC(=O)C=C[C@]4(C)[C@@]3(F)[C@@H](O)C[C@@]12C]
or pharmaceutically acceptable salt, solvate or stereoisomeric form thereof. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.
An antibody-drug conjugate (ADC) according to the formulas:

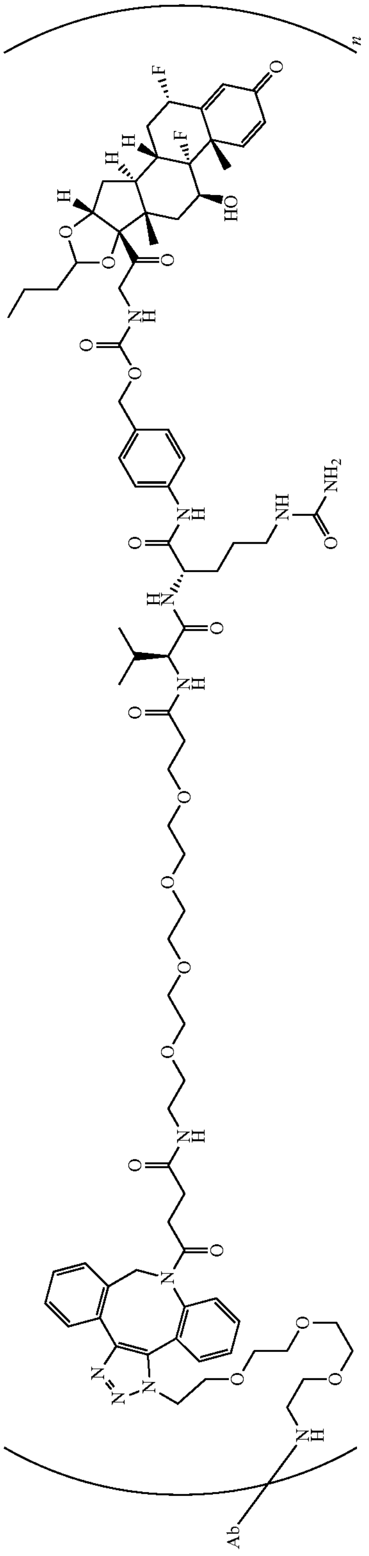
and/or
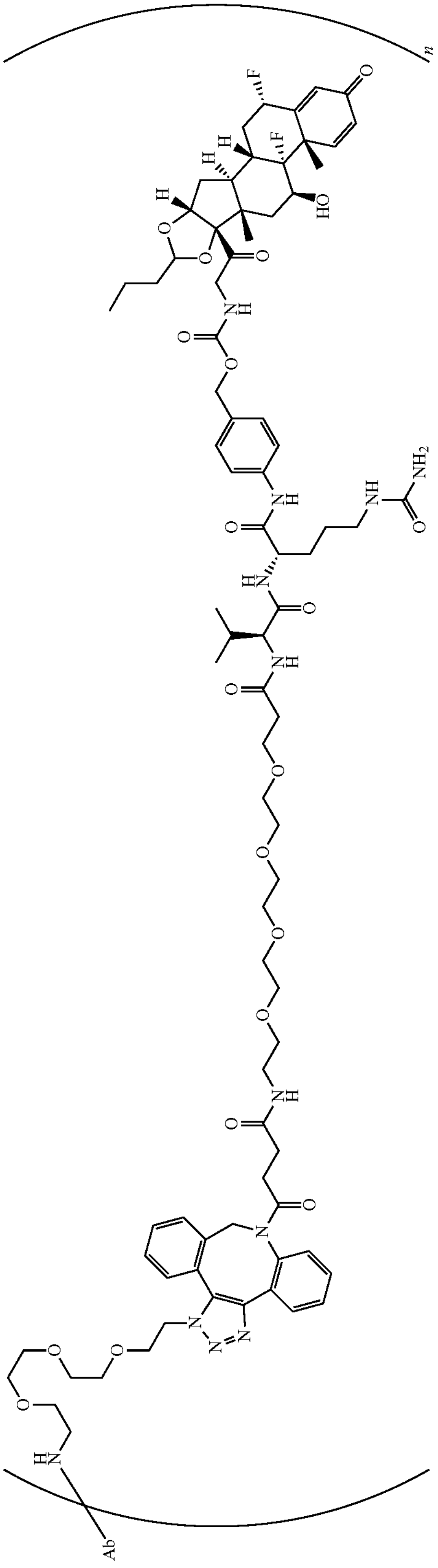

or pharmaceutically acceptable salt, solvate, stereoisomeric form, or regioisomer thereof, or mixtures thereof; wherein the antibody is an anti-MSR1 antibody, or antigen binding fragment thereof. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises an N297Q mutation.

An antibody-drug conjugate (ADC) according to the formulas:

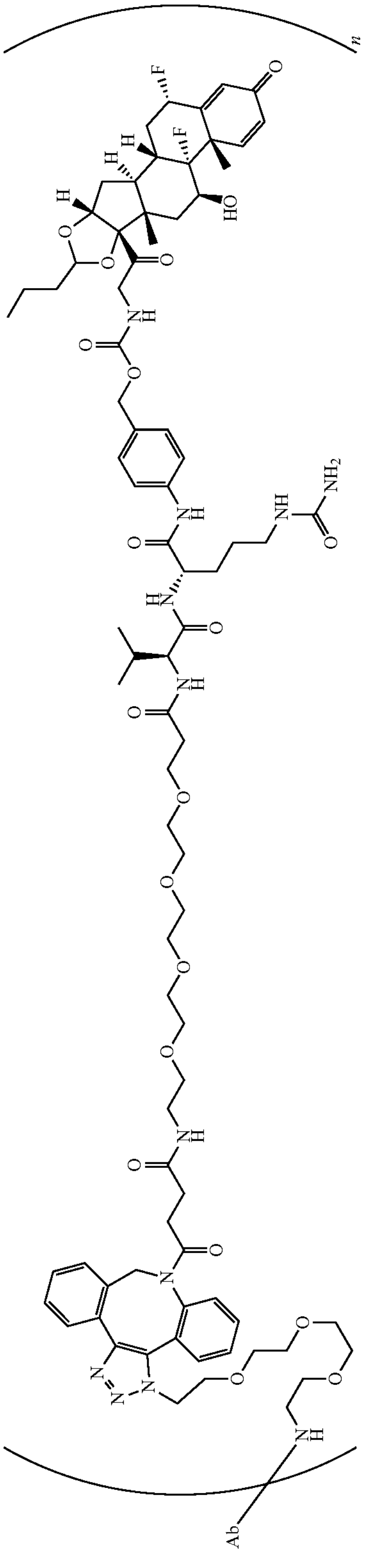
and/or
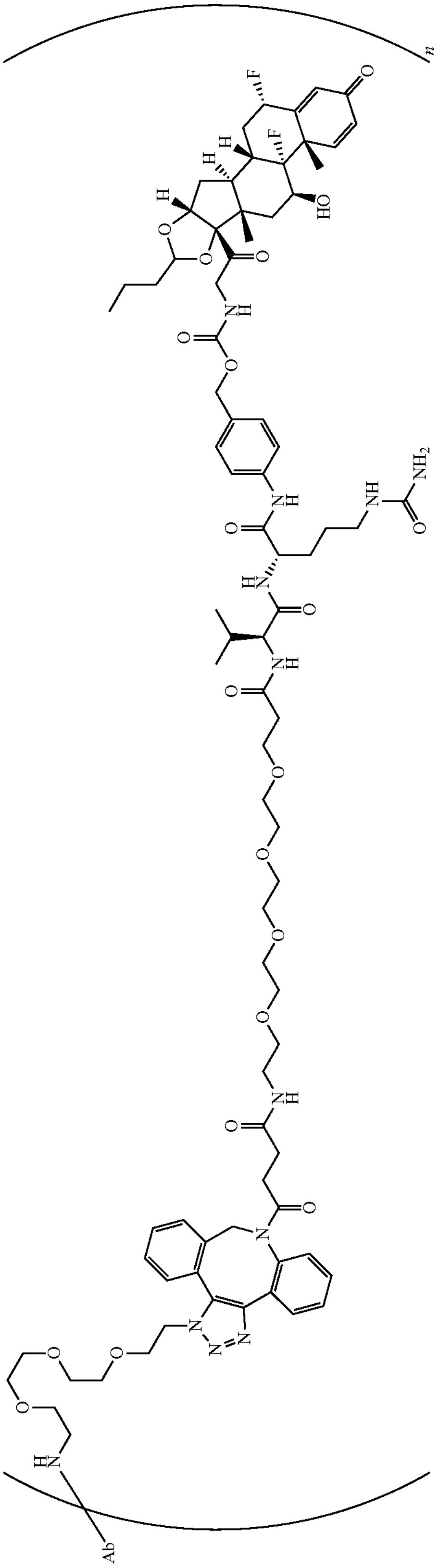

or pharmaceutically acceptable salt, solvate, stereoisomeric form, or regioisomer thereof, or mixtures thereof; wherein the antibody is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

An antibody-drug conjugate (ADC) according to the formulas:

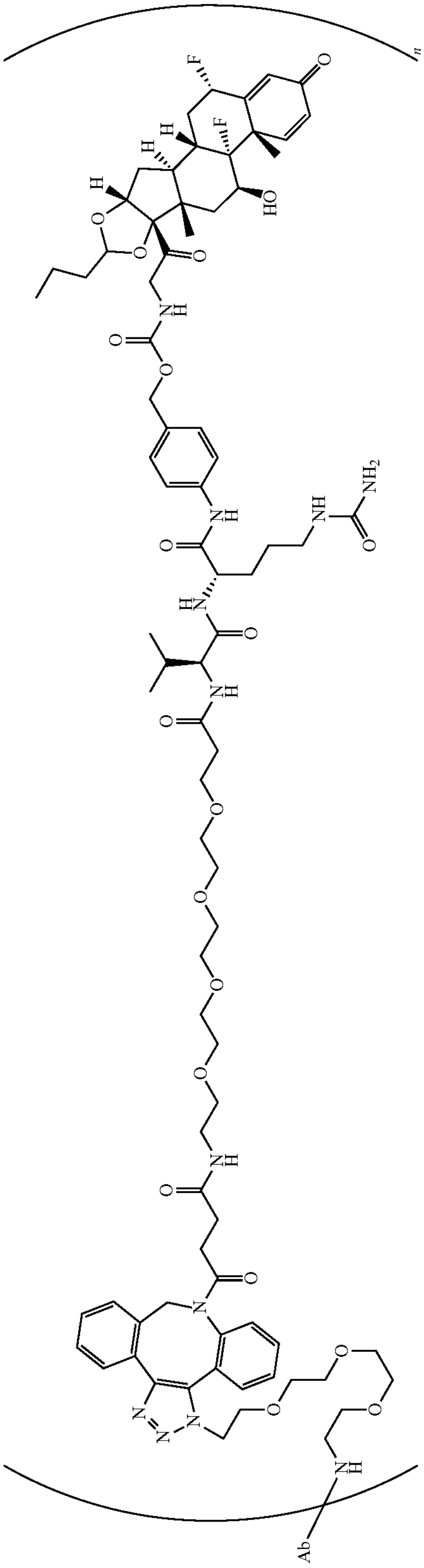
and/or
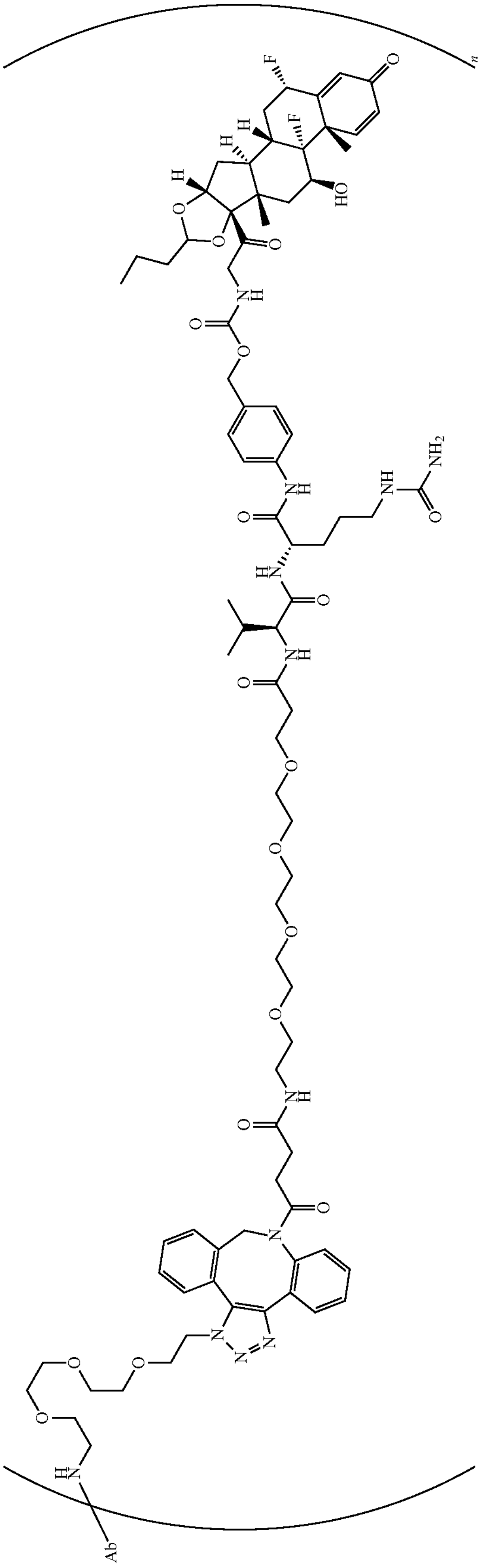

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

An antibody-drug conjugate (ADC) according to the formulas:

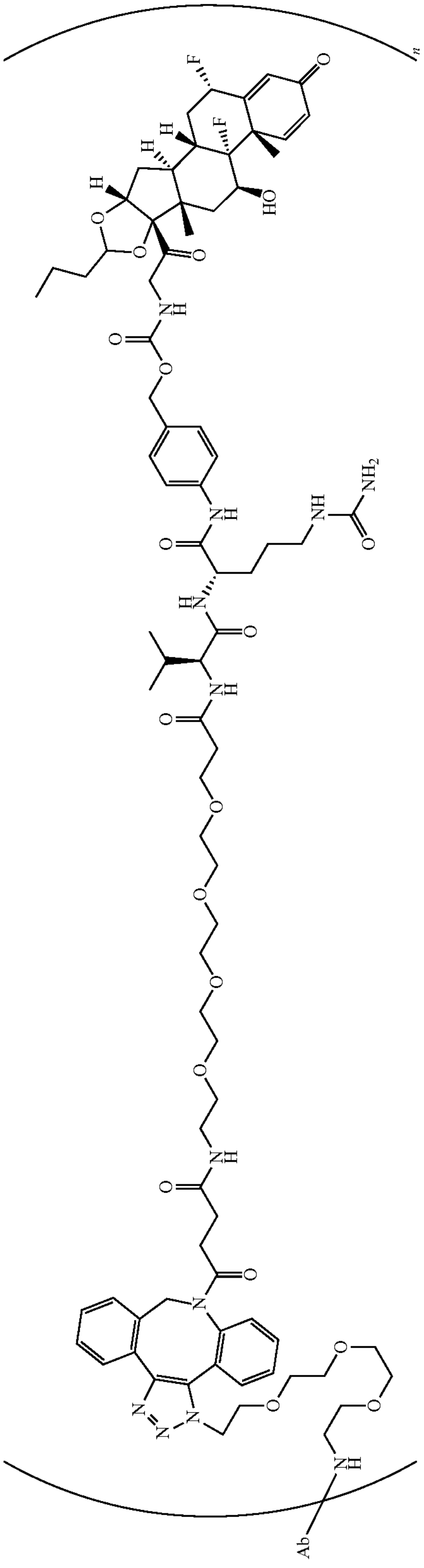
and/or
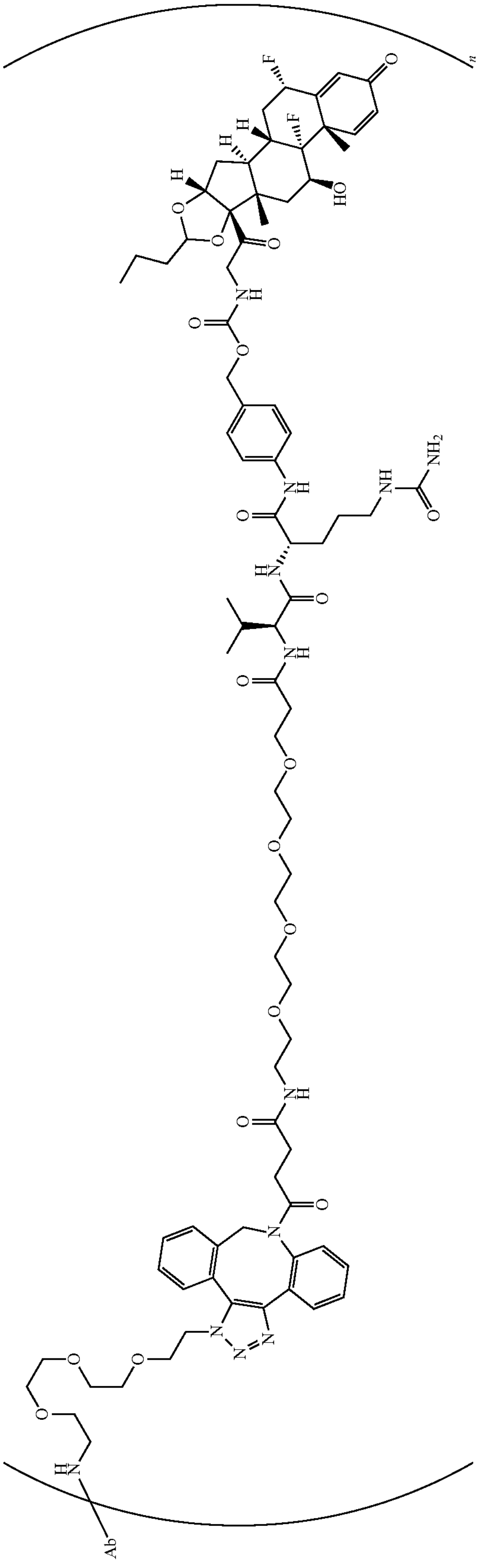

or pharmaceutically acceptable salt, solvate, stereoisomeric form, or regioisomer thereof, or mixtures thereof; wherein the antibody is an anti-MSR1 antibody, or antigen binding fragment thereof, comprising a set of variable regions heavy chain variable regions (HCVR) and a set of light chain variable regions (LCVR) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

An antibody-drug conjugate (ADC) according to the formulas:

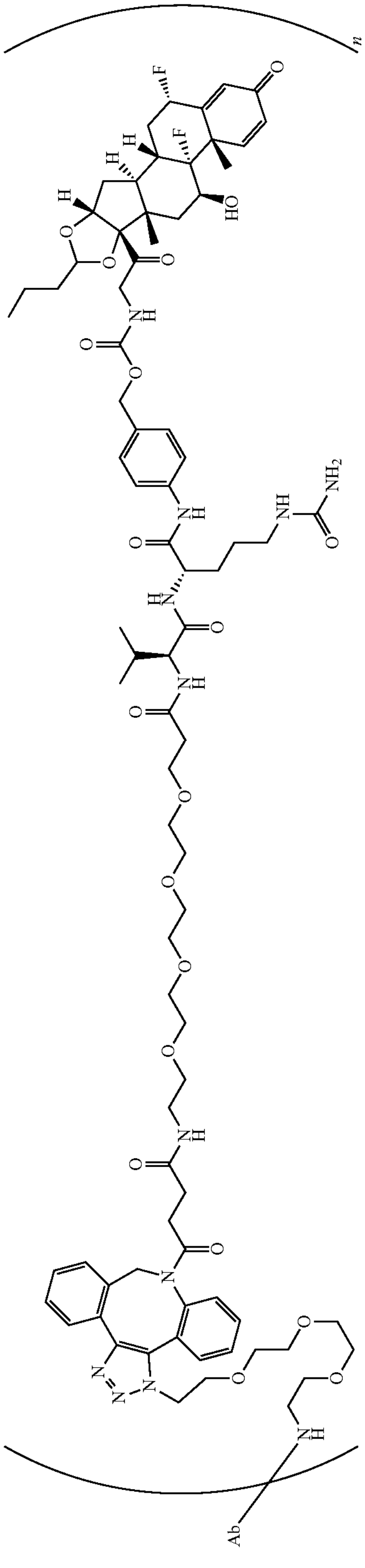
and/or
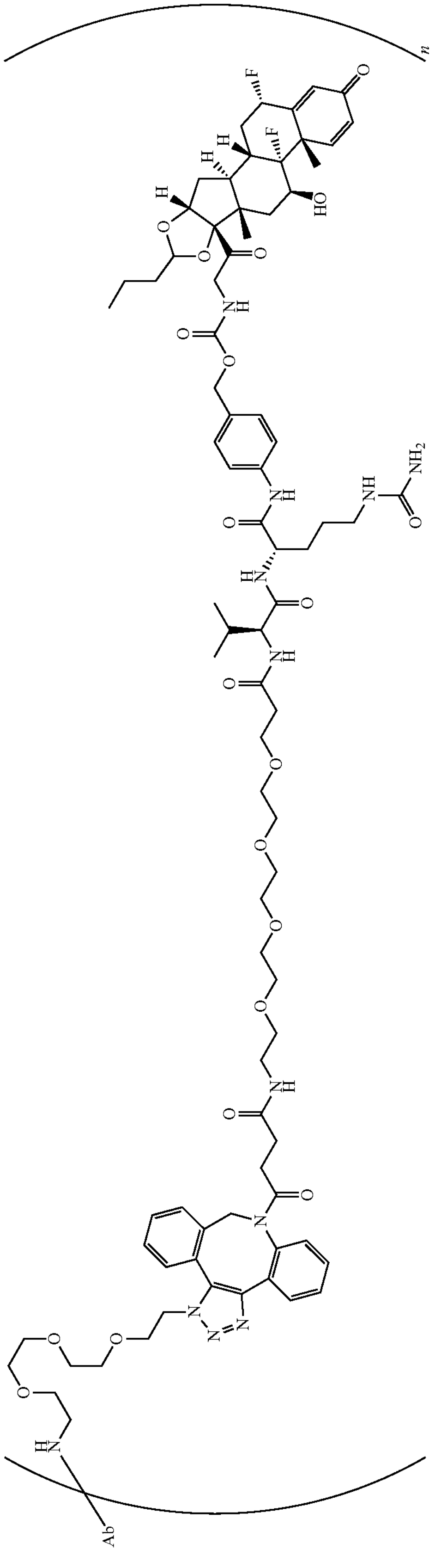

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain variable region (HCVR) comprising SEQ ID NO: 50 and a light chain variable region (LCVR) SEQ ID NO: 58. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

Provided herein is an anti-MSR1 antibody, or antigen binding fragment thereof, conjugated to the payload

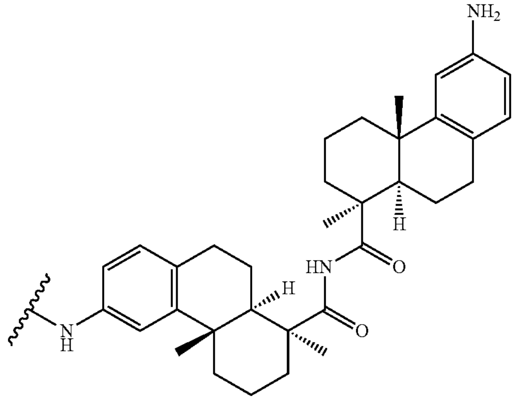

, or pharmaceutically acceptable salt, solvate or stereoisomeric form thereof. In some embodiments, the anti-MSR1 antibody, or antigen binding fragment thereof, comprises an N297Q mutation.

Provided herein is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4 and conjugated to the payload

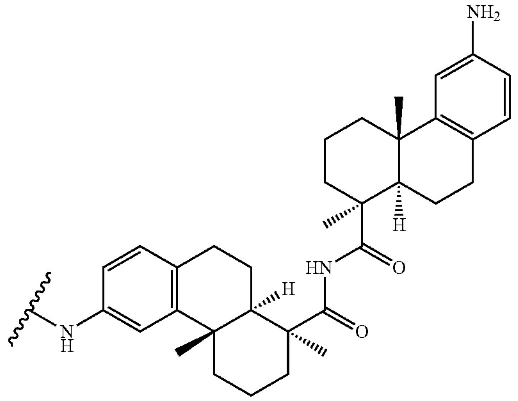

, or pharmaceutically acceptable salt, solvate or stereoisomeric form thereof. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

Provided herein is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64 and conjugated to the payload

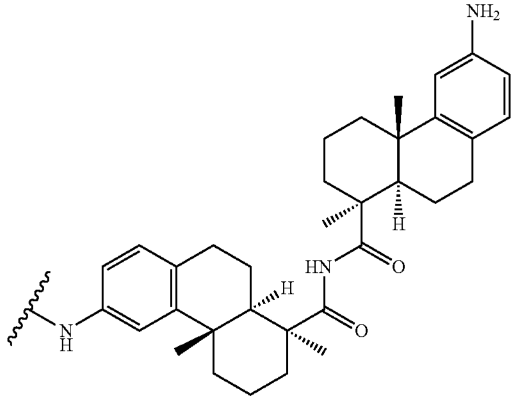

, or pharmaceutically acceptable salt, solvate or stereoisomeric form thereof. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

Provided herein is an anti-MSR1 antibody, or antigen binding fragment thereof, comprising a set of variable regions heavy chain variable regions (HCVR) and a set of light chain variable regions (LCVR) from Table 4 and conjugated to the payload

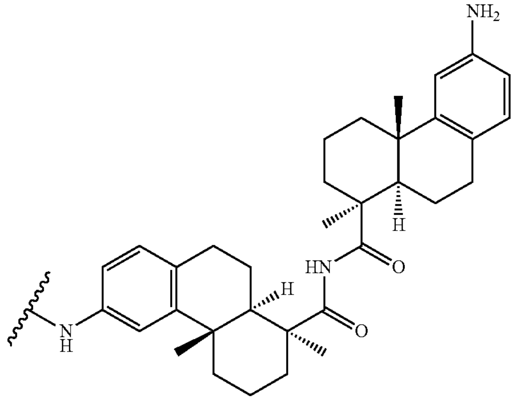

, or pharmaceutically acceptable salt, solvate or stereoisomeric form thereof. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

Provided herein is an anti-MSR1 antibody, or antigen binding fragment thereof, comprising a heavy chain variable region (HCVR) comprising SEQ ID NO: 50 and a light chain variable region (LCVR) SEQ ID NO: 58 and conjugated to the payload

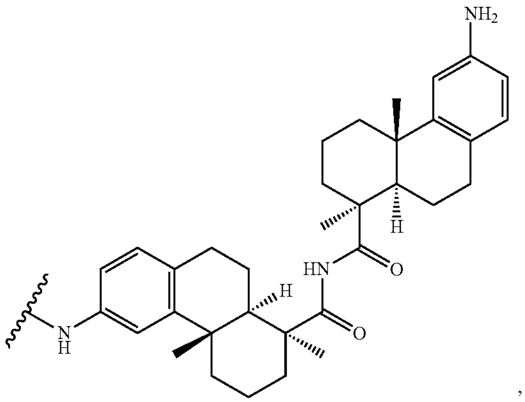

, or pharmaceutically acceptable salt, solvate or stereoisomeric form thereof. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

An antibody-drug conjugate (ADC) according to the formulas:

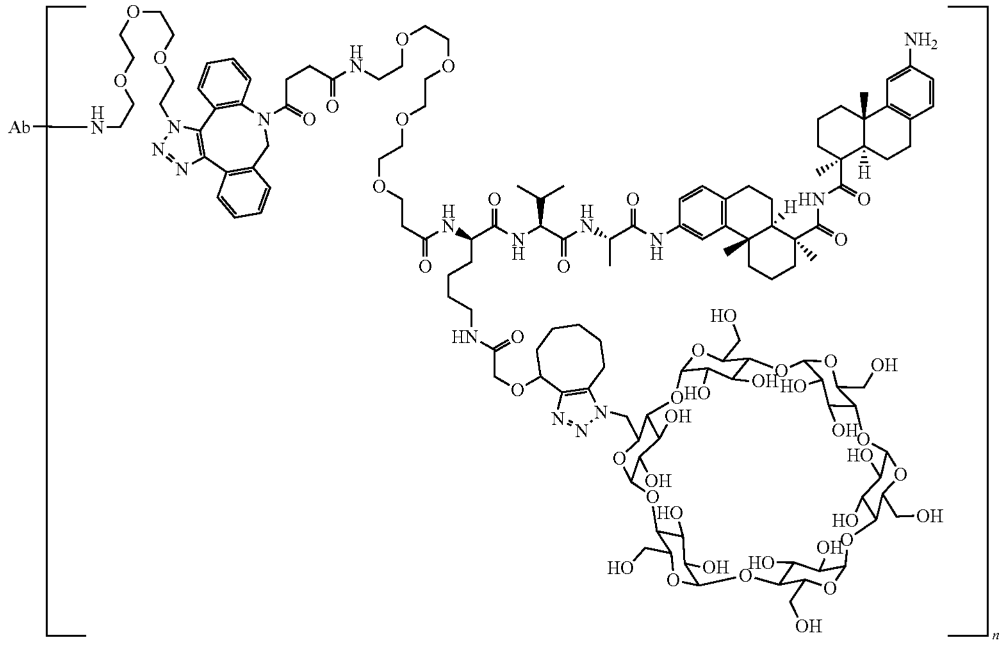

and/or

-continued

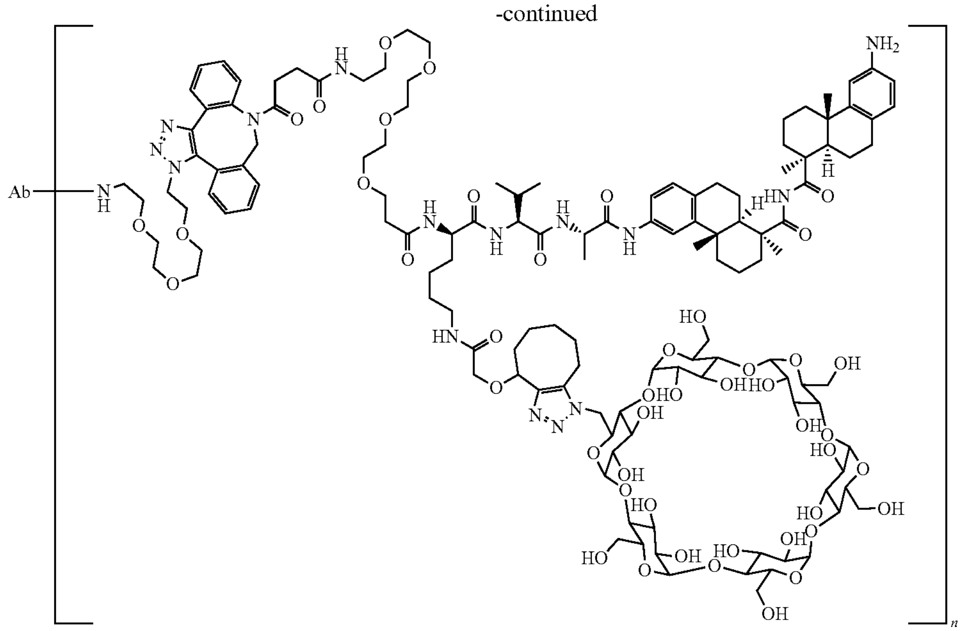

or pharmaceutically acceptable salt, solvate, stereoisomeric form, or regioisomer thereof, or mixtures thereof; wherein the antibody is an anti-MSR1 antibody, or antigen binding fragment thereof. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises an N297Q mutation.

An antibody-drug conjugate (ADC) according to the formulas:

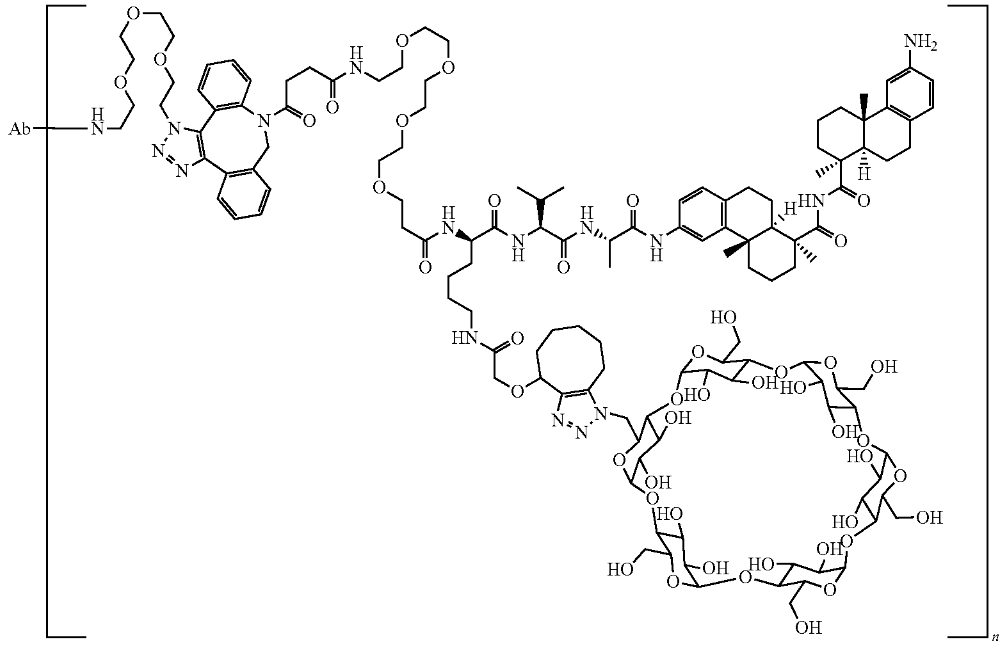

and/or

-continued

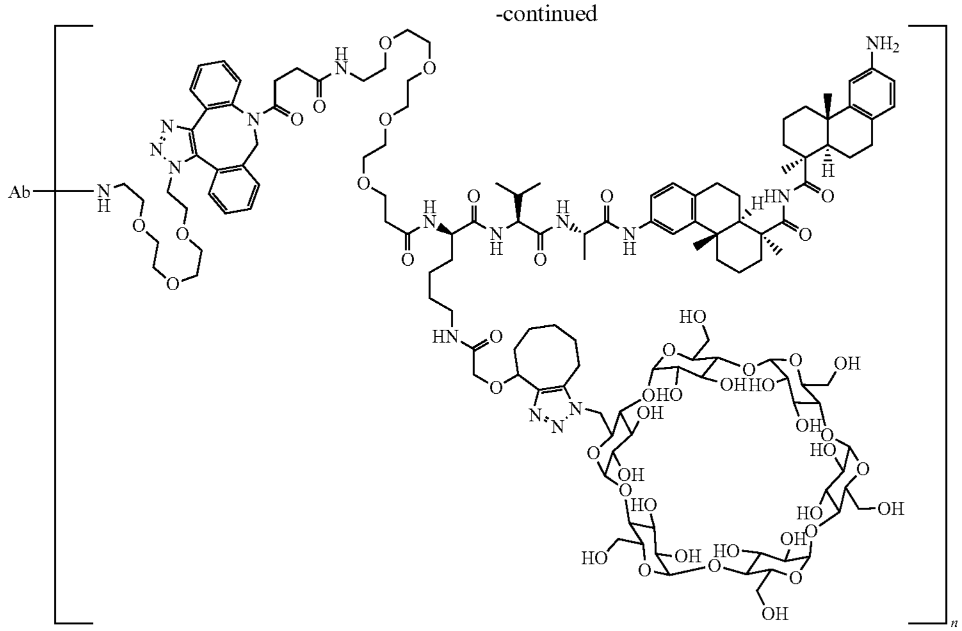

or pharmaceutically acceptable salt, solvate, stereoisomeric form, or regioisomer thereof, or mixtures thereof; wherein the antibody is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

An antibody-drug conjugate (ADC) according to the formulas:

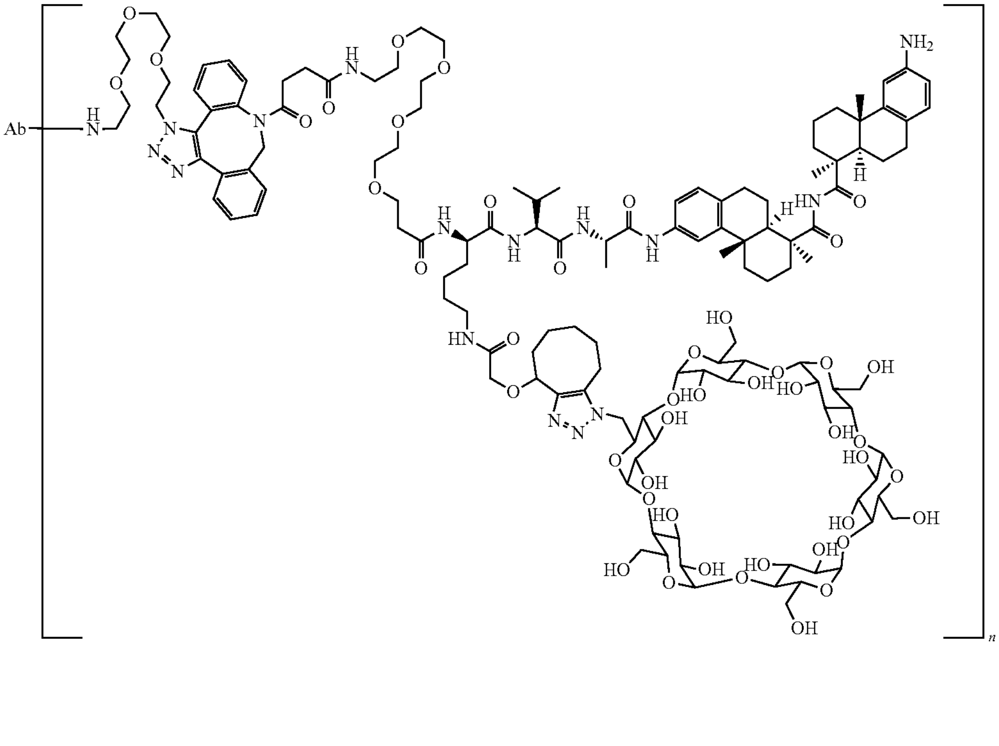

and/or

-continued

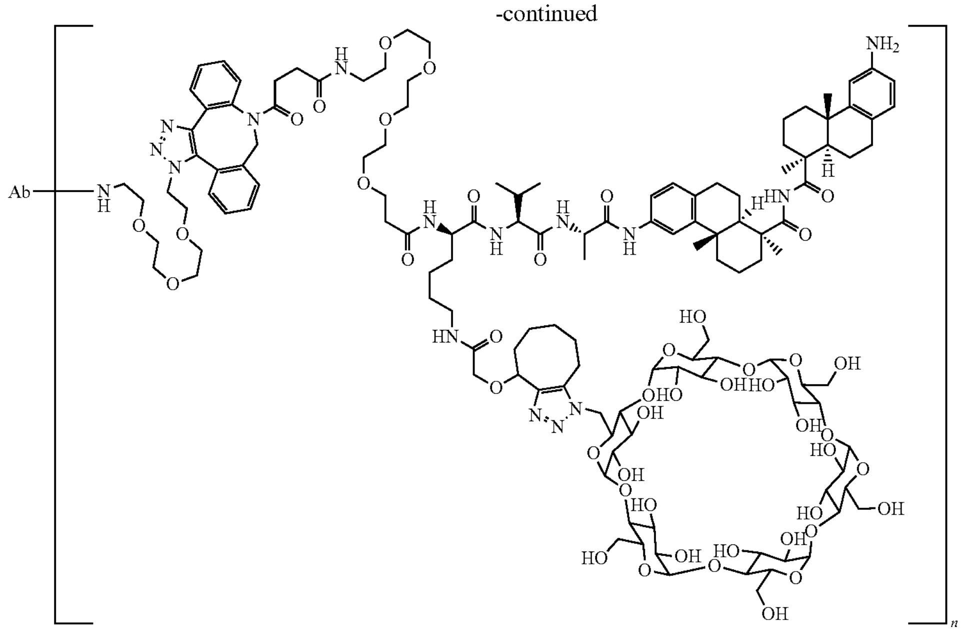

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

An antibody-drug conjugate (ADC) according to the formulas:

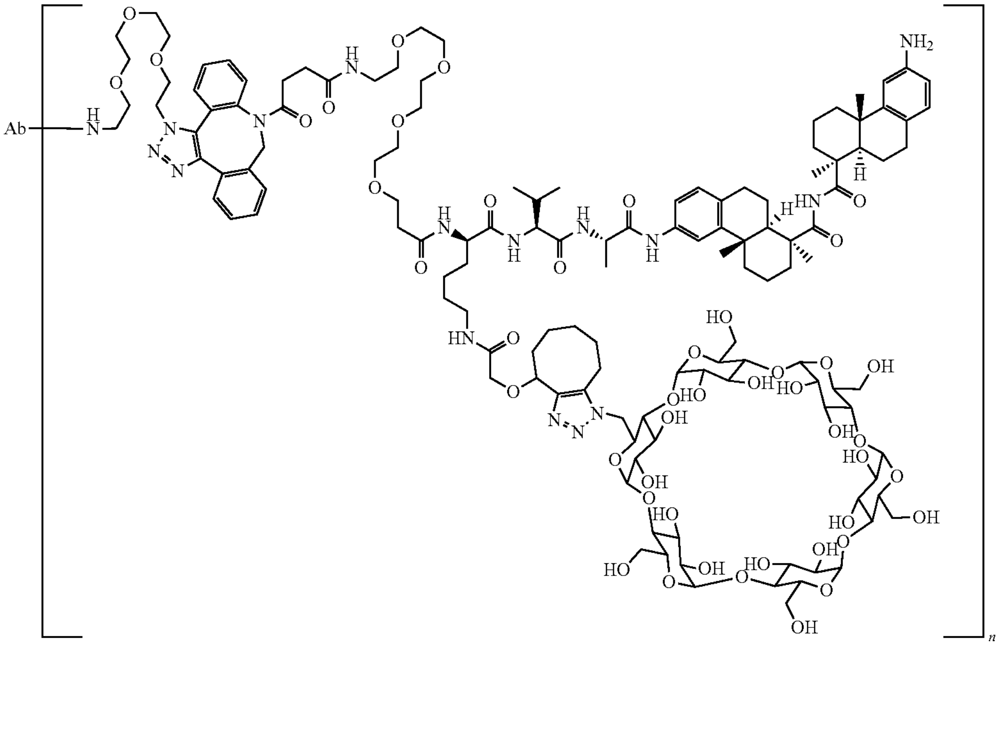

and/or

-continued

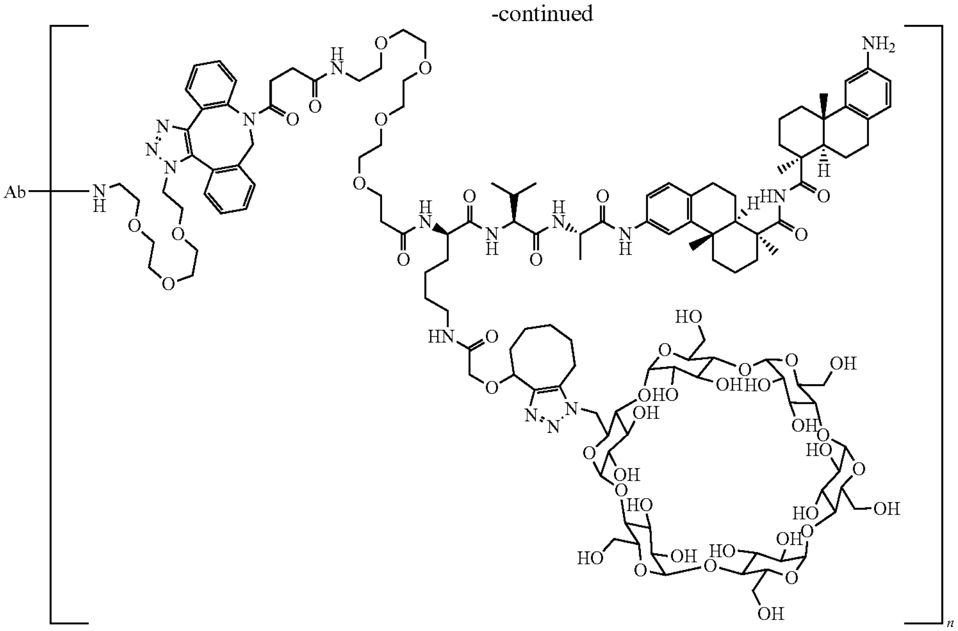

or pharmaceutically acceptable salt, solvate, stereoisomeric form, or regioisomer thereof, or mixtures thereof; wherein the antibody is an anti-MSR1 antibody, or antigen binding fragment thereof, comprising a set of variable regions heavy chain variable regions (HCVR) and a set of light chain variable regions (LCVR) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

An antibody-drug conjugate (ADC) according to the formulas:

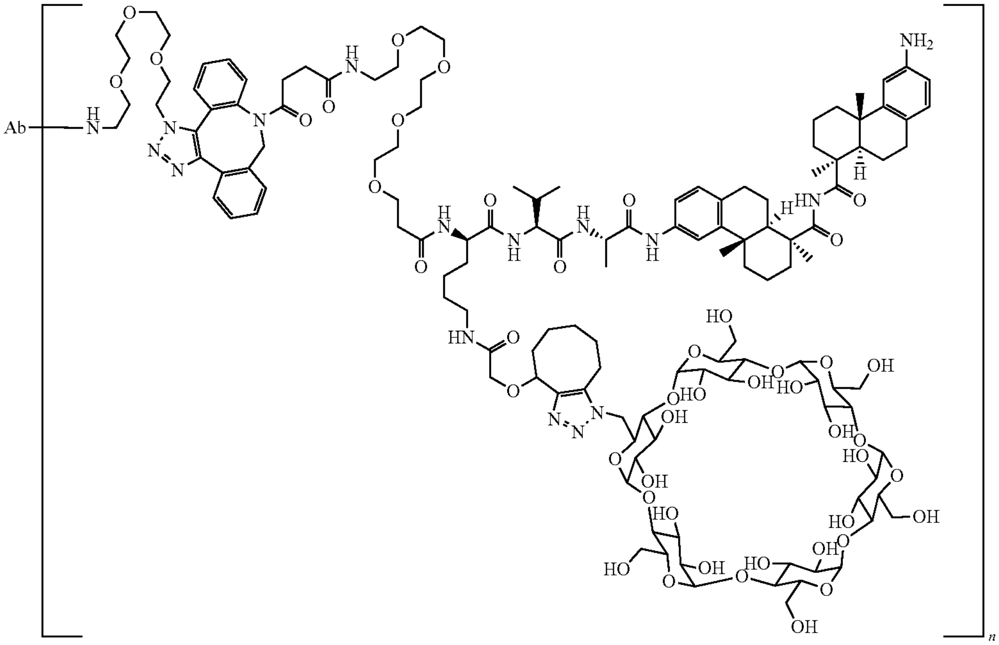

and/or

-continued

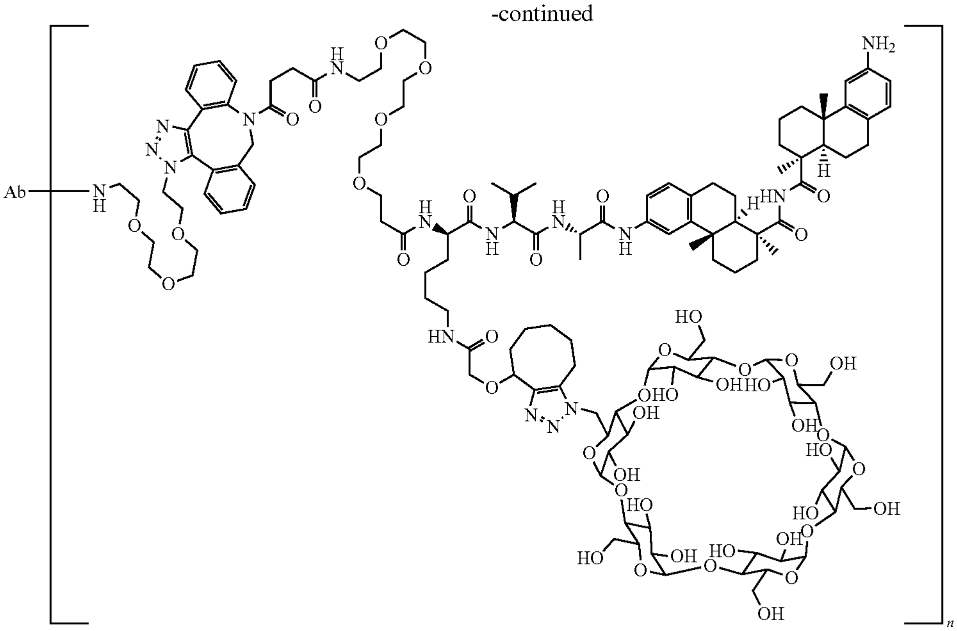

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain variable region (HCVR) comprising SEQ ID NO: 50 and a light chain variable region (LCVR) SEQ ID NO: 58. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

Provided herein is an anti-MSR1 antibody, or antigen binding fragment thereof, conjugated to the payload

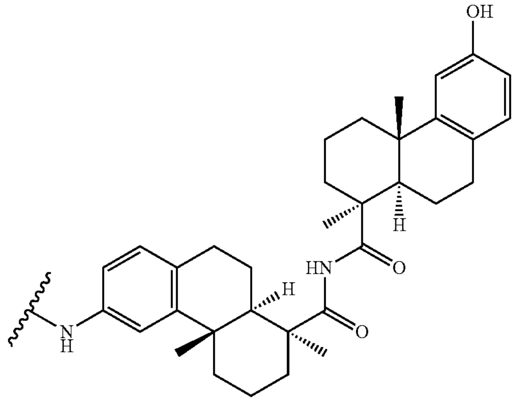

, or pharmaceutically acceptable salt, solvate or stereoisomeric form thereof. In some embodiments, the anti-MSR1 antibody, or antigen binding fragment thereof, comprises an N297Q mutation.

Provided herein is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4 and conjugated to the payload

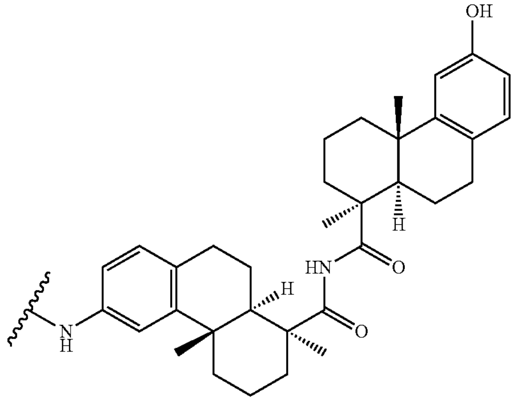

, or pharmaceutically acceptable salt, solvate or stereoisomeric form thereof. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

Provided herein is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64 and conjugated to the payload

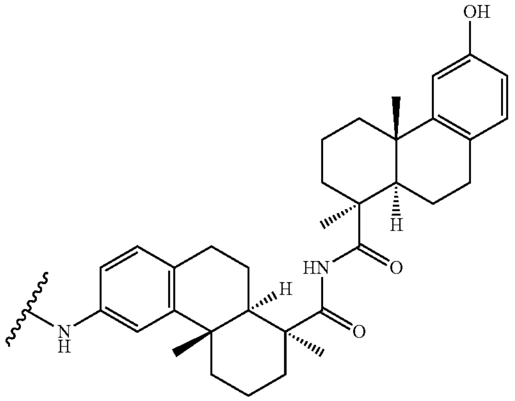

, or pharmaceutically acceptable salt, solvate or stereoisomeric form thereof. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

Provided herein is an anti-MSR1 antibody, or antigen binding fragment thereof, comprising a set of variable regions heavy chain variable regions (HCVR) and a set of light chain variable regions (LCVR) from Table 4 and conjugated to the payload

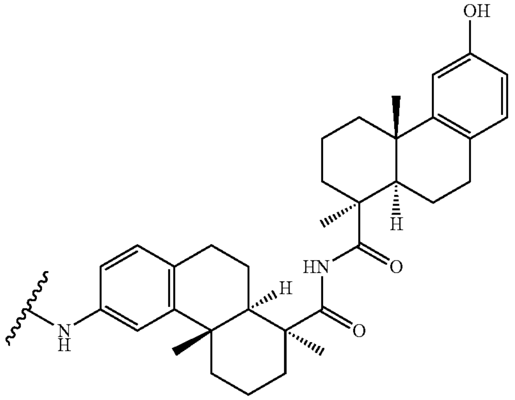

, or pharmaceutically acceptable salt, solvate or stereoisomeric form thereof. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

Provided herein is an anti-MSR1 antibody, or antigen binding fragment thereof, comprising a heavy chain variable region (HCVR) comprising SEQ ID NO: 50 and a light chain variable region (LCVR) SEQ ID NO: 58 and conjugated to the payload

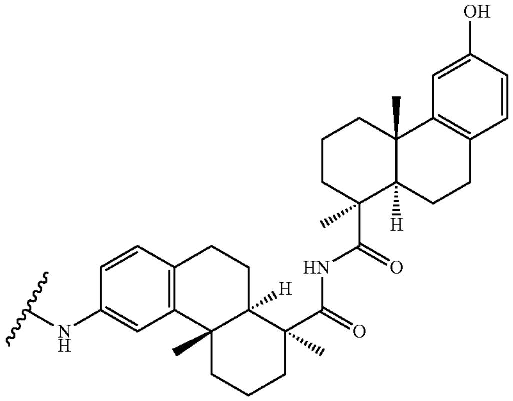

, or pharmaceutically acceptable salt, solvate or stereoisomeric form thereof. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

An antibody-drug conjugate (ADC) according to the formulas:

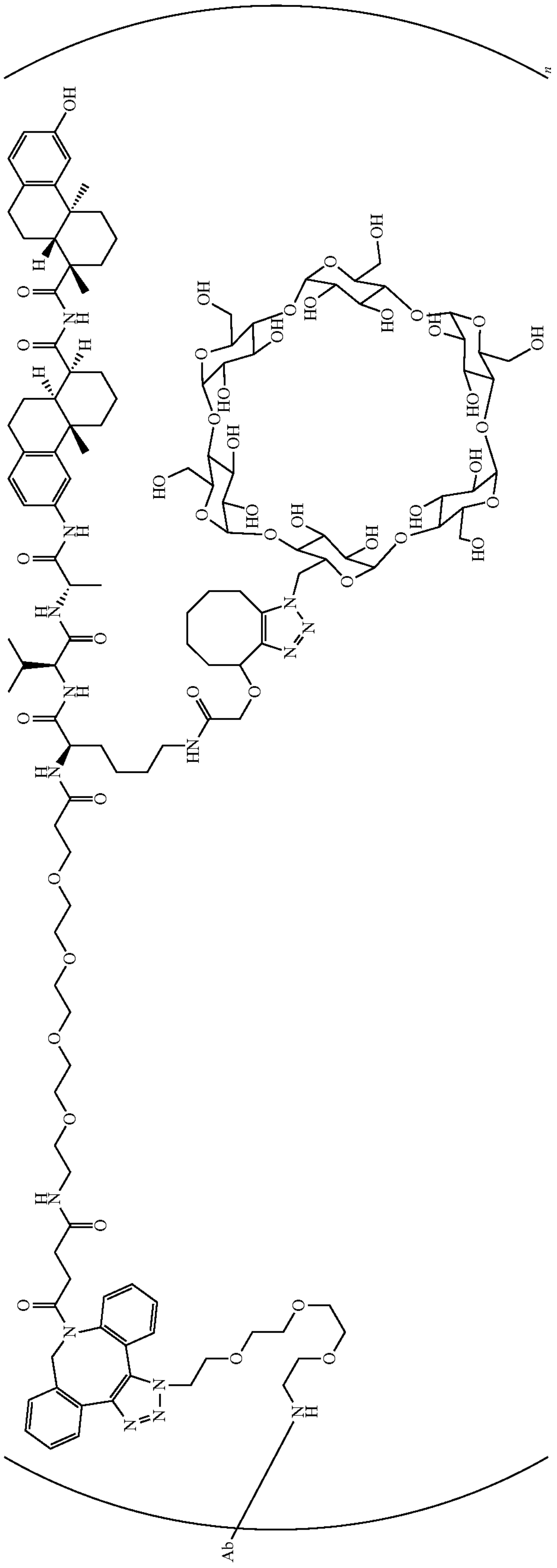
and/or

-continued
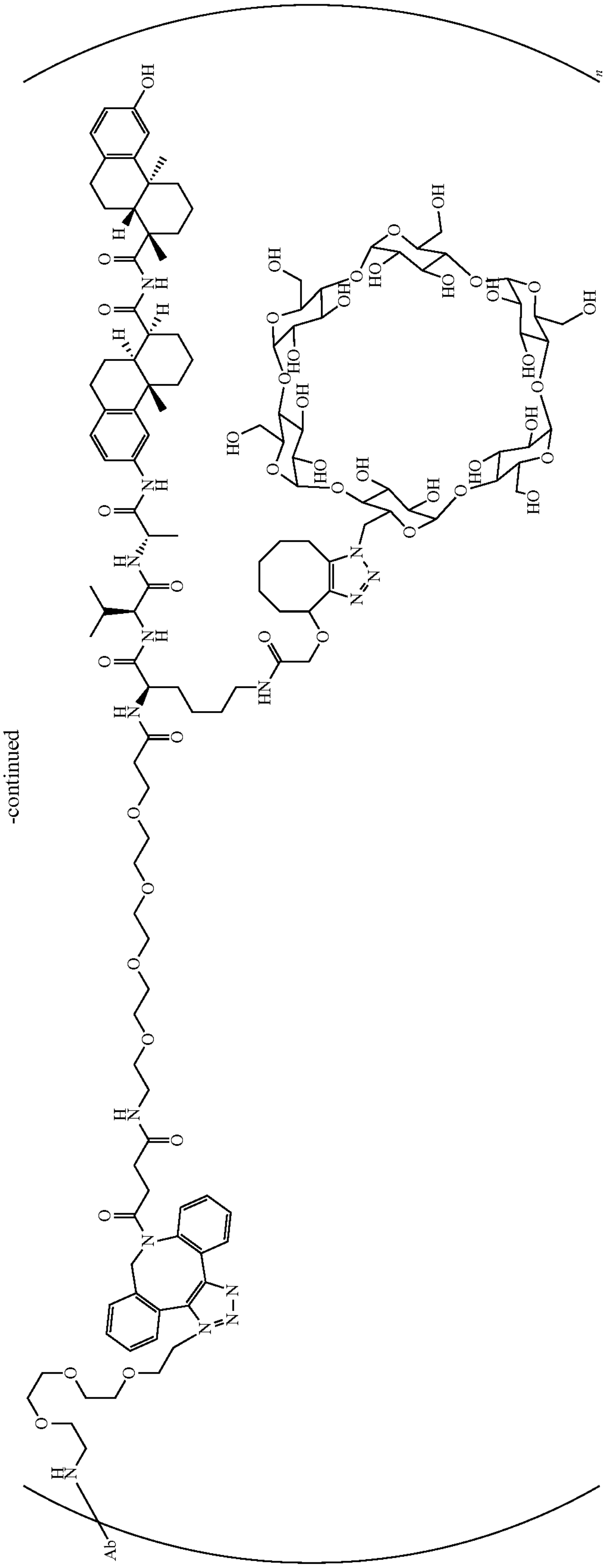

or pharmaceutically acceptable salt, solvate, stereoisomeric form, or regioisomer thereof, or mixtures thereof; wherein the antibody is an anti-MSR1 antibody, or antigen binding fragment thereof. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises an N297Q mutation.

An antibody-drug conjugate (ADC) according to the formulas:

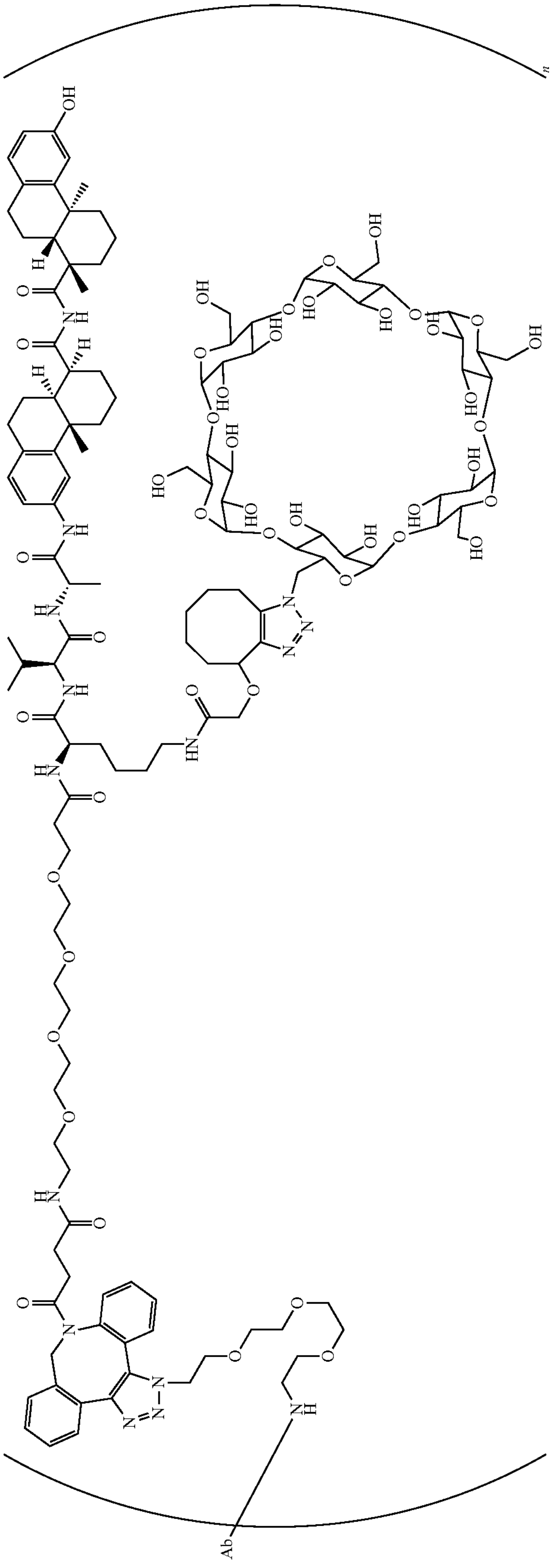
and/or

-continued
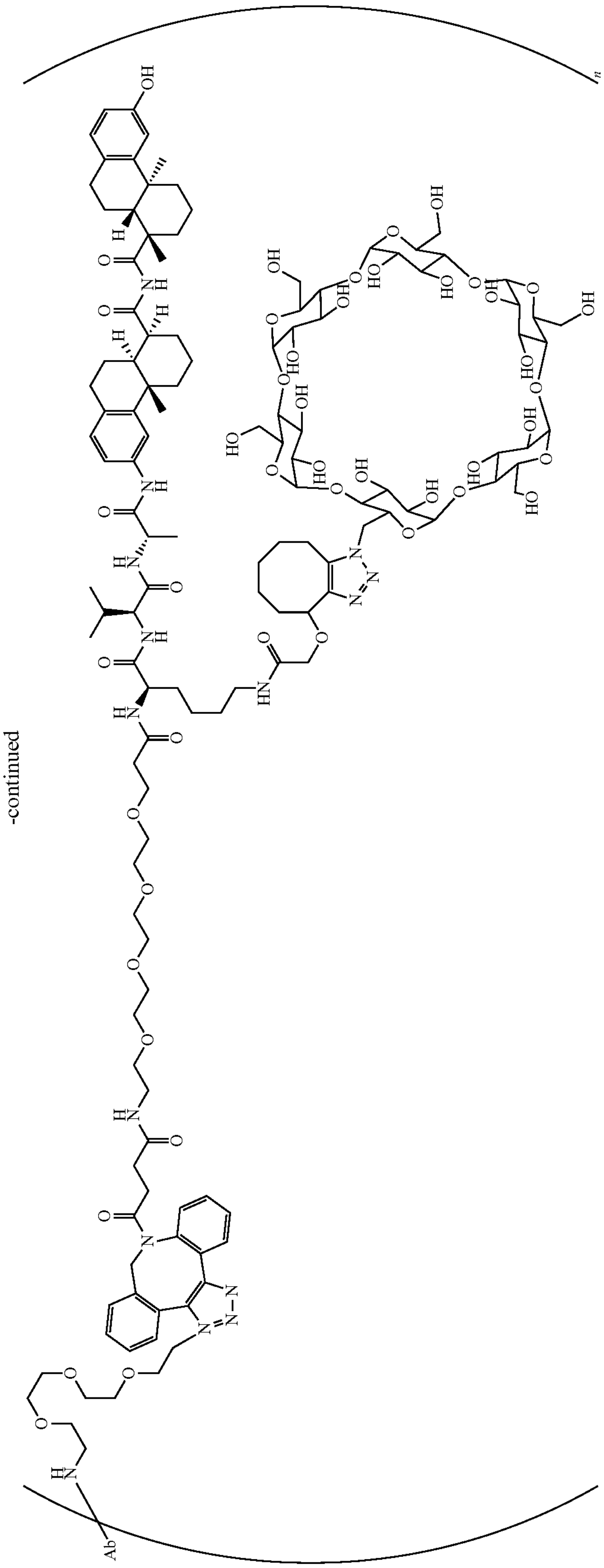

or pharmaceutically acceptable salt, solvate, stereoisomeric form, or regioisomer thereof, or mixtures thereof; wherein the antibody is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

An antibody-drug conjugate (ADC) according to the formulas:

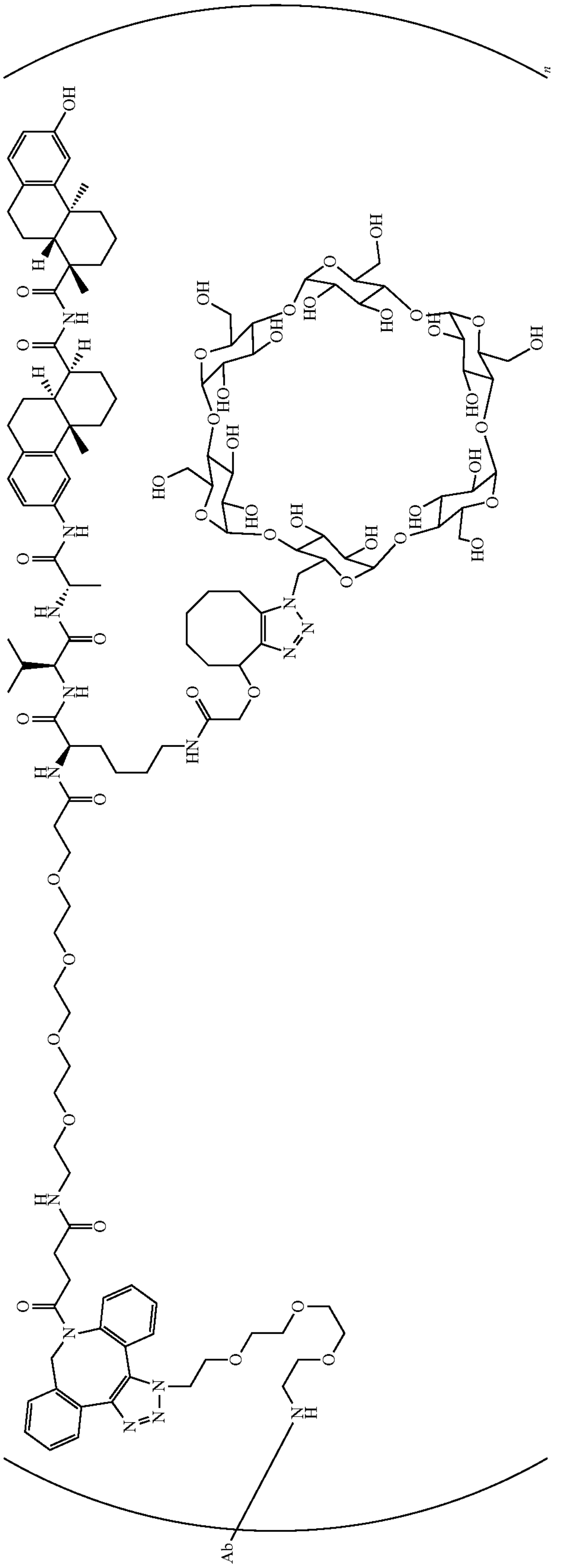
and/or

-continued
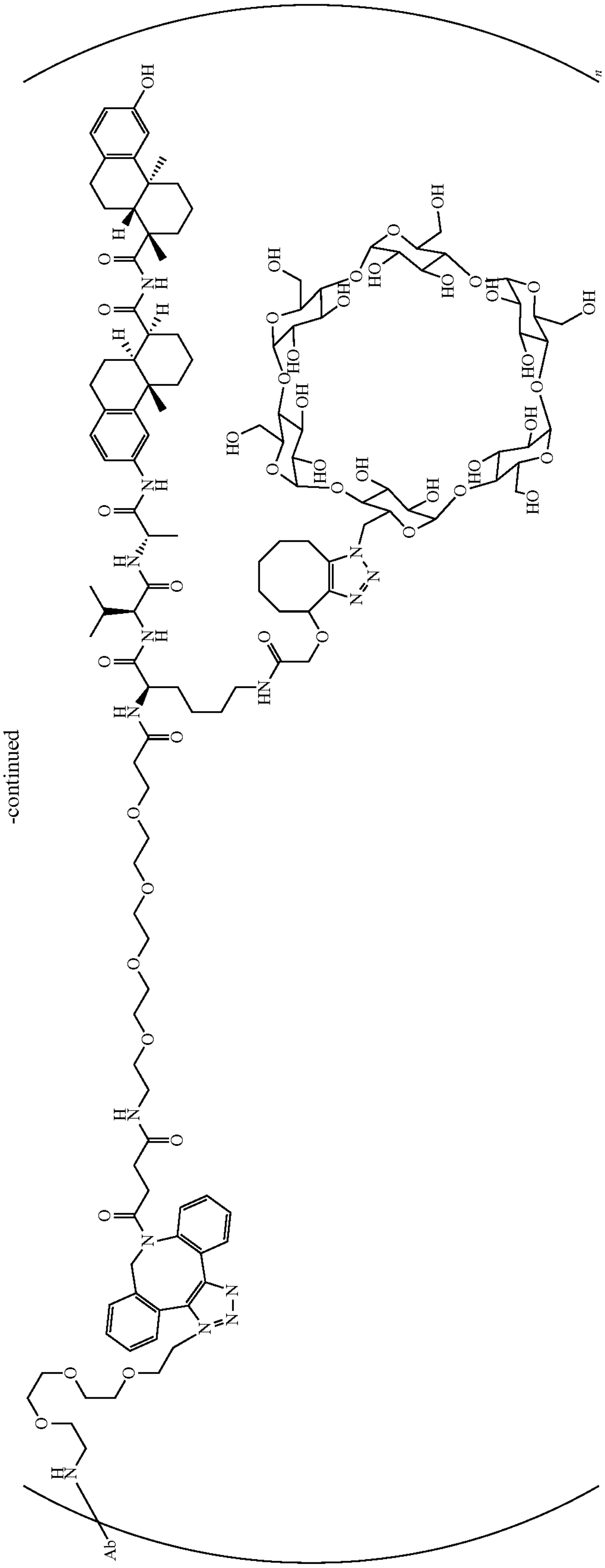

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56 a light chain complementarity determining region (LCDR)-1 comprising SEQ ID NO: 60; an LCDR2 comprising SEQ ID NO: 62; and an LCDR3 comprising SEQ ID NO: 64. In some of such embodiments, the drug antibody ratio (OAR) is from 1-4. In some embodiments, the OAR is 1. In some embodiments, the OAR is 2. In some embodiments, the OAR is 3. In some embodiments, the OAR is 4. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

An antibody-drug conjugate (ADC) according to the formulas:

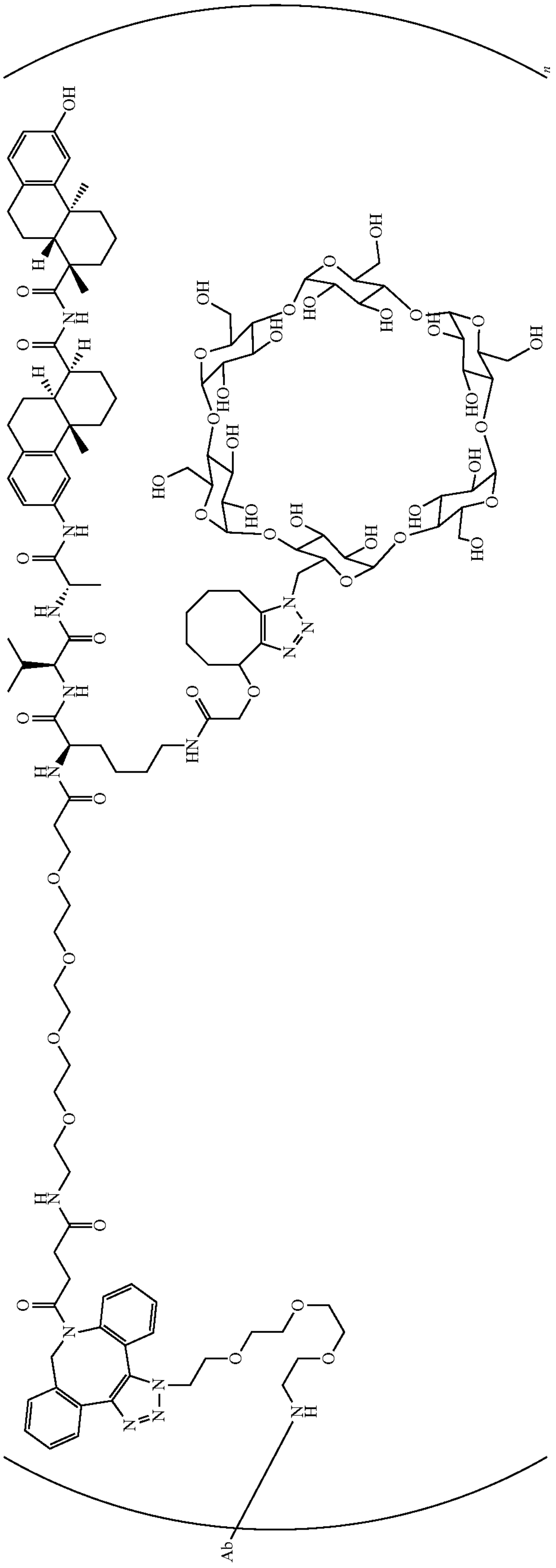
and/or

-continued
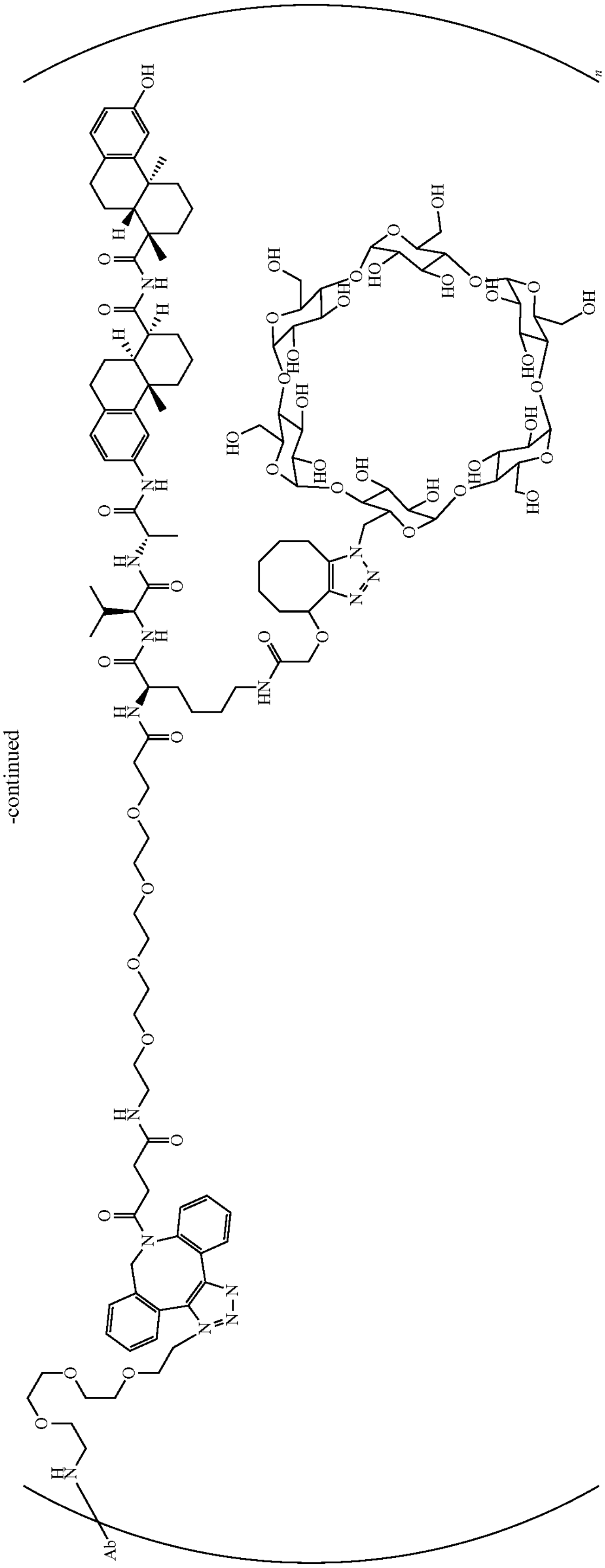

or pharmaceutically acceptable salt, solvate, stereoisomeric form, or regioisomer thereof, or mixtures thereof; wherein the antibody is an anti-MSR1 antibody, or antigen binding fragment thereof, comprising a set of variable regions heavy chain variable regions (HCVR) and a set of light chain variable regions (LCVR) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

An antibody-drug conjugate (ADC) according to the formulas:

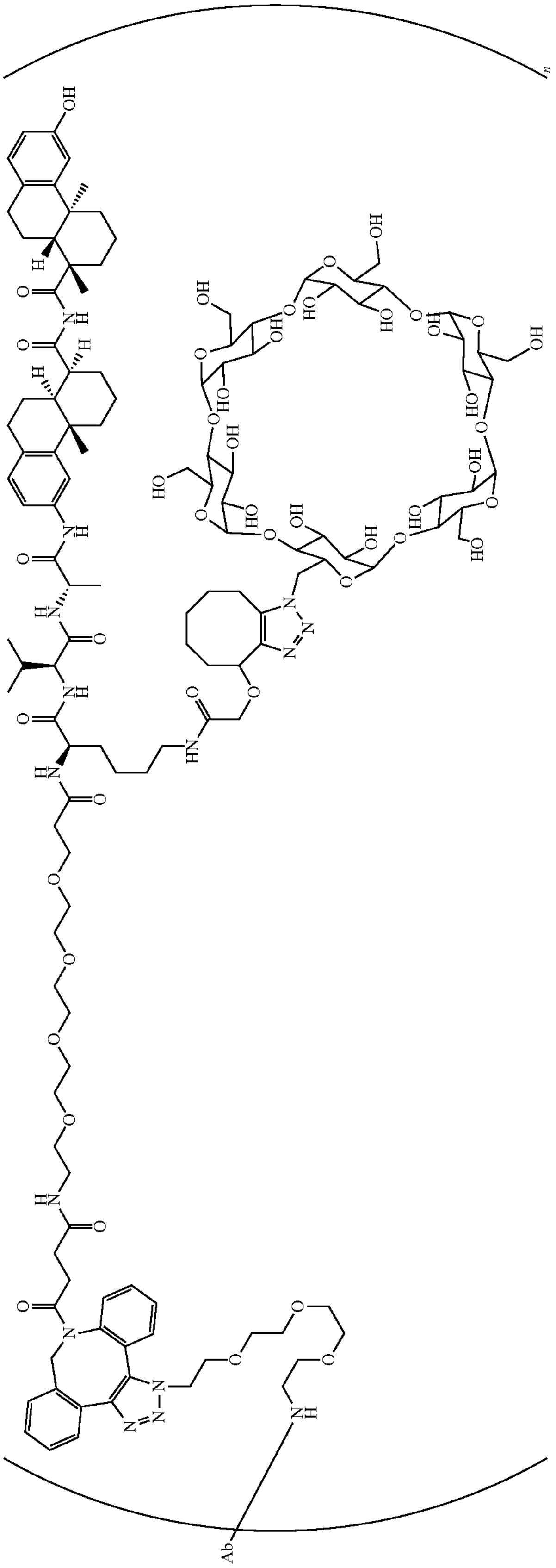
and/or

-continued
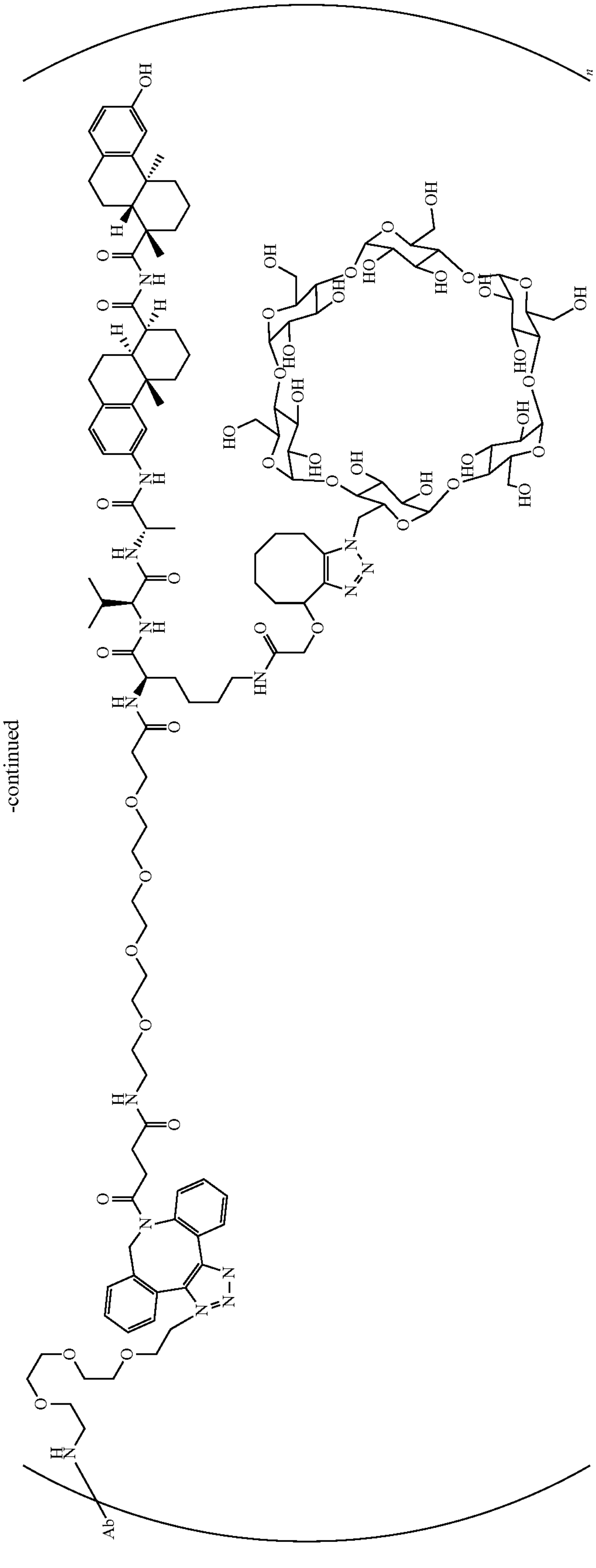

or pharmaceutically acceptable salt, solvate, stereoisomeric form, or regioisomer thereof, or mixtures thereof; wherein the antibody is an anti-MSR1 antibody, or antigen binding fragment thereof, comprising a heavy chain variable region (HCVR) comprising SEQ ID NO: 50 and a light chain variable region (LCVR) SEQ ID NO: 58. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

Provided herein is an anti-MSR1 antibody, or antigen binding fragment thereof, conjugated to the payload

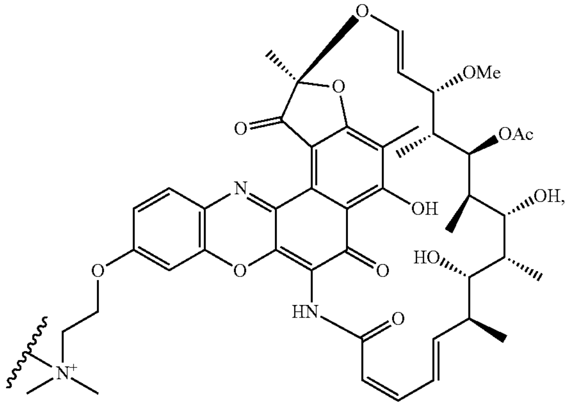 [SMILES: *[N+](C)(C)CCOc1ccc2nc3c4c5c6c(C)c(O)c4c(=O)c(c-3oc2c1)NC(=O)/C=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O]

or pharmaceutically acceptable salt, solvate or stereoisomeric form thereof. In some embodiments, the anti-MSR1 antibody, or antigen binding fragment thereof, comprises an N297Q mutation.

Provided herein is an anti-MSR1 antibody, or antigen binding fragment thereof, comprising a set of six complementarity determining regions (CDRs) (HCDR1, HCDR2, HCDR3, LCDR1, LCDR2, LCDR3 from Table 4 and conjugated to the payload

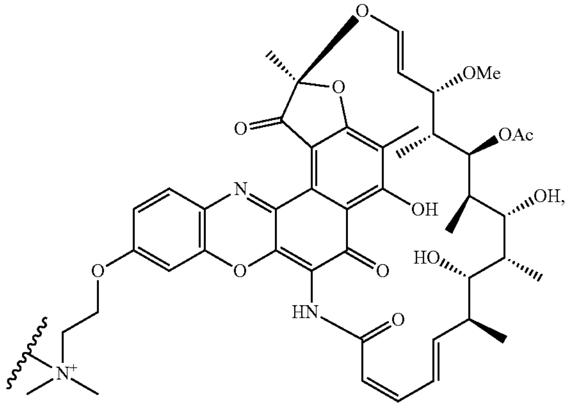 [SMILES: *[N+](C)(C)CCOc1ccc2nc3c4c5c6c(C)c(O)c4c(=O)c(c-3oc2c1)NC(=O)/C=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O]

or pharmaceutically acceptable salt, solvate or stereoisomeric form thereof. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

Provided herein is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64 and conjugated to the payload

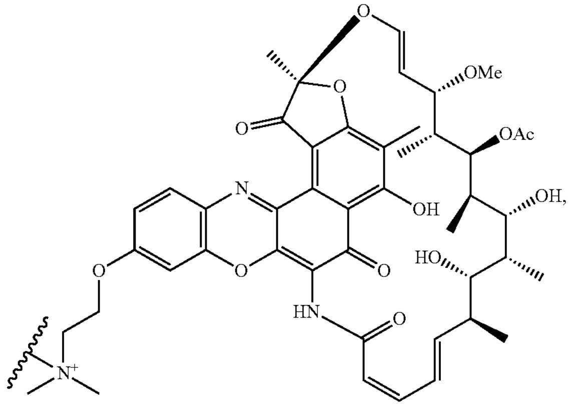 [SMILES: *[N+](C)(C)CCOc1ccc2nc3c4c5c6c(C)c(O)c4c(=O)c(c-3oc2c1)NC(=O)/C=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O]

or pharmaceutically acceptable salt, solvate or stereoisomeric form thereof. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

Provided herein is an anti-MSR1 antibody, or antigen binding fragment thereof, comprising a set of variable regions heavy chain variable regions (HCVR) and a set of light chain variable regions (LCVR) from Table 4 and conjugated to the payload

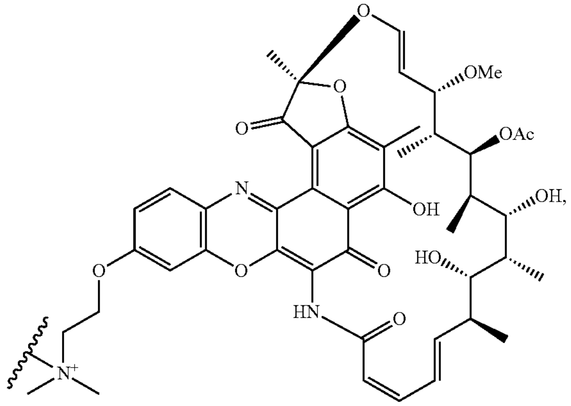 [SMILES: *[N+](C)(C)CCOc1ccc2nc3c4c5c6c(C)c(O)c4c(=O)c(c-3oc2c1)NC(=O)/C=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O]

or pharmaceutically acceptable salt, solvate or stereoisomeric form thereof. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

Provided herein is an anti-MSR1 antibody, or antigen binding fragment thereof, comprising a heavy chain variable region (HCVR) comprising SEQ ID NO: 50 and a light chain variable region (LCVR) SEQ ID NO: 58 and conjugated to the payload

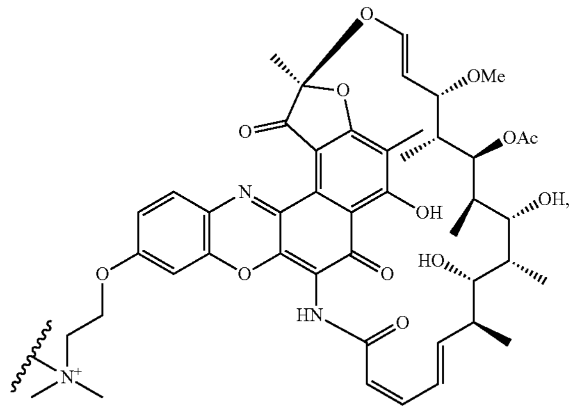 [SMILES: *[N+](C)(C)CCOc1ccc2nc3c4c5c6c(C)c(O)c4c(=O)c(c-3oc2c1)NC(=O)/C=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O]

or pharmaceutically acceptable salt, solvate or stereoisomeric form thereof. In some embodiments, the anti-MSR1 antibody, or antigen binding fragment thereof, comprises a heavy chain variable region (HCVR) comprising SEQ ID NO: 50 and a light chain variable region (LCVR) SEQ ID NO: 58, and an N297Q mutation.

An antibody-drug conjugate (ADC) according to the formula:

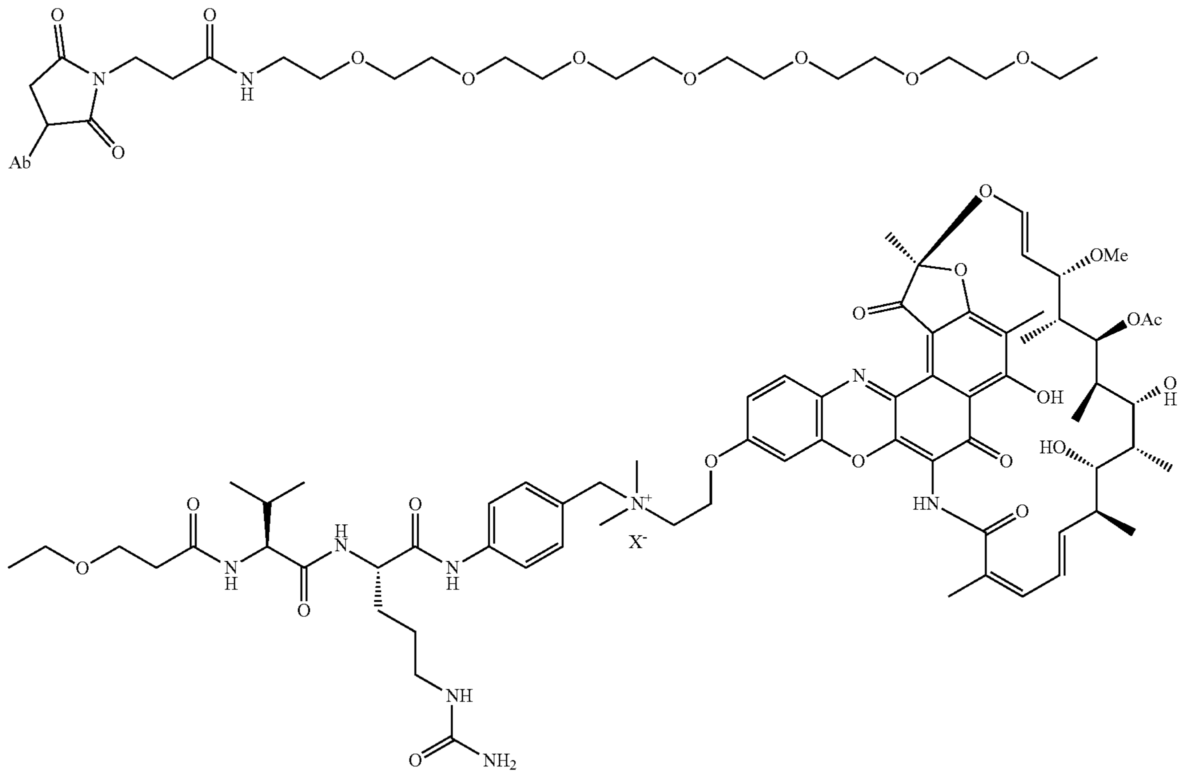

or pharmaceutically acceptable salt, solvate, stereoisomeric form, or regioisomer thereof, or mixtures thereof; wherein $X^-$ is a pharmaceutically acceptable counter ion and wherein the antibody is an anti-MSR1 antibody, or antigen binding fragment thereof. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises an N297Q mutation.

An antibody-drug conjugate (ADC) according to the formula:

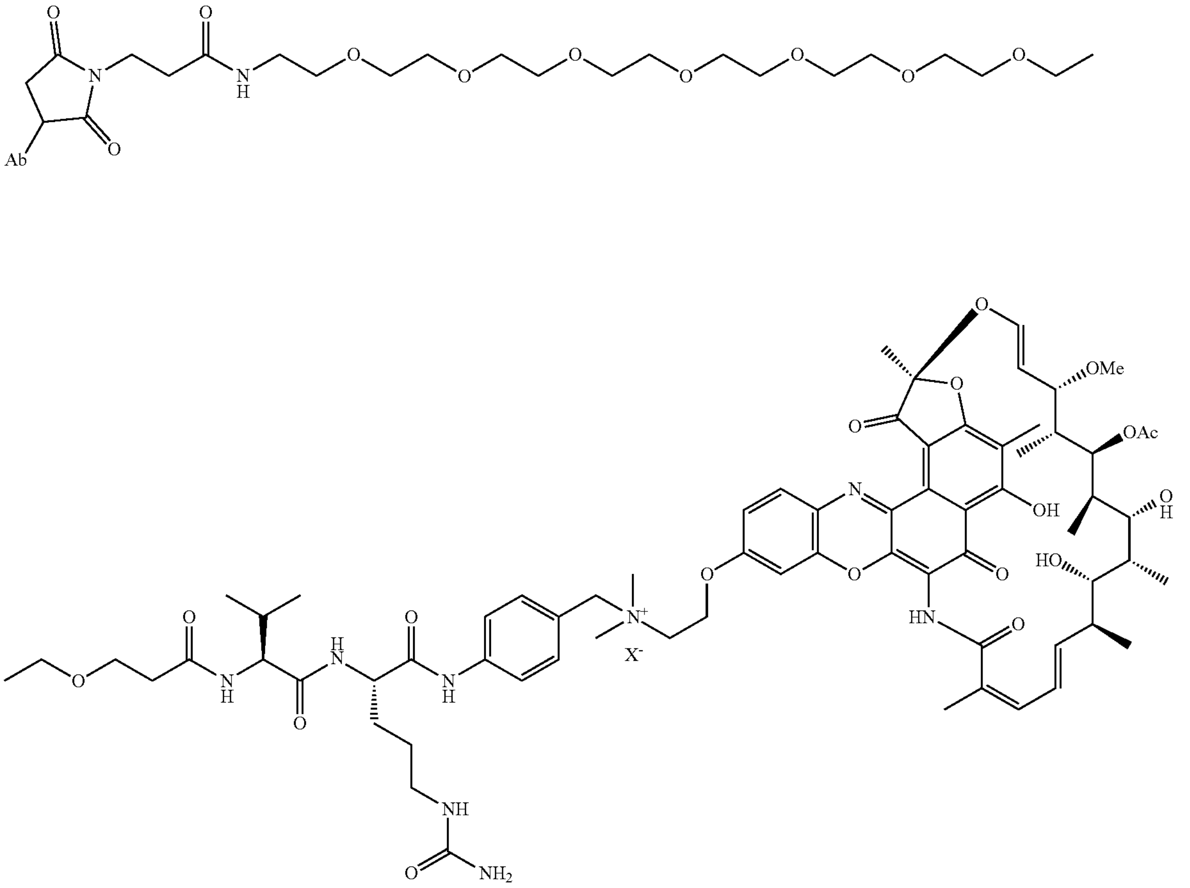

or pharmaceutically acceptable salt, solvate, stereoisomeric form, or regioisomer thereof, or mixtures thereof; wherein $X^-$ is a pharmaceutically acceptable counter ion and wherein the antibody is an anti-MSR1 antibody, or antigen binding fragment thereof, comprising a set of six complementarity determining regions (CDRs) (HCDR1, HCDR2, HCDR3, LCDR1, LCDR2, LCDR3) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of six complementarity determining regions (CDRs) (HCDR1, HCDR2, HCDR3, LCDR1, LCDR2, LCDR3) from Table 4, and an N297Q mutation.

An antibody-drug conjugate (ADC) according to the formula:

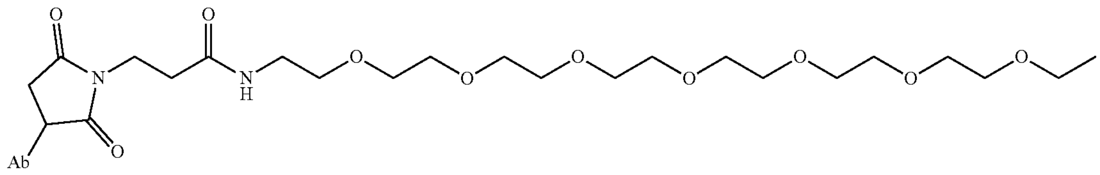

-continued

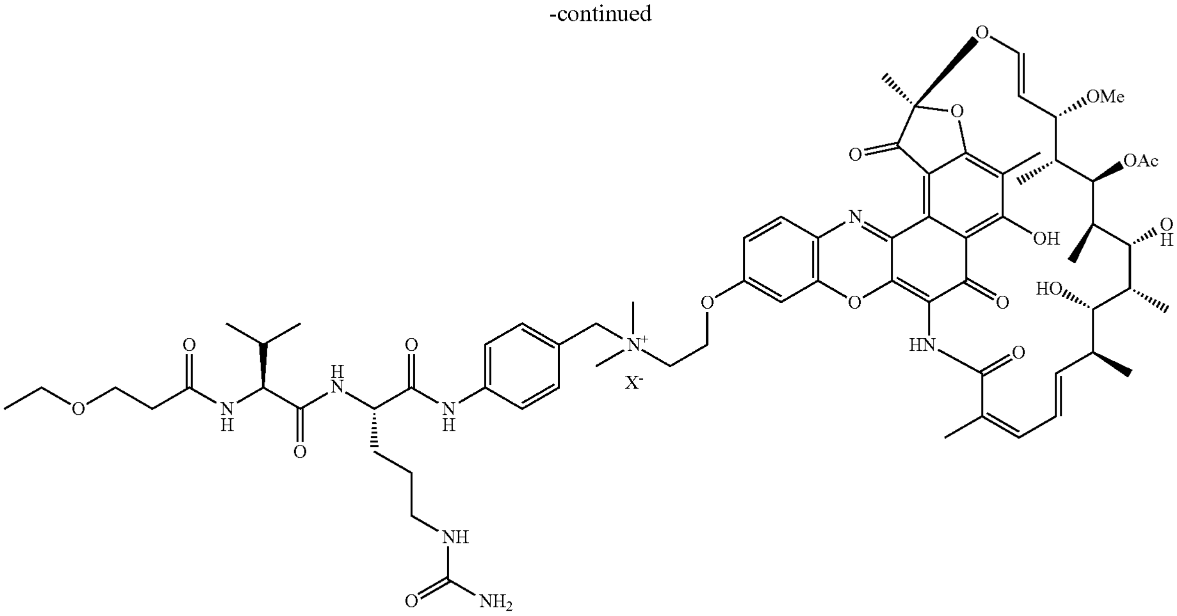

or pharmaceutically acceptable salt, solvate, stereoisomeric form, or regioisomer thereof, or mixtures thereof; wherein $X^-$ is a pharmaceutically acceptable counter ion and wherein the antibody is an anti-MSR1 antibody, or antigen binding fragment thereof, comprising a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain complementarity determining region (HCDR)-1 comprising SEQ ID NO: 52; an HCDR2 comprising SEQ ID NO: 54; an HCDR3 comprising SEQ ID NO: 56; a light chain complementarity determining region (LCDR)-1 comprising SEQ ID NO: 60; an LCDR2 comprising SEQ ID NO: 62; and an LCDR3 comprising SEQ ID NO: 64, and an N297Q mutation.

An antibody-drug conjugate (ADC) according to the formula:

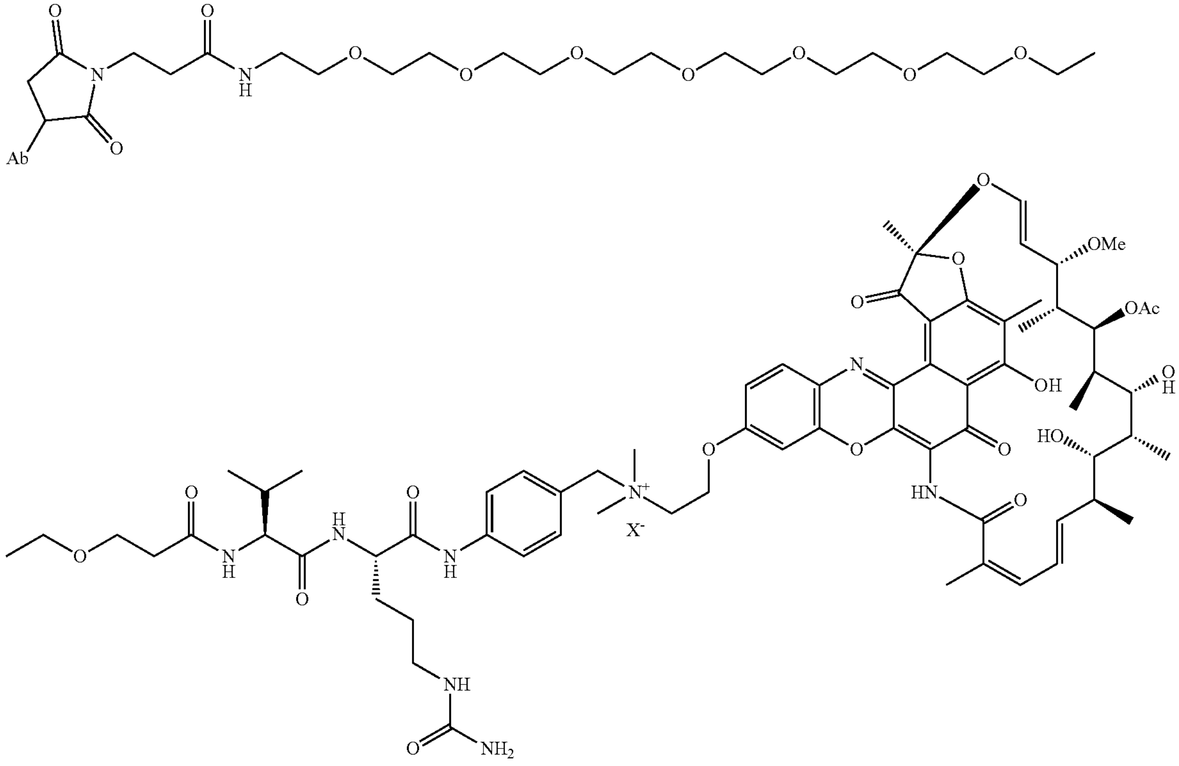

or pharmaceutically acceptable salt, solvate, stereoisomeric form, or regioisomer thereof, or mixtures thereof; wherein $X^-$ is a pharmaceutically acceptable counter ion and wherein the antibody is an anti-MSR1 antibody, or antigen binding fragment thereof, comprising a set of variable regions heavy chain variable regions (HCVR) and a set of light chain variable regions (LCVR) from Table 4. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a set of variable regions heavy chain variable regions (HCVR) and a set of light chain variable regions (LCVR) from Table 4, and an N297Q mutation.

An antibody-drug conjugate (ADC) according to the formula:

the antibody is an anti-MSR1 antibody, or antigen binding fragment thereof, comprising a heavy chain variable region (HCVR) comprising SEQ ID NO: 50 and a light chain variable region (LCVR) SEQ ID NO: 58. In some of such embodiments, the drug antibody ratio (DAR) is from 1-4. In some embodiments, the DAR is 1. In some embodiments, the DAR is 2. In some embodiments, the DAR is 3. In some embodiments, the DAR is 4. In some embodiments, the anti-MSR1 antibody, or antigen binding fragment thereof, comprises a heavy chain variable region (HCVR) comprising SEQ ID NO: 50; a light chain variable region (LCVR) SEQ ID NO: 58; and an N297Q mutation.

As used herein, in certain embodiments, where an amino acid is bonded to the spacer $SP^1$, e.g., in the moiety $—SP^1\text{-}AA^1\text{-}AA^2\text{-}$, the amino acid $AA^1$ is bonded via its amino group to the spacer $SP^1$. The spacer residue includes

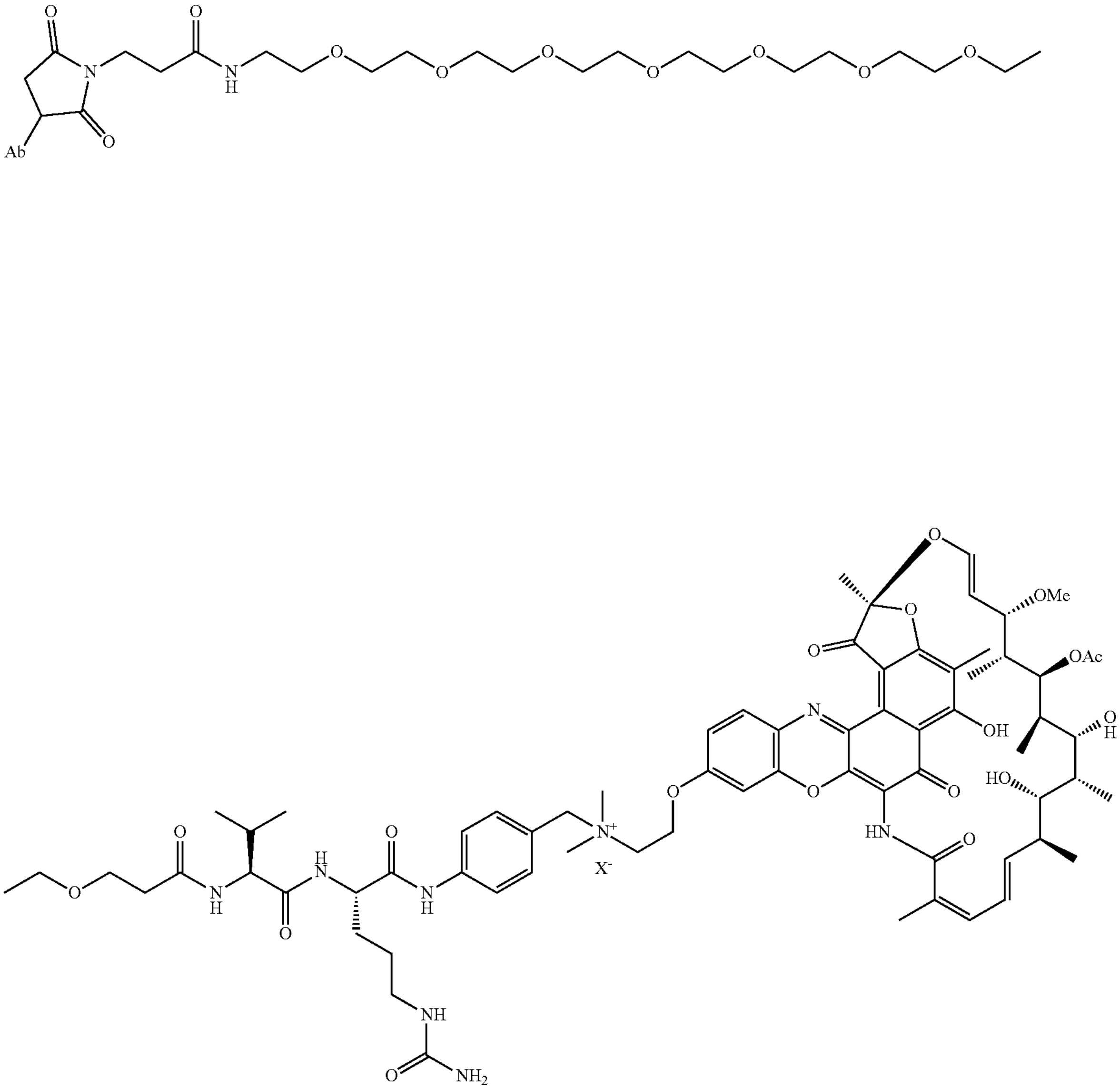

or pharmaceutically acceptable salt, solvate, stereoisomeric form, or regioisomer thereof, or mixtures thereof; wherein $X^-$ is a pharmaceutically acceptable counter ion and wherein portions of a functional group that formed the bond with the amino group in the amino acid. By way of example only, in the following structure:

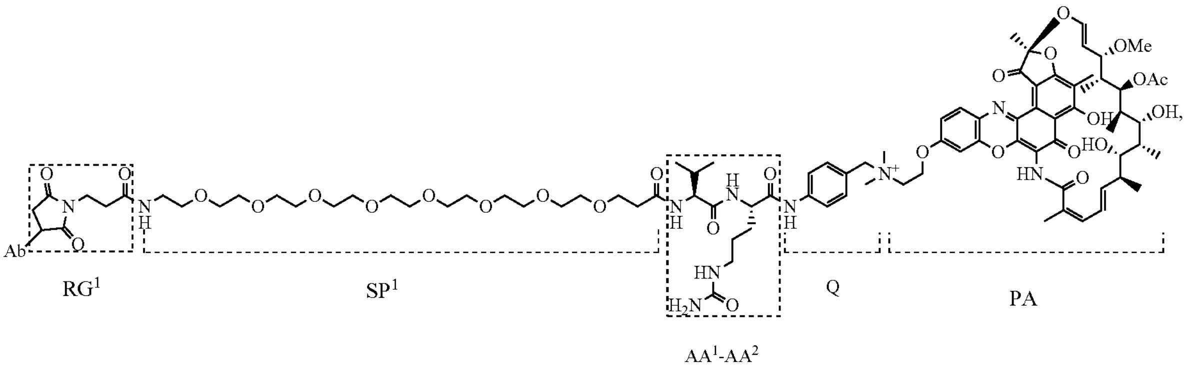

the valine residue is bonded to $SP^1$ as shown, and the $SP^1$ residue, in this example, comprises a (C=O) moiety. Also, in this example, the $SP^1$ residue comprises a functional group suitable for forming a bond with the reactive group and the $SP^1$ residue comprises a —NH— moiety. Those of skill in the art will recognize that similar groupings can apply to all other formulae described herein.

The antibody drug conjugates described herein can be prepared using conjugation conditions known to those of ordinary skill in the art, (see, e.g., Doronina et al. Nature Biotechnology 2003, 21, 7, 778, which is incorporated herein by reference in its entirety). In some embodiments an ADC is prepared by contacting an anti-MSR1 antibody or an antigen-binding fragment thereof with a compound comprising the desired linker and payload, wherein said linker possesses a moiety that is reactive with the antibody or antigen-binding protein, e.g., at the desired residue of the antibody or antigen-binding protein. Exemplary conditions are described in the Examples below.

Preparation of Antibody-Drug Conjugates

In some embodiments, provided herein are processes for preparing an antibody-drug conjugate comprising contacting an anti-MSR1 antibody, or a PEG-modified anti-MSR1 antibody, or an antigen binding fragment thereof with a linker-payload or a linker-spacer-payload selected from Table 3. Also provided herein is an antibody drug conjugate prepared by conjugating an anti-MSR1 antibody or a PEG-modified anti-MSR1 antibody, or an antigen binding fragment thereof, with a linker payload, or a linker-spacer-payload, or a stereoisomeric form thereof, or a regioisomer thereof, or a mixture of regioisomers thereof, selected from Table 3.

TABLE 3

| List of linker-payloads (LPs) and their structures | |
|---|---|
| LP1 | 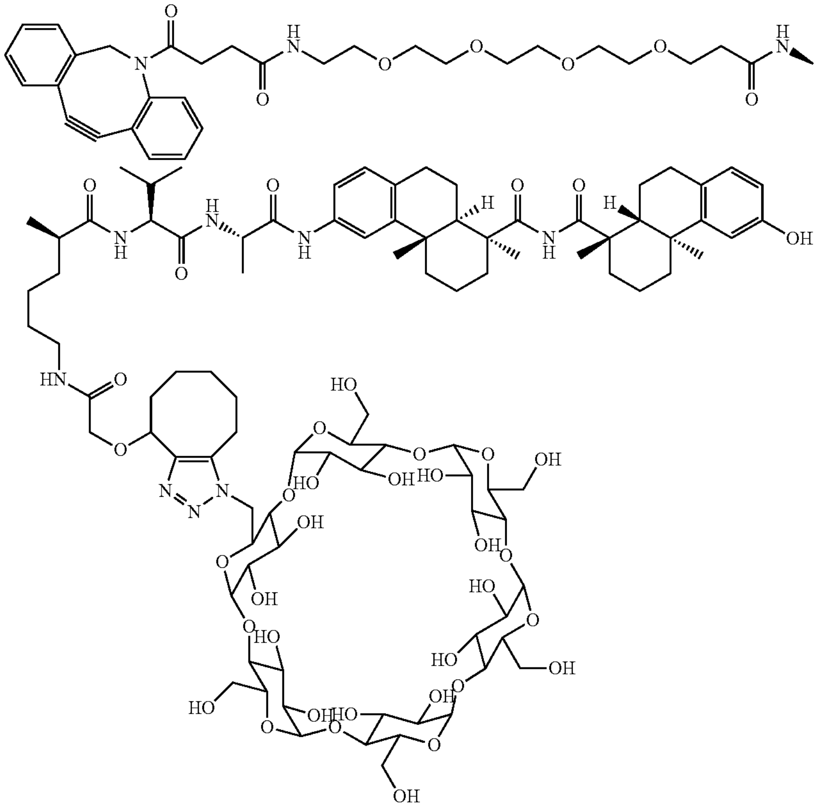 |

TABLE 3-continued
| List of linker-payloads (LPs) and their structures | |
|---|---|
| LP2 | 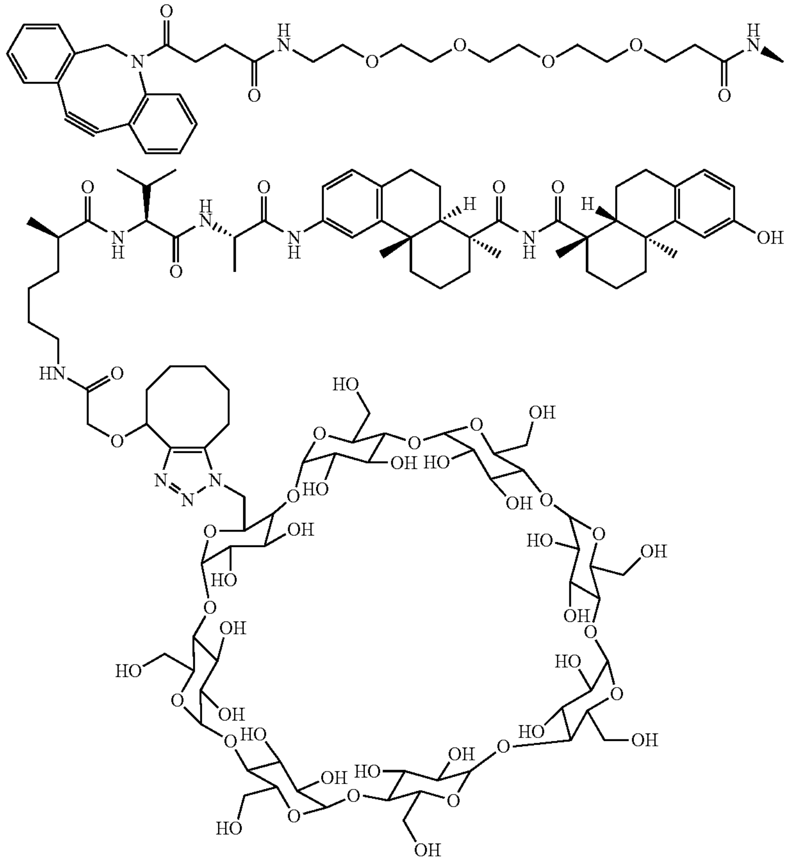 |
| LP5 | 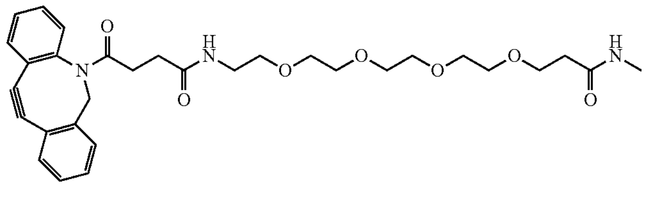 |

TABLE 3-continued
| List of linker-payloads (LPs) and their structures |
|---|
| 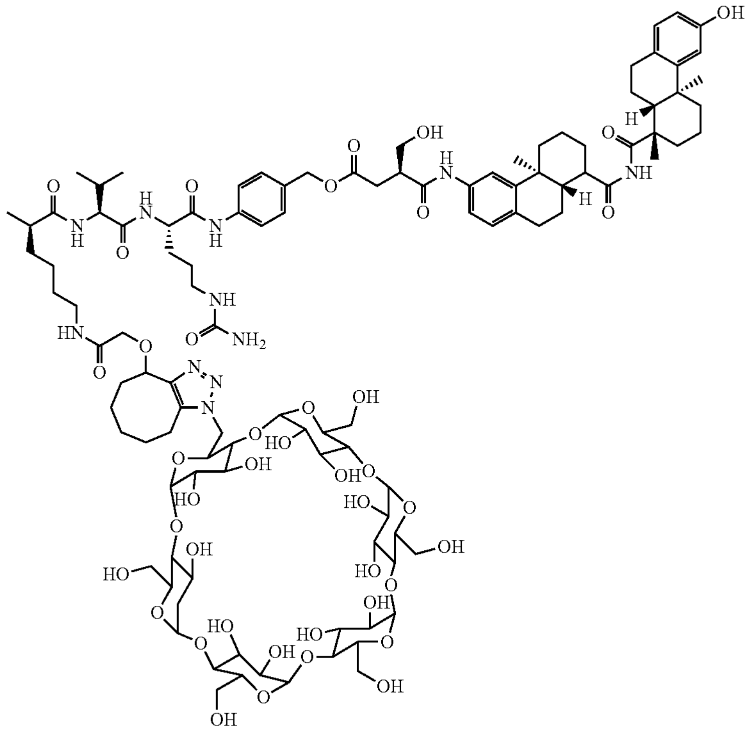 |
| LP6 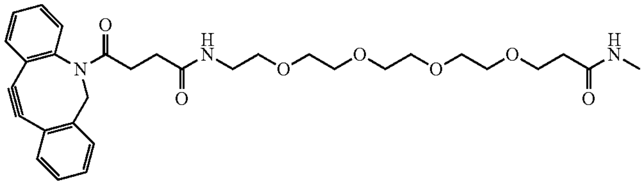 |
| 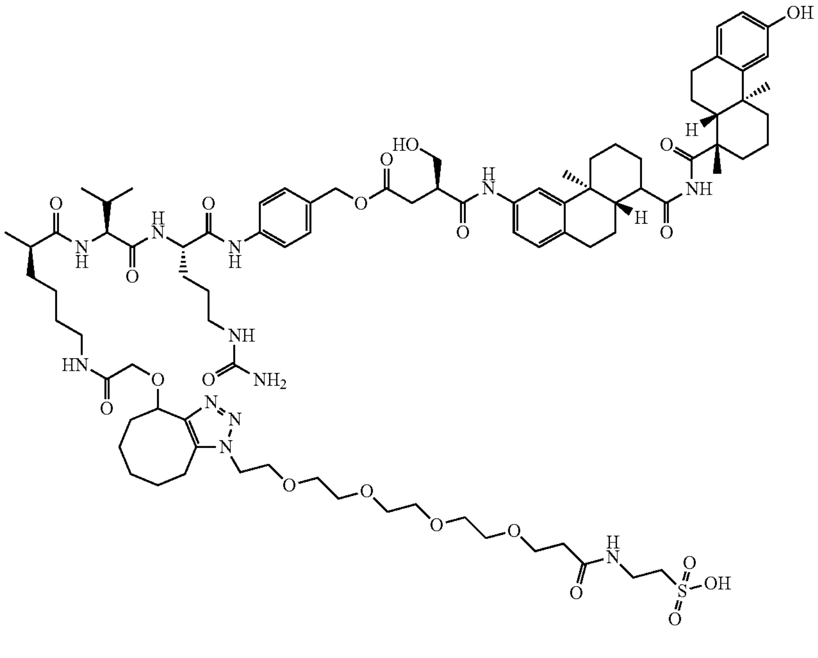 |

TABLE 3-continued
List of linker-payloads (LPs) and their structures
LP18
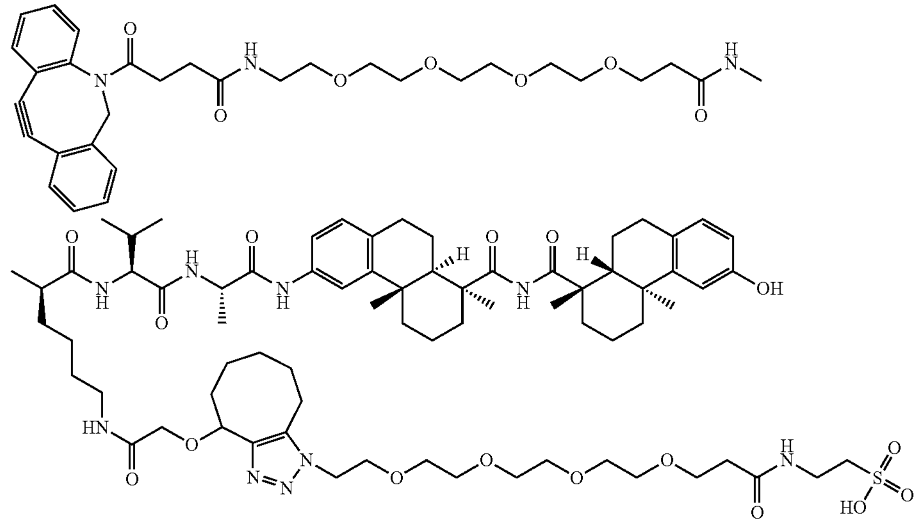
LP4
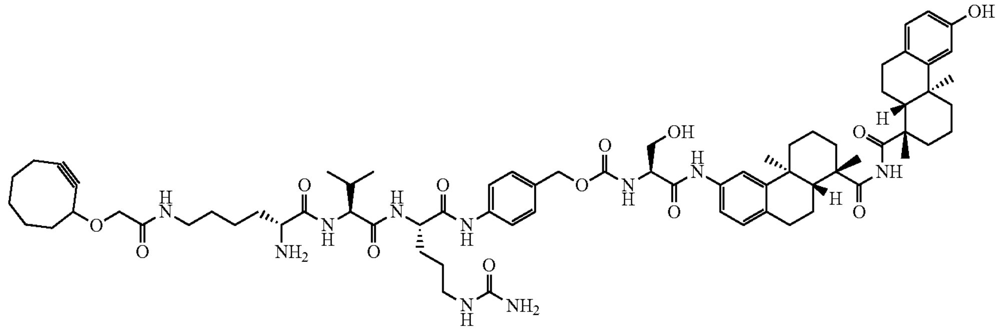 [SMILES: CC(C)[C@H](NC(=O)[C@H](N)CCCCNC(=O)COC1C#CCCCCC1)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]
LP11
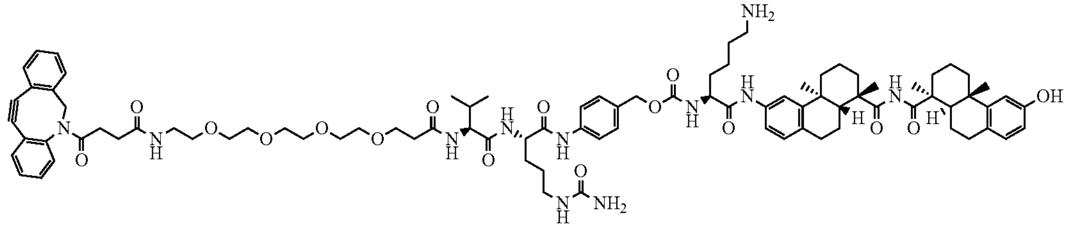 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCCCN)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]
LP9
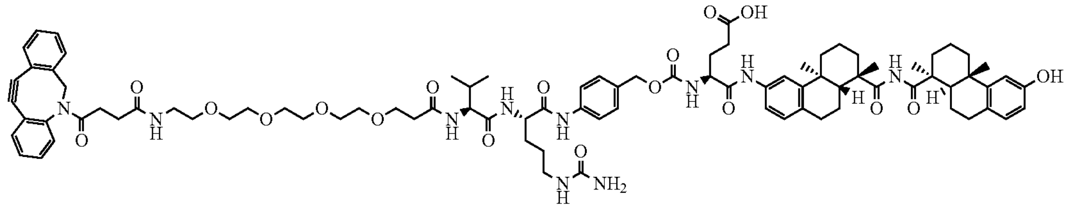 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]
LP12
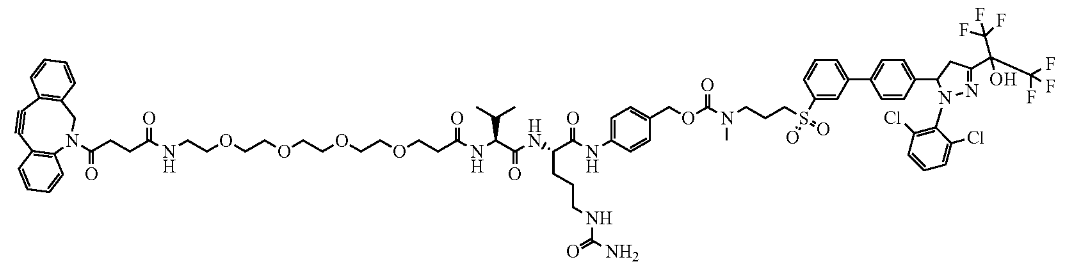 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N(C)CCCS(=O)(=O)c2cccc(-c3ccc(C4CC(C(O)(C(F)(F)F)C(F)(F)F)=NN4c4c(Cl)cccc4Cl)cc3)c2)cc1]

TABLE 3-continued
| List of linker-payloads (LPs) and their structures | |
|---|---|
| LP3 | 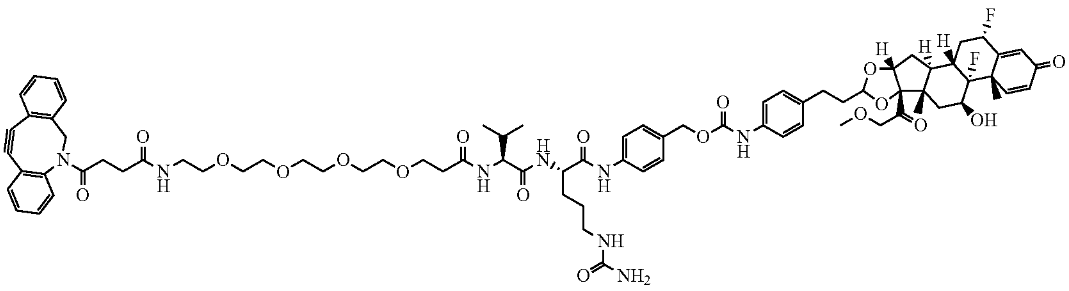 |
| LP13 | 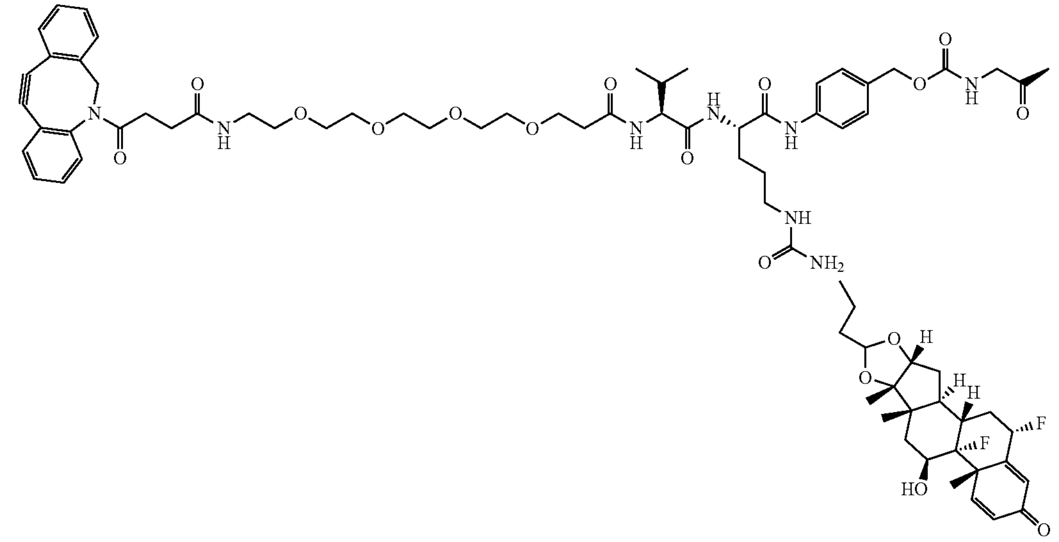 |
| | 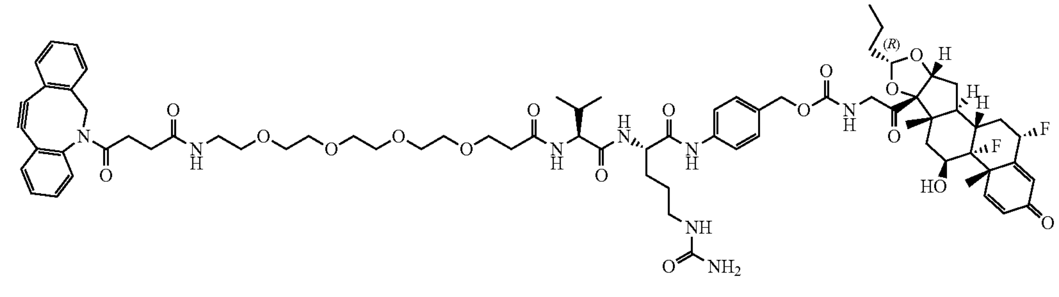 |
| | 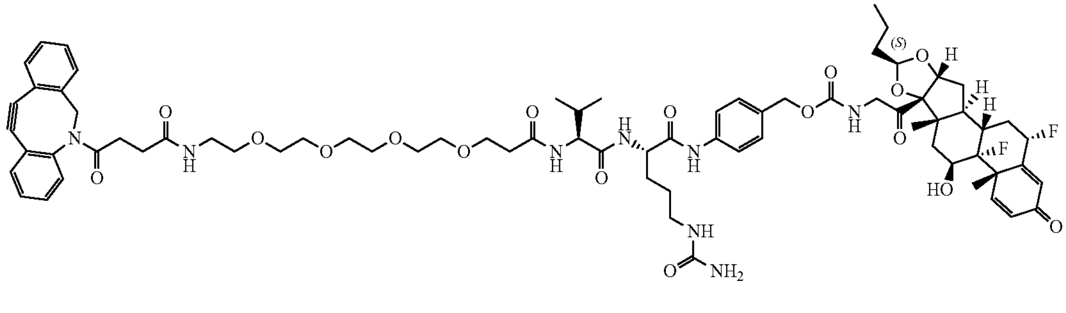 |

TABLE 3-continued
List of linker-payloads (LPs) and their structures
LP14
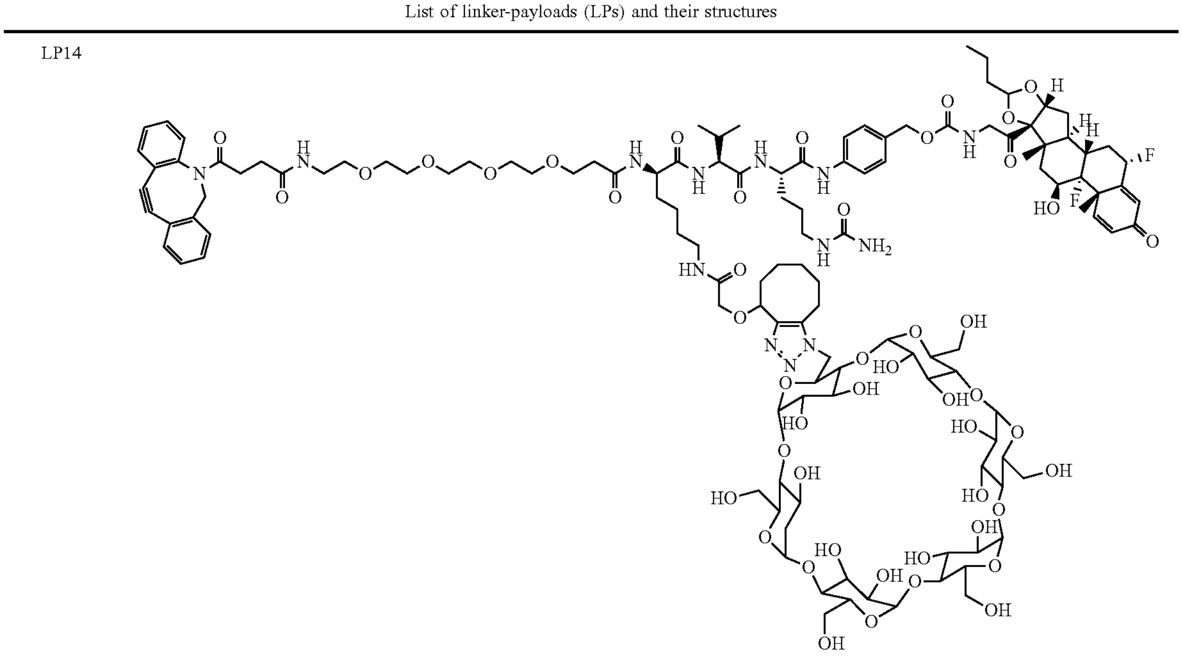
LP15
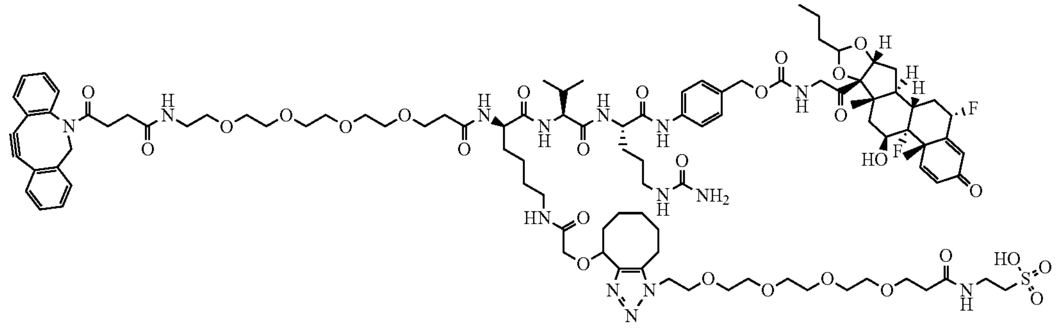 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CCOCCOCCOCCOCCC(=O)NCCS(=O)(=O)O)NC(=O)CCOCCOCCOCCOCCNC(=O)CCC(=O)N3Cc4ccccc4C#Cc4ccccc43)C(C)C)cc2)O1]
2a
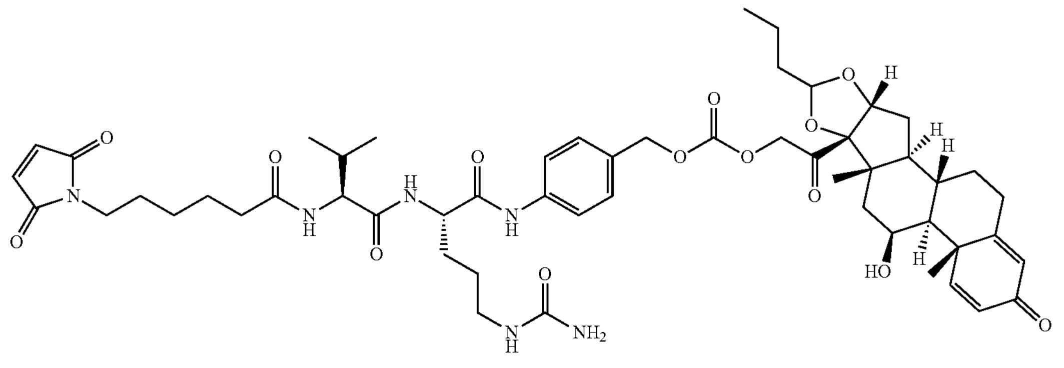 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)CCCCCN3C(=O)C=CC3=O)C(C)C)cc2)O1]
2b
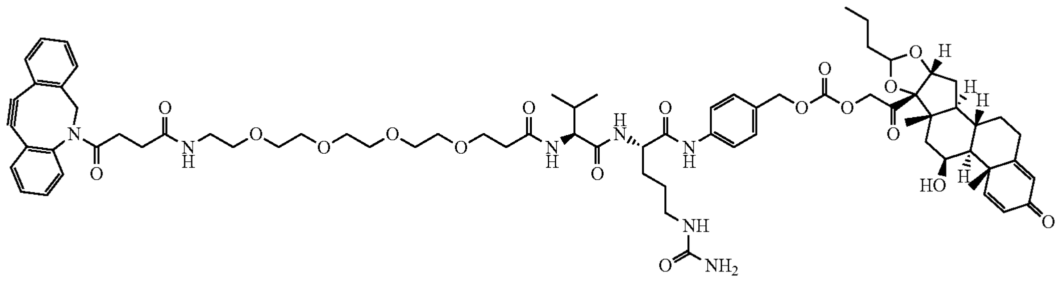 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

TABLE 3-continued
List of linker-payloads (LPs) and their structures
2f
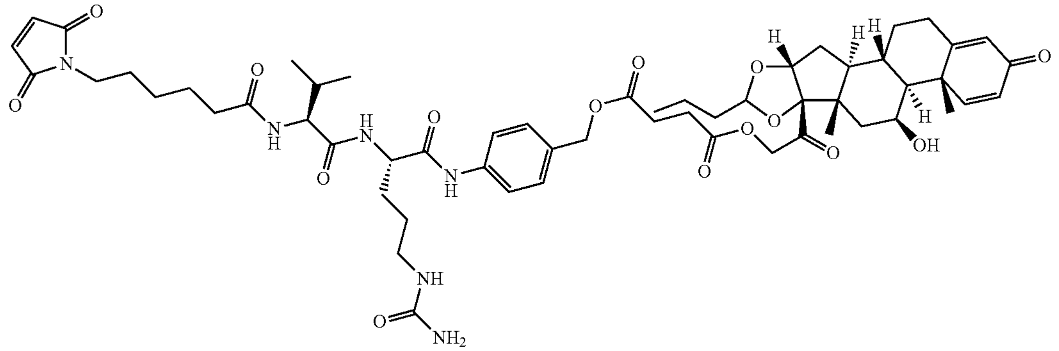 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCCCCN3C(=O)C=CC3=O)C(C)C)cc2)O1]
2g
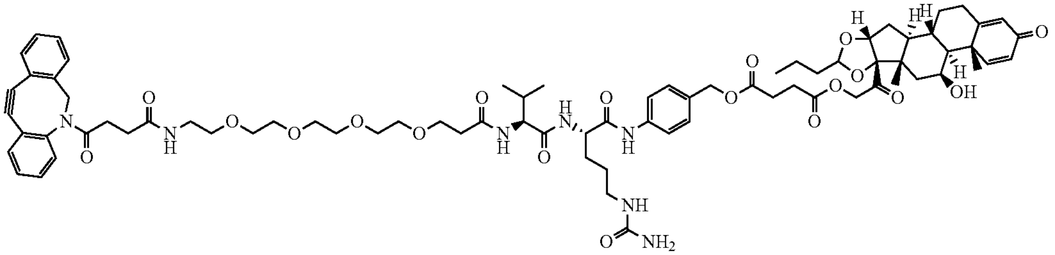 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]
2j
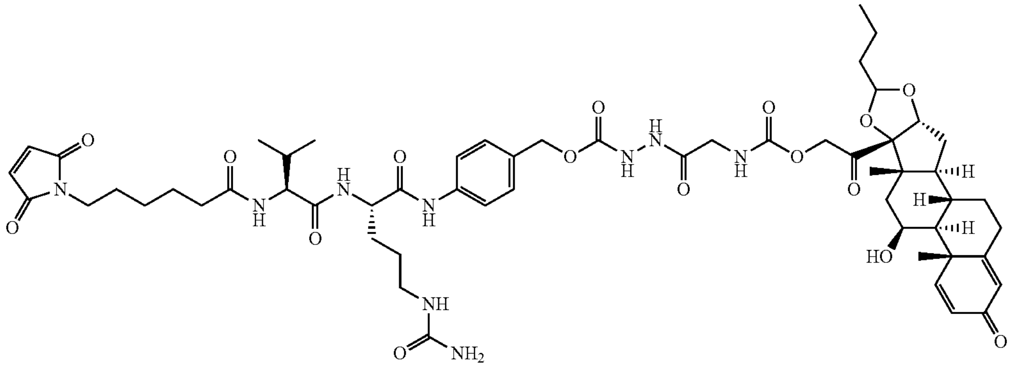
2k
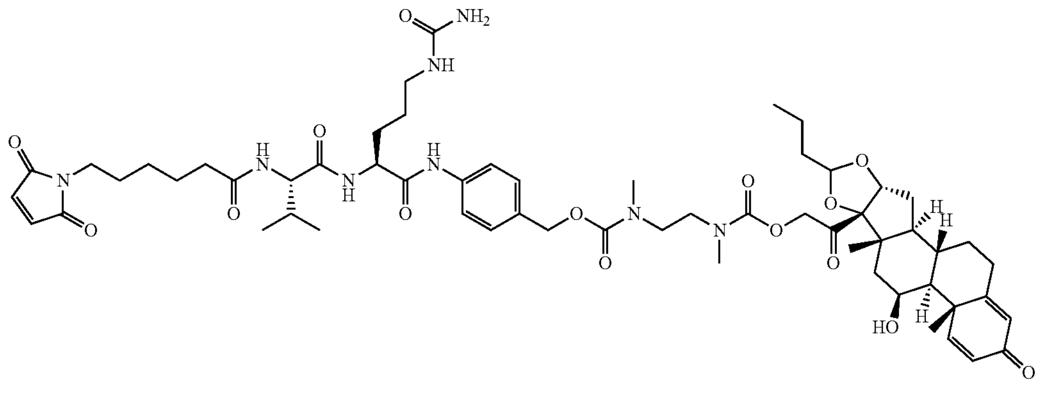 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCCCCN3C(=O)C=CC3=O)C(C)C)cc2)O1]

TABLE 3-continued
List of linker-payloads (LPs) and their structures
2l
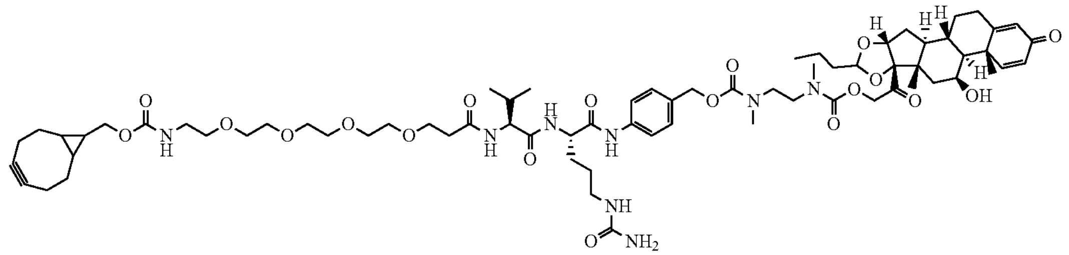 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)OCC3C4CCC#CCCC43)C(C)C)cc2)O1]
2m
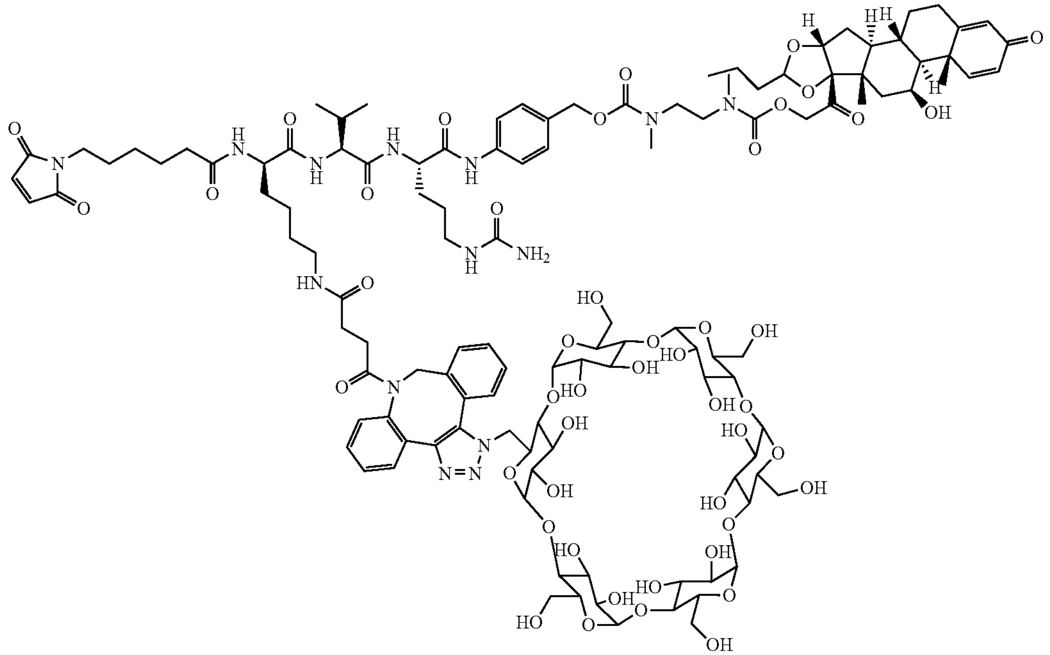 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)[C@@H](CCCCNC(=O)CCC(=O)N3Cc4ccccc4-c4c(nnn4CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)-c4ccccc43)NC(=O)CCCCCN3C(=O)C=CC3=O)C(C)C)cc2)O1]
2n
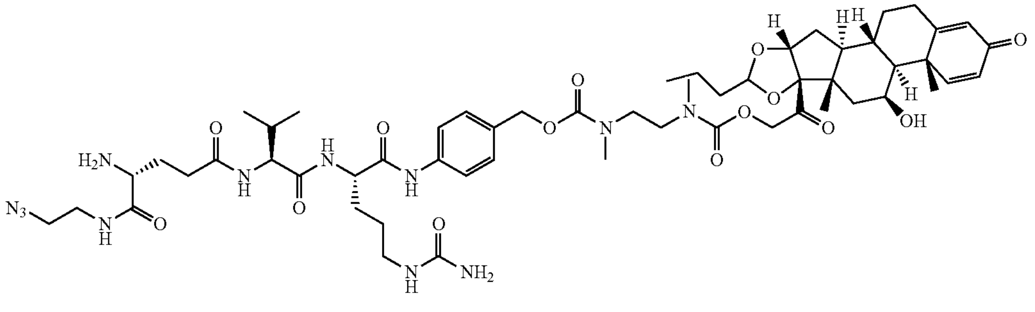
or a mixture thereof
2q
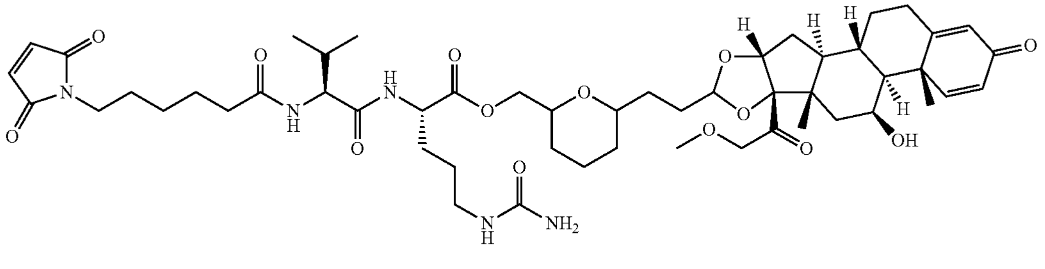 [SMILES: COCC(=O)[C@@]12OC(CCC3CCCC(COC(=O)[C@H](CCCNC(N)=O)NC(=O)[C@@H](NC(=O)CCCCCN4C(=O)C=CC4=O)C(C)C)O3)O[C@@H]1C[C@H]1[C@@H]3CCC4=CC(=O)C=C[C@]4(C)[C@H]3[C@@H](O)C[C@@]12C]

TABLE 3-continued
List of linker-payloads (LPs) and their structures
LP1A
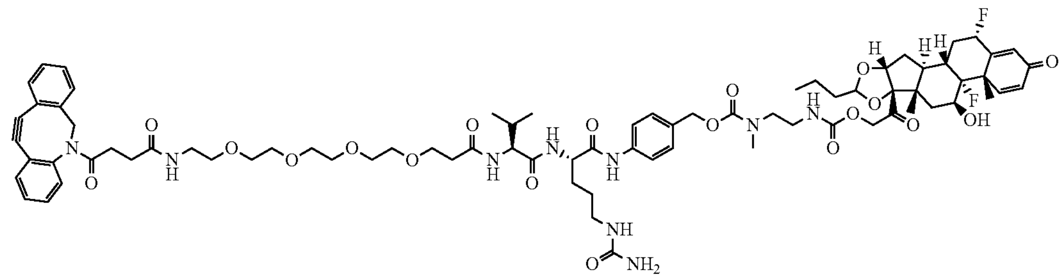 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCN(C)C(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]
LP2A
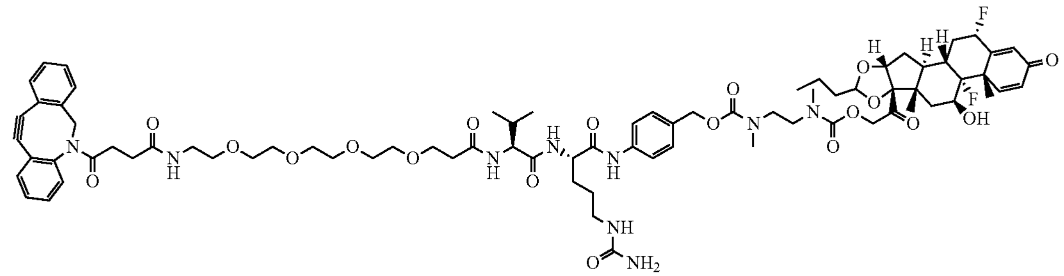 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]
LP3A
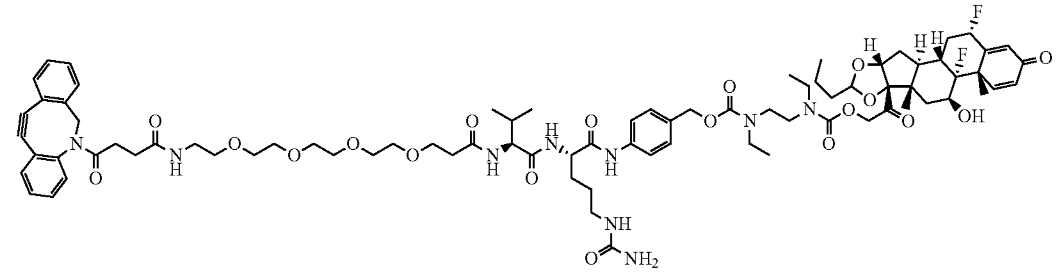
LP4A
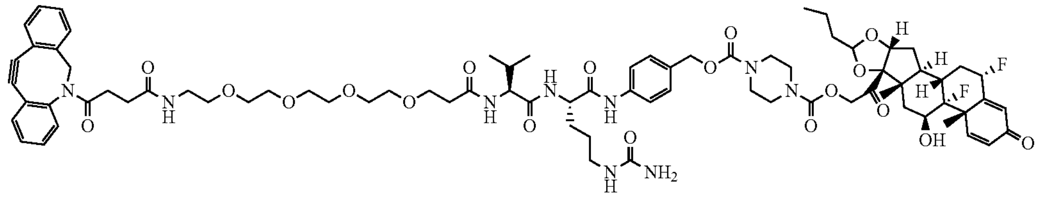
LP5A
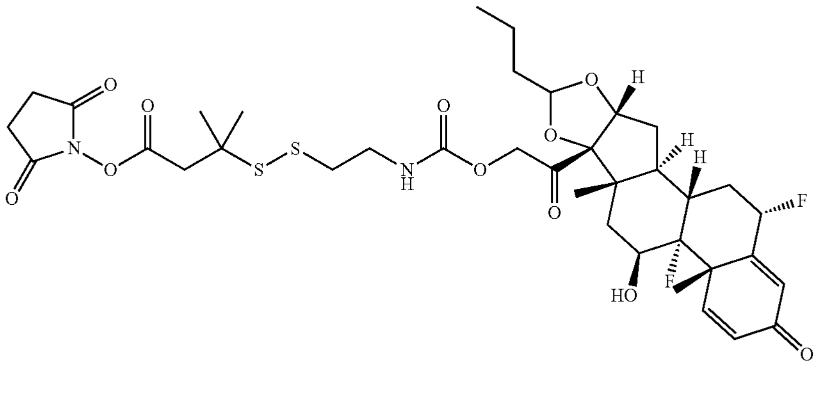

TABLE 3-continued
| List of linker-payloads (LPs) and their structures | |
|---|---|
| LP6A | 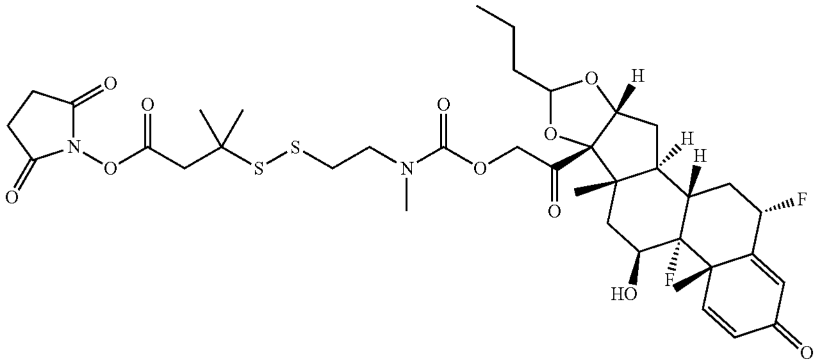 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)ON2C(=O)CCC2=O)O1] |
| LP7A | 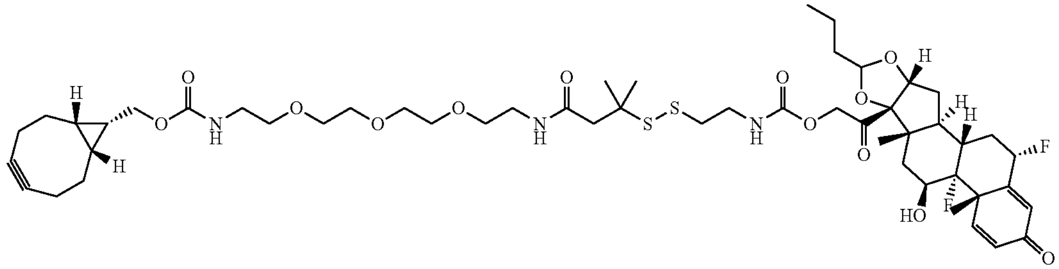 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)NCCOCCOCCOCCNC(=O)OC[C@@H]2[C@@H]3CCC#CCC[C@@H]32)O1] |
| LP8A | 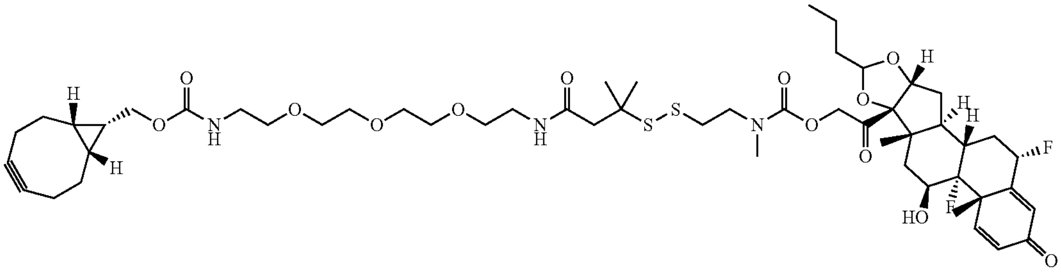 |
| LP9A | 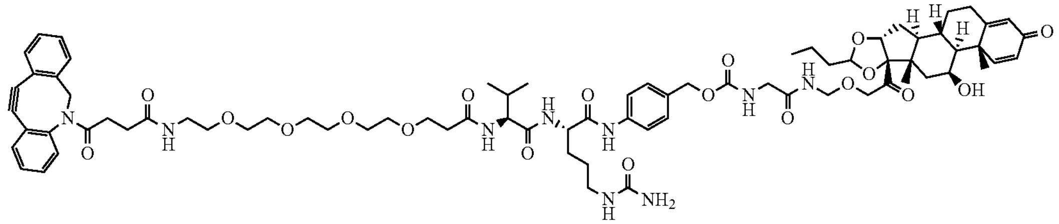 |
| LP10A | 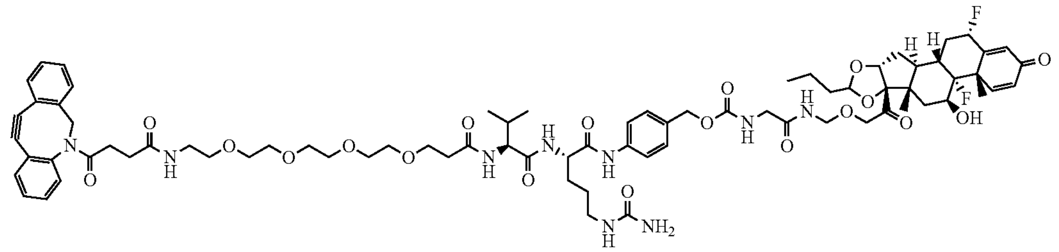 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COCNC(=O)CNC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1] |

TABLE 3-continued
List of linker-payloads (LPs) and their structures
LP11A
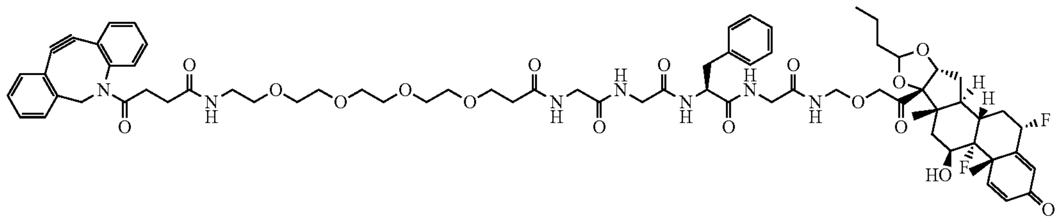 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COCNC(=O)CNC(=O)[C@H](Cc2ccccc2)NC(=O)CNC(=O)CNC(=O)CCOCCOCCOCCOCCNC(=O)CCC(=O)N2Cc3ccccc3C#Cc3ccccc32)O1]
LP12A
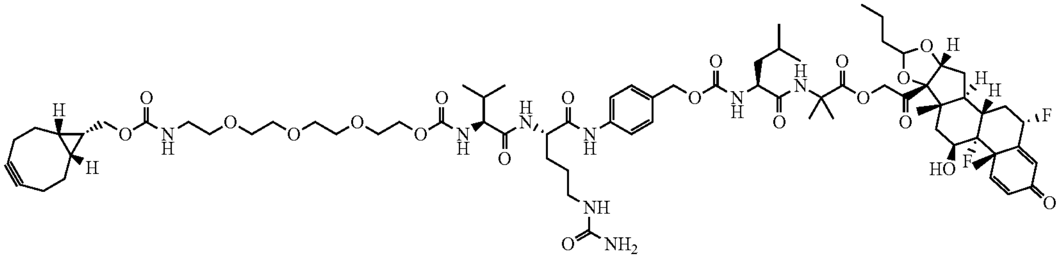 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](NC(=O)OCCOCCOCCOCCNC(=O)OC[C@@H]3[C@@H]4CCC#CCC[C@@H]43)C(C)C)cc2)O1]
LP13A
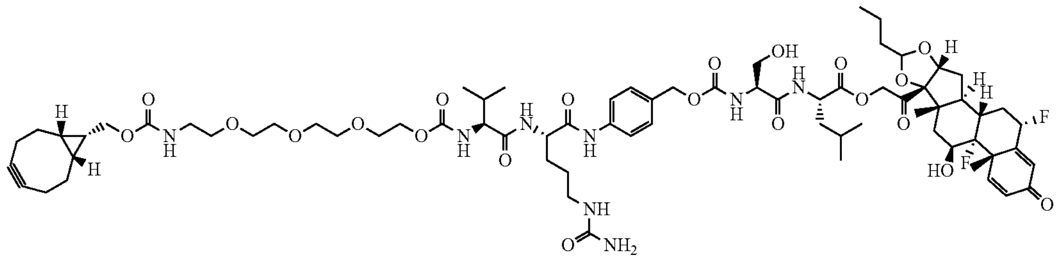 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](NC(=O)OCCOCCOCCOCCNC(=O)OC[C@@H]3[C@@H]4CCC#CCC[C@@H]43)C(C)C)cc2)O1]
LP18A
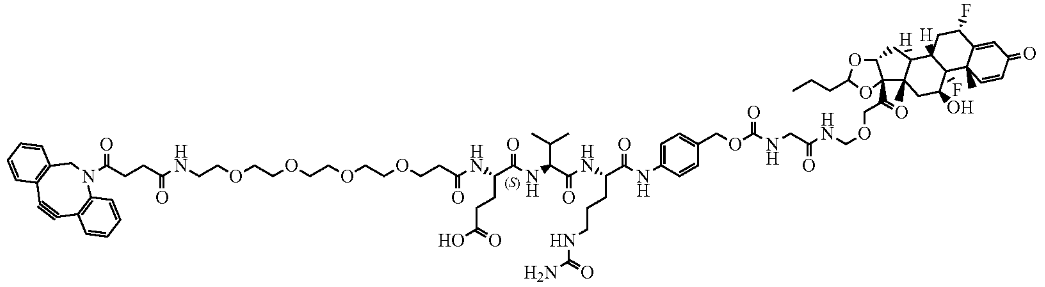
LP19A
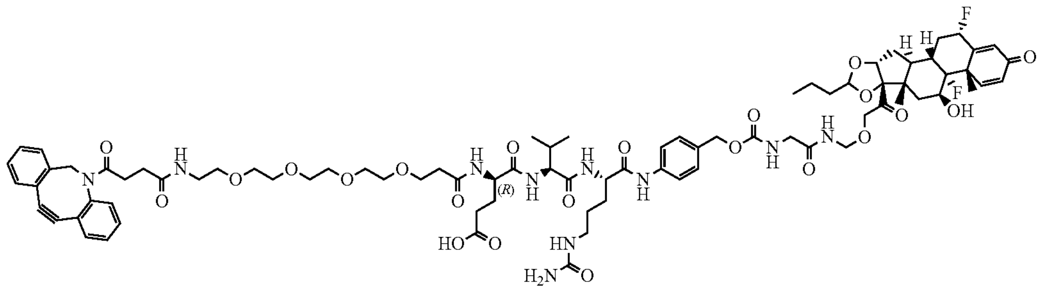
LP20A
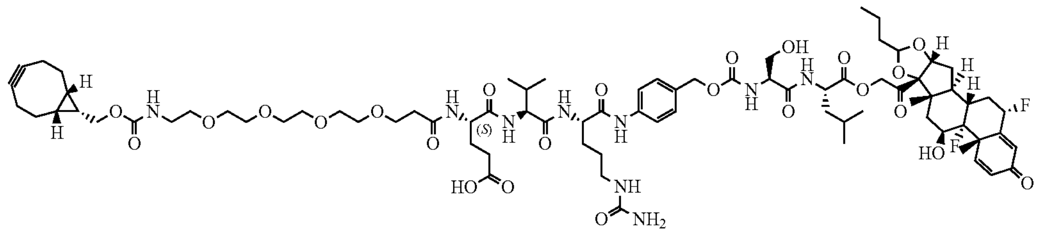

TABLE 3-continued
| List of linker-payloads (LPs) and their structures |
| --- |
LP21A
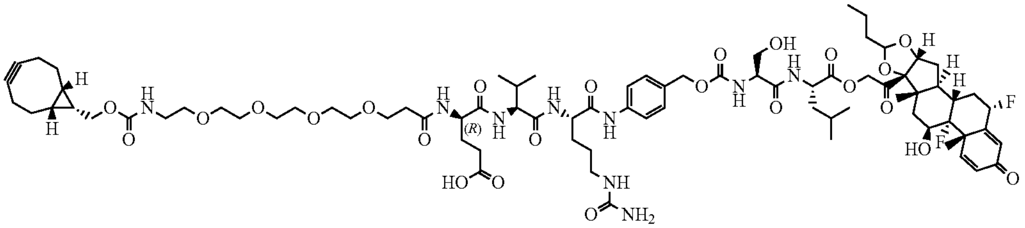
LP22A
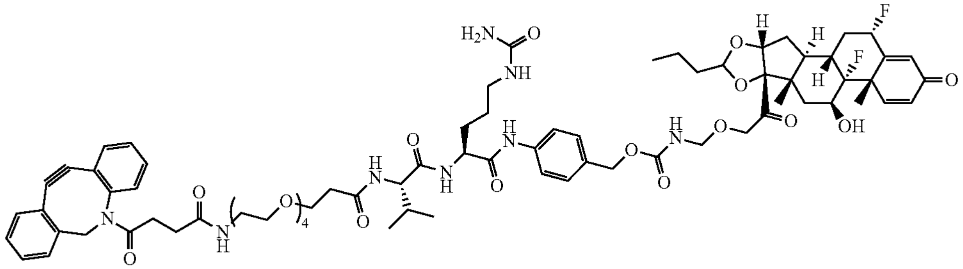
LP23A
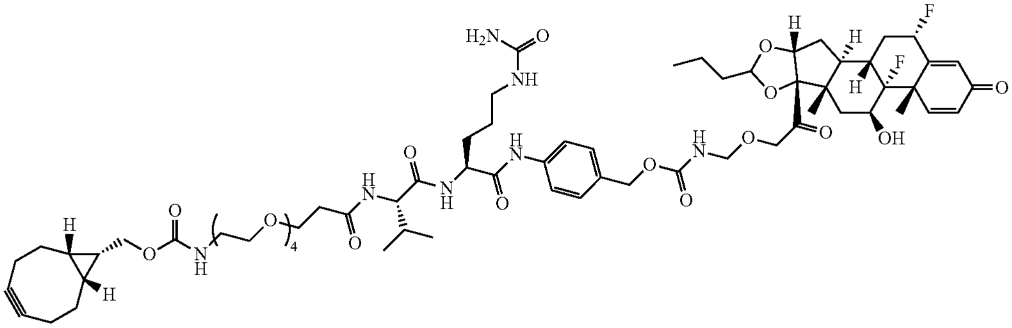
LP24A
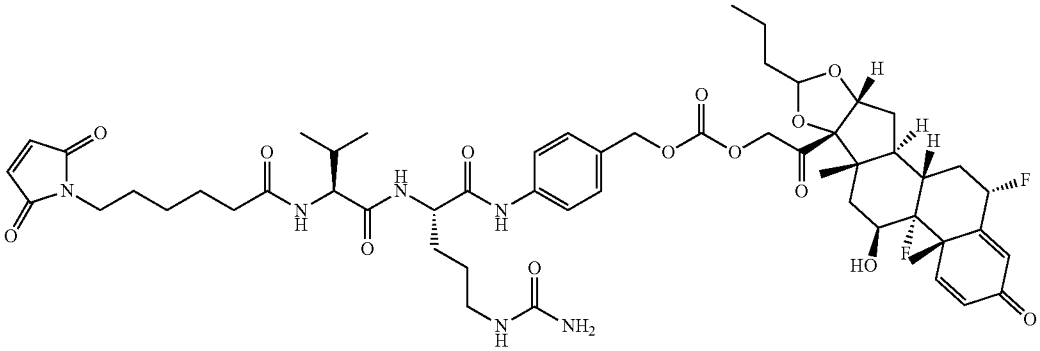 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)OCc2ccc(NC(=O)[C@H](CCCNC(N)=O)NC(=O)[C@@H](NC(=O)CCCCCN3C(=O)C=CC3=O)C(C)C)cc2)O1]
LP25A
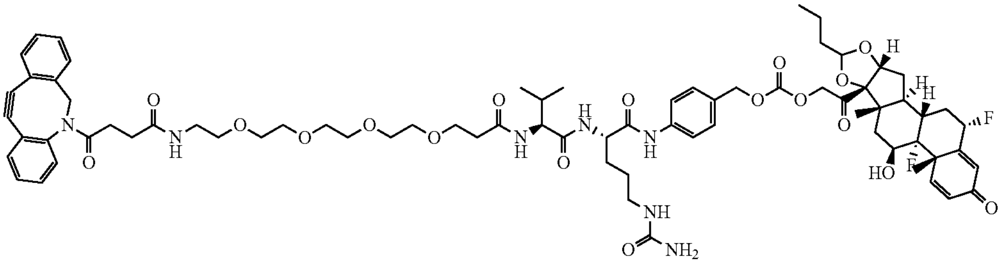 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

TABLE 3-continued
| List of linker-payloads (LPs) and their structures |
|---|
LP26A
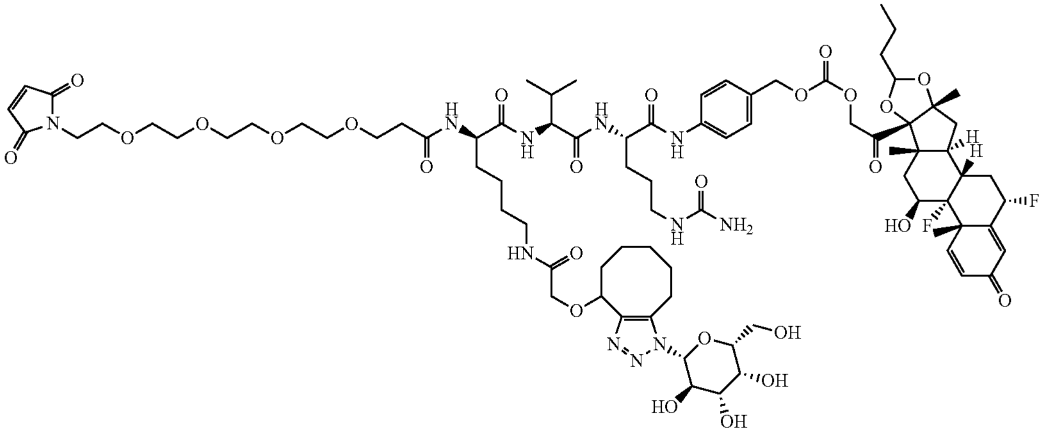 [SMILES: CCCC1O[C@]2(C(=O)COC(=O)OCc3ccc(NC(=O)[C@H](CCCNC(N)=O)NC(=O)[C@@H](NC(=O)[C@@H](CCCCNC(=O)COC4CCCCCc5c4nnn5[C@@H]4O[C@H](CO)[C@H](O)[C@H](O)[C@H]4O)NC(=O)CCOCCOCCOCCOCCN4C(=O)C=CC4=O)C(C)C)cc3)[C@@](C)(C[C@H]3[C@@H]4C[C@H](F)C5=CC(=O)C=C[C@]5(C)[C@@]4(F)[C@@H](O)C[C@@]32C)O1]
LP27A
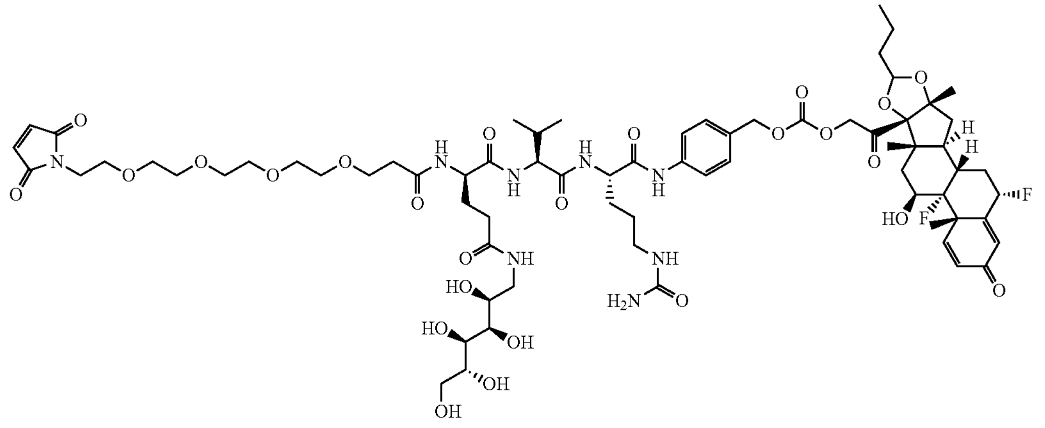 [SMILES: CCCC1O[C@]2(C(=O)COC(=O)OCc3ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN4C(=O)C=CC4=O)C(C)C)cc3)[C@@](C)(C[C@H]3[C@@H]4C[C@H](F)C5=CC(=O)C=C[C@]5(C)[C@@]4(F)[C@@H](O)C[C@@]32C)O1]
LP28A
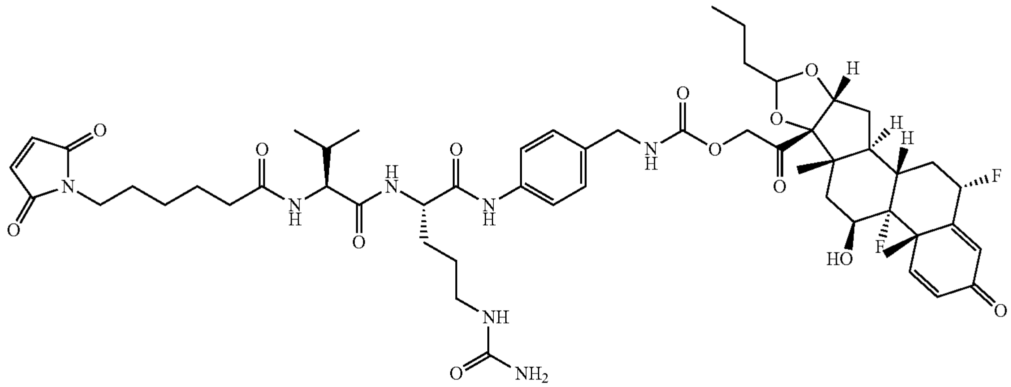 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCc2ccc(NC(=O)[C@H](CCCNC(N)=O)NC(=O)[C@@H](NC(=O)CCCCCN3C(=O)C=CC3=O)C(C)C)cc2)O1]
LP29A
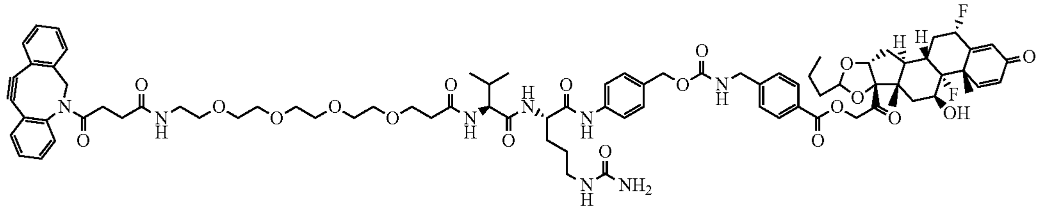 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)c2ccc(CNC(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)cc2)O1]

TABLE 3-continued
List of linker-payloads (LPs) and their structures
LP30A
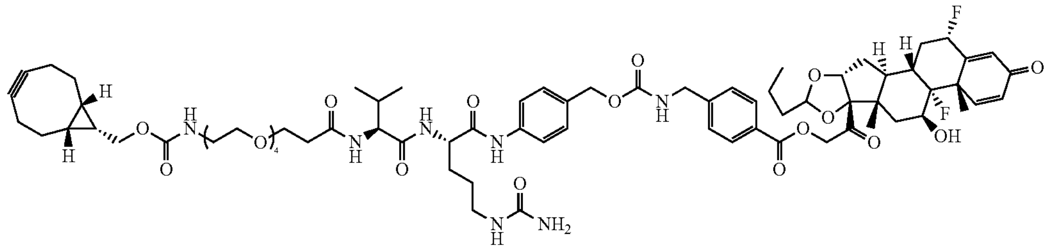
LP31A
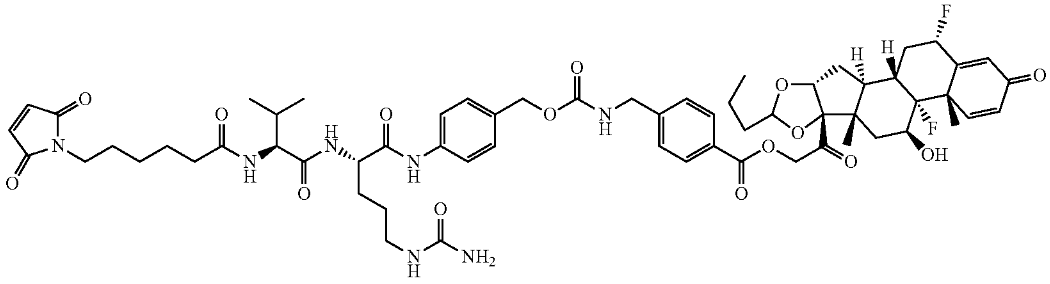 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)c2ccc(CNC(=O)OCc3ccc(NC(=O)[C@H](CCCNC(N)=O)NC(=O)[C@@H](NC(=O)CCCCCN4C(=O)C=CC4=O)C(C)C)cc3)cc2)O1]
LP1B
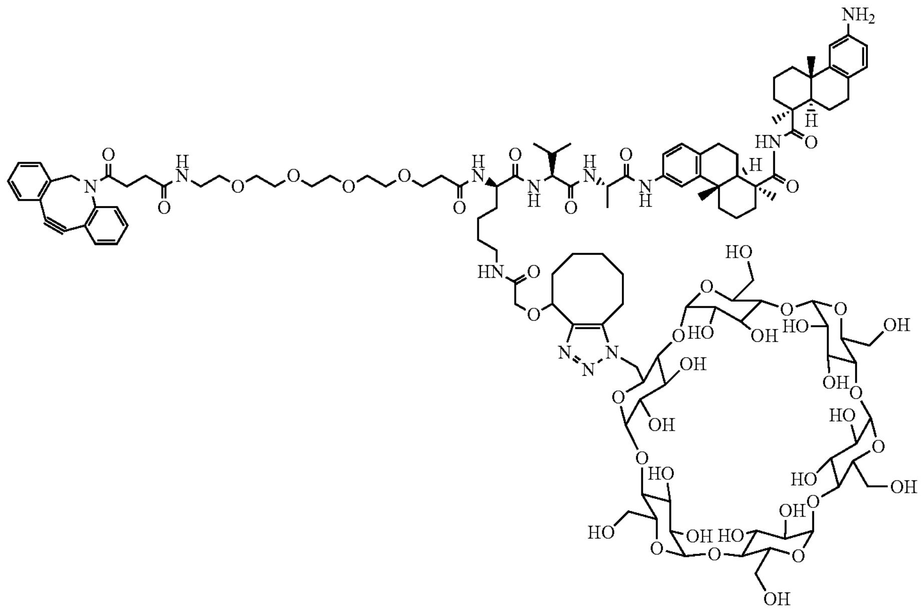 [SMILES: CC(C)[C@H](NC(=O)[C@@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

TABLE 3-continued
| List of linker-payloads (LPs) and their structures |
|---|
| LP2B 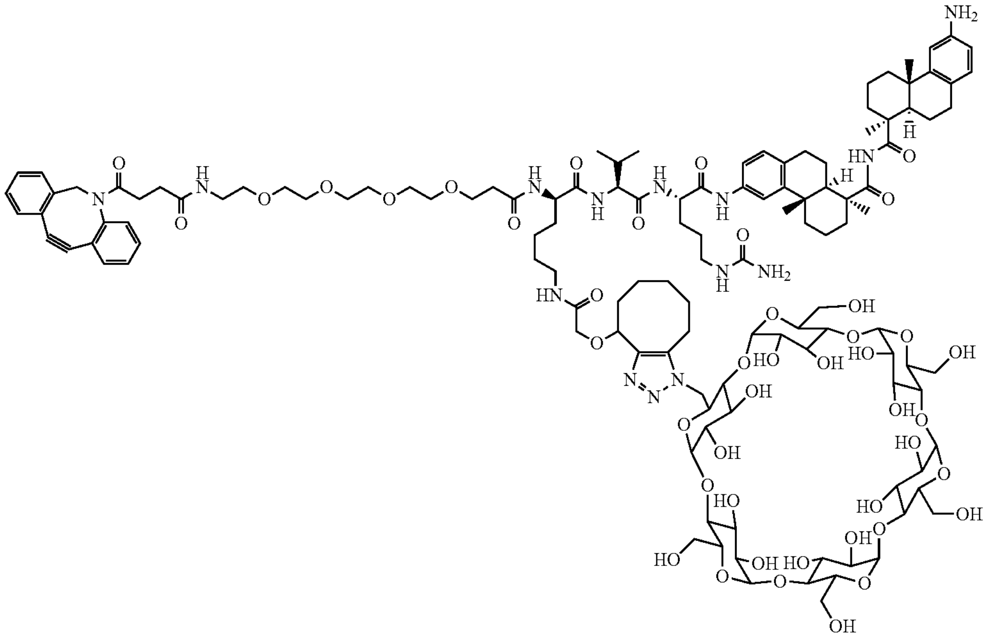 |
| LP3B 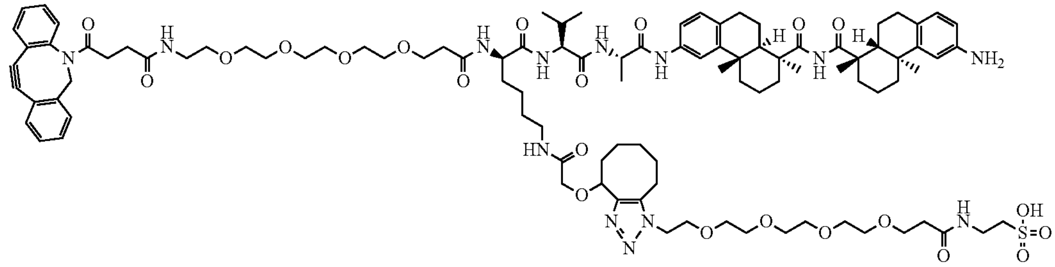 |
| LP4B 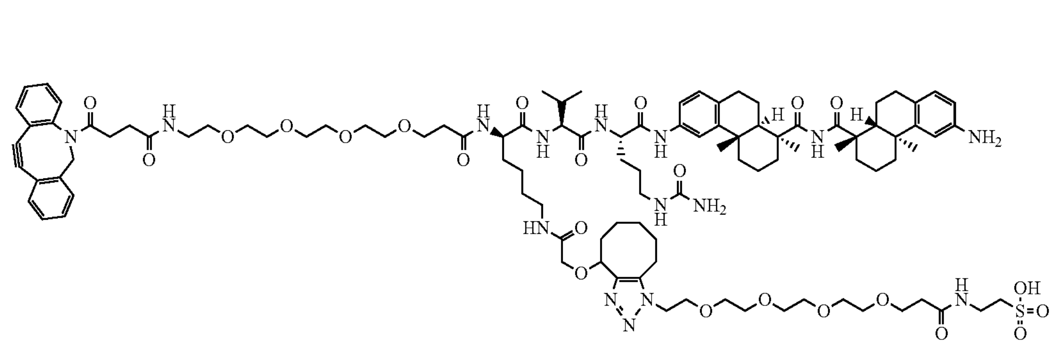 |

TABLE 3-continued
| List of linker-payloads (LPs) and their structures | |
|---|---|
| LP5B | 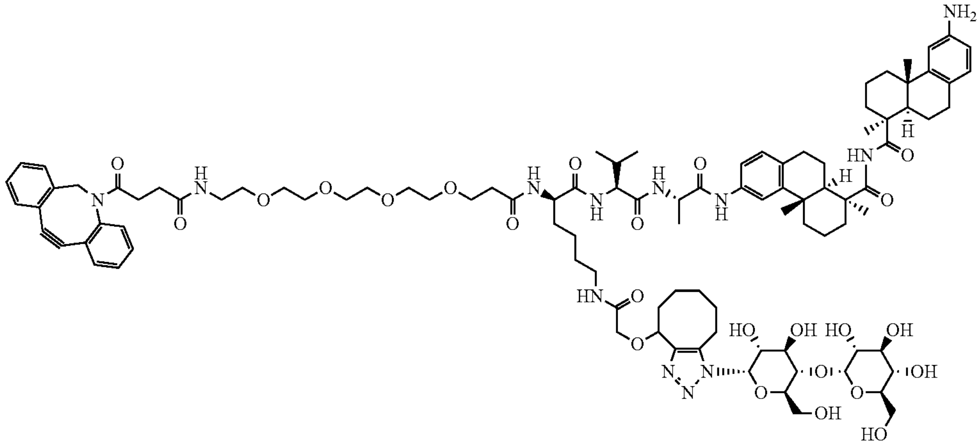 [SMILES: CC(C)[C@H](NC(=O)[C@@H](CCCCNC(=O)COC1CCCCCc2c1nnn2[C@H]1O[C@H](CO)[C@@H](O[C@H]2O[C@H](CO)[C@@H](O)[C@H](O)[C@H]2O)[C@H](O)[C@H]1O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] |
| LP6B | 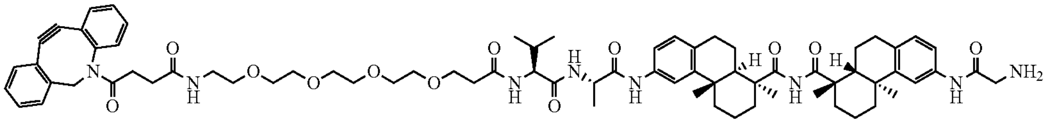 [SMILES: CC(C)[C@H](NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(NC(=O)CN)ccc5CC[C@@H]34)[C@@H]1CC2] |
| LP7B | 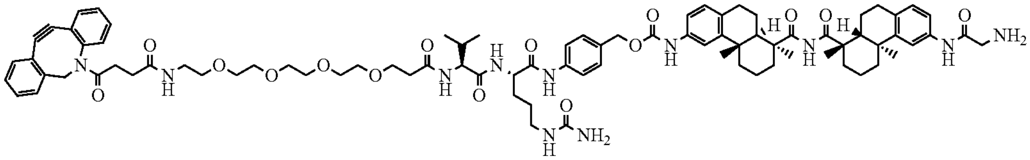 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Nc2ccc3c(c2)[C@@]2(C)CCC[C@](C)(C(=O)NC(=O)[C@@]4(C)CCC[C@]5(C)c6cc(NC(=O)CN)ccc6CC[C@@H]45)[C@@H]2CC3)cc1] |
| LP8B | 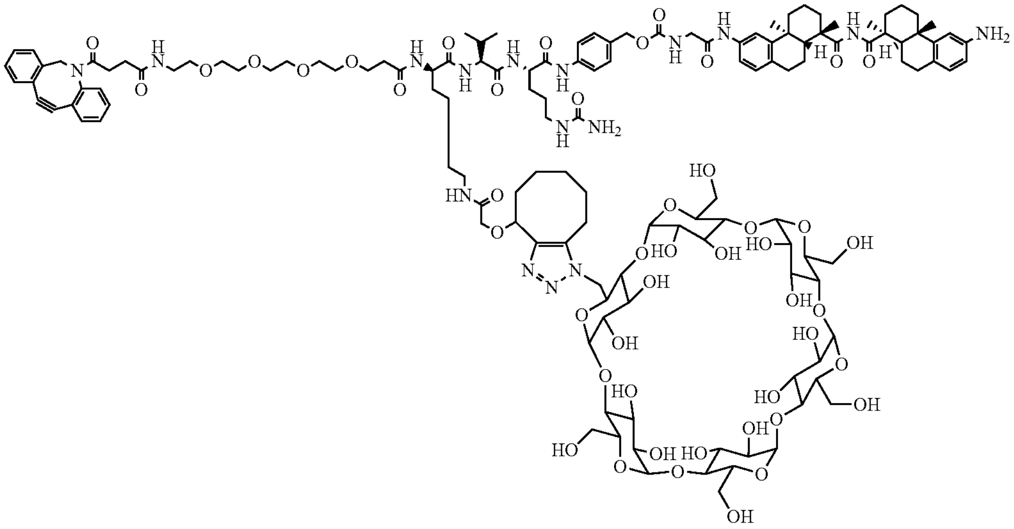 [SMILES: CC(C)[C@H](NC(=O)[C@@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1] |
| LP9B | 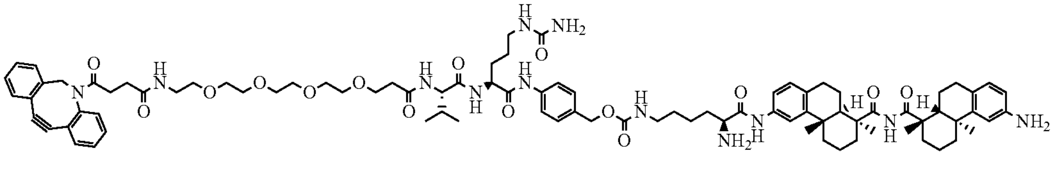 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)NCCCC[C@H](N)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1] |

TABLE 3-continued
List of linker-payloads (LPs) and their structures
LP10B
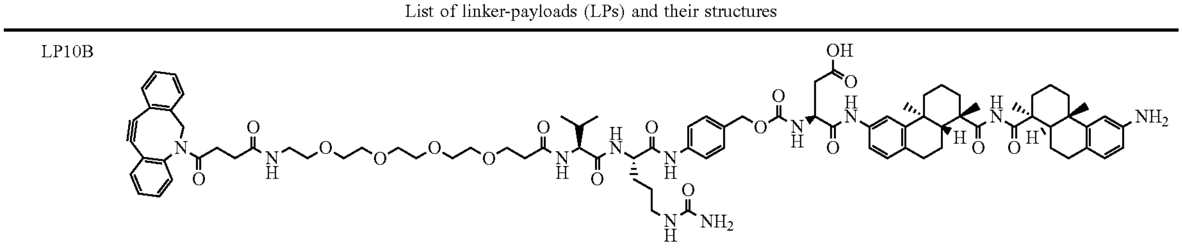
LP11B
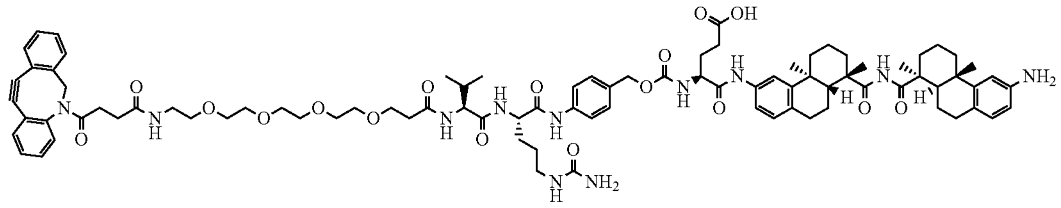 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]
LP12B
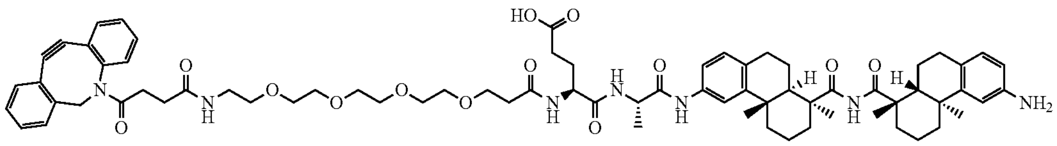 [SMILES: C[C@H](NC(=O)[C@H](CCC(=O)O)NC(=O)CCOCCOCCOCCOCCNC(=O)CCC(=O)N1Cc2ccccc2C#Cc2ccccc21)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]
R20
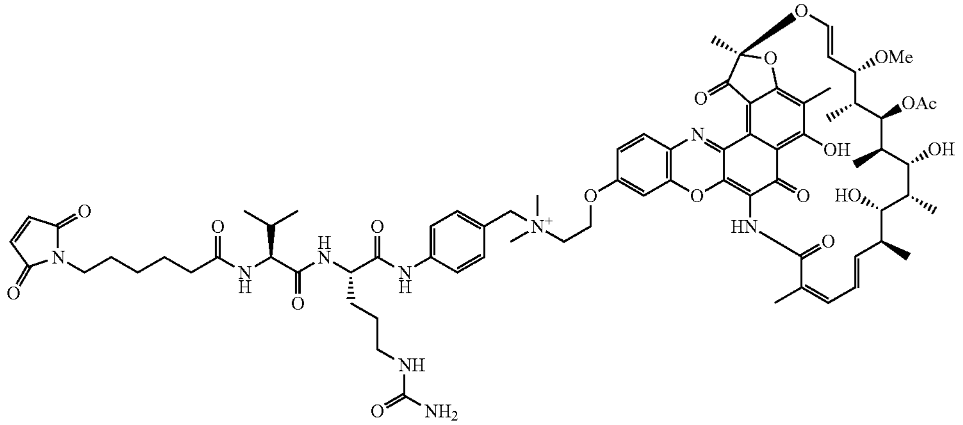
and
R25
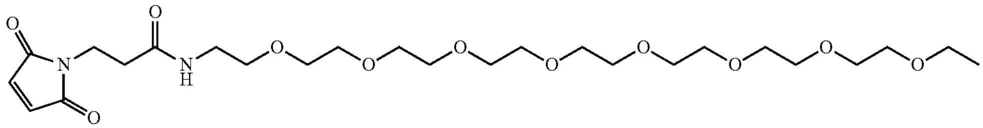

TABLE 3-continued

List of linker-payloads (LPs) and their structures

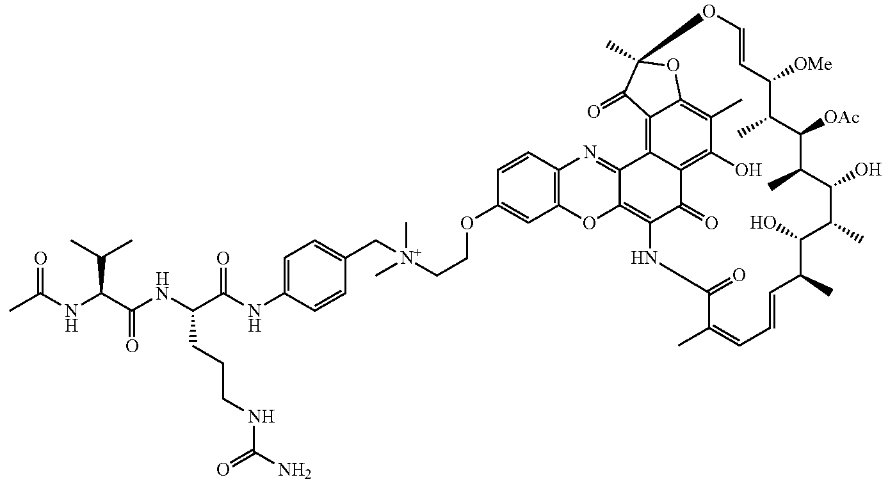

The compounds in the tables above can be prepared as described in the Examples herein.

Also provided herein is a method of preparing an antibody-drug conjugate of a rifamycin analog (e.g., rifampicin), comprising the step of contacting an anti-MSR1 antibody, or antigen-binding fragment thereof, with a linker payload according to Formula (D):

Formula (D)

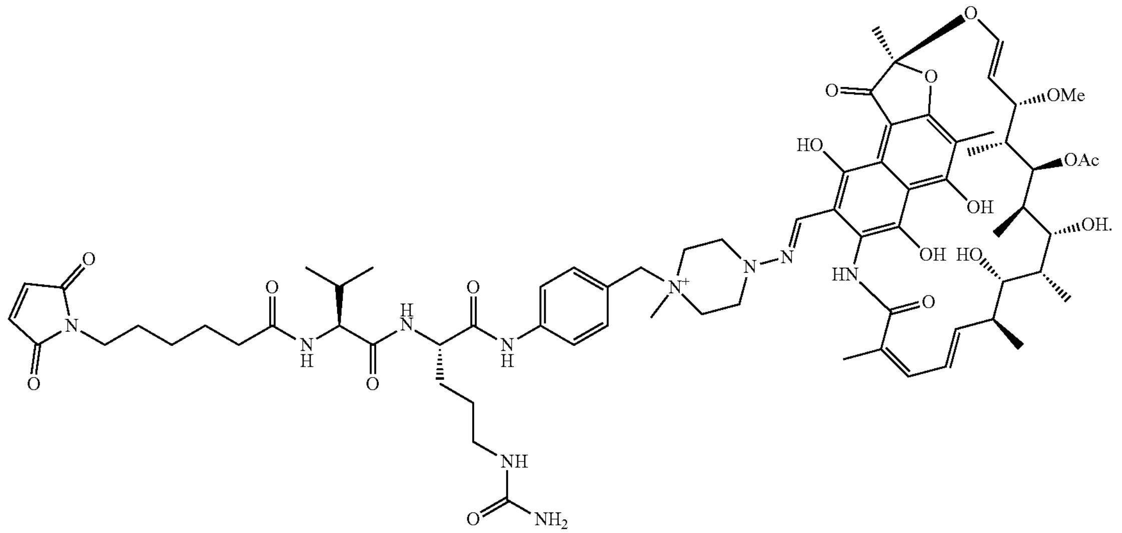

under conditions suitable for forming a bond between anti-MSR1 antibody, or antigen-binding fragment thereof.

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of an MSR1 protein. Alternatively, the epitope may consist of a plurality of non-contiguous amino acids (or amino acid sequences) of MSR1. In some embodiments, the epitope is located on or near the modified LDL-binding domain of MSR1. In other embodiments, the epitope is located outside of the modified LDL-binding domain of MSR1, e.g., at a location on the surface of MSR1 at which an antibody, when bound to such an epitope, does not interfere with modified-LDL binding to MSR1.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

Embodiments include anti-MSR1 antibodies that bind to the same epitope as any of the specific exemplary antibodies described herein (e.g. antibodies comprising any of the amino acid sequences as set forth in Table 4 herein). Likewise, embodiments also include anti-MSR1 antibodies that compete for binding to MSR1 with any of the specific exemplary antibodies described herein (e.g. antibodies comprising any of the amino acid sequences as set forth in Table 4 herein).

One can easily determine whether an antibody binds to the same epitope as, or competes for binding with, a reference anti-MSR1 antibody by using routine methods known in the art and exemplified herein at, e.g., Example 7. For example, to determine if a test antibody binds to the same epitope as a reference anti-MSR1 antibody disclosed herein, the reference antibody is allowed to bind to a MSR1 protein. Next, the ability of a test antibody to bind to the MSR1 molecule is assessed. If the test antibody is able to bind to MSR1 following saturation binding with the reference anti-MSR1 antibody, it can be concluded that the test antibody binds to a different epitope than the reference anti-MSR1 antibody. On the other hand, if the test antibody is not able to bind to the MSR1 molecule following saturation binding with the reference anti-MSR1 antibody, then the test antibody may bind to the same epitope as the epitope bound by the reference anti-MSR1 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-MSR1 antibody, the above-described binding methodology is performed in two orientations. In a first orientation, the reference antibody is allowed to bind to a MSR1 protein under saturating conditions followed by assessment of binding of the test antibody to the MSR1 molecule. In a second orientation, the test antibody is allowed to bind to a MSR1 molecule under saturating conditions followed by assessment of binding of the reference antibody to the MSR1 molecule. If, in both orientations, only the first (saturating) antibody is capable of binding to the MSR1 molecule, then it is concluded that the test antibody and the reference antibody compete for binding to MSR1. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-MSR1 antibodies disclosed herein can be fully human antibodies. Methods for generating monoclonal antibodies, including fully human monoclonal antibodies are known in the art. Any such known methods can be used in the context of the present invention to make human antibodies that specifically bind to human MSR1.

Using VELOCIMMUNE™ technology, for example, or any other similar known method for generating fully human monoclonal antibodies, high affinity chimeric antibodies to MSR1 are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-MSR1 antibody. While the constant region selected may vary according to specific use, high affinity antigen-binding and target specificity characteristics reside in the variable region. In certain instances, fully human anti-MSR1 antibodies are isolated directly from antigen-positive B cells.

Bioequivalents

The anti-MSR1 antibodies and antibody fragments disclosed herein encompass proteins having amino acid sequences that vary from those of the described antibodies but that retain the ability to bind human MSR1. Such variant antibodies and antibody fragments comprise one or more additions, deletions, or substitutions of amino acids when compared to parent sequence, but exhibit biological activity that is essentially equivalent to that of the described antibodies. Likewise, the anti-MSR1 antibody-encoding DNA sequences disclosed herein encompass sequences that comprise one or more additions, deletions, or substitutions of nucleotides when compared to the disclosed sequence, but that encode an anti-MSR1 antibody or antibody fragment that is essentially bioequivalent to an anti-MSR1 antibody or antibody fragment disclosed herein. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-MSR1 antibodies disclosed herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-MSR1 antibody variants comprising amino acid changes which modify the glycosylation characteristics of the antibodies, e.g., mutations which eliminate or remove glycosylation.

Species Selectivity and Species Cross-Reactivity

According to certain embodiments, provided herein are anti-MSR1 antibodies that bind to human MSR1 but not to MSR1 from other species. Embodiments also include anti-MSR1 antibodies that bind to human MSR1 and to MSR1 from one or more non-human species. For example, the anti-MSR1 antibodies disclosed herein may bind to human MSR1 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee MSR1. According to certain exemplary embodiments, anti-MSR1 antibodies are provided which specifically bind human MSR1 and cynomolgus monkey (e.g., *Macaca fascicularis*) MSR1. Other anti-MSR1 antibodies disclosed herein bind human MSR1 but do not bind, or bind only weakly, to cynomolgus monkey MSR1.

Multispecific Antibodies

The antibodies disclosed herein may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The anti-MSR1 antibodies disclosed herein can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

Embodiments include bispecific antibodies wherein one arm of an immunoglobulin binds human MSR1, and the other arm of the immunoglobulin is specific for a second antigen. The MSR1-binding arm can comprise any of the HCVR/LCVR or CDR amino acid sequences as set forth in Table 4 herein. In certain embodiments, the MSR1-binding arm binds human MSR1 and blocks modified LDL binding to MSR1. In other embodiments, the MSR1-binding arm binds human MSR1 but does not block modified LDL binding to MSR1. In some embodiments, the MSR1 binding arm binds human MSR1 and activates MSR1 signaling. In other embodiments, the MSR1 binding arm blocks MSR1-mediated receptor stimulation. Embodiments also include bispecific antibodies wherein one arm of an antibody binds a first epitope of human MSR1, and the other arm of said antibody binds a second distinct epitope of human MSR1.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

Embodiments relate to pharmaceutical compositions comprising the anti-MSR1 antibodies or antigen-binding fragments thereof disclosed herein. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-MSR1 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical compositions disclosed herein, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition as disclosed herein can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition disclosed herein. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™ OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L.P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of Antibodies

Embodiments include methods comprising administering to a subject in need thereof a therapeutic composition comprising an anti-MSR1 antibody or an antibody-drug conjugate comprising an anti-MSR1 antibody (e.g., an anti-MSR1 antibody or ADC comprising any of the HCVR/LCVR or CDR sequences as set forth in Table 4 herein). The therapeutic composition can comprise any of the anti-MSR1 antibodies, antigen-binding fragments thereof, or ADCs disclosed herein (e.g., ADCs of Formula (I), (IA), (IB), (IB-1), (IB-2), (IC), (ID), (IE), (III), (3000), (5001), (5002), (5003), (5004), (6001), (6002), (6003), (6004), (6005), (7001), (7002), (7003), (7004) and/or (7005)), and a pharmaceutically acceptable carrier or diluent.

The antibodies and ADCs disclosed herein are useful, inter alia, for the treatment, prevention and/or amelioration of any disease or disorder associated with or mediated by MSR1 expression or activity, or treatable by binding MSR1 without competing against modified LDL, or and/or promoting MSR1 receptor internalization and/or decreasing cell surface receptor number. For example, the antibodies and ADCs disclosed herein are useful for the treatment, attenuation, or amelioration of atherosclerosis, proliferative disorders, neurodegenerative disorders, and inflammation by targeting cells that express MSR1 and/or that respond to MSR1-mediated signaling, e.g., macrophages.

In the context of the methods of treatment described herein, the anti-MSR1 antibody, or an ADC thereof, may be administered as a monotherapy (i.e., as the only therapeutic agent) or in combination with one or more additional therapeutic agents (examples of which are described elsewhere herein).

Provided herein is a method of treating a proliferative disease, a metabolic disease, inflammation, a neurodegenerative disease, or disease, disorder, or condition associated with glucocorticoid receptor signaling, in a subject comprising administering to the subject an effective treatment amount of a compound described herein (e.g., an anti-MSR1 ADC), or a pharmaceutical composition comprising a compound described herein.

In some embodiments, where the payload is a steroid, the disease, disorder, or condition is allergic state, including but not limited to asthma, atopic dermatitis, contact dermatitis, allergic dermatitis, drug hypersensitivity reactions, anaphylactic rhinitis, perennial or seasonal allergic rhinitis, and serum sickness; dermatologic diseases and conditions, including but not limited to skin itching, seborrheic dermatitis, neurodermatitis, eczema, bullous dermatitis herpetiformis, exfoliative erythroderma, mycosis fungoides, pemphigus, and severe erythema multiforme (Stevens-Johnson syndrome); endocrine disorders, including but not limited to primary or secondary adrenocortical insufficiency, congenital adrenal hyperplasia, hypercalcemia associated with cancer, and nonsuppurative thyroiditis; gastrointestinal diseases; hematologic disorders, including but not limited to acquired (autoimmune) hemolytic anemia, congenital (erythroid) hypoplastic anemia (Diamond-Blackfan anemia), idiopathic thrombocytopenic purpura in adults, pure red cell aplasia, and secondary thrombocytopenia; trichinosis; tuberculous meningitis with subarachnoid block or impending block; neoplastic diseases, including but not limited to leukemias and lymphomas; nervous system disorders, including but not limited to acute exacerbations of multiple sclerosis, cerebral edema associated with primary or metastatic brain tumor, craniotomy, or head injury; ophthalmic diseases, including but not limited to sympathetic ophthalmia, temporal arteritis, uveitis, xerophthalmia, and ocular inflammatory conditions unresponsive to topical corticosteroids; renal diseases, including but not limited to for inducing a diuresis or remission of proteinuria in idiopathic nephrotic syndrome or that due to lupus erythematosus; respiratory diseases, including but not limited to berylliosis, fulminating or disseminated pulmonary tuberculosis when used concurrently with appropriate antituberculous chemotherapy, idiopathic eosinophilic pneumonias, symptomatic sarcoidosis; and Rheumatic disorders, including but not limited to use as adjunctive therapy for short-term administration (to tide the patient over an acute episode or exacerbation) in acute gouty arthritis, acute rheumatic carditis, ankylosing spondylitis, psoriaticarthritis, rheumatoid arthritis, including juvenile rheumatoid arthritis, and for use in dermatomyositis, polymyositis, stomatitis, and systemic lupus erythematosus. In certain embodiments, provided herein are methods of treating or preventing arthritis.

In some embodiments, set forth herein is a method for treating a disease, disorder, or condition selected from an autoimmune disease, an allergy, arthritis, asthma, a breathing disorder, a blood disorder, a cancer, a collagen disease, a connective tissue disorders, a dermatological disease, an eye disease, an endocrine problem, an immunological disease, an inflammatory disease, an intestinal disorders, a gastrointestinal disease, a neurological disorder, an organ transplant condition, a rheumatoid disorder, a skin disorder, a swelling condition, a wound healing condition, and a combination thereof comprising administering a steroid payload or conjugate thereof described herein.

In some embodiments, the autoimmune disorder is selected from multiple sclerosis, autoimmune hepatitis, shingles, systemic lupus erythematosus (i.e., lupus), myasthenia gravis, Duchenne muscular dystrophy, and sarcoidosis. In some embodiments, the breathing disorder is selected from asthma, chronic respiratory disease, chronic obstructive pulmonary disease, bronchial inflammation, and acute bronchitis. In some embodiments, the cancer is selected from leukemia, lymphoblastic leukemia, acute lymphoblastic leukemia, chronic lymphoblastic leukemia, Hodgkin's lymphoma, Non-Hodgkin's lymphoma (NHL), and multiple myeloma. In some embodiments, the collagen disease is systemic lupus erythematosus. In some embodiments, the eye disease is keratitis. In some embodiments, the endocrine problem is selected from Addison's Disease, adrenal insufficiency, adrenal cortical dysfunction, adrenocortical, and congenital adrenal hyperplasia. In some embodiments, the inflammatory disease is selected from inflammation after cataract surgery, joint inflammation, immune inflammation, tendon inflammation, bursitis, epicondylitis, Crohn's disease, inflammatory bowels disease, lipid pneumonitis thyroiditis, urticaria (hives), pericarditis, nephrotic syndrome, and uveitis. In some embodiments, the intestinal disorder is selected from collagenous colitis, ulcerative colitis, Crohn's disease, and inflammatory bowels disease. In some embodiments, the rheumatoid disorder is selected from rheumatoid arthritis, polymyalgia rheumatic, psoriatic arthritis, ankylosing spondylitis, and systemic lupus erythematosus. In some embodiments, the skin disorder is selected from psoriasis, eczema, and poison ivy. In some embodiments, the neurological disorder is chronic inflammatory demyelinating polyradiculoneuropathy.

In some embodiments, the compounds described herein are administered to a patient to treat an acute inflammatory event, including but not limited to shock, brain edema, and graft-vs-host disease. In some embodiments, the compounds described herein are administered to treat lympholytic effects, including but not limited to those associated with hematological malignancies, e.g., leukemias, lymphomas, and myelomas.

In some embodiments, set forth herein is a method for reducing inflammation in a subject in need thereof, comprising administering to a subject in need thereof a therapeutically effective amount of a steroid or conjugate thereof described herein. In some embodiments, set forth herein is a method for modulating the immune system in a subject in need thereof, comprising administering to a subject in need thereof a therapeutically effective amount of a steroid or conjugate thereof described herein. In some embodiments, set forth herein is a method for modulating cortisol levels in a subject in need thereof, comprising administering to a subject in need thereof a therapeutically effective amount of a steroid or conjugate thereof described herein. In some embodiments, set forth herein is a method of reducing lymphocyte migration in a subject in need thereof, comprising administering to a subject in need thereof a therapeutically effective amount of a steroid or conjugate thereof described herein. In some embodiments, set forth herein is a method of treating hypercalcemia due to cancer, Meniere's disease, a migraine headache, a cluster headache, a severe aphthous ulcer, laryngitis, severe tuberculosis, a Herxheimer reaction to syphilis, a decompensated heart failure, allergic rhinitis or nasal polyps, comprising administering to a subject in need thereof a steroid payload or conjugate thereof described herein. In some embodiments, the compounds disclosed herein can be used for treating inflammatory bowel disease, Crohn's disease, or ulcerative colitis. In some embodiments, the disease, disorder, or condition is a chronic inflammatory condition, including but not limited to asthma, skin infections, and ocular infections. In some embodiments, compounds described herein are used for immunosuppression in patients undergoing organ transplantation.

In some embodiments, the steroid payloads and conjugates thereof described herein are administered to a patient to treat a nervous disorder associated with GR signaling, including but not limited to psychiatric disorders such as schizophrenia, drug addiction, post-traumatic stress disorder (PTSD), and mood disorders, substance abuse, stress, and anxiety.

In some embodiments, the steroid payloads and conjugates thereof described herein are administered to a patient to treat a visual system disorder, including but not limited to ocular inflammation (e.g., conjunctivitis, keratitis, uveitis), macular edema, and macular degeneration. In some embodiments, the steroid payloads and conjugates thereof described herein are administered to a patient to treat a cardiovascular disorder. In some embodiments, the steroid payloads and conjugates thereof described herein are administered to a patient to treat a glucose and/or liver metabolism disorder. In some embodiments, the steroid payloads and conjugates thereof described herein are administered to a patient to treat a musculoskeletal system disorder. In some embodiments, the steroid payloads and conjugates thereof described herein are administered to a patient to treat a cutaneous inflammatory condition, such as eczema and psoriasis.

The protein conjugates described herein provide a means for targeted delivery of its steroid payload to particular cells or organ systems, thereby reducing or preventing side effects that result from administration of the free unconjugated steroid payload. Examples of such potential side effects to be reduced or prevented include those listed in the approved drug label for Decadron® (dexamethasome), which is incorporated herein by reference in its entirety. In some embodiments, the side effect to be reduced or prevented is selected from elevation of blood pressure; sodium retention; water/fluid retention (edema, angioedema, pulmonary edema); increased excretion of potassium; reversible hypothalamic-pituitary adrenal (HPA) axis suppression; potential corticosteroid insufficiency after withdrawal of treatment; susceptibility to infections; exacerbation of systemic fungal infections; worsening of severity of chickenpox in pediatric and adult patients; worsening of severity of measles in pediatric and adult patients; posterior subcapsular cataracts; glaucoma with possible damage to the optic nerves; enhancement of the establishment of secondary ocular infections due to bacteria, fungi, or viruses; increase in new episodes of optic neuritis; Kaposi's sarcoma; drug-induced secondary adrenocortical insufficiency; increased risk of a perforation when active or latent peptic ulcers, diverticulitis, fresh intestinal anastomoses, and nonspecific ulcerative colitis, are present; peritoneal irritation following gastrointestinal perforation; decreased bone formation; increased bone resorption; inhibition of osteoblast function; inhibition of bone growth in pediatric patients; development of osteoporosis at any age; acute myopathy (possibly involving ocular and respiratory muscles, and potentially resulting in quadriparesis); elevation of creatinine kinase; psychic derangements, ranging from euphoria, insomnia, mood swings, personality changes, and severe depression, to frank psychotic manifestations; aggravation of existing emotional instability or psychotic tendencies; elevated intraocular pressure; bradycardia; cardiac arrest; cardiac arrhythmias; cardiac enlargement; circulatory collapse; congestive heart failure; fat embolism; hypertension; hypertrophic cardiomyopathy in premature infants; myocardial rupture following recent myocardial infarction; syncope; tachycardia; thromboembolism; thrombophlebitis; vasculitis; acne; allergic dermatitis; dry scaly skin; ecchymoses and petechiae; erythema; impaired wound healing; increased sweating; rash; striae; suppression of reactions to skin tests; thin fragile skin; thinning scalp hair; urticarial; decreased carbohydrate and glucose tolerance; development of cushingoid state; hyperglycemia; glycosuria; hirsutism; hypertrichosis; increased requirements for insulin or oral hypoglycemic agents in diabetes (insulin resistance); manifestations of latent diabetes mellitus; menstrual irregularities; secondary adrenocortical and pituitary unresponsiveness (particularly in times of stress; as in trauma; surgery; or illness); suppression of growth in pediatric patients; congestive heart failure in susceptible patients; fluid retention; hypokalemic alkalosis; potassium loss; sodium retention; abdominal distention; elevation in serum liver enzyme levels (usually reversible upon discontinuation); hepatomegaly; increased appetite; nausea; pancreatitis; peptic ulcer with possible perforation and hemorrhage; perforation of the small and large intestine (particularly in patients with inflammatory bowel disease); ulcerative esophagitis; negative nitrogen balance due to protein catabolism; aseptic necrosis of femoral and humeral heads; loss of muscle mass; muscle weakness; osteoporosis; pathologic fracture of long bones; steroid myopathy; tendon rupture; vertebral compression fractures; convulsions; depression; emotional instability; euphoria; headache; increased intracranial pressure with papilledema (pseudotumor cerebri) usually following discontinuation of treatment; insomnia; mood swings; neuritis; neuropathy; paresthesia; personality changes; psychic disorders; vertigo; exophthalmos; glaucoma; increased intraocular pressure; posterior subcapsular cataracts; abnormal fat deposits;

decreased resistance to infection; hiccups; increased or decreased motility and number of spermatozoa; malaise; moon face; and weight gain; and those side effects associated with drug-drug interactions. In some embodiments, the side effect to be reduced or prevented are those associated with drug-drug interactions. In some embodiments, the side effect to be reduced or prevented is associated with drug-drug interactions from the use of a corticosteroid with aminoglutethimide including diminishment of adrenal suppression by corticosteroids; amphotericin B injection and potassium-depleting agents, including development of hypokalemia, cardiac enlargement, and congestive heart failure; antibiotics including a significant decrease in corticosteroid clearance; anticholinesterases including producing severe weakness in patients with myasthenia gravis; oral anticoagulants including inhibition of response to warfarin; antidiabetics including increased blood glucose concentrations; antitubercular drugs including decreased serum concentrations of isoniazid; cholestyramine including increased clearance of corticosteroids; cyclosporine including increased activity of both cyclosporine and corticosteroids, and incidence of convulsions; dexamethasone suppression test (DST) interference including false-negative results in patients being treated with indomethacin; digitalis glycosides including increased risk of arrhythmias due to hypokalemia; ephedrine including enhancement of the metabolic clearance of corticosteroids, resulting in decreased blood levels and lessened physiologic activity; estrogens, including oral contraceptives, including decreased hepatic metabolism of certain corticosteroids and associated increase in their effect; hepatic enzyme inducers, inhibitors and substrates (drugs which induce cytochrome P450 3A4 (CYP 3A4) enzyme activity e.g., barbiturates, phenytoin, carbamazepine, rifampin), including enhancing of metabolism of corticosteroids; drugs which inhibit CYP 3A4 (e.g., ketoconazole, macrolide antibiotics such as erythromycin), including the potential for increased plasma concentrations of corticosteroids; drugs that are metabolized by CYP 3A4 (e.g., indinavir, erythromycin), including increase in their clearance, resulting in decreased plasma concentration; ketoconazole including decreased metabolism of certain corticosteroids by up to 60%, leading to increased risk of corticosteroid side effects, and inhibition of adrenal corticosteroid synthesis potentially causing adrenal insufficiency during corticosteroid withdrawal; nonsteroidal anti-inflammatory agents (NSAIDS), including increased risk of gastrointestinal side effects and increased clearance of salicylates; phenytoin, including increases or decreases in phenytoin level, altered seizure control; skin tests, including suppression of reactions to skin tests; thalidomide including toxic epidermal necrolysis; and vaccines including a diminished response to toxoids and live or inactivated vaccines due to inhibition of antibody response or potentiation of the replication of some organisms contained in live attenuated vaccines).

Thus, provided herein are methods for treating a disease, disorder, or condition associated with the glucocorticoid receptor comprising administering a conjugate of Formula (I), (IA), (IB), (IB-1), (IB-2), (IC), (ID), (IE), Formula (III) or Formula (3000), to a patient having said disease, disorder, or condition, wherein the side effects associated with administration of the free steroid payload of said conjugate is reduced. Furthermore, provided herein are methods of delivering a compound of Formula (III), or Formula (3000), to a cell comprising contacting said cell with a protein conjugate the compound of Formula (3000), or Formula (III), wherein the protein conjugate comprises an antibody or antigen binding fragment thereof that binds a surface antigen of said cell.

In some examples, where the payload is an LXR modulator, set forth herein is a method of treating a disease, disorder or condition comprising administering to a patient having said disorder a therapeutically effective amount of a compound and/or an ADC (e.g., ADCs of Formula (I), (IA), (IB), (IB-1), (IB-2), (IC), (ID), (IE), (5001), (5002), (5003), (5004), (6001), (6002), (6003), (6004), or (6005)) or a pharmaceutical composition thereof.

In some examples, set forth herein is a method of preventing a disease, disorder or condition comprising administering to a patient having said disorder a prophylactically effective amount of a compound and/or an ADC (e.g., ADCs of Formula (I), (IA), (IB), (IB-1), (IB-2), (IC), (ID), (IE), (5001), (5002), (5003), (5004), (6001), (6002), (6003), (6004), or (6005), or a pharmaceutical composition thereof.

In some examples, set forth herein are methods for treating or preventing any disease, disorder, or condition responsive to modulation of LXR signaling. In some examples, the disease or disorder is associated with LXR function, LXR polymorphisms, LXR agonist activity, or LXR antagonist activity. In some examples, set forth herein is a method of treating or preventing a disease, disorder, or condition selected from the group consisting of a proliferative disorder, a neurodegenerative disorder, an immunological disorder, an autoimmune disease, an inflammatory disorder, a dermatological disease, a metabolic disease, cardiovascular disease, and a gastrointestinal disease.

The proliferative disorder can be any proliferative disorder known to those of skill. In certain embodiments, proliferative disorders include, without limitation, oncology disorders, where the oncology disorder can be any cancer disorder known to those of skill. In certain embodiments, provided herein are methods of treating or preventing a melanoma. In certain embodiments, provided herein are methods of treating or preventing metastatic melanoma. In certain embodiments, provided herein are methods of treating or preventing lung cancer. In certain embodiments, provided herein are methods of treating or preventing EGFR-tyrosine kinase inhibitor resistant lung cancer. In certain embodiments, provided herein are methods of treating or preventing oral cancer. In certain embodiments, provided herein are methods of treating or preventing oral squamous cell carcinoma. In certain embodiments, provided herein are methods of treating or preventing prostate cancer. In certain embodiments, provided herein are methods of treating or preventing Hodgkin's lymphoma. In certain embodiments, provided herein are methods of treating or preventing breast cancer.

The neurodegenerative disorder can be any neurodegenerative disorder known to those of skill. In certain embodiments, provided herein are methods of treating or preventing Alzheimer's disease. In certain embodiments, provided herein are methods of treating or preventing Parkinson's disease. In certain embodiments, provided herein are methods of treating or preventing Huntington's disease. In certain embodiments, provided herein are methods of treating or preventing amyotrophic lateral sclerosis. In certain embodiments, provided herein are methods of treating or preventing myelin gene expression. In certain embodiments, provided herein are methods of treating or preventing myelination and remyelination conditions, diseases, or disorders.

The immunological disorder can be any immunological disorder known to those of skill. In certain embodiments, provided herein are methods of treating or preventing inflammatory bowel disease. In certain embodiments, provided herein are methods of treating or preventing ulcerative colitis. In certain embodiments, provided herein are methods of treating or preventing Crohn's disease.

The inflammatory disorder can be any inflammatory disorder known to those of skill. In certain embodiments, provided herein are methods of treating or preventing arthritis. In certain embodiments, provided herein are methods of treating or preventing rheumatoid arthritis.

The metabolic disease can be any metabolic disease known to those of skill. In certain embodiments, the metabolic disease is dyslipidemia. Dyslipidemia can be any dyslipidemia known to those of skill. In certain embodiments, dyslipidemia is selected from the group consisting of hyperlipidemia, hypercholesterolemia, hypertriglyceridemia, hyperlipoproteinemia, HDL deficiency, ApoA-I deficiency, and cardiovascular disease such as coronary artery disease (including, for example, treatment and prevention of angina, myocardial infarction, and sudden cardiac death); atherosclerosis (including, for example, treatment and prevention of atherosclerosis); and restenosis (including, for example, preventing or treating atherosclerotic plaques which develop as a consequence of medical procedures such as balloon angioplasty). In certain embodiments, provided herein are methods of treating or preventing diabetes.

The cardiovascular disease can be any cardiovascular disease known to those of skill. In certain embodiments, provided herein are methods of treating or preventing atherosclerosis. In certain embodiments, provided herein are methods of treating or preventing atherosclerosis derived from abnormal macrophage processing. In certain embodiments, provided herein are methods of treating or preventing atherosclerosis derived from the formation of oxidized low-density lipoproteins (oxLDLs), where marcrophages fail to process oxLDLs. In certain embodiments, provided herein are methods of treating or preventing ischemic heart disease. In certain embodiments, provided herein are methods of treating or preventing stroke. In certain embodiments, provided herein are methods of treating or preventing hypertensive heart disease. In certain embodiments, provided herein are methods of treating or preventing aortic aneurysm. In certain embodiments, provided herein are methods of treating or preventing endocarditis. In certain embodiments, provided herein are methods of treating or preventing peripheral artery disease. In certain embodiments, provided herein are methods of treating or preventing combinations of any of the diseases provided in this paragraph.

In some examples, set forth herein is a method for modulating the function of a nuclear receptor. By way of non-limiting example, the function may be selected from expression/secretion of inflammatory mediators (e.g. cytokines, chemokines), cholesterol regulation, cholesterol intake, cholesterol efflux, cholesterol oxidation, migration, chemotaxis, apoptosis and necrosis, an inflammatory activity, lipid regulation, apoptosis, migration, chemotaxis, gene transcription, and protein expression.

In some examples, set forth herein is a method of preventing a disease, disorder or condition comprising administering to a patient having said disorder a therapeutically effective amount of a compound and/or an ADC of Formula (I), (IA), (IB), (IB-1), (IB-2), (IC), (ID), (IE), (7001), (7002), (7003), (7004), and/or (7005), or a pharmaceutical composition thereof.

*S. aureus* is a facultative intracellular bacterium that can survive phagocytosis by macrophages and other cells types (Horn, J., et al., Inside job: *Staphylococcus aureus* host-pathogen interactions. Int J Med Microbiol, 2018. 308(6): p. 607-624; Jubrail, J., et al., *Inability to sustain intraphagolysosomal killing of Staphylococcus aureus predisposes to bacterial persistence in macrophages*. Cell Microbiol, 2016. 18(1): p. 80-96). Intravital imaging has demonstrated that macrophages can serve as a reservoir where *S. aureus* replicates and then seeds other organs during infection (Surewaard, B. G., et al., *Identification and treatment of the Staphylococcus aureus reservoir in vivo*. J Exp Med, 2016. 213(7): p. 1141-51). Most antibiotics do not penetrate cells, including macrophages, very well, indicating that the intracellular *S. aureus* reservoir can evade treatment with standard of care antibiotics (Lehar, S. M., et al., Novel antibody-antibiotic conjugate eliminates intracellular *S. aureus*. Nature, 2015. 527(7578): p. 323-8). However, liposomal formulation of vancomycin increased penetration of the antibiotic into macrophages and reduced *S. aureus* organ burden more effectively than standard of care vancomycin (Surewaard, B. G., et al., Identification and treatment of the *Staphylococcus aureus* reservoir in vivo. J Exp Med, 2016. 213(7): p. 1141-51). Together, these data indicate that delivering an antibiotic to macrophages may be an effective method to eliminate the intracellular *S. aureus* reservoir.

Antibiotic resistant *S. aureus* remains a public health problem and roughly 40% blood stream infections are caused by methicillin-resistant *S. aureus* (MRSA) in the USA. Few FDA approved treatment options exist for MRSA blood stream infections, with vancomycin remaining an antibiotic of choice. In spite of appropriate antibiotic treatment, mortality from *S. aureus* blood stream infections is ~18%, prompting investigation into combinations that can improve treatment.

The rifamycin class of antibiotics inhibit bacterial RNA polymerase (RNAP) and have potent activity against *S. aureus*. Monotherapy with this class of antibiotics, however, can lead to selection of a resistant population during treatment. Therefore, rifamycin antibiotics can be used in combination with first line antibiotics to improve outcomes, commonly in infections involving prostheses or foreign devices.

The ADCs described herein comprising rifamycin analogs are useful for preventing or treating growth of a bacterium and/or bacterial infection in a subject. In some instances, the bacterium is a gram positive bacterium (a gram positive bacterium is the cause of the bacterial infection). In some instances, the bacterium is a pencillin-resistant bacterium (a penicillin-resistant bacterium is the cause of the bacterial infection). In some instances, the bacterium is a *Staphylococcus aureus*, methicillin resistant *Staphylococcus aureus* (MRSA) bacterium (a MRSA bacterium is the cause of the bacterial infection). In some instances, the bacterium is a methicillin susceptible *Staphylococcus aureus* (MSSA) bacterium (a MSSA bacterium is the cause of the bacterial infection). In some instances, the bacterium is a vancomycin-resistant *Staphylococcus aureus* (VRSA) bacterium (a VRSA bacterium is the cause of the bacterial infection). In some instances, the bacterium is multi-drug resistant *M. tuberculosis* (a multi-drug resistant *M. tuberculosis* bacterium is the cause of the bacterial infection). In further instances, the bacterium is *Chlamydia trachomatis* resistant to, e.g., azithromycin (*Chlamydia trachomatis* resistant to, e.g., azithromycin is the cause of the bacterial infection). In more instances, the bacterium is *Clostridium difficile* resistant to, e.g., metronidazole, vancomycin, and/or fidaxomicin (*Clostridium difficile* resistant to, e.g., metronidazole, vancomycin, and/or fidaxomicin is the cause of the bacterial infection).

Provided herein is a method of preventing or treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of an antibody-drug conjugate comprising a rifamycin analog (e.g., ADCs of Formula (I), (IA), (IB), (IB-1), (IB-2), (IC), (ID), (IE), (7001), (7002), (7003), (7004) and/or (7005)). Also provided herein is a method of preventing or treating an intracellular bacterial infection in a subject comprising administering to the subject an effective treatment amount of an antibody-drug conjugate of an antibody-drug conjugate comprising a rifamycin analog (e.g., ADCs of Formula (I), (IA), (IB), (IB-1), (IB-2), (IC), (ID), (IE), (7001), (7002), (7003), (7004) and/or (7005)).

In some instances, provided herein are therapeutic methods comprising administration an anti-MSR1 antibody, an antigen-binding portion of an MSR1 antibody, or an ADC comprising an anti-MSR1 antibody of MSR1 antigen-binding fragment thereof, to a subject in need thereof are useful for the treatment, and/or prevention of bacterial infection in a subject, and/or a disease or disorder or condition associated with Staphylococcal infection, for example, a *S. aureus* infection and/or for ameliorating at least one symptom associated with such disease, disorder or condition. Such disease, disorder or condition can be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some instances, the subject has a prosthetic joint and the antibodies disclosed herein are used for treating and/or preventing *S. aureus* infection of the tissue surrounding the prosthetic joint. In some instances, the subject has a catheter and the antibodies disclosed herein are used for treating and/or preventing *S. aureus* infection of the catheter and/or the tissue surrounding the catheter. In some instances, the subject has a foreign body implanted, and the antibodies disclosed herein are used for treating and/or preventing *S. aureus* infection of the foreign body and/or the tissue surrounding the foreign body. In some instances, the subject has mastitis, and the antibodies disclosed herein are useful for treating mastitis.

In some instances, the rifamycin analogs and/or anti-MSR1 ADCs thereof are administered in combination with one or more additional antibiotics (e.g., antibiotics that may be used for MRSA infections) such as vancomycin, trimethoprim-sulfamethoxazole, tetracycline, doxycycline/minocycline, clindamycin, cephalosporins (e.g. cephalexin), naficillin, fidaxomicin, linezolid, and the like, and/or any other suitable antibiotic(s). In some instances, the ADCs described herein comprising rifamycin analogs are administered in combination with vancomycin and are useful for preventing or treating bacterial infection in a subject.

Combination Therapies and Formulations

Embodiments include compositions and therapeutic formulations comprising any of the anti-MSR1 antibodies described herein in combination with one or more additional therapeutically active components, and methods of treatment comprising administering such combinations to subjects in need thereof.

The anti-MSR1 antibodies disclosed herein may be co-formulated with and/or administered in combination with one or more additional therapeutically active component(s) selected from the group consisting of: cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The anti-MSR1 antibodies disclosed herein may also be administered and/or co-formulated in combination with anti-inflammatory agents, immunomodulatory agents, analgesics, corticosteroids, steroids, antioxidants, COX inhibitors, cardioprotectants, metal chelators, IFN-gamma, and/or NSAIDs. In some embodiments, the anti-MSR1 antibodies can be administered and/or co-formulated in combination with anti-PCSK9 antibodies, anti-ANGPTL3 antibodies, statins, ezetimibe and other lipid lowering therapies.

The additional therapeutically active component(s), e.g., any of the agents listed above or derivatives thereof, may be administered just prior to, concurrent with, or shortly after the administration of an anti-MSR1 antibody disclosed herein; (for purposes of the present disclosure, such administration regimens are considered the administration of an anti-MSR1 antibody "in combination with" an additional therapeutically active component). Embodiments include pharmaceutical compositions in which an anti-MSR1 antibody disclosed herein is co-formulated with one or more of the additional therapeutically active component(s) as described elsewhere herein.

Administration Regimens

According to certain embodiments, multiple doses of an anti-MSR1 antibody (or an ADC or a pharmaceutical composition comprising a combination of an anti-MSR1 antibody and any of the additional therapeutically active agents mentioned herein) may be administered to a subject over a defined time course. The methods comprise sequentially administering to a subject multiple doses of an anti-MSR1 antibody disclosed herein. As used herein, "sequentially administering" means that each dose of anti-MSR1 antibody is administered to the subject at a different point in time, e.g., on different days separated by a predetermined interval (e.g., hours, days, weeks or months). Embodiments include methods which comprise sequentially administering to the patient a single initial dose of an anti-MSR1 antibody, followed by one or more secondary doses of the anti-MSR1 antibody, and optionally followed by one or more tertiary doses of the anti-MSR1 antibody.

The terms "initial dose," "secondary doses," and "tertiary doses," refer to the temporal sequence of administration of the anti-MSR1 antibody disclosed herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-MSR1 antibody, but generally may differ from one another in terms of frequency of administration. In certain embodiments, however, the amount of anti-MSR1 antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-MSR1 antibody which is administered to a patient prior to the administration of the very next dose in the sequence with no intervening doses.

The methods according to this aspect of the invention may comprise administering to a patient any number of secondary and/or tertiary doses of an anti-MSR1 antibody. For example, in certain embodiments, a single secondary dose is administered to the patient. In other embodiments, two or more (e.g., 2, 3, 4, 5, 6, 7, 8, or more) secondary doses are administered to the patient. Likewise, in certain embodiments, a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments, the frequency at which the secondary and/or tertiary doses are administered to a patient can vary over the course of the treatment regimen. The frequency of administration may also be adjusted during the course of treatment by a physician depending on the needs of the individual patient following clinical examination.

Embodiments include administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-MSR1 antibodies disclosed herein may also be used to detect and/or measure MSR1, or MSR1-expressing cells in a sample, e.g., for diagnostic purposes. For example, an anti-MSR1 antibody, or fragment thereof, may be used to diagnose a condition or disease characterized by aberrant expression (e.g., over-expression, under-expression, lack of expression, etc.) of MSR1. Exemplary diagnostic assays for MSR1 may comprise, e.g., contacting a sample, obtained from a patient, with an anti-MSR1 antibody disclosed herein, wherein the anti-MSR1 antibody is labeled with a detectable label or reporter molecule. Alternatively, an unlabeled anti-MSR1 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein, or rhodamine; or an enzyme such as alkaline phosphatase, beta-galactosidase, horseradish peroxidase, or luciferase. Specific exemplary assays that can be used to detect or measure MSR1 in a sample include enzyme-linked immunosorbent assay (ELISA), radioimmunoassay (RIA), immuno-PET (e.g., $^{89}Zr$, $^{64}Cu$, etc.), and fluorescence-activated cell sorting (FACS).

Samples that can be used in MSR1 diagnostic assays according to the present invention include any tissue or fluid sample obtainable from a patient which contains detectable quantities of MSR1 protein, or fragments thereof, under normal or pathological conditions. Generally, levels of MSR1 in a particular sample obtained from a healthy patient (e.g., a patient not afflicted with a disease or condition associated with abnormal MSR1 levels or activity) will be measured to initially establish a baseline, or standard, level of MSR1. This baseline level of MSR1 can then be compared against the levels of MSR1 measured in samples obtained from individuals suspected of having a MSR1-related disease or condition.

EXAMPLES

The following examples are put forth so as to provide those of ordinary skill in the art with a complete disclosure and description of how to make and use the methods and compositions provided herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric. The examples should not be construed as limiting, as the examples merely provide specific understanding and practice of the embodiments and their various aspects.

As used herein, the symbols and conventions used in the processes, and Examples, herein, are consistent with those used in the contemporary scientific literature, for example, the Journal of the American Chemical Society or the *Journal of Biological Chemistry* unless specified otherwise to the contrary. Specifically, but without limitation, the following abbreviations may be used in the Examples and throughout the specification:

| Abbreviation | Term |
|---|---|
| ADC | Antibody-drug conjugate |
| Aglycosylated antibody | Antibody does not have any glycan |
| aq | Aqueous |
| BARAC | Biarylazacyclooctynone |
| BCN | (1R,8S,9s)-Bicyclo[6.1.0]non-4-yn-9-yl |
| Boc | N-tert-butoxycarbonyl |

-continued

| Abbreviation | Term |
|---|---|
| BupHTM | Thermo Scientific Prod# 28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAR | Drug to antibody ratio. |
| DCM | Dichloromethane |
| DIBAC | Dibenz[b,f]azocine, 11,12-didehydro-5,6-dihydro- or Dibenzocyclooctyne or Dibenz[b,f]azocine-5(6H)-butanoic acid, 11,12-didehydro |
| DIBAC-Suc | Dibenz[b,f]azocine-5(6H)-butanoic acid, 11,12-didehydro |
| DIBACT | 3H-Benzo[c]-1,2,3-triazolo[4,5-e][1]benzazocine, 8,9-dihydro- |
| DIBO | Dibenzocyclooctyne |
| DIFO | Difluorinated cyclooctyne |
| DIPEA | Diisopropylethylamine |
| DMF | N,N-dimethylformamide |
| DMSO | Dimethylsulfoxide |
| ESI | Electrospray ionization |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Light chain of immunoglobulin |
| LC | Liquid chromatography |
| MC | Maleimidocaproyl |
| mg | Milligrams |
| min | Minutes |
| mL | Milliliters |
| mM | Millimolar |
| MMAE | Monomethyl auristatin E |
| MS | Mass spectrometry |
| MSD | Mass-selective detector |
| MTG | Microbial transglutaminase |
| MW | Molecular weight |
| ncADC | Non-Cytotoxic antibody drug conjugation |
| NHS | N-hydroxy succinimide |
| nM | nanomolar |
| NMR | Nuclear magnetic resonance |
| NOESY | Nuclear Overhauser effect spectroscopy |
| PAB | Para-aminobezyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| ppm | Parts per million (chemical shift) |
| RP | Reversed phase |
| RT or rt | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-Aniline |
| VC | Valine-citrulline |
| μL | Microliters |
| μM | micromolar |

Reagents and solvents were obtained from commercial sources such as Sinopharm Chemical Reagent Co. (SCRC), Sigma-Aldrich, Alfa, or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethylsilane (TMS).

HPLC-MS measurements were run on an Agilent 1200 HPLC/6100 SQ System using the follow conditions:

Method A for HPLC-MS measurements included, as the Mobile Phase: A: Water (0.01% trifluoroacetic acid (TFA)), B: acetonitrile (0.01% TFA); Gradient Phase: 5% of B increased to 95% of B within 15 minutes (min); Flow Rate: 1.0 mL/min; Column: SunFire C18, 4.6×50 mm, 3.5 μm; Column Temperature: 50° C. Detectors: Analog to Digital Converter (ADC) Evaporative Light-scattering Detector (ELSD), Diode array detector (DAD) (214 nm and 254 nm), electrospray ionization-atmospheric ionization (ES-API).

Method B for HPLC-MS measurements included, as the Mobile Phase: A: Water (10 mM $NH_4HCO_3$), B: acetonitrile; Gradient Phase: 5% to 95% of B within 15 min; Flow Rate: 1.0 mL/min; Column: XBridge C18, 4.6×50 mm, 3.5 μm; Column Temperature: 50° C. Detectors: ADC ELSD, DAD (214 nm and 254 nm), mass selective detector (MSD) (ES-API).

LC-MS measurements were run on an Agilent 1200 HPLC/6100 SQ System using the following conditions:

Method A for LC-MS measurements included, as the Instrument: WATERS 2767; column: Shimadzu Shim-Pack, PRC-ODS, 20×250 mm, 15 μm, two connected in series; Mobile Phase: A: Water (0.01% TFA), B: acetonitrile (0.01% TFA); Gradient Phase: 5% of B increased to 95% of B within 3 min; Flow Rate: 1.8-2.3 mL/min; Column: SunFire C18, 4.6×50 mm, 3.5 μm; Column Temperature: 50° C. Detectors: ADC ELSD, DAD (214 nm and 254 nm), ES-API.

Method B for LC-MS measurement included, as the Instrument: Gilson GX-281; column: Xbridge Prep C18 10 μm OBD, 19×250 mm; Mobile Phase: A: Water (10 mM $NH_4HCO_3$), B: Acetonitrile; Gradient Phase: 5% to 95% of B within 3 min; Flow Rate: 1.8-2.3 mL/min; Column: XBridge C18, 4.6×50 mm, 3.5 μm; Column Temperature: 50° C. Detectors: ADC ELSD, DAD (214 nm and 254 nm), MSD (ES-API).

Preparative high-pressure liquid chromatography (Prep-HPLC) in an acidic or basic solvent system was utilized on a Gilson GX-281 instrument. The acidic solvent system used a Waters SunFire 10 μm C18 column (100 Å, 250×19 mm), and solvent A for prep-HPLC was water/0.05% TFA and solvent B was acetonitrile. The elution conditions were a linear gradient increase of solvent B from 5% to 100% over a time period of 20 min at a flow rate of 30 mL/min. The basic solvent system included a Waters Xbridge 10 μm C18 column (100 Å, 250×19 mm), and solvent A used for prep-HPLC was water/10 mM ammonium bicarbonate ($NH_4HCO_3$) and solvent B was acetonitrile. The elution conditions were a linear gradient increase of solvent B from 5% to 100% over a time period of 20 min at a flow rate of 30 mL/min.

Flash chromatography was performed on a Biotage instrument, with Agela Flash Column silica-CS cartridges; Reversed phase flash chromatography was performed on Biotage instrument, with Boston ODS or Agela C18 cartridges.

Analytical chiral HPLC method-SFC conditions:

a) Instrument: SFC Method Station (Thar, Waters)

b) Column: CHIRALPAK AD-H/AS-H/OJ-H/OD-H 4.6×100 mm, 5 μm (Daicel)

c) Column temperature: 40° C.

d) Mobile phase: $CO_2$/IPA (0.1% DEA)=55/45 e) Flow: 4.0 ml/min f) Back Pressure: 120 Bar g) Injection volume: 2 μL.

Preparative chiral HPLC method-SFC conditions:

a) Instrument: SFC-80 (Thar, Waters)

b) Column: CHIRALPAK AD-H/AS-H/OJ-H/OD-H 20×250 mm, 10 μm (Daicel)

c) Column temperature: 35° C.

d) Mobile phase: $CO_2$/IPA (0.2% Methanol Ammonia) =30/70 e) Flow rate: 80 g/min f) Back pressure: 100 bar g) Detection wavelength: 214 nm h) Cycle time: 6.0 min i) Sample solution: 1500 mg dissolved in 70 mL Methanol j) Injection volume: 2 mL (loading: 42.86 mg/injection).

As used herein, the symbols and conventions used in these processes, schemes, and examples, regardless of whether a particular abbreviation is specifically defined, are consistent with those used in the contemporary scientific literature, for example, the Journal of the American Chemical Society or the *Journal of Biological Chemistry.*

Example 1. Generation of Anti-MSR1 Antibodies

Anti-MSR1 antibodies were obtained by immunizing a genetically engineered mouse comprising DNA encoding human immunoglobulin heavy and kappa light chain variable regions with an immunogen comprising recombinant human MSR1 extracellular domain fused to an N-terminal nonahistidine tag (R&D Systems, Catalog #2708-MS-050, Minneapolis, MN). The mice used for the immunizations were Velocimmune mice or mice which expressed a "universal light chain" ("ULC" mice). Antibodies produced ULC mouse have different heavy chain variable regions but essentially identical light chain variable domains.

The antibody immune response was monitored by a MSR1-specific immunoassay. When a desired immune response was achieved splenocytes were harvested and fused with mouse myeloma cells to preserve their viability and form hybridoma cell lines. The hybridoma cell lines were screened and selected to identify cell lines that produce MSR1-specific antibodies. Using this technique several anti-MSR1 chimeric antibodies (i.e., antibodies possessing human variable domains and mouse constant domains) were obtained. In addition, several fully human anti-MSR1 antibodies were isolated directly from antigen-positive B cells without fusion to myeloma cells, as described in US 2007/0280945A1.

Certain biological properties of the exemplary anti-MSR1 antibodies generated in accordance with the methods of this Example are described in detail in the Examples set forth below.

Example 2. Heavy and Light Chain Variable Region Amino Acid and Nucleic Acid Sequences Table 4 sets forth the amino acid sequence identifiers of the heavy and light chain variable regions and CDRs of selected anti-MSR1 antibodies described herein. The corresponding nucleic acid sequence identifiers are set forth in Table 5.

TABLE 4

Amino Acid Sequence Identifiers

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1H21227N | 2 | 4 | 6 | 8 | 10 | 12 | 14 | 16 |
| H1H21228N | 18 | 20 | 22 | 24 | 26 | 28 | 30 | 32 |

TABLE 4-continued

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H21231N | 34 | 36 | 38 | 40 | 42 | 44 | 46 | 48 |
| H1H21234N | 50 | 52 | 54 | 56 | 58 | 60 | 62 | 64 |
| H1H21235N | 66 | 68 | 70 | 72 | 74 | 76 | 78 | 80 |
| H1H25685N | 82 | 84 | 86 | 88 | 90 | 92 | 94 | 96 |
| H1H25690N | 98 | 100 | 102 | 104 | 106 | 108 | 110 | 112 |
| H1H25695N | 114 | 116 | 118 | 120 | 122 | 124 | 126 | 128 |
| H1H25700N | 130 | 132 | 134 | 136 | 138 | 140 | 142 | 144 |
| H1H27729P | 146 | 148 | 150 | 152 | 154 | 156 | 158 | 160 |
| H1H27731P | 162 | 164 | 166 | 168 | 170 | 172 | 174 | 176 |
| H1H27732P | 178 | 180 | 182 | 184 | 186 | 188 | 190 | 192 |
| H1H27734P | 194 | 196 | 198 | 200 | 202 | 204 | 206 | 208 |
| H1H27736P | 210 | 212 | 214 | 216 | 218 | 220 | 222 | 224 |
| H1H27739P | 226 | 228 | 230 | 232 | 234 | 236 | 238 | 240 |
| H1H27747P | 242 | 244 | 246 | 248 | 250 | 252 | 254 | 256 |
| H1H27749P | 258 | 260 | 262 | 264 | 266 | 268 | 270 | 272 |
| H1H27751P | 274 | 276 | 278 | 280 | 282 | 284 | 286 | 288 |
| H1H27754P | 290 | 292 | 294 | 296 | 298 | 300 | 302 | 304 |
| H1H27756P | 306 | 308 | 310 | 312 | 314 | 316 | 318 | 320 |
| H1H27760P2 | 322 | 324 | 326 | 328 | 90 | 92 | 94 | 96 |
| H1H27761P2 | 330 | 332 | 334 | 336 | 90 | 92 | 94 | 96 |
| H1H27762P2 | 338 | 340 | 342 | 344 | 90 | 92 | 94 | 96 |
| H1H27766P2 | 346 | 348 | 350 | 352 | 90 | 92 | 94 | 96 |
| H1H27771P2 | 354 | 356 | 358 | 360 | 362 | 364 | 366 | 368 |
| H1xH27759P2 | 370 | 372 | 374 | 376 | 90 | 92 | 94 | 96 |
| H1xH27773P2 | 378 | 380 | 382 | 384 | 362 | 364 | 366 | 368 |
| H1xH27778P2 | 386 | 388 | 390 | 392 | 362 | 364 | 366 | 368 |
| H1xH29273P2 | 394 | 396 | 397 | 400 | 90 | 92 | 94 | 96 |
| H1xH29282P2 | 402 | 404 | 406 | 408 | 90 | 92 | 94 | 96 |
| H1xH29283P2 | 410 | 412 | 414 | 416 | 90 | 92 | 94 | 96 |
| H2M21229N | 420 | 422 | 424 | 426 | 428 | 430 | 432 | 434 |
| H2M21230N | 436 | 438 | 440 | 442 | 444 | 446 | 448 | 450 |
| H2M21232N | 452 | 454 | 456 | 458 | 460 | 462 | 464 | 466 |

TABLE 5

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H21227N | 1 | 3 | 5 | 7 | 9 | 11 | 13 | 15 |
| H1H21228N | 17 | 19 | 21 | 23 | 25 | 27 | 29 | 31 |
| H1H21231N | 33 | 35 | 37 | 39 | 41 | 43 | 45 | 47 |
| H1H21234N | 49 | 51 | 53 | 55 | 57 | 59 | 61 | 63 |
| H1H21235N | 65 | 67 | 69 | 71 | 73 | 75 | 77 | 79 |
| H1H25685N | 81 | 83 | 85 | 87 | 89 | 91 | 93 | 95 |
| H1H25690N | 97 | 99 | 101 | 103 | 105 | 107 | 109 | 111 |
| H1H25695N | 113 | 115 | 117 | 119 | 121 | 123 | 125 | 127 |
| H1H25700N | 129 | 131 | 133 | 135 | 137 | 139 | 141 | 143 |
| H1H27729P | 145 | 147 | 149 | 151 | 153 | 155 | 157 | 159 |
| H1H27731P | 161 | 163 | 165 | 167 | 169 | 171 | 173 | 175 |
| H1H27732P | 177 | 179 | 181 | 183 | 185 | 187 | 189 | 191 |
| H1H27734P | 193 | 195 | 197 | 199 | 201 | 203 | 205 | 207 |
| H1H27736P | 209 | 211 | 213 | 215 | 217 | 219 | 221 | 223 |
| H1H27739P | 225 | 227 | 229 | 231 | 233 | 235 | 237 | 239 |
| H1H27747P | 241 | 243 | 245 | 247 | 249 | 251 | 253 | 255 |
| H1H27749P | 257 | 259 | 261 | 263 | 265 | 267 | 269 | 271 |
| H1H27751P | 273 | 275 | 277 | 279 | 281 | 283 | 285 | 287 |
| H1H27754P | 289 | 291 | 293 | 295 | 297 | 299 | 301 | 303 |
| H1H27756P | 305 | 307 | 309 | 311 | 313 | 315 | 317 | 319 |
| H1H27760P2 | 321 | 323 | 325 | 327 | 89 | 91 | 93 | 95 |
| H1H27761P2 | 329 | 331 | 333 | 335 | 89 | 91 | 93 | 95 |
| H1H27762P2 | 337 | 339 | 341 | 343 | 89 | 91 | 93 | 95 |
| H1H27766P2 | 345 | 347 | 349 | 351 | 89 | 91 | 93 | 95 |
| H1H27771P2 | 353 | 355 | 357 | 359 | 361 | 363 | 365 | 367 |
| H1xH27759P2 | 369 | 371 | 373 | 375 | 89 | 91 | 93 | 95 |
| H1xH27773P2 | 377 | 379 | 381 | 383 | 361 | 363 | 365 | 367 |
| H1xH27778P2 | 385 | 387 | 389 | 391 | 361 | 363 | 365 | 367 |
| H1xH29273P2 | 393 | 395 | 397 | 399 | 89 | 91 | 93 | 95 |

TABLE 5-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1xH29282P2 | 401 | 403 | 405 | 407 | 89 | 91 | 93 | 95 |
| H1xH29283P2 | 409 | 411 | 413 | 415 | 89 | 91 | 93 | 95 |
| H2M21229N | 419 | 421 | 423 | 425 | 427 | 429 | 431 | 433 |
| H2M21230N | 435 | 437 | 439 | 441 | 443 | 445 | 447 | 449 |
| H2M21232N | 451 | 453 | 455 | 457 | 459 | 461 | 463 | 465 |

Antibodies are typically referred to herein according to the following nomenclature: Fc prefix (e.g. "H1H," "H2aM," etc.), followed by a numerical identifier (e.g. "21227," "21228," "21231," etc.), followed by a "P," "N," or "P2" suffix, as shown in Tables 4 and 5. Thus, according to this nomenclature, an antibody may be referred to herein as, e.g., "H1H21227N," "H2aM21228N," "H1H27729P," "H1H27760P2," etc. The prefix on the antibody designations used herein indicate the particular Fc region isotype of the antibody. In particular, an "H1H" antibody has a human IgG1 Fc (all variable regions are fully human as denoted by the first 'H' in the antibody designation), while an "H2aM" antibody has a mouse IgG2a Fc. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 4 and 5—will remain the same, and the binding properties are expected to be identical or substantially similar regardless of the nature of the Fc domain.

Antibody Modifications. Three anti-MSR1 antibodies described in Example 1 (21227N, 21231N, 21234N) were produced with the original human Fcγ portion, as well as a version with an N297Q single point mutation for all three anti-MSR1 antibodies. All other antibodies described herein were made with an N297Q single point mutation in human Fcγ portion. A third version, an N297D mutation was produced for the 21227N antibody only.

Example 3. Surface Plasmon Resonance Derived Binding Affinities and Kinetic Constants of Human Monoclonal Anti-MSR1 Antibodies Binding affinities and kinetic constants of human anti-MSR1 antibodies for different MSR1 reagents were determined by real-time surface plasmon resonance (Biacore 4000). All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM4 sensor chip surface was first derivatized by amine coupling with the goat anti-human Fcγ specific polyclonal antibody (Jackson ImmunoResearch Laboratories, Cat #BR-1008-39) to capture anti-MSR1 monoclonal antibodies. Binding studies were performed on human MSR1 extracellular domain expressed with a N-terminal nonahistidine tag (His9-hMSR1; R&D Systems, Cat #2708-MS), and monkey MSR1 extracellular domain expressed with a N-terminal hexahistidine-myc-myc tag (HMM-mfMSR1; SEQ ID NO: 418). Different concentrations of His9-hMSR1 and HMM-mfMSR1 (100 nM-3.7 nM; 3-fold serial dilution) were first prepared in HBS-ET running buffer and were injected over anti-human Fcγ captured anti-MSR1 monoclonal antibody surface for 3 minutes at a flow rate of 30 μL/minute, while the dissociation of monoclonal antibody bound MSR1 reagent was monitored for 10 minutes in HBS-ET running buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60 * kd}$$

Binding kinetics parameters for His9-hMSR1 or HMM-mfMSR1 binding to different anti-MSR1 monoclonal antibodies at 25° C. and 37° C. are shown in Tables 6 and 7, respectively.

TABLE 6

Biacore Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H21227N- | His9-hMSR1 | 1.23E+06 | 4.89E−05 | 3.97E−11 | 236 |
| N297Q | HMM-mfMSR1 | 1.36E+06 | 7.51E−05 | 5.53E−11 | 154 |
| H1H21227N- | His9-hMSR1 | 1.14E+06 | 3.79E−05 | 3.33E−11 | 305 |
| N297D | HMM-mfMSR1 | 1.35E+06 | 4.03E−05 | 2.99E−11 | 287 |
| H1H21231N- | His9-hMSR1 | 3.99E+05 | 5.88E−05 | 1.47E−10 | 196 |
| N297Q | HMM-mfMSR1 | 2.40E+05 | 9.03E−05 | 3.76E−10 | 128 |
| H1H21234N- | His9-hMSR1 | 4.97E+05 | 1.00E−05* | 2.01E−11 | 1155 |
| N297Q | HMM-mfMSR1 | 4.08E+05 | 1.95E−05 | 4.66E−11 | 593 |
| H1H27729P- | His9-hMSR1 | 1.97E+05 | 1.07E−03 | 5.45E−09 | 11 |
| N297Q | HMM-mfMSR1 | 2.69E+05 | 2.12E−03 | 7.90E−09 | 5 |
| H1H27731P- | His9-hMSR1 | 1.29E+05 | 2.24E−05 | 1.74E−10 | 515 |
| N297Q | HMM-mfMSR1 | 9.82E+04 | 4.69E−05 | 4.77E−10 | 247 |

TABLE 6-continued

Biacore Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H27732P- | His9-hMSR1 | 1.25E+05 | 1.00E−05* | 8.01E−11 | 1155 |
| N297Q | HMM-mfMSR1 | 1.28E+05 | 3.17E−05 | 2.48E−10 | 364 |
| H1H27734P- | His9-hMSR1 | 4.20E+05 | 1.11E−03 | 2.64E−09 | 10 |
| N297Q | HMM-mfMSR1 | 4.23E+05 | 2.91E−03 | 6.88E−09 | 4 |
| H1H27736P- | His9-hMSR1 | 5.15E+05 | 2.31E−04 | 4.48E−10 | 50 |
| N297Q | HMM-mfMSR1 | 4.64E+05 | 5.87E−04 | 1.27E−09 | 20 |
| H1H27739P- | His9-hMSR1 | 3.75E+05 | 1.03E−03 | 2.74E−09 | 11 |
| N297Q | HMM-mfMSR1 | 3.52E+05 | 1.44E−04 | 4.10E−10 | 80 |
| H1H27747P- | His9-hMSR1 | 2.43E+05 | 6.52E−04 | 2.69E−09 | 18 |
| N297Q | HMM-mfMSR1 | 2.31E+05 | 8.74E−04 | 3.78E−09 | 13 |
| H1H27749P- | His9-hMSR1 | 3.18E+05 | 1.76E−05 | 5.54E−11 | 656 |
| N297Q | HMM-mfMSR1 | 2.49E+05 | 4.27E−05 | 1.71E−10 | 271 |
| H1H27751P- | His9-hMSR1 | 1.78E+06 | 3.05E−04 | 1.72E−10 | 38 |
| N297Q | HMM-mfMSR1 | 7.44E+05 | 7.49E−04 | 1.01E−09 | 15 |
| H1H27754P- | His9-hMSR1 | 2.90E+05 | 1.00E−05* | 3.44E−11 | 1155 |
| N297Q | HMM-mfMSR1 | 2.35E+05 | 1.76E−05 | 7.50E−11 | 657 |
| H1H27756P- | His9-hMSR1 | 3.00E+05 | 1.22E−04 | 4.06E−10 | 94 |
| N297Q | HMM-mfMSR1 | 3.58E+05 | 2.44E−03 | 6.81E−09 | 5 |
| H1H27760P- | His9-hMSR1 | 4.54E+05 | 9.09E−04 | 2.00E−09 | 13 |
| N297Q | HMM-mfMSR1 | 3.63E+05 | 7.01E−04 | 1.93E−09 | 16 |
| H1H27759P- | His9-hMSR1 | 5.99E+05 | 1.22E−03 | 2.03E−09 | 9 |
| N297Q | HMM-mfMSR1 | 4.17E+05 | 9.19E−04 | 2.20E−09 | 13 |
| H1H27761P- | His9-hMSR1 | 3.12E+05 | 5.10E−04 | 1.63E−09 | 23 |
| N297Q | HMM-mfMSR1 | 3.18E+05 | 5.97E−04 | 1.88E−09 | 19 |
| H1H27762P- | His9-hMSR1 | 9.89E+05 | 1.83E−03 | 1.85E−09 | 6 |
| N297Q | HMM-mfMSR1 | 1.25E+06 | 1.99E−03 | 1.59E−09 | 6 |
| H1H27766P- | His9-hMSR1 | 2.34E+05 | 1.86E−05 | 7.96E−11 | 620 |
| N297Q | HMM-mfMSR1 | 1.57E+05 | 7.94E−05 | 5.06E−10 | 145 |
| H1H27771P- | His9-hMSR1 | 6.86E+05 | 9.58E−04 | 1.40E−09 | 12 |
| N297Q | HMM-mfMSR1 | 5.19E+05 | 5.26E−03 | 1.01E−08 | 2.2 |
| H1H27773P- | His9-hMSR1 | 6.58E+05 | 2.63E−03 | 3.99E−09 | 4 |
| N297Q | HMM-mfMSR1 | 6.43E+05 | 1.96E−03 | 3.05E−09 | 6 |
| H1H27778P- | His9-hMSR1 | 5.75E+05 | 3.94E−04 | 6.85E−10 | 29 |
| N297Q | HMM-mfMSR1 | 4.67E+05 | 1.36E−03 | 2.91E−09 | 8 |
| H1H21234N | His9-hMSR1 | 6.04E+05 | 1.00E−05* | 1.66E−11 | 1155 |
| | HMM-mfMSR1 | 3.36E+05 | 1.00E−05* | 2.98E−11 | 1155 |
| H1H21231N | His9-hMSR1 | 4.77E+05 | 1.00E−05* | 2.10E−11 | 1155 |
| | HMM-mfMSR1 | 2.74E+05 | 6.39E−05 | 2.33E−10 | 181 |
| H1H21227N | His9-hMSR1 | 1.20E+06 | 1.44E−05 | 1.20E−11 | 800 |
| | HMM-mfMSR1 | 1.27E+06 | 4.41E−05 | 3.48E−11 | 262 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

TABLE 7

Biacore Binding Affinities of Anti-MSR1 mAbs at 37° C.
Binding at 37° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H21227N- | His9-hMSR1 | 2.67E+06 | 1.23E−05 | 4.60E−12 | 941 |
| N297Q | HMM-mfMSR1 | 2.74E+06 | 1.08E−05 | 3.95E−12 | 1069 |
| H1H21227N- | His9-hMSR1 | 2.73E+06 | 1.00E−05* | 3.66E−12 | 1155 |
| N297D | HMM-mfMSR1 | 2.68E+06 | 2.42E−05 | 9.03E−12 | 477 |
| H1H21231N- | His9-hMSR1 | 5.34E+05 | 1.15E−04 | 2.15E−10 | 101 |
| N297Q | HMM-mfMSR1 | 5.87E+05 | 1.09E−04 | 1.86E−10 | 106 |
| H1H21234N- | His9-hMSR1 | 7.87E+05 | 1.00E−05* | 1.27E−11 | 1155 |
| N297Q | HMM-mfMSR1 | 7.50E+05 | 1.00E−05* | 1.33E−11 | 1155 |
| H1H27729P- | His9-hMSR1 | 2.39E+05 | 2.04E−03 | 8.53E−09 | 6 |
| N297Q | HMM-mfMSR1 | 4.07E+05 | 3.49E−03 | 8.58E−09 | 3.3 |
| H1H27731P- | His9-hMSR1 | 2.86E+05 | 1.32E−04 | 4.62E−10 | 88 |
| N297Q | HMM-mfMSR1 | 2.78E+05 | 1.87E−04 | 6.74E−10 | 62 |
| H1H27732P- | His9-hMSR1 | 2.81E+05 | 3.12E−05 | 1.11E−10 | 370 |
| N297Q | HMM-mfMSR1 | 3.34E+05 | 1.06E−04 | 3.17E−10 | 109 |
| H1H27734P- | His9-hMSR1 | 1.09E+06 | 1.90E−03 | 1.74E−09 | 6 |
| N297Q | HMM-mfMSR1 | 9.49E+05 | 3.20E−03 | 3.37E−09 | 4 |
| H1H27736P- | His9-hMSR1 | 1.02E+06 | 7.33E−04 | 7.17E−10 | 16 |
| N297Q | HMM-mfMSR1 | 2.01E+06 | 1.28E−03 | 6.37E−10 | 9 |
| H1H27739P- | His9-hMSR1 | 7.76E+05 | 2.88E−03 | 3.72E−09 | 4 |
| N297Q | HMM-mfMSR1 | 2.25E+06 | 8.42E−04 | 3.74E−10 | 14 |

TABLE 7-continued

Biacore Binding Affinities of Anti-MSR1 mAbs at 37° C.
Binding at 37° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H27747P- | His9-hMSR1 | 5.13E+05 | 2.76E−03 | 5.37E−09 | 4 |
| N297Q | HMM-mfMSR1 | 6.57E+05 | 2.28E−03 | 3.47E−09 | 5 |
| H1H27749P- | His9-hMSR1 | 4.97E+05 | 2.42E−04 | 4.86E−10 | 48 |
| N297Q | HMM-mfMSR1 | 4.77E+05 | 1.72E−04 | 3.61E−10 | 67 |
| H1H27751P- | His9-hMSR1 | 1.45E+06 | 9.43E−04 | 6.50E−10 | 12 |
| N297Q | HMM-mfMSR1 | 1.17E+06 | 1.80E−03 | 1.55E−09 | 6 |
| H1H27754P- | His9-hMSR1 | 6.63E+05 | 2.53E−05 | 3.81E−11 | 457 |
| N297Q | HMM-mfMSR1 | 7.01E+05 | 3.53E−05 | 5.04E−11 | 327 |
| H1H27756P- | His9-hMSR1 | 6.63E+05 | 7.71E−04 | 1.16E−09 | 15 |
| N297Q | HMM-mfMSR1 | 8.02E+05 | 3.19E−03 | 3.97E−09 | 4 |
| H1H27760P- | His9-hMSR1 | 1.08E+06 | 1.89E−03 | 1.74E−09 | 6 |
| N297Q | HMM-mfMSR1 | 1.52E+06 | 1.59E−03 | 1.05E−09 | 7 |
| H1H27759P- | His9-hMSR1 | 1.03E+06 | 2.30E−03 | 2.24E−09 | 5 |
| N297Q | HMM-mfMSR1 | 1.46E+06 | 1.88E−03 | 1.28E−09 | 6 |
| H1H27761P- | His9-hMSR1 | 6.81E+05 | 2.22E−03 | 3.26E−09 | 5 |
| N297Q | HMM-mfMSR1 | 9.20E+05 | 2.14E−03 | 2.32E−09 | 5 |
| H1H27762P- | His9-hMSR1 | 3.06E+06 | 1.96E−03 | 6.40E−10 | 6 |
| N297Q | HMM-mfMSR1 | 2.82E+06 | 1.97E−03 | 6.98E−10 | 6 |
| H1H27766P- | His9-hMSR1 | 3.40E+05 | 7.72E−05 | 2.27E−10 | 150 |
| N297Q | HMM-mfMSR1 | 3.43E+05 | 5.89E−04 | 1.72E−09 | 20 |
| H1H27771P- | His9-hMSR1 | 1.35E+06 | 2.04E−03 | 1.51E−09 | 6 |
| N297Q | HMM-mfMSR1 | 4.94E+05 | 9.07E−03 | 1.84E−08 | 1.3 |
| H1H27773P- | His9-hMSR1 | 9.19E+05 | 3.07E−03 | 3.34E−09 | 4 |
| N297Q | HMM-mfMSR1 | 9.60E+05 | 5.06E−03 | 5.27E−09 | 2.3 |
| H1H27778P- | His9-hMSR1 | 1.19E+06 | 6.55E−04 | 5.49E−10 | 18 |
| N297Q | HMM-mfMSR1 | 1.19E+06 | 1.25E−03 | 1.05E−09 | 9 |
| H1H21234N | His9-hMSR1 | 6.76E+05 | 1.00E−05* | 1.48E−11 | 1155 |
| | HMM-mfMSR1 | 7.26E+05 | 1.00E−05* | 1.38E−11 | 1155 |
| H1H21231N | His9-hMSR1 | 7.02E+05 | 9.09E−05 | 1.30E−10 | 127 |
| | HMM-mfMSR1 | 7.12E+05 | 7.82E−05 | 1.10E−10 | 148 |
| H1H21227N | His9-hMSR1 | 2.56E+06 | 1.85E−05 | 7.24E−12 | 624 |
| | HMM-mfMSR1 | 2.76E+06 | 1.00E−05* | 3.62E−12 | 1155 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

At 25° C., all of the anti-MSR1 monoclonal antibodies of the invention bound to His9-hMSR1 with $K_D$ values ranging from 12 pM to 5.45 nM, as shown in Table 6. At 37° C., all of the anti-MSR1 monoclonal antibodies of the invention bound to His9-hMSR1 with $K_D$ values ranging from 3.66 pM to 8.53 nM, as shown in Table 7.

At 25° C., all of the anti-MSR1 monoclonal antibodies of the invention bound to HMM-mfMSR1 with $K_D$ values ranging from 29.9 pM to 10.1 nM, as shown in Table 6. At 37° C., all of the anti-MSR1 monoclonal antibodies of the invention bound to HMM-mfMSR1 with $K_D$ values ranging from 3.62 pM to 18.4 nM, as shown in Table 7.

Example 4. Octet-Derived Binding Affinities and Kinetic Constants of Human Monoclonal Anti-MSR1 Antibodies Binding affinities and kinetic constants of human anti-MSR1 antibodies for different MSR1 reagents were determined using a real time, label-free bio-layer interferometry assay on an OCTET® HTX biosensor platform (Pall FortéBio Corp., Menlo Park, CA). The experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. Binding studies were performed on human MSR1 extracellular domain expressed with a N-terminal nonahistidine tag (His9-hMSR1; R&D Systems, Cat #2708-MS), monkey MSR1 extracellular domain expressed with a N-terminal myc-myc-hexahistidine tag (HMM-mfMSR1; SEQ ID NO: 418), and mouse MSR1 extracellular domain expressed with a N-terminal nonahistidine tag (His9-mMSR1; R&D Systems, Cat #1797-MS). The anti-MSR1 monoclonal antibodies were captured by dipping either anti-human Fc (AHC) or anti-mouse Fc (AMC) Octet biosensors in wells containing 5 μg/mL or 10 μg/mL of anti-MSR1 monoclonal antibody for 45-90 seconds. The AHC captured anti-MSR1 monoclonal antibodies were then dipped in wells containing 50 nM of His9-mMSR1, while the AMC captured anti-MSR1 monoclonal antibodies were dipped in wells containing different concentrations of His9-hMSR1 or HMM-mfMSR1 (100 nM, 25 nM) or 100 nM His9-mMSR1. The binding of different MSR1 reagents to the captured anti-MSR1 monoclonal antibody was measured for 4 minutes and the dissociation of monoclonal antibody bound MSR1 reagent was monitored for 8-10 minutes in HBS-EBT buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60 * kd}$$

Binding kinetics parameters for His9-hMSR1, HMM-mfMSR1 or His9-mMSR1 binding to different anti-MSR1 monoclonal antibodies of the invention at 25° C. are shown in Tables 8 and 9.

TABLE 8

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-hMSR1 | 1.22E+05 | 1.16E−04 | 9.54E−10 | 100 |
| | HMM-mfMSR1 | 1.00E+05 | 1.46E−04 | 1.45E−09 | 79 |
| H2aM21229N | His9-hMSR1 | 3.00E+05 | 2.10E−04 | 7.00E−10 | 55 |
| | HMM-mfMSR1 | 1.35E+05 | 2.22E−03 | 1.64E−08 | 5 |
| H2aM21230N | His9-hMSR1 | 6.47E+05 | 2.87E−04 | 4.43E−10 | 40 |
| | HMM-mfMSR1 | 2.37E+05 | 3.76E−04 | 1.59E−09 | 31 |
| H2aM21232N | His9-hMSR1 | 1.30E+05 | 2.86E−04 | 2.20E−09 | 40 |
| | HMM-mfMSR1 | 9.75E+04 | 3.27E−04 | 3.35E−09 | 35 |
| H2aM21235N | His9-hMSR1 | 1.21E+05 | 4.58E−05 | 3.78E−10 | 252 |
| | HMM-mfMSR1 | 1.02E+05 | 6.27E−05 | 6.12E−10 | 184 |
| H2aM25700N | His9-hMSR1 | 5.58E+05 | 1.14E−04 | 2.05E−10 | 101 |
| | HMM-mfMSR1 | 5.53E+05 | 1.15E−04 | 2.08E−10 | 100 |
| H2aM25690N | His9-hMSR1 | 2.29E+05 | 3.11E−04 | 1.36E−09 | 37 |
| | HMM-mfMSR1 | 1.64E+05 | 5.47E−04 | 3.35E−09 | 21 |
| H2aM25695N | His9-hMSR1 | 3.60E+05 | 5.27E−04 | 1.46E−09 | 22 |
| | HMM-mfMSR1 | 3.12E+05 | 5.71E−04 | 1.83E−09 | 20 |
| H2aM25685N | His9-hMSR1 | 2.01E+05 | 3.97E−04 | 1.98E−09 | 29 |
| | HMM-mfMSR1 | 6.49E+04 | 1.28E−03 | 1.97E−08 | 9 |
| mIgG Isotype | His9-hMSR1 | NB$ | NB$ | NB$ | NB$ |
| Control | HMM-mfMSR1 | NB$ | NB$ | NB$ | NB$ |

$indicates that no binding was observed under the current experimental conditions.

TABLE 9

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-mMSR1 | NB$ | NB$ | NB$ | NB$ |
| H2aM21229N | His9-mMSR1 | NB$ | NB$ | NB$ | NB$ |
| H2aM21230N | His9-mMSR1 | NB$ | NB$ | NB$ | NB$ |
| H2aM21232N | His9-mMSR1 | NB$ | NB$ | NB$ | NB$ |
| H2aM21235N | His9-mMSR1 | NB$ | NB$ | NB$ | NB$ |
| H2aM25700N | His9-mMSR1 | 3.60E+04 | 1.85E−04 | 5.20E−09 | 63 |
| H2aM25690N | His9-mMSR1 | NB$ | NB$ | NB$ | NB$ |
| H2aM25695N | His9-mMSR1 | NB$ | NB$ | NB$ | NB$ |
| H2aM25685N | His9-mMSR1 | NB$ | NB$ | NB$ | NB$ |
| mIgG Isotype Control | His9-mMSR1 | NB$ | NB$ | NB$ | NB$ |
| H1H21227N-N297Q | His9-mMSR1 | 3.74E+05 | 7.08E−04 | 1.89E−09 | 16 |
| H1H21227N-N297D | His9-mMSR1 | 4.61E+05 | 7.86E−04 | 1.71E−09 | 15 |
| H1H21231N-N297Q | His9-mMSR1 | IC# | IC# | IC# | IC# |
| H1H21234N-N297Q | His9-mMSR1 | 3.82E+04 | 5.00E−05* | 1.31E−09 | 231 |
| H1H27729P N297Q | His9-mMSR1 | NB$ | NB$ | NB$ | NB$ |
| H1H27731P-N297Q | His9-mMSR1 | NB$ | NB$ | NB$ | NB$ |
| H1H27732P-N297Q | His9-mMSR1 | NB$ | NB$ | NB$ | NB$ |
| H1H27734P-N297Q | His9-mMSR1 | NB$ | NB$ | NB$ | NB$ |
| H1H27736P-N297Q | His9-mMSR1 | IC# | IC# | IC# | IC# |
| H1H27739P-N297Q | His9-mMSR1 | NB$ | NB$ | NB$ | NB$ |
| H1H27747P-N297Q | His9-mMSR1 | NB$ | NB$ | NB$ | NB$ |
| H1H27749P-N297Q | His9-mMSR1 | IC# | IC# | IC# | IC# |
| H1H27751P-N297Q | His9-mMSR1 | NB$ | NB$ | NB$ | NB$ |
| H1H27754P-N297Q | His9-mMSR1 | NB$ | NB$ | NB$ | NB$ |
| H1H27756P-N297Q | His9-mMSR1 | NB$ | NB$ | NB$ | NB$ |
| H1H27760P-N297Q | His9-mMSR1 | NB$ | NB$ | NB$ | NB$ |
| H1H27759P-N297Q | His9-mMSR1 | NB$ | NB$ | NB$ | NB$ |
| H1H27761P-N297Q | His9-mMSR1 | IC# | IC# | IC# | IC# |
| H1H27762P-N297Q | His9-mMSR1 | NB$ | NB$ | NB$ | NB$ |
| H1H27766P-N297Q | His9-mMSR1 | NB$ | NB$ | NB$ | NB$ |
| H1H27771P-N297Q | His9-mMSR1 | IC# | IC# | IC# | IC# |

TABLE 9-continued

| OCTET ® Binding Affinities of Anti-MSR1 mAbs at 25° C. Binding at 25° C./Antibody-Capture Format | | | | | |
|---|---|---|---|---|---|
| Antibody | Analyte | ka ($M^{-1}s^{-1}$) | kd ($s^{-1}$) | $K_D$ (Molar) | t½ (min) |
| H1H27773P-N297Q | His9-mMSR1 | NB$ | NB$ | NB$ | NB$ |
| H1H27778P-N297Q | His9-mMSR1 | NB$ | NB$ | NB$ | NB$ |
| H1H21234N | His9-mMSR1 | 4.60E+04 | 5.00E−05* | 1.09E−09 | 231 |
| H1H21231N | His9-mMSR1 | IC# | IC# | IC# | IC# |
| H1H21227N | His9-mMSR1 | 4.15E+05 | 8.16E−04 | 1.97E−09 | 14 |
| Non-binding Control | His9-mMSR1 | NB$ | NB$ | NB$ | NB$ |

*indicates that no dissociation of His9-mMSR1 was observed under the current experimental conditions and the $k_d$ value was manually fixed at 5.00E−05 while fitting the data $indicates that no binding was observed under the current experimental conditions.

#indicates that the binding data is inconclusive (IC)

The anti-MSR1 monoclonal antibodies bound to His9-hMSR1 with $K_D$ values ranging from 205 pM to 2.2 nM, as shown in Table 8. The anti-MSR1 monoclonal antibodies bound to HMM-mfMSR1 with $K_D$ values ranging from 208 pM to 19.7 nM, as shown in Table 8.

As shown in Table 9, 23 out of 35 anti-MSR1 monoclonal antibodies did not bind to His9-mMSR1, while the binding data for 6 anti-MSR1 monoclonal antibodies was inconclusive. Six (6) out of 35 anti-MSR1 monoclonal antibodies bound to His9-mMSR1 with $K_D$ values ranging from 1.09 nM to 5.2 nM, as shown in Table 9.

Example 5. Anti-MSR1 Antibodies Display Specific Binding to Cell Surface-Expressed Human and Monkey MSR1

The ability of anti-MSR1 monoclonal antibodies to bind to human or monkey MSR1 expressing cells was determined using electrochemiluminescence (ECL) based detection.

Generation of MSR1-expressing cell lines. Two cell lines overexpressing either human or monkey MSR1 were generated. To generate the human MSR1 overexpressing cell line, human embryonic kidney (HEK) 293 cells were engineered by transduction with hygromycin resistant lentiviral vector encoding full length human MSR1 (hMSR1, amino acids M1-L451 of accession number NP_619729.1) with a C-terminal Myc tag. The resulting cell line is referred to as HEK293.Myc.hMSR1. Similarly, to generate the monkey MSR1 overexpressing cell line, HEK293 cells were engineered by transfection with the geneticin resistant expression plasmid encoding full length monkey MSR1 (*Macaca fascicularis*, mfMSR1, amino acids M1-L451 of accession number XP_005562705.1). The resulting cell line is referred to as HEK293.mfMSR1 cells. To measure the ability of antibodies to bind to endogenously expressed human MSR1, THP-1 human monocytic cells were treated with 200 nM of phorbol 12-myristate 13-acetate (PMA; Sigma, Cat #P8139) for 72 hours to induce high MSR1 expression prior to antibody binding. Non-transfected HEK293 cells were included as non-specific binding controls as they have no detectable expression of MSR1 by next-generation sequencing of gene expression (data not shown).

Antibody binding assay. To perform the antibody binding assay, cells from each of the cell lines described above were rinsed once in PBS buffer without $Ca^{2+}/Mg^{2+}$ and incubated for 5 minutes at 37° C. with Enzyme Free Cell Dissociation Solution (Millipore, Cat. #S-004-C, Burlington, MA) to detach cells from a flask. All cells were washed once with 1×PBS with $Ca^{2+}/Mg^{2+}$ and counted with a Cellometer™ Auto T4 cell counter (Nexcelom Bioscience). Approximately $1.0\times10^4$ cells were seeded separately onto 96-well carbon electrode plates [MULTI-ARRAY high bind plate, Meso Scale Diagnostics] and incubated for 1 hour at 37° C. Non-specific binding sites were then blocked by 2% BSA (w/v) in PBS with $Ca^{2+}/Mg^{2+}$ for 1 hour at room temperature. THP-1 cells were pre-incubated for 0.5 hours at room temperature in sample dilution buffer with: 1) 1 mg/mL Fc receptor block reagents to block Fc gamma receptors on THP-1 cell surface [whole molecule human IgG (Jackson Immunoresearch, Cat #009-000-003) for wells being tested with anti-MSR1-mFc antibodies or 2) whole molecule mIgG (Jackson Immunoresearch, Cat #015-000-003) for wells being tested with anti-MSR1-hFc antibodies. Antibody binding on HEK293.Myc.hMSR1, HEK293.mfMSR1 and HEK293 cells was tested without Fc receptor block reagents. To the plate-bound HEK293.Myc.hMSR1, HEK293.mfMSR1 and HEK293 cells or THP-1+Fc block, solutions of anti-MSR1 or control antibodies in serial dilutions ranging from 1.7 pM to 100 nM, and solutions without the presence of antibodies were added in duplicate, and the plates were incubated for 1 hour at room temperature. Plates were then washed to remove unbound antibodies an AquaMax2000 plate washer with a cell washing head (MDS Analytical Technologies). The plate-bound antibodies were detected with either a SULFO-TAG™-conjugated goat polyclonal anti-human IgG antibody specific for Fcγ fragment (Jackson Immunoresearch, Cat #109-005-098) or a SULFO-TAG™-conjugated goat polyclonal anti-mouse IgG antibody specific for Fcγ fragment (Jackson Immunoresearch, Cat #115-005-164) for 1 hour at room temperature. Plates were washed and developed with Read Buffer (Meso Scale Diagnostics, Cat #R92TD-2) according to manufacturer's recommended procedure and luminescent signals were recorded with a SECTOR Imager 600 (Meso Scale Diagnostics). Luminescence intensity, measured in relative light units (RLU), was recorded to indicate the binding intensity of each antibody at the range of concentrations. The ratio of signal detected for cell-surface binding of each anti-MSR antibody compared to isotype control antibody (both at 11 nM) was reported as an indication of specificity of MSR1 binding. Antibodies with the binding ratio on MSR-1 expressing cells of greater than or equal to 2-fold compared to the ratio on parental HEK293 cells were classified as specific binders. Antibodies with a binding ratio of less than 2-fold compared to the ratio on parental HEK293 cells were classified as non-binders as shown in. (See Table 10).

TABLE 10

Binding of Anti-MSR1 Antibodies to MSR1-Expressing Cells

| Antibody | Ratio of 11 nM Antibody Binding Signal (RLU) on MSR1-expressing cells and parental HEK293 to isotype control | | | |
|---|---|---|---|---|
| | HEK293.Myc.h MSR1 | PMA-treated THP-1 | HEK293.m fMSR1 | HEK293 |
| Specific Human and monkey MSR1 binders | | | | |
| H1H21227N-N297Q | 37 | 5 | 23 | 1 |
| H1H21227N-N297D | 34 | 6 | 25 | 1 |
| H1H21227N | 37 | 7 | 26 | 1 |
| H1H21231N-N297Q | 64 | 45 | 69 | 4 |
| H1H21231N | 61 | 42 | 75 | <1 |
| H1H21234N-N297Q | 43 | 25 | 35 | 9 |
| H1H21234N | 32 | 18 | 31 | 3 |
| H1H27729P-N297Q | 17 | 8 | 6 | 3 |
| H1H27731P-N297Q | 48 | 38 | 43 | 7 |
| H1H27732P-N297Q | 72 | 56 | 46 | 6 |
| H1H27734P-N297Q | 40 | 21 | 28 | 14 |
| H1H27736P-N297Q | 58 | 48 | 45 | 12 |
| H1H27739P-N297Q | 22 | 9 | 20 | 1 |
| H1H27747P-N297Q | 26 | 13 | 21 | 5 |
| H1H27749P-N297Q | 27 | 33 | 24 | 3 |
| H1H27751P-N297Q | 63 | 54 | 49 | 15 |
| H1H27754P-N297Q | 55 | 66 | 53 | 18 |
| H1H27756P-N297Q | 38 | 21 | 20 | 6 |
| H1H27759P2-N297Q | 23 | 9 | 25 | 2 |
| H1H27760P2-N297Q | 29 | 15 | 25 | 3 |
| H1H27761P2-N297Q | 23 | 10 | 15 | 3 |
| H1H27762P2-N297Q | 33 | 11 | 25 | 3 |
| H1H27771P2-N297Q | 42 | 21 | 7 | 2 |
| H1H27773P2-N297Q | 5 | 3 | 10 | 2 |
| H1H27778P2-N297Q | 51 | 32 | 29 | 4 |
| H1xH27759P2 | 22 | 6 | 21 | <1 |
| H1xH29283P2 | 26 | 9 | 24 | 1 |
| H2aM25685N | 75 | 11 | 25 | 2 |
| H2aM25690N | 166 | 25 | 77 | 5 |
| H2aM25695N | 35 | 8 | 45 | 5 |
| H2aM25700N | 46 | 3 | 39 | 1 |
| H2aM21228N | 66 | 16 | 60 | 2 |
| H2aM21230N | 78 | 21 | 55 | 5 |
| H2aM21232N | 86 | 21 | 51 | 1 |
| H2aM21235N | 68 | 20 | 40 | 6 |
| Specific Human MSR1 only binders | | | | |
| H2aM21229N | 78 | 56 | 27 | 36 |
| H1xH29282P2 | 9 | 3 | 1 | <1 |
| H1H27766P2-N297Q | 20 | 9 | 13 | 8 |
| Non-specific binder | | | | |
| H1xH29273P2 | 20 | 24 | 27 | |
| Isotype controls | | | | |
| hIgG1 Isotype Control | 1 | 1 | 1 | 1 |
| mIgG Isotype Control | 1 | 1 | 1 | 1 |

As illustrated in Table 10, thirty-eight of thirty-nine tested anti-MSR1 antibodies bound specifically to HEK293.Myc.hMSR1 cells with binding ratios ranging from 5- to 166-fold above isotype control at 11 nM anti-MSR1 antibody concentration. Thirty-three of these anti-MSR1 antibodies specifically bound to THP-1 cells endogenously expressing human MSR1 after PMA cell differentiation with cell binding ratios ranging from 3- to 66-fold above isotype control at 11 nM. Thirty-five anti-MSR1 antibodies that bound to engineered hMSR1 cells also bound specifically to mfMSR1 engineered cells with cell binding ratios ranging from 6- to 77-fold above isotype control at 11 nM. Twelve anti-MSR1 antibodies (H1H21234N-N297Q, H1H27731P-N297Q, H1H27732P-N297Q, H1H27734P-N297Q, H1H27736P-N297Q, H1H27751P-N297Q, H1H27754P-N297Q, H1H27756P-N297Q, H2aM25695N, H2aM21235N, H2aM21229N, H1H27766P2-N297Q) bound to parental HEK293 cells with ratios 5-fold or greater above isotype control. Anti-MSR1 antibodies produced with a human IgG1 containing a N297Q or a N297D single point mutation bound cells comparable to their corresponding unmodified parental antibodies.

One anti-MSR1 antibody, H1xH29273P2, was characterized as a non-specific binder, as it bound to MSR1 cells with ratios less than 2 compared to the HEK293 cells at 11 nM antibody concentration. The hlgG1 and mlgG1 isotype controls were not specific, as expected.

Example 6. Relative Binding of Anti-MSR1 Antibodies to Cell Surface-Expressed Mouse MSR1

Relative cell surface binding of the anti-MSR1 antibodies to mouse MSR1 expressing cells was determined by flow cytometry using MSR1 positive RAW264.7 cells (ATCC, Catalog #TIB-71) and MSR1 negative B16F10.9 cells (Lin et al. 1998. PNAS 95:8829-8834). For the assay, cells were plated in PBS without calcium and magnesium (VWR Cat #45000-446) and 2% FBS (Saradigm Cat #1500-500) (Staining Buffer) in 96 well V-bottom plates (Axygen Scientific, Cat #P-96-450-V-C-S). To block binding to Fc receptors, RAW264.7 cells were incubated for 30 minutes at 4° C. with 500 μg/mL mouse IgG (Jackson ImmunoResearch, Cat #015-000-003) diluted in staining buffer, while B16F10.9 cells remained in staining buffer. Following Fc receptor blocking, 10 μg/mL of anti-MSR1 antibodies or an isotype control antibody were added to the cells and were subsequently incubated for 30 minutes on ice. For a positive control, a commercial anti-mouse MSR1 (Sino Biological, Cat #50129-R004) antibody was used, while a rabbit IgG antibody (Thermo Scientific, Cat #26102) was used as a negative control. The cells were then washed once with staining buffer and were incubated with either an APC conjugated anti-human Fc secondary antibody (Jackson ImmunoResearch, Cat #109-136-170) or an Alexa-Flour 647 conjugated anti-rabbit Fc secondary antibody [Jackson ImmunoResearch Cat #111-606-046] at 10 μg/mL for 30 minutes at 4° C. Cells were subsequently washed and fixed using a 50% solution of Cytofix (BD Biosciences, Cat #554655) diluted in PBS. Samples were run on the Beckman Coulter Cytoflex and results were analyzed in Flowjo 10.2 software (BD) to calculate the mean fluorescent intensity (MFI; Table 11). The signal to noise (S/N) was determined by calculating the ratio of the anti-MSR1 antibodies or the control antibodies MFI to the unstained sample MFI (Table 11).

TABLE 11

Binding of Anti-MSR1 Antibodies to RAW264.7 Cells (Flow Cytometry)

| Antibody | RAW264.7 MFI | B16F10.9 MFI | RAW264.7 S/N | B16F10.9 S/N |
|---|---|---|---|---|
| Unstained | 2524 | 3657 | 1 | 1 |
| Anti-human IgG secondary antibody only | 3095 | 3174 | 1 | 1 |
| Non-binding control | 3402 | 3829 | 1 | 1 |
| H1H21227N-N297Q | 12810 | 3287 | 5 | 1 |
| H1H21231N-N297Q | 3582 | 3374 | 1 | 1 |
| H1H21234N-N297Q | 7052 | 3499 | 3 | 1 |
| Anti-mouse MSR antibody | 245149 | 6161 | 97 | 2 |
| Anti-rabbit IgG secondary antibody only | 8720 | 5389 | 3 | 1 |
| H1H27729P-N297Q | 3484 | 3459 | 1 | 1 |
| H1H27731P-N297Q | 3510 | 3688 | 1 | 1 |
| H1H27732P-N297Q | 3425 | 3730 | 1 | 1 |
| H1H27734P-N297Q | 4783 | 4505 | 1 | 1 |
| H1H27736P-N297Q | 3554 | 3759 | 1 | 1 |
| H1H27739P-N297Q | 3271 | 3580 | 1 | 1 |
| H1H27747P-N297Q | 3630 | 3875 | 1 | 1 |
| H1H27749P-N297Q | 3789 | 3693 | 1 | 1 |
| H1H27751P-N297Q | 3823 | 4992 | 1 | 1 |
| H1H27754P-N297Q | 5406 | 4091 | 1 | 1 |
| H1H27756P-N297Q | 4573 | 3782 | 1 | 1 |

TABLE 11-continued

Binding of Anti-MSR1 Antibodies to RAW264.7 Cells (Flow Cytometry)

| Antibody | RAW264.7 MFI | B16F10.9 MFI | RAW264.7 S/N | B16F10.9 S/N |
|---|---|---|---|---|
| H1H27759P-N297Q | 3288 | 3425 | 1 | 1 |
| H1H27760P-N297Q | 3429 | 3521 | 1 | 1 |
| H1H27761P-N297Q | 3837 | 3734 | 1 | 1 |
| H1H27762P-N297Q | 3519 | 3608 | 1 | 1 |
| H1H27766P-N297Q | 3812 | 3793 | 1 | 1 |
| H1H27771P-N297Q | 4055 | 3865 | 1 | 1 |
| H1H27773P-N297Q | 3367 | 3735 | 1 | 1 |
| H1H27778P-N297Q | 3648 | 4138 | 1 | 1 |

As illustrated in Table 11, two anti-MSR1 antibodies (H1H21227N-N297Q and H1H21234N-N297Q) bound weakly to RAW264.7 cells with S/N values of 5 and 3, respectively. The non-binding control antibody did not bind RAW264.7 cells. None of the 22 anti-MSR1 antibodies bound to B16F10.9 cells. A reference positive control (mouse MSR1/CD204 antibody, Sino Biological, Cat. #50129-R004) bound Raw 264.7 cells with a S/N of 97.

Example 7. Anti-MSR1 Antibodies Bind to Distinct Epitopes on MSR1 Receptor/Cross-Competition Between Anti-MSR1 Antibodies Binding competition between different anti-MSR1 antibodies was assessed using a real time, label-free bio-layer interferometry assay on an OCTET® HTX biosensor platform (Pall FortéBio Corp., Menlo Park, CA). The experiment was performed at 25° C. in 10 mM HEPES, 150 mM NaCl, 3 mM EDTA, 0.05% v/v Surfactant Tween-20, and 1 mg/mL BSA, pH 7.4 (HBS-EBT) buffer with the plate shaking at the speed of 1000 rpm.

To assess whether different antibodies are able to compete with one another for binding to their respective epitopes on the recombinant human MSR1 extracellular domain expressed with a N-terminal nonahistidine tag (His9-hMSR1; R&D Systems, Cat #2708-MS), around 0.59-0.79 nM of His9-hMSR1 was first captured onto anti-Penta-His antibody coated OCTET® biosensor tips (Pall FortéBio Corp., #18-5122) by submerging the biosensor tips for 45 seconds into wells containing a 20 μg/mL solution of His9-hMSR1. The antigen-captured biosensor tips were then saturated with a first anti-MSR1 monoclonal antibody (subsequently referred to as "mAb-1") by immersion into wells containing a 50 μg/mL solution of mAb-1 for 4 minutes. The biosensor tips were then submerged into wells containing a 50 μg/mL solution of a second anti-MSR1 monoclonal antibody (subsequently referred to as "mAb-2") for 4 minutes. All of the biosensor tips were washed in HBS-EBT buffer in between each step of the experiment. The real-time binding response was monitored during the course of the experiment and the binding response at the end of each step was recorded. The response of mAb-2 binding to His9-hMSR1 pre-complexed with mAb-1 was compared, and the competitive/non-competitive behavior of the different anti-MSR1 monoclonal antibodies was determined using a 50% inhibition threshold. Table 12 explicitly defines the relationships of antibodies competing in both directions, independent of the order of binding.

TABLE 12

Cross-competition of Anti-MSR1 Antibodies for Binding to His9-hMSR1

| First mAb (mAb-1) Captured using Anti-Penta-His Octet Biosensors | mAb-2 antibodies which Compete with mAb-1 | First mAb (mAb-1) Captured using Anti-Penta-His Octet Biosensors | mAb-2 antibodies which Compete with mAb-1 |
|---|---|---|---|
| H1H27756P-N297Q | H1H21231N | H1H27751P-N297Q | H1H21234N-N297Q |
| | H1H27760P-N297Q | | H1H27734P-N297Q |
| | H1H27762P-N297Q | | H1H27732P-N297Q |
| | H1H21231N-N297Q | | H1H27731P-N297Q |
| | H1H27747P-N297Q | | H1H27754P-N297Q |
| | H1H27749P-N297Q | | H1H27766P-N297Q |
| H1H21231N | H1H27756P-N297Q | | H1H21227N-N297D |
| | H1H27760P-N297Q | H1H27732P-N297Q | H1H27734P-N297Q |
| | H1H27762P-N297Q | | H1H27751P-N297Q |
| | H1H21231N-N297Q | | H1H27731P-N297Q |
| | H1H27747P-N297Q | | H1H27754P-N297Q |
| | H1H27749P-N297Q | H1H27731P-N297Q | H1H27734P-N297Q |
| H1H27760P-N297Q | H1H27756P-N297Q | | H1H27751P-N297Q |
| | H1H21231N | | H1H27732P-N297Q |
| | H1H27762P-N297Q | | H1H27754P-N297Q |
| | H1H21231N-N297Q | H1H27754P-N297Q | H1H27734P-N297Q |
| | H1H27747P-N297Q | | H1H27751P-N297Q |
| | H1H27749P-N297Q | | H1H27732P-N297Q |
| H1H27762P-N297Q | H1H27756P-N297Q | | H1H27731P-N297Q |
| | H1H21231N | H1H27761P-N297Q | H1H27736P-N297Q |
| | H1H27760P-N297Q | | H1H27771P-N297Q |
| | H1H21231N-N297Q | | H1H27778P-N297Q |
| | H1H27747P-N297Q | | H1H27773P-N297Q |
| | H1H27749P-N297Q | | H1H27739P-N297Q |
| | H1H27766P-N297Q | H1H27736P-N297Q | H1H27761P-N297Q |
| H1H21231N-N297Q | H1H27756P-N297Q | | H1H27771P-N297Q |
| | H1H21231N | | H1H27778P-N297Q |
| | H1H27760P-N297Q | | H1H27759P-N297Q |
| | H1H27762P-N297Q | | H1H27773P-N297Q |
| | H1H27747P-N297Q | | H1H27773P-N297Q |
| | H1H27749P-N297Q | H1H27771P-N297Q | H1H27761P-N297Q |
| H1H27747P-N297Q | H1H27760P-N297Q | | H1H27736P-N297Q |
| | H1H27762P-N297Q | | H1H27778P-N297Q |
| | H1H21231N-N297Q | | H1H27759P-N297Q |
| H1H27749P-N297Q | H1H27760P-N297Q | | H1H27773P-N297Q |
| | H1H27762P-N297Q | | H1H27739P-N297Q |
| | H1H21231N-N297Q | H1H27778P-N297Q | H1H27761P-N297Q |
| H1H21234N-N297Q | H1H21234N | | H1H27736P-N297Q |
| H1H21234N | H1H21234N-N297Q | | H1H27771P-N297Q |
| H1H27734P-N297Q | H1H21234N-N297Q | | H1H27759P-N297Q |
| | H1H27751P-N297Q | | H1H27773P-N297Q |
| | H1H27732P-N297Q | | H1H27739P-N297Q |
| | H1H27731P-N297Q | H1H27759P-N297Q | H1H27736P-N297Q |
| | H1H27754P-N297Q | | H1H27771P-N297Q |
| | H1H27766P-N297Q | | H1H27778P-N297Q |
| | H1H21227N-N297D | | H1H27773P-N297Q |
| H1H27766P-N297Q | No mAb* | | H1H27739P-N297Q |
| H1H21227N-N297D | H1H21234N-N297Q | H1H27773P-N297Q | H1H27749P-N297Q |
| | H1H21234N | | H1H27766P-N297Q |
| | H1H27766P-N297Q | | H1H21227N-N297D |
| H1H27739P-N297Q | H1H27759P-N297Q | H1H27729P-N297Q | Data Inconclusive** |
| H1H21227N | Data Inconclusive** | H1H21227N-N297Q | Data Inconclusive** |

*Does not cross compete with any other mAb for binding to MSR1 when captured as 'mAb-1'

**mAb failed to saturate MSR1 surface or did not bind to MSR1 surface

Example 8. Ligand Uptake of Anti-MSR1 Antibodies

MSR1 can binds and internalize chemically modified or altered polyanionic molecules, including modified low density lipoproteins (LDL) (Platt, N. and S. Gordon. 2001. J C/in Invest. 108(5):649-654). A bioassay was generated to assess the ability of the exemplary anti-MSR1 antibodies to regulate the uptake of certain MSR1 ligands.

Generation of MSR1-expressing cell lines for assay. Human embryonic kidney cells (HEK293) were transduced to stably express human MSR1 (amino acids 1-451 of UniProtKB accession number NP_619729.1) with a C-terminal Myc tag. The resulting cell line, referred to here as "HEK293.Myc.hMSR1", was selected and maintained in DMEM containing 10% FIBS, NEAA, penicillin/streptomycin, L-glutamine, and 100 μg/mL hygromycin.

Ligand uptake assay. For the bioassay, HEK293.Myc.hMSR1 cells were plated onto 96-well poly-D-lysine-coated assay plates (Greiner Bio One, Cat #655946) at 20,000 cells per well in Opti-MEM containing 0.1% FBS, penicillin/streptomycin, and L-Glutamine (assay media) and incubated at 37° C. in 5% $CO_2$ overnight. The following day, antibodies were serially diluted from 300 nM to 5.08 pM (1:3 serial dilution) and pre-incubated with the cells, along with a negative control consisting of assay media alone, for 30 minutes at 37° C. in 5% $CO_2$. After 30 minutes, either oxidized or acetylated low-density lipoprotein (LDL) labeled with 1,1'dioctadecyl-3,3,3',3'-tetramethylindocarbocyanine perchlorate (referred to as "Dil-OxLDL" or "Dil-AcLDL," respectively) was added to the cells at a constant concentration of 10 μg/mL. To determine the dose response of ligand uptake, Dil-OxLDL or Dil-AcLDL was serially diluted from 25 μg/mL to 24.4 μg/mL (plus assay media alone without LDL) and added to cells not with antibodies. After an overnight incubation at 37° C. in 5% $CO_2$, cells were fixed with BD CytoFix™ (BD Biosciences, Cat #554655) for 2 hours at 4° C., and ligand uptake was evaluated using a Flexstation3 plate reader (Molecular Devices) with excitation at 514 nm and emission at 565 nm. Results were analyzed using nonlinear regression (4-parameter logistics) with the Prism 7 program to obtain $EC_{50}$ and $IC_{50}$ values. The percentage of inhibition was calculated with the Relative Fluorescent Unit (RFU) values by using the following equation:

$$\text{Max \% Inhibition} = 100 \times \frac{RLU_{Baseline} - RLU_{Inhibition}}{RLU_{Baseline} - RLU_{Background}}$$

In the equation, "$RFU_{Baseline}$" is the fluorescence value from the cells treated with 10 μg/mL ligand without antibodies, "$RFU_{Inhibition}$" is the minimum fluorescence value with for a particular antibody with 10 μg/mL ligand, and "$RFU_{Background}$" is the fluorescence value from cells without any ligand or antibodies. The results and calculated values of the ligand uptake assay are provided in Table 13.

TABLE 13

Antibody Inhibition of Dil-OxLDL and Dil-AcLDL Uptake in HEK293.Myc.hMSR1 Cells

| | | Dil-Oxidized LDL | | Dil-Acetylated LDL | |
|---|---|---|---|---|---|
| Row | Antibodies | % Inhibition | $IC_{50}$ (M) | % Inhibition | $IC_{50}$ (M) |
| 1 | H2aM21227N | 90 | 3.1E−09 | 62 | 3.7E−09 |
| 2 | H2aM21228N | 79 | 3.1E−09 | 10 | >1.0E−07 |
| 3 | H2aM21229N | 26 | >1.0E−07 | no inhibition | no inhibition |
| 4 | H2aM21230N | 70 | 2.3E−09 | 47 | >1.0E−08 |
| 5 | H1M21231N | 79 | 3.7E−09 | 50 | >2.0E−08 |
| 6 | H2aM21232N | 79 | 4.8E−09 | 54 | >1.0E−08 |
| 7 | H2bM21234N | 61 | 4.5E−09 | 19 | 1.8E−09 |
| 8 | H2aM21235N | 64 | 3.2E−09 | 24 | >1.0E−07 |
| 9 | Mouse IgG2a Isotype control mAb 1 | no inhibition | no inhibition | no inhibition | no inhibition |
| 10 | Mouse IgG1 Isotype control mAb | no inhibition | no inhibition | no inhibition | no inhibition |
| 11 | H2aM25685N | 43 | >1.0E−07 | 22 | >1.0E−07 |
| 12 | H2aM25690N | 83 | 1.7E−09 | 53 | 2.1E−09 |
| 13 | H2aM25695N | 69 | >1.6E−08 | 40 | >1.7E−07 |
| 14 | H2aM25700N | 91 | 2.2E−09 | 79 | 2.4E−09 |
| 15 | Mouse IgG2a isotype control mAb 2 | no inhibition | no inhibition | no inhibition | no inhibition |
| 16 | H1H21227N-N297Q | 94 | 1.8E−09 | 65 | 2.4E−09 |
| 17 | H1H21231N-N297Q | 88 | 3.7E−09 | 62 | 3.7E−09 |
| 18 | H1H21234N-N297Q | 52 | 6.1E−09 | 34 | 1.3E−09 |
| 19 | H1H21227N | 89 | 2.0E−09 | 65 | 2.1E−09 |
| 20 | H1H21231N | 78 | 3.6E−09 | 63 | 3.5E−09 |
| 21 | H1H21234N | 64 | 4.3E−09 | 36 | 7.1E−10 |
| 22 | H1H27729P-N297Q | no inhibition | no inhibition | 28 | 1.2E−09 |
| 23 | H1H27731P-N297Q | 62 | >1.0E−08 | 37 | 1.8E−09 |
| 24 | H1H27732P-N297Q | 86 | 1.7E−09 | 62 | 2.2E−09 |
| 25 | H1H27734P-N297Q | 22 | 5.5E−09 | no inhibition | no inhibition |
| 26 | H1H27736P-N297Q | 83 | 3.2E−09 | 49 | 3.4E−09 |
| 27 | H1H27739P-N297Q | 55 | >1.0E−07 | no inhibition | no inhibition |
| 28 | H1H27747P-N297Q | 42 | >1.0E−07 | 26 | >1.0E−07 |
| 29 | H1H27749P-N297Q | 42 | 1.7E−09 | 35 | 4.2E−10 |
| 30 | H1H27751P-N297Q | 85 | 2.9E−09 | 59 | 1.6E−09 |
| 31 | H1H27754P-N297Q | 73 | 4.6E−09 | 38 | 1.8E−09 |
| 32 | H1H27756P-N297Q | 76 | 3.4E−09 | 42 | >1.0E−07 |
| 33 | H1H27759P-N297Q | 74 | >1.0E−08 | 48 | >1.0E−07 |
| 34 | H1H27760P-N297Q | 70 | 4.9E−09 | 46 | 2.6E−09 |
| 35 | H1H27761P-N297Q | 43 | 9.5E−09 | 29 | >1.0E−07 |
| 36 | H1H27762P-N297Q | 78 | 4.0E−09 | 38 | 2.9E−09 |
| 37 | H1H27766P-N297Q | 72 | 3.7E−09 | 38 | 3.5E−09 |
| 38 | H1H27771P-N297Q | 73 | 3.0E−09 | 49 | 1.9E−09 |
| 39 | H1H27773P-N297Q | 41 | >1.0E−07 | 31 | >1.0E−07 |
| 40 | H1H27778P-N297Q | 88 | 2.2E−09 | 54 | 1.5E−09 |
| 41 | Human IgG1-N297Q, Isotype Control mAb | no inhibition | no inhibition | no inhibition | no inhibition |
| 42 | Human IgG1 Isotype Control mAb | no inhibition | no inhibition | no inhibition | no inhibition |

Suitable antibody candidates illustrate relatively efficient inhibition (e.g., an $IC_{50}$ value of less than about 10 nM). In some embodiments, suitable antibody candidates also illustrate less than about 65% maximum inhibition of ligand uptake.

As shown in Table 13 (rows 1-10), eight antibodies showed inhibition of Dil-OxLDL uptake on the HEK293.Myc.hMSR1 cells with maximum inhibition ranging from 26% to 90% and $IC_{50}$ values ranging from 2.3 nM to >100 nM. Seven of the 8 antibodies showed inhibition of Dil-AcLDL uptake with maximum inhibition ranging from 10% to 62% and $IC_{50}$ values ranging from 1.8 nM to >100 nM. Antibody H2aM21229N showed no inhibition of Dil-AcLDL uptake.

As shown in Table 13 (rows 11-15), four antibodies showed inhibition of MSR1-mediated Dil-OxLDL uptake with maximum inhibition ranging from 43% to 91% and $IC_{50}$ values ranging from 1.7 nM to >100 nM. Four antibodies of the invention showed inhibition of MSR1-mediated Dil-AcLDL uptake with maximum inhibition ranging from 22% to 79% and $IC_{50}$ values ranging from 2.1 nM to >100 nM.

As shown in Table 13 (rows 16-42), twenty-four out of 25 antibodies showed inhibition of MSR1-mediated uptake of Dil-OxLDL with maximum inhibition ranging from 22% to 94% and $IC_{50}$ values ranging from 1.7 nM to >100 nM. Twenty-three of the 25 antibodies showed inhibition of Dil-AcLDL uptake with maximum inhibition ranging from 26% to 65% and $IC_{50}$ values ranging from 0.42 nM to >100 nM. Antibody H1H27729P-N297Q showed no inhibition of Dil-OxLDL uptake while antibodies H1H27739P-N297Q and H1H27734P-N297Q showed no inhibition of Dil-AcLDL uptake on HEK293.Myc.hMSR1 cells.

Human and mouse Isotype control antibodies did not show inhibition of Dil-OxLDL and Dil-AcLDL uptake by HEK293.Myc.hMSR1 cells in any of the assays.

Example 9. Binding and Internalization of Cell-Surface Expressed MSR1 by Anti-MSR1 Antibodies Exemplary anti-MSR1 antibodies were assessed for their ability to bind and internalize MSR1 on MSR1-expressing cells.

For the assay, THP-1 cells [ATCC, Cat #TIB-202] were seeded into 96 well PDL coated plates (Perkin Elmer, Cat #6055500) in RPMI (Irvine Scientific, Cat #9160) containing 10% FBS (ATCC, Cat #30-2020), pencillin/streptomycin/L-glutamine (Gibco, Cat #10378-016), 50 μM Beta-Mercaptoethanol (Sigma, Cat #M7522) (growth media) plus 200 nM Phorbol Myristate Acetate (PMA; Sigma, Cat #P1585). The THP-1 cells were allowed to differentiate for 4 days at 37° C. in 5% $CO_2$. To stain, quadruplicate plates of cells were incubated with 10 μg/mL of anti-MSR1 antibodies diluted in 2% FBS in PBS, without Calcium and Magnesium (Irving, Cat #9240) (staining buffer) for 30 minutes at 4° C. Cells were washed twice with staining buffer incubated with an Alexa-Flour 488 conjugated secondary Ab (Jackson Immunoresearch, Cat #115-547-003 or Jackson Immunoresearch, Cat #109-547-003) at 10 μg/mL for 30 minutes at 4° C., and subsequently washed twice more with staining buffer. Two plates were immediately fixed and stained with 4% paraformaldehyde (PFA; ThermoFisher, Cat #28908)+5 μM DRAQ5 (ThermoFisher, Cat #62251) in PBS for 20 minutes (non-internalization plates). The remaining two plates were incubated at 37° C. for 1 hour followed by fixation and staining for 20 minutes using a solution of 4% PFA+5 μM DRAQ5 diluted in PBS (internalization plates). After fixation, all plates were washed once with PBS. One non-internalization plate and one internalization plate were incubated with an anti-Alexa Fluor 488 antibody (Regeneron) at 50 μg/mL in PBS overnight at 4° C. to quench surface Alexa Fluor 488 fluorescence. The remaining plates were incubated with PBS only. Confocal images were acquired on the Opera Phenix (Perkin Elmer) at 40× magnification. Harmony analysis software (Perkin Elmer) was utilized to identify DRAQ5-labeled cells and the total Alexa-Fluor 488 relative fluorescent units (RFU) per cell was determined. The total binding at 4° C. (RFU values of 4° C. unquenched wells), total binding at 37° C. (RFU values of 37° C. unquenched wells), the total internalized RFU, and % Internalization were determined for each antibody as shown in Table 14.

For all calculations, background fluorescence from unstained wells was subtracted from every well. Total internalized RFU was calculated as follows: Total RFU of 37° C. unquenched samples−Surface RFU at 37° C. Surface RFU is defined as unquenched RFU at 37° C.−quenched RFU at 37° C.)/QE. QE (quenching efficiency) is defined as: 1−(Total RFU of 4° C. quenched sample/Total RFU of 4° C. unquenched sample). The % Internalization was determined from the following formula: (Total internalized RFU at 37° C./Total RFU at 37° C.)*100.

TABLE 14

Internalization and Surface Binding of Anti-MSR1 Antibodies in Differentiated THP-1 Cells

| Antibody | Total Binding at 4° C. | Total Binding at 37° C. | Total Internalized RFU | % Internalization |
|---|---|---|---|---|
| H1H27729P-N297Q | 1930685 | 6607625 | 3763127 | 57.0 |
| H1H27731P-N297Q | 1215319 | 1802404 | 977543 | 54.2 |
| H1H27732P-N297Q | 2513511 | 4924734 | 2414132 | 49.0 |
| H1H27734P-N297Q | 482859 | 1151348 | 737425 | ND* |
| H1H27736P-N297Q | 9514681 | 12267400 | 14468087 | 117.9** |
| H1H27739P-N297Q | 3702857 | 5608380 | 4016378 | 71.6 |
| H1H27747P-N297Q | 2518361 | 5917858 | 3444330 | 58.2 |
| H1H27749P-N297Q | 4478384 | 12799899 | 5704834 | 44.6 |
| H1H27751P-N297Q | 5831744 | 7998767 | 6787876 | 84.9 |
| H1H27754P-N297Q | 3077308 | 7161570 | 6446236 | 90.0 |
| H1H27756P-N297Q | 6691792 | 11904608 | 9039171 | 75.9 |
| H1H27759P-N297Q | 4028970 | 2480463 | 1861578 | 75.0 |
| H1H27760P-N297Q | 1297337 | 6011876 | 3707164 | 61.7 |
| H1H27761P-N297Q | 1940392 | 2764577 | 1625899 | 58.8 |
| H1H27762P-N297Q | 2529645 | 3856573 | 3767717 | 97.7 |
| H1H27766P-N297Q | 1877240 | 3224247 | 2062539 | 64.0 |
| H1H27771P-N297Q | 6272656 | 7535203 | 6991358 | 92.8 |
| H1H27773P-N297Q | 490905 | 962752 | −67811 | ND* |
| H1H27778P-N297Q | 9910952 | 16552831 | 12518725 | 75.6 |
| H1H21227N-N297Q | 1800012 | 4110990 | 3226161 | 78.5 |
| H1H21234N-N297Q | 1953248 | 5451125 | 722651 | 13.3 |
| Isotype control | 185971 | 1087469 | 1704047 | ND* |

ND*: % internalization could not be determined due to weak binding and/or inability to determine quenching efficiency

**A % internalized value >100% is due to the total internalized values being slightly higher than total values at 37° C. An internalization of 100% was confirmed visually by the appearance of all Alex488 fluorescence into vesicular structures at 37° C.

As shown in Table 14, 19 of 21 assayed anti-MSR1 antibodies demonstrated internalization into differentiated THP-1 cells ranging from 13.3% to 117.9% internalization. For two of the 21 anti-MSR1 antibodies, internalization could not be determined due to weak binding and/or inability to determine quenching efficiency. As a control, the isotype control did not demonstrate any measurable internalization.

Example 10. Assessing Blocking Ability of Anti-MSR1 Antibodies for Human MSR1

The ability of anti-MSR1 antibodies disclosed herein to block the binding of various ligands to human MSR1 was measured using three competition sandwich ELISA assays. The ligands used in the assays were: (1) acetylated LDL (Ac-LDL), (2) oxidized LDL (Ox-LDL), and (3) advanced glycation end-products of bovine serum albumin (AGE-BSA).

For the assay, recombinant monomeric human MSR1 protein comprised of a portion of the human MSR1 extracellular domain expressed with a N-terminal 9-Histidine tag (His9-hMSR1; R&D Systems, Cat #2708-MS) was coated at a concentration of 2 μg/mL in PBS on a 96-well microtiter plate overnight at 4° C. for use in competition ELISA assays with Ac-LDL, Ox-LDL, or biotinylated-AGE-BSA ("biot-AGE-BSA"). Nonspecific binding sites were subsequently blocked using a 0.5% (w/v) solution of bovine serum albumin (BSA) in phosphate-buffered saline (PBS). Anti-MSR1 antibodies or isotype control antibodies were serially diluted as appropriate for each tested ligand and added in duplicate for each serial dilution set to microtiter plates coated with His9-hMSR1. Buffer alone was also added to wells on each coat. After 1 hour incubation at room temperature, without wash, a final constant concentration of 50 pM Ac-LDL (Life Technologies/ThermoFisher Scientific, Cat #L-35354), 5 nM or 10 nM Ox-LDL (Alfa Aesar, Cat #J65591), or 400 pM biot-AGE-BSA (R&D Systems, Cat #BT4127) were added to plates with His9-hMSR1, and the plates were incubated for an additional 1 hour at room temperature. (Concentrations of Ac-LDL, Ox-LDL and biot-AGE-BSA for antibody inhibition assays were selected from the approximate midway point within the linear portion of individual binding curves of Ac-LDL, Ox-LDL or biot-AGE-BSA to plate-coated His9-hMSR1.) Wells were washed, and plate-bound Ac-LDL or Ox-LDL were detected with anti-LDL rabbit antibody (Alfa Aesar, Cat #J64398) in combination with anti-rabbit IgG (H+L) specific donkey polyclonal antibodies conjugated with horseradish peroxidase (HRP) (JacksonImmunoResearch, Cat #711-035-152) and biot-AGE-BSA was detected with a streptavidin-HRP (ThermoFisher Scientific, Cat #N200). Plates were developed using TMB substrate solution (BD Biosciences, Cat #51-2606KC & Cat #51-2607KC) according to manufacturer's recommendation and absorbance at 450 nm was measured on a Victor™ Multilabel Plate Reader (PerkinElmer™). This assay was conducted in four different assay runs.

Data analysis was performed using a sigmoidal dose-response model within Prism™ software (GraphPad). Percent blockade at maximum concentration of the antibody tested in each assay was calculated as an indicator of the ability of the antibodies to block the binding of Ac-LDL, Ox-LDL or biot-AGE-BSA to His9-hMSR1 on the plate relative to the baseline of the assay. In the calculation, binding signal of the same concentrations of Ac-LDL, Ox-LDL, or biot-AGE-BSA used for the assays in the absence of antibody was referenced as 100% binding or 0% blocking, while the baseline of the assay, defined as binding signal of the sample of buffer without MSR1 ligands or antibody, was referenced as 0% binding or 100% blocking. The maximum percent blockade at the highest concentration of antibody tested in each assay are reported for all antibodies. Negative percent blockade numbers reflected higher MSR1 ligands binding to plate coated His9-hMSR1 in the presence of antibodies. The blocking results are summarized in Table 15.

TABLE 15

Blocking Ability of Anti-MSR1 Antibodies in Competition ELISA Assays

| | anti-MSR1 antibody blocking of Ox-LDL binding to His9-hMSR1 | | | Anti-MSR1 antibody (100 nM) blocking of Ac-LDL | Anti-MSR1 antibody (300 nM) blocking of biot-AGE-BSA binding to His9- |
|---|---|---|---|---|---|
| Antibody | anti-MSR1 antibody concentration | Ox-LDL concentration | % Blocking | binding to His9-hMSR1 % Blocking | hMSR1 % Blocking |
| Blocked > 50% in all assay formats | | | | | |
| H2aM25700N | 500 nM | 10 nM | 98 | 104 | 101 |
| H1H21227N-N297Q | 500 nM | 10 nM | 97 | 105 | 96 |
| H1H21227N-N297D | 500 nM | 10 nM | 99 | 101 | 97 |
| H1H21227N | 500 nM | 10 nM | 100 | 105 | 99 |
| Blocked > 50% in some assay formats | | | | | |
| H2aM25695N | 500 nM | 10 nM | 96 | 65 | 16 |
| H1H27766P2-N297Q | 1 μM | 10 nM | 54 | 52 | 27 |
| H1H21234N-N297Q | 500 nM | 10 nM | 49 | 75 | −27 |
| H1H21234N | 500 nM | 10 nM | 98 | 70 | 21 |
| Blocked < 50% in all assay formats | | | | | |
| H2aM21228N | 500 nM | 5 nM | 41 | −32 | −1 |
| H2aM21229N | 500 nM | 5 nM | 38 | −11 | 3 |
| H2aM21230N | 500 nM | 5 nM | 45 | −14 | 9 |
| H2aM21232N | 500 nM | 5 nM | 16 | 25 | −50 |

TABLE 15-continued

Blocking Ability of Anti-MSR1 Antibodies in Competition ELISA Assays

| Antibody | anti-MSR1 antibody blocking of Ox-LDL binding to His9-hMSR1: anti-MSR1 antibody concentration | Ox-LDL concentration | % Blocking | Anti-MSR1 antibody (100 nM) blocking of Ac-LDL binding to His9-hMSR1 % Blocking | Anti-MSR1 antibody (300 nM) blocking of biot-AGE-BSA binding to His9-hMSR1 % Blocking |
|---|---|---|---|---|---|
| H2aM21235N | 500 nM | 5 nM | −4 | 24 | −24 |
| H2aM25685N | 500 nM | 10 nM | 28 | −33 | −86 |
| H2aM25690N | 500 nM | 10 nM | 8 | −76 | −96 |
| H1H21231N-N297Q | 500 nM | 10 nM | 26 | −60 | −50 |
| H1H21231N | 500 nM | 10 nM | 22 | −62 | −44 |
| H1H27729P-N297Q | 1 μM | 10 nM | 36 | 8 | 15 |
| H1H27731P-N297Q | 1 μM | 10 nM | −1 | −41 | 4 |
| H1H27732P-N297Q | 1 μM | 10 nM | −60 | −61 | −9 |
| H1H27734P-N297Q | 1 μM | 10 nM | −15 | −38 | −4 |
| H1H27736P-N297Q | 1 μM | 10 nM | 3 | −31 | −3 |
| H1H27739P-N297Q | 1 μM | 10 nM | −41 | −47 | −9 |
| H1H27747P-N297Q | 1 μM | 10 nM | −31 | −44 | −2 |
| H1H27749P-N297Q | 1 μM | 10 nM | −21 | −51 | −1 |
| H1H27751P-N297Q | 1 μM | 10 nM | −31 | −51 | −11 |
| H1H27754P-N297Q | 1 μM | 10 nM | −44 | −42 | −9 |
| H1H27756P-N297Q | 1 μM | 10 nM | −45 | −54 | −8 |
| H1H27759P2-N297Q | 1 μM | 10 nM | −62 | −45 | −19 |
| H1H27760P2-N297Q | 1 μM | 10 nM | −47 | −43 | −4 |
| H1H27761P2-N297Q | 1 μM | 10 nM | −21 | −36 | −4 |
| H1H27762P2-N297Q | 1 μM | 10 nM | −65 | −58 | −16 |
| H1H27771P2-N297Q | 1 μM | 10 nM | −23 | −21 | −1 |
| H1H27773P2-N297Q | 1 μM | 10 nM | 2 | −11 | 1 |
| H1H27778P2-N297Q | 1 μM | 10 nM | −59 | −40 | −8 |
| Isotype control antibodies | | | | | |
| hIgG1 isotype control | 1 μM | 10 nM | 3 | −8 | 4 |
| mIgG1 isotype control | 1 μM | 10 nM | 16 | −4 | 7 |

Four of 35 assayed anti-MSR1 antibodies were identified as blocking >50% of Ac-LDL, Ox-LDL, and biot-AGE-BSA binding to hMSR1. These four anti-MSR1 antibodies blocked greater than 95% of 50 pM Ac-LDL, 10 nM Ox-LDL and 400 pM biot-AGE-BSA binding to His9-hMSR1.

At the maximum concentration of antibody tested, four of the 35 anti-MSR1 antibodies blocked >50% Ac-LDL and/or Ox-LDL binding to hMSR1 but did not block biot-AGE-BSA binding to hMSR1. Three of these antibodies blocked both 50 pM Ac-LDL and 10 nM Ox-LDL binding to hMSR1 with 52% to 98% blockade. One antibody (H1H21234N-N297Q) blocked only 50 pM Ac-LDL binding to hMSR1 with 75% blockade.

Twenty-seven (27) of the 35 anti-MSR1 antibodies and the irrelevant isotype control antibodies blocked <50% of Ac-LDL, Ox-LDL, and biot-AGE-BSA binding to hMSR1.

Three anti-MSR1 antibodies (21227N, 21231N, 21234N) were produced both with the original human Fcγ portion and a version with a N297Q single point mutation. The 21227N antibody was also produced as a third version with a N297D mutation. The modified versions of 21227N (H1H21227N-N297Q and H1H21227N-N297D) and 21231N (H1H21231N-N297Q) anti-MSR1 antibodies retained parental characteristics. Antibodies H1H21227N-N297Q and H1H21227N-N297D blocked >50% of Ac-LDL, Ox-LDL, and biot-AGE-BSA binding to hMSR1, while antibody H1H21231N-N297Q blocked <50% of Ac-LDL, Ox-LDL, and biot-AGE-BSA binding to hMSR1. Anti-MSR1 modified antibody H1H21234N-N297Q blocked only 50 pM Ac-LDL binding to hMSR1 in comparison to unmodified H1H21234N antibody, which blocked >50% for both Ac-LDL and Ox-LDL binding to hMSR1.

Example 11. Synthesis of Payload P1 and P2B (FIG. 1)

Methyl (1S,4aS,10aR)-6-hydroxy-1,4a-dimethyl-1,2,3,4,4a,9,10,10a-octahydrophenanthrene-1-carboxylate (P1-2)

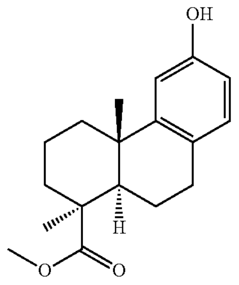 [SMILES: COC(=O)[C@@]1(C)CCC[C@]2(C)c3cc(O)ccc3CC[C@@H]12]

To a solution of podocarpic acid (P1-1, 90 g, 0.33 mol) in methanol (200 mL) and toluene (600 mL) was added with (trimethylsilyl)diazomethane (2 M in hexane, 200 mL). The reaction mixture was stirred at room temperature for 2 hours. The podocarpic acid was then totally consumed according to LCMS. The volatiles were removed in vacuo, and the residue was triturated from petroleum ether (2 L) to give compound P1-2 (91 g, 96% yield) as a white solid. ESI m/z: 289 $(M+H)^+$. $^1H$ NMR (400 MHz, $DMSO_{d6}$) δ 8.95 (s, 1H), 6.79 (d, J=8.2 Hz, 1H), 6.63 (d, J=2.4 Hz, 1H), 6.48 (dd, J=8.2, 2.4 Hz, 1H), 3.58 (s, 3H), 2.80-2.55 (m, 2H), 2.20-2.02 (m, 3H), 1.96-1.71 (m, 2H), 1.56-1.45 (m, 2H), 1.27 (t, J=13.5 Hz, 1H), 1.21 (s, 3H), 1.09 (td, J=13.5, 4.1 Hz, 1H), 0.91 (s, 3H) ppm.

Methyl (1S,4aS,10aR)-1,4a-dimethyl-6-(trifluoromethanesulfonyloxy)-1,2,3,4,4a,9,10,10a-octahydrophenanthrene-1-carboxylate (P1-3)

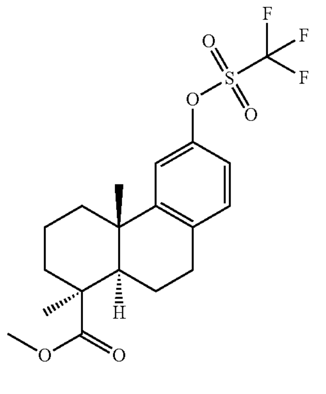 [SMILES: COC(=O)[C@@]1(C)CCC[C@]2(C)c3cc(OS(=O)(=O)C(F)(F)F)ccc3CC[C@@H]12]

To a solution of compound P1-2 (10 g, 35 mmol) in methylene chloride (200 mL) were added pyridine (3.3 g, 42 mmol) and DMAP (0.84 g, 6.9 mmol) under nitrogen atmosphere. The mixture was cooled to −78° C. and was added triflic anhydride (12 g, 42 mmol), and the resulting mixture was allowed to warm to 25° C. and stirred at 25° C. for another 4 hours. The reaction mixture was diluted with DCM (500 mL), washed with water (100 mL), aq. hydrochloride (1 N, 150 mL) and brine (100 mL), dried over sodium sulfate and concentrated in vacuo to give crude compound P1-3 (14 g, 97% crude yield) as viscous oil, which was pure enough for the next step. The crude compound P1-3 could be purified by flash chromatography (0-10% ethyl acetate in petroleum ether) to give pure product as viscous oil. ESI m/z: 421.2 $(M+1)^+$. $^1H$ NMR (400 MHz, $CDCl_3$) δ 7.12 (d, J=2.5 Hz, 1H), 7.10 (d, J=8.5 Hz, 1H), 6.97 (dd, J=8.5, 2.5 Hz, 1H), 3.67 (s, J=3.4 Hz, 3H), 2.93 (dd, J=17.2, 4.4 Hz, 1H), 2.85-2.71 (m, 1H), 2.29 (d, J=13.5 Hz, 1H), 2.25-2.14 (m, 2H), 2.03-1.89 (m, 2H), 1.71-1.61 (m, 1H), 1.56-1.48 (m, 1H), 1.40 (td, J=13.4, 4.2 Hz, 1H), 1.30-1.22 (m, 3H), 1.09 (td, J=13.6, 4.2 Hz, 1H), 1.02 (s, 3H) ppm.

Methyl (1S,4aS,10aR)-6-((tert-butoxycarbonyl)amino)-1,4a-dimethyl-1,2,3,4,4a,9,10,10a-octahydrophenanthrene-1-carboxylate (P1-4)

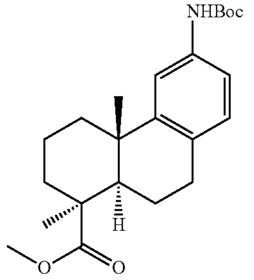 [SMILES: COC(=O)[C@@]1(C)CCC[C@]2(C)c3cc(NC(=O)OC(C)(C)C)ccc3CC[C@@H]12]

To a solution of compound P1-3 (14 g, 34 mmol) and tert-butyl carbamate ($BocNH_2$, 7.9 g, 68 mmol) in tert-butanol (100 mL) were added, successively cesium carbonate (22 g, 68 mmol), tris(dibenzylideneacetone)dipalladium (0) ($Pd_2(dba)_3$, 1.8 g, 2.0 mmol) and X-Phos (1.8 g, 4.0 mmol) at room temperature. The mixture was de-gassed and purged with argon three times and was then stirred at 80° C. under argon (balloon) overnight until compound P1-3 was totally consumed, as monitored by TLC. After cooling to room temperature, the reaction mixture was diluted with ethyl acetate and filtered through Celite. The solid was washed with ethyl acetate for 3 times. The combined filtrate was concentrated in vacuo and the residue was purified by silica gel column chromatography (0-6.25% ethyl acetate in petroleum ether) to give compound P1-4 (11 g, 82% yield) as a white solid. ESI m/z: 410 $(M+23)^+$. $^1H$ NMR (500 MHz, $DMSO_{d6}$) δ 9.07 (s, 1H), 7.39 (s, 1H), 7.13 (d, J=8.5 Hz, 1H), 6.87 (d, J=8.3 Hz, 1H), 3.59 (s, 3H), 2.76 (dd, J=16.4, 4.5 Hz, 1H), 2.70-2.61 (m, 1H), 2.16-2.05 (m, 3H), 2.00-1.75 (m, 2H), 1.65-1.50 (m, 2H), 1.45 (s, 9H), 1.31-1.25 (m, 1H), 1.21 (s, 3H), 1.10 (td, J=13.5, 4.1 Hz, 1H), 0.92 (s, 3H) ppm.

(1S,4aS,10aR)-6-{[(tert-Butoxy)carbonyl]amino}-1,4a-dimethyl-1,2,3,4,4a,9,10,10a-octahydro-phenanthrene-1-carboxylic acid (P1-5)

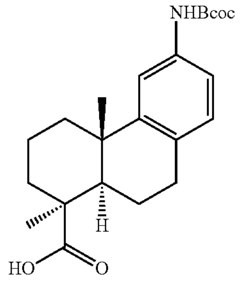

To a solution of compound P1-4 (4.9 g, 13 mmol) in DMSO was added potassium tert-butoxide (15 g, 0.13 mol) in one portion at room temperature. The reaction mixture was stirred at 60° C. for 3 hours under argon until the reaction was completed according to LCMS. After cooling to room temperature, the reaction mixture was poured into ice and acidified slowly with aq. hydrochloride (0.5 M) to pH 5, during which the temperature did not exceed 25° C. The precipitates were collected by filtration and washed with water several times. The crude product was further purified by silica gel column chromatography (0-20% ethyl acetate in petroleum ether) to give compound P1-5 (4.5 g, 93% yield) as a white solid. ESI m/z: 318 $(M-55)^+$. $^1H$ NMR (500 MHz, $DMSO_{d6}$) δ 12.08 (s, 1H), 9.08 (s, 1H), 7.40 (s, 1H), 7.11 (s, 1H), 6.87 (d, J=8.3 Hz, 1H), 2.79-2.68 (m, 1H), 2.65 (d, J=12.6 Hz, 1H), 2.17-2.03 (m, 4H), 1.94-1.76 (m, 2H), 1.53 (d, J=13.7 Hz, 1H), 1.46 (d, J=7.4 Hz, 9H), 1.29-1.14 (m, 5H), 1.04 (s, 3H) ppm.

tert-Butyl N-[(4bS,8S,8aR)-8-carbamoyl-4b,8-dimethyl-4b,5,6,7,8,8a,9,10-octahydrophenanthren-3-yl] carbamate (P1-6)

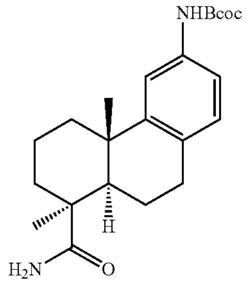

To a solution of P1-5 (4.5 g, 12 mmol) and HATU (4.9 g, 13 mmol) in DMF (50 mL) was added diisopropylethylamine (20 mL, 0.12 mol), and the mixture was stirred at 25° C. for an hour. To the mixture was then added ammonium chloride (16 g, 0.30 mol) and the mixture was stirred at room temperature overnight. The resulting mixture was diluted with ethyl acetate, washed with water and brine, dried over sodium sulfate and concentrated in vacuo. The residue was purified by flash chromatography (0-20% ethyl acetate in petroleum ether) to give compound P1-6 (4.2 g, 94% yield) as a white solid. ESI m/z: 373.3 $(M+1)^+$. $^1H$ NMR (500 MHz, $methanol_{d4}$) δ7.20 (s, 1H), 6.97 (d, J=7.7 Hz, 1H), 6.80 (d, J=8.3 Hz, 1H), 2.77-2.68 (m, 2H), 2.66-2.55 (m, 1H), 2.20 (d, J=12.9 Hz, 1H), 2.13 (dd, J=13.2, 5.3 Hz, 1H), 2.08 (d, J=14.0 Hz, 1H), 2.03-1.86 (m, 2H), 1.54 (d, J=11.1 Hz, 1H), 1.40 (s, 9H), 1.26 (t, J=26.7 Hz, 1H), 1.18 (s, 3H), 1.14-1.03 (m, 4H) ppm.

Methyl (1S,4aS,10aR)-6-amino-1,4a-dimethyl-1,2,3,4,4a,9,10,10a-octahydrophenanthrene-1-carboxylate trifluoroacetic acid salt (P1-7)

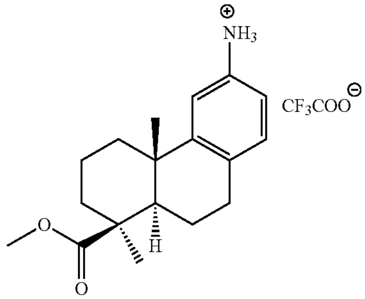

To a solution of compound P1-4 (6.0 g, 15 mmol) in DCM (60 mL) was added TFA (12 mL) at RT. The resulting mixture was stirred at RT for 2 h until Boc was totally removed, as monitored by TLC. The reaction mixture was concentrated in vacuo to give crude compound P1-7 as a TFA salt, which was used in the next step without further purification. ESI m/z: 288 $(M+1)^+$.

Methyl (1S,4aS,10aR)-6-(benzyloxy)-1,4a-dimethyl-1,2,3,4,4a,9,10,10a-octahydrophenanthrene-1-carboxylate (P1-8a)

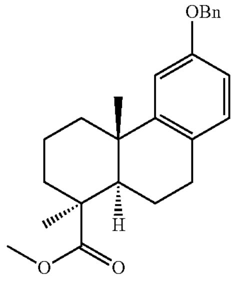 [SMILES: COC(=O)[C@@]1(C)CCC[C@]2(C)c3cc(OCc4ccccc4)ccc3CC[C@@H]12]

A mixture of compound P1-2 (12 g, 40 mmol) and cesium carbonate (14 g, 44 mmol) in DMF (100 mL) was stirred at 20-25° C. for 15 minutes. To the mixture was added benzyl bromide (7.1 mL, 60 mmol) at room temperature. After stirring at room temperature for 4 hours, the resulting mixture was poured into cold water and extracted with ethyl acetate. The combined organic solution was washed with water and brine, dried over sodium sulfate and concentrated in vacuo. The crude product was purified by flash chromatography (0-10% ethyl acetate in petroleum ether) to give the title compound P1-8a (13 g, 89% yield) as a white solid. ESI m/z: 379 $(M+H)^+$. $^1H$ NMR (500 MHz, $methanol_{d4}$) δ 7.60-7.20 (m, 5H), 7.00-6.82 (m, 2H), 6.73 (d, J=7.1 Hz, 1H), 5.03 (s, 2H), 3.66 (s, 3H), 2.95-2.58 (m, 2H), 2.36-2.10 (m, 3H), 2.10-1.85 (m, 2H), 1.70-1.48 (m, 2H), 1.44-1.21 (m, 4H), 1.15 (t, J=17.2 Hz, 1H), 1.01 (s, 3H) ppm.

Methyl (1S,4aS,10aR)-6-(dibenzylamino)-1,4a-dimethyl-1,2,3,4,4a,9,10,10a-octahydrophenanthrene-1-carboxylate (8b)

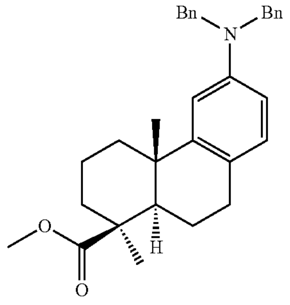 [SMILES: COC(=O)[C@@]1(C)CCC[C@]2(C)c3cc(N(Cc4ccccc4)Cc4ccccc4)ccc3CC[C@@H]12]

To a solution of the crude compound P1-7 obtained above (calc. 15 mmol) in DMF (60 mL) were added potassium carbonate (6.4 g, 46 mmol) and benzylbromide (5.8 g, 34 mmol) at RT. The reaction mixture was stirred at 80° C. overnight until the reaction was complete as monitored by TLC. After cooling to RT, the mixture was poured into cold water (300 mL) and extracted with ethyl acetate (×3). The combined organic solution was washed with water and brine, dried over sodium sulfate, and concentrated in vacuo to give crude product 8b, which was used in the next step without further purification. ESI m/z: 468 (M+1)$^+$.

1S,4aS,10aR)-6-(Benzyloxy)-1,4a-dimethyl-1,2,3,4,4a,9,10,10a-octahydrophenanthrene-1-carboxylic acid (P1-9a)

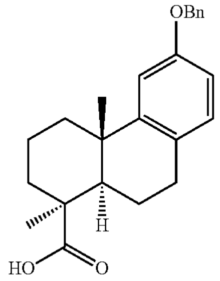 [SMILES: C[C@]1(C(=O)O)CCC[C@]2(C)c3cc(OCc4ccccc4)ccc3CC[C@@H]12]

A mixture of compound P1-8a (11 g, 29 mmol) and potassium tert-butoxide (33 g, 0.29 mol) in DMSO (0.19 L) was stirred at 100° C. for an hour until the methyl group was totally removed, as monitored by LCMS and TLC. After cooling to 25° C., the mixture was quenched with aqueous hydrochloride (1 N) and extracted with ethyl acetate. The combined organic solution was washed with brine, dried over sodium sulfate and concentrated in vacuo. The residue was purified by silica gel column chromatography (0-24% ethyl acetate in petroleum ether) to give compound P1-9a (7.5 g, 71% yield) as a white solid. ESI m/z: 365 (M+H)$^+$. 1H NMR (500 MHz, methanol$_{d4}$) δ 7.42 (d, J=7.4 Hz, 2H), 7.36 (t, J=7.5 Hz, 2H), 7.30 (t, J=7.3 Hz, 1H), 6.92 (d, J=8.4 Hz, 1H), 6.87 (d, J=2.5 Hz, 1H), 6.72 (dd, J=8.4, 2.5 Hz, 1H), 5.02 (s, 2H), 2.82 (dd, J=16.3, 4.4 Hz, 1H), 2.77-2.65 (m, 1H), 2.24 (d, J=13.2 Hz, 2H), 2.19 (dd, J=13.8, 6.0 Hz, 1H), 2.11-1.96 (m, 2H), 1.64-1.56 (m, 1H), 1.53 (d, J=11.0 Hz, 1H), 1.35 (td, J=13.3, 3.7 Hz, 1H), 1.30 (s, 3H), 1.13 (s, 3H), 1.11-1.05 (m, 1H) ppm.

(1S,4aS,10aR)-6-(Dibenzylamino)-1,4a-dimethyl-1,2,3,4,4a,9,10,10a-octahydrophenanthrene-1-carboxylic acid (9b)

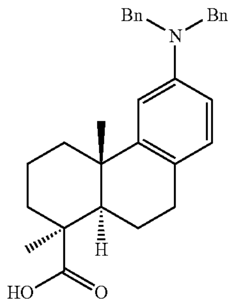 [SMILES: C[C@]1(C(=O)O)CCC[C@]2(C)c3cc(N(Cc4ccccc4)Cc4ccccc4)ccc3CC[C@@H]12]

To a solution of the crude compound 8b obtained above (calc. 15 mmol) in DMSO (100 mL) was added potassium tert-butoxide (17 g, 0.15 mol) in one portion at RT. The reaction mixture was stirred at 100° C. for 2 h under argon until the reaction was complete according to LCMS. After cooling to RT, the reaction mixture was poured into ice and acidified slowly with aq. hydrochloride (4 M) to pH 5, during which the temperature was not allowed to reach higher than 25° C. The mixture was extracted with ethyl acetate and the combined organic solution was washed with water and brine, dried over sodium sulfate, and concentrated in vacuo. The crude product was purified by silica gel column chromatography (0-20% ethyl acetate in petroleum ether) to give compound 9b (6.8 g, 99% yield in 3 steps from compound P1-4) as a white solid. ESI m/z: 454 (M+1)$^+$.

Pentafluorophenyl (1S,4aS,10aR)-6-(benzyloxy)-1,4a-dimethyl-1,2,3,4,4a,9,10,10a-octahydrophenanthrene-1-carboxylate (P1-10a)

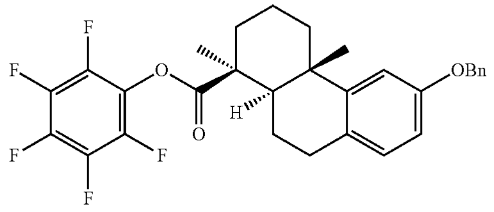 [SMILES: C[C@]1(C(=O)Oc2c(F)c(F)c(F)c(F)c2F)CCC[C@]2(C)c3cc(OCc4ccccc4)ccc3CC[C@@H]12]

To a solution of P1-9a (9.6 g, 26 mmol) in DMF (100 mL) was added DIPEA (14 mL, 79 mmol), and perfluorophenyl 2,2,2-trifluoroacetate (15 g, 53 mmol). This mixture was stirred at room temperature overnight and monitored by LCMS. The reaction mixture was then diluted with ether (200 mL) and washed with water (300 mL) and brine (200 mL). The organic solution was dried over sodium sulfate, and concentrated in vacuo. The residue was purified by flash chromatography (0-10% ethyl acetate in petroleum ether) to give compound P1-10a (12 g, 88% yield) as a white solid. ESI m/z: 531 (M+H)$^+$. $^1$H NMR (500 MHz, DMSO$_{d6}$) δ 7.43 (d, J=7.1 Hz, 2H), 7.38 (t, J=7.4 Hz, 2H), 7.31 (t, J=7.2 Hz, 1H), 6.93 (dd, J=10.2, 5.5 Hz, 2H), 6.76 (dd, J=8.4, 2.5 Hz, 1H), 5.05 (s, 2H), 2.81 (dd, J=16.3, 4.5 Hz, 1H), 2.77-2.68 (m, 1H), 2.28-2.19 (m, 2H), 2.18 (dd, J=13.4, 5.6

Hz, 1H), 2.00-1.83 (m, 2H), 1.74 (d, J=11.8 Hz, 1H), 1.65 (d, J=14.1 Hz, 1H), 1.47 (s, 3H), 1.38-1.27 (m, 2H), 1.08 (s, 3H) ppm.

Pentafluorophenyl (1S,4aS,10aR)-6-(dibenzylamino)-1,4a-dimethyl-1,2,3,4,4a,9,10,10a-octahydrophenanthrene-1-carboxylate (10b)

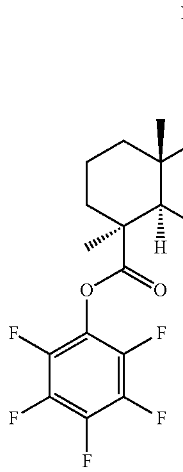

To a solution of 9b (6.8 g, 15 mmol) in DMF (100 mL) was added DIPEA (10 mL, 0.61 mol), and perfluorophenyl 2,2,2-trifluoroacetate (10 mL, 58 mmol). This mixture was stirred at 25° C. overnight under nitrogen, and was then diluted with ether. The organics were washed with water and brine, dried over sodium sulfate, and concentrated in vacuo. The residue was purified by silica gel column chromatography (0-10% ethyl acetate in petroleum ether) to give compound 10b (7.5 g, 81% yield) as a white solid. ESI m/z: 620 $(M+1)^+$. $^1$H NMR (400 MHz, $CDCl_3$) δ 7.36-7.25 (m, 10H), 6.92 (d, J=8.4 Hz, 1H), 6.67 (d, J=2.8 Hz, 1H), 6.63 (dd, J=8.4, 2.6 Hz, 1H), 4.63 (m, 4H), 2.85-2.73 (m, 2H), 2.41-2.37 (m, 1H), 2.22-2.20 (m, 1H), 2.15-1.91 (m, 3H), 1.71-1.65 (m, 2H), 1.51 (s, 3H), 1.37-1.19 (m, 2H), 1.10 (s, 3H) ppm.

tert-Butyl N-[(4bS,8S,8aR)-8-({[(1S,4aS,10aR)-6-(benzyloxy)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P1-11a)

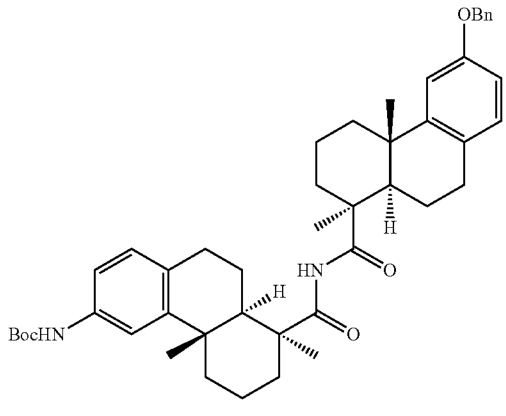 [SMILES: CC(C)(C)OC(=O)Nc1ccc2c(c1)[C@@]1(C)CCC[C@](C)(C(=O)NC(=O)[C@@]3(C)CCC[C@]4(C)c5cc(OCc6ccccc6)ccc5CC[C@@H]34)[C@@H]1CC2]

To a solution of compound P1-6 (2.3 g, 6.2 mmol) in THF (20 mL) was added dropwise n-BuLi (2.5 M in hexane, 5.5 mL, 14 mmol) at −78° C. The reaction was stirred at this temperature for 1 hour. To the mixture was added a solution of P1-10a (3.0 g, 5.6 mmol) in THF (20 mL), and the resulting mixture was then stirred at 10-20° C. overnight until compound P1-10a was consumed, as monitored by LCMS. The reaction was quenched with sat. aq. ammonium chloride and extracted with ethyl acetate. The combined organic solution was washed with water and brine, dried over sodium sulfate and concentrated in vacuo. The residue was purified by flash chromatography (0-30% ethyl acetate in petroleum ether) to give compound P1-11a (1.59 g, 51% yield) as a white solid. ESI m/z: 719 $(M+1)^+$.

(Compared with the procedure of 11b below, n-BuLi was used here instead of LiHMDS. Although P1-6 was not completely consumed, this procedure led to less side-product and the yield of P1-11a was increased from ca. 40% to 51%. The unreacted compound P1-6 was recovered (recovered yield: 10-20%).

tert-Butyl N-[(4bS,8S,8aR)-8-({[(1S,4aS,10aR)-6-(dibenzylamino)-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (11b)

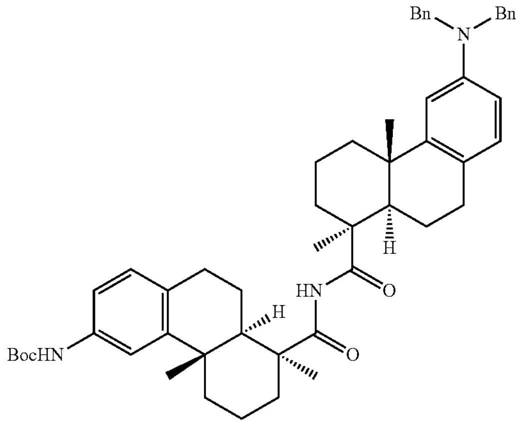 [SMILES: CC(C)(C)OC(=O)Nc1ccc2c(c1)[C@@]1(C)CCC[C@](C)(C(=O)NC(=O)[C@@]3(C)CCC[C@]4(C)c5cc(N(Cc6ccccc6)Cc6ccccc6)ccc5CC[C@@H]34)[C@@H]1CC2]

To a solution of compound P1-6 (1 g, 2.7 mmol) in THF (15 mL) was added dropwise lithium bis(trimethylsilyl) amide (1 M in hexane, 8.0 mL) at 0° C. The reaction was stirred at 0° C. for an hour. To the mixture was added a solution of compound 10b (2.5 g, 4.0 mmol) in THF (10 mL), and the resulting mixture was then stirred at RT overnight. The reaction was then quenched with sat. aq. ammonium chloride and extracted with ethyl acetate. The combined organic solution was washed with water and brine, dried over sodium sulfate, and concentrated in vacuo. The residue was purified by flash chromatography (0-35% ethyl acetate in petroleum ether) to give compound 11b (0.95 g, 44% yield) as a white solid; and recovered compound P1-6 (recovered yield 37%). ESI m/z: 808 $(M+1)^+$. $^1$H NMR (400 MHz, $CDCl_3$) δ 8.16 (s, 1H), 7.35-7.24 (m, 10H), 7.12 (d, J=8 Hz, 1H), 7.00 (d, J=8.4 Hz, 1H), 6.91 (d, J=8.4 Hz, 1H), 6.62-6.59 (m, 2H), 6.42 (s, 1H), 4.62 (s, 3H), 2.98-2.75 (m, 4H), 2.31-2.22 (m, 5H), 2.10-1.97 (m, 5H), 1.69-1.63 (m, 4H), 1.56 (s, 9H), 1.32-1.27 (m, 9H), 1.43-1.27 (m, 5H), 1.05 (s, 3H) ppm.

tert-Butyl N-[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (P1-12a)

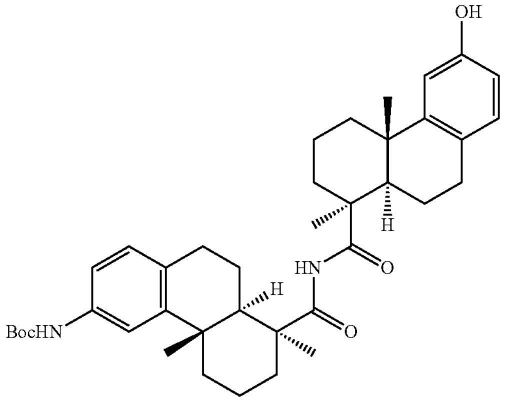 [SMILES: CC(C)(C)OC(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of P1-11a (2.0 g, 2.78 mmol) in ethyl acetate (40 mL) was added wet palladium on carbon (10% Pd, 0.9 g) under nitrogen protection. The mixture was degassed and purged with hydrogen and stirred at room temperature under hydrogen balloon overnight until P1-11a was totally consumed, which was monitored by LCMS. The mixture was filtered through Celite and the filtration was concentrated in vacuo. The residue was purified by silica gel column chromatography (0-55% ethyl acetate in petroleum ether) to give P1-12a (1.06 g, 61% yield) as a white solid. ESI m/z: 629 $(M+H)^+$. $^1$H NMR (500 MHz, $DMSO_{d6}$) δ 9.10 (s, 1H), 8.98 (s, 1H), 8.11 (s, 1H), 7.40 (s, 1H), 7.15 (d, J=7.5 Hz, 1H), 6.90 (d, J=8.4 Hz, 1H), 6.81 (d, J=8.3 Hz, 1H), 6.63 (d, J=2.3 Hz, 1H), 6.50 (dd, J=8.2, 2.4 Hz, 1H), 2.84 (td, J=16.3, 3.8 Hz, 2H), 2.77-2.64 (m, 2H), 2.30-2.22 (m, 2H), 2.14 (t, J=10.9 Hz, 4H), 2.00-1.80 (m, 4H), 1.65-1.54 (m, 4H), 1.45 (s, 9H), 1.34-1.28 (m, 2H), 1.27 (d, J=2.5 Hz, 6H), 1.15-1.08 (m, 2H), 0.99 (s, 6H) ppm.

tert-Butyl N-[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate (12b)

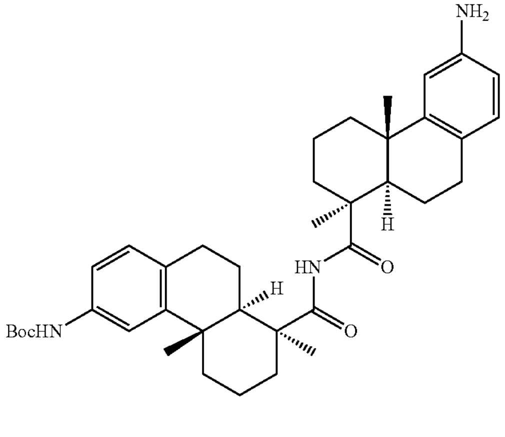 [SMILES: CC(C)(C)OC(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

To a solution of 11b (0.45 g, 0.56 mmol) in ethyl acetate (5 mL) was added wet palladium on carbon (10% Pd, 50 mg) under nitrogen. The mixture was degassed, purged with hydrogen 3 times, and was stirred at RT under a hydrogen balloon overnight. The mixture was filtered through Celite and the filtrate was concentrated in vacuo to give compound 12b (0.33 g, 94% yield) as a white solid. ESI m/z: 628 $(M+1)^+$.

(1S,4aS,10aR)-N-[(1S,4aS,10aR)-6-Amino-1,4a-dimethyl-1,2,3,4,4a,9,10,10a-octahydrophenanthrene-1-carbonyl]-6-hydroxy-1,4a-dimethyl-1,2,3,4,4a,9,10,10a-octahydrophenanthrene-1-carboxamide (P1)

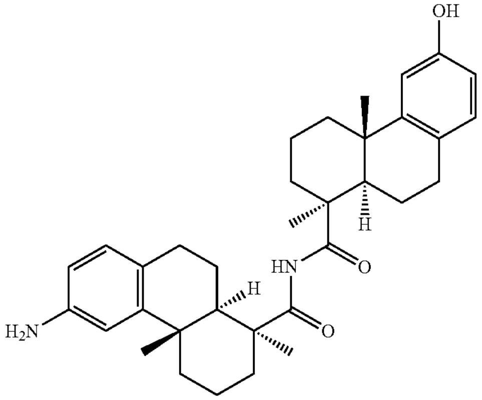

To the solution of compound P1-2a (0.17 g, 0.27 mmol) in DCM (10 mL) was added dropwise TFA (3 mL) at room temperature. The reaction mixture was stirred at room temperature for an hour until Boc was removed according to LCMS. The volatiles were removed in vacuo and the residue was purified by prep-HPLC (method B) to give P1 (0.10 g, 70% yield) as a white solid.

ESI m/z: 529.3 $(M+1)^+$.

$^1$H NMR (400 MHz, $CDCl_3$) δ 8.14 (s, 1H), 6.92 (d, J=8.3 Hz, 1H), 6.86 (d, J=8.1 Hz, 1H), 6.73 (d, J=2.5 Hz, 1H), 6.65-6.57 (m, 2H), 6.50 (dd, J=8.1, 2.3 Hz, 1H), 4.75 (s, 1H), 3.49 (s, 1H), 2.99-2.85 (m, 2H), 2.79 (tt, J=11.6, 5.8 Hz, 2H), 2.34-2.14 (m, 6H), 2.15-1.95 (m, 4H), 1.74-1.51 (m, 5H), 1.46-1.34 (m, 2H), 1.30 (s, 6H), 1.21-1.06 (m, 8H) ppm.

$^1$H NMR (400 MHz, $DMSO_{d6}$) δ 8.99 (s, 1H), 8.09 (s, 1H), 6.81 (d, J=8.0 Hz, 1H), 6.68 (d, J=8.0 Hz, 1H), 6.63 (d, J=2.5 Hz, 1H), 6.50 (dd, J=8.0, 2.5 Hz, 1H), 6.48 (d, J=2.5 Hz, 1H), 6.34 (dd, J=8.0, 2.5 Hz, 1H), 4.69 (s, 2H), 2.86-2.60 (m, 4H), 2.28-2.10 (m, 6H), 1.94-1.75 (m, 4H), 1.65-1.53 (m, 4H), 1.35-1.20 (m, 8H), 1.20-1.06 (m, 2H), 0.98 (s, 6H) ppm.

$^{13}$C NMR (100 MHz, $DMSO_{d6}$) δ 174.03, 173.92, 155.34, 148.39, 147.63, 146.43, 129.56, 129.09, 124.60, 121.65, 113.23, 112.58, 111.81, 110.77, 52.32, 52.09, 45.56, 45.52, 39.20, 39.36, 38.23, 38.17, 37.18, 37.12, 31.08, 31.00, 27.65, 27.64, 23.08, 23.03, 21.43, 21.27, 19.64, 19.61 ppm.

HPLC (method B): Retention time: 8.92 min, purity: 99.4%. chiral HPLC: >99.9% (in column AD, AS, OD, and OJ).

Optical rotation (α): +2.53° (1.7 g/100 mL THF, 25° C.).

(1S,4aS,10aR)-6-Amino-N-((1S,4aS,10aR)-6-amino-1,4a-dimethyl-1,2,3,4,4a,9,10,10a-octahydro-phenanthrene-1-carbonyl)-1,4a-dimethyl-1,2,3,4,4a,9,10,10a-octahydrophenanthrene-1-carboxamide (P2B)

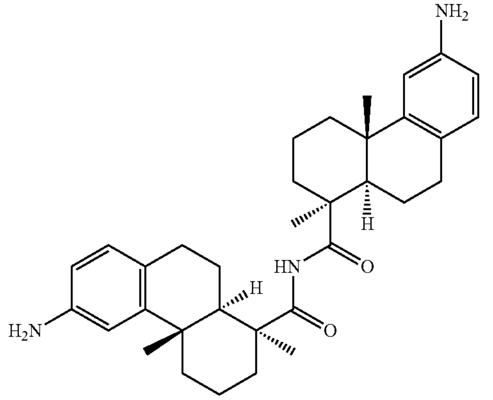

To the solution of compound 12b (0.63 g, 1.0 mmol) in DCM (10 mL) was added dropwise TFA (3 mL) at RT. The reaction mixture was stirred at RT for 4 h until Boc was removed according to LCMS. The mixture was directly purified by prep-HPLC (method B) to give P2B (0.42 g, 79% yield) as a white solid. ESI m/z: 528.2 $(M+1)^+$. $^1H$ NMR (500 MHz, $DMSO_{d6}$) δ 8.28 (s, 1H), 6.67 (d, J=8.0 Hz, 2H), 6.47 (d, J=2.0 Hz, 2H), 6.33 (dd, J=8.0, 2.0 Hz, 2H), 4.69 (s, 4H), 2.80-2.75 (m, 2H), 2.70-2.60 (m, 2H), 2.26-2.20 (m, 2H), 2.19-2.05 (m, 4H), 1.95-1.75 (m, 4H), 1.62-1.50 (m, 4H), 1.33-1.20 (m, 8H), 1.12 (t, J=8.8 Hz, 2H), 0.98 (s, 6H) ppm.

Example 11-2. Synthesis of P3B

This example demonstrates general methods for the synthesis of the podocarpic acid derivative P3B in Table C, below. This example refers to the compounds numbered from 11b and P3B in FIG. 23.

(3S,8R,9S,10R,13S,14S)-17-imino-10,13-dimethyl-2,3,4,7,8,9,10,11,12,13,14,15,16,17-tetradecahydro-1H-cyclopenta[a]phenanthren-3-ol, trifluoroacetic acid salt (P3B)

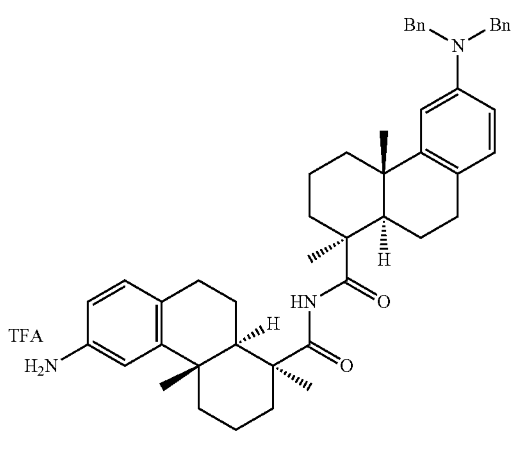 [SMILES: C[C@]1(C(=O)NC(=O)[C@@]2(C)CCC[C@]3(C)c4cc(N(Cc5ccccc5)Cc5ccccc5)ccc4CC[C@@H]23)CCC[C@]2(C)c3cc(N)ccc3CC[C@@H]12]

To a solution of compound 11b (10 mg, 12 μmol) in DCM (2 mL) was added TFA (1 mL). The reaction mixture was stirred at RT for 2 h until Boc was removed according to LCMS. The volatiles were removed in vacuo and the residue was dissolved in 5% acetonitrile in water. The solution was lyophilized to afford compound P3B (7 mg, 80% yield) as a light yellow solid. ESI m/z: 354.8 $(M/2+H)^+$. $^1H$ NMR (400 MHz, $DMSO_{d6}$) δ 9.38 (br s, 2H), 8.08 (s, 1H), 7.35-7.06 (m, 12H), 6.97 (d, J=8.8 Hz, 1H), 6.73 (d, J=8.8 Hz, 1H), 6.51 (s, 1H), 6.46 (d, J=6.4 Hz, 1H), 4.68-4.55 (m, 4H), 3.00-2.50 (m, 4H), 2.40-2.00 (m, 6H), 1.94-1.73 (m, 5H), 1.70-1.50 (m, 3H), 1.50-1.00 (m, 11H), 0.98 (s, 3H), 0.83 (s, 3H) ppm. $^{19}F$ NMR (376 MHz, $DMSO_{d6}$) δ −74.08 ppm.

Example 11-3

This example demonstrates general methods for the synthesis of the podocarpic acid derivatives P4B-P8B in Table C, below. This example refers to the compounds numbered from 12b and P4B-P8B in FIG. 23.

Example 11-3a

Intermediates 13a-e

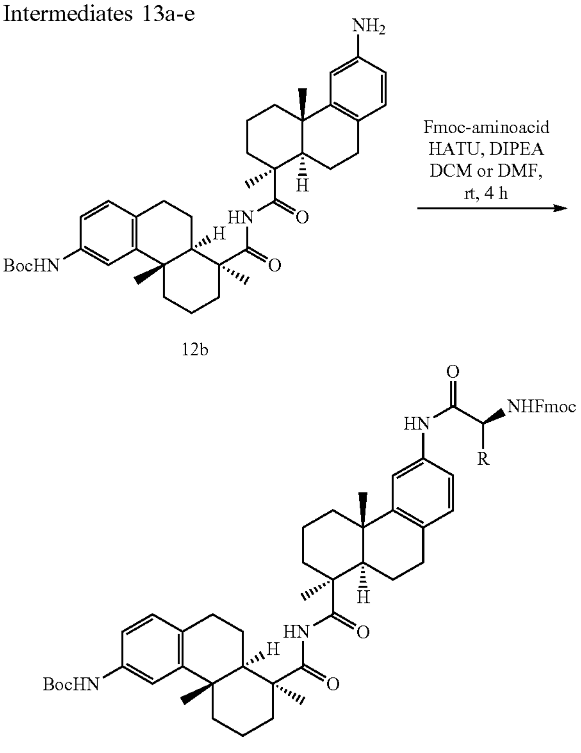

12b

13a, R = H
13b, R = $CH_2OH$
13c, R = $(CH_2)_4NHFmoc$
13d, R = $CH_2COOtBu$
13e, R = $CH_2CH_2COOtBu$ To a solution of compound 12b (1.0 equiv.) in DMF or DCM were added Fmoc-aminoacid (1.1-1.2 equiv.), HATU (1.2-1.5 equiv.) and DIPEA (2.0-3.0 equiv.) successively. The reaction mixture was stirred at RT for 4 h, which was monitored by LCMS. The mixture was concentrated in vacuo (when DCM was solvent) and the residue was purified by silica gel column chromatography (0-90% ethyl acetate in petroleum ether); or the reaction mixture (when DMF was solvent) was directly purified by reverse phase flash chromatography (50-90% acetonitrile in aq. ammonium bicarbonate (10 mM)) to give compound 13 as white solids.

| 12b | Fmoc-aminoacid | | HATU | DIPEA | | | | Product | | |
|---|---|---|---|---|---|---|---|---|---|---|
| g (mmol) | R | g (mmol) | g (mmol) | g (mmol) | Solvent (mL) | Time (h) | purifica-tion | # | g | Yield (%) |
| 0.13 (0.20) | H | 0.071 (0.24) | 0.11 (0.29) | 0.077 (0.60) | DMF (10) | 4 | RP-B | 13a | 0.14 | 78 |
| 0.31 (0.50) | $CH_2OH$ | 0.18 (0.55) | 0.23 (0.60) | 0.19 (1.50) | DCM (20) | 4 | SGC | 13b | 0.39 | 83 |
| 0.20 (0.32) | $(CH_2)_4NHFmoc$ | 0.21 (0.35) | 0.15 (0.38) | 0.083 (0.64) | DMF (20) | 4 | RP-B | 13c | 0.30 | 78 |
| 0.31 (0.50) | $CH_2COOtBu$ | 0.22 (0.55) | 0.23 (0.60) | 0.19 (1.50) | DCM (20) | 4 | SGC | 13d | 0.43 | 85 |
| 0.31 (0.50) | $(CH_2)_2COOtBu$ | 0.23 (0.55) | 0.23 (0.60) | 0.19 (1.50) | DCM (20) | 4 | SGC | 13e | 0.42 | 82 |

9H-Fluoren-9-ylmethyl N-({[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl)carbamate (13a)

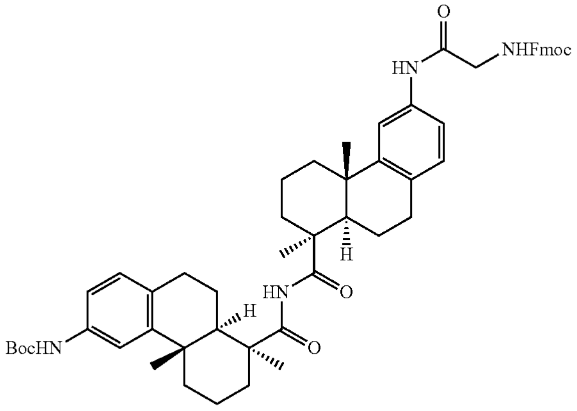

Following the general procedure for Intermediates 13a-e, compound 13a (0.14 g, 78% yield) was obtained as a white solid. ESI m/z: 907 $(M+H)^+$.

9H-Fluoren-9-ylmethyl N-[(1S)-1-{[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (13b)

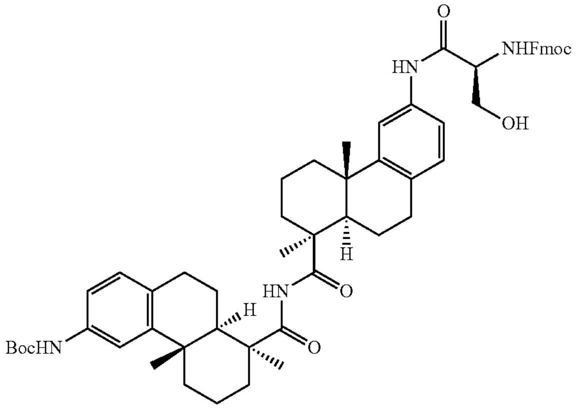

Following the general procedure for Intermediates 13a-e, compound 13b (0.39 g, 83% yield) was obtained as a white solid. ESI m/z: 938 $(M+H)^+$.

9H-Fluoren-9-ylmethyl N-[(5S)-5-{[(4bS,8S,8aR)-8-({[(1S,4aS,10aR)-6-{[(tert-butoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-5-{[(9H-fluoren-9-ylmethoxy)carbonyl]amino}pentyl]carbamate (13c)

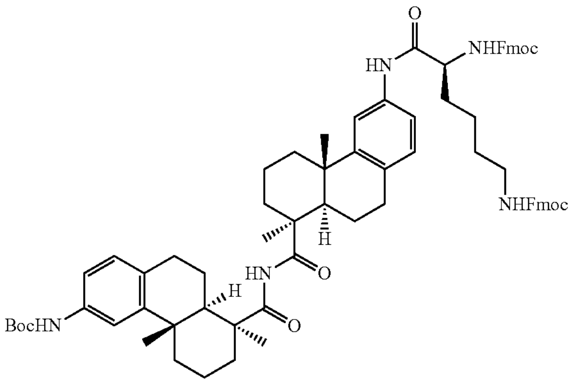

Following the general procedure for Intermediates 13a-e, compound 13c (0.30 g, 78% yield) was obtained as a white solid. ESI m/z: 1201 $(M+H)^+$.

(S)-tert-Butyl 3-(((9H-fluoren-9-yl)methoxy)carbonylamino)-4-((4bS,8S,8aR)-8-((1S,4aS,10aR)-6-(tert-butoxycarbonylamino)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoate (13d)

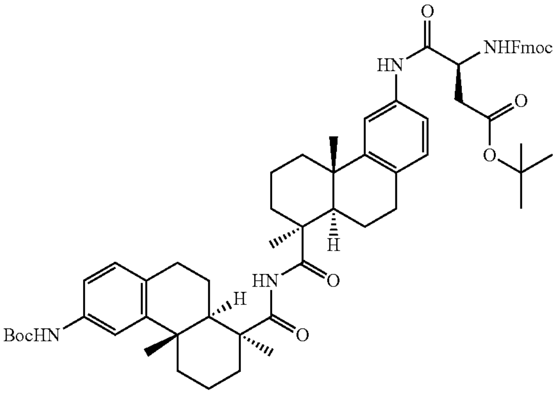

Following the general procedure for Intermediates 13a-e, compound 13d (0.43 g, 85% yield) was obtained as a white solid. ESI m/z: 1021 $(M+H)^+$.

(S)-tert-Butyl 4-(((9H-fluoren-9-yl)methoxy)carbonylamino)-5-((4bS,8S,8aR)-8-((1S,4aS,10aR)-6-(tert-butoxycarbonylamino)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoate (13e)

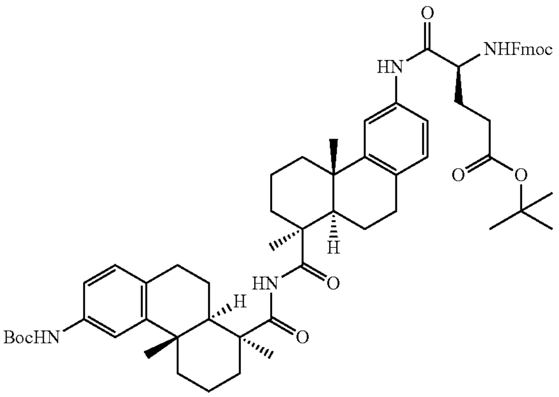

Following the general procedure for Intermediates 13a-e, compound 13e (0.42 g, 82% yield) was obtained as a white solid. ESI m/z: 1036 $(M+H)^+$.

Example 11-3b

Intermediates 14a-e

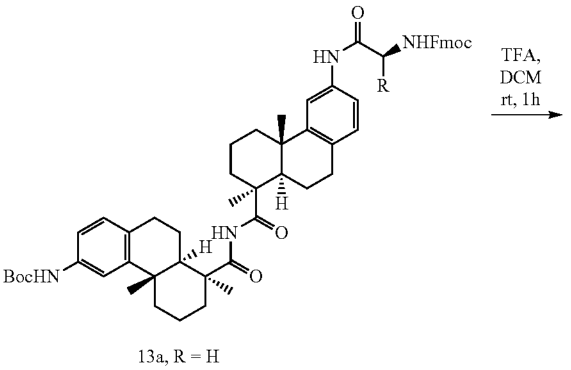

13a, R = H
13b, R = $CH_2OH$
13c, R = $(CH_2)_4NHFmoc$
13d, R = $CH_2COOtBu$
13e, R = $CH_2CH_2COOtBu$

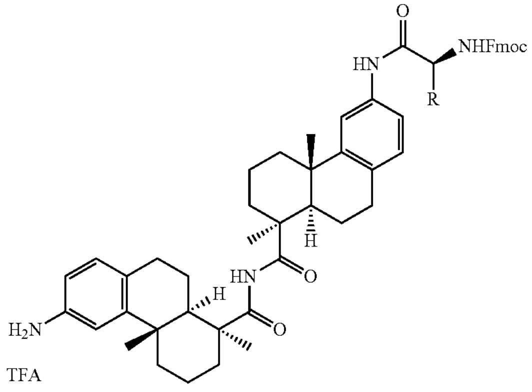

14a, R = H
14b, R = $CH_2OH$
14c, R = $(CH_2)_4NHFmoc$
14d, R = $CH_2COOH$
14e, R = $CH_2CH_2COOH$ To a solution of compound 13 (1.0 equiv.) in DCM was added TFA at RT. The reaction mixture was stirred at RT for an hour and concentrated in vacuo to give crude product 14 as colorless oil, which was used for the next step without further purification.

| 13 | | | | | Crude Product 14 | | |
|---|---|---|---|---|---|---|---|
| # | R | g (mmol) | TFA (mL) | DCM (mL) | # | R | g |
| 13a | H | 0.14 (0.16) | 3 | 10 | 14a | H | 0.13 |
| 13b | $CH_2OH$ | 0.10 (0.11) | 3 | 10 | 14b | $CH_2OH$ | 0.09 |
| 13c | $(CH_2)_4NHFmoc$ | 0.24 (0.20) | 3 | 10 | 14c | $(CH_2)_4NHFmoc$ | 0.22 |
| 13d | $CH_2COOtBu$ | 0.12 (0.12) | 3 | 10 | 14d | $CH_2COOH$ | 0.10 |

-continued

| 13 | | | | | Crude Product 14 | | |
|---|---|---|---|---|---|---|---|
| | | g | TFA | DCM | | | |
| # R | | (mmol) | (mL) | (mL) | # | R | g |
| 13e | $(CH_2)_2COOtBu$ | 0.10 (0.10) | 3 | 20 | 14e | $(CH_2)_2COOH$ | 0.08 |

9H-Fluoren-9-ylmethyl N-({[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate, trifluoroacetic acid salt (14a)

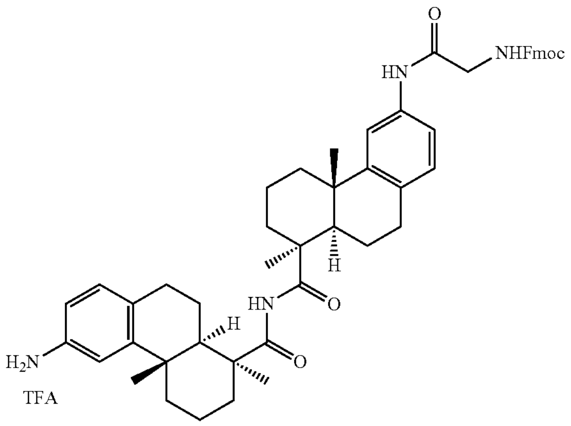

Following the general procedure for Intermediates 14a-e, crude compound 14a (0.14 g, 99% yield, TFA salt) was obtained as colorless oil. ESI m/z: 807 $(M+1)^+$.

9H-Fluoren-9-ylmethyl (S)-1-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-3-hydroxy-1-oxopropan-2-ylcarbamate, trifluoroacetic acid salt (14b)

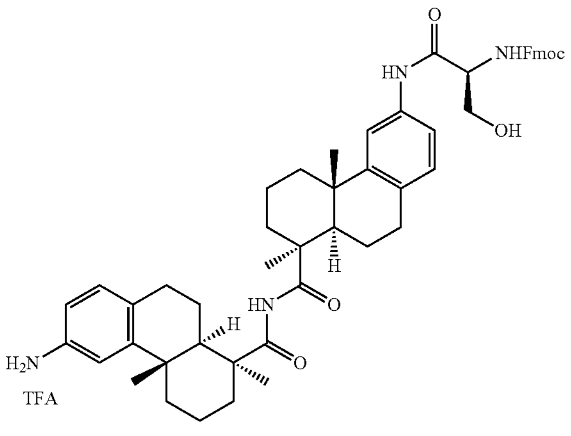

Following the general procedure for Intermediates 14a-e, crude compound 14b (0.14 g, 99% yield, TFA salt) was obtained as colorless oil. ESI m/z: 837 $(M+1)^+$.

9H-Fluoren-9-ylmethyl N-[(5S)-5-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-5-{[(9H-fluoren-9-ylmethoxy)carbonyl]amino}pentyl] carbamate, trifluoroacetic acid salt (14c)

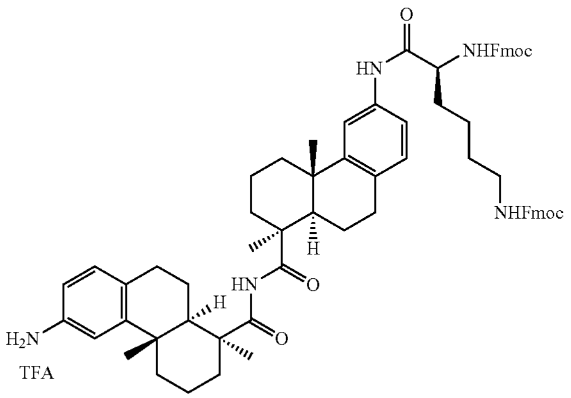

Following the general procedure for Intermediates 14a-e, crude compound 14c (0.22 g, 92% yield, TFA salt) was obtained as colorless oil. ESI m/z: 1101 $(M+1)^+$.

(S)-3-(((9H-Fluoren-9-yl)methoxy)carbonylamino)-4-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoic acid, trifluoroacetic acid salt (14d)

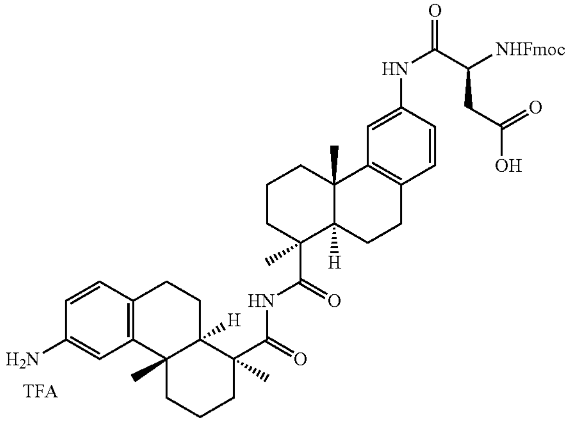

Following the general procedure for Intermediates 14a-e, crude compound 14d (0.10 g, 87% yield, TFA salt) was obtained as colorless oil. ESI m/z: 866 $(M+1)^+$.

(S)-4-(((9H-Fluoren-9-yl)methoxy)carbonylamino)-5-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoic acid, trifluoroacetic acid salt (14e)

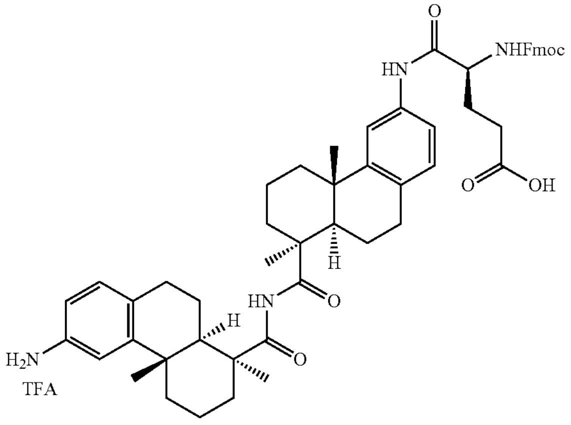

Following the general procedure for Intermediates 14a-e, crude compound 14e (84 mg, 86% yield, TFA salt) was obtained as colorless oil. ESI m/z: 880 $(M+1)^+$.

Example 11-3c

Payloads P4B-P8B

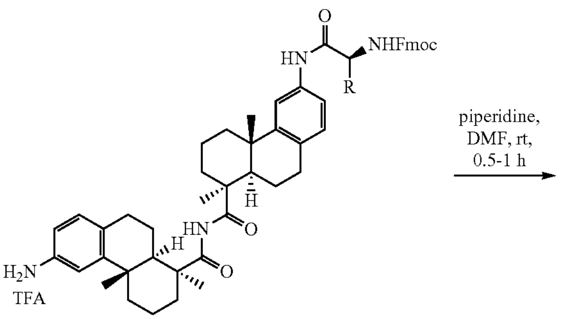

14a, R = H
14b, R = $CH_2OH$
14c, R = $(CH_2)_4NHFmoc$
14d, R = $CH_2COOH$
14e, R = $CH_2CH_2COOH$

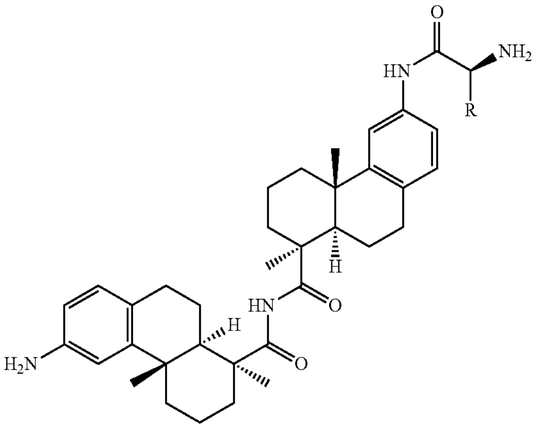

P4B, R = H
P5B, R = $CH_2OH$
P6B, R = $(CH_2)_4NH_2$
P7B, R = $CH_2COOH$
P8B, R = $CH_2CH_2COOH$

To a solution of crude 14, obtained above, in DMF was added piperidine. The mixture was stirred at RT for half an hour, which was monitored by LCMS. The mixture was directly purified by prep-HPLC (method B) to give payloads P4-8 as white solids.

| Crude 14 | | | piperidine | | | | | | |
|---|---|---|---|---|---|---|---|---|---|
| # | R | g (mmol) | (mL) | DMF (mL) | Time (hour) | purification | # | R | mg (Yield) |
| 14a | H | 0.066 (0.073) | 0.5 | 3 | 0.5 | Prep-B | P4B | H | 12 (28%) |
| 14b | $CH_2OH$ | 0.10 (0.11) | 0.5 | 3 | 0.5 | Prep-B | P5B | $CH_2OH$ | 41 (67%) |

-continued

| Crude 14 | | | piper- | | | | | | |
|---|---|---|---|---|---|---|---|---|---|
| # | R | g (mmol) | idine (mL) | DMF (mL) | Time (hour) | purification | # | R | mg (Yield) |
| 14c | $(CH_2)_4NHFmoc$ | 0.050 (0.045) | 0.5 | 5 | 1 | Prep-B | P6B | $(CH_2)_4NH_2$ | 5 (17%) |
| 14d | $CH_2COOH$ | 0.10 (0.12) | 0.5 | 3 | 0.5 | Prep-B | P7B | $CH_2COOH$ | 39 (51%) |
| 14e | $(CH_2)_2COOH$ | 0.10 (0.12) | 0.5 | 3 | 0.5 | Prep-B | P8B | $(CH_2)_2COOH$ | 44 (58%) |

(1S,4aS,10aR)-N-[(1S,4aS,10aR)-6-(2-Aminoacetamido)-1,4a-dimethyl-1,2,3,4,4a,9,10,10a-octahydrophenanthrene-1-carbonyl]-6-amino-1,4a-dimethyl-1,2,3,4,4a,9,10,10a-octahydrophenanthrene-1-carboxamide (P4B)

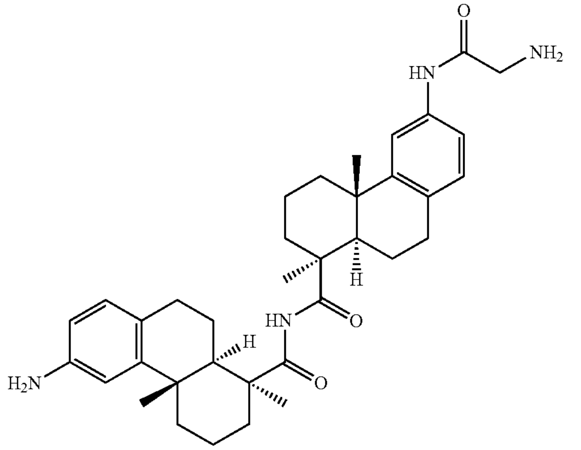 [SMILES: C[C@]1(C(=O)NC(=O)[C@@]2(C)CCC[C@]3(C)c4cc(NC(=O)CN)ccc4CC[C@@H]23)CCC[C@]2(C)c3cc(N)ccc3CC[C@@H]12]

Following the general procedure for Payloads P4B-8B, compound P4B (12 mg, 28% yield) was obtained as a white solid. ESI m/z: 585 $(M+1)^+$. $^1H$ NMR (500 MHz, $DMSO_{d6}$) δ 9.79 (s, 1H), 8.12 (s, 1H), 7.50 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 3.20 (s, 3H), 2.95-2.83 (m, 1H), 2.80-2.70 (m, 2H), 2.70-2.60 (m, 1H), 2.30-2.20 (m, 2H), 2.20-2.10 (m, 4H), 2.05-1.70 (m, 4H), 1.70-1.50 (m, 4H), 1.31-1.25 (m, 8H), 1.20-1.10 (m, 2H), 1.05 (d, J=7.5 Hz, 6H) ppm.

(1S,4aS,10aR)-6-Amino-N-((1S,4aS,10aR)-6-((S)-2-amino-3-hydroxypropanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P5B)

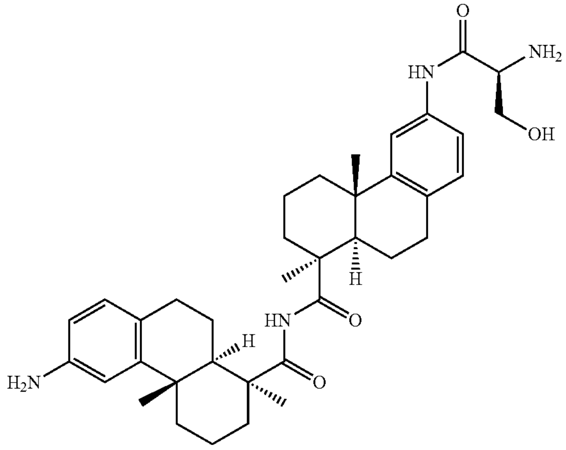 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(N)ccc3CC[C@@H]12]

Following the general procedure for Payloads P4B-8B, compound P5B (41 mg, 67% yield) was obtained as a white solid. ESI m/z: 615 $(M+1)^+$. $^1H$ NMR (500 MHz, $DMSO_{d6}$) b 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.84-4.76 (m, 1H), 4.67 (s, 2H), 3.60-3.45 (m, 2H), 2.95-2.83 (m, 1H), 2.80-2.60 (m, 4H), 2.30-2.20 (m, 3H), 2.20-2.10 (m, 4H), 1.95-1.75 (m, 5H), 1.70-1.50 (m, 4H), 1.40-1.30 (m, 2H), 1.28 (s, 3H), 1.26 (s, 3H), 1.20-1.10 (m, 3H), 1.01 (s, 3H), 0.98 (s, 3H) ppm.

(1S,4aS,10aR)-6-Amino-N-((1S,4aS,10aR)-6-((S)-2,6-diaminohexanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P6B)

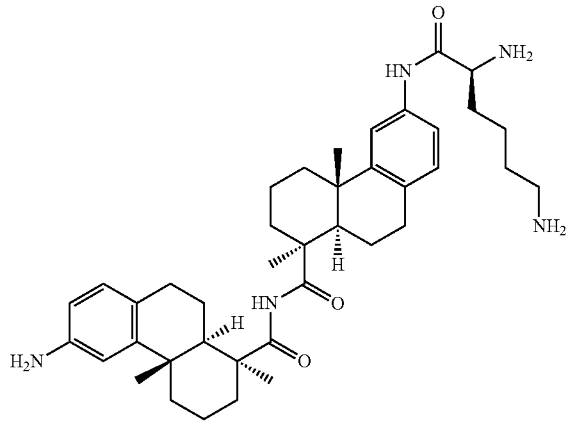 [SMILES: C[C@]1(C(=O)NC(=O)[C@@]2(C)CCC[C@]3(C)c4cc(NC(=O)[C@@H](N)CCCCN)ccc4CC[C@@H]23)CCC[C@]2(C)c3cc(N)ccc3CC[C@@H]12]

Following the general procedure for Payloads P4B-8B, compound P6B (5 mg, 17% yield) was obtained as a white solid. ESI m/z: 656 $(M+1)^+$. $^1$H NMR (500 MHz, $DMSO_{d6}$) δ 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 3.20 (s, 2H), 2.95-2.83 (m, 2H), 2.80-2.70 (m, 2H), 2.70-2.60 (m, 2H), 2.37-2.35 (m, 1H), 2.30-2.20 (m, 3H), 2.20-2.10 (m, 5H), 2.05-1.95 (m, 2H), 1.95-1.75 (m, 5H), 1.70-1.50 (m, 6H), 1.31-1.25 (m, 8H), 1.20-1.10 (m, 3H), 1.05 (d, J=7.5 Hz, 6H), 0.85 (t, J=6.0 Hz, 1H) ppm.

(S)-3-Amino-4-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-oxobutanoic acid (P7B)

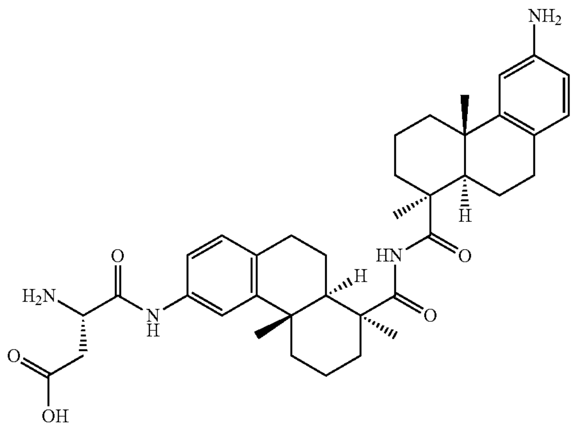 [SMILES: C[C@]1(C(=O)NC(=O)[C@@]2(C)CCC[C@]3(C)c4cc(NC(=O)[C@@H](N)CC(=O)O)ccc4CC[C@@H]23)CCC[C@]2(C)c3cc(N)ccc3CC[C@@H]12]

Following the general procedure for Payloads P4B-8B, compound P7B (39 mg, 51% yield) was obtained as a white solid. ESI m/z: 643 $(M+1)^+$. $^1$H NMR (500 MHz, $DMSO_{d6}$) δ 10.5-10.0 (br, 1H), 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.84-4.50 (m, 2H), 3.75-3.68 (m, 2H), 2.95-2.83 (m, 1H), 2.80-2.60 (m, 4H), 2.40-2.20 (m, 4H), 2.20-2.10 (m, 5H), 1.95-1.70 (m, 5H), 1.70-1.50 (m, 5H), 1.27 (d, J=7.5 Hz, 6H), 1.20-1.10 (m, 2H), 1.01 (s, 3H), 0.98 (s, 3H) ppm.

(S)-4-Amino-5-((4bS,8S,8aR)-8-((1S,4aS,10aR)-6-Amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoic acid (P8B)

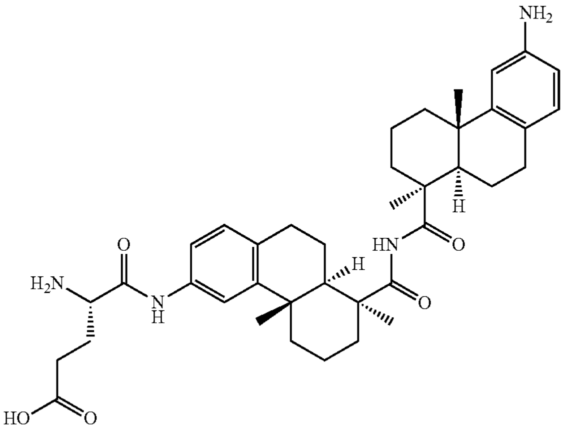

Following the general procedure for Payloads P4B-8B, compound P8B (44 mg, 58% yield) was obtained as a white solid. ESI m/z: 657 $(M+1)^+$. $^1$H NMR (500 MHz, $DMSO_{d6}$) δ 8.09 (s, 1H), 7.52 (s, 1H), 7.41 (dd, J=8.5 Hz, 1.5 Hz, 1H), 6.96 (d, J=8.5 Hz, 1H), 6.68 (d, J=8.5 Hz, 1H), 6.48 (d, J=1.5 Hz, 1H), 6.34 (dd, J=7.5 Hz, 1.5 Hz, 1H), 4.70 (m, 2H), 2.95-2.83 (m, 1H), 2.80-2.60 (m, 5H), 2.30-2.20 (m, 4H), 2.20-2.10 (m, 5H), 1.95-1.75 (m, 5H), 1.70-1.50 (m, 5H), 1.50-1.40 (m, 4H), 1.27 (d, J=7.5 Hz, 6H), 1.20-1.10 (m, 2H), 1.01 (s, 3H), 0.98 (s, 3H) ppm.

(1S,4aS,10aR)-6-amino-N-((1S,4aS,10aR)-6-((S)-2-amino-3-(1H-imidazol-4-yl)propanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P9B)

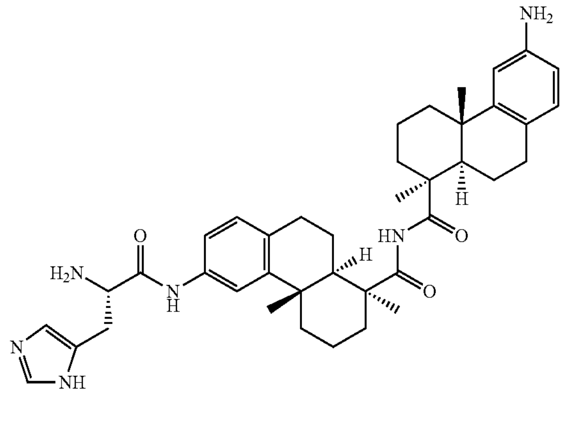 [SMILES: C[C@]1(C(=O)NC(=O)[C@@]2(C)CCC[C@]3(C)c4cc(NC(=O)[C@@H](N)Cc5cnc[nH]5)ccc4CC[C@@H]23)CCC[C@]2(C)c3cc(N)ccc3CC[C@@H]12]

To a solution of Fmoc-His-OH (0.38 g, 1.0 mmol) in DCM (5 mL) were added Fmoc-OSu (0.37 g, 1.1 mmol) and DIPEA (0.26 g, 2.0 mmol). The reaction mixture was stirred at RT overnight. The volatiles were removed in vacuo and the residue was purified by flash chromatography (5-10% methanol in DCM) to give Fmoc-His(Fmoc)-OH (0.50 g, 84% yield, ESI m/z: 600 $(M+1)^+$) as a white solid.

To a solution of compound 12b (0.31 g, 0.50 mmol) in DCM (20 mL) were added the Fmoc-His(Fmoc)-OH (0.33 g, 0.55 mmol), obtained above, HATU (0.23 g, 0.60 mmol) and DIPEA (0.19 g, 1.5 mmol) successively. The resulting mixture was stirred at RT for 4 h, which was monitored by LCMS. To the reaction mixture was added piperidine (0.5 mL) and the mixture was stirred at RT for an hour until Fmoc was totally removed, as monitored by LCMS. The mixture was concentrated in vacuo and the residue was purified by reverse phase flash chromatography (50-80% acetonitrile in water) to give Boc-P9B (0.15 g) as a white solid, half of which was dissolved in DCM (20 mL). To the solution was added TFA (3 mL). The mixture was stirred at RT for an hour until Boc was removed according to LCMS. The volatiles were removed in vacuo and the residue was purified by prep-HPLC (method B) to give compound P9B (17 mg, 12% yield) as a white solid. ESI m/z: 665 $(M+1)^+$. $^1$H NMR (500 MHz, $DMSO_{d6}$) δ 11.82 (s, 1H), 9.75 (s, 1H), 8.09 (s, 1H), 7.52-7.50 (m, 2H), 7.41 (dd, J=8.5 Hz, 1.5 Hz, 1H), 6.96 (d, J=8.5 Hz, 1H), 6.90-6.80 (m, 1H), 6.68 (d, J=8.5 Hz, 1H), 6.48 (d, J=1.5 Hz, 1H), 6.34 (dd, J=7.5 Hz, 1.5 Hz, 1H), 4.84-4.50 (m, 2H), 3.60-3.45 (m, 2H), 2.95-2.83 (m, 2H), 2.80-2.70 (m, 2H), 2.70-2.60 (m, 2H), 2.40-2.10 (m, 8H), 1.95-1.70 (m, 5H), 1.70-1.50 (m, 4H), 1.27 (d, J=7.5 Hz, 6H), 1.20-1.10 (m, 2H), 1.01 (s, 3H), 0.98 (s, 3H) ppm.

Example 11-4

This example demonstrates general methods for the synthesis of the podocarpic acid derivatives P10B and P11B in Table C, below. This example refers to the compounds numbered from 14a, 15a-b, and P10B and P11B in FIG. 24.

(S)-tert-Butyl 4-amino-5-((4bS,8S,8aR)-8-((1S,4aS,10aR)-6-(2-aminoacetamido)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoate, di-trifluoroacetic acid salt (15a)

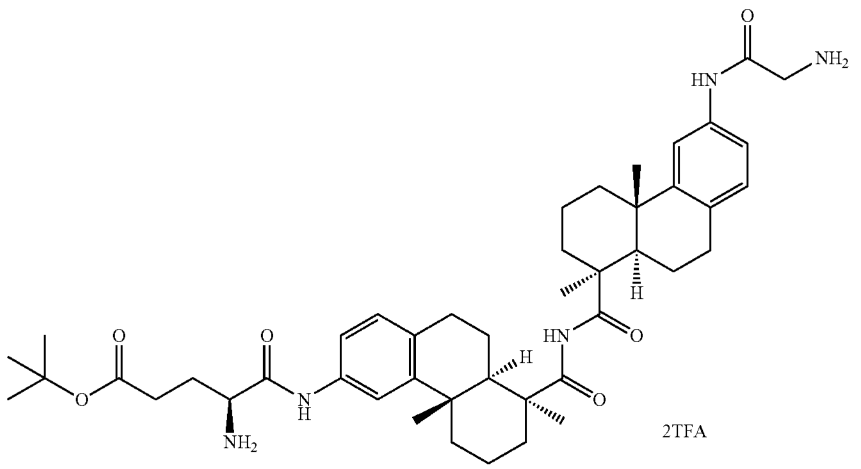 [SMILES: CC(C)(C)OC(=O)CC[C@H](N)C(=O)Nc1ccc2c(c1)[C@@]1(C)CCC[C@](C)(C(=O)NC(=O)[C@@]3(C)CCC[C@]4(C)c5cc(NC(=O)CN)ccc5CC[C@@H]34)[C@@H]1CC2]

To a solution of Fmoc-Glu(OtBu)-OH (74 mg, 0.17 mmol) and DIPEA (55 μL, 0.32 mmol) in DMF (5.0 mL) was added HATU (91 mg, 0.24 mmol). The mixture was stirred at RT for 15 min before the addition of compound 14a (0.14 g, 0.16 mmol). The reaction mixture was stirred at RT overnight, which was monitored by LCMS. To the reaction mixture was then added piperidine (1 mL) dropwise. The reaction mixture was stirred at RT for an hour until Fmoc was totally removed according to LCMS. The resulting mixture was directly separated by reverse phase flash chromatography (0-100% acetonitrile in aq. TFA (0.01%)) to give compound 15a (0.13 g, 80% yield) as a yellow solid. ESI m/z: 770.5 $(M+1)^+$.

(4S,4'S)-tert-Butyl 5,5'-(4bS,4b'S,8S,8aR,8'S,8a'R)-8,8'-(azanediylbis(oxomethylene))bis(4b,8-dimethyl-4b,5,6,7,8,8a,9,10-octahydrophenanthrene-8,3-diyl) bis(azanediyl)bis(4-amino-5-oxopentanoate) di-trifluoroacetic acid salt (15b)

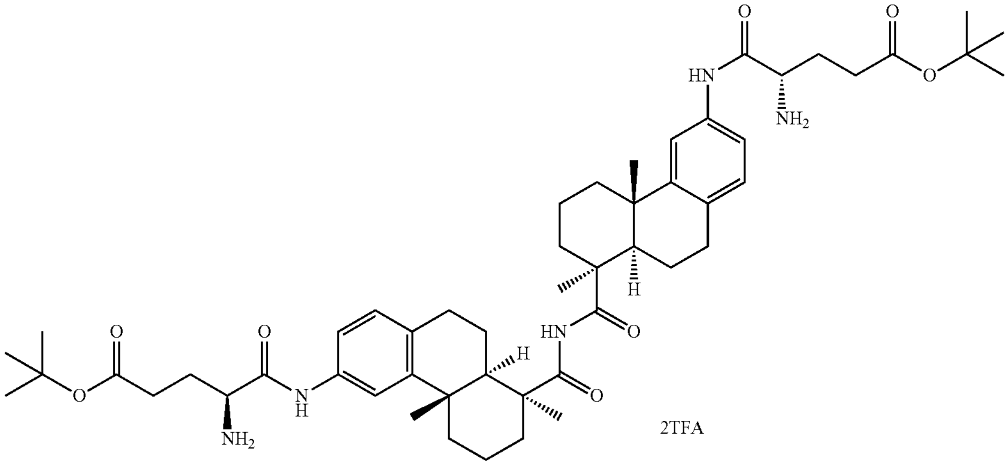 [SMILES: CC(C)(C)OC(=O)CC[C@H](N)C(=O)Nc1ccc2c(c1)[C@@]1(C)CCC[C@](C)(C(=O)NC(=O)[C@@]3(C)CCC[C@]4(C)c5cc(NC(=O)[C@@H](N)CCC(=O)OC(C)(C)C)ccc5CC[C@@H]34)[C@@H]1CC2]

2TFA

To a solution of Fmoc-Glu(OtBu)-OH (0.15 g, 0.35 mmol) and DIPEA (83 μL, 0.48 mmol) in DMF (5.0 mL) was added HATU (0.15 g, 0.40 mmol). The mixture was stirred at RT for 30 min before the addition of compound P2B (0.10 g, 0.16 mmol). The reaction mixture was stirred at RT overnight, which was monitored by LCMS. To the reaction mixture was then added piperidine (1 mL) dropwise. The reaction mixture was stirred at RT for 3 h until Fmoc was totally removed according to LCMS. The resulting mixture was directly separated by reverse phase flash chromatography (0-100% acetonitrile in aq. TFA (0.01%)) to give compound 15b (0.14 g, 78% yield) as a yellow solid. ESI m/z: 899 $(M+1)^+$.

(S)-4-Amino-5-((4bS,8S,8aR)-8-((1S,4aS,10aR)-6-(2-aminoacetamido)-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-5-oxopentanoic acid (P10B)

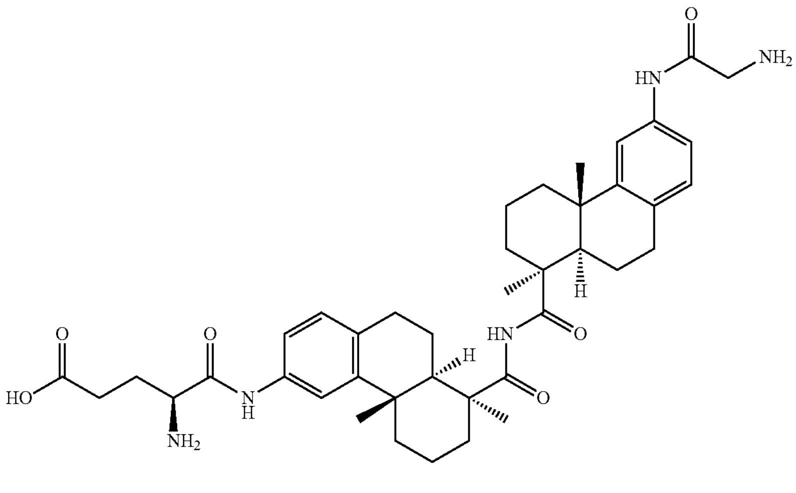 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)CN)ccc3CC[C@@H]12]

A mixture of compound 15a (0.13 g, 0.13 mmol) in neat TFA (2.0 mL) was stirred at RT for an hour, which was monitored by LCMS. The resulting mixture was diluted with DCM (20 mL) and concentrated in vacuo. The residue was purified by reversed phase flash chromatography (0-100% acetonitrile in aq. sodium bicarbonate (10 mM)) to give P10B (20 mg, 22% yield) as a white solid. ESI m/z: 358 $(M/2+1)^+$; 714.5 $(M+1)^+$. $^1H$ NMR (400 MHz, $DMSO_{d6}$) δ 9.85 (br s, 1H), 8.12 (s, 1H), 7.51 (s, 2H), 7.42-7.36 (m, 2H), 6.96 (dd, J=8.0 Hz and 3.0 Hz, 2H), 3.67 (br s, 8H), 3.36-3.33 (m, 1H), 3.22 (s, 2H), 2.91-2.87 (m, 2H), 2.80-2.71 (m, 2H), 2.31-2.28 (m, 4H), 2.17-2.14 (m, 4H), 1.91-1.82 (m, 5H), 1.69-1.58 (m, 5H), 1.34-1.23 (m, 6H), 1.19-1.12 (m, 2H), 1.01 (s, 6H) ppm.

(4S,4'S)-5,5'-(4bS,4b'S,8S,8aR,8'S,8a'R)-8,8'-(Azanediylbis(oxomethylene))bis(4b,8-dimethyl-4b,5,6,7,8,8a,9,10-octahydrophenanthrene-8,3-diyl)bis(azanediyl)bis(4-amino-5-oxopentanoic acid) (P11B)

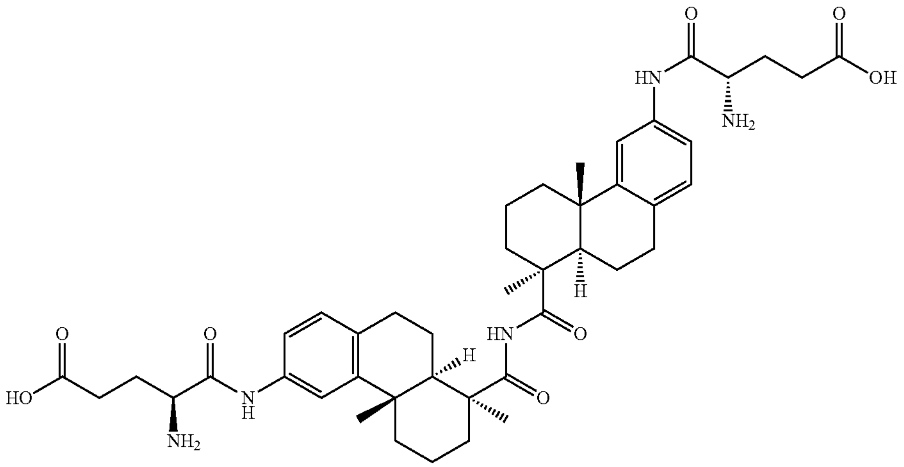 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)[C@@H](N)CCC(=O)O)ccc3CC[C@@H]12]

A mixture of compound 15b (0.14 g, 0.14 mmol) in neat TFA (3.0 mL) was stirred at RT for an hour, which was monitored by LCMS. The resulting mixture was diluted with DCM (30 mL) and concentrated in vacuo. The residue was purified by reverse phase flash chromatography (0-100% acetonitrile in aq. sodium bicarbonate (10 mM)) to give P11B (20 mg, 18% yield) as a white solid. ESI m/z: 394 $(M/2+1)^+$. $^1H$ NMR (400 MHz, $DMSO_{d6}$) δ 9.85 (br s, 2H), 8.12 (s, 1H), 7.51 (s, 2H), 7.9 (dd, J=8.4 Hz and 1.6 Hz, 2H), 6.97 (d, J=8.0 Hz, 2H), 3.5 (br s, 6H), 3.40-3.37 (m, 2H), 3.16 (s, 1H), 2.91-2.88 (m, 2H), 2.79-2.66 (m, 2H), 2.33-2.29 (m, 7H), 2.18-2.15 (m, 4H), 1.91-1.84 (m, 6H), 1.71-1.59 (m, 6H), 1.35-1.23 (m, 6H), 1.18-1.12 (m, 2H), 1.01 (s, 6H) ppm.

Example 11-5

This example demonstrates methods for the synthesis of the linker-payloads LP1B-LP5B in Table 3, above. This example refers to the compounds numbered 12b and from 102a-b to 106a-e and linker-payloads LP1B-LP5B in FIG. 25.

Example 5a

Intermediates 102a-b

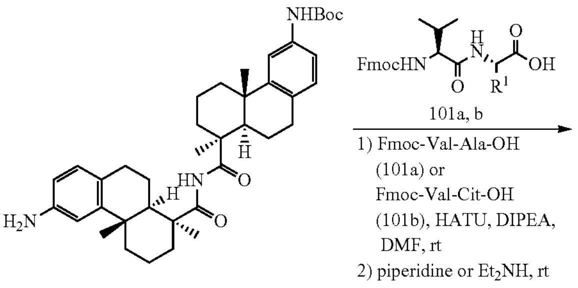

12b

-continued

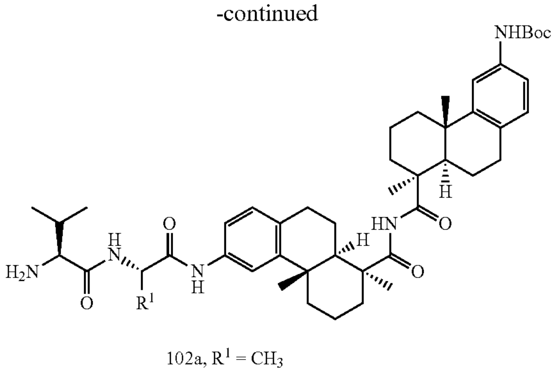

102a, $R^1 = CH_3$
102b, $R^1 = (CH_2)_3NHCONH_2$

To a solution of acid (Fmoc-Val-Ala-OH (101a, 1.2 equiv.) or Fmoc-Val-Cit-OH (101b, 1.2 equiv.) in DMF were added HATU (1.2 equiv.) and DIPEA (2.0-3.0 equiv.) at RT. After the mixture was stirred at RT for 5 min, compound 12b (1.0 equiv.) was added. The resulting mixture was stirred at RT for 4-20 h until the amine was consumed according to LCMS. To the mixture was then added piperidine (excess), and the mixture was stirred at RT for 1-6 h until Fmoc was totally removed, as monitored by LCMS. The reaction mixture was filtered through a membrane and the filtrate was directly purified by prep-HPLC (method B) or reverse phase flash chromatography to give compound 102 (38-72% yield) as a white solid.

| | | | | Step 1 | | | | Step 2 | | | | |
|---|---|---|---|---|---|---|---|---|---|---|---|---|
| Amine | | Acid | | HATU | DIPEA | | | Piper- | | | Product | |
| | g (mmoL) | | g (mmoL) | g (mmol) | g (mmol) | DMF (mL) | Time (hr) | idine (mL) | Time (hr) | Purifica-tion | # | g (yield) |
| 12b | 0.31 (0.50) | 101a | 0.25 (0.60) | 0.23 (0.60) | 0.19 (1.5) | 20 | 4 | 0.5 | 1 | RP | 102a | 0.29 (72%) |
| 12b | 0.50 (0.80) | 101b | 0.48 (0.96) | 0.36 (0.96) | 0.28 mL (1.6) | 6 | 20 | 0.5 | 6 | Prep-B | 102b | 0.27 (38%) |

tert-Butyl N-[(4bS,8S,8aR)-8-({[(1S,4aS,10aR)-6-[(2S)-2-[(2S)-2-amino-3-methylbutanamido]propanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (102a)

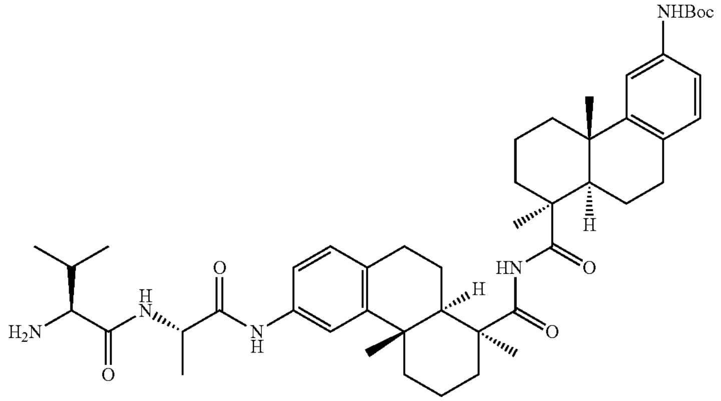 [SMILES: CC(C)[C@H](N)C(=O)N[C@@H](C)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

Following the general procedure for Intermediates 102a, b, compound 102a (0.29 g, 72% yield) was obtained as a white solid. ESI m/z: 799 $(M+1)^+$.

tert-Butyl N-[(4bS,8S,8aR)-8-({[(1S,4aS,10aR)-6-[(2S)-2-[(2S)-2-amino-3-methylbutanamido]-5-(carbamoylamino)pentanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (102b)

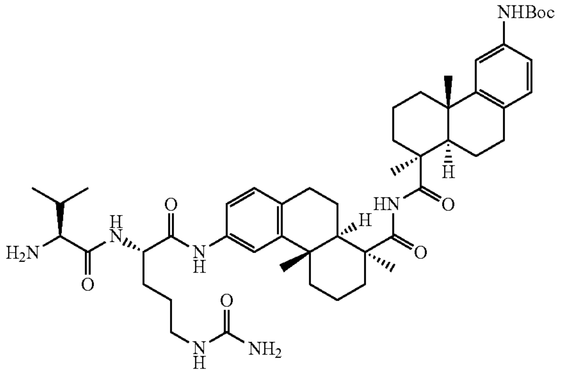 [SMILES: CC(C)[C@H](N)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

Following the general procedure for Intermediates 102a, b, compound 102b (0.27 g, 38% yield) was obtained as a white solid. ESI m/z: 885 $(M+1)^+$.

Example 5b

Intermediates 104a-b tert-Butyl N-[(4bS,8S,8aR)-8-({[(1S,4aS,10aR)-6-[(2S)-2-[(2S)-2-{2-amino-6-[2-(cyclooct-2-yn-1-yloxy)acetamido]hexanamido}-3-methylbutanamido]propanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (104a)

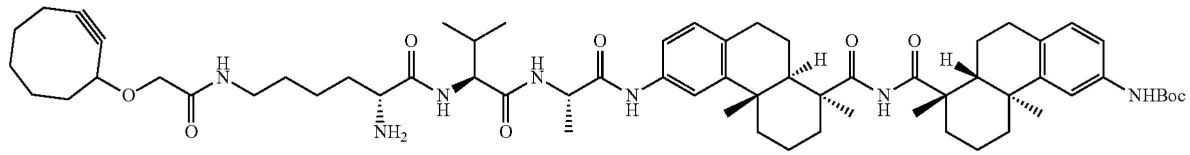 [SMILES: CC(C)[C@H](NC(=O)[C@H](N)CCCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

To a solution of compound 103 (70 mg, 0.13 mmol) in DMF (2 mL) were added HATU (68 mg, 0.18 mmol) and DIPEA (44 μL, 0.24 mmol) at RT. The mixture was stirred at RT for 5 min before the addition of compound 102a (95 mg, 0.12 mmol). The reaction mixture was then stirred at RT for 3 h until compound 102a was totally consumed, as monitored by LCMS. To the reaction mixture was then added piperidine (0.5 mL, excess). The mixture was stirred at RT for 2 h. The mixture was then filtered and the filtrate was concentrated. The residue was purified by reverse phase flash chromatography (0-100% acetonitrile in aq. ammonium bicarbonate (10 mM)) to give compound 104a (0.13 g, 96% yield) as a white solid. ESI m/z: 518.0 $((M-55)/2)^+$.

tert-Butyl N-[(4bS,8S,8aR)-8-({[(1S,4aS,10aR)-6-[(2S)-2-[(2S)-2-{2-amino-6-[2-(cyclooct-2-yn-1-yloxy)acetamido]hexanamido}-3-methylbutanamido]-5-(carbamoylamino)pentanamido]-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamate (104b)

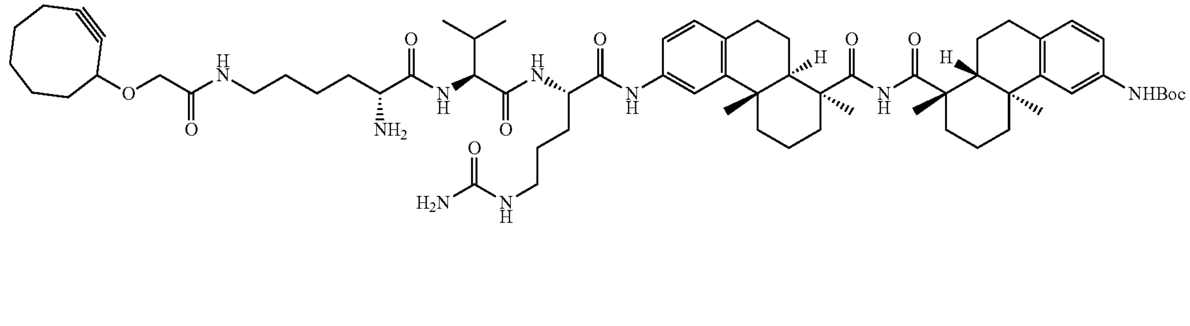 [SMILES: CC(C)[C@H](NC(=O)[C@H](N)CCCCNC(=O)COC1C#CCCCCC1)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

To a solution of compound 103 (0.27 g, 0.31 mmol) and DIPEA (0.11 mL, 0.61 mmol) in DMF (6 mL) was added compound 102b (0.18 g, 0.34 mmol) followed by the addition of HATU (0.14 g, 0.37 mmol). The reaction mixture was stirred at RT for 3 h, which was monitored by LCMS. The resulting solution was directly purified by reverse phase flash chromatography to give compound Fmoc-104b (0.30 g, ESI m/z: 711 $((M+Na)/2+1)^+$) as a pale yellow solid, which was dissolved in DCM (6.0 mL). To the solution was added piperidine (0.5 mL) and the reaction mixture was stirred at RT for 2 h until Fmoc was totally removed according to LCMS. The volatiles were removed in vacuo and the residue was triturated with petroleum ether to give compound 104b (0.26 g, 65% yield) as a light yellow solid. ESI m/z: 1177.6 $((M+H)^+$.

Example 5c

Intermediates 105a-c

Azido intermediate a-CD-$N_3$ (105a) was synthesized according to J. Am. Chem. Soc., 2012, 134(46), 19108-19117 (FIG. 32).

Azido-15-oxo-3,6,9,12-tetraoxa-16-azaoctadecane-18-sulfonic acid (105b), FIG. 33

To a solution of 2,5-dioxopyrrolidin-1-yl 1-azido-3,6,9,12-tetraoxapentadecan-15-oate ($N_3$—$PEG_4$-OSu, 0.10 g, 0.26 mmol) and taurine (39 mg, 0.31 mmol) in anhydrous DMF (4 mL) was added DIPEA (15 mg, 0.52 mmol). The mixture was stirred at RT overnight. The reaction mixture was filtered and the solution was purified by prep-HPLC (method A) to give intermediate 105b (0.80 g, yield 78%) as colorless oil. ESI m/z: 399.1 $(M+H)^+$. $^1H$ NMR (500 MHz, $D_2O$) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

Azido intermediate maltose-$N_3$ (105c) was synthesized according to Tetrahedron Letters, 2001, 42 (7), 1325-1328 (FIG. 34).

Example 5d

Intermediates 106a-e

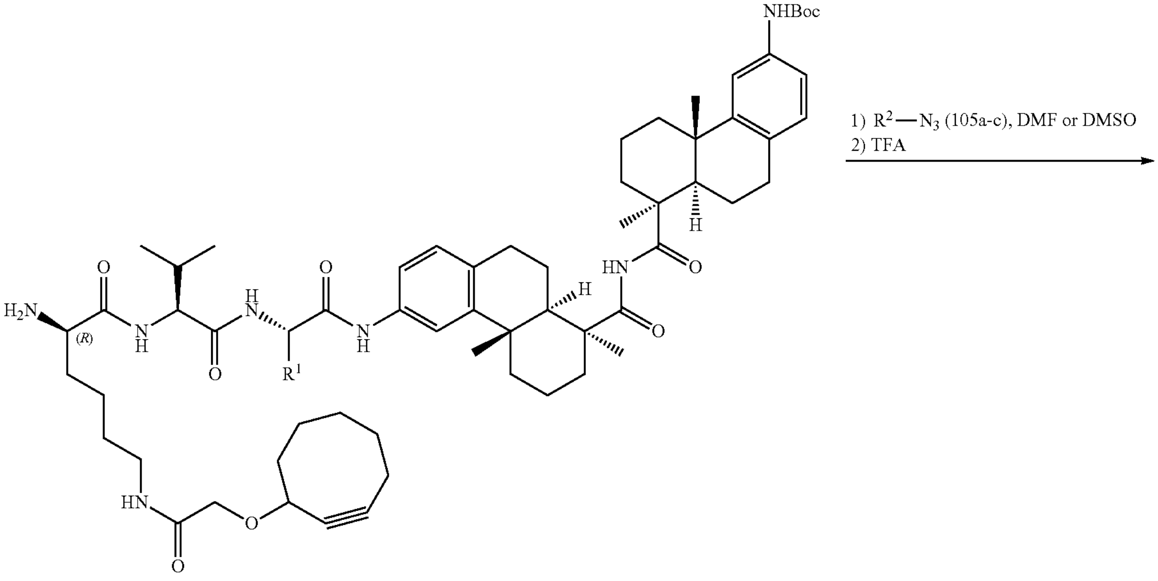

104a, $R^1 = CH_3$
104b, $R^1 = (CH_2)_3NHCONH_2$

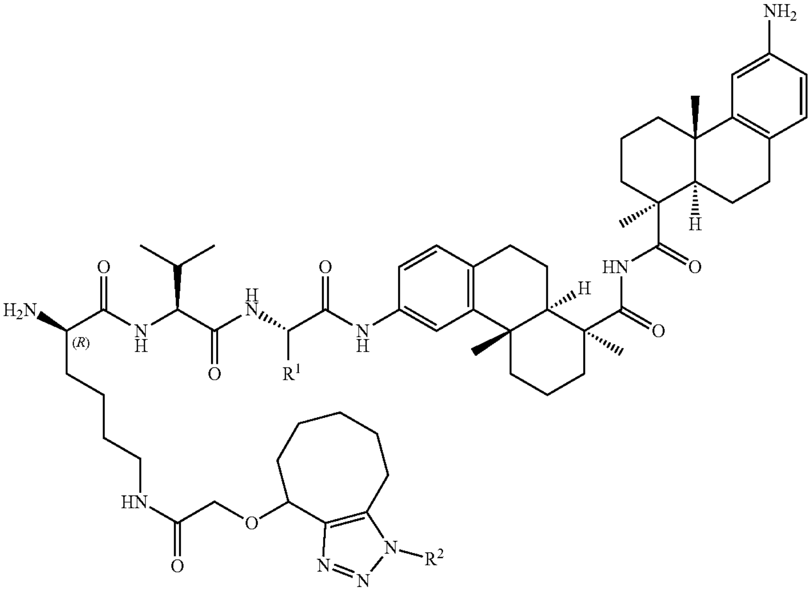

106a, $R^1 = CH_3$, $R^2$ = aCD
106b, $R^1 = (CH_2)_3NHCONH_2$, $R^2$ = aCD
106c, $R^1 = CH_3$, $R^2$ = $PEG_4$-taurine
106d, $R^1 = (CH_2)_3NHCONH_2$, $R^2$ = $PEG_4$-taurine
106e, $R^1 = CH_3$, $R^2$ = maltose To a solution of compound 104 in DMF were added azido intermediate 105 at RT. The reaction was stirred at RT for 3-48 h until LCMS showed complete reaction. The reaction mixture was directly purified by prep-HPLC to give compound Boc-106 as a white solid, which was dissolved in TEA solution (or neat TEA). The solution was stirred at RT for 0.5-20 h until Boc was removed according to LCMS. The solution was concentrated to give 106 (as the TEA salt).

| Alkyne | | Azide | | Step 1 | | | | Step 2 | | | Product | |
|---|---|---|---|---|---|---|---|---|---|---|---|---|
| | g (mmoL) | | g (mmoL) | DMF (mL) | T (° C.) | Time (hr) | Purification | TFA (mL) | solvent (mL) | Time (hr) | # | g (yield) |
| 104a | 0.050 (0.045) | 105a | 0.11 (0.12) | 4 | RT | 48 | RP-A | 1 | DCM (3 mL) | 1 | 106a | 0.019* (69%) |
| 104b | 0.050 (0.042) | 105a | 0.085 (0.085) | 4 | RT | 20 | RP | 2 | / | 0.5 | 106b | 0.076 (87%) |
| 104a | 0.17 (0.16) | 105b | 0.12 (0.31) | 6 | RT | 20 | RP-A | 2 | / | 1 | 106c | 0.090 (39%) |
| 104b | 0.050 (0.042) | 105b | 0.034 (0.084) | 2 | RT | 3 | RP | 1 | MeOH (2 mL) | 20 | 106d | 0.022 (36%) |
| 104a | 0.035 (0.032) | 105c | 0.024 (0.064) | DMSO 5 mL | RT | 4 | RP | 3 | / | 2 | 106e | 0.034 (77%) |

*not all Boc-106a was used for de-Boc.

(1S,4aS,10aR)-N-[(1S,4aS,10aR)-6-Amino-1,4a-dimethyl-2,3,4,9,10,10a-hexahydrophenanthrene-1-carbonyl]-6-[(2S)-2-[(2S)-2-[(2R)-2-amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-4H,5H,6H,7H,8H,9H-cycloocta[d][1,2,3]triazol-4-yl)oxy]acetamido}hexanamido]-3-methylbutanamido]propanamido]-1,4a-dimethyl-2,3,4,9,10,10a-hexahydrophenanthrene-1-carboxamide trifluoroacetic acid salt (106a)

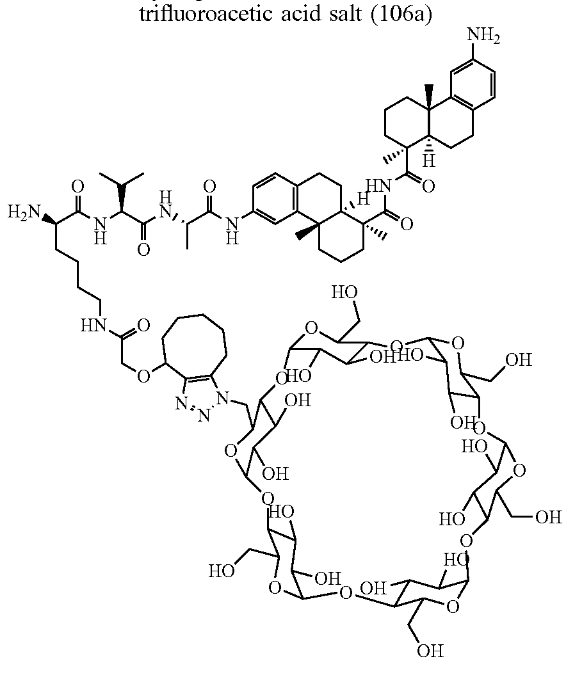

Following the general procedure for Intermediates 106a-e, compound Boc-106a (72 mg, 76% yield, as a mixture of triazole regioisomers) was obtained as a white solid (ESI m/z: 1045 $(M/2+1)^+$). A small amount of the pure major isomer (7 mg) could be obtained after further purification by reverse phase flash chromatography (0-60% acetonitrile in aq. TFA (0.01%)), which was determined by $^1$H NMR (500 MHz, $DMSO_{d6}$) ((with regioisomers) δ 9.92 (s, 0.5H), 9.82 (s, 0.5H), 9.10 (s, 1H), 8.58-8.53 (m, 1H), 8.50-8.35 (m, 1H), 8.12 (s, 1H), 8.04 (s, 3H), 7.88-7.82 (m, 1H), 7.55 (s, 0.5H), 7.46 (s, 0.5H), 7.41 (s, 1H), 7.40-7.26 (m, 1H), 7.14 (d, J=7.0 Hz, 1H), 6.97 (d, J=8.0 Hz, 1H), 6.90 (d, J=8.5 Hz, 1H), 5.51 (br, 12H), 4.83-4.70 (m, 8H), 4.57-4.51 (m, 3H), 4.44-4.36 (m, 4H), 4.00-3.98 (m, 1H), 3.88-3.55 (m, 27H), 3.26-3.09 (m, 6H), 2.91-2.85 (m, 4H), 2.76-2.63 (m, 3H), 2.29-2.25 (m, 2H), 2.17-1.99 (m, 4H), 1.96-1.93 (m, 6H), 1.88-1.63 (m, 9H), 1.56-1.54 (m, 15H), 1.33-1.28 (m, 15H), 1.18-1.13 (m, 3H), 1.01-0.99 (m, 6H), 0.89-0.83 (m, 7H) ppm.). To a mixture of Boc-106a (as a mixture of regioisomers) (20 mg, 9.6 μmol) in DCM (3 mL) was added TFA (1 mL). The resulting mixture was stirred at RT for an hour until Boc was removed, as monitored by LCMS. The volatiles were removed in vacuo to give compound 106a (19 mg, 69% yield from 104a) as a pale-yellow solid, which was used for the next step without further purification. ESI m/z: 995 $(M/2+1)^+$.

(1S,4aS,10aR)-N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]-1,4a-dimethyl-1,2,3,4,4a,9,10,10a-octahydrophenanthren-1-yl]carbonyl}-6-amino-1,4a-dimethyl-1,2,3,4,4a,9,10,10a-octahydrophenanthrene-1-carboxamide trifluoroacetic acid salt (106b)

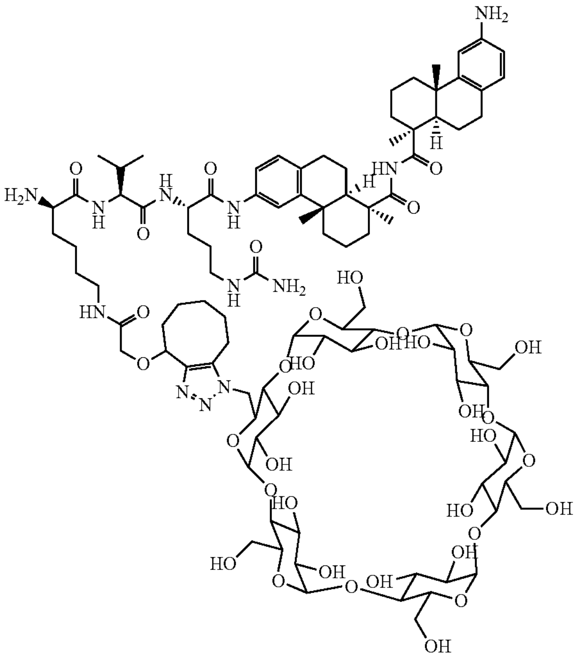 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106b (76 mg, 87% yield from 104b) was obtained as a yellow solid. ESI m/z: 692 (M/3+1)$^+$.

1-(4-(2-(((R)-5-Amino-6-(((S)-1-(((S)-1-(((4bS,8S,8aR)-8-(((1S,4aS,10aR)-6-amino-1,4a-dimethyl-1,2,3,4,4a,9,10,10a-octahydrophenanthrene-1-carbonyl)carbamoyl)-4b,8-dimethyl-4b,5,6,7,8,8a,9,10-octahydrophenanthren-3-yl)amino)-1-oxopropan-2-yl)amino)-3-methyl-1-oxobutan-2-yl)amino)-6-oxohexyl)amino)-2-oxoethoxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (106c)

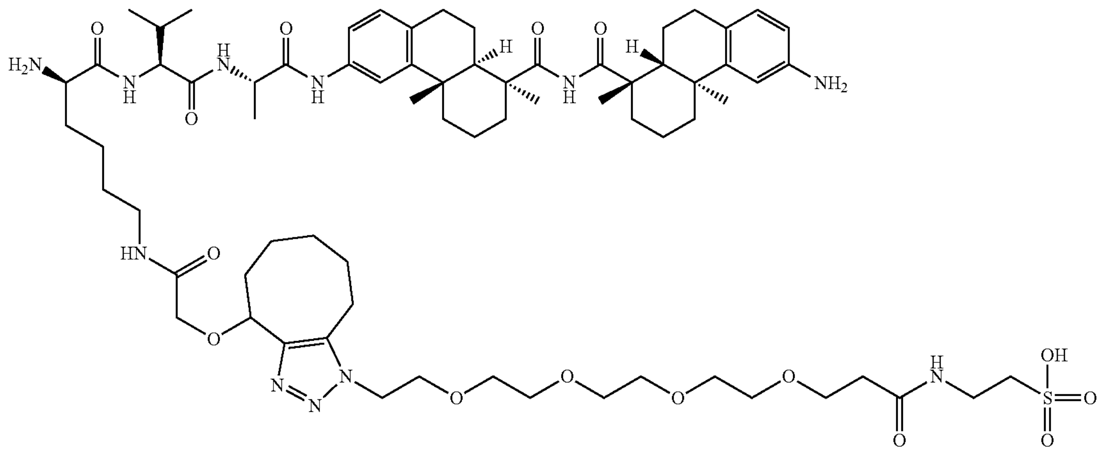 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106c (90 mg, 39% yield from 104c) was obtained as a yellow solid. ESI m/z: 463.8 $(M/3+1)^+$.

1-(4-(((6S,9S,12R)-1,12-Diamino-6-(((4bS,8S,8aR)-8-(((1S,4aS,10aR)-6-amino-1,4a-dimethyl-1,2,3,4,4a,9,10,10a-octahydrophenanthrene-1-carbonyl)carbamoyl)-4b,8-dimethyl-4b,5,6,7,8,8a,9,10-octahydrophenanthren-3-yl)carbamoyl)-9-isopropyl-1,8,11,18-tetraoxo-2,7,10,17-tetraazanonadecan-19-yl)oxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (106d)

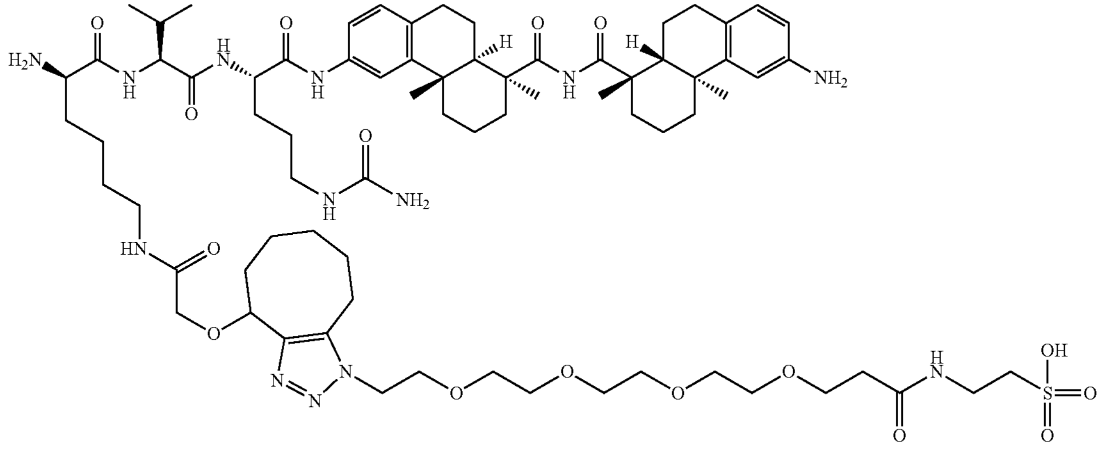 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106d as its TFA salt (22 mg, 36% yield) was obtained as a white solid after purification by reverse phase flash chromatography (0-80% acetonitrile in water during 25 minutes). ESI m/z: 788 (M/2+H)+.

(1S,4aS,10aR)-6-Amino-N-((1S,4aS,10aR)-6-((2S)-2-((2S)-2-((2R)-2-amino-6-(2-((1-((2S,3R,4R,5S,6R)-3,4-dihydroxy-6-(hydroxymethyl)-5-(((2R,3R,4S,5S,6R)-3,4,5-trihydroxy-6-(hydroxymethyl)tetrahydro-2H-pyran-2-yl)oxy)tetrahydro-2H-pyran-2-yl)-3a,4,5,6,7,8,9,9a-octahydro-1H-cycloocta[d][1,2,3]triazol-4-yl)oxy)acetamido)hexanamido)-3-methylbutanamido)propanamido)-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (106e)

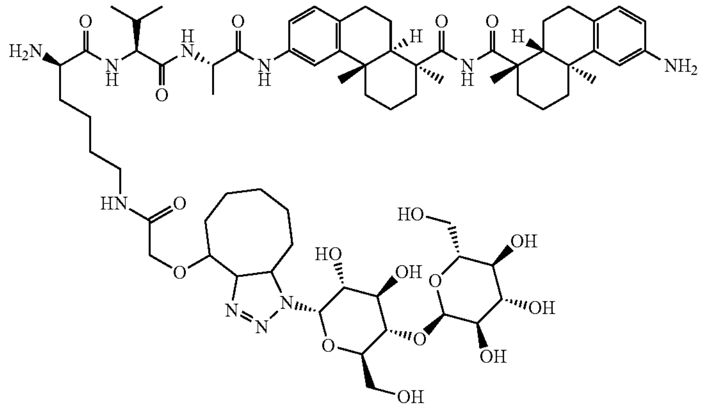 [SMILES: CC(C)[C@H](NC(=O)[C@H](N)CCCCNC(=O)COC1CCCCCC2C1N=NN2[C@H]1O[C@H](CO)[C@@H](O[C@H]2O[C@H](CO)[C@@H](O)[C@H](O)[C@H]2O)[C@H](O)[C@H]1O)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Intermediates 106a-e, compound 106e as its TFA salt (34 mg, 77% yield) was obtained as colorless oil. ESI m/z: 1358 (M+H)+.

Example 5e

Linker-Payloads LP1B-LP5B

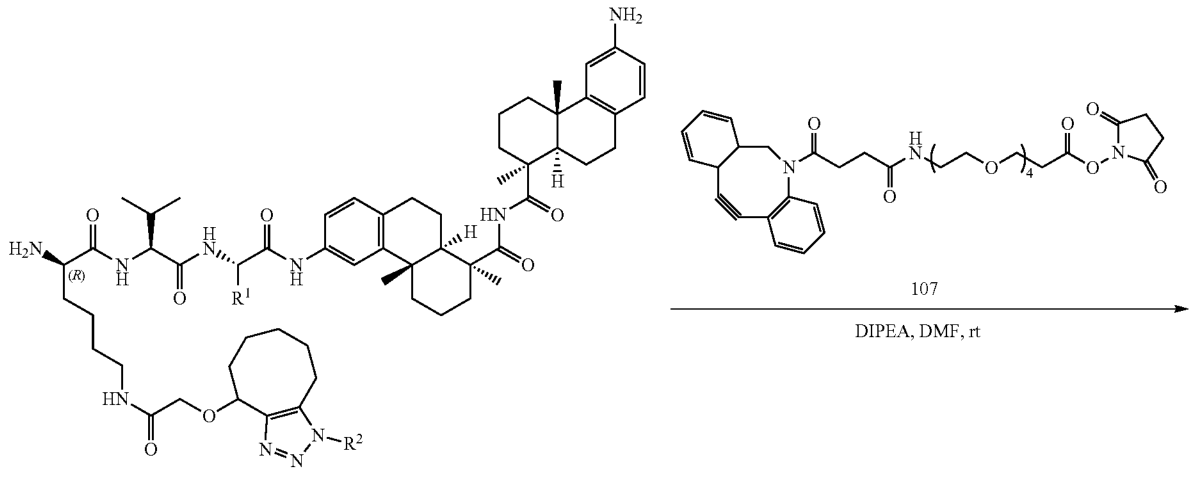

106a, $R^1$ = $CH_3$, $R^2$ = aCD
106b, $R^1$ = $(CH_2)_3NHCONH_2$, $R^2$ = aCD
106c, $R^1$ = $CH_3$, $R^2$ = $PEG_4$-taurine
106d, $R^1$ = $(CH_2)_3NHCONH_2$, $R^2$ = $PEG_4$-taurine
106e, $R^1$ = $CH_3$, $R^2$ = maltose -continued

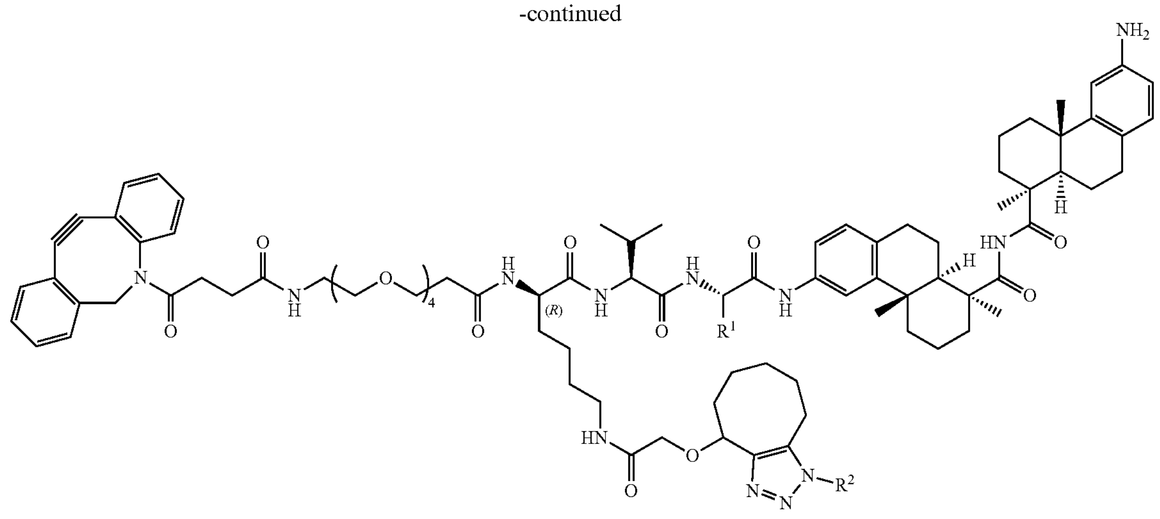

LP1B-5B

To a solution of compound 106 in DMF were added compound DIBAC-PEG$_4$-NHS 107 and DIPEA at RT. The reaction mixture was stirred at RT for 3 h. The reaction mixture was directly purified by prep-HPLC (method B) or reverse phase flash chromatography (method B) to give compound LP1B-5B.

| Amine 106 | | NHS ester | | | | | Product LP | |
|---|---|---|---|---|---|---|---|---|
| # | mg (μmol) | 107 mg (μmol) | DIPEA (mmol) | DMF (mL) | Time (hr) | Purification | # | mg (yield) |
| 106a | 19 (8.7) | 7.0 (11) | 4.0 mg (0.031) | 1.5 | 1.5 | RP-B (twice) | LP1B | 8 (36%)* |
| 106b | 76 (37) | 24 (37) | 12 μL (0.073) | 5 | 1.5 | Prep-B (twice) | LP2B | 20 (21%) |
| 106c | 90 (65) | 39 (60) | 0.02 mL (0.12) | 5 | 1.5 | Prep-B | LP3B | 60 (52%) |
| 106d | 22 (15) | 9.7 (15) | 5 μL (0.030) | 2 | 1.5 | Prep-B | LP4B | 6 (20%) |
| 106e | 40 (29) | 23 (35) | 7.6 mg (59) | 5 | 4 | Prep-B | LP5B | 15 (27%) |

*7 mg of compound 106a as free base was recycled.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-{[(1S,4aS,10aR)-6-amino-1,4a-dimethyl-2,3,4,9,10,10a-hexahydrophenanthrene-1-carbonyl]carbamoyl}-4b,8-dimethyl-5,6,7,8a,9,10-hexahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-4H,5H,6H,7H,8H,9H-cycloocta[d][1,2,3]triazol-4-yl)oxy]acetamido}pentyl]-3,6,9,12-tetraoxapentadecan-15-amide (LP1B)

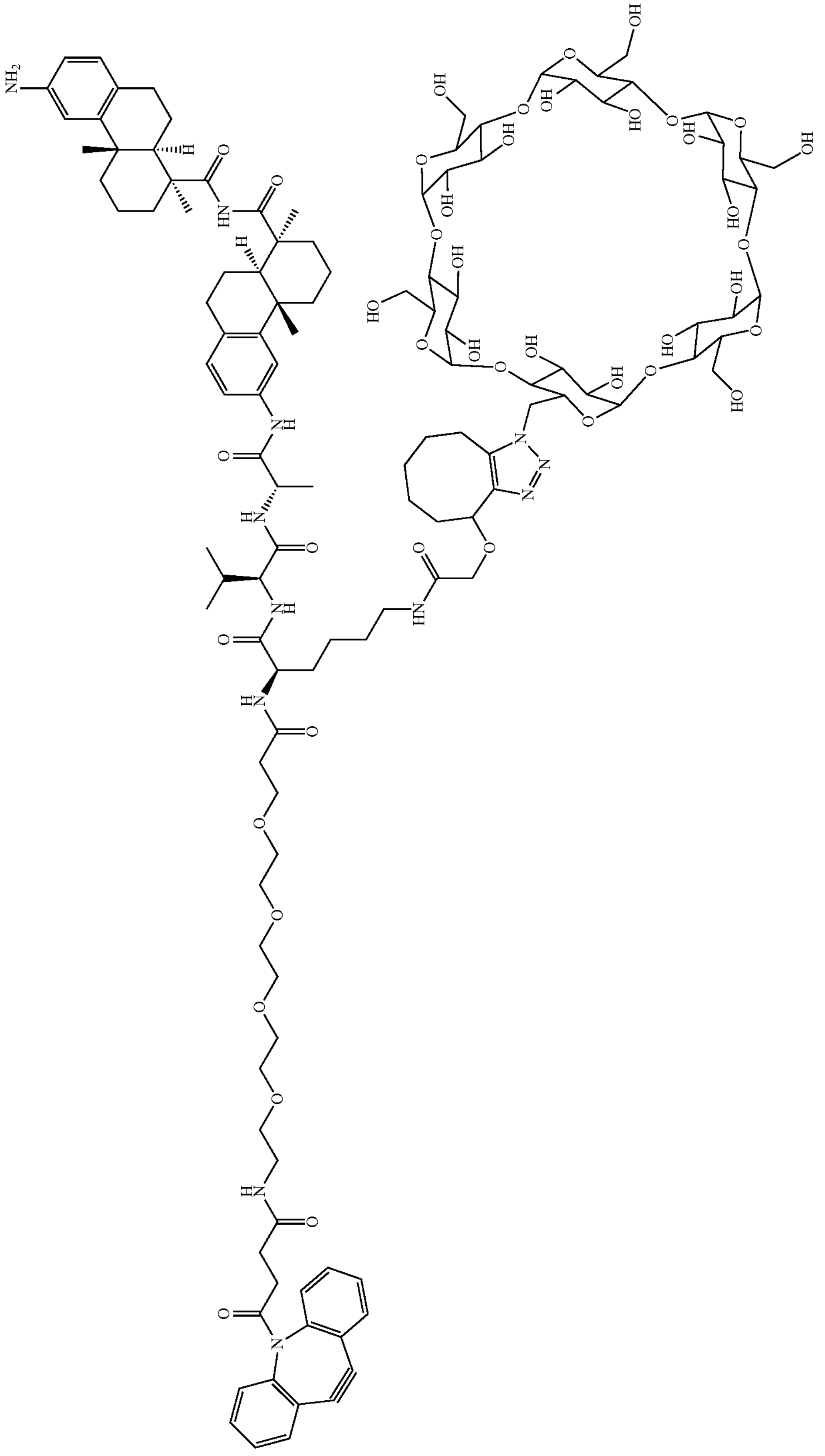

Following the general procedure for Linker-payloads LP1-5, linker-payload LP1B (8 mg, 36% yield) was obtained as a white solid. ESI m/z: 842 $(M/3+1)^+$; 1262 $(M/2+1)^+$. $^1$H NMR (400 MHz, DMSO$_{d6}$) δ 9.69 (s, 0.5H), 9.28 (s, 0.5H), 8.20-8.00 (m, 5H), 7.81-7.75 (m, 2H), 7.66 (d, J=7.6 Hz, 1H), 7.60 (d, J=7.6 Hz, 1H), 7.53-7.27 (m, 9H), 6.96-6.92 (m, 1H), 6.67 (d, J=8.0 Hz, 1H), 6.47 (s, 1H), 6.32 (d, J=8.4 Hz, 1H), 5.57-5.47 (m, 14H), 5.13-4.99 (m, 2H), 4.81-4.68 (m, 11H), 4.59-4.52 (m, 5H), 4.36-4.29 (m, 3H), 4.16-4.08 (m, 1H), 3.99-3.98 (m, 1H), 3.84-3.53 (m, 30H), 3.45-3.38 (m, 12H), 3.13-3.03 (m, 4H), 2.90-2.66 (m, 5H), 2.36-2.32 (m, 1H), 2.26-2.20 (m, 3H), 2.15-2.12 (m, 4H), 2.00-1.99 (m, 2H), 1.88-1.72 (m, 6H), 1.64-1.40 (m, 14H), 1.33-1.24 (m, 17H), 1.14-1.09 (m, 3H), 1.00-0.97 (m, 7H), 0.89-0.81 (m, 8H) ppm.

Anal. HPLC: 95%, Retention time: 7.93 min (method B).

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-4-(carbamoylamino)butyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP2B)

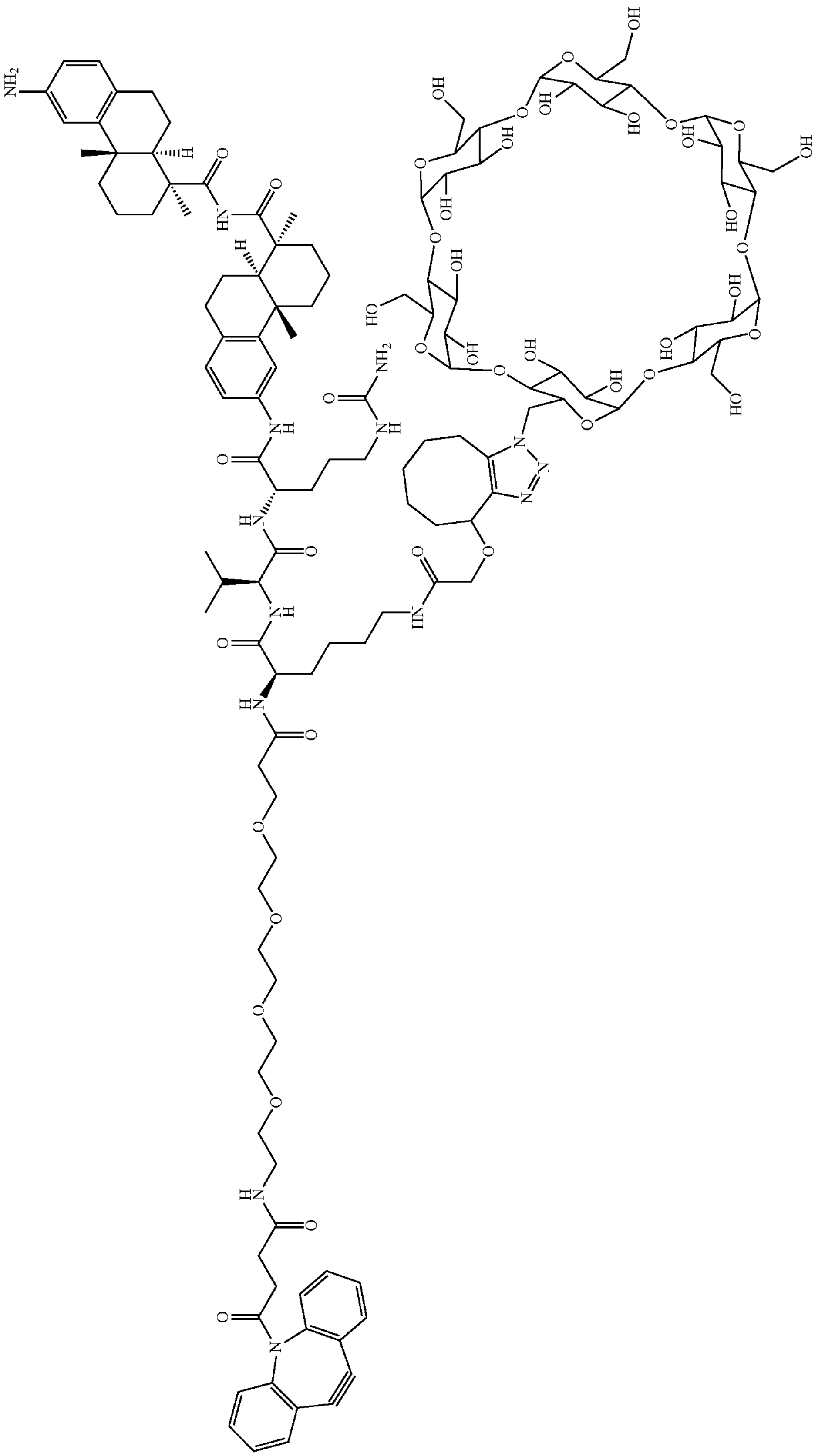

Following the general procedure for Linker-payloads LP1-5, linker-payload LP2B (20 mg, 21% yield) was obtained as a white solid. ESI m/z: 870 $(M/3+H)^+$. $^1$H NMR (400 MHz, $DMSO_{d6}$) δ 9.76 (s, 1H), 9.31 (s, 1H), 8.26-8.16 (m, 1H), 8.11-8.07 (m, 1H), 8.03-7.98 (m, 1H), 7.78-7.75 (m, 1H), 7.68-7.66 (m, 1H), 7.62-7.60 (d, J=7.2 Hz, 1H), 7.55-7.52 (m, 1H), 7.48-7.44 (m, 4H), 7.39-7.30 (m, 4H), 6.96-6.93 (m, 1H), 6.68-6.77 (d, J=8.4 Hz, 1H), 6.47 (m, 1H), 6.34-6.32 (dd, J=8.0 Hz, 1.6 Hz, 1H), 5.96 (br s, 1H), 5.59-5.56 (m, 5H), 5.52-5.45 (m, 7H), 5.38 (s, 2H), 5.13 (br s, 1H), 5.04-5.00 (d, J=14.0 Hz, 1H), 4.81-4.69 (m, 10H), 4.60-4.51 (m, 5H), 4.36-4.11 (m, 5H), 3.98 (br s, 2H), 3.85-3.77 (m, 11H), 3.70-3.58 (m, 10H), 3.45-3.40 (m, 20H), 3.30-3.27 (m, 4H), 3.12-3.04 (m, 5H), 2.98-2.86 (m, 4H), 2.77-2.67 (m, 4H), 2.27-2.19 (m, 4H), 2.16-2.10 (m, 4H), 2.02-1.96 (m, 2H), 1.89-1.73 (m, 8H), 1.64-1.57 (m, 11H), 1.50-1.43 (m, 7H), 1.26-1.20 (m, 12H), 1.15-1.10 (m, 4H), 1.01-0.97 (m, 6H), 0.89-0.82 (m, 6H) ppm. Anal. HPLC: 100%, Retention time: 7.35 min (method B). Solubility: <0.1 mg/mL water.

2-{1-[4-({[(5R)-5-[1-(4-{2-Azatricyclo[10.4.0.04'1] hexadeca-1(12),4(9),5,7,13,15-hexaen-10-yn-2-yl}-4-oxobutanamido)-3,6,9,12-tetraoxapentadecan-15-amido]-5-{[(1 S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl] carbonyl}carbamoyl)-4b,8-dimethyl-4b,5,6,7,8,8a,9,10-octahydrophenanthren-3-yl]carbamoyl}ethyl] carbamoyl}-2-methylpropyl]carbamoyl}pentyl] carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP3B)

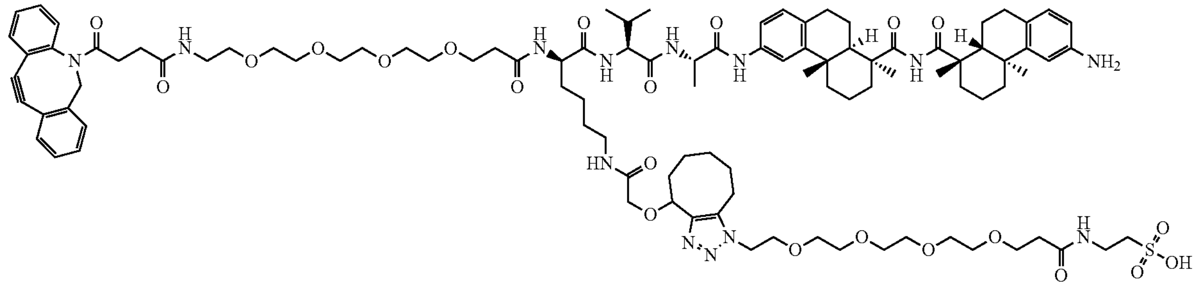 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, linker-payload LP3B (60 mg, 52% yield) was obtained as a white solid. ESI m/z: 642 $(M/3+H)^+$. $^1$H NMR (500 MHz, $CDCl_3$) δ 9.68 (s, 0.6H), 9.25 (s, 0.4H), 8.22-8.07 (m, 3H), 8.02-7.86 (m, 2H), 7.77-7.72 (m, 2H), 7.68-7.60 (m, 2H), 7.54-7.52 (m, 1H), 7.50-7.42 (m, 4H), 7.39-7.27 (m, 4H), 7.22 (s, 1H), 7.08 (s, 1H), 6.97-6.94 (m, 2H), 6.74 (d, J=10.5 Hz, 1H), 6.58 (s, 1H), 6.43 (dd, J=10.0 Hz, 2.0 Hz, 1H), 5.62 (br s, 1H), 5.04-5.00 (m, 1H), 4.93-4.90 (m, 0.4H), 4.76-4.72 (m, 0.6H), 4.52-4.26 (m, 4H), 4.16-4.08 (m, 1H), 3.81-3.75 (m, 4H), 3.61-3.55 (m, 4H), 3.46-3.44 (m, 24H), 3.30-3.27 (m, 5H), 3.08-3.06 (m, 5H), 2.97-2.89 (m, 2H), 2.80-2.74 (m, 4H), 2.54-2.52 (m, 2H), 2.40-2.31 (m, 2H), 2.27-2.22 (m, 4H), 2.16-2.13 (m, 4H), 2.02-1.71 (m, 8H), 1.69-1.45 (m, 10H), 1.40-1.21 (m, 14H), 1.17-1.08 (m, 4H), 1.01-0.98 (m, 6H), 0.89-0.82 (m, 6H) ppm.

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1 S)-1-{[(1S)-1-{[(4bS,8S,8aR)-8-({[(1S,4aS,10aR)-6-amino-1,4a-dimethyl-1,2,3,4,4a,9,10,10a-octahydrophenanthren-1-yl]carbonyl}carbamoyl)-4b,8-dimethyl-4b,5,6,7,8,8a,9,10-octahydrophenanthren-3-yl]carbamoyl}-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP4B)

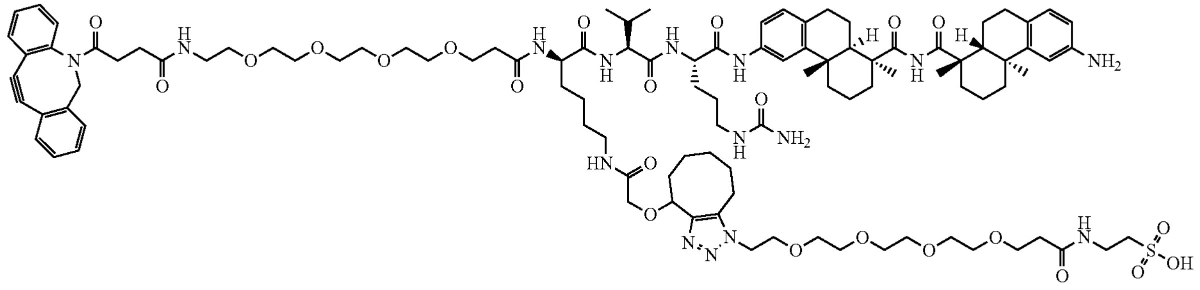 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, compound LP4B (6.0 mg, 20% yield) was obtained as a white solid. ESI m/z: 671 (M/3+H)$^+$. $^1$H NMR (500 MHz, $CDCl_3$) δ 9.37 (s, 1H), 9.29 (s, 1H), 8.24-8.22 (m, 1H), 8.18-8.17 (m, 2H), 8.09 (s, 2H), 8.01-7.99 (m, 1H), 7.97-7.94 (m, 2H), 7.89-7.84 (m, 1H), 7.76 (m, 5H), 7.68 (d, J=7.5 Hz, 2H), 7.62 (d, J=7.5 Hz, 2H), 7.55 (m, 2H), 7.51-7.43 (m, 7H), 7.39-7.28 (m, 7H), 7.08 (m, 4H), 6.96-6.93 (t, J=7.0 Hz, 2H), 6.68 (d, J=8.5 Hz, 2H), 6.48 (s, 2H), 6.35-6.33 (m, 2H), 5.97-5.95 (m, 2H), 5.37 (s, 4H), 5.04-5.01 (m, 2H), 4.74-4.69 (m, 5H), 4.52 (m, 1H), 4.42 (t, J=5.5 Hz, 2H), 4.34-4.27 (m, 4H), 4.18 (m, 1H), 4.13-4.11 (m, 1H), 3.82-3.77 (m, 5H), 3.58-3.55 (m, 6H), 3.49-3.44 (m, 14H), 3.10-3.05 (m, 4H), 2.98-2.93 (m, 4H), 2.77-2.75 (m, 4H), 2.28-2.25 (m, 4H), 2.03-1.99 (m, 2H), 1.64-1.51 (m, 6H), 1.27-1.24 (m, 11H), 1.01-0.98 (m, 11H), 0.89-0.82 (m, 8H) ppm.

1-(4-{2-Azatricyclo[10.4.0.0$^{4,9'}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]carbamoyl}-5-[2-({1-[(2S,3R,4R,5S,6R)-3,4-dihydroxy-6-(hydroxymethyl)-5-{[(2R,3R,4S,5S,6R)-3,4,5-trihydroxy-6-(hydroxymethyl)oxan-2-yl]oxy}oxan-2-yl]-1H,4H,5H,6H,7H,8H,9H-cycloocta[d][1,2,3]triazol-4-yl}oxy)acetamido]pentyl]-3,6,9,12-tetraoxapentadecan-15-amide (LP5B)

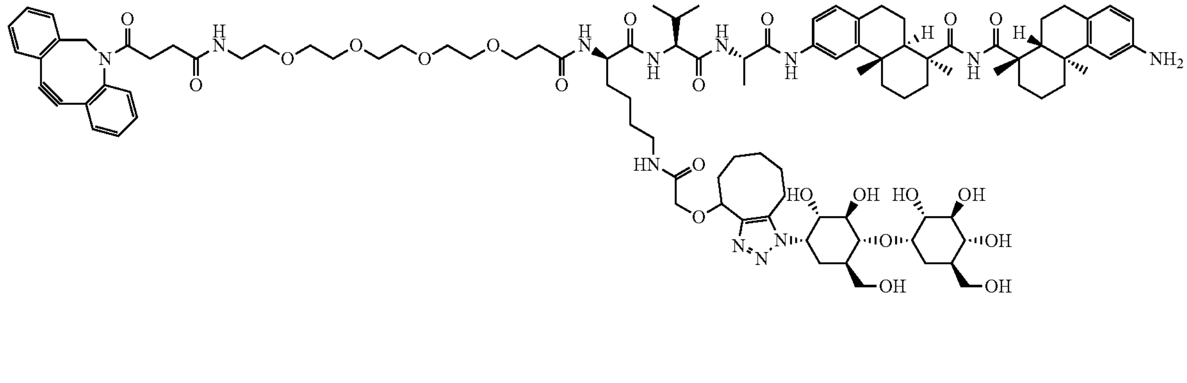 [SMILES: CC(C)[C@H](NC(=O)[C@@H](CCCCNC(=O)COC1CCCCCc2c1nnn2[C@H]1C[C@H](CO)[C@@H](O[C@H]2C[C@H](CO)[C@@H](O)[C@H](O)[C@H]2O)[C@H](O)[C@H]1O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

Following the general procedure for Linker-payloads LP1-5, compound LP5B (15 mg, 27% yield) was obtained as a white solid. ESI m/z: 947 $(M/2+H)^+$. $^1H$ NMR (400 MHz, $DMSO_{d6}$) b 9.69 (s, 0.55H), 9.27 (s, 0.45H), 8.25-8.15 (m, 2H), 8.15-8.05 (m, 2H), 8.05-7.90 (m, 1H), 7.90-7.80 (m, 1H), 7.76 (t, J=6.4 Hz, 1H), 7.66 (d, J=8.0 Hz, 1H), 7.60 (d, J=6.8 Hz, 1H), 7.55-7.40 (m, 4H), 7.40-7.25 (m, 3H), 7.00-6.90 (m, 1H), 6.67 (d, J=8.4 Hz, 1H), 6.47 (s, 1H), 6.32 (d, J=8.0 Hz, 1H), 5.75-5.70 (m, 1H), 5.56 (d, J=6.0 Hz, 1H), 5.50-5.40 (m, 2H), 5.20-4.92 (m, 4H), 4.80-4.70 (m, 1H), 4.70-4.65 (m, 2H), 4.65-4.55 (m, 2H), 4.40-4.25 (m, 2H), 4.20-3.95 (m, 2H), 3.80-3.75 (m, 2H), 3.75-3.45 (m, 23H), 3.30-3.20 (m, 3H), 3.20-2.90 (m, 5H), 2.90-2.65 (m, 3H), 2.60-2.55 (m, 1H), 2.40-1.95 (m, 12H), 1.90-1.70 (m, 5H), 1.70-1.35 (m, 14H), 1.35-1.20 (m, 15H), 1.15-1.05 (m, 3H), 1.00-0.90 (m, 7H), 0.90-0.80 (m, 7H) ppm.

Example 11-6

Linker-Payload LP6B

This example demonstrates methods for the synthesis of the linker-payload LP6B in Table 3, above. This example refers to the compounds numbered from 109 to 113 and linker-payload LP6B in FIG. 26.

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (110)

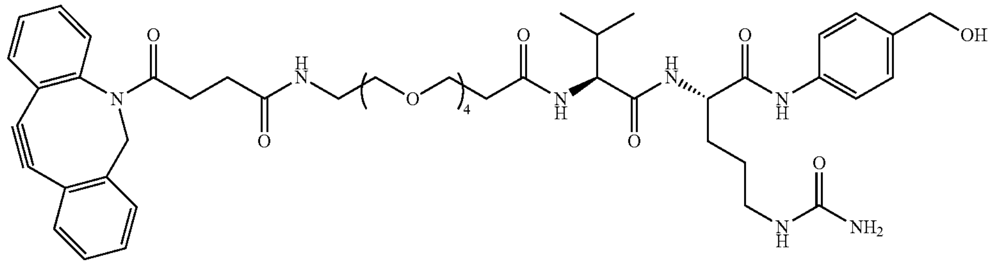

To a solution of compound 108 (0.30 g, 0.54 mmol) in DMF (10 mL) were added HATU (0.31 g, 0.81 mmol) and DIPEA (0.14 g, 1.1 mmol) successively at RT. The mixture was stirred at RT for 15 min. To the reaction solution was then added VC-PAB-OH 109 (CAS: 159857-79-1, 0.21 g, 0.54 mmol) at RT, and the resulting mixture was stirred at RT for 3 h until 108 or 109 were consumed, as monitored by LCMS. The reaction mixture was then filtered through a filtering membrane and the filtrate was concentrated and directly purified by reverse phase flash chromatography (0-100% acetonitrile in water (with 10 mmol/L ammonium bicarbonate)) to give compound 110 (0.30 g, 60% yield) as a white solid. ESI m/z: 617 $(M+H)^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate (112)

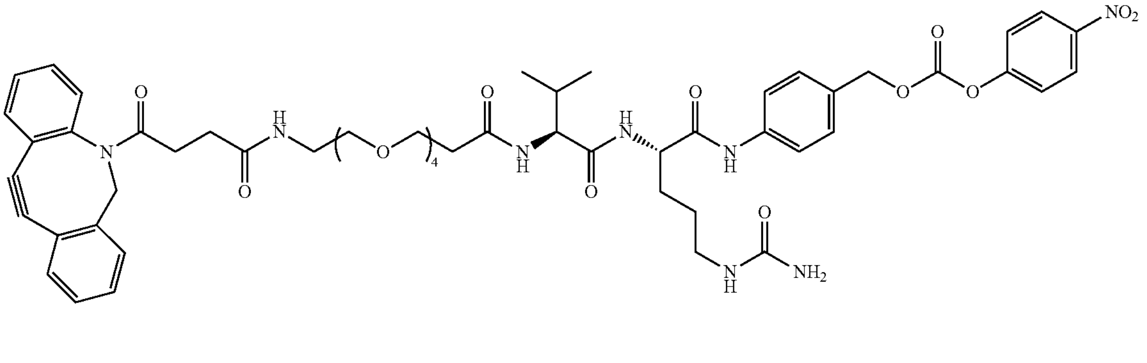

To a solution of compound 110 (0.15 g, 0.16 mmol) in DMF (10 mL) were added bis(4-nitrophenyl) carbonate 111 (0.15 g, 0.49 mmol) and DIPEA (63 mg, 0.49 mmol) successively at 0° C. The mixture was then stirred at RT for 3 h until 110 was consumed, as monitored by LCMS. The reaction mixture was filtered through a filtering membrane and the filtrate was concentrated and directly purified by reverse phase flash chromatography (0-100% acetonitrile in water (with 10 mmol/L ammonium bicarbonate)) to give compound 112 (50 mg, 28% yield) as a white solid. ESI m/z: 1079 $(M+H)^+$.

9H-Fluoren-9-ylmethyl N-({[(4bS,8S,8aR)-8-({[(1S,4aS,10aR)-6-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl)carbamate (113)

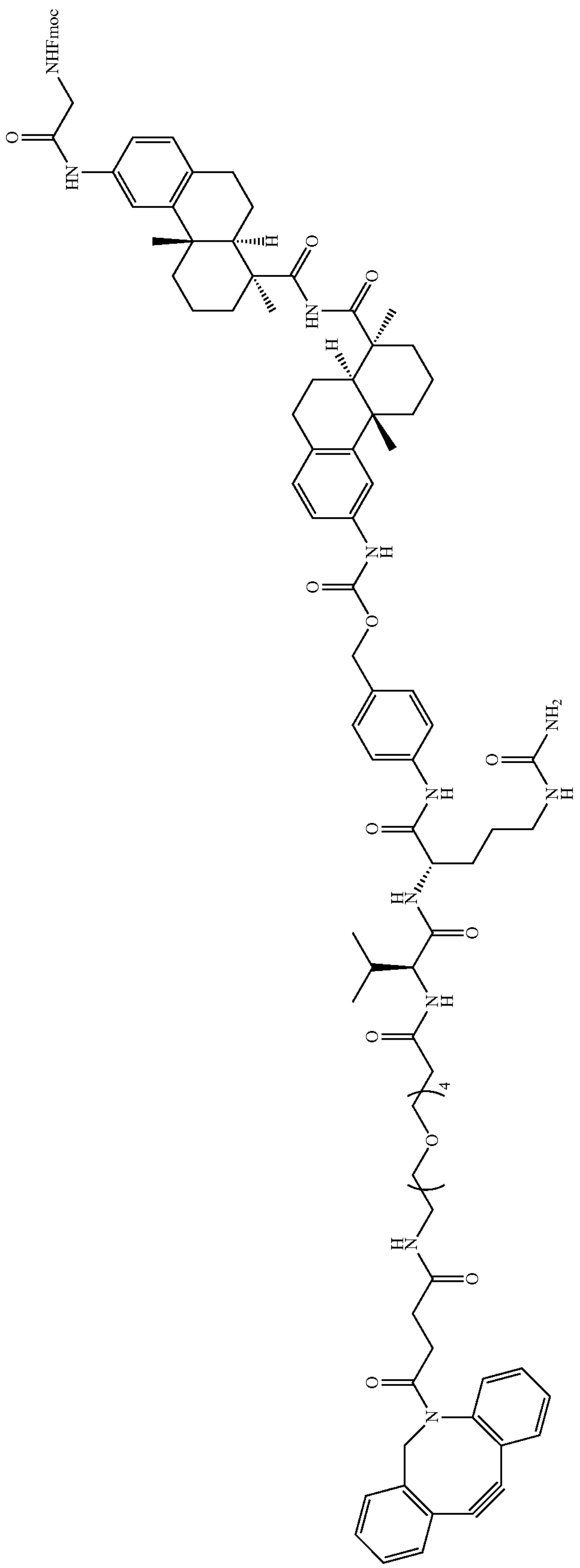

To a mixture of compound 14a (0.10 g, 0.12 mmol) and compound 112 (0.15 g, 0.14 mmol) in DMF (5 mL) were added HOBt (20 mg, 0.15 mmol) and DIPEA (48 mg, 0.37 mmol), and the mixture was stirred at RT for 4 h, which was monitored by LCMS. The reaction mixture was purified by prep-HPLC (method B) to give compound 113 (0.16 g, 72% yield) as a light yellow solid. ESI m/z: 874 $(M/2+1)^+$.

{4-[(2S)-2-[(2S)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(4bS,8S,8aR)-8-{[(1S,4aS,10aR)-6-(2-aminoacetamido)-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamate (LP6B)

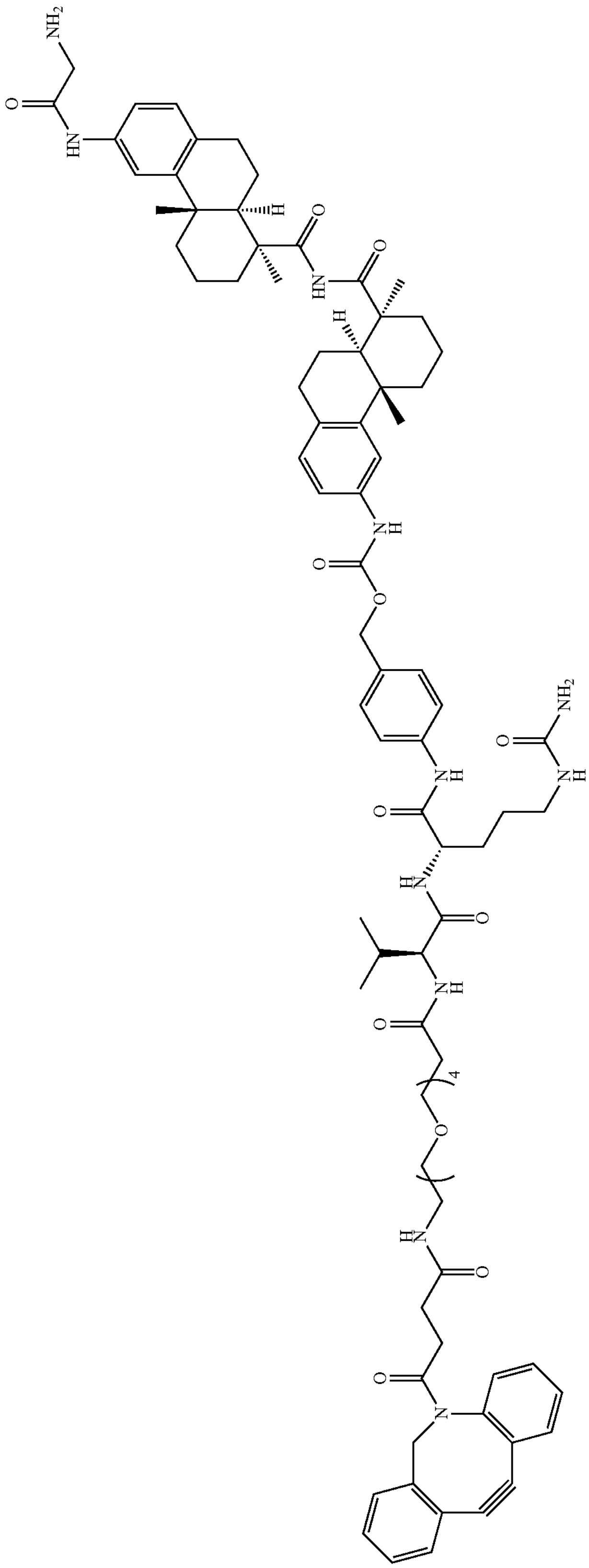

To a solution of compound 113 (0.10 g, 0.057 mmol) in DMF (5 mL) was added piperidine (1 mL) and the mixture was stirred at RT for half an hour until Fmoc was totally removed according to LCMS. The reaction mixture was directly purified by Prep-HPLC (method B) to give compound LP6B (35 mg, 23% yield) as a white solid. ESI m/z: 763 $(M/2+1)^+$. $^1H$ NMR (500 MHz, $DMSO_{d6}$) δ 10.0 (s, 1H), 9.51 (s, 1H), 8.15-8.08 (m, 2H), 7.87 (d, J=8.5 Hz, 1H), 7.76 (t, J=5.0 Hz, 1H), 7.70-7.65 (m, 1H), 7.61 (t, J=8.5 Hz, 3H), 7.51-7.42 (m, 4H), 7.41-7.30 (m, 8H), 7.20-7.10 (m, 1H), 7.00-6.90 (m, 2H), 6.00-5.95 (m, 1H), 5.40 (s, 2H), 5.35-5.30 (m, 1H), 5.10-5.00 (m, 3H), 4.40-4.35 (m, 1H), 4.25-4.20 (m, 1H), 3.65-3.55 (m, 3H), 3.50-3.40 (m, 14H), 3.25 (s, 3H), 3.10-3.00 (m, 4H), 3.00-2.85 (m, 4H), 2.80-2.70 (m, 2H), 2.63-2.61 (m, 1H), 2.60-2.55 (m, 1H), 2.45-2.35 (m, 3H), 2.31-2.20 (m, 3H), 2.20-2.10 (m, 4H), 2.10-1.92 (m, 5H), 1.90-1.82 (m, 4H), 1.68-1.53 (m, 6H), 1.50-1.40 (m, 2H), 1.20-1.10 (m, 2H), 1.02-0.96 (m, 6H), 0.90-0.80 (m, 8H) ppm.

Example 11-7

Linker-Payload LP7B

This example demonstrates methods for the synthesis of the linker-payload LP7B in Table 2, above. This example refers to the compounds numbered 14a, 107, 114 and 115 and linker-payload LP7B in FIG. 27.

9H-Fluoren-9-ylmethyl N-({[(4bS,8S,8aR)-8-({[(1S,4aS,10aR)-6-[(2S)-2-[(2S)-2-{[(tert-butoxy)carbonyl]amino}-3-methylbutanamido]propanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate (114)

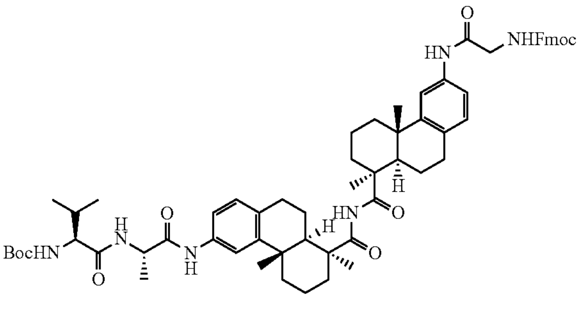

To a solution of compound 14a (66 mg, 0.082 mmol) in DMF (10 mL) were added Boc-Val-Ala-OH 101c (28 mg, 0.098 mmol), DIPEA (32 mg, 0.25 mmol) and HATU (47 mg, 0.12 mmol). The reaction mixture was stirred at RT for 4 h, and monitored by LCMS. The mixture was directly purified by reverse phase flash chromatography (50-90% acetonitrile in aq. ammonium bicarbonate (10 mM)) to give compound 114 (74 mg, 84% yield) as a white solid. ESI m/z: 978 $(M-Boc+1)^+$.

9H-Fluoren-9-ylmethyl N-({[(4bS,8S,8aR)-8-({[(1S,4aS,10aR)-6-[(2S)-2-[(2S)-2-amino-3-methylbutanamido]propanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}methyl) carbamate trifluoroacetic acid salt (115)

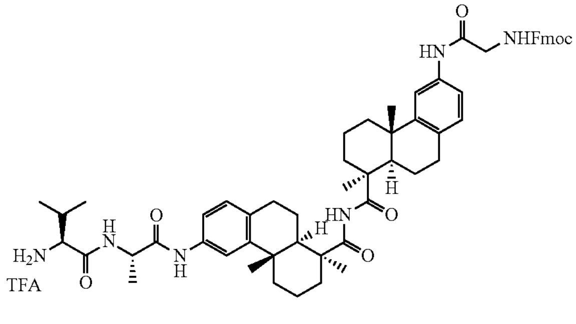

To a solution of compound 114 (74 mg, 0.069 mmol) in DCM (3 mL) was added TFA (1 mL). The reaction mixture was stirred at RT for an hour until Boc was totally removed according to LCMS. The volatiles were removed in vacuo to give crude product 115 (66 mg, 97% yield as TFA salt) as colorless oil. ESI m/z: 978 $(M+1)^+$.

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-{[(4bS,8S,8aR)-8-{[(1S,4aS,10aR)-6-(2-aminoacetamido)-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}ethyl]carbamoyl}-2-methylpropyl]-3,6,9,12-tetraoxapentadecan-15-amide (LP7B)

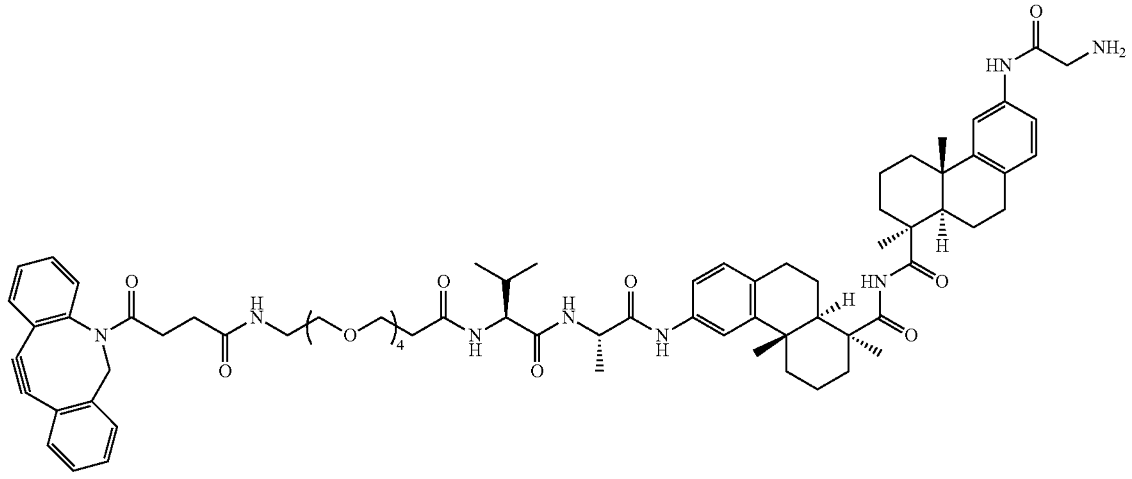

To a solution of compound 115 (60 mg, 61 μmol) in DMF (5 mL) was added DIBAC-suc-PEG4-OSu 107 (48 mg, 74 μmol) and DIPEA (24 mg, 0.18 mmol). The reaction mixture was stirred at RT for 4 h, and monitored by LCMS. To the reaction was then added piperidine (0.2 mL, excess). The reaction mixture was stirred at RT for 30 min until Fmoc was totally removed according to LCMS. The reaction mixture was directly purified by Prep-HPLC (method B) to give LP7B (22 mg, 28% yield) as a white solid. ESI m/z: 1292 $(M+H)^+$. $^1H$ NMR (500 MHz, $DMSO_{d6}$) (with regioisomers) δ 9.66 (s, 0.5H), 9.51 (s, 0.5H), 8.43 (d, J=7.5 Hz, 0.5H), 8.15-8.10 (m, 1.5H), 8.05 (d, J=7.5 Hz, 0.5H), 7.90 (d, J=7.5 Hz, 0.5H), 7.77 (t, J=5.5 Hz, 1H), 7.70-7.65 (m, 1H), 7.65-7.60 (m, 1H), 7.55-7.25 (m, 11H), 6.97 (d, J=8.5 Hz, 2H), 5.02 (d, J=14.5 Hz, 1H), 4.40-4.35 (m, 1H), 4.18 (t, J=7.5 Hz, 0.5H), 4.04 (t, J=7.5 Hz, 0.5H), 3.65-3.50 (m, 3H), 3.50-3.40 (m, 14H), 3.23 (s, 3H), 3.15-3.05 (m, 3H), 2.95-2.85 (m, 3H), 2.80-2.70 (m, 3H), 2.60-2.55 (m, 1H), 2.40-2.10 (m, 12H), 2.00-1.80 (m, 5H), 1.80-1.70 (m, 1H), 1.70-1.55 (m, 5H), 1.24 (s, 1H), 1.20-1.10 (m, 3H), 1.10-0.90 (m, 8H), 0.90-0.80 (m, 8H) ppm.

Example 11-8

Linker-Payload LP8B

This example demonstrates methods for the synthesis of the linker-payload LP8B in Table 3, above. This example refers to the compounds numbered P4B, 117-120 and linker-payload LP8B in FIG. 28.

{4-[(2S)-2-[(2S)-2-Amino-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (117)

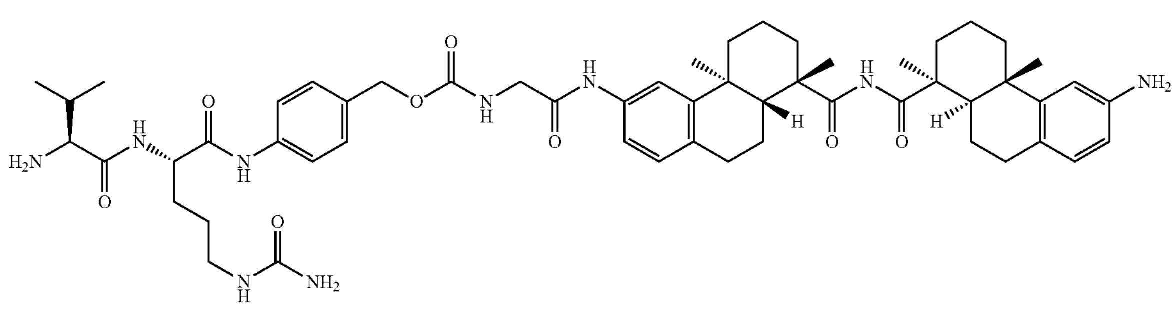 [SMILES: CC(C)[C@H](N)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of Fmoc-vc-PAB-PNP 116 (0.14 g, 0.18 mmol) and payload P4B (0.11 g, 0.18 mmol) in DMF (2 mL) were added HOBt (24 mg, 0.18 mmol) and DIPEA (70 mg, 0.54 mmol) at RT by syringe. The mixture was stirred at RT for 2 h and compound P4B was consumed according to LCMS. To the resulting mixture was added piperidine (42 mg, 0.50 mmol) and the reaction was stirred at RT for 2 h until Fmoc was totally removed, as monitored by LCMS. After filtering through a membrane, the filtrate was concentrated and directly purified by prep-HPLC (method B) to give a compound 117 (45 mg, 27% yield) as a white solid. ESI m/z: 991 $(M+1)^+$. $^1H$ NMR (400 MHz, $DMSO_{d6}$) δ 10.11 (s, 1H), 9.80 (s, 1H), 8.20-8.04 (m, 2H), 7.60 (d, J=8.4 Hz, 2H), 7.52-7.44 (m, 2H), 7.36-7.20 (m, 3H), 6.96 (d, J=8.4 Hz, 1H), 6.68 (d, J=8.2 Hz, 1H), 6.48 (d, J=1.7 Hz, 1H), 6.36-6.29 (m, 1H), 5.98 (t, J=5.6 Hz, 1H), 5.41 (s, 2H), 4.97 (s, 2H), 4.70 (s, 2H), 4.52-4.42 (m, 1H), 3.75 (d, J=6.0 Hz, 2H), 3.07-2.85 (m, 4H), 2.82-2.61 (m, 3H), 2.31-2.06 (m, 6H), 2.00-1.78 (m, 6H), 1.72-1.52 (m, 6H), 1.44-1.09 (m, 13H), 0.99 (d, J=8.5 Hz, 6H), 0.87 (d, J=8.1 Hz, 3H), 0.78 (d, J=6.8 Hz, 3H) ppm.

2,5-Dioxopyrrolidin-1-yl (2R)-6-[2-(cyclooct-2-yn-1-yloxy)acetamido]-2-{[(9H-fluoren-9-ylmethoxy) carbonyl]amino}hexanoate (118)

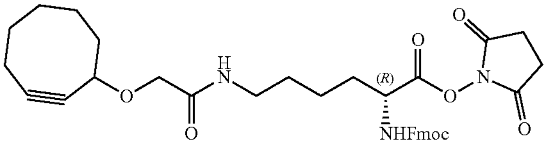

A mixture of compound 103 (0.10 g, 0.19 mmol), EDCI (72 mg, 0.38 mmol) and HOSu (43 mg, 0.38 mmol) in DCM (3 mL) was stirred at RT for 3 h. The reaction mixture was concentrated and the residue was purified by silica gel column chromatography (70% of ethyl acetate in petroleum ether) to give intermediate 118 (55 mg, 47% yield) as a white solid, which was used in the next step without purification. ESI m/z: 630 $(M+1)^+$.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido] phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (119)

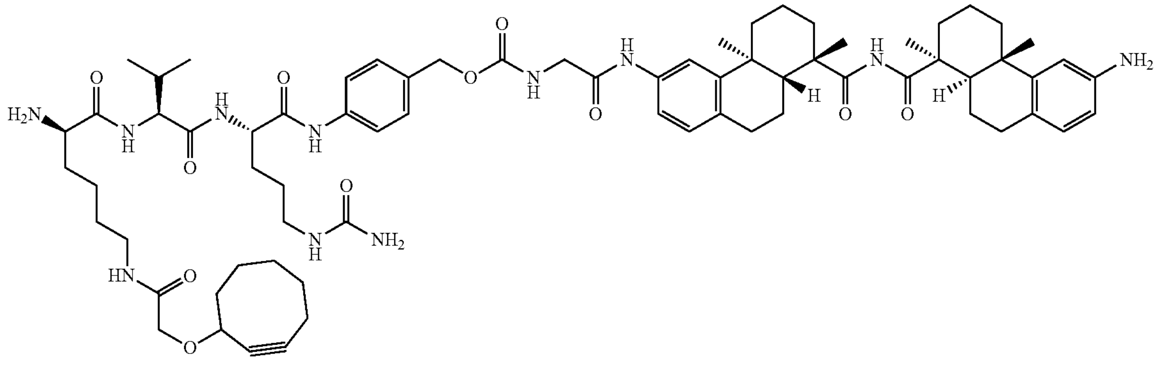 [SMILES: CC(C)[C@H](NC(=O)[C@H](N)CCCCNC(=O)COC1C#CCCCCC1)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of compound 117 (55 mg, 56 μmol) and DIPEA (24 mg, 0.19 mmol) in DMF (1.5 mL) was added the crude intermediate 118 (40 mg, 63 μmol). The reaction mixture was stirred at RT for 2 h until 118 was consumed according to LCMS. The reaction mixture was directly purified by reverse phase flash chromatography (0-100% acetonitrile in water) to give Fmoc-119 (60 mg, ESI m/z: 753 $(M/2+1)^+$) as a white solid, which was dissolved in DMF (1.5 mL). To the solution was added diethylamine (24 mg, 0.33 mmol) and the solution was stirred at RT for 2 h until Fmoc was totally removed according to LCMS. The reaction mixture was directly purified by reverse phase flash chromatography (0-100% acetonitrile in aq. ammonium bicarbonate) to give compound 119 (35 mg, 50% yield from compound 117) as a white solid. ESI m/z: 1282 $(M+H)^+$.

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl)carbamate (120)

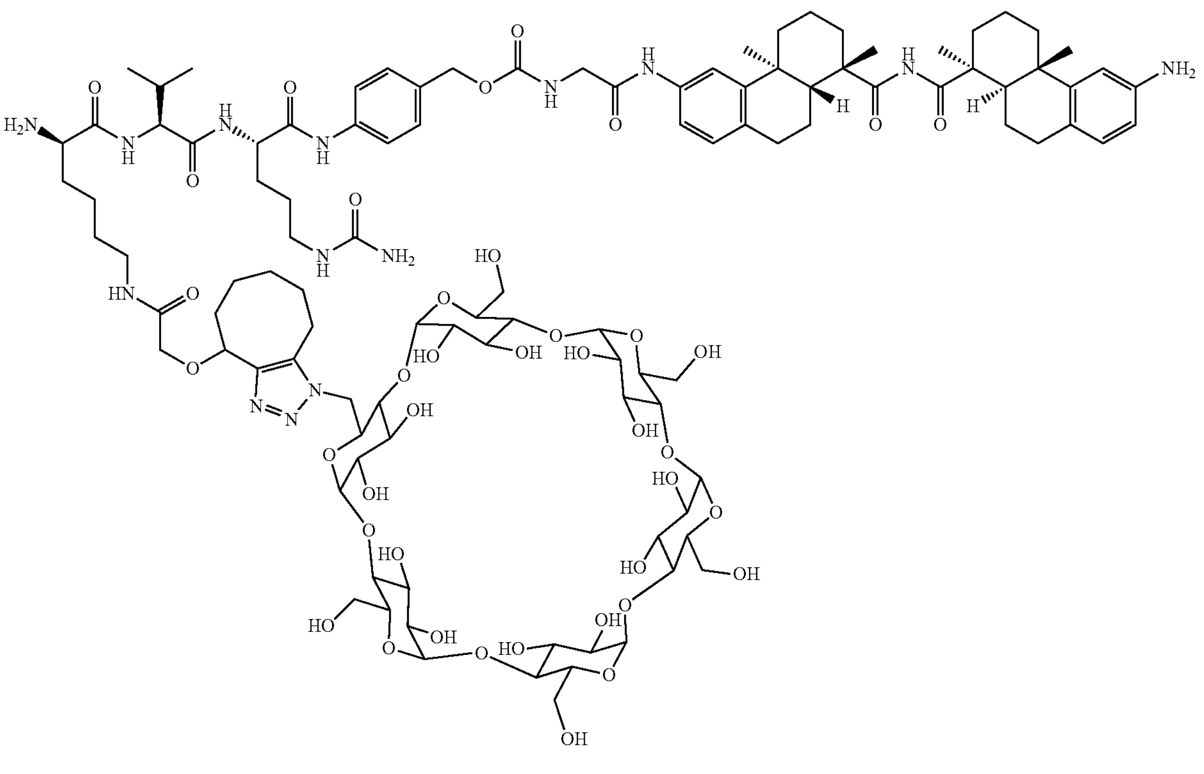 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of compound 119 (70 mg, 54 μmol) in DMF (3 mL) was added a-CD-$N_3$ 105a (0.16 g, 0.16 mmol). The reaction mixture was stirred at 50° C. for 3 days, which was monitored by LCMS. The resulting mixture was then directly purified by reverse phase flash chromatography (0-100% acetonitrile in aq. ammonium bicarbonate (10 mM) to give compound 120 (20 mg, 16% yield) as a white solid. ESI m/z: 1141 $(M/2+1)^+$.

{4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxa-pentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-({[(4bS,8S,8aR)-8-{[(1S,4aS,10aR)-6-amino-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}methyl) carbamate (LP8B)

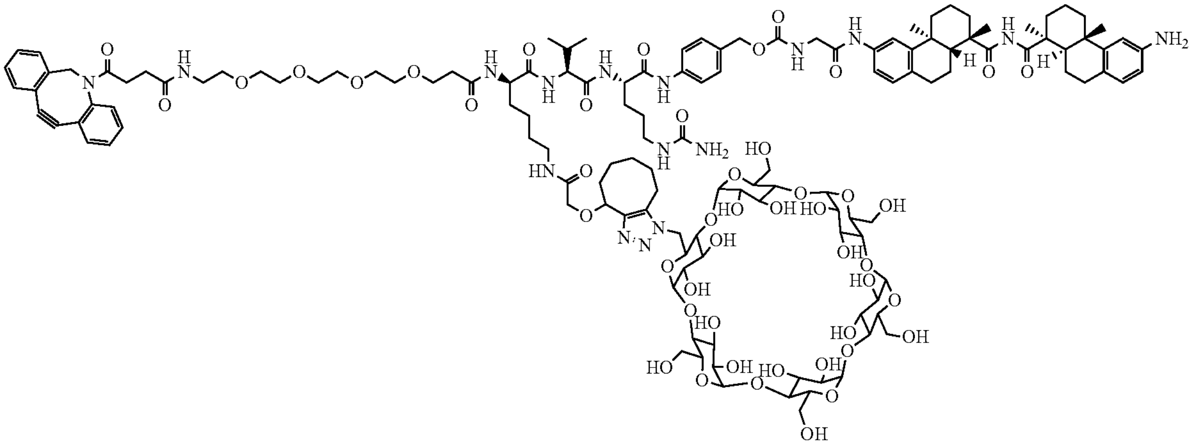 [SMILES: CC(C)[C@H](NC(=O)[C@@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)NCC(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of compound 120 (10 mg, 4.4 μmol) and intermediate 107 (5 mg, 7.7 μmol) in DMF (2 mL) was added DIPEA (16 mg, 0.12 mmol) and the mixture was stirred at room temperature for 16 h. The reaction mixture was directly purified by prep-HPLC (method B) twice to give LP8B (1.5 mg, 12% yield) as a white solid. ESI m/z: 939 (M/3+H)$^+$. $^1$H NMR (500 MHz, DMSO$_{d6}$) δ 9.87-9.66 (m, 1H), 8.22-8.08 (m, 4H), 7.91-7.76 (m, 2H), 7.71-7.61 (m, 4H), 7.56-7.45 (m, 4H), 7.40-7.28 (m, 5H), 6.96 (d, J=8.5 Hz, 1H), 6.68 (d, J=8.1 Hz, 1H), 6.48 (s, 1H), 6.34 (d, J=8.2 Hz, 1H), 6.03-5.96 (m, 1H), 5.67-5.31 (m, 12H), 5.06-4.95 (m, 3H), 4.87-4.66 (m, 7H), 4.63-4.50 (m, 3H), 4.38-4.29 (m, 3H), 4.22-4.13 (m, 1H), 4.06-3.93 (m, 1H), 3.86-3.40 (m, 54H), 3.30-3.19 (m, 4H), 3.17-2.85 (m, 4H), 2.81-2.62 (m, 2H), 2.60-2.54 (m, 3H), 2.41-1.95 (m, 11H), 1.92-1.71 (m, 5H), 1.68-1.40 (m, 13H), 1.33-1.09 (m, 22H), 1.02-0.93 (m, 10H), 0.89-0.78 (m, 9H) ppm. Anal. HPLC (as a mixture of triazole regioisomers): 63%, Retention time: 6.03 min; 36%, Retention time: 6.13 min (method B).

Example 11-9

Linker-Payload LP9B

This example demonstrates methods for the synthesis of the linker-payload LP9B in Table 3, above. This example refers to the compounds numbered 12b, 15, 112, 121, and 122 and linker-payload LP9B in FIG. 29.

9H-Fluoren-9-ylmethyl N-[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate, trifluoroacetic acid salt (15)

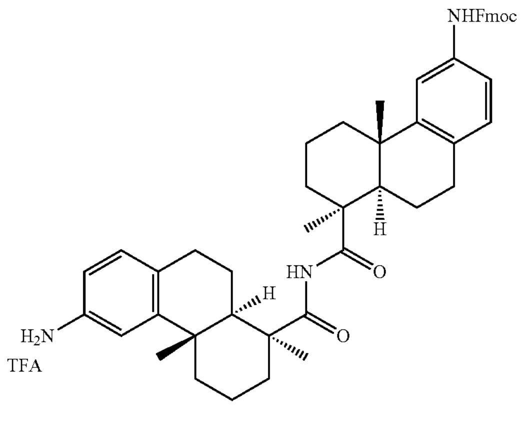

To a solution of compound 12b (0.63 g, 1.0 mmol) in DCM (50 mL) were added Fmoc-OSu (0.40 g, 1.2 mmol) and DIPEA (0.26 g, 2.0 mmol). The mixture was stirred at RT for 16 h, which was monitored by LCMS. The mixture was concentrated in vacuo and the residue was purified by silica gel column chromatography (50-80% ethyl acetate in petroleum ether) to give Boc-15 (0.71 g) as a white solid, which was dissolved in DCM (10 mL). To the solution was added TFA (3 mL) at RT. The reaction mixture was stirred at RT for 4 h until Boc was totally removed according to LCMS. The volatiles were removed in vacuo to give compound 15 as a TFA salt (0.62 g, 74% yield) and colorless oil. ESI m/z: 751 $(M+H)^+$.

9H-Fluoren-9-ylmethyl N-[(4bS,8S,8aR)-8-({[(1S,4aS,10aR)-6-[(2S)-6-amino-2-{[(9H-fluoren-9-yl-methoxy)carbonyl]amino}hexanamido]-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamate, trifluoroacetic acid salt (122)

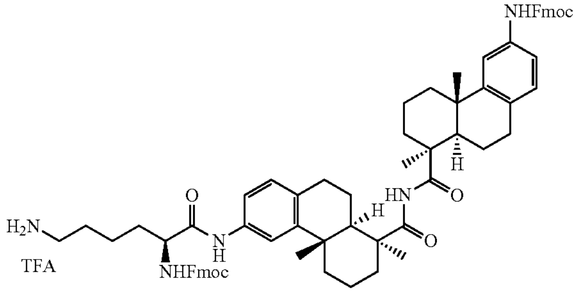

To the solution of compound 15 (0.30 g, 0.40 mmol) in DMF (20 mL) were added Fmoc-Lys(Boc)-OH 121 (0.23 g, 0.48 mmol), HATU (228 mg, 0.60 mmol) and DIPEA (0.16 g, 1.2 mmol) successively at RT. The reaction mixture was stirred at RT for 4 h, and monitored by LCMS. The resulting mixture was directly purified by reverse phase flash chromatography (50-90% acetonitrile in aq. ammonium bicarbonate (10 mM)) to give Boc-122 (0.41 g) as a white solid, 0.24 g of which was dissolved in DCM (20 mL). To the solution was added TFA (3 mL) and the reaction mixture was stirred at RT for an hour until Boc was totally removed according to LCMS. The volatiles were removed in vacuo to give compound 122 as a TFA salt (0.22 g, 79% yield) and colorless oil. ESI m/z: 1101 $(M+H)^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(5S)-5-amino-5-{[(4bS,8S,8aR)-8-{[(1S,4aS,10aR)-6-amino-1,4a-dimethyl-1,2,3,4,4a,9,10,10a-octahydro-phenanthrene-1-carbonyl]carbamoyl}-4b,8-dimethyl-4b,5,6,7,8,8a,9,10-octahydrophenanthren-3-yl]carbamoyl}pentyl]carbamate (LP9B)

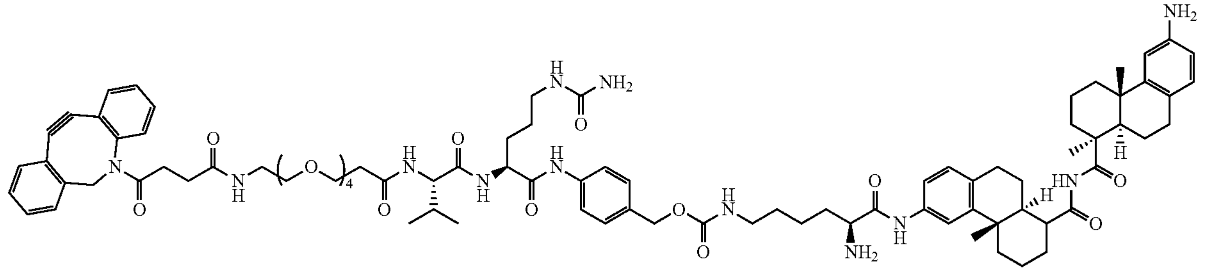

To a mixture of compound 122 (14 mg, 12 μmol) and compound 112 (15 mg, 14 μmol) in DMF (5 mL) were added HOBt (2 mg, 15 μmol) and DIPEA (5 mg, 37 μmol), and the mixture was stirred at RT for 4 h, which was monitored by LCMS. To the reaction mixture was then added piperidine (0.5 mL) and the mixture was stirred at RT for 0.5 h until Fmoc was totally removed according to LCMS. The reaction mixture was then filtered through a membrane and the filtrate was concentrated and directly purified by prep-HPLC (method B) to give LP9B (6 mg, 31% yield) as a white solid. ESI m/z: 798 $(M/2+H)^+$. $^1$H NMR (500 MHz, $DMSO_{d6}$) δ 10.0 (s, 1H), 8.15-8.08 (m, 2H), 7.87 (d, J=8.5 Hz, 1H), 7.76 (t, J=5.0 Hz, 1H), 7.67 (d, J=7.0 Hz, 1H), 7.61 (d, J=7.0 Hz, 1H), 7.60-7.56 (m, 2H), 7.51-7.42 (m, 4H), 7.41-7.24 (m, 6H), 7.20-7.16 (m, 1H), 6.95 (d, J=8.5 Hz, 1H), 6.68 (d, J=8.0 Hz, 1H), 6.50-6.46 (m, 1H), 6.36-6.32 (m, 1H), 6.00-5.96 (m, 1H), 5.40 (s, 2H), 5.02 (d, J=9.0 Hz, 1H), 4.91 (s, 2H), 4.69 (s, 2H), 4.40-4.35 (m, 1H), 4.25-4.20 (m, 1H), 3.65-3.55 (m, 3H), 3.50-3.40 (m, 14H), 3.24-3.20 (m, 2H), 3.10-3.05 (m, 2H), 3.00-2.92 (m, 3H), 2.92-2.85 (m, 1H), 2.80-2.70 (m, 2H), 2.65-2.55 (m, 2H), 2.45-2.35 (m, 2H), 2.31-2.20 (m, 4H), 2.20-2.10 (m, 4H), 2.10-1.92 (m, 3H), 1.90-1.70 (m, 6H), 1.68-1.53 (m, 6H), 1.50-1.30 (m, 8H), 1.25-1.20 (m, 7H), 1.20-1.10 (m, 3H), 1.02-0.96 (m, 6H), 0.90-0.80 (m, 6H) ppm.

Example 11-10

Linker-Payloads LP10B and LP11B

This example demonstrates methods for the synthesis of the linker-payloads LP10B-LP11B in Table 3, above. This example refers to the compounds numbered P7B, P8B, 116, 123a-b, linker-payloads LP10B and LP11B in FIG. 30.

(S)-4-((4bS,8S,8aR)-8-((1S,4aS,10aR)-6-Amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-3-((4-((S)-2-((S)-2-amino-3-methylbutanamido)-5-ureidopentanamido)benzyloxy)carbonylamino)-4-oxobutanoic acid (123a)

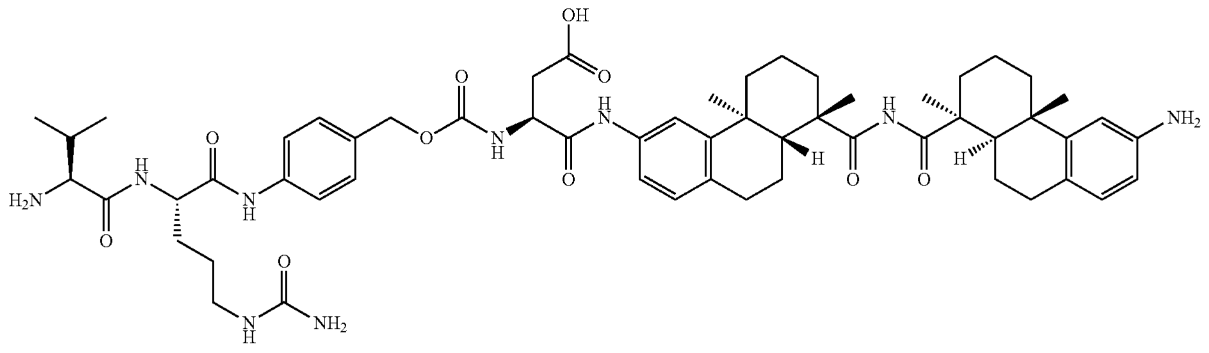 [SMILES: CC(C)[C@H](N)C(=O)N[C@@H](CCCNC(N)=O)C(=O)Nc1ccc(COC(=O)N[C@@H](CC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

To a solution of payload P7 (64 mg, 0.10 mmol) in DMF (5 mL) were added intermediate 116 (92 mg, 0.12 mmol) and DIPEA (26 mg, 0.20 mmol) successively at RT. The reaction mixture was stirred at RT for 4 h, and monitored by LCMS. To the mixture was then added piperidine (0.5 mL), and the reaction mixture was stirred at RT for 10 min until Fmoc was totally removed according to LCMS. The mixture was directly purified by reverse phase flash chromatography (40-70% acetonitrile in aq. ammonium bicarbonate (10 mM)) to give compound 123a (41 mg, 39% yield) as a white solid. ESI m/z: 1049 $(M+H)^+$.

(S)-5-((4bS,8S,8aR)-8-((1S,4aS,10aR)-6-Amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-4-((4-((S)-2-((S)-2-amino-3-methylbutanamido)-5-ureidopentanamido)benzyloxy)carbonylamino)-5-oxopentanoic acid (123b)

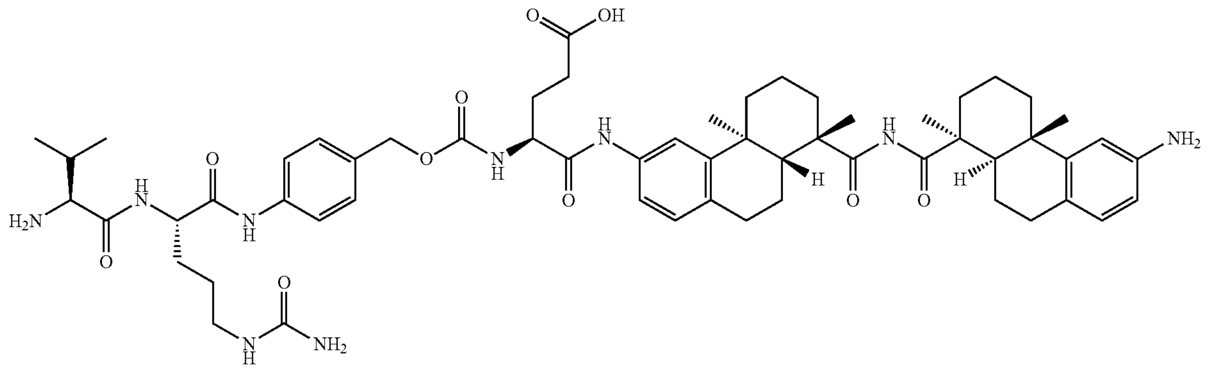 [SMILES: CC(C)[C@H](N)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(N)ccc6CC[C@@H]45)[C@@H]2CC3)cc1]

Following a similar procedure for 123a except substituting P8 (0.53 g, 0.81 mmol) for P7, provides compound 123b (0.61 g, 71% yield) as a white solid. ESI m/z: 1063 $(M+H)^+$.

(3S)-3-{[({4-[(2S)-2-[(2S)-2-[1-(4-{2-Azatricyclo [10.4.0.0$^{4,9}$]hexadeca-1(12),4(9),5,7,13,15-hexaen-10-yn-2-yl}-4-oxobutanamido)-3,6,9,12-tetraoxa-pentadecan-15-amido]-3-methylbutanamido]-5-(carbamoylamino)pentanamido]phenyl}methoxy) carbonyl]amino}-3-{[(4bS,8S,8aR)-8-{[(1S,4aS, 10aR)-6-amino-1,4a-dimethyl-1,2,3,4,4a,9,10,10a-octahydrophenanthrene-1-carbonyl]carbamoyl}-4b, 8-dimethyl-4b,5,6,7,8,8a,9,10-octahydrophenanthren-3-yl]carbamoyl}propanoic acid (LP10B)

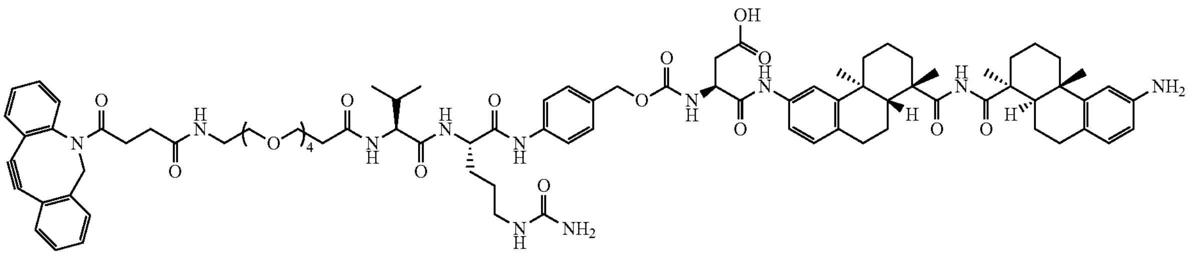

To a solution of compound 123 (21 mg, 20 μmol) in DMF (2 mL) was added intermediate 107 (16 mg, 24 μmol) and DIPEA (5 mg, 40 μmol) successively at RT. The reaction mixture was stirred at RT for 4 h, and monitored by LCMS. The resulting mixture was directly purified by Prep-HPLC (method B) to give compound LP10B (12 mg, 38% yield) as a white solid. ESI m/z: 792 $(M/2+H)^+$. $^1H$ NMR (400 MHz, $DMSO_{d6}$) δ 10.0 (s, 1H), 8.14 (d, J=7.2 Hz, 1H), 8.09 (s, 1H), 7.90 (d, J=8.8 Hz, 1H), 7.85-7.75 (m, 1H), 7.68 (d, J=8.0 Hz, 1H), 7.65-7.55 (m, 3H), 7.55-7.40 (m, 4H), 7.40-7.25 (m, 5H), 6.95 (d, J=8.8 Hz, 1H), 6.67 (d, J=8.0 Hz, 1H), 6.47 (s, 1H), 6.32 (d, J=8.0 Hz, 1H), 6.05-5.95 (m, 1H), 5.43 (s, 2H), 5.05-4.90 (m, 3H), 4.80-4.60 (m, 1H), 4.40-4.35 (m, 2H), 4.25-4.20 (m, 1H), 3.65-3.55 (m, 3H), 3.50-3.40 (m, 25H), 3.20-2.85 (m, 4H), 2.80-2.55 (m, 3H), 2.40-2.30 (m, 3H), 2.30-2.20 (m, 3H), 2.20-2.05 (m, 4H), 2.0-1.50 (m, 12H), 1.50-1.30 (m, 3H), 1.30-1.20 (m, 6H), 1.20-1.05 (m, 2H), 1.05-0.90 (m, 5H), 0.90-0.80 (m, 6H) ppm.

(4S)-4-{[({4-[(2S)-2-[(2S)-2-[1-(4-{2-Azatricyclo [10.4.0.0$^{4,9}$]hexadeca-1(12),4(9),5,7,13,15-hexaen-10-yn-2-yl}-4-oxobutanamido)-3,6,9,12-tetraoxa-pentadecan-15-amido]-3-methylbutanamido]-5-(carbamoylamino)pentanamido]phenyl}methoxy) carbonyl]amino}-4-{[(4bS,8S,8aR)-8-{[(1S,4aS, 10aR)-6-amino-1,4a-dimethyl-1,2,3,4,4a,9,10,10a-octahydrophenanthrene-1-carbonyl]carbamoyl}-4b, 8-dimethyl-4b,5,6,7,8,8a,9,10-octahydrophenanthren-3-yl]carbamoyl}butanoic acid (LP11B)

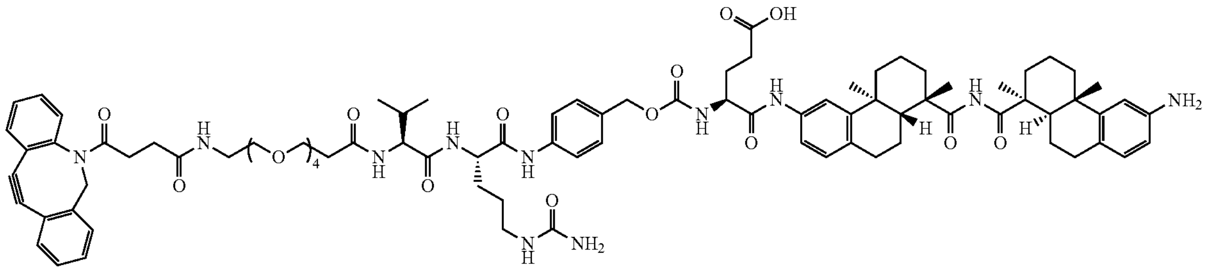

Following a similar procedure for LP10B except substituting 123b (0.10 g, 94 μmol) for 123a, provides compound LP11B (50 mg, 33% yield) as a white solid. ESI m/z: 799 $(M/2+H)^+$. $^1H$ NMR (400 MHz, $DMSO_{d6}$) δ 10.0 (s, 1H), 9.91 (s, 1H), 8.14 (d, J=7.2 Hz, 1H), 8.09 (s, 1H), 7.90 (d, J=8.8 Hz, 1H), 7.85-7.75 (m, 1H), 7.68 (d, J=8.0 Hz, 1H), 7.65-7.55 (m, 3H), 7.55-7.40 (m, 4H), 7.40-7.25 (m, 6H), 6.95 (d, J=8.8 Hz, 1H), 6.67 (d, J=8.0 Hz, 1H), 6.47 (s, 1H), 6.32 (d, J=8.0 Hz, 1H), 6.05-5.95 (m, 1H), 5.43 (s, 2H), 5.05-4.90 (m, 3H), 4.40-4.35 (m, 2H), 4.25-4.20 (m, 1H), 3.65-3.55 (m, 4H), 3.50-3.40 (m, 25H), 3.20-2.85 (m, 4H), 2.80-2.55 (m, 3H), 2.40-2.30 (m, 3H), 2.30-2.20 (m, 3H), 2.20-2.05 (m, 4H), 2.00-1.50 (m, 12H), 1.50-1.30 (m, 3H), 1.30-1.20 (m, 6H), 1.20-1.05 (m, 2H), 1.05-0.90 (m, 5H), 0.90-0.80 (m, 6H) ppm.

Example 11-11

Payload P12B and Linker-Payload LP12B

This example demonstrates methods for the synthesis of the payload P12B in Table C, below, and the linker-payload LP12B in Table C, above. This example refers to the compounds numbered 12b, 107, 124, 125, and 126 and payload P12B linker-payload LP12B in FIG. 31.

((S)-2-((((9H-Fluoren-9-yl)methoxy)carbonyl)amino)-5-(tert-butoxy)-5-oxopentanoyl)-L-alanine (125)

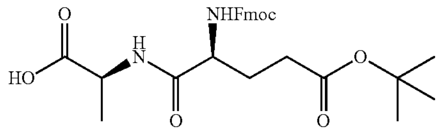

To a solution of Fmoc-Glu(OtBu)-OH (6.0 g, 14 mmol) in DCM (300 mL) were added HOSu (3.2 g, 28 mmol) and EDCI (5.4 g, 28 mmol). The reaction mixture was stirred at RT overnight, and monitored by LCMS. The resulting mixture was diluted with DCM (200 mL) and washed with water (100 mL×2) and brine (100 mL). The organic solution was dried over anhydrous sodium sulfate, filtered, and concentrated in vacuo to give crude compound 124 (8.5 g, ESI m/z: 545 $(M+23)^+$), which was dissolved into DMF (10 mL). To the solution were added alanine (4.2 g, 48 mmol) and DIPEA (6.2 g, 48 mmol). The reaction mixture was stirred at RT overnight, and monitored by LCMS. The resulting mixture was poured into water (100 mL) and acidified with acetic acid to pH 5-6. The mixture was extracted with ethyl acetate and the combined organic solution was concentrated in vacuo. The crude product was purified by reverse phase flash chromatography (0-60% acetonitrile in aq. TFA (0.01%)) to give compound 125 (1 g, 15% yield) as a white solid. ESI m/z: 497 $(M+H)^+$.

(S)-tert-Butyl 4-amino-5-((S)-1-((4bS,8S,8aR)-8-((1S,4aS,10aR)-6-(tert-butoxycarbonylamino)-1,4a-dimethyl-1,2,3,4,4a,9,10,10a-octahydro-phenanthrene-1-carbonylcarbamoyl)-4b,8-dimethyl-4b,5,6,7,8,8a,9,10-octahydrophenanthren-3-ylamino)-1-oxopropan-2-ylamino)-5-oxopentanoate (126)

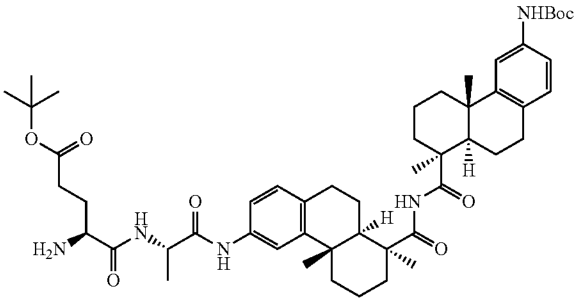 [SMILES: C[C@H](NC(=O)[C@@H](N)CCC(=O)OC(C)(C)C)C(=O)Nc1ccc2c(c1)[C@@]1(C)CCC[C@](C)(C(=O)NC(=O)[C@@]3(C)CCC[C@]4(C)c5cc(NC(=O)OC(C)(C)C)ccc5CC[C@@H]34)[C@@H]1CC2]

To a solution of compound 125 (42 mg, 84 μmol) and DIPEA (28 μl, 0.16 mmol) in DMF (3.0 mL) was added HATU (36 mg, 95 μmol). The reaction mixture was stirred at RT for 10 min before the addition of compound 12b (50 mg, 80 μmol), and the mixture was stirred at RT overnight, which was monitored by LCMS. To the reaction mixture was then added piperidine (1.0 mL) and the mixture was stirred at RT for 3 h until Fmoc was totally removed according to LCMS. The resulting mixture was directly purified by reverse phase flash chromatography (0-100% acetonitrile in aq. TFA (0.01%)) to give compound 126 (20 mg, 28% yield) as a yellow solid. ESI m/z: 885 $(M+H)^+$.

(S)-4-Amino-5-((S)-1-((4bS,8S,8aR)-8-((1S,4aS,10aR)-6-amino-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-1-oxopropan-2-ylamino)-5-oxopentanoic acid (P12B)

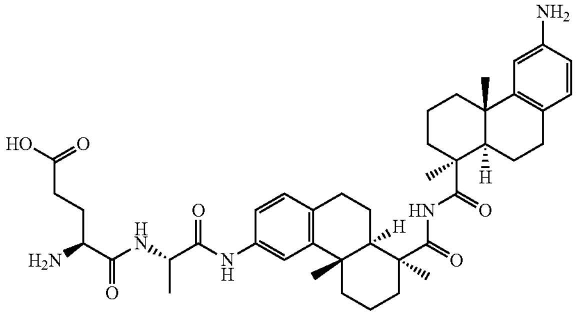 [SMILES: C[C@H](NC(=O)[C@@H](N)CCC(=O)O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2]

A mixture of compound 126 (57 mg, 64 μmol) in neat TFA (2.0 mL) was stirred at RT for an hour, and monitored by LCMS. The resulting mixture was diluted with DCM (20 mL) and concentrated in vacuo. The residue was purified by reverse phase flash chromatography (0-100% acetonitrile in aq. sodium bicarbonate (10 mM)) to give P12B (20 mg, 43% yield) as a white solid. ESI m/z: 365 $(M/2+H)^+$. $^1H$ NMR (400 MHz, $DMSO_{d6}$) δ 9.90 (s, 1H), 8.30 (br s, 1H), 8.09 (s, 1H), 7.50 (s, 1H), 7.33 (d, J=8.4 Hz, 1H), 6.96 (d, J=8.4 Hz, 1H), 6.67 (d, J=8.0 Hz, 1H), 6.46 (s, 1H), 6.33 (dd, J=7.6 Hz and 2.0 Hz, 1H), 4.70 (br s, 1H), 4.41-4.36 (m, 1H), 3.42-3.30 (m, 6H), 2.91-2.85 (m, 1H), 2.78-2.75 (m, 2H), 2.67-2.61 (m, 1H), 2.32-2.27 (m, 4H), 2.16-2.13 (m, 4H), 1.88-1.77 (m, 4H), 1.65-1.58 (m, 4H), 1.29-1.23 (m, 12H), 1.14-1.11 (m, 2H), 1.01 (d, J=7.6 Hz, 6H) ppm.

(4S)-4-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-4-{[(1 S)-1-{[(4bS,8S,8aR)-8-({[(1S,4aS,10aR)-6-amino-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}butanoic acid (LP12B)

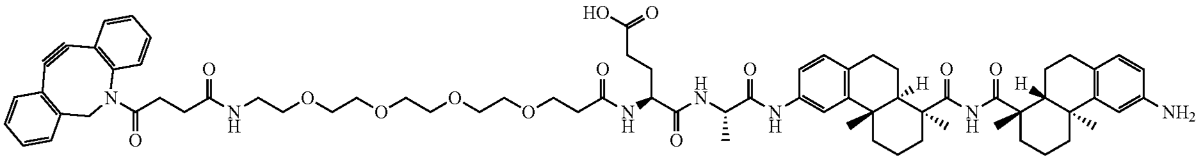

To a solution of compound P12B (10 mg, 14 μmol) in DMF (2.0 ml) were added DIPEA (6 μl, 21 μmol) and compound 107 (11 mg, 16 μmol). The reaction mixture was stirred at RT for 3 h, and monitored by LCMS. The resulting mixture was directly purified by Prep-HPLC (method B) to give compound LP12B (3.5 mg, 20% yield) as a white solid. ESI m/z: 632 $(M/2+H)^+$. $^1H$ NMR (400 MHz, $DMSO_{d6}$) δ 9.64 (s, 1H), 9.49 (s, 1H), 8.41-8.39 (m, 1H), 8.12-8.09 (m, 1H), 7.79 (br s, 1H), 7.67 (d, J=7.2 Hz, 1H), 7.61 (d, J=7.2 Hz, 1H), 7.60 (br s, 1H), 7.52-7.27 (m, 8H), 6.95 (d, J=8.4 Hz, 1H), 6.67 (d, J=8.4 Hz, 1H), 6.47 (s, 1H), 6.33 (dd, J=8.4 Hz and 1.6 Hz, 1H), 5.02 (d, J=14.0 Hz, 1H), 4.70-4.67 (br s, 1H), 4.36-4.30 (m, 1H), 4.21-4.14 (m, 1H), 3.61-3.58 (m, 3H), 3.46-3.45 (m, 15H), 3.08-3.06 (m, 2H), 2.90-2.55 (m, 5H), 2.42-2.09 (m, 12H), 1.98-1.73 (m, 7H), 1.65-1.54 (m, 3H), 1.29-1.25 (m, 12H), 1.17-1.11 (m, 2H), 0.99-0.97 (m, 6H) ppm.

TABLE C

| LXR modulator payloads | | | | |
| --- | --- | --- | --- | --- |
| Cpd code | Structures | MF | FW | Exact Mass |
| P1 | 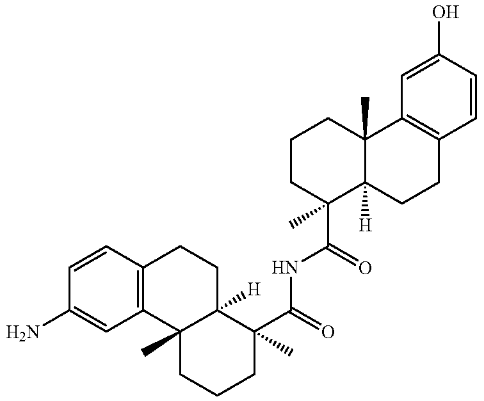 [SMILES: C[C@]1(C(=O)NC(=O)[C@@]2(C)CCC[C@]3(C)c4cc(O)ccc4CC[C@@H]23)CCC[C@]2(C)c3cc(N)ccc3CC[C@@H]12] | $C_{34}H_{44}N_2O_3$ | 528.72 | 528.72 |

TABLE C-continued
| LXR modulator payloads | | | | |
|---|---|---|---|---|
| Cpd code | Structures | MF | FW | Exact Mass |
| P2B | 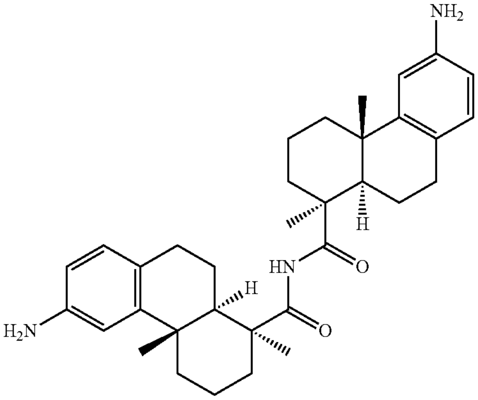 [SMILES: C[C@]1(C(=O)NC(=O)[C@@]2(C)CCC[C@]3(C)c4cc(N)ccc4CC[C@@H]23)CCC[C@]2(C)c3cc(N)ccc3CC[C@@H]12] | $C_{34}H_{45}N_3O_2$ | 527.74 | 527.74 |
| P3B | 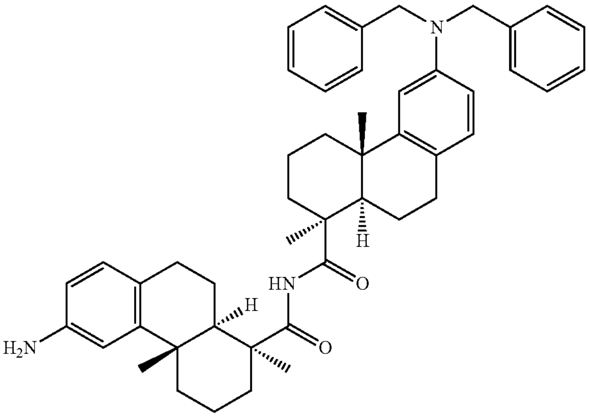 [SMILES: C[C@]1(C(=O)NC(=O)[C@@]2(C)CCC[C@]3(C)c4cc(N(Cc5ccccc5)Cc5ccccc5)ccc4CC[C@@H]23)CCC[C@]2(C)c3cc(N)ccc3CC[C@@H]12] | $C_{48}H_{57}N_3O_2$ | 707.99 | 707.45 |
| P4B | 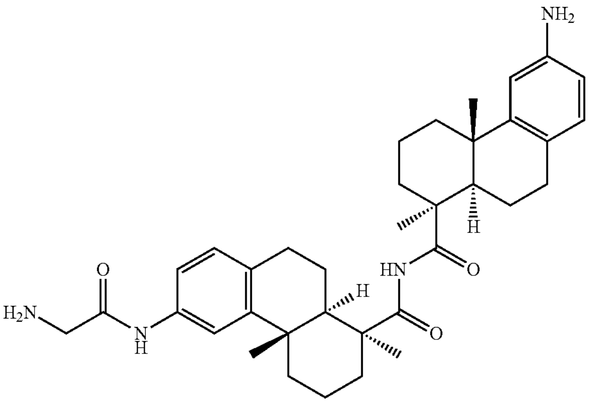 [SMILES: C[C@]1(C(=O)NC(=O)[C@@]2(C)CCC[C@]3(C)c4cc(NC(=O)CN)ccc4CC[C@@H]23)CCC[C@]2(C)c3cc(N)ccc3CC[C@@H]12] | $C_{36}H_{48}N_4O_3$ | 584.79 | 584.37 |

TABLE C-continued
| LXR modulator payloads | | | | |
|---|---|---|---|---|
| Cpd code | Structures | MF | FW | Exact Mass |
| P5B | 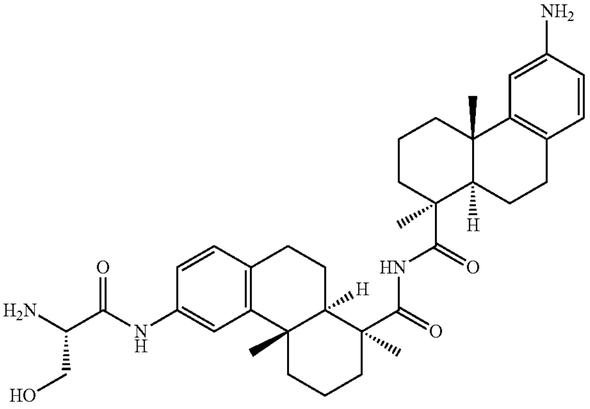 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(N)ccc3CC[C@@H]12] | $C_{37}H_{50}N_4O_4$ | 614.82 | 614.38 |
| P6B | 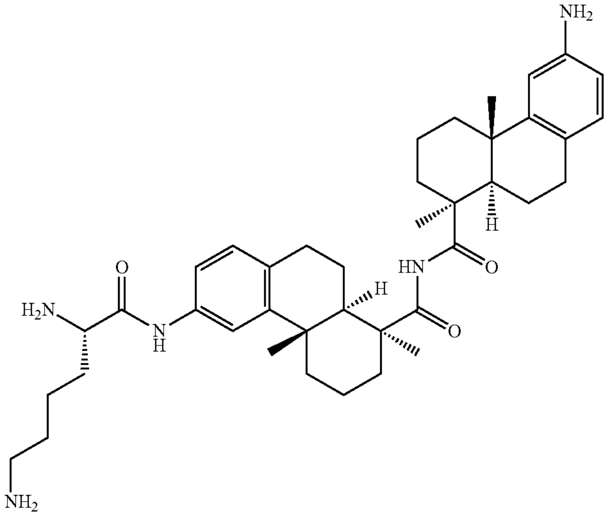 [SMILES: C[C@]1(C(=O)NC(=O)[C@@]2(C)CCC[C@]3(C)c4cc(NC(=O)[C@@H](N)CCCCN)ccc4CC[C@@H]23)CCC[C@]2(C)c3cc(N)ccc3CC[C@@H]12] | $C_{40}H_{57}N_5O_3$ | 655.91 | 655.45 |
| P7B | 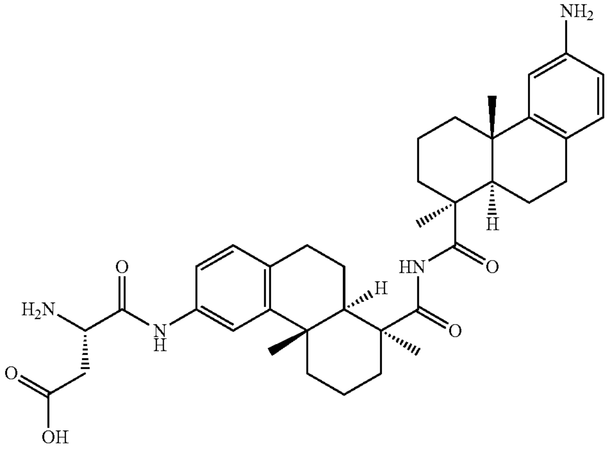 [SMILES: C[C@]1(C(=O)NC(=O)[C@@]2(C)CCC[C@]3(C)c4cc(NC(=O)[C@@H](N)CC(=O)O)ccc4CC[C@@H]23)CCC[C@]2(C)c3cc(N)ccc3CC[C@@H]12] | $C_{38}H_{50}N_4O_5$ | 642.83 | 642.38 |

TABLE C-continued
| LXR modulator payloads | | | | |
|---|---|---|---|---|
| Cpd code | Structures | MF | FW | Exact Mass |
| P8B | 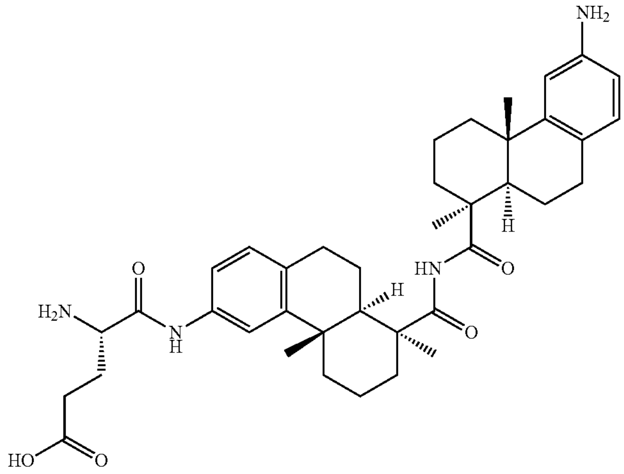 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(N)ccc3CC[C@@H]12] | $C_{39}H_{52}N_4O_5$ | 656.85 | 656.39 |
| P9B | 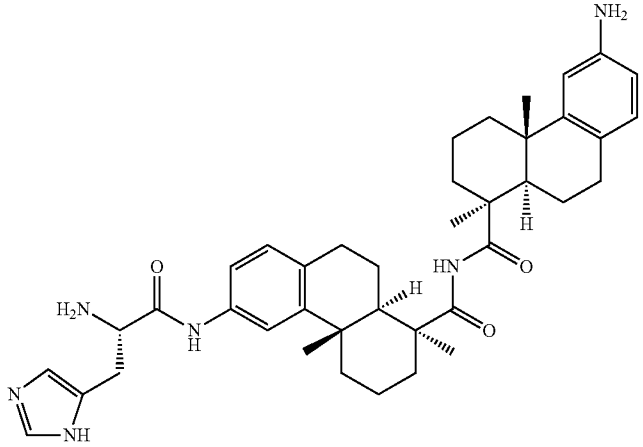 [SMILES: C[C@]1(C(=O)NC(=O)[C@@]2(C)CCC[C@]3(C)c4cc(NC(=O)[C@@H](N)Cc5cnc[nH]5)ccc4CC[C@@H]23)CCC[C@]2(C)c3cc(N)ccc3CC[C@@H]12] | $C_{40}H_{52}N_6O_3$ | 664.88 | 664.41 |
| P10B | 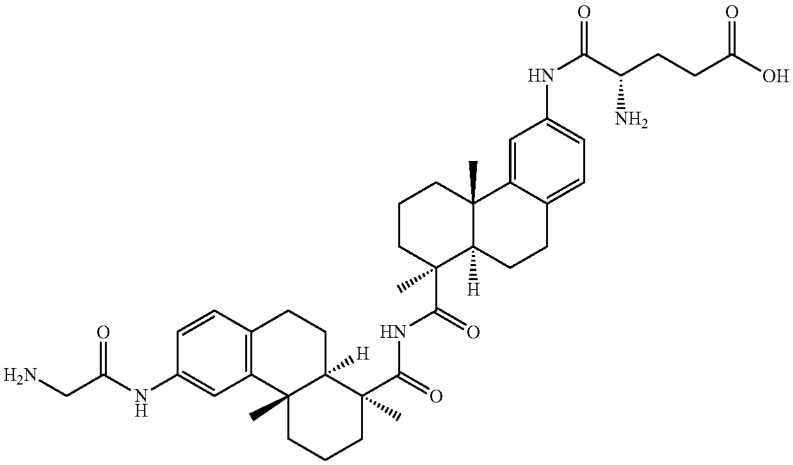 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)CN)ccc3CC[C@@H]12] | $C_{41}H_{55}N_5O_6$ | 713.91 | 713.42 |

TABLE C-continued
| LXR modulator payloads | | | | |
|---|---|---|---|---|
| Cpd code | Structures | MF | FW | Exact Mass |
| P11B | 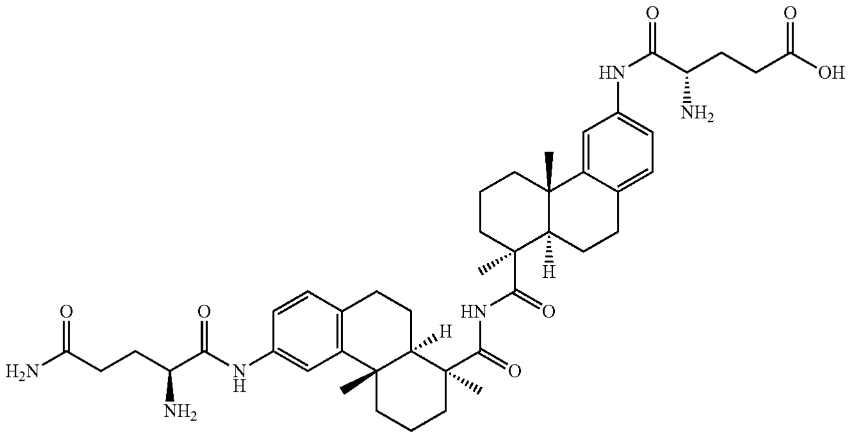 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(NC(=O)[C@@H](N)CCC(N)=O)ccc3CC[C@@H]12] | $C_{44}H_{59}N_5O_8$ | 785.97 | 785.44 |
| P12B | 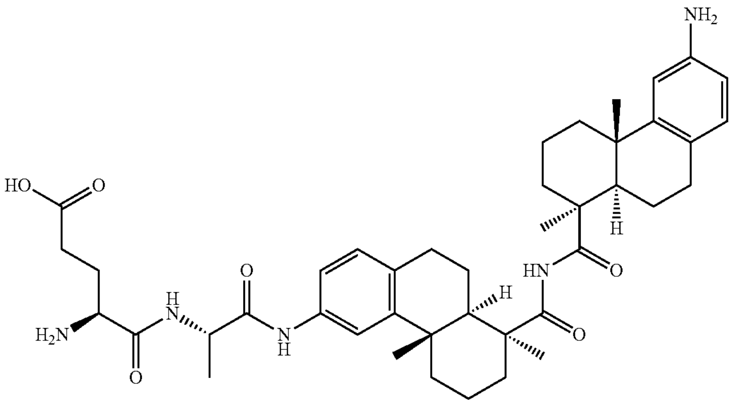 [SMILES: C[C@H](NC(=O)[C@@H](N)CCC(=O)O)C(=O)Nc1ccc2c(c1)[C@@]1(C)CCC[C@](C)(C(=O)NC(=O)[C@@]3(C)CCC[C@]4(C)c5cc(N)ccc5CC[C@@H]34)[C@@H]1CC2] | $C_{42}H_{57}N_5O_6$ | 727.93 | 727.43 |
The structures, calculated Log P values, MS and HPLC results for the above payload compounds are summarized in Table D.

TABLE D

Chemical-Physical Properties of Payloads

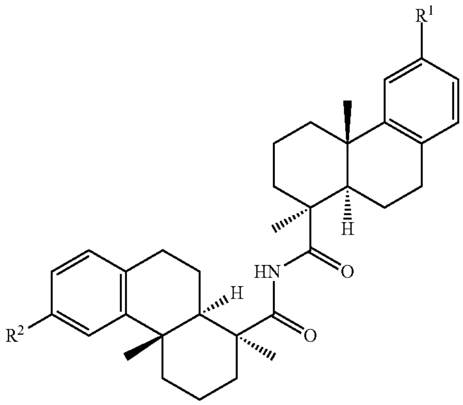

| Cpd | R1 | R2 | cLogP | MS (M + H) | HPLC Purity (%) | HPLC RT (min) |
|---|---|---|---|---|---|---|
| P1 | OH | $NH_2$ | +++ | 529.3 | 95 | 8.66 |
| P2B | $NH_2$ | $NH_2$ | +++ | 528.2 | 95 | 9.11 |
| P3B | $NH_2$ | $NBn_2$ | +++ | 354.8 (M/2 + H) | 95 | 8.87 |
| P4B | $NH_2$ | $NHC(O)CH_2NH_2$ (Gly) | ++ | 585.4 | 98 | 8.20 |
| P5B | $NH_2$ | NHC(O)(S)— $CH(CH_2OH)NH_2$ (Ser) | ++ | 615.4 | 100 | 7.86 |
| P6B | $NH_2$ | $NHC(O)CH((CH_2)_4NH_2)NH_2$ (Lys) | +++ | 656.5 | 100 | 8.89 |
| P7B | $NH_2$ | $NHC(O)CH(CH_2CO_2H)NH_2$ (Asp) | + | 643.4 | 100 | 6.64 |
| P8B | $NH_2$ | $NHC(O)CH(CH_2CH_2COOH)$ $NH_2$ (Glu) | + | 657.4 | 97 | 6.69 |
| P9B | $NH_2$ | $NHC(O)CH(CH_2$— imidazole)$NH_2$ (His) | ++ | 665.3 | 97 | 5.94 |
| P10B | $NHC(O)CH_2NH_2$ (Gly) | $NHC(O)CH(CH_2CH_2COOH)$ $NH_2$ (Glu) | + | 714.5 | 100 | 6.12 |
| P11B | $NHC(O)CH(CH_2CH_2$ $COOH)NH_2$ (Glu) | $NHC(O)CH(CH_2CH_2COOH)$ $NH_2$ (Glu) | + | 393.8 (M/2 + H) | 100 | 5.45 |
| P12B | $NH_2$ | $NHC(O)CH(CH_3)NHC(O)CH$ $(CH_2CH_2COOH)NH_2$ (AlaGlu) | + | 728.5 | 100 | 6.61, 6.67 |

6 < +++ < 12; 4 < ++ < 6; 0 < + < 4

The molecular formulae, molecular weights, calculated Log P values, MS, and HPLC results for the above linker-payload compounds are summarized in Table E.

TABLE E

Chemical-Physical Properties of Payloads

| Cpd | MF | MW | cLogP | Purity (%) | MS m/z (100%) | highest MS m/z | HPLC RT (min) |
|---|---|---|---|---|---|---|---|
| LP1 | $C_{124}H_{176}N_{12}O_{43}$ | 2522.81 | + | 95 | 841.7 [M/3 + H] | 1262.0 [M/2 + H] | 7.93 (B) |
| LP2B | $C_{127}H_{182}N_{14}O_{44}$ | 2608.87 | + | 100 | 870.3 [M/3 + H] | 870.3 [M/3 + H] | 7.35 (B) |
| LP3B | $C_{101}H_{143}N_{13}O_{22}S$ | 1923.36 | +++ | 100 | 641.8 [M/3 + H] | 962.5 [M/2 + H] | 6.20 (B) |
| LP4B | $C_{104}H_{149}N_{15}O_{23}S$ | 2009.45 | ++ | 99 | 670.5 [M/3 + H] | 1004.9 [M/2 + H] | 5.94 (B) |
| LP5B | $C_{100}H_{138}N_{12}O_{24}$ | 1892.23 | ++ | 95 | 631.5 [M/3 + H] | 946.6 [M/2 + H] | 6.94 (B) |
| LP6B | $C_{85}H_{109}N_{11}O_{15}$ | 1524.84 | +++ | 96 | 763.0 [M/2 + H] | 763.0 [M/2 + H] | 8.63 (B) |

TABLE E-continued

| Chemical-Physical Properties of Payloads | | | | | | | |
|---|---|---|---|---|---|---|---|
| Cpd | MF | MW | cLogP | Purity (%) | MS m/z (100%) | highest MS m/z | HPLC RT (min) |
| LP7B | $C_{74}H_{96}N_8O_{12}$ | 1289.60 | +++ | 97 | 645.4 [M/2 + H] | 1290.7 [M + H] (23%) | 8.67 (B) |
| LP8B | $C_{137}H_{192}N_{16}O_{47}$ | 2815.07 | + | 99 | 939.2 [M/2 + H] | 939.2 [M/2 + H] | 7.60 (B) |
| LP9B | $C_{89}H_{118}N_{12}O_{15}$ | 1595.96 | +++ | 100 | 798.3 [M/2 + H] | 798.3 [M/2 + H] | 8.58 (B) |
| LP10B | $C_{87}H_{111}N_{11}O_{17}$ | 1582.88 | +++ | 97 | 528.4 [M/3 + H] | 792.0 [M/2 + H] | 7.11 (B) |
| LP11B | $C_{88}H_{113}N_{11}O_{17}$ | 1596.90 | +++ | 96 | 799.2 [M/2 + H] | 799.2 [M/2 + H] | 7.10 (B) |
| LP12B | $C_{72}H_{91}N_7O_{13}$ | 1262.53 | +++ | 100 | 631.8 [M/2 + H] | 631.8 [M/2 + H] | 7.51 (B) |

6 < +++ < 12; 4 < ++ < 6; −2 < + < 4

Figure 2:
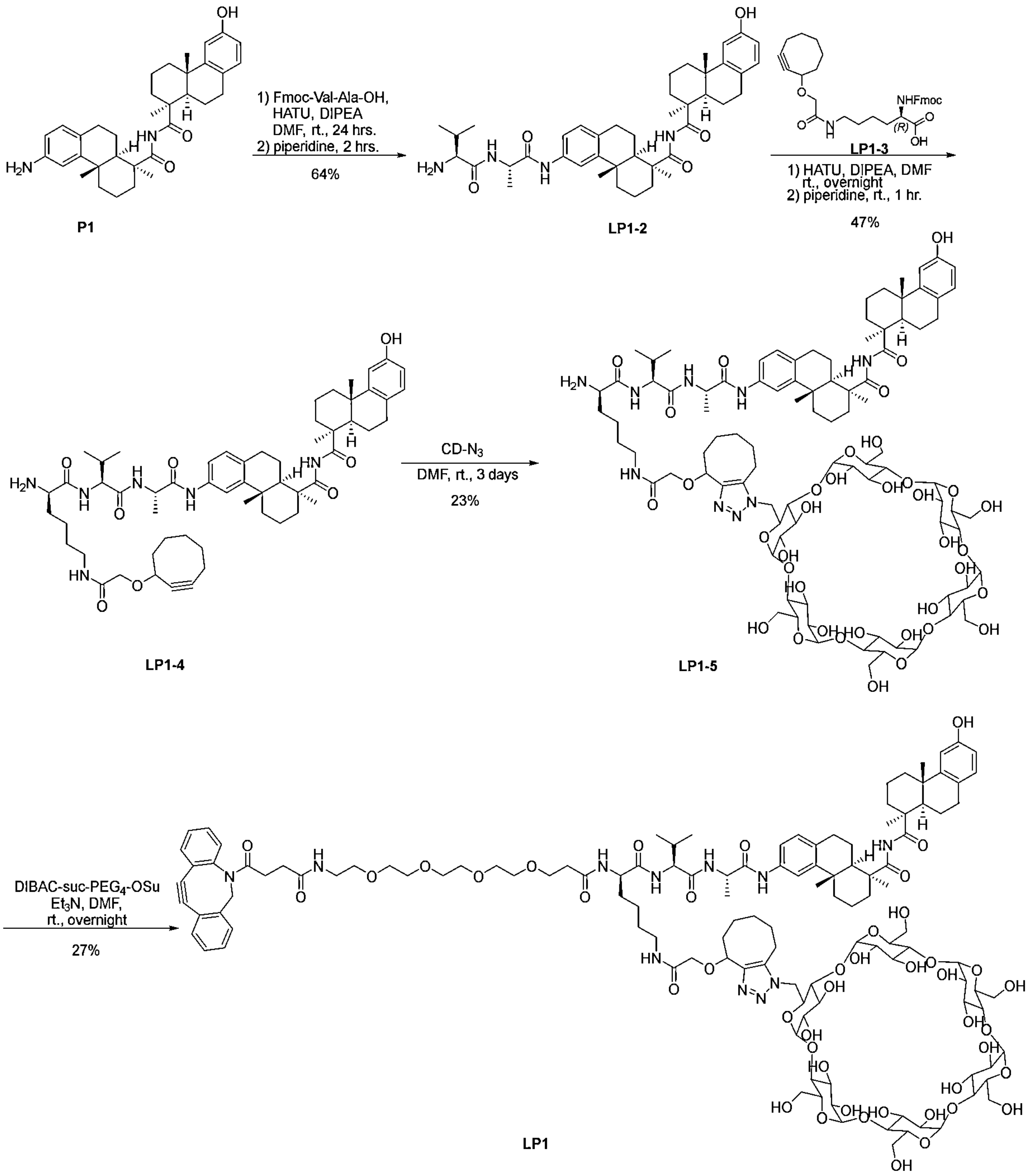
FIG. 2 provides a scheme for the synthesis of LP1.

Example 12. Synthesis of LP1 (FIG. 2)

(1S,4aS,10aR)-6-((S)-2-((S)-2-Amino-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (LP1-2)

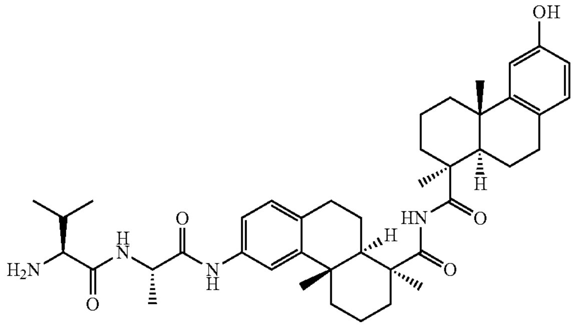 [SMILES: CC(C)[C@H](N)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of P1 (53 mg, 0.10 mmol) in DMF (1 mL) were added Fmoc-Val-Ala-OH (41 mg, 0.10 mmol), HATU (38 mg, 0.1 mmol) and diisopropylethylamine (26 mg, 0.20 mmol) successively. After stirring at 25° C. for 24 hours until P1 was consumed according to LCMS, the mixture was added piperidine (0.1 mL) and the resulting solution was stirred at 25° C. for another 3 hours. After filtration, the filtrate was directly purified by prep-HPLC (method B) to give compound LP1-2 (45 mg, 64% yield) as a white solid. ESI m/z: 699 $(M+1)^+$. $^1$H NMR (500 MHz, methanol$_{d4}$) δ 8.40 (s, 1H), 7.47 (s, 1H), 7.32 (d, J=8.0 Hz, 1H), 7.03 (d, J=8.3 Hz, 1H), 6.88 (d, J=8.2 Hz, 1H), 6.72 (d, J=2.4 Hz, 1H), 6.56 (dd, J=8.3, 2.4 Hz, 1H), 4.60-4.48 (m, 1H), 3.22-3.11 (m, 1H), 3.02-2.93 (m, 1H), 2.92-2.76 (m, 3H), 2.74-2.70 (m, 1H), 2.43-2.31 (m, 3H), 2.28 (d, J=14.1 Hz, 3H), 2.16-1.96 (m, 3H), 1.81 (s, 1H), 1.78-1.65 (m, 4H), 1.53-1.42 (m, 4H), 1.38 (d, J=5.3 Hz, 6H), 1.33-1.22 (m, 2H), 1.14 (d, J=6.6 Hz, 6H), 1.09 (d, J=18.6 Hz, 6H) ppm.

(1S,4aS,10aR)-6-((2S)-2-((2S)-2-((2R)-2-Amino-6-(2-(cyclooct-2-ynyloxy)acetamido)hexanamido)-3-methylbutanamido)propanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (LP1-4)

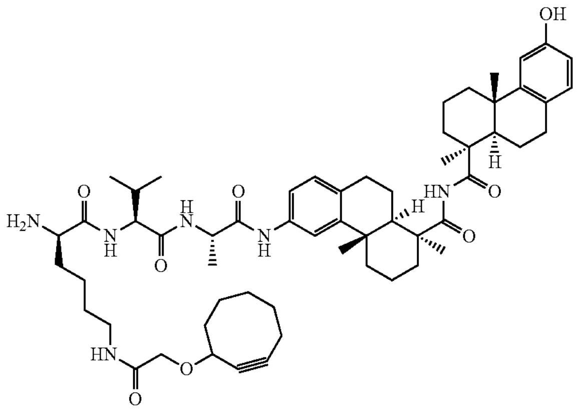 [SMILES: CC(C)[C@H](NC(=O)[C@H](N)CCCCNC(=O)COC1C#CCCCCC1)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-3 (35 mg, 0.064 mmol) in DMF (1 mL) were added HATU (24 mg, 0.064 mmol) and compound LP1-2 (45 mg, 0.064 mmol) in succession at room temperature. The mixture was stirred for a few minutes at room temperature until the mixture was homogenous. To this mixture was added diisopropylethylamine (41 mg, 0.32 mmol) at room temperature by syringe. The resulting mixture was stirred at room temperature overnight (16 hours) until LP1-2 was mostly consumed according to LCMS. To this reaction mixture was then added piperidine (0.1 mL, excess) dropwise at room temperature and the mixture was stirred for another 3 hours until Fmoc was removed, as monitored by LCMS. The reaction mixture was directly purified by reversed phase flash chromatography or prep-HPLC (method B, basic condition) to give compound LP1-4 (30 mg, 47% yield) as a white solid. ESI m/z: 991 $(M+1)^+$. $^1$H NMR (500 MHz, methanol$_4$) δ 7.51 (d, J=1.5 Hz, 1H), 7.37 (dd, J=8.3, 2.0 Hz, 1H), 7.02 (d, J=8.3 Hz, 1H), 6.89 (d, J=8.4 Hz, 1H), 6.72 (d, J=2.4 Hz, 1H), 6.56 (dd, J=8.3, 2.5 Hz, 1H), 4.64-4.57 (m, 1H), 4.48 (q, J=7.1 Hz, 1H), 4.33-4.27 (m, 1H), 4.20 (d, J=6.7 Hz, 1H), 3.93 (m, 2H), 3.43 (t, J=6.6 Hz, 1H), 3.24 (t, J=6.9 Hz, 2H), 3.02-2.93 (m, 2H), 2.92-2.76 (m, 3H), 2.40-2.32 (m, 2H), 2.33-2.23 (m, 4H), 2.22-2.12 (m, 3H), 2.12-2.00 (m, 5H), 1.99-1.91 (m, 1H), 1.91-1.81 (m, 2H), 1.78-1.66 (m, 6H), 1.66-1.58 (m, 1H), 1.58-1.49 (m, 2H), 1.45 (d, J=7.1 Hz, 6H), 1.38 (d, J=4.0 Hz, 6H), 1.34-1.22 (m, 4H), 1.14 (d, J=7.0 Hz, 6H), 1.06-0.98 (m, 6H) ppm.

(1S,4aS,10aR)-N-{[(1S,4aS,10aR)-6-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (LP1-5)

To a solution of compound LP1-4 (30 mg, 30 μmol) in DMF (0.5 mL) was added a solution of CD-$N_3$ (60 mg, 60 μmol) in DMF (0.5 mL) at room temperature by syringe. The mixture was stirred at 20-25° C. for 3 days. Compound LP1-4 was mostly consumed according to LCMS. The reaction mixture was directly purified by prep-HPLC (method B) to give compound LP1-5 (14 mg, 23% yield) as a white solid. ESI m/z: 995 $(M/2+1)^+$. 1H NMR (500 MHz, methanol$_{d4}$) δ 8.40 (s, 1H), 7.56-7.52 (m, 1H), 7.32 (t, J=7.7 Hz, 1H), 7.03 (d, J=8.4 Hz, 1H), 6.88 (d, J=8.3 Hz, 1H), 6.72 (d, J=2.4 Hz, 1H), 6.56 (dd, J=8.2, 2.3 Hz, 1H), 5.24-5.16 (m, 1H), 5.01-4.95 (m, 6H), 4.65-4.59 (m, 1H), 4.52-4.44 (m, 1H), 4.31-4.22 (m, 2H), 4.13-3.73 (m, 22H), 3.63-3.43 (m, 14H), 3.14-2.72 (m, 7H), 2.45-2.32 (m, 3H), 2.28 (d, J=13.8 Hz, 3H), 2.22-1.85 (m, 11H), 1.82-1.59 (m, 9H), 1.55-1.41 (m, 8H), 1.38 (d, J=5.3 Hz, 6H), 1.31-1.26 (m, 3H), 1.14 (d, J=7.2 Hz, 6H), 1.06-0.93 (m, 6H) ppm.

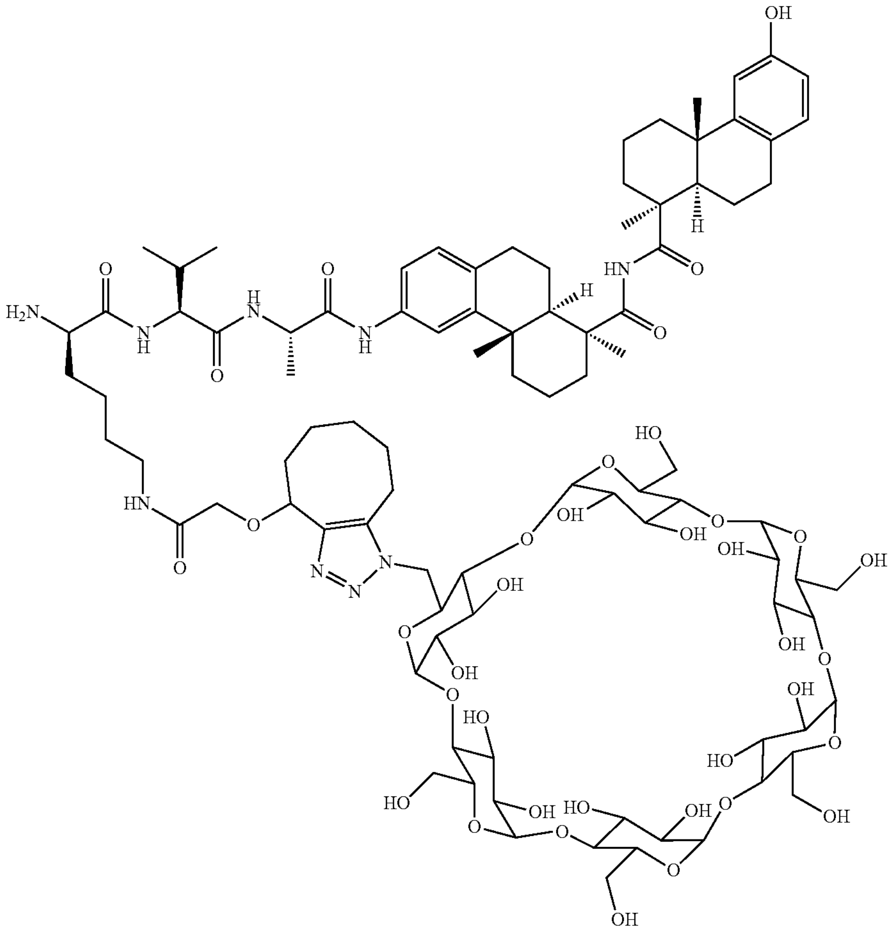 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1 S)-1-{[(1 S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP1)

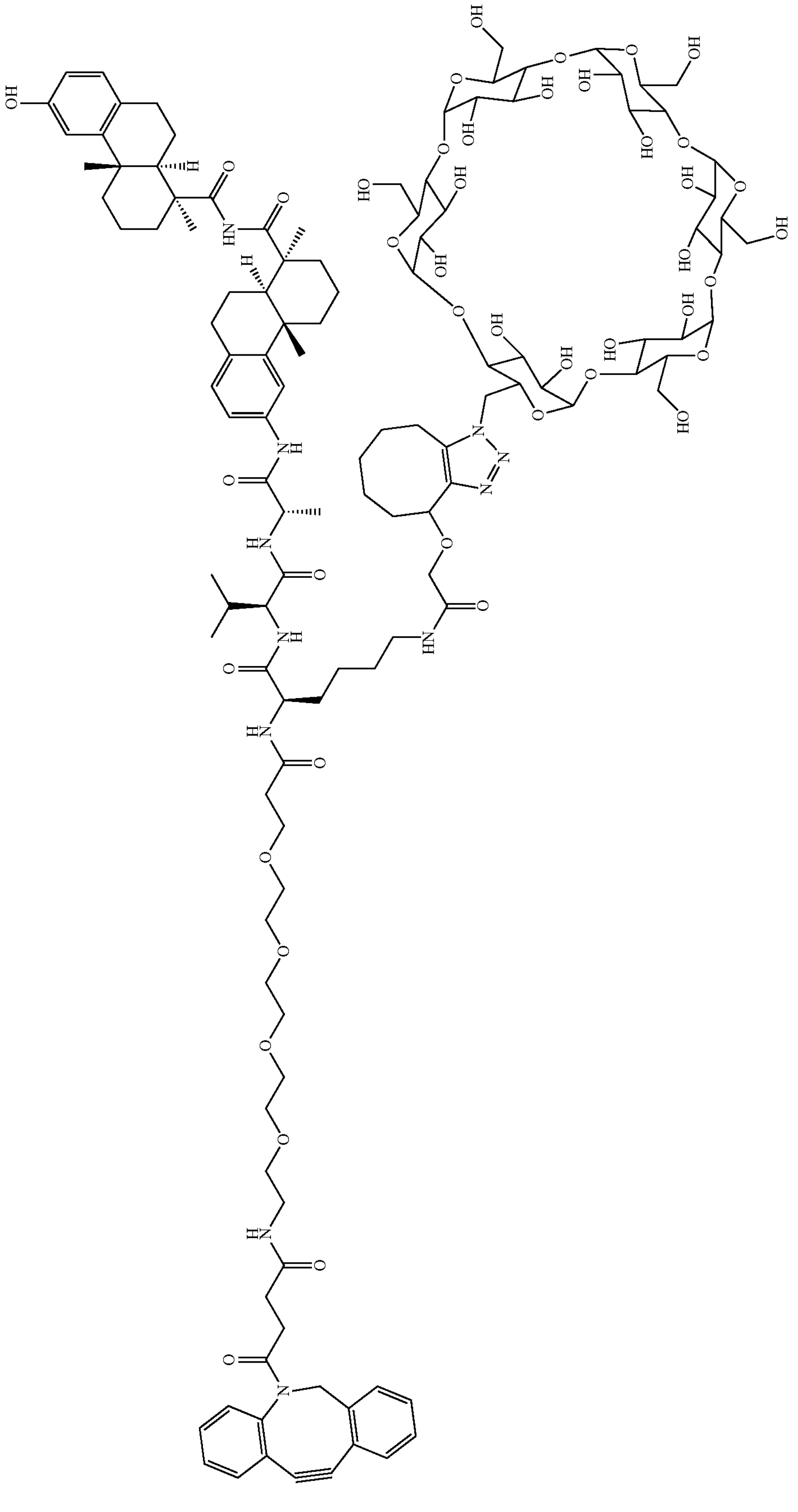

To a solution of compound LP1-5 (14 mg, 7.4 μmol) and DIBAC-Suc-PEG$_4$-OSu (6.5 mg, 10 μmol) in DMF (1 mL) was added triethylamine (2.0 mg, 20 μmol) and the mixture was stirred at 20-25° C. for 16 hours. Most of the volatiles were removed in vacuo and the residue was purified by prep-HPLC (method B) to give compound LP1 (5.0 mg, 27% yield) as a white solid. ESI m/z: 1261 $(M/2+1)^+$. $^1$H NMR (500 MHz, methanol$_{d4}$) δ 7.69-7.44 (m, 6H), 7.41-7.30 (m, 3H), 7.26 (d, J=6.8 Hz, 1H), 7.04-6.96 (m, 1H), 6.88 (d, J=8.4 Hz, 1H), 6.72 (d, J=1.9 Hz, 1H), 6.56 (dd, J=8.3, 2.4 Hz, 1H), 5.25-5.18 (m, 1H), 5.17-5.08 (m, 1H), 5.01-4.94 (m, 4H), 4.61 (s, 16H), 4.53-4.13 (m, 5H), 4.03-3.80 (m, 18H), 3.74-3.64 (m, 3H), 3.63-3.41 (m, 23H), 3.28-2.76 (m, 12H), 2.76-2.65 (m, 1H), 2.56-2.44 (m, 2H), 2.42-2.31 (m, 4H), 2.30-2.23 (m, 4H), 2.18-1.92 (m, 9H), 1.79-1.55 (m, 9H), 1.49-1.34 (m, 9H), 1.33-1.22 (m, 3H), 1.18-1.10 (m, 6H), 1.06-0.94 (m, 6H) ppm.

Figure 3:
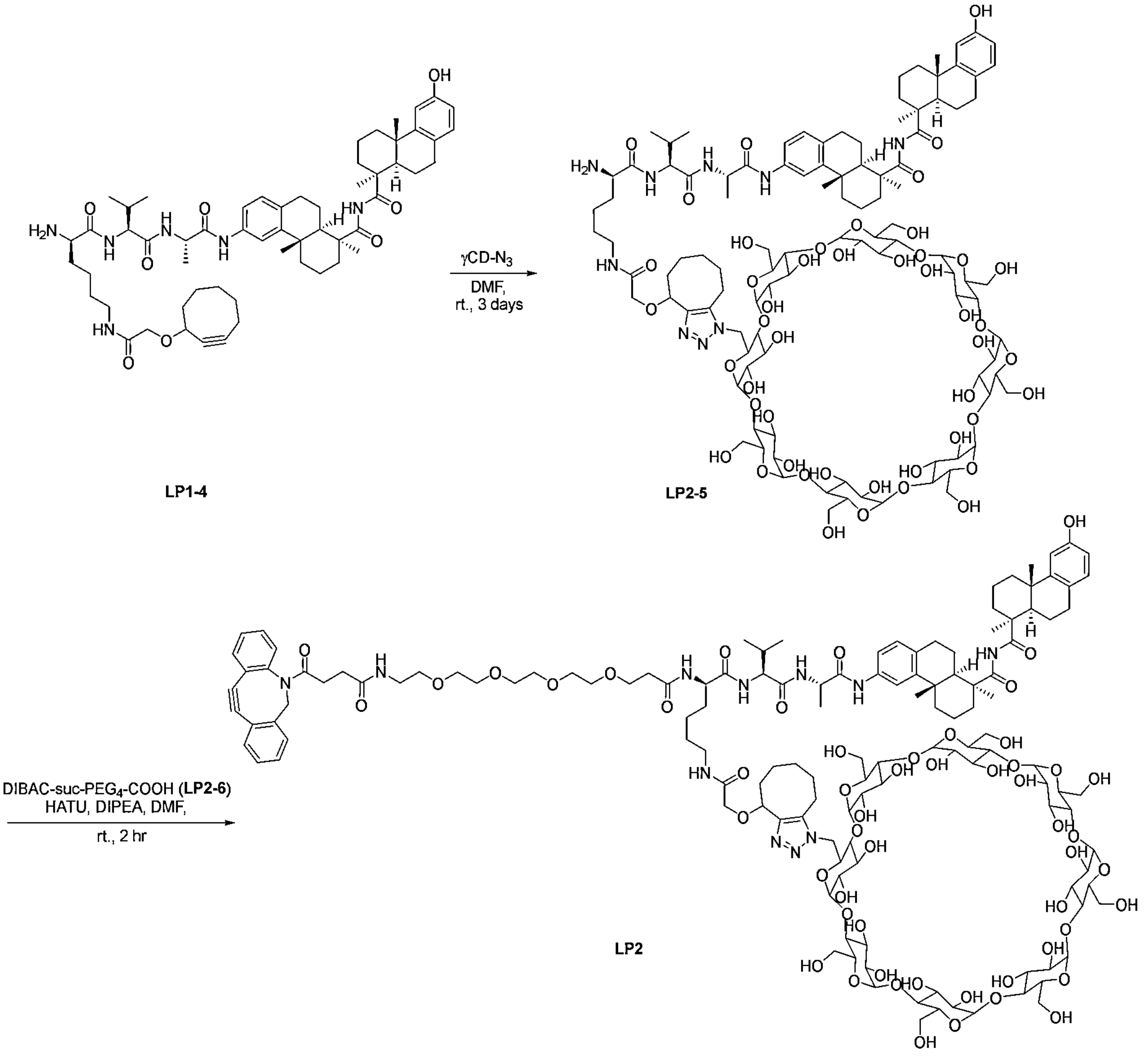
FIG. 3 provides a scheme for the synthesis of LP2.

Example 13. Synthesis of LP2 (FIG. 3)

(1S,4aS,10aR)-N-{[(1S,4aS,10aR)-6-[(2S)-2-[(2S)-2-[(2R)-2-Amino-6-{2-[(1-{[41,42,43,44,45,46,47,48,49,50,51,52,53,54,55,56-hexadecahydroxy-10,15,20,25,30,35,40-heptakis(hydroxymethyl)-2,4,7,9,12,14,17,19,22,24,27,29,32,34,37,39-hexadecaoxanonacyclo[36.2.2.2$^{3,6}$.2$^{8,11}$.2$^{13,16}$.2$^{18,21}$.2$^{23,26}$.2$^{28,31}$.2$^{33,36}$]hexapentacontan-5-yl]methyl}-1H,4H,5H,6H,7H,8H,9H-cycloocta[d][1,2,3]triazol-4-yl)oxy]acetamido}hexanamido]-3-methylbutanamido]propanamido]-1,4a-dimethyl-1,2,3,4,4a,9,10,10a-octahydrophenanthren-1-yl]carbonyl}-6-hydroxy-1,4a-dimethyl-1,2,3,4,4a,9,10,10a-octahydrophenanthrene-1-carboxamide (LP2-5)

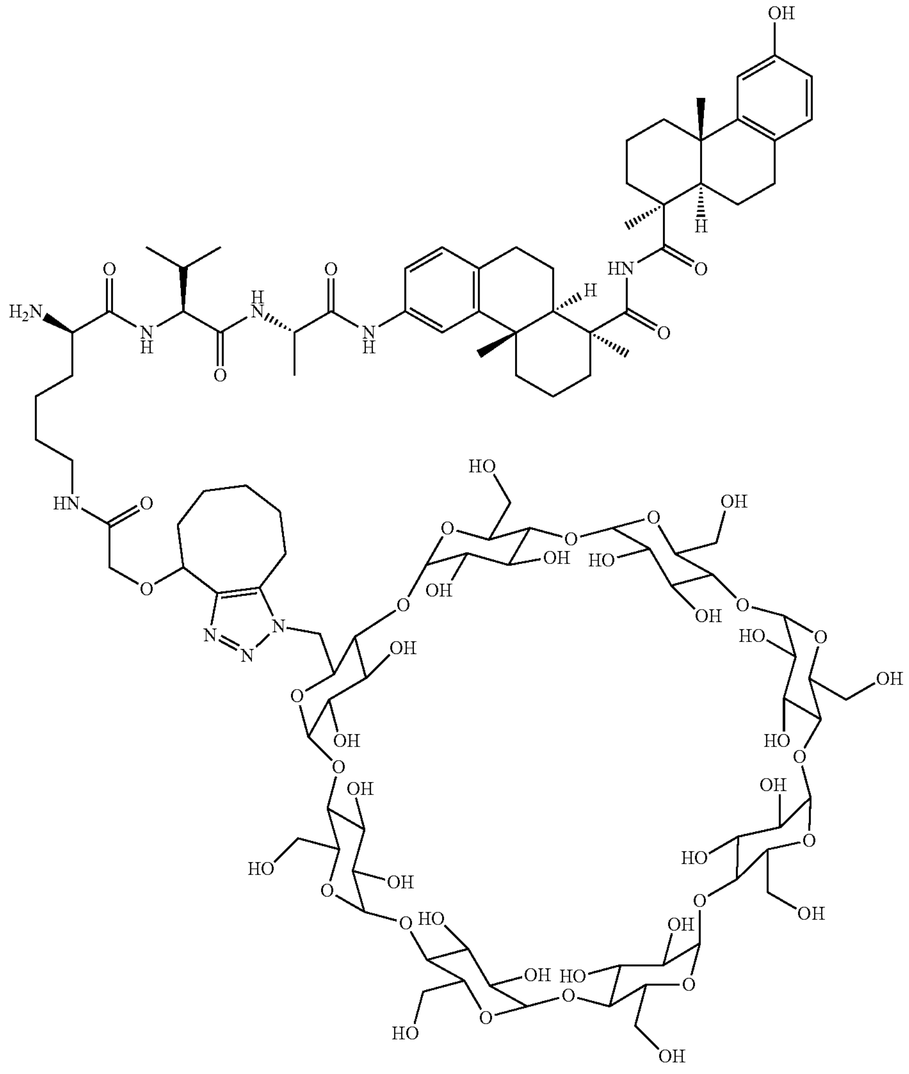 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-4 (30 mg, 0.030 mmol) in DMF (2 mL) was added γCD-$N_3$ (0.12 mg, 0.091 mmol). The mixture was stirred at RT for 16 hours, which was monitored by LCMS. The mixture was filtered through membrane and the filtrate was then purified by prep-HPLC (method A) to give compound LP2-5 (40 mg, 57% yield) as a white solid. ESI m/z: 1157.6 $(M/2+1)^+$. $^1H$ NMR (500 MHz, $DMSO_{d6}$) δ 9.82 (s, 1H), 9.00 (s, 1H), 8.55 (d, J=9.0 Hz, 1H), 8.39 (d, J=6.5 Hz, 1H), 8.11-8.04 (m, 4H), 7.93-7.88 (m, 1H), 7.45 (s, 1H), 7.35 (d, J=8.0 Hz, 1H), 6.97 (d, J=8.5 Hz, 1H), 6.81 (d, J=8.5 Hz, 1H), 6.63 (s, 1H), 6.50 (d, J=11 Hz, 1H), 5.89-5.68 (m, 16H), 5.16-4.32 (m, 19H), 3.94-3.80 (m, 4H), 3.69-3.51 (m, 50H), 3.18-2.64 (m, 8H), 2.33-1.85 (m, 12H), 1.65-1.11 (m, 25H), 0.99 (d, J=9.5 Hz, 6H), 0.89-0.83 (m, 6H) ppm.

1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}-5-{2-[(1-{[41,42,43,44,45,46,47,48,49,50,51,52,53,54,55,56-hexadecahydroxy-10,15,20,25,30,35,40-heptakis(hydroxymethyl)-2,4,7,9,12,14,17,19,22,24,27,29,32,34,37,39-hexadecaoxanonacyclo[36.2.2.2$^{3,6}$.2$^{8,11}$.2$^{13,16}$.2$^{18,21}$.2$^{23,26}$.2$^{28,31}$.2$^{33,36}$]hexapentacontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide (LP2)

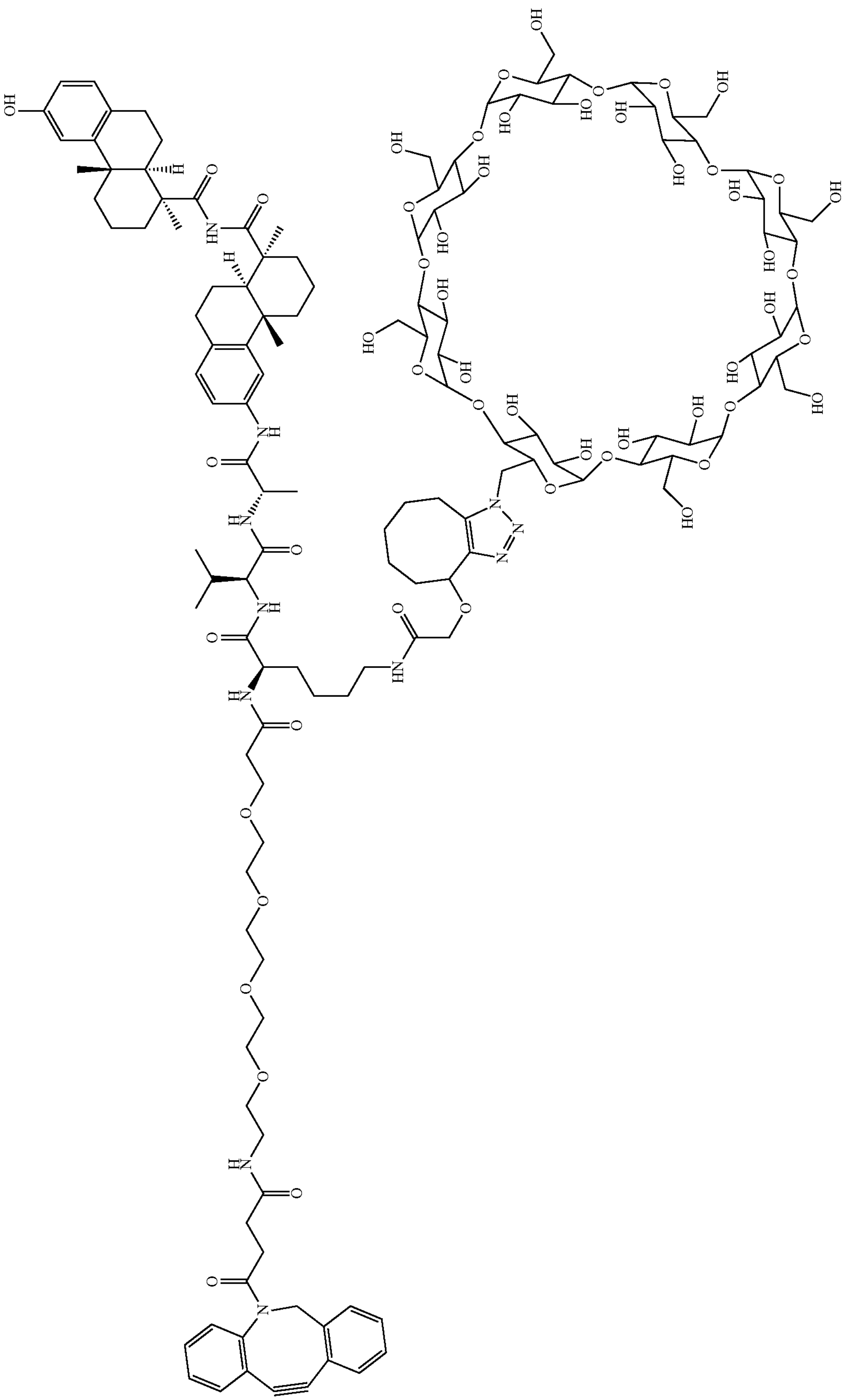

To a solution of compound LP2-6 (4.3 mg, 7.8 μmol) in anhydrous DMF (1 mL) was added HATU (3.0 mg, 7.8 μmol). The mixture was stirred at 10° C. for 10 minutes before compound LP2-5 (15 mg, 6.5 μmol) and DIPEA (1.7 mg, 13 μmol) was added. The mixture was stirred at RT for 2 hours until LP2-5 was totally consumed, as monitored by LCMS. The mixture was filtered through a membrane and the filtrate was purified by prep-HPLC (method B) to give compound LP3 (6.0 mg, 32% yield) as a white solid. ESI m/z: 1424.2 $(M/2+1)^+$. $^1H$ NMR (500 MHz, $DMSO_{d6}$) δ 9.26 (s, 1H), 8.95 (s, 1H), 8.24-7.98 (m, 4H), 7.81 (d, J=5.6 Hz, 1H), 7.72 (t, J=5.5 Hz, 1H), 7.67 (d, J=8.1 Hz, 1H), 7.61 (d, J=7.4 Hz, 1H), 7.55 (s, 1H), 7.53-7.25 (m, 7H), 6.95 (d, J=8.5 Hz, 1H), 6.81 (d, J=8.4 Hz, 1H), 6.63 (d, J=2.1 Hz, 1H), 6.50 (dd, J=8.2, 2.1 Hz, 1H), 5.94-5.58 (m, 15H), 5.39-4.43 (m, 17H), 4.37-4.24 (m, 3H), 4.13-4.08 (m, 1H), 3.98-3.33 (m, 52H), 3.26-2.52 (m, 18H), 2.40-1.18 (m, 48H), 1.18-0.63 (m, 19H) ppm. Solubility: 0.075 mg/mL $H_2O$.

Figure 4:
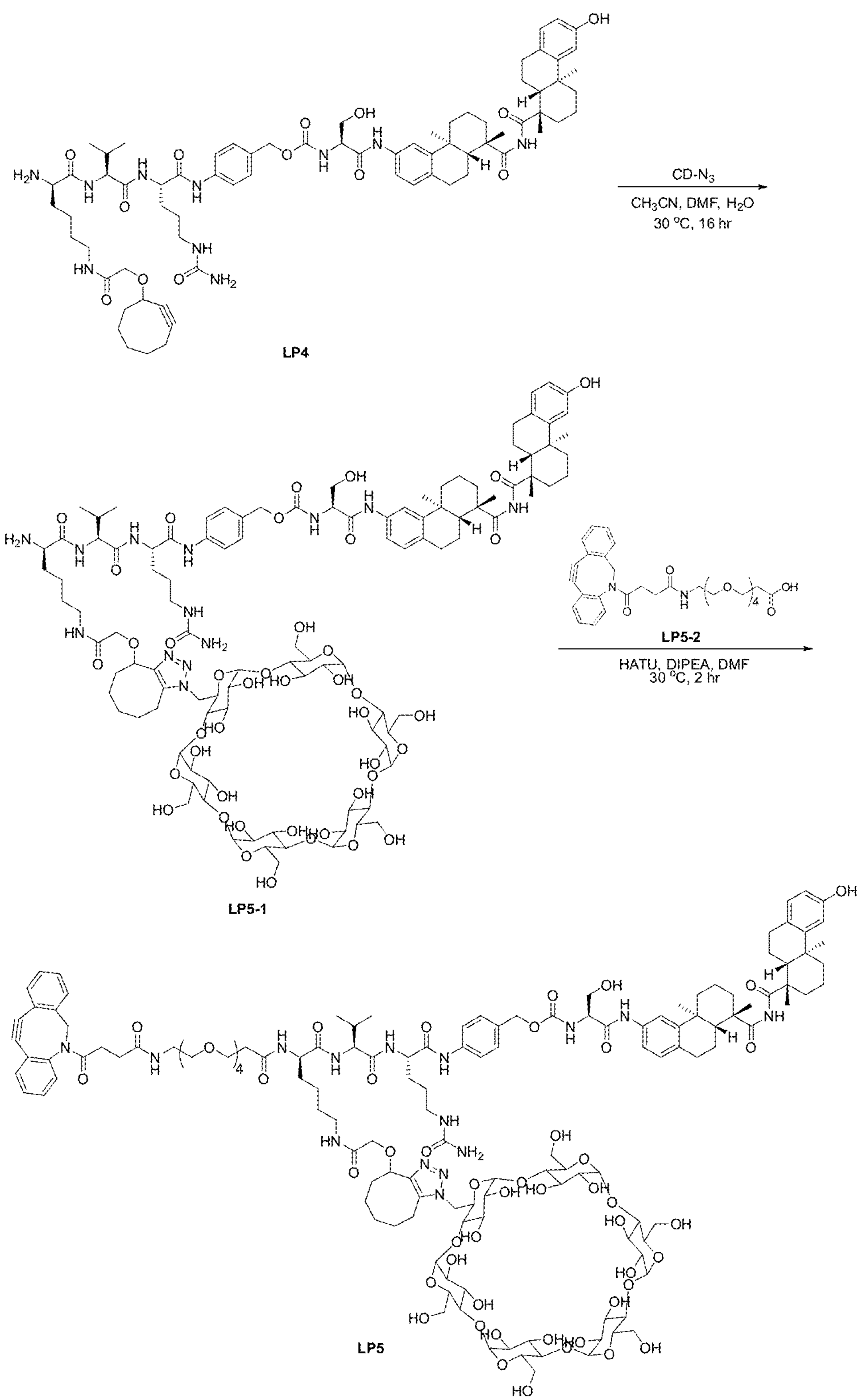
FIG. 4 provides a scheme for the synthesis of LP5.

Example 14. Synthesis of LP5 (FIG. 4)

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP5-1)

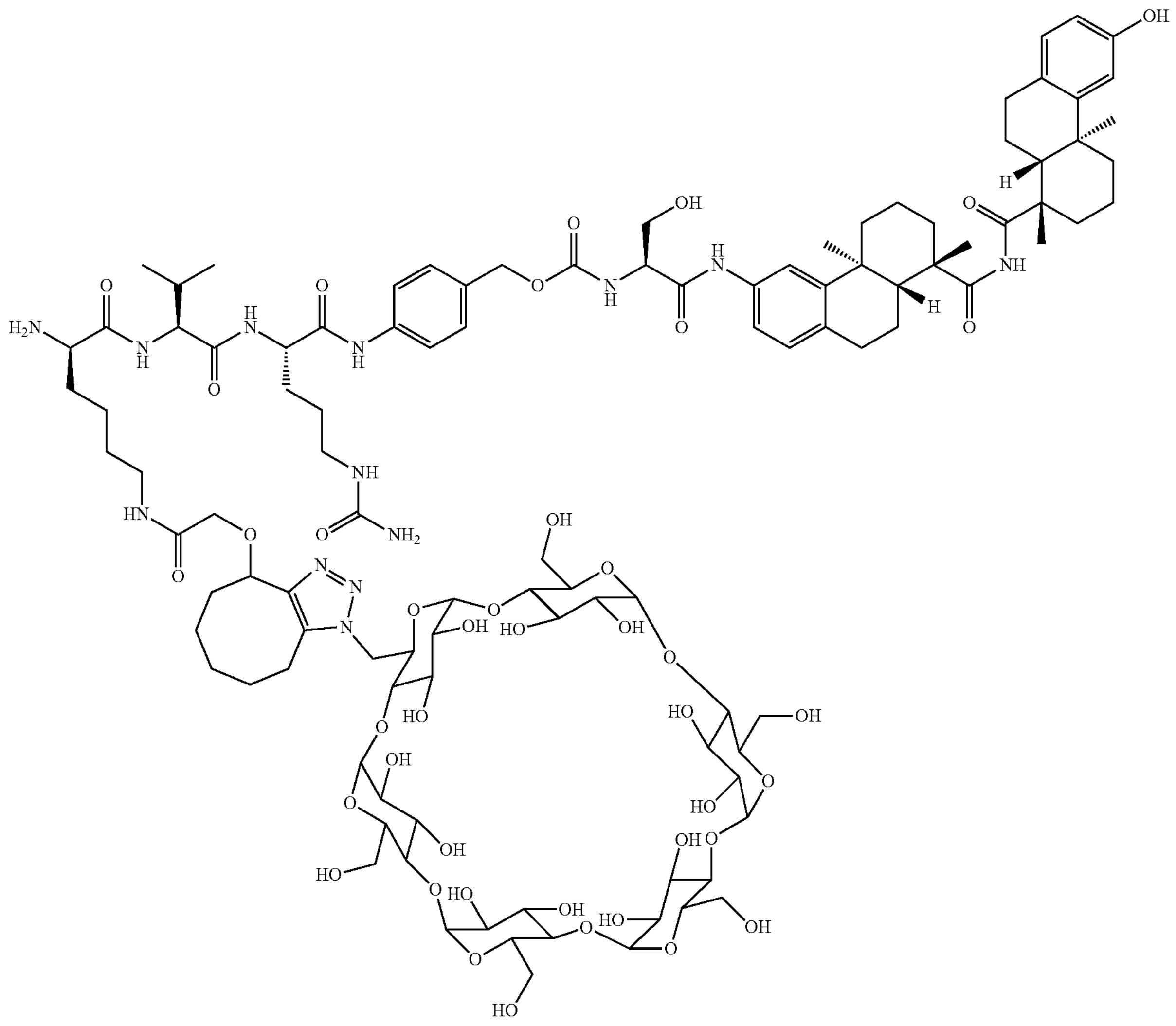 [SMILES: CC(C)[C@H](NC(=O)[C@H](N)CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP4 (20 mg, 15 μmol) in DMF (1 mL) was added a solution of CD-$N_3$ (46 mg, 45 μmol) in acetonitrile (2 mL) and water (2 mL) at RT. The mixture was stirred at 30° C. for 16 hours. Compound LP4 was mostly consumed according to LCMS. The reaction mixture was directly purified by prep-HPLC (method B) to give compound LP5-1 (20 mg, 57% yield) as a white solid. ESI m/z: 1156.0 $(M/2+1)^+$.

{4-[(2S)-2-[(2S)-2-[(2R)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,8}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP5)

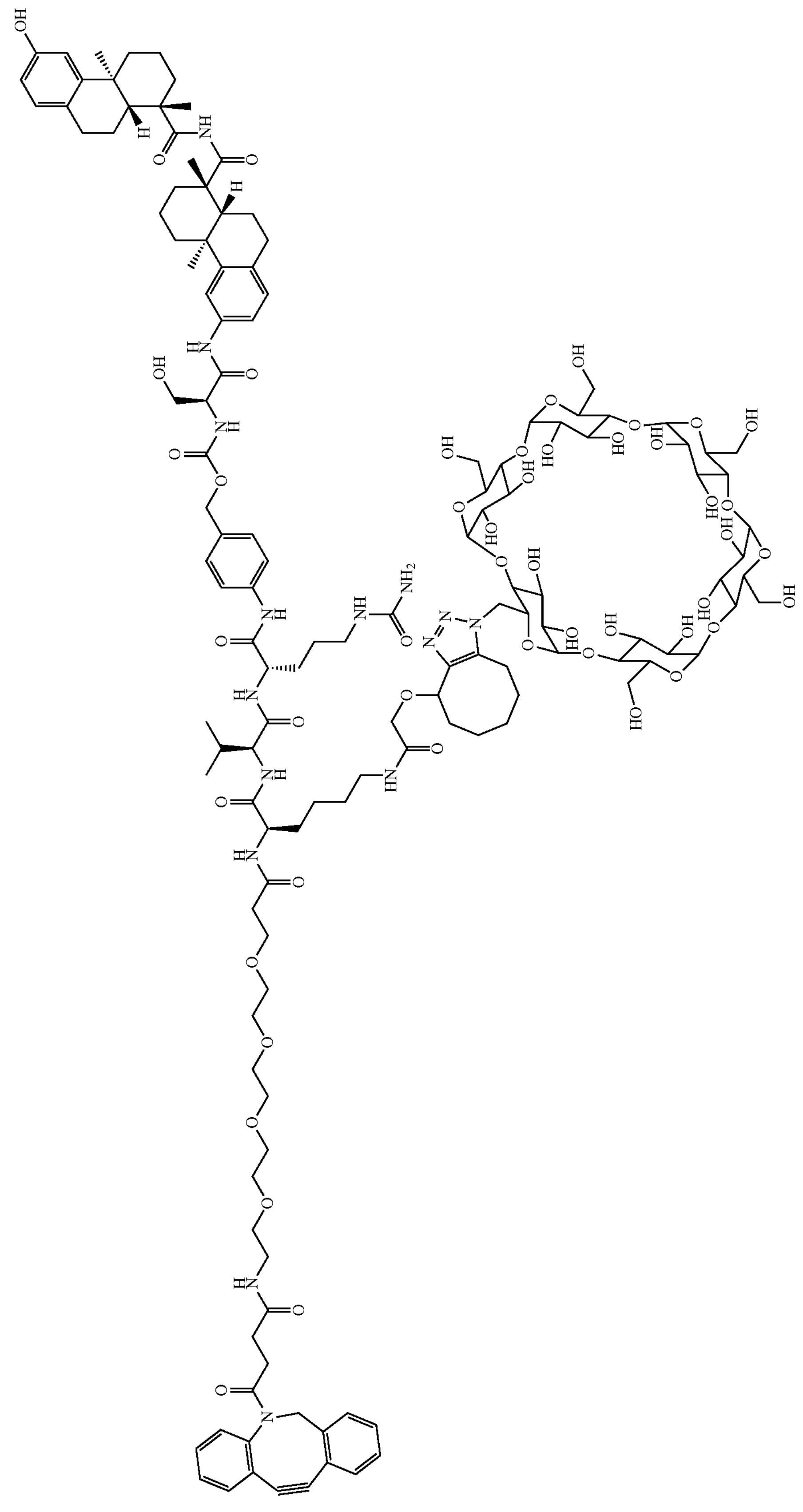

To a solution of DIBAC-PEG$_4$-acid LP5-2 (4.3 mg, 7.8 μmol) in DMF (1 mL) were added HATU (3.0 mg, 3.6 μmol) and DIPEA (1.7 mg, 13 μmol) at RT. The resulting mixture was stirred at RT for 10 minutes. To the mixture was then added LP5-1 (15 mg, 6.5 μmol). The reaction mixture was stirred at 30° C. for 2 hours until the reaction completed, as monitored by LCMS. The reaction mixture was filtered and purified by prep-HPLC (method B) to give LP5 (10 mg, 42% yield) as a white solid. ESI m/z: 1424.3 $(M/2+1)^+$. $^1$H NMR (500 MHz, DMSO$_{d6}$) δ 9.81-9.67 (m, 2H), 8.99 (s, 1H), 8.20-8.06 (m, 5H), 7.85-7.22 (m, 18H), 6.97-6.49 (m, 2H), 5.98 (s, 1H), 5.65-5.33 (m, 15H), 5.14-4.92 (m, 5H), 4.82-4.72 (m, 6H), 4.60-4.54 (m, 4H), 4.36-4.28 (m, 3H), 4.18-3.96 (m, 3H), 3.85-3.55 (m, 27H), 3.49-3.39 (m, 23H), 3.28-3.08 (m, 8H), 2.94-2.57 (m, 4H), 2.42-2.07 (m, 8H), 1.99-1.45 (m, 22H), 1.28-1.11 (m, 23H), 1.05-0.95 (m, 6H), 0.89-0.79 (i, 7H) ppm.

Figure 5:
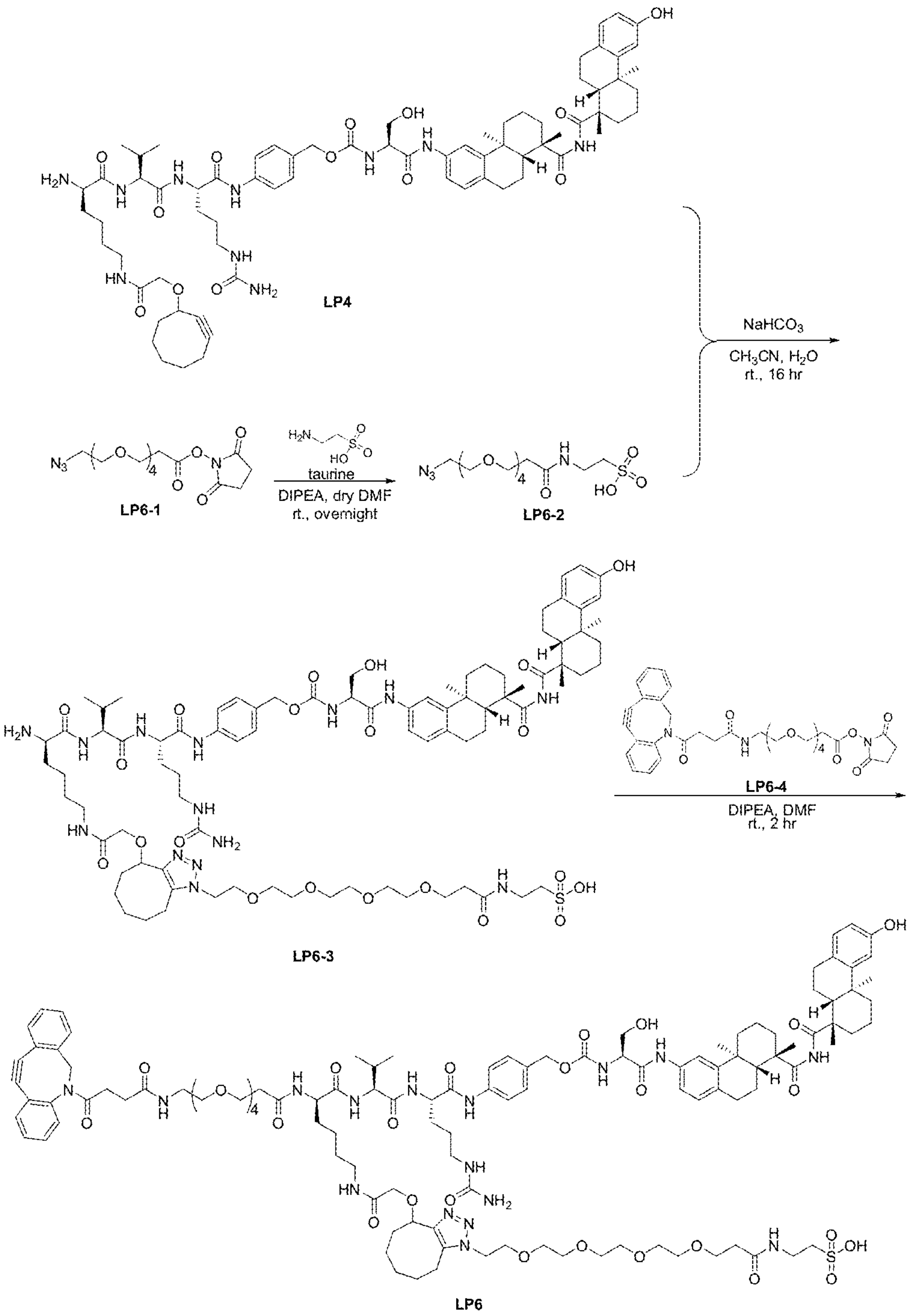
FIG. 5 provides a scheme for the synthesis of LP6.

Example 15. Synthesis of LP6 (FIG. 5)

1-Azido-15-oxo-3,6,9,12-tetraoxa-16-azaoctadecane-18-sulfonic acid (L6-2)

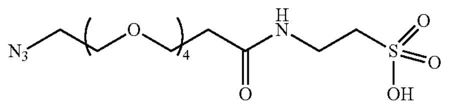

To a solution of azido-PEG$_4$-NHS (L6-1, 0.10 g, 0.26 mmol) in anhydrous DMF (4 mL) were added taurine (39 mg, 0.31 mmol) and DIPEA (15 mg, 0.52 mmol). The mixture was stirred at 25° C. overnight. The mixture was filtered and the filtrate was purified by prep-HPLC (method A) to give compound LP6-2 (80 mg, 78% yield) as colorless oil. ESI m/z: 399.1 $(M+H)^+$. $^1$H NMR (500 MHz, $D_2O$) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

2-{1-[4-({[(5R)-5-Amino-5-{[(1S)-1-{[(1S)-1-({4-[({[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP6-3)

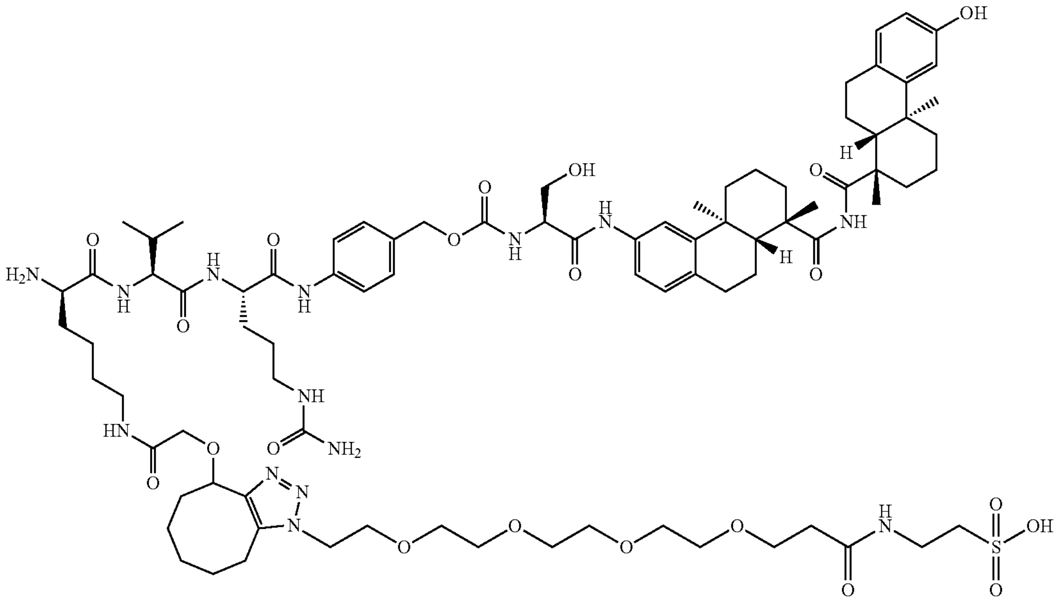 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP6-2 (20 mg, 50 μmol) in water (1 mL) was added dropwise sat. aq. sodium bicarbonate solution at 0° C. until pH~7. To the stirred solution was then added a solution of compound LP4 (28 mg, 21 μmol) in acetonitrile (1 mL) by syringe. The mixture was stirred at 25° C. overnight. The reaction mixture was monitored by LCMS until compound LP4 was totally consumed. The reaction mixture was filtered and purified by prep-HPLC (method A) to give compound LP6-3 (15 mg, 41% yield) as a white solid. ESI m/z: 856.5 $(M/2+1)^+$.

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1 S)-1-{[(1S)-1-({4-[({[(1 S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamoyl}oxy)methyl]phenyl}carbamoyl)-4-(carbamoylamino)butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP6)

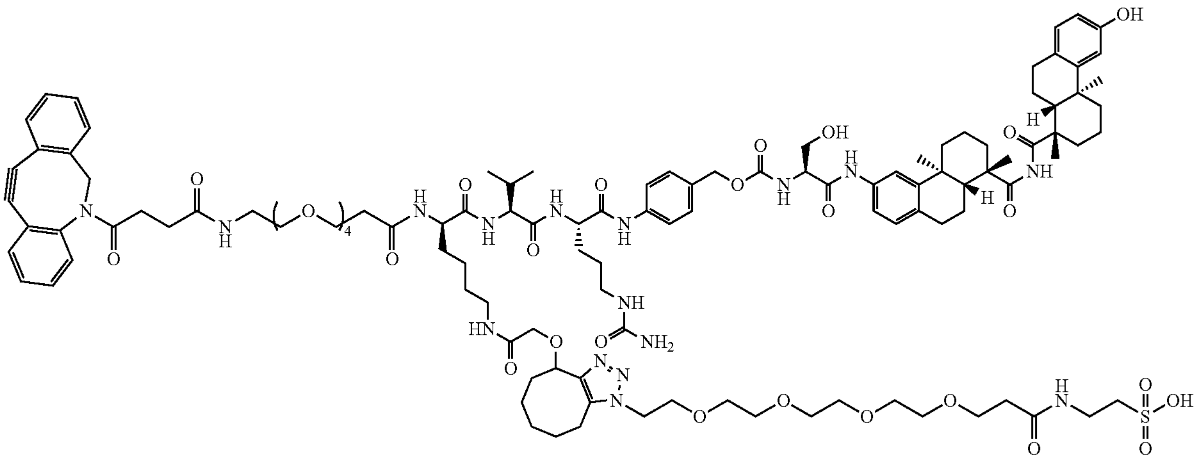

To a solution of compound LP6-3 (15 mg, 8.8 μmol) and commercially available DIBAC-Suc-PEG$_4$-OSu LP6-4 (5.7 mg, 8.8 μmol, CAS 1427004-19-0) in DMF (1 mL) was added DIPEA (2.3 mg, 18 μmol) and the mixture was stirred at RT for 2 hours. Most of the volatiles were removed in vacuo and the residue was purified by prep-HPLC (method B) to give LP6 (6.0 mg, 30% yield) as a white solid. ESI m/z: 1123.8 $(M/2+H)^+$, 749.5 $(M/3+H)^+$. $^1$H NMR (500 MHz, methanol$_{d4}$) δ 7.76-7.16 (m, 14H), 7.06-7.00 (m, 1H), 6.88 (d, J=8.5 Hz, 1H), 6.72-6.71 (m, 1H), 6.56-6.55 (m, 1H), 5.39-5.33 (m, 1H), 5.14-5.09 (m, 5H), 4.61 (s, 18H), 4.50-4.43 (m, 2H), 4.33-4.30 (m, 1H), 3.99 (s, 2H), 3.89-3.85 (m, 3H), 3.73-3.42 (m, 28H), 3.25-2.72 (m, 8H), 2.45 (t, J=7.5 Hz, 2H), 2.36-1.96 (m, 18H), 1.81-1.51 (m, 12H), 1.45-1.32 (m, 15H), 1.12-0.89 (m, 12H) ppm.

Figure 6:
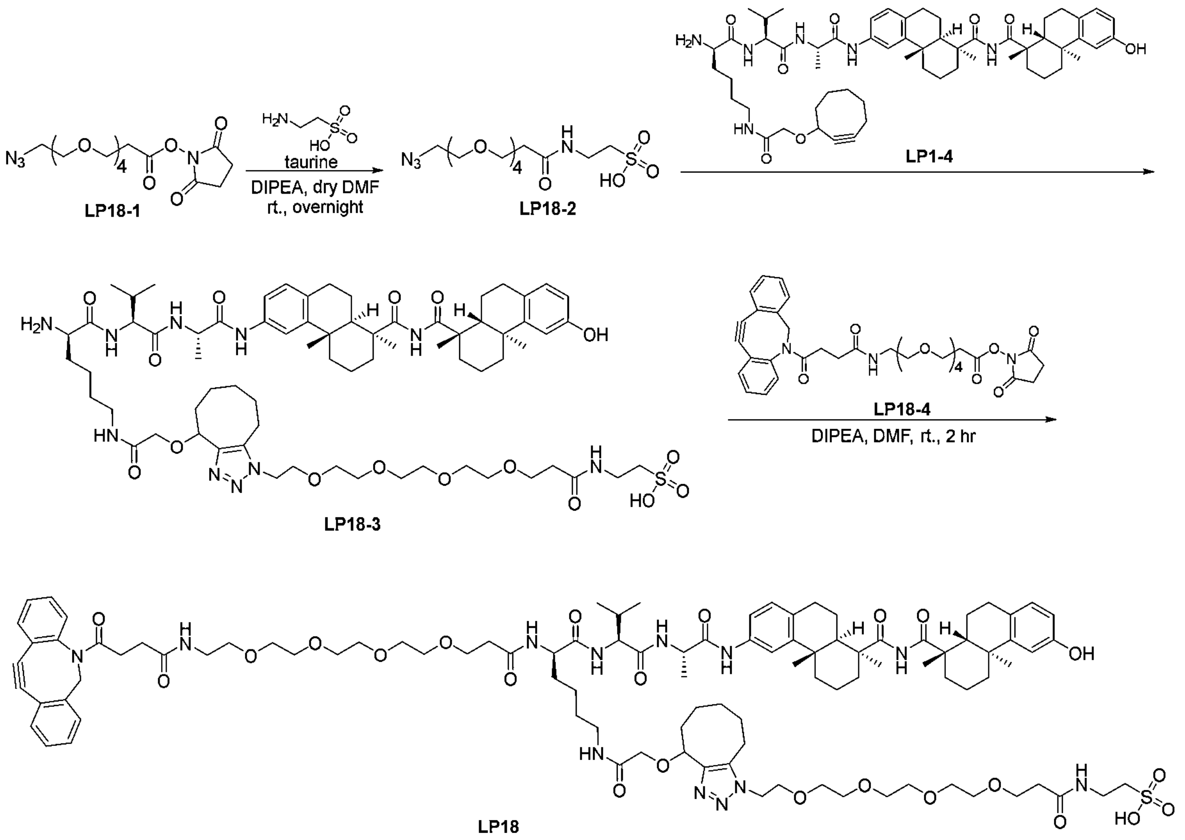
FIG. 6 provides a scheme for the synthesis of LP18.

Example 16. Synthesis of LP18 (FIG. 6)

1-Azido-15-oxo-3,6,9,12-tetraoxa-16-azaoctadecane-18-sulfonic acid (L18-2)

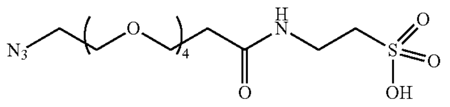

To a solution of azido-PEG$_4$-NHS (L18-1, 0.10 g, 0.26 mmol) in anhydrous DMF (4 mL) were added taurine (39 mg, 0.31 mmol) and DIPEA (15 mg, 0.52 mmol). The mixture was stirred at 25° C. overnight. The mixture was filtered and the filtrate was purified by prep-HPLC (method A) to give compound LP18-2 (80 mg, 78% yield) as colorless oil. ESI m/z: 399.1 $(M+H)^+$. $^1$H NMR (500 MHz, $D_2O$) δ 3.69 (t, J=6.0 Hz, 2H), 3.64-3.59 (m, 14H), 3.49 (t, J=6.5 Hz, 2H), 3.41 (t, J=4.5 Hz, 2H), 3.00 (t, J=7.0 Hz, 2H), 2.45 (t, J=6.0 Hz, 2H) ppm.

1-(4-(2-((R)-5-Amino-6-((S)-1-((S)-1-((4bS,8S,8aR)-8-((1S,4aS,10aR)-6-hydroxy-1,4a-dimethyl-1,2,3,4,4a,9,10,10a-octahydrophenanthrene-1-carbonylcarbamoyl)-4b,8-dimethyl-4b,5,6,7,8,8a,9,10-octahydrophenanthren-3-ylamino)-1-oxopropan-2-ylamino)-3-methyl-1-oxobutan-2-ylamino)-6-oxohexylamino)-2-oxoethoxy)-4,5,6,7,8,9-hexahydro-1H-cycloocta[d][1,2,3]triazol-1-yl)-15-oxo-3,6,9,12-tetraoxa-16-azaoctadecane-18-sulfonic acid (LP18-3)

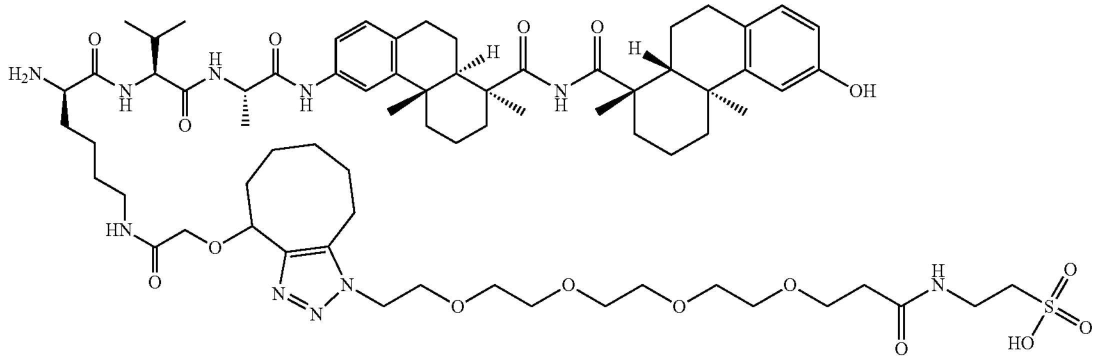 [SMILES: CC(C)[C@H](NC(=O)[C@H](N)CCCCNC(=O)COC1CCCCCc2c1nnn2CCOCCOCCOCCOCCC(=O)NCCS(=O)(=O)O)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

To a solution of compound LP1-4 (40 mg, 40 μmol) in DMF (1 mL) was added azide LP18-2 (40 mg, 0.10 mmol) at RT. The reaction was stirred at RT for 16 hours, until LCMS showed complete reaction. The reaction mixture was directly purified by prep-HPLC to give compound LP18-3 (43 mg, 77% yield) as a white solid. ESI m/z: 695.4 $(M/2+H)^+$.

To a solution of compound LP18-3 (30 mg, 22 μmol) in DMF (1 mL) were added a solution of DIBAC-suc-$PEG_4$-OSu (LP18-4, 14 mg, 22 μmol) in DMF (1 mL) and DIPEA (4 mg, 32 μmol) successively at RT. The reaction mixture was stirred at RT for 2 hours. The reaction mixture was directly purified by prep-HPLC (method B) to give compound LP18 (15 mg, 37% yield) as a white solid. ESI m/z: 642 $(M/3+H)^+$. $^1H$ NMR (400 MHz, $DMSO_{d6}$) δ 9.68-9.27 (m, 1H), 8.99 (s, 1H), 8.23-7.85 (m, 4H), 7.79-7.71 (m, 2H), 7.76-7.42 (m, 6H), 7.39-7.28 (m, 3H), 7.21 (s, 1H), 7.09 (s, 1H), 6.96-6.93 (m, 2H), 6.81 (d, J=8.4 Hz, 1H), 6.63 (d, J=2.4 Hz, 1H), 6.50 (dd, J=8.4 Hz, 2.4 Hz, 1H), 5.02 (d, J=14.0 Hz, 1H), 4.93-4.72 (m, 1H), 4.53-4.09 (m, 5H), 3.82-3.75 (m, 4H), 3.62-3.53 (m, 3H), 3.51-3.38 (m, 23H), 3.30-3.27 (m, 6H), 3.12-2.67 (m, 10H), 2.61-2.54 (m, 4H), 2.39-1.52 (m, 31H), 1.45-1.08 (m, 18H), 1.01-0.98 (m, 6H), 0.90-0.82 (m, 6H) ppm.

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1 S)-1-{[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}ethyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP18)

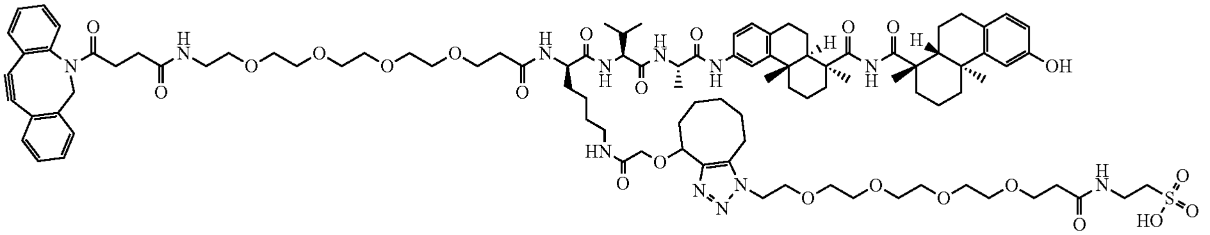 [SMILES: CC(C)[C@H](NC(=O)[C@@H](CCCCNC(=O)COC1CCCCCc2c1nnn2CCOCCOCCOCCOCCC(=O)NCCS(=O)(=O)O)NC(=O)CCOCCOCCOCCOCCNC(=O)CCC(=O)N1Cc2ccccc2C#Cc2ccccc21)C(=O)N[C@@H](C)C(=O)Nc1ccc2c(c1)[C@@]1(C)CCC[C@](C)(C(=O)NC(=O)[C@@]3(C)CCC[C@]4(C)c5cc(O)ccc5CC[C@@H]34)[C@@H]1CC2]

Example 17. Synthesis of Payload P5, Payload P6, and Payload P7

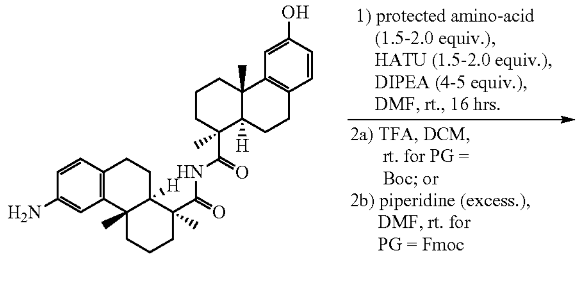

P1

-continued

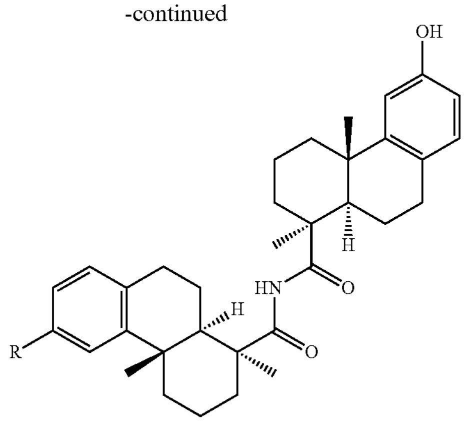

P5-P7

| Cpd | R | PG | Yield |
|---|---|---|---|
| P5 | NHC(O)(S)—CH($CH_2OH$)$NH_2$ (Ser) | Fmoc | 51% |
| P6 | NHC(O)(S)—CH($CH_2CH_2COOH$)$NH_2$ (Glu) | tBu, Boc | 46% |
| P7 | NHC(O)(S)—CH(($CH_2$)$_4NH_2$)$NH_2$ (Lys) | Boc, Boc | 49% |

Payload P5

(1S,4aS,10aR)-6-((S)-2-Amino-3-hydroxypropanamido)-N-((1S,4aS,10aR)-6-hydroxy-1,4a-dimethyl-1,2,3,4,4a,9,10,10a-octahydrophenanthrene-1-carbonyl)-1,4a-dimethyl-1,2,3,4,4a,9,10,10a-octahydrophenanthrene-1-carboxamide (P5)

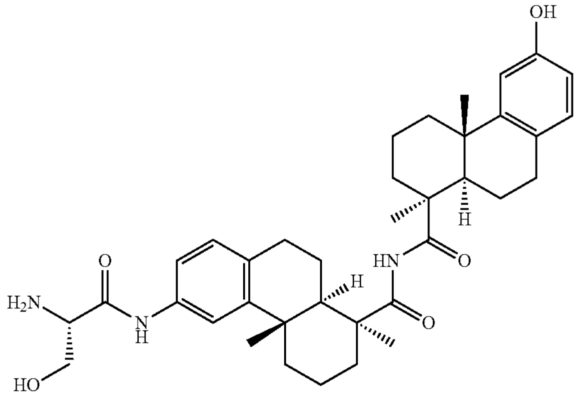 [SMILES: C[C@]1(C(=O)NC(=O)[C@@]2(C)CCC[C@]3(C)c4cc(NC(=O)[C@@H](N)CO)ccc4CC[C@@H]23)CCC[C@]2(C)c3cc(O)ccc3CC[C@@H]12]

To a solution of Fmoc-Ser-OH (33 mg, 0.1 mmol) in DMF (1 mL) were added HATU (38 mg, 0.1 mmol) and DIPEA (39 mg, 0.3 mmol) at 25° C. The resulting mixture was stirred at this temperature for an hour. To the mixture was then added P1 (30 mg, 0.06 mmol). After the reaction mixture was stirred at 25° C. for 16 hours and P1 was totally consumed (monitored by LCMS), piperidine (0.2 mL) was added into the mixture, which was stirred for another 30 min at room temperature. The residue was directly purified by prep-HPLC (method B) to give P5 (18 mg, 51% yield) as a white solid. ESI m/z: 616 $(M+1)^+$. $^1$H NMR (500 MHz, $DMSO_{d6}$) δ 9.74 (br s, 1H), 9.00 (s, 1H), 8.11 (s, 1H), 7.58 (s, 1H), 7.41 (dd, J=8.2, 2.0 Hz, 1H), 6.96 (d, J=8.4 Hz, 1H), 6.82 (d, J=8.3 Hz, 1H), 6.63 (d, J=2.3 Hz, 1H), 6.50 (dd, J=8.2, 2.4 Hz, 1H), 4.82 (t, J=5.5 Hz, 1H), 3.62-3.45 (m, 2H), 2.97-2.67 (m, 4H), 2.67-2.61 (m, 2H), 2.33-2.21 (m, 2H), 2.21-2.03 (m, 4H), 1.96-1.77 (m, 4H), 1.70-1.50 (m, 4H), 1.43-1.37 (m, 1H), 1.36-1.20 (m, 8H), 1.23-1.06 (m, 2H), 1.06-0.93 (m, 6H) ppm.

Payload P6

(4S)-4-Amino-4-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}butanoic acid; trifluoroacetic acid salt (P6)

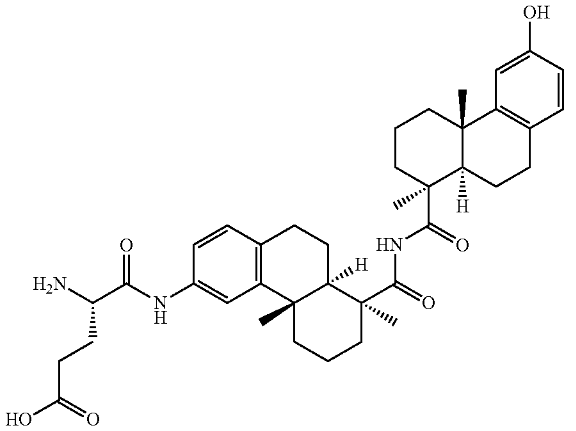 [SMILES: C[C@]1(C(=O)NC(=O)[C@@]2(C)CCC[C@]3(C)c4cc(NC(=O)[C@@H](N)CCC(=O)O)ccc4CC[C@@H]23)CCC[C@]2(C)c3cc(O)ccc3CC[C@@H]12]

To a solution of OtBu-N-Boc-Glu-OH (15 mg, 0.05 mmol) in DMF (1 mL) were added HATU (19 mg, 0.05 mmol) and DIPEA (13 mg, 0.1 mmol) at 25° C. The resulting mixture was stirred at this temperature for an hour. To the mixture was then added P1 (14 mg, 0.026 mmol). After stirring at 25° C. for 16 hours and P1 was totally consumed (monitored by LCMS), the reaction mixture was diluted with ethyl acetate and washed with water and brine. The organic solution was dried over sodium sulfate and concentrated in vacuo. The residue was dissolved in DCM (1 mL) and to the solution was added TFA (0.1 mL) slowly at room temperature. The mixture was stirred at room temperature for 2 hours. The volatiles were removed in vacuo and the residue was purified by prep-HPLC (method A) to give P6 (8 mg, 46% yield) as a white solid. ESI m/z: 658.3 $(M+1)^+$. $^1$H NMR (400 MHz, $DMSO_{d6}$) δ 10.32 (s, 1H), 9.00 (s, 1H), 8.12 (s, 1H), 7.48 (s, 1H), 7.35 (d, J=8.2 Hz, 1H), 7.02 (d, J=8.4 Hz, 1H), 6.82 (d, J=8.3 Hz, 1H), 6.63 (d, J=2.1 Hz, 1H), 6.50 (dd, J=8.2, 2.3 Hz, 1H), 3.87 (t, J=6.5 Hz, 1H), 2.97-2.67 (m, 4H), 2.41-2.22 (m, 4H), 2.22-2.08 (m, 4H), 2.05-1.97 (m, 2H), 1.94-1.80 (m, 4H), 1.69-1.52 (m, 4H), 1.42-1.22 (m, 8H), 1.22-1.06 (m, 2H), 1.02 (s, 3H), 0.99 (s, 3H) ppm. $^{19}$F NMR (376 MHz, $DMSO_{d6}$) δ −73.50 ppm.

Payload P7

(1S,4aS,10aR)-N-[(1S,4aS,10aR)-6-Hydroxy-1,4a-dimethyl-1,2,3,4,4a,9,10,10a-octahydro-phenanthrene-1-carbonyl]-6-[(2S)-2,6-diamino-hexanamido]-1,4a-dimethyl-1,2,3,4,4a,9,10,10a-octahydrophenanthrene-1-carboxamide; trifluoroacetic acid salt (P7)

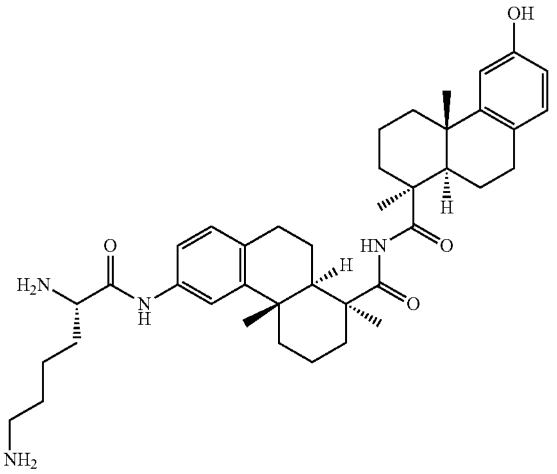 [SMILES: C[C@]1(C(=O)NC(=O)[C@@]2(C)CCC[C@]3(C)c4cc(NC(=O)[C@@H](N)CCCCN)ccc4CC[C@@H]23)CCC[C@]2(C)c3cc(O)ccc3CC[C@@H]12]

To a solution of Boc-Lys-OH (15 mg, 0.05 mmol) in DMF (1 mL) were added HATU (19 mg, 0.05 mmol) and DIPEA (13 mg, 0.1 mmol) at 25° C. The resulting mixture was stirred at this temperature for an hour. To the mixture was then added P1 (15 mg, 0.028 mmol). After stirring at 25° C. for 16 hours and P1 was totally consumed (monitored by LCMS), the reaction mixture was diluted with ethyl acetate and washed with water and brine. The organic solution was dried over sodium sulfate and concentrated in vacuo. The residue (Boc-P7) was dissolved in DCM (1 mL) and to the solution was added TFA (0.1 mL) slowly at room temperature. The mixture was stirred at room temperature for 2 hours. The volatiles were removed in vacuo and the residue was purified by prep-HPLC (method A) to give P7 (9 mg, 49% yield) as a white solid. ESI m/z: 657.5 $(M+1)^+$. $^1$H NMR (400 MHz, $DMSO_{d6}$) δ 10.33 (s, 1H), 9.01 (s, 1H), 8.13 (s, 1H), 7.78 (br s, 6H), 7.51 (s, 1H), 7.34 (d, J=8.1 Hz, 1H), 7.02 (d, J=8.5 Hz, 1H), 6.82 (d, J=8.6 Hz, 1H), 6.63 (s, 1H), 6.51 (d, J=8.3 Hz, 1H), 3.82 (s, 1H), 2.89 (s, 1H), 2.82-2.67 (m, 5H), 2.29 (s, 2H), 2.15 (s, 4H), 1.85 (s, 6H), 1.64-1.51 (m, 6H), 1.28 (d, J=6.8 Hz, 10H), 1.13 (s, 2H), 1.01 (s, 3H), 0.99 (s, 3H) ppm. $^{19}$F NMR (376 MHz, $DMSO_{d6}$) δ −73.53 ppm.

Figure 7:
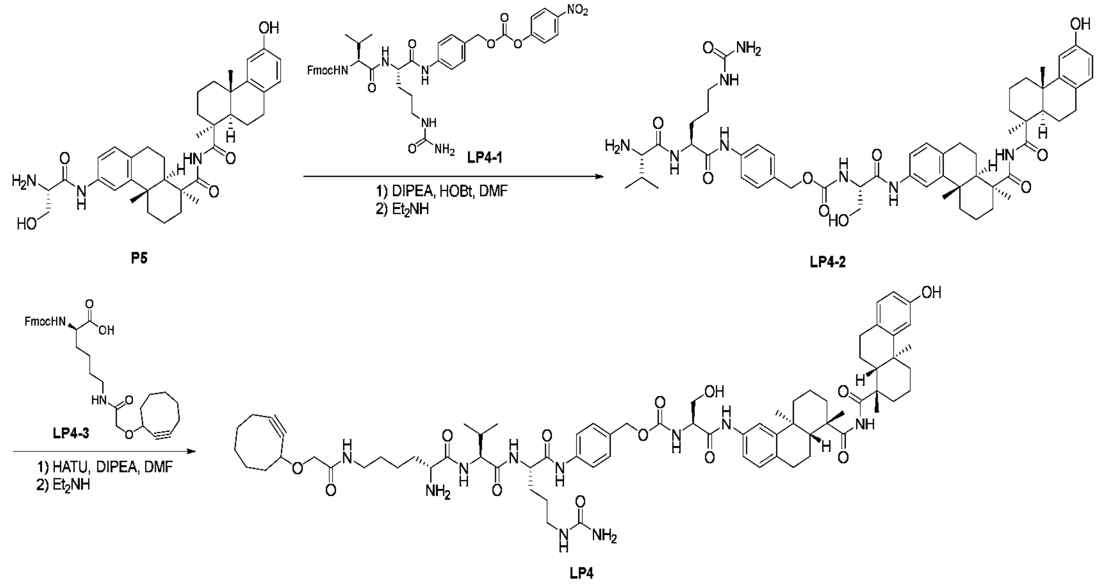
FIG. 7 provides a scheme for the synthesis of LP4.

Example 18. Synthesis of LP4 (FIG. 7)

{4-[(2S)-2-[(2S)-2-Amino-3-methylbutanamido]-5-(carbamoylamino)pentanamido]phenyl}methyl N-[(1 S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP4-2)

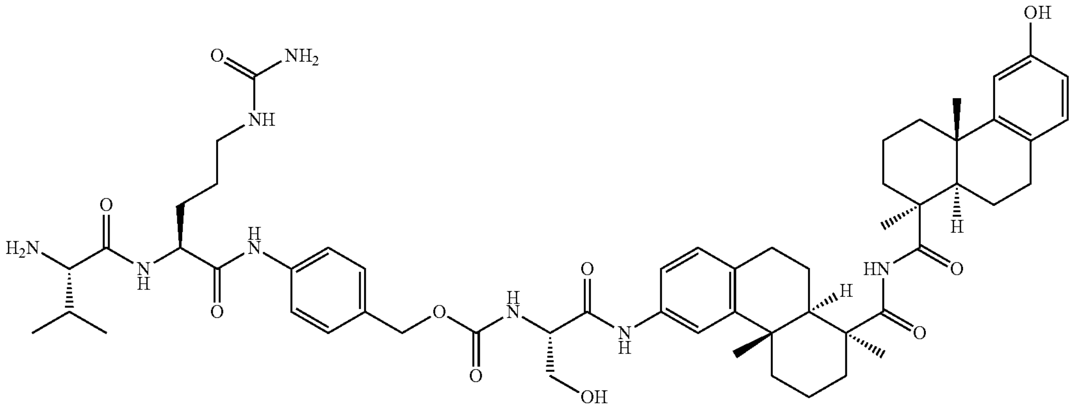 [SMILES: CC(C)[C@H](N)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of Fmoc-vc-PAB-PNP (LP4-1, 58 mg, 76 μmol) and P5 (36 mg, 58 μmol) in DMF (3 mL) were added HOBt (7.9 mg, 58 μmol) and DIPEA (15 mg, 0.12 mmol), and the mixture was stirred at 30° C. for 16 hours. Compound P5 was then totally consumed according to LCMS. To the resulting mixture was added diethylamine (0.1 mL), and the reaction was stirred at RT for an hour until Fmoc was removed, as monitored by LCMS. After the reaction was filtered, the filtrate was directly purified by prep-HPLC (method B) to give compound LP4-2 (36 mg, 48% yield) as a light yellow solid. ESI m/z: 1021 $(M+1)^+$. $^1$H NMR (400 MHz, $DMSO_{d6}$) δ 10.02 (s, 1H), 9.82 (s, 1H), 9.00 (s, 1H), 8.69-8.65 (m, 1H), 8.11-8.00 (m, 4H), 7.65-7.53 (m, 3H), 7.40-7.30 (m, 3H), 7.30-7.20 (m, 1H), 6.96 (d, J=8.0 Hz, 1H), 6.81 (d, J=8.0 Hz, 1H), 6.65-6.61 (m, 1H), 6.50 (dd, J=8.0 Hz, 2.0 Hz, 1H), 6.00-5.95 (m, 1H), 5.48 (s, 2H), 5.00-4.95 (m, 3H), 4.60-4.40 (m, 1H), 4.25-4.20 (m, 1H), 3.65-3.55 (m, 4H), 3.15-2.55 (m, 10H), 2.40-2.20 (m, 3H), 2.20-2.00 (m, 5H), 2.00-1.80 (m, 4H), 1.86-1.55 (m, 6H), 1.27 (d, J=4.8 Hz, 9H), 1.20-1.10 (m, 2H), 0.97-0.90 (m, 6H) ppm.

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-[(1S)-1-{[(4bS,8S,8aR)-8-({[(1S,4aS,10aR)-6-hydroxy-1,4a-dimethyl-1,2,3,4,4a,9,10,10a-octahydrophenanthren-1-yl]formamido}carbonyl)-4b,8-dimethyl-4b,5,6,7,8,8a,9,10-octahydrophenanthren-3-yl]carbamoyl}-2-hydroxyethyl]carbamate (LP4)

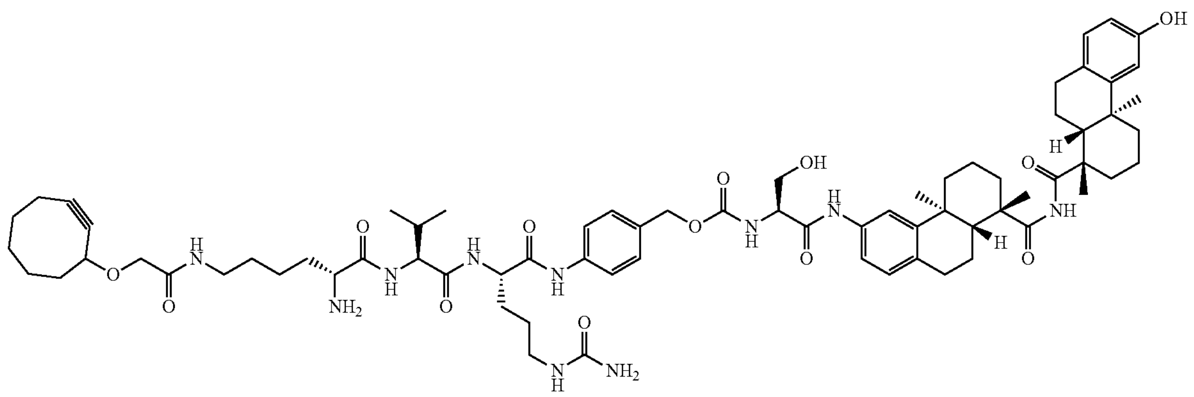 [SMILES: CC(C)[C@H](NC(=O)[C@H](N)CCCCNC(=O)COC1C#CCCCCC1)C(=O)N[C@@H](CCCNC(N)=O)C(=O)Nc1ccc(COC(=O)N[C@@H](CO)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP4-3 (24 mg, 44 μmol) in DMF (2 mL) were added HATU (17 mg, 44 μmol) and compound LP4-2 (35 mg, 34 μmol) in succession at RT. The mixture was stirred for a few minutes at RT until the mixture was homogenous. To this mixture was added DIPEA (8.8 mg, 68 μmol) at RT by syringe. The resulting mixture was stirred at RT for 2 hours until the LP4-2 was mostly consumed according to LCMS. To this reaction mixture was then added diethylamine or piperidine (0.1 mL, excess) dropwise at RT and the mixture was stirred for an hour until Fmoc group was removed, as monitored by LCMS. (Note: Both diethylamine and piperidine were equally effective.) The reaction mixture was directly purified by prep-HPLC (method B) to give compound LP4 (15 mg, 33% yield) as a white solid. ESI m/z: 1313.6 $(M+H)^+$. $^1H$ NMR (500 MHz, methanol$_{d4}$) δ 7.59 (d, J=8.5 Hz, 2H), 7.51 (s, 1H), 7.36-7.26 (m, 3H), 7.01 (d, J=8.5 Hz, 1H), 6.88 (d, J=8.0 Hz, 1H), 6.72-6.71 (m, 1H), 6.57-6.54 (m, 1H), 5.09 (s, 2H), 4.64-4.52 (m, 1H), 4.35-4.28 (m, 2H), 4.21 (d, J=7.0 Hz, 1H), 4.01-3.98 (m, 1H), 3.88-3.84 (m, 3H), 3.43 (t, J=6.5 Hz, 1H), 3.26-3.10 (m, 4H), 3.00-2.76 (m, 3H), 2.38-2.24 (m, 7H), 2.19-2.02 (m, 9H), 1.98-1.78 (m, 4H), 1.74-1.54 (m, 12H), 1.45-1.26 (m, 14H), 1.13 (s, 6H), 1.00 (t, J=7.5 Hz, 6H) ppm.

Figure 8:
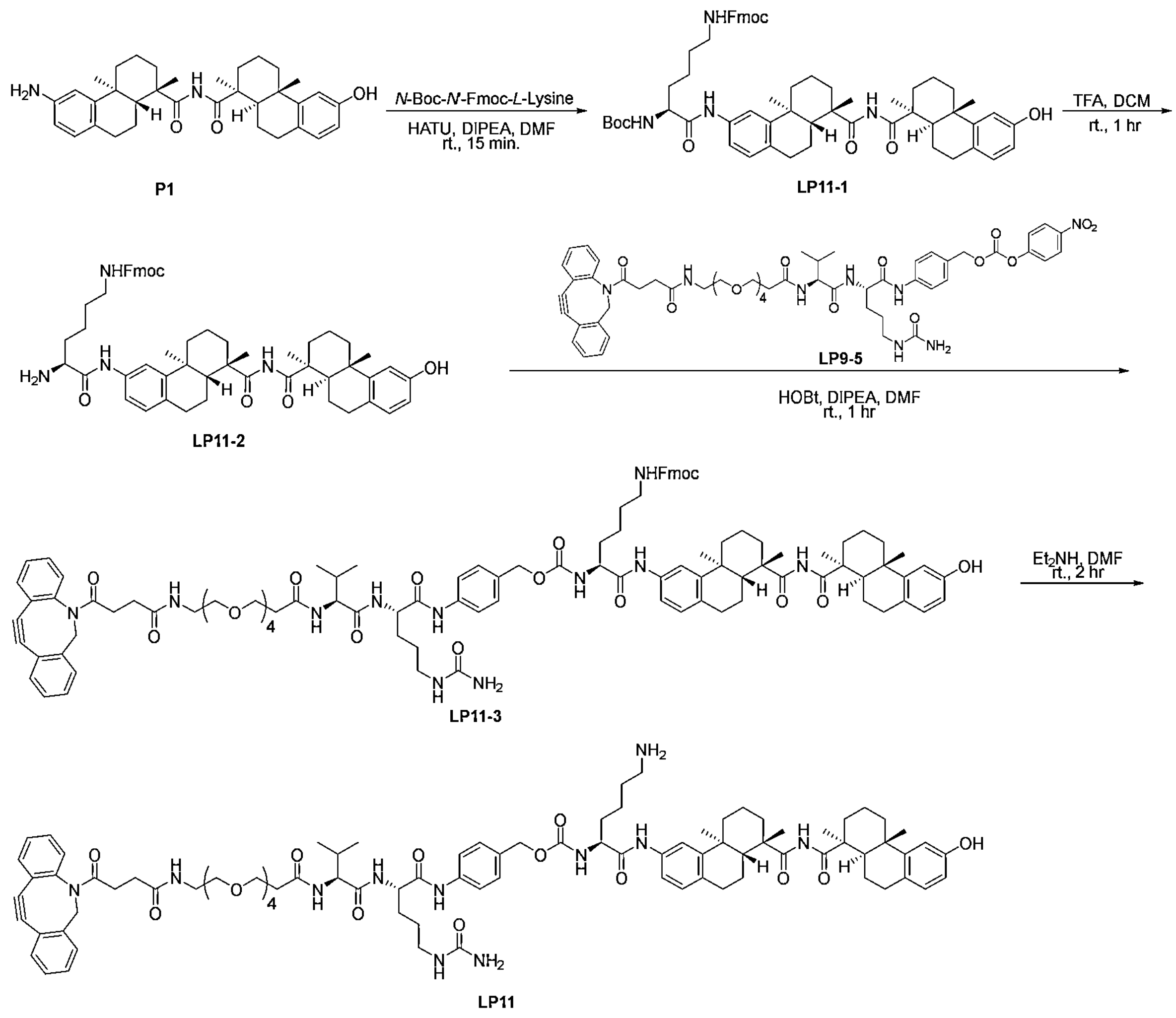
FIG. 8 provides a scheme for the synthesis of LP11.

Example 19. Synthesis of LP11 (FIG. 8)

tert-Butyl N-[(1S)-1-{[(4bS,8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}-5-{[(9H-fluoren-9-ylmethoxy)carbonyl]amino}pentyl] carbamate (LP11-1)

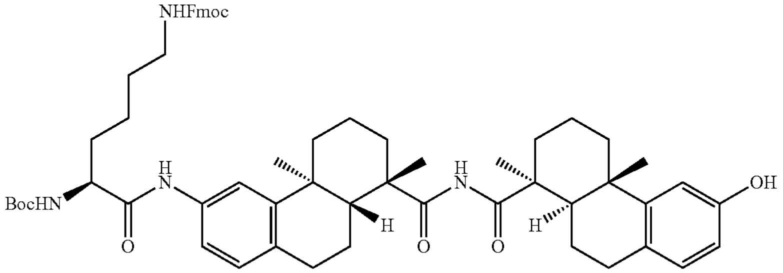

To a solution of N-Boc-N'-Fmoc-L-Lysine (0.21 g, 0.45 mmol) in DMF (2 mL) were added HATU (0.24 g, 0.64 mmol) and DIPEA (0.15 g, 1.1 mmol) at RT. The resulting mixture was stirred at RT for 3 minutes. To the mixture was then added payload P1 (0.20 g, 0.38 mmol). The reaction mixture was stirred at RT for 15 minutes until the reaction completed, as monitored by LCMS. The reaction mixture was filtered and purified by prep-HPLC (method B) to give compound LP11-1 (0.10 g, 27% yield) as a white solid. ESI m/z: 979 $(M+1)^+$.

9H-Fluoren-9-ylmethyl N-[(5S)-5-amino-5-{[(4bS, 8S,8aR)-8-{[(1S,4aS,10aR)-6-hydroxy-1,4a-dimethyl-1,2,3,4,4a,9,10,10a-octahydrophenanthrene-1-carbonyl]carbamoyl}-4b,8-dimethyl-4b,5,6,7,8,8a,9,10-octahydrophenanthren-3-yl]carbamoyl}pentyl] carbamate (LP11-2)

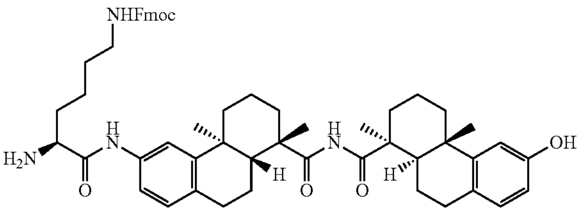

To a solution of compound LP11-1 (0.10 g, 0.10 mmol) in DCM was added TFA (2 mL) at RT. The resulting mixture was stirred at RT for an hour until Boc was totally removed according to LCMS. The volatiles were removed in vacuo. The residue was purified by reversed phase flash chromatography (0-100% acetonitrile in aq. ammonium bicarbonate (10 mM)) to give compound LP11-2 (77 mg, 86% yield) as a white solid. ESI m/z: 879 $(M+1)^+$. $^1$H NMR (400 MHz, $DMSO_{d6}$) δ 9.87-9.52 (m, 1H), 9.00 (s, 1H), 8.11 (s, 1H), 7.92-7.81 (m, 2H), 7.71-7.48 (m, 3H), 7.44-7.22 (m, 6H), 7.00-6.90 (m, 1H), 6.82 (d, J=8.3 Hz, 1H), 6.66-6.60 (m, 1H), 6.54-6.47 (m, 1H), 4.38-4.14 (m, 3H), 3.27-3.17 (m, 1H), 3.01-2.93 (m, 2H), 2.90-2.66 (m, 4H), 2.33-2.06 (m, 7H), 1.94-1.78 (m, 4H), 1.67-1.51 (m, 5H), 1.48-1.07 (m, 16H), 1.03-0.92 (m, 6H) ppm.

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-[(1S)-1-{[(4bS,8S, 8aR)-8-{[(1S,4aS,10aR)-6-hydroxy-1,4a-dimethyl-1, 2,3,4,4a,9,10,10a-octahydrophenanthrene-1-carbonyl]carbamoyl}-4b,8-dimethyl-4b,5,6,7,8,8a,9, 10-octahydrophenanthren-3-yl]carbamoyl}-5-{[(9H-fluoren-9-ylmethoxy)carbonyl]amino}pentyl] carbamate (LP11-3)

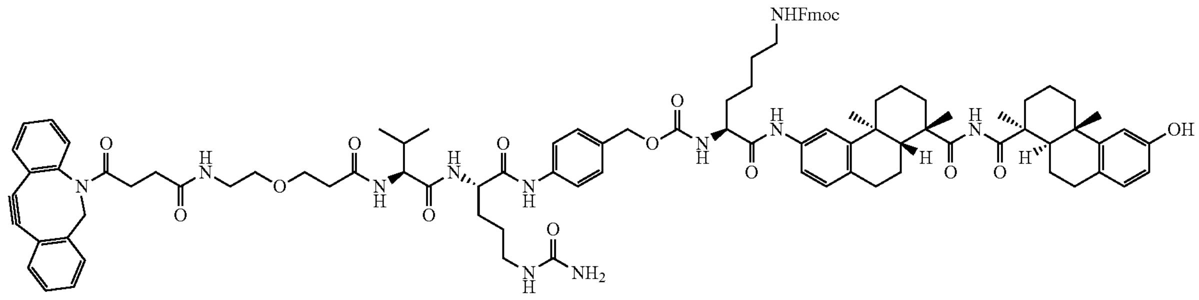

To a mixture of compound LP11-2 (57 mg, 65 μmol) and compound LP9-5 (0.10 g, 96 μmol) in DMF (3 mL) were added HOBt (30 mg, 0.22 mmol) and DIPEA (0.11 g, 0.81 mmol), and the mixture was stirred at RT for an hour, which was monitored by LCMS. The reaction mixture was purified by reversed phase flash chromatography (0-100% acetonitrile in aq. ammonium bicarbonate (10 mM)) to give compound LP11-3 (97 mg, 81% yield) as a white solid. ESI m/z: 909 $(M/2+1)^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[(1S)-5-amino-1-{[(4bS,8S,8aR)-8-{[(1S,4aS,10aR)-6-hydroxy-1,4a-dimethyl-1,2,3,4,4a,9,10,10a-octahydro-phenanthrene-1-carbonyl]carbamoyl}-4b,8-dim-ethyl-4b,5,6,7,8,8a,9,10-octahydrophenanthren-3-yl]carbamoyl}pentyl]carbamate (LP11)

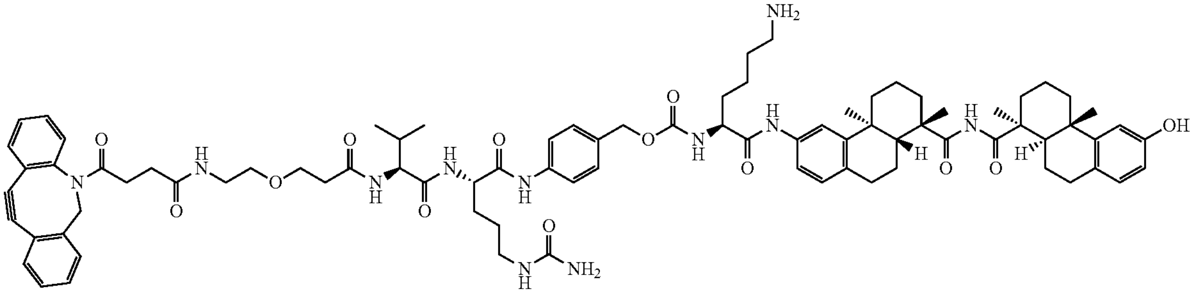 [SMILES: CC(C)[C@H](NC(=O)CCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCCCN)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

To a solution of compound LP11-3 (97 mg, 53 μmol) in DMF (3 mL) was added diethylamine (45 mg, 0.62 mmol). The mixture was stirred at RT for 2 hours until Fmoc was totally removed according to LCMS. The reaction mixture was directly purified by prep-HPLC (method B) to give compound LP11 (40 mg, 47% yield) as a white solid. ESI m/z: 798 $(M/2+1)^+$. $^1$H NMR (500 MHz, DMSO$_{d6}$) δ 9.99 (s, 1H), 9.85 (s, 1H), 9.00 (s, 1H), 8.21-8.10 (m, 2H), 7.88 (d, J=8.5 Hz, 1H), 7.82-7.59 (m, 6H), 7.55-7.43 (m, 5H), 7.41-7.29 (m, 5H), 6.98 (d, J=8.2 Hz, 1H), 6.84 (d, J=8.3 Hz, 1H), 6.66 (s, 1H), 6.53 (d, J=8.1 Hz, 1H), 6.06-5.96 (m, 1H), 5.50-5.38 (m, 2H), 5.09-4.92 (m, 3H), 4.45-4.35 (m, 1H), 4.28-4.21 (m, 1H), 4.14-4.04 (m, 1H), 3.67-3.58 (m, 4H), 3.52-3.45 (m, 13H), 3.14-2.69 (m, 9H), 2.63-2.56 (m, 1H), 2.50-2.44 (m, 1H), 2.43-2.37 (m, 1H), 2.33-2.13 (m, 7H), 2.06-1.85 (m, 6H), 1.82-1.56 (m, 9H), 1.51-1.23 (m, 17H), 1.21-1.13 (m, 2H), 1.10-0.80 (m, 12H) ppm.

Figure 9:
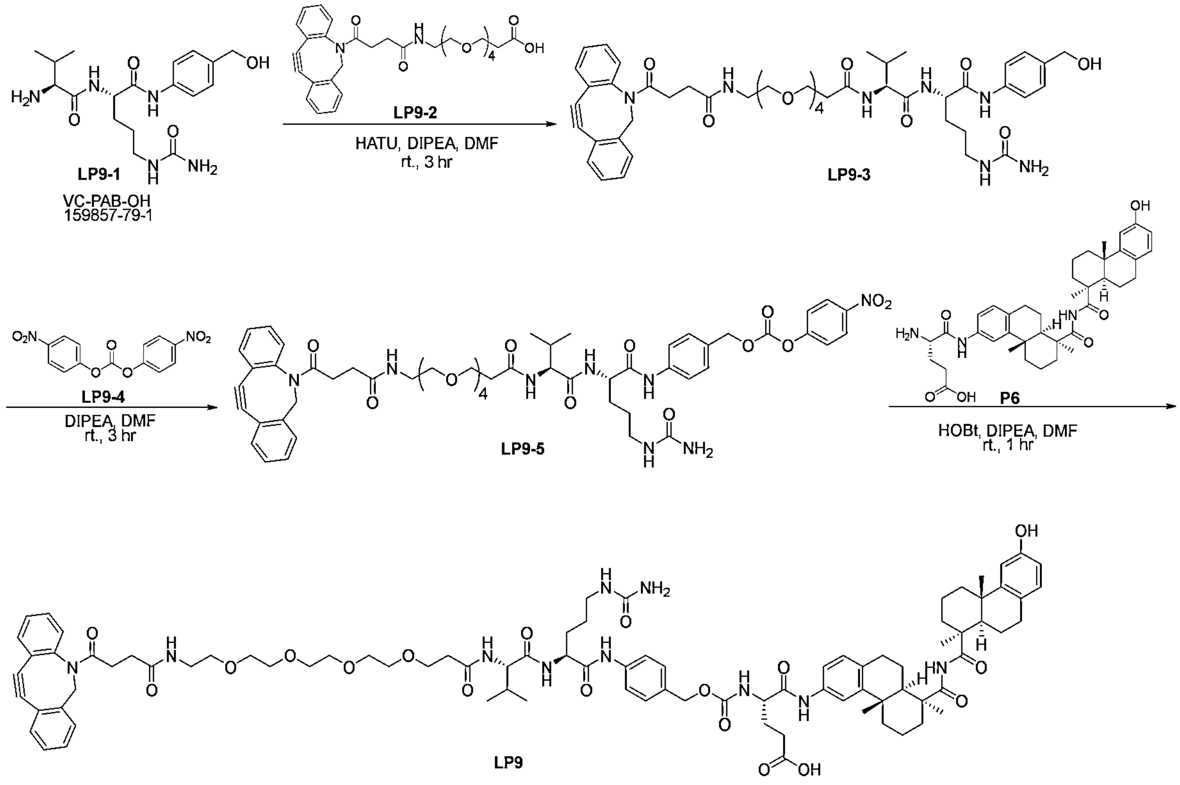
FIG. 9 provides a scheme for the synthesis of LP9.

Example 20. Synthesis of LP9 (FIG. 9)

1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (LP9-3)

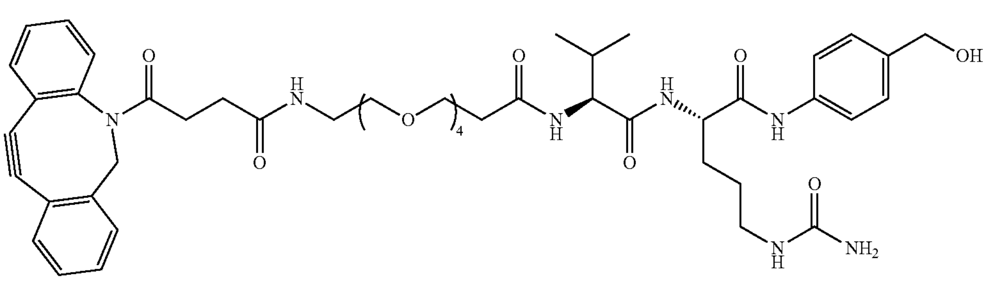

To a solution of compound LP9-2 (0.30 g, 0.54 mmol) in DMF (10 mL) were added HATU (0.31 g, 0.81 mmol) and DIPEA (0.14 g, 1.1 mmol) successively at room temperature. The mixture was stirred at room temperature for 15 minutes. To the reaction solution was added VC-PAB-OH (LP9-1, CAS: 159857-79-1, 0.21 g, 0.54 mmol) at RT, and the resulting mixture was stirred at RT for 3 hours until LP9-2 was consumed, as monitored by LCMS. The reaction mixture was filtered through filtering a membrane and the filtrate was directly purified by reversed flash chromatography (0-100% acetonitrile in water (with 10 mmol/L ammonium bicarbonate)) to give compound LP9-2 (0.30 g, 60% yield) as a white solid. ESI m/z: 617 $(M+H)^+$.

{4-[(2S)-2-[(2S)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate (LP9-5)

To a mixture of compound P6 (50 mg, 76 μmol) and compound LP9-5 (0.10 g, 96 μmol) in DMF (1 mL) were added HOBt (16 mg, 0.12 mmol) and DIPEA (39 mg, 0.31 mmol), and the mixture was stirred at RT for an hour, which was monitored by LCMS. The reaction mixture was purified by prep-HPLC (method B) to give compound LP9 (40 mg, 33% yield) as a white solid. ESI m/z: 799 $(M/2+1)^+$. $^{1}H$ NMR (500 MHz, $DMSO_{d6}$) δ 10.02 (s, 1H), 9.03 (s, 1H), 8.20-8.07 (m, 2H), 7.94-7.87 (m, 1H), 7.82-7.76 (m, 1H), 7.70-7.57 (m, 4H), 7.54-7.42 (m, 4H), 7.40-7.26 (m, 6H), 6.99-6.91 (m, 1H), 6.85-6.79 (m, 1H), 6.63 (s, 1H), 6.53-6.47 (m, 1H), 6.03 (s, 1H), 5.44 (s, 2H), 5.07-4.88 (m, 3H), 4.42-4.32 (m, 1H), 4.27-4.20 (m, 1H), 4.11-4.02 (m, 1H), 3.63-3.55 (m, 3H), 3.51-3.41 (m, 13H), 3.11-2.58 (m, 10H), 2.40-2.10 (m, 11H), 2.00-1.55 (m, 15H), 1.46-1.09 (m, 14H), 1.05-0.94 (m, 6H), 0.99-0.77 (m, 7H) ppm.

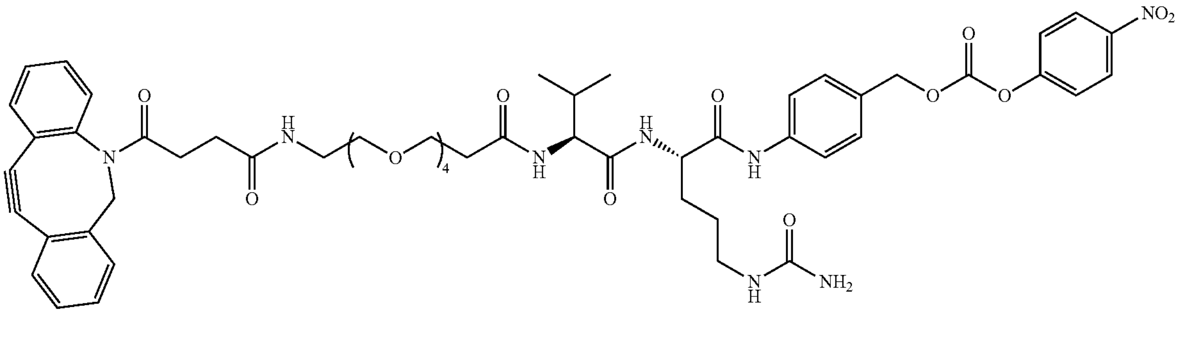

To a solution of compound LP9-3 (0.15 g, 0.16 mmol) in DMF (10 mL) were added bis(4-nitrophenyl) carbonate (LP9-4, 0.15 g, 0.49 mmol) and DIPEA (63 mg, 0.49 mmol) successively at 0° C. The mixture was then stirred at RT for 3 hours until LP9-3 was mostly consumed, as monitored by LCMS. The reaction mixture was filtered through a filtering membrane and the filtrate was directly purified by reversed flash chromatography (0-100% acetonitrile in water (with 10 mmol/L ammonium bicarbonate)) to give compound LP9-5 (50 mg, 28% yield) as a white solid. ESI m/z: 1079 $(M+H)^+$.

(4S)-4-{[({4-[(2S)-2-[(2S)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl]amino}-4-{[(4bS,8S,8aR)-8-{[(1S,4aS,10aR)-6-hydroxy-1,4a-dimethyl-1,2,3,4,4a,9,10,10a-octahydrophenanthrene-1-carbonyl] carbamoyl}-4b,8-dimethyl-4b,5,6,7,8,8a,9,10-octahydrophenanthren-3-yl]carbamoyl}butanoic acid (LP9)

Figure 10:
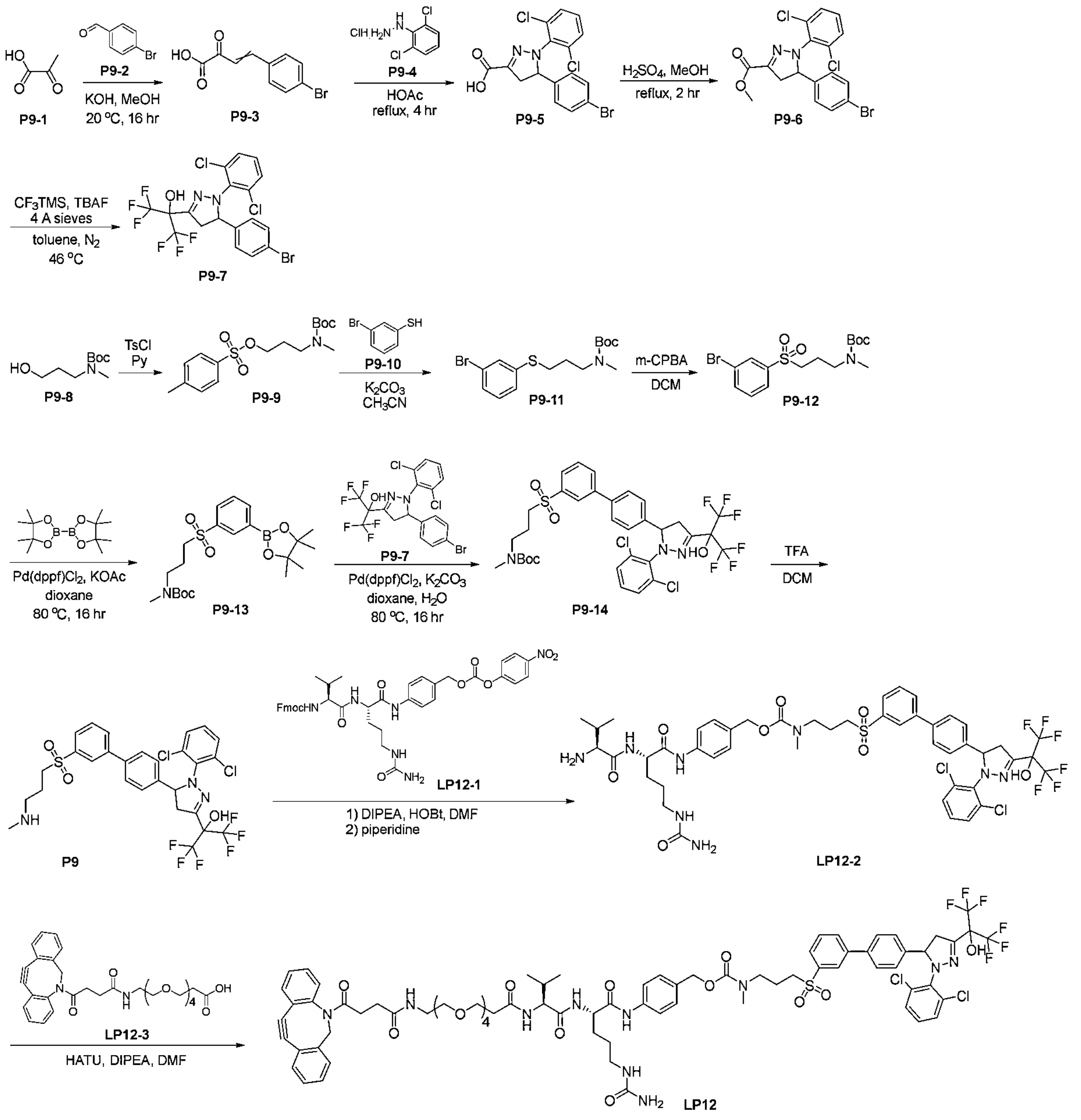
FIG. 10 provides a scheme for the synthesis of LP12.

Example 21. Synthesis of Payload P9 and Linker-Payload LP12 (FIG. 10)

Payload P9

Synthesis of Payload P9 is based, at least in part, on US 2015/0291563A1, incorporated herein by reference in its entirety. 4-(4-Bromophenyl)-2-oxobut-3-enoic acid (P9-3)

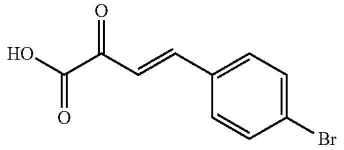

To a solution of 4-bromobenzaldehyde P9-2 (5.5 g, 30 mmol) and pyruvic acid P9-1 (2.8 g, 32 mmol) in methanol (100 mL) was added a solution of potassium hydroxide (2.5 g, 45 mmol) in methanol (100 mL) at 0° C. Precipitation

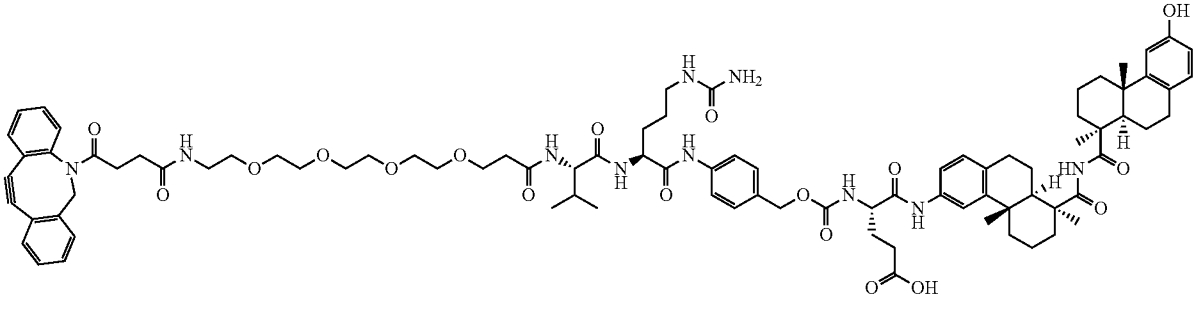 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N[C@@H](CCC(=O)O)C(=O)Nc2ccc3c(c2)[C@@]2(C)CCC[C@](C)(C(=O)NC(=O)[C@@]4(C)CCC[C@]5(C)c6cc(O)ccc6CC[C@@H]45)[C@@H]2CC3)cc1]

occurred during addition of the base and the mixture was allowed to reach RT for an hour. The mixture was allowed to stirred at RT for 16 hours and then concentrated in vacuo to remove volatiles. The residue was diluted with water (200 mL) and acidified with aq. HCl (1 M) to pH 3. The mixture was extracted with ethyl acetate (100 mL×3). The combined organic solution was dried over sodium sulfate and concentrated in vacuo to give compound P9-3 (7.1 g, 93% yield) as viscous oil. ESI m/z: 255 $(M+1)^+$.

5-(4-Bromophenyl)-1-(2,6-dichlorophenyl)-4,5-dihydro-1H-pyrazole-3-carboxylic acid (P9-5)

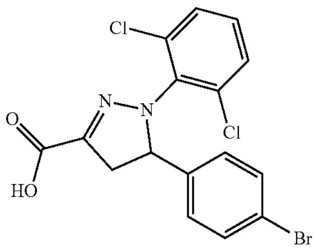 [SMILES: O=C(O)C1=NN(c2c(Cl)cccc2Cl)C(c2ccc(Br)cc2)C1]

A mixture of compound P9-3 (5.1 g, 20 mmol) and (2,6-dichlorophenyl)hydrazine hydrochloride P9-4 (4.1 g, 20 mmol) in glacial acetic acid (100 mL) were refluxed under a nitrogen atmosphere for 4 hours. After cooled to 25° C., the reaction mixture was poured into ice-water, whereby a sticky mass was obtained, which was extracted with DCM. The combined organic solutions were washed with water, dried with sodium sulfate and concentrated. The residue was dried in air to give compound P9-5 (5.4 g, 65% yield) as a pale yellow solid. ESI m/z: 413 $(M+1)^+$.

Methyl 5-(4-bromophenyl)-1-(2,6-dichlorophenyl)-4,5-dihydro-1H-pyrazole-3-carboxylate (P9-6)

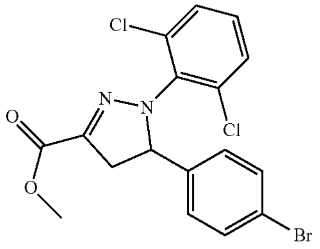 [SMILES: COC(=O)C1=NN(c2c(Cl)cccc2Cl)C(c2ccc(Br)cc2)C1]

To the solution of compound P9-5 (8.2 g, 20 mmol) in methanol (200 mL) was added sulfuric acid (0.5 mL) dropwise. The mixture was refluxed for 4 hours, which was monitored by LCMS. The reaction mixture was cooled to RT and the volatiles were removed in vacuo. The residue was extracted with ethyl acetate (300 mL) and subsequently washed with sat. aq. ammonium chloride and water. The organic layer was dried over sodium sulfate and concentrated in vacuo. The residue was purified by silica gel column chromatography (ethyl acetate/n-hexane=1/4) to give compound P9-6 (2.1 g, 25% yield) as yellow oil. ESI m/z 429 $(M+1)^+$. $^1$H NMR (500 MHz, $DMSO_{d6}$) δ7.50-7.45 (m, 4H), 7.35-7.25 (m, 3H), 5.70-5.52 (m, 1H), 3.77 (s, 3H), 1.75-1.65 (m, 1H), 3.32-3.24 (m, 1H) ppm.

2-(5-(4-Bromophenyl)-1-(2,6-dichlorophenyl)-4,5-dihydro-1H-pyrazol-3-yl)-1,1,1,3,3,3-hexafluoropropan-2-ol (P9-7)

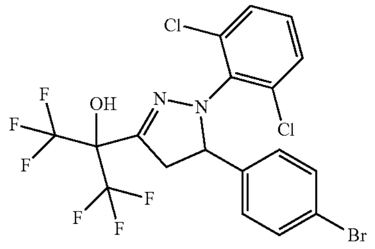 [SMILES: OC(C1=NN(c2c(Cl)cccc2Cl)C(c2ccc(Br)cc2)C1)(C(F)(F)F)C(F)(F)F]

To a mixture of compound P9-6 (0.49 g, 1.2 mmol) in toluene (20 mL) were added (trifluoromethyl)trimethylsilane (0.68 mL, 4.6 mmol), 4 Å molecular sieves (100 mg) and TBAF (1 M in THF, 4.6 mL) slowly under nitrogen atmosphere. The resulting mixture was stirred at 46° C. for 16 hours. The resulting mixture was filtered through celite pad and the filtrate was diluted with DCM. The solution was washed with distilled water and brine, dried over anhydrous magnesium sulfate and concentrated in vacuo. The yellow residue was purified by silica gel column chromatography (ethyl acetate/n-hexane=1/8) to give compound P9-7 (0.15 g, 25% yield) as brown oil. $^1$H NMR (400 MHz, $CDCl_3$) δ 7.43-7.38 (m, 2H), 7.25 (s, 1H), 7.24 (s, 1H), 7.22-7.17 (m, 2H), 7.12-7.06 (m, 1H), 5.75-5.95 (m, 1H), 4.88 (s, 1H), 3.65-3.55 (m, 1H), 3.26-3.16 (m, 1H) ppm.

tert-Butyl 3-(3-bromophenylthio)propyl(methyl)carbamate (P9-11)

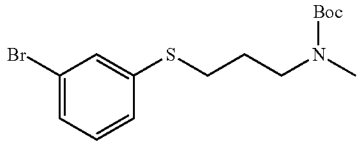 [SMILES: CN(CCCSc1cccc(Br)c1)C(=O)OC(C)(C)C]

To the solution of tert-butyl 3-hydroxypropyl(methyl) carbamate P9-8 (1.9 g, 10 mmol) in Pyridine (5 mL) was added tosyl chloride (2.1 g, 11 mmol) dropwise at 0° C. The mixture was stirred at RT for 2 hours, which was monitored by LCMS. The mixture was concentrated in vacuo to remove Pyridine to give crude product P9-9 (ESI m/z: 244 $(M-Boc+1)^+$), which was dissolved in acetonitrile (100 mL). To the solution were added 3-bromobenzenethiol P9-10 (1.9 g, 10 mmol) and cesium carbonate (6.5 g, 20 mmol). The mixture was refluxed for 4 hours, which was monitored by LCMS. After cooled to RT, the reaction mixture was filtered and the filtrate was concentrated in vacuo. The residue was purified by silica gel column chromatography (8-10% ethyl acetate in petroleum ether) to give compound P9-11 (2.2 g, 61% yield) light yellow oil. ESI m/z: 260 $(M-Boc+1)^+$.

tert-Butyl 3-(3-bromophenylsulfonyl)propyl(methyl)carbamate (P9-12)

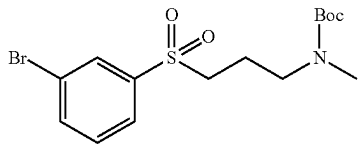 [SMILES: CN(CCCS(=O)(=O)c1cccc(Br)c1)C(=O)OC(C)(C)C]

To a solution of compound P9-11 (0.36 g, 1.0 mmol) in DCM (20 mL) was added mCPBA (1.0 g, 0.4 mmol) slowly at 0° C. The mixture was stirred at RT for 4 hours, which was monitored by LCMS. The reaction mixture was washed with sat. aq. sodium carbonate (20 mL×3) and brine. The organic solution was dried over sodium sulfate, filtered and concentrated in vacuo. The crude product was purified by silica gel column chromatography (8-10% ethyl acetate in petroleum ether) to give compound P9-12 (0.22 g, 56% yield) as light yellow oil. ESI m/z: 294 $(M-Boc+1)^+$.

tert-Butyl methyl(3-(3-(4,4,5,5-tetramethyl-1,3,2-dioxaborolan-2-yl)phenylsulfonyl)propyl)carbamate (P9-13)

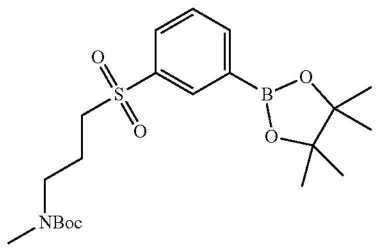

To a solution of compound P9-12 (0.20 g, 0.51 mmol) in 1,4-dioxane (20 mL) were added bis(pinacolato)diboron (0.26 g, 1.0 mmol), $Pd(dppf)Cl_2$ (37 mg, 0.051 mmol) and potassium acetate (0.20 g, 2.0 mmol) under nitrogen atmosphere. The reaction mixture was stirred at 80° C. for 16 hours under nitrogen atmosphere. After cooled to RT, the mixture was filtered through celite pad. To the filtrate was added distilled water and the mixture was extracted with diethyl ether three times. The combined extracts were washed with distilled water and brine, dried over anhydrous magnesium sulfate, and concentrated in vacuo to give a yellow liquid residue. The residue was purified by silica gel column chromatography (8-10% ethyl acetate in petroleum ether) to give compound P9-13 (0.20 g, 87% yield) as colorless oil. ESI m/z: 340 $(M-Boc+1)^+$. $^1H$ NMR (500 MHz, $DMSO_{d6}$) δ 8.10 (s, 1H), 8.05-8.0 (m, 2H), 7.70 (t, J=7.5 Hz, 1H), 3.30-3.25 (m, 2H), 3.20-3.14 (m, 2H), 2.70 (s, 3H), 1.75-1.67 (m, 2H), 1.32 (s, 9H), 1.16 (s, 12H) ppm.

tert-Butyl 3-(4'-(1-(2,6-dichlorophenyl)-3-(1,1,1,3,3,3-hexafluoro-2-hydroxypropan-2-yl)-4,5-dihydro-1H-pyrazol-5-yl)biphenyl-3-ylsulfonyl)propyl (methyl)carbamate (P9-14)

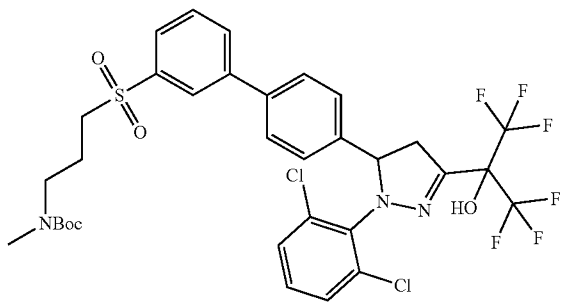 [SMILES: CN(CCCS(=O)(=O)c1cccc(-c2ccc(C3CC(C(O)(C(F)(F)F)C(F)(F)F)=NN3c3c(Cl)cccc3Cl)cc2)c1)C(=O)OC(C)(C)C]

To a mixture of compound P9-13 (0.20 g, 0.51 mmol) and compound P9-7 (0.27 g, 0.51 mmol) in 1,4-dioxane (20 mL) and water (3 mL) were added $Pd(dppf)Cl_2$ (37 mg, 0.051 mmol) and potassium carbonate (0.28 g, 2.0 mmol) under nitrogen protection. The reaction mixture was exchanged with nitrogen 3 times and was stirred at 80° C. under nitrogen atmosphere for 16 hours. After cooled to RT, the reaction mixture was filtered through celite pad. The filtrate was diluted with distilled water and extracted with diethyl ether three times. The combined extracts were washed with distilled water and brine, dried over anhydrous magnesium sulfate and concentrated in vacuo. The residue was purified by silica gel column chromatography (8-10% ethyl acetate in petroleum ether) to give compound P9-14 (0.33 g, 84% yield) as colorless oil. ESI m/z: 667 $(M-Boc+1)^+$.

2-(1-(2,6-Dichlorophenyl)-5-(3'-(3-(methylamino)propylsulfonyl)biphenyl-4-yl)-4,5-dihydro-1H-pyrazol-3-yl)-1,1,1,3,3,3-hexafluoropropan-2-ol, trifluoroacetic acid salt (P9)

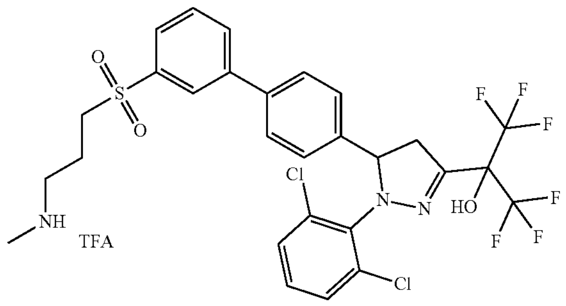 [SMILES: CNCCCS(=O)(=O)c1cccc(-c2ccc(C3CC(C(O)(C(F)(F)F)C(F)(F)F)=NN3c3c(Cl)cccc3Cl)cc2)c1]

To a solution of compound P9-14 (0.20 g, 0.26 mmol) in DCM (10 mL) was added TFA (3 mL). The reaction mixture was stirred at RT for an hour, which was monitored by LCMS. The volatiles were removed in vacuo. The resulting yellow residue was purified by prep-HPLC (method A) to give compound P9 (55 mg, 32% yield as its TFA salt) as a white solid. ESI m/z: 667 $(M+1)^+$. $^1H$ NMR (400 MHz, $DMSO_{d6}$) δ 8.77 (s, 1H), 8.34 (s, 2H), 8.10-8.00 (m, 2H), 7.90-7.83 (m, 1H), 7.80-7.77 (m, 3H), 7.50-7.40 (m, 4H), 7.30-7.20 (m, 1H), 5.58 (t, J=10.4 Hz, 1H), 3.80-3.66 (m, 1H), 3.52 (t, J=8.0 Hz, 2H), 3.26-3.18 (m, 1H), 3.00-2.90 (m, 2H), 2.56-2.52 (m, 3H), 1.92-1.82 (m, 2H) ppm. (H of TFA was not revealed).

Linker-Payload LP12

4-((S)-2-((S)-2-Amino-3-methylbutanamido)-5-ureidopentanamido)benzyl 3-(4'-(1-(2,6-dichlorophenyl)-3-(1,1,1,3,3,3-hexafluoro-2-hydroxypropan-2-yl)-4,5-dihydro-1H-pyrazol-5-yl)biphenyl-3-ylsulfonyl)propyl(methyl)carbamate (LP12-2)

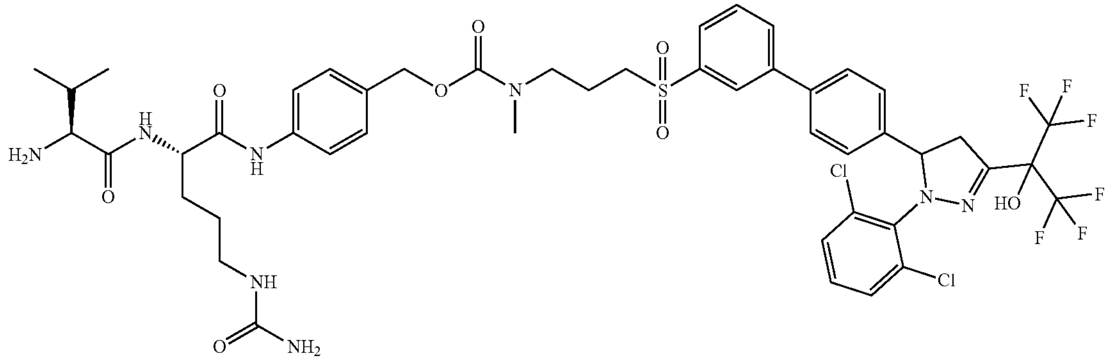 [SMILES: CC(C)[C@H](N)C(=O)N[C@@H](CCCNC(N)=O)C(=O)Nc1ccc(COC(=O)N(C)CCCS(=O)(=O)c2cccc(-c3ccc(C4CC(C(O)(C(F)(F)F)C(F)(F)F)=NN4c4c(Cl)cccc4Cl)cc3)c2)cc1]

To a solution of compound P9 (50 mg, 0.075 mmol) in DMF (5 mL) were added Fmoc-VC-PAB-PNP P12-1 (63 mg, 0.083 mmol), DIPEA (19 mg, 0.15 mmol) and HOBt (15 mg, 0.11 mmol). The reaction mixture was stirred at RT for 4 hours, which was monitored by LCMS. Piperidine (1 mL, excess) was then added into the reaction mixture. The mixture was stirred at RT for an hour until Fmoc was totally removed according to LCMS. The mixture was directly purified by reversed phase flash chromatography (0-50% acetonitrile in aq. ammonium bicarbonate (10 mM)) to give compound LP12-2 (48 mg, 60% yield) as a white solid. ESI m/z: 1073 $(M+1)^+$.

{4-[(2S)-2-[(2S)-2-[1-(4-{2-Azatricyclo[10.4.0.0$^4$,]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-[3-(3-{4-[1-(2,6-dichlorophenyl)-3-(1,1,1,3,3,3-hexafluoro-2-hydroxypropan-2-yl)-4,5-dihydro-1H-pyrazol-5-yl]phenyl}benzenesulfonyl)propyl]-N-methylcarbamate (LP12)

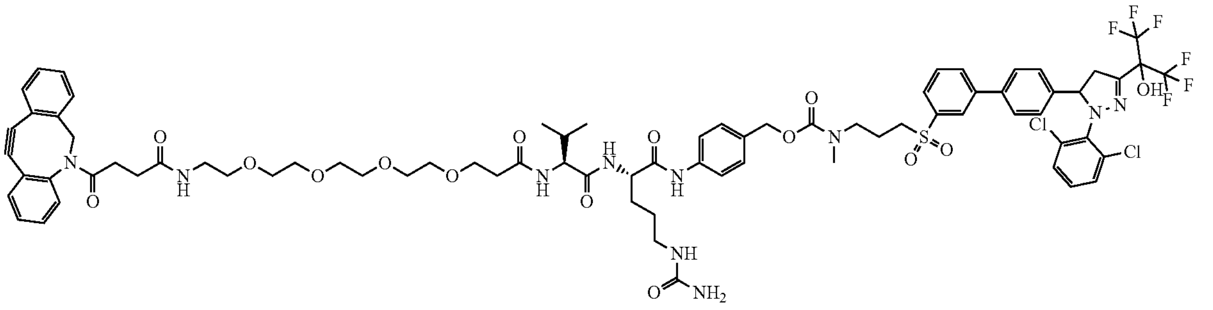 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)N(C)CCCS(=O)(=O)c2cccc(-c3ccc(C4CC(C(O)(C(F)(F)F)C(F)(F)F)=NN4c4c(Cl)cccc4Cl)cc3)c2)cc1]

To a solution of DIBAC-PEG4-acid LP12-3 (18 mg, 32 μmol) in DMF (5 mL) were added HATU (15 mg, 39 μmol) and DIPEA (14 mg, 0.11 mmol) at RT. The resulting mixture was stirred at RT for 30 minutes. To the mixture was then added LP12-2 (29 mg, 27 μmol). The reaction mixture was stirred at RT for an hour until the reaction completed, which was monitored by LCMS. The reaction mixture was filtered and purified by prep-HPLC (method B) to give LP12 (25 mg, 58% yield) as a white solid. ESI m/z: 805 $(M/2+1)^+$. $^1$H NMR (500 MHz, $DMSO_{d6}$) δ 9.99 (s, 1H), 8.75 (s, 1H), 8.13 (d, J=7.5 Hz, 1H), 8.09 (s, 1H), 8.03 (d, J=7.0 Hz, 1H), 7.90-7.80 (m, 2H), 7.80-7.65 (m, 5H), 7.65-7.60 (m, 1H), 7.60-7.52 (m, 2H), 7.52-7.43 (m, 5H), 7.43-7.39 (m, 2H), 7.39-7.31 (m, 2H), 7.31-7.20 (m, 4H), 5.98 (t, J=5.5 Hz, 1H), 5.57 (t, J=10.5 Hz, 1H), 5.41 (s, 2H), 5.03 (d, J=14.0 Hz, 1H), 5.0-4.90 (m, 2H), 4.43-4.34 (m, 1H), 4.23 (t, J=7.0 Hz, 1H), 3.75-3.65 (m, 1H), 3.65-3.53 (m, 3H), 3.53-3.40 (m, 12H), 3.32-3.20 (m, 6H), 3.10-3.05 (m, 2H), 3.05-3.00 (m, 1H), 3.00-2.90 (m, 1H), 2.80-2.70 (m, 3H), 2.60-2.53 (m, 1H), 2.49-2.42 (m, 1H), 2.40-2.30 (m, 1H), 2.30-2.20 (m, 1H), 2.04-1.90 (m, 2H), 1.80-1.65 (m, 4H), 1.65-1.50 (m, 1H), 1.50-1.30 (m, 2H), 1.23 (s, 1H), 0.90-0.80 (m, 6H) ppm.

Example 22. Synthesis of Payload P3 and Payload P4 (FIG. 11)

Figure 11:
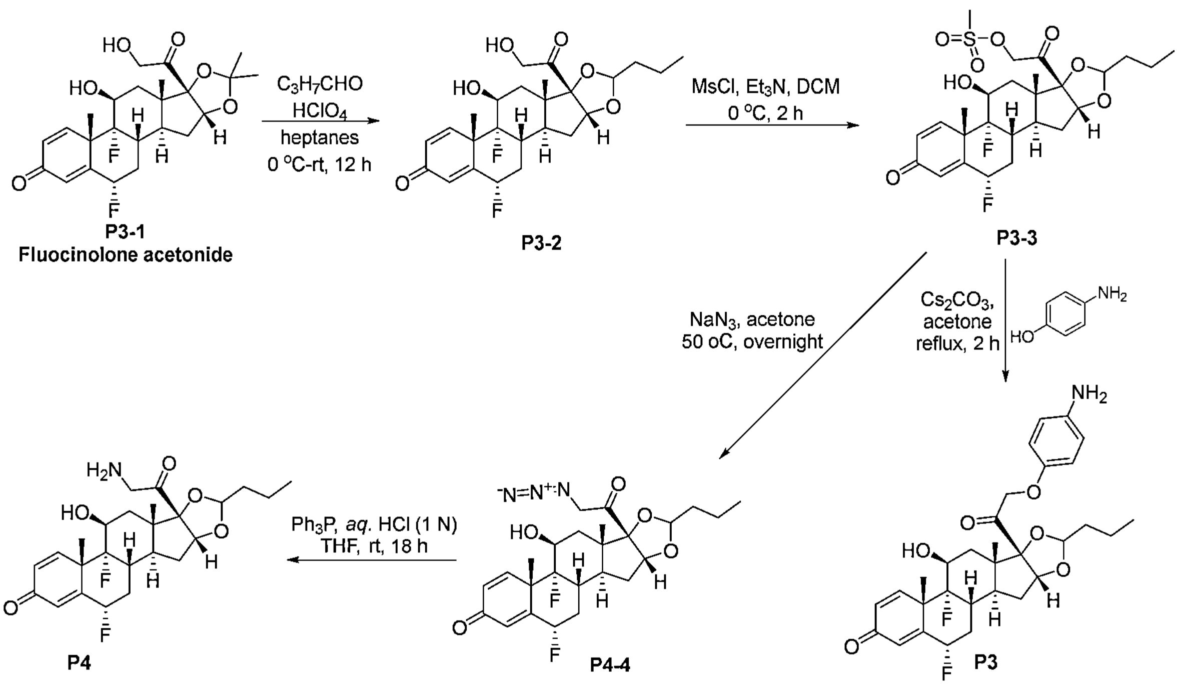
FIG. 11 provides a scheme for the synthesis of P3 and P4.

This example refers to FIG. 11. Certain steroidal payloads were prepared starting from commercial fluocinolone acetonide P3-1 (CAS: 67-73-2). Compound P3-2, obtained from P3-1 by ketal-exchange with butyraldehyde in the presence of perchloric acid, was converted to mesylate P3-3 followed by replacement of the mesylate group with azide moiety to form P4-4 that was reduced to amine P4. Otherwise, the mesylate moiety in P3-3 was also replaced by 4-amino-phenol to afford aniline P3.

Payload P3

(1S,2S,4R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.$0^{2,9}$. $0^{4,8}$.$0^{13,18}$] icosa-14,17-dien-16-one (P3-2)

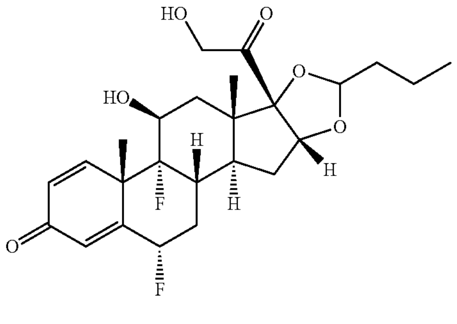

To a mixture of fluocinolone acetonide (P3-1, 0.90 g, 2.0 mmol) and silica gel (18 g) in heptanes (90 mL) was added butyraldehyde (0.27 mL, 3.0 mmol) at 10° C. and the suspension was stirred at 10-20° C. for 10 minutes. To the mixture was added perchloric acid (70%, 0.68 mL, 8.3 mmol) dropwise at 0° C. The reaction mixture was then stirred at 10-20° C. overnight. Most of fluocinolone acetonide P3-1 was consumed according to TLC and LCMS. The reaction mixture was diluted with petroleum ether and quenched with sat. aq. $Na_2CO_3$. The suspension was filtered and the solid was washed with DCM/methanol (v/v=1). The combined filtrate was concentrated in vacuo. The residue was purified by flash chromatography on silica gel (0-100% ethyl acetate in petroleum ether) to give compound P3-2 (0.15 g, 16% yield) as a white solid. ESI m/z: 467.1 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethyl methanesulfonate (P3-3)

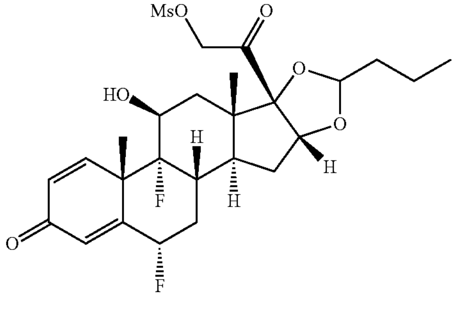

To a solution of compound P3-2 (0.28 g, 0.65 mmol)) and triethylamine (0.13 g, 1.3 mmol) in DCM (3 mL) was added methanesulfonyl chloride (89 mg, 0.78 mmol) at 0° C. After stirred at 0° C. for 0.5 h, the reaction mixture was diluted with DCM (20 mL). The mixture was washed with $H_2O$ (20 mL×2), dried over anhydrous $Na_2SO_4$, filtered and concentrated in vacuo. The residue was purified by silica gel column chromatography on silica gel (0-50% ethyl acetate in petroleum ether) to give compound P3-3 (0.26 g, >99% yield) as a white solid. ESI m/z: 545 $(M+H)^+$.

(1S,2S,4R,8S,9S,11S,12R,13S,19S)-8-[2-(4-Aminophenoxy)acetyl]-12,19-difluoro-11-hydroxy-9,13-dimethyl-6-propyl-5,7-dioxapentacyclo[10.8.0.$0^{2,9}$.$0^{4,8}$.$0^{13,18}$]icosa-14,17-dien-16-one (P3)

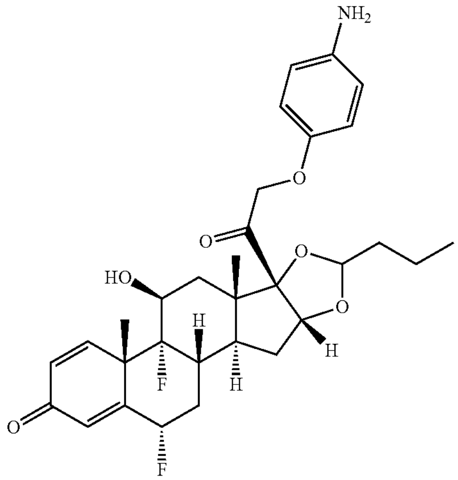

A mixture of compound P3-3 (93 mg, 0.17 mmol), 4-aminophenol (37 mg, 0.34 mmol) and cesium carbonate (0.11 g, 0.34 mmol) in acetone (0.5 mL) was refluxed for 2 hours. The mixture was cooled to RT and diluted with $H_2O$ (10 mL). The mixture was extracted with ethyl acetate (10 mL×3). The combined organic layer was washed with water (20 mL) and brine (20 mL), dried over $Na_2SO_4$, filtered and concentrated in vacuo. The residue was purified by prep-HPLC to give payload P3 (6.0 mg, 6.3% yield) as a white solid. ESI m/z: 298 $(M/2+H)^+$, 558 $(M+H)^+$ (10%). $^1H$ NMR (500 MHz, $MeOD_{d4}$) δ 7.34 (d, J=10.0 Hz, 1H), 6.78-6.71 (m, 4H), 6.37-6.33 (m, 2H), 5.63-5.49 (m, 1H), 5.10-4.99 (m, 1H), 4.77-4.63 (m, 2H), 4.33 (d, J=9.1 Hz, 1H), 2.74-2.57 (m, 1H), 2.39-2.13 (m, 3H), 1.98-1.31 (m, 12H), 1.03-0.93 (m, 6H) ppm. Anal. HPLC: purity 97.4%, Retention time: 7.55 min (method B).

Payload P4

(1S,2S,4R,8S,9S,11S,12R,13S,19S)-8-(2-Azidoacetyl)-12,19-difluoro-11-hydroxy-9,13-dimethyl-6-propyl-5,7-dioxapentacyclo[10.8.0.$0^{2,9}$.$0^{4,8}$.$0^{13,18}$] icosa-14,17-dien-16-one (P4-4)

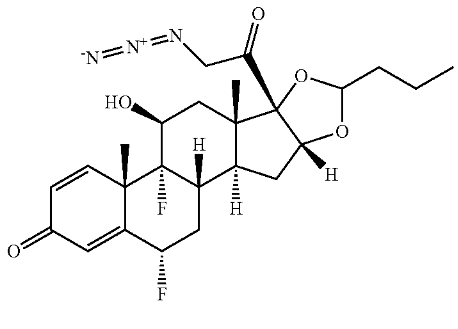

A suspension of compound P3-3 (1.0 g, 1.8 mmol) and sodium azide (1.2 g, 18 mmol) in acetone (15 mL) was stirred at 50° C. overnight. The mixture was cooled to RT and poured into water (80 mL). The aqueous mixture was extracted with ethyl acetate (50 mL×3). The combined organic layer was washed with brine (30 mL), dried over anhydrous $Na_2SO_4$, filtered and concentrated in vacuo to afford crude azido precursor compound P4-4 (0.90 g, >99% yield) as a yellow solid, which was used for the next step without further purification. ESI m/z: 492 $(M+H)^+$.

(1S,2S,4R,6R,8S,9S,11S,12R,13S,19S)-8-(2-Aminoacetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid salt (P4)

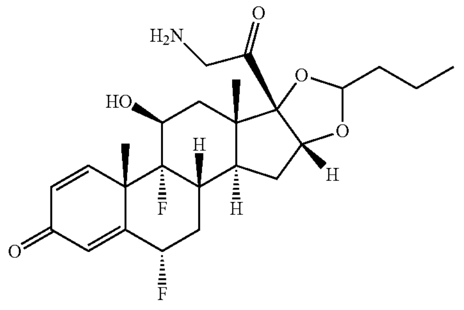

To a solution of compound P4-4 (0.85 g, 1.7 mmol) in THF (20 mL) was added aq. hydrochloride (1 N, 10 mL). The mixture was stirred at 28-32° C. until it turned clear, to the mixture was then added triphenylphosphine (0.68 g, 2.6 mmol). The resulting yellow clear solution was stirred at RT for 18 h. The mixture was concentrated in vacuo and the residue was purified by reversed phase flash chromatography (0-50% acetonitrile in aq. TFA (0.05%)) to give compound P4 (R/S) (0.56 g, 57% yield, TFA salt) as an off-white solid. ESI m/z: 466 $(M+H)^+$. $^1$H NMR (400 MHz, MeOD$_{d4}$) δ 7.33 (d, J=9.9 Hz, 1H), 6.40-6.29 (m, 2H), 5.69-5.45 (m, 1H), 4.93-4.92 (m, 1H), 4.71 (t, J=4.3 Hz, 1H), 4.35-4.27 (m, 2H), 3.90-3.84 (m, 1H), 2.81-2.54 (m, 1H), 2.42-2.06 (m, 3H), 1.82-1.32 (m, 11H), 1.09-0.87 (m, 6H) ppm. $^{19}$F NMR (376 MHz, $CD_3OD$) δ −77.01, −166.24, −166.92, −188.81, −188.83 ppm. Anal. HPLC: 100%, Retention time: 6.86 min (method A).

Payload P4 is optionally subjected to chiral separation by HPLC and/or supercritical fluid chromatography (SFC). Stereochemically pure epimers of P4, i.e., P4-1 (R) and P4-2 (S) or enriched mixtures thereof, P4-3, were obtained by chiral separation from a mixture of their corresponding R/S isomers. The absolute stereochemistry for each compound was determined by 2D-NOESY. Reference is made to US Application Publication Number US 2018/0155389, which shows that in the 2D-NOESY spectra for compounds 11-5R/S therein, $H^{22}$ and $H^{18}$ were correlated for a compound 11-5R, and that there was no correlation between $H^{22}$ and $H^{18}$ in 11-5S. Using a similar analysis as depicted in US 2018/0155389 for compounds 11-5R/S, the chiral centers at $C^{22}$-position are identified for compounds P4-1 and P4-2 herein by 2D-NOESY.

P4-1

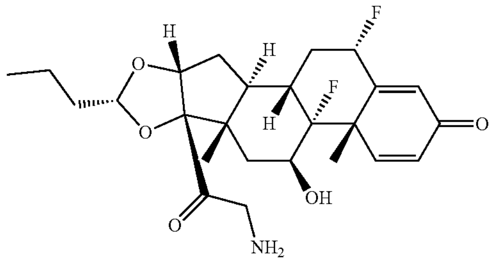

(R isomer)

P4-2

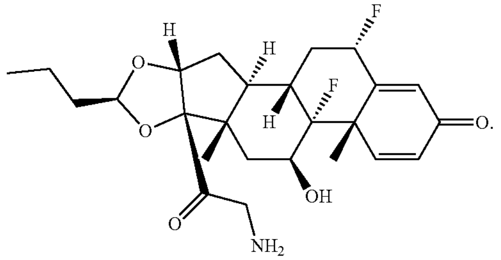

(S isomer)

P4-3: R:S 3:1 to 4:1

Alternate synthesis (1S,2S,4R,6R,8S,9S,11S,12R,13S,19S)-8-(2-Aminoacetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid salt P4-1 (R)

Step 1: Using the same procedure described above, the azido precursor P4-4 (R) (0.12 g, 87% yield) was obtained from compound (P3-3R) as a white solid after purification by flash chromatography (0-50% ethyl acetate in petroleum ether). ESI m/z: 492 $(M+H)^+$. $^1$H NMR (500 MHz, $CDCl_3$) δ 7.10 (dd, J=10.2, 1.3 Hz, 1H), 6.44 (s, 1H), 6.38 (dd, J=10.2, 1.8 Hz, 1H), 5.48-5.31 (m, 1H), 4.92 (d, J=5.4 Hz, 1H), 4.62 (t, J=4.4 Hz, 1H), 4.43 (dd, J=5.6, 2.7 Hz, 1H), 4.22 (d, J=18.7 Hz, 1H), 3.94 (d, J=18.7 Hz, 1H), 2.56-2.39 (m, 2H), 2.32-2.18 (m, 2H), 1.85-1.71 (m, 3H), 1.67-1.54 (m, 7H), 1.46-1.37 (m, 2H), 0.97-0.90 (m, 6H) ppm.

Step 2: Using the same procedure described above, compound P4-1 (R) (30 mg, 66% yield) was obtained as a white solid after purification by prep-HPLC (method A). ESI m/z: 466 $(M+H)^+$. $^1$H NMR (500 MHz, MeOD$_{d4}$) δ 7.34 (d, J=10.0 Hz, 1H), 6.40-6.30 (m, 2H), 5.65-5.46 (m, 1H), 4.94-4.91 (m, 1H), 4.72 (t, J=4.3 Hz, 1H), 4.34-4.28 (m, 2H), 3.88 (d, J=18.8 Hz, 1H), 2.78-2.60 (m, 1H), 2.39-2.34 (m, 1H), 2.33-2.18 (m, 2H), 1.77-1.54 (m, 9H), 1.53-1.40 (m, 2H), 0.99-0.95 (m, 6H) ppm. Anal. HPLC: 100%, Retention time: 6.85 min (method A).

P4-2 (S) is obtained using a similar procedure.

The Table below provides a comparison of $^1$H NMR chemical shifts (ppm in d6-DMSO) of R-P4 (P4-1 herein) and S-P4 (P4-2 herein) isolated by SFC of P4 (R/S).

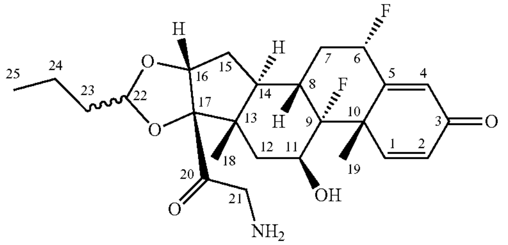

| Proton # | P4 (rac-) in DMSO-d6 | P4-1 (R) in DMSO-d6 | P4-2 (S)-in DMSO-d6 |
|---|---|---|---|
| | 8.14 (s, 3H) | 8.14 (s, 3H) | 8.12 (brs, 3H), |
| $C^1$—H | 7.31 (d, J = 10.2 Hz, 1H) | 7.30 (d, J = 10.0 Hz, 1H) | 7.30 (d, J = 10.0 Hz, 1H), |
| $C^2$—H | 6.31 (dd, J = 10.1 Hz, 1.6 Hz, 1H) | 6.31 (dd, J = 10.0 Hz, 1.6 Hz, 1H) | 6.30 (dd, J = 1.6 Hz, 10.0 Hz, 1H), |
| $C^4$—H | 6.11 (s, 1H) | 6.11 (s, 1H) | 6.11 (s, 1H), |
| $C^6$—H | 5.71-5.54 (m, 1H) | 5.71-5.55 (m, 1H) | 5.71-5.54 (m, 1H), |
| $C^7$—H | 2.28-2.26 (m, 1H), 1.68-1.56 (m, 1H) | 2.28-2.26 (m, 1H), 1.68-1.56 (m, 1H) | 2.25-2.22 (m, 1H), 1.72-1.52 (m, 1H) |
| $C^8$—H | 1.87-1.79 (m, 1H) | 1.44-1.31 (m, 1H) | 1.87-1.79 (m, 1H) |
| $C^{11}$—H | 4.18 (m, 1H) | 4.22 (m, 1H) | 4.18 (m, 1H) |
| $C^{12}$—H | 2.09-2.01 (m, 1H) 1.68-1.56 (m, 1H) | 2.09-2.01 (m, 1H), 1.68-1.56 (m, 1H) | 2.03-1.97 (m, 1H), 1.72-1.52 (m, 1H) |
| $C^{14}$—H | 2.09-2.01 (m, 1H) | 2.09-2.01 (m, 1H) | 2.03-1.97 (m, 1H) |
| $C^{15}$—$H_2$ | 2.67-2.50 (m, 1H), 1.68-1.56 (m, 1H) | 2.67-2.50 (m, 1H), 1.68-1.56 (m, 1H) | 2.58-2.53 (m, 1H), 1.72-1.52 (m, 1H) |
| $C^{16}$—H | 4.78 (m, 0.6H) 5.15 (d, J = 7.6 Hz, 0.4 H), | 4.78 (m, 1H) | 5.15 (d, J = 7.6 Hz, 1 H) |
| $C^{18}$—$H_3$ | 0.85 (s, 3H) | 0.85 (s, 3H) | 0.91 (s, 3H) |
| $C^{19}$—$H_3$ | 1.48 (s, 3H) | 1.48 (s, 3H) | 1.48 (s, 3H) |
| $C^{21}$—$H_2$ | 4.20 (m, 1H), | 4.20 (d, J = 19 Hz, 1H), | 4.15 (d, J = 19 Hz, 1H), |
| | 3.77 (m, 1H) | 3.77 (d, J = 19 Hz, 1H) | 3.74 (d, J = 19 Hz, 1H) |
| $C^{22}$—H | 4.67 (t, J = 4.4 Hz, 0.6H) 5.22 (t, J = 4.8 Hz, , 0.4H) | 4.67 (t, J = 4.4 Hz, 1H) | 5.22 (t, J = 4.8 Hz, , 1H) |

-continued

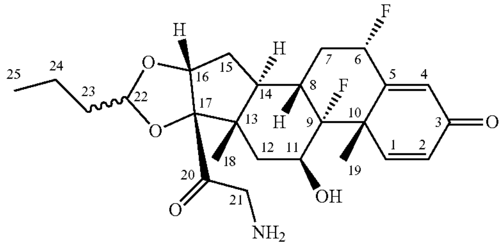

| Proton # | P4 (rac-) in DMSO-d6 | P4-1 (R) in DMSO-d6 | P4-2 (S)-in DMSO-d6 |
|---|---|---|---|
| $C^{23}$—$H_2$ | 1.68-1.56 (m, 2H) | 1.68-1.56 (m, 2H) | 1.48 (m, 2H) |
| $C^{24}$—$H_2$ | 1.44-1.31 (m, 2H) | 1.44-1.31 (m, 2H) | 1.34-1.28 (m, 1H) |
| $C^{25}$—$H_3$ | 0.87 (t, J = 7.2 Hz, 3H) | 0.87 (t, J = 7.2 Hz, 3H) | 0.88 (t, J = 7.6 Hz, 3 H) |

S-isomer: ESI m/z: 522 $(M + H)^+$; chiral SFC (CC4): 99.5 d.e. %; $^1H$ NMR (400 MHz, $CDCl_3$) δ 7.21 (d, J = 10.1 Hz, 1H), 6.77 (d, J = 8.8 Hz, 2H), 6.63 (d, J = 8.8 Hz, 2H), 6.24 (dd, J = 10.1, 1.6 Hz, 1H), 6.02 (s, 1H), 5.20 (d, J = 6.8 Hz, 1H), 5.18 (t, J = 4.8 Hz, 1H), 4.99 (d, J = −17.9 Hz, 1H), 4.61 (d, J = −17.9 Hz, 1H), 4.43 (s, 1H), 3.46 (s, 2H), 2.57 (td, J = 13.2, 4.4 Hz, 1H), 2.34 (dd, J = 13.4, 3.2 Hz, 1H), 2.16-2.01 (m, 4H), 1.85-1.68 (m, 3H), 1.59-1.49 (m, 3H), 1.44 (s, 3H), 1.44-1.26 (m, 2H), 1.18-1.09 (m, 2H), 1.00 (s, 3H), 0.91 (t, J = 7.3 Hz, 3H) ppm.
R-isomer: ESI m/z: 522 $(M + H)^+$; chiral SFC (CC4): 98.1 d.e. %; $^1H$ NMR (400 MHz, $CDCl_3$) δ 7.23 (d, J = 10.1 Hz, 1H), 6.79 (dd, J = 8.8 Hz, 2H), 6.65 (d, J = 8.8 Hz, 2H), 6.27 (dd, J = 10.1, 1.7 Hz, 1H), 6.04 (s, 1H), 4.94 (d, J = 4.4 Hz, 1H), 4.89 (d, J = 18.0 Hz, 1H), 4.65 (d, J = 18.0 Hz, 1H), 4.61 (t, J = 4.4 Hz, 1H) 4.48 (d, J = 2.1 Hz, 1H), 3.51 (s, 2H), 2.58 (td, J = 13.3 Hz, 4.9 Hz, 1H), 2.35 (dd, J = 13.4 Hz, 2.8 Hz, 1H), 2.23-1.99 (m, 4H), 1.79-1.61 (m, 6H), 1.46-1.38 (m, 2H), 1.44 (s, 3H), 1.23-1.09 (m, 2H), 0.95 (s, 3H), 0.93 (t, J = 7.3 Hz, 3H) ppm.

Figure 12:
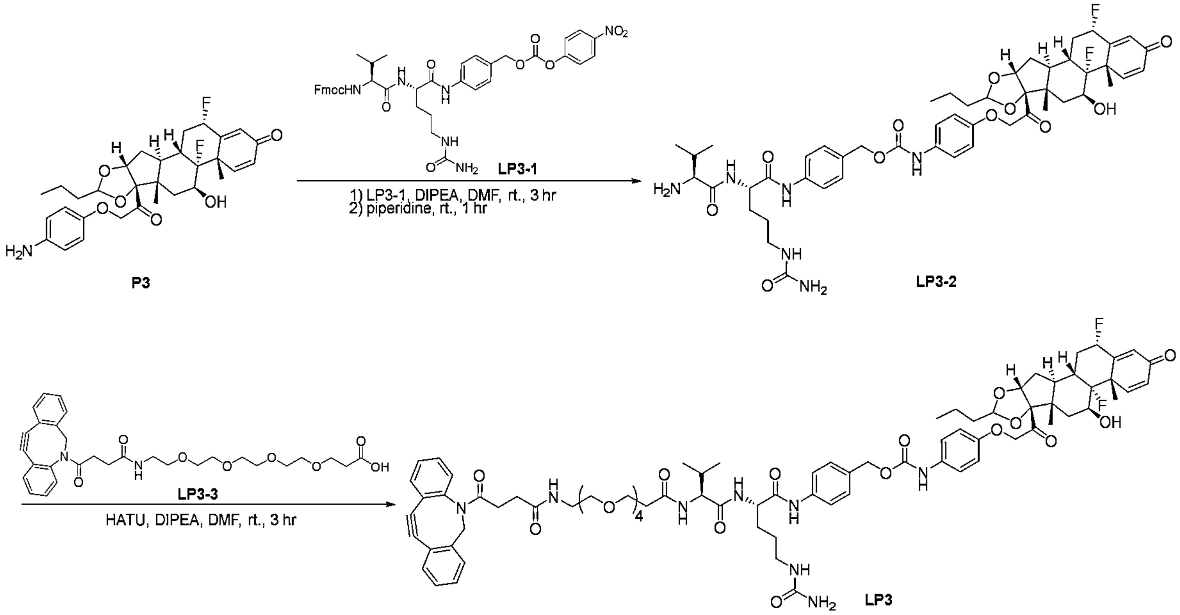
FIG. 12 provides a scheme for the synthesis of LP3.

Example 23. Synthesis of Linker-Payload LP3 (FIG. 12)

{4-[(2S)-2-[(2S)-2-Amino-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}phenyl)carbamate (LP3-2)

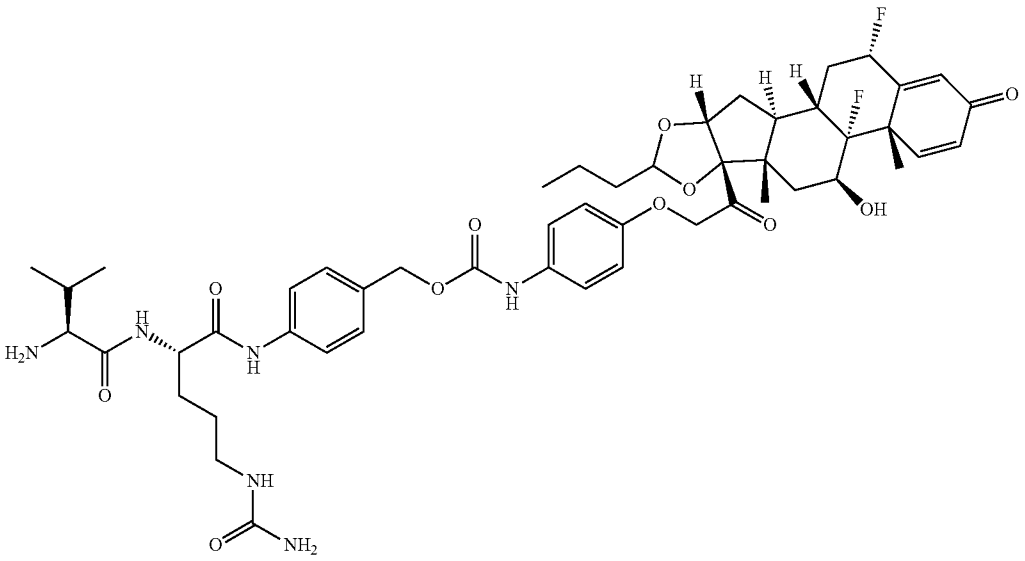

To a solution of Fmoc-vc-PAB-PNP (LP3-1, 100 mg, 0.13 mmol) and compound P3 (87 mg, 0.15 mmol) in DMF (5 mL) was added with DIPEA (67 mg, 0.52 mmol) at RT by syringe. The mixture was stirred at RT for 3 hours and most of LP3-1 was consumed according to LCMS. To the resulting mixture was added piperidine (1 mL, excess) and it was stirred at 25° C. for 2 hours until Fmoc was totally removed, which was monitored by LCMS. After filtering through a membrane, the filtrate was directly purified by prep-HPLC (method B) to give a compound LP3-2 (80 mg, 64% yield) as a white solid. ESI m/z: 963 $(M+1)^+$. $^1H$ NMR (500 MHz, $DMSO_{d6}$) δ 10.22 (s, 1H), 9.57 (s, 1H), 8.69 (d, J=7.5 Hz, 1H), 8.08 (s, 3H), 7.61 (d, J=6.8 Hz, 2H), 7.36 (d, J=6.8 Hz, 3H), 7.27 (d, J=8.0 Hz, 1H), 7.22-7.00 (m, 1H), 6.84 (d, J=7.2 Hz, 2H), 6.30 (dd, J=8.0 Hz, 1.6 Hz, 1H), 6.11 (s, 1H), 6.10-6.00 (m, 1H), 5.72-5.55 (m, 1H), 5.52 (s, 1H), 5.48 (s, 1H), 5.16-5.05 (m, 3H), 4.88-4.80 (m, 1H), 4.80-4.76 (m, 1H), 4.75-4.70 (m, 1H), 4.55-4.48 (m, 1H), 4.25-4.20 (m, 1H), 3.70-3.60 (m, 1H), 3.12-2.90 (m, 2H), 2.70-2.55 (m, 1H), 2.40-2.20 (m, 1H), 2.15-2.00 (m, 3H), 1.86-1.75 (m, 1H), 1.75-1.65 (m, 1H), 1.64-1.54 (m, 5H), 1.49 (s, 4H), 1.46-1.34 (m, 4H), 0.97-0.91 (m, 5H), 0.90-0.85 (m, 4H), 0.85-0.80 (m, 3H) ppm.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate (LP3)

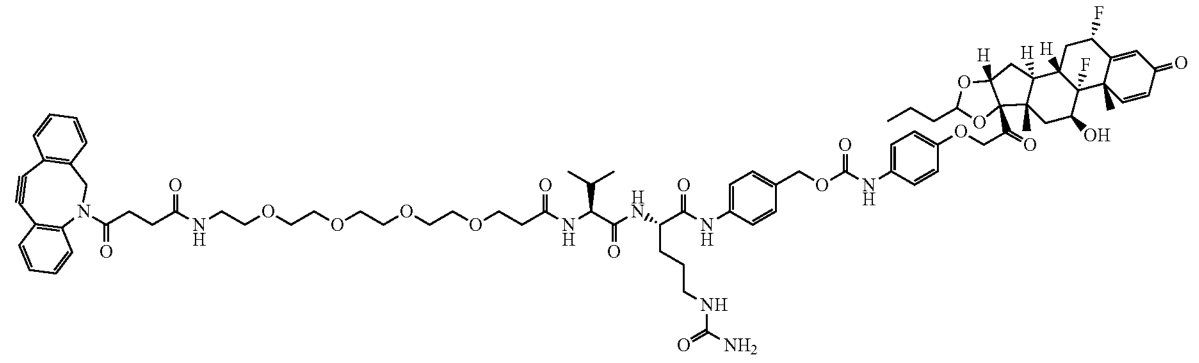

To a solution of acid LP3-3 (37 mg, 67 μmol) in DMF (5 mL) were added DIPEA (15 mg, 0.12 mmol) and HATU (34 mg, 90 μmol) at RT successively. The resulting mixture was stirred at this temperature for 0.5 hour before the amine LP3-2 (58 mg, 60 μmol) was added. The reaction mixture was stirred at RT for 3 hours until the amine was totally consumed, which was monitored by LCMS. The reaction mixture was filtered through membrane and the filtrate was then separated by prep-HPLC to give compound LP3 (20 mg, 22% yield) as a white solid. ESI m/z: 1499 $(M+H)^+$. $^1H$ NMR (400 MHz, $DMSO_{d6}$) δ 10.02 (s, 1H), 9.59 (s, 1H), 8.14 (d, J=7.6 Hz, 1H), 7.88 (d, J=8.8 Hz, 1H), 7.80-7.75 (m, 1H), 7.70-7.66 (m, 1H), 7.65-7.60 (m, 3H), 7.53-7.45 (m, 3H), 7.40-7.28 (m, 7H), 6.84 (d, J=9.2 Hz, 2H), 6.30 (dd, J=10.4 Hz, 1.6 Hz, 1H), 6.11 (s, 1H), 6.10-6.00 (m, 1H), 5.72-5.55 (m, 1H), 5.52 (s, 1H), 5.43 (s, 2H), 5.16-5.05 (m, 4H), 4.88-4.70 (m, 3H), 4.43-4.33 (m, 1H), 4.25-4.20 (m, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.75 (m, 2H), 1.64-1.54 (m, 5H), 1.49 (s, 4H), 1.46-1.34 (m, 4H), 1.23 (s, 2H), 0.90-0.80 (m, 12H) ppm. Anal. HPLC: 100%, Retention time: 7.99 min (method B). Solubility: <0.01 mg/mL water.

Figure 13:
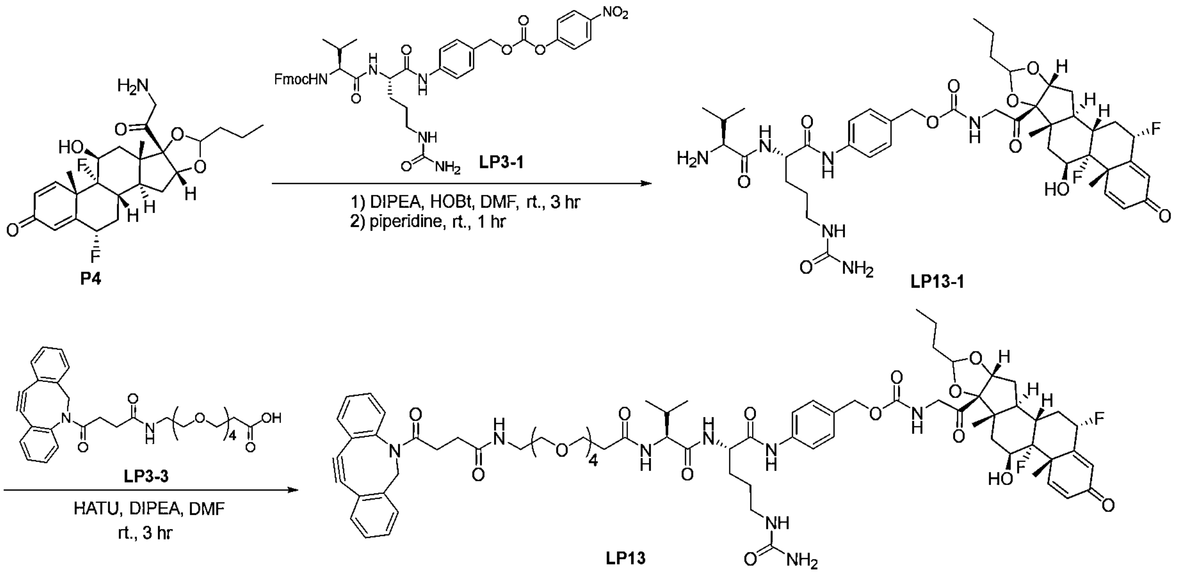
FIG. 13 provides a scheme for the synthesis of LP13.

Example 24. Synthesis of Linker-Payload LP13 (FIG. 13)

{4-[(2S)-2-[(2S)-2-Amino-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (LP13-1)

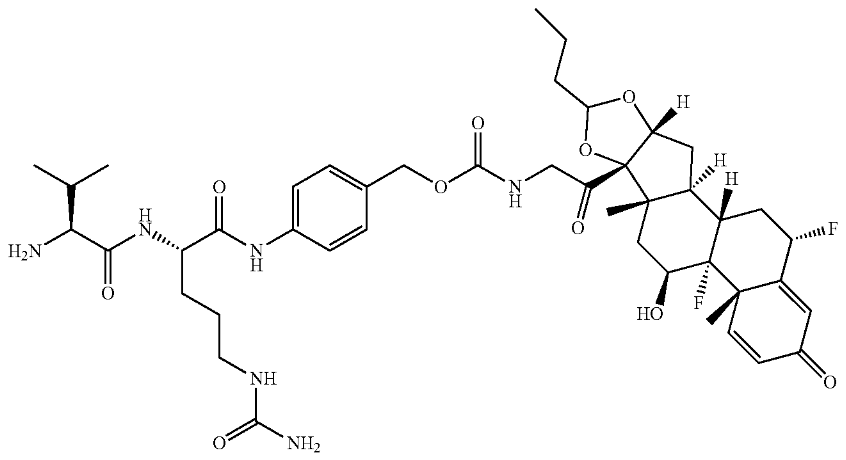 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](N)C(C)C)cc2)O1]

To a solution of Fmoc-VC-PAB-PNP (LP3-1, 0.17 g, 0.22 mmol) and compound P4 (93 mg, 0.20 mmol) in DMF (3 mL) was added with DIPEA (51 mg, 0.40 mmol) at RT by syringe. The mixture was stirred at RT for 3 hours and most of materials were consumed according to LCMS. To the resulting mixture was added piperidine (0.3 mL, excess) and it was stirred at RT for an hour until Fmoc was totally removed, which was monitored by LCMS. After filtering through a membrane, the filtrate was directly purified by prep-HPLC (method B) to give compound LP13-1 (0.13 g, 73% yield) as a white solid. ESI m/z: 871 $(M+1)^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (LP13)

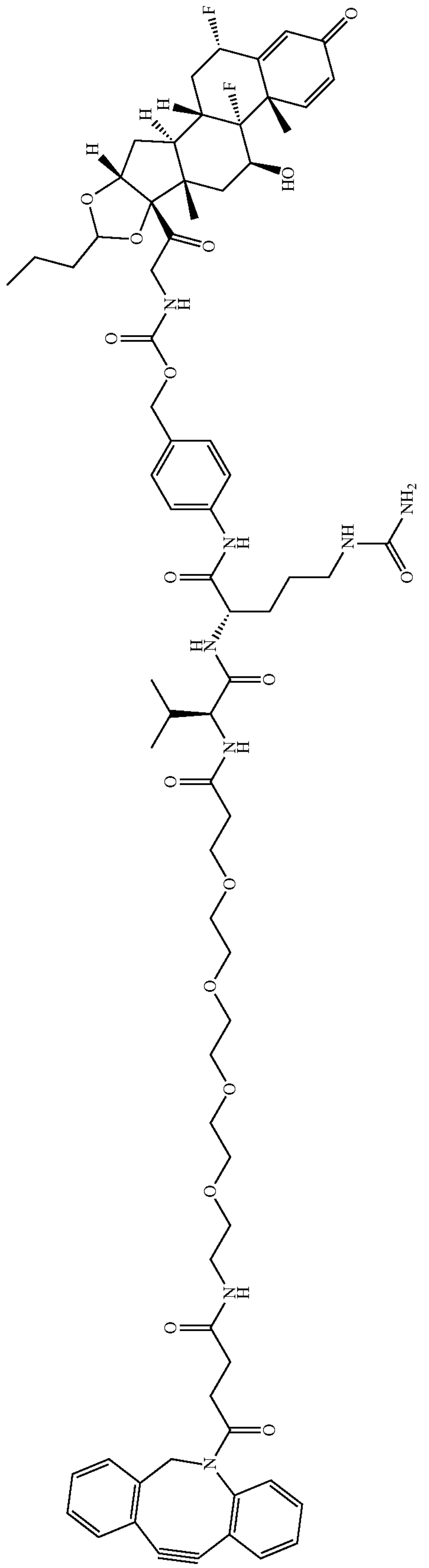

To a solution of acid LP3-3 (30 mg, 54 μmol) in DMF (5 mL) were added DIPEA (13 mg, 0.10 mmol) and HATU (31 mg, 81 μmol) at RT successively. The resulting mixture was stirred at this temperature for 0.5 hour before the amine LP13-1 (43 mg, 50 μmol) was added. The reaction mixture was stirred at RT for 3 hours until the amine was totally consumed, which was monitored by LCMS. The reaction mixture was filtered through membrane and the filtrate was then separated by prep-HPLC (method B) to give compound LP13 (16 mg, 23% yield) as a white solid. ESI m/z: 1406 $(M+H)^+$. $^1H$ NMR (500 MHz, $DMSO_{d6}$) δ 9.99 (s, 1H), 8.11 (d, J=7.5 Hz, 1H), 7.88 (d, J=8.5 Hz, 1H), 7.80-7.75 (m, 1H), 7.70-7.66 (m, 1H), 7.65-7.60 (m, 3H), 7.53-7.33 (m, 6H), 7.33-7.28 (m, 3H), 6.30 (dd, J=10.0 Hz, 1.5 Hz, 1H), 6.11 (s, 1H), 6.10-6.00 (m, 1H), 5.72-5.55 (m, 2H), 5.41 (s, 2H), 5.05-5.01 (m, 1H), 4.97 (s, 2H), 4.80-4.72 (m, 1H), 4.60-4.58 (m, 1H), 4.43-4.33 (m, 1H), 4.25-4.10 (m, 3H), 3.88-3.80 (m, 1H), 3.65-3.55 (m, 3H), 3.50-3.40 (m, 12H), 3.30-3.25 (m, 2H), 3.12-2.90 (m, 4H), 2.70-2.55 (m, 2H), 2.48-2.35 (m, 2H), 2.30-2.20 (m, 2H), 2.15-1.95 (m, 4H), 1.86-1.65 (m, 3H), 1.64-1.54 (m, 5H), 1.49 (s, 4H), 1.46-1.34 (m, 5H), 0.90-0.80 (m, 12H) ppm. Anal. HPLC: 100%, Retention time: 7.40 min (method B). Solubility: 0.02 mg/mL water.

Figure 14:
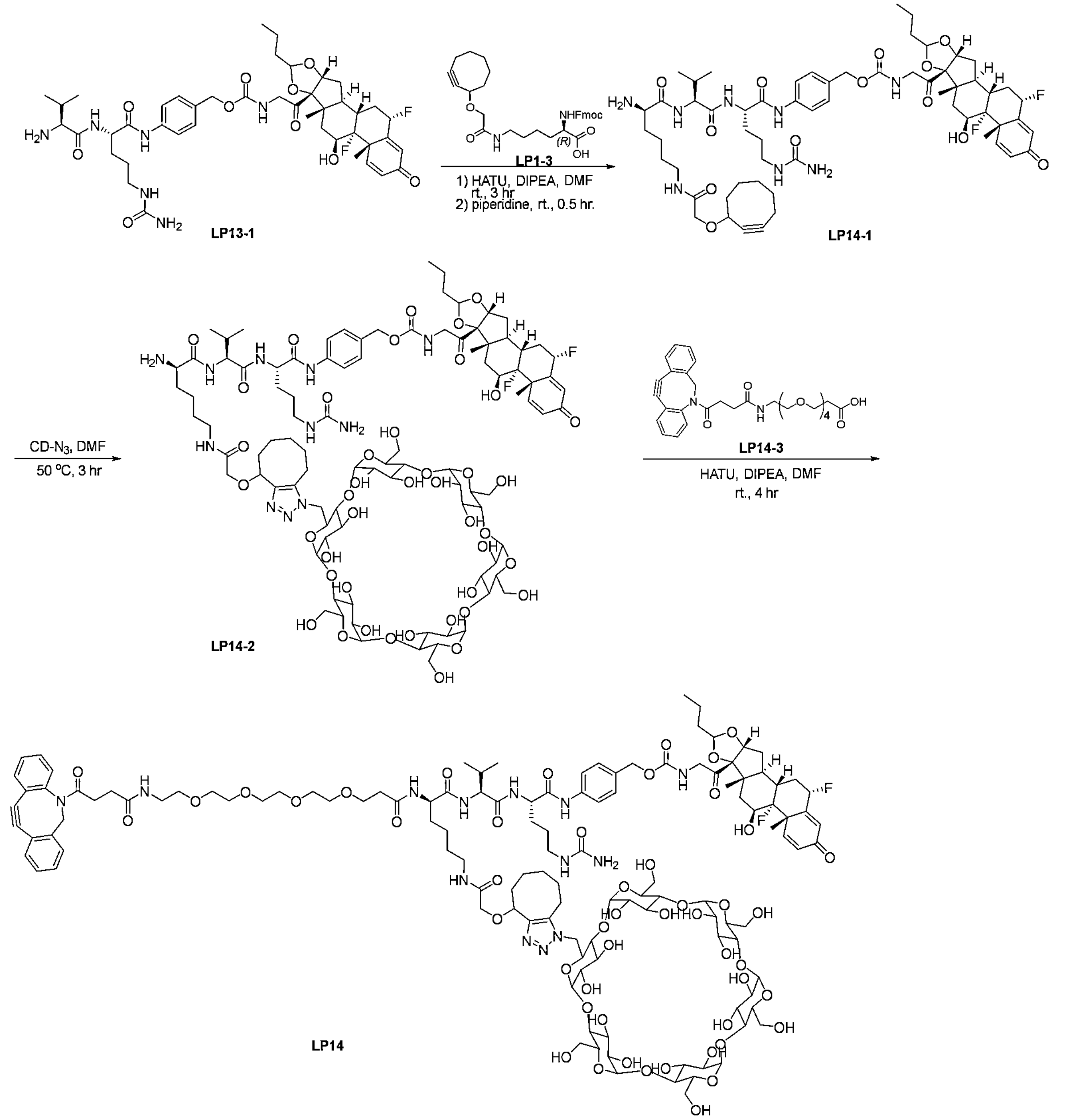
FIG. 14 provides a scheme for the synthesis of LP14.

Example 25. Synthesis of Linker-Payload LP14 (FIG. 14)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate (LP14-1)

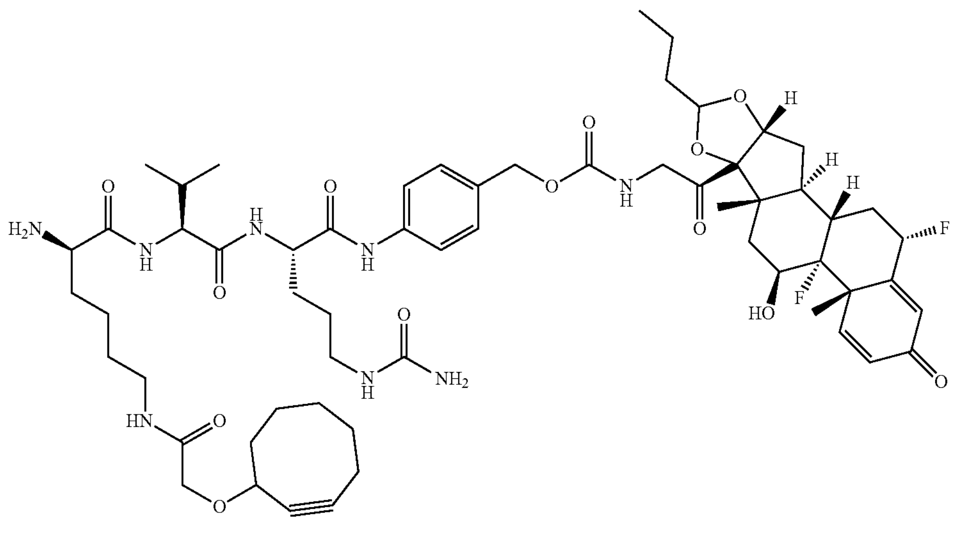

To a solution of acid LP1-3 (0.12 g, 0.22 mmol) in DMF (5 mL) were added HATU (0.11 g, 0.30 mmol) and DIPEA (77 mg, 0.60 mmol) at RT. After the mixture was stirred at RT for 30 minutes, a solution of amine LP13-1 (0.17 g, 0.20 mmol) in DMF (5 mL) was added by syringe. The resulting mixture was stirred at RT for 3 hours until the amine was mostly consumed according to LCMS. To the mixture was then added piperidine (1 mL, excess), and the mixture was stirred at RT for half an hour until Fmoc was totally removed, which was monitored by LCMS. The reaction mixture was filtered through a membrane and the filtrate was directly purified by reversed phase flash chromatography (0-100% acetonitrile in aq. ammonium bicarbonate (10 mM)) to give compound LP14-1 (0.12 g, 52% yield) as a white solid. ESI m/z: 1163 $(M+1)^+$. $^1H$ NMR (400 MHz, $MeOD_{d4}$) δ 7.65-7.55 (m, 2H), 7.40-7.26 (m, 3H), 6.39-6.27 (m, 2H), 5.65-5.45 (m, 1H), 5.13-5.01 (m, 2H), 4.71-4.50 (m, 2H), 4.40-4.14 (m, 4H), 4.11-3.82 (m, 3H), 3.46-3.39 (m, 1H), 3.29-3.09 (m, 4H), 2.76-2.54 (m, 1H), 2.41-2.10 (m, 7H), 2.09-1.99 (m, 1H), 1.96-1.80 (m, 5H), 1.78-1.21 (m, 23H), 1.06-0.82 (m, 12H) ppm.

{4-[(2S)-2-[(2S)-2-[(2R)-2-Amino-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23}$,$2^{6}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethyl}carbamate (LP14-2)

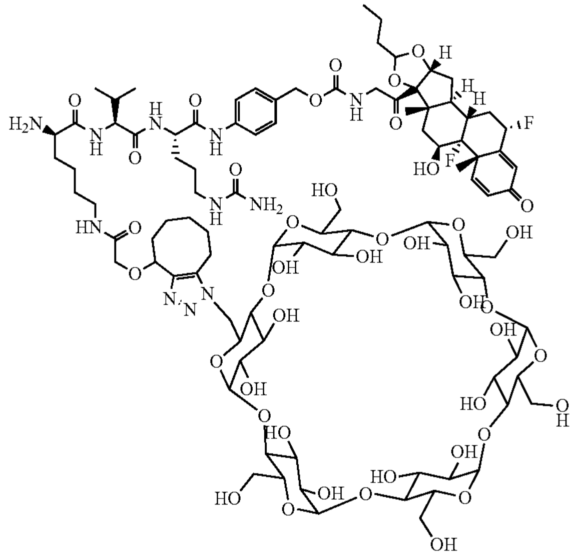

To a solution of alkyne LP14-1 (0.12 g, 0.10 mmol) in DMF (5 mL) was added a-cyclodextrin-azide (0.30 g, 0.30 mmol). The resulting mixture was then stirred at 50° C. for 3 hours until the compound LP14-1 was mostly consumed and desired mass was detected, which was monitored by LCMS. After filtered, the resulting mixture was directly purified by reversed phase flash chromatography (0-100% acetonitrile in aq. ammonium bicarbonate (10 mM)) to give compound LP14-2 (0.11 g, 51% yield) as a white solid. ESI m/z: 1081 $(M/2+1)^+$. $^1$H NMR (500 MHz, $DMSO_{d6}$) δ 10.05 (s, 1H), 8.30-7.80 (m, 3H), 7.80-7.55 (m, 2H), 7.50-7.40 (m, 1H), 7.40-7.25 (m, 3H), 6.30 (d, J=12.5 Hz, 1H), 6.11 (s, 1H), 6.00 (s, 1H), 5.80-5.35 (m, 16H), 5.25-5.05 (m, 1H), 4.97 (s, 2H), 4.90-4.50 (m, 13H), 4.50-4.00 (m, 5H), 3.95-3.55 (m, 22H), 3.30-3.20 (m, 8H), 3.20-3.00 (m, 4H), 3.00-2.85 (m, 5H), 2.25-2.20 (m, 2H), 2.10-1.95 (m, 4H), 1.80-1.00 (m, 30H), 1.00-0.90 (m, 4H), 0.90-0.80 (m, 14H) ppm.

{4-[(2S)-2-[(2S)-2-[(2R)-2-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.$2^{3,6}$.$2^{8,11}$.$2^{13,16}$.$2^{18,21}$.$2^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethyl}carbamate (LP14)

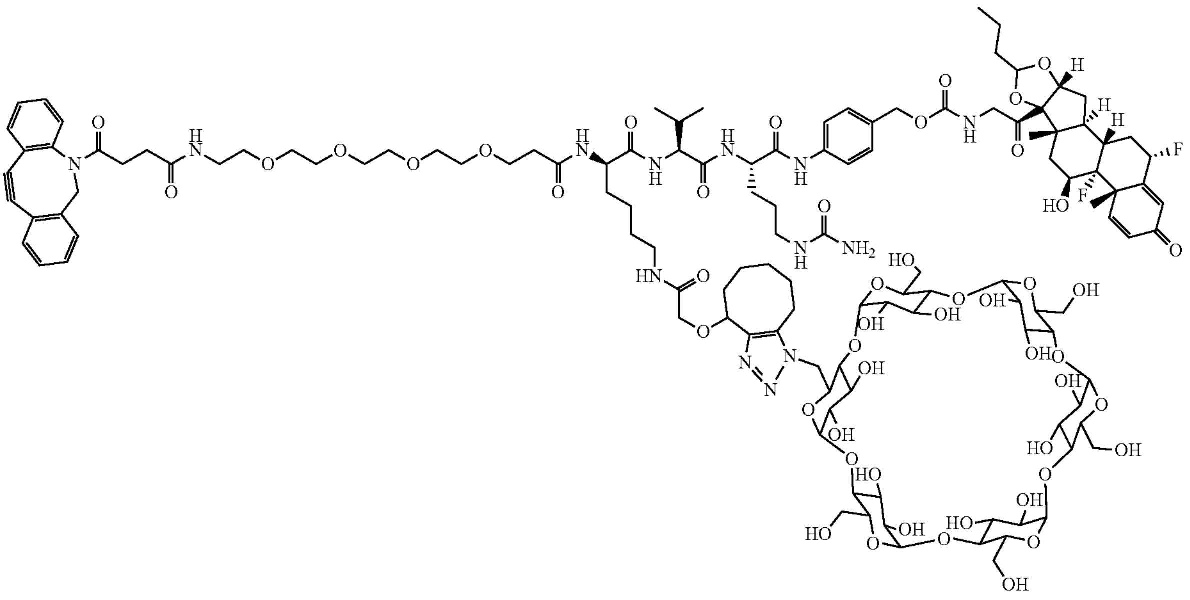

To a solution of acid LP14-3 (30 mg, 54 μmol) in DMF (5 mL) were added DIPEA (18 mg, 0.14 mmol) and HATU (26 mg, 69 μmol) at RT successively. The resulting mixture was stirred at this temperature for 0.5 hour before the amine LP14-2 (0.10 g, 46 μmol) was added. The reaction mixture was stirred at RT for 4 hours until the amine was totally consumed, which was monitored by LCMS. The reaction mixture was filtered through membrane and the filtrate was then separated by prep-HPLC (method B) to give compound LP14 (26 mg, 22% yield) as a white solid. ESI m/z: 1349 $(M+H)^+$. $^1H$ NMR (500 MHz, $DMSO_{d6}$) δ 9.71 (s, 1H), 8.30-8.00 (m, 3H), 8.00-7.74 (m, 2H), 7.70-7.58 (m, 5H), 7.52-7.20 (m, 12H), 6.35-6.20 (m, 2H), 6.15-5.85 (m, 3H), 5.80-5.35 (m, 18H), 5.25-4.90 (m, 6H), 4.90-4.50 (m, 14H), 4.40-4.25 (m, 4H), 4.25-4.10 (m, 3H), 4.10-3.95 (m, 2H), 3.95-3.55 (m, 22H), 3.55-3.40 (m, 22H), 3.20-3.00 (m, 6H), 3.00-2.85 (m, 3H), 2.65-2.55 (m, 1H), 2.25-2.20 (m, 4H), 2.10-1.95 (m, 6H), 1.80-1.70 (m, 5H), 1.70-1.50 (m, 10H), 1.50-1.45 (m, 9H), 0.90-0.80 (m, 14H) ppm. Anal. HPLC: 100%, Retention time: 6.23 min (method B). Solubility: 0.026 mg/mL water.

Figure 15:
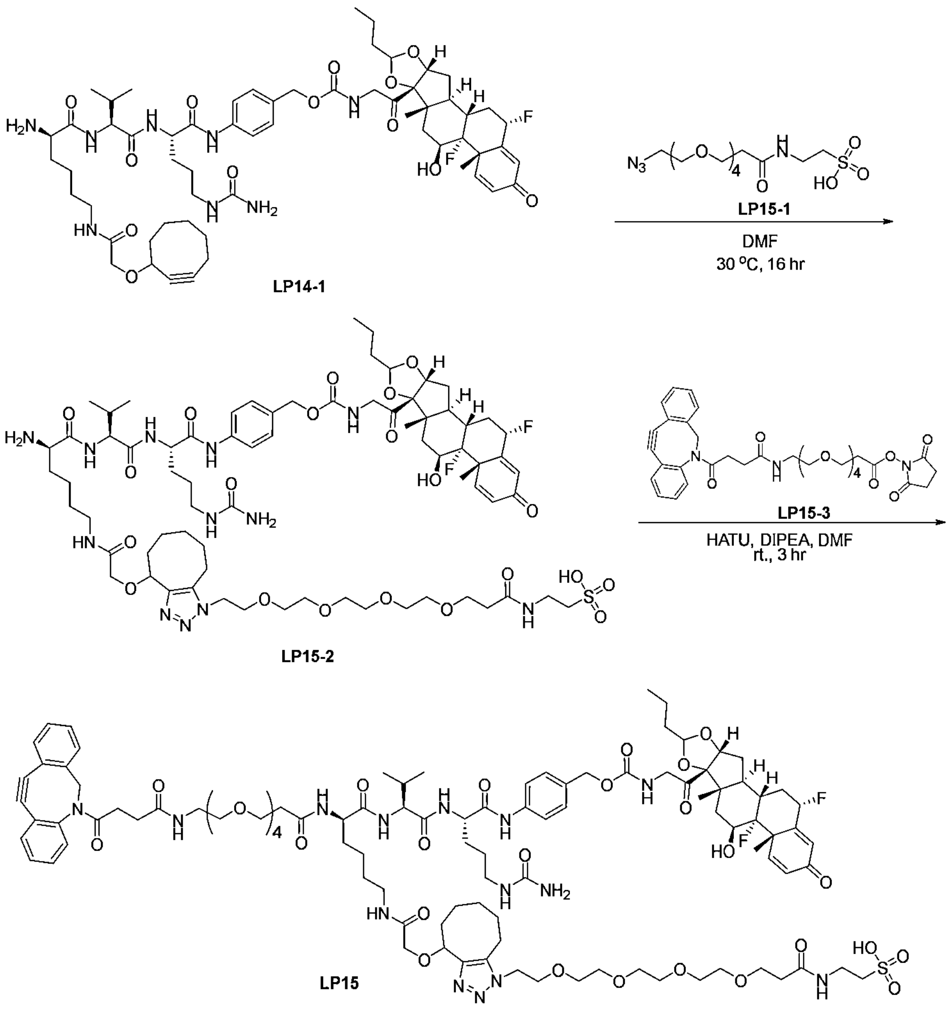
FIG. 15 provides a scheme for the synthesis of LP15.

Example 26. Synthesis of Linker-Payload LP15 (FIG. 15)

2-{1-[4-({[(5R)-5-Amino-5-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo [10.8.0.0$^{2,9}$.0$^{48}$.0$^{13}$'1$^{8}$]icosa-14,17-dien-8-yl]-2-oxoethyl}carbamoyl)oxy]methyl}phenyl)carbamoyl] butyl]carbamoyl}-2-methylpropyl] carbamoyl}pentyl]carbamoyl}methoxy)-1H,4H,5H, 6H,7H,8H,9H-cycloocta[d][1,2,3]triazol-1-yl]-3,6,9, 12-tetraoxapentadecan-15-amido}ethane-1-sulfonic acid (LP15-2)

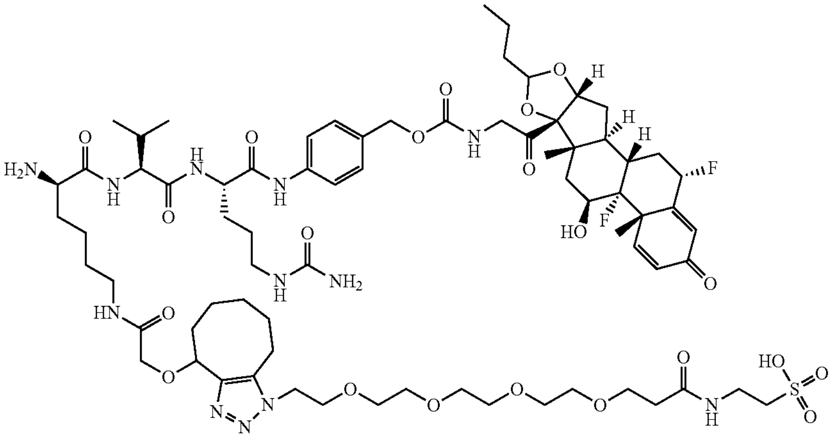 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CCOCCOCCOCCOCCC(=O)NCCS(=O)(=O)O)C(C)C)cc2)O1]

To a solution of compound LP14-1 (60 mg, 52 μmol) in DMF (2 mL) was added azido compound LP15-1 (62 mg, 0.16 mmol). The reaction was stirred at 30° C. overnight. LCMS showed the completion of reaction. The reaction mixture was directly purified by prep-HPLC (method B) to give compound LP15-2 (60 mg, 74% yield) as a white solid. ESI m/z: 781 $(M/2+H)^+$. $^1H$ NMR (400 MHz, $MeOD_{d4}$) δ 7.61 (d, J=8.5 Hz, 2H), 7.39-7.28 (m, 3H), 6.39-6.30 (m, 2H), 5.66-5.46 (m, 1H), 5.29-5.13 (m, 1H), 5.12-5.04 (m, 3H), 4.72-4.60 (m, 2H), 4.56-4.49 (m, 2H), 4.36-3.84 (m, 8H), 3.76-3.70 (m, 2H), 3.66-3.54 (m, 14H), 3.30-3.23 (m, 2H), 3.21-3.04 (m, 3H), 3.03-2.97 (m, 2H), 2.96-2.84 (m, 1H), 2.75-2.52 (m, 1H), 2.50-2.42 (m, 2H), 2.39-2.01 (m, 6H), 1.99-1.78 (m, 6H), 1.74-1.22 (m, 22H), 1.03-0.87 (m, 12H) ppm.

2-{1-[4-({[(5R)-5-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-5-{[(1 S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamoyl)oxy]methyl}phenyl)carbamoyl]butyl]carbamoyl}-2-methylpropyl]carbamoyl}pentyl]carbamoyl}methoxy)-1H,4H,5H,6H,7H,8H,9H-cycloocta[d][1,2,3]triazol-1-yl]-3,6,9,12-tetraoxapentadecan-15-amido}ethane-1-sulfonic acid (LP15)

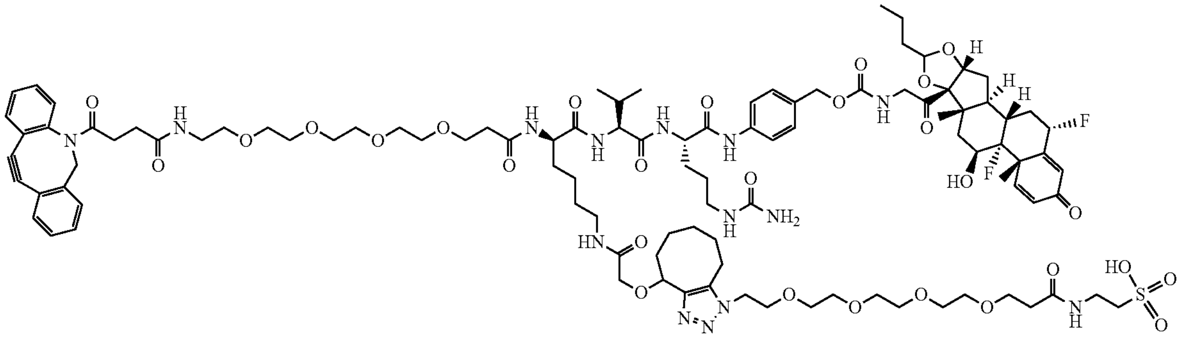 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](CCCCNC(=O)COC3CCCCCc4c3nnn4CCOCCOCCOCCOCCC(=O)NCCS(=O)(=O)O)NC(=O)CCOCCOCCOCCOCCNC(=O)CCC(=O)N3Cc4ccccc4C#Cc4ccccc43)C(C)C)cc2)O1]

To a solution of compound LP15-2 (47 mg, 30 μmol) in DMF (1 mL) were added compound LP15-3 (21 mg, 33 μmol) and DIPEA (19 mg, 0.15 mmol) at RT. The reaction mixture was stirred at RT for 3 hours. The reaction mixture was directly purified by prep-HPLC (method B) to give compound LP15 (28 mg, 45% yield) as a white solid. ESI m/z: 1049 (M/2+H)$^+$. 1H NMR (500 MHz, MeOD$_{d4}$) δ 7.75-7.57 (m, 4H), 7.48-7.43 (m, 3H), 7.38-7.23 (m, 6H), 6.37-6.28 (m, 2H), 5.65-5.43 (m, 1H), 5.17-5.03 (m, 3H), 4.69-4.59 (m, 2H), 4.52-4.47 (m, 1H), 4.45-4.41 (m, 1H), 4.34-4.25 (m, 2H), 4.23-4.13 (m, 2H), 4.07-3.86 (m, 5H), 3.77-3.68 (m, 4H), 3.64-3.54 (m, 22H), 3.52-3.47 (s, 3H), 3.46-3.40 (m, 4H), 3.29-3.21 (m, 4H), 3.20-3.14 (m, 2H), 3.10-3.01 (m, 1H), 3.00-2.95 (m, 2H), 2.92-2.84 (m, 1H), 2.76-2.60 (m, 2H), 2.47-2.42 (m, 2H), 2.40-2.25 (m, 5H), 2.23-2.13 (m, 3H), 2.07-1.97 (m, 3H), 1.90-1.79 (m, 4H), 1.71-1.55 (m, 14H), 1.52-1.42 (m, 3H), 1.40-1.29 (m, 8H), 1.07-0.85 (m, 12H) ppm. Anal. HPLC: 98%, Retention time: 5.88 min (method B).

Example 26A: Synthesis of Budenoside Spacers (See FIG. 22)

Figure 22:
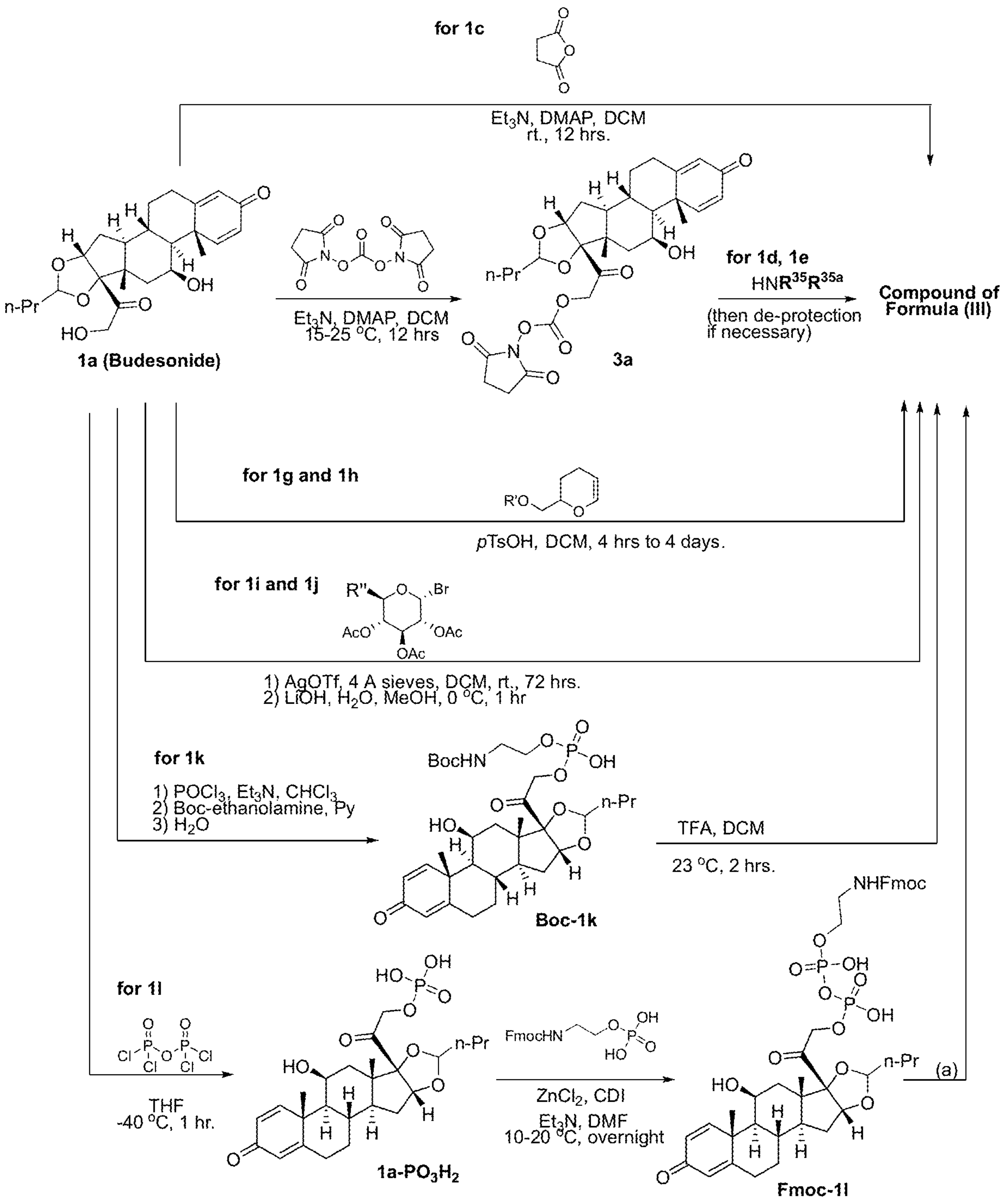
FIG. 22 provides a scheme for the synthesis of Budesonide-spacers containing the reactive groups, suc-acid (compound 1c), carbamate analogues (1d, 1e), THP-analogues (1g and 1h), glucose analogues (1i and 1j), phosphate analogues (1k and 1l), and a commercial phosphate analogue (1m).

FIG. 22 shows Scheme 1 for the synthesis of Budesonide-spacers containing the reactive groups, suc-acid (compound 1c), carbamate analogues (1d, 1e), THP-analogues (1g and 1h), glucose analogues (1i and 1j), phosphate analogues (1k and 1l), and a commercial phosphate analogue (1m).

Intermediate 3a

1-[({2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]pyrrolidine-2,5-dione (3a)

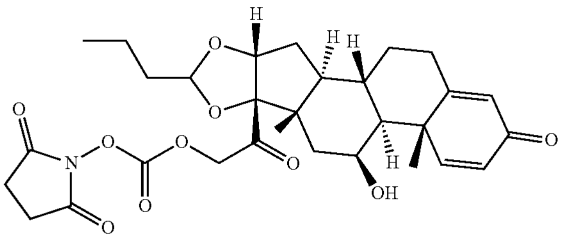 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)ON2C(=O)CCC2=O)O1]

To a solution of budesonide 1a (0.10 g, 0.26 mmol) in DCM (1 mL) were added bis(2,5-dioxopyrrolidin-1-yl) carbonate (71 mg, 0.30 mmol), triethylamine (47 mg, 0.52 mmol) and DMAP (3.0 mg, cat.). The reaction mixture was stirred at 15-25° C. for 12 hours until budesonide was consumed, which was monitored by LCMS. The reaction mixture was then diluted with DCM and washed by water. The organic solution was dried over sodium sulfate. After filtered, the solution was concentrated in vacuo and the residue (crude 3a) was used for the next step directly without purification. (93 mg, yield 71%). ESI m/z: 572.2 (M+H)$^+$.

Example 1c

4-{2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-4-oxobutanoic acid (1c)

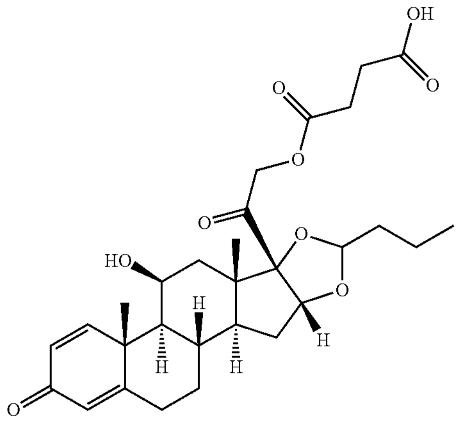

See WO2015005459; WO2013074988; *Research in Pharmaceutical Science,* 2011, 6(2), 107-116; and *International Journal of Pharmaceutics,* 2009, 365(1-2), 69-76.

To a solution of budesonide (1a, 0.10 g, 0.26 mmol) in DCM (1 mL) were added succinic anhydride (30 mg, 0.30 mmol), triethylamine (47 mg, 0.52 mmol) and DMAP (3 mg, catalyst, 0.02 mmol). The mixture was stirred at RT for 12 hours until budesonide was consumed, which was monitored by TLC and LCMS. The reaction mixture was then diluted with DCM and washed with water. The organic solution was dried over sodium sulfate. After filtered, the solution was concentrated in vacuo and the residue was purified by prep-HPLC to give title compound 1c (22 mg, yield 18%) as a white solid. ESI m/z: 531.3 $(M+H)^+$. $^1H$ NMR (500 MHz, $CDCl_3$) δ 7.48 (d, J=10 Hz, 1H), 6.28-6.26 (m, 1H), 6.04-6.02 (m, 1H), 5.23-5.11 (m, 1H), 5.06-4.99 (m, 1H), 4.83-4.68 (m, 1H), 4.45-4.43 (m, 1H), 2.76-2.63 (m, 5H), 2.41-2.39 (m, 1H), 2.26-2.12 (m, 2H), 1.99-1.66 (m, 6H), 1.57-1.38 (m, 6H), 1.32 (s, 1H), 1.16-0.94 (m, 8H) ppm.

Example 1d

2-[(1S,2S,4R,8S,9S,11S,12S,13R)-11-Hydroxy-9,13-dimethyl-16-oxo-6-propyl-5,7-dioxapentacyclo[$10.8.0.0^{2,9}.0^{4,8}.0^{13,18}$]icosa-14,17-dien-8-yl]-2-oxoethyl N-methyl-N-[2-(methylamino)ethyl]carbamate (1d)

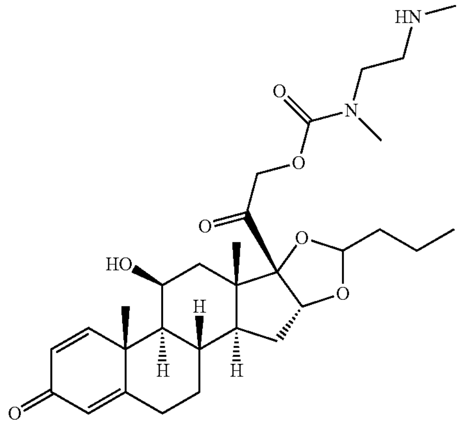

To a solution of crude intermediate 3a (63 mg, 0.11 mmol) in DCM (5 mL) were added N,N'-dimethylethane-1,2-diamine (28 mg, 0.32 mmol) and triethylamine (38 mg, 0.38 mmol) at RT. The resulting mixture was stirred at RT for 2 hours until most of 3a was consumed, which was monitored by LCMS. The volatiles were removed in vacuo and the residue was purified by prep-HPLC (method B) to give 1d (4 mg, yield 4.5%) as a white solid. ESI m/z: 545.3 $(M+H)^+$. $^1H$ NMR (500 MHz, $CDCl_3$) δ 7.32-7.30 (m, 1H), 6.28-6.25 (m, 1H), 6.02-6.01 (m, 1H), 4.42 (br s, 1H), 3.50-3.23 (m, 3H), 3.10-3.02 (m, 3H), 2.82-2.71 (m, 3H), 2.57-2.55 (m, 1H), 2.35-2.33 (m, 1H), 2.15-2.06 (m, 2H), 1.96-1.79 (m, 12H), 1.60-1.56 (m, 3H), 1.46 (m, 3H), 1.37-1.33 (m, 2H), 1.23-1.04 (m, 4H), 0.92-0.86 (m, 3H) ppm.

Example 1e

2-[(1S,2S,4R,8S,9S,11S,13R)-11-Hydroxy-9,13-dimethyl-16-oxo-6-propyl-5,7-dioxapentacyclo[$10.8.0.0^{2,9}.0^{4,8}.0^{13,18}$]icosa-14,17-dien-8-yl]-2-oxoethyl N-[(hydrazinecarbonyl)methyl]carbamate (1e)

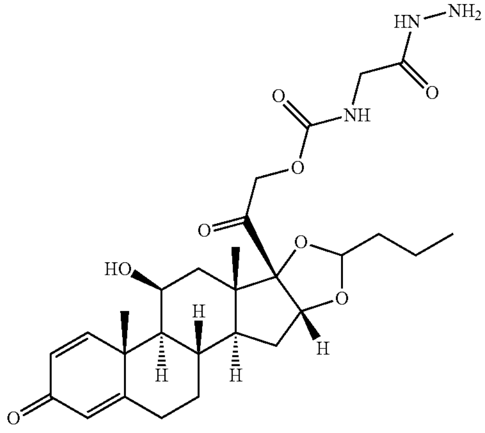

To a mixture of crude 3a (0.16 g, 0.28 mmol) in DMF (3 mL) were added Boc-2-(2-aminoacetyl)hydrazine (80 mg, 0.42 mmol) and triethylamine (85 mg, 0.84 mmol). The reaction mixture was stirred at 25° C. for 16 hours and intermediate 3a was consumed, which was monitored by LCMS. The mixture was then quenched with water and extracted with ethyl acetate. The combined organic solution was dried over anhydrous sodium sulfate. After filtered, the solution was concentrated in vacuo. The residue was purified by silica gel column chromatography (30-50% ethyl acetate in petroleum ether) to give Boc-1e (70 mg) as a white solid (ESI m/z: 646 $(M+H)^+$), which was dissolved in DCM (2 mL). To the solution was added dropwise TFA (1 mL) at 0° C. The mixture was stirred at 25° C. for 2 hours until Boc-1e was consumed, which was monitored by LCMS. The volatiles were removed in vacuo and the residue was purified by prep-HPLC to give title compound 1e (7 mg, yield 12%) as a white solid. ESI m/z: 546 $(M+H)^+$.

Example 1g (1S,2S,4R,8S,9S,11S,12S,13R)-11-Hydroxy-8-(2-{[6-(hydroxymethyl)oxan-2-yl]oxy}acetyl)-9,13-dimethyl-6-propyl-5,7-dioxapentacyclo[10.8.0.$0^{2,9}$.$0^{4,8}$.$0^{13,18}$]icosa-14,17-dien-16-one (1g)

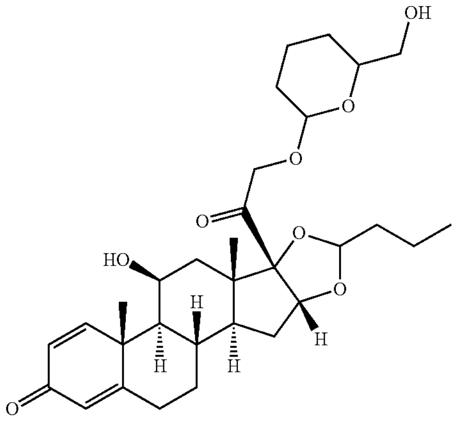

To a solution of budesonide (1a, 50 mg, 0.12 mmol) in anhydrous DCM (4 mL) were added (3,4-dihydro-2H-pyran-2-yl)methanol (0.11 g, 0.93 mmol) and p-toluene-sulfonic acid (31 mg, 0.18 mmol) at 0° C. The reaction mixture was stirred at RT for 4 days, which was monitored by LCMS. The volatiles were removed in vacuo and the residue was dissolved in DMF and separated by prep-HPLC (method B) to give title compound 1g (13 mg, yield 20%) as a white solid. ESI m/z: 545 $(M+H)^+$.

Example 1h

Methyl 2-[(6-{2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}oxan-2-yl)methoxy]acetate (1h)

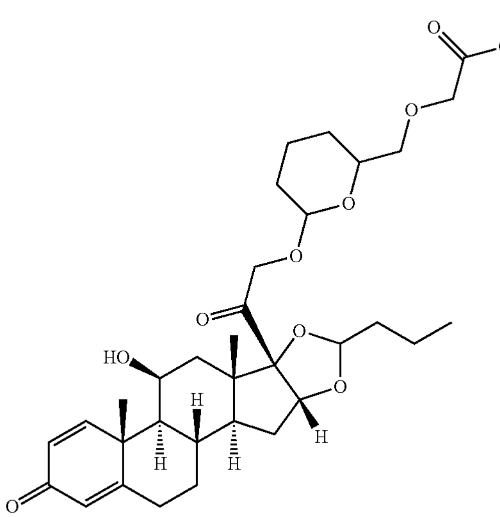

To a solution of (3,4-dihydro-2H-pyran-2-yl)methanol (2.0 g, 18 mmol) in THF (30 mL) was added sodium hydride (60% in mineral oil, 0.88 g, 22 mmol) portion wise at 0° C. under nitrogen protection. The suspension was stirred at 0° C. until the end of hydrogen evolution. To the resulting mixture was then added a solution of ethyl 2-bromoacetate (4.0 g, 26 mmol) in THF (18 mL). The mixture was stirred at RT overnight until the starting material was mostly consumed according to LCMS. After cooled to 0° C., the reaction was quenched with water under nitrogen protection and extracted with ethyl acetate. The combined organic solution was washed with water and brine, dried over sodium sulfate and concentrated in vacuo. The residue was purified by flash chromatography (0-8% ethyl acetate in petroleum ether) to give ethyl 2-((3,4-dihydro-2H-pyran-2-yl)methoxy)acetate (0.70 g, 21% yield) as colorless oil. ($^1H$ NMR (500 MHz, $DMSO_{d6}$) δ 6.36 (d, J=6.0 Hz, 1H), 4.67 (m, 1H), 4.16 (s, 2H), 3.92 (m, 1H), 3.65 (s, 3H), 3.57 (d, J=5.5 Hz, 2H), 2.50-1.99 (m, 1H), 1.93-1.82 (m, 1H), 1.80 (m, 1H), 1.60 (m, 1H) ppm.)

To a solution of budesonide (1a, 0.11 g, 0.25 mmol) in anhydrous DCM (8 mL) were added ethyl 2-((3,4-dihydro-2H-pyran-2-yl)methoxy)acetate (0.35 g, 1.9 mmol) obtained above and p-toluenesulfonic acid (66 mg, 0.35 mmol) at 0° C. The reaction mixture was stirred at RT for 4 hours, which was monitored by LCMS. The volatiles were removed in vacuo and the residue was dissolved in DMF and separated by prep-HPLC (method A) to give title compound 1h (46 mg, yield 29%) as a white solid. ESI m/z: 617 $(M+H)^+$.

Example 1i (1S,2S,4R,8S,9S,11S,12S,13R)-11-Hydroxy-9,13-dimethyl-6-propyl-8-(2-{[(2R,3R,4S,5S,6R)-3,4,5-tri hydroxy-6-(hydroxymethyl)oxan-2-yl]oxy}acetyl)-5,7-dioxapentacyclo[10.8.0$0^{2,9}$.$0^{4,8}$.$0^{13,18}$]icosa-14,17-dien-16-one (1i, with epimers)

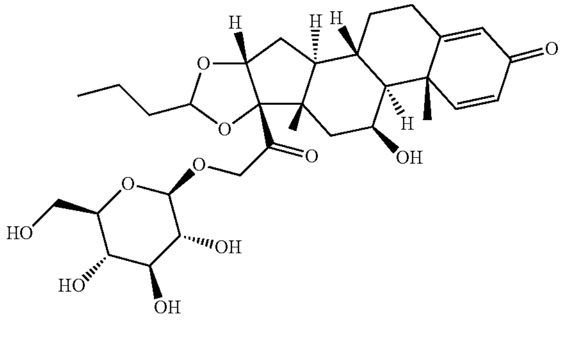 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1]

To a mixture of budesonide (1a, 0.22 g, 0.50 mmol) and acetobromo-a-D-Glucose (0.33 g, 0.80 mmol) in DCM (15 mL) was added 4 Å molecular sieves (1.0 g), and the mixture was stirred at RT for half an hour followed by the addition of silver trifluoromethanesulfonate (0.19 g, 0.75 mmol) at 0° C. The suspension was stirred in dark at RT over weekend (72 hours) under nitrogen protection. The mixture was filtered through Celite and the filtrate was concentrated in vacuo. The residue was purified by prep-HPLC (method B) to give Ac-1i (25 mg, yield 9.2%) as a white solid. ESI m/z: 761 $(M+H)^+$. $^1H$ NMR ($DMSO_{d6}$, 400 MHz) (with epimers) δ 7.34-7.30 (m, 1H), 6.19-6.14 (m, 1H), 5.91 (s, 1H), 5.29 (t, J=9.2 Hz, 1H), 5.17-5.15 (m, 0.5H), 5.03-5.01 (m, 0.5H), 4.96-4.90 (m, 1H), 4.85-4.74 (m, 3H), 4.70-4.67 (m, 1H), 4.64-4.63 (m, 0.5H), 4.59-4.56 (m, 0.5H), 4.39-4.28 (m, 2H), 4.20-4.16 (m, 1H), 4.05-3.99 (m, 2H), 2.56-2.40 (m, 1H), 2.32-2.26 (m, 1H), 2.13-1.89 (m, 14H), 1.83-1.63 (m, 3H), 1.59-1.48 (m, 3H), 1.44-1.21 (m, 6H), 1.15-0.91 (m, 2H), 0.86-0.81 (m, 6H) ppm.

To a solution of the compound Ac-1i (30 mg, 39 μmol) obtained above in water (1 mL) and methanol (3 mL) was added lithium hydroxide monohydrate (17 mg, 0.40 mmol) at 0° C. After stirred at 0° C. for an hour, the mixture was directly purified by prep-HPLC (method B) to give 1i (24 mg, 98% yield) as a white solid. ESI m/z: 593 $(M+H)^+$. $^1H$ NMR ($MeOD_{d4}$, 400 MHz) (with epimers) δ 7.46 (t, J=10.4 Hz, 1H), 6.26 (dt, J=10.0 and 2.0 Hz, 1H), 6.02 (s, 1H), 5.21 and 4.64 (t, J=4.8 Hz, 1H), 5.16 (t, J=7.2 Hz, 0.5H), 4.94-4.80 (m, 2.5H), 4.57-4.47 (m, 1H), 4.44-4.41 (m, 1H), 4.34-4.31 (m, 1H), 3.90-3.87 (m, 1H), 3.70-3.64 (m, 1H), 3.39-3.24 (m, 4H), 2.70-2.62 (m, 1H), 2.41-2.36 (m, 1H), 2.27-2.08 (m, 2H), 2.00-1.93 (m, 1H), 1.88-1.81 (m, 1H), 1.74-1.32 (m, 9H), 1.22-0.90 (m, 8H) ppm.

Example 1j (2S,3S,4S,5R,6R)-3,4,5-Trihydroxy-6-{2-[(1S,2S, 4R,8S,9S,11S,12S,13R)-11-hydroxy-9,13-dimethyl-16-oxo-6-propyl-5,7-dioxapentacyclo[10.8.00$^{2,9}$.0$^{4,8}$.0$^{13,18}$]icosa-14,17-dien-8-yl]-2-oxoethoxy}oxane-2-carboxylic acid (1j, with epimers)

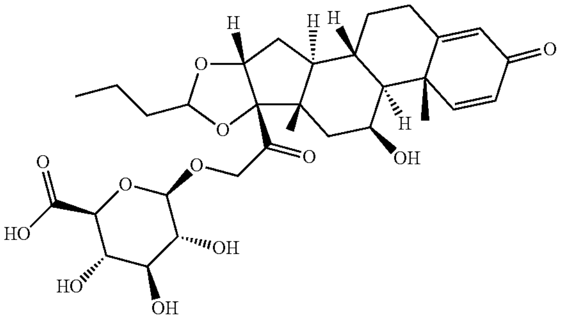 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](C(=O)O)[C@@H](O)[C@H](O)[C@H]2O)O1]

Following the similar procedures as 1i except substituting acetobromo-α-D-Glucuronic acid methyl ester for acetobromo-α-D-Glucose, the compound 1j (24 mg, 9.2% yield in 2 steps) as a white solid was obtained. ESI m/z: 607 $(M+H)^+$. $^1H$ NMR ($MeOD_{d4}$, 400 MHz) δ 7.48 (t, J=10.0 Hz, 1H), 6.28-6.24 (m, 1H), 6.02 (s, 1H), 5.22-5.15 (m, 1H), 4.98-4.81 (m, 2.5H), 4.65-4.56 (m, 1.5H), 4.45-4.39 (m, 2H), 3.62-3.59 (m, 1H), 3.52-3.46 (m, 1H), 3.41 (t, J=8.8 Hz, 1H), 3.30-3.28 (m, 1H), 2.70-2.62 (m, 1H), 2.40-2.36 (m, 1H), 2.27-2.10 (m, 2H), 1.95-1.92 (m, 2H), 1.75-1.54 (m, 3H), 1.50 (s, 3H), 1.51-1.32 (m, 3H), 1.12-0.90 (m, 8H) ppm.

Example 1k (2, 2113ethoxy)({2 1H)S,2S,4R,8S,9S,11S,12S, 13R)13oxy)({2 1H), 3.30-3.28 (m, 1H), 2.70-2.62 (m, 1H), 2.40-2.36 (m, 1H)$^{2,9}$.0$^{4,8}$.0$^{13,18}$]icosa)({2 1H), 3.30-3.28 oxoethoxy})phosphinic acid (1k)

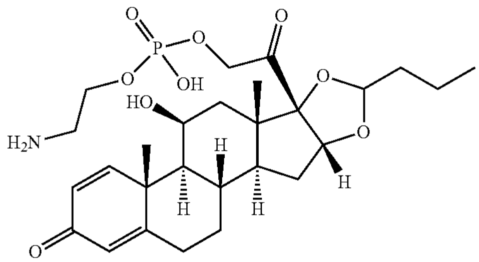

To a solution of triethylamine (0.67 g, 6.6 mmol) in chloroform (4 mL) was added phosphorus oxychloride (0.51 mg, 3.3 mmol) at 0° C., followed by the addition of a solution of budesonide (1a, 1.3 g, 3.0 mmol) in chloroform (4 mL). After stirred at 20° C. for 2 hours, the mixture was cooled to 0° C. and was added a solution of Boc-ethanolamine (0.41 mg, 2.6 mmol) in chloroform (4 mL) and pyridine (3 mL). After stirred at 20° C. for an hour until the reaction was completed according to LCMS, the reaction mixture was quenched by the addition of water (2 mL) at 0° C. The mixture was stirred at 20° C. overnight. The volatiles were removed in vacuo and the residue was purified by prep-HPLC (method B) to afford crude Boc-1k (330 mg, 17%) as yellow film. ESI m/z: 676 $(M+Na)^+$.

To a solution of Boc-1k (0.18 g, 0.28 mmol) in DCM (5 mL) was added trifluoroacetic acid (0.5 mL) at 0° C. The resulting mixture was stirred at 23° C. for 2 hours until Boc was totally removed according to LCMS. The volatiles were removed in vacuo. The residue was purified by prep-HPLC (method B) to afford 1k as a white solid (90 mg, 59% yield). ESI m/z: 554 $(M+H)^+$. $^1H$ NMR (500 MHz, $MeOD_{d4}$) δ 7.49 (d, J=10.1 Hz, 1H), 6.28 (d, J=10.1 Hz, 1H), 6.03 (s, 1H), 5.24-5.15 (m, 1H), 4.87-4.62 (m, 3H), 4.45 (d, J=6.1 Hz, 1H), 4.18-4.15 (m, 2H), 3.22-3.20 (m, 2H), 2.71-2.64 (m, 1H), 2.40 (d, J=13.4 Hz, 1H), 2.29-1.71 (m, 6H), 1.65-1.32 (m, 9H), 1.22-0.91 (m, 7H) ppm. Anal. HPLC: >99.9%, Retention time: 3.90 min (method B).

Example 1l (2-{[(9H-Fluoren-9-ylmethoxy)carbonyl] amino}ethoxy)phosphonic acid

See J. Am. Chem. Soc., 2016, 138(4), 1430-1445; WO2015153401; and Phosphorus, Sulfur and Silicon and the Related Elements, 2000, 165, 83-90.

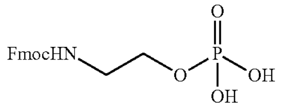

To a mixture of Fmoc-ethanolamine (1.1 g, 3.9 mmol) in THF (16 mL) was added diphosphoryl chloride (2.2 g, 8.8 mmol) by syringe at −40° C. After stirred at −40° C. for an hour until the starting material was totally consumed, which was monitored by LCMS, the reaction mixture was quenched with water (1 mL) at −40° C., treated with saturated aqueous sodium bicarbonate solution (200 mL) and kept at 10-20° C. overnight. The resulting mixture was acidified with conc. HCl to pH 2 and was then extracted with ethyl acetate. The combined organic solution was dried over sodium sulfate and concentrated to afford the crude title compound (1.6 g, crude) as a white solid, which was used for the next step without purification. ESI m/z: 364 $(M+H)^+$.

(2-{[(9H-Fluoren-9-ylmethoxy)carbonyl]amino}ethoxy)({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (Fmoc-11)

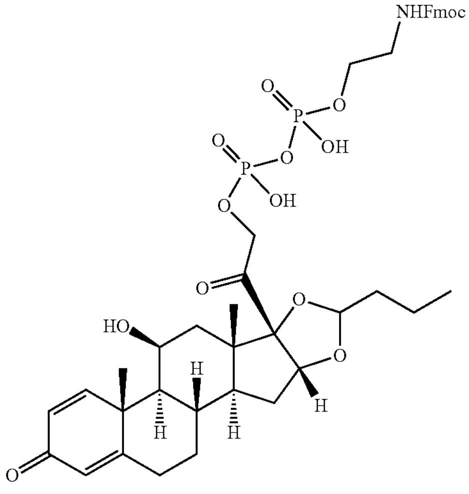

Following the above procedure except substituting budesonide (1a, 0.86 g, 20 mmol) for Fmoc-ethanolamine, the phosphonic budesonide intermediate 1a-$PO_3H_2$ (1.1 g, crude) as a white solid (ESI m/z: 551 $(M+H)^+$) was obtained.

To a solution of crude (2-{[(9H-Fluoren-9-ylmethoxy)carbonyl]amino}ethoxy)phosphonic acid (0.29 g, 0.80 mmol) in DMF (5 mL) were added triethylamine (81 mg, 0.80 mmol) and 1,1'-carbonyldiimidazole (CDI, 0.32 g, 2.0 mmol) at 10° C. The mixture was stirred at 10-20° C. for 30 minutes before the phosphonic budesonide intermediate 1a-$PO_3H_2$ obtained above (0.41 g, 0.80 mmol) and zinc chloride (0.87 g, 6.4 mmol) were added into the reaction mixture. The resulting mixture was stirred at 10-20° C. overnight and starting material was totally consumed according to LCMS. The reaction was then quenched with diluted aq. HCl (1 N, 50 mL) and extracted with ethyl acetate. The combined organic solution was concentrated and the residue was purified by prep-HPLC (method B) to afford Fmoc-11 (0.32 g, yield 47%) as a white solid. ESI m/z: 856 $(M+H)^+$.

(2-Aminoethoxy)({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (11)

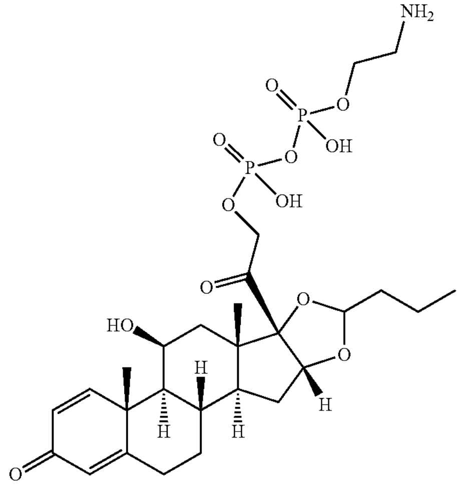

See WO2015153401.

To a solution of Fmoc-11 (0.10 g, 0.12 mmol) in DCM (2 mL) was added piperidine (67 mg, 0.79 mmol) at 10° C. The reaction mixture was stirred at 10-20° C. for 16 hours. Compound Fmoc-11 was totally consumed according to LCMS. The volatiles were removed in vacuo and the residue was purified by prep-HPLC (method B) to afford 11 (50 mg, yield 68%) as a white solid. ESI m/z: 634 $(M+H)^+$. $^1H$ NMR (500 MHz, $MeOD_{d4}$) δ 7.50 (d, J=10.0 Hz, 1H), 6.28 (d, J=9.9 Hz, 1H), 6.03 (s, 1H), 5.23-5.16 (m, 1H), 5.02-4.97 (m, 1H), 4.88-4.67 (m, 1H), 4.45 (d, J=3.4 Hz, 1H), 4.23 (s, 2H), 3.24 (s, 2H), 2.67 (dd, J=13.5, 8.3 Hz, 1H), 2.40 (d, J=11.3 Hz, 1H), 2.28-1.32 (m, 15H), 1.23-0.92 (m, 8H) ppm. Anal. HPLC: >99.9%, Retention time: 2.74 min (method B).

Table 1a below presents steroids made using the methods described herein.

TABLE 1a

Structure and Chemical-Physical Properties of Compounds

| # | Structure | HPLC purity | cLog P | MF | MW (Cal.) | MS (M + H) |
|---|---|---|---|---|---|---|
| 1a | 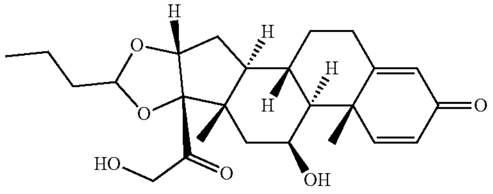 | 95 | 2.73 | $C_{25}H_{34}O_6$ | 430.55 | 431.3 |

TABLE 1a-continued
Structure and Chemical-Physical Properties of Compounds
| # | Structure | HPLC purity | cLog P | MF | MW (Cal.) | MS (M + H) |
|---|---|---|---|---|---|---|
| 1c | 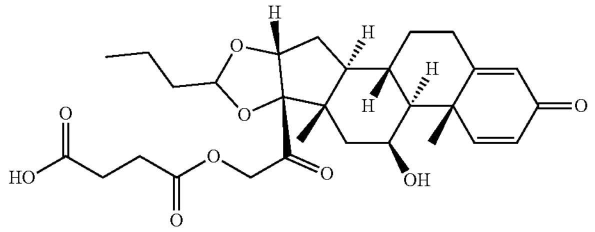 | 98 | 3.00 | $C_{29}H_{38}O_9$ | 530.25 | 531.2 |
| 1d | 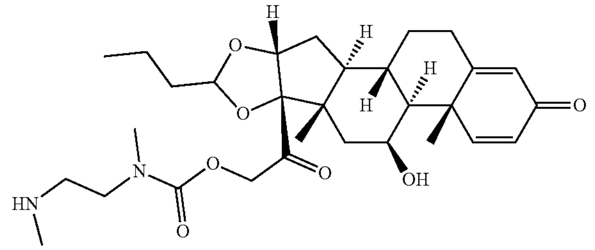 | 93 | 2.92 | $C_{30}H_{44}N_2O_7$ | 544.69 | 545.3 |
| 1e | 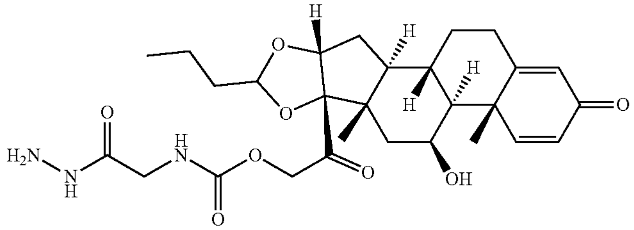 | 100 | 1 .44 | $C_{28}H_{39}N_3O_8$ | 545.62 | 546.2 |
| 1g | 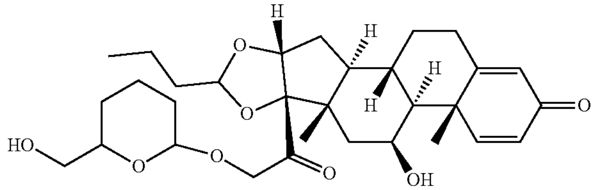 | 92 | 3.65 | $C_{31}H_{44}O_8$ | 544.68 | 545.3 |
| 1h | 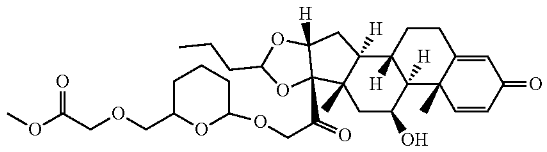 | 98 | 3.19 | $C_{34}H_{48}O_{10}$ | 616.32 | 616.32 |
| 1i | 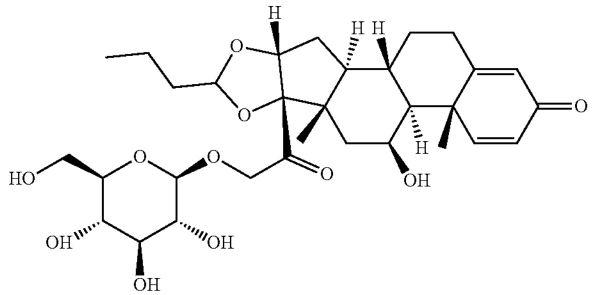 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](CO)[C@@H](O)[C@H](O)[C@H]2O)O1] | 100 | 0.96 | $C_{31}H_{44}O_{11}$ | 592.67 | 593.4 |

TABLE 1a-continued
Structure and Chemical-Physical Properties of Compounds
| # | Structure | HPLC purity | cLog P | MF | MW (Cal.) | MS (M + H) |
|---|---|---|---|---|---|---|
| 1j | 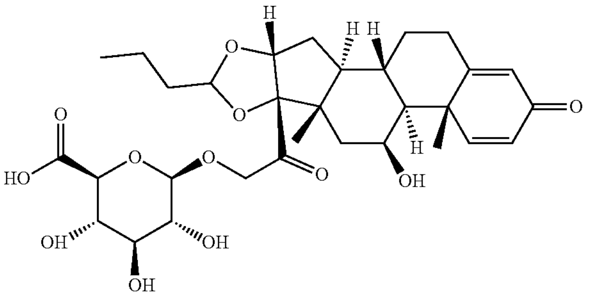 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO[C@@H]2O[C@H](C(=O)O)[C@@H](O)[C@H](O)[C@H]2O)O1] | 98 | 1. 28 | $C_{31}H_{42}O_{12}$ | 606.66 | 607.3 |
| 1k | 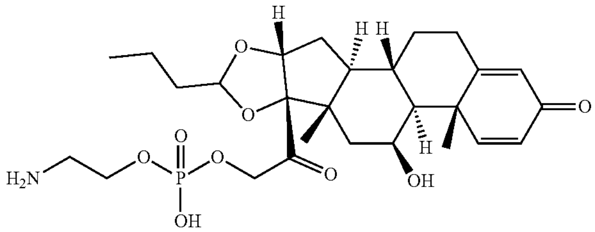 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCN)O1] | 100 | 1.18 | $C_{27}H_{40}NO_9P$ | 553.58 | 554.1 |
| 1l | 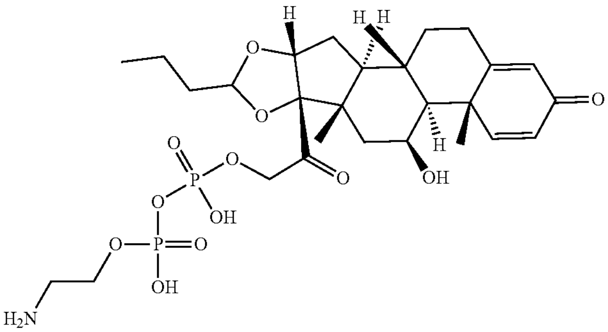 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OP(=O)(O)OCCN)O1] | 100 | 0.55 | $C_{27}H_{41}NO_{12}P_2$ | 633.56 | 634.0 |
| 1m | 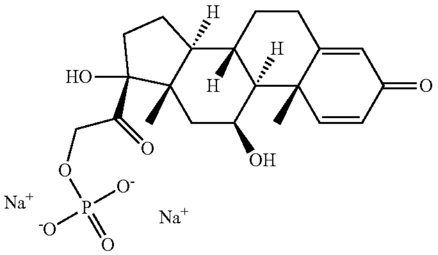 | 100 | 1.15 | $C_{21}H_{27}Na_2O_8P$ | 484.39 | 590.3 |
| 100 | 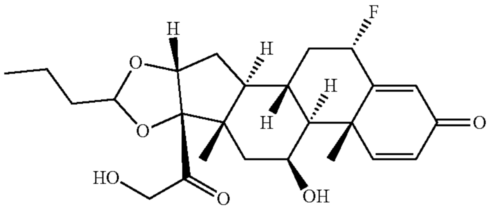 | 100 | 2.44 | $C_{25}H_{32}F_2O_6$ | 466.51 | 467 |

TABLE 1a-continued
| Structure and Chemical-Physical Properties of Compounds | | | | | | |
|---|---|---|---|---|---|---|
| # | Structure | HPLC purity | cLog P | MF | MW (Cal.) | MS (M + H) |
| 101a | 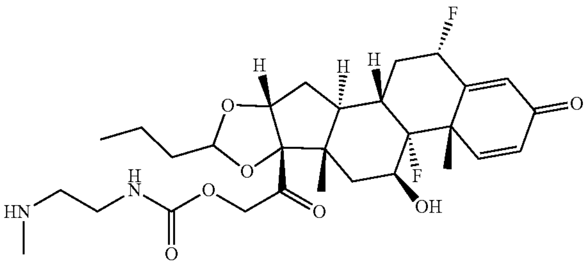 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1] | >95 | 2.40 | $C_{29}H_{40}F_2N_2O_7 \cdot C_2HF_3O_2$ | 663.66 | 567 |
| 101b | 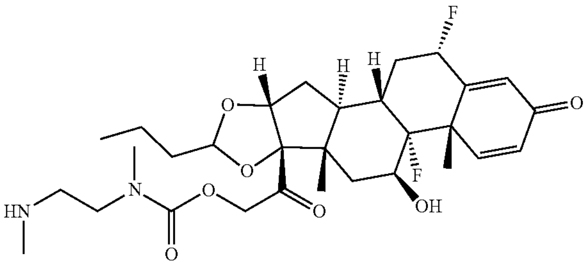 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1] | >95 | 2.63 | $C_{30}H_{42}F_2N_2O_7 \cdot C_2HF_3O_2$ | 678.69 | 581 |
| 101c | 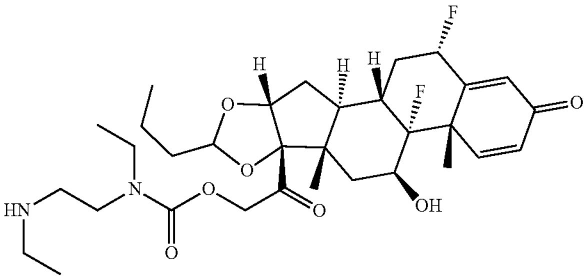 | 100 | 3.34 | $C_{32}H_{46}F_2N_2O_7 \cdot C_2HF_3O_2$ | 722.74 | 609 |
| 101d | 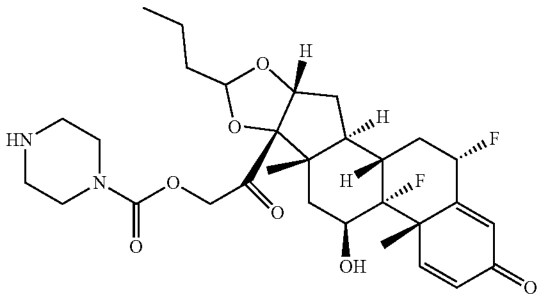 | 100 | 2.46 | $C_{30}H_{40}F_2N_2O_7$ | 578.64 | 579 |
| 102c | 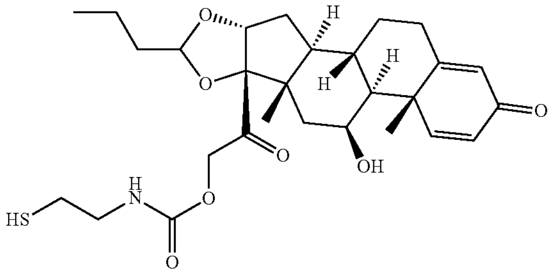 | >95 | 3.47 | $C_{28}H_{39}NO_7S$ | 533.68 | 531 |

TABLE 1a-continued
| # | Structure | HPLC purity | cLog P | MF | MW (Cal.) | MS (M + H) |
|---|---|---|---|---|---|---|
| | Structure and Chemical-Physical Properties of Compounds | | | | | |
| 102d | 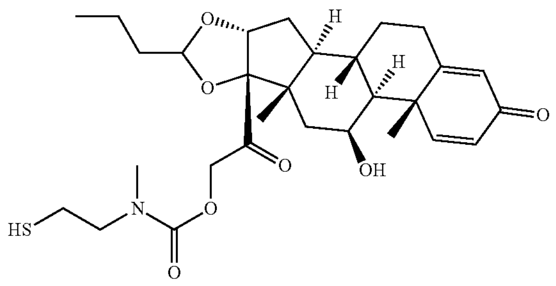 | >95 | 3.69 | $C_{29}H_{41}NO_7S$ | 547.71 | 548 |
| 102e | 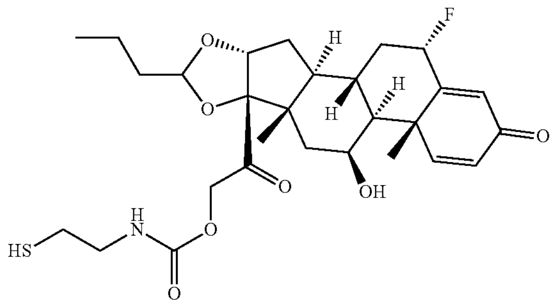 | >95 | 3.17 | $C_{29}H_{37}F_2NO_7S$ | 569.66 | 570 |
| 102f | 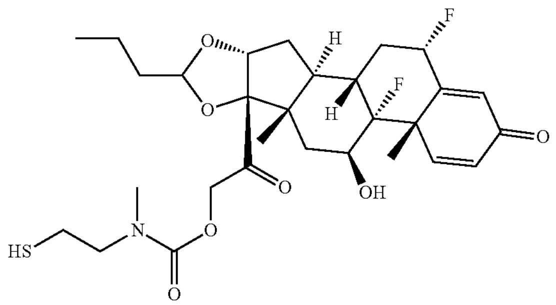 | >95 | 3.40 | $C_{29}H_{39}F_2NO_7S$ | 583.69 | 584 |
| 103a | 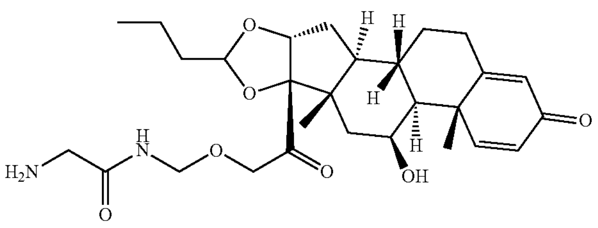 | 98 | 1.58 | $C_{28}H_{40}N_2O_7$ | 516.64 | 517 |
| 103b | 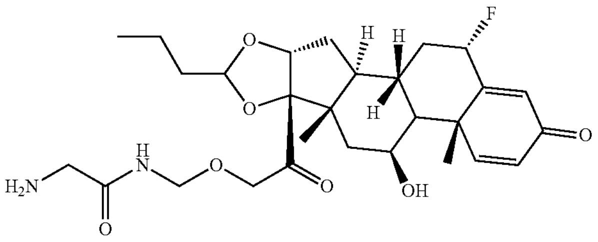 | 98 | 1.29 | $C_{29}H_{38}F_2N_2O_7$ | 552.62 | 553 |

TABLE 1a-continued
Structure and Chemical-Physical Properties of Compounds
| # | Structure | HPLC purity | cLog P | MF | MW (Cal.) | MS (M + H) |
|---|---|---|---|---|---|---|
| 104a | 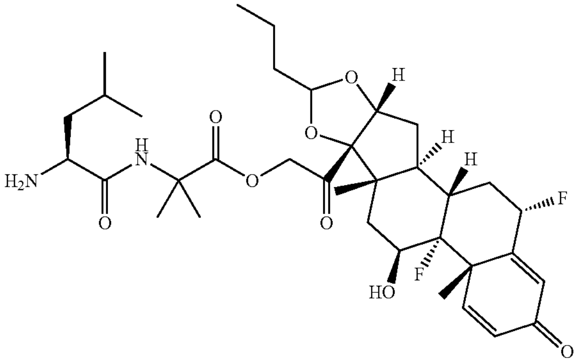 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@@H](N)CC(C)C)O1] | >90 | 3.67 | $C_{35}H_{50}F_2N_2O_8$ | 664.79 | 665 |
| 104b | 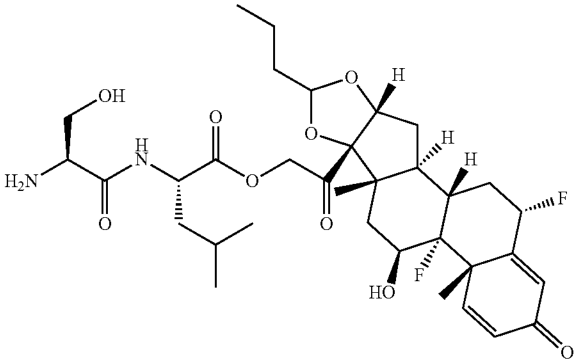 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@@H](N)CO)O1] | >95 | 2.19 | $C_{34}H_{48}F_2N_2O_9$ | 666.76 | 667 |

Scheme 2. Synthesis of VC-PAB Spacer-Budesonide
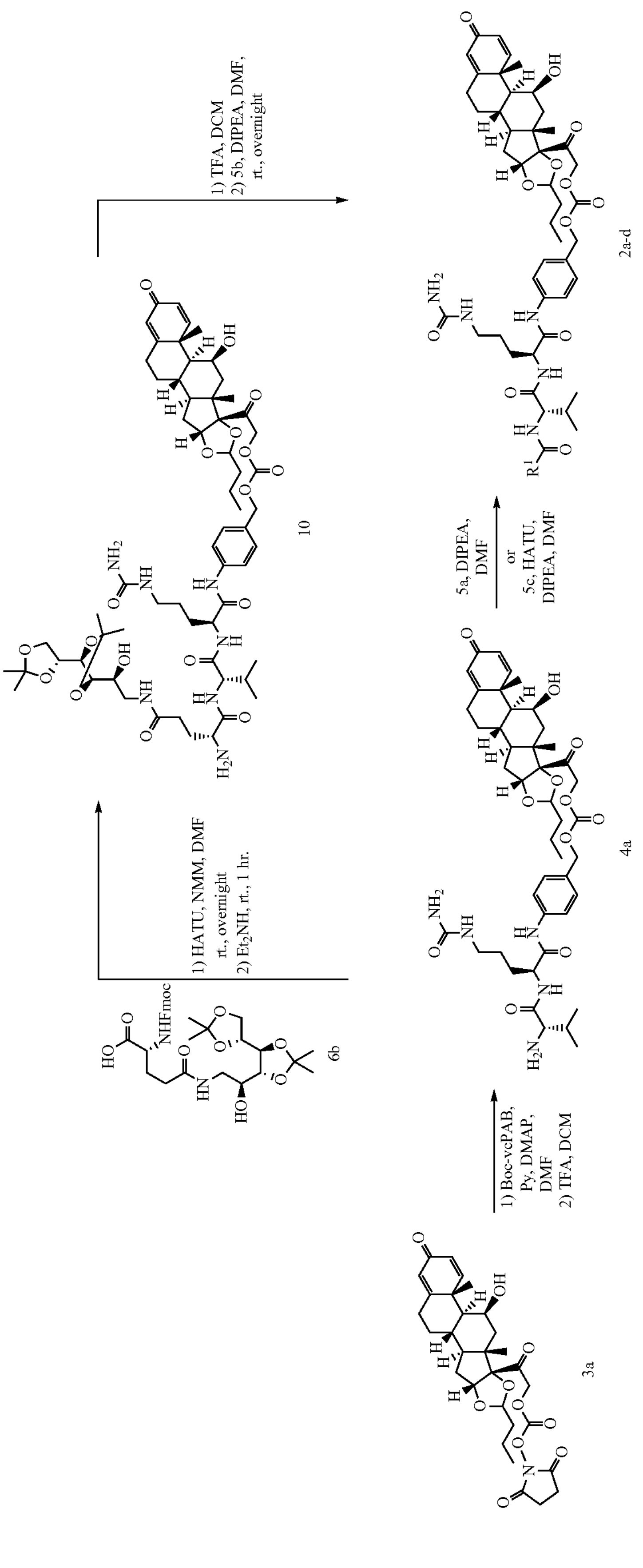
6b
10
3a
4a
2a-d

-continued
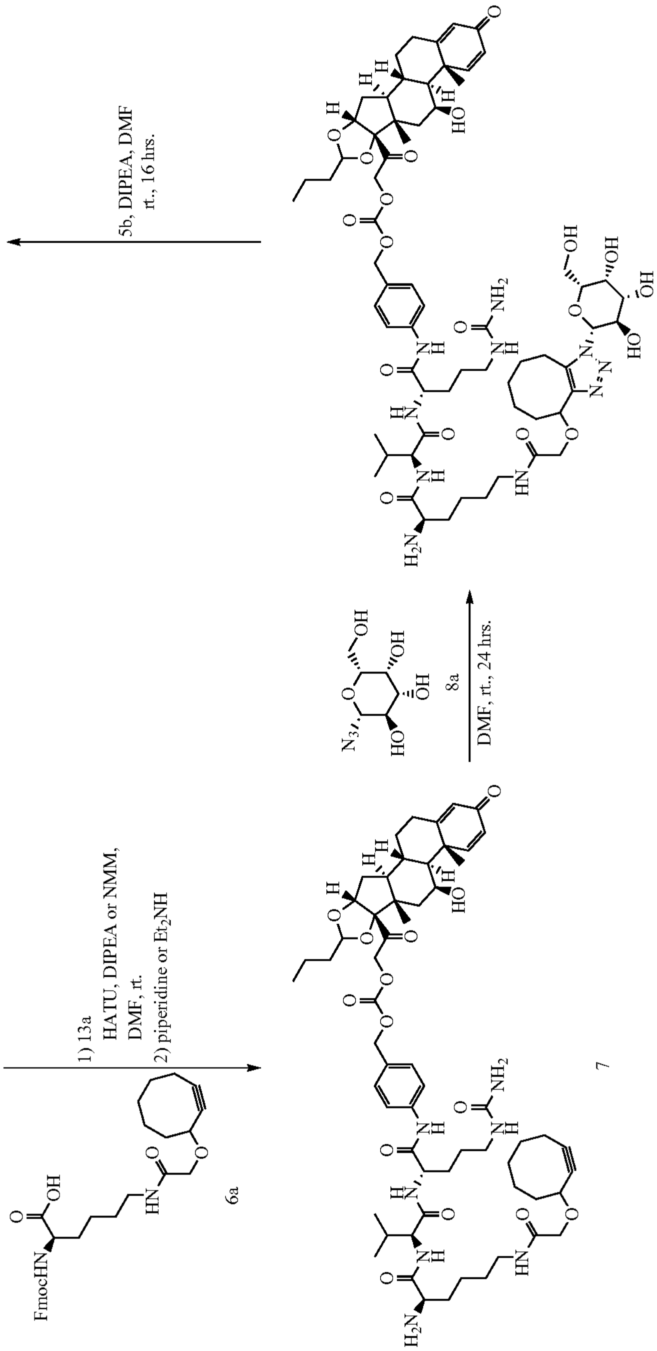
6a
7
8a
9
Boc-vcPAB:
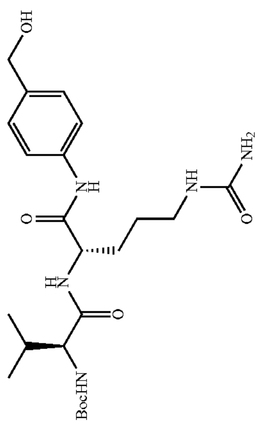

General Procedure A for Synthesis of MC-Spacer-Budesonide (2a and 2c)

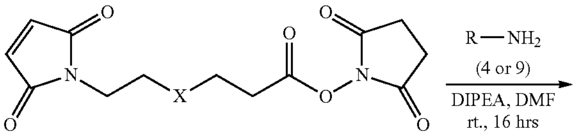

5a, X = $CH_2$
5b, X = $(OCH_2CH_2)_3O$

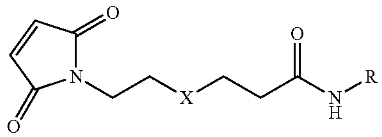

2a, c

To a solution of vcPAB-Budesonide (4a A=CO, 1.0 equiv.) or amine 9 (1.0 equiv.) in Scheme 2 in DMF (ca. 1 mL per 10 mg amine) were added activated NHS ester 5 (1.5-3.0 equiv.) in the table below and DIPEA (2.0 equiv.) at RT. The reaction mixture was stirred at RT overnight when NHS ester and most of amine were consumed according to LCMS spectra. After filtration, the reaction solution was directly purified by prep-HPLC or reversed phase flash chromatography to give the desired amide 2 (ca. 17% yield) as a white solid.

| Amines | | Activated ester 5 | | Base/reagents | Solvent | Time (hr) | Purification | Product 2 |
|---|---|---|---|---|---|---|---|---|
| 4a[c] | 50 mg, 56 μmol | 5a | 28 mg, 91 μmol | DIPEA (23 mg, 0.18 mmol) | DMF (3 mL) | 16 | Prep-HPLC (method A) | 2a (10 mg, 17%) |
| rxn solution of 9 | | 5b | 8.8 mg, 20 μmol | DIPEA (4.0 mg, 31 μmol) | DMF (1 mL) | 16 | Prep-HPLC (method A) | 2d (3.5 mg, 4%) |

[c]TFA salt

General Procedure B for Synthesis of Amides 2b, 21, 2m-Precursor from Acid

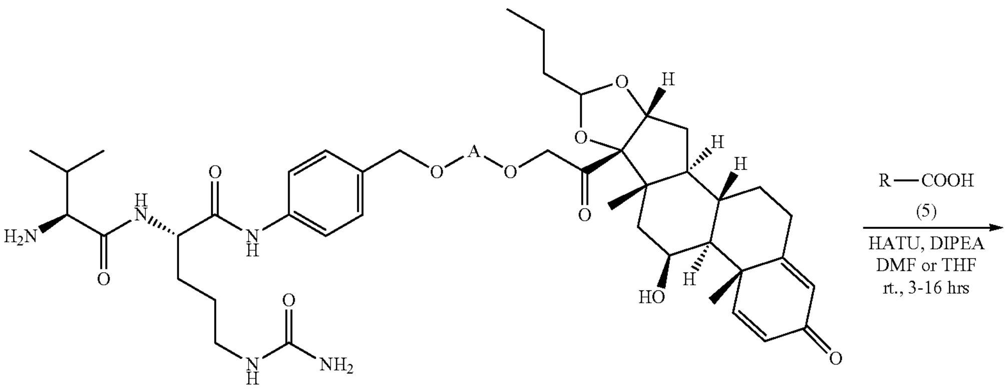

4a-c

-continued

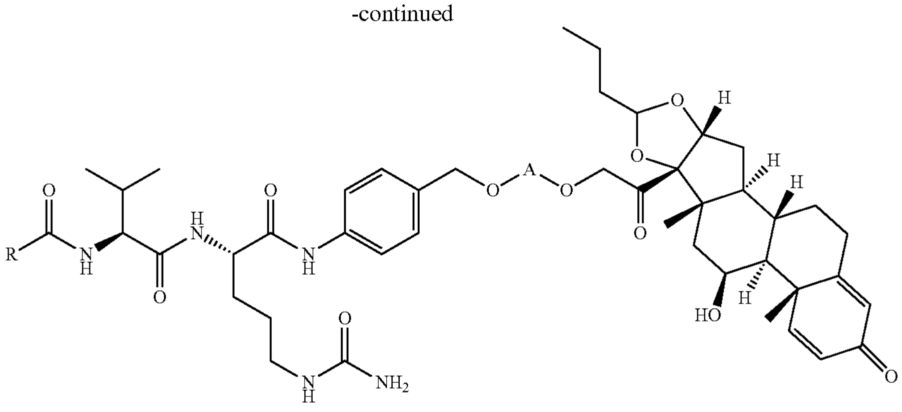

2b, 21, 2m-precursor

| Products | Amines | Acids | A | R |
|---|---|---|---|---|
| 2b | 4a | 5c | 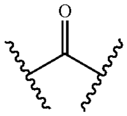 [SMILES: *C(*)=O] | 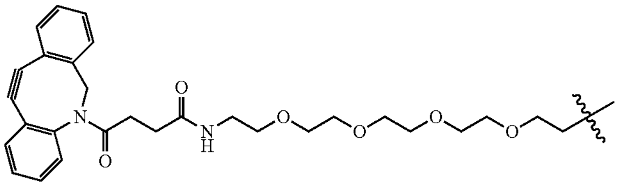 [SMILES: *CCOCCOCCOCCOCCNC(=O)CCC(=O)N1Cc2ccccc2C#Cc2ccccc21] |
| 21 | 4c | 5d | 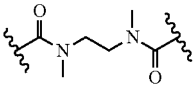 [SMILES: *C(=O)N(C)CCN(C)C(*)=O] | 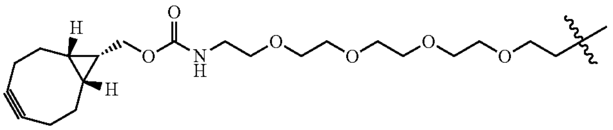 [SMILES: *CCOCCOCCOCCOCCNC(=O)OC[C@@H]1[C@@H]2CCC#CCC[C@@H]21] |
| 2m-precursor | 4c | 5e | 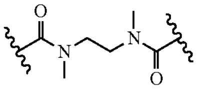 [SMILES: *C(=O)N(C)CCN(C)C(*)=O] | 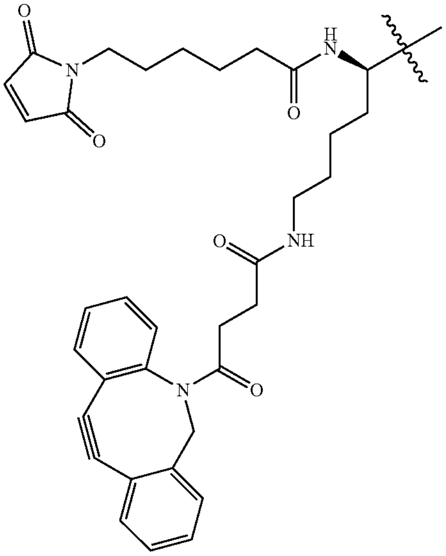 [SMILES: *[C@@H](CCCCNC(=O)CCC(=O)N1Cc2ccccc2C#Cc2ccccc21)NC(=O)CCCCCN1C(=O)C=CC1=O] |

To a solution of acid 5 (1.0-1.5 equiv.) in DMF or DCM or THF (1 mL per 5 mg 5) were added DIPEA (2.0-5.0 equiv.) and HATU (1.4-2.2 equiv.) at RT. The resulting mixture was stirred at this temperature for 0.5-1 hour before the vcPAB-Budesonide (4, 1.0 equiv.) was added. The reaction mixture was stirred at RT for 3-16 hours until the amine was totally consumed, which was monitored by LCMS. The reaction mixture was filtered through membrane and the filtration was then separated by prep-HPLC or reversed phase flash chromatography to give the amide 2 (21-54% yield) as a white solid. In the table below are additional details.

| | Amines | | acid | Base/reagents | Solvent | Time (hr) | Purification | Product 2 |
|---|---|---|---|---|---|---|---|---|
| 4b | 10 mg, 11 μmol | 5c | 10 mg, 18 μmol | DIPEA (6.2 mg, 48 μmol) HATU (9.0 mg, 24 μmol) | DMF (1 mL) | 16 | Prep-HPLC (method B) | 2b (3.0 mg, 21%) |
| 4c | 58 mg, 61 μmol | 5c | 37 mg, 67 μmol | DIPEA (15 mg, 0.12 mmol) HATU (34 mg, 89 μmol) | DMF (5 mL) | 3 | Prep-HPLC (method B) | 2i (21 mg, 24%) |
| 4c | 8.9 mg, 9.4 μmol | 5d | 6.3 mg, 14 μmol | DIPEA (3.6 mg, 27 μmol) HATU (8.0 mg, 20 μmol) | DMF (1 mL) | 16 | Prep-HPLC (method B) | 2l (7 mg, 54%) |
| 4c | 20 mg, 21 μmol | 5e | 13 mg, 21 μmol | DIPEA (8.0 mg, 62 μmol) HATU (12 mg, 31 μmol) | THF (5 mL) | 16 | Prep-HPLC (method A) | 2m-precursor (5 mg) |

General Procedure C for Synthesis of Intermediate 7 and 10

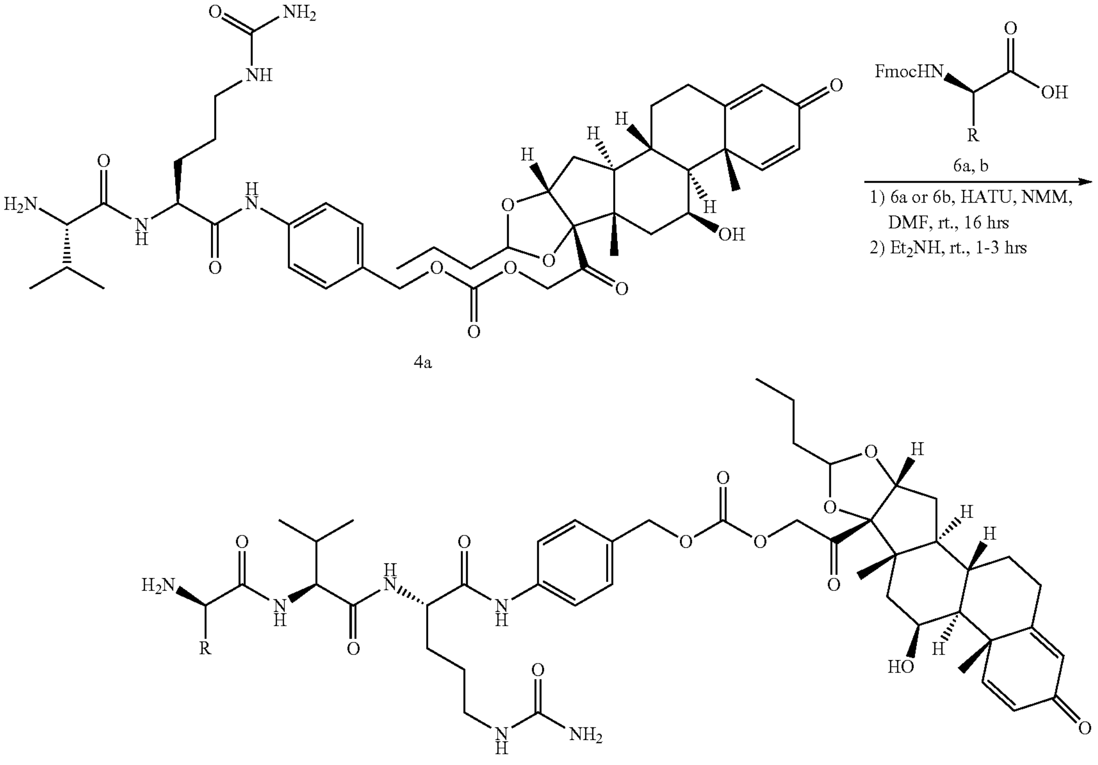

4a 7, 10

| Fmoc-Aminoacid 6 | Product | R |
|---|---|---|
| 6a | 7 | 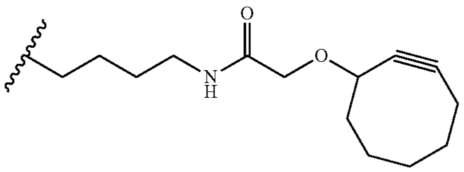 [SMILES: *CCCCNC(=O)COC1C#CCCCCC1] |

-continued

| Fmoc-Aminoacid 6 | Product | R |
|---|---|---|
| 6b | 10 | 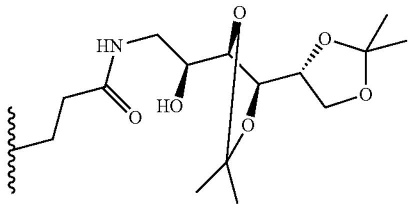 |

To a solution of intermediate 6 (1.2-1.4 equiv.) in DMF was added HATU (1.5-1.7 equiv.) at RT. The solution obtained was stirred at RT for an hour. To this suspension were added a solution of vcPAB-budesonide (4a, 1.0 equiv.) in DMF (0.10 mL per mg of 4a) and subsequently NMM (2.3-3.0 equiv.). The reaction mixture was stirred at RT for 16 hours and turned clear. The reaction was monitored by LCMS until compound 4a was totally consumed. To the reaction mixture was then added diethylamine (excess), and the resulting mixture was then stirred at RT for 1-3 hours until Fmoc was removed according to LCMS. The volatiles were removed in vacuo and the residue was purified by prep-HPLC (method A) to give compound 7 (18% yield from compound 4a) or purified by prep-HPLC (method B) to give compound 10 (5-% yield) as a white solid. In the table below are additional details.

| Amines | | Intermediate 6 | | Base/reagents | Solvent | Time | Purification | Product |
|---|---|---|---|---|---|---|---|---|
| 4a | 60 mg, 64 μmol | 6a | 46 mg, 86 μmol | NMM (15 mg, 0.15 mmol) HATU (41 mg, 0.11 mmol) then $Et_2NH$ (0.5 mL) | DMF (3 mL) | 16 hrs then 3 hrs | Prep-HPLC (method A) | 7 (13 mg, 18%) |
| 4a | 0.19 g, 0.20 mmol | 6b | 0.15 g, 0.24 mmol | NMM (61 mg, 0.60 mmol) HATU (0.11 g, 0.29 mmol) then $Et_2NH$ (1 mL) | DMF (5 mL) | 16 hrs then 1 hr | Prep-HPLC (method B) | 10 (13 mg, 5%) |

General Procedure D for Synthesis of Carbamates 2j, 2k, 2r, and 2s

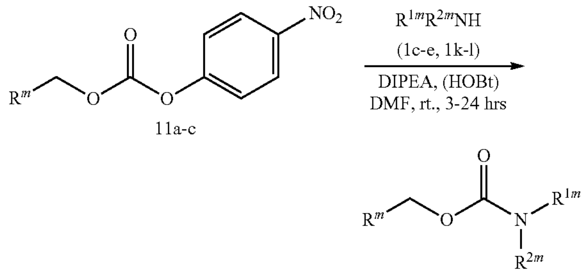

11a-c 2j, 2k, 2r, 2s

The mixture was stirred at RT for 3-24 hours until PNP activated ester was totally consumed, which was monitored by LCMS. The reaction mixture was filtered through membrane and the filtrate was separated directly by prep-HPLC to give compound 2 (with or without diastereoisomers, 11-63% yield) as a white solid(s). In the table below are additional details.

| | Spacer-budesonide 21 | | Activated ester 23 | Base/reagents | Solvent | Time (hr) | Purification | Product 2 |
|---|---|---|---|---|---|---|---|---|
| 1e | 15 mg, 28 µmol | 11a | 15 mg, 20 µmol | DIPEA (12 mg, 93 µmol) HOBt (4.0 mg, 30 µmol) | DMF (1 mL) | 12 | Prep-HPLC (method A) | 2j (3.0 mg, 13%) |
| 1d | 20 mg, 37 µmol | 11a | 22 mg, 30 µmol | DIPEA (12 mg, 93 µmol) HOBt (6.0 mg, 44 µmol) | DMF (1 mL) | 12 | Prep-HPLC (method A) | 2k-A (3.3 mg, 10%) 2k-B (4.1 mg, 12%) |
| 1k | 50 mg, 90 µmol | 11c | 30 mg, 95 µmol | DIPEA (50 mg, 0.39 mmol) | DMF (1 mL) | 3 | Prep-HPLC (method B) | 2r (40 mg, yield 61%) |

Synthesis of 2a-d

Budesonide-Linkers 2a-d were prepared from three approaches according to Scheme 2. The first approach was directly amide coupling reactions from vcPAB-Budesonide (4a), which was obtained from the activated ester of budesonide 3a with linkers 5. The second approach was via initial amide coupling reactions from vcPAB-Budesonide (4a) with intermediate 6a to generate Budesonide-Linkers 7, followed by 3+2 cyclization with galactose-azide (8a) to generate intermediates 9, and finally by secondary amide coupling reactions with 5. The third approach was via first amide coupling reactions of 4 with intermediate 6b, followed by amide formation with 5b and sequentially deprotection of acetone to give 2d.

Intermediate 4a

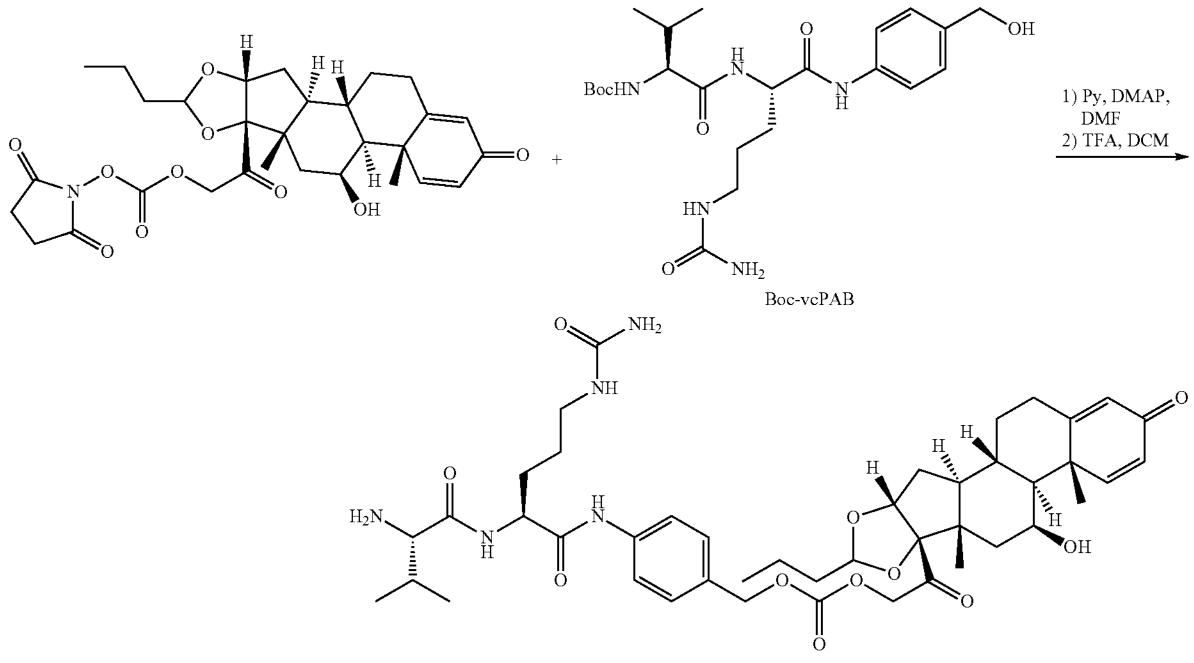

Boc-vcPAB

4a 1.4 mmol) in dry DMF (10 mL) were added Boc-vc-PAB (12a) [WO2008/34124 A2](0.59 g, 1.2 mmol), DMAP (0.30 g, 2.4 mmol) and pyridine (0.29 g, 3.7 mmol). The mixture was stirred at RT for 16 hours until 3a was totally consumed according to LCMS. The reaction mixture was directly purified by reversed phase flash chromatography (50-80% acetonitrile in water) to give intermediate Boc-4a (0.74 g, yield 38%, ESI m/z: 936 $(M+H)^+$) as a white solid, which was dissolved in DCM (40 mL). To 5 mL of the DCM solution (containing 94 mg Boc-4a) was added TFA (0.5 mL) dropwise at 0° C. After stirred at RT for 1.5 hours until the Boc-4a was consumed, which was monitored by LCMS, the resulting mixture was concentrated in vacuo to give crude title product 4a (83 mg, yield 34% from budesonide) as its TFA salt as colorless oil, which can be used without purification for next step synthesis. 20 mg of the crude 4a was purified by prep-HPLC (method B) to give pure 4a (8 mg) as free base for plasma stability test. ESI m/z: 836 $(M+H)^+$. $^1H$ NMR (400 MHz, $DMSO_{d6}$) δ 10.17 (s, 1H), 8.12 (br s, 1H), 7.62 (d, J=8.5 Hz, 2H), 7.31 (d, J=10.2 Hz, 3H), 6.17 (d, J=10.1 Hz, 1H), 5.97 (t, J=5.7 Hz, 1H), 5.92 (s, 1H), 5.40 (s, 2H), 5.22-5.01 (m, 4H), 4.89-4.62 (m, 3H), 4.53-4.40 (m, 1H), 4.30 (s, 1H), 3.09-2.87 (m, 3H), 2.36-2.22 (m, 1H), 2.14-1.87 (m, 4H), 1.81 (d, J=5.6 Hz, 2H), 1.75 (s, 2H), 1.62-1.52 (m, 4H), 1.51-1.41 (m, 2H), 1.40-1.19 (m, 8H), 1.18-0.92 (m, 2H), 0.92-0.82 (m, 9H), 0.78 (d, J=6.8 Hz, 3H) ppm.

Example 2a

N-[(1 S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-6-(2,5-dioxo-2,5-dihydro-1H-pyrrol-1-yl)hexanamide (2a)

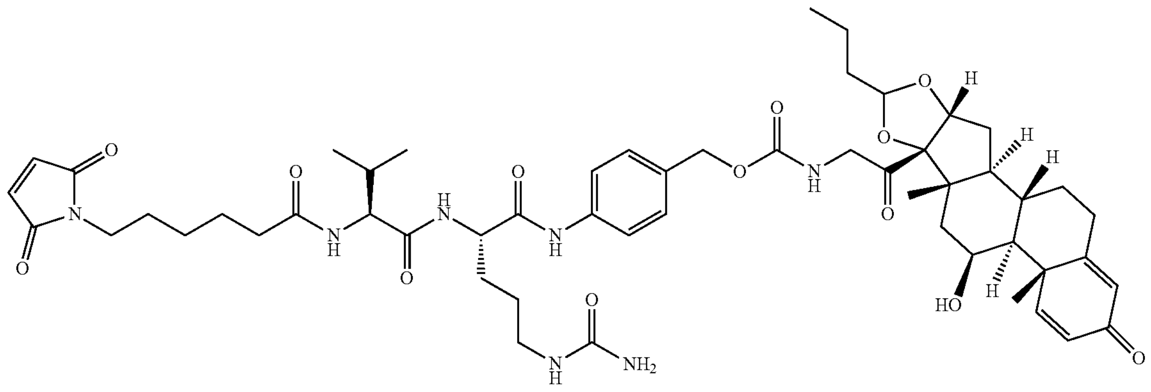 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CNC(=O)OCc2ccc(NC(=O)[C@H](CCCNC(N)=O)NC(=O)[C@@H](NC(=O)CCCCCN3C(=O)C=CC3=O)C(C)C)cc2)O1]

Following the general procedure A, the title compound 2a (10 mg, 17% yield) was obtained as a white solid. ESI m/z: 1029 (M+H)$^+$. Anal. HPLC: 92.5%, Retention time: 7.66 min (method A).

Example 2b 1-(4-{2-Azatricyclo[10.4.0.0$^{4,9}$]hexadeca-1(12),4(9),5,7,13,15-hexaen-10-yn-2-yl}-4-oxobutanam-[(1S,2S,4R,8S,9S,11S,12S,13R)-11-hydroxy-9,13-dimethyl-16-oxo-6-propyl-5,7-ido)-N-[(1S)-1-{[(1 S)-4-(carbamoylamino)-1-[(4-{[({2dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-3,6,9,12-tetraoxapentadecan-15-amide (2b)

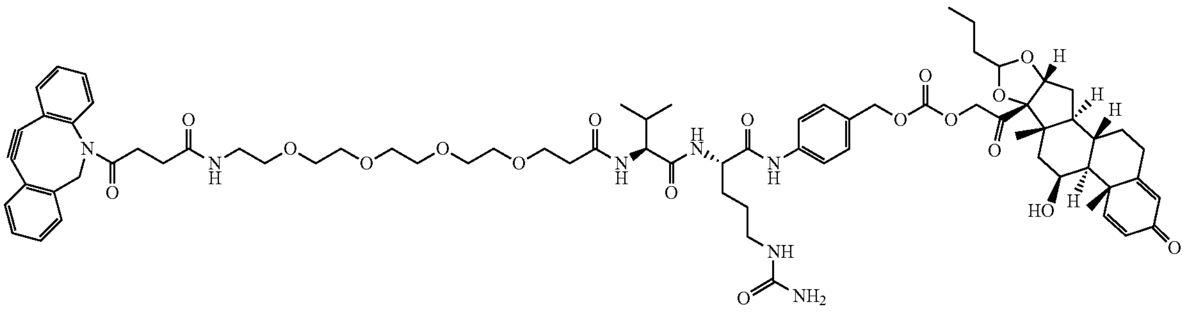 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

Following the general procedure B, the title compound 2b (3.0 mg, 21% yield) was obtained as a white solid. ESI m/z: 686 (M/2+H)$^+$. $^1$H NMR (400 MHz, DMSO$_{d6}$) δ 10.05 (s, 1H), 8.15 (d, J=7.5 Hz, 1H), 7.88 (d, J=8.8 Hz, 1H), 7.77 (t, J=5.7 Hz, 1H), 7.71-7.66 (m, 1H), 7.66-7.59 (m, 3H), 7.52-7.27 (m, 9H), 6.17 (d, J=10.0 Hz, 1H), 6.03-5.95 (m, 1H), 5.92 (s, 1H), 5.79-5.74 (m, 1H), 5.43 (s, 2H), 5.22-4.99 (m, 6H), 4.88-4.84 (m, 1H), 4.84-4.60 (m, 2H), 4.42-4.34 (m, 1H), 4.33-4.26 (m, 1H), 4.26-4.20 (m, 1H), 3.65-3.55 (m, 3H), 3.48-3.44 (m, 12H), 3.32-3.26 (m, 2H), 3.12-2.91 (m, 4H), 2.63-2.54 (m, 1H), 2.41-2.19 (m, 3H), 2.03-1.94 (m, 4H), 1.84-1.78 (m, 2H), 1.63-1.22 (m, 14H), 1.03-0.82 (m, 15H) ppm. Anal. HPLC: 96.9%, Retention time: 8.10 min (method B).

Example 2c (2R)-2-Amino-N-[(1S)-1-{[(1 S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-6-[2-(cyclooct-2-yn-1-yloxy)acetamido]hexanamide (7)

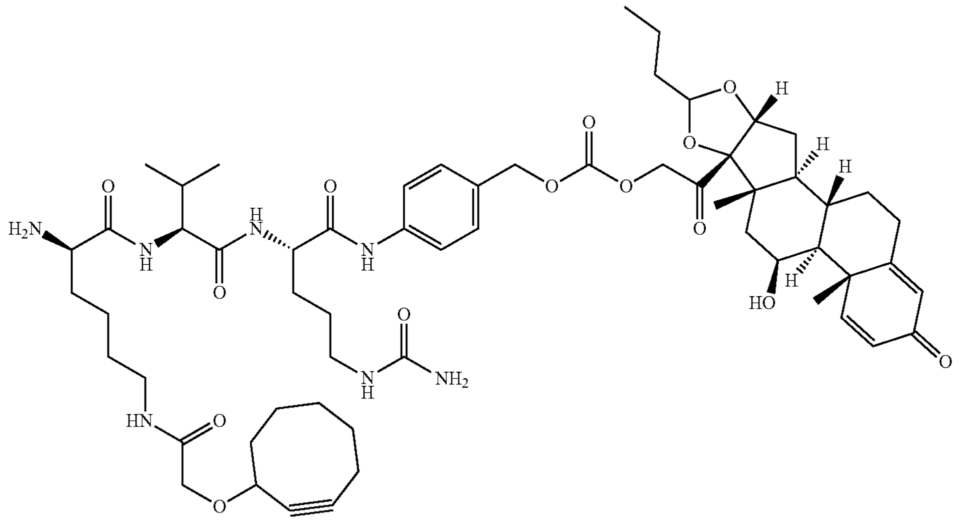 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCCCNC(=O)COC3C#CCCCCC3)C(C)C)cc2)O1]

ESI m/z: 565 (M/2+H)$^+$. $^1$H NMR (500 MHz, DMSO$_{d6}$) δ 10.17-10.00 (m, 1H), 8.47-7.73 (m, 2H), 7.69-7.57 (m, 3H), 7.38-7.26 (m, 3H), 6.17 (d, J=10.0 Hz, 1H), 5.99 (s, 1H), 5.92 (s, 1H), 5.76 (s, 1H), 5.42 (s, 2H), 5.23-5.01 (m, 4H), 4.88-4.61 (m, 3.4H), 4.43-4.16 (m, 4.6H), 3.85 (d, J=14.7 Hz, 1H), 3.73 (d, J=14.5 Hz, 1H), 3.23-3.18 (m, 1H), 3.09-2.90 (m, 4H), 2.33-2.18 (m, 3H), 2.18-2.04 (m, 3H), 2.03-1.66 (m, 10H), 1.64-1.50 (m, 7H), 1.49-1.22 (m, 13H), 1.17-0.90 (m, 4H), 0.90-0.79 (m, 12H) ppm.

(2R)-2-Amino-N-[(1S)-1-{[(1 S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-6-[2-({1-[(2R,3R,4S,5R,6R)-3,4,5-trihydroxy-6-(hydroxymethyl)oxan-2-yl]-1H,4H,5H,6H,7H,8H,9H-cycloocta[d][1,2,3]triazol-4-yl}oxy)acetamido]hexanamide (9)

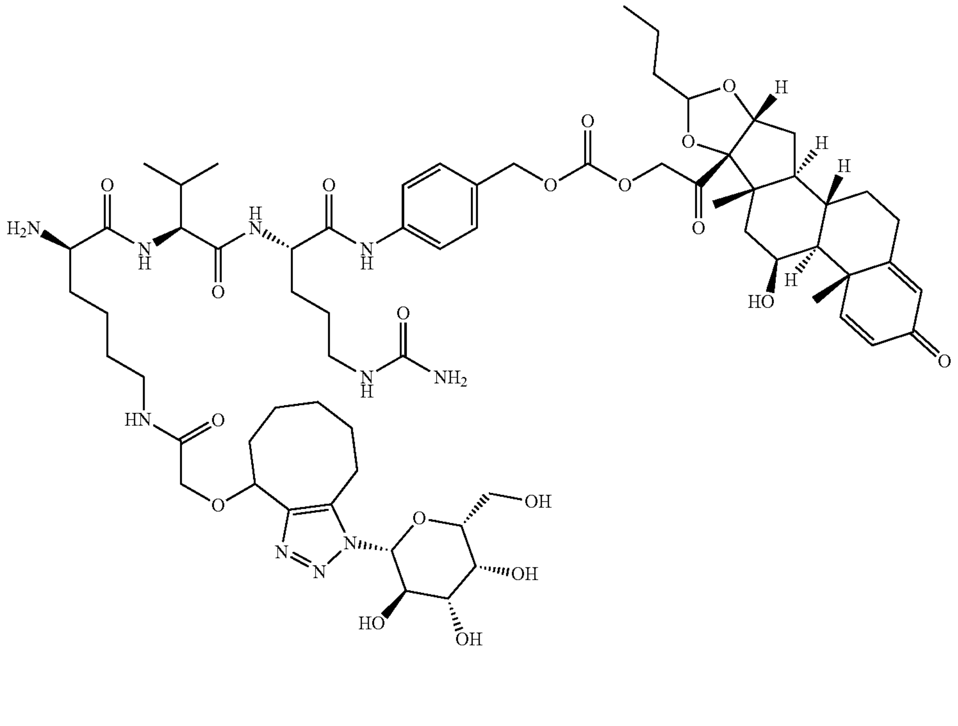 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCCCNC(=O)COC3CCCCCc4c3nnn4[C@@H]3O[C@H](CO)[C@H](O)[C@H](O)[C@H]3O)C(C)C)cc2)O1]

After filtration, the resulting solution of 9 was directly used directly for the next step. ESI m/z: 667 $(M/2+H)^+$ N-[(1R)-1-{[(1S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}carbonyl)oxy]methyl}phenyl)carbamoyl]butyl]carbamoyl}-2-methylpropyl]carbamoyl}-5-[2-({1-[(2R,3R,4S,5R,6R)-3,4,5-trihydroxy-6-(hydroxymethyl)oxan-2-yl]-4H,5H,6H,7H,8H,9H-cycloocta[d][1,2,3]triazol-4-yl}oxy)acetamido]pentyl]-1-(2,5-dioxopyrrol-1-yl)-3,6,9,12-tetraoxapentadecan-15-amide (Mc-PEG$_4$-N(sugar-COT)Lys-vc-PAB-Budesonide) (2c)

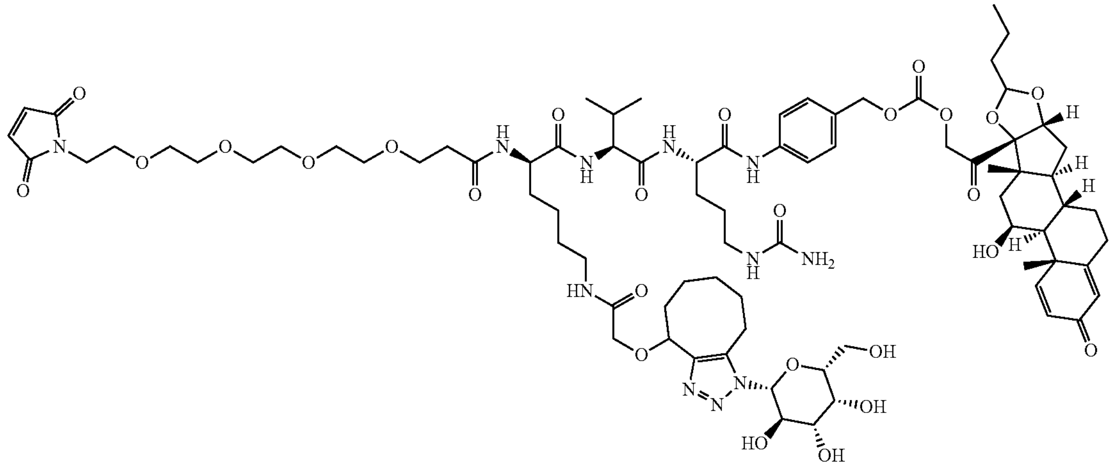 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@@H](CCCCNC(=O)COC3CCCCCc4c3nnn4[C@@H]3O[C@H](CO)[C@H](O)[C@H](O)[C@H]3O)NC(=O)CCOCCOCCOCCOCCN3C(=O)C=CC3=O)C(C)C)cc2)O1]

ESI m/z: 831 $(M/2+H)^+$. $^1H$ NMR (400 MHz, DMSO$_{d6}$) δ 9.73 (s, 1H), 8.21-8.07 (m, 3H), 7.94-7.82 (m, 1H), 7.71-7.59 (m, 3H), 7.39-7.26 (m, 4H), 7.02 (s, 1H), 6.17 (d, J=10.0 Hz, 1H), 6.09-5.98 (m, 1H), 5.92 (s, 1H), 5.56-5.28 (m, 4H), 5.25-5.01 (in, 4H),4.90-4.62 (m, 5H), 4.39-4.13 (m, 5H), 3.84-3.69 (m, 4H), 3.59-3.40 (m, 16H), 3.17-2.79 (m, 9H), 2.43-1.71 (m, 13H), 1.71-1.42 (m, 15H), 1.40-1.19 (m, 11H), 1.04-0.77 (in, 15H) ppm. Anal. HPLC: 97.6%, Retention time: 7.63 min (method A).

Example 2d (2R)-2-Amino-N-[(1S)-1-{[(1 S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}carbonyl)oxy]methyl}phenyl)carbamoyl]butyl]carbamoyl}-2-methylpropyl]-N'-[(2S)-2-[(4R,5R)-5-[(4R)-2,2-dimethyl-1,3-dioxolan-4-yl]-2,2-dimethyl-1,3-dioxolan-4-yl]-2-hydroxyethyl]pentanediamide (10)

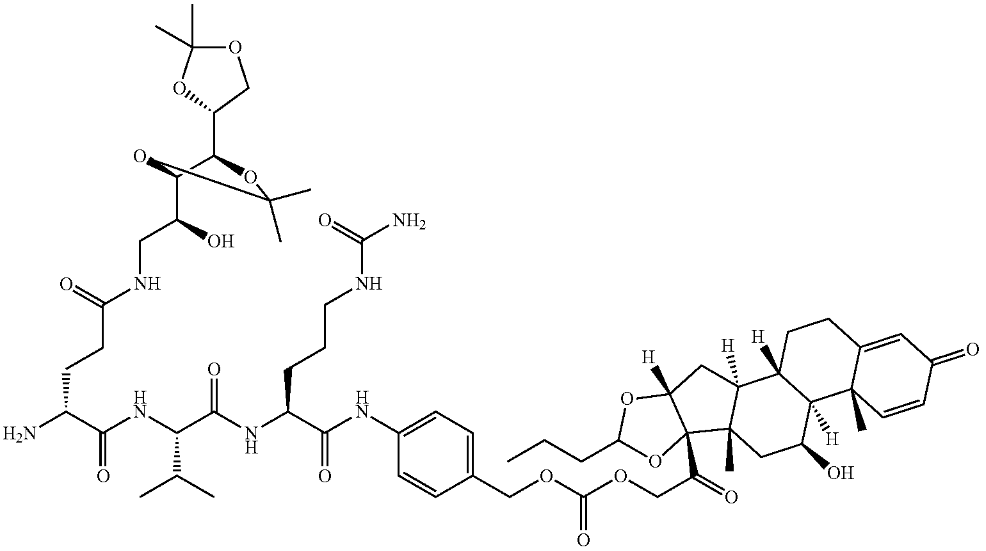

Following the general procedure C, compound 10 (13 mg, 5% yield) was obtained as a white solid. ESI m/z: 605 $(M/2+H)^+$. $^1H$ NMR (500 MHz, $DMSO_{d6}$) 10.08 (s, 1H), 8.34-8.17 (m, 1H), 7.98 (s, 1H), 7.93-7.81 (m, 1H), 7.62 (d, J=8.4 Hz, 2H), 7.42-7.26 (m, 3H), 6.17 (d, J=10.1 Hz, 1H), 5.99 (s, 1H), 5.92 (s, 1H), 5.76 (s, 1H), 5.42 (s, 2H), 5.23-5.01 (m, 4H), 4.91-4.61 (m, 4H), 4.43-4.20 (m, 3H), 4.10-3.72 (m, 6H), 3.60-3.54 (m, 1H), 3.24-3.09 (m, 2H), 3.07-2.91 (m, 2H), 2.32-2.25 (m, 1H), 2.22-2.10 (m, 2H), 2.04-1.93 (m, 2H), 1.88-1.67 (m, 5H), 1.64-1.22 (m, 27H), 1.17-0.93 (m, 3H), 0.91-0.81 (m, 12H) ppm.

(2R)-2-Amino-N-[(1S)-1-{[(1 S)-4-(carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}carbonyl)oxy]methyl}phenyl)carbamoyl]butyl]carbamoyl}-2-methylpropyl]-N'-[(2S,3R,4R,5R)-2,3,4,5,6-pentahydroxyhexyl]pentanediamide (10A)

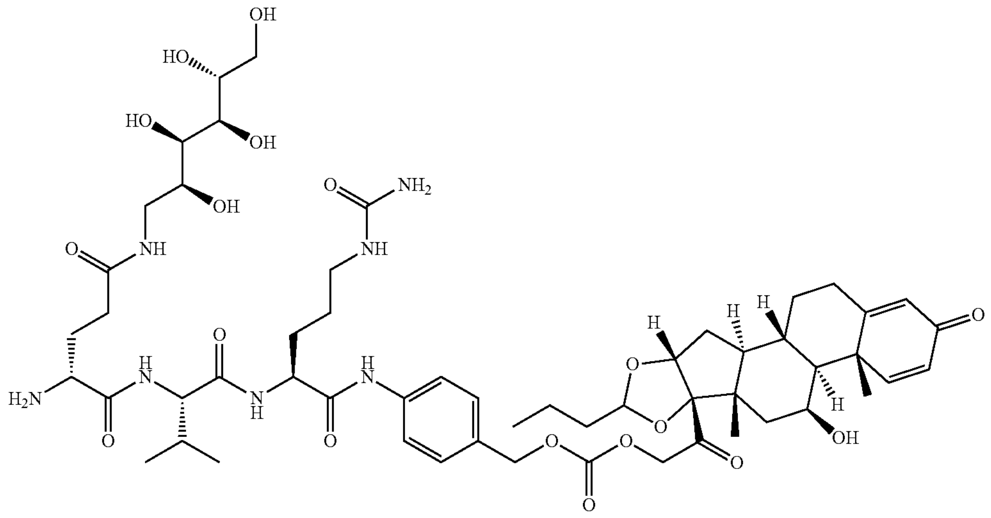 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@H](N)CCC(=O)NC[C@H](O)[C@@H](O)[C@H](O)[C@H](O)CO)C(C)C)cc2)O1]

To a mixture of compound 10 (13 mg, 11 μmol) in DCM (1 mL) was added TFA (1 mL) dropwise. The mixture was stirred at RT for an hour which was monitored by LCMS. The volatiles were removed in vacuo to give crude deprotection product 10A (13 mg) as a light yellow oil, which was used for the next step without further purification. ESI m/z: 565 $(M/2+H)^+$.

(2R)-N-[(1S)-1-{[(1S)-4-(Carbamoylamino)-1-[(4-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)oxy]methyl}phenyl)carbamoyl]butyl]carbamoyl}-2-methylpropyl]-2-[1-(2,5-dioxopyrrol-1-yl)-3,6,9,12-tetraoxapentadecan-15-amido]-N'-[(2S,3R,4R,5R)-2,3,4,5,6-pentahydroxyhexyl]pentanediamide (2d)

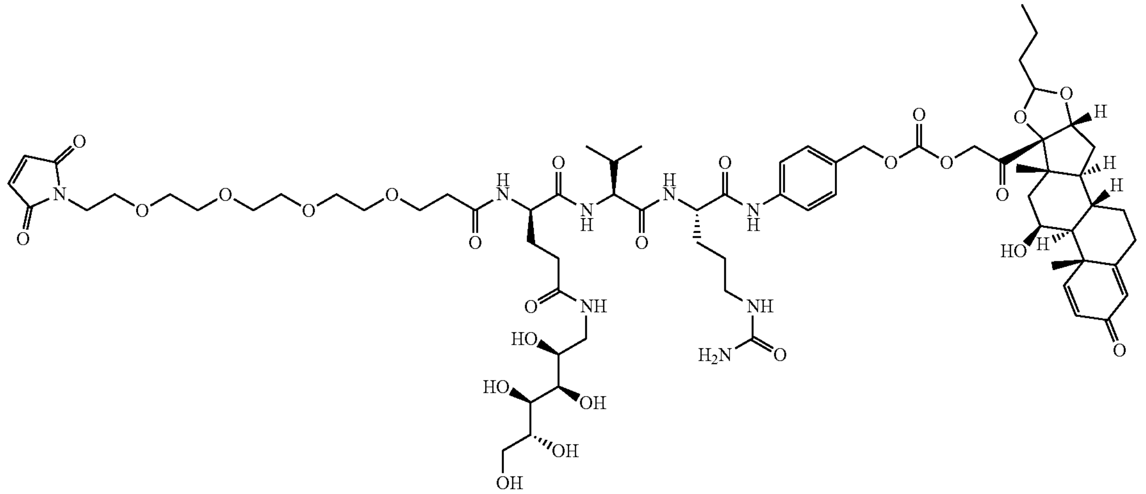 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)[C@@H](CCC(=O)NC[C@H](O)[C@@H](O)[C@H](O)[C@H](O)CO)NC(=O)CCOCCOCCOCCOCCN3C(=O)C=CC3=O)C(C)C)cc2)O1]

Following the general procedure A, the title compound 2d (3.5 mg, 1% total yield from 4a) was obtained as a white solid. ESI m/z: 829.7 $(M/2+H)^+$. $^1H$ NMR (400 MHz, $DMSO_{d6}$) δ 10.10 (s, 0.25H), 9.79 (s, 0.75H), 8.22 (d, J=7.1 Hz, 1H), 8.12 (d, J=7.5 Hz, 1H), 8.07 (d, J=7.8 Hz, 1H), 7.79-7.71 (m, 1H), 7.69-7.60 (m, 2H), 7.38-7.27 (m, 4H), 7.02 (d, J=1.4 Hz, 2H), 6.17 (dt, J=7.6, 1.6 Hz, 1H), 6.03-5.97 (m, 1H), 5.92 (s, 1H), 5.46-5.40 (m, 2H), 5.35-5.02 (m, 4H), 4.89-4.61 (m, 4H), 4.50-4.45 (m, 1H), 4.40-4.16 (m, 7H), 3.65-3.37 (m, 21H), 3.07-2.90 (m, 3H), 2.44-2.23 (m, 4H), 2.17-1.93 (m, 6H), 1.90-1.71 (m, 4H), 1.62-1.20 (m, 15H), 1.06-0.76 (m, 15H) ppm. Anal. HPLC: >99%, Retention time: 6.40 min (method A).

Scheme 3. Synthesis of 2e

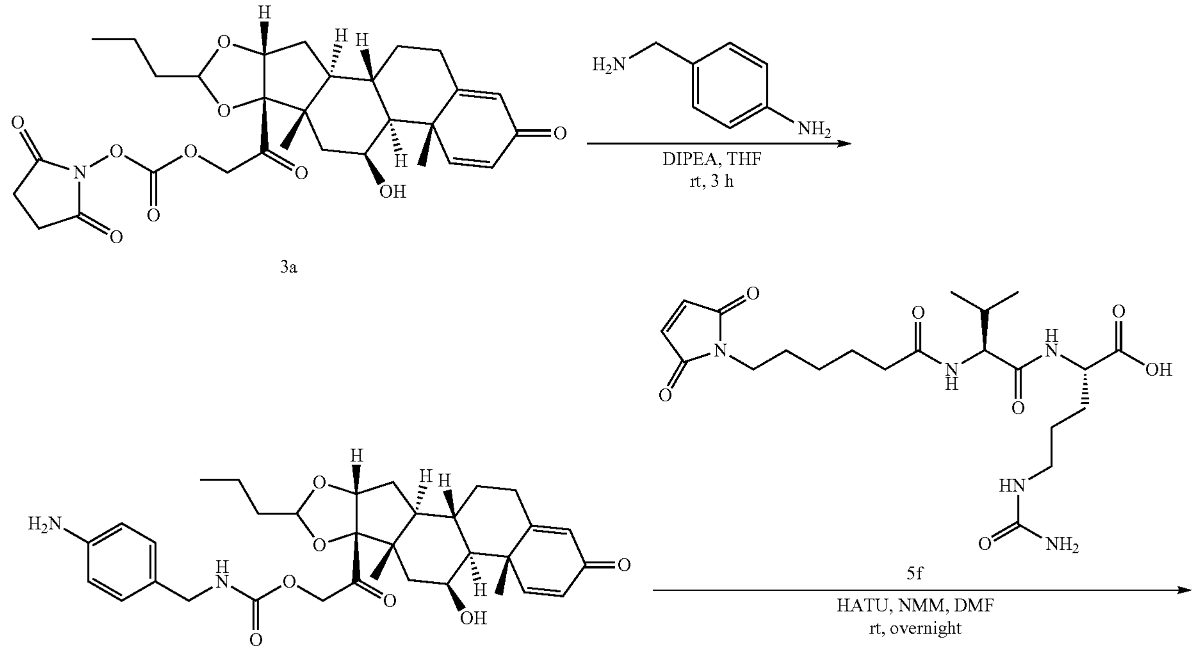

3a

5f

13

-continued

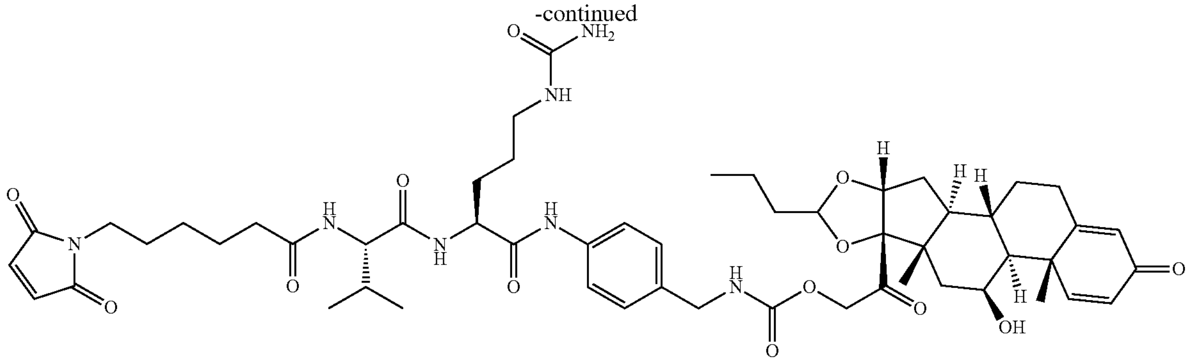

2e

Example 2e

2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxo-ethyl N-[(4-aminophenyl)methyl]carbamate (13)

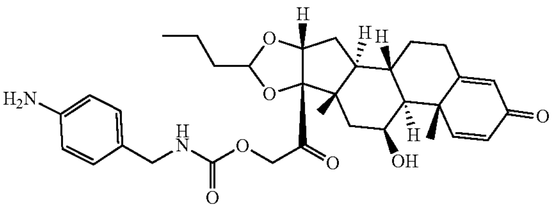 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)NCc2ccc(N)cc2)O1]

To a solution of 4-aminobenzylamine (9.7 mg, 79 μmol) and DIPEA (12 mg, 93 μmol) in THF (10 mL) was added a solution of 3a (24 mg, 44 μmol) in THF (5.0 mL) dropwise at RT. The mixture was stirred at RT for 3 hours until 3a was totally consumed, which was monitored by LCMS. The volatiles were removed in vacuo and residue was purified via prep-HPLC (method B) to give compound 13 (5.6 mg, yield 22%) as a white solid. ESI m/z: 579.2 $(M+H)^+$. $^1$H NMR (400 MHz, MeOD$_{d4}$) δ 7.48-7.45 (m, 3H), 7.31-7.28 (m, 2H), 6.27-6.24 (m, 1H), 6.02 (s, 1H), 5.22 (m, 1H), 5.12-5.11 (m, 1H), 4.96 (m, 1H), 4.86-4.81 (m, 2H), 4.66 (m, 1H), 4.44-4.35 (m, 3H), 2.66-2.65 (m, 1H), 2.40-2.36 (m, 1H), 2.15-2.10 (m, 2H), 1.97-1.60 (m, 6H), 1.53-1.36 (m, 6H), 1.09-0.92 (m, 7H) ppm.

2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxo-ethyl N-({4-[(2S)-5-(carbamoylamino)-2-[(2S)-2-[6-(2,5-dioxo-2,5-dihydro-1H-pyrrol-1-yl) hexanamido]-3-methylbutanamido]pentanamido] phenyl}methyl)carbamate (2e)

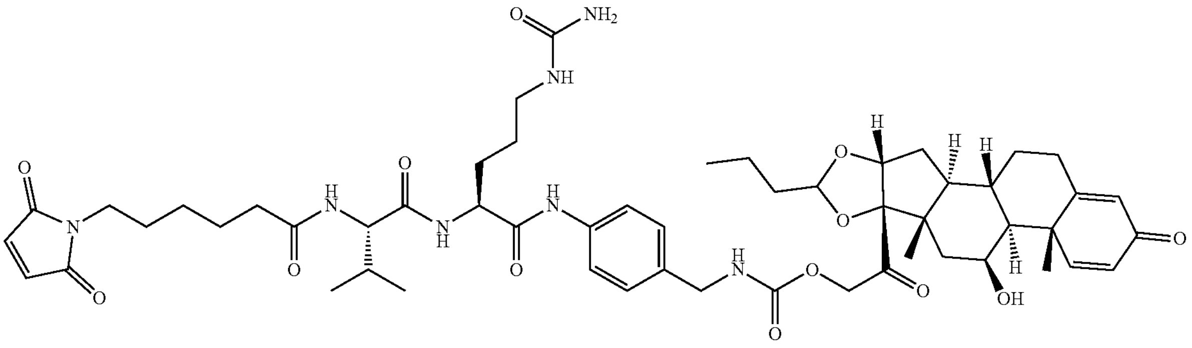 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)NCc2ccc(NC(=O)[C@H](CCCNC(N)=O)NC(=O)[C@@H](NC(=O)CCCCCN3C(=O)C=CC3=O)C(C)C)cc2)O1]

To a mixture of MC-VC-OH 5f (WO2014/191578 A1) (5.7 mg, 12 μmol) in dry DMF (1.5 mL) were added HATU (4.6 mg, 12 μmol) and NMM (4.0 mg, 40 μmol) at RT. The mixture was stirred at RT for 10 minutes before compound 13 (4.7 mg, 8.1 μmol) was added into the reaction mixture. The resulting mixture was stirred at RT overnight. Compound 13 was totally consumed and desired product was detected as major product according to LCMS. The mixture was directly purified by prep-HPLC to give title compound 2e (2.9 mg, yield 35%) as a white solid. ES m/z: 1029.1 $(M+H)^+$, 514.7 $(M/2+H)^+$. Anal. HPLC: >99%, Retention time: 7.54 min (method A).

Scheme 4.
Synthesis of linker-spacer-budesonide (via ester) 2f and 2g

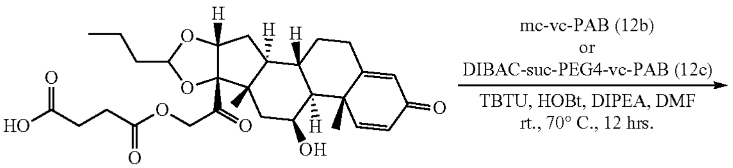

1c

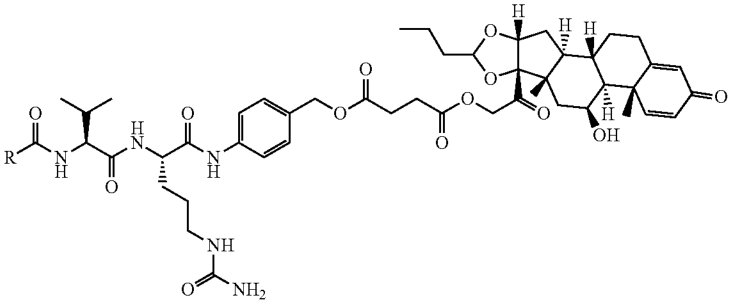

2f, 2g

| Compd # | R |
|---|---|
| 2f | MC |
| 2g | DIBAC-suc-PEG4 |

Example 2f

1-{4-[(2S)-5-(Carbamoylamino)-2-[(2S)-2-[6-(2,5-dioxo-2,5-dihydro-1H-pyrrol-1-yl)hexanamido]-3-methylbutanamido]pentanamido]phenyl}methyl 4-{2-[(1S,2S,4R,8S,9S,11S,12S,13R)-11-hydroxy-9,13-dimethyl-16-oxo-6-propyl-5,7-dioxapentacyclo $[10.8.0.0^{2,9}.0^{4,8}.0^{13,18}]$icosa-14,17-dien-8-yl]-2-oxoethyl} butanedioate (2f)

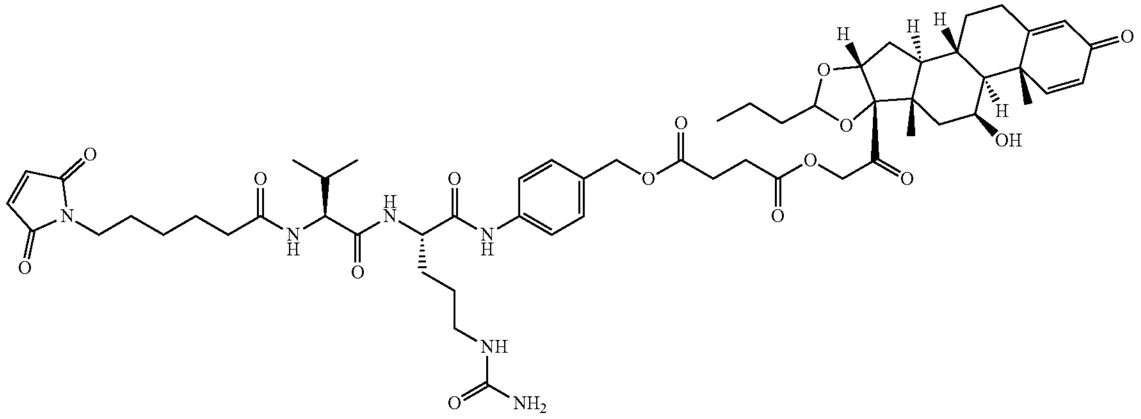 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCCCCN3C(=O)C=CC3=O)C(C)C)cc2)O1]

To a solution of 1c (20 mg, 38 μmol) in DMF (2 mL) were added MC-VCPAB (12b, 0.11 g, 0.19 mmol), TBTU (63 mg, 0.19 mmol), HOBt (26 mg, 0.19 mmol) and DIPEA (41 mg, 0.19 mmol) at RT. The resulting mixture was stirred at 70° C. for 12 hours. No more product 2f was formed, which was monitored by LCMS. The reaction mixture was directly purified by prep-HPLC (method A) to give title compound 2f (2.6 mg, yield 6%) as a white solid. ESI m/z: 1085.3 $(M+H)^+$. $^1H$ NMR (400 MHz, $CDCl_3$) δ 7.55-7.52 (m, 1H), 7.34-7.30 (m, 1H), 6.67 (br s, 1H), 6.30-6.27 (m, 1H), 6.03 (br s, 1H), 5.16-5.11 (m, 2H), 5.09-4.87 (m, 2H), 4.80-4.61 (m, 1H), 4.60-4.30 (m, 2H), 3.47-3.44 (m, 1H), 3.21-3.10 (m, 1H), 3.03-2.96 (m, 2H), 2.79-2.55 (m, 4H), 2.35-1.73 (m, 28H), 1.71-1.32 (m, 15H), 1.29-1.07 (m, 4H), 0.99-0.85 (m, 9H) ppm.

Example 2g

1-{4-[(2S)-2-[(2S)-2-[1-(4-{2-Azatricyclo[10.4.0.$0^{4,9}$]hexadeca-1 (12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-{2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethyl} butanedioate (2g)

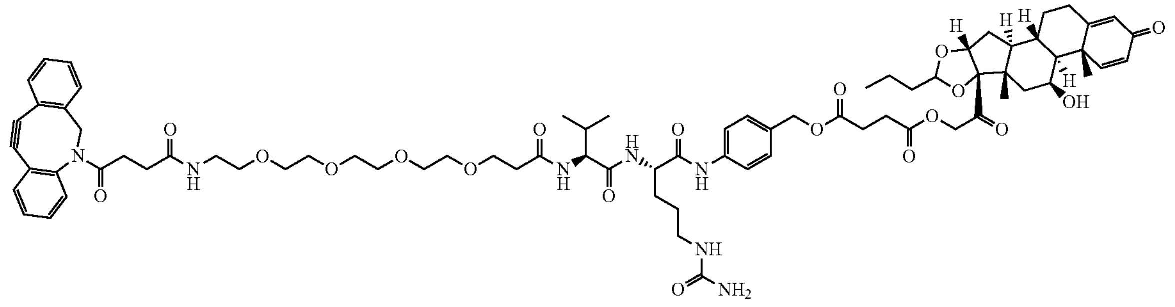 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1]

Following the procedures of example 2f except substituting DIBAC-suc-PEG4-vc-PAB (12c) for 12b, the title compound 2g (15 mg, yield 19%) as a white solid. ESI m/z: 714 $(M/2+H)^+$. $^1H$ NMR (500 MHz, $MeOD_{d4}$) δ 7.67-7.60 (m, 4H), 7.48-7.46 (m, 4H), 7.38-7.32 (m, 4H), 7.26 (d, J=6.8 Hz, 1H), 6.27 (d, J=10.0 Hz, 1H), 6.03 (s, 1H), 5.24-5.10 (m, 4H), 5.02-4.97 (m, 1H), 4.85-4.66 (m, 2H), 4.61 (s, 1H), 4.53 (dd, J=9.1, 4.9 Hz, 1H), 4.45-4.43 (m, 1H), 4.22 (dd, J=6.7, 4.7 Hz, 1H), 3.78-3.69 (m, 3H), 3.60-3.55 (m, 11H), 3.47-3.40 (m, 2H), 3.26-3.10 (m, 4H), 2.78-2.54 (m, 8H), 2.41-2.35 (m, 2H), 2.25-2.11 (m, 4H), 2.02-1.31 (m, 17H), 1.21-0.92 (m, 14H) ppm. Anal. HPLC: 99.5%, Retention time: 7.86 min (method B).

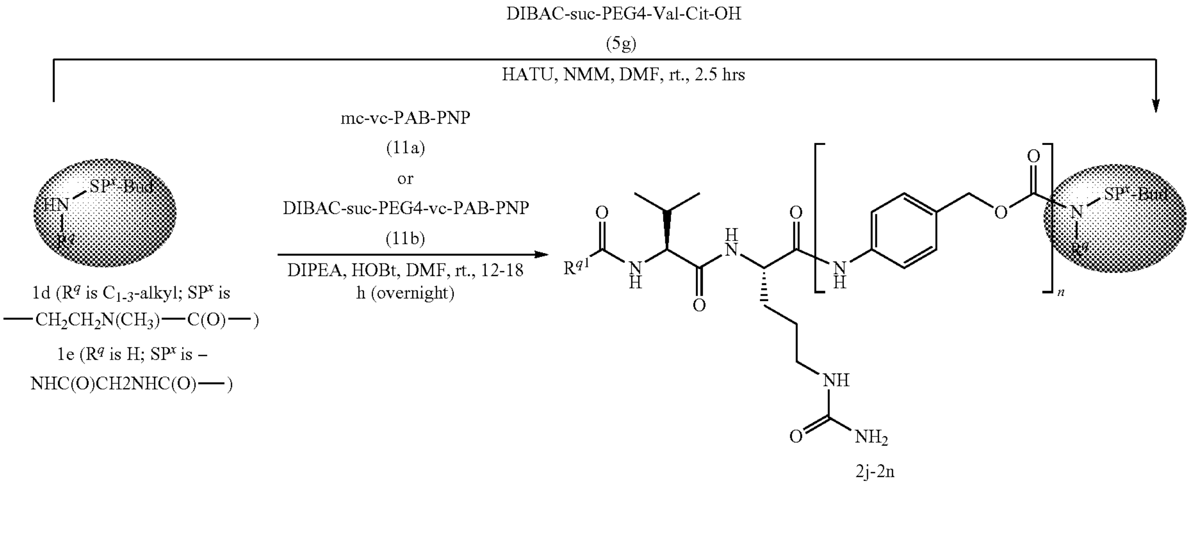

1d ($R^q$ is $C_{1-3}$-alkyl; $SP^x$ is —$CH_2CH_2N(CH_3)$—C(O)—)

1e ($R^q$ is H; $SP^x$ is –NHC(O)CH2NHC(O)—)

2j-2n

-continued

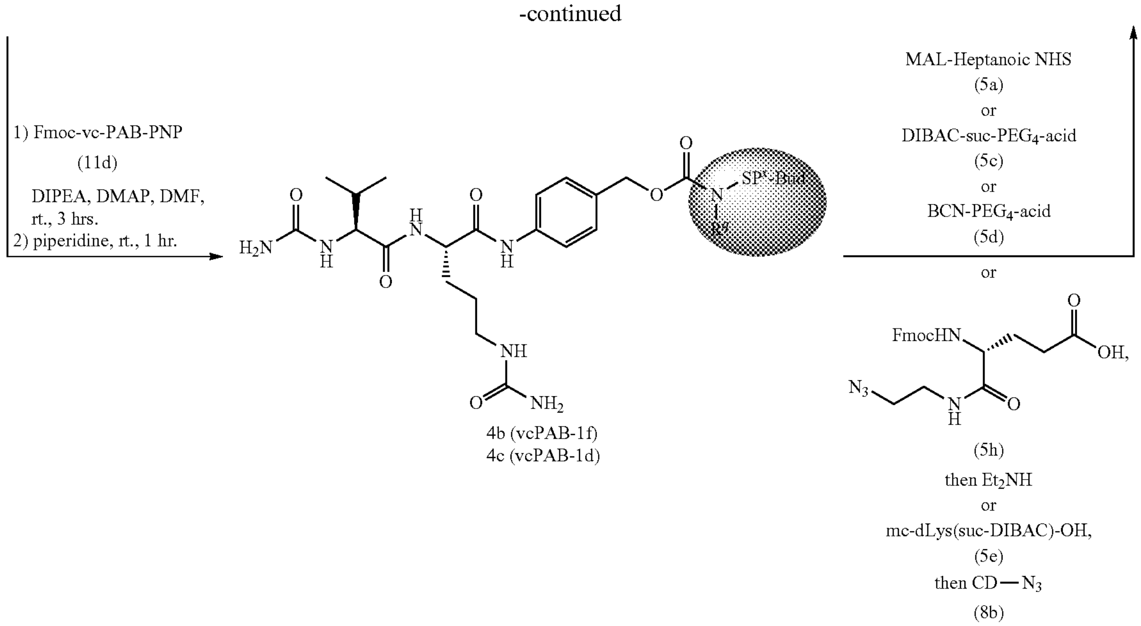

4b (vcPAB-1f)
4c (vcPAB-1d)

In Scheme 5, Bud refers to budesonide.

Most Budesonide-Linkers (2) having VC-PAB moiety were synthesized from three approaches via amide or carbamate (Scheme 5). The compounds 1d, 1e were separately conjugated with linkers by amide coupling to give amide or carbamate (Scheme 5). In the table below are additional details.

| Compd No | $R^{q1}$ in 2j, 2k, 2l, 2m, 2n | n in 2j-n | $R^q$-NH-Spacer-Budesonide |
|---|---|---|---|
| 2j | 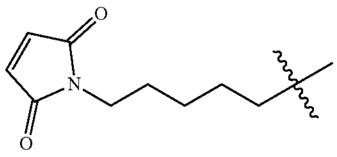 [SMILES: *CCCCCN1C(=O)C=CC1=O] | 1 | 1e |
| 2k | 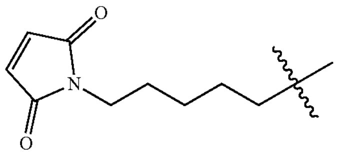 [SMILES: *CCCCCN1C(=O)C=CC1=O] | 1 | 1d |
| 2l | 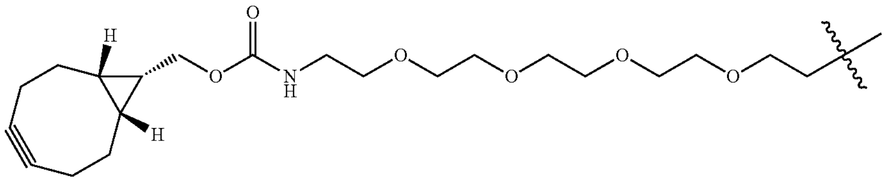 [SMILES: *CCOCCOCCOCCOCCNC(=O)OC[C@@H]1[C@@H]2CCC#CCC[C@@H]21] | 1 | 1d |

-continued

| Compd No | $R^{q1}$ in 2j, 2k, 2l, 2m, 2n | n in 2j-n | $R^q$-NH-Spacer-Budesonide |
|---|---|---|---|
| 2m | 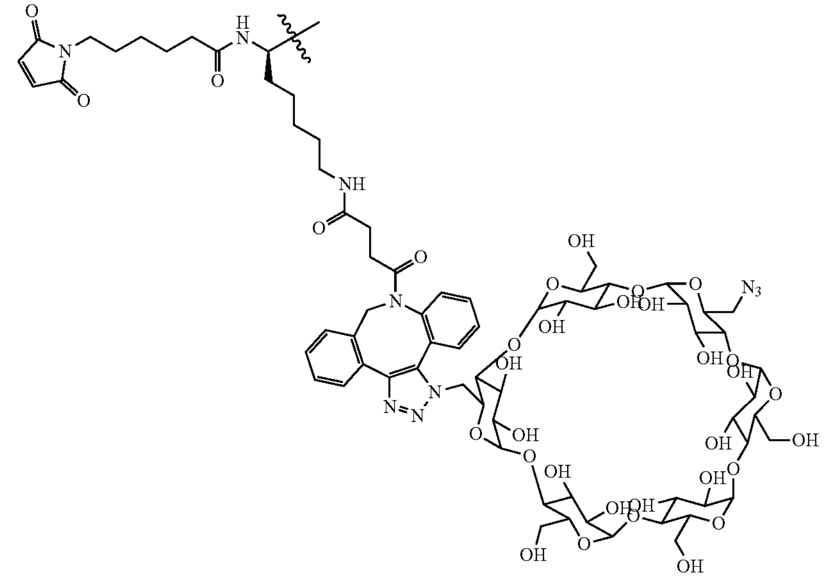 [SMILES: *[C@@H](CCCCCNC(=O)CCC(=O)N1Cc2ccccc2-c2nnn(CC3OC4OC5C(CO)OC(OC6C(CO)OC(OC7C(CO)OC(OC8C(CN=[N+]=[N-])OC(OC9C(CO)OC(OC3C(O)C4O)C(O)C9O)C(O)C8O)C(O)C7O)C(O)C6O)C(O)C5O)c2-c2ccccc21)NC(=O)CCCCCN1C(=O)C=CC1=O] | 1 | 1d |
| 2n | 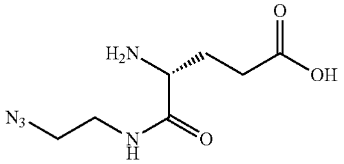 [SMILES: [N-]=[N+]=NCCNC(=O)[C@H](N)CCC(=O)O] | 1 | 1d |

Intermediate 4c

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl N-(2-{[({4-[(2S)-2-[(2S)-2-amino-3-methylbutanamido]-5-(carbamoylamino)pentanamido]phenyl}methoxy)carbonyl](methyl)amino}ethyl)-N-methylcarbamate (4c)

To a solution of compound 1d (40 mg, 73 μmol) in DMF (3 mL) were added Fmoc-vcPAB-PNP (11d, 60 mg, 78 μmol), DMAP (9.0 mg, 74 μmol) and DIPEA (20 mg, 0.16 mmol) at room temperature. The mixture was stirred at room temperature for 3 hours until most of starting materials were consumed, which was monitored by LCMS. To the reaction mixture was then added piperidine (1 mL). After stirred at room temperature for an hour until the de-Fmoc reaction was completed, which was monitored by LCMS, the reaction mixture was directly purified by prep-HPLC (method B) to give compound 4c (9.0 mg, yield 13%, the 2$^{nd}$ peak in LC) as a white solid. ESI m/z: 951 $(M+H)^+$, 973 $(M+Na)^+$.

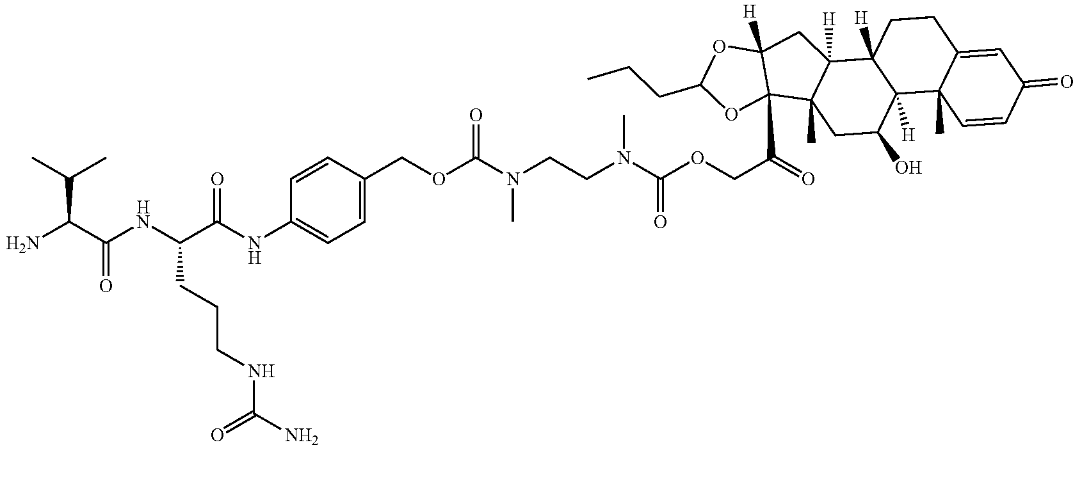 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](N)C(C)C)cc2)O1]

Example 2j

2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{48}$.0$^{13,18}$]icosa-14,17-dien-8-yl]-2-oxo-ethyl N-({N'-[({4-[(2S)-5-(carbamoylamino)-2-[(2S)-2-[6-(2,5-dioxo-2,5-dihydro-1H-pyrrol-1-yl) hexanamido]-3-methylbutanamido]pentanamido] phenyl}methoxy)carbonyl] hydrazinecarbonyl}methyl)carbamate (2j)

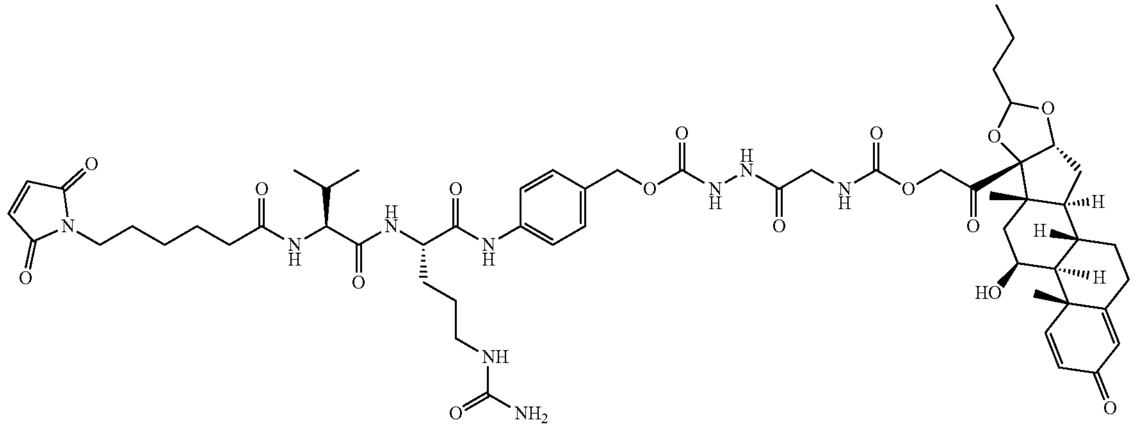

ESI m/z: 1144.3 $(M+H)^+$. $^1$H NMR (400 MHz, $CDCl_3$) δ 10.02 (s, 1H), 9.77 (s, 1H), 9.18 (s, 1H), 8.12 (d, J=7.2 Hz, 1H), 7.83 (d, J=8.4 Hz, 1H), 7.73-7.70 (m, 1H), 7.61-7.59 (m, 2H), 7.32-7.29 (m, 3H), 7.01 (s, 2H), 6.19-6.16 (m, 1H), 6.00-5.92 (m, 2H), 5.05-5.00 (m, 2H), 4.95-4.85 (m, 2H), 4.71-4.62 (m, 2H), 4.40-4.17 (m, 3H), 3.71-3.58 (m, 2H), 3.45-3.39 (m, 2H), 3.06-2.89 (m, 3H), 2.33-2.28 (m, 2H), 2.20-2.07 (m, 3H), 2.02-1.91 (m, 3H), 1.81-1.75 (m, 2H), 1.75-1.62 (m, 2H), 1.60-1.44 (m, 11H), 1.42-1.20 (m, 6H), 1.19-1.12 (m, 4H), 1.00-0.92 (m, 2H), 0.88-0.81 (m, 10H) ppm.

Example 2k

2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxo-ethyl N-(2-{[({4-[(2S)-5-(carbamoylamino)-2-[(2S)-2-[6-(2,5-dioxo-2,5-dihydro-1H-pyrrol-1-yl) hexanamido]-3-methylbutanamido]pentanamido] phenyl}methoxy)carbonyl](methyl)amino}ethyl)-N-methylcarbamate (2k-A and 2k-B)

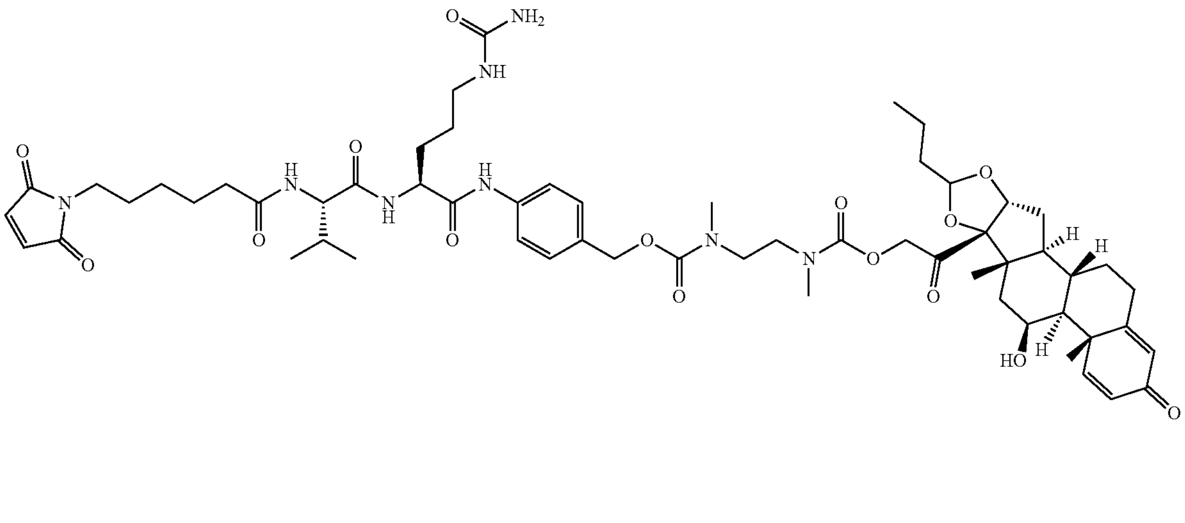 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCCCCN3C(=O)C=CC3=O)C(C)C)cc2)O1]

Following the general procedure D, the title compounds 2k-A (3.3 mg, yield 10%, the second peak in LC) and 2k-B (4.1 mg, yield 12%, the first peak in LC) as diastereoisomers were obtained as white solids.

2k-A: ESI m/z: 1143.4 $(M+H)^+$, Retention time: 1.70 min (method A).

2k-B: ESI m/z: 1143.4 $(M+H)^+$, Retention time: 1.65 min (method A).

Example 21

Bicyclo[6.1.0]non-4-yn-9-ylmethyl N-(14-{[(1S)-1-{[(1 S)-4-(carbamoylamino)-1-[(4-{[({2-[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}(methyl)carbamoyl)oxy]methyl}phenyl)carbamoyl]butyl]carbamoyl}-2-methylpropyl]carbamoyl}-3,6,9,12-tetraoxatetradecan-1-yl)carbamate (2l)

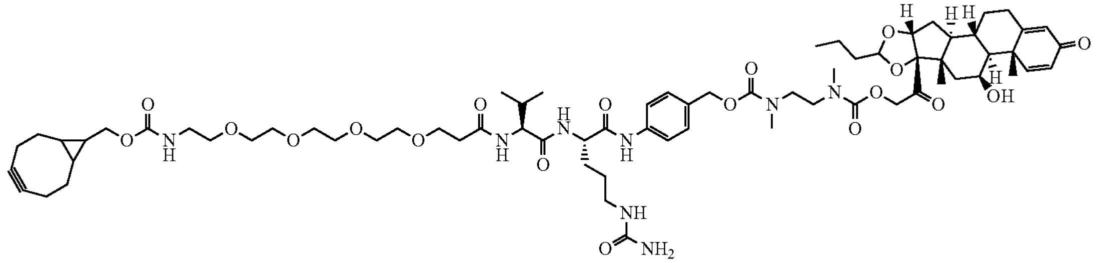 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)OCC3C4CCC#CCCC43)C(C)C)cc2)O1]

ESI m/z: 687.5 $(M/2+H)^+$, 1396.8 $(M+Na)^+$ (50%), $^1H$ NMR (500 MHz, MeOD$_{d4}$) δ 7.66 (d, J=7.5 Hz, 2H), 7.50 (d, J=10.0 Hz, 1H), 7.36 (d, J=7.0 Hz, 2H), 6.28 (d, J=10.0 Hz, 1H), 6.04 (s, 1H), 5.15-5.05 (m, 2H), 4.87-4.62 (m, 4H), 4.53 (s, 1H), 4.46 (s, 1H), 4.21 (d, J=6.5 Hz, 1H), 4.16 (d, J=8.0 Hz, 2H), 3.83-3.72 (m, 2H), 3.66-3.60 (m, 12H), 3.56-3.52 (m, 3H), 3.49-3.42 (m, 1H), 3.30 (s, 3H), 3.25-3.09 (m, 3H), 3.02-2.96 (m, 4H), 2.87 (dd, J=16.6, 4.8 Hz, 2H), 2.72-2.64 (m, 1H), 2.58 (t, J=6.0 Hz, 2H), 2.40 (d, J=13.1 Hz, 1H), 2.31-2.10 (m, 9H), 2.01-1.91 (m, 3H), 1.81-1.70 (m, 2H), 1.63 (s, 7H), 1.51 (s, 3H), 1.48-1.30 (m, 4H), 1.11 (s, 1H), 1.02-0.91 (m, 15H) ppm. Anal. HPLC: >99.9%, Retention time: 9.40 min (method A).

Example 2m

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[(2R)-6-(4-{2-azatricyclo[10.4.0.0$^{4,9}$]hexadeca-1(12),4(9),5,7,13,15-hexaen-10-yn-2-yl}-4-oxobutanamido)-2-[6-(2,5-dioxo-2,5-dihydro-1H-pyrrol-1-yl)hexanamido]hexanamido]-3-methylbutanamido]-5-(carbamoylamino)pentanamido]phenyl}methoxy)carbonyl](methyl) amino}ethyl)-N-methylcarbamate (2m-precursor)

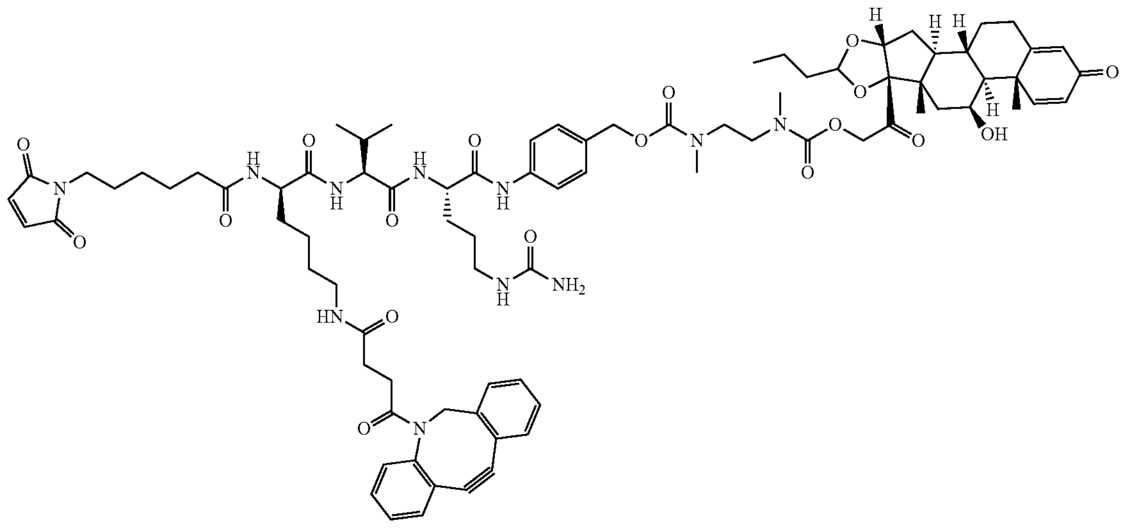 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)[C@@H](CCCCNC(=O)CCC(=O)N3Cc4ccccc4C#Cc4ccccc43)NC(=O)CCCCCN3C(=O)C=CC3=O)C(C)C)cc2)O1]

Following the general procedure B, the crude compound 2m-precursor (the precursor of 2m) (5 mg) was obtained as light yellow oil, which was used directly for the next step. ESI m/z: 780 $(M/2+H)^+$ 2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl N-(2-{[({4-[(2S)-5-(carbamoylamino)-2-[(2S)-2-[(2R)-2-[6-(2,5-dioxo-2,5-dihydro-1H-pyrrol-1-yl)hexanamido]-6-[4-(3-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-3,4,5,13-tetraazatetracyclo[13.4.0.0$^{2,6}$.0$^{7,12}$]nonadeca-1(15),2(6),4,7(12),8,10,16,18-octaen-13-yl)-4-oxobutanamido]hexanamido]-3-methylbutanamido]pentanamido]phenyl}methoxy) carbonyl](methyl)amino}ethyl)-N-methylcarbamate (2m)

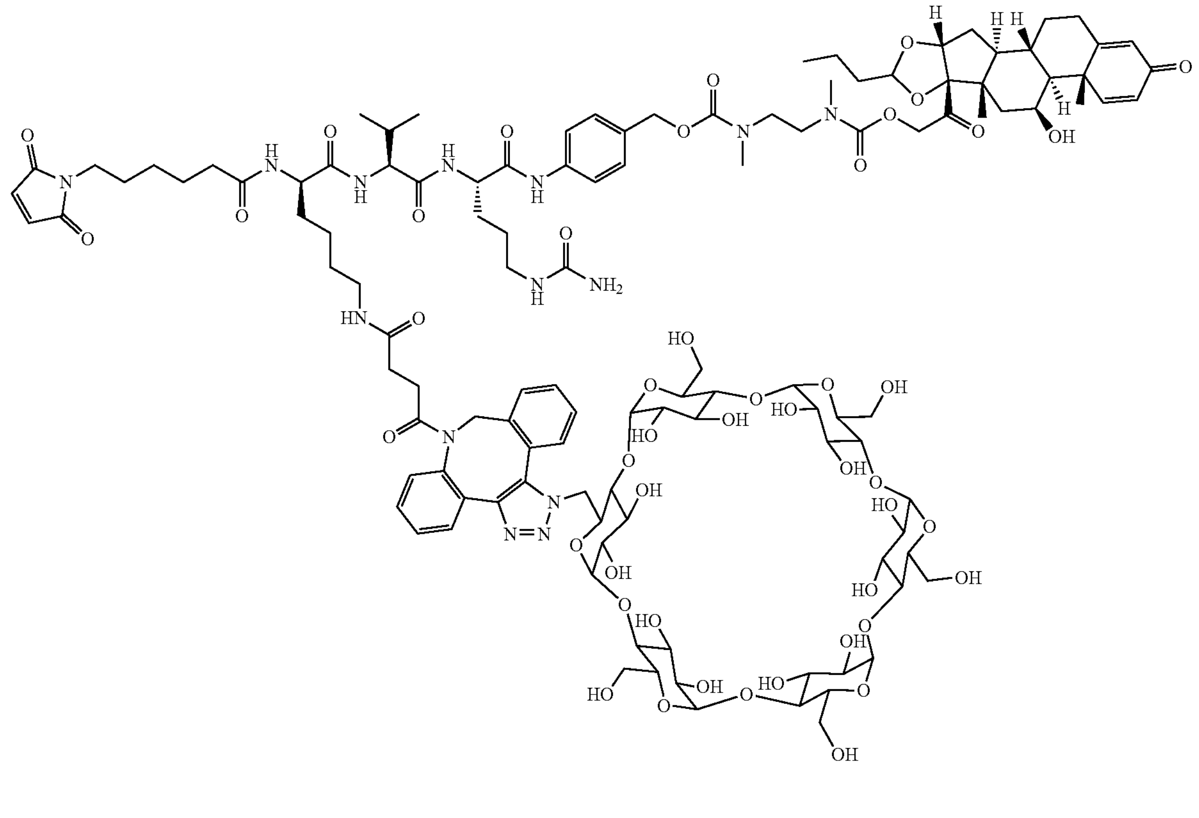 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)[C@@H](CCCCNC(=O)CCC(=O)N3Cc4ccccc4-c4c(nnn4CC4OC5OC6C(CO)OC(OC7C(CO)OC(OC8C(CO)OC(OC9C(CO)OC(OC%10C(CO)OC(OC4C(O)C5O)C(O)C%10O)C(O)C9O)C(O)C8O)C(O)C7O)C(O)C6O)-c4ccccc43)NC(=O)CCCCCN3C(=O)C=CC3=O)C(C)C)cc2)O1]

To a solution of crude 2m (5 mg) in DMF (1 mL) was added CD-$N_3$ (8b, 63 mg, 63 μmol). The resulting mixture was stirred at RT for 72 hours, which was monitored by LCMS. The resulting mixture was directly purified by prep-HPLC (method A) to give compound 2m (2 mg, 4% yield from 4c) as a white solid. ESI m/z: 1278.8 $(M/2+H)^+$. Anal. HPLC: 97.9%, Retention time: 6.49 min (method A).

Example 2n

2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl N-(2-{[({4-[(2S)-2-[(2S)-2-[(4R)-4-amino-4-[(2-azidoethyl)carbamoyl]butanamido]-3-methylbutanamido]-5-(carbamoylamino)pentanamido]phenyl}methoxy)carbonyl](methyl)amino}ethyl)-N-methylcarbamate (2n)

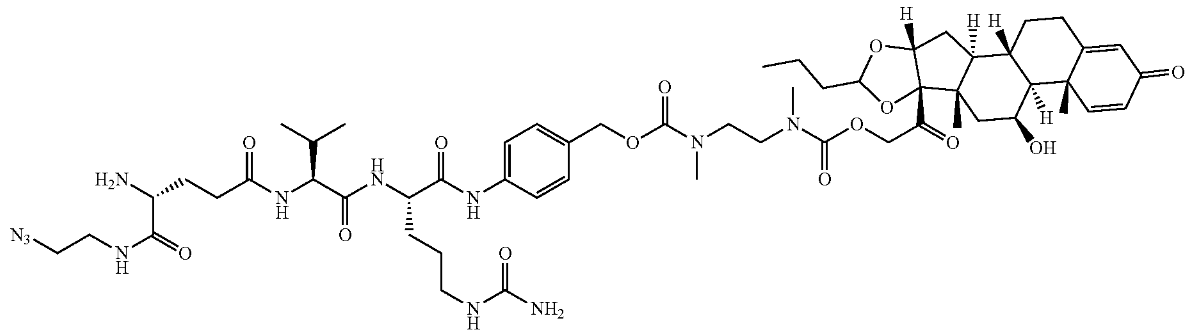 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CC[C@@H](N)C(=O)NCCN=[N+]=[N-])C(C)C)cc2)O1]

The reaction mixture was then stirred at RT overnight. Compound 4c was totally consumed according to LCMS. The mixture was separated by prep-HPLC (method A) and after lyophilization, Fmoc-2n was obtained (20 mg), which was dissolved in DMF (2 mL). To the DMF solution was added diethylamine (4 drops, c.a. 0.08 mL). The reaction mixture was stirred at RT for 2 hours until de-Fmoc reaction was completed, which was monitored by LCMS. The mixture was filtered through filter membrane and the solution was purified by prep-HPLC (method A) to give the title compound 2n (10 mg, yield 8.4%) as a white solid. ESI m/z: 1147 $(M+H)^+$. Anal. HPLC: 99.6%, Retention time: 5.67 min (method A); 7.72 min (method B).

Scheme 6. Synthesis of Linker-Budesonide 2q (THP analog)

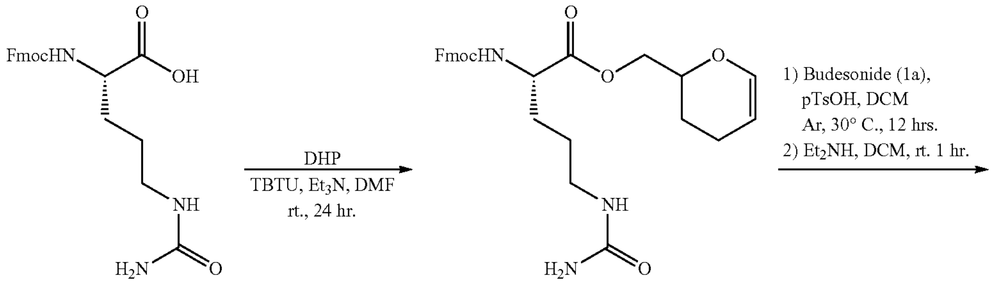

14 15

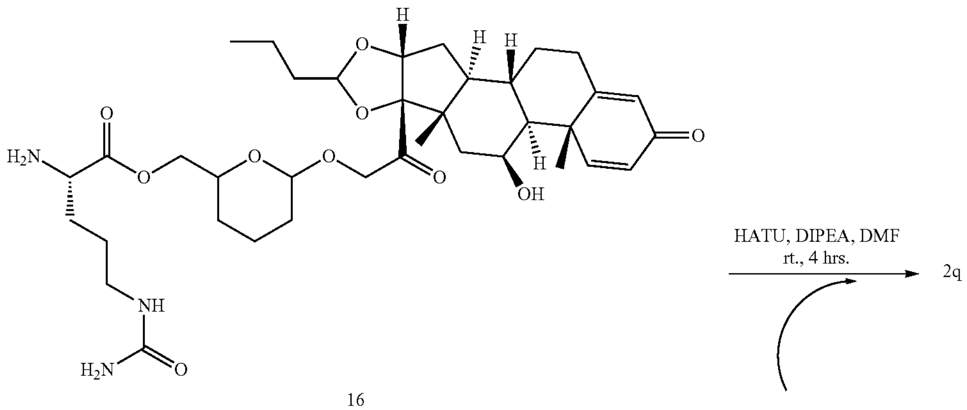

16

-continued

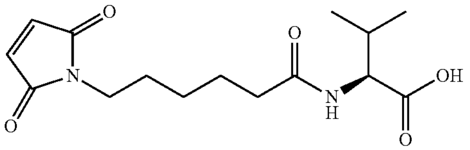

5i

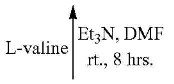

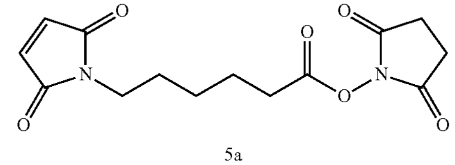

5a

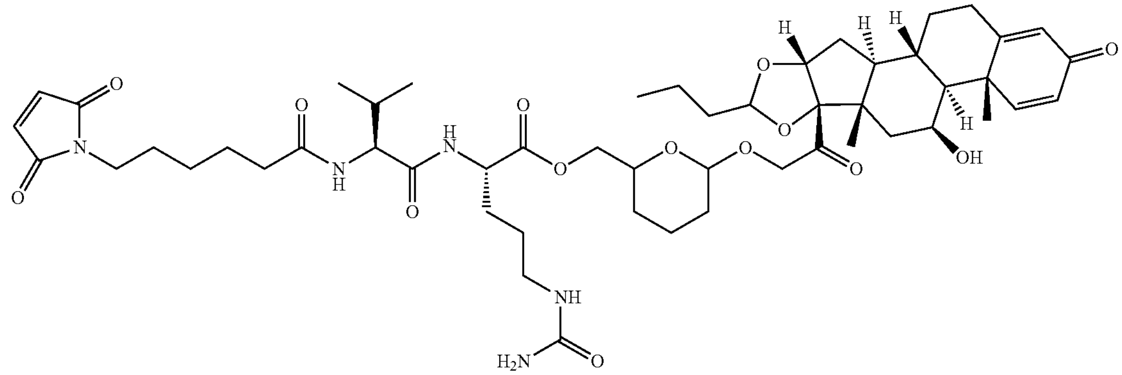

2q

Example 2q (2S)-(3,4-Dihydro-2H-pyran-2-yl)methyl 2-(((9H-fluoren-9-yl)methoxy)carbonylamino)-5-ureidopentanoate (15)

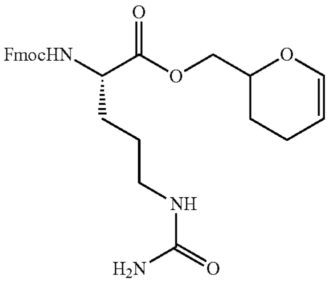

To a mixture of Fmoc-Cit-OH (14, 0.29 g, 0.73 mmol) in DMF (5 mL) were added DHP (0.10 mg, 0.88 mmol), TBTU (0.70 g, 2.2 mmol) and triethylamine (0.37 g, 3.7 mmol) at RT. The resulting mixture was stirred at RT for 24 hours. 15% of desired mass was detected by LCMS. The reaction was quenched with water (30 mL) and extracted with ethyl acetate (10 mL×3). The combined organic solution was washed with water and brine, dried over sodium sulfate and concentrated in vacuo. The crude product was purified by reversed phase flash chromatography (0-100% acetonitrile in water) to give title compound 15 (110 mg, yield 30%) as colorless oil. ESI m/z: 494 $(M+H)^+$.

(6-{2-[(1S,2S,4R,8S,9S,11S,12S,13R)-11-Hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethoxy}oxan-2-yl)methyl (2S)-2-amino-5-(carbamoylamino)pentanoate (16)

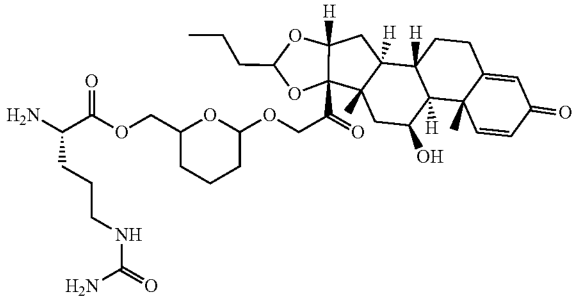 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC2CCCC(COC(=O)[C@@H](N)CCCNC(N)=O)O2)O1]

To a solution of compound 15 (80 mg, 0.16 mmol) in anhydrous DCM (3 mL) was added a solution of budesonide (1a, 70 mg, 0.16 mmol) and p-toluenesulfonic acid (42 mg, 0.24 mmol) in anhydrous DCM (2 mL) by syringe under protection of argon balloon at RT. The reaction mixture was stirred at 30° C. under argon balloon for 12 hours. Most of compound 15 was consumed according to LCMS. The reaction mixture was cooled to RT, and to the reaction mixture was added diethylamine (1 mL). The reaction mixture was stirred at RT for 1 hours until de-Fmoc reaction was completed, which was monitored by LCMS. The volatiles were removed in vacuo and the residue was purified by prep-HPLC (method B) to give the title compound 16 (17 mg, yield 31%) as a white solid. ESI m/z: 702 $(M+H)^+$.

(S)-2-(6-(2,5-Dioxo-2,5-dihydro-1H-pyrrol-1-yl)hexanamido)-3-methylbutanoic acid (5i)

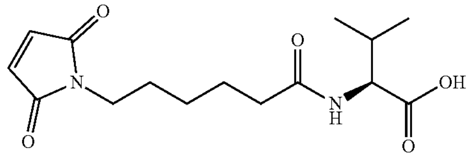 [SMILES: CC(C)[C@H](NC(=O)CCCCCN1C(=O)C=CC1=O)C(=O)O]

To a solution of L-valine (0.12 g, 1.0 mmol) in anhydrous DMF (2 mL) were added compound 5a (0.31 g, 1.0 mmol) and triethylamine (0.51 g, 5.0 mmol) at RT. The reaction mixture was stirred at RT for 8 hours until compound 5a was totally consumed, which was monitored by LCMS. The reaction mixture was filtered through filtering membrane and the filtrate was directly purified by prep-HPLC (method A) to give the title compound 5i (0.14 g, yield 46%) as colorless oil. ESI m/z: 311 $(M+H)^+$.

6-{2-[(1S,2S,4R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}oxan-2-yl)methyl (2S)-5-(carbamoylamino)-2-[(2S)-2-[6-(2,5-dioxo-2,5-dihydro-1H-pyrrol-1-yl)hexanamido]-3-methylbutanamido]pentanoate (2q)

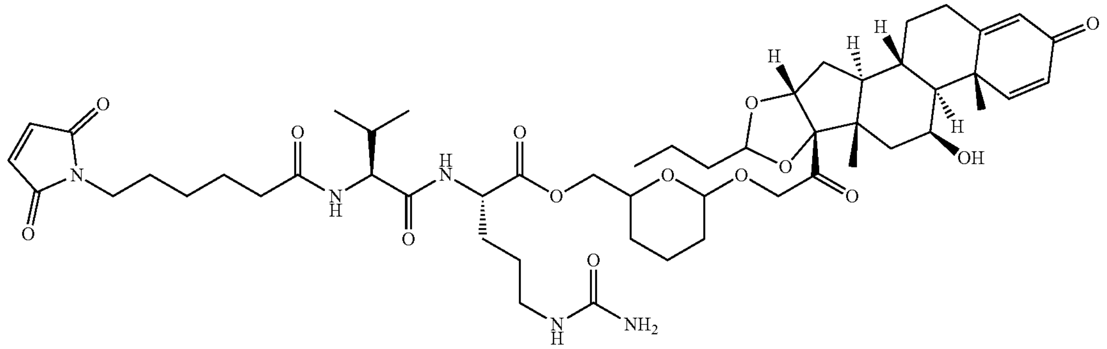 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC2CCCC(COC(=O)[C@H](CCCNC(N)=O)NC(=O)[C@@H](NC(=O)CCCCCN3C(=O)C=CC3=O)C(C)C)O2)O1]

To a solution of compound 5i (5.8 mg, 19 μmol) in DMF (1 mL) were added HATU (10 mg, 26 μmol) and DIPEA (6.6 mg, 51 μmol) at RT. The mixture was stirred at RT for 15 minutes, and to the solution was then added compound 16 (12 mg, 17 μmol) at RT. The resulting mixture was stirred at RT for 4 hours until compound 5i was totally consumed, which was monitored by LCMS. The reaction mixture was then filtered though filtering membrane and the filtrate was directly purified by prep-HPLC (method A) twice to give the title compound 2q (2 mg, yield 12%) as a white solid. ESI m/z: 995.3 $(M+H)^+$. Anal. HPLC: 83.5%, Retention time: 10.36 min (method B).

Scheme 7. Synthesis of linker-phosphate-budesonide 2r and 2s

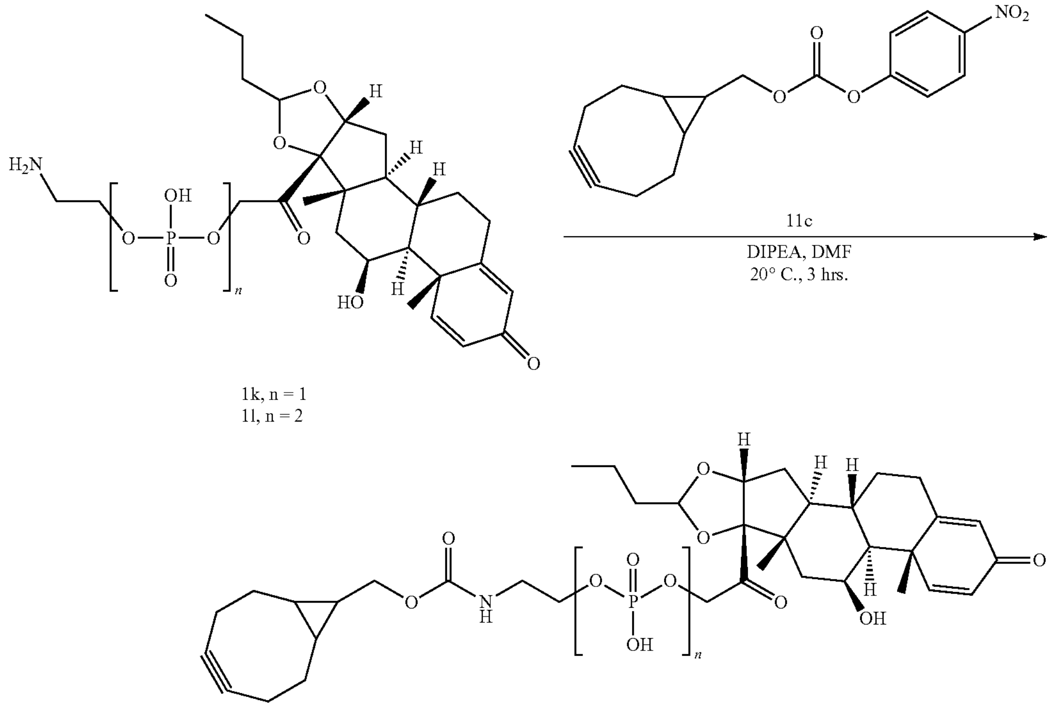

1k, n = 1
1l, n = 2

2r, n = 1
2s, n = 2

Phosphate-budesonides were coupled with BCN-PNP (11c) to give BCN-phosphate-Budesonides (compound 2r and 2s) (scheme 7).

Example 2r

{2-[({Bicyclo[6.1.0]non-4-yn-9-ylmethoxy}carbonyl)amino]ethoxy}({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}) phosphinic acid (2r)

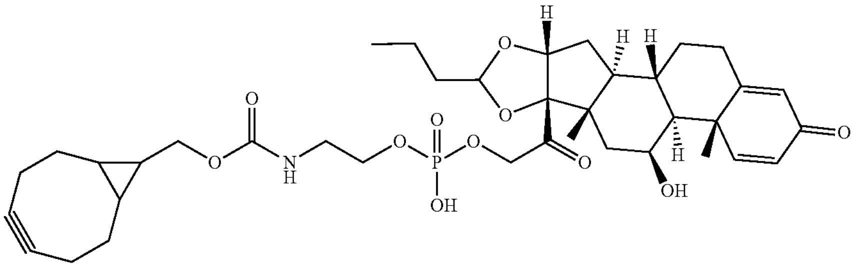 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OCCNC(=O)OCC2C3CCC#CCCC32)O1]

Following the general procedure D, compound 2r (40 mg, 61% yield) was obtained as a white solid. ESI m/z: 730 $(M+H)^+$. $^1H$ NMR (500 MHz, $MeOD_{d4}$) δ 7.49 (d, J=10.1 Hz, 1H), 6.29-6.26 (m, 1H), 6.03 (s, 1H), 5.23-5.16 (m, 1H), 4.88-4.64 (m, 3H), 4.45 (dd, J=8.0, 3.1 Hz, 1H), 4.23-4.13 (m, 2H), 3.97 (dd, J=11.9, 5.7 Hz, 2H), 3.36 (t, J=4.7 Hz, 2H), 2.67 (td, J=13.4, 5.3 Hz, 1H), 2.40 (d, J=9.6 Hz, 1H), 2.30-1.34 (m, 23H), 1.21-0.92 (m, 10H) ppm. Anal. HPLC: >99.9%, Retention time: 5.26 min (method B).

Example 2s

{2-[({Bicyclo[6.1.0]non-4-yn-9-ylmethoxy}carbonyl)amino]ethoxy}({[hydroxy({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy})phosphoryl]oxy})phosphinic acid (2s)

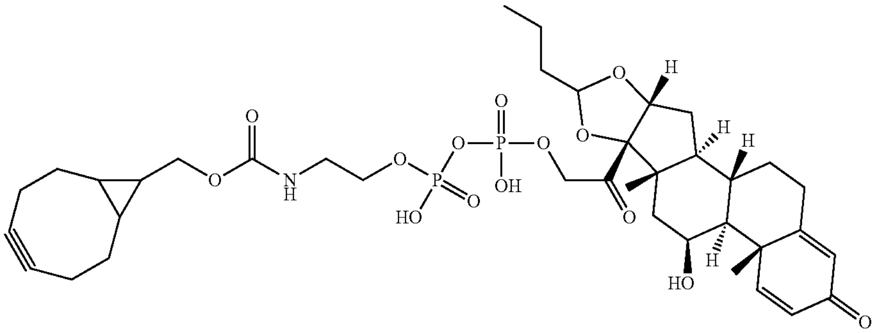 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COP(=O)(O)OP(=O)(O)OCCNC(=O)OCC2C3CCC#CCCC32)O1]

ESI m/z: 810 $(M+H)^+$. $^1H$ NMR (500 MHz, $MeOD_{d4}$) δ 7.51 (d, J=10.1 Hz, 1H), 6.28 (d, J=10.0 Hz, 1H), 6.03 (s, 1H), 5.22-5.16 (m, 1H), 4.98-4.66 (m, 3H), 4.46 (s, 1H), 4.12 (dt, J=45.0, 13.0 Hz, 4H), 3.39 (t, J=11.9 Hz, 2H), 2.67 (dd, J=13.3, 8.0 Hz, 1H), 2.40 (d, J=11.2 Hz, 1H), 2.30-1.32 (m, 23H), 1.22-0.92 (m, 10H) ppm. Anal. HPLC: >99.9%, Retention time: 4.03 min (method B).

Experimental Procedures for Intermediates

TABLE 4

| Key intermediates and starting materials | | |
|---|---|---|
| Structures | Intermediate No. | References or synthesis |
| 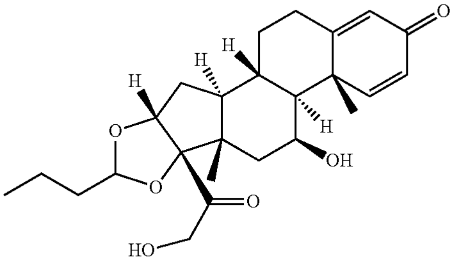 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CO)O1] | 1a (budesonide) | Commercially available (51333-22-3) |
| 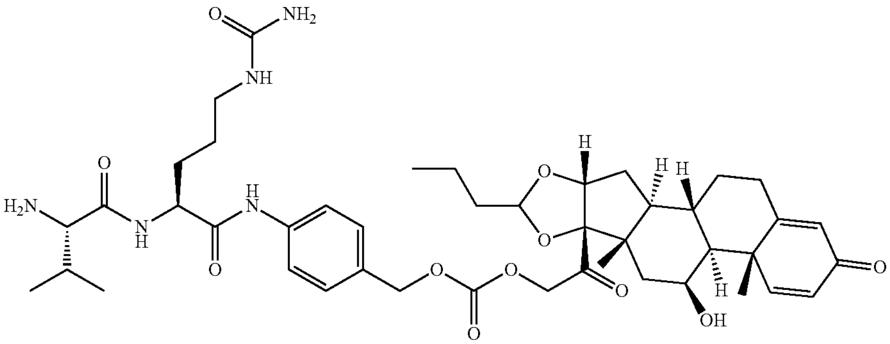 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](N)C(C)C)cc2)O1] | 4a (vcPAB-budesonide) | See scheme 2 |

TABLE 4-continued
Key intermediates and starting materials
| Structures | Intermediate No. | References or synthesis |
|---|---|---|
| 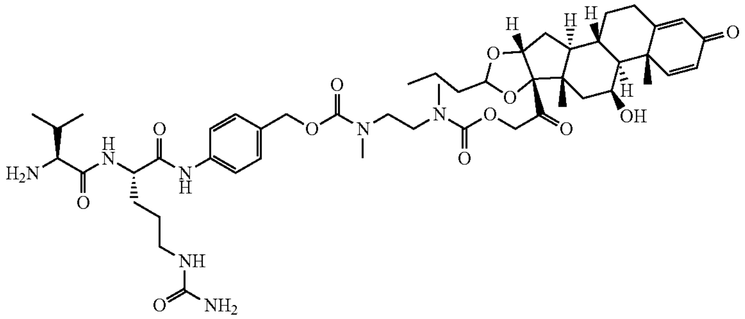 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](N)C(C)C)cc2)O1] | 4c (vcPAB-1d) | See scheme 5 |
| 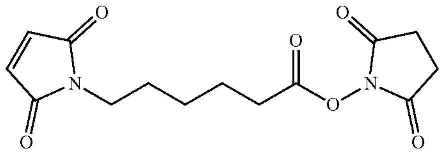 [SMILES: O=C(CCCCCN1C(=O)C=CC1=O)ON1C(=O)CCC1=O] | 5a (mc-NHS) | Commercially available (55750-63-5) |
| 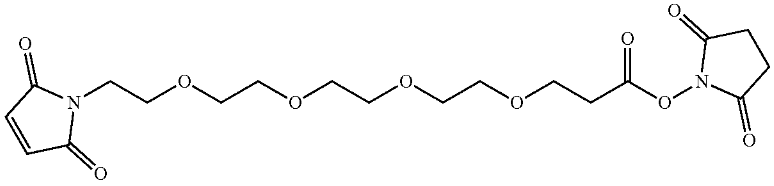 [SMILES: O=C(CCOCCOCCOCCOCCN1C(=O)C=CC1=O)ON1C(=O)CCC1=O] | 5b (MAL-PEG4-NHS) | Commercially available (1325208-25-0) |
| 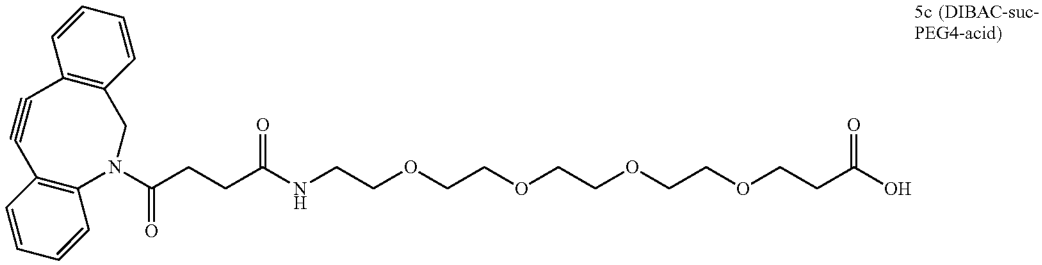 | 5c (DIBAC-suc-PEG4-acid) | Commercially available (1537170-85-6 |
| 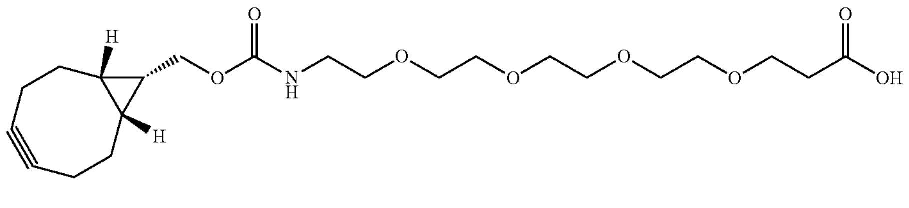 [SMILES: O=C(O)CCOCCOCCOCCOCCNC(=O)OC[C@@H]1[C@@H]2CCC#CCC[C@@H]21] | 5d (BCN-PEG4-acid) | Commercially available (1421932-54-8) |

TABLE 4-continued
| Key intermediates and starting materials | | |
|---|---|---|
| Structures | Intermediate No. | References or synthesis |
| 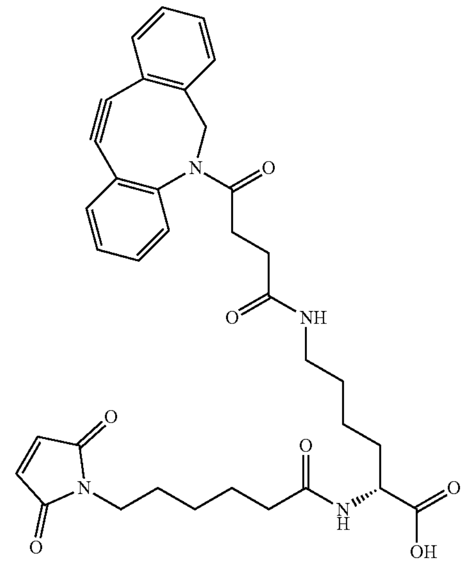 [SMILES: O=C(CCC(=O)N1Cc2ccccc2C#Cc2ccccc21)NCCCC[C@@H](NC(=O)CCCCCN1C(=O)C=CC1=O)C(=O)O] | 5e | Scheme 8 |
| 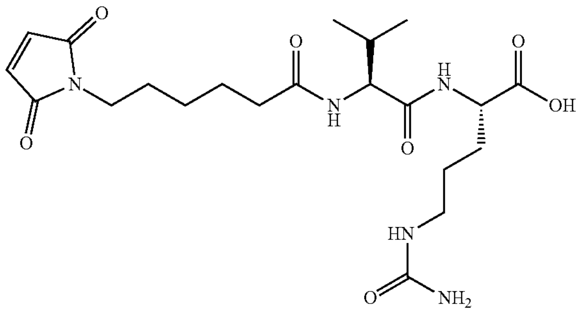 [SMILES: CC(C)[C@H](NC(=O)CCCCCN1C(=O)C=CC1=O)C(=O)N[C@@H](CCCNC(N)=O)C(=O)O] | 5f (mc-Val-Cit-OH) | WO2014/191578 A1 |
| 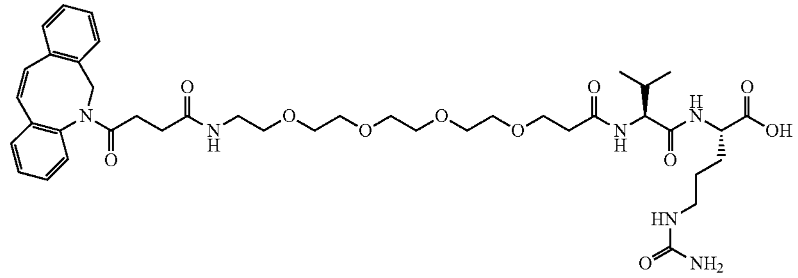 [SMILES: CC(C)[C@H](NC(=O)CCOCCOCCOCCOCCNC(=O)CCC(=O)N1Cc2ccccc2/C=C\c2ccccc21)C(=O)N[C@@H](CCCNC(N)=O)C(=O)O] | 5g (DIBAC-suc-PEG4-Val-Cit-OH) | Scheme 9 |
| 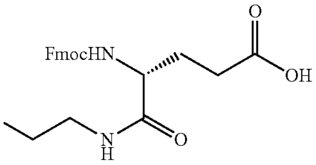 | 5h | Scheme 10 |
| 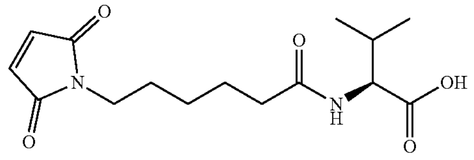 [SMILES: CC(C)[C@H](NC(=O)CCCCCN1C(=O)C=CC1=O)C(=O)O] | 5i | See scheme 6 |

TABLE 4-continued
| Key intermediates and starting materials | | |
|---|---|---|
| Structures | Intermediate No. | References or synthesis |
| 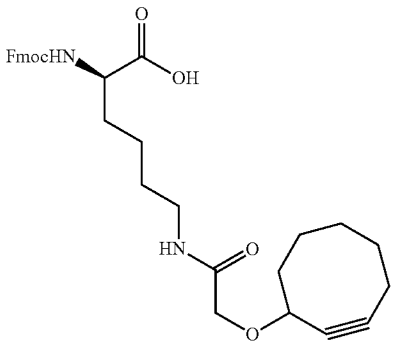 | 6a | Scheme 11 |
| 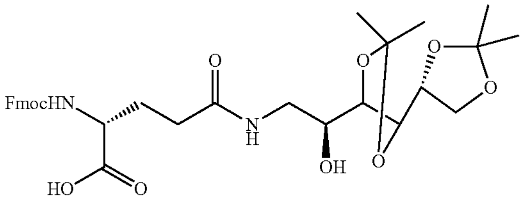 | 6b | *J. Org. Chem.* 2010, 75, 3685-3691 |
| 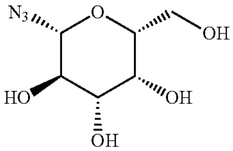 [SMILES: [N-]=[N+]=N[C@@H]1O[C@H](CO)[C@H](O)[C@H](O)[C@H]1O] | 8a | Commercially available (35899-89-9) |
| 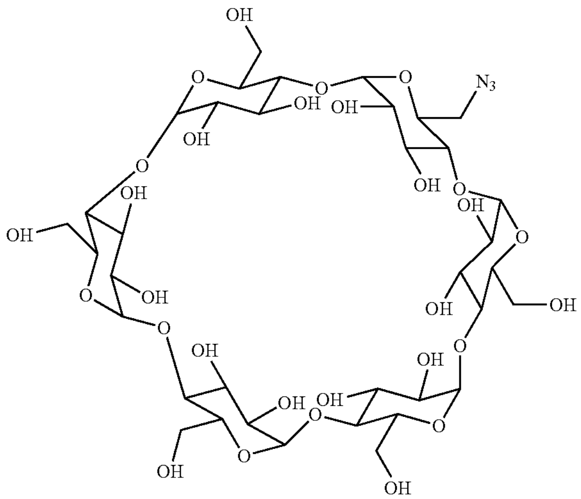 [SMILES: [N-]=[N+]=NCC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O] | 8b | *Synth. Commun.*, 2002, 32(21), 3367-3372 *J. Am. Chem. Soc.*, 2012, 134(46), 19108-19117 *J. Med. Chem.*, 1997, 40(17), 2755-2761 *J. Am. Chem. Soc.*, 1993, 115(12), 5035-5040 |
| 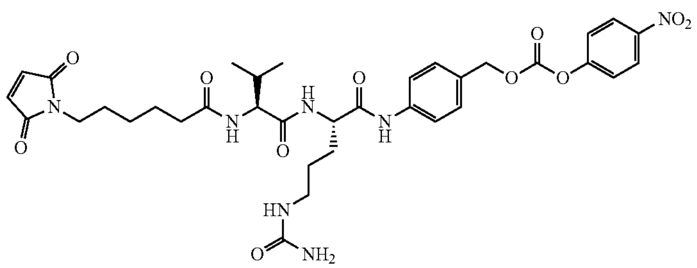 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1] | 11a (MC-VC-PAB-PNP) | Commercially available (159857-81-5) WO2014/191578 A1 |

TABLE 4-continued
| Key intermediates and starting materials | | |
|---|---|---|
| Structures | Intermediate No. | References or synthesis |
| 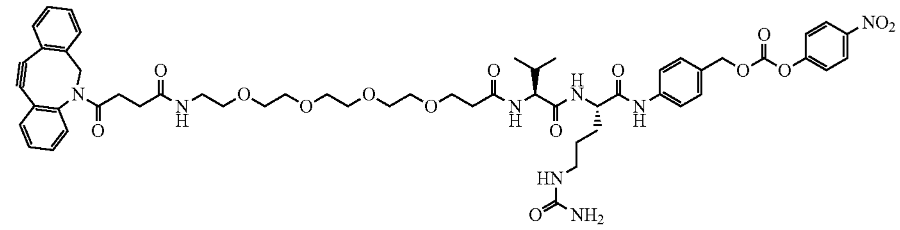 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Oc2ccc([N+](=O)[O-])cc2)cc1] | 11b (DIBAC-suc-PEG4-vc-PAB-PNP) | Scheme 12 |
| 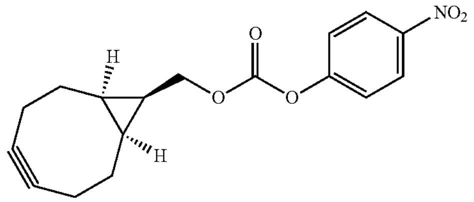 [SMILES: O=C(OC[C@@H]1[C@@H]2CCC#CCC[C@@H]21)Oc1ccc([N+](=O)[O-])cc1] | 11c (BCN-PNP) | WO2013/181697A1 *Angew. Chem. Int. Ed.*, 2010, 49 (49), 9422-9425 |
| 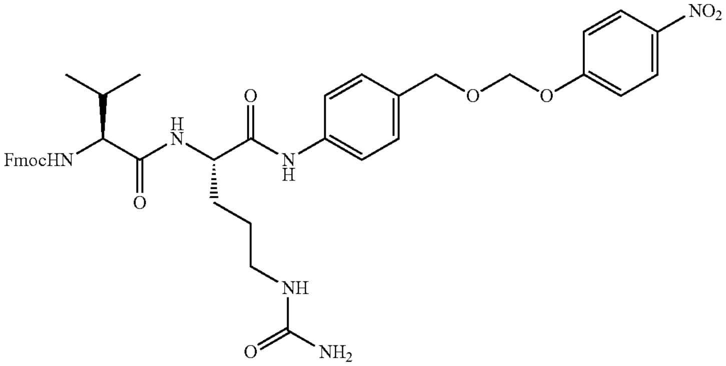 | 11d (Fmoc-vc-PAB-PNP) | Commercially available 863971-53-3 |
| 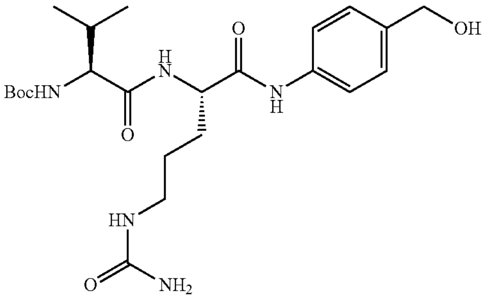 [SMILES: CC(C)[C@H](NC(=O)OC(C)(C)C)C(=O)N[C@@H](CCCNC(N)=O)C(=O)Nc1ccc(CO)cc1] | 12a (Boc-vc-PAB) | Commercially available (870487-09-5) WO2008/34124 A2 |
| 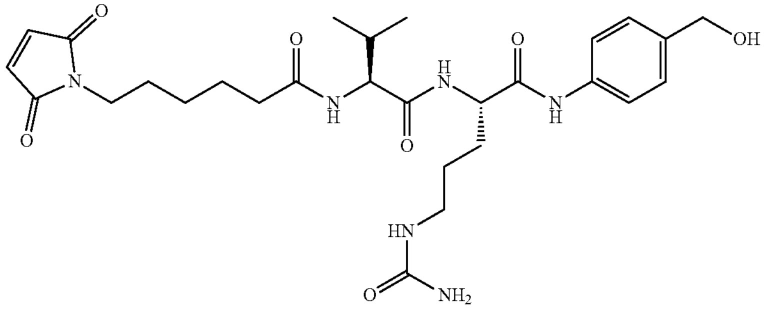 [SMILES: CC(C)[C@H](NC(=O)CCCCCN1C(=O)C=CC1=O)C(=O)N[C@@H](CCCNC(N)=O)C(=O)Nc1ccc(CO)cc1] | 12b (MC-VC-PAB) | Commercially available 159857-80-4 |

TABLE 4-continued
| Key intermediates and starting materials | | |
|---|---|---|
| Structures | Intermediate No. | References or synthesis |
| 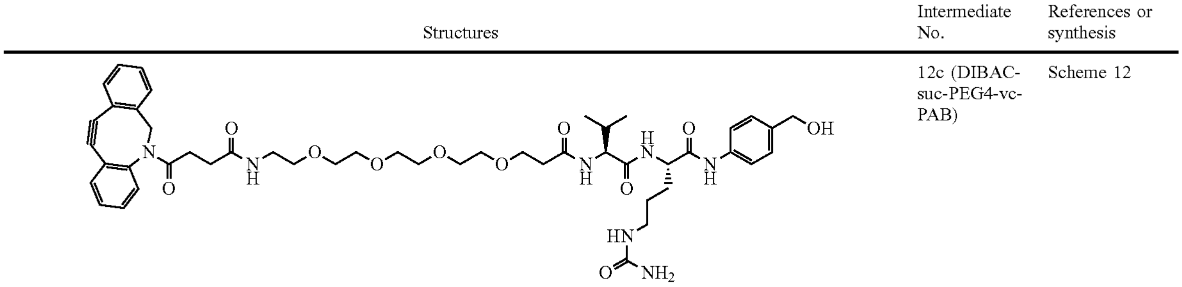 | 12c (DIBAC-suc-PEG4-vc-PAB) | Scheme 12 |
Scheme 8. Synthesis of 5e
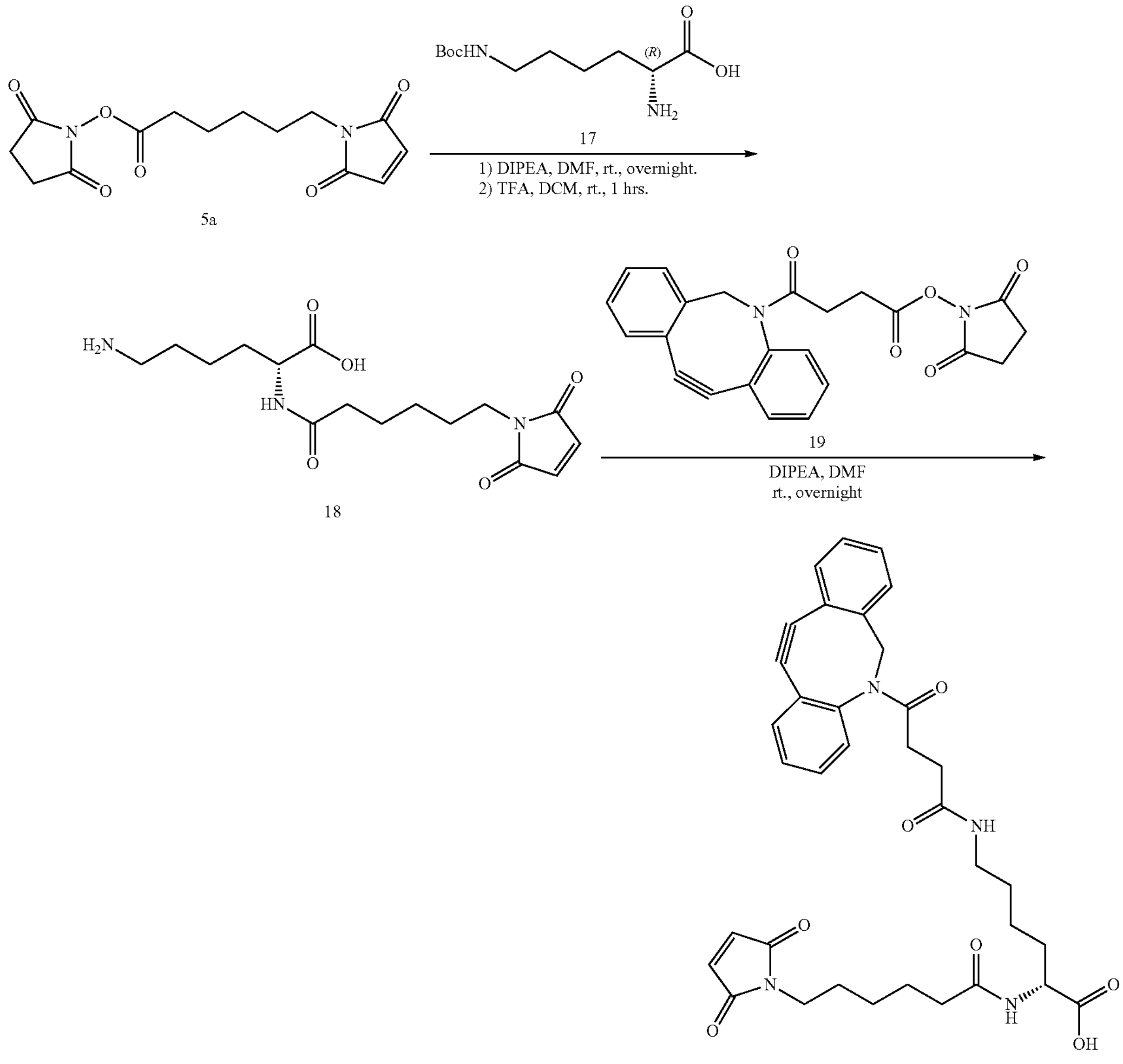
5e (2R)-6-(4-{2-Azatricyclo[10.4.0.04,]hexadeca-1(12), 4,6,8,13,15-hexaen-10-yn-2-yl}-4-oxobutanamido)-2-[6-(2,5-dioxo-2,5-dihydro-1H-pyrrol-1-yl)hexanamido]hexanoic acid (5e)

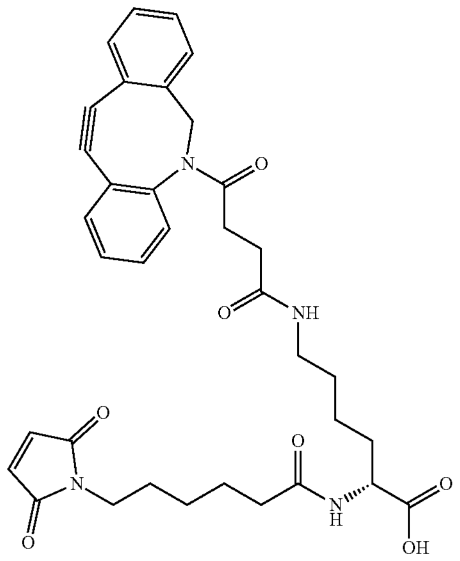 [SMILES: O=C(CCC(=O)N1Cc2ccccc2C#Cc2ccccc21)NCCCC[C@@H](NC(=O)CCCCCN1C(=O)C=CC1=O)C(=O)O]

To a mixture of H-D-Lys(Boc)-OH (17, 0.25 g, 1.0 mmol) in DMF (10 mL) were added 6-Maleimidocarproic acid-NHS (5a, 0.31 g, 1.0 mmol) and diisopropylethylamine (DIPEA, 0.26 g, 2.0 mmol) at RT. After the reaction was stirred at RT overnight, compound 5a was totally consumed. The mixture was directly separated by reversed phase flash chromatography (0-100% acetonitrile in water (0.05% TFA)) to give intermediate Boc-18 (ESI m/z: 440 $(M+H)^+$) as colorless oil, which was dissolved in DCM (5 mL). To the solution was added TFA (0.5 mL) dropwise at 0° C., and the mixture was stirred at RT for an hour. The reaction was monitored by LCMS and intermediate Boc-18 was totally consumed. The volatiles were removed in vacuo to give crude 18 (ESI m/z: 340 $(M/2+H)^+$), which was used for the next step without further purification. To the mixture of crude compound 18 (0.21 g, 0.62 mmol) in DMF (5 mL) was added activated ester 19 (0.20 g, 0.50 mmol) and DIPEA (50 mg, 0.39 mmol) at RT. After the reaction mixture was stirred at RT overnight, compound 19 was totally consumed, which was monitored by LCMS. The reaction mixture was then directly separated by reversed phase flash chromatography (0-100% acetonitrile in water) to give title compound 5e (0.10 g, 20% yield in 3 steps from 5a) as a white solid. ESI m/z: 627 $(M+H)^+$. $^1$H NMR ($DMSO_{d6}$, 400 MHz): δ 7.89 (d, J=13.2 Hz, 1H), 7.69-7.62 (m, 3H), 7.48-7.47 (m, 3H), 7.36-7.28 (m, 3H), 6.99 (s, 2H), 5.03 (d, J=13.6 Hz, 1H), 4.09-4.04 (m, 1H), 3.60 (d, J=13.6 Hz, 1H), 3.38-3.34 (m, 1H), 2.90-2.87 (m, 2H), 2.61-2.55 (m, 1H), 2.25-2.17 (m, 1H), 2.08-1.51 (m, 5H), 1.46-1.15 (m, 12H) ppm.

Scheme 9. Synthesis of 5g

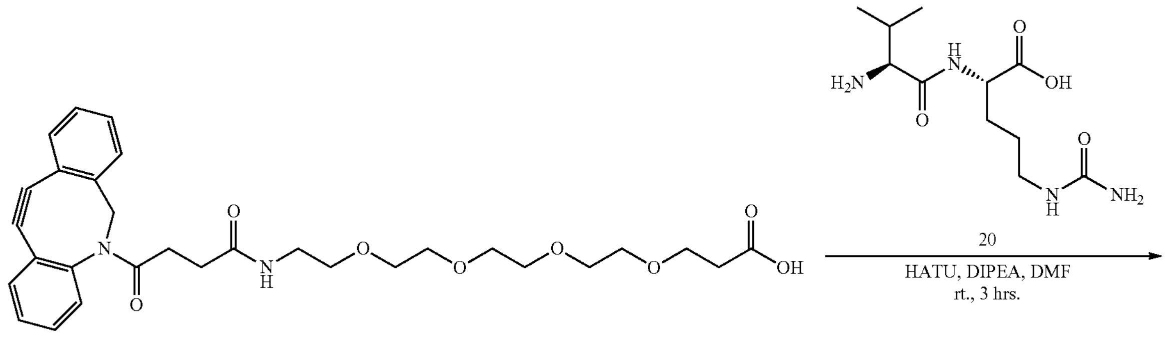

5c

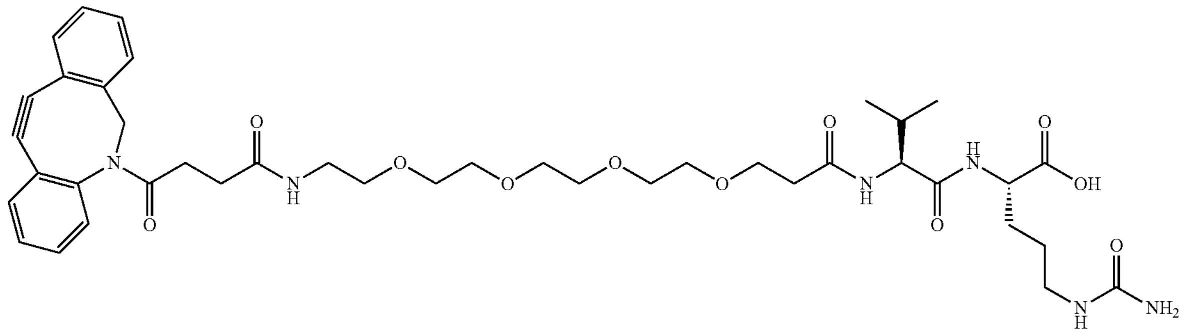

5g (2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanoic acid (5g)

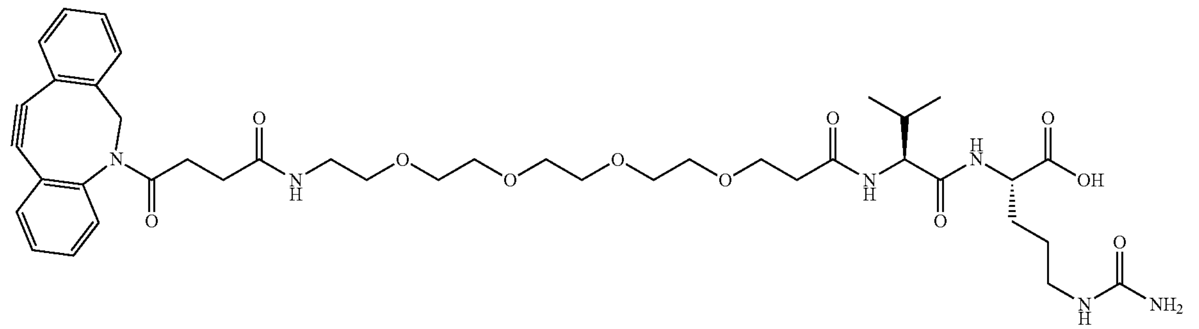 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)O]

To a solution of compound 5c (0.30 g, 0.54 mmol) in DMF (10 mL) were added HATU (0.31 g, 0.81 mmol) and DIPEA (0.14 g, 1.1 mmol) at RT. The mixture was stirred at RT for 15 minutes. To the reaction solution was added Val-Cit-OH (20 (CAS #159858-33-0), 0.21 g, 0.76 mmol) at RT, and the resulting mixture was stirred at RT for 3 hours until most materials were consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 5g (0.25 g, yield 57%) as a white solid. ESI m/z: 809.5 $(M+H)^+$.

Scheme 10. Synthesis of intermediates 5h

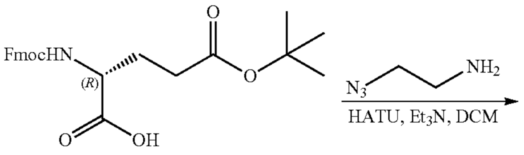

21

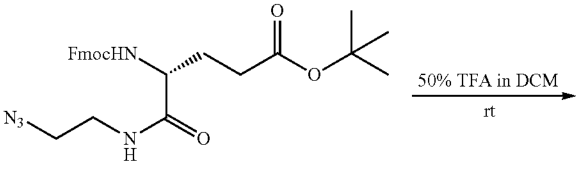

22

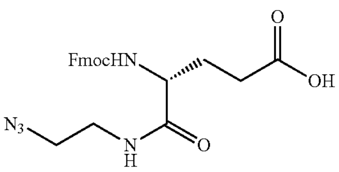

5h tert-Butyl (4R)-4-[(2-azidoethyl)carbamoyl]-4-{[(9H-fluoren-9-ylmethoxy)carbonyl]amino}butanoate (22)

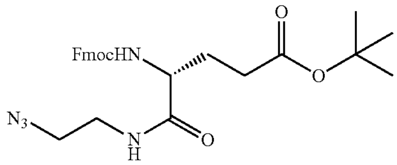

To a mixture of Fmoc-D-Glu(OTBU)-OH (21, (104091-08-9), 0.30 g, 0.71 mmol) and 2-azidoethanamine (87156-40-9, 73 mg, 0.85 mmol) in DCM (50 mL) were added HATU (0.41 g, 1.1 mmol) and triethylamine (0.3 mL) at RT. The reaction mixture was stirred at RT overnight. Most of compound 21 was then consumed according to TLC and LCMS. After the reaction mixture was quenched with water (50 mL) at RT, the organic solution was washed with water and brine, dried over sodium sulfate and concentrated in vacuo. The residue was purified by prep-TLC (silica gel, eluting with petroleum ether/ethyl acetate (v/v=1)) to give the title compound 22 (0.30 g, yield 76%) as yellow viscous oil. ESI m/z: 494 $(M+H)^+$. $^1H$ NMR (400 MHz, $DMSO_{d6}$): δ 8.09 (m, 1H), 7.84-7.90 (m, 4H), 7.33-7.44 (m, 4H), 6.28 (s, 2H), 3.35 (m, 6H), 3.26 (m, 1H), 2.50 (m, 2H), 2.25 (m, 1H), 1.80 (m, 1H), 1.39 (s, 9H) ppm.

(4R)-4-[(2-Azidoethyl)carbamoyl]-4-{[(9H-fluoren-9-ylmethoxy)carbonyl]amino}butanoic acid (5h)

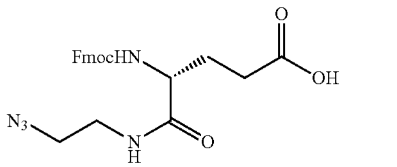

The resulting mixture was stirred at RT for 2 hours until compound 22 was totally consumed, which was monitored by TLC and LCMS. The volatiles were removed in vacuo to give crude compound 5h (17 mg, yield 96%) as yellow oil, which was used for the next step without further purification. ESI m/z: 438 $(M+H)^+$.

Scheme 11. Synthesis of Intermediates 6a

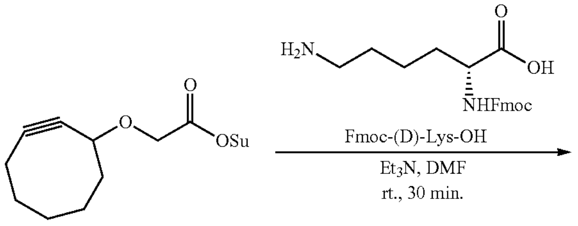

23

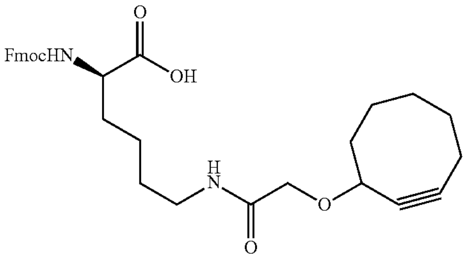

6a (2R)-6-[2-(Cyclooct-2-yn-1-yloxy)acetamido]-2-{[(9H-fluoren-9-ylmethoxy)carbonyl]amino}hexanoic acid (6a)

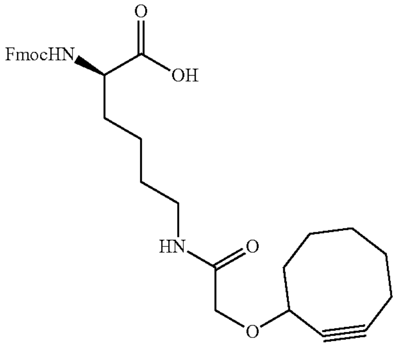

To a mixture of commercial compound 23 (65 mg, 0.23 mmol, CAS: 1425803-45-7) in DMF (2 mL) were added Fmoc-D-Lys-OH (85 mg, 0.23 mmol) and triethylamine (52 mg, 0.51 mmol). The reaction mixture was stirred at RT for 30 minutes. The mixture was directly separated by reversed phase flash chromatography (0-100% acetonitrile in water (0.05% TFA)) to give intermediate 6a (85 mg, yield 70%) as a white solid. ESI m/z: 533 $(M+H)^+$. $^1H$ NMR ($MeOD_{d4}$, 500 MHz): δ 7.70 (d, J=7.5 Hz, 2H), 7.59 (t, J=8.0 Hz, 2H), 7.30 (t, J=7.5 Hz, 2H), 7.22 (t, J=7.4 Hz, 2H), 4.35-4.22 (m, 2H), 4.22-4.09 (m, 2H), 4.09-3.99 (m, 1H), 3.94-3.81 (m, 1H), 3.79-3.67 (m, 1H), 3.15 (t, J=6.9 Hz, 2H), 2.17-1.96 (m, 3H), 1.96-1.86 (m, 1H), 1.85-1.66 (m, 4H), 1.66-1.41 (m, 5H), 1.41-1.25 (m, 3H) ppm.

Scheme 12. Synthesis of intermediates 11b and 12c
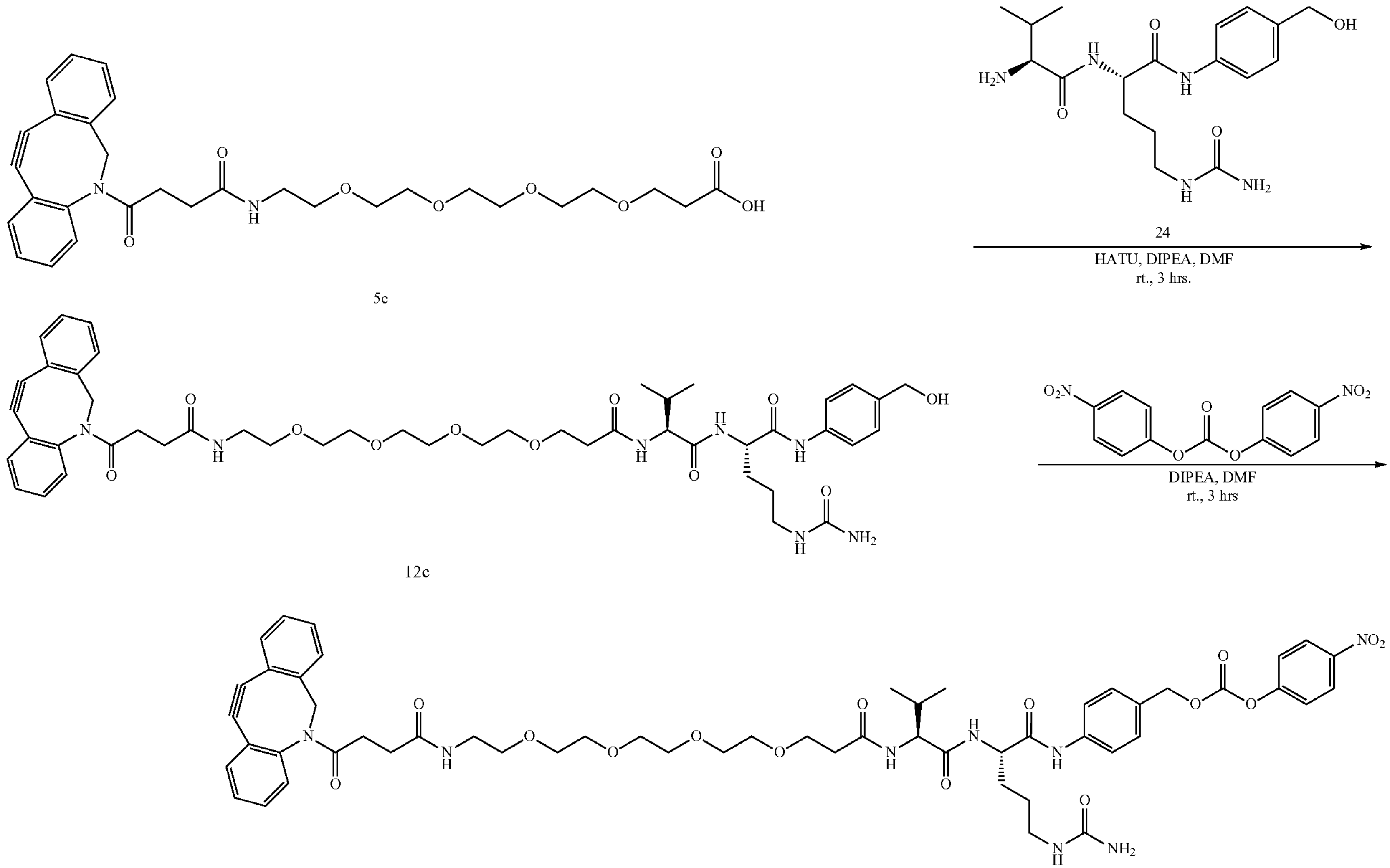
5c
12c
11b 1-(4-{2-Azatricyclo[10.4.0.049]hexadeca-1(12),4(9),5,7,13,15-hexaen-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (12c)

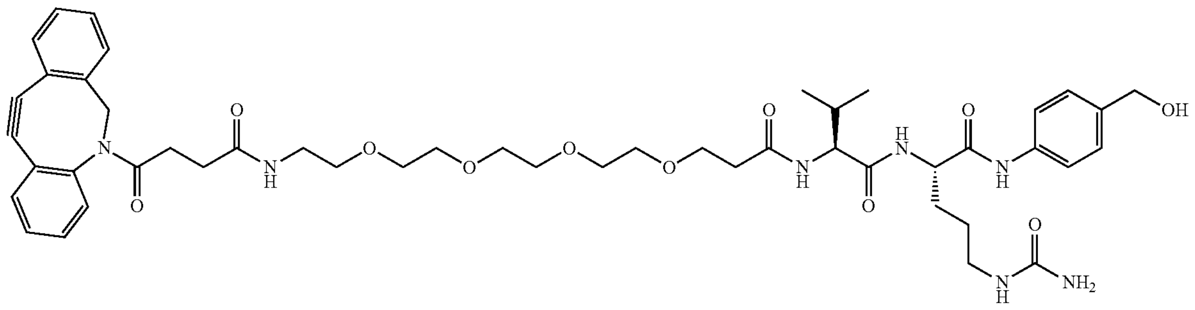 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(CO)cc1]

The mixture was stirred at RT for 15 minutes. To the reaction solution was added vc-PAB (24 (159857-79-1), 0.21 g, 0.54 mmol) at RT, and the resulting mixture was stirred at RT for 3 hours until most materials were consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 12c (0.30 g, yield 60%) as a white solid. ESI m/z: 617 $(M+H)^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate (11b)

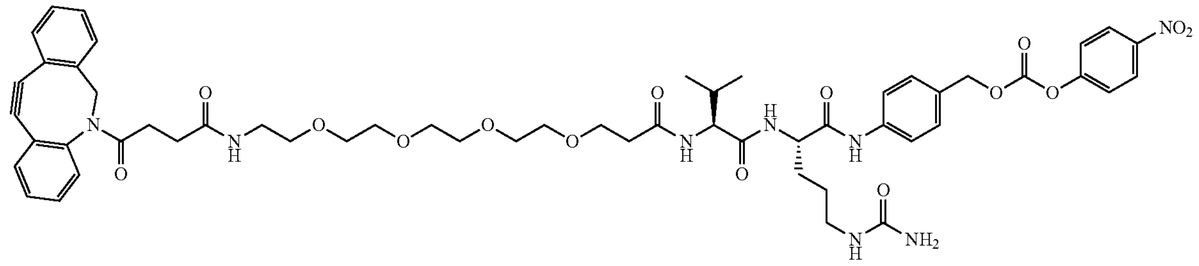 [SMILES: CC(C)[C@H](NC(=O)CCOCCOCCOCCOCCNC(=O)CCC(=O)N1Cc2ccccc2C#Cc2ccccc21)C(=O)N[C@@H](CCCNC(N)=O)C(=O)Nc1ccc(COC(=O)Oc2ccc([N+](=O)[O-])cc2)cc1]

To a solution of compound 12c (0.15 g, 0.16 mmol) in DMF (10 mL) were added bis(4-nitrophenyl) carbonate (0.15 g, 0.49 mmol) and DIPEA (63 mg, 0.49 mmol) at 0° C. The mixture was then stirred at RT for 3 hours until 12c was mostly consumed, which was monitored by LCMS. The reaction mixture was filtered through filtering membrane and the filtrate was directly purified by reversed flash chromatography (0-100% acetonitrile in water (with 10 mmol/L ammonium bicarbonate)) to give title intermediate 11b (50 mg, yield 28%) as a white solid. ESI m/z: 1079 $(M+H)^+$.

Table 5A below presents linker payloads made using the methods described herein.

TABLE 5A
Examples of Linker-Payloads
| LP | Payload | Linker name | Structures |
|---|---|---|---|
| 2a | 1a | MC-VC-PAB | 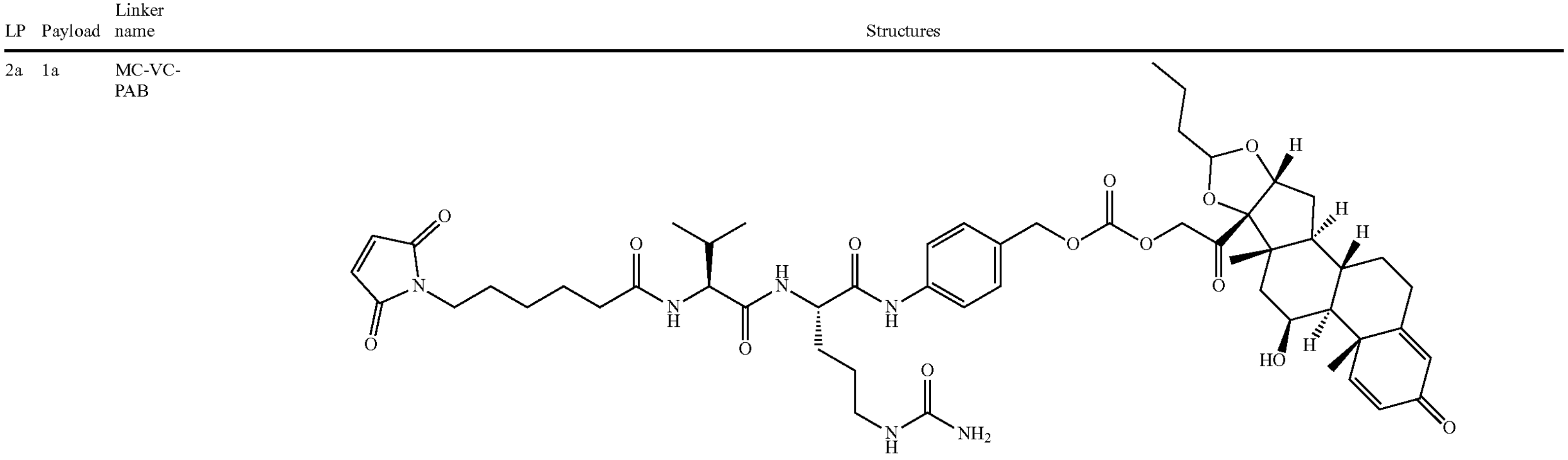 |
| 2b | 1a | DIBAC-suc-vc-PAB | 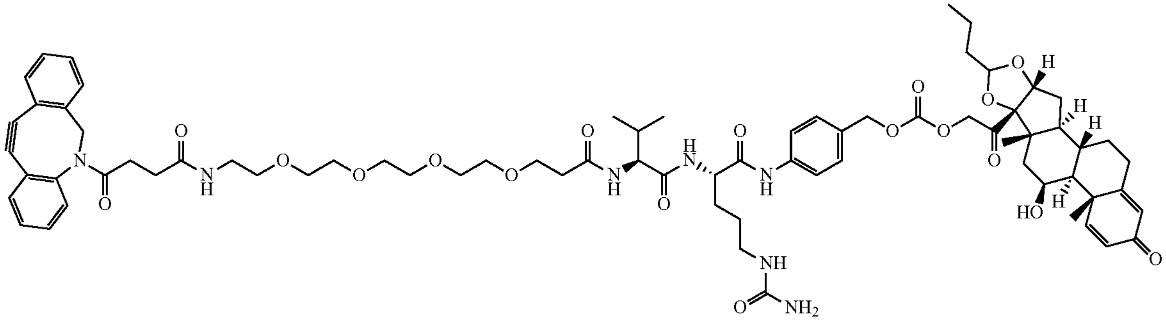 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1] |

TABLE 5A-continued
| Examples of Linker-Payloads | | | |
|---|---|---|---|
| LP | Payload | Linker name | Structures |
| 2c | 1a | mc-PEG4-(sugar-COT)dLys-vc-PAB | 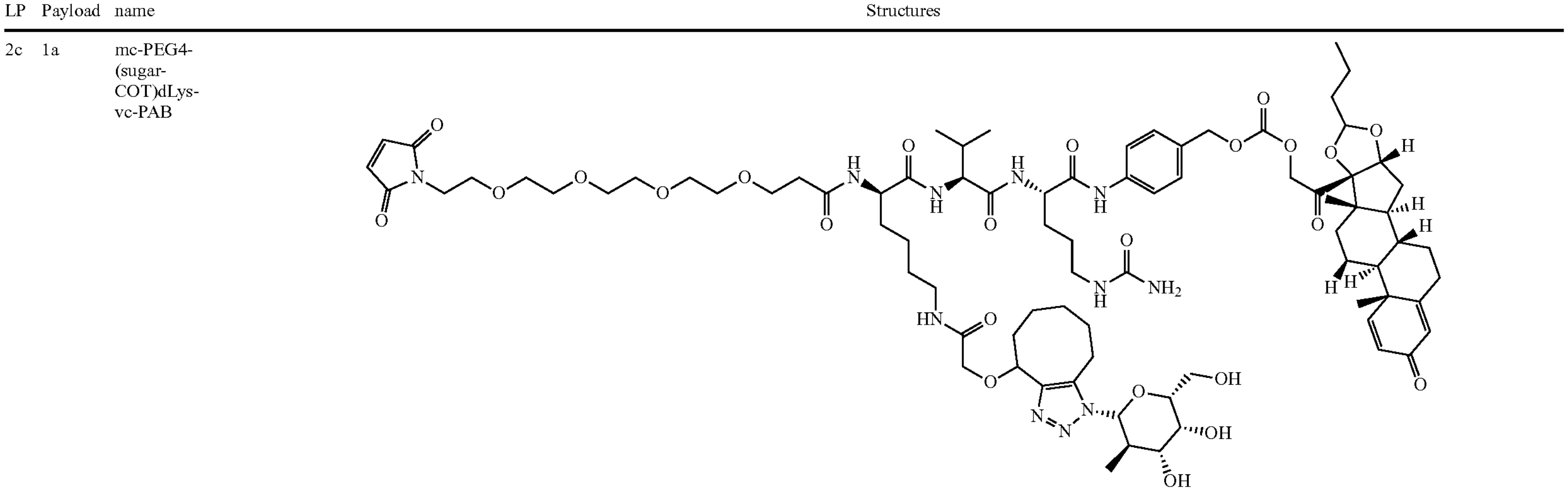 |
| 2d | 1a | mc-PEG4-(sugar2)dGlu-vc-PAB | 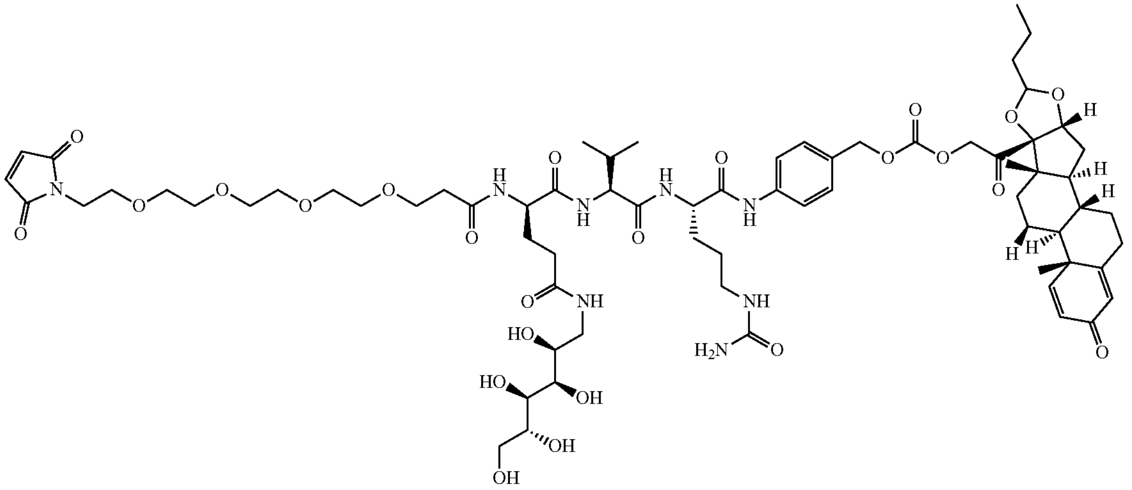 |

TABLE 5A-continued
| Examples of Linker-Payloads | | | |
|---|---|---|---|
| LP | Payload | Linker name | Structures |
| 2e | 1a | MC-VC-PABA | 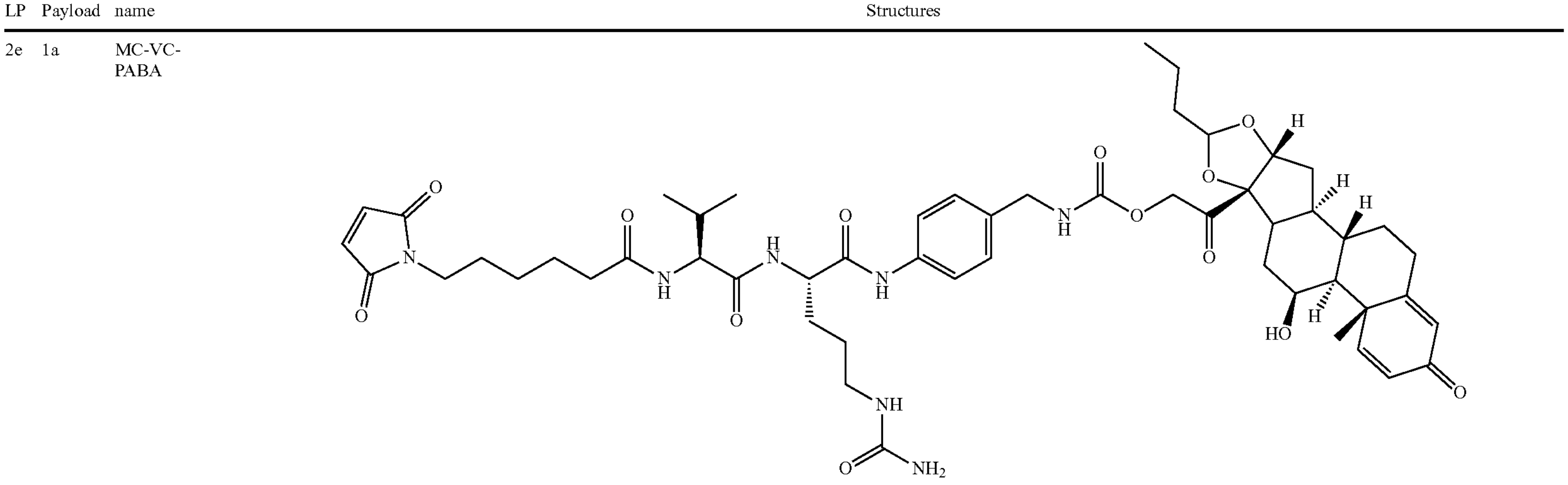 |
| 2f | 1c | MC-VC-PAB | 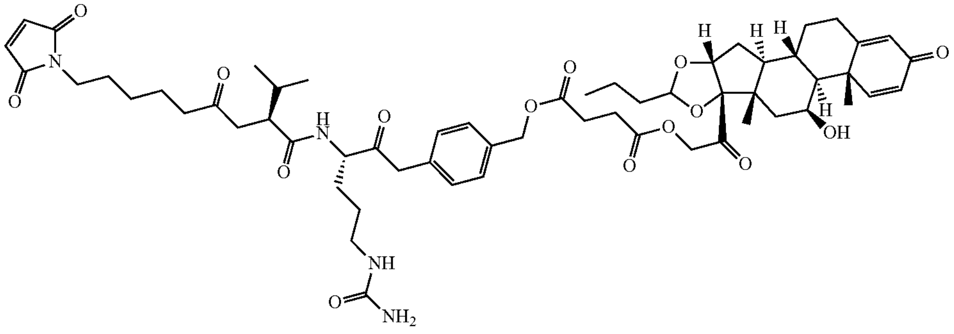 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC(=O)CCC(=O)OCc2ccc(CC(=O)[C@H](CCCNC(N)=O)NC(=O)[C@@H](CC(=O)CCCCCN3C(=O)C=CC3=O)C(C)C)cc2)O1] |

TABLE 5A-continued
| Examples of Linker-Payloads | | | |
|---|---|---|---|
| LP | Payload | Linker name | Structures |
| 2g | 1c | DIBAC-suc-vc-PAB | 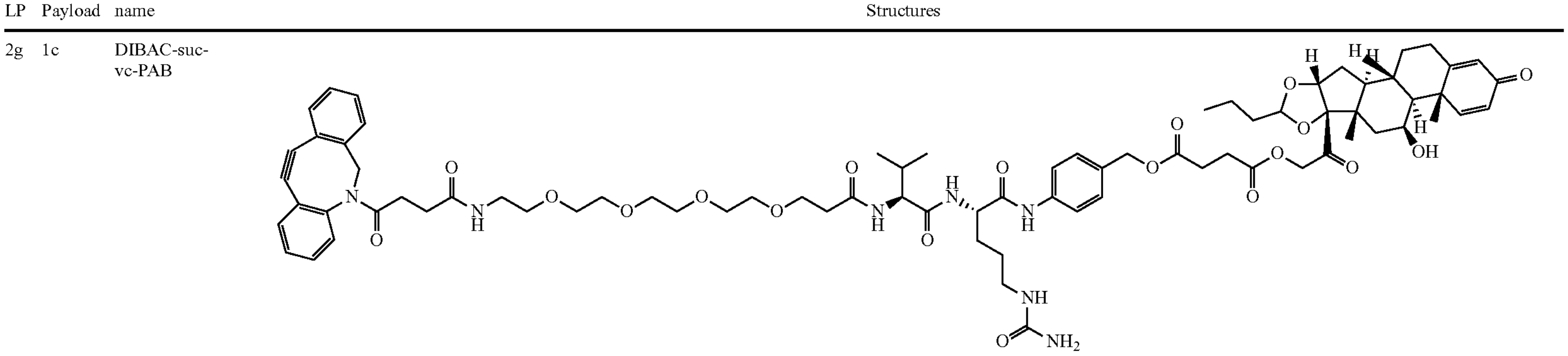 |
| 2j | 1e | MC-VC-PAB | 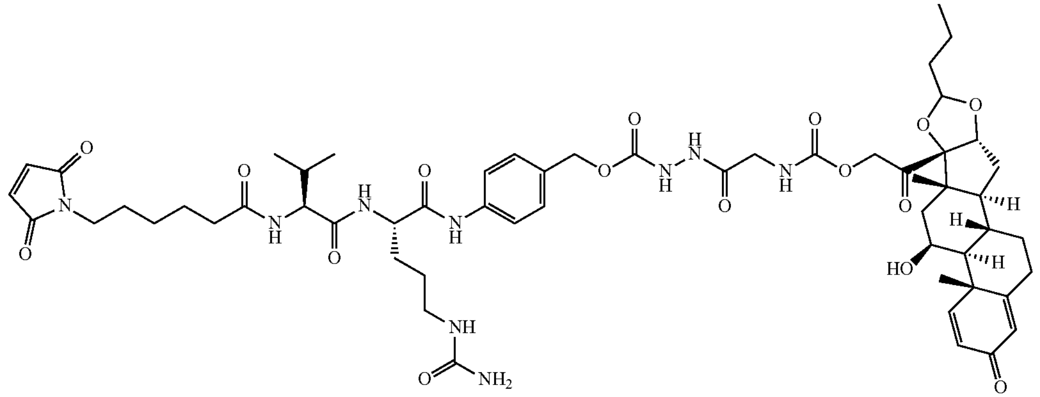 |

TABLE 5A-continued
Examples of Linker-Payloads
| LP | Payload | Linker name | Structures |
|---|---|---|---|
| 2k | 1d | MC-VC-PAB | 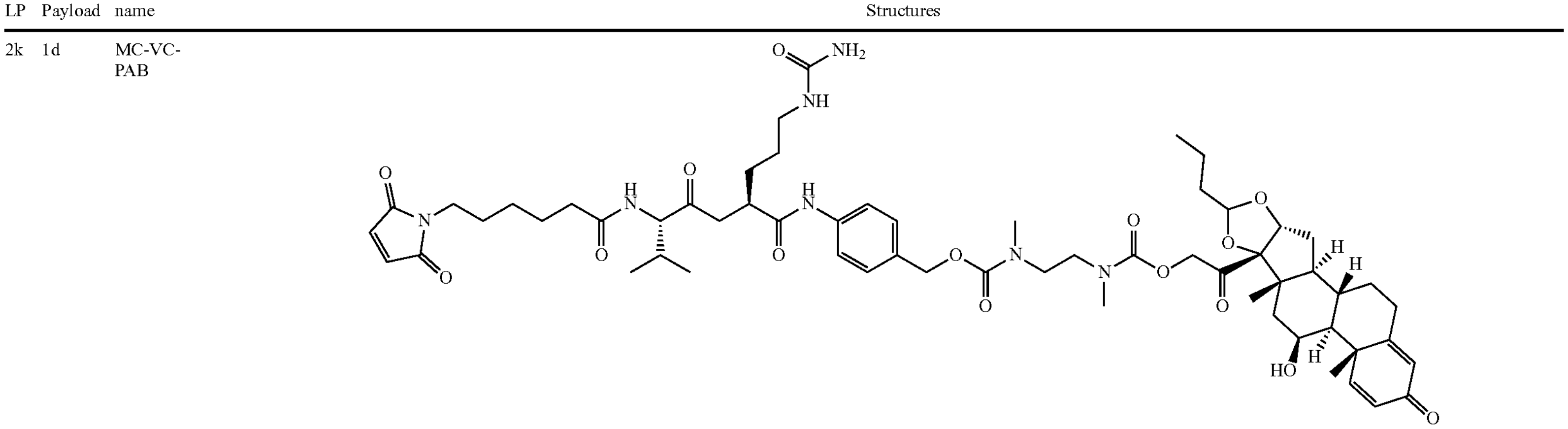 |
| 2l | 1d | BCN-PEG4-vc-PAB | 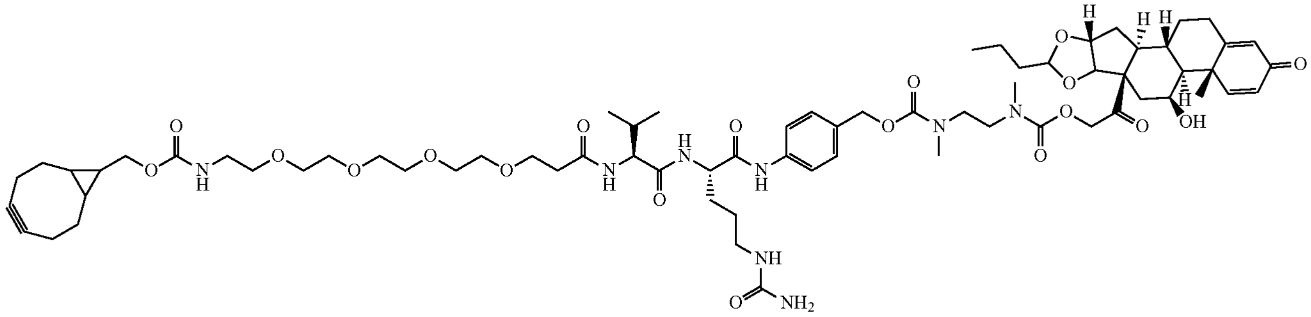 [SMILES: CCCC1OC2[C@@H](C[C@H]3[C@@H]4CCC5=CC(=O)C=C[C@]5(C)[C@H]4[C@@H](O)C[C@]23C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)OCC3C4CCC#CCCC43)C(C)C)cc2)O1] |

TABLE 5A-continued
| Examples of Linker-Payloads | | | |
|---|---|---|---|
| LP | Payload | Linker name | Structures |
| 2m | 1d | mc-N5(CD-DIBAC-suc)Lys-vc-PAB | 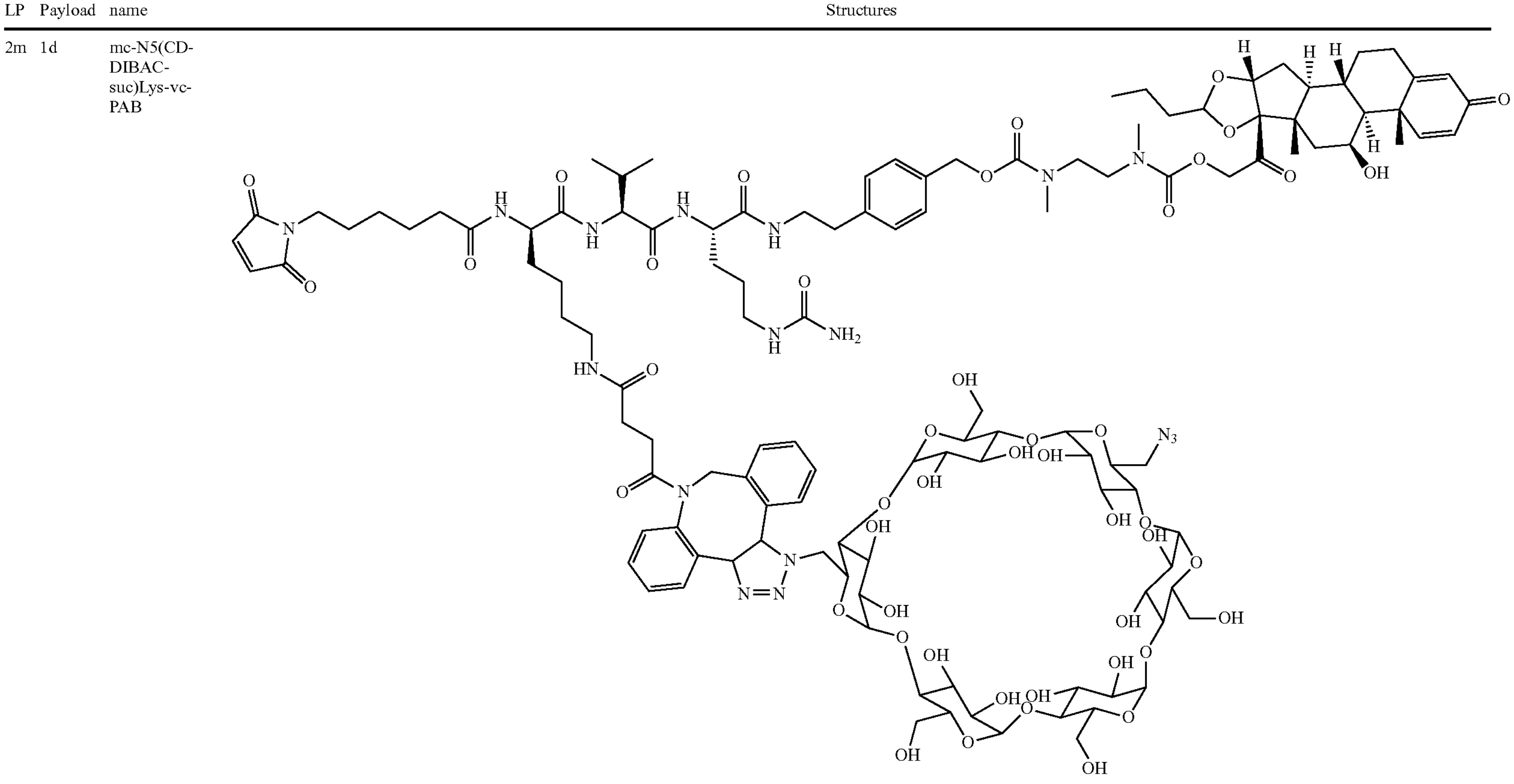 |

TABLE 5A-continued
Examples of Linker-Payloads
| LP | Payload | Linker name | Structures |
|---|---|---|---|
| 2n | 1d | azidoethyl-GLu-vc-PAB | 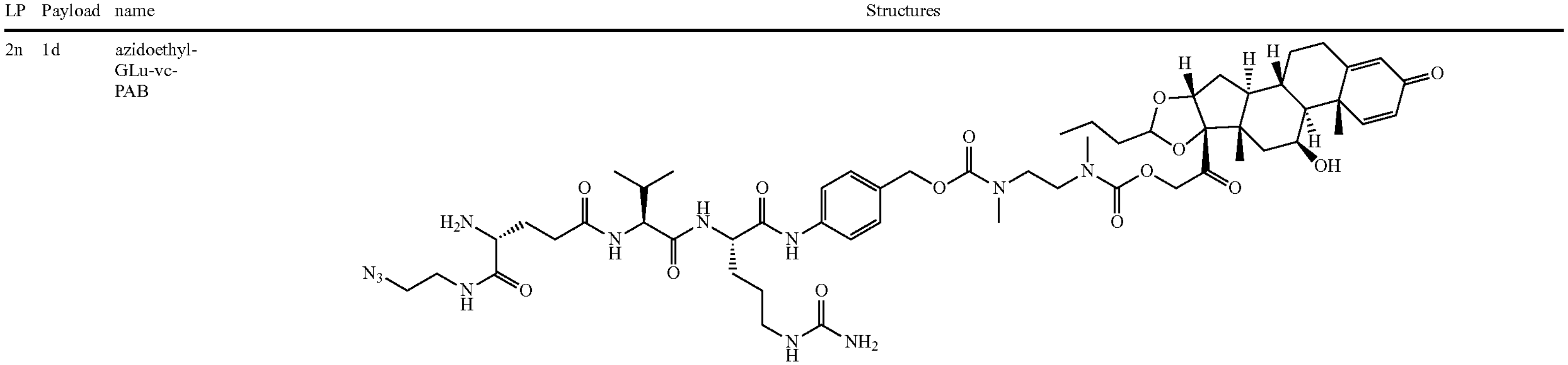 |
| 2q | 1g | MC-VC | 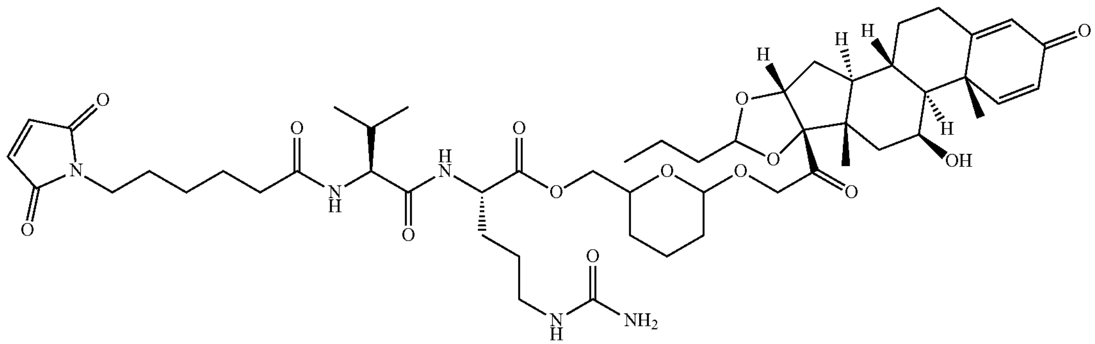 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)COC2CCCC(COC(=O)[C@H](CCCNC(N)=O)NC(=O)[C@@H](NC(=O)CCCCCN3C(=O)C=CC3=O)C(C)C)O2)O1] |
| 2r | 1k | BCN | 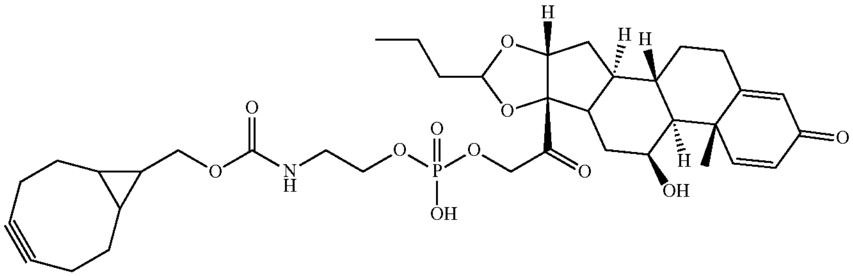 [SMILES: CCCC1O[C@@H]2C[C@@H]3C(C[C@H](O)[C@H]4[C@H]3CCC3=CC(=O)C=C[C@@]34C)[C@]2(C(=O)COP(=O)(O)OCCNC(=O)OCC2C3CCC#CCCC32)O1] |

TABLE 5A-continued
| Examples of Linker-Payloads | | | |
|---|---|---|---|
| LP | Payload | Linker name | Structures |
| 2s | 11 | BCN | 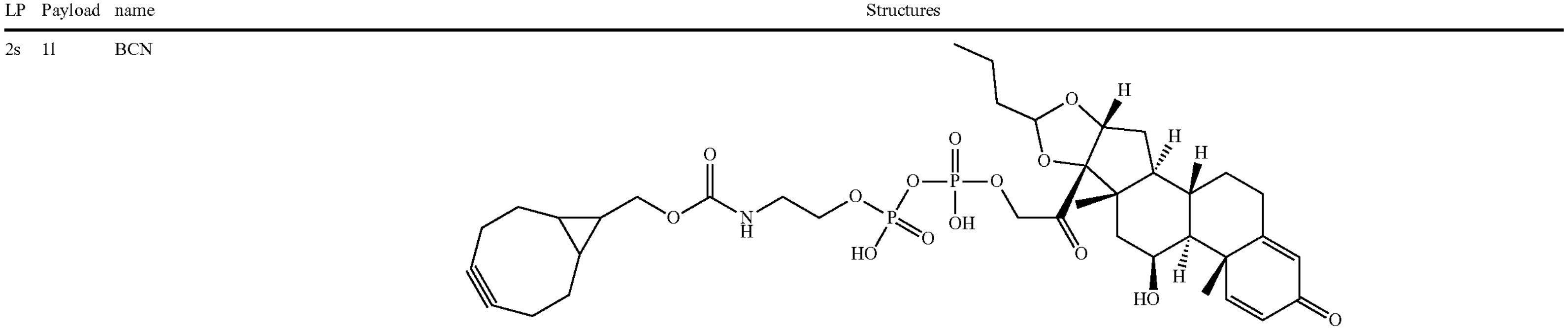 |

TABLE 6A

Characterization Data for Linker-Payloads

| LP | cLogP | MF | MW | HPLC purity (%) | HPLC RT (min) | MS (m/z) 100% | Highest m/z peak |
|---|---|---|---|---|---|---|---|
| 2a | 4.18 | $C_{54}H_{72}N_6O_{14}$ | 1029.2 | 92 | 7.6 (A) | 1029 (M + H) | 1029 (M + H) |
| 2b | 5.42 | $C_{74}H_{95}N_7O_{18}$ | 1370.6 | 97 | 8.1 (B) | 685.8 (M/2 + H) | 685.8 (M/2 + H) |
| 2c | 1.03 | $C_{81}H_{117}N_{11}O_{26}$ | 1660.9 | 97 | 7.0 (A) | 830.8 (M/2 + H) | 830.8 (M/2 + H) |
| 2d | −1.87 | $C_{70}H_{102}N_8O_{25}$ | 1455.6 | 100 | 6.48 (A) | 728 (M/2 + H) | 1456 (M + H) (10%) |
| 2e | 3.45 | $C_{54}H_{73}N_7O_{13}$ | 1028.2 | 100 | 7.54 (A) | 1028.3 (M + H) | 1028.3 (M + H) |
| 2f | 3.54 | $C_{57}H_{76}N_6O_{15}$ | 1085.2 | 98 | 1.71 (LCMS) | 1085.3 (M + H) | 1085.3 (M + H) |
| 2g | 4.77 | $C_{77}H_{99}N_7O_{19}$ | 1426.7 | >99 | 7.86 (B) | 714.0 (M/2 + H) | 1427 (M + H) (15%) |
| 2j | 2.16 | $C_{57}H_{77}N_9O_{16}$ | 1144.3 | 98 | 1.57 (LCMS) | 1144.3 (M + H) | 1144.3 (M + H) |
| 2k | 3.54 | $C_{59}H_{82}N_8O_{15}$ | 1143.3 | 98 | 1.70 (LCMS) | 1143.4 (M + H) | 1143.4 (M + H) |
| 2l | 4.66 | $C_{71}H_{104}N_8O_{19}$ | 1373.6 | 100 | 9.40 (A) | 687.5 (M/2 + H) | 1396.8 (M + Na) (50%) |
| 2m | −4.89 | $C_{120}H_{166}N_{14}O_4$ | 2556.7 | 100 | 6.49 (A) | 1278.8 (M/2 + H) | 1278.8 (M/2 + H) |
| 2n | 1.68 | $C_{56}H_{82}N_{12}O_{14}$ | 1147.3 | 100 | 7.72 (B) | 1147.5 (M + H) | 1147.5 (M + H) |
| 2q | 3.52 | $C_{52}H_{75}N_5O_{14}$ | 994.2 | 79 | 10.36 (B) | 995.3 (M + H) | 995.3 (M + H) |
| 2r | 4.88 | $C_{38}H_{52}NO_{11}P$ | 729.8 | 100 | 5.26 (B) | 686.2 (weak mass) | 1459.1 (2M + H) |
| 2s | 0.55 | $C_{38}H_{53}NO_{14}P_2$ | 809.8 | 100 | 4.03 (B) | 766.1 (M − 44) | 810.1 (M + H) (70%) |

Synthesis of Linker-Payloads LP1A-4A

Scheme 101. Synthesis of Payload 100, spacer-payload 101a-d and linker-payloads LP1A-4A
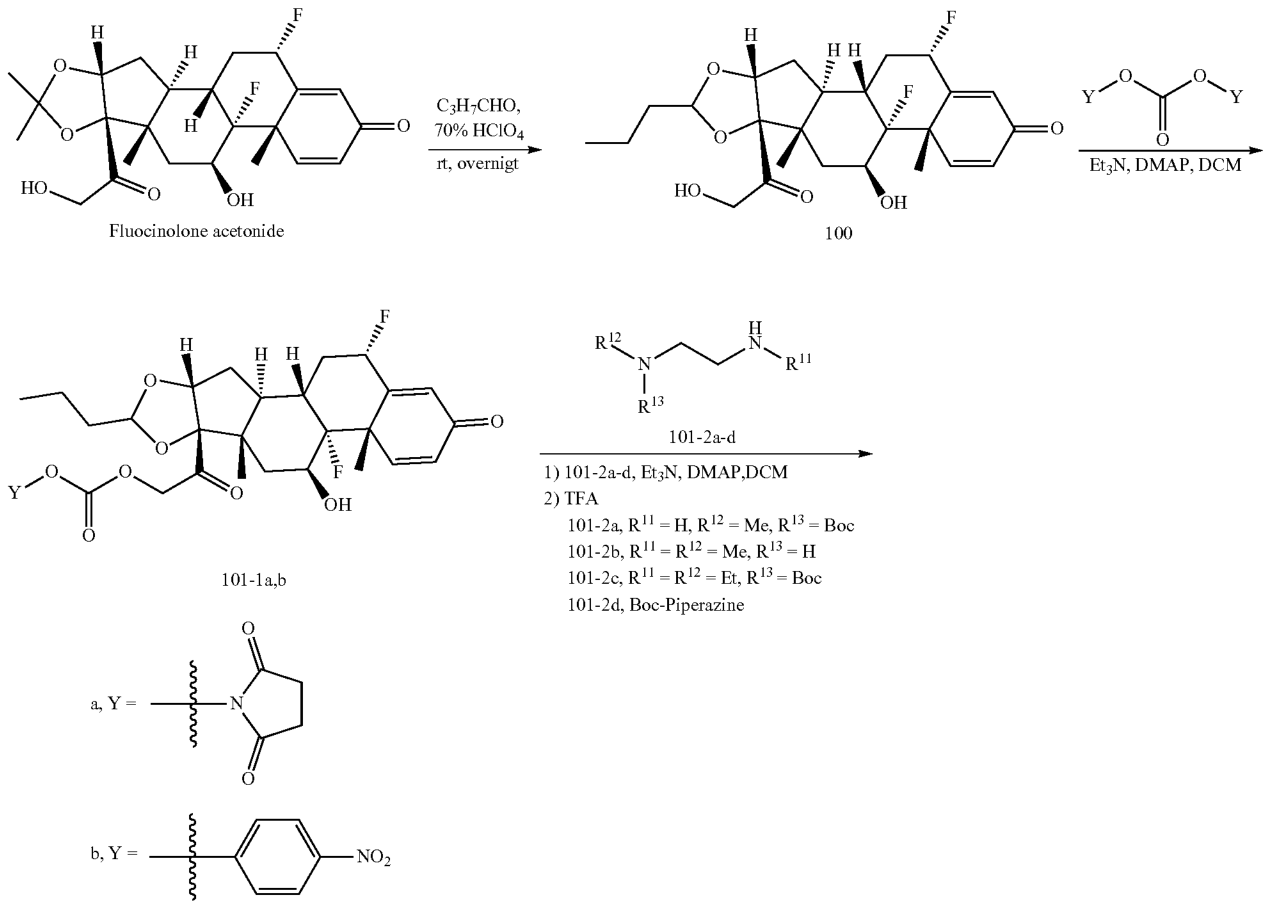
Fluocinolone acetonide
100
101-1a,b
a, Y =
b, Y =

-continued
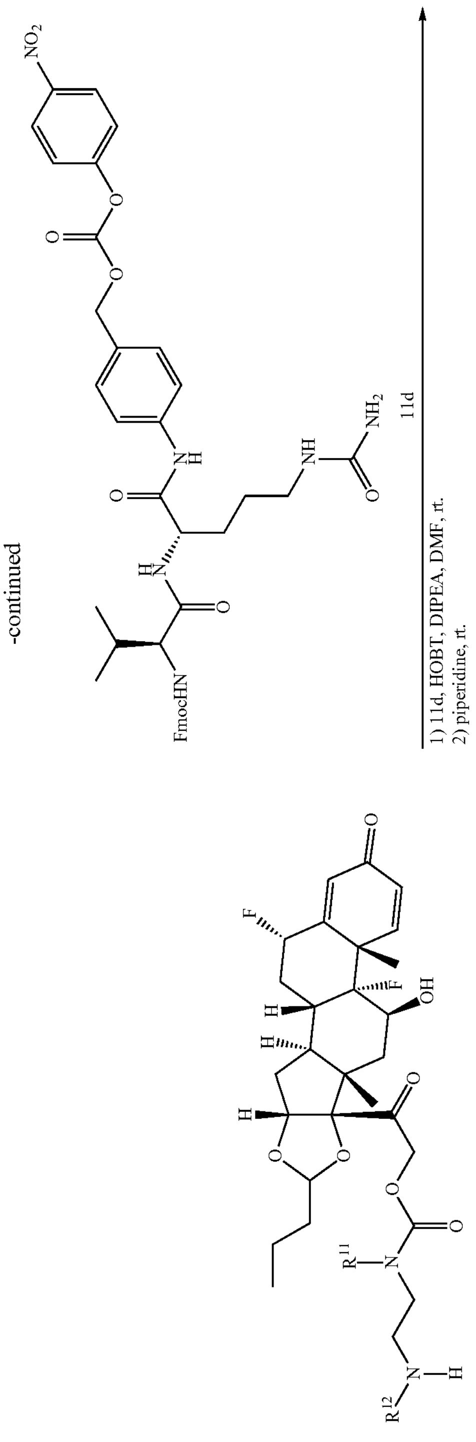
101a-d
101a, $R^{11}$ = H, $R^{12}$ = Me
101b, $R^{11}$ = $R^{12}$ = Me
101c, $R^{11}$ = $R^{12}$ = Et
101d, $R^{11}$, $R^{12}$ together =
—$CH_2CH_2$-(forming piperazine)

-continued
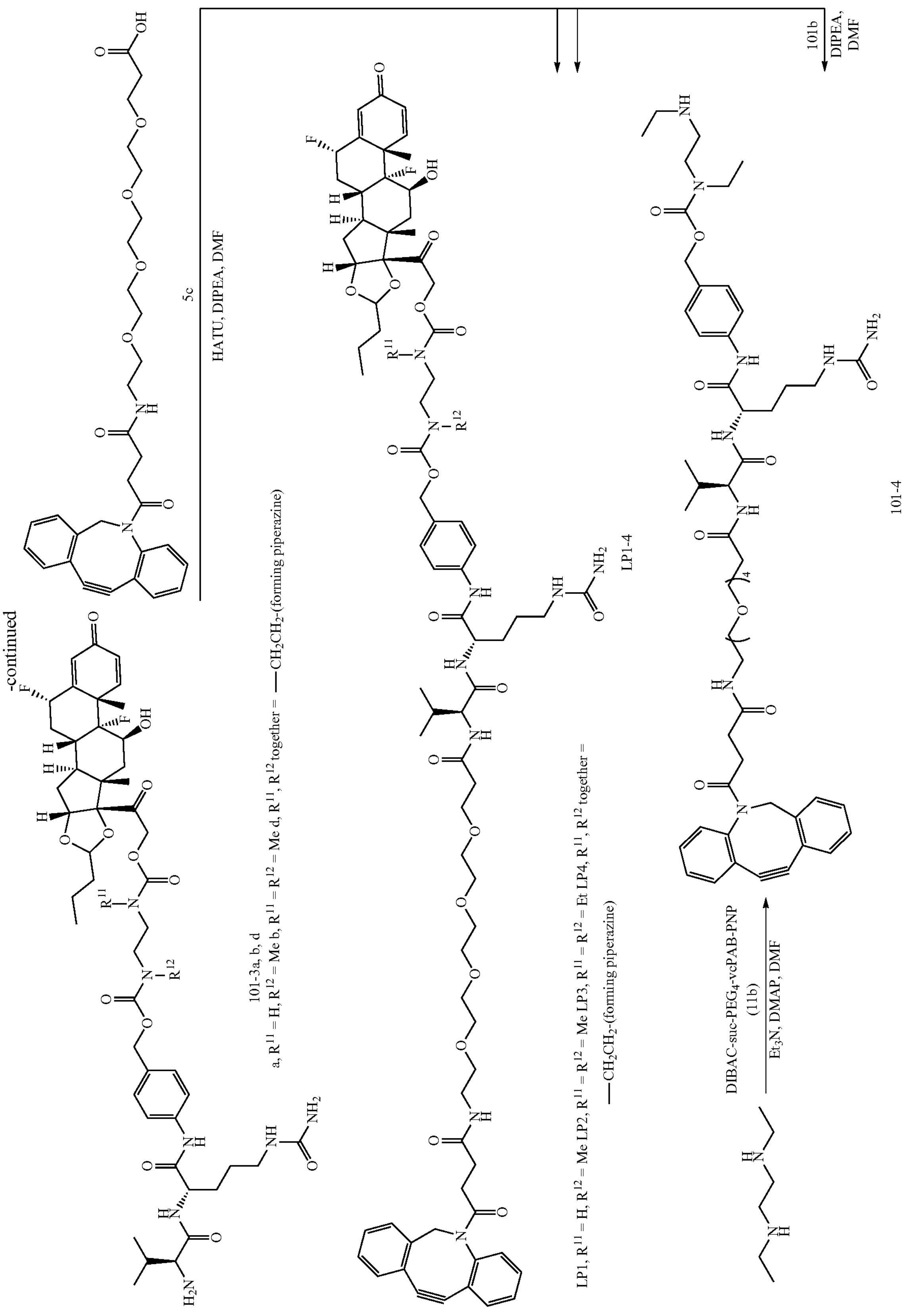
101-3a, b, d
a, $R^{11}$ = H, $R^{12}$ = Me b, $R^{11}$ = $R^{12}$ = Me d, $R^{11}$, $R^{12}$ together = —$CH_2CH_2$-(forming piperazine)
LP1-4
LP1, $R^{11}$ = H, $R^{12}$ = Me LP2, $R^{11}$ = $R^{12}$ = Me LP3, $R^{11}$ = $R^{12}$ = Et LP4, $R^{11}$, $R^{12}$ together = —$CH_2CH_2$-(forming piperazine)
101-4

(1S,2S,4R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.$0^{2,9}$.$0^{4,8}$.$0^{13,18}$]icosa-14,17-dien-16-one (100)

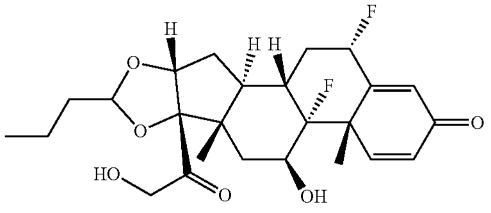

To a mixture of fluocinolone acetonide (10 g, 22 mmol) and silica gel (100 g) in heptanes (900 mL) was added butyraldehyde (3.0 mL, 33 mmol) below 10° C. and the suspension was stirred at 10-20° C. for 30 minutes. To the mixture was added perchloric acid (70%, 7.6 mL, 91 mmol) dropwise at 0° C. The reaction mixture was then stirred at RT overnight. Most of fluocinolone acetonide was consumed according to TLC and LCMS. The reaction mixture was diluted with petroleum ether and quenched with sat. aq. sodium carbonate. The suspension was filtered and the solid was washed with DCM/methanol (v/v=1:1). The combined filtrate was concentrated in vacuo. The residue was purified by flash chromatography (0-1.5% methanol in DCM) to give compound 100 (8.0 g, yield: 78%) as a white solid. ESI m/z: 467.1 $(M+H)^+$.

1-[({2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}carbonyl)oxy]pyrrolidine-2,5-dione (101-1a)

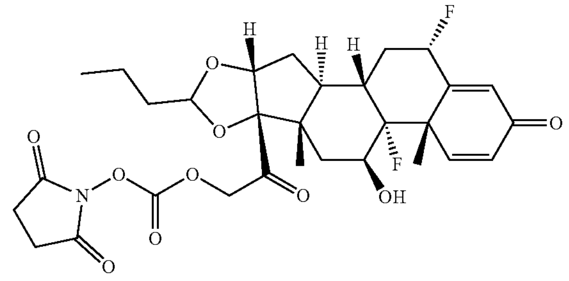 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)ON2C(=O)CCC2=O)O1]

To a solution of compound 100 (0.47 g, 1.0 mmol) in DCM (20 mL) were added bis(2,5-dioxopyrrolidin-1-yl) carbonate (0.28 g, 1.1 mmol), triethylamine (0.40 g, 4.0 mmol) and DMAP (3.0 mg, cat.). The reaction mixture was stirred at RT for 4 hours until compound 100 was consumed, which was monitored by LCMS. The reaction mixture was then diluted with DCM and washed by water. The organic solution was dried over sodium sulfate. After filtered, the solution was concentrated in vacuo and the residue (crude 101-1a) was used for the next step directly without purification. ESI m/z: 608.2 $(M+H)^+$.

(1S,2S,4R,8S,9S,11S,12R,13S,19S)-12,19-Difluoro-11-hydroxy-9,13-dimethyl-8-{2-[(4-nitrophenoxycarbonyl)oxy]acetyl}-6-propyl-5,7-dioxapentacyclo[10.8.0.$0^{2,9}$.$0^{4,8}$.$0^{13,18}$]icosa-14,17-dien-16-one (101-1b)

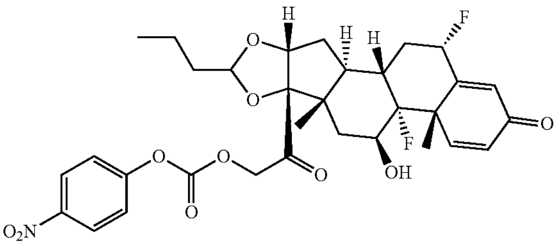 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)Oc2ccc([N+](=O)[O-])cc2)O1]

A mixture of compound 100 (0.80 g, 1.7 mmol), bis(4-nitrophenyl) carbonate (1.6 g, 5.2 mmol) and DIPEA (1.1 g, 8.6 mmol) in THF (20 mL) was stirred at RT for 4 hours, which was monitored by LCMS. The mixture was concentrated in vacuo. The crude product was purified by silica gel column chromatography (50% ethyl acetate in petroleum ether) to give compound 101-1b (0.75 g, 69% yield) as colorless oil. ESI m/z: 632 $(M+H)^+$.

General Procedure for Compound 101
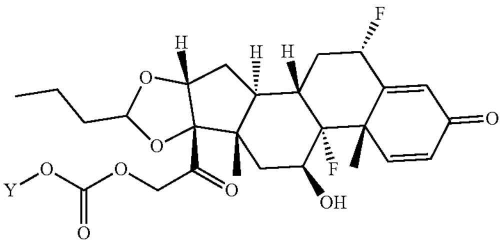
101-1a,b
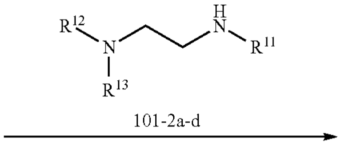
1) 101-2a-d, $Et_3N$, DMAP, DCM
2) TFA
101-2a, $R^{11}$ = H, $R^{12}$ = Me, $R^{13}$ = Boc
101-2b, $R^{11}$ = $R^{12}$ = Me, $R^{13}$ = H
101-2c, $R^{11}$ = $R^{12}$ = Et, $R^{13}$ = Boc
101-2d, piperazine
a, Y = 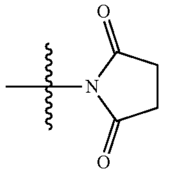
b, Y = 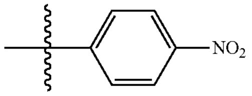
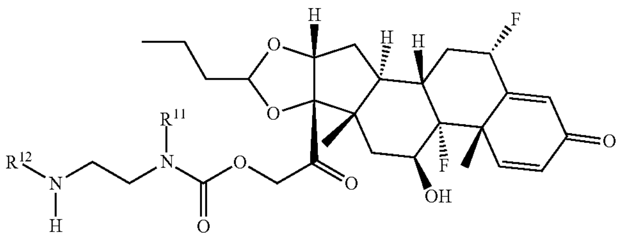
101a-d
101a, $R^{11}$ = H, $R^{12}$ = Me
101b, $R^{11}$ = $R^{12}$ = Me
101c, $R^{11}$ = $R^{12}$ = Et
101d, $R^{11}$, $R^{12}$ together =
—$CH_2CH_2$-(forming piperazine)

To a solution of compound 101-1a or 101-1b (crude, calculated as 1.0 mmol) in DCM (20 mL) were added diamine 101-2(a, b, c, or d) (1.1 mmol) and DMAP (0.1 mmol). The reaction mixture was stirred at RT for 4 hours before TFA (1 mL) was added into. The mixture was stirred at RT for half an hour (for $R^{13}$=Boc, the reaction was stirred until Boc was totally removed, which monitored by LCMS). The resulting mixture was concentrated in vacuo and the residue was purified by reversed phase flash chromatography (50-80% acetonitrile in aq. TFA (0.5%)) to give compound 101(a, b, c, or d) as colorless oil.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-[2-(methylamino)ethyl]carbamate (101a)

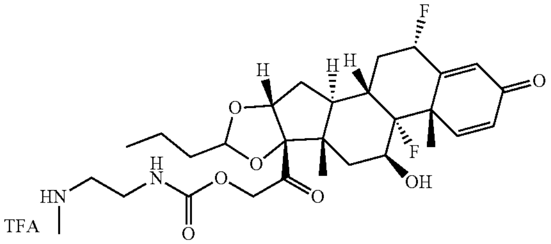 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCNC)O1]

Following the general procedure and using compound 101-1a with Boc-diamine 101-2a, compound 101a (0.38 g, 57% in 2 steps, TFA salt) was obtained as colorless oil. ESI m/z: 567 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-[2-(methylamino)ethyl]carbamate (101b)

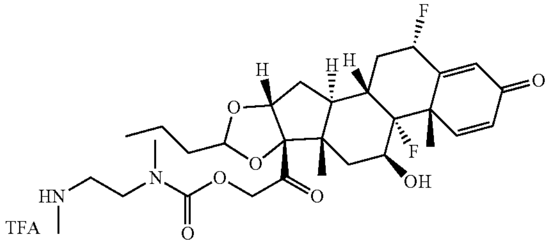 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCNC)O1]

Following the general procedure and using compound 101-1a with diamine 101-2b, compound 101b (0.45 g, 66% yield in 2 steps, TFA salt) was obtained as colorless oil. ESI m/z: 581 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-ethyl-N-[2-(ethylamino)ethyl]carbamate (101c)

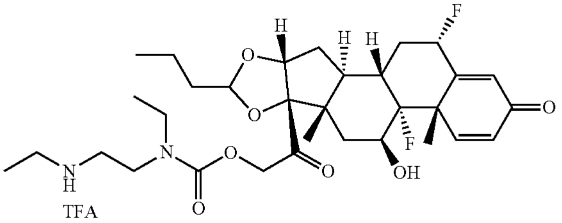 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(CC)CCNCC)O1]

Following the general procedure and using compound 101-1b with diamine 101-2c, compound 101c (24 mg, 18% yield in 2 steps, TFA salt) was obtained as colorless oil. ESI m/z: 609 $(M+H)^+$. $^1$H NMR (500 MHz, DMSO$_{d6}$) δ 8.38 (s, 2H), 7.30 (d, J=10.5 Hz, 1H), 6.24 (dd, J=10.5 Hz, 2.0 Hz, 1H), 6.11 (s, 1H), 5.70-5.54 (m, 2H), 5.10-4.91 (m, 1H), 4.85-4.65 (m, 3H), 4.25-4.16 (m, 1H), 3.60-3.40 (m, 2H), 3.33-3.20 (m, 4H), 3.20-2.90 (m, 4H), 2.67-2.53 (m, 1H), 2.30-2.20 (m, 1H), 2.10-2.00 (m, 2H), 1.80-1.70 (m, 1H), 1.64-1.51 (m, 4H), 1.49 (s, 3H), 1.40-1.30 (m, 2H), 1.20-1.10 (m, 4H), 1.10-1.00 (m, 1H), 0.90-0.80 (m, 6H) ppm.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl piperazine-1-carboxylate (101d)

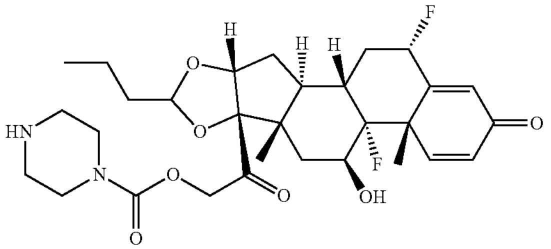 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N2CCNCC2)O1]

Following the general procedure and using compound 101-1b with piperazine (101-2d) without treatment with TFA and purified by silica gel column chromatography (0-10% methanol in DCM), compound 101d (0.21 g, 49% yield in 2 steps, free base) was obtained as colorless oil. ESI m/z: 579 $(M+H)^+$.

General Procedure for Compound 101-3

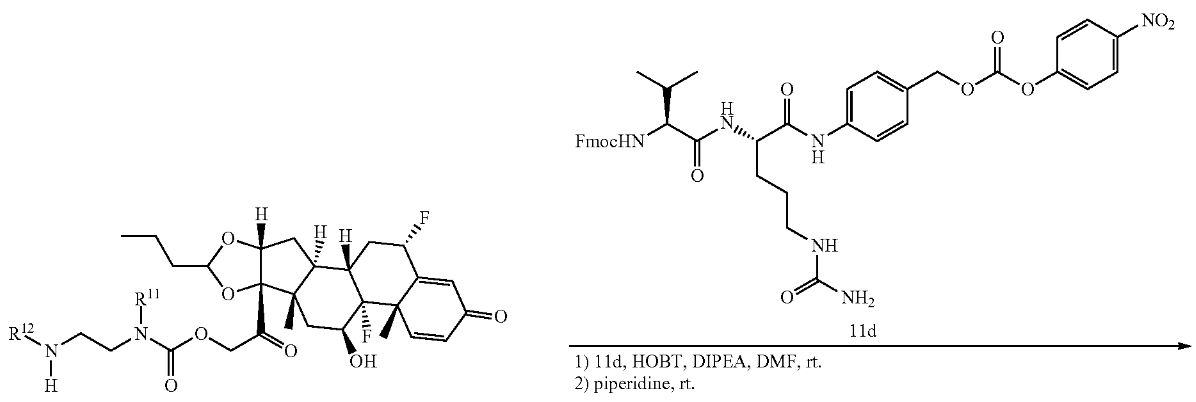

101a, b, d
101a, $R^{11}$ = H, $R^{12}$ = Me
101b, $R^{11}$ = $R^{12}$ = Me
101d, $R^{11}$, $R^{12}$ =
$—CH_2CH_2$-(piperazine)

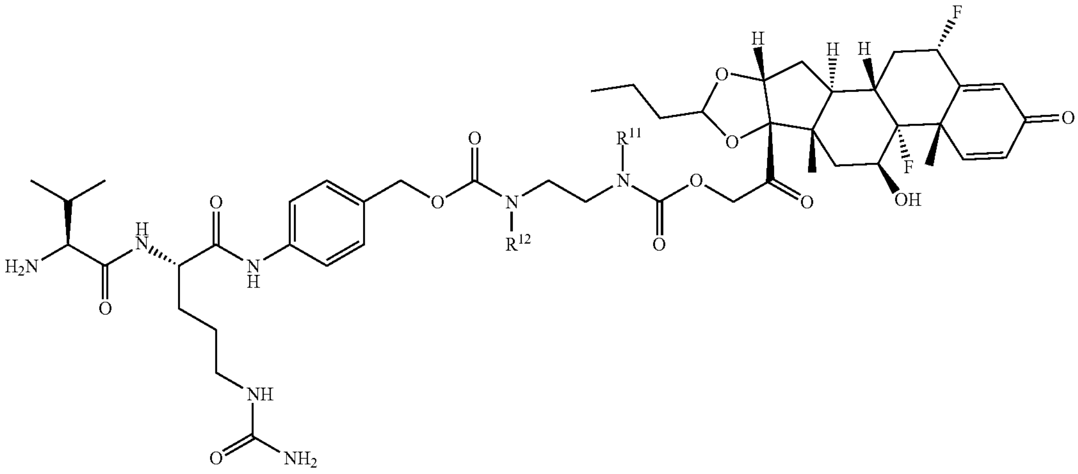

101-3a, b, d
a, $R^{11}$ = H, $R^{12}$ = Me
b, $R^{11}$ = $R^{12}$ = Me
d, $R^{11}$, $R^{12}$ together = $—CH_2CH_2$-(forming piperazine)

To a solution of compound 101a, b or d (0.20 mmol) in DMF (3 mL) were added Fmoc-VC-PAB-PNP 11d (0.17 g, 0.22 mmol), HOBT (41 mg, 0.30 mmol) and DIPEA (77 mg, 0.60 mmol). The mixture was stirred at RT for 3 hours, which was monitored by LCMS. To the mixture was then added piperidine (0.3 mL). The reaction mixture was stirred at RT for an hour until Fmoc was totally removed according to LCMS. The resulting mixture was directly purified by reversed phase flash chromatography (50-80% acetonitrile in aq. $NH_4HCO_3$ (10 mM)) to give compound 101-3a, b or d as a white solid.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-amino-3-methylbutanamido]-5-(carbamoylamino)pentanamido]phenyl}methoxy)carbonyl](methyl)amino}ethyl)carbamat e (101-3a)

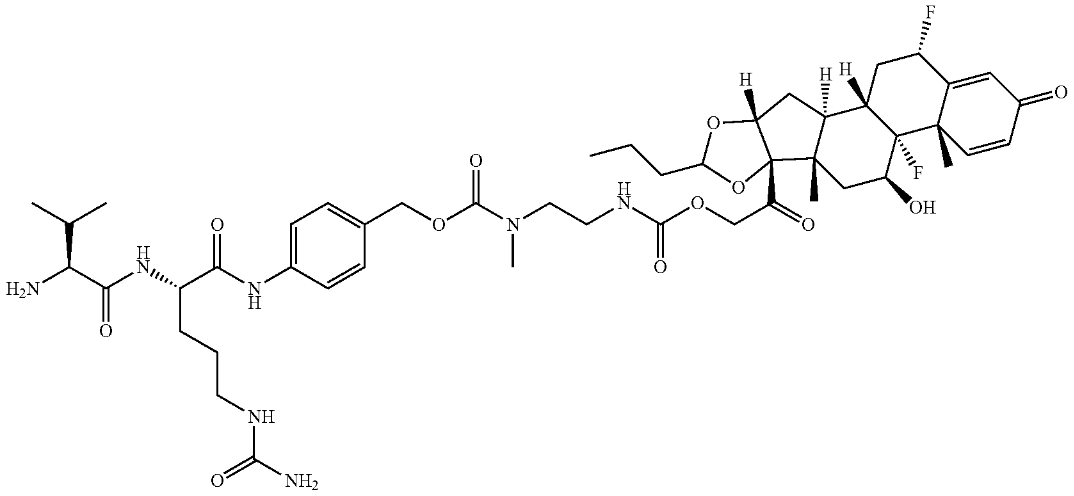 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCN(C)C(=O)OCc2ccc(NC(=O)[C@H](CCCNC(N)=O)NC(=O)[C@@H](N)C(C)C)cc2)O1]

Following the general procedure and using compound 101a, compound 101-3a (0.11 g, 57% yield) was obtained as a white solid. ESI m/z: 972 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-[2-(methylamino)ethyl]carbamate (101-3b)

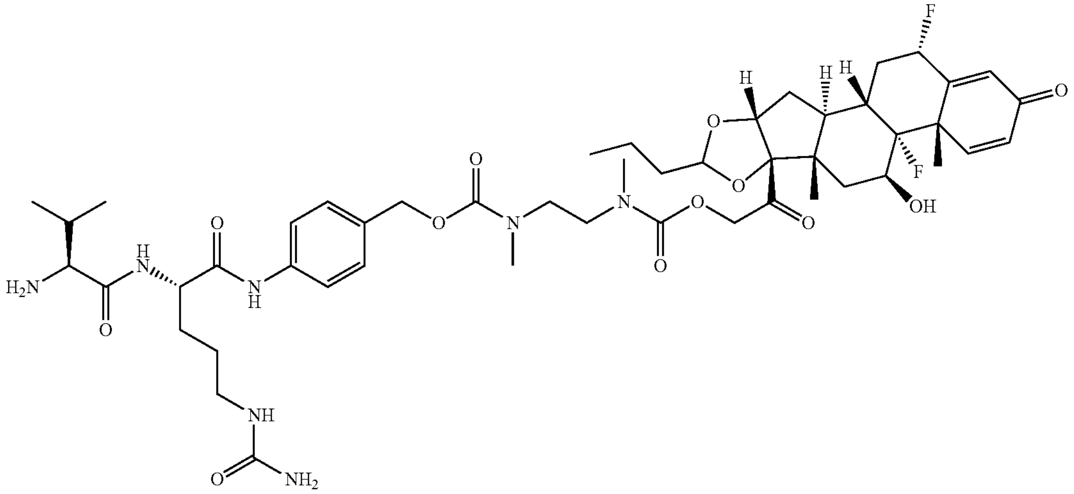 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](N)C(C)C)cc2)O1]

Following the general procedure and using compound 101b, compound 101-3b (0.13 g, 65% yield) was obtained as a white solid. ESI m/z: 986 (M+H)$^+$.

1-{4-[(2S)-2-[(2S)-2-Amino-3-methylbutanamido]-5-(carbamoylamino)pentanamido]phenyl}methyl 4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl} piperazine-1,4-dicarboxylate (101-3d)

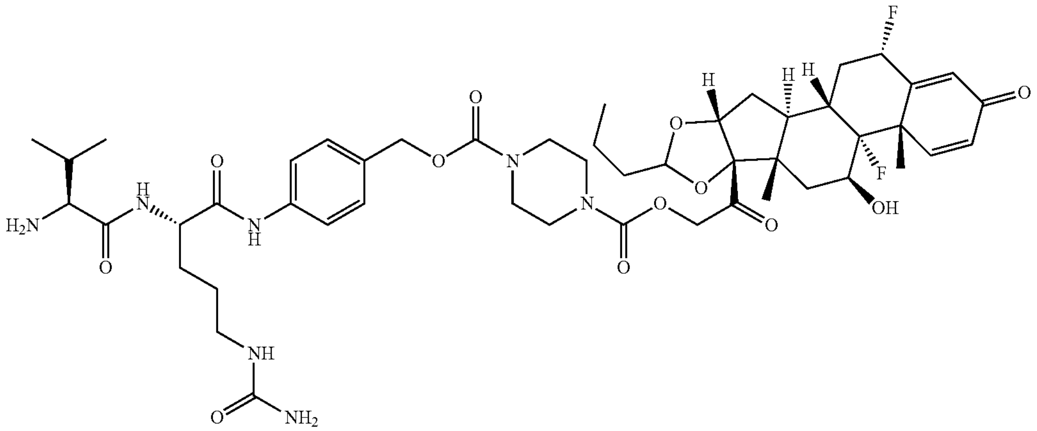 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N2CCN(C(=O)OCc3ccc(NC(=O)[C@H](CCCNC(N)=O)NC(=O)[C@@H](N)C(C)C)cc3)CC2)O1]

Following the general procedure and using compound 101d (58 mg, 0.10 mmol), compound 101-3d (52 mg, 53% yield) was obtained as a white solid. ESI m/z: 984 $(M+H)^+$. $^1H$ NMR (500 MHz, $DMSO_{d6}$) δ 10.0 (s, 1H), 8.14 (d, J=7.5 Hz, 1H), 7.60 (d, J=8.5 Hz, 2H), 7.31 (d, J=8.5 Hz, 2H), 7.26 (d, J=8.5 Hz, 1H), 6.30 (dd, J=1.5 Hz, 10.5 Hz, 1H), 6.11 (s, 1H), 6.02-5.88 (m, 1H), 5.70-5.50 (m, 2H), 5.42 (s, 2H), 5.20-4.92 (m, 3H), 4.80-4.62 (m, 3H), 4.50-4.45 (m, 1H), 4.25-4.15 (m, 1H), 3.50-3.35 (m, 8H), 3.05-2.90 (m, 3H), 2.70-2.54 (m, 2H), 2.32-2.20 (m, 1H), 2.10-1.50 (m, 10H), 1.46 (s, 3H), 1.45-1.30 (m, 5H), 0.95 (d, J=7.5 Hz, 1H), 0.90-0.80 (m, 9H), 0.77 (d, J=7.0 Hz, 3H) ppm.

General Procedure for Compounds LP1A, LP2A and LP4A

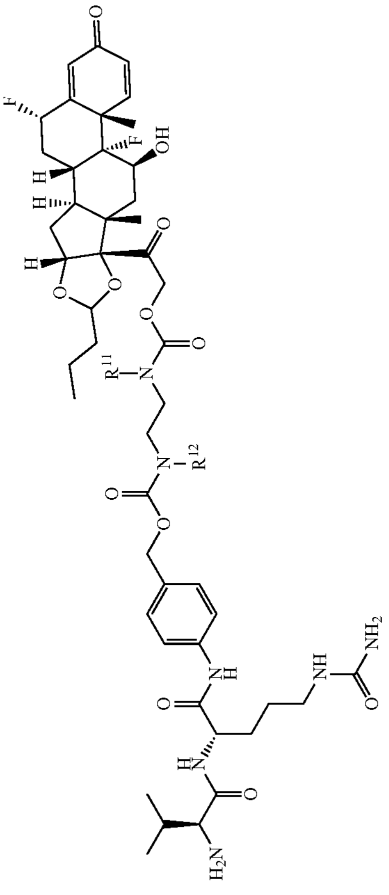
101-3a, b, d
a, $R^{11}$ = H, $R^{12}$ = Me
b, $R^{11}$ = $R^{12}$ = Me
d, $R^{11}$, $R^{12}$ =
—$CH_2CH_2$-(piperazine)
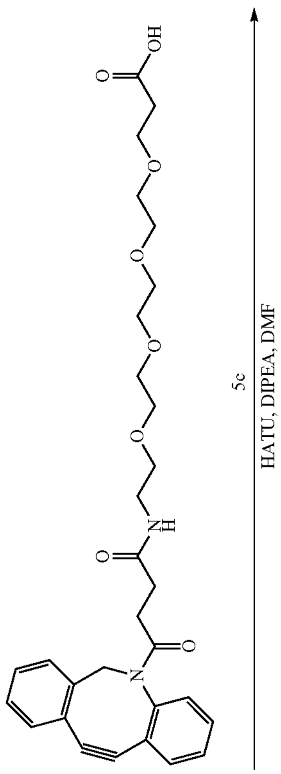
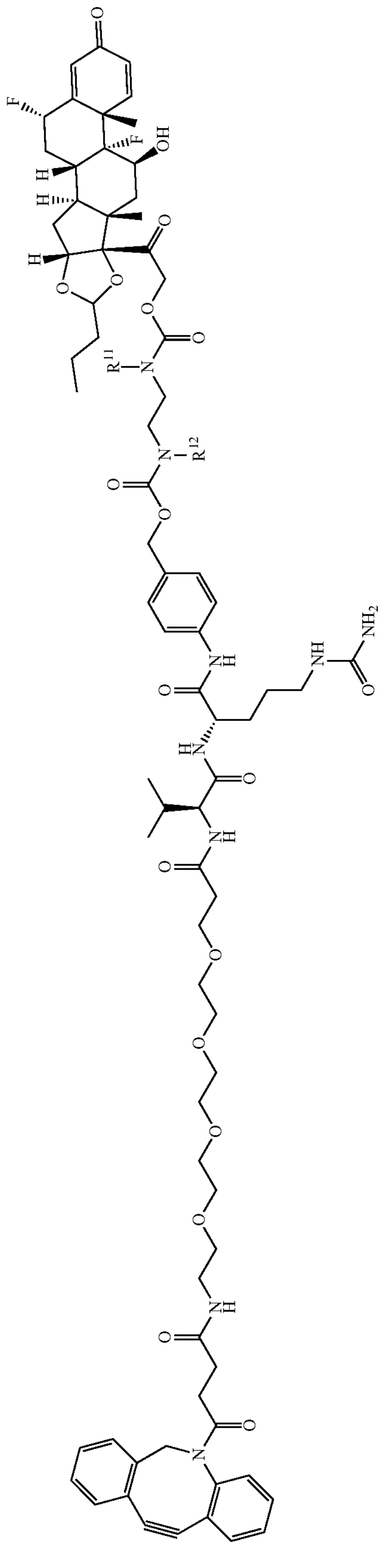
LP1A, 2A, 4A
LP1A, $R^{11}$ = H, $R^{12}$ = Me
LP2A, $R^{11}$ = $R^{12}$ = Me
LP4A, $R^{11}$, $R^{12}$ together =
—$CH_2CH_2$-(forming piperazine)

To a solution of compound 5c (34 mg, 60 μmol) in DMF (1 mL) were added HATU (27 mg, 71 μmol) and DIPEA (20 mg, 0.15 mmol). The mixture was stirred at RT for 5 minutes before compound 101-3a, b, or d (50 μmol) was added into the mixture. The mixture was stirred at RT for 2 hours, which was monitored by LCMS. The resulting mixture was directly purified by prep-HPLC (method B) to give compound LP1A, 2A or 4A as a white solid.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](methyl)amino}ethyl)carbamate (LP1A)

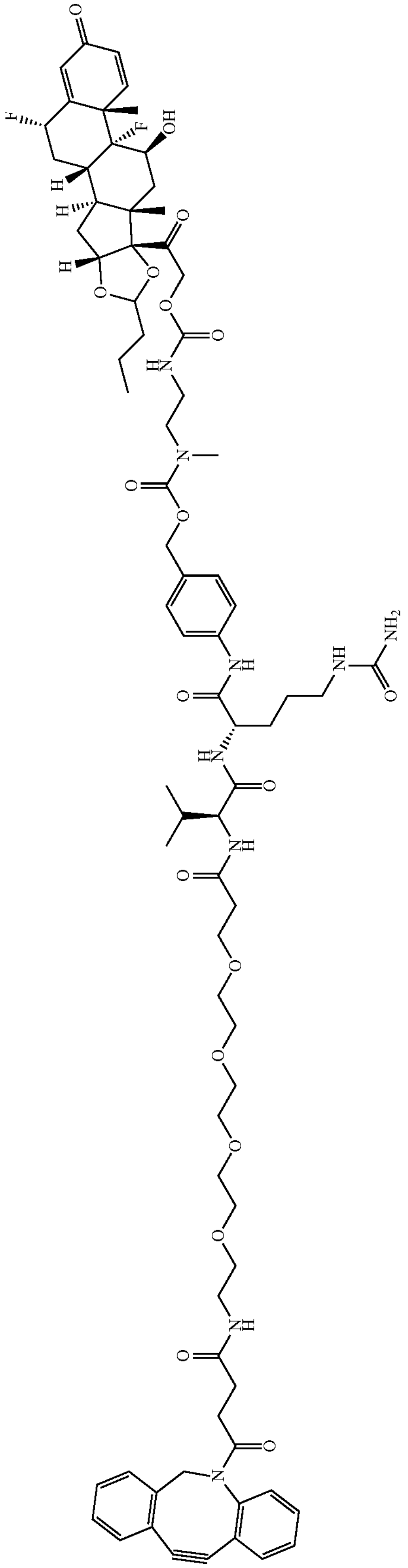

Following the general procedure and using compound 101-3a, linker-payload LP1A (20 mg, 26% yield) was obtained as a white solid. ESI m/z: 754 $(M/2+H)^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](methyl)amino}ethyl)-N-methylcarbamate (LP2A)

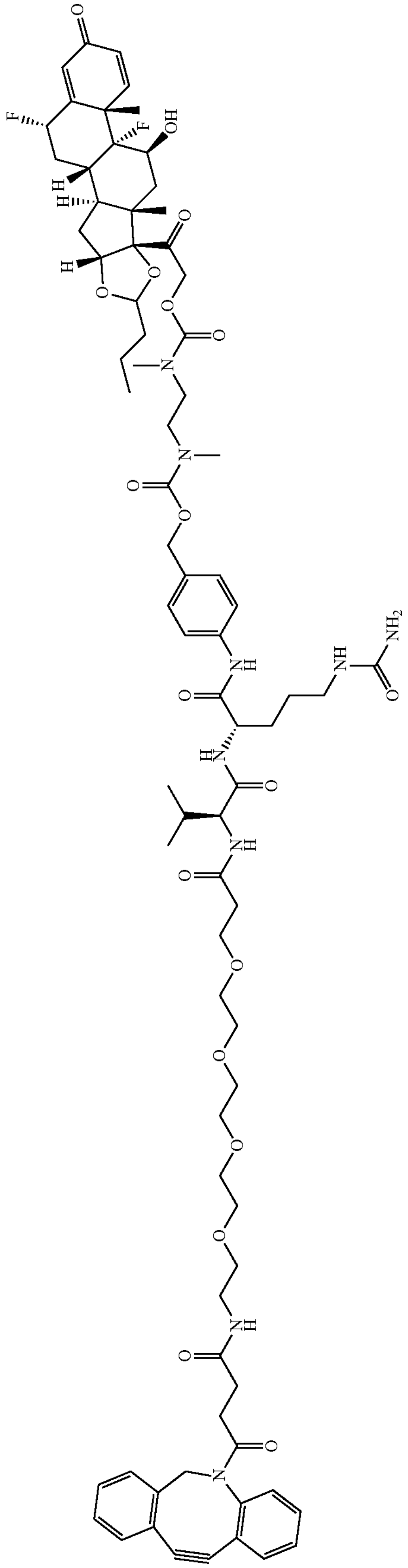

Following the general procedure and using compound 101-3b, linker-payload LP2A (20 mg, 26% yield) was obtained as a white solid. ESI m/z: 761 $(M/2+H)^+$. $^1H$ NMR (500 MHz, $DMSO_{d6}$) δ 9.98 (s, 1H), 8.12 (d, J=7.4 Hz, 1H), 7.87 (d, J=8.6 Hz, 1H), 7.76 (t, J=5.4 Hz, 1H), 7.69-7.66 (m, 1H), 7.64-7.57 (m, 3H), 7.51-7.44 (m, 3H), 7.40-7.33 (m, 2H), 7.32-7.25 (m, 4H), 6.33-6.27 (m, 1H), 6.11 (s, 1H), 5.98 (t, J=5.5 Hz, 1H), 5.70-5.55 (m, 2H), 5.41 (s, 2H), 5.08-4.91 (m, 4H), 4.79-4.66 (m, 2H), 4.41-4.35 m, 1H), 4.25-4.17 (m, 2H), 3.64-3.56 (m, 3H), 3.49-3.41 (m, 15H), 3.30-3.27 (m, 2H), 3.13-3.00 (m, 3H), 2.98-2.75 (m, 8H), 2.65-2.54 (m, 2H), 2.48-2.43 (m, 1H), 2.41-2.34 (m, 1H), 2.28-2.19 (m, 2H), 2.07-1.94 (m, 4H), 1.81-1.67 (m, 3H), 1.63-1.53 (m, 5H), 1.48 (s, 3H), 1.45-1.31 (m, 5H), 0.88-0.82 (m, 13H) ppm.

1-{4-[(2S)-2-[(2S)-2-[1-(4-{2-Azatricyclo [10.4.0.0$^4$,]hexadeca-1(12),4(9),5,7,13,15-hexaen-10-yn-2-yl}-4-oxobutanamido)-3,6,9,12-tetraoxa-pentadecan-15-amido]-3-methylbutanamido]-5-(carbamoylamino)pentanamido]phenyl}methyl 4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}piperazine-1,4-dicarboxylate (LP4A)

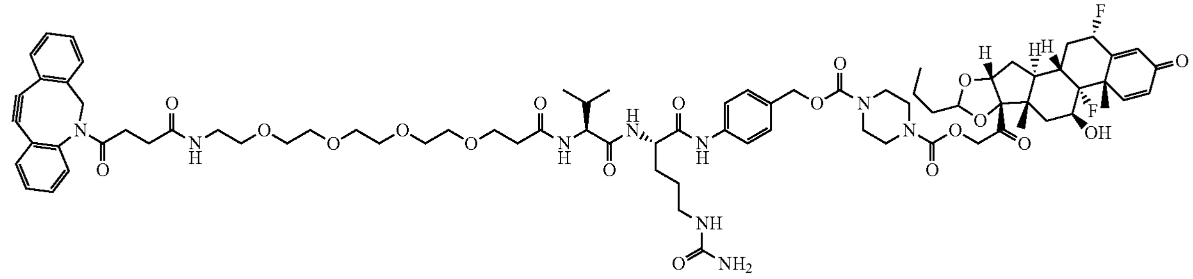 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N2CCN(C(=O)OCc3ccc(NC(=O)[C@H](CCCNC(N)=O)NC(=O)[C@@H](NC(=O)CCOCCOCCOCCOCCNC(=O)CCC(=O)N4Cc5ccccc5C#Cc5ccccc54)C(C)C)cc3)CC2)O1]

Following the general procedure and using compound 101-3d, linker-payload LP4A (35 mg, 44% yield) was obtained as a white solid. ESI m/z: 760 $(M/2+H)^+$. $^1H$ NMR (500 MHz, $DMSO_{d6}$) δ 10.0 (s, 1H), 8.14 (d, J=7.5 Hz, 1H), 7.88 (d, J=8.5 Hz, 1H), 7.77 (t, J=5.0 Hz, 1H), 7.70-7.66 (m, 1H), 7.63-7.55 (m, 3H), 7.52-7.43 (m, 3H), 7.40-7.27 (m, 6H), 6.30 (d, J=10.5 Hz, 1H), 6.11 (s, 1H), 6.02-5.88 (m, 1H), 5.70-5.50 (m, 2H), 5.42 (s, 2H), 5.20-4.92 (m, 4H), 4.80-4.62 (m, 3H), 4.40-4.35 (m, 1H), 4.26-4.20 (m, 2H), 3.64-3.55 (m, 3H), 3.50-3.35 (m, 17H), 3.30-3.25 (m, 3H), 3.15-2.90 (m, 4H), 2.64-2.54 (m, 2H), 2.50-2.45 (m, 1H), 2.41-2.34 (m, 1H), 2.32-2.20 (m, 2H), 2.10-1.92 (m, 4H), 1.80-1.68 (m, 3H), 1.62-1.50 (m, 5H), 1.46 (s, 3H), 1.45-1.40 (m, 2H), 1.40-1.30 (m, 3H), 1.22-1.20 (m, 1H), 0.90-0.80 (m, 13H) ppm.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-ethyl-N-[2-(ethylamino)ethyl]carbamate (101-4)

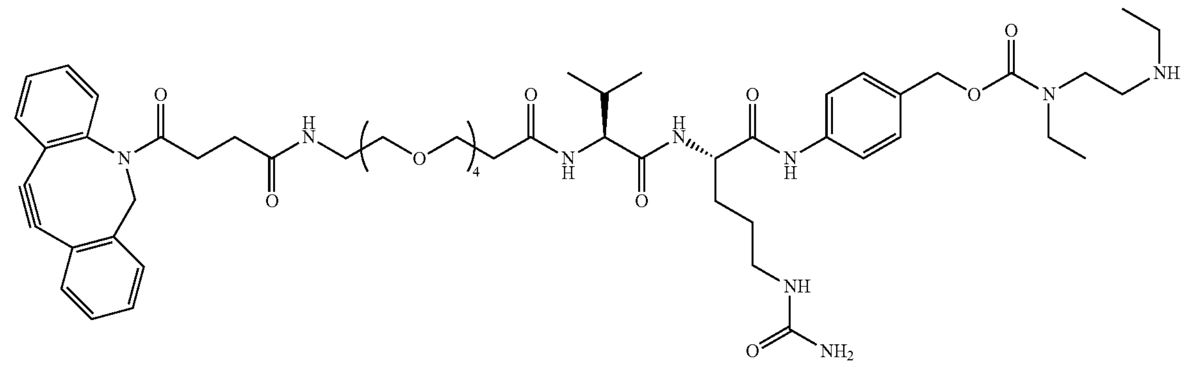

To a solution of DIBAC-suc-PEG$_4$-vcPAB-PNP 11b (0.11 g, 0.10 mmol) in DMF (5 mL) were added N,N'-diethylethylenediame (58 mg, 0.50 mmol) and DMAP (1 mg, 0.01 mmol). The reaction mixture was stirred at RT for 4 hours, which was monitored by LCMS. The resulting mixture was directly purified by prep-HPLC (method B) to give compound 101-4 as colorless oil. ESI m/z: 1056.6 (M+H)$^+$, 529 (M/2+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-{[({4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methoxy)carbonyl](ethyl)amino}ethyl)-N-ethylcarbamate (LP3A)

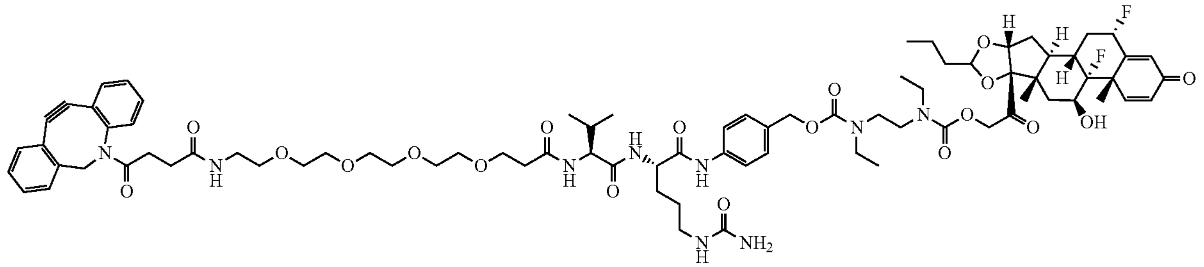

A mixture of compound 101-4 (16 mg, 15 μmol), 101-1b (11 mg, 17 μmol) and DIPEA (4.0 mg, 31 μmol) in DMF (5 mL) was stirred at RT for 4 hours, which was monitored by LCMS. The reaction mixture was directly purified by prep-HPLC (method B) to give linker-payload LP3A (3 mg, 13% yield) as a white solid. ESI m/z: 775 (M/2+H)$^+$. $^1$H NMR (500 MHz, DMSO$_{d6}$) δ 10.0 (s, 1H), 8.14 (d, J=7.5 Hz, 1H), 7.88 (d, J=8.5 Hz, 1H), 7.77 (t, J=5.0 Hz, 1H), 7.70-7.66 (m, 1H), 7.63-7.55 (m, 3H), 7.52-7.43 (m, 3H), 7.40-7.27 (m, 7H), 6.30 (d, J=10.5 Hz, 1H), 6.11 (s, 1H), 6.02-5.88 (m, 1H), 5.70-5.50 (m, 2H), 5.42 (s, 2H), 5.20-4.92 (m, 4H), 4.80-4.62 (m, 3H), 4.40-4.35 (m, 1H), 4.26-4.20 (m, 2H), 3.64-3.55 (m, 4H), 3.50-3.35 (m, 18H), 3.12-2.90 (m, 7H), 2.64-2.54 (m, 3H), 2.41-2.34 (m, 2H), 2.32-2.20 (m, 3H), 2.10-1.92 (m, 5H), 1.88-1.68 (m, 3H), 1.62-1.50 (m, 6H), 1.50-1.40 (m, 6H), 1.40-1.30 (m, 4H), 1.22-1.20 (m, 1H), 1.02-0.90 (m, 4H), 0.90-0.78 (m, 6H) ppm.

Synthesis of Cysteamine Prodrugs: Linker-Payloads LP5A, 6A, 7A and LP8A

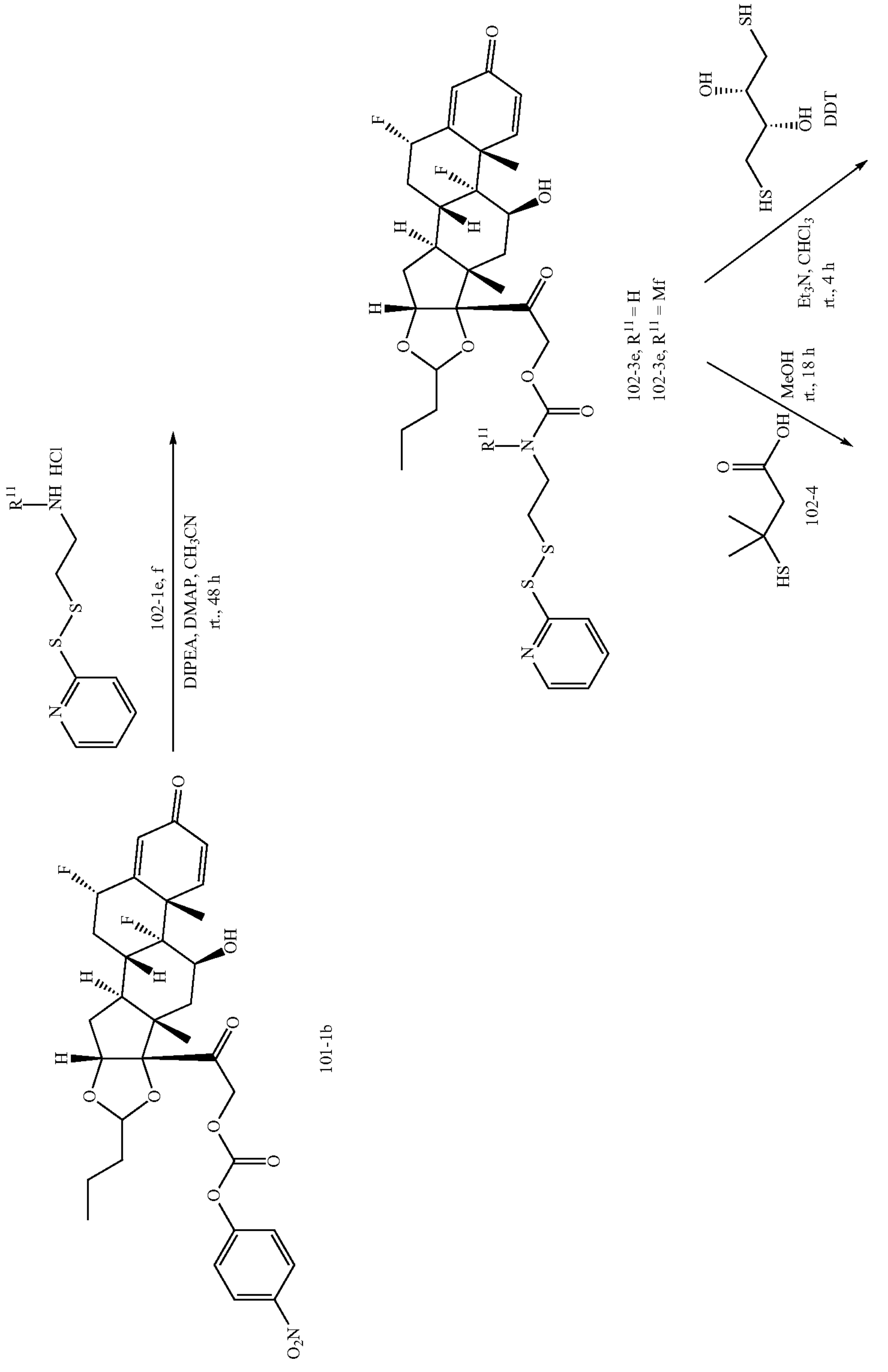
101-1b
102-1e, f
102-3e, $R^{11}$ = H
102-3e, $R^{11}$ = Mf
102-4
DDT -continued
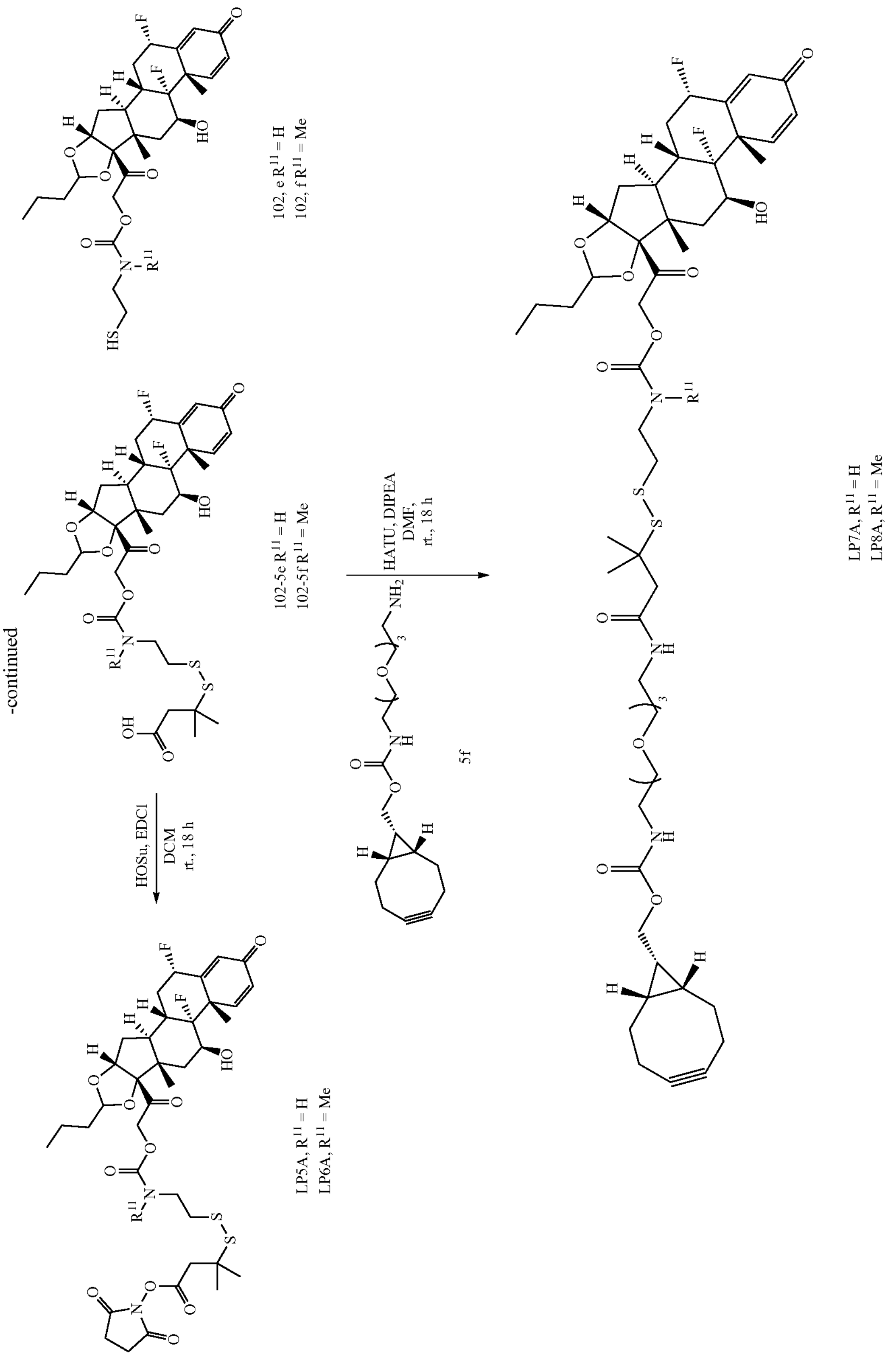
102, e $R^{11}$ = H
102, f $R^{11}$ = Me
102-5e $R^{11}$ = H
102-5f $R^{11}$ = Me
5f
LP5A, $R^{11}$ = H
LP6A, $R^{11}$ = Me
LP7A, $R^{11}$ = H
LP8A, $R^{11}$ = Me 2-(pyridin-2-yldisulfanyl)ethanamine hydrochloride (102-1e) was commercially available with CAS 83578-21-6. tert-butyl (2-mercaptoethyl)(methyl)carbamate (102-1f) was synthesized according to *Eur. J. Med. Chem.*, 2015, 95, 483-491.

endo-bicyclo[6.1.0]non-4-yn-9-ylmethyl N-(2-{2-[2-(2-aminoethoxy)ethoxy]ethoxy}ethyl)carbamate (5f) was synthesized according to WO2016168769.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-[2-(pyridin-2-yldisulfanyl)ethyl]carbamate (102-3e)

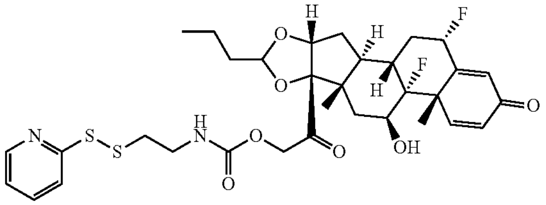

To a solution of compound 101-1b (0.54 g, 0.86 mmol) in acetonitrile (10 mL) were added DIPEA (0.22 g, 1.7 mmol), 102-1e (0.19 g, 0.86 mmol) and DMAP (10 mg, 86 μmol). The reaction mixture was stirred at RT for 48 hours until 101-1b was totally consumed according to LCMS. The mixture was then filtered and the filtrate was concentrated in vacuo. The residual oil was purified by silica gel column chromatography (20-50% ethyl acetate in hexane) to give compound 102-3e (0.47 g, 80% yield) as a white solid. ESI m/z: 679.2 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-[2-(pyridin-2-yldisulfanyl)ethyl]carbamate (102-3f)

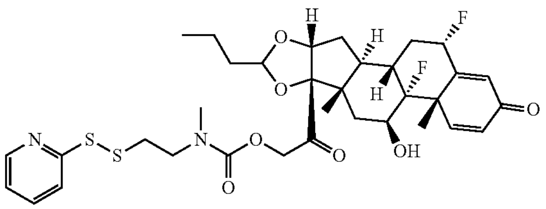

Following the similar procedure as 102-3e except substituting 102-1f for 102-1e, compound 102-3f (0.45 g, 75% yield) was obtained as a white solid. ESI m/z: 693.2 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-(2-sulfanylethyl)carbamate (102e)

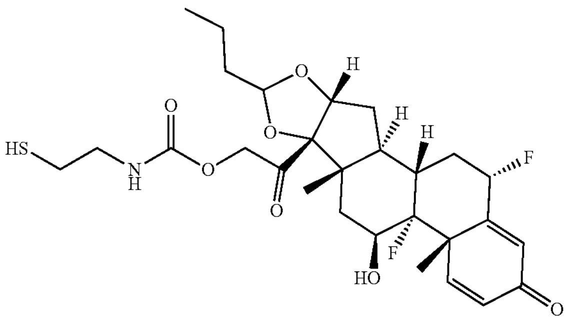 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCS)O1]

To a solution of compound 102-3e (1.4 g, 2.1 mmol) in chloroform (30 mL) were added triethylamine (0.82 mL, 5.9 mmol) and 1,4-dithiothreitol (Cleland's reagent, DTT) (1.2 g, 7.8 mmol). The reaction mixture was stirred at RT under nitrogen for 4 hours, which was monitored by LCMS. The resulting mixture was concentrated in vacuo. The residue was purified by silica gel column chromatography (50-70% ethyl acetate in hexane) to give compound 102e (0.95 g, 83% yield) as a white solid. ESI m/z: 570.2 (M+H)$^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl N-methyl-N-(2-sulfanylethyl)carbamate (102f)

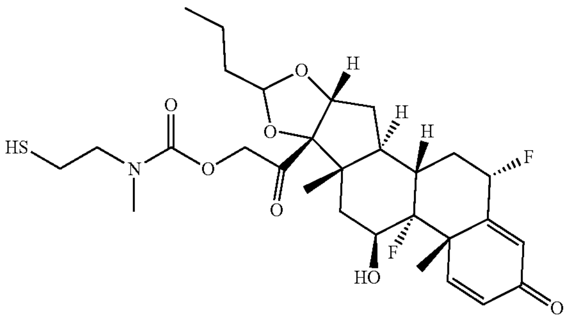 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCS)O1]

Following the similar procedure as 102e except substituting 102-3f for 102-3e, compound 102f (0.97 g, 83% yield) was obtained as a white solid. ESI m/z: 584.3 (M+H)$^+$.

3-({2-[({2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanoic acid (102-5e)

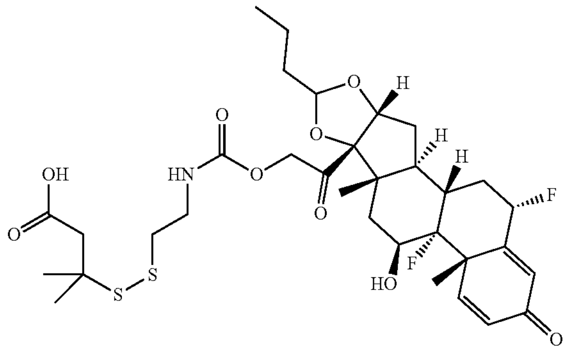 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)O)O1]

To a solution of compound 102-3e (0.68 g, 1.0 mmol) in methanol (5 mL) were added compound 102-4 (0.13 g, 1.0 mmol). The reaction mixture was stirred at RT for 18 hours, which was monitored by LCMS. The resulting mixture was then directly purified by prep-HPLC (method B) to give compound 102-5e (0.39 g, 55% yield) as a white solid. ESI m/z: 702.2 $(M+H)^+$.

3-({2-[({2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanoic acid (102-5f)

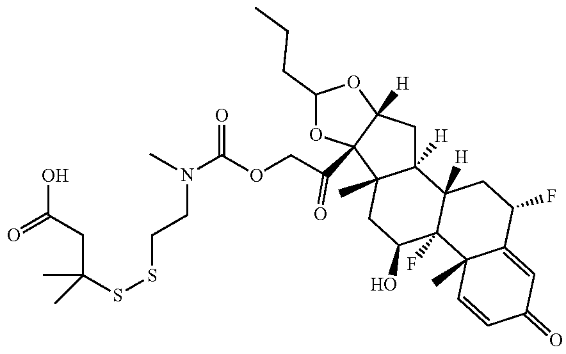 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)O)O1]

Following the similar procedure as 102-5e except substituting 102-3f for 102-3e, compound 102-5f (0.29 g, 40% yield) was obtained as a white solid. ESI m/z: 716.3 $(M+H)^+$.

2,5-Dioxopyrrolidin-1-yl 3-({2-[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanoate (LP5A)

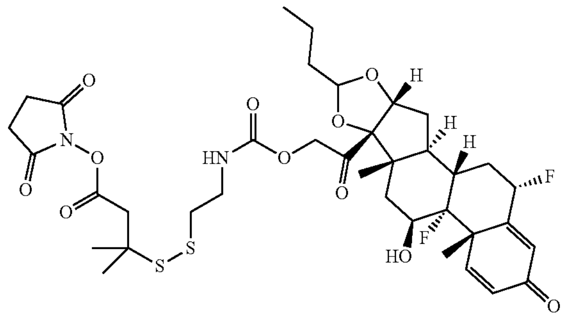 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)ON2C(=O)CCC2=O)O1]

To a solution of compound 102-5e (0.20 g, 0.29 mmol) in DCM (10 mL) were added HOSu (73 mg, 0.64 mmol) and EDCI (0.12 g, 0.64 mmol), and the mixture was stirred at RT for 24 hours, which was monitored by LCMS. The resulting mixture was diluted with DCM (50 mL) and the organic solution was washed with water and brine, dried over anhydrous sodium sulfate and concentrated in vacuo. The residue was purified by prep-HPLC (method A) to give LP5A (85 mg, 37% yield) as colorless oil. ESI m/z: 799.3 $(M+H)^+$.

2,5-Dioxopyrrolidin-1-yl 3-({2-[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanoate (LP6A)

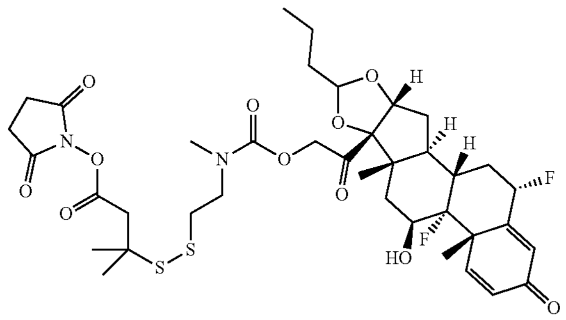 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)ON2C(=O)CCC2=O)O1]

Following the similar procedure as LP5A except substituting 102-5f for 102-5e, compound LP6A (86 mg, 36% yield) was obtained as colorless oil. ESI m/z: 813.3 $(M+H)^+$.

endo-Bicyclo[6.1.0]non-4-yn-9-ylmethyl N-{2-[2-(2-{2-[3-({2-[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)amino]ethyl}disulfanyl)-3-methylbutanamido]ethoxy}ethoxy)ethoxy]ethyl}carbamate (LP7A)

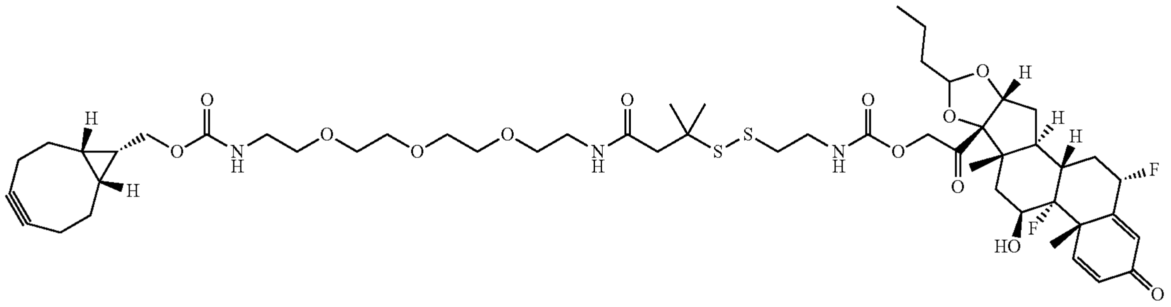 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)NCCSSC(C)(C)CC(=O)NCCOCCOCCOCCNC(=O)OC[C@@H]2[C@@H]3CCC#CCC[C@@H]32)O1]

To a solution of compound 102-5e (0.20 g, 0.29 mmol) in DMF (10 mL) were added HATU (0.11 g, 0.29 mmol) and DIPEA (75 mg, 0.58 mmol). The reaction mixture was stirred at RT for 10 minutes before compound 5f (0.11 g, 0.29 mmol) was added into. The reaction mixture was stirred at RT for 18 hours, which was monitored by LCMS. The resulting mixture was then directly purified by prep-HPLC (method B) to give compound LP7A (0.16 g, 55% yield) as a white solid. ESI m/z: 526.7 $(M/2+H)^+$.

endo-Bicyclo[6.1.0]non-4-yn-9-ylmethyl N-{2-[2-(2-{2-[3-({2-[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}carbonyl)(methyl)amino]ethyl}disulfanyl)-3-methylbutanamido]ethoxy}ethoxy)ethoxy]ethyl}carbamate (LP8A)

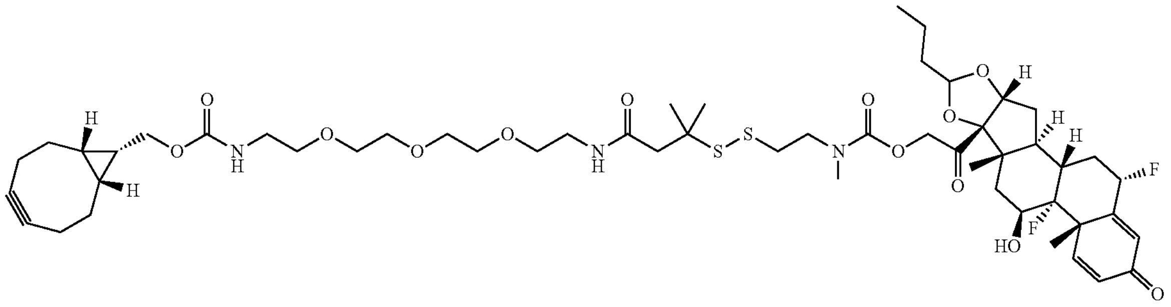 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)NCCOCCOCCOCCNC(=O)OC[C@@H]2[C@@H]3CCC#CCC[C@@H]32)O1]

Following the similar procedure as LP7A except substituting 102-5f for 102-5e, compound LP8A (0.13 g, 41% yield) was obtained as a white solid. ESI m/z: 533.8 $(M/2+H)^+$.

Synthesis of AMO Linker-Payloads LP9A-11A

Scheme 103A. Synthesis of Payloads 103a, b and Linker-payloads LP9A-10A
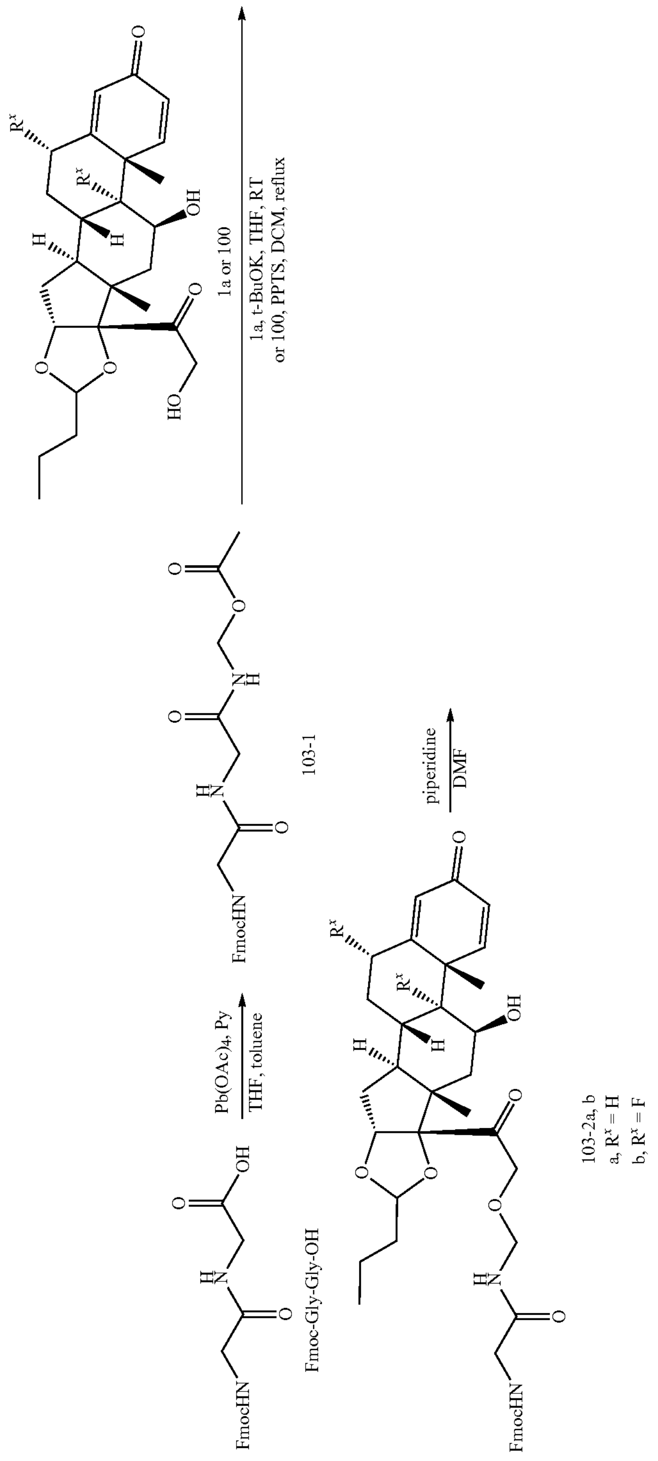
Fmoc-Gly-Gly-OH
103-1
103-2a, b
a, $R^x$ = H
b, $R^x$ = F -continued
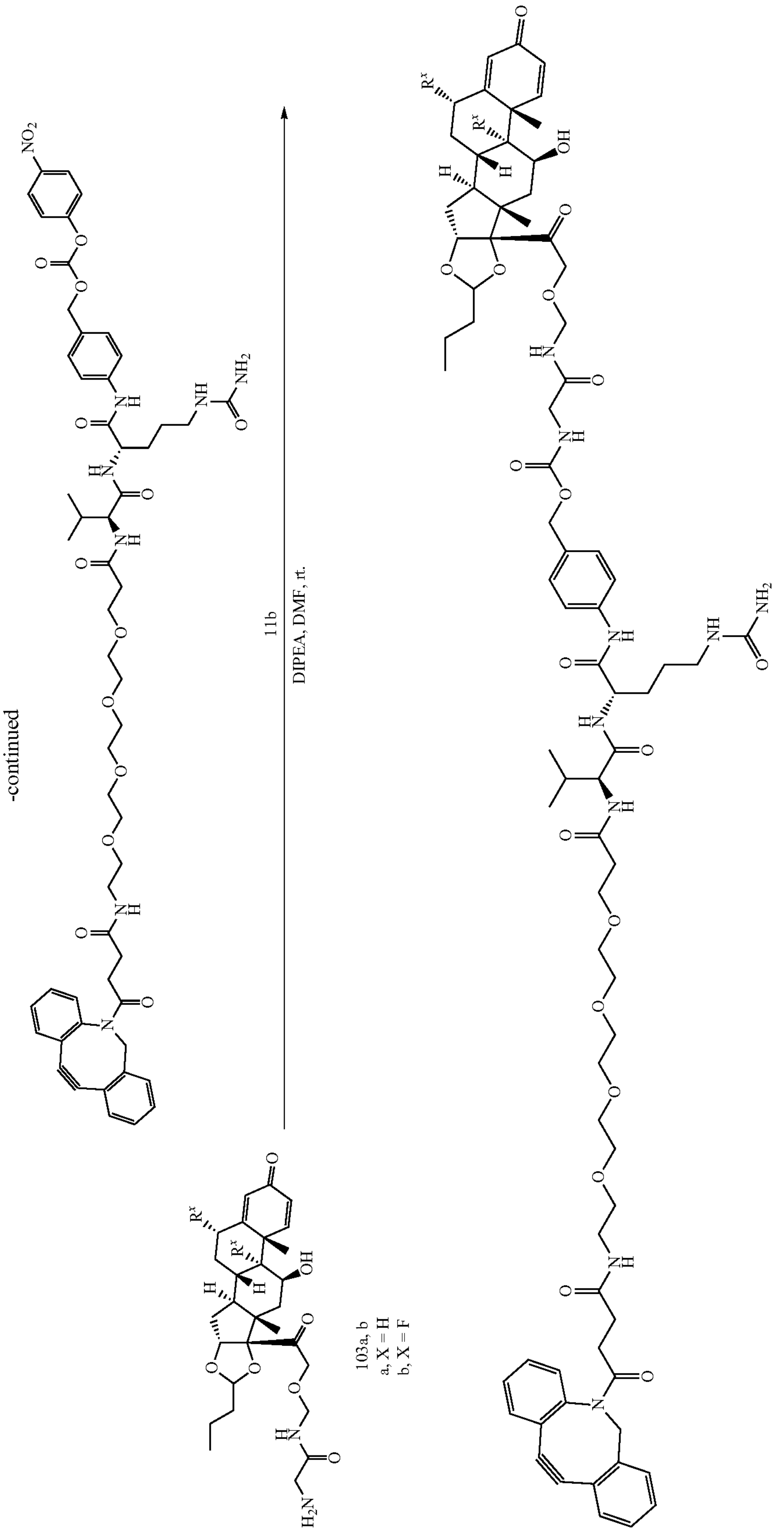
103a, b
a, X = H
b, X = F
LP9A, 10A
LP9A, $R^x$ = H
LP10A, $R^x$ = F (2-(((9H-Fluoren-9-yl)methoxy)carbonylamino)acetamido)methyl acetate (103-1)

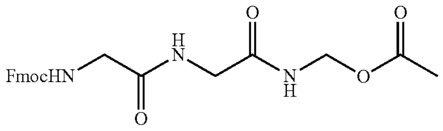

To a mixture of Fmoc-Gly-Gly-OH (4.3 g, 12 mmol) in THF (0.12 L) and toluene (40 mL) were added pyridine (1.2 mL, 15 mmol) and lead tetraacetate (6.8 g, 15 mmol). The reaction mixture was refluxed for 5 hours, which was monitored by LCMS. After cooled to RT, the reaction mixture was filtered through Celite to remove the insoluble material, and the filtrate was concentrated in vacuo. The residue was dissolved in ethyl acetate, and the solution was washed with water and brine. The organic solution was dried over sodium sulfate and concentrated in vacuo. The residue was purified by silica gel column chromatography (10% ethyl acetate in petroleum ether) to provide compound 103-1 (3.0 g, 67% yield) as a colorless solid. ESI m/z: 391 $(M+Na)^+$.

9H-Fluoren-9-ylmethyl N-{[({2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}methyl)carbamoyl]methyl}carbamate (103-2a)

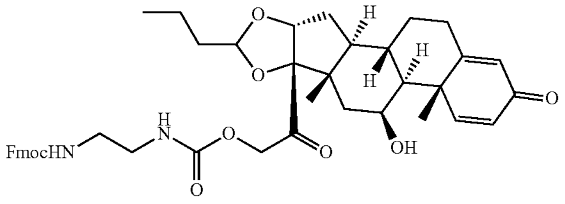

To a solution of compound 103-1 (0.37 g, 1.0 mmol) and budesonide 1a (1.3 g, 3.0 mmol) in THF (4 mL) was added potassium tert-butoxide (0.22 g, 2.0 mmol) at 0° C. The reaction mixture was stirred at RT for 15 minutes, which was monitored by TLC. The reaction solution was charged with ethyl acetate and water at 0° C., and extracted with ethyl acetate and chloroform. The combined organic solution was dried over sodium sulfate and concentrated in vacuo. The residue was purified by silica gel column chromatography (30-35% ethyl acetate in petroleum ether) to give compound 103-2a (0.19 g, 40% yield) as a white solid. ESI m/z: 739 $(M+H)^+$.

9H-Fluoren-9-ylmethyl N-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}methyl)carbamoyl]methyl}carbamate (103-2b)

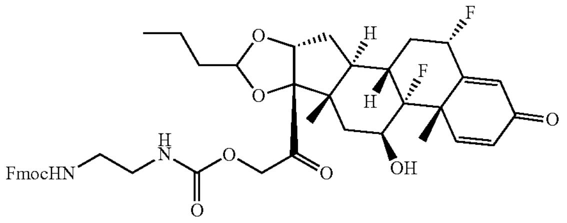

To a sealed tube were added a solution of compound 103-1 (0.30 g, 0.81 mmol) and compound 100 (0.38 g, 0.81 mmol) in DCM (4 mL) and pyridinium p-toluenesulfonate (21 mg, 81 μmol) at RT. The reaction tube was sealed and stirred at 50° C. for 24 hours, which was monitored by LCMS. After cooled, the reaction mixture was concentrated in vacuo and the residue was purified by prep-HPLC (method A) to give compound 103-2b (0.23 g, 37% yield) as a white solid. ESI m/z: 775 $(M+H)^+$.

2-Amino-N-({2-[(1S,2S,4R,8S,9S,11S,12S,13R)-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}methyl)acetamide (103a)

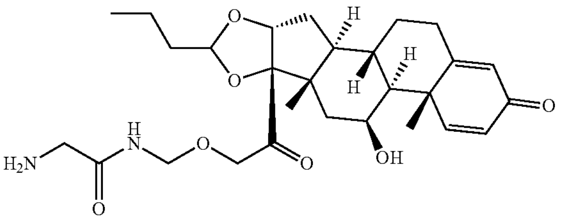

To a solution of compound 103-2a (0.10 g, 0.14 mmol) in DMF (2 mL) was added piperidine (35 mg, 0.41 mmol). The reaction mixture was stirred at RT for 2 hours until Fmoc was totally removed, which was monitored by LCMS. The resulting mixture was directly purified by reversed phase flash chromatography (0-100% acetonitrile in aq. TFA (0.05%)) to give compound 103a (50 mg, 70% yield) as a white solid. ESI m/z: 517.6 $(M+H)^+$.

2-Amino-N-({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)acetamide (103b)

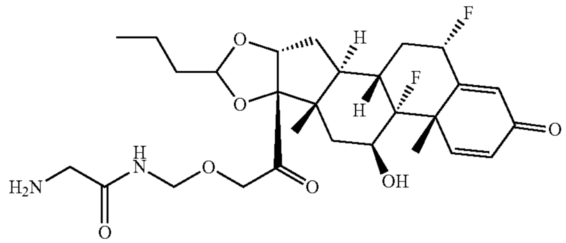

Following the similar procedure as 103a except substituting 103-2b for 103-2a, compound 103b (0.26 g, 65% yield) was obtained as a white solid. ESI m/z: 553.2 (M/2+H)$^+$.

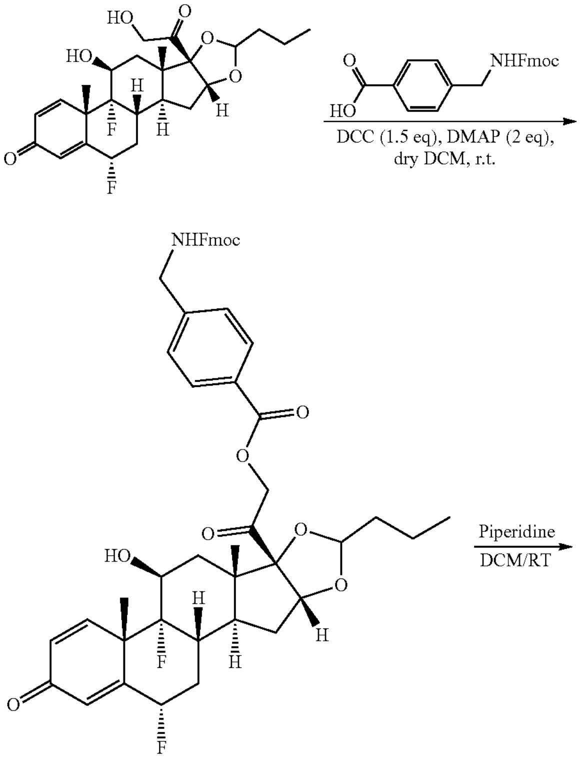

-continued

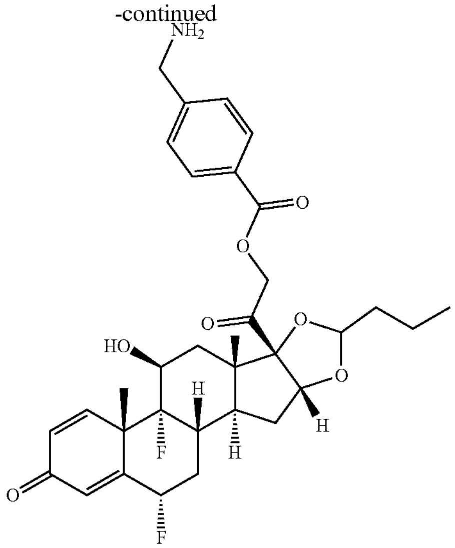

105b

Compound 105(b) was prepared according to the above procedure.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{[({2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamate (LP9A)

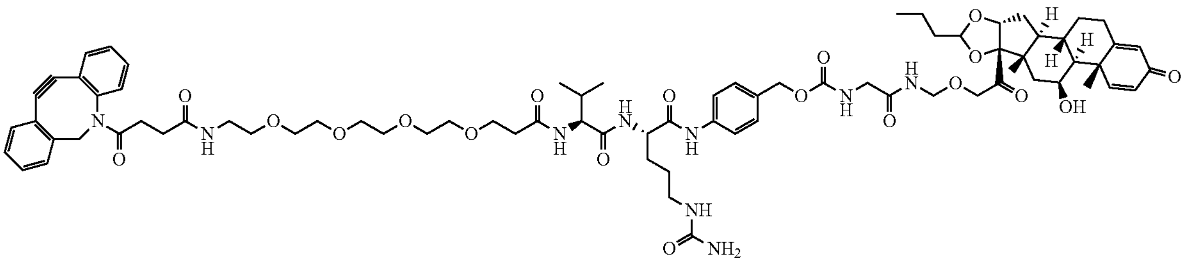

To a solution of compound 103a (15 mg, 29 μmol) in DMF (1.0 mL) were added compound 11b (30 mg, 28 μmol), HOBT (2.0 mg, 15 μmol) and DIPEA (7.7 mg, 60 μmol). The reaction mixture was stirred at RT for 2 hours, which was monitored by LCMS. The mixture was directly purified by prep-HPLC (method B) to give linker-payload LP9A (5.0 mg, 11% yield) as a white solid. ESI m/z: 729 (M/2+H)$^+$.

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamate (LP10A)

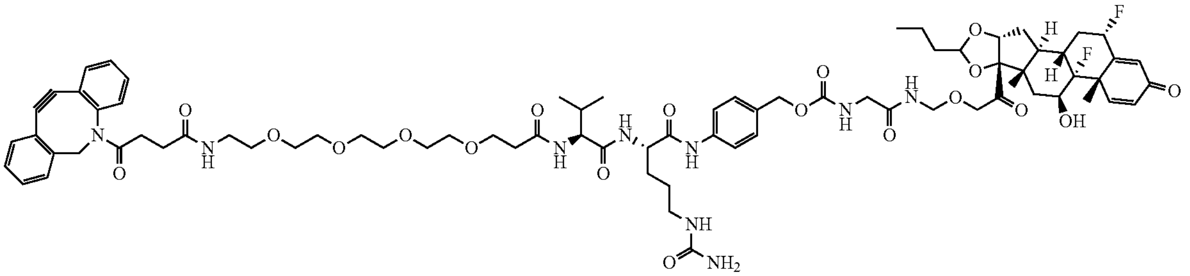

Following the similar procedure as LP9A except substituting 103b for 103a, linker-payload LP10A (23 mg, 58% yield) was obtained as a white solid. ESI m/z: 747.0 (M/2+H)$^+$; 513.8 (fragment cleaved by LCMS, piece cleaved at $NHCH_2$—O) $^1$HNMR (400 MHz, DMSO$_{d6}$) δ 10.02 (s, 1H), 8.80-8.72 (m, 1H), 8.15 (d, J=6.8 Hz, 1H), 7.89 (d, J=8.8 Hz, 1H), 7.80-7.75 (m, 1H), 7.68 (d, J=7.6 Hz, 1H), 7.64-7.58 (m, 3H), 7.54-7.22 (m, 9H), 6.29 (d, J=10.0 Hz, 1H), 6.10 (s, 1H), 6.04-5.96 (m, 1H), 5.78-4.10 (m, 15H), 3.66-3.54 (m, 5H), 3.54-3.42 (m, 13H), 3.32-3.26 (m, 2H), 3.20-2.50 (m, 7H), 2.42-2.20 (m, 4H), 2.05-1.90 (m, 4H), 1.85-1.25 (m, 15H), 0.90-0.80 (m, 13H) ppm.

Scheme 103B. Synthesis of Linker-payload LP11A

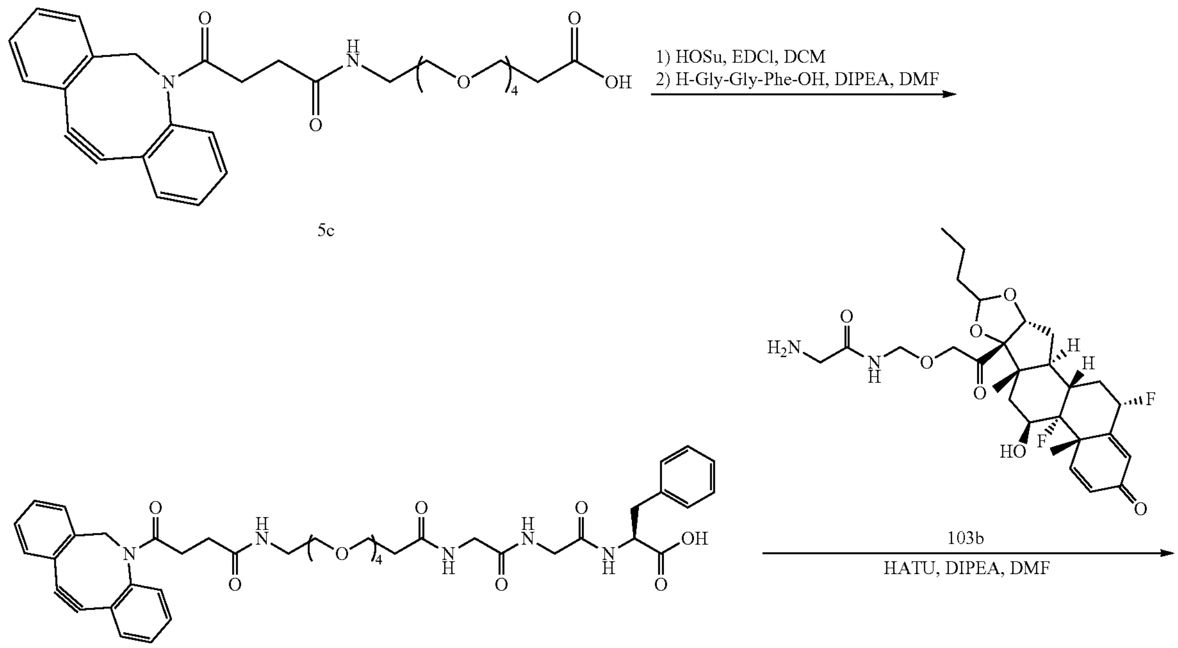

5c 103-3

-continued

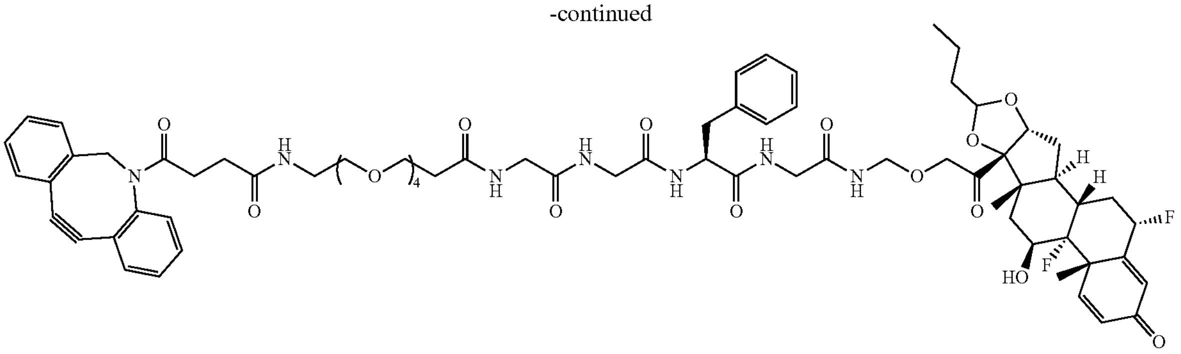

LP11A (2S)-2-(2-{2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]acetamido}acetamido)-3-phenylpropanoic acid (103-3)

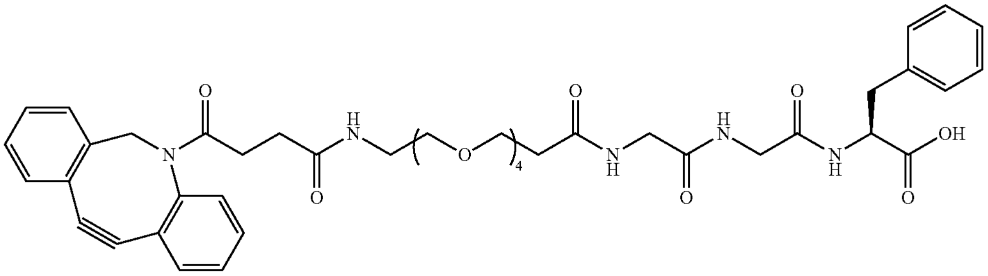

To a solution of compound 5c (0.16 g, 0.29 mmol) in DCM (20 mL) were added HOSu (73 mg, 0.64 mmol) and EDCI (0.12 g, 0.64 mmol). The mixture was stirred at RT for 24 hours until compound 5c was totally consumed according to LCMS. The resulting mixture was diluted with DCM (50 mL) and the organic solution was washed with water (50 mL) and brine (50 mL), dried with anhydrous sodium sulfate and concentrated in vacuo to give the OSu active ester (0.16 g, 84% yield) as colorless oil, which was used for next step directly. To a solution of H-Gly-Gly-Phe-OH (10 mg, 36 μmol) in DMF (0.5 mL) were added the OSu active ester (23 mg, 36 μmol) obtained above and DIPEA (9.0 mg, 72 μmol). The reaction mixture was stirred at RT overnight. The mixture was directly purified by prep-HPLC (method B) to give compound 103-3 (15 mg, 51% yield) as a white solid. ESI m/z: 408.2 (M/2+H)$^+$.

1-(4-{2-Azatricyclo[10.4.0.0$^{4,9}$]hexadeca-1(12),4(9),5,7,13,15-hexaen-10-yn-2-yl}-4-oxobutanamido)-N-{[({[(1 S)-1-({[({2-[(19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl)-2-phenylethyl]carbamoyl}methyl)carbamoyl]methyl}-3,6,9,12-tetraoxapentadecan-15-amide (LP11A)

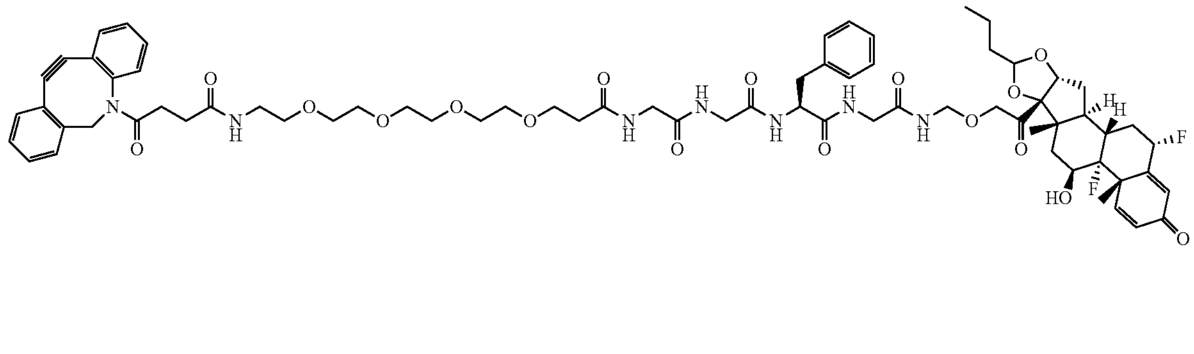 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COCNC(=O)CNC(=O)[C@H](Cc2ccccc2)NC(=O)CNC(=O)CNC(=O)CCOCCOCCOCCOCCNC(=O)CCC(=O)N2Cc3ccccc3C#Cc3ccccc32)O1]

To a solution of compound 103-3 (15 mg, 18 μmol) in DMF (0.5 mL) were added HATU (14 mg, 36 μmol) and DIPEA (9.3 mg, 72 μmol). The reaction mixture was stirred at RT for 10 min before compound 103b (10 mg, 18 μmol) was added into the mixture. The reaction mixture was then stirred at RT overnight. The resulting mixture was directly purified by prep-HPLC (method B) to give linker-payload LP11A (5.0 mg, 20% yield) as a white solid. ESI m/z: 420.2 $(M/3+H)^+$.

Synthesis of Dipeptide Prodrug: Linker-Payload LP12A

Scheme 104A. Synthesis of payload 104a

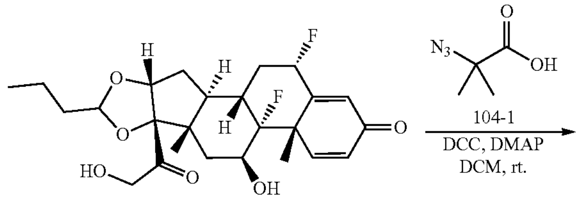

100

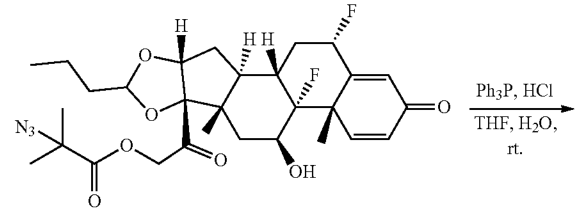

104-2a

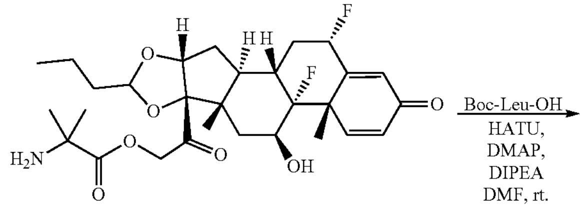

104-3a

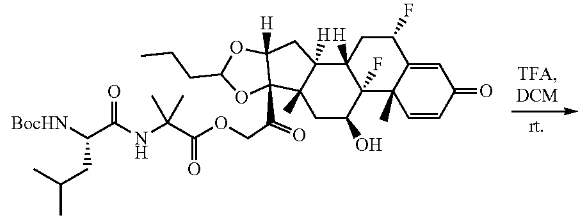

104-4a

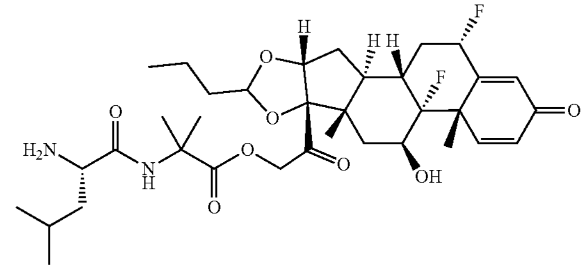

104a

Alpha-Azidoisobutyric acid 104-1 was synthesized according to *Org. Lett.,* 2001, 3(5), 781-783.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-azido-2-methylpropanoate (104-2a)

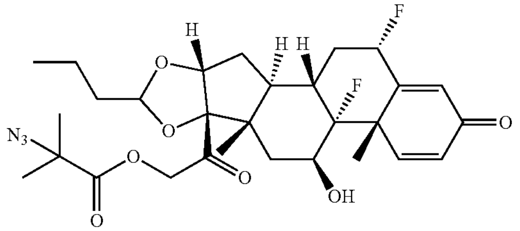

To a solution of compound 100 (0.10 g, 0.21 mmol) in DCM (30 mL) were added compound 104-1 (52 mg, 0.40 mmol), DCC (90 mg, 0.44 mmol) and DMAP (10 mg) and the mixture was stirred at RT overnight, which was monitored by LCMS. The resulting mixture was concentrated in vacuo and the residue was purified by prep-HPLC (method A) to give compound 104-2a (80 mg, 70% yield) as a white solid. ESI m/z: 578.3 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-amino-2-methylpropanoate (104-3a)

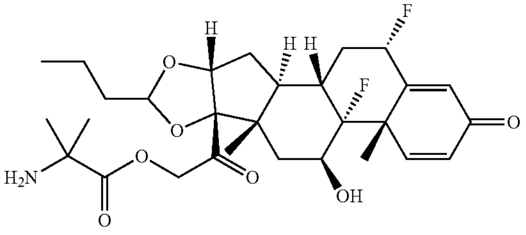

To a solution of compound 104-2a (75 mg, 0.15 mmol) in THF (5 mL) were added $PPh_3$ (0.15 g, 0.57 mmol), water (5 mL) and conc. HCl (1 drop), and the reaction mixture was stirred at RT overnight. The mixture was concentrated in vacuo and diluted with DMF. The precipitated was removed off by filtration. The filtrate was purified by prep-HPLC (method A) to give compound 104-3a (45 mg, 54% yield) as a white solid. ESI m/z: 552.3 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-{[(tert-butoxy)carbonyl]amino}-4-methylpentanamido]-2-methylpropanoate (104-4a)

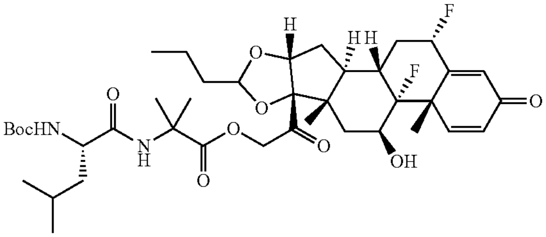

To a mixture of Boc-Leu-OH (20 mg, 87 μmol) and HATU (50 mg, 0.13 mmol) in DMF (3 mL) were added DIPEA (30 mg, 0.23 mmol), DMAP (2 mg) and compound 104-3a (30 mg, 54 μmol). The mixture was stirred at RT for an hour, which was monitored by LCMS. The mixture was directly purified by prep-HPLC (method A) to give compound 104-4a (25 mg, 55% yield) as a white solid. ESI m/z: 787.4 (M+Na)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-amino-4-methylpentanamido]-2-methylpropanoate (104a)

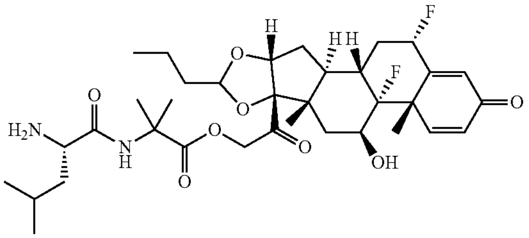

To a mixture of compound 104-4a (25 mg, 33 μmol) in DCM (1.5 mL) was added TFA (0.15 mL), and the mixture was stirred at RT for an hour until Boc was totally removed according to LCMS. The reaction mixture was concentrated in vacuo and the residue was purified by prep-HPLC (method A) to give compound 104a (13 mg, 61% yield) as a white solid. ESI m/z: 665.4 (M+H)$^+$. $^1$H NMR (400 MHz, DMSO$_{d6}$) δ 8.39 (s, 1H), 8.26 (s, 1H), 7.27 (d, J=10.0 Hz, 1H), 6.31 (d, J=10.1 Hz, 1H), 6.11 (s, 1H), 5.63 (t, J=24.2 Hz, 2H), 5.30-5.05 (m, 1H), 4.96 (d, J=17.7 Hz, 1H), 4.81-4.65 (m, 2H), 4.20 (s, 1H), 2.69-2.54 (m, 1H), 2.36-2.15 (m, 1H), 2.12-1.94 (m, 2H), 1.85-1.63 (m, 2H), 1.63-1.53 (m, 3H), 1.52-1.41 (m, 11H), 1.41-1.10 (m, 6H), 0.97-0.76 (m, 12H) ppm.

Scheme 104B. Synthesis of Linker-payload LP12A
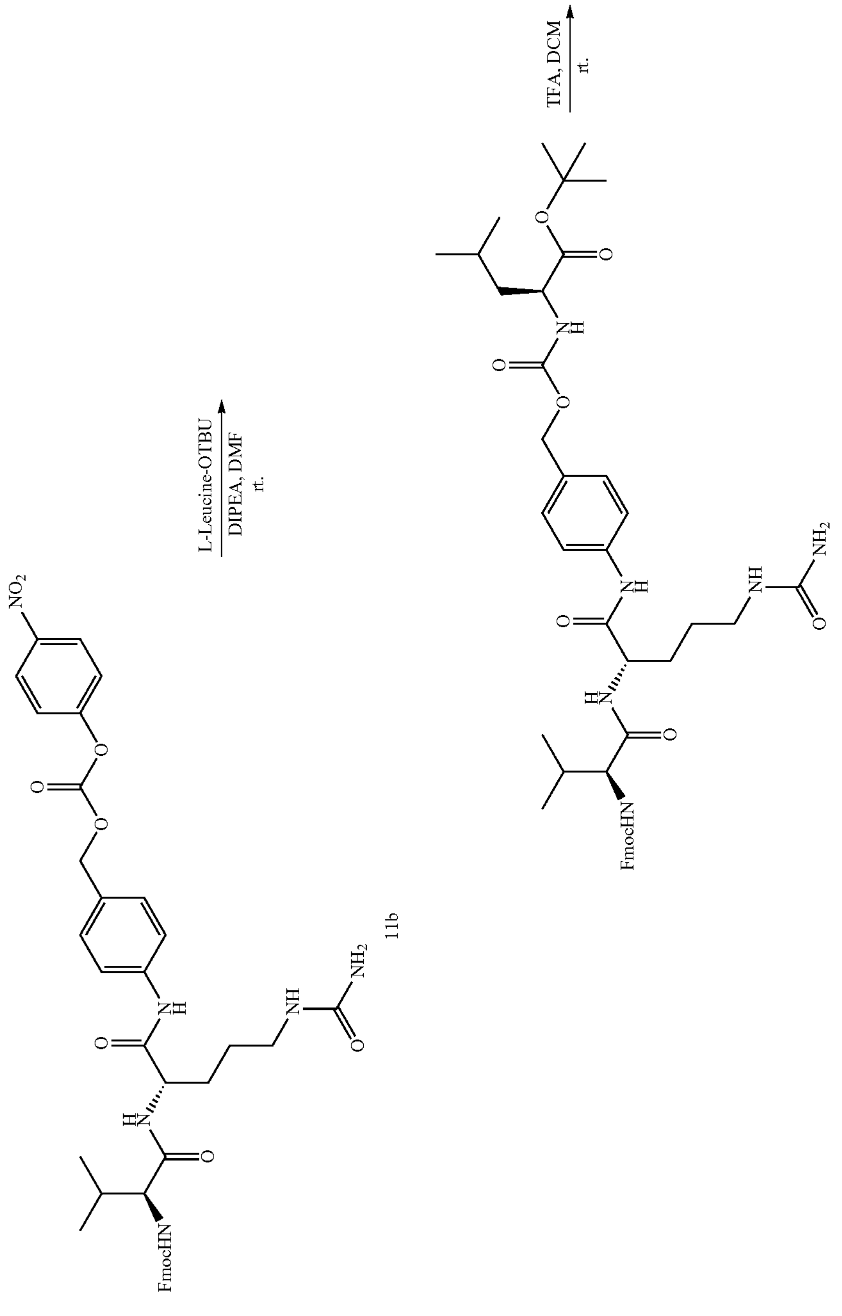
11b
104-5

-continued
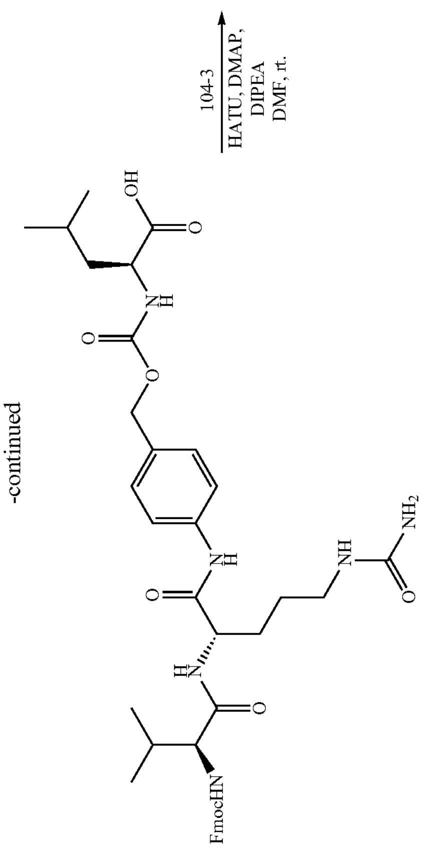
104-6
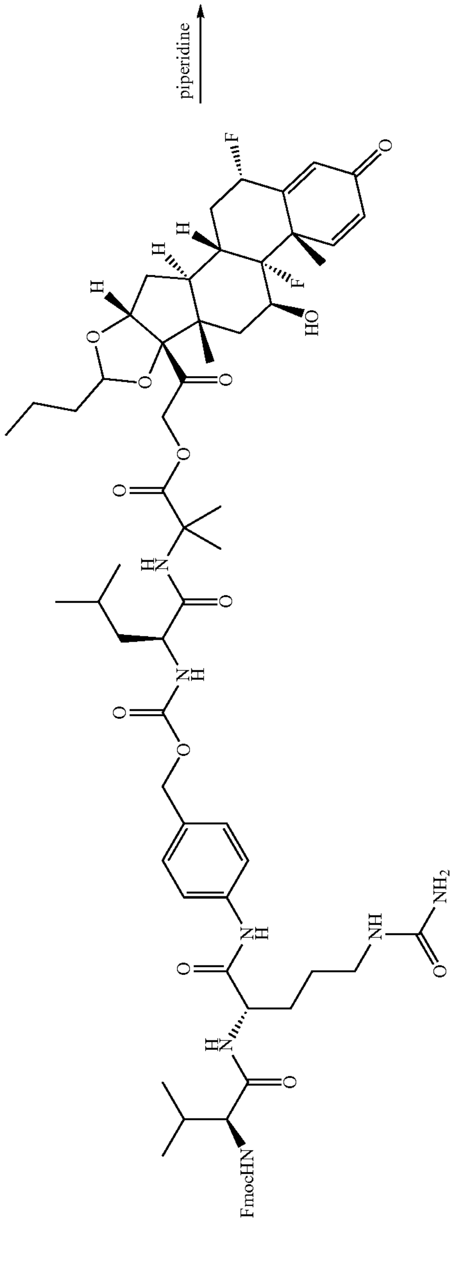
104-7a

-continued
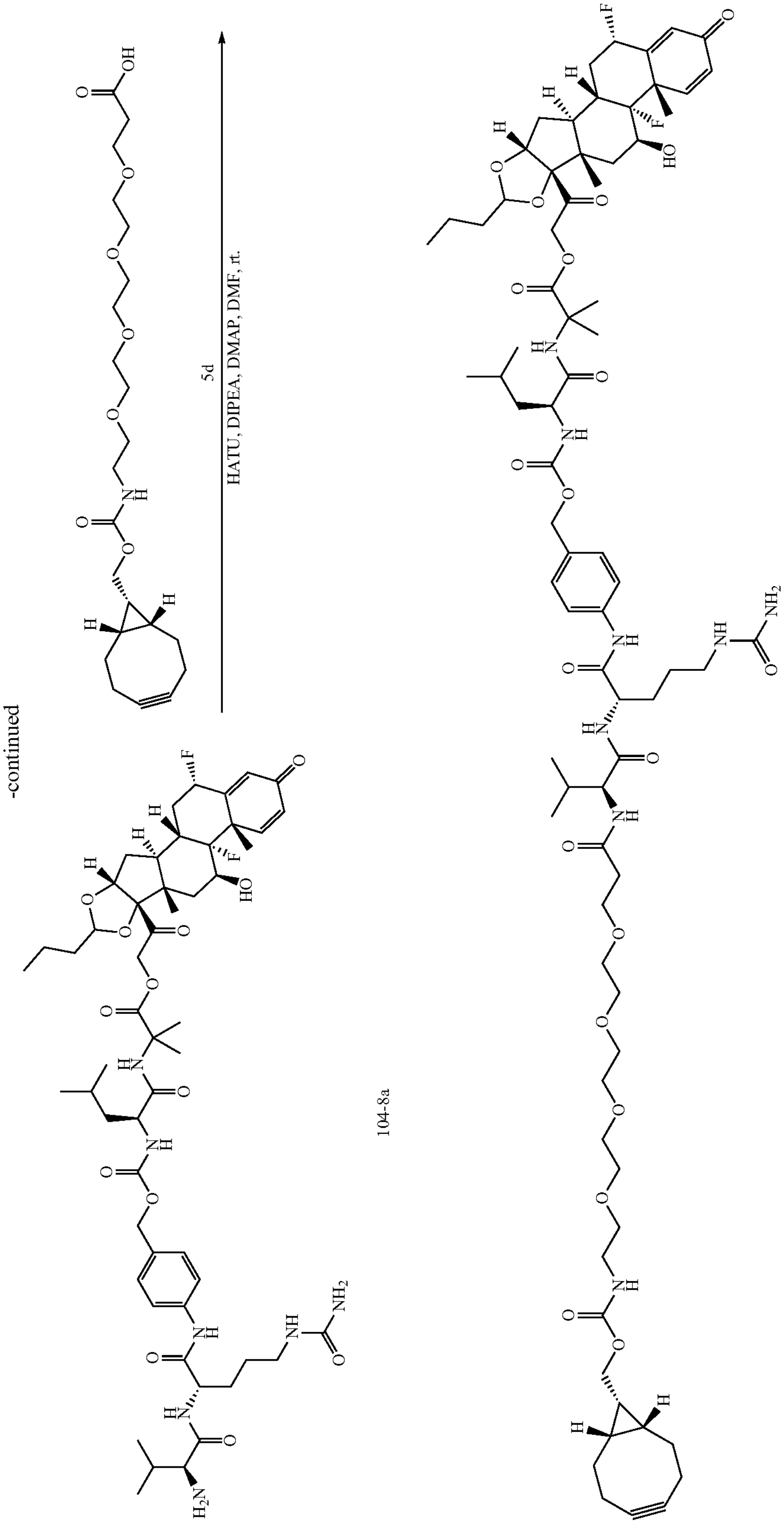
104-8a
LP12A tert-Butyl (2S)-2-{[({4-[(2S)-5-(carbamoylamino)-2-[2 S)-2-{[(9H-fluoren-9-ylmethoxy)carbonyl]amino}-3-methylbutanamido]pentanamido]phenyl}methoxy)carbonyl]amino}-4-methylpentanoate (104-5)

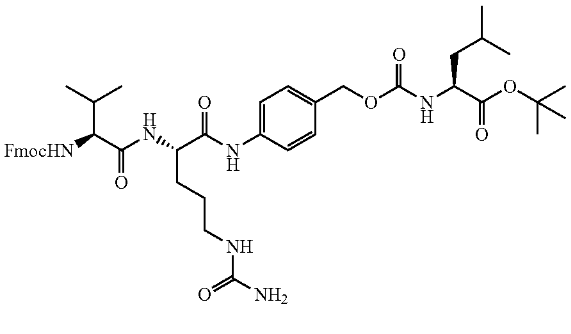

To a solution of compound 11b (0.30 g, 0.39 mmol) and H-Leu-OTBU-OH (0.14 g, 0.63 mmol) in DMF (3 mL) was added DIPEA (0.26 g, 2.0 mmol), and the reaction mixture was stirred at RT for 2 hours. The resulting mixture was directly purified by prep-HPLC (method A) to give compound 104-5 (0.11 g, 35% yield) as a white solid. ESI m/z: 815.4 $(M+H)^+$.

(2S)-2-{[({4-[(2S)-5-(Carbamoylamino)-2-[(2S)-2-{[(9H-fluoren-9-ylmethoxy)carbonyl]amino}-3-methylbutanamido]pentanamido]phenyl}methoxy)carbonyl]amino}-4-methylpentanoic acid (104-6)

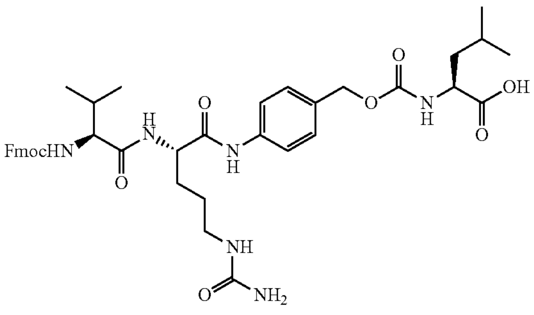

To a solution of compound 104-5 (25 mg, 31 μmol) in DCM (4 mL) was added TFA (0.8 mL) and the mixture was stirred at RT for 2 hours. The resulting mixture was concentrated in vacuo and the residue was purified by prep-HPLC (method A) to give compound 104-6 (15 mg, 67% yield) as a white solid. ESI m/z: 759.3 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-{[({4-[(2S)-5-(carbamoylamino)-2-[(2S)-2-{[(9H-fluoren-9-ylmethoxy)carbonyl]amino}-3-methylbutanamido]pentanamido]phenyl}methoxy)carbonyl]amino}-4-methylpentanamido]-2-methylpropanoate (104-7a)

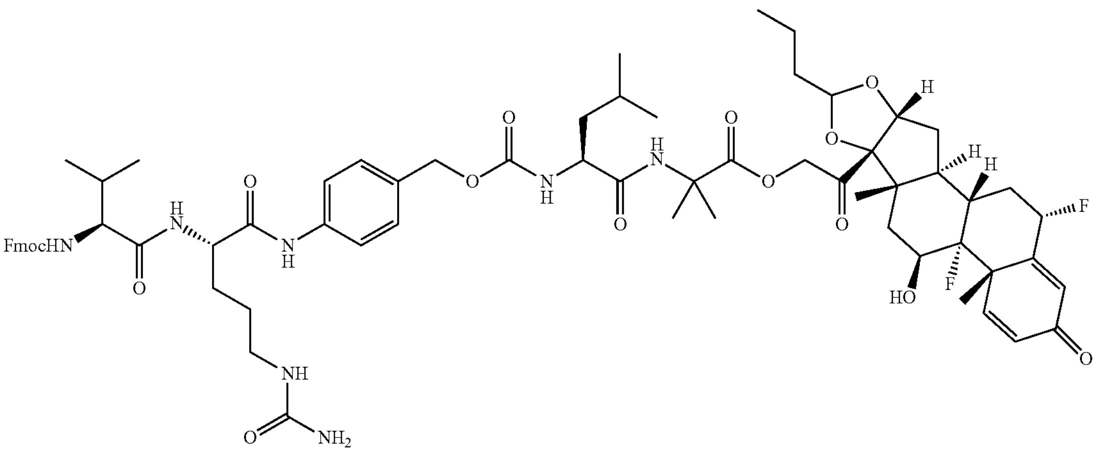

To a solution of compound 104-5 (20 mg, 26 μmol) and compound 104-3 (17 mg, 32 μmol) in DMF (2 mL) were added HATU (20 mg, 52 μmol), DIPEA (13 mg, 0.10 mmol) and DMAP (1 mg), and the reaction mixture was stirred at RT for an hour, which was monitored by LCMS. The resulting mixture was directly purified by prep-HPLC (method A) to give compound 104-7a (30 mg, 89% yield) as a white solid. ESI m/z: 1293 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-{[({4-[(2S)-2-[(2S)-2-amino-3-methylbutanamido]-5-(carbamoylamino)pentanamido]phenyl}methoxy)carbonyl]amino}-4-methylpentanamido]-2-methylpropanoate (104-8a)

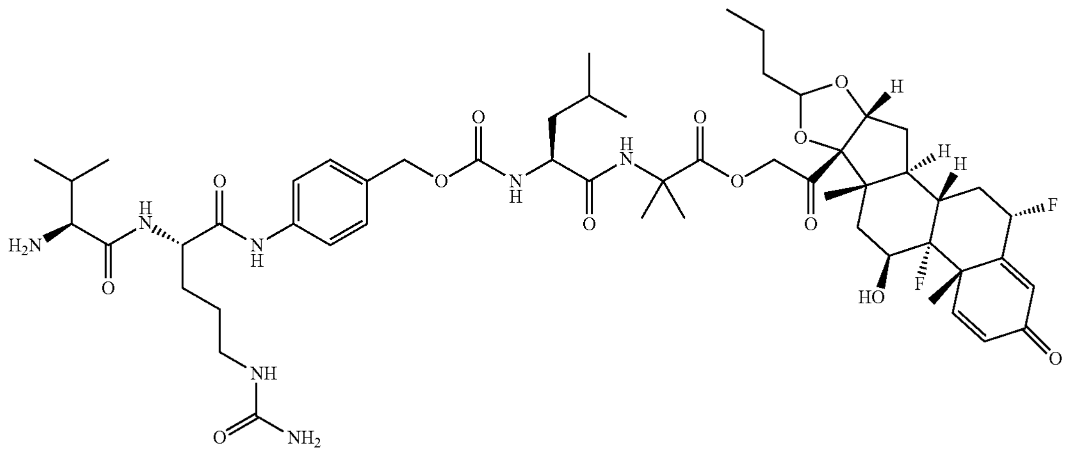 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](N)C(C)C)cc2)O1]

To a solution of compound 104-7a (25 mg, 19 μmol) in DMF (2 mL) was added piperidine (0.2 mL), and the mixture was stirred at RT for half an hour until Fmoc was totally removed according to LCMS. The reaction mixture was immediately purified by reversed phase flash chromatography (0-50% acetonitrile in aq. TFA (0.03%)) to give compound 104-8a (20 mg, 95% yield) as a white solid. ESI m/z: 1070.5 $(M+H)^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl 2-[(2S)-2-{[({4-[(2S)-2-[(2S)-2-[1-({[endo-bicyclo[6.1.0]non-4-yn-9-ylmethoxy]carbonyl}amino)-3,6,9,12-tetraoxapentadecan-15-amido]-3-methylbutanamido]-5-(carbamoylamino)pentanamido]phenyl}methoxy)carbonyl]amino}-4-methylpentanamido]-2-methylpropanoate (LP12A)

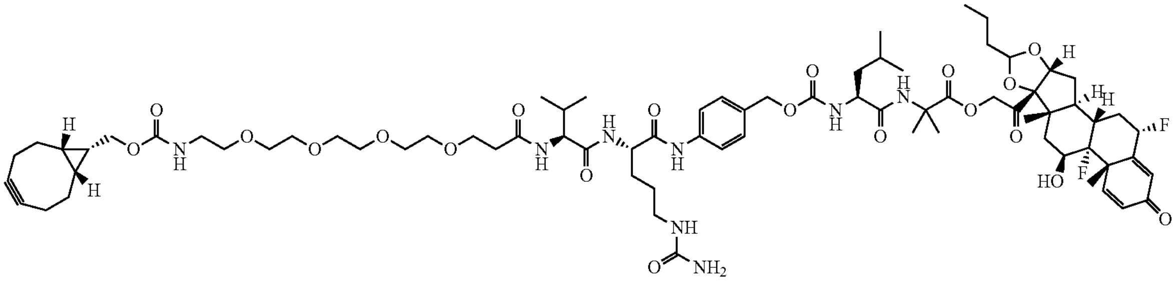 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1]

To a solution of compound 104-8a (20 mg, 26 μmol) and compound 5d (14 mg, 32 μmol) in DMF (2 mL) were added HATU (22 mg, 58 μmol), DIPEA (15 mg, 0.12 mmol) and DMAP (1 mg), and the reaction mixture was stirred at RT for 2 hours, which was monitored by LCMS. The resulting mixture was directly purified by prep-HPLC (method A) to give linker-payload LP12A (10 mg, 21% yield) as a white solid. ESI m/z: 747.6 $(M/2+H)^+$. $^1H$ NMR (400 MHz, $DMSO_{d6}$) δ 9.97 (s, 1H), 8.35-8.25 (m, 1H), 8.11 (d, J=7.4 Hz, 1H), 7.87 (d, J=8.6 Hz, 1H), 7.58 (d, J=8.2 Hz, 2H), 7.34-7.18 (m, 4H), 7.17-7.04 (m, 1H), 6.30 (d, J=10.1 Hz, 1H), 6.11 (s, 1H), 6.03-5.90 (s, 1H), 5.72-5.50 (m, 2H), 5.41 (s, 2H), 5.34-3.91 (m, 12H), 3.66-3.38 (m, 15H), 3.15-2.88 (m, 4H), 2.73-2.53 (m, 1H), 2.50-2.45 (m, 1H), 2.41-2.31 (m, 1H), 2.30-1.90 (m, 9H), 1.83-1.62 (m, 2H), 1.63-1.17 (m, 27H), 0.92-0.77 (m, 20H) ppm.

Scheme 104C. Synthesis of Payload 104b and its linker-payload LP13A
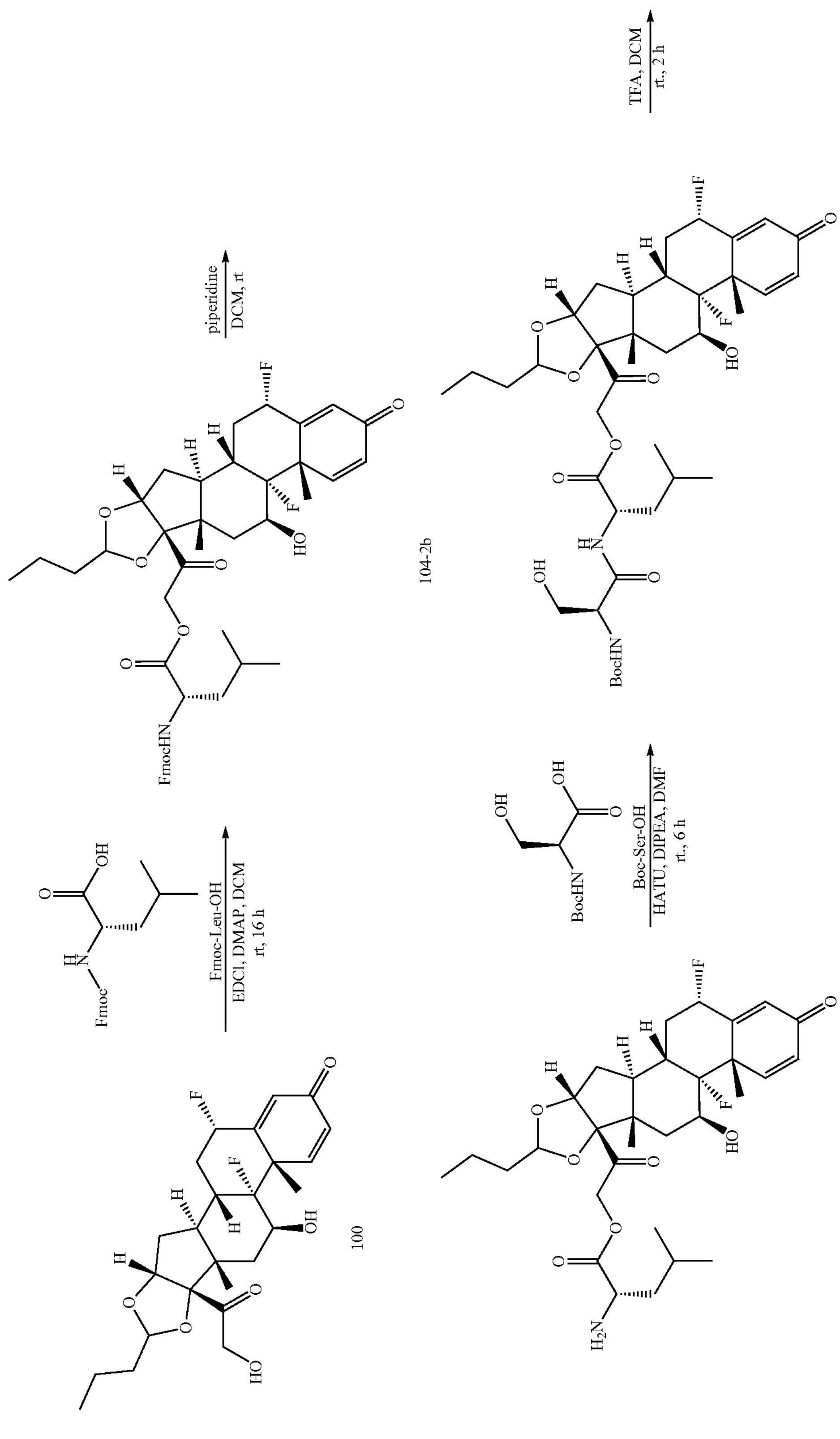
100
104-2b
104-3b
104-4b -continued
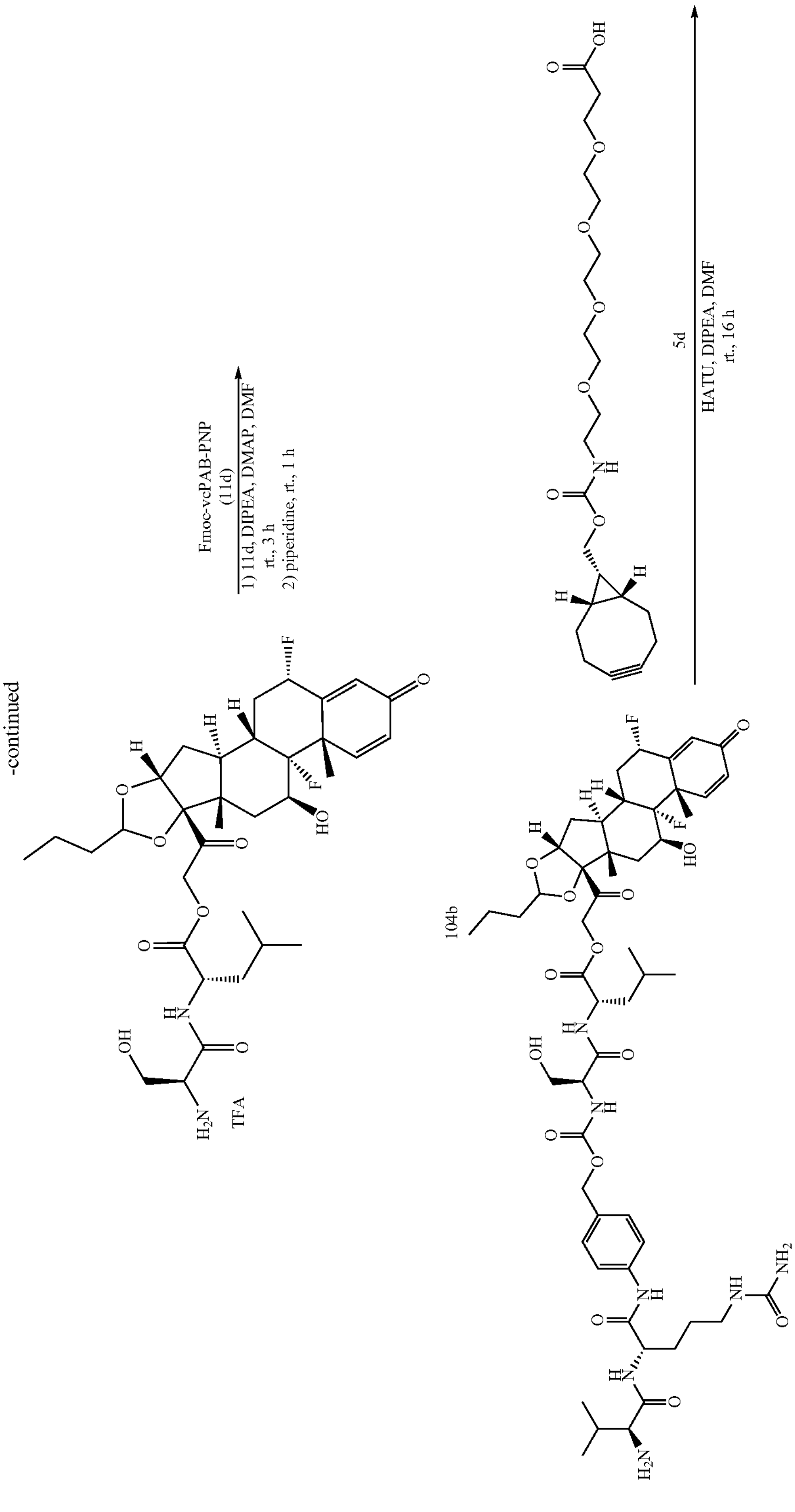
104b
104-8b -continued
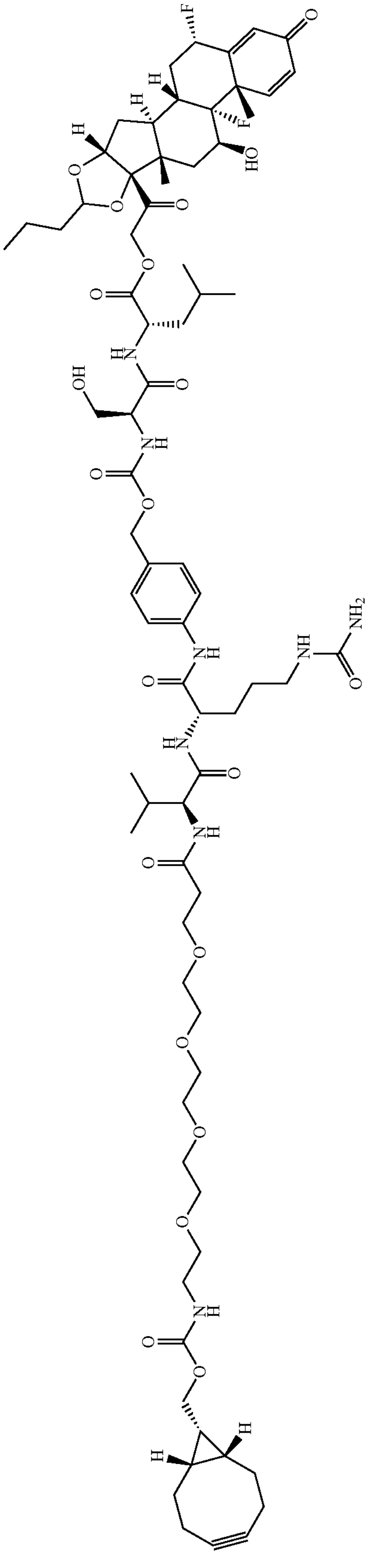
LP13A 2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-{[(9H-fluoren-9-ylmethoxy)carbonyl]amino}-4-methylpentanoate (104-2b)

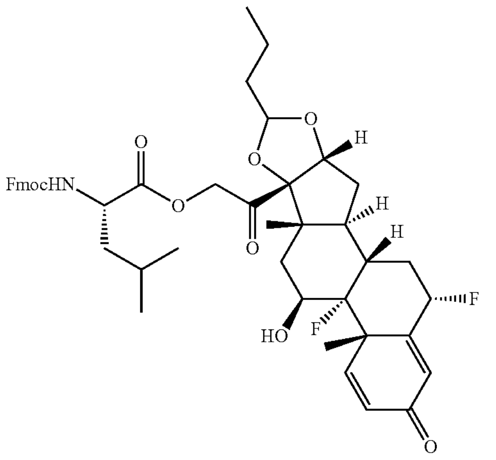

To a solution of compound 100 (0.47 g, 1.0 mmol) and Fmoc-Leu-OH (0.39 g, 1.1 mmol) in DCM (10 mL) were added EDCI (0.23 g, 1.2 mmol) and DMAP (12 mg, 0.10 mmol). The mixture was stirred at RT for 16 hours, which was monitored by LCMS. The resulting mixture was diluted with water (50 mL) and extracted with DCM (50 mL×2). The combined organic solution was dried over sodium sulfate and concentrated in vacuo. The residue was purified silica gel column chromatography (10-50% ethyl acetate in petroleum ether) to give compound 104-2b (0.52 g, 65% yield) as a white solid. ESI m/z: 802.4 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-amino-4-methylpentanoate (104-3b)

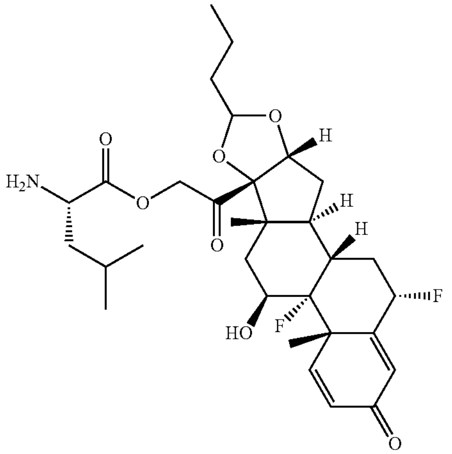 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@@H](N)CC(C)C)O1]

To a solution of compound 104-2b (0.50 g, 0.62 mmol) in DCM (9 mL) was added piperidine (1 mL) and the reaction mixture was stirred at RT for 30 minutes until Fmoc was totally removed according to LCMS. The resulting mixture was concentrated in vacuo. The residue was purified by silica gel column chromatography (5-10% methanol in DCM) to give compound 104-3b (0.32 g, 90% yield) as a white solid. ESI m/z: 580.3 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[(tert-butoxy)carbonyl]amino}-3-hydroxypropanamido]-4-methylpentanoate (104-4b)

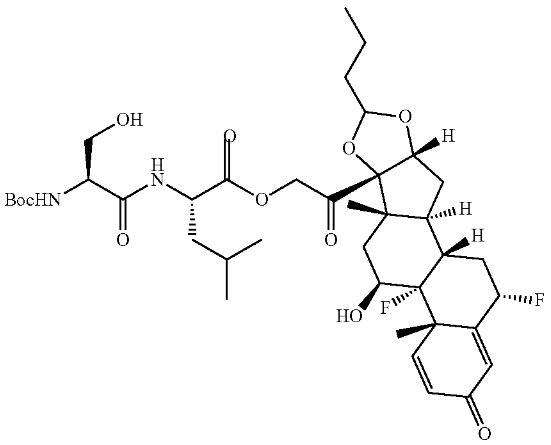

To a mixture of compound 104-3b (0.32 g, 0.55 mmol) and Boc-Ser-OH (0.14 g, 0.66 mmol) in DMF (3 mL) were added HATU (0.25 g, 0.66 mmol) and DIPEA (0.21 g, 1.6 mmol) at RT. The mixture was stirred at RT for 6 hours, which was monitored by LCMS. The resulting mixture was concentrated in vacuo, and the residue was purified silica gel column chromatography (10-50% ethyl acetate in petroleum ether) to give compound 104-4b (0.34 mg, 80% yield) as a white solid. ESI m/z: 767.4 $(M+H)^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-amino-3-hydroxypropanamido]-4-methylpentanoate trifluoroacetic acid salt (104b)

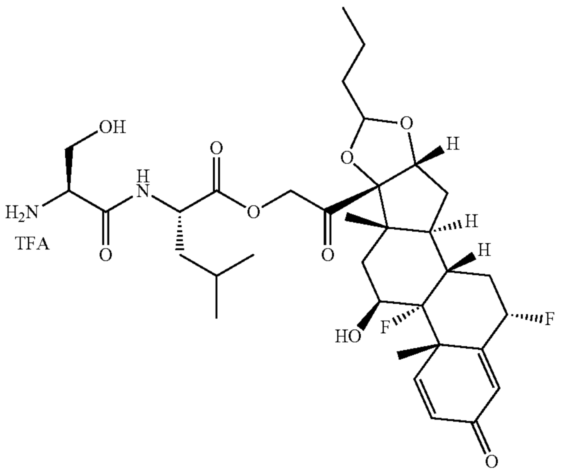 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@@H](N)CO)O1]

To a solution of compound 104-4b (0.34 g, 0.44 mmol) in DCM (5 mL) was added TFA (1 mL). The reaction mixture was stirred at RT for 2 hours until Boc was totally removed according to LCMS. The resulting mixture was concentrated and the residue (0.33 g, 95% yield) was pure enough for the next step. 100 mg of crude product was further purified by prep-HPLC (method A) to give compound 104b (80 mg, 80% yield) as a yellow solid. ESI m/z: 667.3 (M+H)$^+$.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[({4-[(2S)-2-[(2S)-2-amino-3-methylbutanamido]-5-(carbamoylamino)pentanamido]phenyl}methoxy)carbonyl]amino}-3-hydroxypropanamido]-4-methylpentanoate (104-8b)

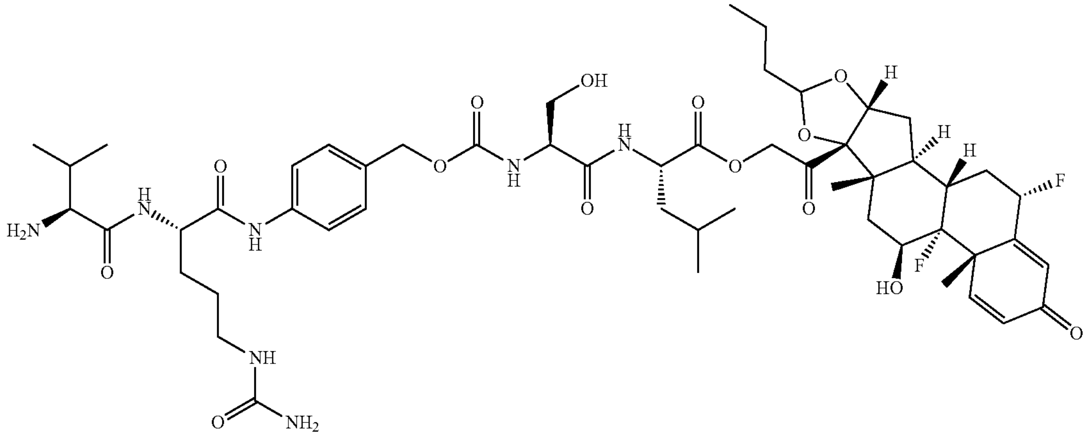 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](N)C(C)C)cc2)O1]

To a solution of crude compound 104b (0.10 g, 0.13 mmol) freshly obtained above in DMF (3 mL) were added Fmoc-vcPAB-PNP (11d) (0.12 g, 0.16 mmol), DMAP (16 mg, 0.13 mmol) and DIPEA (50 mg, 0.39 mmol) at RT. The mixture was stirred at RT for 3 hours until most of starting materials were consumed, which was monitored by LCMS. To the reaction mixture was then added piperidine (1 mL). After stirred at room temperature for an hour until the Fmoc was totally removed according to LCMS. The reaction mixture was directly purified by prep-HPLC (method B) to give compound 104-8b (28 mg, 20% yield) as a white solid. ESI m/z: 536.8 (M/2+H)$^+$.

2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl (2S)-2-[(2S)-2-{[({4-[(2S)-2-[(2S)-2-[1-({[endo-bicyclo[6.1.0]non-4-yn-9-ylmethoxy]carbonyl}amino)-3,6,9,12-tetraoxapentadecan-15-amido]-3-methylbutanamido]-5-(carbamoylamino)pentanamido]phenyl}methoxy)carbonyl]amino}-3-hydroxypropanamido]-4-methylpentanoate (LP13A)

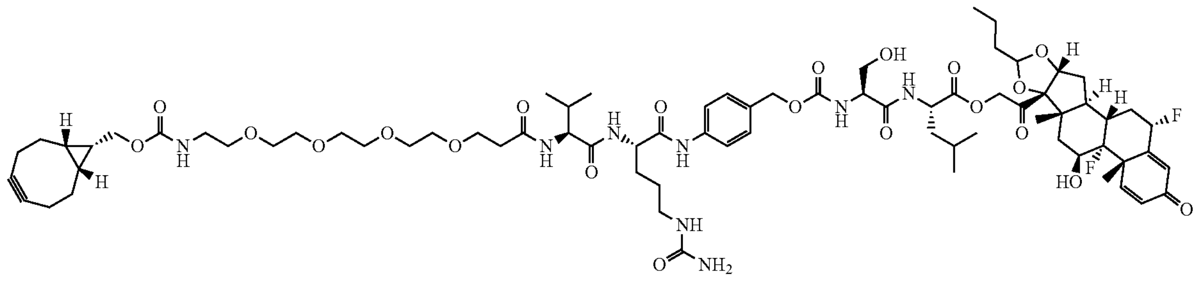 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1]

To a solution of compound 5d (10 mg, 22 μmol) in DMF (1 mL) were added HATU (9 mg, 22 μmol) and DIPEA (8.0 mg, 62 μmol) successively at RT. The mixture was stirred at RT for half an hour followed by the addition of a solution of compound 104-8b (20 mg, 19 μmol) in DMF (1 mL). The resulting mixture was stirred at RT for 2 hours until compound 104-8b was consumed, which was monitored by LCMS. After filtered through membrane, the filtrate was directly purified by prep-HPLC (method B) to give linker-payload LP13A (10 mg, 35% yield) as a white solid. ESI m/z: 748.4 (M/2+H)$^+$.

Scheme 105. Synthesis of LP18A-21A
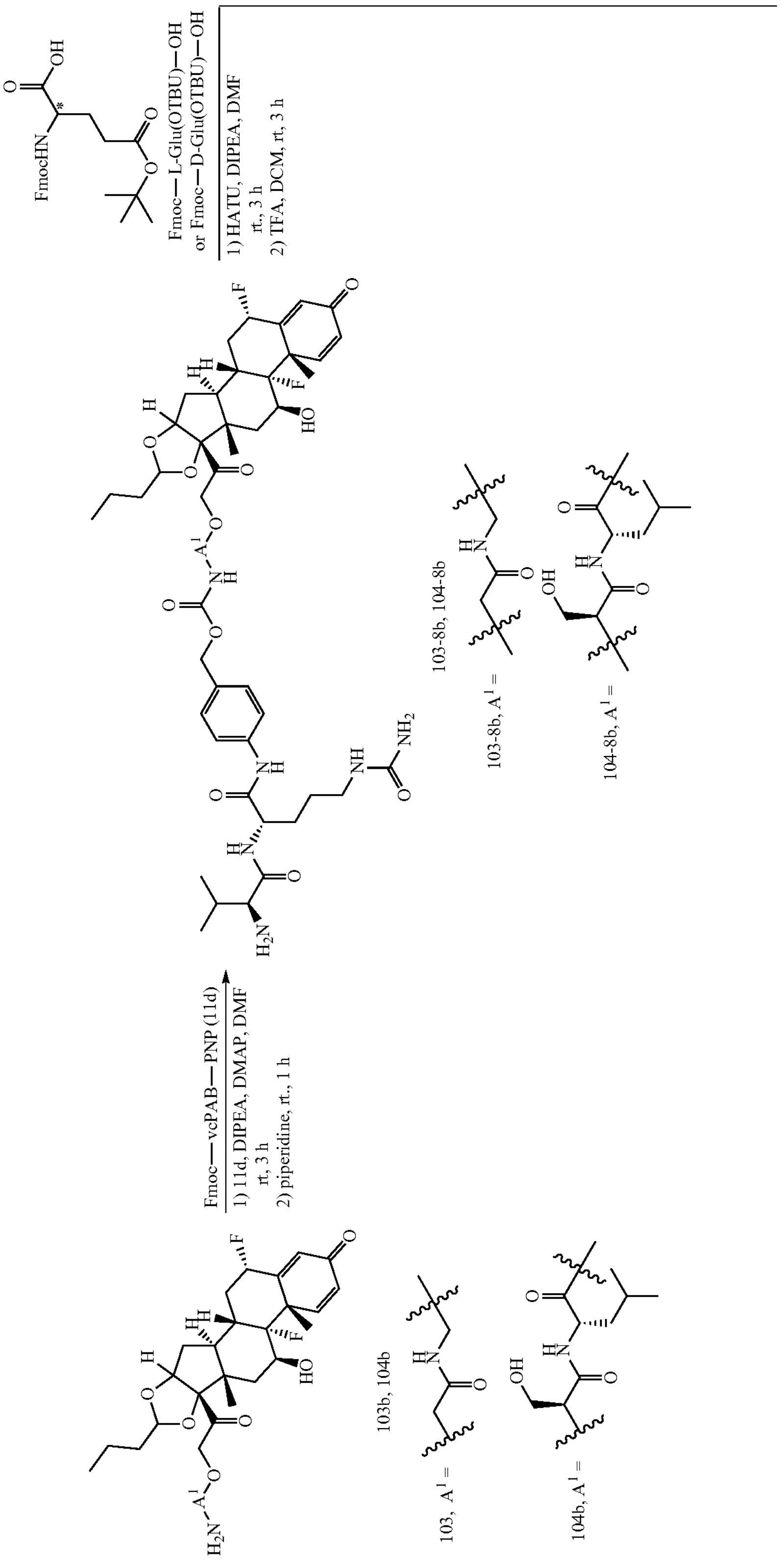

-continued
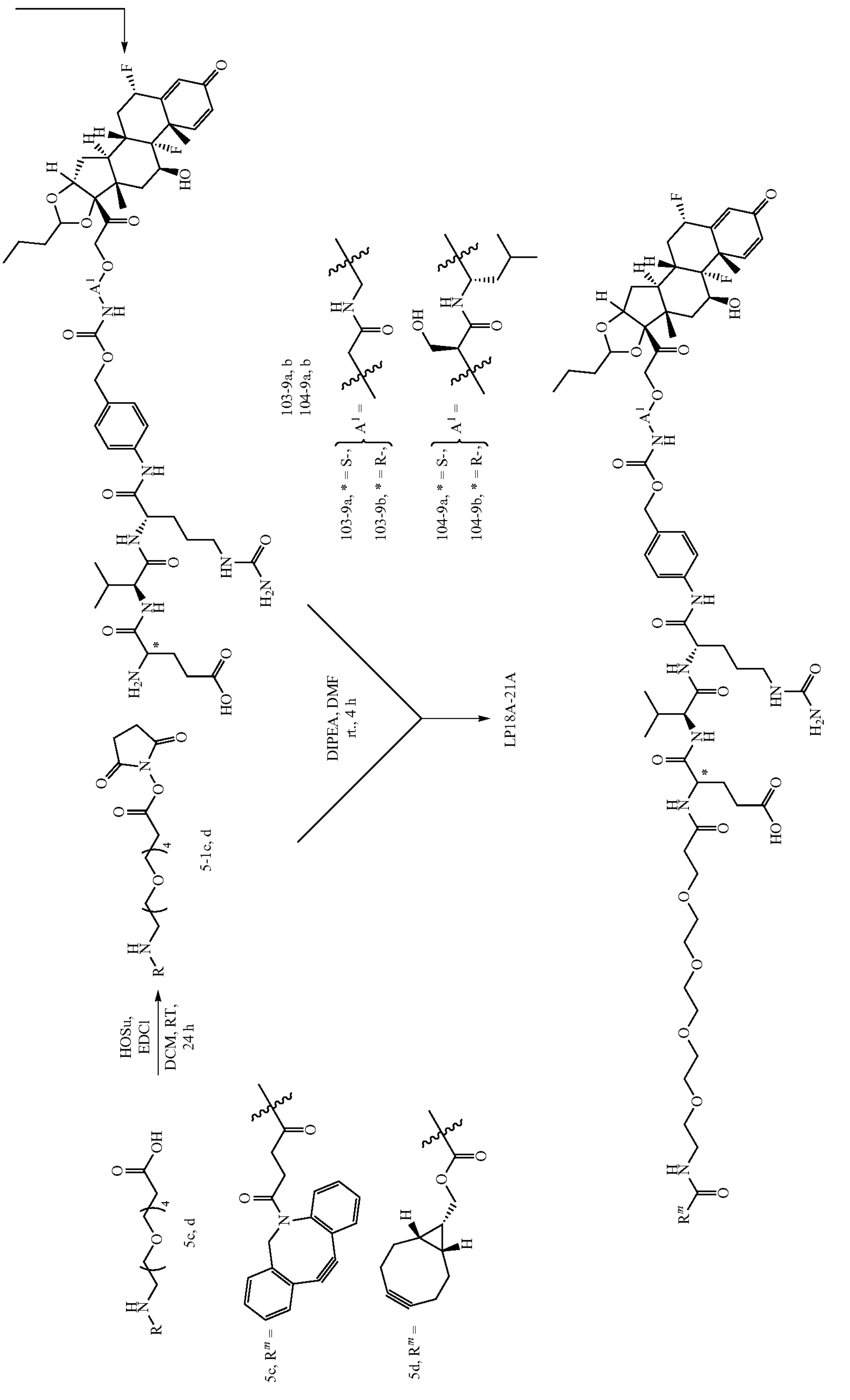

-continued
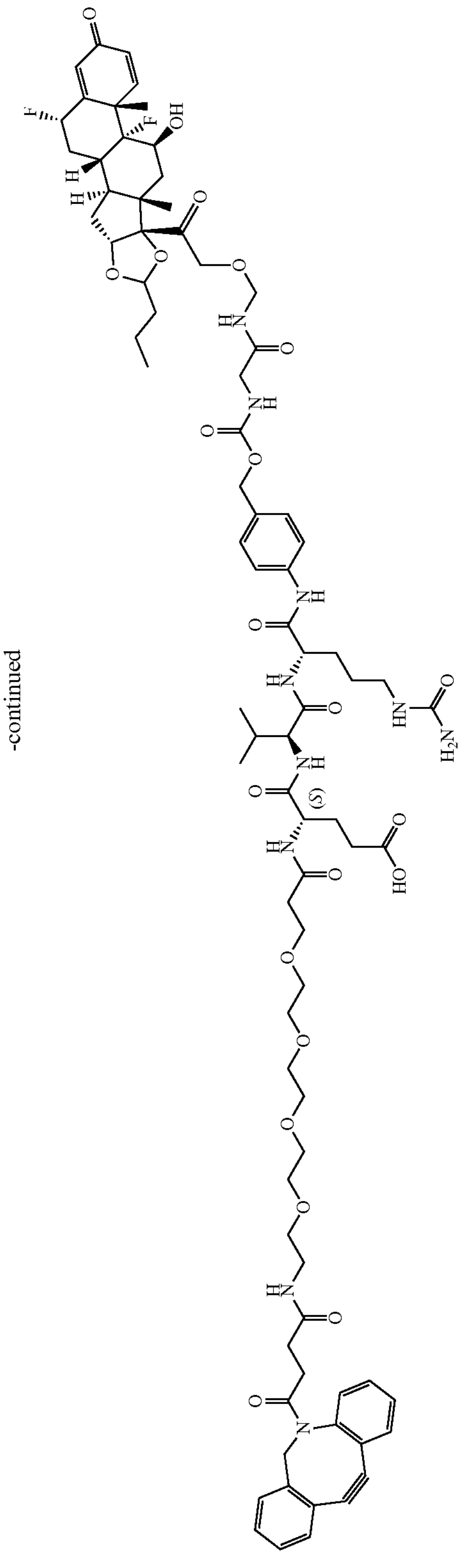
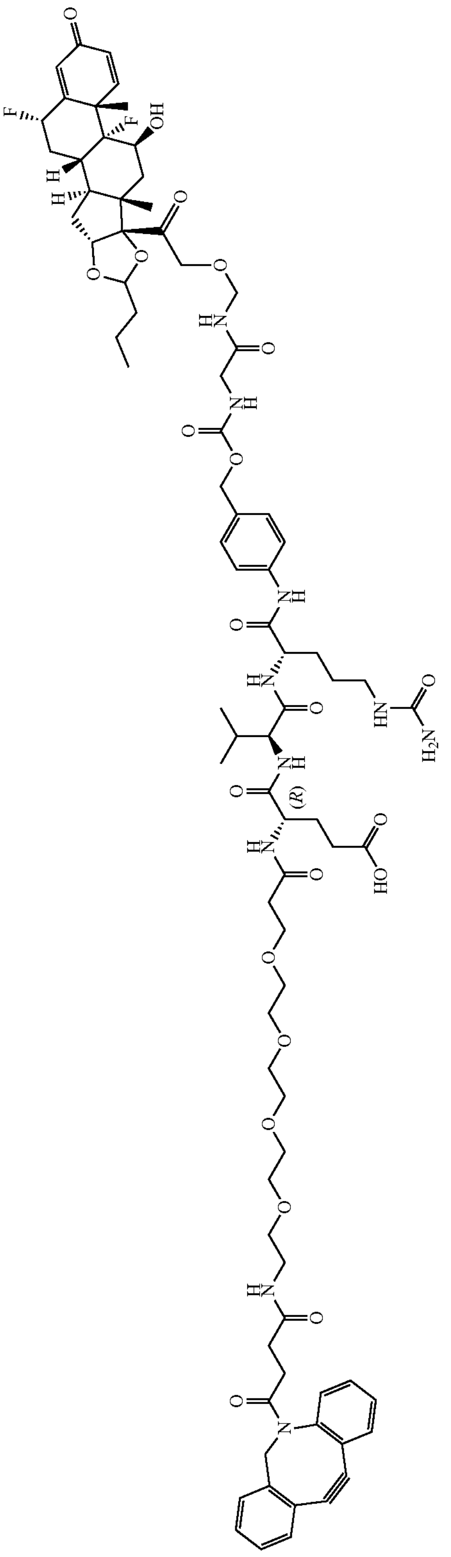

-continued
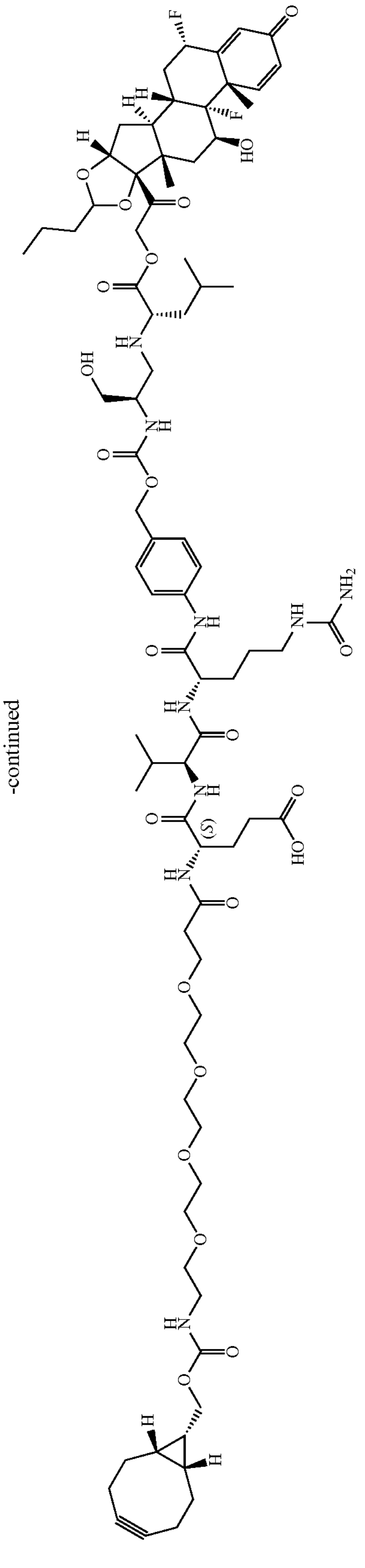
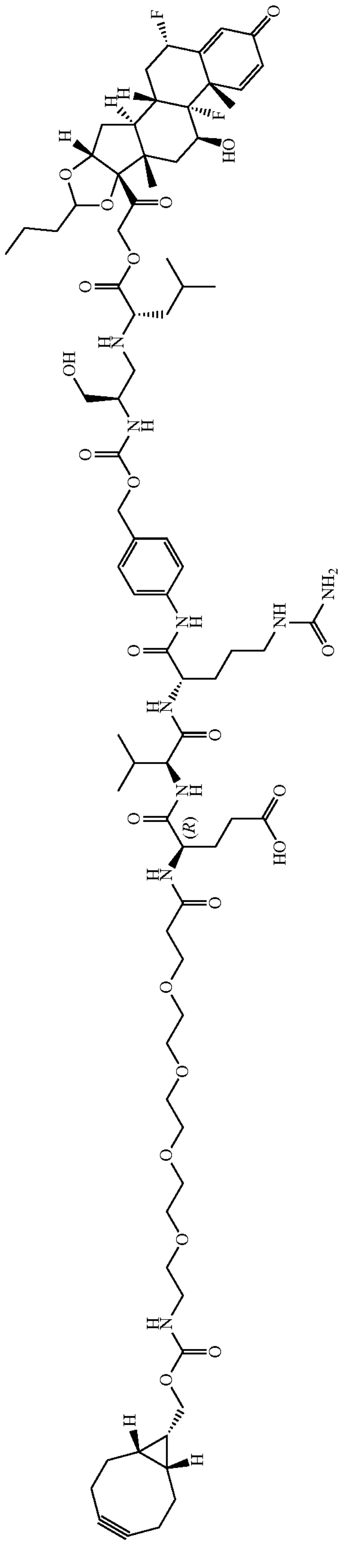

2,5-Dioxopyrrolidin-1-yl 1-(4-{2-azatricyclo [10.4.0.0$^{4,9}$]hexadeca-1(12),4(9),5,7,13,15-hexaen-10-yn-2-yl}-4-oxobutanamido)-3,6,9,12-tetraoxa-pentadecan-15-oate (5-1c)

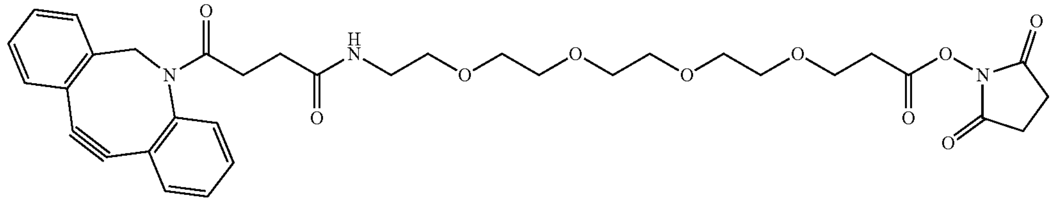 [SMILES: O=C(CCC(=O)N1Cc2ccccc2C#Cc2ccccc21)NCCOCCOCCOCCOCCC(=O)ON1C(=O)CCC1=O]

To a solution of compound 5c (160 mg, 0.290 mmol) in DCM (20 mL) were added HOSu (73.3 mg, 0.637 mmol) and EDCI (122 mg, 0.637 mmol), and the mixture was stirred at RT for 24 hours, which was monitored by LCMS. The reaction mixture was diluted with DCM (50 mL) and the organic layer was washed with water (50 mL) and brine, dried with anhydrous Na2SO4 and concentrated in vacuo to give compound 5-1c (159 mg, 84% yield) as colorless oil, which was used for the next step directly. ESI m/z: 650 $(M+H)^+$.

2,5-Dioxopyrrolidin-1-yl 1-[({endo-bicyclo[6.1.0] non-4-yn-9-ylmethoxy}carbonyl)amino]-3,6,9,12-tetraoxapentadecan-15-oate (5-1d)

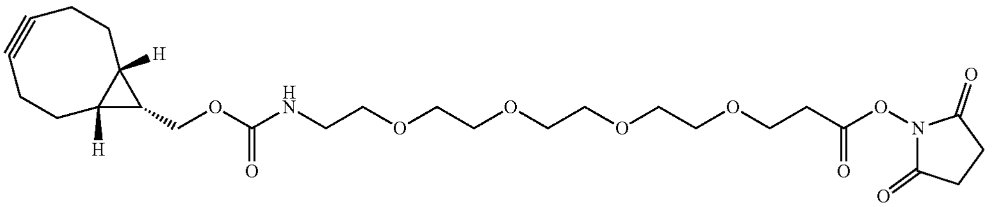 [SMILES: O=C(CCOCCOCCOCCOCCNC(=O)OC[C@@H]1[C@@H]2CCC#CCC[C@@H]21)ON1C(=O)CCC1=O]

Following the similar procedure as 5-1c except substituting 5d for 5c, compound 5-1d (150 mg, 54% yield) was obtained as colorless oil, which was used for the next step directly without further purification. ESI m/z: 539 $(M+H)^+$.

{4-[(2S)-2-[(2S)-2-Amino-3-methylbutanamido]-5-(carbamoylamino)pentanamido]phenyl}methyl N-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl] methyl}carbamate (103-8b)

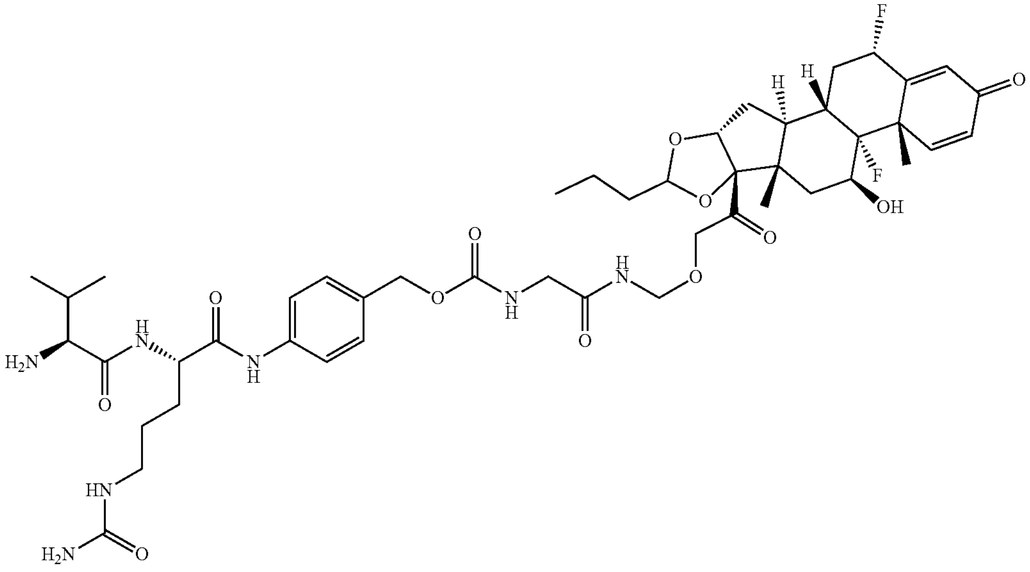 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COCNC(=O)CNC(=O)OCc2ccc(NC(=O)[C@H](CCCNC(N)=O)NC(=O)[C@@H](N)C(C)C)cc2)O1]

Following the similar procedure as 104-8b (see scheme 104C) except substituting 103b for 104b, compound 103-8b (28 mg, 20% yield) was obtained as a white solid. ESI m/z: 480 $(M/2+H)^+$.

(4S)-4-Amino-4-{[(1S)-1-{[(1S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (103-9a)

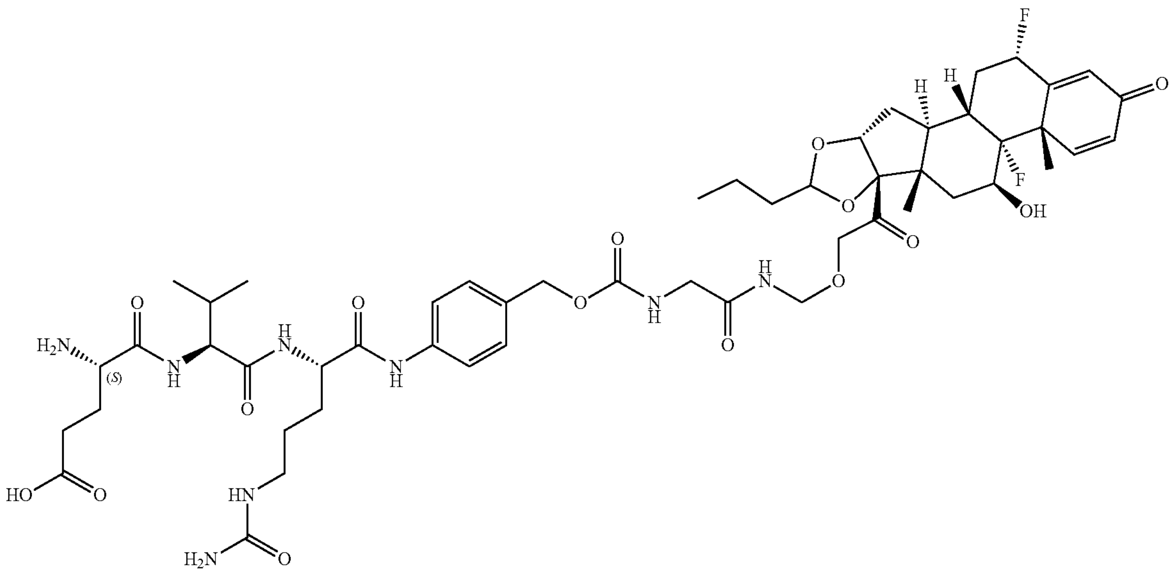

To a solution of compound Boc-L-Glu(OTBU)-OH (0.15 g, 0.50 mmol) in DMF (5 mL) were added HATU (0.19 g, 0.50 mmol) and DIPEA (0.13 g, 1.0 mmol). The reaction mixture mixture was stirred at RT for 10 minutes, before compound 103-8b (0.48 g, 0.50 mmol) was added into the reaction mixture. The reaction mixture was then stirred at RT for 3 hours until 103-8b was totally consumed according to LCMS. The mixture was extracted with EtOAc, and the combined organic solution was washed with water, dried over anhydrous sodium sulfate and concentrated in vacuo. The residue was dissolved into DCM (10 mL). To the solution was added TFA (2 mL), and the reaction mixture was stirred at RT for 3 hours, which was monitored by LCMS. The reaction mixture was concentrated, and the residue was directly purified by prep-HPLC (method B) to give compound 103-9a (0.41 g, 75% yield) as a white solid. ESI m/z: 536.8 $(M/2+H)^+$.

(4R)-4-Amino-4-{[(1S)-1-{[(1 S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl)oxy]methyl}phenyl) carbamoyl]butyl]carbamoyl}-2-methylpropyl]carbamoyl}butanoic acid (103-9b)

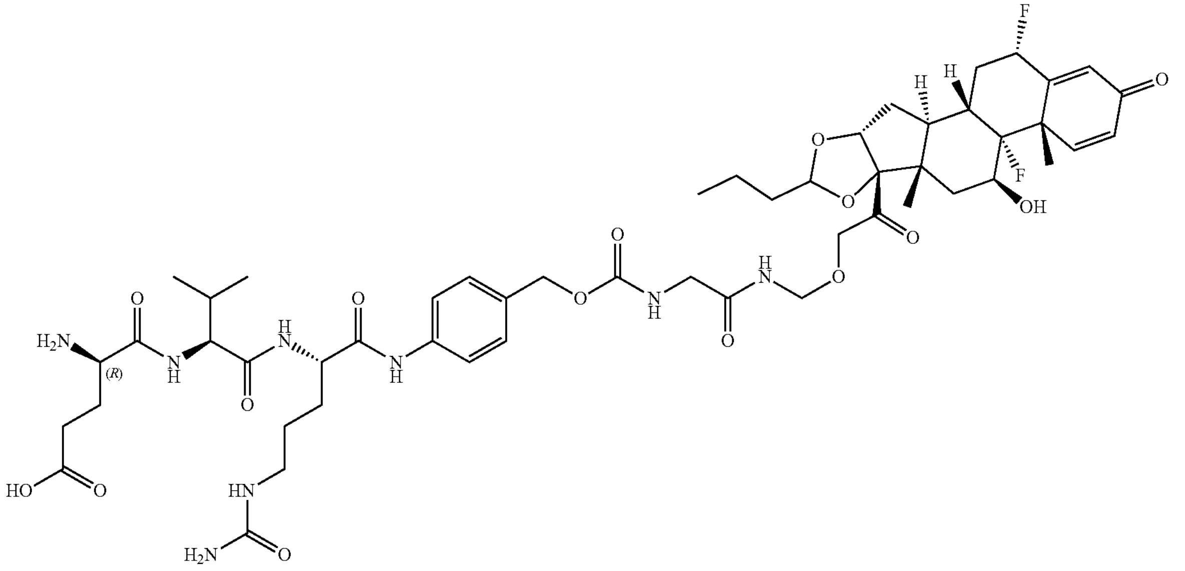

Following the similar procedure as 103-9a except substituting Boc-D-Glu(OTBU)-OH for Boc-L-Glu(OTBU)-OH, compound 103-9b (0.40 g, 74% yield) as a white solid. ESI m/z: 536.8 (M/2+H)$^+$.

(4S)-4-Amino-4-{[(1S)-1-{[(1S)-4-(carbamoylamino)-1-({4-[({[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (104-9a)

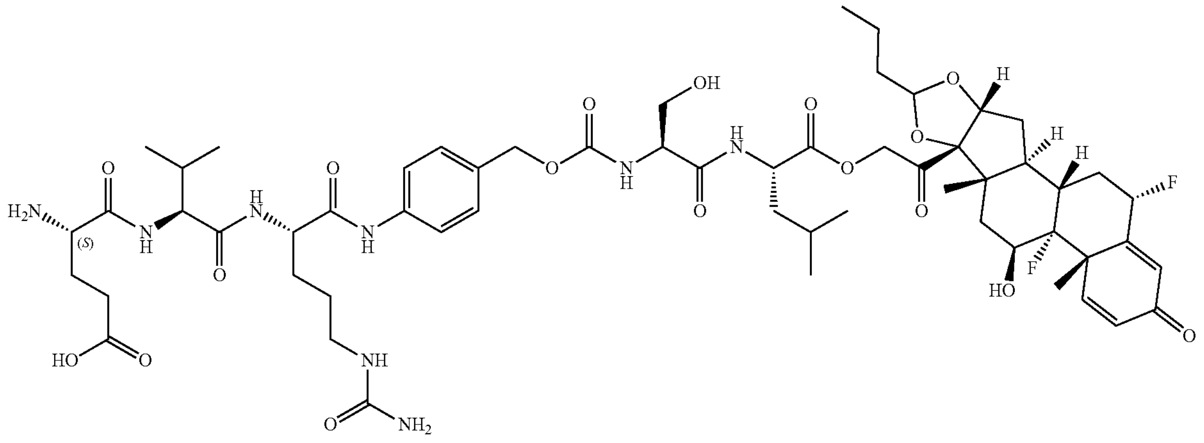

Following the similar procedure as 103-9a except substituting 104-8b for 103-8b, compound 104-9a (0.39 g, 65% yield) as a white solid. ESI m/z: 601.3 (M/2+H)$^+$.

(4R)-4-Amino-4-{[(1S)-1-{[(1S)-4-(carbamoylamino)-1-({4-[({[(1 S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (104-9b)

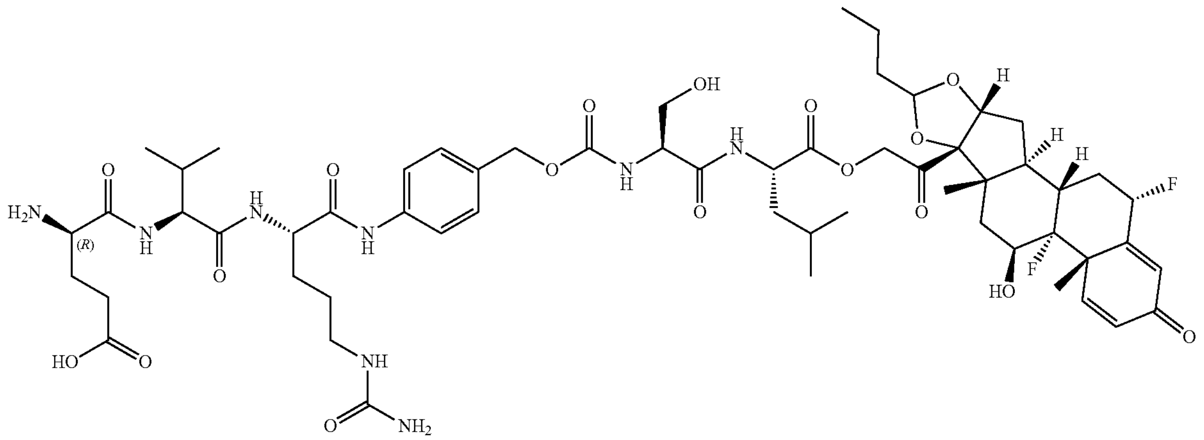

Following the similar procedure as 103-9a except substituting 104-8b for 103-8b, Boc-D-Glu(OTBU)-OH for Boc-L-Glu(OTBU)-OH, compound 104-9b (0.39 g, 65% yield) as a white solid. ESI m/z: 601.3 (M/2+H)$^+$.

(4S)-4-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (LP18A)

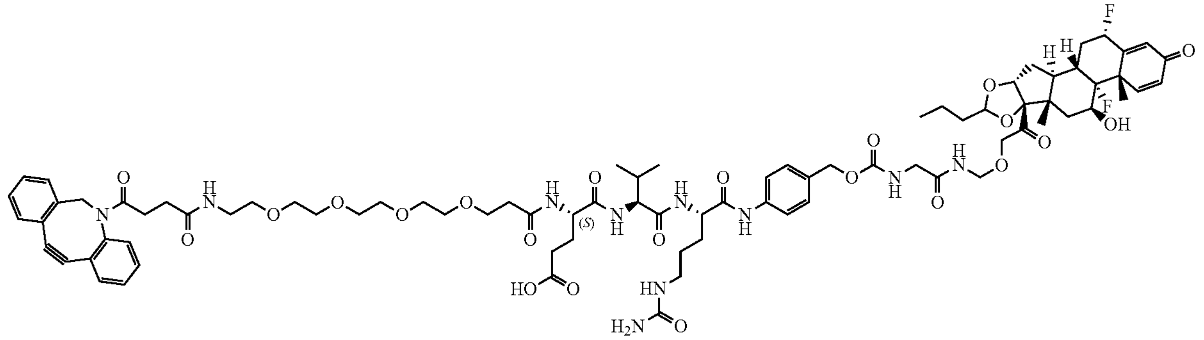

To a solution of compound 103-9a (57 mg, 53 μmol) in DMF (1 mL) were added compound 5-1c (36 mg, 56 μmol) and DIPEA (27 mg, 0.21 mmol). The reaction mixture was stirred at RT for 4 hours, which was monitored by LCMS. The resulting mixture was then directly purified by prep-HPLC (method B) to give compound LP18A (12 mg, 15% yield) as a white solid. ESI m/z: 811.4 (M/2+H)$^+$.

(4R)-4-[1-(4-{2-Azatricyclo[10.4.0.$0^{4,9}$]hexadeca-1(12),4(9),5,7,13,15-hexaen-10-yn-2-yl}-4-oxobutanamido)-3,6,9,12-tetraoxapentadecan-15-amido]-4-{[(1S)-1-{[(1S)-4-(carbamoylamino)-1-[(4-{[({[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}methyl)carbamoyl]methyl}carbamoyl)oxy]methyl}phenyl)carbamoyl]butyl]carbamoyl}-2-methylpropyl]carbamoyl}butanoic acid (LP19A)

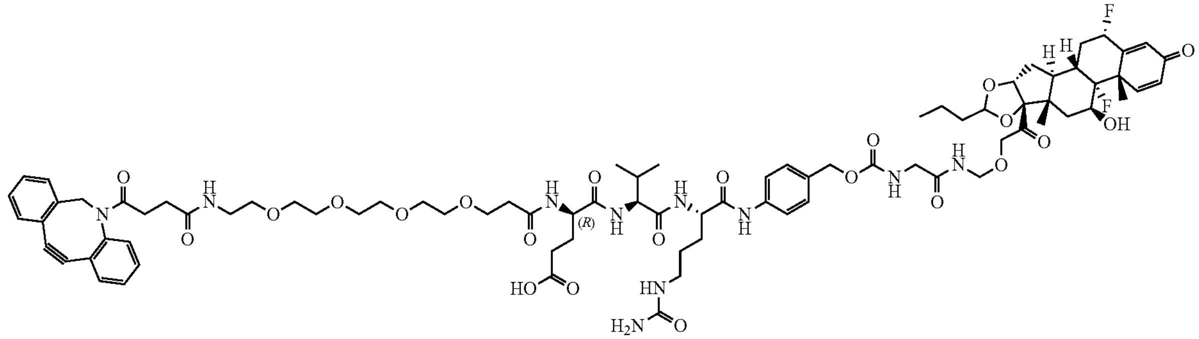

Following the similar procedure as LP18A except substituting 103-9b for 103-9a, compound LP19A (14 mg, 17% yield) as a white solid. ESI m/z: 811.4 $(M/2+H)^+$.

(4S)-4-{1-[({endo-Bicyclo[6.1.0]non-4-yn-9-ylmethoxy}carbonyl)amino]-3,6,9,12-tetraoxapentadecan-15-amido}-4-{[(1S)-1-{[(1S)-4-(carbamoylamino)-1-({4-[({[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (LP20A)

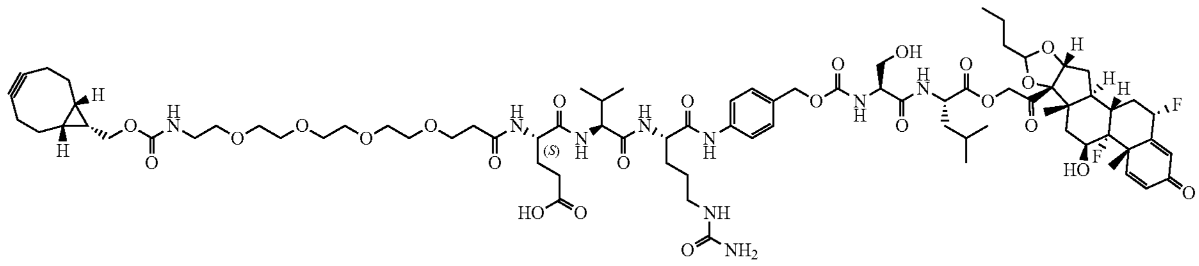

To a solution of compound 104-9a (64 mg, 53 μmol) in DMF (1 mL) were added compound 5-1d (30 mg, 56 μmol) and DIPEA (27 mg, 0.21 mmol). The reaction mixture was stirred at RT for 4 hours, which was monitored by LCMS. The resulting mixture was then directly purified by prep-HPLC (method B) to give compound LP20A (17 mg, 20% yield) as a white solid. ESI m/z: 813.0 $(M/2+H)^+$.

(4R)-4-{1-[({endo-Bicyclo[6.1.0]non-4-yn-9-ylmethoxy}carbonyl)amino]-3,6,9,12-tetraoxapentadecan-15-amido}-4-{[(1S)-1-{[(1S)-4-(carbamoylamino)-1-({4-[({[(1S)-1-{[(2S)-1-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.$0^{2,9}$.$0^{4,8}$.$0^{13,18}$]icosa-14,17-dien-8-yl]-2-oxoethoxy}-4-methyl-1-oxopentan-2-yl]carbamoyl}-2-hydroxyethyl]carbamoyl}oxy)methyl]phenyl}carbamoyl)butyl]carbamoyl}-2-methylpropyl]carbamoyl}butanoic acid (LP21A)

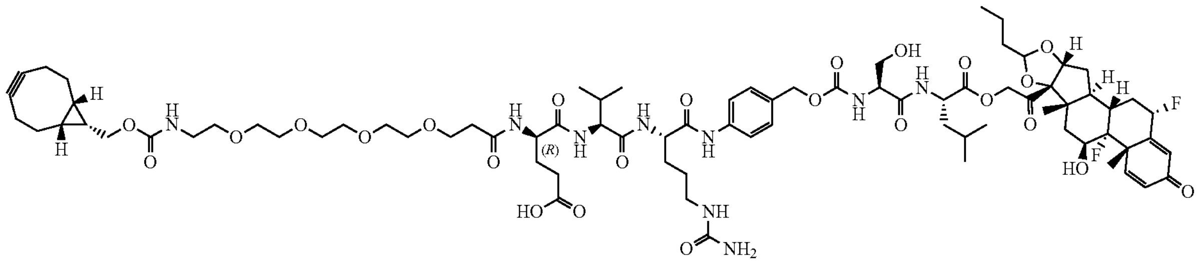

Following the similar procedure as LP20A except substituting 104-9b for 104-9a, compound LP21A (14 mg, 17% yield) as a white solid. ESI m/z: 813.0 $(M/2+H)^+$.

Table 5B below presents linker payloads made using the methods described herein.

TABLE 5B
| Examples of Linker-Payloads | | | |
|---|---|---|---|
| LP | Pay-load | Linker name | Structures |
| LP1 A | 101a | DIBAC-suc-PEG4-vcPAB-MEDA-100 | 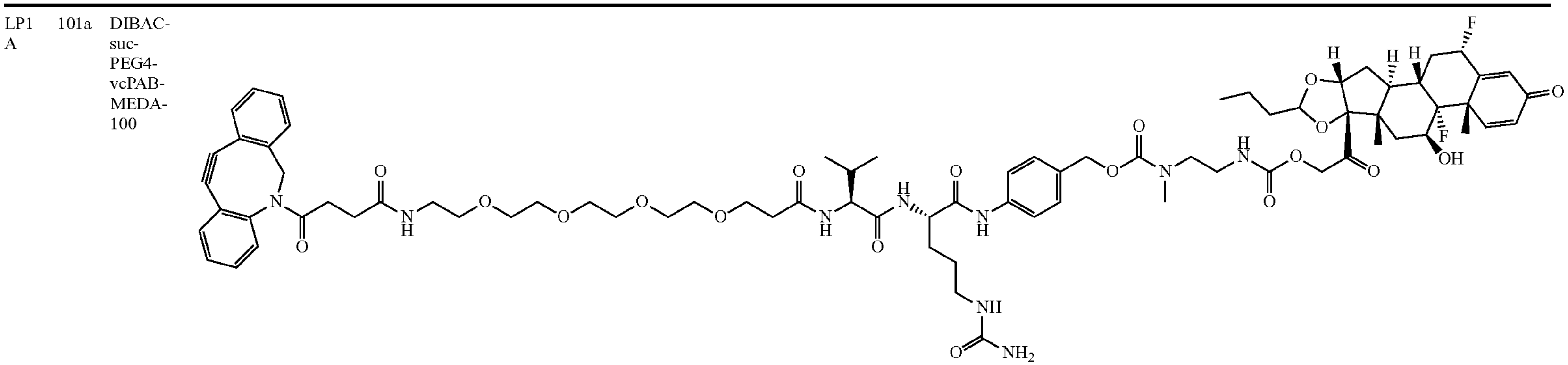 |
| LP2 A | 101b | DIBAC-suc-PEG4-vcPAB-DMEDA-100 | 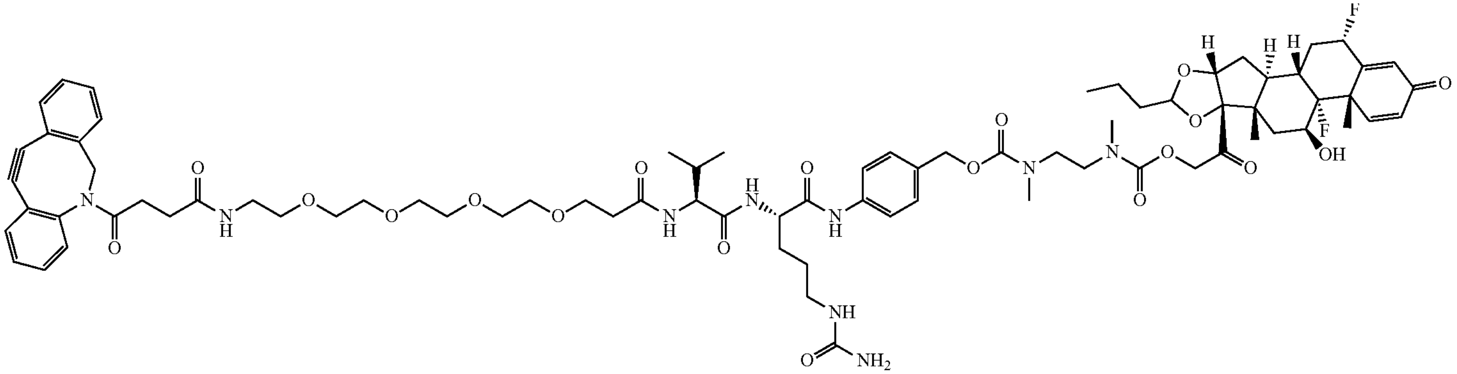 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCN(C)C(=O)OCc2ccc(NC(=O)[C@H](CCCNC(N)=O)NC(=O)[C@@H](NC(=O)CCOCCOCCOCCOCCNC(=O)CCC(=O)N3Cc4ccccc4C#Cc4ccccc43)C(C)C)cc2)O1] |

TABLE 5B-continued
| Examples of Linker-Payloads | | | |
|---|---|---|---|
| LP | Payload | Linker name | Structures |
| LP3A | 101c | DIBAC-suc-PEG4-vcPAB-DEEDA-100 | 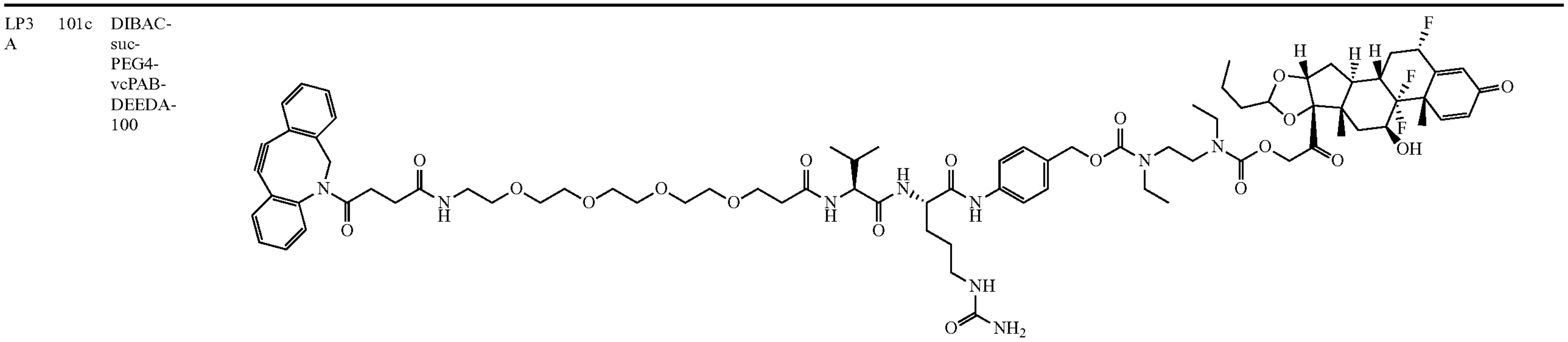 |
| LP4A | 101d | DIBAC-suc-PEG4-vcPAB-Pip-100 | 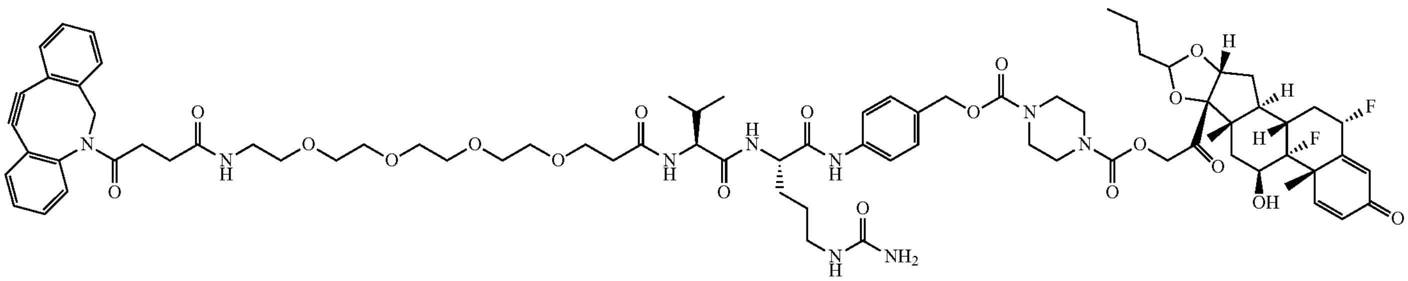 |
| LP5A | 102e | NHS-disulfide-SEA-100 | 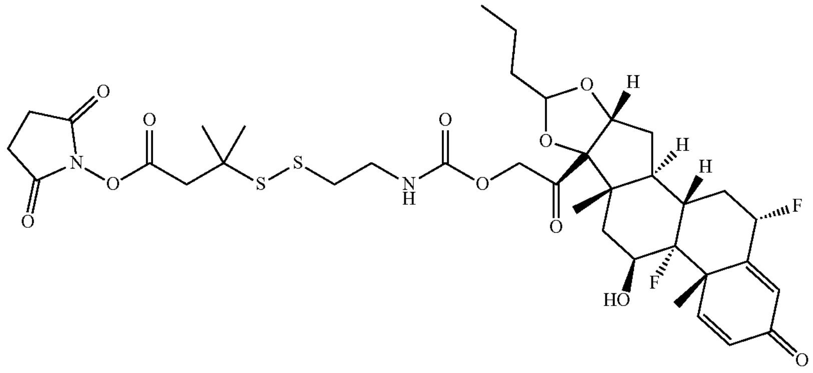 |

TABLE 5B-continued
| Examples of Linker-Payloads | | | |
|---|---|---|---|
| LP | Pay-load | Linker name | Structures |
| LP6 A | 102f | NHS-disulfide-SEMA-100 | 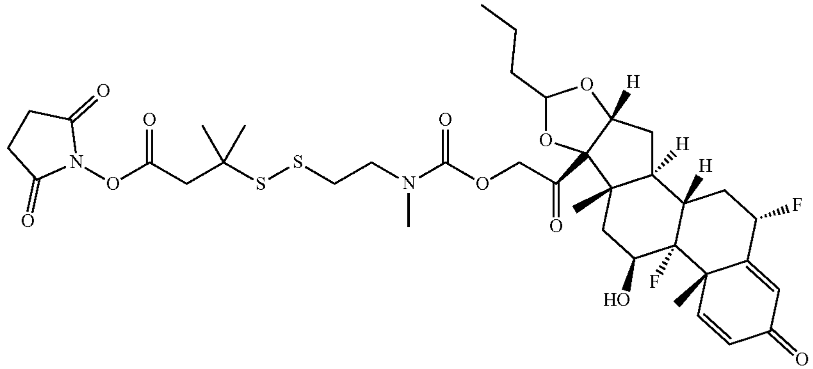 |
| LP7 A | 102e | BCN-PEG3-disulfide-SEA-100 | 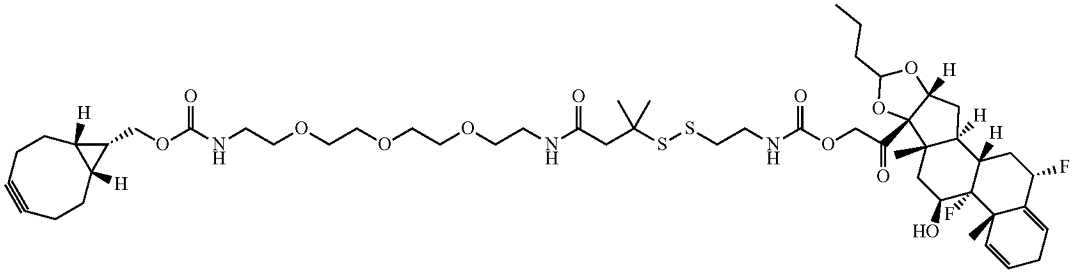 [SMILES: CCCC1O[C@@H]2C[C@H]3[C@@H]4C[C@H](F)C5=CCC=C[C@]5(C)[C@@]4(F)[C@@H](O)C[C@]3(C)[C@]2(C(=O)COC(=O)NCCSSC(C)(C)CC(=O)NCCOCCOCCOCCNC(=O)OC[C@@H]2[C@@H]3CCC#CCC[C@@H]32)O1] |
| LP8 | 102f | BCN-PEG3-disulfide-SEMA-100 | 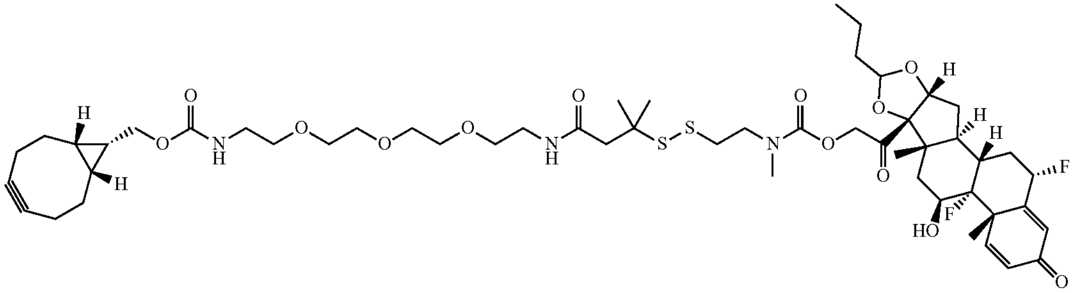 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)N(C)CCSSC(C)(C)CC(=O)NCCOCCOCCOCCNC(=O)OC[C@@H]2[C@@H]3CCC#CCC[C@@H]32)O1] |

TABLE 5B-continued
Examples of Linker-Payloads
| LP | Pay-load | Linker name | Structures |
|---|---|---|---|
| LP9A | 103a | DIBAC-suc-PEG4-vcPAB-Gly-AMO-Bud | 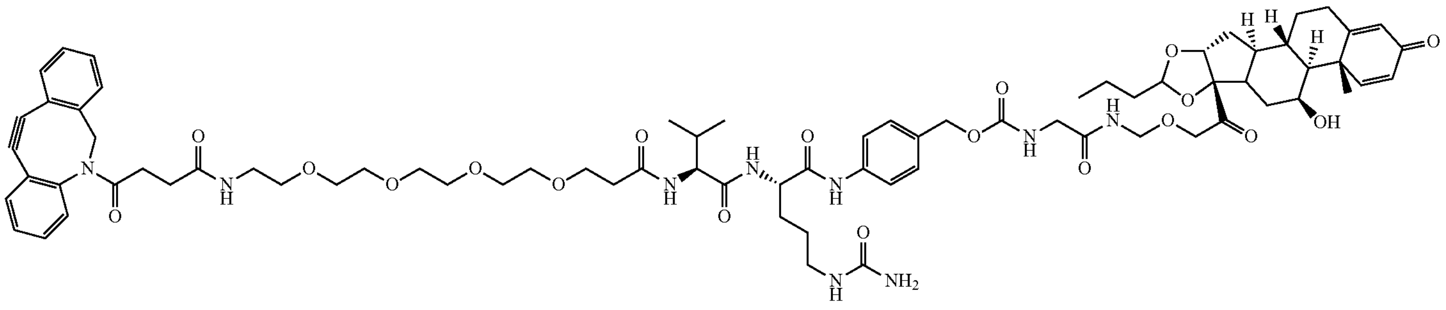 |
| LP10A | 103b | DIBAC-suc-PEG4-vcPAB-Gly-AMO-100 | 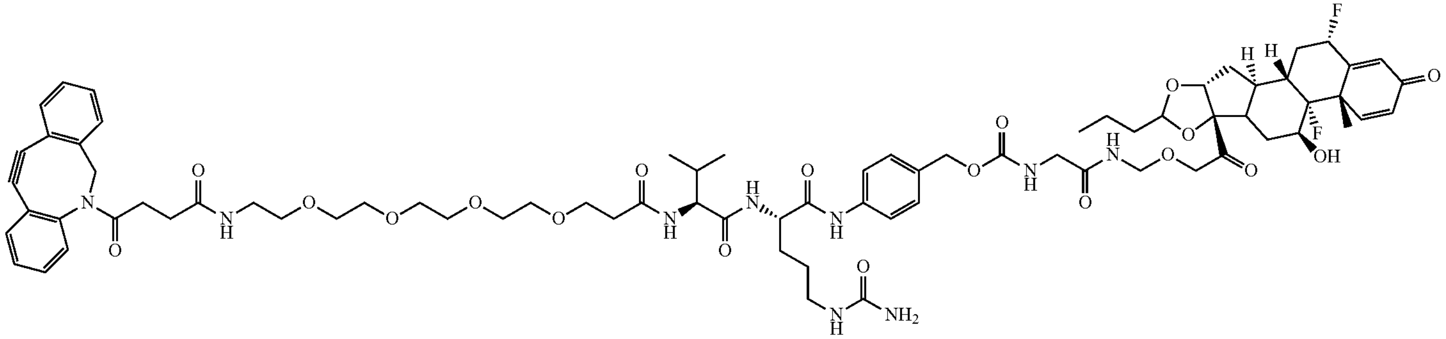 |
| LP11A | 103b | DIBAC-suc-PEG4-GGFG-AMO-100 | 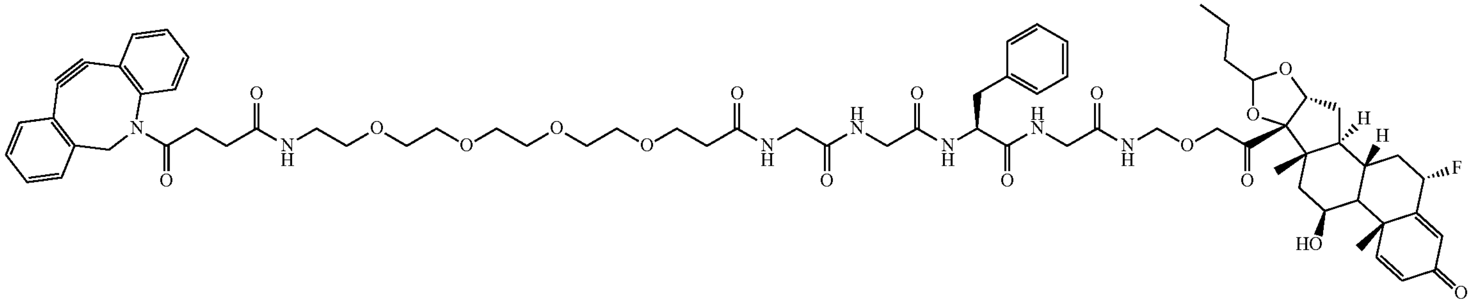 [SMILES: CCCC1O[C@@H]2C[C@H]3[C@@H]4C[C@H](F)C5=CC(=O)C=C[C@]5(C)C4[C@@H](O)C[C@]3(C)[C@]2(C(=O)COCNC(=O)CNC(=O)[C@H](Cc2ccccc2)NC(=O)CNC(=O)CNC(=O)CCOCCOCCOCCOCCNC(=O)CCC(=O)N2Cc3ccccc3C#Cc3ccccc32)O1] |

TABLE 5B-continued
| Examples of Linker-Payloads | | | |
|---|---|---|---|
| LP | Pay-load | Linker name | Structures |
| LP12A | 104a | BCN-PEG4-vcPAB-Leu-Aib-100 | 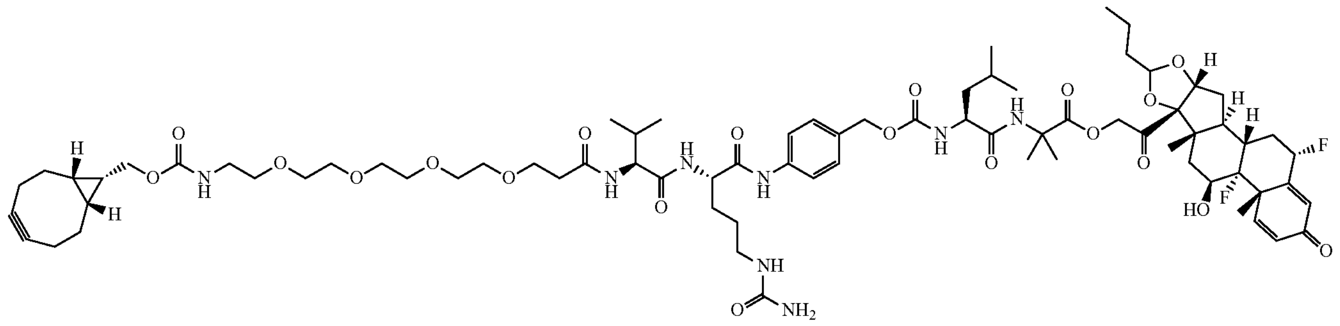 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)C(C)(C)NC(=O)[C@H](CC(C)C)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1] |
| LP13A | 104b | BCN-PEG4-vcPAB-Ser-Leu-100 | 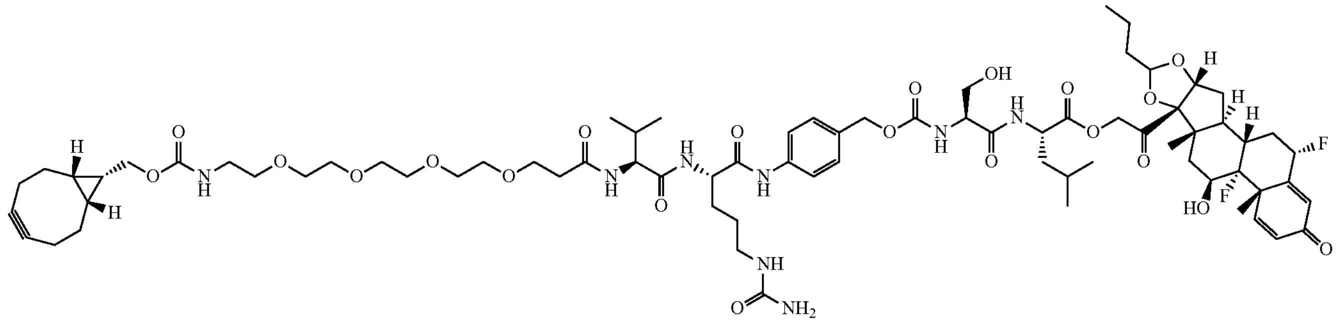 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COC(=O)[C@H](CC(C)C)NC(=O)[C@H](CO)NC(=O)OCc2ccc(NC(=O)[C@H](CCCNC(N)=O)NC(=O)[C@@H](NC(=O)CCOCCOCCOCCOCCNC(=O)OC[C@@H]3[C@@H]4CCC#CCC[C@@H]43)C(C)C)cc2)O1] |

TABLE 5B-continued
| Examples of Linker-Payloads | | | |
|---|---|---|---|
| LP | Pay-load | Linker name | Structures |
| LP18A | 103b | DIBAC-suc-PEG4-EVC-PAB-Gly-AMO-100 | 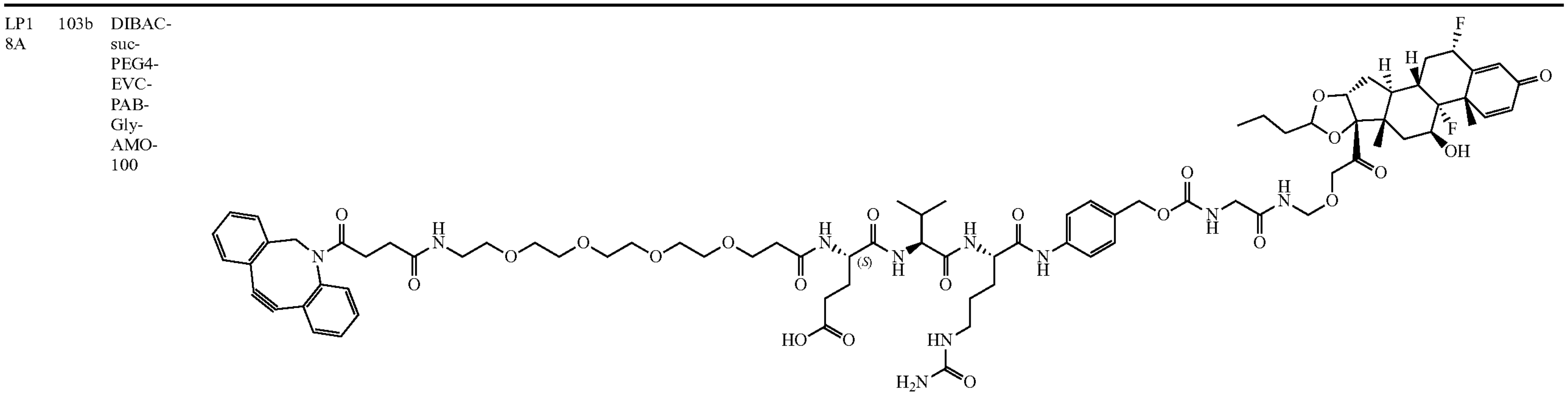 |
| LP19A | 103b | DIBAC-suc-PEG4-dEVC-PAB-Gly-AMO-100 | 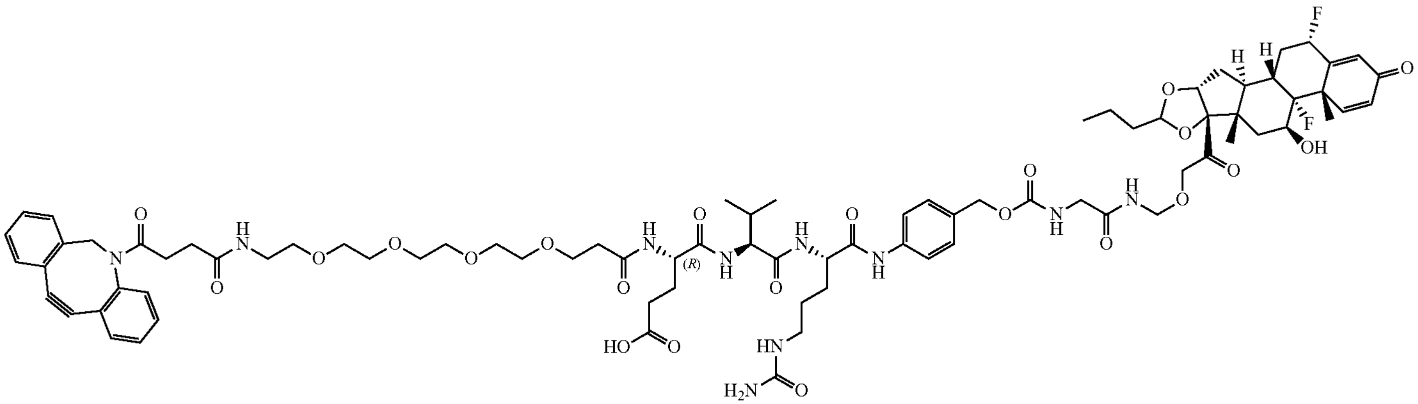 |

TABLE 5B-continued
| Examples of Linker-Payloads | | | |
|---|---|---|---|
| LP | Pay-load | Linker name | Structures |
| LP20A | 104b | BCN-PEG4-EVC-PAB-Ser-Leu-100 | 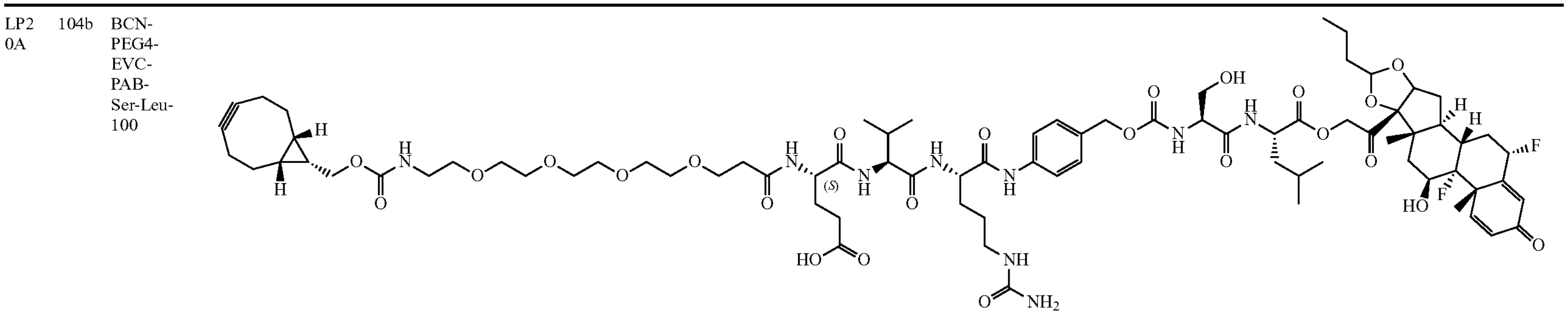 |
| LP21A | 104b | BCN-PEG4-dEVC-PAB-Ser-Leu-100 | 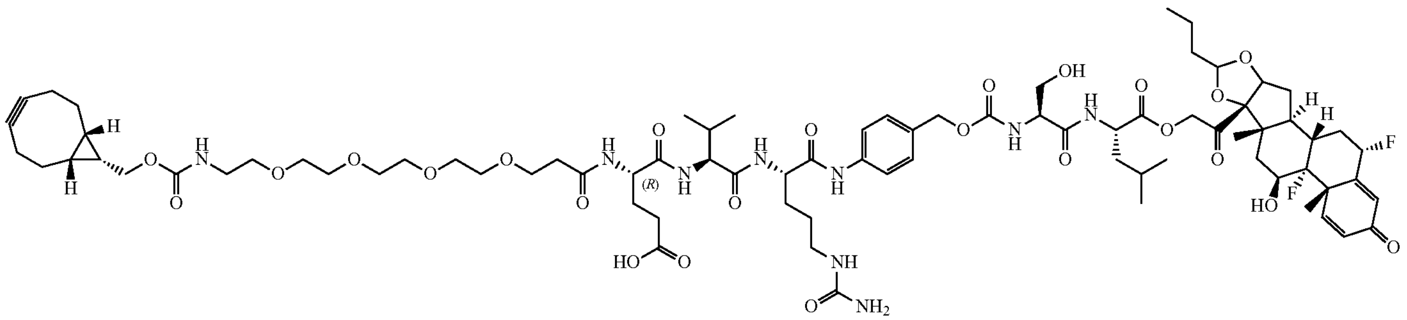 |

Example 27. Characterization of Linker-Payloads

Table 16 summarizes the results of the Linker-Payloads HPLC purity and LC retention time on HPLC, M/Z from mess spectra. The analytical HPLC and MS methods were described in general procedures as disclosed herein.

TABLE 16

Chemical-physical property of Linker-payloads

| LP | cLogP | MF | MW | HPLC purity (%) | HPLC RT (min)[1] | MS (m/z) 100% | Highest m/z peak |
|---|---|---|---|---|---|---|---|
| 13 | 4.39 | C74H94F2N8O17 | 1405.60 | >99 | 7.40[1] | 703.5 (M/2 + H) | 703.5 (M/2 + H) |
| 15 | 2.98 | C103H144F2N14O28S | 2096.38 | 98 | 5.88 | 699.6 (M/3 + H) | 1049.0 (M/2 + H) (67%) |
| 3 | 6.25 | $C_{80}H_{98}F_2N_8O_{18}$ | 1497.70 | 99 | 7.99[1] | 1498.7 (M/2 + H) | 1498.7 (M + H) (10%) |
| 6 | 6.59 | $C_{115}H_{160}N_{16}O_{28}S$ | 2245.13 | 99 | 7.24 | 749.5 (M/3 + H) | 1123.8 $(M/2 + H)^+$ |

[1]Method B for HPLC-MS

TABLE 17

Linker-Payload Properties

| LP | cLogP | MF | MW | HPLC purity (%) | HPLC RT (min) | MS (m/z) 100% | Highest m/z peak |
|---|---|---|---|---|---|---|---|
| LP1 | −0.38 | $C_{124}H_{175}N_{11}O_{44}$ | 2523.76 | 98 | 6.45, 6.55 (B) | 841.8 [M/3 + H] | 1262.4 [M/2 + H] (30%) |
| LP2 | −3.92 | $C_{136}H_{195}N_{11}O_{54}$ | 2848.04 | 96 | 7.48 (B) | 955.0 [(M + 18)/3] 949.5 (M/3 + H) | 1424.2 (M/2 + H) (30%) |
| LP3 | 6.25 | $C_{80}H_{98}F_2N_8O_{18}$ | 1497.67 | 100 | 7.99 (B) | 749.5 (M/2 + H) | 1497.7 (M + H) (5%) |
| LP4 | 7.53 | $C_{72}H_{100}N_{10}O_{13}$ | 1313.62 | 96 | 8.16 (B) | 657.5 (M/2 + H) | 1313.6 (M + H) (5%) |
| LP5 | −1.48 | $C_{138}H_{193}N_{15}O_{49}$ | 2846.08 | 100 | 6.11, 6.21 (B) | 949.0 (M/3 + H) | 1423.3 (M/2 + H) (5%) |
| LP6 | 6.59 | $C_{115}H_{160}N_{16}O_{28}S$ | 2246.66 | 100 | 7.24 (B) | 749.5 (M/3 + H) | 1123.8 (M/2 + H) (5%) |
| LP9 | 8.70 | $C_{88}H_{112}N_{10}O_{18}$ | 1597.89 | 95 | 5.67 (B) | 799.0 (M/2 + H) | 799.0 (M/2 + H) |
| LP11 | 8.17 | $C_{89}H_{117}N_{11}O_{16}$ | 1596.95 | 95 | 8.51 (B) | 798.5 (M/2 + H) | 798.5 (M/2 + H) |
| LP12 | 8.77 | $C_{77}H_{86}Cl_2F_6N_{10}O_{15}S$ | 1608.53 | 99 | 9.36 (B) | 804.2 (M/2 + H) | 804.2 (M/2 + H) |
| LP13 | 4.39 | $C_{74}H_{94}F_2N_8O_{17}$ | 1405.58 | 100 | 7.40 (B) | 703.5 (M/2 + H) | 1405.7 (M + H) (5%) |
| LP14 | −5.09 | $C_{126}H_{177}F_2N_{13}O_{49}$ | 2695.81 | 100 | 6.23 (B) | 899.2 (M/3 + H) | 1348.6 (M/2 + H) (40%) |
| LP15 | 2.98 | $C_{103}H_{144}F_2N_{14}O_{28}S$ | 2096.38 | 98 | 5.88 (B) | 699.6 (M/3 + H) | 1049.0 (M/2 + H) (67%) |
| LP18 | 6.49 | $C_{101}H_{142}N_{12}O_{23}S$ | 1924.34 | 97 | 7.57 (B) | 642.2 (M/3 + H) | 962.5 (M/2 + H) (70%) |

TABLE 17A

Characterization Data for Linker-Payloads

| LP | cLogP | MF | MW | HPLC purity (%) | HPLC RT (min) | MS (m/z) 100% | Highest m/z peak |
|---|---|---|---|---|---|---|---|
| LP1A | 4.26 | $C_{78}H_{101}F_2N_9O_{19}$ | 1506.71 | 95 | | 753.9 (m/2 + H) | 753.9 (m/2 + H) |
| LP2A | 4.48 | $C_{79}H_{103}F_2N_9O_{19}$ | 1520.71 | 97 | | 761.0 (m/2 + H) | 761.0 (m/2 + H) |
| LP3A | 5.20 | $C_{81}H_{107}F_2N_9O_{19}$ | 1548.76 | 95 | | 775.0 (m/2 + H) | 775.0 (m/2 + H) |
| LP4A | 4.31 | $C_{79}H_{101}F_2N_9O_{19}$ | 1518.69 | 99 | | 760.0 (m/2 + H) | 760.0 (m/2 + H) |
| LP5A | 3.40 | $C_{37}H_{48}F_2N_2O_{11}S_2$ | 798.91 | 99 | | 799.3 (m + H) | 799.3 (m + H) |
| LP6A | 3.62 | $C_{38}H_{50}F_2N_2O_{11}S_2$ | 812.94 | 97 | | 813.3 (m + H) | 813.3 (m + H) |
| LP7A | 5.20 | C52H75F2N3O13S2 | 1052.29 | 97 | | 526.7 (m/2 + H) | 526.7 (m/2 + H) |
| LP8A | 5.42 | C53H77F2N3O13S2 | 1066.32 | 98 | | 533.8 (m/2 + H) | 533.8 (m/2 + H) |
| LP9A | 3.65 | $C_{77}H_{101}N_9O_{19}$ | 1456.70 | 96 | | 729.0 (m/2 + H) | 729.0 (m/2 + H) |
| LP10A | 3.35 | $C_{77}H_{99}F_2N_9O_{19}$ | 1492.68 | 95 | | 513.8 (fragment) | 747.0 (m/2 + H) |
| LP11A | 1.96 | $C_{71}H_{87}F_2N_7O_{17}$ | 1348.51 | 95 | | 450.2 (m/3 + H) | 675.2 (m/2 + H) |
| LP12A | 5.61 | $C_{76}H_{110}F_2N_8O_{20}$ | 1493.75 | 90 | | 747.6 (m/2 + H) | 747.6 (m/2 + H) |
| LP13A | 4.13 | $C_{75}H_{108}F_2N_8O_{21}$ | 1495.70 | 95 | | 748.4 (m/2 + H) | 748.4 (m/2 + H) |
| LP18A | 2.46 | $C_{82}H_{106}F_2N_{10}O_{22}$ | 1621.77 | 95 | | 811 (m/2 + H) | 811 (m/2 + H) |
| LP19A | 2.46 | $C_{82}H_{106}F_2N_{10}O_{22}$ | 1621.77 | 95 | | 811 (m/2 + H) | 811 (m/2 + H) |
| LP20A | 3.25 | $C_{80}H_{115}F_2N_9O_{24}$ | 1624.81 | 95 | | 813 (m/2 + H) | 813 (m/2 + H) |
| LP21A | 3.25 | $C_{80}H_{115}F_2N_9O_{24}$ | 1624.81 | 95 | | 813 (m/2 + H) | 813 (m/2 + H) |

Example 28. ADC Conjugation

Figure 16:
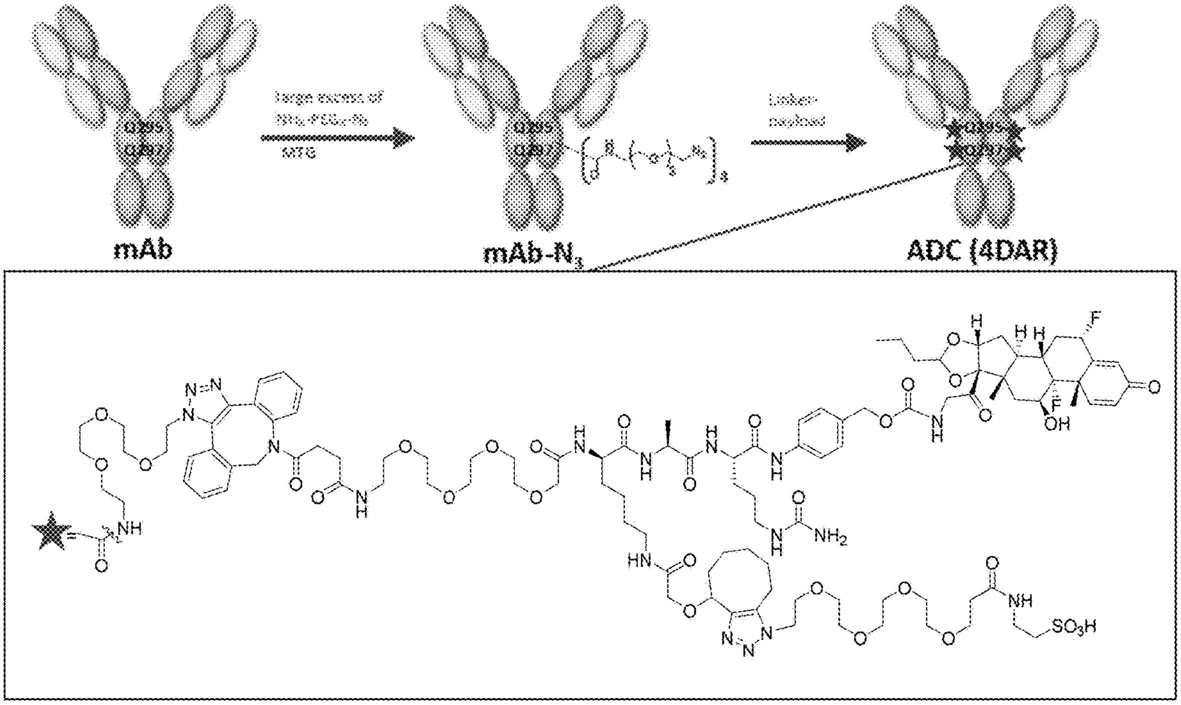
FIG. 16 provides a scheme for the synthesis of antibody-drug conjugates (ADCs).

This example demonstrates a method for site-specific conjugation, generally, of a payload to an antibody or antigen-binding fragment thereof. See FIG. 16.

Generated anti-MSR1 antibodies (Table 4) were mutated (N297Q) to incorporate a transglutaminase site for conjugation with a therapeutic payload. The site-specific aglycosylated antibodies containing an N297Q mutation were conjugated with amine-$PEG_3$-$N_3$ to generate the azido-functionalized antibody conjugates (mAb-$N_3$), including anti MSR1 Ab-$PEG_3$-$N_3$.

The present example demonstrates a method for making the conjugates. Aglycosylated antibody with a human IgG1 isotype in BupH™ (pH 7-8) was mixed with >200 molar equivalents of azido-d$PEG_3$-amine (MW. 218.26 g/mol). The resulting solution was mixed with transglutaminase (25 U/mL; 5U MTG per mg of antibody) resulting in a final concentration of the antibody at 0.5-10 mg/mL, and the solution was then incubated at 37° C. for 4-24 hours while gently shaking. The reaction was monitored by SDS-PAGE or ESI-MS. Upon the completion, the excess amine and MTG were removed by Size Exclusion Chromatography (SEC) to generate the azido-functionalized antibody (mAb-$N_3$). This product was analyzed on SDS-PAGE and ESI-MS. The azido-d$PEG_3$-amine added to two sites—Q295 and Q297—of the antibody resulting in an 804 Da increase for the 4DAR aglycosylated antibody-$PEG_3$-azide conjugate. The conjugation sites were identified and confirmed at $EEQ^{Linker}YQ^{Linker}STYR$ for the 4DAR azido-functionalized antibody via peptide sequence mapping of trypsin digested heavy chains.

The site-specific aglycosylated antibody drug conjugates (ADCs) with a human IgG1 containing an N297Q mutation were prepared by a [2+3] click reaction between the azido-functionalized antibody (mAb-$N_3$) with an alkyne containing linker-payload (LP).

A site-specific antibody conjugate with linker-payload (LP) was prepared by incubating mAb-$PEG_3$-$N_3$ (1-12 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for 30 min to 24 hr. The progress of the reaction was monitored by ESI-MS and the absence of mAb-$PEG_3$-$N_3$ indicated the completion of the conjugation. The excess amount of the LP and organic solvent were removed by SEC via elution with PBS, or via protein A column chromatography via elution with acidic buffer followed by neutralization with Tris (pH 8.0). The purified conjugates were analyzed by SEC, SDS-PAGE, and ESI-MS. Shown in Table 19 is a list of the MMAE antibody conjugates, steroid antibody conjugates, and LXR agonist antibody conjugates from the corresponding LPs, their molecular weights and ESI-DAR values.

In a specific example, the azido-functionalized antibody (1 mg) in 0.800 mL PBSg (PBS, 5% glycerol, pH 7.4) was treated with six molar equivalents of linker payload (LP) in Table 1 (conc. 10 mg/mL in DMSO) for 2 hours at RT and the excess linker payload (LP) was removed by size exclusion chromatography (SEC, Superdex 200 HR, GE Health-care). The final product was concentrated by ultra-centrifugation and characterized by UV, SEC, SDS-PAGE and ESI-MS.

Example 28A: ADC Conjugation

This example demonstrates a method for making a non-site-specific conjugation of a drug to an antibody using a thiol-maleimide reaction.

Conjugation through antibody cysteines is performed in two steps using the methods described similar to those described in Mol Pharm. 2015 Jun. 1; 12(6):1863-71.

A monoclonal antibody (mAb, 10 mg/ml in 50 mM HEPES, 150 mM NaCl) at pH 7.5 is reduced with 1 mM dithiothreitol (0.006 mg per mg of antibody) or TCEP (2.5 molar equivalent to antibody) at 37° C. for 30 minutes. The concentration of the antibody was calculated based on the absorbance at 280 nm on Nanodrop (ThermoFisher Scientific) and an extinction coefficient of the antibody. After gel filtration (G-25, pH 4.5 sodium acetate), the LP compound in DMSO (10 mg/mL) is added to the reduced antibody, and the mixture was adjusted to pH 7.0 with 1 M HEPES (pH 7.4). The reaction is allowed to react for 3-14 hours. The resulting conjugate was purified by SEC. The DAR (UV) values are determined using the measured absorbances of the ncADC and the extinction coefficients of the antibody and LP compound.

Example 29. Characterization of ADCs by LC-ESI-MS

Measurement of intact mass for the ADC samples by LC-ESI-MS was performed to determine the drug-payload distribution profile and to calculate the average DAR. Each testing sample (20-50 ng, 5 uL) was loaded onto an Acquity UPLC Protein BEH C4 column (10K psi, 300 Å, 1.7 μm, 75 μm×100 mm; Cat No. 186003810). After 3 minutes of desalting, the protein was eluted and mass spectra were acquired by a Waters Synapt G2-Si mass spectrometer. As summarized in Table 18, most site-specific ADCs have 3.9-4 DAR for the site specific conjugates.

TABLE 18

| ADC Properties | | | | |
|---|---|---|---|---|
| LP # | MW (LP) | Ab, Ab-$N_3$, or ncADC | MS m/z (ncADC) | DAR (ESI-MS) |
| | | H1H27729P | | |
| | | H1H27729P-$N_3$ | 144166 | 4 |
| 1 | 2523.8 | H1H27729P-LP1 | | |
| | | H1H27731P | 144620 | 4 |
| | | H1H27731P-$N_3$ | | |
| 1 | 2523.8 | H1H27731P-LP1 | | |
| | | H1H27732P | 144176 | 5.7 |
| | | H1H27732P-$N_3$ | | |
| 1 | 2523.8 | H1H27732P-LP1 | | |
| | | H1H27734P | 145110 | 4.4 |
| | | H1H27734P-$N_3$ | | |
| 1 | 2523.8 | H1H27734P-LP1 | | |
| | | H1H27736P | 145940 | 4 |
| | | H1H27736P-$N_3$ | | |
| 1 | 2523.8 | H1H27736P-LP1 | | |
| | | H1H27739P | 145251 | 4 |
| | | H1H27739P-$N_3$ | | |
| 1 | 2523.8 | H1H27739P-LP1 | | |
| | | H1H27747P | 145214 | 5.3 |
| | | H1H27747P-$N_3$ | | |
| 1 | 2523.8 | H1H27747P-LP1 | | |
| | | H1H27749P | 143441 | 4 |
| | | H1H27749P-$N_3$ | | |

TABLE 18-continued

| ADC Properties | | | | |
|---|---|---|---|---|
| LP # | MW (LP) | Ab, Ab-$N_3$, or ncADC | MS m/z (ncADC) | DAR (ESI-MS) |
| 1 | 2523.8 | H1H27749P-LP1 | | |
| | | H1H17751P | 146092 | 3.8 |
| | | H1H17751P-$N_3$ | | |
| 1 | 2523.8 | H1H17751P-LP1 | | |
| | | H1H27754P | 145477 | 4.2 |
| | | H1H27754P-$N_3$ | | |
| 1 | 2523.8 | H1H27754P-LP1 | | |
| | | H1H27756P | 145503 | |
| | | H1H27756P-$N_3$ | 146310 | 4 |
| 1 | 2523.8 | H1H27756P-LP1 | 156424 | 4 |
| | | H1H17759P2 | 145126 | |
| | | H1H17759P2-$N_3$ | 145930 | 4 |
| 1 | 2523.8 | H1H17759P2-LP1 | 156046 | 4 |
| | | H1H17760P | 145611 | |
| | | H1H17760P2-$N_3$ | 146431 | 4 |
| 1 | 2523.8 | H1H17760P2-LP1 | 156533 | 4 |
| | | H1H17761P2 | 145508 | |
| | | H1H17761P2-$N_3$ | 146717 | 6 |
| 1 | 2523.8 | H1H17761P-LP1 | 161884 | 5.34 |
| | | | 159158 | |
| | | H1H27762P2 | 144371 | |
| | | H1H27762P2-$N_3$ | 145177 | 4 |
| 1 | 2523.8 | H1H27762P2-LP1 | 155294 | 4 |
| | | H1H27766P2 | 146314 | |
| | | H1H27766P2-$N_3$ | 147121 | 4 |
| 1 | 2523.8 | H1H27766P2-LP1 | 157236 | 4 |
| | | H1H27771P2 | 145966 | |
| | | H1H27771P2-$N_3$ | 146774 | 4 |
| 1 | 2523.8 | H1H27771P2-LP1 | 156890 | 4 |
| | | H1H27773P2 | 145533 | |
| | | H1H27773P2-$N_3$ | 146337 | 4 |
| 1 | 2523.8 | H1H27773P2-LP1 | 156453 | 4 |
| | | H1H27778P2 | 145310 | |
| | | H1H27778P2-$N_3$ | 146115 | 4 |
| 1 | 2523.8 | H1H27778P2-LP1 | 156227 | 4 |
| | | H1H21231N | | |
| | | H1H21231N-$N_3$ | Lot2 | 2 |
| 1 | 2523.8 | H1H21231N-LP1 | Lot4 | 1.9 |
| | | H1H21227N | | |
| | | H1H21227N-$N_3$ | Lot2 | 4 |
| 1 | 2523.8 | H1H21227N-LP1 | Lot3 | 3.7 |
| | | H1H21231N | | |
| | | H1H21231N-$N_3$ | Lot2 | 6 |
| 1 | 2523.8 | H1H21231N-LP1 | Lot3 | 5.9 |
| | | H1H21235N | 145487 | |
| | | H1H21235N-$N_3$ | 146288 | 4 |
| 1 | 2523.8 | H1H21235N-LP1 | 156390 | 4.1 |
| | | H1H25700N | 145484 | |
| | | H1H25700N-$N_3$ | 146688 | 6 |
| 1 | 2523.8 | H1H25700N-LP1 | 161873 | 6 |
| | | H1H25690N | 145157 | |
| | | H1H25690N-$N_3$ | 145969 | 4 |
| 1 | 2523.8 | H1H25690N-LP1 | 156060 | 4.1 |
| | | H1H25695N | 145736 | |
| | | H1H25695N-$N_3$ | 146537 | 4 |
| 1 | 2523.8 | H1H25695N-LP1 | 156637 | 3.9 |
| | | H1H25685N | 145380 | |
| | | H1H25685N-$N_3$ | 146582 | 6 |
| 1 | 2523.8 | H1H25685N-LP1 | 161767 | 5.8 |
| | | H1H21228N | 144830 | |
| | | H1H21228N-$N_3$ | 145631 | 4 |
| 1 | 2523.8 | H1H21228N-LP1 | 155732 | 4.2 |
| | | H1H21234N | 145790 | |
| | | H1H21234N-$N_3$ | 146583 | 4 |
| 1 | 2523.8 | H1H21234N-LP1 | 156691 | 4 |
| 2 | 2848.1 | H1H21234N-LP2 | 157983 | 3.9 |
| 4 | 1313.7 | H1H21234N-LP4 | 151841 | 3.9 |
| 5 | 2846.2 | H1H21234N-LP5 | 157963 | 3.9 |
| 6 | 2246.7 | H1H21234N-LP6 | 155570 | 3.9 |
| 9 | 1597.9 | H1H21234N-LP9 | 152975 | 3.9 |
| 11 | 1597.0 | H1H21234N-LP11 | 152979 | 3.9 |
| 12 | 1608.6 | H1H21234N-LP12 | 153019 | 3.9 |
| 13 | 1405.6 | H1H21234N-LP13 | 152218 | 3.9 |
| 14 | 2695.9 | H1H21234N-LP14 | 157369 | 3.6 |
| 15 | 2096.4 | H1H21234N-LP15 | 154964 | 3.9 |

TABLE 18-continued

| ADC Properties | | | | |
|---|---|---|---|---|
| LP # | MW (LP) | Ab, Ab-$N_3$, or ncADC | MS m/z (ncADC) | DAR (ESI-MS) |
| 3 | 1497.7 | H1H21234N-LP3 | 152568 | 3.9 |
| Fel D1 | | Isotype Control-N297Q | | |
| | | Isotype Control-N297Q-$N_3$ | 146251 | 4 |
| 1 | 2523.8 | Isotype Control-N297Q-LP1 | 156352 | 3.9 |
| 13 | 1405.6 | Isotype Control-N297Q-LP13 | 152218 | 3.9 |
| 14 | 2695.9 | Isotype Control-N297Q-LP14 | 157369 | 3.6 |
| 15 | 2096.4 | Isotype Control-N297Q-LP15 | 154964 | 3.9 |
| 3 | 1496.7 | Isotype Control-N297Q-LP3 | 152568 | 4 |

Example 30. Biacore Surface Plasmon Resonance Derived Binding Kinetics of Anti-MSR1 Antibody-Drug Conjugates The MSR1 antibodies disclosed herein were conjugated to various liver X receptor (LXR) payloads or various steroid payloads. This example describes how equilibrium dissociation constant ($K_D$) values for human MSR1 reagents binding to human anti-MSR1 antibody-drug conjugates and their corresponding unconjugated parental antibodies were determined using a real-time surface plasmon resonance-based Biacore T200 biosensor.

All binding studies were performed in 10 mM HEPES, 300 mM NaCl, 3 mM EDTA, and 0.05% v/v Surfactant Tween-20, pH 7.4 (HBS-ET) running buffer at 25° C. The Biacore CM4 sensor chip surface was first derivatized by amine coupling with the goat anti-human Fcγ specific polyclonal antibody (Jackson ImmunoResearch Laboratories, Cat #BR-1008-39) to capture anti-MSR1 monoclonal antibodies. Binding studies were performed on human MSR1 extracellular domain expressed with a N-terminal nonahistidine tag (His9-hMSR1; R&D Systems, Cat #2708-MS). Different concentrations of His9-hMSR1 (100 nM-3.7 nM or 30 nM-3.33 nM; 3-fold serial dilution) were first prepared in HBS-ET running buffer and were injected over anti-human Fcγ captured anti-MSR1 monoclonal antibody surface for 3 minutes at a flow rate of 50 μL/minute, while the dissociation of monoclonal antibody bound MSR1 reagent was monitored for about 8-10 minutes in HBS-ET running buffer.

The association rate ($k_a$) and dissociation rate ($k_d$) were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\text{min}) = \frac{\ln(2)}{60*kd}$$

Binding kinetics parameters for His9-hMSR1 binding to different anti-MSR1 antibody-LXR ADCs and their unconjugated parental antibodies at 25° C. are shown in Table 19. “LP1” represents a linker-payload for which the payload structure is provided in Example 11.

TABLE 19

Binding kinetics of His-hMSR1 binding to MSR1 Antibody-LXR ADCs and Corresponding Unconjugated Antibodies at 25° C.

| Antibody Captured | ka ($M^{-1}s^{-1}$) | kd ($s^{-1}$) | $K_D$ (Molar) | t½ (min) |
|---|---|---|---|---|
| H1H27729P-N297Q | 1.05E+05 | 9.06E−04 | 8.67E−09 | 12.8 |
| H1H27729P-N297Q-LP1 | 5.47E+04 | 7.18E−04 | 1.31E−08 | 16.1 |
| H1H27731P-N297Q | 1.17E+05 | 1.00E−05 | 8.55E−11 | 1155.2 |
| H1H27731P-N297Q-LP1 | 1.28E+05 | 1.00E−05* | 7.80E−11 | 1155.2 |
| H1H27732P-N297Q | 2.20E+05 | 1.00E−05* | 4.50E−11 | 1155.2 |
| H1H27732P-N297Q-LP1 | 1.50E+05 | 1.00E−05* | 6.60E−11 | 1155.2 |
| H1H27734P-N297Q | 7.72E+04 | 5.96E−04 | 7.72E−09 | 19.4 |
| H1H27734P-N297Q-LP1 | 6.93E+04 | 4.49E−04 | 6.49E−09 | 25.7 |
| H1H27736P-N297Q | 1.14E+05 | 1.47E−04 | 1.29E−09 | 78.7 |
| H1H27736P-N297Q-LP1 | 9.59E+04 | 1.21E−04 | 1.26E−09 | 95.5 |
| H1H27739P-N297Q | 1.19E+05 | 5.55E−04 | 4.68E−09 | 20.8 |
| H1H27739P-N297Q-LP1 | 8.88E+04 | 7.22E−04 | 8.14E−09 | 16.0 |
| H1H27747P-N297Q | 1.17E+05 | 2.62E−04 | 2.24E−09 | 44.1 |
| H1H27747P-N297Q-LP1 | 1.36E+05 | 2.03E−04 | 1.49E−09 | 56.9 |
| H1H27749P-N297Q | 1.43E+05 | 1.00E−05* | 6.99E−11 | 1155.2 |
| H1H27749P-N297Q-LP1 | 1.40E+05 | 1.00E−05* | 7.16E−11 | 1155.2 |
| H1H27751P-N297Q | 2.10E+05 | 1.75E−04 | 8.33E−10 | 66.1 |
| H1H27751P-N297Q-LP1 | 2.29E+05 | 1.52E−04 | 6.64E−10 | 76.1 |
| H1H27754P-N297Q | 2.00E+05 | 1.00E−05* | 4.99E−11 | 1155.2 |
| H1H27754P-N297Q-LP1 | 1.77E+05 | 1.00E−05* | 5.64E−11 | 1155.2 |
| H1H27756P-N297Q | 7.21E+04 | 1.19E−04 | 1.65E−09 | 97.4 |
| H1H27756P-N297Q-LP1 | 6.27E+04 | 1.10E−04 | 1.76E−09 | 104.7 |
| H1H27759P-N297Q | 1.03E+05 | 4.35E−04 | 4.23E−09 | 26.6 |
| H1H27759P-N297Q-LP1 | 1.30E+05 | 5.95E−04 | 4.57E−09 | 19.4 |
| H1H27760P-N297Q | 2.31E+05 | 3.83E−04 | 1.66E−09 | 30.2 |
| H1H27760P-N297Q-LP1 | 2.59E+05 | 4.34E−04 | 1.67E−09 | 26.6 |
| H1H27761P-N297Q | 5.95E+05 | 3.62E−04 | 6.09E−10 | 31.9 |
| H1H27761P-N297Q-LP1 | 2.53E+05 | 5.11E−04 | 2.02E−09 | 22.6 |
| H1H27762P-N297Q | 4.05E+05 | 5.60E−04 | 1.38E−09 | 20.6 |
| H1H27762P-N297Q-LP1 | 4.83E+05 | 6.23E−04 | 1.29E−09 | 18.5 |
| H1H27766P-N297Q | 1.72E+05 | 1.00E−05* | 5.83E−11 | 1155.2 |
| H1H27766P-N297Q-LP1 | 4.16E+05 | 2.70E−05 | 6.49E−11 | 427.4 |
| H1H27771P-N297Q | 3.83E+05 | 3.55E−04 | 9.26E−10 | 32.6 |
| H1H27771P-N297Q-LP1 | 3.38E+05 | 4.42E−04 | 1.31E−09 | 26.1 |
| H1H27773P-N297Q | 5.49E+04 | 7.52E−04 | 1.37E−08 | 15.4 |
| H1H27773P-N297Q-LP1 | 2.72E+04 | 9.47E−04 | 3.48E−08 | 12.2 |
| H1H27778P-N297Q | 1.66E+05 | 2.71E−04 | 1.63E−09 | 42.6 |
| H1H27778P-N297Q-LP1 | 2.85E+05 | 2.76E−04 | 9.70E−10 | 41.8 |
| H1H21234N-N297Q | 2.20E+05 | 1.00E−05* | 4.54E−11 | 1155.2 |
| H1H21234N-N297Q-LP1 | 4.90E+05 | 1.00E−05* | 2.04E−11 | 1155.2 |
| H1xH29273P2 | 8.20E+04 | 7.63E−03 | 9.30E−08 | 1.5 |
| H1xH29282P2 | 8.28E+04 | 3.62E−03 | 4.37E−08 | 3.2 |
| H1xH29283P2 | 1.39E+05 | 1.85E−03 | 1.34E−08 | 6.2 |

*indicates that no dissociation of His9-hMSR1 was observed under the current experimental conditions and the $k_d$ value was manually fixed at 1.00E−05 while fitting the data $indicates that no binding was observed under the current experimental conditions.

At 25° C., different anti-MSR1 antibody-LXR conjugates bound to 9×His-hMSR1 with $K_D$ values ranging from less than or equal to 0.6 pM to 34.8 nM, while the unconjugated parental antibodies bound to 9×His-hMSR1 with $K_D$ values ranging from less than or equal to 0.6 pM to 13.7 nM as shown in Table 19.

The binding studies were repeated with anti-MSR1 antibody H1H21234-N297Q and steroid linker payloads (LPs). Binding kinetics parameters for His9-hMSR1 binding at 25° C. are shown in Table 20. “LP3” represents a linker-payload for which the structure is provided in Example 23, and “LP13” represents a linker-payload for which the structure is provided in Example 24.

TABLE 20

Binding kinetics of His-hMSR1 binding to MSR1 Antibody-Steroid ADCs and Corresponding Unconjugated Antibody at 25° C.

| Antibody Captured | ka ($M^{-1}s^{-1}$) | kd ($s^{-1}$) | $K_D$ (Molar) | t½ (min) |
|---|---|---|---|---|
| H1H21234N-N297Q* | 3.00E+05 | 1.00E−05 | 3.33E−11 | 1155.2 |
| H1H21234N-N297Q-LP3* | 4.17E+05 | 1.00E−05 | 2.40E−11 | 1155.2 |
| H1H21234N-N297Q-LP13* | 4.00E+05 | 1.00E−05 | 2.50E−11 | 1155.2 |

*indicates that no dissociation of His9-hMSR1 was observed under the current experimental conditions and the $k_d$ value was manually fixed at 1.00E−05 while fitting the data $indicates that no binding was observed under the current experimental conditions.

At 25° C., an anti-MSR1 monoclonal antibody conjugated with LP3 and LP13 bound to His9-hMSR1 with $K_D$ values ranging from 25.0 pM and 24.0 pM, respectively, as shown in Table 20. In comparison, the corresponding unconjugated anti-MSR1 monoclonal antibody bound to His9-hMSR1 with a $K_D$ value of 33.3 pM.

Example 31. Anti-MSR1 Antibody-LXR Conjugates Activate LXR Signaling in a LXR-Luciferase Reporter Bioassay Generation of assay cell line. To test the efficacy of anti-MSR1 antibody-LXR conjugates in vitro, a cell-based LXR responsive luciferase reporter assay was developed. To generate the assay cell line, a LXR regulated luciferase reporter gene [Cignal Lenti LXR Reporter (luc) kit (Qiagen, Cat #CLS-001 L)] was transduced into THP1 cells, and cells were selected for two weeks in puromycin. The lentivirus expresses the firefly luciferase gene under the control of a minimal CMV promoter and tandem repeats of the LXR transcriptional response element. The resulting cell line is referred to as THP1/LXR-Luc cells.

Assay protocol. THP1/LXR-Luc cells were seeded onto 96 well plates at 40,000 cells/well in media containing RPMI supplemented with 10% FBS and pencillin/streptomycin and subsequently differentiated with 200 nM Phorbol Myristate Acetate (PMA) for 3 days. After the 3-day differentiation period, three-fold serial dilutions of antibody drug conjugates, unconjugated antibodies, or free payloads in fresh media were added to the cells at final concentration ranging from 100 nM to 0.01 nM. Media alone served as a blank control. Forty-eight hours later, luciferase activity was determined after the addition of One-Glo™ reagent (Promega, Cat #E6130) to each well. Relative light units (RLUs) were measured on a Victor luminometer (PerkinElmer) and $EC_{50}$ values were determined using a four-parameter logistic equation over a 10-point dose response curve (GraphPad Prism). The $EC_{50}$ value of each reagent tested is shown in Table 21. The signal to noise (S/N) was determined by calculating the ratio of RLU of standard one over RLU of standard eight for each of the unconjugated anti-MSR1 antibodies or free payloads. "LP #" represents a linker-payload for which the corresponding structures are provided elsewhere herein, and "P #" represents a payload for which the corresponding structures are provided elsewhere herein.

TABLE 21

Agonist Activity of Anti-MSR1 Antibody-LXR Conjugates, Payloads, and Unconjugated Antibodies

| Molecule tested | $EC_{50}$ (M) | S/N |
|---|---|---|
| H1H21231N-N297Q-LP1 | 8.6E−10 | 14.5 |
| H1H21227N-N297Q-LP1 | 8.9E−10 | 31.0 |
| H1H21231N-N297Q-LP1 | 1.73E−09 | 38.6 |
| H1H21234N-N297Q-LP1 | 3.65E−09 | 18.4 |
| H1H21234N-N297Q-LP4 | 6.3E−10 | 9.0 |
| H1H21234N-N297Q-LP5 | 9.8E−10 | 9.6 |
| H1H21234N-N297Q-LP6 | 1.02E−09 | 9.2 |
| H1H21234N-N297Q-LP12 | No activation | 1.5 |
| H1H21234N-N297Q-LP9 | 1.12E−09 | 8.3 |
| H1H21234N-N297Q-LP11 | 8.1E−10 | 10.0 |
| H1H21234N-N297Q-LP2 | 8.7E−10 | 9.1 |
| H1H27729P-N297Q-LP1 | 1.64E−09 | 14.5 |
| H1H27731P-N297Q-LP1 | 1.46E−09 | 15.5 |
| H1H27732P-N297Q-LP1 | 8.2E−10 | 19.1 |
| H1H27734P-N297Q-LP1 | 5.19E−09 | 17.8 |
| H1H27736P-N297Q-LP1 | 1.01E−09 | 16.4 |
| H1H27739P-N297Q-LP1 | 1.60E−09 | 21.0 |
| H1H27747P-N297Q-LP1 | 4.77E−09 | 20.6 |
| H1H27749P-N297Q-LP1 | 1.46E−09 | 13.1 |
| H1H27751P-N297Q-LP1 | 1.54E−09 | 17.9 |
| H1H27754P-N297Q-LP1 | 1.30E−09 | 17.3 |
| H1H27756P-N297Q-LP1 | 1.61E−09 | 18.6 |
| H1H27759P-N297Q-LP1 | 5.94E−09 | 18.9 |
| H1H27760P-N297Q-LP1 | 6.34E−09 | 21.5 |
| H1H27761P-N297Q-LP1 | 5.72E−09 | 20.7 |
| H1H27762P-N297Q-LP1 | 7.02E−09 | 16.4 |
| H1H27766P-N297Q-LP1 | 1.277E−08 | 11.3 |
| H1H27771P-N297Q-LP1 | 2.41E−09 | 17.3 |
| H1H27773P-N297Q-LP1 | >4.05E−08 | 12.9 |
| H1H27778P-N297Q-LP1 | 1.51E−09 | 16.1 |
| H1H21235N-N297Q-LP1 | 8.3E−10 | 8.2 |
| H1H25700N-N297Q-LP1 | 1.13E−09 | 7.4 |
| H1H25690N-N297Q-LP1 | 2.5E−10 | 8.0 |
| H1H25695N-N297Q-LP1 | 1.87E−09 | 9.8 |
| H1H25685N-N297Q-LP1 | 7.8E−10 | 8.3 |
| H1H21228N-N297Q-LP1 | 1.8E−09 | 8.6 |
| Isotype Control-N297Q-LP1 | >6.6E−08 | 2.7 |
| H1H21234N-N297Q | No activation | No activation |
| P1 | 1.14E−09 | 15.9 |
| P5 | 4.6E−10 | 5.7 |
| P7 | 2.09E−09 | 8.9 |
| P6 | 3.7E−10 | 8.3 |

As shown in Table 21, at 48-hour time point, all of the anti-MSR1 antibodies conjugated with LP1 demonstrated stimulation of the THP1/Luc cells with $EC_{50}$ values ranging from 0.2 nM to greater than 140.5 nM with S/N values ranging from 7.4 to 38.6. One exemplary anti-MSR1 antibody-LXR conjugate (H1H21234N-N297Q-LP1) demonstrated stimulation of the THP1/Luc cells with an $EC_{50}$ value of 3.7 nM and S/N of 18.4. The free payload, P1, demonstrated stimulation of the THP1/Luc cells with an average $EC_{50}$ of 15.9 nM. The isotype control antibody conjugated with LP1 (Isotype control-LP1) had an average $EC_{50}$ value of >66 nM and S/N of 2.7. Additionally, H1H21234N-N297Q conjugated with additional LXR agonist linker-payloads (H1H21234N-N297Q-LP4, H1H21234N-N297Q-LP5, H1H21234N-N297Q-LP6, H1H21234N-N297Q-LP12, H1H21234N-N297Q-LP9, H1H21234N-N297Q-LP11, and H1H21234N-N297Q-LP2) tested demonstrated stimulation of the THP1/Luc cells with $EC_{50}$ values ranging from 0.63 nM to greater than 73 nM and S/N ranging from 1.4 to 10. In contrast, an anti-MSR1 antibody conjugated to an LXR agonist linker-payload (H1H21234N-N297Q-LP12), which acted as comparators in the assay, did not demonstrate any activation of the THP1/Luc cells. Additional LXR agonist payloads tested (P5, P7, and P6) demonstrated stimulation of the THP1/Luc cells with $EC_{50}$ values ranging from 0.37 nM to 2.09 nM and S/N ranging from 5.7 to 8.9. One unconjugated anti-MSR1 antibody (H1H21234N) alone did not have any impact on stimulation of the THP/Luc cells.

Example 32. Anti-MSR1 Antibody-Steroid Conjugates Inhibit Release of LPS-Mediated IL-1β In Vitro To test the anti-inflammatory properties of anti-MSR1 antibody-steroid conjugates in vitro, a lipopolysaccharide (LPS)-mediated IL-1β release assay was performed. For the assay, THP-1 cells were seeded onto 96 well plates at 40,000 cells/well in media containing RPMI supplemented with 10% FBS and pencillin/streptomycinin and differentiated with 200 nM Phorbol Myristate Acetate (PMA) for 3 days. After the 3-day differentiation period, three-fold serial dilutions of antibody drug conjugates, unconjugated antibodies, or free payloads in fresh media were added to the cells at final concentration ranging from 100 nM to 0.01 nM. Media alone served as a blank control. Subsequently at 24, 48, or 72 hours later, cells were treated with 100 ng/ml LPS (InVivoGen, Cat #tlrl-eklps) for 5 hours. The cell media was then collected, and IL-1β levels were measured using a V-PLEX Proinflammatory Panel 1 human kit (Meso Scale Diagnostics, Cat #15049D-2) as per manufacturer's instructions. Subsequently, the plate was read on a Meso Scale Diagnostics instrument.

$IC_{50}$ values were determined from a four-parameter logistic equation over a 10-point response curve (GraphPad Prism). All $IC_{50}$ values are expressed in M (molar) concentration. The $IC_{50}$ values and IL-1β amount at the maximum concentration of antibody-steroid conjugates or controls are shown in Table 22 each of the time point tested.

TABLE 22

LPS-induced IL-1β Release of Anti-MSR1 Antibody-Steroid Conjugates

| | 24 hour | | 48 hour | | 72 hour | |
|---|---|---|---|---|---|---|
| Molecule | $EC_{50}$ (M) | IL1beta released at max concentration tested (pg/mL) | $EC_{50}$ (M) | IL1beta released at max concentration tested (pg/mL) | $EC_{50}$ (M) | IL1beta released at max concentration tested (pg/mL) |
| H1H21234N-N297Q-LP13 | 6.287E−09 | 119.43 | 3.586E−09 | 69.3 | 1.7E−09 | 70.31 |
| Isotype control-N297Q-LP13 | NA | 209.6 | NA | 279.4 | NA | 276.27 |
| H1H21234N-N297Q | NA | 234.21 | NA | 267.7 | NA | 355.76 |
| P4 | 8.486E−10 | 43.39 | 1.017E−09 | 9.3 | 1.199E−09 | 12.95 |
| Dexamethasone | 4.199E−10 | 45.33 | 7.941E−10 | 11.8 | 5.433E−10 | 13.34 |

As shown in Table 22, at 24-hour time point, the anti-MSR1 antibody-steroid conjugate (H1H21234N-N297Q-LP13) inhibited LPS-induced IL-1β secretion with an $IC_{50}$ of 6.287 nM. The free payload P4 and free payload control Dexamethasone, inhibited LPS-induced IL-1β secretion with $IC_{50}$ values of 0.8486 nM and 0.4199 nM, respectively. Neither the isotype control antibody conjugated with LP13 (Isotype control-N297Q-LP13) nor the unconjugated anti-MSR1 antibody (H1H21234N-N297Q) had any impact on LPS-induced IL-1β release.

As shown in Table 22, at 48-hour time point, the anti-MSR1 antibody-steroid conjugate (H1H21234N-N297Q-LP13) inhibited LPS-induced IL-1β secretion with an $IC_{50}$ of 3.586 nM. The free payload P4 and free payload control Dexamethasone, inhibited LPS-induced IL-1β secretion with $IC_{50}$ values of 1.017 nM and 0.7941 nM, respectively. Neither the isotype control antibody conjugated with LP13 (Isotype control-N297Q-LP13) nor the unconjugated anti-MSR1 antibody (H1H21234N-N297Q) had any impact on LPS-induced IL-1β release.

As shown in Table 22, at 72-hour time point, the anti-MSR1 antibody-steroid conjugate (H1H21234N-N297Q-LP13) inhibited LPS-induced IL-1β secretion with an $IC_{50}$ of 1.7 nM. The free payload P4 and free payload control Dexamethasone inhibited LPS-induced IL-1β secretion with $IC_{50}$ values of 1.199 nM and 0.5433 nM, respectively. Neither the isotype control antibody conjugated with LP13 (Isotype control-N297Q-LP13) nor the unconjugated anti-MSR1 antibody (H1H21234N-N297Q) had any impact on LPS-induced IL-1β release.

Example 33. Anti-MSR1 Antibody-Steroid Conjugates Inhibit Release of LPS-Mediated Inflammatory Responses In Vivo To examine the anti-inflammatory effect of the anti-MSR1 antibody-steroid conjugates, an ex-vivo and in vivo LPS-induced inflammatory immune response model was performed.

Generation of a mouse inflammatory immune response model. Mice homozygously expressing human MSR1 extracellular domain in place of the mouse MSR1 extracellular domain and with a homozygous deletion of the ApoE gene were utilized (resulting mice referred to as $Msr1^{hu/hu}$ $ApoE^{-/-}$ mice).

Assay protocol for ex vivo LPS-induced responses. In ex vivo LPS challenge experiments, mice were intraperitoneally administered with 10 μL/g of anti-MSR1 antibody-steroid conjugates (H1H21234N-N297Q-LP13), isotype control steroid conjugate (Isotype control-LP13), unconjugated anti-MSR1 antibody (H1H21234N-N297Q) and isotype control antibodies at different time points (24, 48, and 72 hours) prior to harvesting the peritoneal cells from peritoneal cavity. PBS and free steroids P4 and Dexamethasone (Henry Schein Animal Health, Cat #NDC #11695-4017-1), were intraperitoneally injected at 2 hour prior to peritoneal cell isolation. Experimental dosing and treatment protocol for groups of mice are shown in Table 23. All mice were sacrificed at 0 hour time point and peritoneal cells were obtained from the peritoneum by the peritoneal lavage technique. In brief, 5 mL of ice cold 1×PBS (ThermoFisher Scientific, Cat #20012027) containing 2% BSA (Gibco, Cat #A9576) and 0.6 mM EDTA (ThermoFisher Scientific, Cat #15575020) were injected into the peritoneal cavity using 27 g needle. Peritoneal cells were collected into 15 mL tubes with 20 g needle attached to 5-mL syringe, centrifuged at 300×g for 8 minutes and adjusted to $1\times10^6$ cells/mL in RPMI-1640 (ThermoFisher Scientific, #15140122) containing 10% of FBS (ThermoFisher Scientific, Cat #10082147) and 1% of penicillin-streptomycin (ThermoFisher Scientific, Cat #11875093). The resuspended cells were plated at 500,000 cells per well in 24-well tissues culture plates and incubated with or without 10 ng/mL of LPS for 18 hours.

TABLE 23

Experiment Design, Dosing, and Treatment Protocol for Ex Vivo LPS Challenge Experiment

| | In vivo | | | | Ex vivo LPS |
|---|---|---|---|---|---|
| | Group | Mice (n) | Molecule tested | Dose (mg/kg) | Challenge (10 ng/mL) |
| 72 hour | 1 | 3 | H1H21234N-N297Q-LP13 | 96.08 | +/−LPS |
| | 2 | 3 | Isotype control-N297Q-LP13 | 97.07 | +/−LPS |
| | 3 | 3 | H1H21234N-N297Q | 96.08 | +/−LPS |
| | 4 | 3 | Isotype control-N297Q | 97.07 | +/−LPS |
| 48 hour | 5 | 3 | H1H21234N-N297Q-LP13 | 96.08 | +/−LPS |
| | 6 | 3 | Isotype control-N297Q-LP13 | 97.07 | +/−LPS |
| | 7 | 3 | H1H21234N-N297Q | 96.08 | +/−LPS |
| | 8 | 3 | Isotype control-N297Q | 97.07 | +/−LPS |
| 24 hour | 9 | 3 | H1H21234N-N297Q-LP13 | 96.08 | +/−LPS |
| | 10 | 3 | Isotype control-N297Q-LP13 | 97.07 | +/−LPS |
| | 11 | 3 | H1H21234N-N297Q | 96.08 | +/−LPS |
| | 12 | 3 | Isotype control-N297Q | 97.07 | +/−LPS |
| 2 hour | 13 | 3 | PBS | — | +/−LPS |
| | 14 | 3 | Dexamethasone | 1 | +/−LPS |
| | 15 | 3 | P4 | 1.48 | +/−LPS |

Assay protocol for in vivo LPS-induced responses. In in vivo LPS challenge experiments, mice were intraperitoneally administered with 10 μL/g of decreasing concentrations of anti-MSR1 antibody-steroid conjugates (H1H21234N-N297Q-LP13) and isotype control steroid conjugate (Isotype control-N297Q-LP13) at 24 hours prior to in vivo LPS challenge. PBS and free steroid P4 were intraperitoneally injected at 2 hours prior to in vivo LPS challenge. Experimental dosing and treatment protocol for groups of mice are shown in Table 24. At 0 hour time point, three large drops of blood (volume ~ 100 μL) were collected from the maxillary vein of each mouse into serum gel separator tubes. The tubes were centrifuged at 2200-2500 rpm for 15 minutes, and the serum was collected into 96-well plates for subsequent measurement of cytokines. At 18 hours post in vivo LPS challenge, the peritoneal cells were obtained from periotenal cavity as aforementioned for subsequent flow cytometry analysis.

TABLE 24

Experiment Design, Dosing, and Treatment Protocol for In Vivo LPS Challenge Experiment

| | In vivo | | | | In vivo LPS |
|---|---|---|---|---|---|
| | Group | Mice (n) | Molecule tested | Dose (mg/kg) | Challenge (1 μg/mouse) |
| 24 hour | 1 | 5 | H1H21234N-N297Q-LP13 | 96.08 | + |
| | 2 | 5 | Isotype control-N297Q-LP13 | 97.07 | + |
| | 3 | 5 | H1H21234N-N297Q-LP13 | 32.03 | + |
| | 4 | 5 | Isotype control-N297Q-LP13 | 32.36 | + |
| | 5 | 5 | H1H21234N-N297Q-LP13 | 10.67 | + |
| | 6 | 5 | Isotype control-N297Q-LP13 | 10.79 | + |
| 2 hour | 7 | 3 | PBS | — | − |
| | 8 | 5 | PBS | — | + |
| | 9 | | P4 | 1.48 | + |
| | 10 | 5 | P4 | 0.49 | + |
| | 11 | 5 | P4 | 0.16 | + |

Measurement of cytokines at 18 hours post-LPS ex vivo challenge. Supernatants were collected into 96-well round bottom tissue culture plates at 18 hours post-ex vivo LPS challenge and stored at 20° C. until further analysis. Cytokine concentrations in the supernatants were measured using a Proinflammatory Panel 1 (mouse) multiplex immunoassay kit (MesoScale Diagnostics, Cat #K15048D) according to manufacturer's instructions. Electrochemiluminescence was read on a Meso Scale Diagnostics SECTOR® instrument. Data analysis was performed using GraphPad Prism™ software. Statistical significance within the groups was determined by one-way Anova with Turkey's multiple comparison post-test (*p<0.01; p<0.001; *p<0.0001).

Analysis of expression of activation markers on peritoneal macrophages after LPS ex vivo challenge. Upon collection of supernatants for cytokine analysis, the plates were washed twice with 1×PBS w/o $Ca^{++}$/$Mg2^{++}$ (ThermoFisher Scientific, Cat #14190144), and the adherent peritoneal cells were harvested by addition of 250-300 μL of cold Macrophage Detachment Solution DXF (PromoCell, Cat #C41330) for 40 minutes. The detached cells were collected into 50-mL tubes and centrifuged at 350×g for 15 minutes. After two washes with 1×PBS supplemented with 2 mM EDTA, the cells were resuspended in Cell Staining Buffer (Biolegend, #420201) and plated at $1\times10^6$ cells per well in a 96-well V bottom plate. Cells were centrifuged and cell pellets were resuspended in 100 μL of LIVE/DEAD Blue Fluorescent Reactive Dye (Life Technologies, Cat #L34962) diluted at 1:600 in 1×PBS to determine cell viability. Cells were incubated at room temperature for 20 minutes in dark. After one wash with 1×PBS, cells were incubated in Cell Staining Buffer containing 10 μg/mL of purified rat anti-mouse CD16/CD32 Fc Block (Clone: 2.4G2; BD Biosciences, Cat #553142) for 10 minutes at 4° C. The cells were washed once and incubated in the appropriate antibody mixture diluted in Brilliant Stain Buffer (BD Biosciences, Cat #566345) for 30 minutes at 4° C. in dark. The antibody panel used for flow cytometry analysis is shown in Table 25. The cells were subsequently washed with 1×PBS, resuspended in Cell Staining Buffer and acquired on FACS LSRFortessa X-20 flow cytometer (Becton Dickinson). Data were analyzed using FlowJo (Tree Star).

TABLE 25

| Antibodies used in flow cytometry analysis | | | | |
|---|---|---|---|---|
| Antibody | Fluorochrome | Manu-facturer | Catalog Number | Final Dilution |
| anti-mouse CD45 | BV510 | Biolegend | 103138 | 1/200 |
| anti-mouse B220 | APC-Cy7 | Biolegend | 103224 | 1/200 |
| anti-mouse TCRβ | BV711 | Biolegend | 109243 | 1/200 |
| anti-mouse CD11b | PercP-Cy5.5 | Biolegend | 101228 | 1/300 |
| anti-mouse F4/80 | FITC | Biolegend | 123108 | 1/200 |
| anti-human SR-AI/MSR1 | PE | R&D Systems | FAB2708P | 1/30 |
| anti-mouse TLR4 | APC | Biolegend | 145405 | 1/200 |

TABLE 25-continued

| Antibodies used in flow cytometry analysis | | | | |
|---|---|---|---|---|
| Antibody | Fluorochrome | Manu-facturer | Catalog Number | Final Dilution |
| anti-mouse MHCII | BV421 | Biolegend | 107631 | 1/200 |
| anti-mouse CD80 | PE-Cy7 | Biolegend | 104733 | 1/200 |

Results are provided in Tables 26 to 28. Flow cytometry analysis of peritoneal cells derived from Msr1$^{hu/hu}$ ApoE$^{-/-}$ mice revealed that hMSR1 and TLR4 are predominantly expressed on the surface of F4/80$^{+}$CD11 b$^{+}$ peritoneal macrophages suggesting that MSR1$^{+}$ cells are the main responders to LPS stimulation.

TABLE 26

| Ex Vivo LPS-induced Cytokine Production for Anti-MSR1 Antibody-steroid Conjugates and Controls | | | | |
|---|---|---|---|---|
| | | Cytokine [ng/mL] | | |
| Antibody/Reagent | Time | IL-6 | KC-GRO | TNF-α |
| PBS | 2 hours | 224.8 ± 11.04 | 26.4 ± 2.1 | 1.8 ± 0.3 |
| Dexamethasone | | 134.5 ± 18.2* | 19.9 ± 1.5 | 0.63 ± 0.11* |
| P4 | | 12.98 ± 5.8**** | 2.6 ± 1.3** | 0.43 ± 0.06** |
| H1H21234N-N297Q-LP13 | 24 hours | 21.1 ± 1.38**** | 9.3 ± 1.7 | 0.26 ± 0.08*** |
| Isotype Control-N297Q-LP13 | | 165.6 ± 20.7 | 17.8 ± 1.7 | 0.96 ± 0.14 |
| H1H21234N-N297Q | | 261.9 ± 18.3 | 36.4 ± 2.9 | 2.02 ± 0.4 |
| Isotype Control-N297Q | | 215.8 ± 40.1 | 21.9 ± 5.2 | 1.9 ± 0.1 |
| H1H21234N-N297Q-LP13 | 48 hours | 34.02 ± 7.8** | 6.3 ± 2.3* | 0.58 ± 0.06* |
| Isotype Control-N297Q-LP13 | | 113.4 ± 11.3 | 22.2 ± 4.2 | 1.2 ± 0.2 |
| H1H21234N-N297Q | | 158.3 ± 11.6 | 15.2 ± 0.8 | 1.6 ± 0.3 |
| Isotype Control-N297Q | | 143.4 ± 12.4 | 18.8 ± 1.8 | 1.12 ± 0.1 |
| H1H21234N-N297Q-LP13 | 72 hours | 50.7 ± 14.1* | 13.1 ± 1.1 | 0.47 ± 0.1** |
| Isotype Control-N297Q-LP13 | | 132.1 ± 18.9 | 20.8 ± 2.7 | 0.92 ± 0.07 |
| H1H21234N-N297Q | | 228.6 ± 19.7 | 27.1 ± 3.5 | 1.09 ± 0.2 |
| Isotype Control-N297Q | | 284.5 ± 14.9 | 29.4 ± 8.2 | 1.2 ± 0.2 |

As shown in Table 26, ex vivo LPS challenge induced robust production of IL-6, KC-GRO and TNF-α by peritoneal cells derived from Msr1$^{hu/hu}$ ApoE$^{-/-}$ mice pre-treated with PBS. On the contrary, in vivo administration of MSR1-ncADC conjugates (H1H21234N-N297Q-LP13) at the dose equivalent to 1 mg/kg of Dexamethasone was efficacious in inhibiting LPS-induced cytokine production by peritoneal cells in a time-dependent manner. Comparable inhibition of LPS-induced immune responses was observed between administration of antibody-steroid conjugates at 24, 48, and 72 hours and administration of free payload P4 at 2 hours (Table 26). A similar effect on inhibition of LPS-induced immune response was observed between administration of isotype control-steroid conjugates at 24, 48, and 72 hours and Dexamethasone at 2 hours (Table 26). No effect on LPS-induced cytokine production was observed with isotype control-steroid conjugate (Isotype control-N297Q-LP13), unconjugated anti-MSR1 antibody (H1H21234N-N297Q) and isotype control antibodies administered at different time points (Table 26).

TABLE 27

| In Vivo LPS-induced Cytokine Production in Serum for Anti-MSR1 Antibody-steroid Conjugates and Controls | | | | | |
|---|---|---|---|---|---|
| | Administered Concentration | | Cytokine [ng/mL] | | |
| Antibody/Reagent | (mg/kg) | Time | IL-6 | KC-GRO | TNF-α |
| PBS | — | 2 | 56.94 ± 9.3 | 13.97 ± 1.7 | 1.7 ± 0.3 |
| P4 | 1.48 | hours | 3.51 ± 0.7*** | 4.1 ± 1.5* | 0.09 ± 0.02*** |

TABLE 27-continued

In Vivo LPS-induced Cytokine Production in Serum for Anti-MSR1 Antibody-steroid Conjugates and Controls

| Antibody/Reagent | Administered Concentration (mg/kg) | Time | Cytokine [ng/mL] IL-6 | KC-GRO | TNF-α |
|---|---|---|---|---|---|
| P4 | 0.49 | | 11.89 ± 7.7** | 6.7 ± 2.3 | 0.2 ± 0.04*** |
| P4 | 0.16 | | 19.15 ± 1.1* | 15.1 ± 1.2 | 0.6 ± 0.05*** |
| H1H21234N- | 96.08 | 24 | 7.7 ± 3.1*** | 5.1 ± 1.5* | 0.42 ± 0.14*** |
| N297Q-LP13 | 32.03 | hours | 15.34 ± 5.2*** | 10.6 ± 2.8 | 0.48 ± 0.18*** |
| | 10.67 | | 33 ± 8.1 | 13.3 ± 1.2 | 0.51 ± 0.08*** |
| Isotype Control- | 97.07 | 24 | 33.6 ± 4.1 | 19.2 ± 0.6 | 2.6 ± 0.92 |
| N297Q-LP13 | 32.36 | hours | 65.9 ± 7.8 | 18.2 ± 1.7 | 2 ± 0.67 |
| | 10.79 | | 76.3 ± 9.9 | 19.9 ± 2.1 | 1.9 ± 0.62 |

In vivo administration of MSR1-steroid conjugates (H1H21234N-N297Q-LP13) was also efficacious in inhibiting in vivo LPS-induced cytokine production in a dose-dependent manner in Msr1$^{hu/hu}$ ApoE$^{-/-}$ mice 2 hours post LPS challenge (Table 27). No effect on LPS-induced cytokine production in vivo was observed with isotype control-ncADC (Isotype control-N297Q-LP13, Table 27).

TABLE 28

Ex Vivo LPS-induced Cytokine Production for Anti-MSR1 Antibody-steroid Conjugates and Controls

| Antibody/Reagent | Time | LPS-mediated expression of CD80 [% relative to PBS/LPS-treatment] pMΦ Cells | non-pMΦ Cells |
|---|---|---|---|
| Dexamethasone | 2 hours | 77.69 ± 2.6 | 99.6 ± 5.8 |
| P4 | | 54.7 ± 3.8**** | 93.02 ± 4.4 |
| H1H21234N-N297Q-LP13 | 24 hours | 61.1 ± 1.3*** | 95.5 ± 2.6 |
| Isotype Control-N297Q-LP13 | | 94.9 ± 7.2 | 90.22 ± 5.2 |
| H1H21234N-N297Q | | 76.8 ± 2.3 | 98.9 ± 3.1 |
| Isotype Control-N297Q | | 75.6 ± 4 | 100.8 ± 8.5 |
| H1H21234N-N297Q-LP13 | 48 hours | 58.7 ± 4.2**** | 99 ± 1.8 |
| Isotype Control-N297Q-LP13 | | 75.9 ± 3.8 | 95.4 ± 5.2 |
| H1H21234N-N297Q | | 81.9 ± 2 | 100.4 ± 3.3 |
| Isotype Control-N297Q | | 87.4 ± 0.6 | 107.7 ± 6.7 |
| H1H21234N-N297Q-LP13 | 72 hours | 63.9 ± 1.01*** | 102.3 ± 0.14 |
| Isotype Control-N297Q-LP13 | | 85.3 ± 12.04 | 95.6 ± 2.2 |
| H1H21234N-N297Q | | 82.9 ± 5.9 | 96.3 ± 3.3 |
| Isotype Control-N297Q | | 86.4 ± 4.3 | 96.8 ± 8.8 |

In addition, as illustrated in Table 28, in vivo administration of anti-MSR1 antibody-steroid conjugate (H1H21234N-N297Q-LP13) led to a significant reduction of LPS-mediated expression of CD80 on hMSR1$^+$F4/80$^+$ CD11 b$^+$ peritoneal macrophages (pMΦ), but not on hMSR1$^-$F4/80$^-$CD11b$^-$ cells (non-pMΦ). No effect on CD80 expression was observed with Isotype control antibodies (Table 28).

Example 34. Anti-MSR1 Antibody-LXR Conjugates Activate Cholesterol Efflux in THP-1 Cells The ability of anti-MSR1 antibody-LXR conjugates to activate cholesterol efflux in a human macrophage cell line (THP-1; ATCC Catalog #TIB-202), was assessed using a fluorescent cholesterol analog.

Briefly, THP-1 cells were seeded onto 96-well poly-lysine coated plates (Corning, Catalog #354640) at 100,000 cells/well in RPMI 1640 media (Irvine Scientific, Catalog #9160) containing 10% FBS (Gibco, Catalog #1043010), 10 μg/mL penicillin-streptomycin (Gibco, Catalog #15140122) and incubated at 5% $CO_2$ at 37° C. Cells were differentiated into macrophages by addition of 100 nM Phorbol-12 myristate 13-acetate (Sigma, Catalog #P8139) to the media and subjected to further incubation for 96 hours. Differentiated macrophages were then incubated in phenol red free RPMI 1640 media (Gibco, Catalog #32404-014) containing 25 μM BODIPY-cholesterol (Avanti Polar Lipids, Catalog #810255P), 0.2% bovine serum albumin (BSA; Sigma, Catalog #A7211), and 10 μg/mL penicillin-streptomycin for 24 hours, followed by a 24-hour treatment with serial dilutions of ranging from $1\times10^{7}$ M to $5\times10^{-14}$ M of either free payload, anti-MSR1 antibody-LXR conjugate (H1H21234N-N297Q-LP1), Isotype control-LXR conjugate (Isotype control-N297Q-LP1), and unconjugated anti-MSR1 antibody (H1H21234N-N297Q) in phenol red free RPMI 1640 media containing 0.2% BSA. Cells were washed with phenol red free RPMI 1640 media and incubated with 100 μL of acceptor media containing 50 μg/mL high density lipoprotein (Millipore, Catalog #437641), 10 μg/mL apolipoprotein A1 (Millipore, Catalog #ALP10) in phenol red free RPMI 1640 media for 5 hours, after which, the acceptor media was collected and cells were lysed in 100 μL of RIPA buffer (Millipore, Catalog #20-188) for 2 hours with gentle agitation at room temperature. Fluorescence was measured in these fractions at excitation 482 nm, emission 515 nm in SpectraMax i3 plate reader (Molecular Devices).

Figure 17:
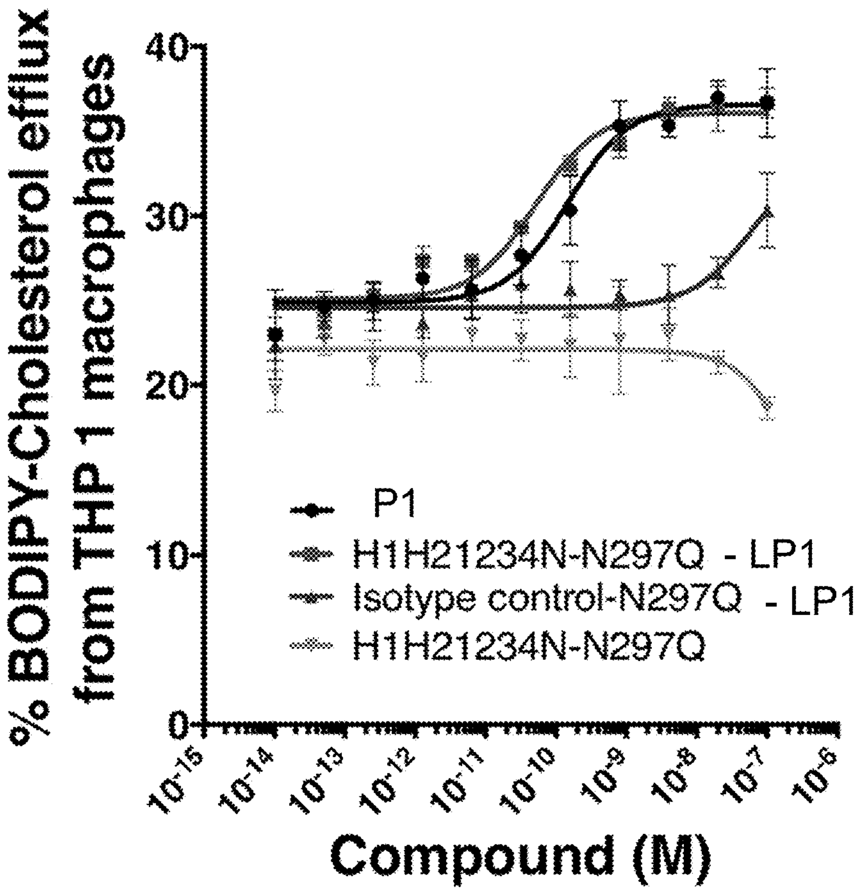
FIG. 17 is a line graph illustrating percentage of dose-dependent cholesterol efflux in THP-1 macrophages for an exemplary MSR1 antibody-LXR conjugate, its unconjugated counterpart, an isotype control-steroid conjugate, and the corresponding free payload.

Percentage of BODIPY-cholesterol efflux was calculated using the following formula: [fluorescence in acceptor media/(fluorescence in acceptor media+fluorescence in cell lysate)]×100. Table 29 provides activated cholesterol efflux for the tested articles, and FIG. 17 illustrates the data in graph form.

TABLE 29

Activation of cholesterol efflux by antibody-LXR conjugates and comparators

| Molecule tested | Cholesterol Efflux activation $EC_{50}$ (M) | Maximum efflux (%) |
|---|---|---|
| P1 | 1.5E−10 | 36.7 |
| H1H21234N-N297Q-LP1 | 5.0E−11 | 36.7 |
| Isotype control-N297Q-LP1 | >6.4E−8 | 30.3 |
| H1H21234N-N297Q | N/A | 18.7 |

As shown in Table 29, after 24 hours, H1H21234N-N297Q-LP1 conjugate demonstrated the largest amount of cholesterol efflux with a maximum percent efflux of 36.6% and an $EC_{50}$ value of 50 pM. The free payload P1 demonstrated the second largest amount of cholesterol efflux with a maximum percent efflux of 36.6% and an $EC_{50}$ value of 150 pM. The Isotype control-N297Q-LP1 conjugate demonstrated a minimal amount of cholesterol efflux with a maximum percent efflux of 30.3%. The unconjugated antibody, H1H21234N-N297Q, did not demonstrated any measurable cholesterol efflux.

Example 34A Activity of LXR Agonist Payloads in a Cell Based LXR Responsive Luciferase Reporter Assay The activity of certain LXR agonist payloads described herein were assessed in a cell based LXR responsive luciferase reporter assay. To generate the assay cell line, an LXR regulated luciferase reporter gene (Cignal Lenti LXR Reporter (luc) kit (Qiagen, Cat #CLS-001L)) was transduced into THP1 cells and the cells were selected for two weeks in puromycin. The lentivirus expresses the firefly luciferase gene under the control of a minimal CMV promoter and tandem repeats of the LXR transcriptional response element. The resulting cell line is referred to as THP1/LXR-Luc cells. For the assay, THP1/LXR-Luc cells were seeded onto 96 well plates at 40,000 cells/well in media containing RPMI supplemented with 10% FBS and penicillin/streptomycin and were then differentiated with 200 nM Phorbol Myristate Acetate (PMA) for 3 days. The media was subsequently removed and replaced with 80 uL of fresh media without PMA. Three-fold serial dilutions of free payloads were prepared in 100% DMSO, transferred to fresh media, and 20 uL were added to the cells at a final constant DMSO concentration of 0.2% and free payloads at final concentrations ranging from 100 nM to 0.015 nM. The last well in the plate served as blank control containing only the media and 0.2% DMSO (untreated well) and was plotted as a continuation of the 3-fold serial dilution. Forty-eight hours later, luciferase activity was determined after the addition of One-Glo™ reagent (Promega, Cat #E6130) to each well. Relative light units (RLUs) were measured on a Victor luminometer (PerkinElmer) and $EC_{50}$ values were determined using a four-parameter logistic equation over a 10-point dose response curve (GraphPad Prism). The $EC_{50}$ value of each molecule tested is shown in the Table 1. The signal to noise (S/N) was determined by taking the ratio of the highest RLU on the dose response curve to the RLU in the untreated wells. As shown in Table 5, all of the tested payload compounds increased LXR-dependent luciferase activity in THP1/LXR-Luc cells with $EC_{50}$ values ranging from 112 pM to 3.51 nM and S/N values ranging from 10.4 to 13.8.

TABLE 30

LXR-Reporter Activity by Payload Compounds in Differentiated THP-1/LXR-Luc cells

| Payload Compound | $EC_{50}$ (M) | S/N |
|---|---|---|
| P1 | 1.14E−09 | 11.4 |
| P2B | 2.92E−10 | 11.3 |
| P4B | 1.25E−10 | 10.4 |
| P6B | 3.34E−09 | 10.9 |
| P5B | 1.74E−10 | 13.8 |
| P7B | 2.53E−10 | 12.5 |

TABLE 30-continued

LXR-Reporter Activity by Payload Compounds in Differentiated THP-1/LXR-Luc cells

| Payload Compound | $EC_{50}$ (M) | S/N |
|---|---|---|
| P9B | 2.34E−10 | 12.8 |
| P8B | 3.51E−09 | 10.8 |
| P10B | 2.22E−10 | 11.1 |
| P12B | 2.96E−10 | 11.4 |
| P11B | 1.12E−10 | 10.7 |

Example 34B Antibody Conjugation

Conjugation through antibody cysteines is performed in two steps using methods similar to those described in Mol. Pharm. 2015, 12(6), 1863-71. In an exemplary procedure, a monoclonal antibody (mAb) is reduced with dithiothreitol or TCEP. After gel filtration, the appropriate linker-payload in DMSO solution is added to the reduced antibody, and the mixture is adjusted to appropriate pH. The reaction is allowed to stir. The resulting conjugate is purified by SEC. The DAR (UV) values are determined using the measured absorbances of the ADC and the extinction coefficients of the antibody linker-payload.

Site-specific antibody conjugation can be performed, e.g., in two steps: (1) microbial transglutaminase e.g., (MTG EC 2.3.2.13, Zedira, Darmstadt, Germany)-based enzymatic attachment of an azido-PEG-amine to a site-specifically mutated antibody and (2) attachment of an appropriate linker-payload to the azido-PEG-amine functionalized antibody via a [2+3]cycloaddition, e.g., 1,3-dipolar cycloaddition between the azido moiety of the functionalized antibody and appropriate cyclooctyne moiety of the linker-payload, e.g., copper-free click chemistry. See, Baskin, J. M.; Prescher, J. A.; Laughlin, S. T.; Agard, N. J.; Chang, P. V.; Miller, I. A.; Lo, A.; Codelli, J. A.; Bertozzi, C. R. *PNAS* 2007, 104 (43), 16793-7. For example, aglycosylated human antibody IgG (IgG1, IgG4, etc.) or a human IgG1 isotype in BupH™ (pH 6.5-8.0) is mixed with ≥200 molar equivalents of azido-dPEG$_3$-amine (MW=218.26 g/mol). The resulting solution is mixed with transglutaminase (25 U/mL; 5U MTG per mg of antibody, from Zedira, Darmstadt, Germany, or Ajinomoto, Japan) resulting in a final concentration of the antibody at 0.5-5 mg/mL, and the solution is kept at pH 6.5-8.0 and then incubated at 37° C. for 4-24 h while gently shaking. The reaction is monitored by ESI-MS. Upon reaction completion, excess amine and MTG is removed by SEC or protein A column eluting with acidic buffer and then neutralizing with Tris buffer (pH 8) to generate the azido-functionalized antibody. This product is analyzed by SDS-PAGE and ESI. The azido-dPEG$_3$-amine adds to two sites—Q295 and Q297—of the antibody resulting in an 804 Da increase for the 4DAR aglycosylated antibody-PEG$_3$-azide conjugate. The conjugation sites are identified and confirmed at EEQ$^{Linker}$YQ$^{Linker}$STYR for the 4DAR azido-functionalized antibody via peptide sequence mapping of trypsin digested heavy chains.

In another example, site-specific aglycosylated antibody drug conjugates with a human IgG (IgG1, IgG4, etc.) containing an N297Q mutation (EU numbering) are prepared by a [2+3] click reaction between azido-functionalized antibodies with an alkyne containing linker-payload. Specifically, an azido-functionalized aglycosylated human IgG1 antibody (mAb-PEG$_3$-N$_3$) is conjugated to an appropriate linker payload by incubating mAb-PEG$_3$-N$_3$ (1-3 mg/mL) in an aqueous medium (e.g., PBS, PBS containing 5% glycerol, HBS) with ≥6 molar equivalents of a linker payload dissolved in a suitable organic solvent, such as DMSO, DMF or DMA (i.e., the reaction mixture contains 5-20% organic solvent, v/v) at 24° C. to 37° C. for over 6 h. The progress of the reaction is monitored by ESI-MS and the absence of mAb-$PEG_3$-$N_3$ indicated the completion of the conjugation. The excess amount of the linker payload and organic solvent are removed by SEC via elution with PBS, or via protein A column eluting with acidic buffer followed by neutralization with Tris (pH 8). The purified conjugates are analyzed by SEC, SDS-PAGE, and ESI-MS.

The antibody and antibody-drug conjugates can be characterized by SDS-PAGE, SEC, and MS (ESI). In one method, SDS-PAGE conditions including non-reduced and reduced samples (2-4 µg) along with BenchMark Pre-Stained Protein Ladder (Invitrogen, cat #10748-010; L #1671922) are loaded per lane in (1.0 mm×10 well) Novex 4-20% Tris-Glycine Gel and are ran at 180 V, 300 mA, for 80 min. An analytic sample is prepared using Novex Tris-Glycine SDS buffer (2×) (Invitrogen, Cat #LC2676) and the reducing sample is prepared with SDS sample buffer (2×) containing 10% 2-mecaptoethanol.

Example 34C

Several linker-payloads (LPs) were derived from the payload compounds in Table C and conjugated to an anti-MSR1 antibody (H1H21234N-N297Q) or a non-binding control using the techniques described in the previous example. The resulting anti-MSR1 LXR agonist antibody drug conjugates (ADCs) were tested for activity in the THP1/LXRLuc reporter assay as described above for the payload compounds. As shown in Table 31, all of the tested anti-MSR1 LXR agonist ADCs demonstrated stimulation of the THP1/LXR-Luc cells with $EC_{50}$ values ranging from 414 pM to 2.11 nM and S/N values ranging from 9.4 to 13.7. The unconjugated anti-MSR1 had no impact on LXR-Luc activity and a nonbinding control antibody conjugated to LP1 (Control ADC-LP1) had $EC_{50}$ values of >100 nM and maximum S/N values <5.0.

Anti-MSR1 antibody H1H21234N has the HCVR according to SEQ ID NO:50 and the LCVR according to SEQ ID NO:58. It comprises HCDR1, HCDR2, HCDR3, LCDR1, LCDR2, and LCDR3 according to SEQ ID NOS:52, 54, 56, 60, 62, and 64, respectively. The polypeptide sequences can be encoded by the polynucleotide sequences SEQ ID NOS: 49, 51, 53, 55, 57, 59, 61, and 63. N297Q indicates that residue 297 is mutated from asparagine (N) to glutamine (Q). All numbering is according to the EU numbering system.

TABLE 31

Anti-MSR1-LXR Agonist Conjugate Activity in Differentiated THP-1/LXR-Luc cells

| Anti-MSR1-LXR agonist ADC | LXR agonist LP | LXR Agonist Payload | $EC_{50}$ (M) | S/N |
|---|---|---|---|---|
| H1H21234N-N297Q-LP1 | LP1 | P2B | 7.38E−10 | 11.8 |
| H1H21234N-N297Q-LP4B | LP4B | P2B | 9.23E−10 | 11.9 |
| H1H21234N-N297Q-LP5B | LP5B | P2B | 1.20E−09 | 11.0 |
| H1H21234N-N297Q-LP2B | LP2B | P2B | 8.68E−10 | 13.7 |
| H1H21234N-N297Q-LP12B | LP12B | P2B | 1.30E−09 | 11.6 |
| H1H21234N-N297Q-LP6B | LP6B | P4B | 6.85E−10 | 12.5 |
| H1H21234N-N297Q-LP7B | LP7B | P4B | 5.60E−10 | 11.6 |
| H1H21234N-N297Q-LP8B | LP8B | P4B | 6.19E−10 | 12.5 |

TABLE 31-continued

Anti-MSR1-LXR Agonist Conjugate Activity in Differentiated THP-1/LXR-Luc cells

| Anti-MSR1-LXR agonist ADC | LXR agonist LP | LXR Agonist Payload | $EC_{50}$ (M) | S/N |
|---|---|---|---|---|
| H1H21234N-N297Q-LP9B | LP9B | P6B | 4.14E−10 | 11.2 |
| H1H21234N-N297Q-LP10B | LP10B | P6B | 9.60E−10 | 12.5 |
| H1H21234N-N297Q-LP11B | LP11B | P8B | 9.78E−10 | 12.4 |
| Unconjugated anti-MSR1 | NA | NA | >1.00E−07 | 0.8 |
| Control ADC-LP1 | LP1 | P2 | >1.00E−07 | 4.4 |

Example 35. In Vivo Effect of Anti-MSR1 Antibody-LXR Conjugates on Atherosclerosis in a Mouse Model The effect of an anti-MSR1 antibody-LXR agonist conjugate, H1H21234N-N297Q-LP1, on atherosclerosis development was evaluated in vivo in mice homozygous for the expression of human MSR1 extracellular domain in place of the mouse MSR1 extracellular domain and homozygous for deletion of the apoE gene (referred to herein as $Msr1^{hu/hu}$ $ApoE^{-/-}$ mice).

Figure 18:
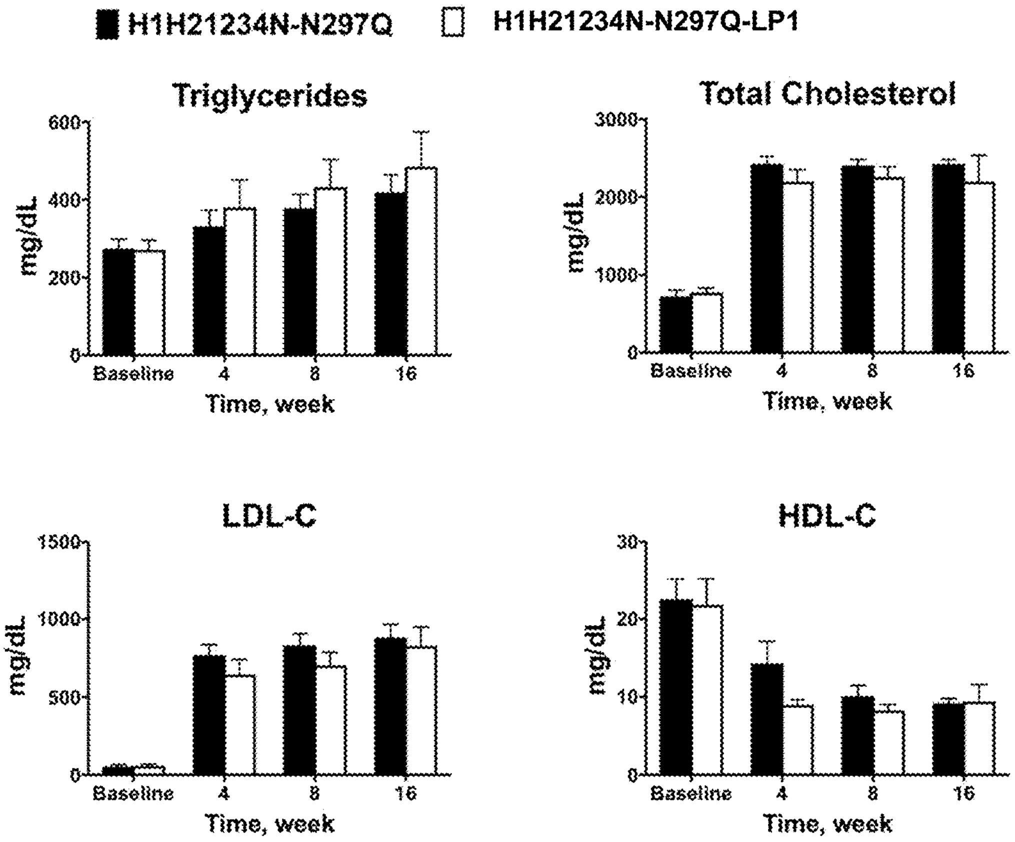
FIG. 18 provides a series of bar graphs illustrating the effect of an exemplary MSR1 antibody-LXR agonist conjugate and its unconjugated counterpart on serum lipid levels in a mouse model of atherosclerosis.

The $Msr1^{hu/hu}$ $ApoE^{-/-}$ mice were pre-bled 6 days before the start of the experiment after 4-hour fast and were then placed on an atherogenic western diet (Research Diets, Cat #106452). The mice were sorted into groups (n=7-9 each) based on their baseline triglycerides (TG) and low-density lipoprotein cholesterol (LDL-C) values. An MSR1 antibody (H1H21234N-N297Q) or MSR1 antibody-LXR agonist conjugate (H1H21234N-N297Q-LP1) were administered by weekly subcutaneous injections at 25 mg/kg dose (based on the antibody concentration) starting on day 0 for 16 weeks. Serum was collected at 4, 8, and 16 weeks of the study after 4-hour fast to evaluate serum lipids using AdviaXPT Chemistry System (Siemens). Average serum lipid values were calculated for each time point. Results, expressed as (mean±SEM) are shown in FIG. 18. FIG. 18 illustrates that administration of the MSR1 antibody-LXR agonist conjugate H1H21234N-N297Q-LP1 did not have an effect on serum lipid levels.

Figure 19:
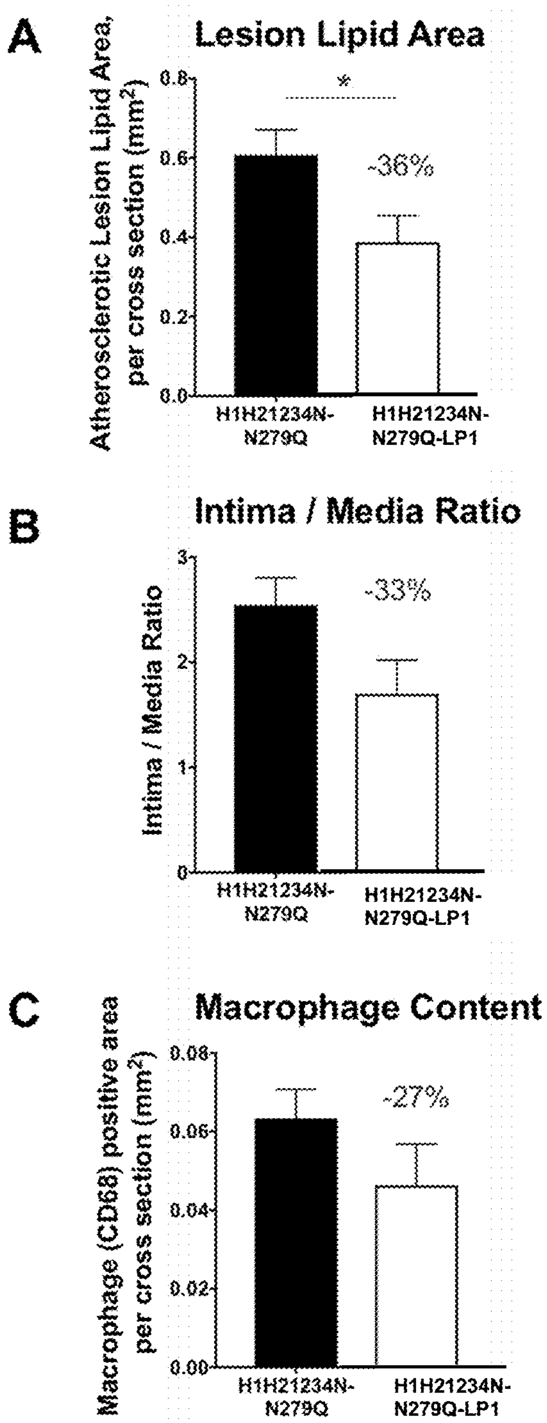
FIG. 19 provides a series of bar graphs illustrating the effect of an exemplary MSR1 antibody-LXR agonist conjugate and its unconjugated counterpart on lesion lipid area and macrophage (CD68) content in a mouse model of atherosclerosis.

Mice were sacrificed at the end of the study under nonfasted conditions 6 days after the last injection anti-MSR1 antibody or MSR1 antibody-LXR agonist ncADC, and their heart and liver were collected. Hearts were imbedded in Optimal cutting temperature compound (OCT), and sectioned perpendicular to the axis of the aorta, starting within the heart and working in the direction of the aortic arch. Once the aortic root was identified by the appearance of aortic valve leaflets, serial cross sections (12 µm thick) were taken and mounted on consecutive slides (VWR International, Cat #16004-406). These sections were stained with hematoxylin and eosin stain (H&E stain), Oil Red O lipid stain, and rat-anti-CD68 antibody, (Abcam, Cat #ab201844) to label macrophages for analysis. An Aperio AT2 slide scanner (Leica Biosystems, Illinois) was used to scan the slides and to generate images. For each mouse, the lipid area was measured using HALO software (Indica Labs, New Mexico) in 7 subsequent cross sections based on Oil Red O staining, and subsequently the average of total lesion lipid area per mouse was calculated using these measurements. All measurements were conducted by an analyst who was blinded to the treatment groups. Results, expressed as (mean±SEM) are shown in FIG. 19, (A). FIG. 19, (A)

illustrates that administration of the MSR1 antibody-LXR agonist conjugate H1H21234N-N297Q-LP1 led to reduction in atherosclerotic lesion area.

In addition, H&E stained slides were used to calculate Intima/Media ratio, which represents the normalized value of plaque size. The internal and external elastic laminas of arterial media and lumen areas were measured in 7 subsequent cross sections for each mouse using the H&E stained sections and the average values were calculated per mouse. Intima/media ratio were calculated using the equation:

Intima/media ratio=(Internal elastic lamina area−Lumen area)/(External elastic lamina area−Internal elastic lamina area)

Results, expressed as (mean±SEM) are shown in FIG. 19, (B).

The macrophage content in the sections was measured using slides stained with rat anti-CD68 antibody. For each mouse, macrophage positive area was measured using HALO software in at least 5 subsequent cross sections, and the average of total macrophage content per mouse was calculated using these measurements. Results, expressed as (mean±SEM) are shown in FIG. 19, (C). FIG. 19, (C) illustrates that administration of the MSR1 antibody-LXR agonist conjugate H1H21234N-N297Q-LP1 led to reduction in macrophage content.

Figure 21:
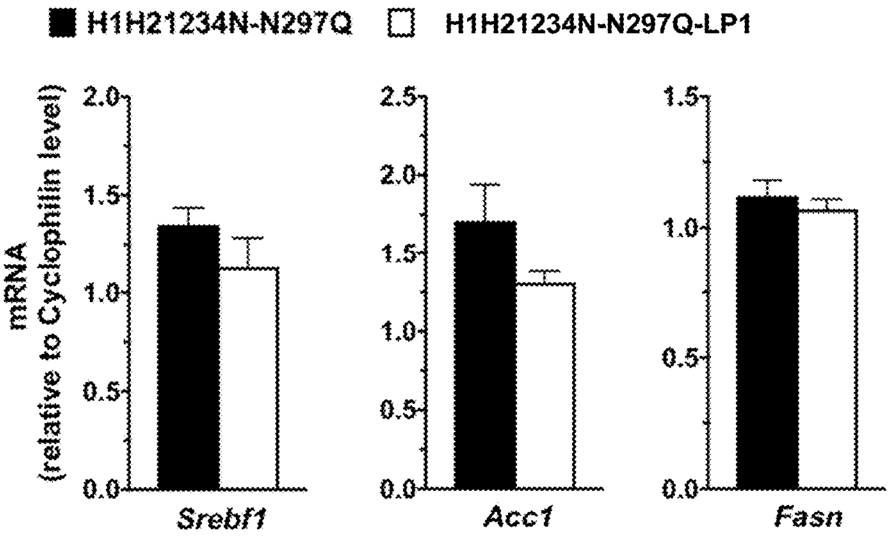
FIG. 21 provides a series of bar graphs illustrating the effect of an exemplary MSR1 antibody-LXR agonist conjugate and its unconjugated counterpart on de novo lipogenesis in a mouse model of atherosclerosis.

Livers collected at sacrifice were used for qRT-PCR and lipid extraction. One piece of liver from each mouse was placed in RNAlader (Invitrogen, Cat #AM7023) for RNA extraction and then the expression of lipogenic genes (Srebfl, Acc, Fasn) to evaluated de novo lipogenesis was evaluated by qRT-PCR using standard methods. Results, expressed as (mean±SEM) are shown in FIG. 21. FIG. 21 illustrates that administration of the MSR1 antibody-LXR agonist conjugate H1H21234N-N297Q-LP1 has no effect on hepatic triglyceride or cholesterol level.

Figure 20:
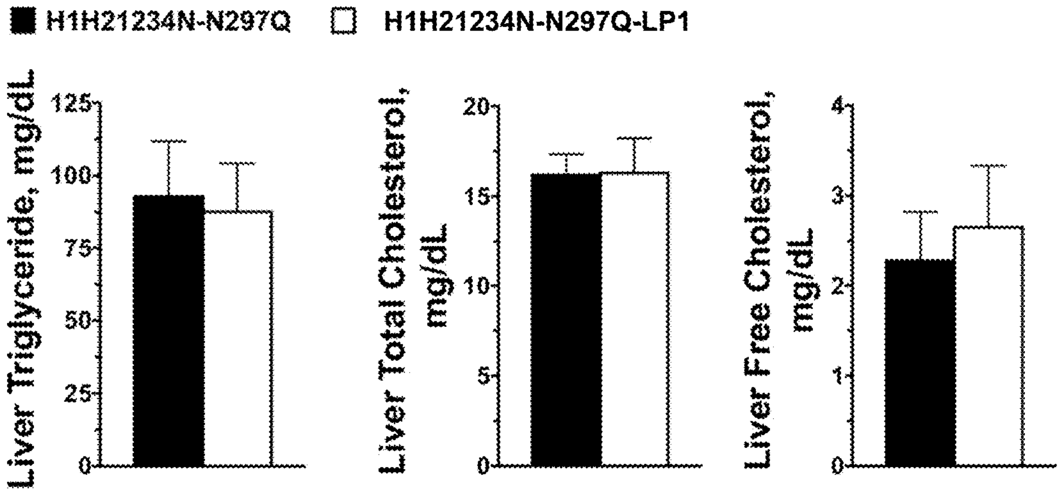
FIG. 20 provides a series of bar graphs illustrating the effect of an exemplary MSR1 antibody-LXR agonist conjugate and its unconjugated counterpart on hepatic triglyceride and cholesterol levels in a mouse model of atherosclerosis.

Lipids were extracted from the second piece of liver from each mouse by Folch's method and solubilized by Carr's method. The levels of TG, total and free cholesterol were measured using enzymatic assays for detection (Teco Diagnostics, Cat #T532-480 (TG); Thermo Fisher Scientific, Cat #TR13421 (total cholesterol); Waco Diagnostics, Cat #993-02501 (free cholesterol)) and normalized to wet tissue weight. Results, expressed as (mean±SEM) are shown in FIG. 20. FIG. 20 illustrates that administration of the MSR1 antibody-LXR agonist conjugate H1H21234N-N297Q-LP1 has no effect on hepatic de novo lipogenesis.

General Methods for Examples 36-41

All the solvents used were purchased either from Sigma Aldrich or Fisher Scientific and were used as is. Rifamycin S was purchased from Bosche Scientific. $^{1}$H-NMR spectra were recorded on a Varian Inova 300 MHz and 500 MHz NMR instruments. The chemical shifts (5) are reported in ppm with respect to the NMR solvents used for analysis and are reported as s—singlet, d—doublet, t—triplet, q—quartet, dd—doublet of doublet, dt—doublet of triplet, dq—doublet of quartet, and m—multiplet. Coupling constants (J) are reported in hertz (Hz). Chromatographic purities were determined on an Agilent 1100, 1260 Infinity, or 1200 Series LC/MS systems using Chromolith® FastGradient RP-18e analytical columns (50×2 mm, Merck KGaA, P/N 1.52007.0001) and the following analytical HPLC method: injection volume 5 or 10 μL; flow rate 1 mL/min; 5-95% acetonitrile in water over 4 min; Agilent diode array detector at λ=254 nm; room temperature. Low resolution mass spectrometry was performed on an Agilent system using electrospray ionization sources and analyzed with either single quadrupole or ion trap mass detectors.

Example 36. Synthesis of Analogs R1a-R1d

Scheme R1, below, depicts the synthesis of exemplary compounds 1a-1d according to the disclosure from commercially available starting materials.

Scheme R1

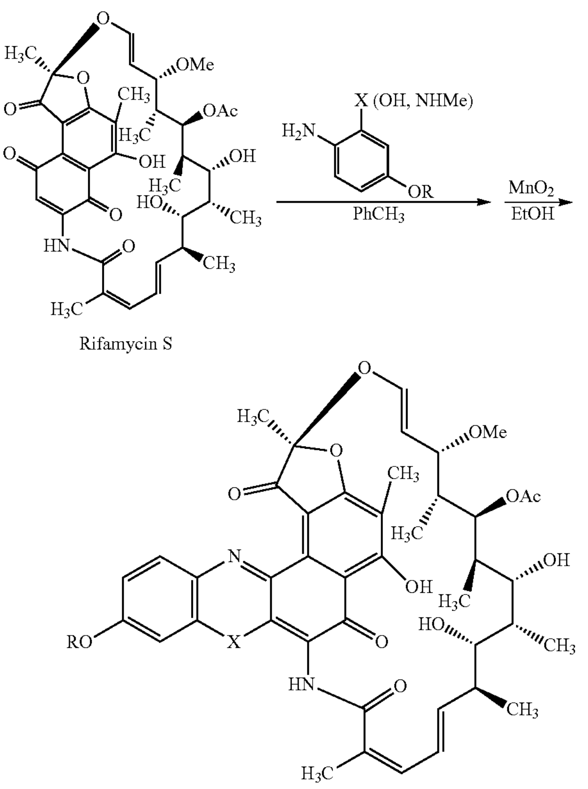

Rifamycin S

R1a, R = Me X = O
R1b, R = Bn X = O
R1c, R = H X = O
R1d, R = H X = NHMe

Example 36A: Rifamycin 4-MeO-Phenol Analog (R1a)

The general coupling procedure of Example 36 is used to prepare the title compound: To a stirring solution under argon of rifamycin S (200 mg, 0.287 mmol) in 15 mL of toluene at room temperature was added 2-amino-5-methoxyphenol (44 mg, 0.316 mmol). The mixture solution was stirred for 3 days at room temperature. The progress of reaction was monitored by LC/MS, then the mixture was evaporated to dryness. The dark residue was dissolved in 10 mL of ethanol, and 100 mg (1.14 mmol) of manganese oxide ($MnO_2$) was added in one portion to the ethanol solution. The sluggish mixture was stirred for 15h at room temperature. After filtration of insoluble materials using a Celite pad, the filtrate was evaporated under reduced pressure. The dark residue was purified on a 40 g HP silica gel Gold RediSep column via ISCO (gradient elution: 5→95% EA in hexanes) and the pure fractions evaporated and dried in vacuo giving the title compound Ria as a dark reddish solid (85 mg, 37%). MS (ESI, pos.): calc'd for $C_{44}H_{50}N_2O_{13}$, 814.33; found 815.3 (M+H), 837.3 (M+Na). $^1H$ NMR (500 MHz; $CDCl_3$) δ 7.96 (d, J=9.0 Hz, 1H), 7.47 (s, 1H), 7.05-7.01 (m, 2H), 6.86 (s, 1H), 5.99 (s, 2H), 4.97 (dd, J=12.4, 7.4 Hz, 2H), 3.93 (s, 3H), 3.08 (s, 3H), 3.00-2.99 (m, 1H), 2.30 (s, 3H), 2.13 (s, 3H), 2.03 (d, J=18.1 Hz, 3H), 1.81 (s, 3H), 1.70-1.67 (m, 1H), 1.59-1.54 (m, 16H), 1.53 (s, 3H), 0.96-0.95 (m, 3H).

Example 36B: Rifamycin 4-BnO-Phenol Analog (R1b)

Analog R1b was prepared using intermediate R2, the synthesis of which is depicted in Scheme R2, below.

Scheme R2

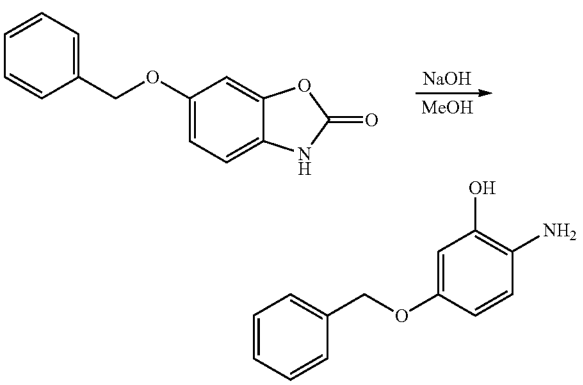

R2

Synthesis of compound R2. The mixture of 6-(benzyloxy) benzo[d]oxazol-2(3H)-one (500 mg, 2.07 mmol) and methanol (6 mL) was treated with a solution of 1.2 g of NaOH in 6 mL of water. The suspension was heated at 90° C. overnight. After cooling at room temperature, the mixture was treated with 6N HCl (5 mL) then filtered. The filtrate was adjusted to afford pH=8-9 with sat. aq. $NaHCO_3$ and the precipitate was filtered, washed with water to give a dark solid, which was purified by 40 g HP silica gel Gold RediSep column (0→90% EA in hexanes) to afford 220 mg (49%) of compound R2. MS (ESI, pos.): calc'd for $C_{13}H_{13}NO_2$, 215.09; found 216.1 (M+H). $^1H$ NMR (500 MHz; DMSO-$d_6$) δ 7.39-7.37 (m, 5H), 7.31 (d, J=7.0 Hz, 1H), 6.49 (d, J=8.4 Hz, 1H), 6.37 (d, J=2.7 Hz, 1H), 6.25 (dd, J=8.4, 2.7 Hz, 1H), 4.91 (s, 2H).

Synthesis of analog R1b. To a stirred solution of rifamycin S (20 mg, 0.0287 mmol) under argon in 1 mL of toluene at room temperature was treated with 2-amino-5-(benzyloxy)phenol R2 (6.8 mg, 0.0316 mmol). The solution was stirred for 3 days at room temperature and additional 2-amino-5-(benzyloxy)phenol (6.8 mg) was added. The progress of reaction was monitored by LC/MS. After 5 days, the mixture was evaporated to dryness. The dark residue was dissolved in 3.5 mL of ethanol and 10 mg (0.11 mmol) of manganese oxide ($MnO_2$) was added in one portion to the ethanol solution. The sluggish mixture was stirred for 3h at room temperature. After filtration of insoluble materials using a Celite pad, the filtrate was evaporated under reduced pressure. The dark residue was purified on a 24 g HP silica gel Gold RediSep column via ISCO (gradient elution: 5→98% EA in hexanes) and the pure fractions evaporated and dried in vacuo giving the title compound R1b as a dark reddish solid (8.5 mg, 33%). MS (ESI, pos.): calc'd for $C_{50}H_{54}N_2O_{13}$, 890.36; found 891.3 (M+H). $^1H$ NMR (500 MHz; $CDCl_3$) δ 7.97 (s, 1H), 7.49 (s, 1H), 7.44-7.41 (m, 5H), 7.14-7.11 (m, 2H), 7.07 (s, 1H), 6.94 (s, 1H), 5.32 (s, 1H), 5.23 (s, 1H), 5.18 (d, J=11.9 Hz, 2H), 4.99 (s, 2H), 3.11 (s, 3H), 3.04 (dd, J=2.0, 0.6 Hz, 1H), 2.32 (s, 3H), 2.07 (s, 6H), 1.83 (s, 3H), 1.71-1.69 (m, 1H), 1.61 (d, J=0.4 Hz, 9H), 1.58-1.52 (m, 6H), 1.28 (s, 1H), 0.97 (td, J=1.9, 1.2 Hz, 3H), 0.79 (t, J=0.8 Hz, 1H).

Example 36C: Rifamycin 4-OH-Phenol Analog (36c)

Analog R1c was prepared using intermediate R4, the synthesis of which is depicted in Scheme R3, below.

Scheme R3

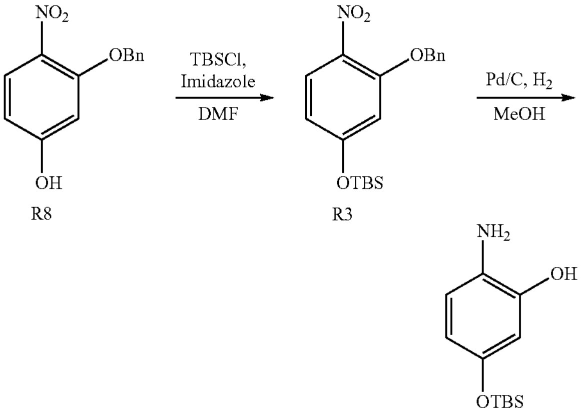

R8 R3

R4

2-amino-5-((tert-butyldimethylsilyl) oxy)phenol (R4):

Synthesis of compound R3. Compound R8 was prepared from the product in Example 36B. To the solution of 3-benzyloxy-4-nitrophenol R8 (400 mg, 1.63 mmol) under argon in DMF (2 mL) was added TBSCI (0.247 mL, 2.44 mmol), imidazole (222 mg, 3.26 mmol), and DMAP (0.5 mg). The mixture was stirred at room temperature overnight then diluted with ethyl acetate (25 mL), washed with water (2×10 mL), brine solution (10 mL), and dried over sodium sulfate. The crude was purified by 40 g HP silica gel Gold RediSep column via ISCO (gradient elution: 0→20% EA in hexanes) and the pure fractions evaporated to afford the desired compound R3 (540 mg, 92%). MS (ESI, pos.): calc'd for $C_{19}H_{25}N_2O_4Si$, 359.16; found 382.1 (M+Na).

Synthesis of compound R4. To the solution under argon of compound R3 (120 mg, 0.33 mmol) in 3 mL of methanol (degassed with argon three times) was added 10% Pd/C (10 mg). The mixture was again degassed and bubbled with hydrogen from a balloon. A hydrogen balloon was inserted through the septa and the mixture was aged for overnight. The mixture was filtered through Celite and concentrated to give a dark greenish solid (71 mg, 90%). MS (ESI, pos.): calc'd for $C_{12}H_{21}NO_2Si$, 239.13; found 240.2 (M+H).

Synthesis of analog R1c. To a stirring solution under argon of rifamycin S (120 mg, 0.172 mmol) in 10 mL of toluene at room temperature was added compound R4 (46 mg, 0.192 mmol). The mixture solution was stirred for 3 days at room temperature. The progress of the reaction was monitored by LC/MS, then the mixture was evaporated to dryness. The dark residue was dissolved in 10 mL of ethanol, and 50 mg (0.6 mmol) of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 24 g HP silica gel Gold RediSep column via ISCO (gradient elution: 5→95% EA in hexanes). The pure fractions were evaporated and dried in vacuo giving the title compound R1c as a dark reddish solid (48 mg, 35%). MS: calc'd for $C_{43}H_{48}N_2O_{13}$, 800.32; found 801.3 (M+H), 799.2 (M−H). $^1H$ NMR (500 MHz; DMSO-$d_6$) δ 11.43 (d, J=1.7 Hz, 1H), 9.33-9.32 (m, 1H), 7.82 (dt, J=2.0, 1.0 Hz, 1H), 7.02-7.01 (m, 1H), 6.89 (t, J=1.3 Hz, 1H), 6.04 (dd, J=2.5, 0.9 Hz, 1H), 5.83 (dt, J=1.9, 1.0 Hz, 1H), 5.25-5.24 (m, 1H), 4.78-4.77 (m, 1H), 4.14-4.14 (m, 1H), 3.52 (d, J=0.8 Hz, 1H), 3.07 (d, J=0.7 Hz, 1H), 3.03 (t, J=0.6 Hz, 3H), 2.89 (s, 1H), 2.78 (t, J=2.7 Hz, 1H), 2.19 (d, J=16.7 Hz, 3H), 1.99 (d, J=12.2 Hz, 4H), 1.95 (t, J=0.5 Hz, 4H), 1.67 (d, J=1.9 Hz, 3H), 1.24 (s, 2H), 0.89 (dd, J=2.5, 1.1 Hz, 2H), 0.85 (d, J=6.5 Hz, 6H), 0.69 (d, J=1.5 Hz, 3H).

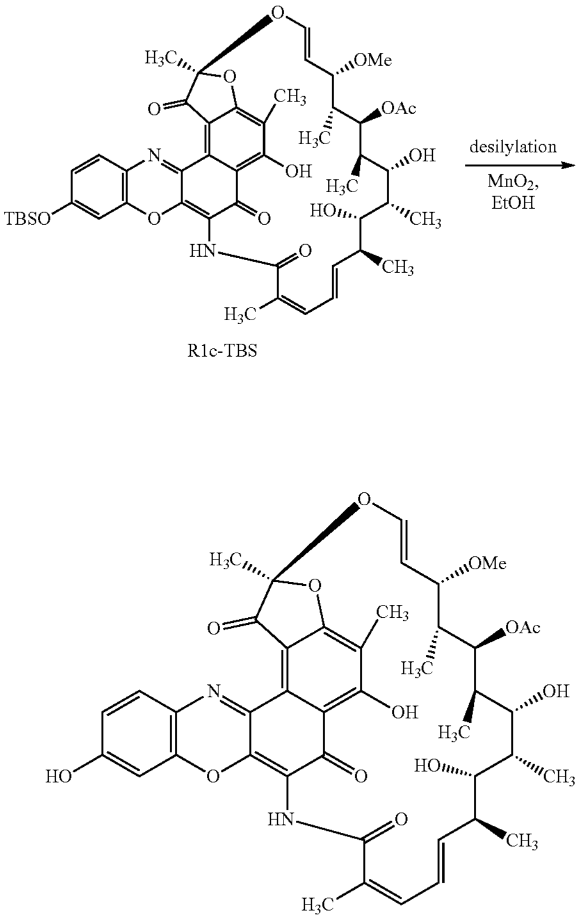

R1c-TBS

R1c

Example 36D: Rifamycin 4-OH-Phenol N-Methyl Analogs (36d)

Analog 36d was prepared using intermediate R7, the synthesis of which is depicted in Scheme R4, below.

Scheme R4

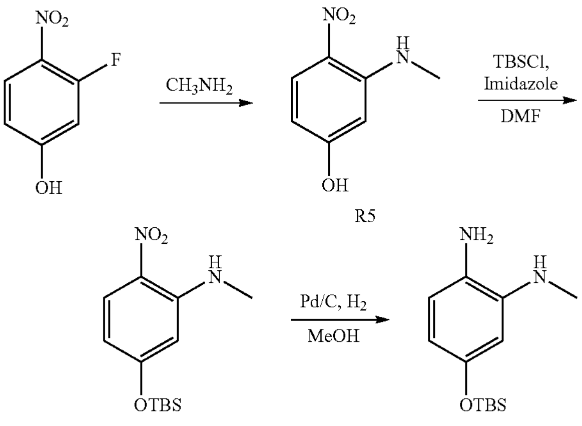

R5

R6

R7

5-((tert-butyldimethylsilyl)oxy)-N1-methylbenzene-1,2-diamine (R7):

Synthesis of compound R5. The title compound was prepared using the method disclosed in PTC *Int. Appl.* 2008051805. In a sealed tube were placed a mixture of 3-fluoro-4-nitrophenyl (1 g, 6.36 mmol) and 2 mL of a 40% methylamine aqueous solution. The flask was sealed via septum, purged with argon, and heated at 80° C. in an oil-bath for 18 h. The reaction was complete by LCMS analysis and cooled to room temperature. The solution was dissolved by the addition of water (15-20 mL) and extracted using ethyl acetate (3×30 mL). The combined organic layer was then washed with water, brine, dried ($Na_2SO_4$), and then concentrated to give a crude product, brown white solid (900 mg, 84%) of R5, which was used in the next step without further purification. MS (ESI, pos.): calc'd for $C_7H_8N_2O_3$, 168.05; found 169.1 (M+H).

Synthesis of compound R6. Under argon 3-(methylamino)-4-nitrophenol R5 (200 mg, 1.19 mmol) and imidazole (162 mg, 2.38 mmol) were dissolved in anhydrous DMF in the presence of catalytic DMAP (0.7 mg). The stirred yellow solution was cooled in an ice-bath and TBSCl (269 mg, 1.79 mmol) was added in one portion to the yellow solution. After 5 min the bath was removed and the solution was allowed to warm to room temperature overnight. The mixture was quenched by saturated $NaHCO_3$ solution and extracted with ethyl acetate (2×25 mL). The combine organics were dried by addition of $Na_2SO_4$ and then concentrated to give a crude product. The residue was purified on a 24 g HP silica gel Gold RediSep column via ISCO (gradient elution: 0→90% EA in hexanes) and the pure fractions evaporated then dried in vacuo giving the title compound R6 as a yellow solid (220 mg, 66%). MS: calc'd for $C_{13}H_{22}N_2O_3Si$, 282.14; found 283.1 (M+H).

Synthesis of compound R7. Under argon 5-((tert-butyldimethylsilyl)oxy)-N1-methylbenzene-1,2-diamine 6 (50 mg, 0.177 mmol) was dissolved in 2 mL of methanol. The solution was degassed with argon three times followed by addition of Pd/C (5 mg). The mixture was further degassed with argon and connected to a hydrogen balloon via septum. After 2.5 h, the analysis by LC/MS from an in-process aliquot indicated the reaction was complete. The mixture was filtered through Celite and concentrated to afford 46 mg of compound R7 quantitatively, which was used in the next step instantly without further purification. MS: calc'd for $C_{13}H_{24}N_2OSi$, 252.17; found 253.2 (M+H).

Synthesis of analog R1d. To a stirring solution under argon of rifamycin S (58 mg, 0.083 mmol) in 3 mL of toluene at room temperature was added compound R7 (21 mg, 0.083 mmol). The solution was stirred for 2 days at room temperature. The progress of the reaction was monitored by LC/MS, then the solution was evaporated to dryness. The dark residue was dissolved in 5 mL of ethanol and 10 mg of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 12 g HP silica gel Gold RediSep column via ISCO (gradient elution: 5→95% EA in hexanes) and the pure fractions evaporated then dried in vacuo giving the title compound R1d as a dark reddish solid (22.3 mg, 33%). This was found to be impure by LC/MS, so it was dissolved in MeCN/water and repurified on a 15.5 g C18 Aq Gold column (gradient elution: 10-95% MeCN in water, 0.05% acetic acid in both, over 20 min). The product fractions were combined, frozen on dry ice, and lyophilized giving the title compound R1d as a white solid (13.5 mg, 20%). MS: calc'd for $C_{44}H_{51}N_3O_{12}$, 813.35; found 814.3 (M+H), 812.3 (M−H). $^1H$ NMR (500 MHz; DMSO-$d_6$) δ 11.31 (b, J=0.8 Hz, 2H), 9.41 (s, 1H), 9.22 (s, 1H), 8.86 (s, 1H), 8.01-7.95 (m, 2H), 7.19-7.13 (m, 2H), 7.04 (s, 2H), 6.79-6.74 (m, 1H), 6.39-6.37 (m, 1H), 6.19 (t, J=11.4 Hz, 2H), 6.08 (d, J=12.4 Hz, 1H), 6.02-5.92 (m, 1H), 5.73 (d, J=26.4 Hz, 1H), 5.49 (d, J=11.2 Hz, 1H), 5.28 (d, J=0.6 Hz, 1H), 5.09-5.02 (m, 2H), 4.82 (dd, J=11.5, 10.2 Hz, 1H), 4.54 (d, J=6.6 Hz, 1H), 4.36 (d, J=2.6 Hz, 1H), 3.96 (d, J=4.4 Hz, 1H), 3.88 (s, 1H), 3.83 (s, 1H), 3.79 (s, 1H), 3.70 (s, 1H), 3.09 (s, 1H), 2.91 (s, 3H), 2.21 (s, 3H), 2.15 (d, J=5.9 Hz, 1H), 1.97 (s, 2H), 1.72 (s, 2H), 1.64 (s, 2H), 1.59 (s, 2H), 0.90 (d, J=7.0 Hz, 1H), 0.70 (d, J=6.6 Hz, 1H), 0.62 (d, J=6.8 Hz, 1H), 0.20-0.18 (m, 1H), 0.07 (d, J=0.7 Hz, 1H).

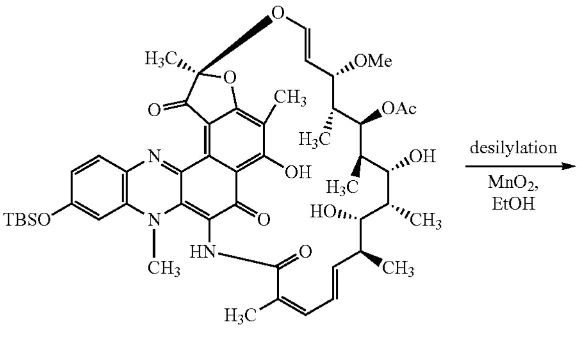

R1d-TBS

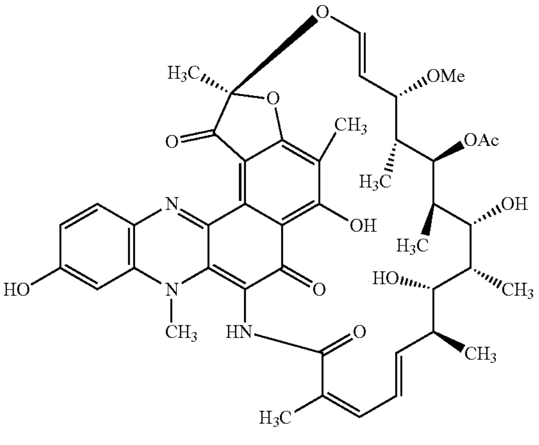

R1d

Example 37: Synthesis of Analog R14

Rifamycin analog R14 was synthesized from rifamycin S as shown in Scheme R5, below, and as described below.

Scheme R5
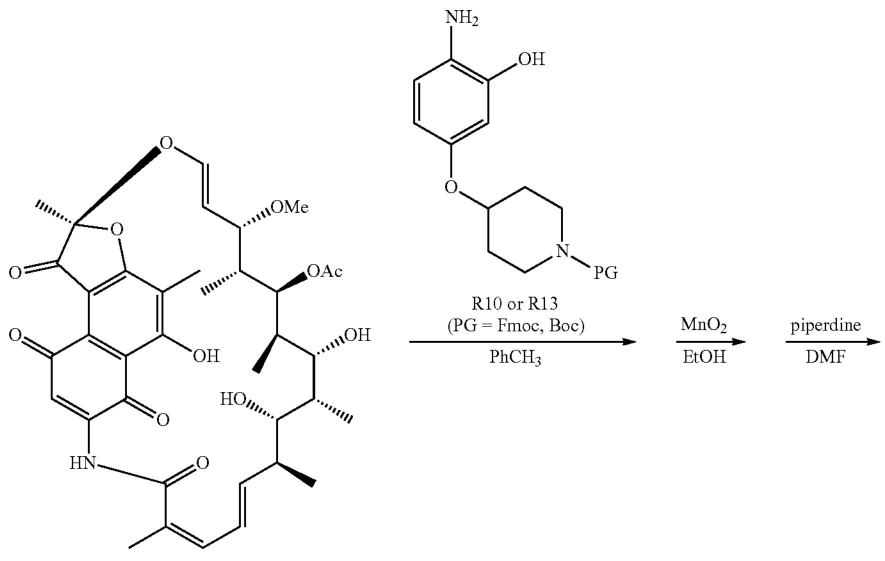
Rifamycin S
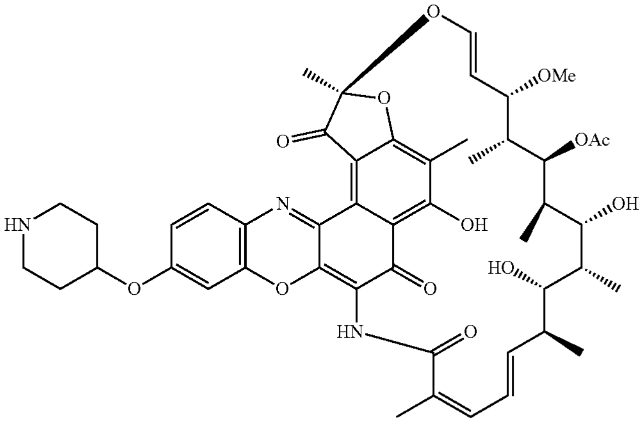
R14
Example 37A: Preparation of Compounds (R10 and R13)
Intermediates R10 and R13 were prepared according to Scheme R6, shown below.
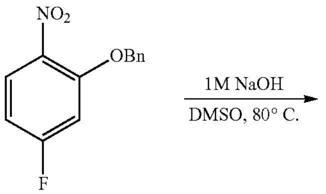
-continued
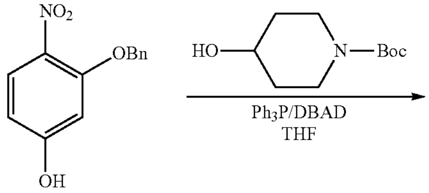
R8

-continued

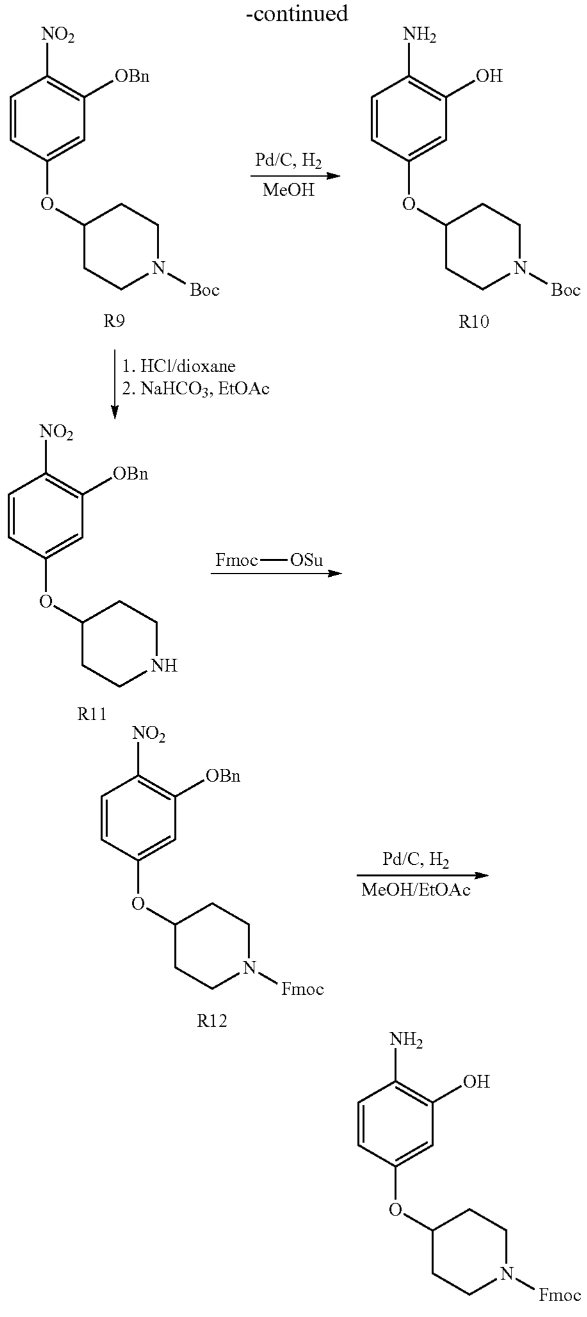

R9 R10 R11 R12 R13

Synthesis of compound R8. The title compound was prepared using a slightly modified method reported by Otten et. al. (*Bioconjugate Chem.* 2001, 12, 76-83). To a solution of 3-fluoro-4-nitrophenyl (2.09 g, 8.45 mmol) in DMSO (10 mL) was added 1M NaOH (10 mL) and heated to 80° C. on a heating block for 18 h. The reaction was complete by LCMS and cooled to room temperature. The reaction was acidified with 1M HCl (15-20 mL) until the pH=3-4 and the resultant solution was extracted using ethyl acetate (3×30 mL). The combined organic layers were washed with water, brine, dried ($Na_2SO_4$), and concentrated in vacuo. The crude oil was then purified on an 80 g HP silica gel Gold RediSep column via ISCO (gradient elution: 0→100% ethyl acetate in hexanes) and the pure fractions evaporated then dried in vacuo giving the title compound R8 as a yellowish white solid (1.51 g, 73%). MS (ESI, pos.): calc'd for $C_{13}H_{11}NO_4$, 245.1; found 268.1 (M+Na), 244.1 (M−H).

Synthesis of compound R9. To a stirring solution under argon of compound R8 (1.51 g, 6.157 mmol) in THF (16 mL) at room temperature were added the BOC-piperidin-4-ol (1.61 g, 8.005 mmol) and $PPh_3$ (2.91 g, 11.083 mmol). A solution of DBAD (2.55 g, 11.083 mmol) in THF (9 mL) was added to the reaction mixture dropwise. After stirring for 16 h, the mixture was evaporated to dryness and the residue was purified on a 40 g HP silica gel Gold RediSep column via ISCO (gradient elution: 0→100% ethyl acetate in hexanes) and the pure fractions evaporated then dried in vacuo giving the title compound R9 as a yellowish white solid (2.41 g, 91%). MS: calc'd for $C_{23}H_{28}N_2O_6$, 428.2; found 451.1 (M+Na).

Synthesis of compound R10. To a degassed solution under argon of compound R9 (100 mg, 0.233 mmol) in 3 mL of methanol was added 5 mg of 10% Pd/C. The mixture was further degassed and connected to a hydrogen balloon. After 2.5 h, the analysis by LC/MS from in-process aliquot indicated the reaction was complete. The mixture was filtered through Celite and concentrated to afford 75 mg of compound R10 quantitatively, which was used in the next step instantly without further purification. MS: calc'd for $C_{16}H_{24}N_2O_4$, 308.17; found 331.2 (M+Na), 307.1 (M−H).

Synthesis of compound R11. To a solution of compound R9 (1100 mg, 2.561 mmol) in 1,4-dioxane (15 mL) was added 4 M HCl in 1,4-dioxane (5 mL). After stirring for 15 h an in-process aliquot indicated the reaction was complete. To the solution was added diethyl ether (50 mL), then the mixture was stirred vigorously for 1 h until a white precipitate formed. The solid was filtered and washed with ether to afford the HCl salt of R11. To the white solid was added EtOAc (10 mL) and sat. $NaHCO_3$ (15 mL) until pH=8-9 and stirred for 15 min. The two layers were separated and the aqueous layer was extracted with EtOAc (3×30 mL). The combined organic layers were dried ($Na_2SO_4$) and concentrated in vacuo to give compound R11 (372 mg, 44%) which was used in the next step instantly without further purification. MS: calc'd for $C_{18}H_{21}N_2O_4$, 328.1; found 329.1 (M+H).

Synthesis of compound R12. To a solution under argon of compound R11 (372 mg, 1.128 mmol) in 1,4-dioxane/water (v/v, 10:1, 11 mL) was added Fmoc-OSu (399 mg, 1.184 mmol). After stirring for 15 h an in-process LC/MS analysis indicated the reaction was complete. The reaction mixture was concentrated in vacuo to give compound R12 which was used in the next step instantly without further purification. MS: calc'd for $C_{33}H_{30}N_2O_6$, 550.2; found 551.2 (M+H).

Synthesis of compound R13. To a solution under argon of compound R12 (72 mg, 0.131 mmol) in 2 mL of methanol and degassed with argon was added 9 mg of 10% Pd/C. The mixture was further degassed with argon and connected to a hydrogen balloon. After 45 min, analysis by LC/MS from an in-process aliquot indicated the reaction was complete. The mixture was filtered through Celite and concentrated in vacuo to afford 55 mg of compound R13 quantitatively, which was used in the next step instantly without further purification. MS: calc'd for $C_{26}H_{26}N_2O_4$, 430.1; found 431.2 (M+H).

Example 37B: Preparation of Analog R14 from Intermediate R10

Synthesis of compound R14-Boc: To a stirring solution of rifamycin S (100 mg, 0.143 mmol) in 5 mL of toluene at room temperature was added compound R10 (44 mg, 0.143 mmol). The mixture solution was stirred for 4 days at room temperature. The progress of the reaction was monitored by LC/MS until complete, then the mixture was evaporated to dryness. The dark residue was dissolved in 10 mL of ethanol and 62 mg (0.715 mmol) of manganese oxide ($MnO_2$) was added at one portion to the ethanol solution. The sluggish mixture was stirred for 15 h at room temperature. After filtration of insoluble materials using Celite pad, the filtrate was evaporated under reduced pressure. The dark residue was purified on a 12 g HP silica gel Gold RediSep column via ISCO (gradient elution: 5%→95% ethyl acetate in hexanes). After concentrating under reduced pressure the crude product (ca. 85% pure) was repurified on a 50 g C18 Aq Gold column (gradient elution: 10-95% MeCN in water, 0.05% acetic acid in both). The pure fractions were combined, frozen on dry ice, and lyophilized to afford R14-Boc as a dark reddish solid (36 mg, 26%). MS: calc'd for $C_{53}H_{65}N_3O_{15}$, 983.44; found 984.4 (M+H).

R14-Boc

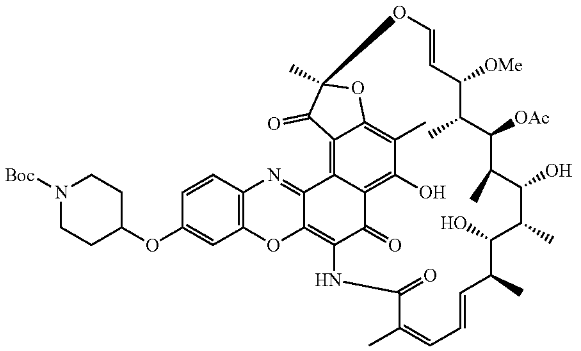

Synthesis of compound R14: R14-Boc (30 mg, 0.03 mmol) was treated with a mixture of TFA/acetonitrile/water (0.25 mL/5 mL/5 mL) at room temperature for 20 h to afford compound R14. The reaction mixture was purified on a 15.5 g C18 Aq. Gold column via ISCO system (gradient elution: 10%-100% MeCN in water, 0.05% acetic acid in both, over 30 min). The product-containing fractions were combined, frozen on dry ice, and lyophilized overnight giving the title compound R14 (10 mg, 37%) as dark reddish solid. MS: calc'd for $C_{48}H_{57}N_3O_{13}$, 883.4; found 884.3 (M+H).

Example 37C: Preparation of Analog R14 from Intermediate R13

Synthesis of compound R14: To a round-bottom flask with hydroxyaniline R13 (55 mg, 0.1278 mmol) were added toluene (1.5 mL) and rifamycin S (67 mg, 0.0956 mmol). The reaction mixture was sonicated for 1 min to dissolve the reaction mixture, sealed via rubber septum, purged with argon, and the reaction stirred at ambient temperature. After 2 days another portion of hydroxyaniline (45 mg, 0.1045 mmol) was added and stirred for 1 d. The reaction was concentrated in vacuo to remove toluene, dissolved in EtOH (6 mL) and $MnO_2$ (20 mg) was added. After stirring for 3 d, the reaction was concentrated in vacuo and purified by chromatography on a 40 g HP silica gel Gold RediSep column via ISCO (gradient elution: 0→100% ethyl acetate in hexanes). The pure fractions were evaporated and dried in vacuo giving the title compound R14-Fmoc as a dark reddish solid (35 mg, 33%). MS (ESI, pos.): calc'd for $C_{63}H_{67}N_3O_{15}$, 1105.4; found 1106.5 (M+H), 1128.5 (M+Na).

R14-Fmoc

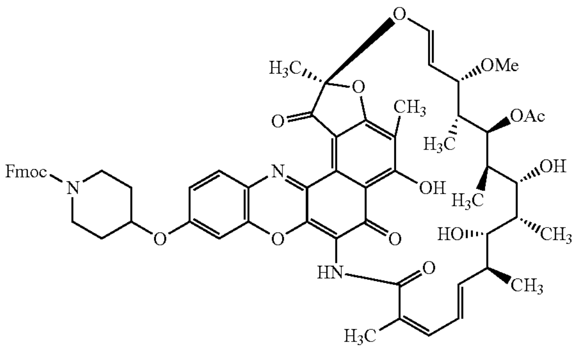

To a stirred solution under argon of Fmoc-rifamycin-piperidine-O-phenol R14-Fmoc of the preceding step (35 mg, 0.0361 mmol) in N,N-dimethylformamide (DMF, 1 mL), was treated with a solution of 2% piperidine (3.5 mg, 0.2 mL, 0.0411 mmol) in DMF and the reaction stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound R14 as dark reddish solid (12 mg, 43%). MS: calc'd for $C_{48}H_{57}N_3O_{13}$, 883.4; found 884.3 (M+H). $^1$H NMR (500 MHz; DMSO-$d_6$) δ 9.40 (s, 1H), 7.87 (d, J=8.9 Hz, 1H), 7.16-7.23 (m, 4H), 5.99-6.05 (m, 2H), 5.76-5.85 (m, 2H), 5.18-5.23 (m, 2H), 4.83-4.95 (m, 2H), 4.80 (br. s, 2H), 4.12 (br. S, 1H), 2.91-3.18 (m, 13H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85-0.92 (m, 12H), 0.69 (br. s, 9H).

Example 38: Synthesis of Analogs R16a-R16e

Rifamycin analogs R16a-R16e were synthesized from rifamycin S as shown in Scheme R7, below, and as described below.

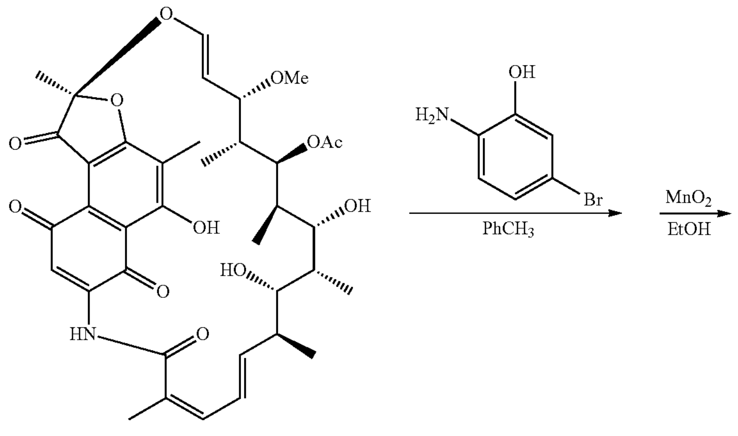
Rifamyin S
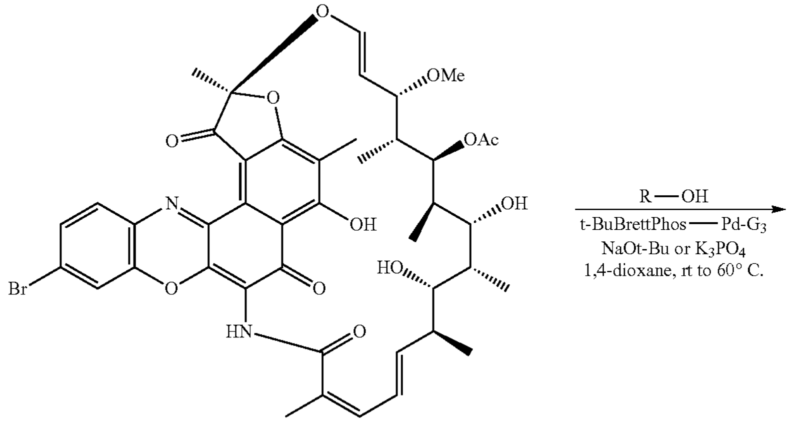
R15
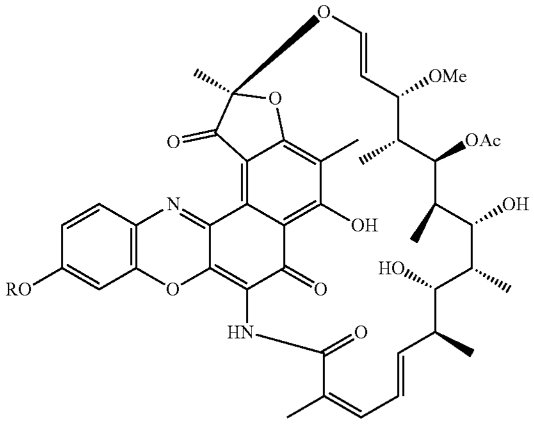
R16
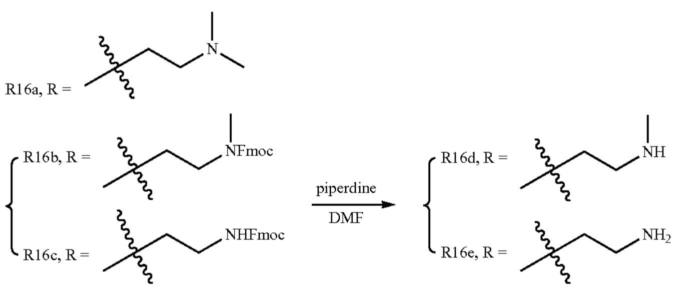

Example 38A: Pd-Catalyzed O-Alkylation (R16a-R16c)

Synthesis of compound R15. To a stirring solution under argon of rifamycin S (2.0 g, 2.87 mmol) in 80 mL of toluene at room temperature was added 2-amino-5-bromophenol (0.54 g, 2.87 mmol). The solution was stirred for 2 days at room temperature. The reaction mixture was then evaporated to dryness and the dark residue dissolved in 20 mL of ethanol and 300 mg of manganese oxide ($MnO_2$) was added in one portion to the ethanol solution. The sluggish mixture was stirred under argon for 15 h at room temperature. After filtration of insoluble materials using a Celite pad, the filtrate was evaporated under reduced pressure. The dark residue was purified on a 120 g HP silica gel Gold RediSep column via ISCO (gradient elution: 5→95% EA in hexanes). The pure fractions were evaporated and dried in vacuo giving the title compound R15 as a dark reddish solid (1.6 g, 65%). MS (ESI, pos.): calc'd for $C_{43}H_{47}BrN_2O_{13}$, 862.23; found 863.1 and 865.1 (M+H), 885.1 and 888.0 (M+Na). $^1$H NMR (500 MHz; DMSO-$d_6$): δ 9.49 (d, J=6.0 Hz, 1H), 7.92 (ddd, J=3.6, 2.9, 1.8 Hz, 1H), 7.86-7.85 (m, 1H), 7.75-7.74 (m, 1H), 6.06-6.05 (m, 1H), 5.84 (dt, J=2.6, 1.4 Hz, 2H), 5.25-5.23 (m, 2H), 4.80 (dt, J=2.5, 1.0 Hz, 1H), 4.23 (td, J=2.4, 1.0 Hz, 1H), 3.49 (d, J=1.1 Hz, 1H), 3.10-3.09 (m, 2H), 3.03 (s, 3H), 2.79 (s, 1H), 2.19 (s, 3H), 2.01 (s, 4H), 1.96 (s, 4H), 1.81 (d, J=2.2 Hz, 1H), 1.68 (s, 3H), 1.60 (dq, J=2.8, 0.9 Hz, 1H), 1.48 (t, J=1.4 Hz, 1H), 0.90 (dt, J=2.1, 1.1 Hz, 2H), 0.84 (d, J=7.1 Hz, 4H), 0.69 (dd, J=2.2, 1.2 Hz, 5H).

Synthesis of compound R16a. Using a similar method reported by Buchwald S. L. et al. (*Org. Lett.* 2018, 20, 1580), a palladium-catalyzed C—O coupling of primary alcohols with compound R15 was employed for title compounds R16a-R16c. To a 2 dram screw-top oven-dried test tube, equipped with a stir bar, and sealed with a screw cap was charged compound R15 (40 mg, 0.0463 mmol, 1.00 eq.), 2-(dimethylamino)ethan-1-ol (42 mg, 0.462 mmol, 10 eq.), tBuBrettPhos Pd G3-palladacycle (11.8 mg, 30 mol %), and NaOt-Bu (5 mg, 0.051 mmol, 1.1 eq.). The reaction tube was recapped with a septum and pierced with a needle attached to evacuate and backfilled with argon (this process was repeated twice) followed by addition of 1,4-dioxane (2.0 mL) via syringe. The reaction was heated at 55° C.±5 in an oil bath under argon pressure for 15 h, the reaction was allowed to cool to room temperature before filtration through a pad of Celite® and rinsed with EtOAc. The crude material was concentrated in vacuo and purified on a 15.5 g C18 Aq Gold column (gradient elution: 10-95% MeCN in water, 0.05% acetic acid in both). The product fractions were combined, frozen on dry ice, and lyophilized giving the title compound R16a as a dark reddish solid (12.5 mg, 32%). MS: calc'd for $C_{47}H_{57}N_3O_{13}$, 871.39; found 872.3 (M+H), 870.2 (M−H). $^1$H NMR (300 MHz; DMSO-$d_6$) δ 9.40 (s, 1H), 7.87 (d, J=8.9 Hz, 1H), 7.23-7.16 (m, 2H), 6.83 (dt, J=2.3, 1.1 Hz, 1H), 6.23 (d, J=4.6 Hz, 1H), 6.06 (dd, J=5.9, 1.1 Hz, 1H), 5.82 (dd, J=2.3, 1.5 Hz, 2H), 5.24 (dt, J=1.4, 0.7 Hz, 1H), 4.83-4.75 (m, 1H), 4.24 (d, J=29.9 Hz, 3H), 3.80 (d, J=1.3 Hz, 1H), 3.03 (t, J=0.5 Hz, 3H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85 (d, J=6.7 Hz, 3H), 0.69 (t, J=1.2 Hz, 3H).

Synthesis of compound R16b. To a 8 mL screw-top oven-dried vial, equipped with a stir bar, and sealed with a screw cap was charged compound R15 (40 mg, 0.0463 mmol, 1.00 eq.), Fmoc-glycinol (131 mg, 0.463 mmol, 10 eq.), t-BuBrettPhos-Pd-G3-palladacycle (16 mg, 0.4 eq.), and $K_3PO_4$ (20 mg, 0.0942 mmol, 2.0 eq.). The reaction vial was capped with a rubber septum, pierced with a needle attached to evacuate and backfilled with argon (this process was repeated twice), followed by the addition of 1,4-dioxane (2.0 mL). The reaction was heated at 60° C. in a heating block under argon pressure for 15h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized giving the title compound R16b as a dark reddish solid (19 mg, 38%). MS (ESI, pos.): calc'd for $C_{60}H_{63}N_3O_{15}$, 1065.4; found 1066.4 (M+H).

Synthesis of compound R16d. Compound R16b of the preceding step (26 mg, 0.0244 mmol) was dissolved in DMF (1 mL), treated with a solution of 2% piperidine (3.1 mg, 0.2 mL, 0.0366 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound R16d as dark blue solid (9 mg, 44%). MS: calc'd for $C_{45}H_{53}N_3O_{13}$, 843.4; found 844.4 (M+H), 842.3 (M−H). $^1$H NMR (500 MHz; $CD_3OD$): δ 7.83 (d, J=8.8 Hz, 1H), 6.91-7.03 (m, 2H), 6.55 (s, 1H), 6.43 (d, J=11.2 Hz, 1H), 6.21-6.30 (m, 2H), 4.98-5.08 (m, 2H), 3.76 (br. s, 3H), 3.43-3.47 (m, 1H), 3.41 (d, J=5.37 Hz, 2H), 3.12 (br. s, 1H), 2.97-3.04 (m, 4H), 2.39 (br. s, 1H), 2.19-2.32 (m, 4H), 2.09-2.14 (m, 4H), 1.95-2.07 (m, 4H), 1.78 (s, 4H), 1.67 (d, J=6.84 Hz, 1H), 1.31 (br. s., 2H), 0.97 (br. s, 8H), 0.66-0.85 (m, 4H), 0.08 (d, J=5.5 Hz, 3H), −0.26 (d, J=6.5 Hz, 3H).

Synthesis of compound R16c. To a 8 mL screw-top oven-dried vial, equipped with a stir bar and sealed with a screw cap was charged compound R15 (80 mg, 0.0926 mmol, 1.00 eq.), Fmoc-sarcosinol (275 mg, 0.9262 mmol, 10 eq.), t-BuBrettPhos-Pd-G3-palladacycle (40 mg, 0.5 eq.), and $K_3PO_4$ (39 mg, 0.1852 mmol, 2 eq.). The reaction vial was capped with a rubber septum, pierced with a needle attached to evacuate and backfilled with argon (this process was repeated twice) followed by addition of 1,4-dioxane (3.0 mL) via syringe. The reaction was heated at 60° C. in a heating block under argon pressure for 15 h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized to give the title compound R16c as a dark reddish solid (49 mg, 49%). MS: calc'd for $C_{61}H_{65}N_3O_{15}$, 1079.4; found 1080.5 (M+H).

Synthesis of compound R16e. Compound R16c of the preceding step (49 mg, 0.045 mmol) was dissolved in DMF (1 mL), treated with a solution of 2% piperidine (7.7 mg, 0.45 mL, 0.091 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound R16e as a dark blue solid (18 mg, 46%). MS: calc'd for $C_{46}H_{55}N_3O_{13}$, 857.3; found 858.3 (M+H). $^1$H NMR (500 MHz; $CD_3OD$): δ 7.84 (d, J=8.79 Hz, 1H), 7.11-7.20 (m, 1H), 6.88-6.96 (m, 1H), 6.64 (s, 1H), 6.42 (d, J=10.26 Hz, 1H), 6.17-6.28 (m, 2H), 4.93-5.06 (m, 2H), 3.86 (br. s, 1H), 3.66-3.84 (m, 8H), 3.18-3.31 (m, 7H), 3.10 (br. s, 2H), 2.94-3.05 (m, 6H), 2.37 (br. s, 1H), 2.25 (d, J=4.88 Hz, 4H), 2.05-2.22 (m, 7H), 1.85-2.05 (m, 7H), 1.78 (s, 6H), 1.65 (br. s, 1H), 1.30 (br. s., 2H), 0.95 (br. s, 8H), 0.82-0.92 (m, 4H), 0.78 (br. s., 1H), 0.70 (br. s, 1H), 0.03 (d, J=5.86 Hz, 3H), −0.28 (d, J=5.86 Hz, 3H).

Example 39: Synthesis of Rifamycin Analogs R17

Rifamycin analogs (R17) were synthesized from compound R14 by use of reductive amination. To a solution of compound R14 (9 mg, 0.0102 mmol) and paraformaldehyde (1.52 mg, 0.051 mmol) in 1.0 mL of anhydrous DCM at room temperature was added $NaBH(OAc)_3$ (4.3 mmol, 0.0204 mmol). The mixture was stirred for 1 h. The reaction progress was monitored by LC/MS to afford the desired product. The crude reaction mixture was quenched by addition of 2-3 drops of water. All volatiles were removed under reduced pressure, then diluted with DMSO (0.5 mL). The crude mixture was purified by preparative HPLC (Gemini, 5 μm, 150 mm×30 mm, eluents: 10-95% MeCN in water, 0.05% AcOH) pure fractions combined and lyophilized to give 6 mg (66%) of R17 as a reddish solid. MS (ESI, pos.): calc'd for $C_{49}H_{59}N_3O_{13}$, 897.40; found 898.4 (M+H). $^1H$ NMR (500 MHz; DMSO-$d_6$): δ 9.38 (br. s., 1H), 7.86 (br. s., 1H), 7.17-7.25 (m, 4H), 6.04 (d, J=6.35 Hz, 1H), 5.81 (br. s., 2H), 4.79 (br. s., 2H), 4.70 (br. s., 2H), 4.15 (br. s., 1H), 3.53 (br. s., 1H), 3.30 (br. s., 5H), 3.09 (br. s., 3H), 3.03 (br. s., 4H), 2.87 (s, 1H), 2.78 (br. s., 2H), 2.58-2.66 (m, 6H), 2.54 (br. s., 8H), 2.37 (d, J=1.47 Hz, 2H), 2.15-2.27 (m, 20H), 2.12 (br. s., 1H), 2.03-2.09 (m, 3H), 2.00 (s, 9H), 1.95 (br. s., 10H), 1.91 (s, 3H), 1.72 (br. s., 3H), 1.67 (br. s., 8H), 1.58 (s, 1H), 1.50 (br. s., 1H), 1.24 (br. s., 2H), 0.81-0.94 (m, 15H), 0.78 (d, J=6.84 Hz, 3H), 0.69 (br. s., 9H).

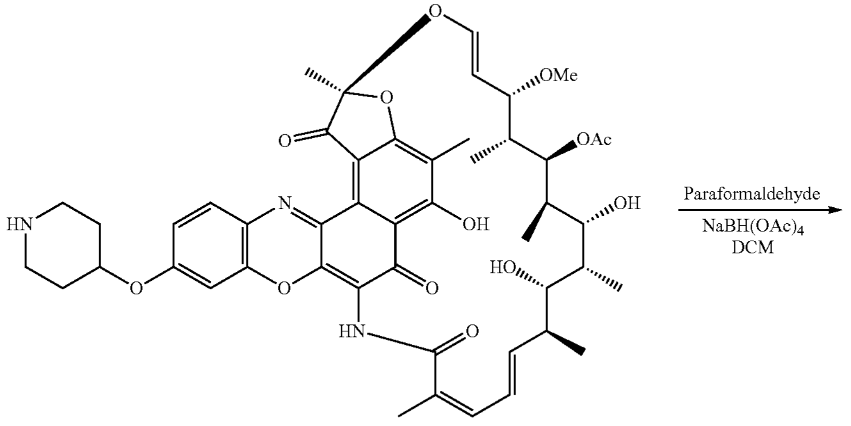

R14

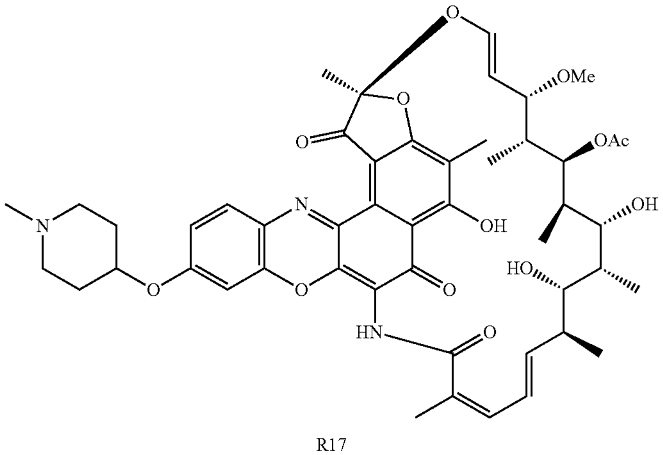

R17

Example 40
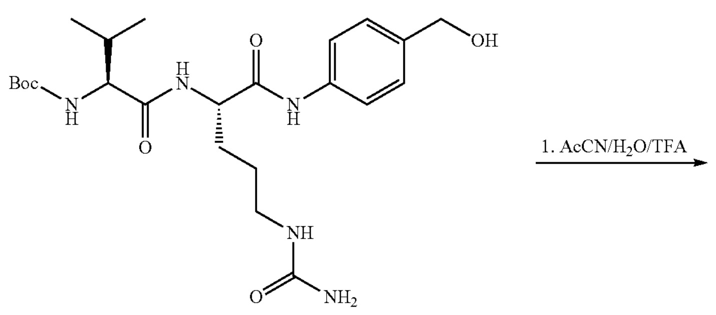
R18a
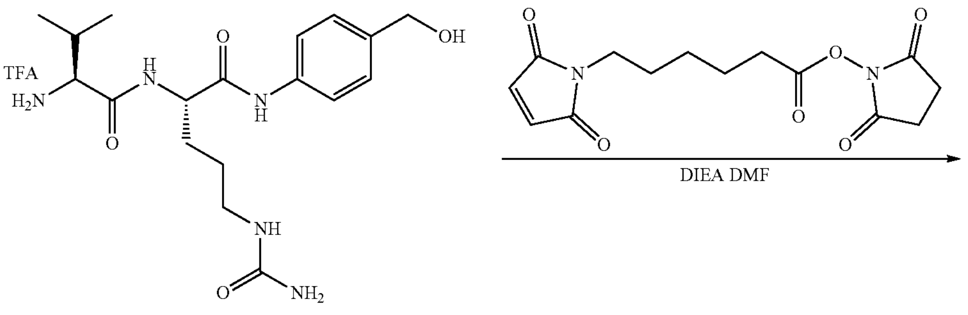
R18b
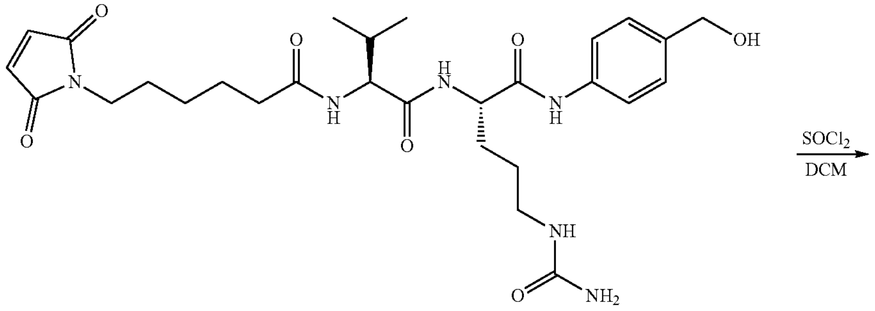
R18
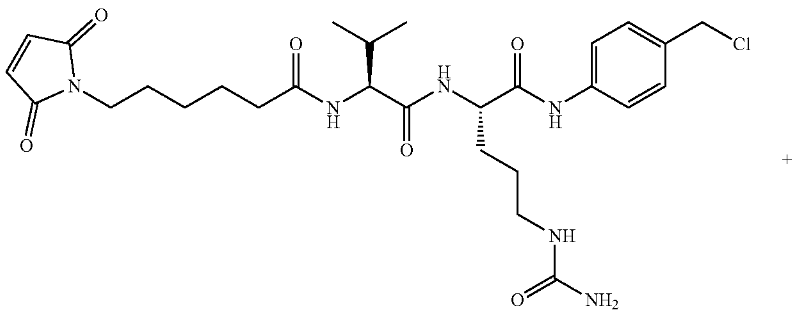
R19

-continued

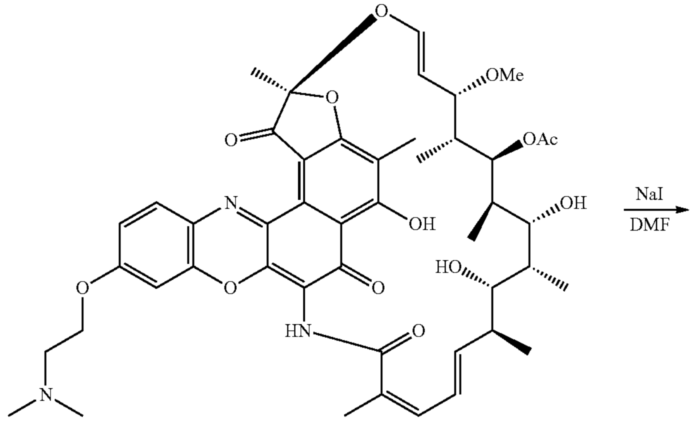

R16a

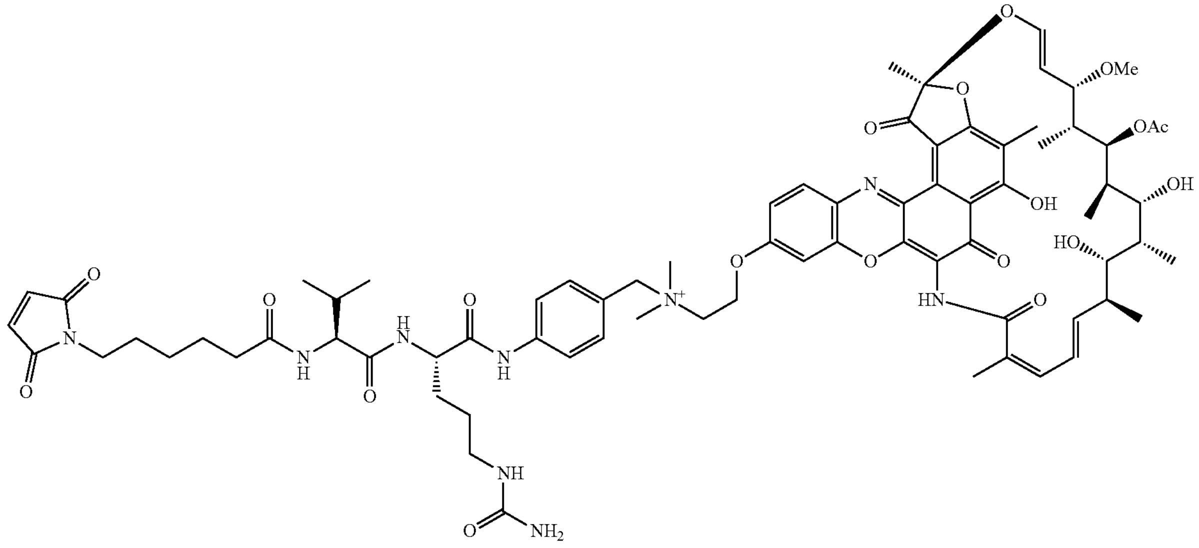

R20

This example describes linker payload chemistry which is used to prepare the title compound R20.

Compound R18: The title compound was prepared using a procedure in PCT Int. Appl., 2014145090. tert-butyl ((S)-1-(((S)-1-((4-(hydroxymethyl) phenyl)amino)-1-oxo-5-ureidopentan-2-yl)amino)-3-methyl-1-oxobutan-2-yl)carbamate R18a, (500 mg, 1.04 mmol) was dissolved in a mixture of $CH_3CN/H_2O/TFA$ (3:1:1=v/v/v, 12 mL/4 mL/4 mL). The reaction mixture was stirred at room temperature for 48 h. The progress of the reaction was determined to be complete by LCMS. After concentrating in vacuo, the crude product R18b (0.9 g wet) was used directly for the next step without further purification. MS (ESI, pos.): calc'd for $C_{18}H_{29}N_5O_4$, 379.22; found 380.2 (M+H).

A solution of R18b (700 mg, 1.47 mmol, 1.0 eq) in water (8 mL) was diluted with 2 mL of aqueous $NaHCO_3$ solution at 4° C. and the mixture (pH=8.0) was treated with commercially available 2,5-dioxopyrrolidin-1-yl 6-(2,5-dioxo-2,5-dihydro-1H-pyrrol-1-yl)hexanoate (408 mg, 0.9 eq) in 10 mL of acetonitrile. The suspension was stirred at room temperature for 16 h until the reaction was complete. The crude product was concentrated under reduced pressure and diluted with DMSO (5 mL). The crude product was purified by an ISCO 150 g C18 column (eluents: 10-95% MeCN in water, 0.05% in AcOH). Pure fractions were combined and lyophilized to afford 368 mg (44%) of compound R18 as a white solid. MS (ESI, pos.): calc'd for $C_{28}H_{40}N_6O_7$, 572.30; found 573.6 (M+H), (2M+H), 1145.9. H NMR (500 MHz; DMSO-$d_6$): δ 9.89 (s, 1H), 8.05 (d, J=7.33 Hz, 1H), 7.81 (d, J=8.79 Hz, 1H), 7.52-7.57 (m, J=8.79 Hz, 2H), 7.21-7.26 (m, J=8.79 Hz, 2H), 6.99-7.02 (m, 2H), 5.98 (br. s., 1H), 5.40 (s, 2H), 5.10 (t, J=5.62 Hz, 1H), 4.35-4.45 (m, 3H), 4.18 (dd, J=6.84, 8.30 Hz, 1H), 3.26-3.33 (m, 2H), 2.91-3.06 (m, 2H), 2.08-2.22 (m, 2H), 1.93-2.01 (m, 1H), 1.66-1.74 (m, 1H), 1.59 (dd, J=4.40, 9.28 Hz, 1H), 1.43-1.55 (m, 5H), 1.32-1.43 (m, 1H), 1.19 (quin, J=7.57 Hz, 2H), 0.84 (d, J=8.30 Hz, 3H), 0.80-0.89 (m, 3H).

Compound R19: To a stirred suspension of R18 (100 mg, 0.174 mmol, 1.0 eq) at room temperature was slowly added $SOCl_2$ (14 μL, 0.192 mmol, 1.1 eq) using a micro syringe. The slurry reaction mixture was stirred for 1.5 h and an aliquot analyzed by LC/MS indicated the formation of the desired. The crude mixture was concentrated to remove all volatiles under reduced pressure. The mixture was diluted with 2 mL of DMSO and loaded on to an ISCO C18 Aq 50 g column for purification (10-95% MeCN in water, 0.05% AcOH). The pure fractions were combined and lyophilized to give 72 mg (71%) of R19 as an off-white solid. MS (ESI, pos.): calc'd for $C_{28}H_{39}ClN_6O_6$, 590.26; found 591.3 (M+H), 1181.5 (2M+H). $^1$H NMR (500 MHz; DMSO-$d_6$) (10.03 (s, 1H), 8.03-8.11 (m, 1H), 7.79 (d, J=8.30 Hz, 1H), 7.57-7.63 (m, J=8.79 Hz, 2H), 7.34-7.38 (m, J=8.79 Hz, 2H), 6.99-7.02 (m, 2H), 5.97 (br. s., 1H), 5.40 (br. s., 2H), 4.71 (s, 2H), 4.34-4.43 (m, 2H), 4.16-4.21 (m, 1H), 3.36-3.42 (m, 3H), 2.90-3.06 (m, 3H), 2.07-2.22 (m, 3H), 1.91-2.00 (m, 1H), 1.66-1.73 (m, 1H), 1.31-1.41 (m, 1H), 1.18 (quin, J=7.69 Hz, 3H), 0.79-0.89 (m, 7H).

Compound R20: The mixture of R19 (13.5 mg, 0.0228 mmol, 1.2 eq), R16a (16.6 mg, 0.0190 mmol, 1.0 eq), and NaI (14.2 mg, 0.095 mmol) in a 2 dram vial was dissolved in 1 mL of anhydrous DMF. A catalytic amount (10 µL) of 0.5 M DIPEA solution in DMF was added by syringe. The mixture was heated at 55° C. in an oil bath overnight. The reaction was complete by LC/MS to afford the desired product. The mixture was cooled to 4° C. and diluted with 1 mL of water. After filtration, the dark crude mixture was purified by an EZ preparative HPLC column (Gemini, 5 µm, 150 mm×30 mm, eluents: 10-95% MeCN in water, 0.05% AcOH). Pure fractions were combined and lyophilized to afford 14.6 mg (55%) of R20 as a dark red solid. MS (ESI, pos.): calc'd for $C_{75}H_{96}N_9O_{19}^+$, 1426.68; found 1427.3 (M+1) and 1425.5 (M−1). $^1$H NMR (500 MHz; DMSO-$d_6$) δ 10.25 (s, 1H), 8.19 (d, J=6.84 Hz, 1H), 7.82 (d, J=8.30 Hz, 2H), 7.76 (d, J=8.79 Hz, 3H), 7.50 (d, J=8.30 Hz, 3H), 7.00 (s, 2H), 6.12 (d, J=12.70 Hz, 1H), 6.03 (br. s., 1H), 5.43 (s, 2H), 4.70-4.80 (m, 2H), 4.58 (br. s., 3H), 4.36-4.41 (m, 1H), 4.18 (t, J=7.82 Hz, 1H), 3.77 (br. s., 2H), 3.36-3.45 (m, 8H), 3.13 (d, J=8.30 Hz, 1H), 2.89-3.06 (m, 12H), 2.78 (t, J=9.04 Hz, 1H), 2.06-2.22 (m, 3H), 2.03 (br. s., 1H), 1.91-2.00 (m, 10H), 1.85 (s, 3H), 1.66-1.74 (m, 1H), 1.56-1.64 (m, 6H), 1.42-1.56 (m, 8H), 1.38 (d, J=6.84 Hz, 2H), 1.15-1.25 (m, 3H), 0.75-0.88 (m, 14H), 0.07 (s, 1H).

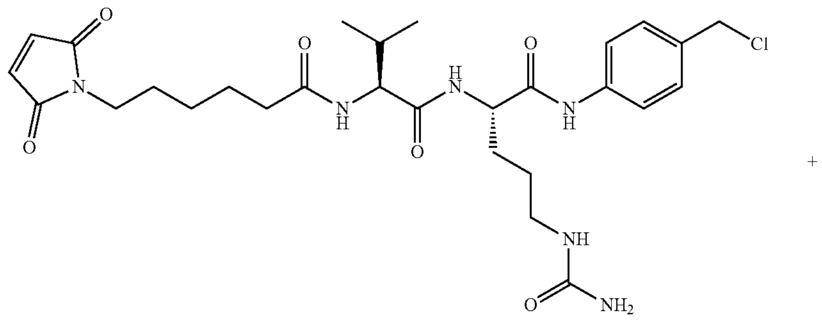

R19

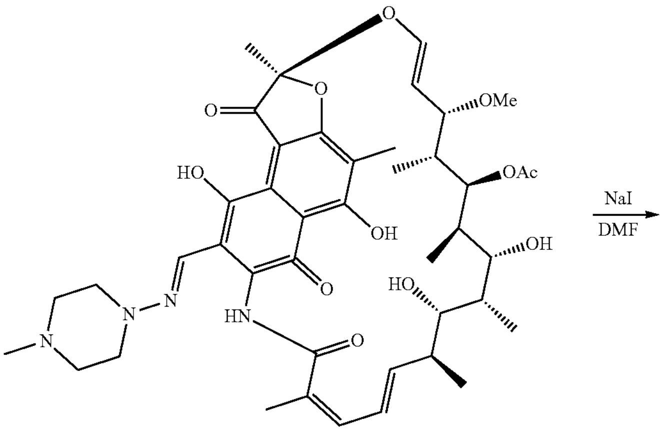

-continued

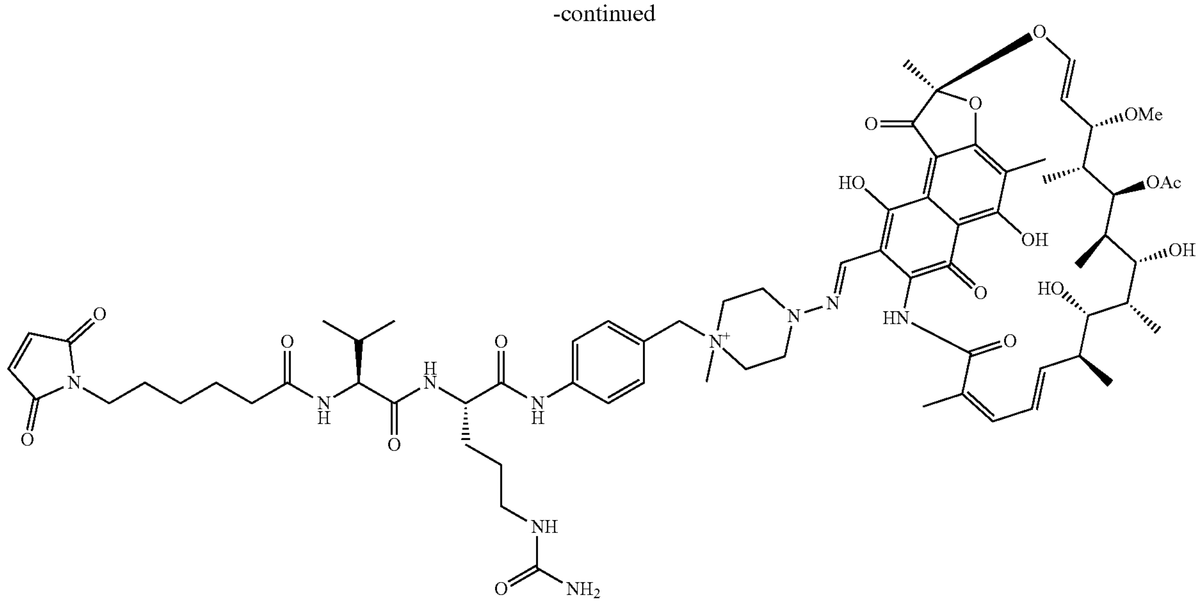

R21

Compound R21: A mixture of R19 (20 mg, 0.0349 mmol, 1.0 eq), rifampicin (25.8 mg, 0.0314 mmol, 0.9 eq), and NaI (39 mg, 0.261 mmol) in 2 dram vial was dissolved in 1 mL of anhydrous DMF. The mixture was heated at 55° C. in an oil bath overnight. The reaction was determined to be complete by LC/MS. The mixture was cooled to 4° C. and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized for 30 h to afford 22 mg (51%) of R21 as a reddish yellow solid. MS (ESI, pos.): calc'd for $C_{71}H_{97}N_{10}O_{18}^{+}$, 1377.70; found 1377.6 (M+H). $^{1}H$ NMR (500 MHz; DMSO-$d_6$) δ 12.55 (s, 1H), 10.20 (s, 1H), 8.81 (s, 1H), 8.13 (s, 2H), 7.77 (dd, J=23.3, 8.4 Hz, 4H), 7.47 (d, J=8.2 Hz, 2H), 7.13-7.07 (m, 1H), 7.00 (s, 2H), 6.25-6.20 (m, 2H), 5.98 (d, J=0.4 Hz, 1H), 5.90 (dd, J=15.9, 6.9 Hz, 1H), 5.42 (s, 2H), 5.08-5.06 (m, 1H), 5.02-5.02 (m, 1H), 4.95-4.91 (m, 1H), 4.58 (dd, J=1.0, 0.4 Hz, 2H), 4.39-4.38 (m, 1H), 4.20-4.15 (m, 2H), 3.74-3.73 (m, 1H), 3.56-3.54 (m, 3H), 3.03-3.01 (m, 2H), 2.96-2.93 (m, 6H), 2.90 (s, 5H), 2.81-2.81 (m, 1H), 2.17 (dd, J=9.5, 5.3 Hz, 3H), 1.97 (s, 5H), 1.91 (d, J=11.0 Hz, 8H), 1.63 (s, 6H), 1.58 (dd, J=6.5, 0.8 Hz, 2H), 1.48 (t, J=7.4 Hz, 8H), 1.37-1.32 (m, 2H), 1.20-1.17 (m, 2H), 1.04 (dd, J=6.1, 0.6 Hz, 1H), 0.86 (td, J=12.9, 6.9 Hz, 14H), 0.77 (d, J=6.5 Hz, 3H), 0.43 (d, J=6.5 Hz, 3H).

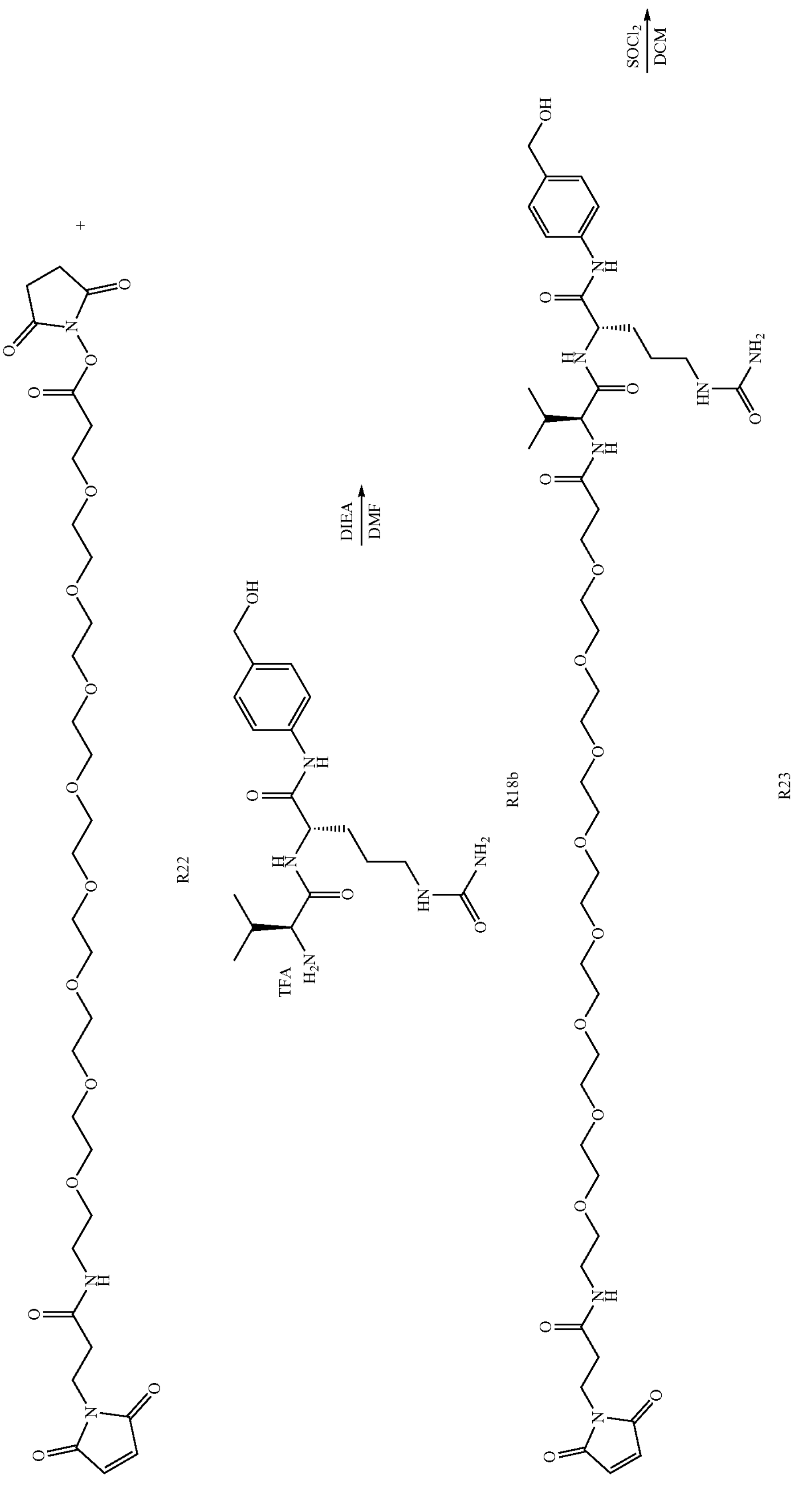
R22
R18b
R23

-continued
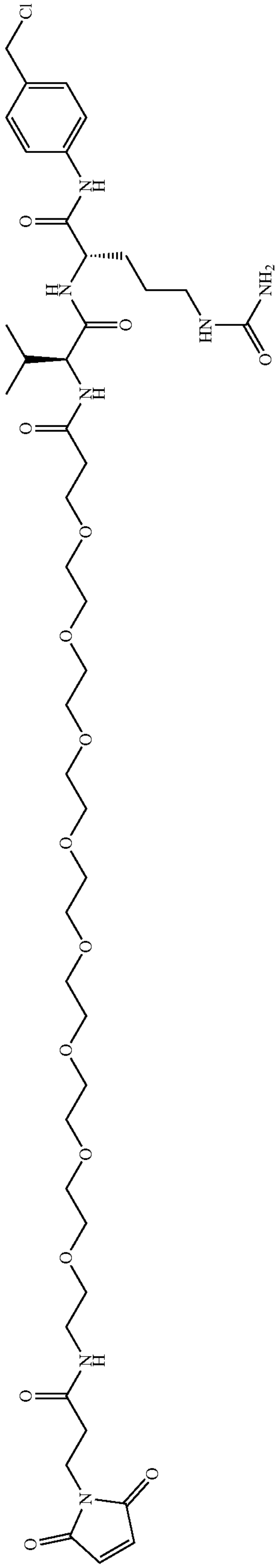
R24
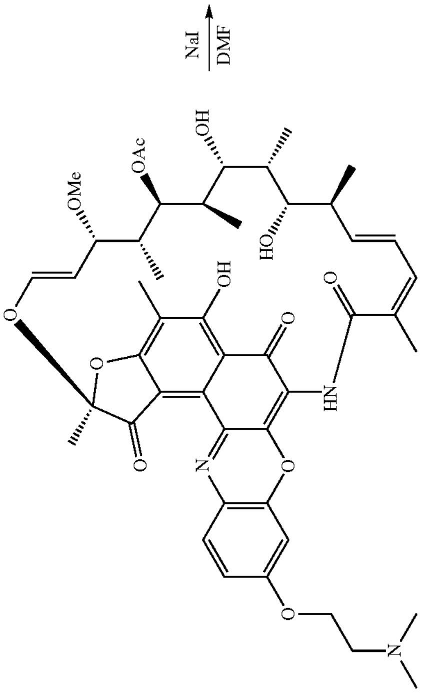
R16a

-continued
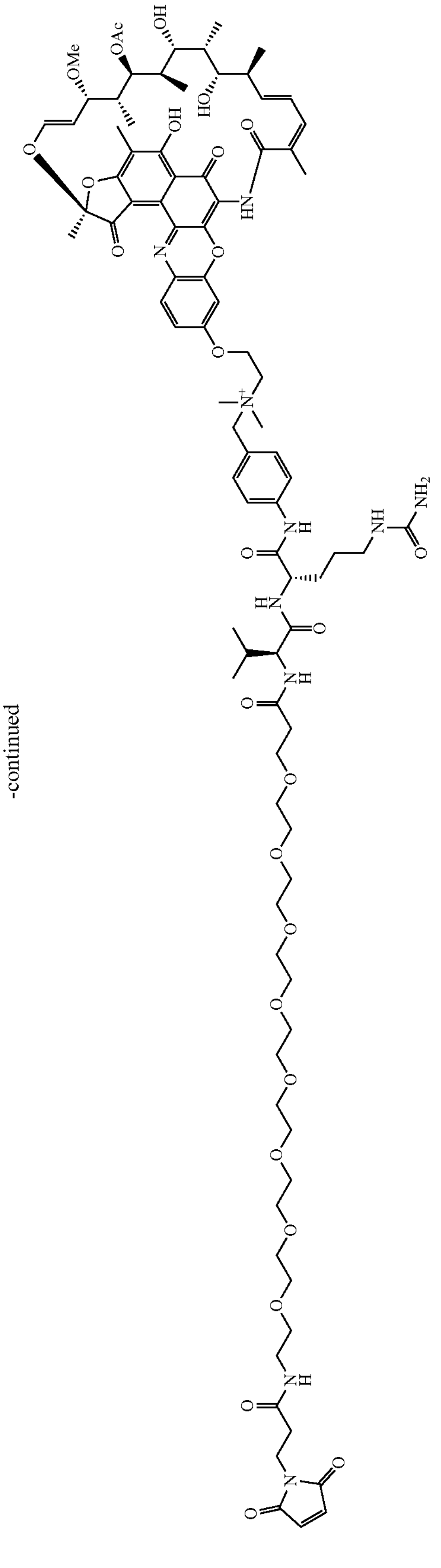
R25

Compound R23: To a mixture of R22 (100 mg, 0.144 mmol) and R18b (82 mg, 0.217 mmol) in anhydrous DMF (1.5 mL) was then treated with DIEA (50 μL, 0.288 mmol) via micro syringe. The reaction mixture was stirred for 2 h at room temperature and determined to afford R23 by LC/MS. The crude mixture was purified by an ISCO C18 100 g Aq column (eluents: 10-95% MeCN in water, 0.05% in AcOH), pure factions combined and lyophilized to yield 84.4 mg (62%) of 23. MS (ESI, pos.): calc'd for $C_{44}H_{71}N_7O_{16}$, 953.50; found 954.4 (M+H), 976.4 (M+Na), 952.4 (M−H). $^1$H NMR (500 MHz; DMSO-$d_6$) δ 9.88 (s, 1H), 8.08 (d, J=7.2 Hz, 1H), 8.00 (s, 1H), 7.86 (d, J=8.5 Hz, 1H), 7.55 (d, J=8.4 Hz, 2H), 7.23 (d, J=8.3 Hz, 2H), 7.00 (s, 2H), 5.98 (s, 1H), 5.40 (s, 1H), 4.43 (s, 2H), 4.39 (d, J=5.4 Hz, 1H), 4.23 (dd, J=8.3, 6.8 Hz, 2H), 3.60 (d, J=6.9 Hz, 6H), 3.44-3.54 (m, 30H), 3.37 (t, J=5.8 Hz, 3H), 3.15 (d, J=5.7 Hz, 2H), 2.99 (d, J=29.6 Hz, 2H), 2.33 (t, J=7.3 Hz, 3H), 1.98 (d, J=6.7 Hz, 1H), 1.71-1.70 (m, 1H), 1.61-1.58 (m, 1H), 1.44-1.36 (m, 2H), 0.85 (dd, J=15.5, 6.7 Hz, 7H).

Compound R24: To a stirred suspension of R23 (15 mg, 0.0157 mmol, 1.0 eq) in a vial at room temperature was slowly added $SOCl_2$ (1.3 μL, 0.0173 mmol, 1.1 eq) via a micro syringe. After 1 h, an aliquot analyzed by LC/MS indicated the formation of the desired product. The crude mixture was concentrated to remove all volatiles under reduced pressure. The crude mixture was diluted with 0.8 mL of MeCN and loaded onto an EZ preparative HPLC column and eluted (Gemini, 5 μm, 150 mm×30 mm, eluents: 10-95% MeCN in water, 0.05% AcOH). Pure fractions were combined and lyophilized to afford 9.5 mg (63%) of R24 as an off-white solid. MS (ESI, pos.): calc'd for $C_{44}H_{70}ClN_7O_{15}$, 971.46; found 972.4 (M+H), 994.4 (M+Na), 970.3 (M−1).

Compound R25: To a mixture of R24 (9.5 mg, 0.00976 mmol, 1.0 eq), R16a (8.51 mg, 0.00976 mmol, 1.0 eq), and NaI (7.3 mg, 0.0488 mmol) in a 1 dram vial was dissolved in 1 mL of anhydrous DMF. A catalytic amount (20 μL) of 0.5M DIEA solution in DMF was added by syringe. The mixture was heated at 55° C. in an oil bath overnight. The reaction was complete by LC/MS to afford the desired product. The mixture was cooled in an ice-bath and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 7.4 mg (42%) of R25 as a dark red solid. MS (ESI, pos.): calc'd for $C_{91}H_{127}N_{10}O_{28}^+$, 1807.88; found 1808.8 (M+H) and 1806.5 (M−1). $^1$H NMR (500 MHz; DMSO-$d_6$) δ 10.23 (s, 1H), 8.22-8.17 (m, 1H), 8.03-7.98 (m, 1H), 7.86 (d, J=8.3 Hz, 1H), 7.75 (d, J=8.2 Hz, 4H), 7.50 (d, J=8.3 Hz, 3H), 7.00 (s, 2H), 6.01 (s, 1H), 5.76 (s, 1H), 5.43 (s, 1H), 4.80-4.80 (m, 1H), 4.58 (s, 1H), 4.43-4.41 (m, 1H), 4.27-4.23 (m, 1H), 3.76 (t, J=0.6 Hz, 2H), 3.59 (t, J=7.3 Hz, 5H), 3.49 (d, J=2.9 Hz, 54H), 3.14 (d, J=5.8 Hz, 4H), 3.03 (s, 8H), 2.90 (t, J=0.7 Hz, 3H), 2.77 (d, J=0.7 Hz, 1H), 2.33 (t, J=7.3 Hz, 4H), 2.08 (d, J=6.1 Hz, 4H), 1.94 (d, J=18.9 Hz, 10H), 1.83 (s, 5H), 1.59 (s, 8H), 0.85 (dd, J=16.1, 6.7 Hz, 8H).

Example 41

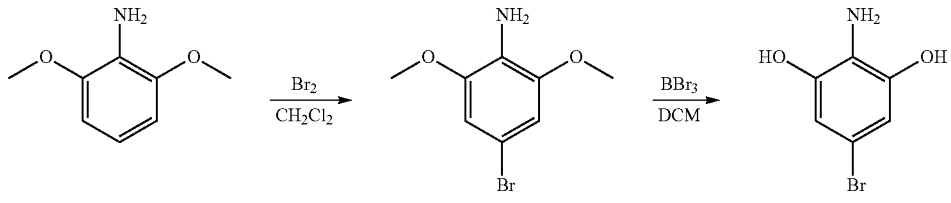

R26

R27

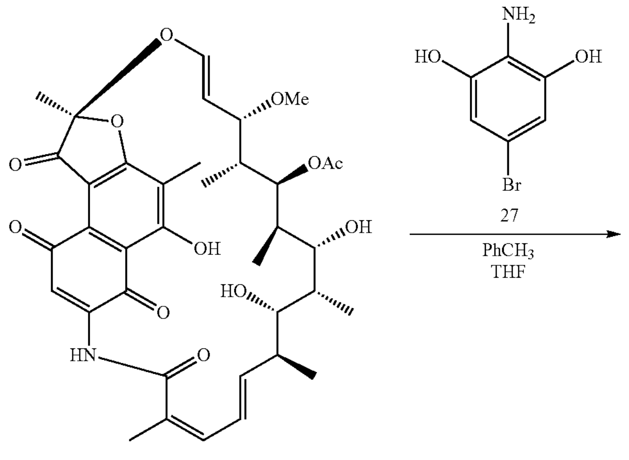

Rifamycin S

-continued

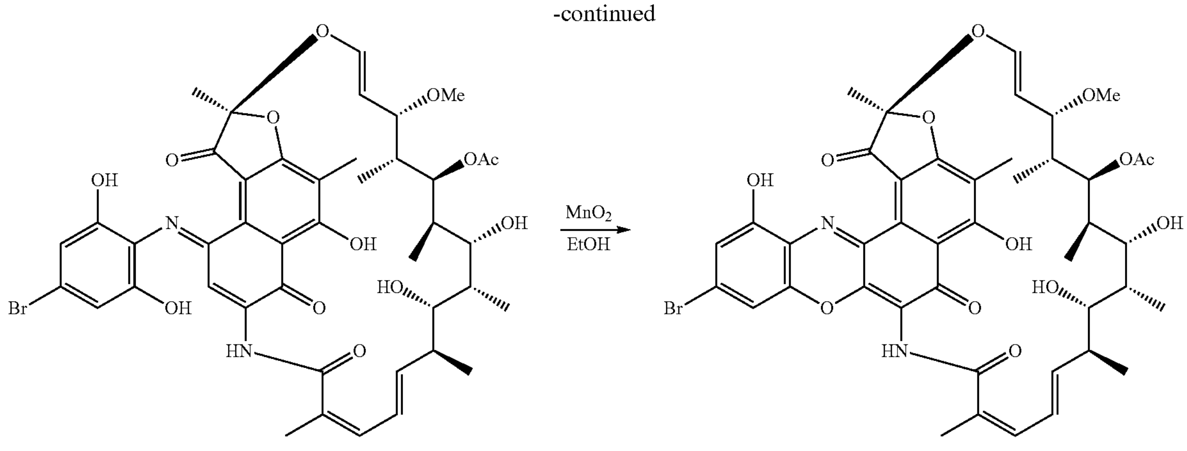

R28a R28

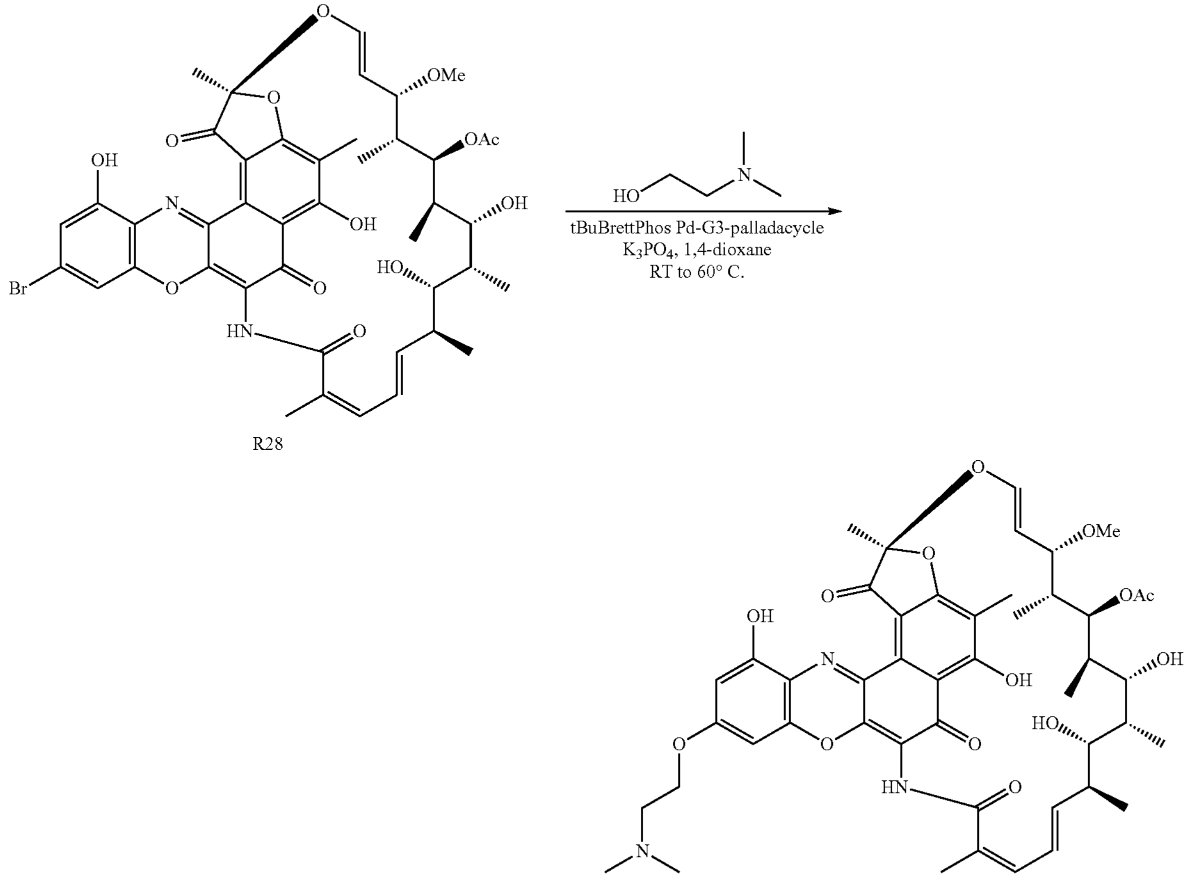

R28

R29

Compound R26: To a stirred solution of 2,6-dimethoxyaniline (9.0 g, 58.7 mmol, 1.0 eq) in 350 mL of anhydrous DCM was dropwise added over 30 min a $Br_2$ solution in 50 mL of anhydrous DCM at 4° C. An additional 200 mL was added to the slurry to achieve a semi-homogeneous solution. The reaction mixture was stirred overnight at room temperature. The dark brown mixture was cooled to 4° C. and basified by addition of 1.0 M NaOH solution (ca. 100 mL) to pH=10-11. The mixture was diluted with 200 mL of DCM and the layers are separated. The aqueous layer was extracted with DCM (200 mL total). The combined DCM layers were washed with water, brine, and dried over $Na_2SO_4$. After concentration in vacuo, the crude product was obtained as a slightly reddish solid. The residue was dissolved in DCM (8 mL) and loaded onto a 220 g HP silica gel Gold RediSep column and purified via ISCO (gradient elution: 5-95% EA in hexanes), pure fractions combined, and the solvent evaporated in vacuo. The solid was triturated with DCM and hexanes and filtered. The off-while solid was dried in vacuo giving the title compound R26 as an off-white solid (9.4 g, 70%). MS (ESI, pos.): calc'd for $C_8H_{10}BrNO_2$, 230.99; found 231.9 and 234.0 (M+H). $^1$H NMR (500 MHz; $CDCl_3$) δ 6.66 (s, 2H), 3.84 (s, 6H)

Compound R27: Compound R26 (2.2 g, 9.47 mmol, 1.0 eq) was dissolved in 10 mL of anhydrous DCM and a $BBr_3$ solution was added dropwise over 10 min (10 mL, 1.0 M solution in DCM) at 4° C. The reaction was exothermic and produced a precipitate. An additional amount of $BBr_3$ (9 mL, 94.7 mmol, 10 eq) was added and the reaction mixture was stirred at room temperature overnight. The reddish suspension was checked by LC/MS to confirm the desired product. The reaction mixture was transferred to a 250 mL flask and cooled to 4° C. The mixture was carefully quenched with water followed by treatment with aqueous saturated $NaHCO_3$ solution to give a pH=7-8. The mixture was extracted with DCM and the aqueous layer cooled to 4° C. to afford a dark brown precipitate. The mixture was filtered and the brown solid was dissolved in 10 mL of methanol and dried over $Na_2SO_4$ to provide the desired product R27 (1.9 g, 100%). MS (ESI, pos.): calc'd for $C_6H_6BrNO_2$, 202.96; found 204.0 and 206.1 (M+H). $^1H$ NMR (500 MHz; $CD_3OD$) δ 6.45 (s, 2H), 4.87 (s, 2H).

Compound R28: To a stirred solution of compound R27 (0.146 g, 0.72 mmol) in a mixture of toluene (20 mL) and THF (20 mL) at room temperature was added rifamycin S (0.5 g, 0.72 mmol). The solution was stirred for 3 days at room temperature to afford the desired product. The solvents were removed in vacuo, the dark residue was dissolved in 10 mL of ethanol followed by 100 mg of manganese dioxide ($MnO_2$). The sluggish mixture was stirred for 5 h at room temperature. After filtration of insoluble materials using a Celite pad, the filtrate was evaporated in vacuo. The dark residue was purified on a 120 g HP silica gel Gold RediSep column via ISCO (gradient elution: 5-95% EA in hexanes). The pure fractions combined and evaporated in vacuo giving the title compound R28 as a dark reddish solid (270 mg, 43%). MS (ESI, pos.): calc'd for $C_{43}H_{47}BrN_2O_{13}$, 878.23; found 879.2 and 880.2 (M+H), 878.1 and 879.1 (M−1). $^1H$ NMR (500 MHz; DMSO-$d_6$) δ 10.22 (br. s., 1H), 9.52 (br. s., 1H), 7.43 (br. s., 1H), 7.35 (br. s., 1H), 6.04 (br. s., 1H), 5.83 (br. s., 2H), 5.21 (d, J=6.35 Hz, 2H), 4.89 (t, J=10.50 Hz, 1H), 4.16 (br. s., 1H), 3.51 (br. s., 1H), 3.15 (br. s., 2H), 3.02 (br. s., 4H), 2.80 (t, J=8.55 Hz, 1H), 2.21 (br. s., 3H), 2.08 (br. s., 1H), 1.96 (s, 4H), 1.99 (s, 4H), 1.78 (br. s., 1H), 1.71 (br. s., 3H), 1.60 (br. s., 1H), 1.47 (br. s., 1H), 0.84 (d, J=6.84 Hz, 6H), 0.69 (br. s., 6H).

Compound R29: To a 8 mL screw-top oven-dried vial, equipped with a stir bar was charged with compound R15 (60 mg, 0.069 mmol, 1.00 eq), 2-(dimethylamino)ethan-1-ol (61 mg, 0.69 mmol, 10 eq), t-BuBrettPhos-Pd-G3-palladacycle (31 mg, 0.0345 mmol, 0.5 eq), and $K_3PO_4$ (30 mg, 0.141 mmol, 2.0 eq.). The reaction vial was capped with a rubber septum. The septum was pierced with a needle attached to evacuate and backfilled with argon (this process was repeated twice) followed by the addition of 1,4-dioxane (1.5 mL). The reaction was heated at 60° C. under argon pressure for 15 h, the reaction was allowed to cool to room temperature, filtered through a pad of Celite®, and rinsed with MeOH. The crude material was concentrated in vacuo and purified on a 50 g C18 Aq column (gradient elution: 10-95% MeCN in water, 0.05% acetic acid in both). The product fractions were combined and lyophilized giving the title compound R29 as a dark reddish solid (21 mg, 35%). MS (ESI, pos.): calc'd for $C_{47}H_{57}N_3O_{14}$, 887.38; found 888.3 (M+H). $^1H$ NMR (500 MHz; DMSO-$d_6$) δ 10.12 (br. s., 1H), 9.39 (br. s., 1H), 6.75 (br. s., 1H), 6.70 (br. s., 1H), 6.03 (br. s., 1H), 5.77 (d, J=15.14 Hz, 1H), 5.21 (br. s., 1H), 4.83-4.90 (m, 1H), 4.15-4.30 (m, 2H), 4.08 (br. s., 1H), 3.53 (br. s., 1H), 3.29 (s, 1H), 3.16 (br. s., 1H), 3.03 (br. s., 3H), 2.87 (br. s., 1H), 2.79 (br. s., 1H), 2.62-2.71 (m, 2H), 2.36 (s, 1H), 2.23 (s, 6H), 2.19 (br. s., 3H), 1.93-2.11 (m, 7H), 1.91 (s, 1H), 1.76 (br. s., 1H), 1.69 (br. s., 3H), 1.53-1.65 (m, 1H), 1.50 (br. s., 1H), 1.32-1.45 (m, 1H), 0.76-0.94 (m, 6H), 0.68 (br. s., 5H).

Example 42: Synthesis of Rifamycin Analog R35

Rifamycin analog R35 was synthesized from rifamycin S as described below.

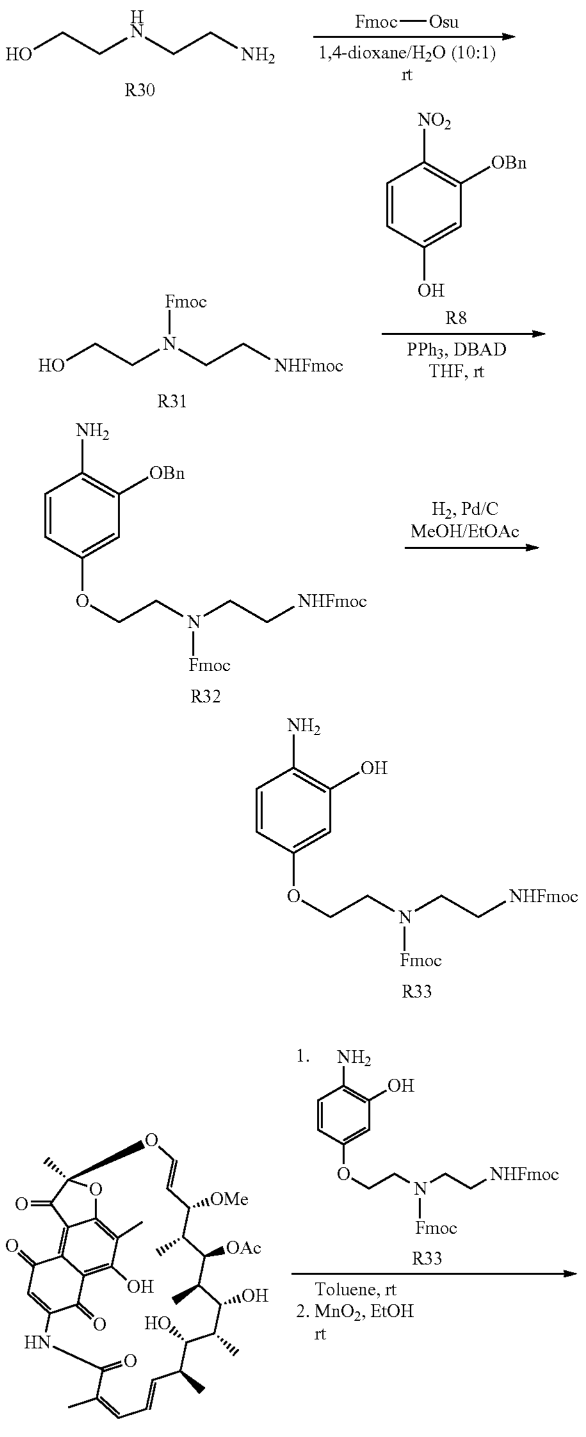

R30

R31

R32

R33

R33 rifamycin S

-continued

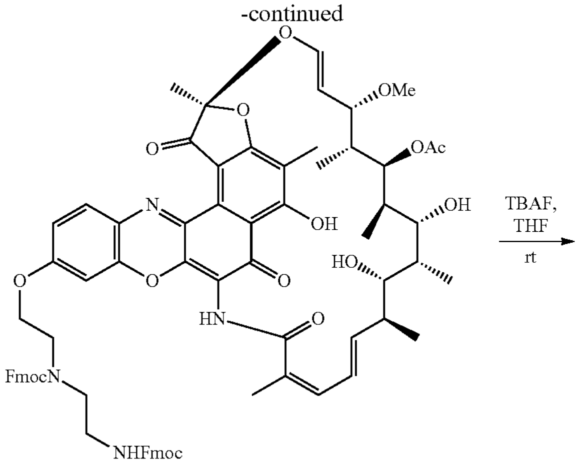

R34

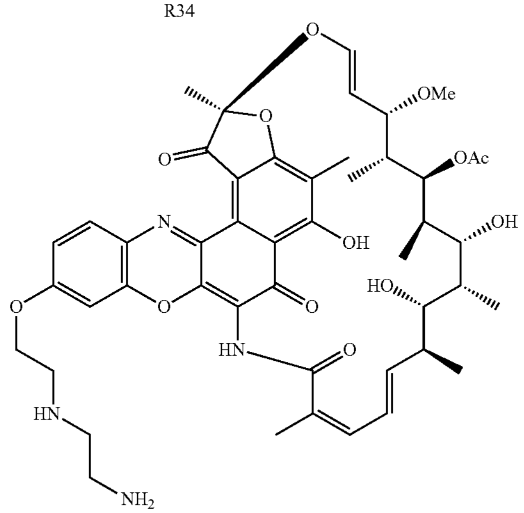

R35

Compound R31: To a solution of compound R30 (200 mg, 1.920 mmol) under argon in 1,4-dioxane/water (v/v, 10:1, 11 mL) was added Fmoc-OSu (1360 mg, 4.032 mmol). After stirring for 5 h an LC/MS analysis indicated the reaction was complete. The reaction mixture was treated with sat. $NaHCO_3$ (5 mL) and extracted with EtOAc (3x15 mL). The combined organic layer was then treated with brine (10 mL), dried ($Na_2SO_4$) and concentrated in vacuo to give crude compound R31 as a white foam (800 mg, 76%), which was used in the next step instantly without further purification. MS: calc'd for $C_{34}H_{32}N_2O_5$, 548.2; found 549.2 (M+H).

Compound R32: To a stirring solution of compound R8 (160 mg, 0.652 mmol) under argon in THF (2 mL) at room temperature were added the alcohol R31 (432 mg, 0.788 mmol) and $PPh_3$ (308 mg, 1.174 mmol). Then a solution of DBAD (270 mg, 1.174 mmol) in THF (1 mL) was added to the reaction mixture dropwise. After stirring for 15 h, the mixture was evaporated to dryness and the residue was purified on a 40 g HP silica gel Gold RediSep column via ISCO (gradient elution: 0-100% ethyl acetate in hexanes), and the pure fractions evaporated and dried in vacuo giving the title compound R32 as a yellowish white solid (286 mg, 56%). MS: calc'd for $C_{47}H_{41}N_3O_8$, 775.3; found 776.3 (M+H), 798.2 (M+Na).

Compound R33: To a solution under argon of compound R32 (220 mg, 0.284 mmol) in 5 mL of methanol/EtOAc (2:3) and degassed with argon was added 31 mg of 10% Pd/C. The mixture was further degassed with argon and connected to a hydrogen balloon. After 2 h, analysis by LC/MS from an in-process aliquot indicated the reaction was complete. The mixture was filtered through Celite and concentrated to afford 150 mg of compound R33 (85% pure by LC/MS) as yellowish oil, which was used in the next step instantly without further purification. MS: calc'd for $C_{40}H_{37}N_3O_6$, 655.3; found 656.3 (M+H).

Compound R34: To a round-bottom flask with hydroxyaniline R33 (150 mg, 0.194 mmol, 85% pure), were added toluene (2 mL) and rifamycin S (129 mg, 0.185 mmol). The reaction mixture was sonicated for 1 min to dissolve the reaction mixture, sealed via rubber septum, purged with argon, and the reaction stirred at ambient temperature. After 1 day another portion of hydroxyaniline R33 (45 mg, 0.059 mmol, 86% pure, synthesized using same procedure describe before) in toluene (2 mL) was added and stirred for 5 d. The reaction was concentrated in vacuo to remove toluene, dissolved in EtOH (4 mL) and $MnO_2$ (20 mg) was added. After stirring for 4 d, the reaction was concentrated in vacuo and purified by chromatography on a 40 g HP silica gel Gold RediSep column via ISCO (gradient elution: 0-100% ethyl acetate in hexanes). The pure fractions were evaporated and dried in vacuo giving the title compound R34 as a dark reddish solid (65 mg, 26%). MS (ESI, pos.): calc'd for $C_{77}H_{78}N_4O_{17}$, 1330.5; found, 1353.5 (M+Na).

Compound R35: To a stirred solution of compound R34 (28 mg, 0.021 mmol) under argon in THF (1 mL), was treated with a solution of TBAF (13 mg, 0.05 mL, 0.050 mmol, 1M in THF) and the reaction was stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 35 as dark reddish solid (9 mg, 48%). MS: calc'd for $C_{47}H_{58}N_4O_{13}$, 886.4; found 887.3 (M+H). $^1$H-NMR (500 MHz; $CD_3OD$): δ 7.86-7.74 (m, 1H), 7.18-7.08 (m, 1H), 6.98-6.84 (m, 1H), 6.78-6.68 (m, 1H), 6.53-6.40 (m, 1H), 6.23-6.15 (m, 1H), 6.23-6.15 (m, 1H), 6.00-5.79 (m, 1H), 6.00-5.79 (m, 1H), 5.30-4.95 (m, 2H), 3.81-3.65 (m, 6H), 3.35 (s, 3H), 3.09-2.93 (m, 7H), 2.25-2.20 (m, 2H), 2.17-2.03 (m, 4H), 2.00-1.87 (m, 5H), 1.76-1.68 (m, 4H), 1.03-0.85 (m, 7H), 0.78-0.65 (m, 2H), 0.14-0.03 (m, 4H), 0.13-0.00 (m, 3H), −0.30 (m, 2H).

Example 43: Broth Minimum Inhibitory Concentration (MIC) Assay

To test the efficacy of rifamycin analogs of the disclosure in vitro, a broth growth inhibition assay was developed. For the assay, *S. aureus* NRS384 was grown in Tryptic Soy Broth (TSB) overnight, then sub-cultured 1:50 in fresh TSB and grown for an additional two hours. The culture was then pelleted via centrifugation and washed twice in PBS. The culture was then diluted to $1 \times 10^4$ cfu/mL in TSB and 50 μL of the suspension was added per well to a 96 well microtiter dish in duplicate. A dilution series of the indicated antibiotic (an analog according to the disclosure or a previously known analog Rifampicin) was added 1:1 for a final starting concentration of $1 \times 10^{-5}$ M with 1:3 dilutions. The plates were incubated at 37° C. with shaking for 24h and then the OD600 nm was read on a Spectramax i3 Minimax 300.

The reagents used and lot numbers are shown in Table R2, below.

TABLE R2

| Reagents and Lot Numbers for MIC Assay | | | |
|---|---|---|---|
| Reagent | Vendor | Catalogue # | Lot |
| PBS | Gibco | 20012-043 | 2003838 |
| *S. aureus* NRS384 | BEI resources | NR-46070 | |
| Tryptic Soy Broth (TSB) | Teknova | T1525 | T014420G1801 |
| Dilution plates | Greiner Bio one | 780261 | B17073CP |

Figure 35:
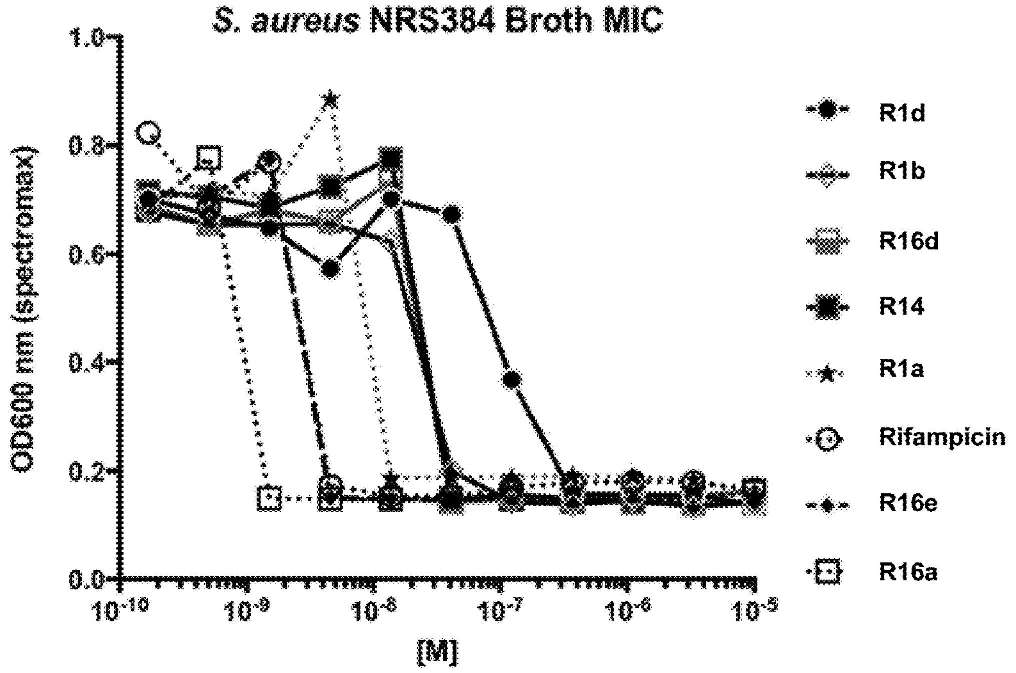
FIG. 35 is a plot of the results of the *S. aureus* growth inhibition assay conducted with rifamycin analogs.

The lowest concentrations that inhibited growth of *S. aureus* (minimum inhibitory concentration, MIC) are listed in Table R3. A plot of the *S. aureus* inhibition assay conducted with rifamycin analogs according to the disclosure is shown as FIG. 35.

TABLE R3

| Minimum inhibitory concentration (MIC) of antibiotics in a broth growth inhibition assay. | | |
|---|---|---|
| Rifamycin analog tested | Mol. Wt. (Da) | *S. aureus* Broth MIC (M) |
| Rifampicin | 823 | 4.6E−09 |
| R1a | 815 | 1.4E−08 |
| R1b | 890 | 1.2E−07 |
| R1d | 813 | 3.7E−07 |
| R14 | 883 | 4.1E−08 |
| R16a | 823 | 1.5E−09 |
| R16d | 843 | 4.1E−08 |
| R16e | 858 | 4.6E−09 |

As shown in Table R3, all rifamycin analogs according to the disclosure are effective at inhibiting growth of *S. aureus* at sub-micromolar to nanomolar concentrations. Analog 6a inhibited growth of *S. aureus* more potently than rifampicin with an MIC of $1.5\times10^{-9}$M.

Example 44: Intracellular Assay

The rifamycin analog compounds' activity against *S. aureus* was tested in an intracellular "killing" assay.

The reagents used and lot numbers are shown in Table R4, below.

TABLE R4

| Reagents and Lot Numbers for Intracellular Assay | | | |
|---|---|---|---|
| Reagent | Vendor | Catalogue # | Lot |
| TSB | Teknova | T1525 | T152517E1701 |
| PBS | Gibco | 20012-043 | 1951145 |
| Triton X-100 | Sigma | TX1568-1 | |
| RPMI | Gibco | 11875-093 | 1989237 |
| FBS | Gibco | 172667 | 138252-100 |
| PMA | Sigma | P8139 | MkBV849TV |
| Costa 96 well plate | Corning | 3904 | 16618025 |
| TSA plates | Teknova | T0144 | T014420G1801 |
| Pen/Strep | Gibco | 15140-122 | 1953095 |
| Dilution plates | Greiner Bio one | 780261 | B17073CP |
| Gentamicin | Gibco | 10131-035 | 1729122 |

THP-1 monocytic cell line was grown in media (RMPI+10% FBS+1% Penicillin/Streptomycin), then seeded at a density of 1e5 cells/well in a 96 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. THP-1 were washed with warm media (RMPI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 ug/mL). After 1h, media was aspirated and the indicated compound was added to infected macrophages in media containing 50 μg/mL gentamicin to prevent extracellular growth of *S. aureus*. After 2h, plates were washed 2× with warm RPMI without FBS, and 100 ul of THP-1 lysis buffer (0.1% Triton in PBS) was added to each well. *S. aureus* survival was enumerated by colony forming units through serial dilution and plating onto TSA.

Figure 36:
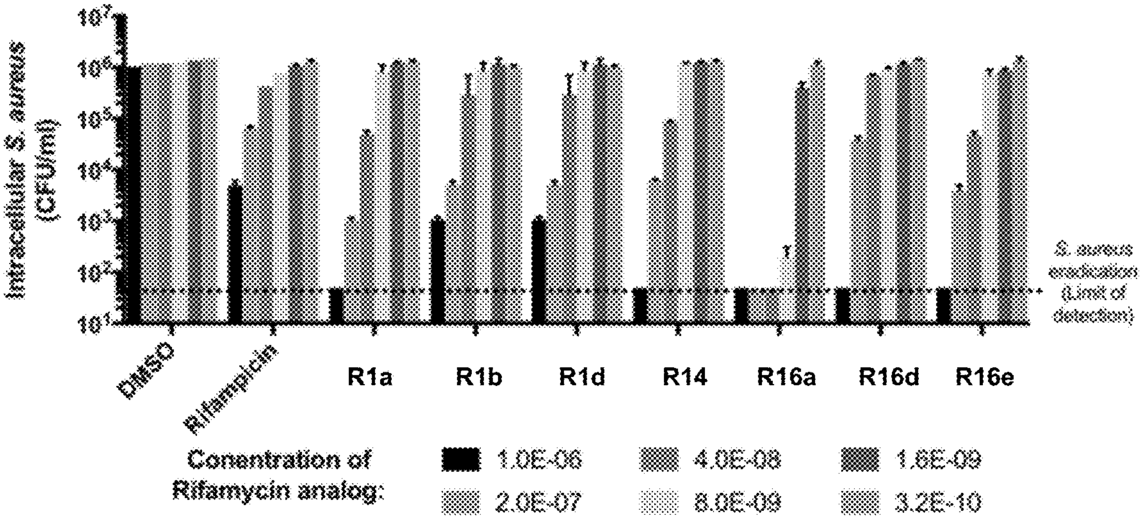
FIG. 36 is a bar graph of the results of the *S. aureus* intracellular killing assay conducted with rifamycin analogs.
Figure 37:
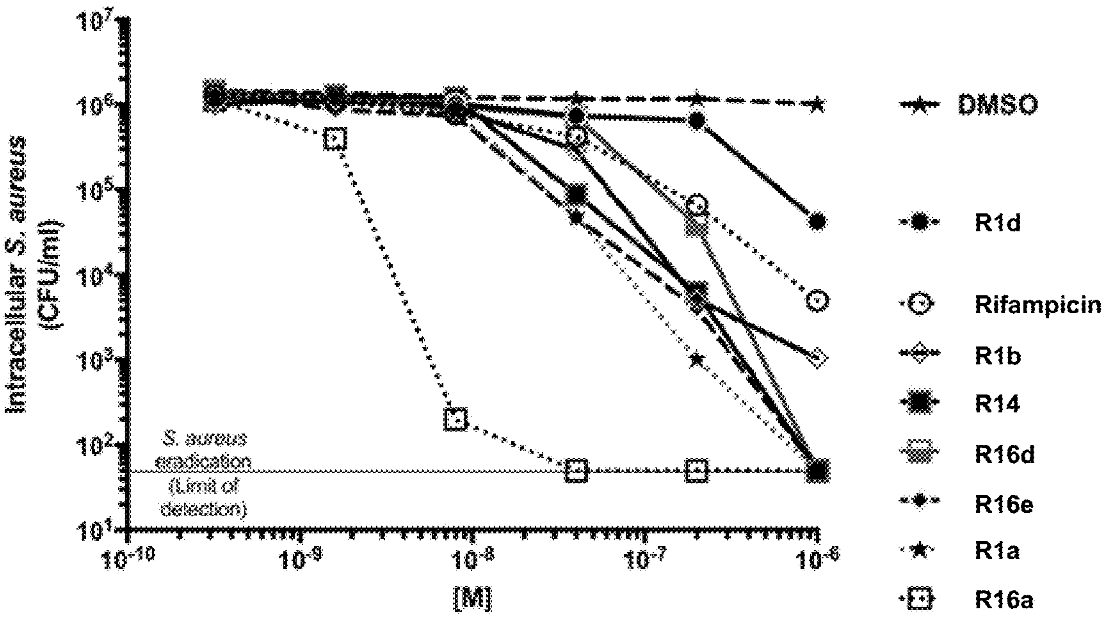
FIG. 37 is a plot of the results of the *S. aureus* intracellular killing assay conducted with rifamycin analogs.

The results of the intracellular killing assay are shown in Table R5 and FIGS. 36 and 37. The minimum inhibitory concentration (MIC) corresponds to the lowest concentration of each compound that resulted in intracellular *S. aureus* eradication.

TABLE R5

| Rifamycin Analog Tested | Intracellular killing MIC |
|---|---|
| Rifampicin | >1.0E−06 |
| R1a | 1.0E−06 |
| R1b | >1.0E−06 |
| R1d | >1.0E−06 |
| R14 | 1.0E−06 |
| R16a | 4.0E−08 |
| R16d | 1.0E−06 |
| R16e | 1.0E−06 |

As Table R5 and FIGS. 36 and 37 demonstrate, compounds R1a, R14, R16a, R16d, and R16e had increased intracellular *S. aureus* killing capacity compared to rifampicin, with compound R16a having the highest activity.

Example 45: Conjugation Method for Maleimides

The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound R25 (1.2 equivalents/SH group) in DMSO (10 mg/ml) was added to the reduced antibody and the mixture adjusted to pH 7.0 with 1 M HEPES (pH 7.4). After 1 h the reaction was quenched with excess N-ethyl maleimide. The conjugates were purified using PBS with 5% glycerol by size exclusion chromatography and sterile filtered. Protein concentrations and payload to antibody ratios were determined by UV spectral analysis. Size-exclusion HPLC established that all conjugates used were >90% monomeric, and RP-HPLC established that there was <1% unconjugated linker payload. All conjugated antibodies were analyzed by HIC for linker payload loading values.

Characterization of Conjugates by Hydrophobic Interaction Chromatography (HIC):

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody. Payload to antibody ratios are reported in Table R6.

TABLE R6

| Percent yield and payload to antibody ratios for each of the antibody drug conjugates | | |
|---|---|---|
| Antibody | Yield (%) | DAR (HIC) |
| H1H21234N-Compound R25 | 50 | 3 |
| Isotype Control-Compound R25 | 50 | 2 |

Example 46

An MSR1-non-cytotoxic antibody drug (ncADC) conjugate was tested in anti-type II collagen antibody-induced arthritis (CAIA) in vivo; cytokine detection in inflamed joints using Proinflammatory Panel 1 (mouse) Multiplex Immunoassay kit (MSD)

Lipopolysaccharide (LPS; 0111:B4) (Chondrex, Cat #53100, Lot #180141). Stock concentration: 2.5 mg/ml; working concentration: 0.5 mg/ml.

To further examine the anti-inflammatory effect of the anti-MSR1 Ab-steroid ncADC, the ncADC was evaluated in a collagen-antibody induced arthritis (CAIA) model in vivo. For the model, mice homozygously expressing human MSR1 extracellular domain and transmembrane domain in place of mouse MSR1 extracellular and transmembrane domains (humanized MSR1) and with a homozygous deletion of the ApoE gene (ApoE-KO) were utilized (resulting mice referred to as hMSR1/ApoE-KO mice).

ncADC Testing in CAIA In Vivo:

To induce CAIA, hMSR1/ApoE-KO mice were intraperitoneally injected with an 8 mg/kg mixture of five anti-type II collagen mAbs (Chondrex, Cat #53100, Lot #180140) on day 0, followed by intraperitoneal administration with 50 μg lipopolysaccharide (LPS; 0111:B4; Chondrex, Cat #53100, Lot #180141) on day 3. Severity of the microscopic levels of arthritis was graded up to 13 days after mAb injection in each of the four limbs per mouse on a 1-4 scale. The criteria for the grading were as follows: 0, normal; 1, mild redness and swelling of ankle/wrist or individual digits; 2, moderate redness and swelling of ankle/wrist; 3, severe redness and swelling of the entire paw including the digits; 4, maximal swelling in limbs involving multiple joints. The maximum value of the sum of the scores obtained from the four limbs of each mouse was 16. Mice developed first signs of arthritis on day 5 and were intraperitoneally treated every other day with 20 μL/g of decreasing concentrations (21 mg/kg, 63 mg/kg, and 191 mg/kg) of anti-MSR1 Ab-steroid ncADC conjugates (H1H21234N-N297Q-P4-3) and isotype control steroid ncADC (Isotype Control-N297Q-P4-3) starting from day 6. PBS, unconjugated anti-MSR1 Ab (H1H21234N-N297Q) and free steroid payload (P4-1), were intraperitoneally injected every other day or daily (referred to as P4-1 ED). Experimental dosing and treatment protocol for groups of mice are shown in Table 32. All mice were sacrificed on day 13 and inflamed patella were collected for subsequent homogenization and cytokine detection.

Measurement of Cytokines in Joint Homogenates:

Inflamed knee patella were collected in 2 mL microcentrifuge tubes containing two tungsten carbide beads (Qiagen, Cat #69997) and 500 μL of T-per buffer (Thermo Scientific, Cat #78510, Lot #QF217759) containing protease inhibitor cocktail and 0.5M EDTA (Thermo Scientific, Cat #78444, Lot #RF231047). Tissues were disrupted at the frequency of $30s^{-1}$ for 10 minutes using Qiagen Tissue Lyser II, centrifuged at 14,000 rpm for 7 minutes, and then supernatants were collected without disturbing the pellet. Cytokine concentrations in the supernatants were measured using a Proinflammatory Panel 1 (mouse) multiplex immunoassay kit (MesoScale Discovery, Cat #K15048D) according to the manufacturer's instructions. In brief, 50 μL/well of calibrators and samples (diluted in Diluent 41) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 μL of Detection Antibody Solution diluted in Diluent 45. After 2-hour incubation at room temperature while shaking, the plates were washed 3 times, and 150 μL of 2× Read Buffer was added to each well. Electrochemiluminescence was immediately read on MSD Spector© instrument. Cytokine concentrations were normalized per total protein content in tissue homogenates measured using Bradford protein assay (BioRad, Cat #5000006, Lot #64144266). Data analysis was performed using GraphPad Prism™ software. Statistical significance within the groups was determined by one-way Anova with Turkey's multiple comparison post-test (*p<0.01; p<0.001; *p<0.0001).

TABLE 32

| Experiment design, dosing, and treatment protocol for CAIA hMSR1/ApoE-KO mice | | | | |
|---|---|---|---|---|
| Group | Mice (n) | Molecule Tested | Dose (mg/kg) | Frequency (d = day) |
| 1 | 5 | PBS | — | every 2 days: d6, d8, d10, d12 |
| 2 | 5 | P4-1ED | 2.95 | everyday: d6, d7, d8, d9, d10, d11, d12 |
| 3 | 5 | P4-1 | 2.95 | every 2 days: d6, d8, d10, d12 |
| 4 | 3 | H1H21234N-N297Q | 191 | every 2 days: d6, d8, d10, d12 |
| 5 | 5 | H1H21234N-N297Q-P4-3 | 191 | every 2 days: d6, d8, d10, d12 |
| 6 | 5 | H1H21234N-N297Q-P4-3 | 63 | every 2 days: d6, d8, d10, d12 |
| 7 | 5 | H1H21234N-N297Q-P4-3 | 21 | every 2 days: d6, d8, d10, d12 |
| 8 | 5 | Isotype Control-N297Q-P4-3 | 191 | every 2 days: d6, d8, d10, d12 |
| 9 | 5 | Isotype Control-N297Q-P4-3 | 63 | every 2 days: d6, d8, d10, d12 |
| 10 | 5 | Isotype Control-N297Q-P4-3 | 21 | every 2 days: d6, d8, d10, d12 |

As shown in Table 33, a mixture of anti-type II collagen mAbs induced robust CAIA in hMSR1/ApoE-KO mice treated with PBS. Therapeutic administration of anti-MSR1 Ab-steroid ncADC (H1H21234N-N297Q-P4-3) in vivo was efficacious in inhibiting the progression and ameliorating the severity of CAIA in a dose-dependent manner with all doses demonstrating a significant effect. Comparable inhibition of CAIA was observed between the anti-MSR1 Ab-steroid ncADC (H1H21234N-N297Q-P4-3) dosed at 21 mg/kg and the free P4-1 dosed every day (P4-1ED). The anti-MSR1 Ab-steroid ncADC (H1H21234N-N297Q-P4-3) dosed at 191 mg/kg and 63 mg/kg demonstrated greater efficacy than the payload dosed every day. Therapeutic administration of 63 mg/kg and 21 mg/kg isotype control-ncADC (Isotype Control-P4-3), unconjugated anti-MSR1 Ab (H1H21234N)

and free P4-1 every other day did not attenuate CAIA in hMSR1/ApoE-KO mice. The highest dose of the isotype control ncADC demonstrated efficacy in ameliorating the severity of CAIA.

As shown in Table 34, in vivo therapeutic administration of anti-MSR1 Ab-steroid ncADC (H1H21234N-N297Q-P4-3) was also efficacious in inhibiting in vivo pro-inflammatory cytokine production in hMSR1/ApoE-KO mice in a dose-dependent manner with all doses tested demonstrating a significant effect on IL-6, IL-1beta and KC-GRO; however, only the highest dose had a significant effect on TNF-alpha. No effect on pro-inflammatory cytokine levels in inflamed joints was observed with unconjugated anti-MSR1 Ab (H1H21234N-N297Q) and free P4-1 administered every other day. The isotype control ncADC demonstrated effects on proinflammatory cytokines at the higher doses tested.

Table 33: Anti-MSR1 Ab-steroid ncADC ameliorates clinical scores of CAIA in hMSR1/ApoE-KO mice in vivo in a dose-dependent manner. Statistical significance to PBS- and Isotype Control-P4-3-treated groups was determined by one-way Anova with Turkey's multiple comparison post-test and standard error of mean (SEM±) calculated.

TABLE 33

| | Molecule Tested | | | | | | | | | |
|---|---|---|---|---|---|---|---|---|---|---|
| | PBS | P4-1ED | P4-1 | H1H21234N-N297Q | H1H21234N-N297Q-P4-3 | | | Isotype Control-N297Q-P4-3 | | |
| Dose (mg/kg) | N/A | 2.95 | 2.95 | 191 | 191 | 63 | 21 | 191 | 63 | 21 |
| Clinical Score | 11.3 ± 2.36 | 5 ± 1.54 | 9.4 ± 2.46 | 13.67 ± 2.02 | 0.5 ± 0.35** | 2.3 ± 0.84** | 5.1 ± 2.1* | 3.2 ± 0.84 | 7.5 ± 0.94 | 9.6 ± 3.96 |

*p < 0.05,
**p < 0.005,
***p < 0.0005,
****p < 0.00001

Table 34: Therapeutic treatment with anti-MSR1 Ab-steroid ncADC inhibits CAIA-induced pro-inflammatory cytokine production in hMSR1/ApoE-KO mice. Statistical significance to PBS- and Isotype Control-N297Q-P4-3-treated groups was determined by one-way Anova with Turkey's multiple comparison post-test and standard error of mean (SEM±) calculated.

TABLE 34

| | | PBS | P4-1ED | P4-1 | H1H21234N | H1H21234N-N297Q-P4-3 | | |
|---|---|---|---|---|---|---|---|---|
| | Dose (mg/kg) | | 2.95 | 2.95 | 191 | 191 | 63 | 21 |
| Cytokines [pg per mg of total protein] | IL-6 | 155.4 ± 41 | 22.8 ± 5.2**** | 131.4 ± 40.9 | 116.3 ± 23.8 | 18.8 ± 3.7**** | 23.5 ± 4.2**** | 51.9 ± 27.8**** |
| | IL-1β | 23.1 ± 6.1 | 1.1 ± 0.6**** | 20.6 ± 4.3 | 23.7 ± 7.9 | 0.5 ± 0.2**** | 1.6 ± 1.3**** | 12.8 ± 2.2** |
| | KC-GRO | 16.6 ± 6.8 | 8 ± 4.4**** | 8.9 ± 9 | 7.8 ± 16 | 5.9 ± 1.5**** | 10.8 ± 6.9**** | 9.9 ± 13* |
| | TNF-α | 7.9 ± 2.8 | 3.5 ± 1.4 | 8.3 ± 1.9 | 10.2 ± 5 | 1.9 ± 0.8* | 3.8 ± 1.9 | 7.9 ± 3.5 |

| | | Isotype Ctrl-N297Q-P4-3 | | |
|---|---|---|---|---|
| | Dose (mg/kg) | 191 | 63 | 21 |
| Cytokines [pg per mg of total protein] | IL-6 | 40.3 ± 15.5**** | 75.2 ± 24.3*** | 99.1 ± 25.5 |
| | IL-1β | 6.3 ± 2.1**** | 13.7 ± 7.3* | 17.3 ± 2.9 |
| | KC-GRO | 11.7 ± 2.7**** | 18.2 ± 8.6 | 15 ± 10 |
| | TNF-α | 4.3 ± 2 | 9.3 ± 4.3 | 9.5 ± 1.6 |

*p < 0.05,
**p < 0.005,
***p < 0.0005,
****p < 0.00001

Example 47

Intracellular *S. aureus* Killing Assay

The following anti-MSR1 ncADcs were tested.

| |
|---|
| H1H21234N-N297Q-R25 |
| Isotype-control antibody-N297Q-R25 |

To test the efficacy of an anti-MSR1 Ab-antibiotic ncADC of the invention in vitro, an intracellular *S. aureus* killing assay was utilized. For the assay, a THP-1 monocytic cell line was grown in media comprised of RPMI containing 10% FBS and 1% Penicillin/Streptomycin, then was seeded at a density of $1\times10^5$ cells/well in a 96 well plate and differentiated into macrophages for three days prior to infection using 200 nM Phorbol Myristate Acetate (PMA). An overnight culture of *S. aureus* MRSA strain NRS384 was grown in RPMI, washed twice with PBS and subsequently resuspended at $1\times10^7$ cfu/mL in PBS. THP-1 cells were washed with warm media (RPMI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media and remaining extracellular *S. aureus* were killed by addition of media containing 100 ug/mL of gentamicin. After 1 hour, media was aspirated and the anti-MSR1 Ab-antibiotic ncADC (H1H21234N-N297Q-R25) at different doses (10 ug/mL, 3.3 ug/mL, 1.1 ug/mL, 0.4 ug/mL, 0.1 ug/mL) and the isotype control-antibiotic ncADC (Isotype control-N297Q-R25) at 10 ug/mL were added to infected macrophages in media containing 50 ug/mL gentamicin to prevent extracellular growth of *S. aureus*. A sample without any ncADC was also included for reference. After 24 hours, plates were washed twice with warm RPMI without FBS and then 100 uL of 0.1% Triton X-100 in PBS was added and incubated for 10 minutes to lyse the THP-1. *S. aureus* survival was enumerated by colony forming units through serial dilution in PBS and plating onto trypticase soy agar plates.

As shown in Table R7, the anti-MSR1 Ab-antibiotic ncADC (H1H21234N-N297Q-R25) at concentrations of 10, 3.3 and 1.1 ug/mL demonstrated the ability to eradicate intracellular *S. aureus* from infected macrophages in vitro. The lower doses of the anti-MSR1 Ab-antibiotic ncADC of 0.4 ug/mL and 0.1 ug/mL demonstrated the ability to reduce intracellular *S. aureus* from infected macrophages in vitro, but not to the limit of detection as the higher doses did. Macrophages treated with the isotype control-antibiotic ncADC (Isotype control-N297Q-R25) at 10 ug/mL harbored intracellular *S. aureus* at a similar level to the untreated control. These data demonstrate that an anti-MSR1 Ab-antibiotic ncADC can be used to effectively kill pathogens residing within a macrophage reservoir.

TABLE R7

Average colony forming units of anti-MSR1 Ab-Antibiotic

| | ncADC dose (ug/mL) | Average cfu/mL | Standard Deviation |
|---|---|---|---|
| *S. aureus* control | none | 275,000 | 0 |
| Isotype Control-N297Q-R25 | 10 | 200,000 | 35,355 |

TABLE R7-continued

Average colony forming units of anti-MSR1 Ab-Antibiotic

| | ncADC dose (ug/mL) | Average cfu/mL | Standard Deviation |
|---|---|---|---|
| MSR1 ncADC | 10 | 50 (limit of detection) | 0 |
| H1H21234N- | 3.3 | 50 (limit of detection) | 0 |
| N297Q-R25 | 1.1 | 50 (limit of detection) | 0 |
| | 0.4 | 663 | 124 |
| | 0.1 | 33,750 | 1,768 |

Example 48

*S. aureus* IV disseminated infection mouse model

The following ADCs were used in this experiment:

| Antibody |
|---|
| MSR1 ncADC H1H21234N-N297Q-R25 |
| Isotype Control-N297Q-R25 |
| MSR1 ncADC H1H21234N 3-N297Q |
| Isotype control-N297Q |

To test the efficacy of an anti-MSR1 Ab-antibiotic ncADC of the invention in vivo, an intravenous disseminated infection model was utilized. *S. aureus* MSRA strain NRS384 was grown overnight in trypic soy broth (TSB) and subcultured to mid-logarithmic phase. Bacteria were then washed twice with PBS and resuspended in PBS at a concentration of 1.2×10ˆ8 cfu/mL. Mice homozygously expressing human MSR1 extracellular domain and transmembrane domain in place of mouse MSR1 extracellular and transmembrane domains (humanized MSR, MAID 7343-MSR1 Humin delHyg) were then infected intravenously through the tail vein with 100 uL of the bacterial suspension, for a final infectious dose of 1.2×10ˆ7 cfu/mouse. From one to three days post infection, mice were treated with 110 mg/kg vancomycin subcutaneously twice daily where indicated. Either the anti-MSR1 monoclonal antibody (H1H21234N-N297Q), anti-MSR1 Ab-antibiotic ncADC (H1H21234N-N297Q-R25), the Isotype control Ab or the ncADC Isotype control (Isotype control-1R25) was administered subcutaneously at the indicated dose, as described in Table R8, one day after infection. Mice were monitored for weight loss and body conditioning score throughout the infection. At four days post infection, mice were euthanized and the *S. aureus* kidney burden was quantified by tissue homogenization followed by enumeration of colony forming units through serial dilution in PBS and plating onto trypicase soy agar plates. The data from this experiment is shown in Table R8.

TABLE R8

Average *S. aureus* kidney burden in mice treated with anti-MSR1 Ab-Antibiotic ncADC in combination with vancomycin

| Treatment | Vancomycin treatment | mAb or conjugate dose (mg/kg) | Average cfu/kidney pair | # of mice with *S. aureus* below the limit of detection | Standard Deviation |
|---|---|---|---|---|---|
| Infected Control | – | (—) | 4.33E+08 | 0/5 | 2.32E+08 |
| Vancomycin | + | (—) | 2.07E+06 | 0/6 | 2.76E+06 |
| Isotype Control 1 mg/kg | + | 1 | 2.44E+06 | 0/4 | 1.51E+06 |
| ncADC Isotype control (Isotype control-N297Q-R25) | + | 1 | 4.01E+05 | 1/5 | 6.49E+05 |
| anti-MSR1 Ab (H1H21234N-N297Q) | + | 1 | 1.55E+05 | 4/8 | 2.72E+05 |
| anti-MSR1 Ab (H1H21234N-N297Q) | + | 0.1 | 2.43E+05 | 0/6 | 2.64E+05 |
| anti-MSR1 Ab-antibiotic ncADC (H1H21234N-N297Q-R25) | + | 1 | 6.17E+03 | 7/9 | 1.69E+04 |
| anti-MSR1 Ab-antibiotic ncADC (H1H21234N-N297Q-R25) | + | 0.1 | 1.16E+03 | 6/8 | 1.78E+03 |

Limit of detection = 250 colony forming units (cfu)

As shown in Table R8, intravenous infection with *S. aureus* MRSA strain NRS384 results in high bacterial burden in the kidneys and treatment of mice with the standard of care antibiotic vancomycin reduces the *S. aureus* kidney burden by approximately 2 logs, but none of the mice had levels of *S. aureus* reduced below the limit of detection (LOD). The anti-MSR1 Ab-antibiotic ncADC (H1H21234N-N297Q-R25) at doses of 1 and 0.1 mg/kg in combination with vancomycin resulted in 77% and 75% of mice with *S. aureus* levels below the LOD, demonstrating improvement in *S. aureus* clearance in mice treated with the Ab-antibiotic ncADC combination therapy. *S. aureus* clearance was less pronounced in mice treated with the isotype control ncADC conjugate (Isotype Control-N297Q-R25) plus vancomycin, demonstrating the benefit of payload targeting to macrophages.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An antibody-drug conjugate comprising an anti-MSR1 antibody, or antigen-binding fragment thereof that binds macrophage scavenger receptor 1 (MSR1), conjugated to a payload residue optionally through a linker or through a linker-spacer, wherein the anti-MSR1 antibody or antigen-binding fragment thereof comprises:

(a) three heavy chain CDRs (HCDR1, HCDR2, and HCDR3) contained within the heavy chain variable region (HCVR) amino acid sequence of SEQ ID NO: 50; and three light chain CDRs (LCDR1, LCDR2, and LCDR3) contained within the light chain variable region (LCVR) amino acid sequence of SEQ ID NO: 58;

(b) three heavy chain CDRs (HCDR1, HCDR2, and HCDR3) contained within the heavy chain variable region (HCVR) amino acid sequence of SEQ ID NO: 2; and three light chain CDRs (LCDR1, LCDR2, and LCDR3) contained within the light chain variable region (LCVR) amino acid sequence of SEQ ID NO: 10;

(c) three heavy chain CDRs (HCDR1, HCDR2, and HCDR3) contained within the heavy chain variable region (HCVR) amino acid sequence of SEQ ID NO: 34; and three light chain CDRs (LCDR1, LCDR2, and LCDR3) contained within the light chain variable region (LCVR) amino acid sequence of SEQ ID NO: 42;

(d) three heavy chain CDRs (HCDR1, HCDR2, and HCDR3) contained within the heavy chain variable region (HCVR) amino acid sequence of SEQ ID NO: 98; and three light chain CDRs (LCDR1, LCDR2, and LCDR3) contained within the light chain variable region (LCVR) amino acid sequence of SEQ ID NO: 106; or (e) three heavy chain CDRs (HCDR1, HCDR2, and HCDR3) contained within the heavy chain variable region (HCVR) amino acid sequence of SEQ ID NO: 290; and three light chain CDRs (LCDR1, LCDR2, and LCDR3) contained within the light chain variable region (LCVR) amino acid sequence of SEQ ID NO: 298.

2. The antibody-drug conjugate of claim 1, wherein the anti-MSR1 antibody or antigen-binding fragment thereof comprises:

(a) a heavy chain comprising the amino acid sequence of SEQ ID NO: 2 and a light chain comprising the amino acid sequence of SEQ ID NO:10;

(b) a heavy chain comprising the amino acid sequence of SEQ ID NO: 34 and a light chain comprising the amino acid sequence of SEQ ID NO: 42;

(c) a heavy chain comprising the amino acid sequence of SEQ ID NO: 50 and a light chain comprising the amino acid sequence of SEQ ID NO: 58;

(d) a heavy chain comprising the amino acid sequence of SEQ ID NO: 98 and a light chain comprising the amino acid sequence of SEQ ID NO: 106; or (e) a heavy chain comprising the amino acid sequence of SEQ ID NO: 290 and a light chain comprising the amino acid sequence of SEQ ID NO: 298.

3. The antibody-drug conjugate of claim 1, having a structure of Formula (I):

Formula (I)

$$BA\left[(L)_{0\text{-}1}PA\right]_n$$

or a pharmaceutically acceptable salt, solvate, or stereoisomeric form thereof, a regioisomer thereof, or a mixture of regioisomers thereof; wherein:

BA is the anti-MSR1 antibody or antigen-binding fragment thereof;

wherein n is one, two, three, or four;

L is a linker;

PA is a payload moiety selected from the group consisting of a steroid residue, a LXR modulator residue, and a rifamycin residue.

4. The antibody-drug conjugate of claim 3, selected from the group consisting of:

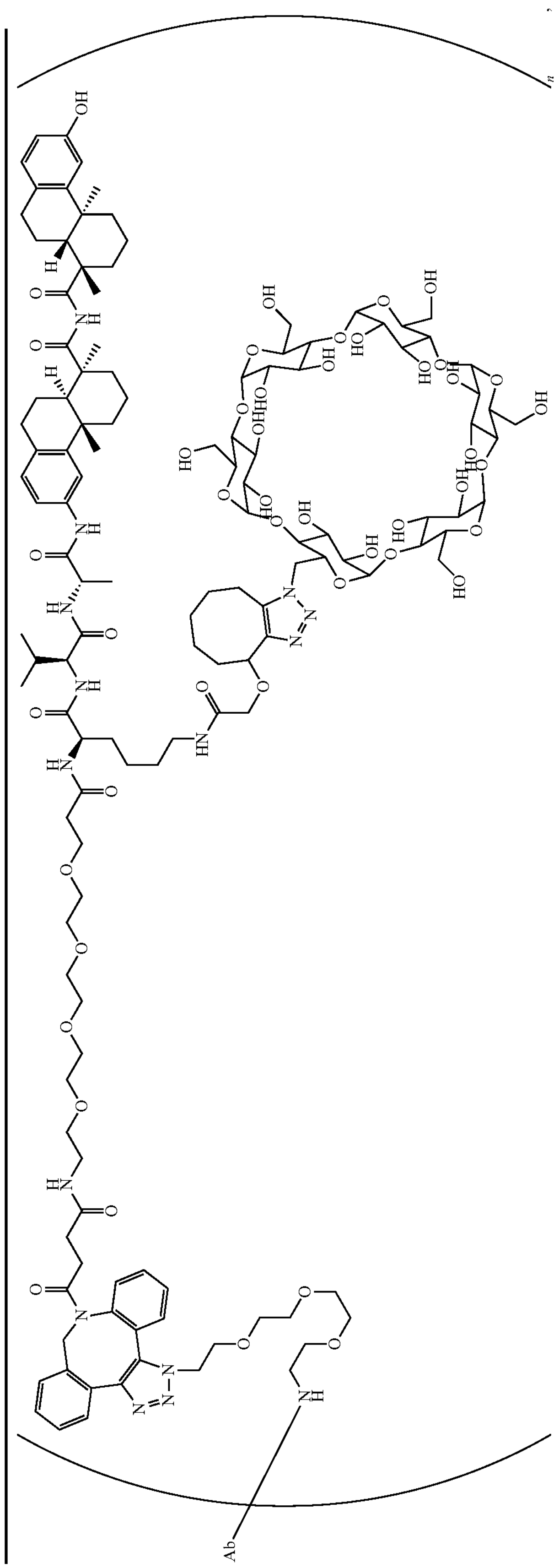

-continued
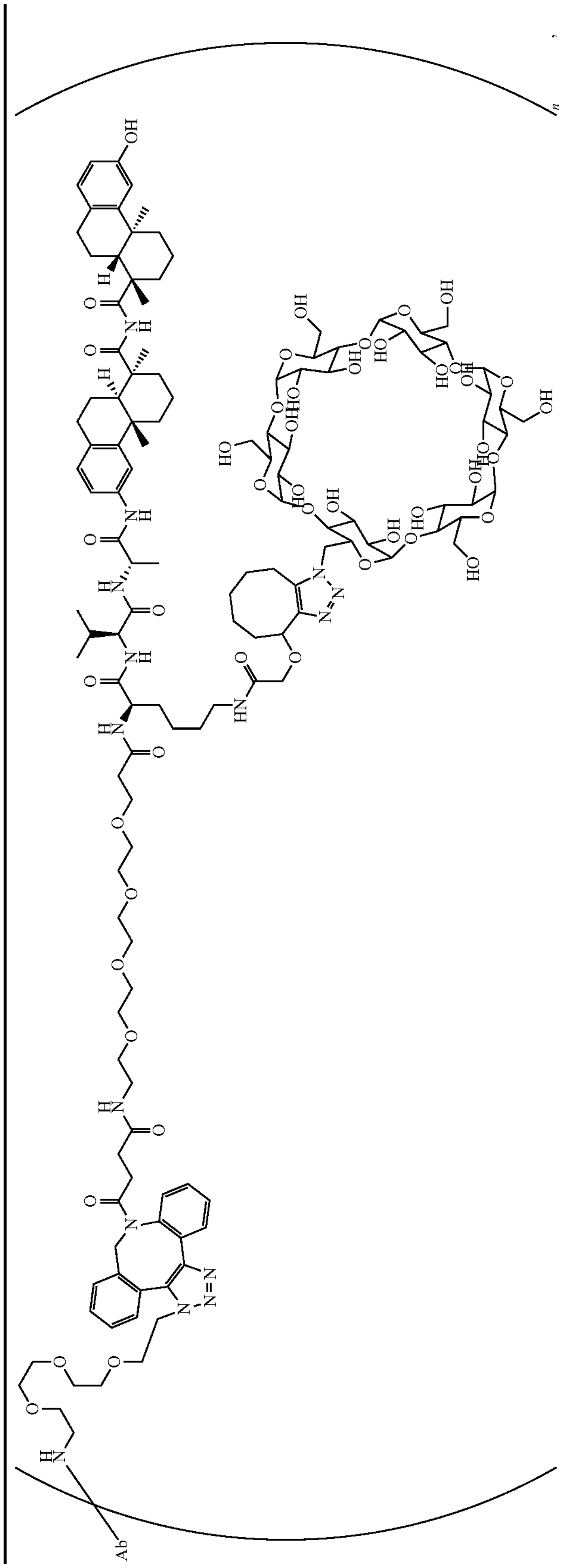

-continued
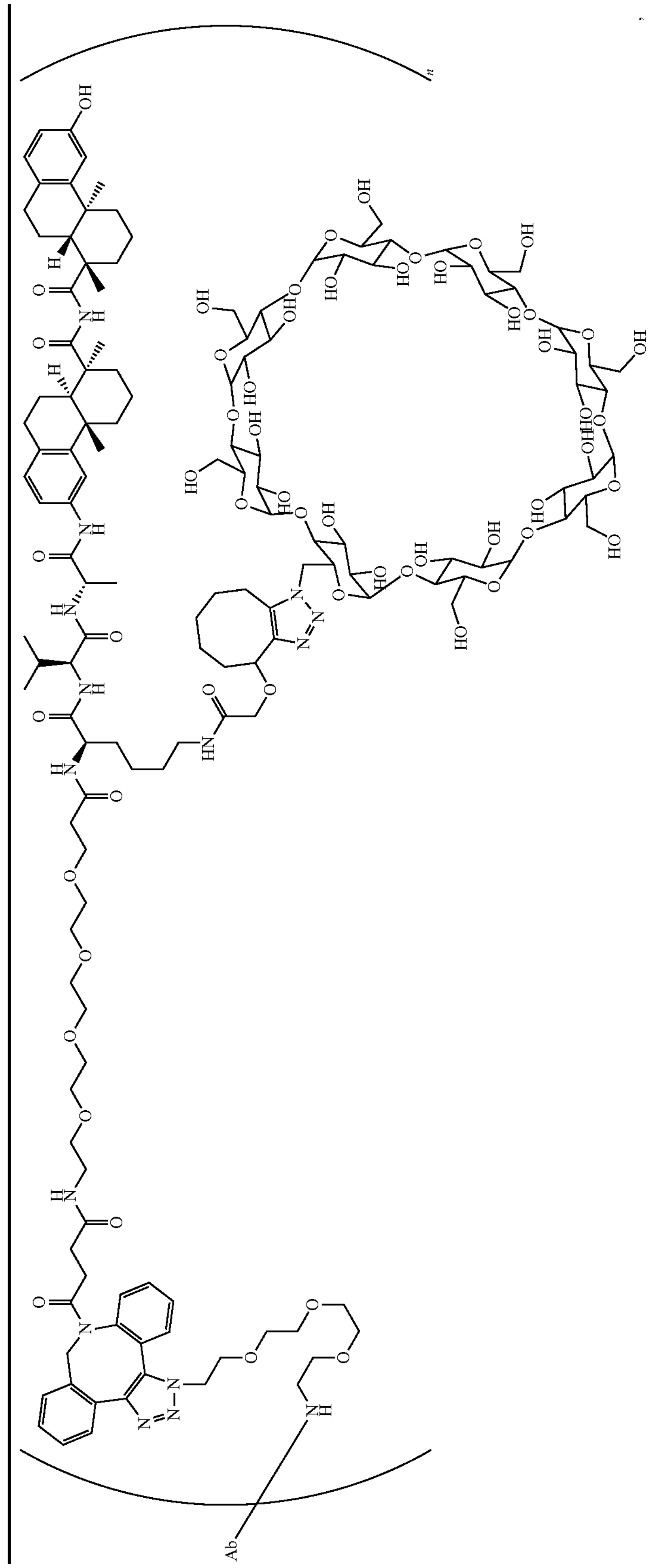
,

-continued
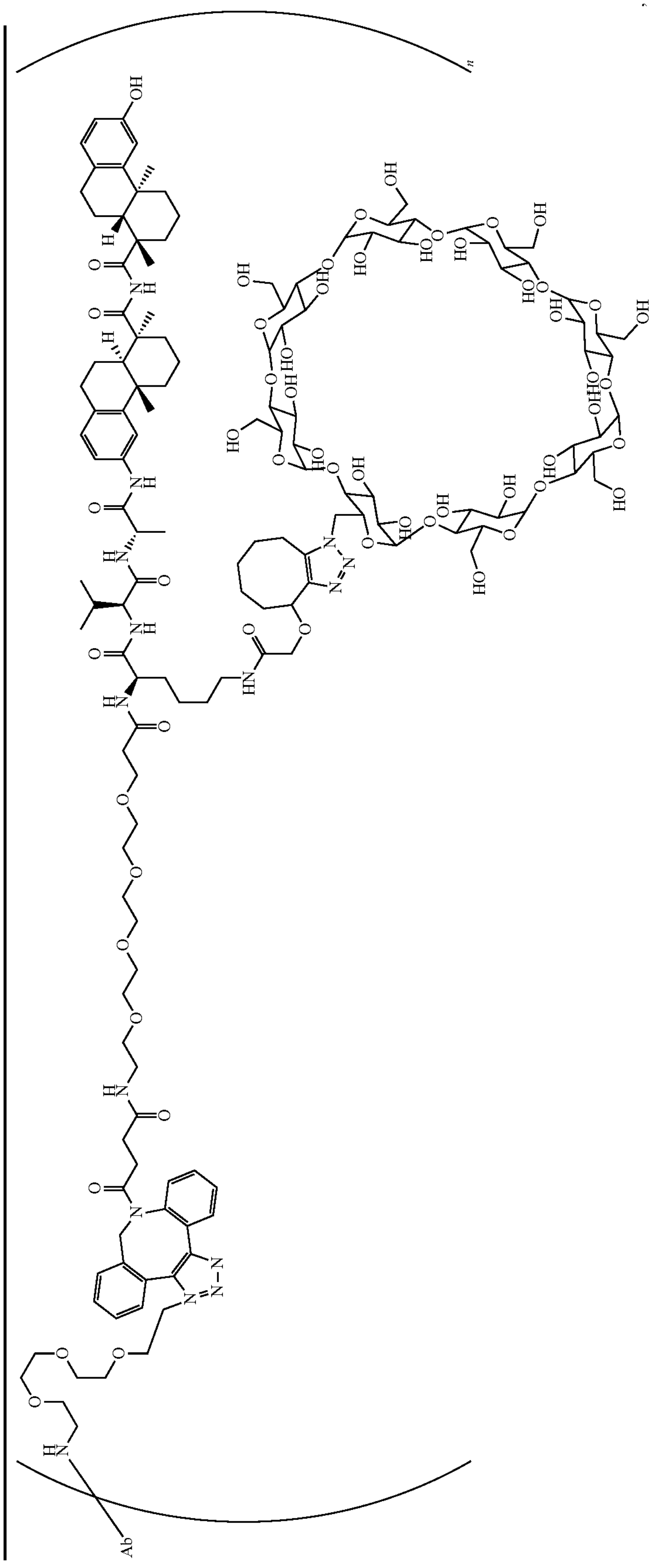

-continued
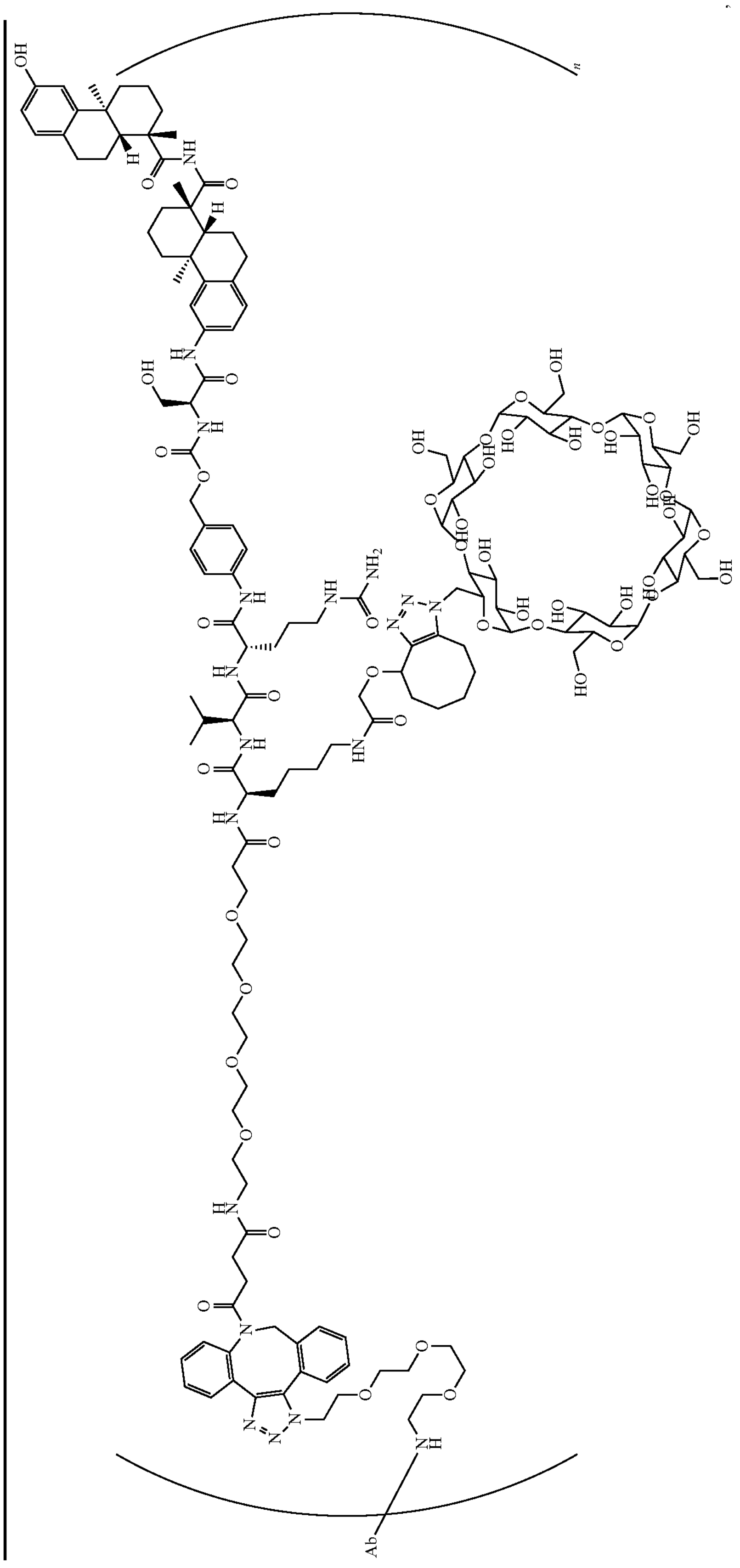

-continued
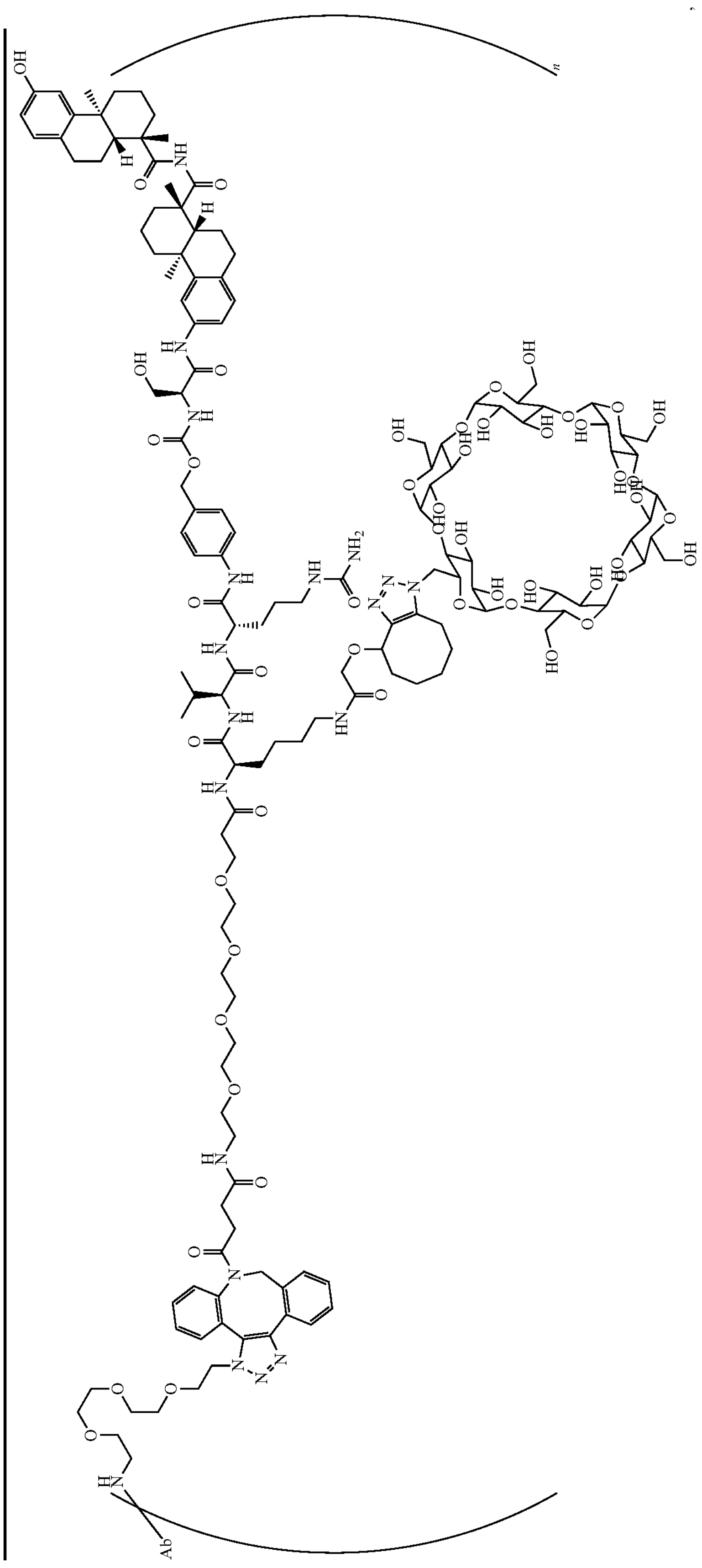

-continued
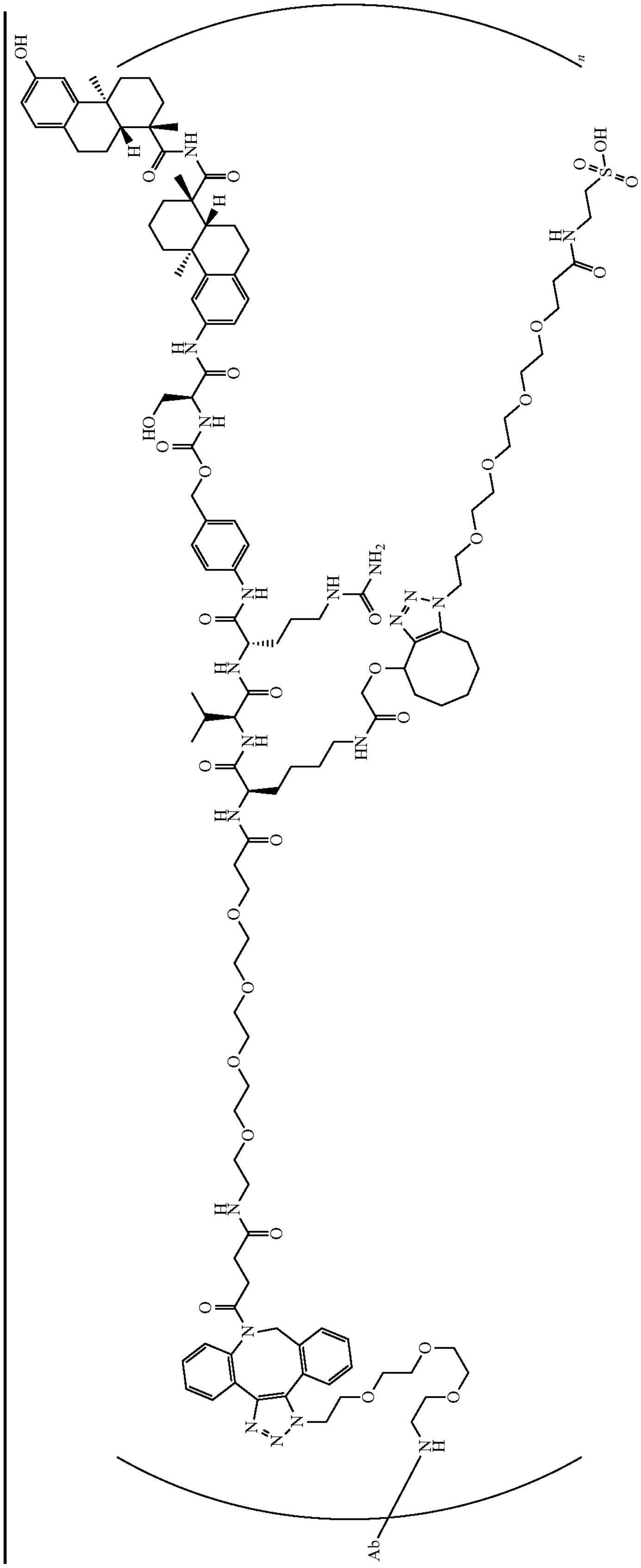
,

-continued
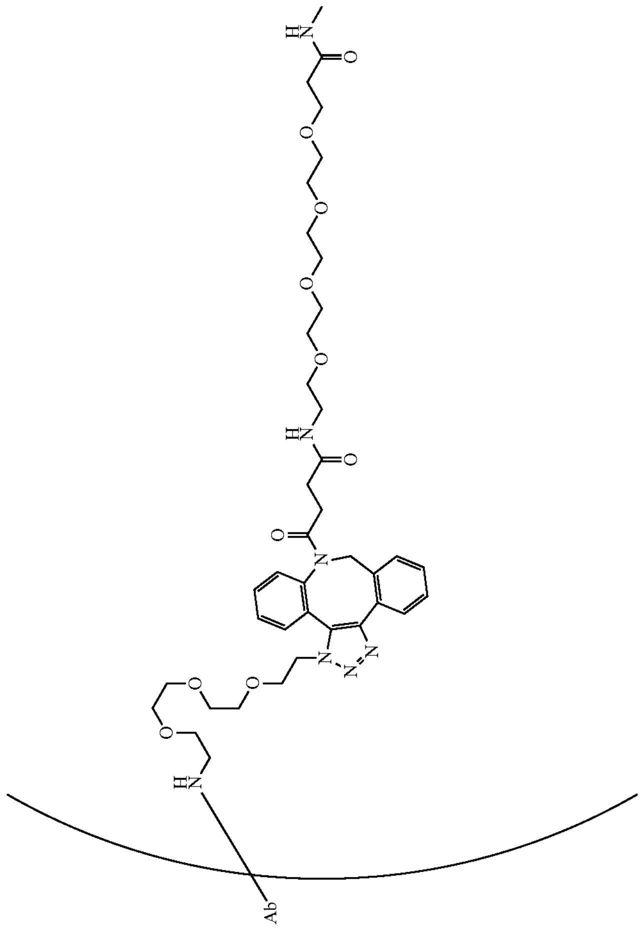

-continued
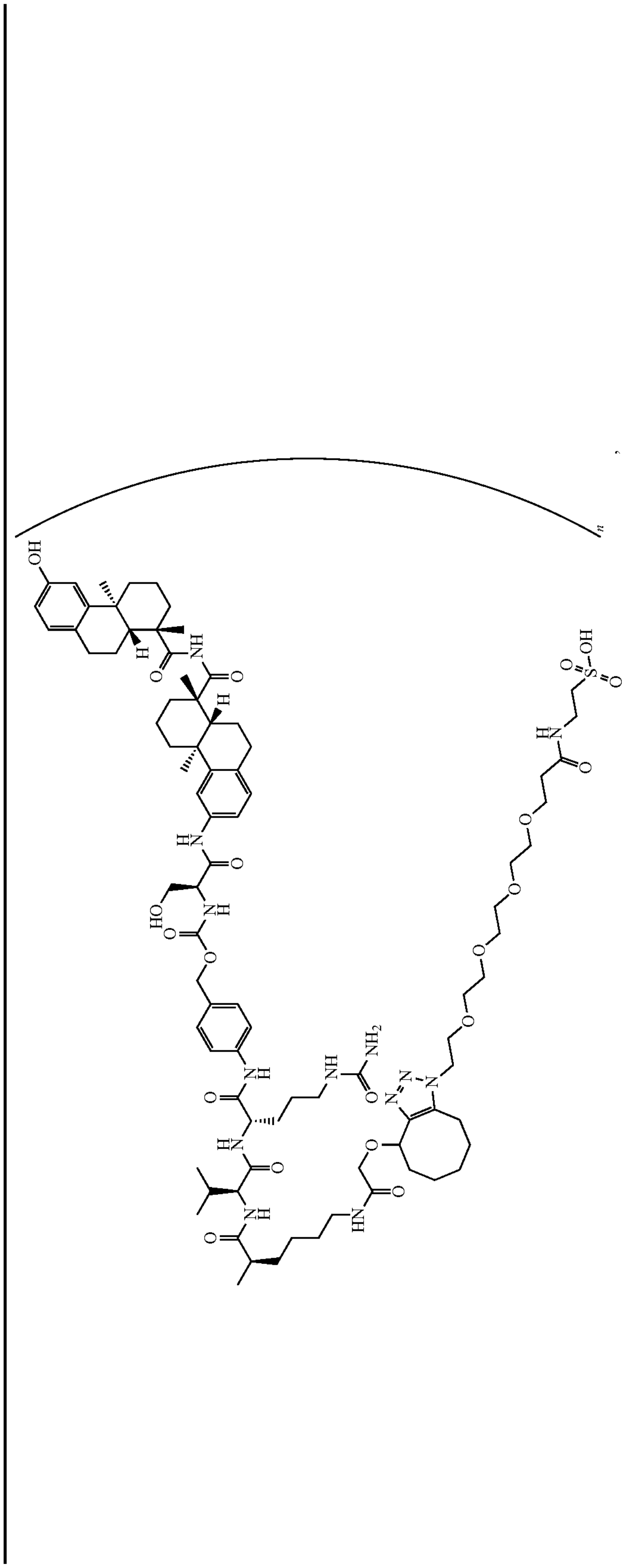
,
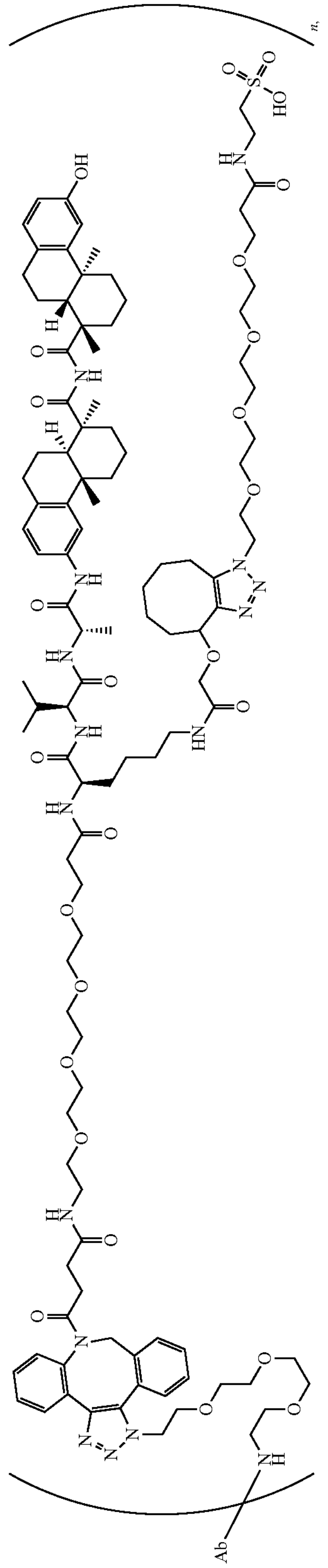
,

-continued
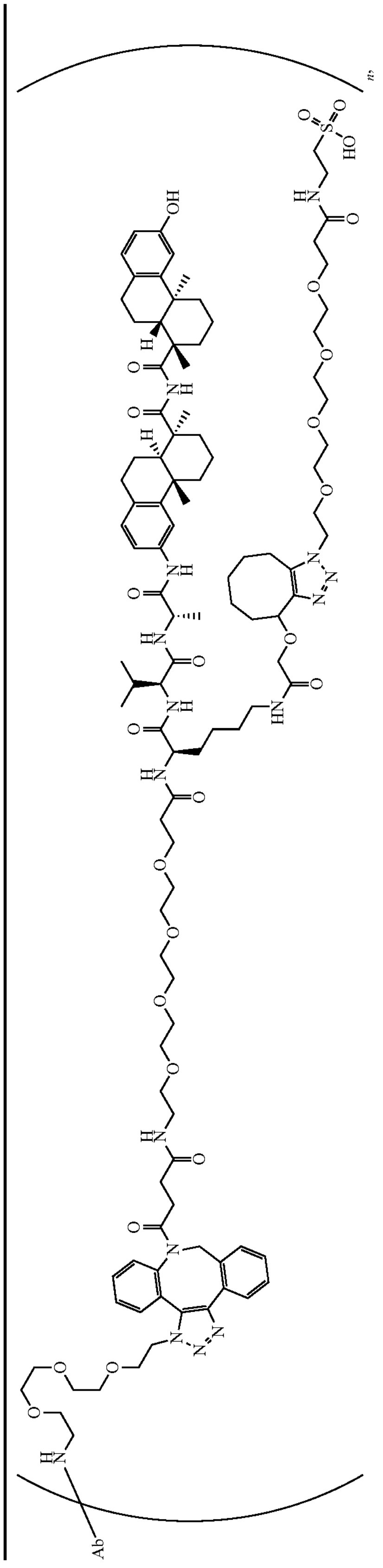
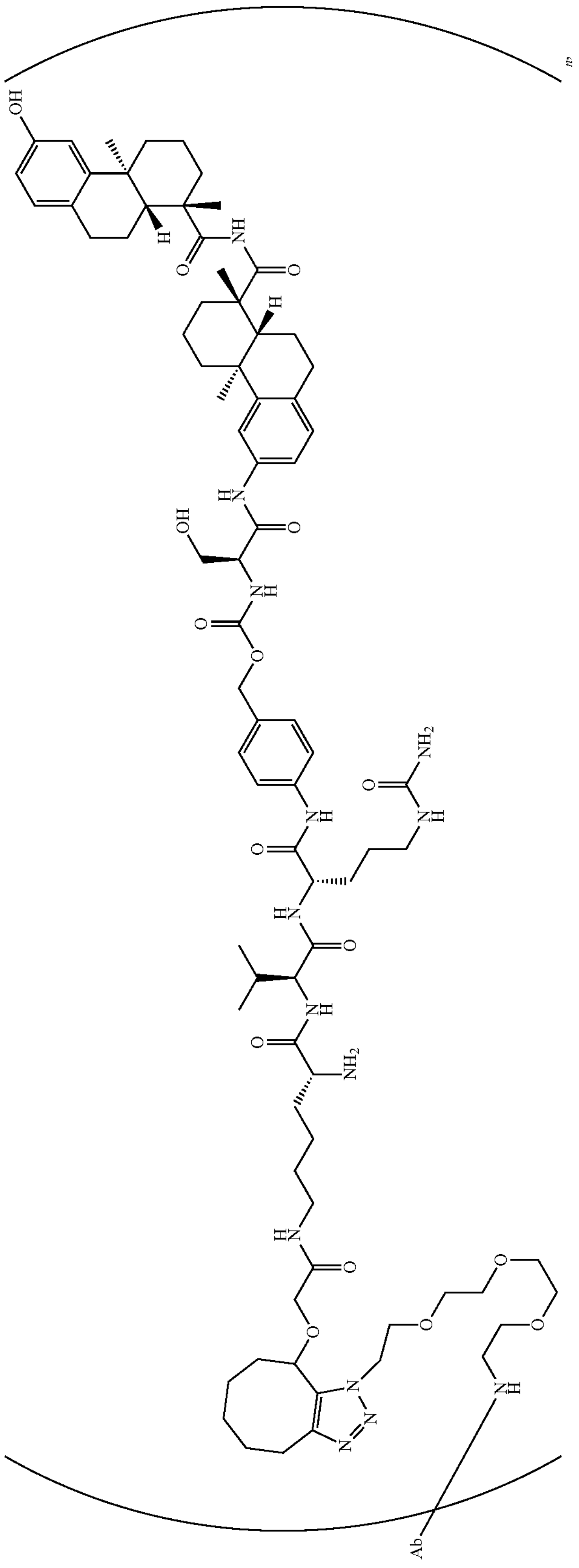

-continued
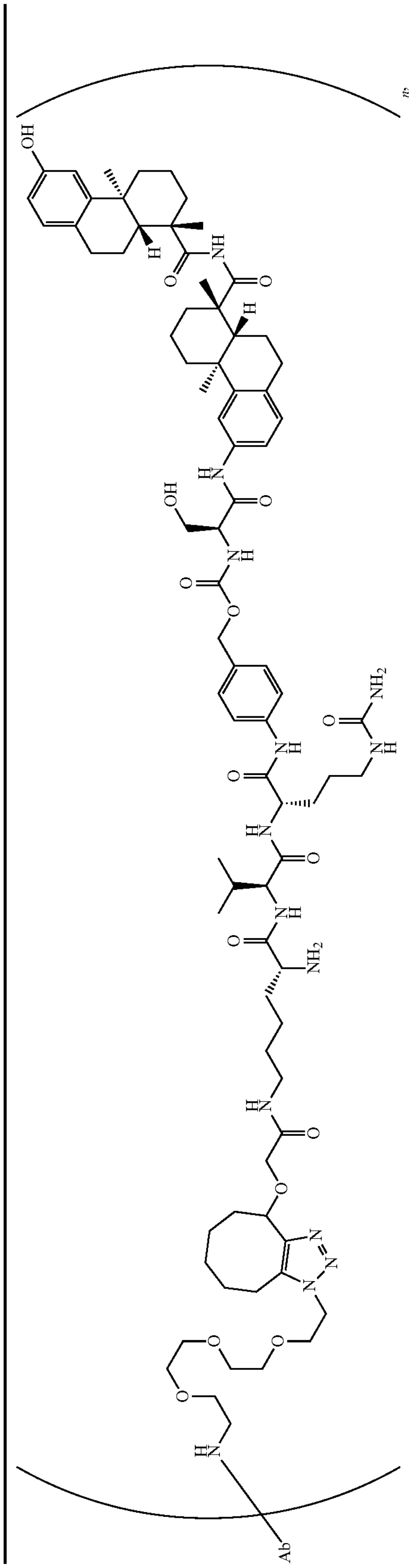
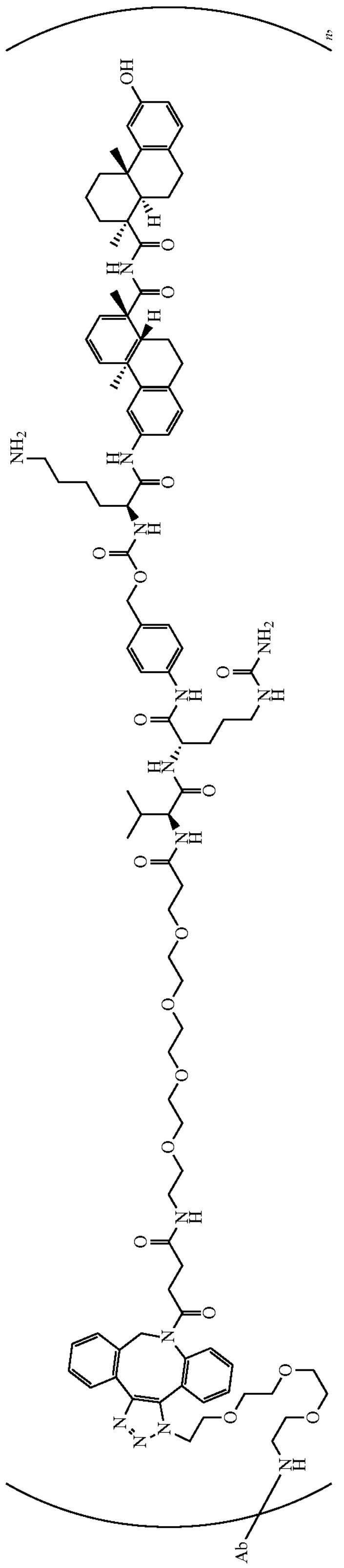

-continued
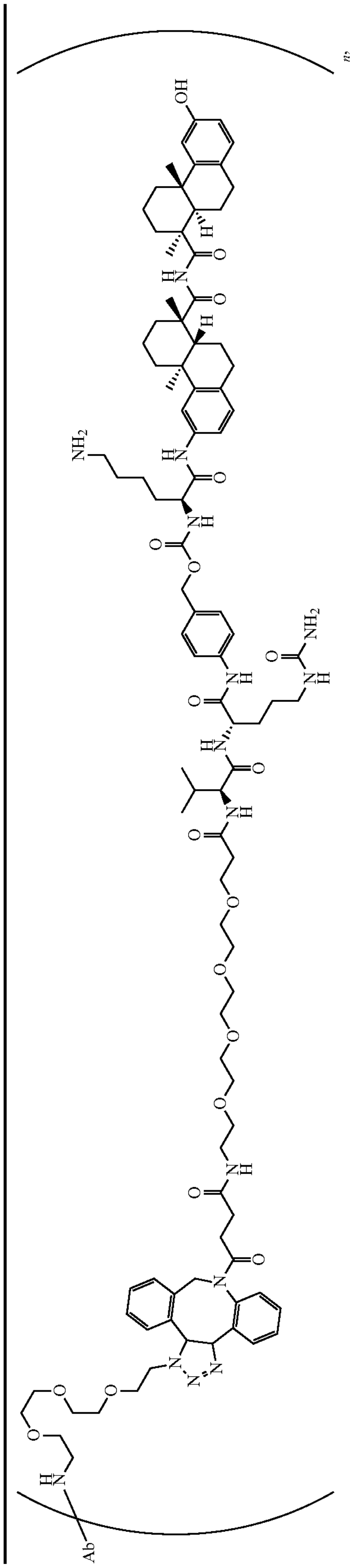
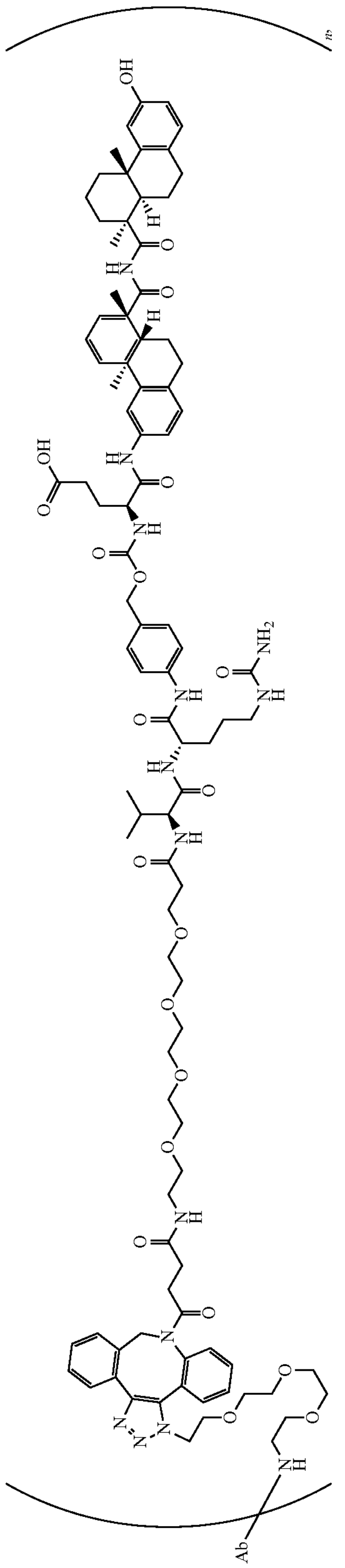
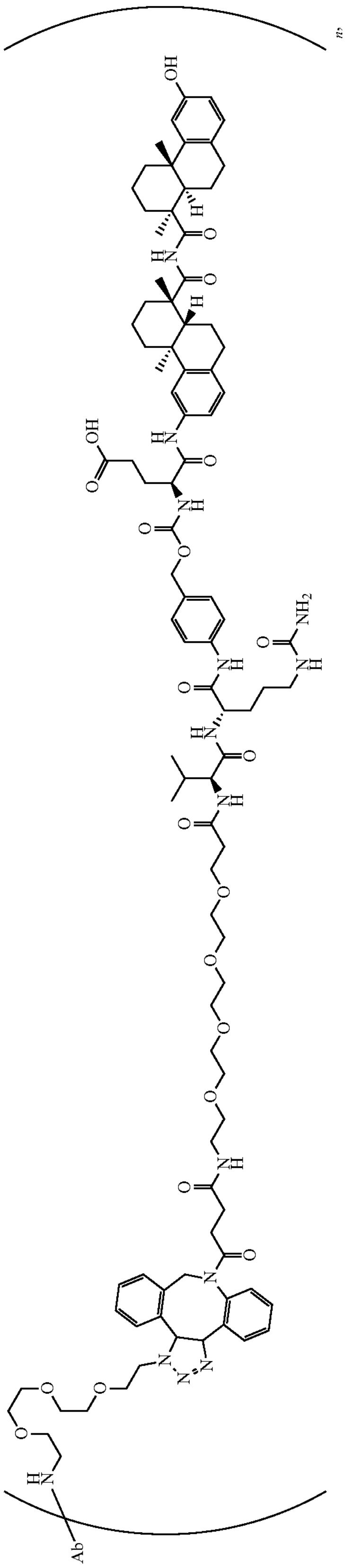

-continued
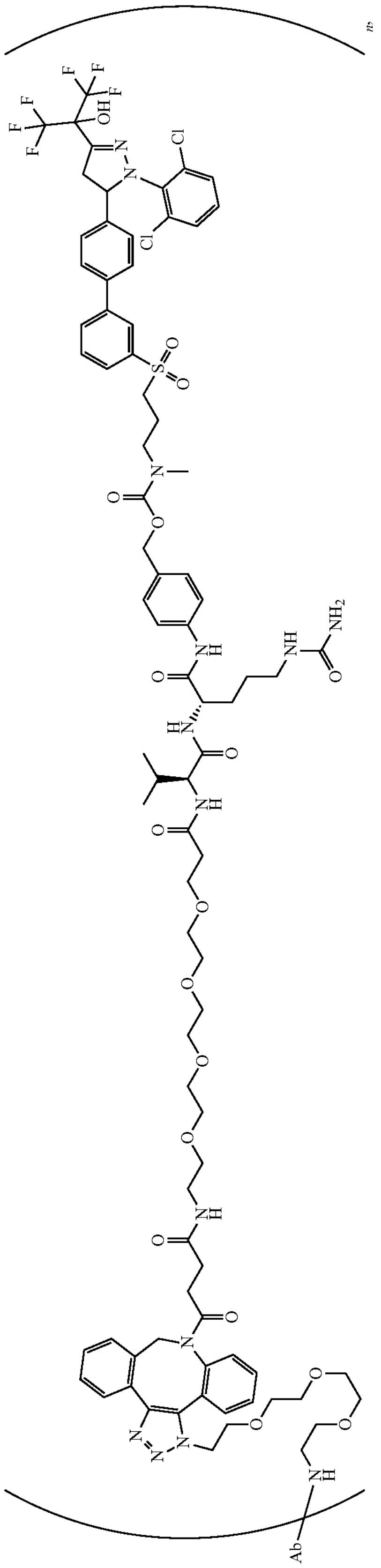
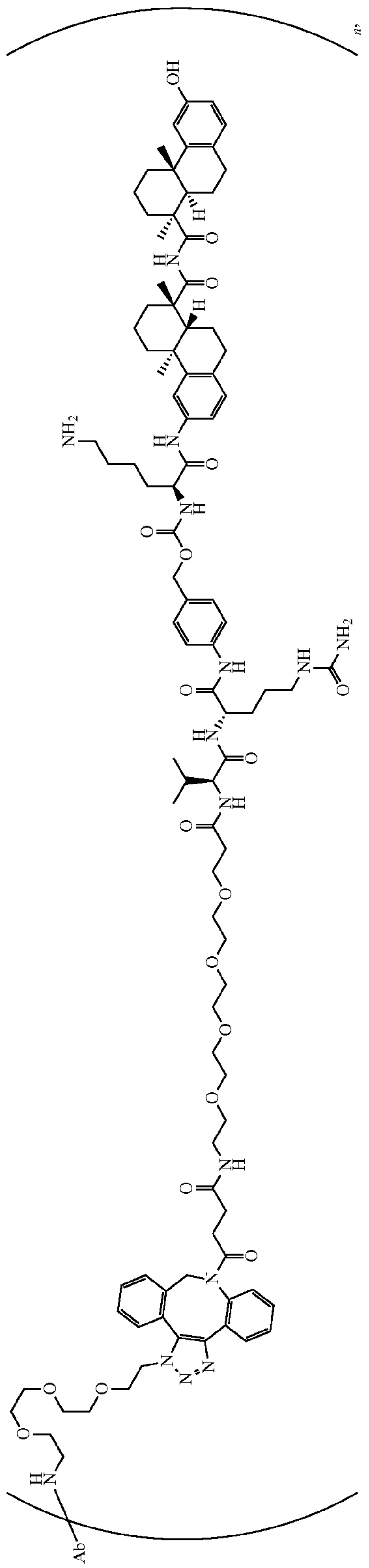

-continued
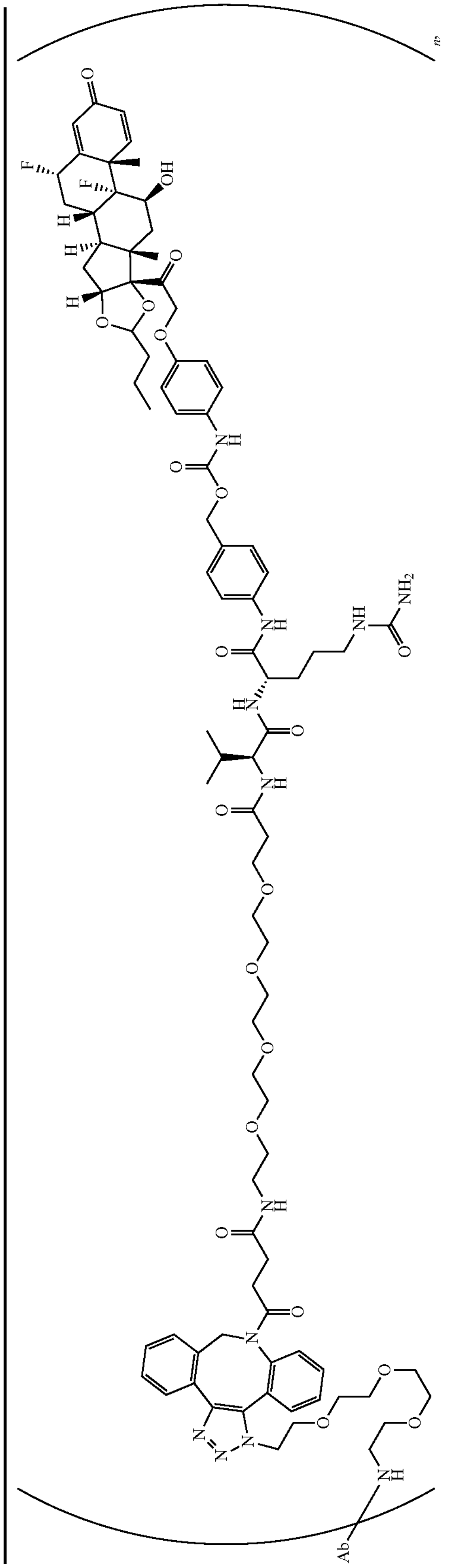
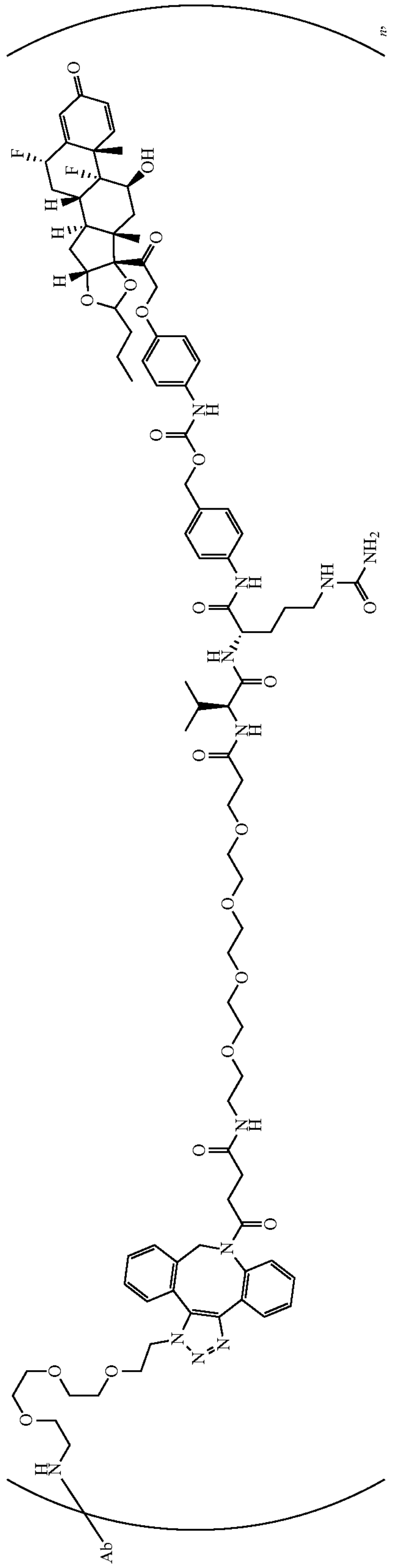

-continued
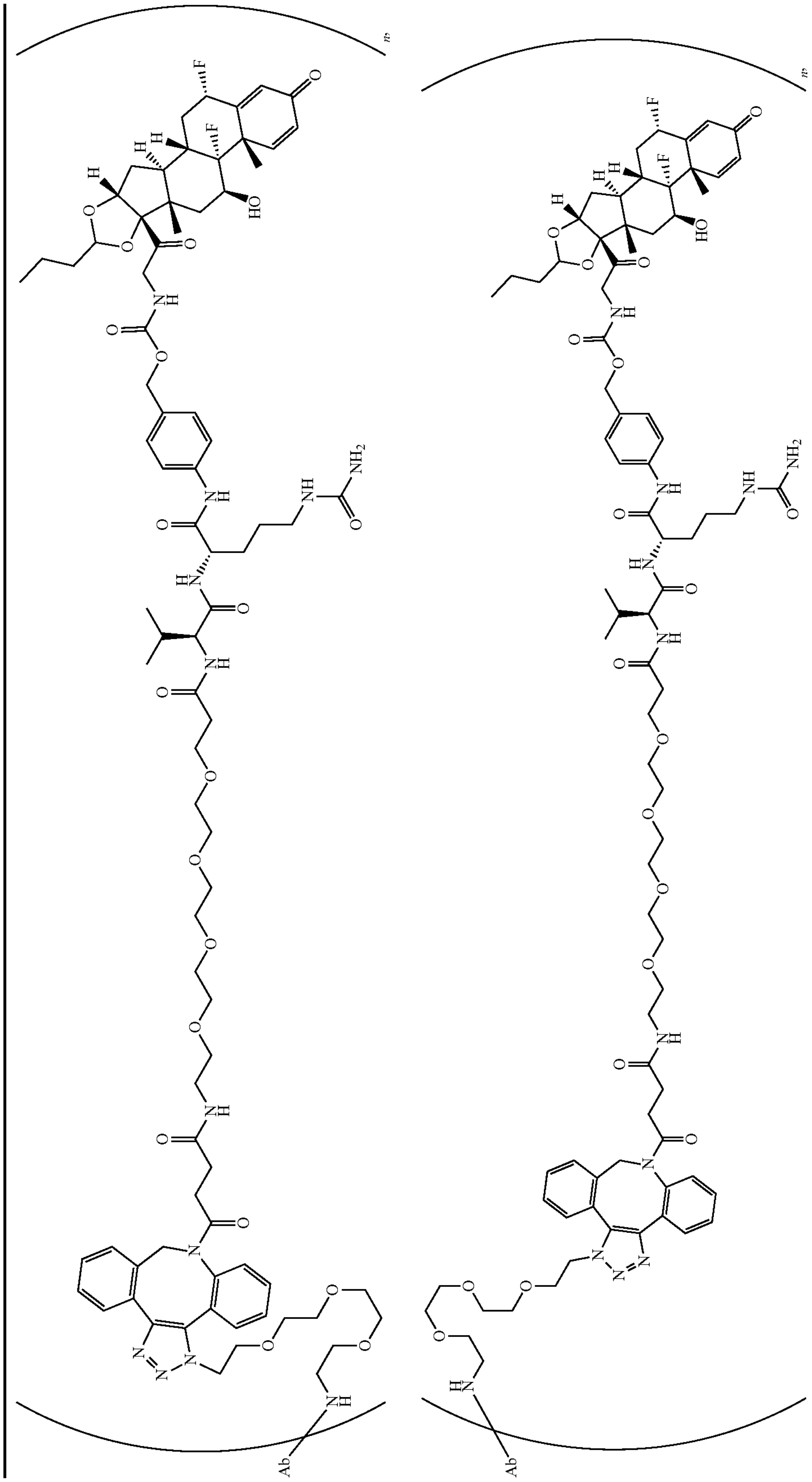

-continued
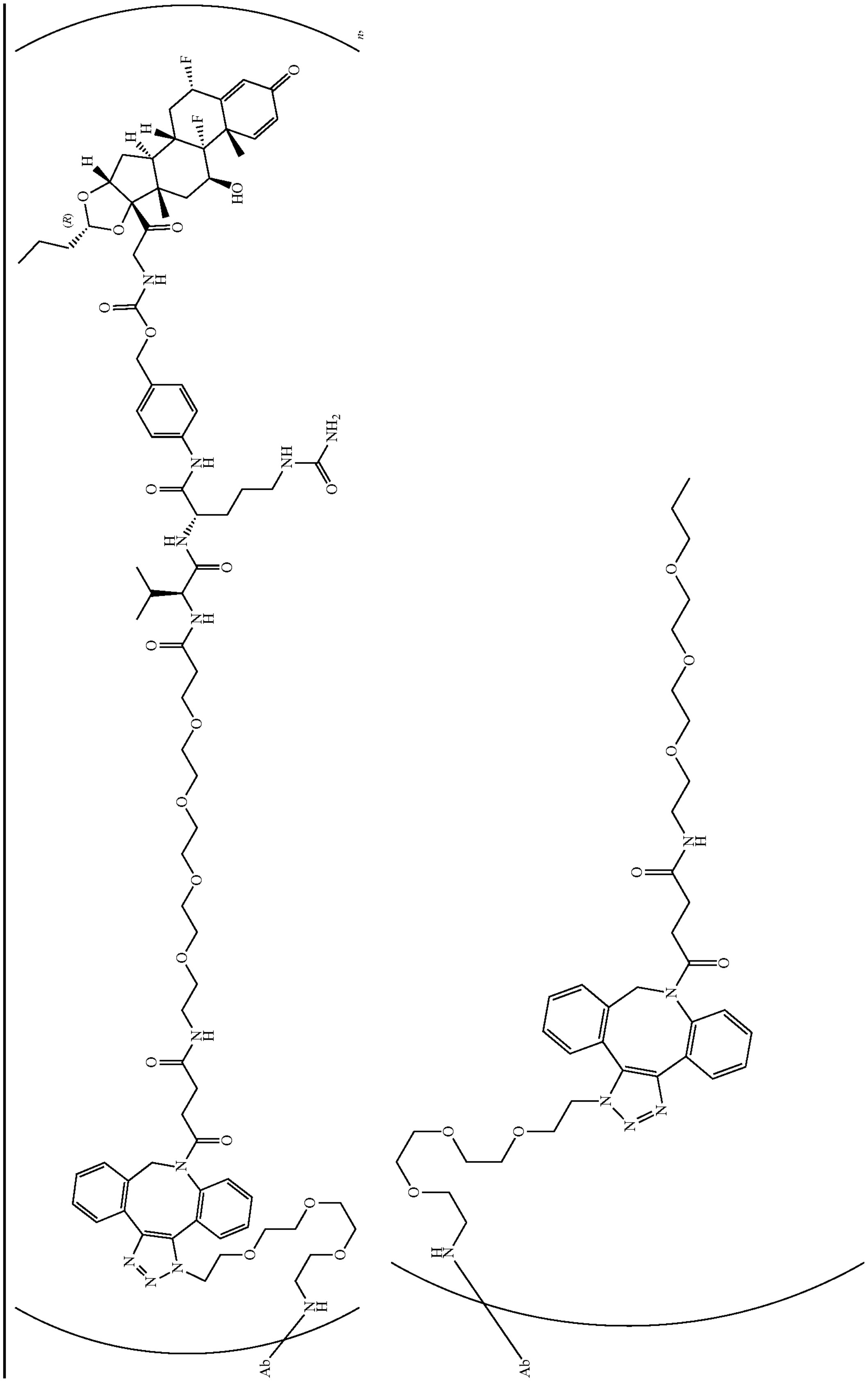

-continued
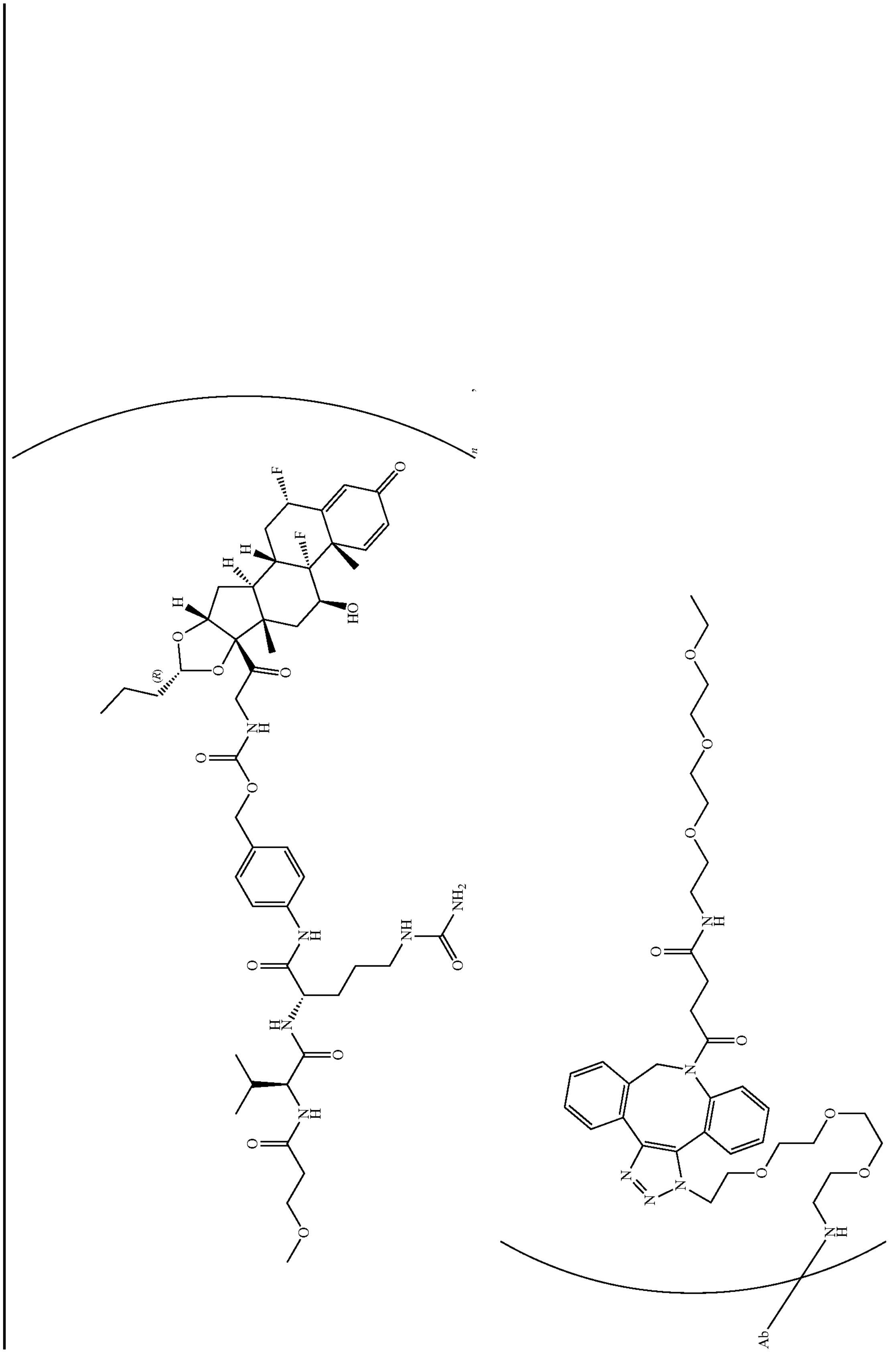

-continued
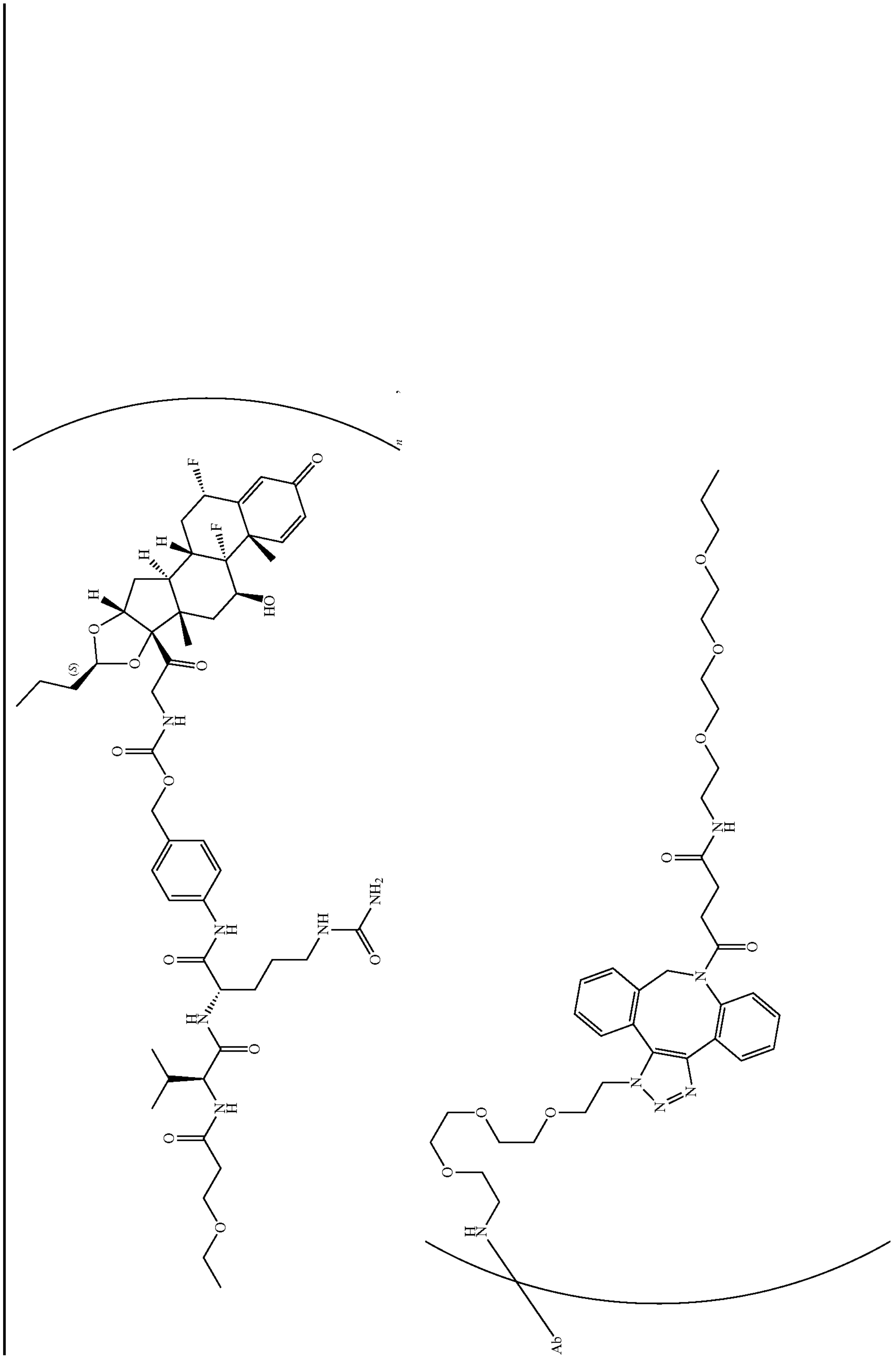

-continued
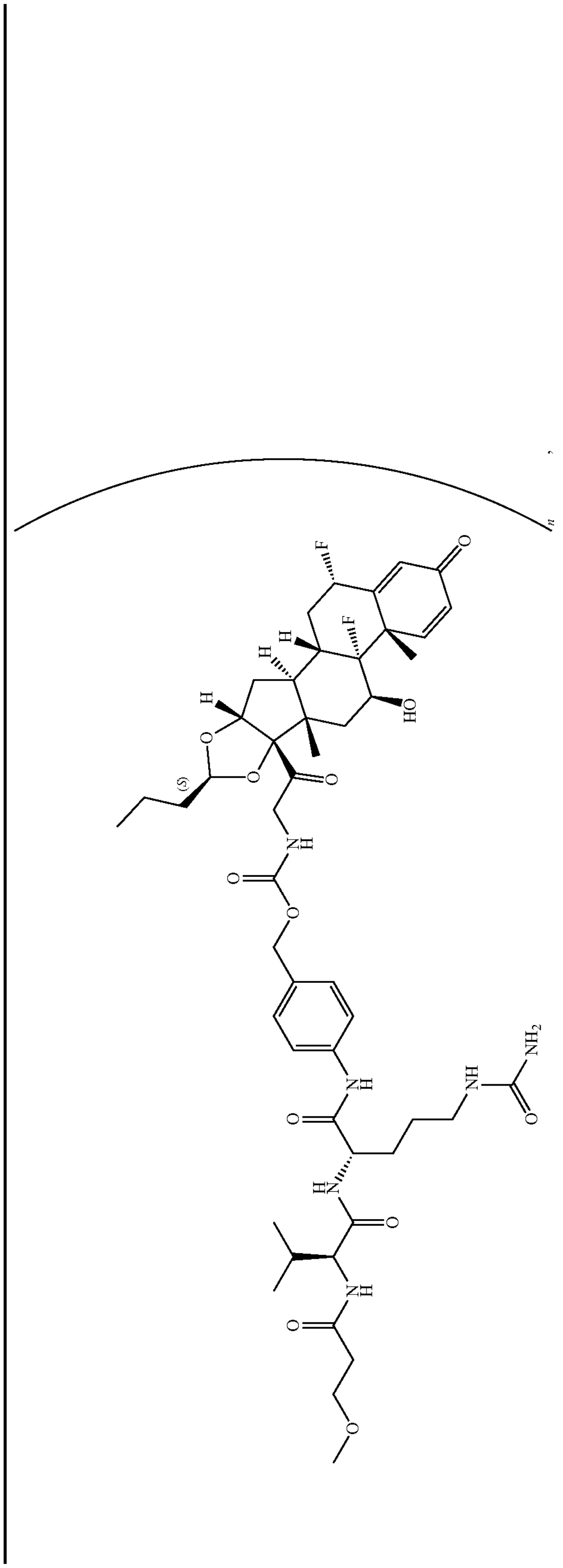

-continued
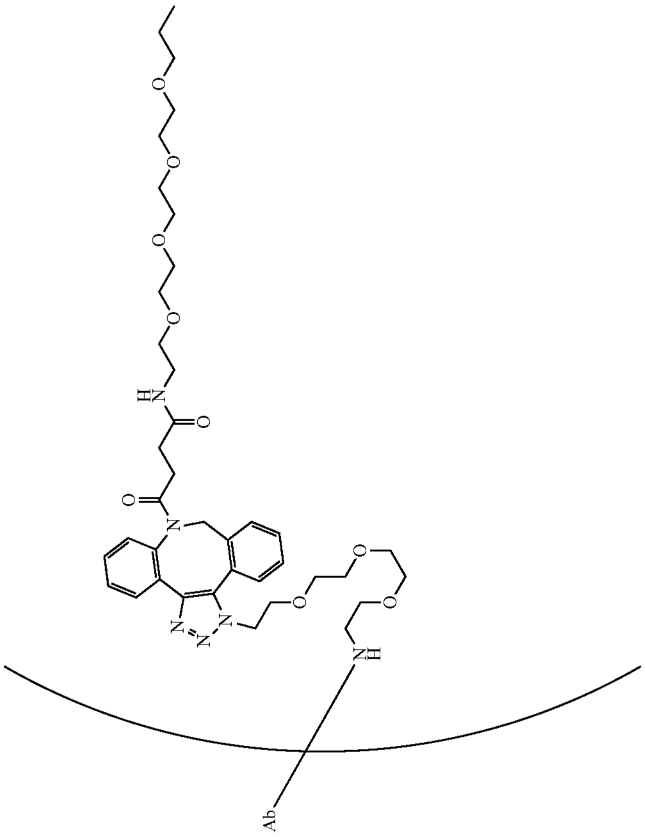

-continued
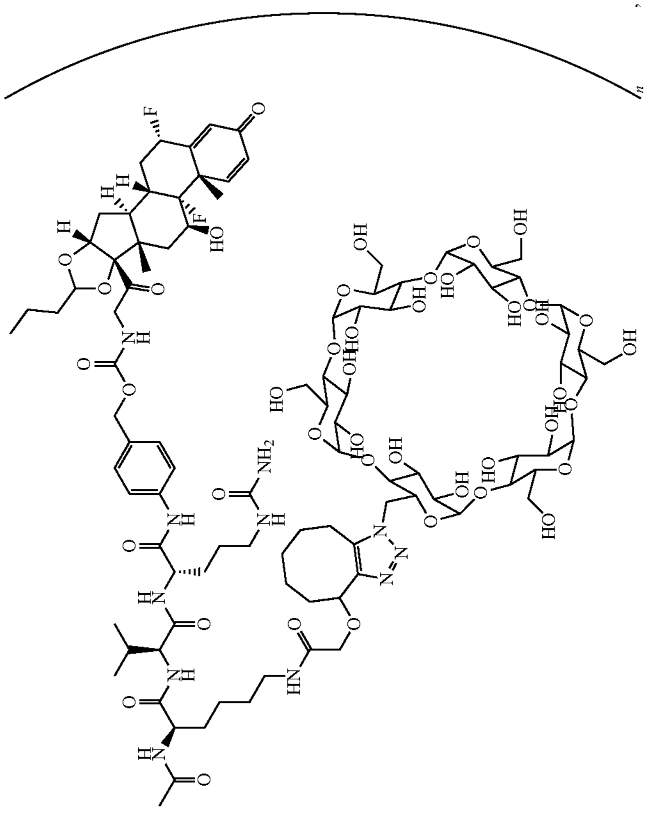

-continued
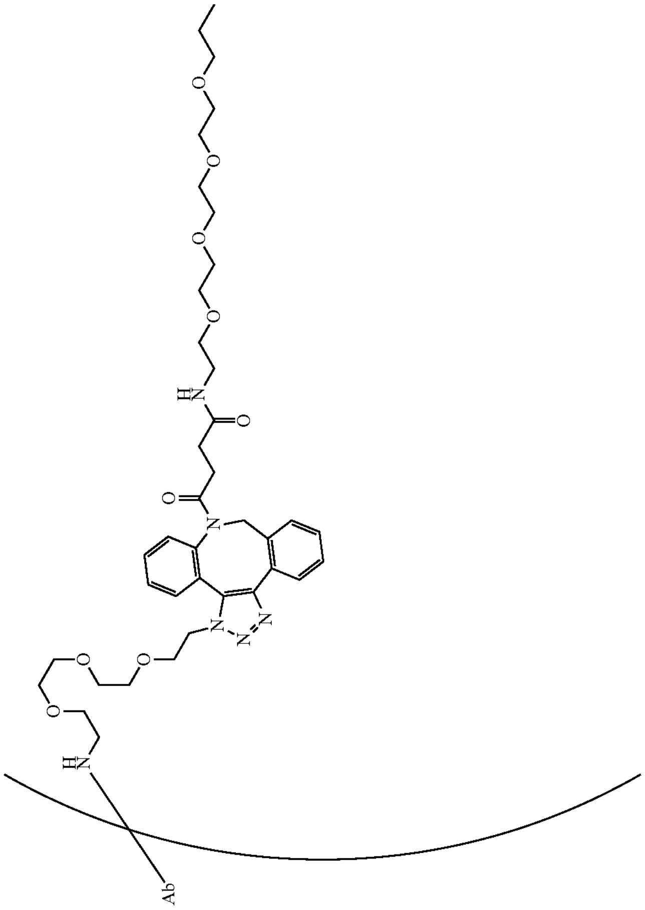

-continued
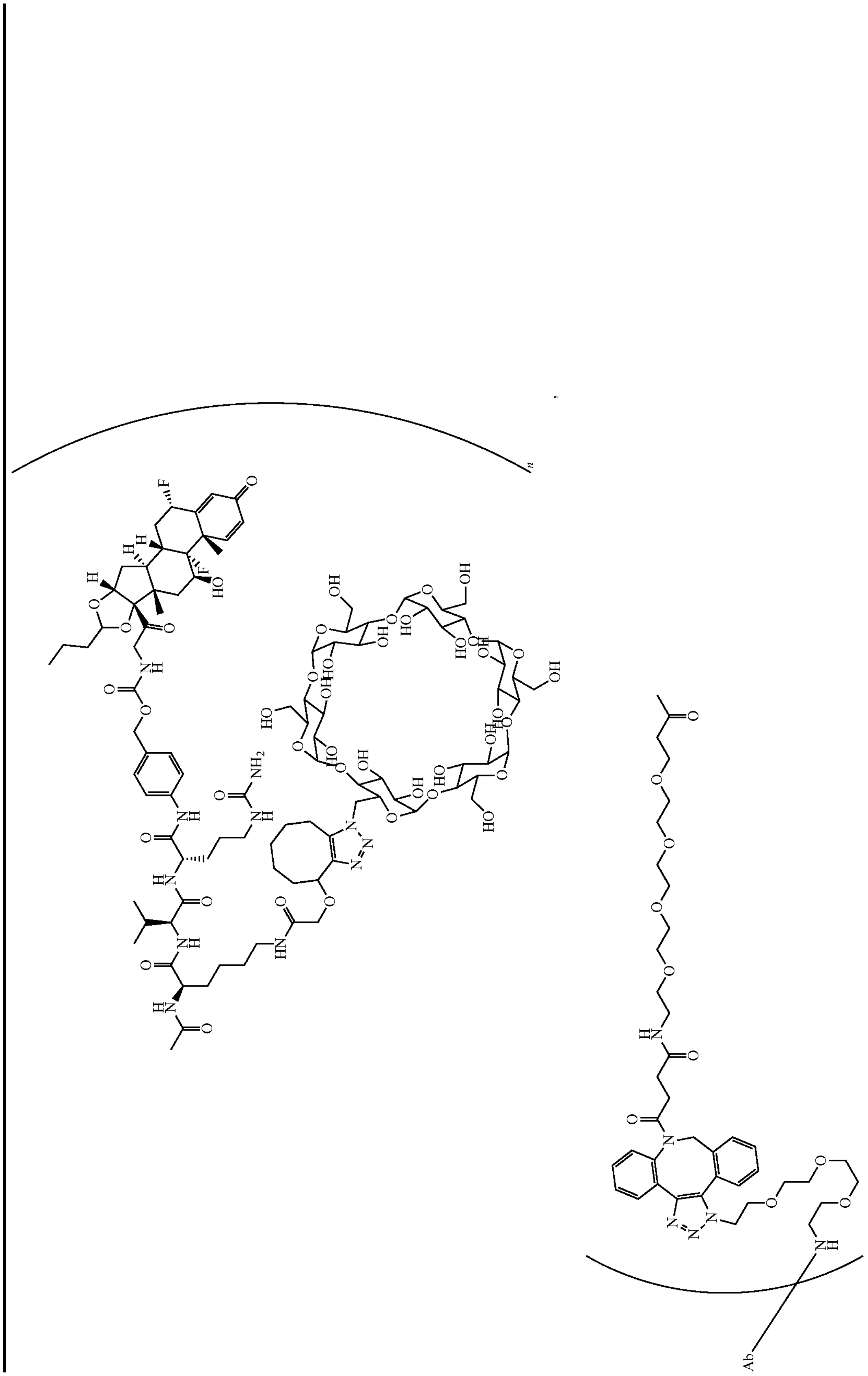

-continued
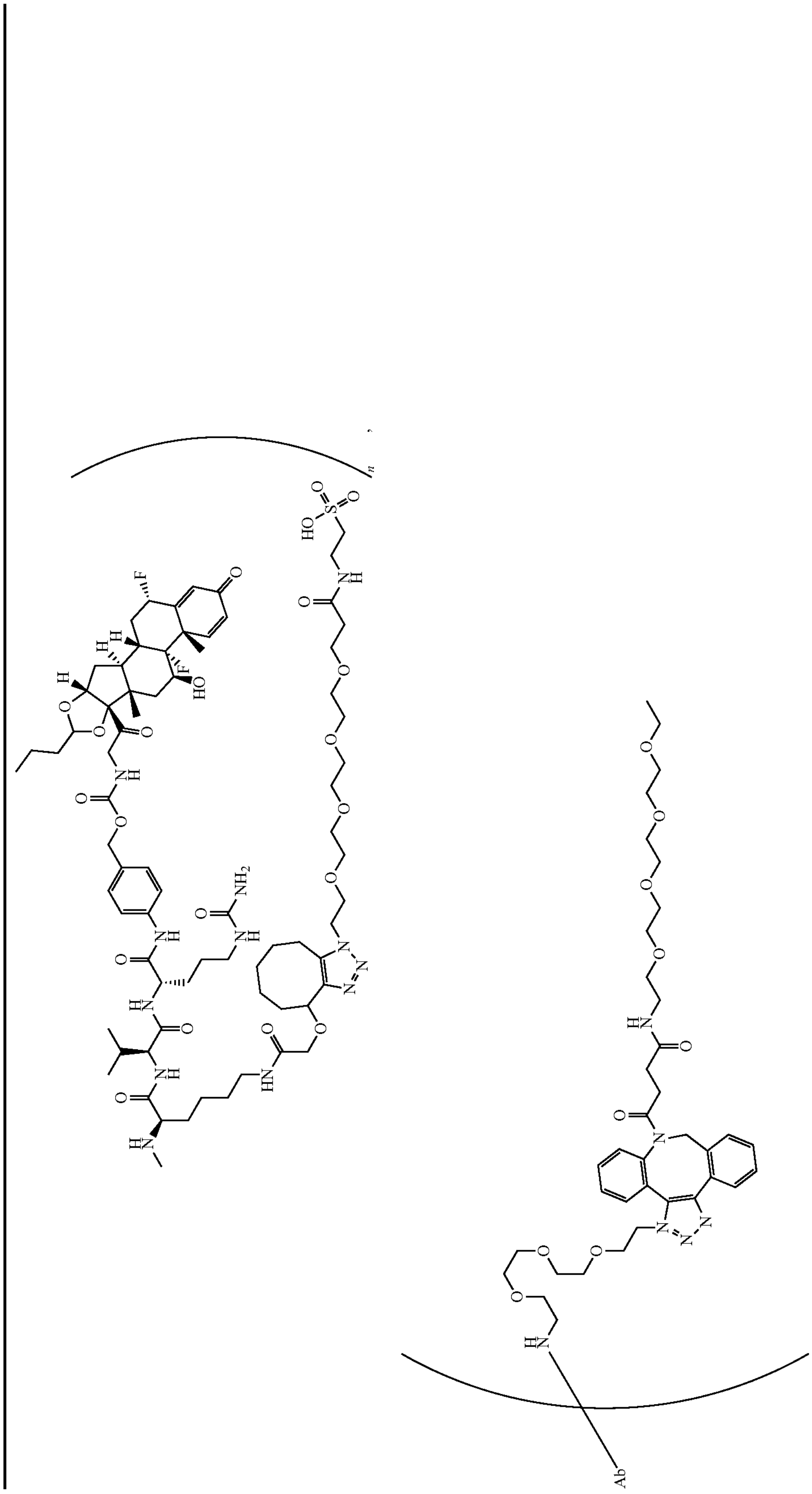

-continued
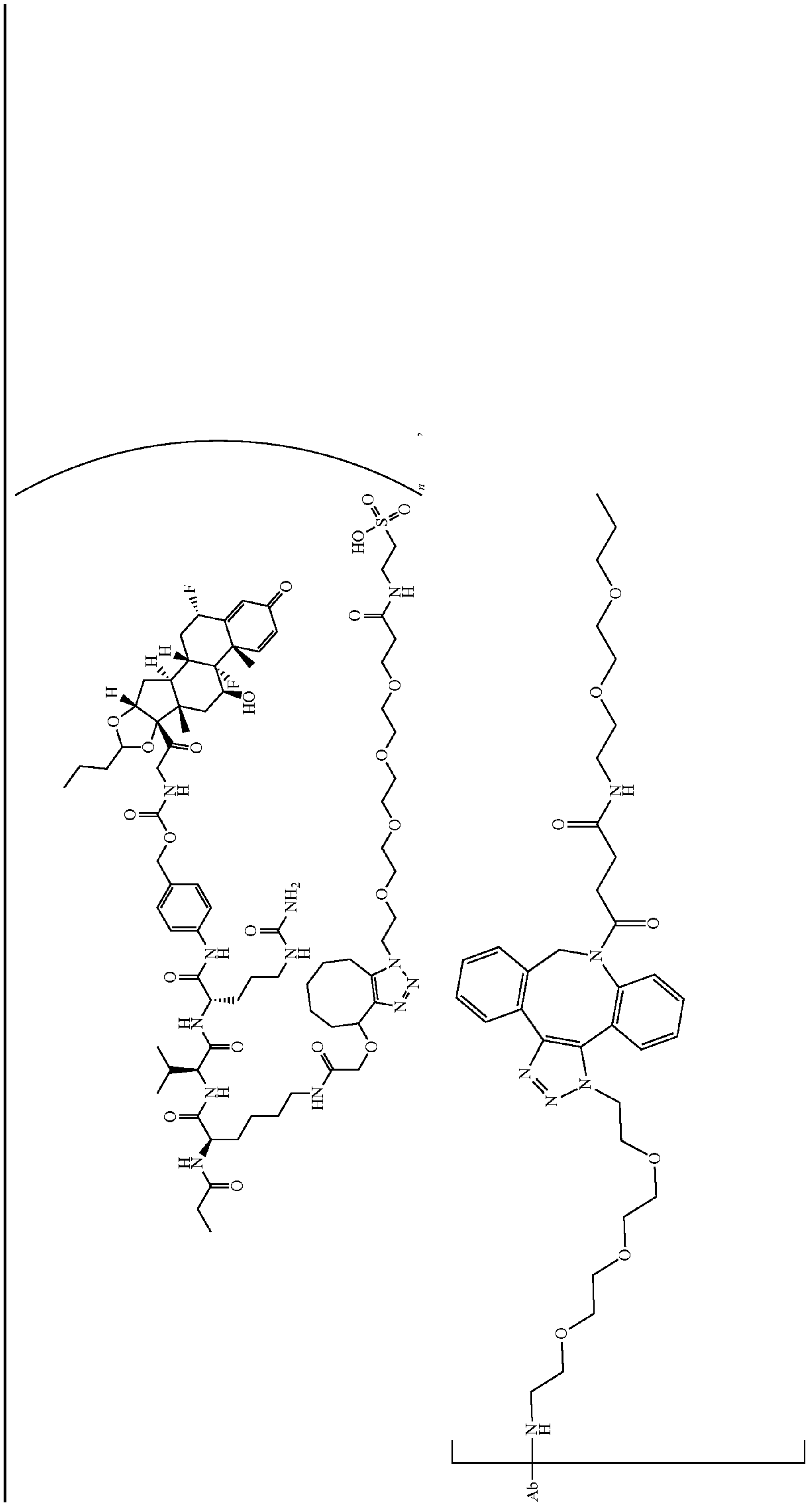

-continued
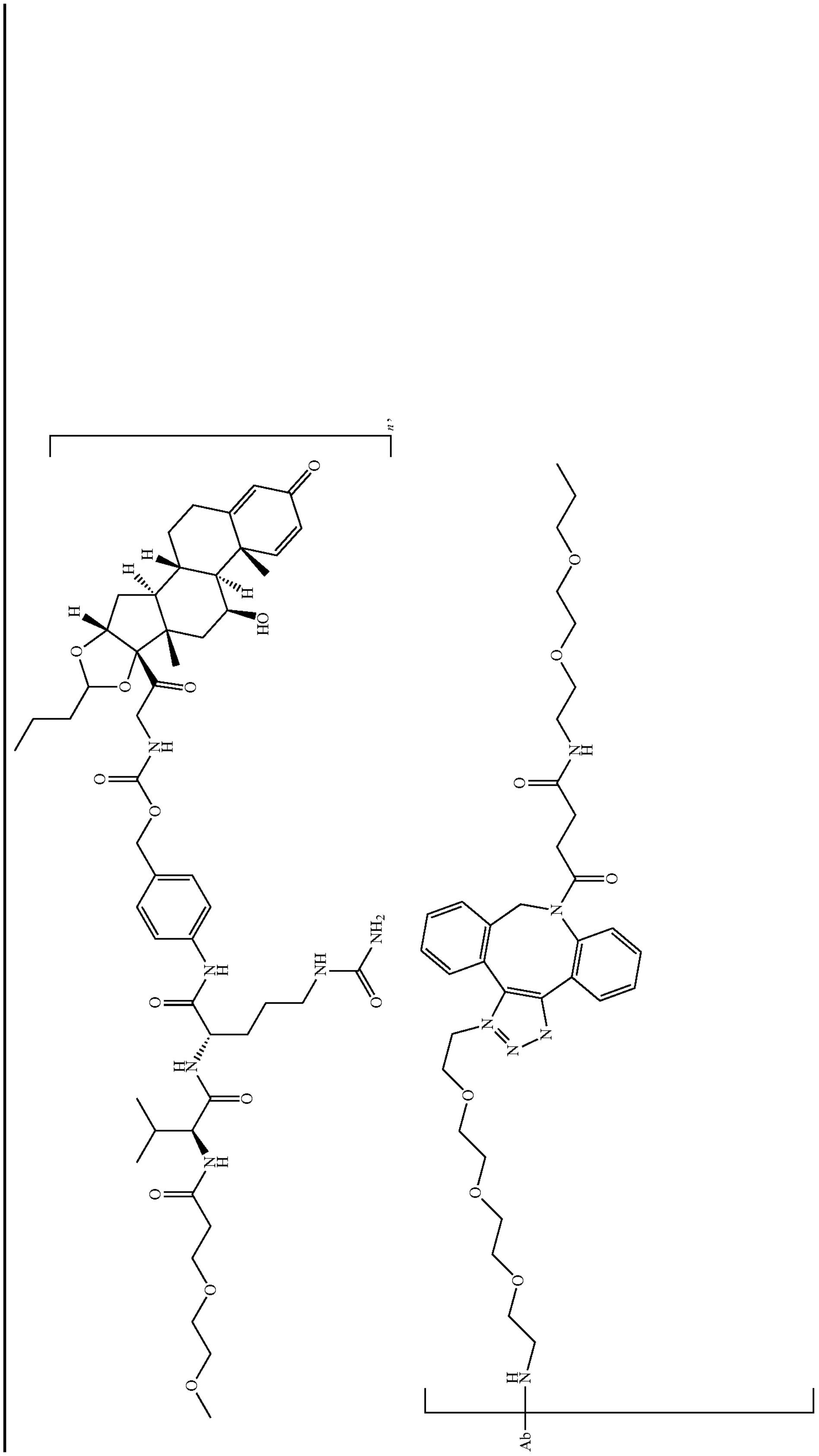

-continued
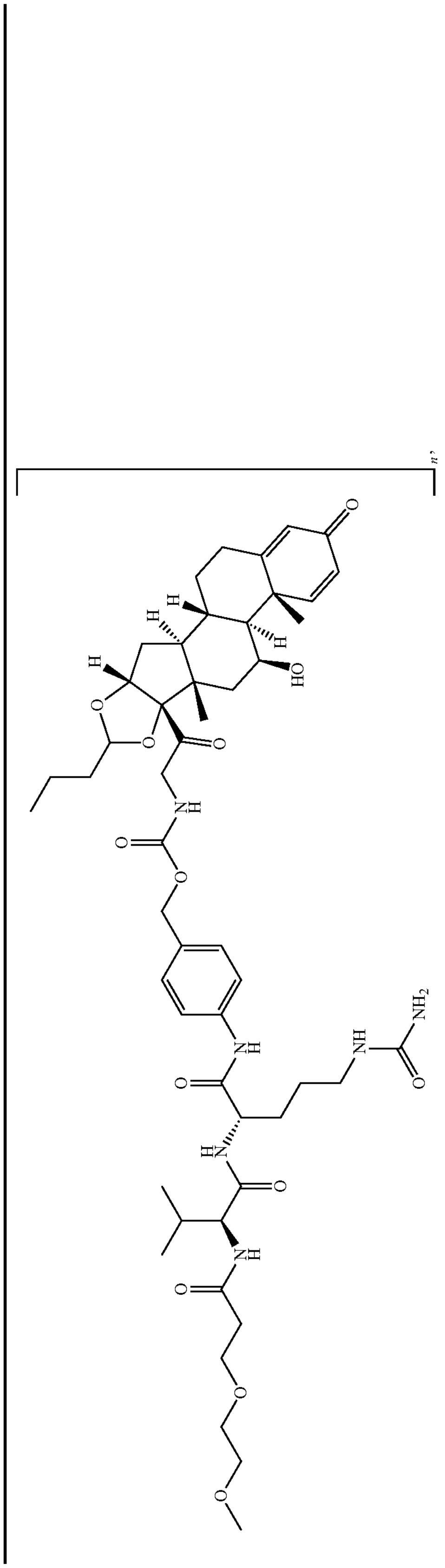
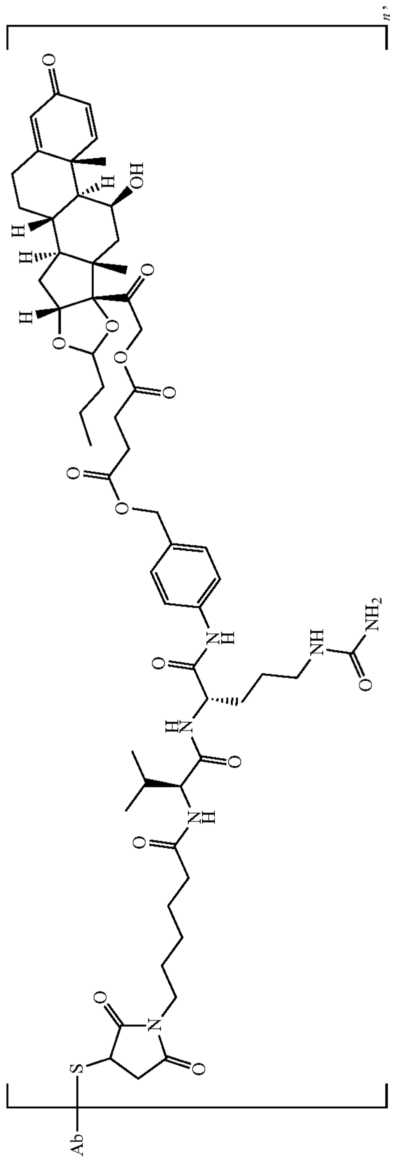

-continued
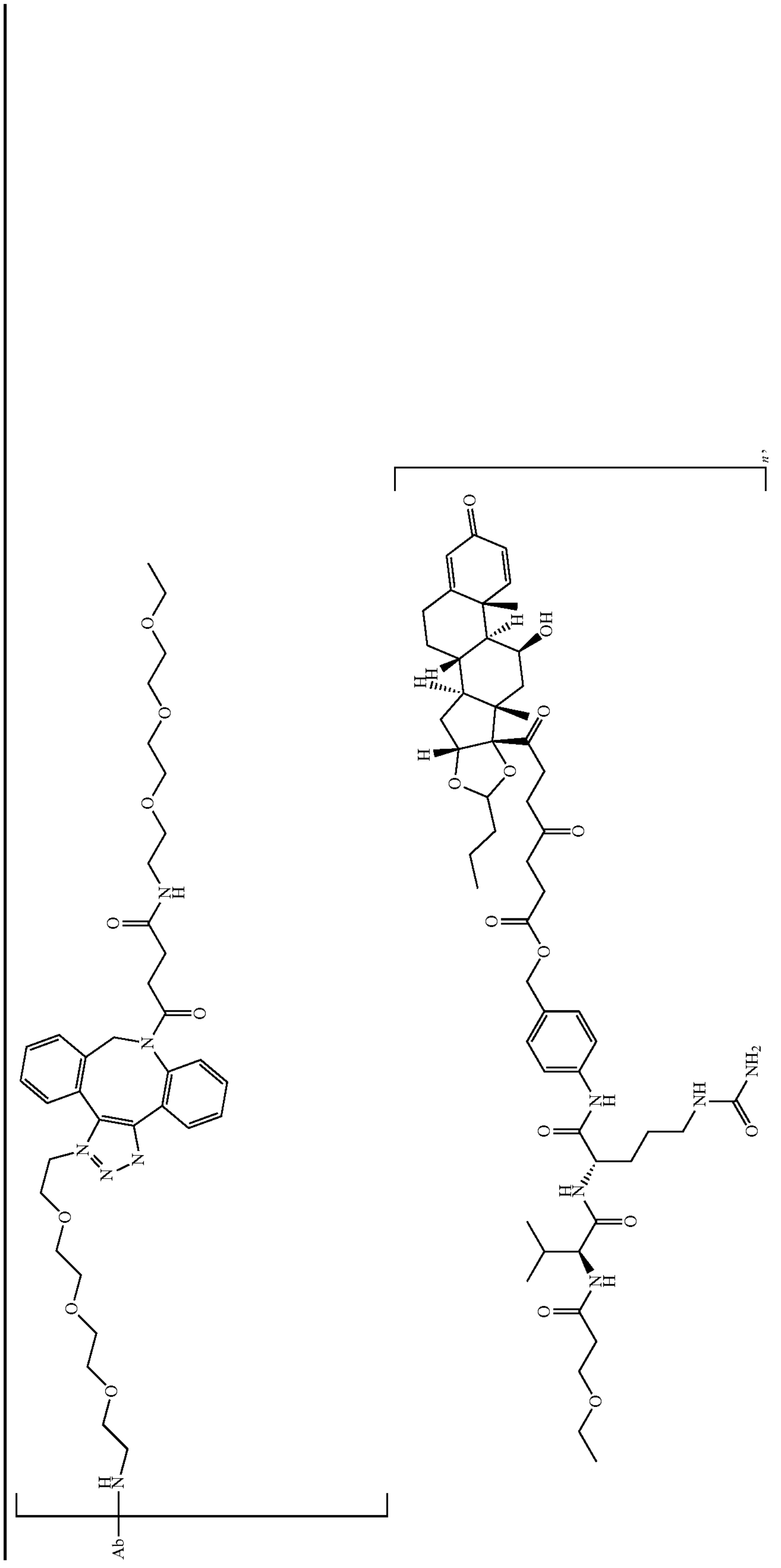

-continued
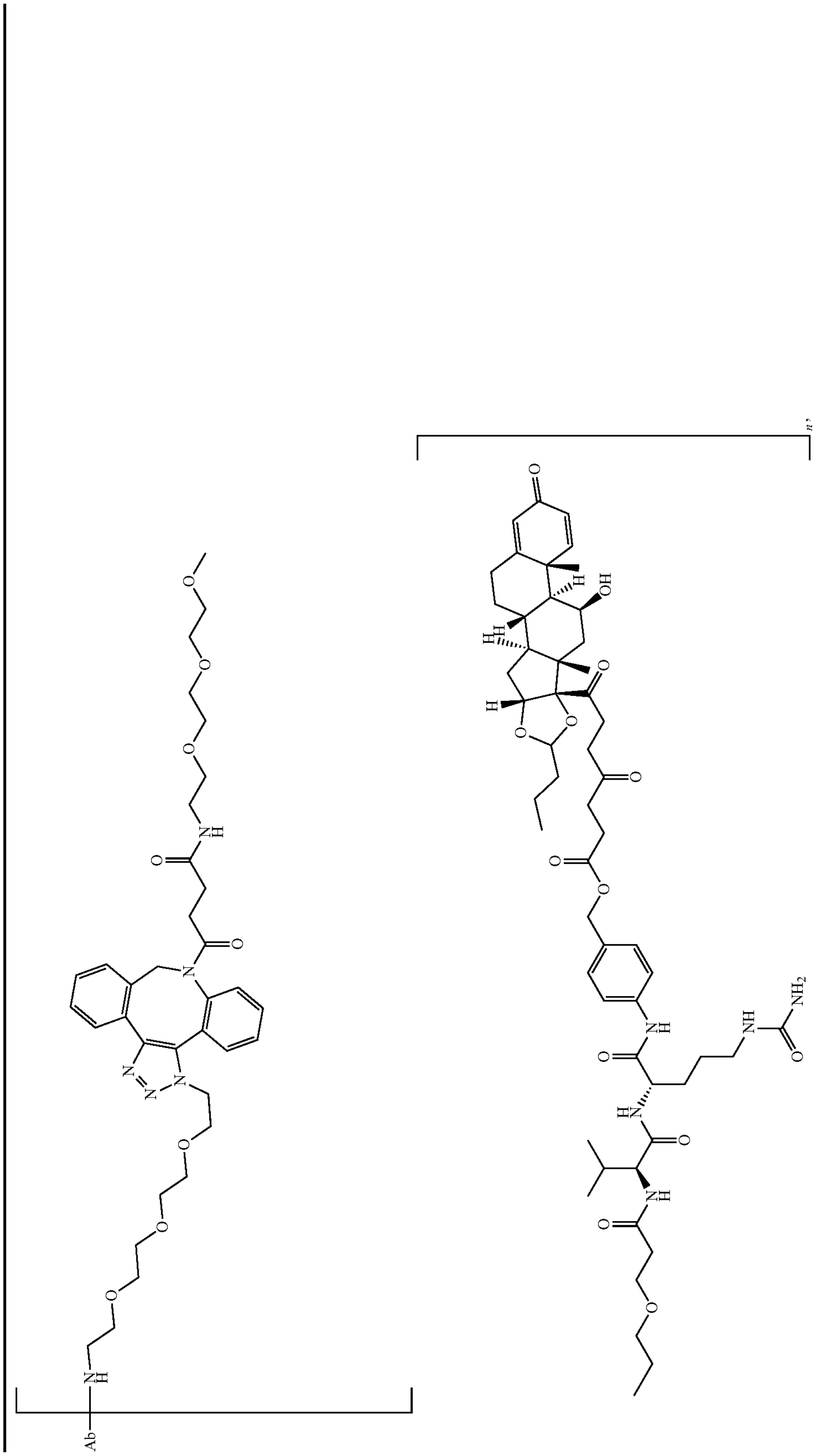

-continued
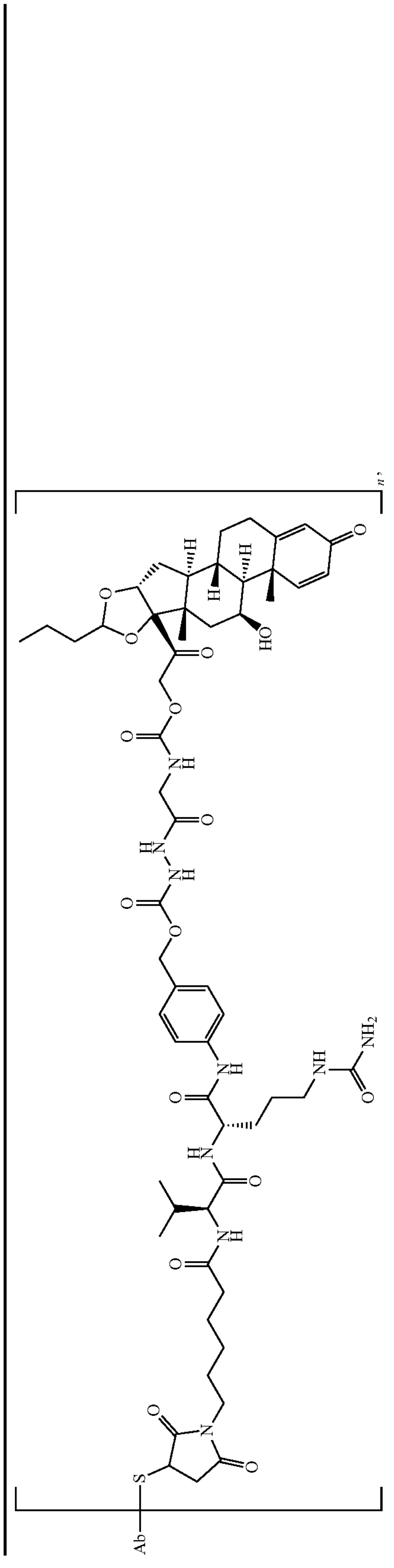
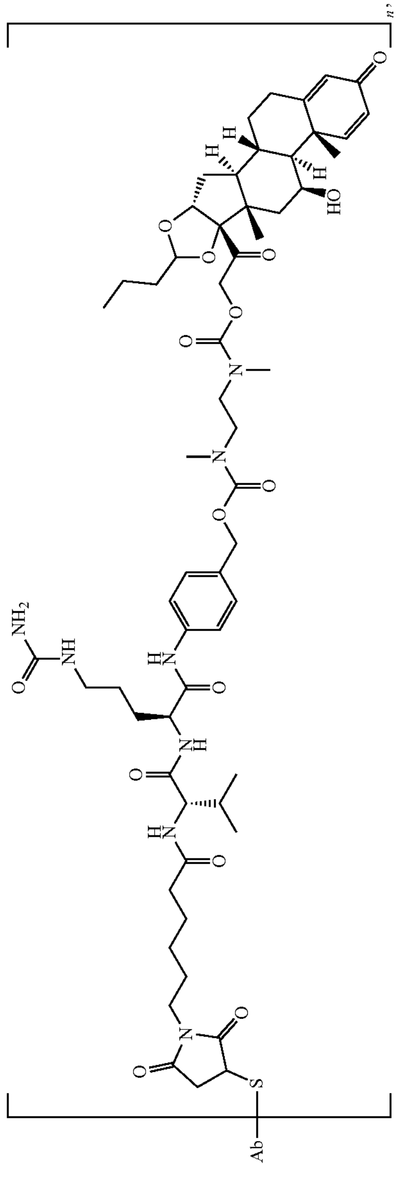

-continued
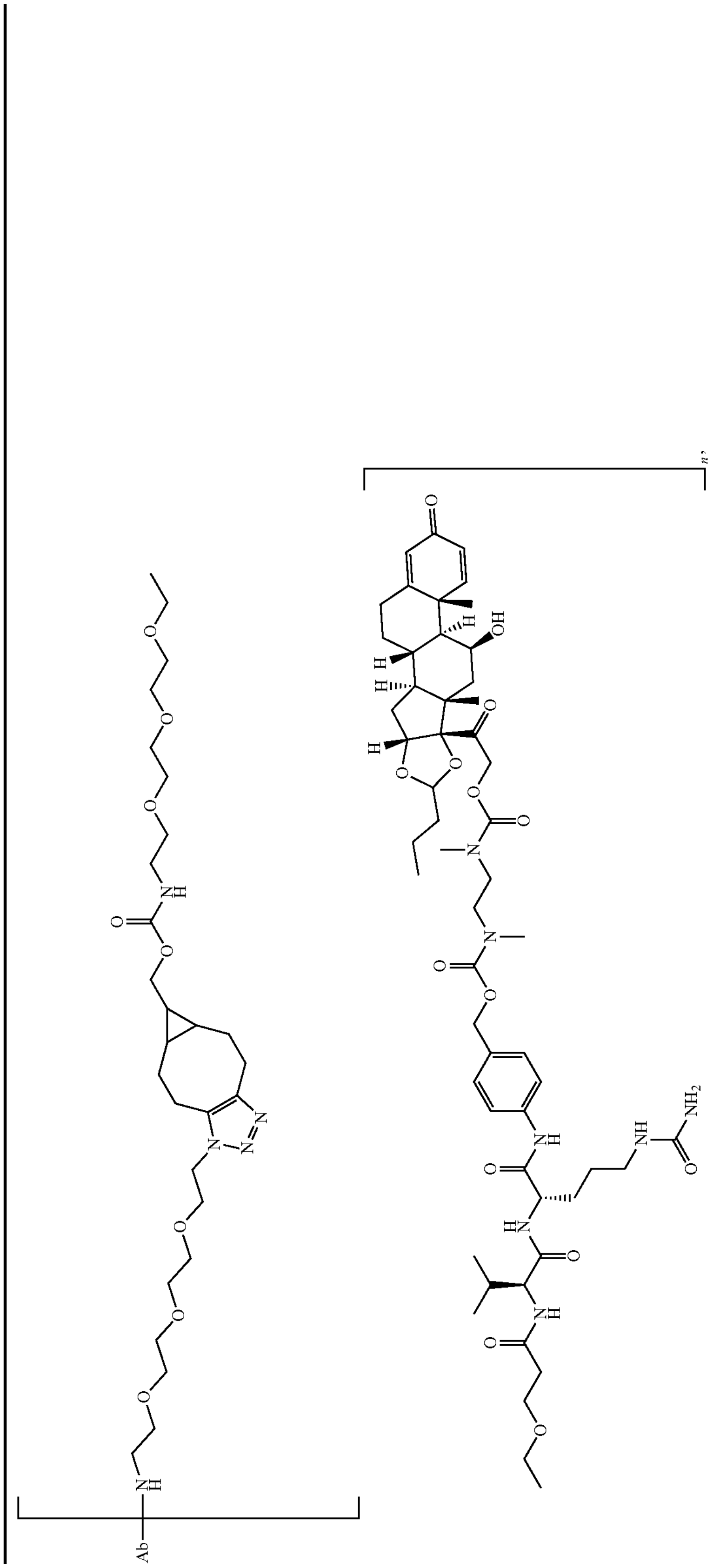

-continued
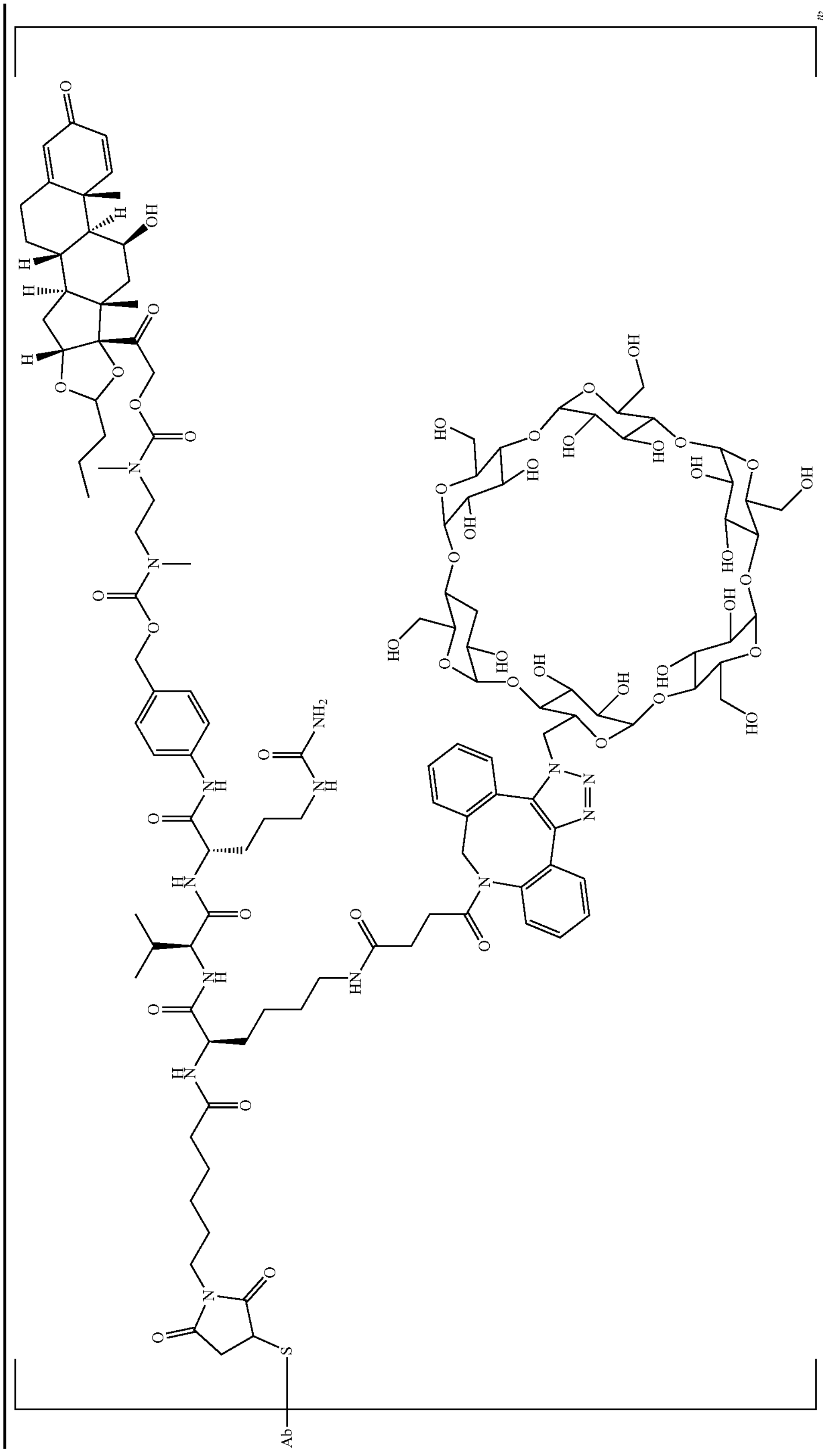

-continued
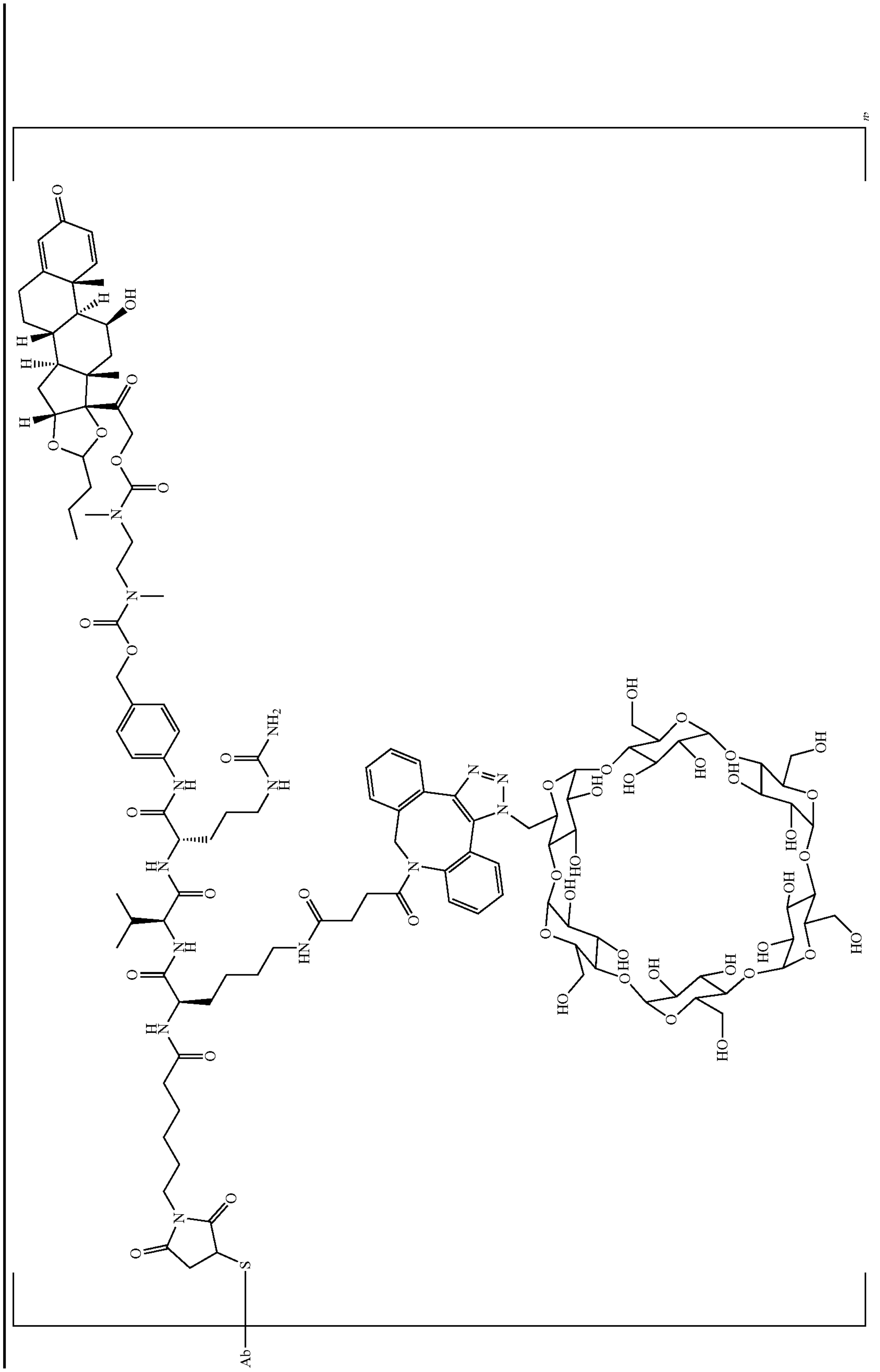

-continued
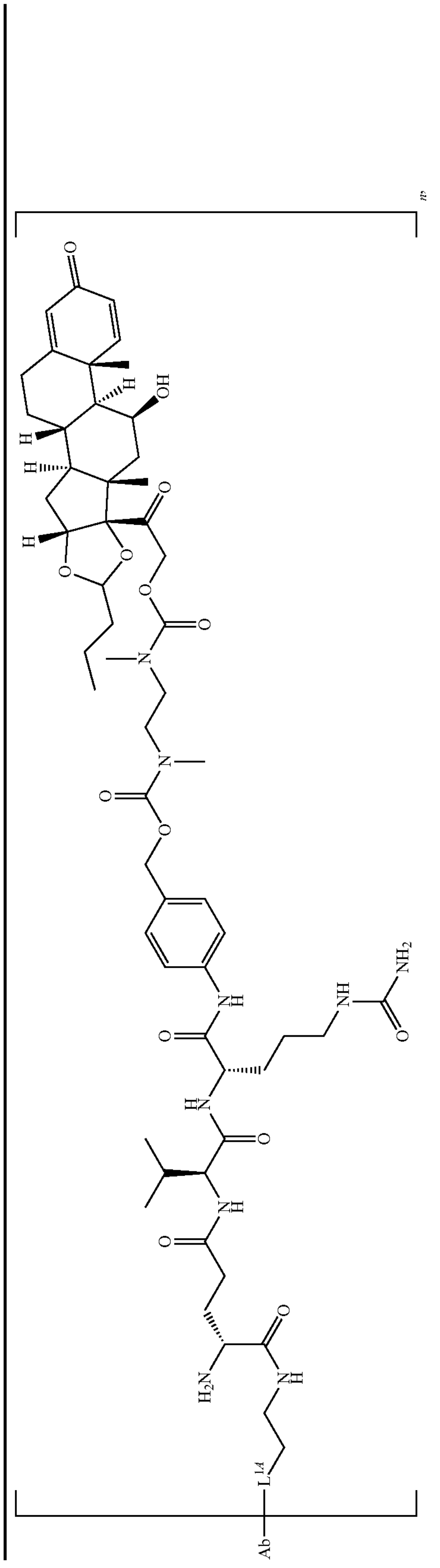
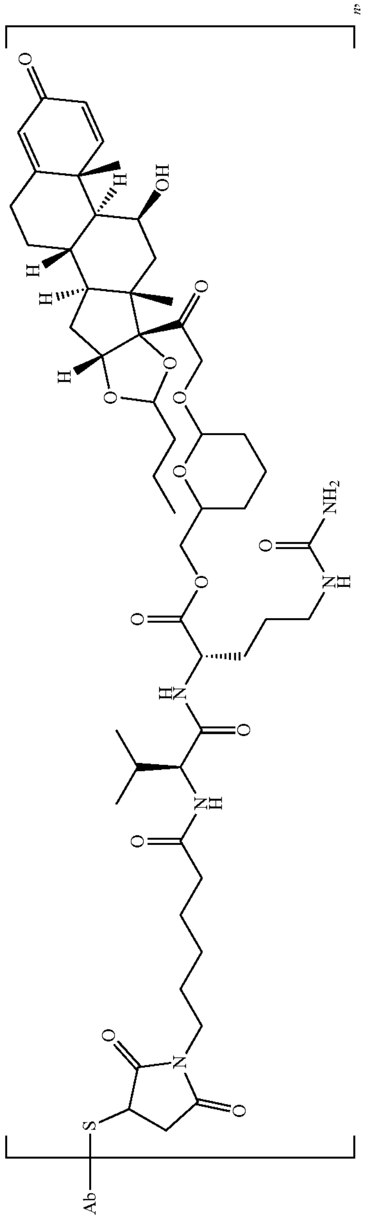

-continued
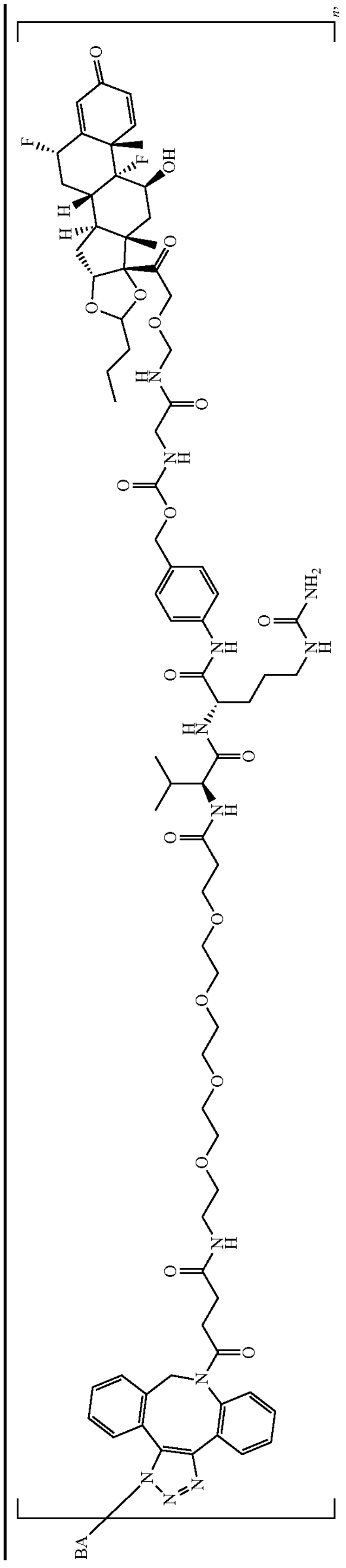
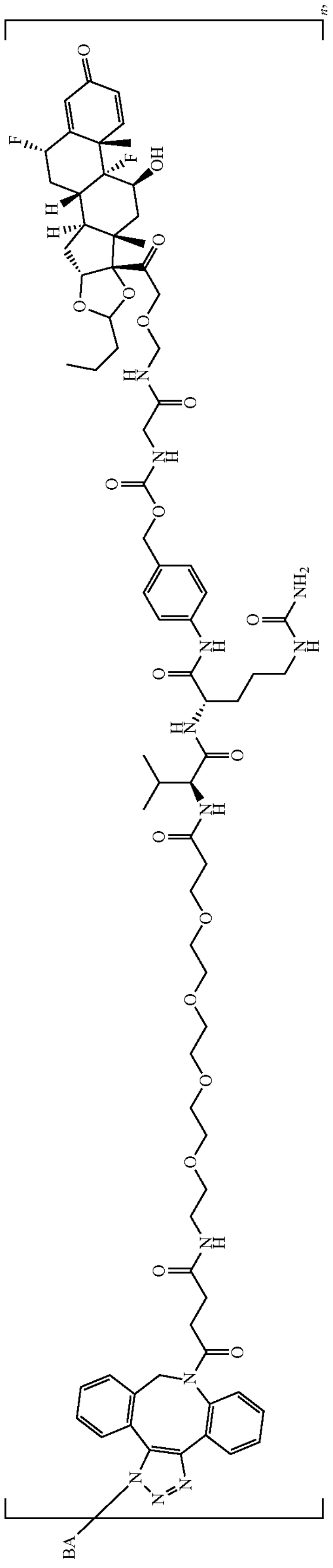
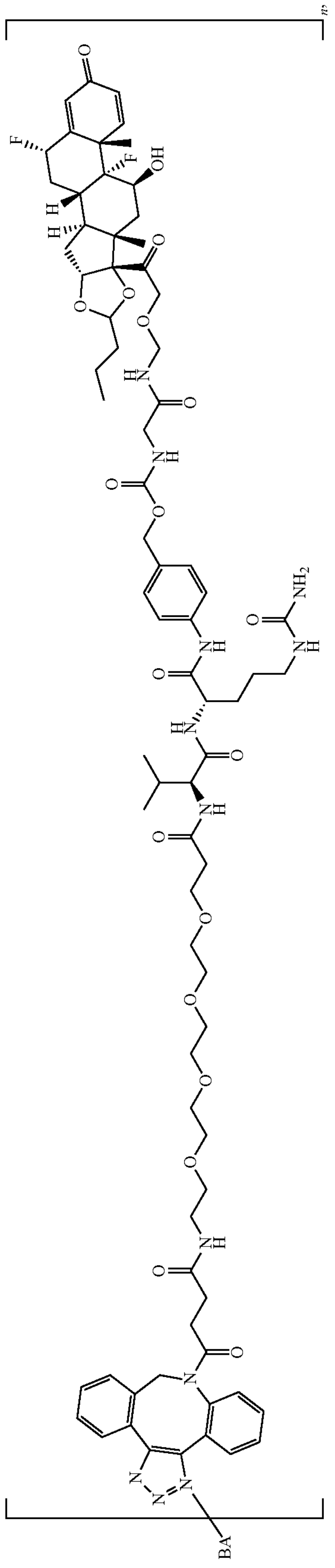

-continued
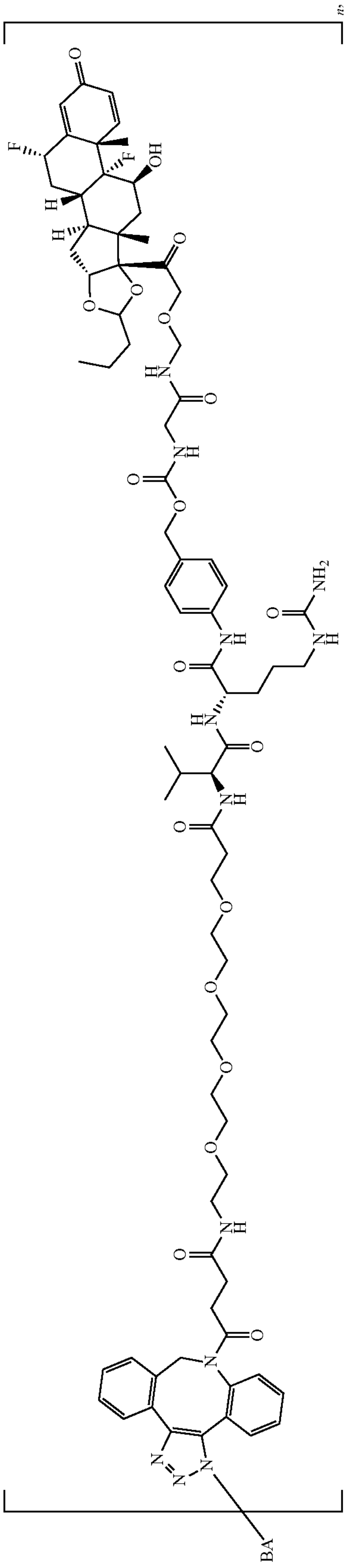
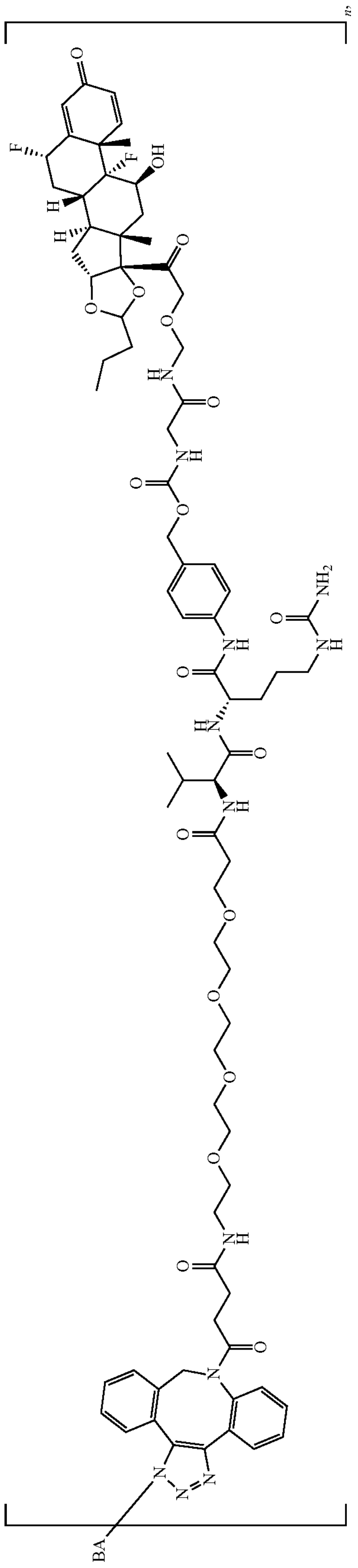

-continued
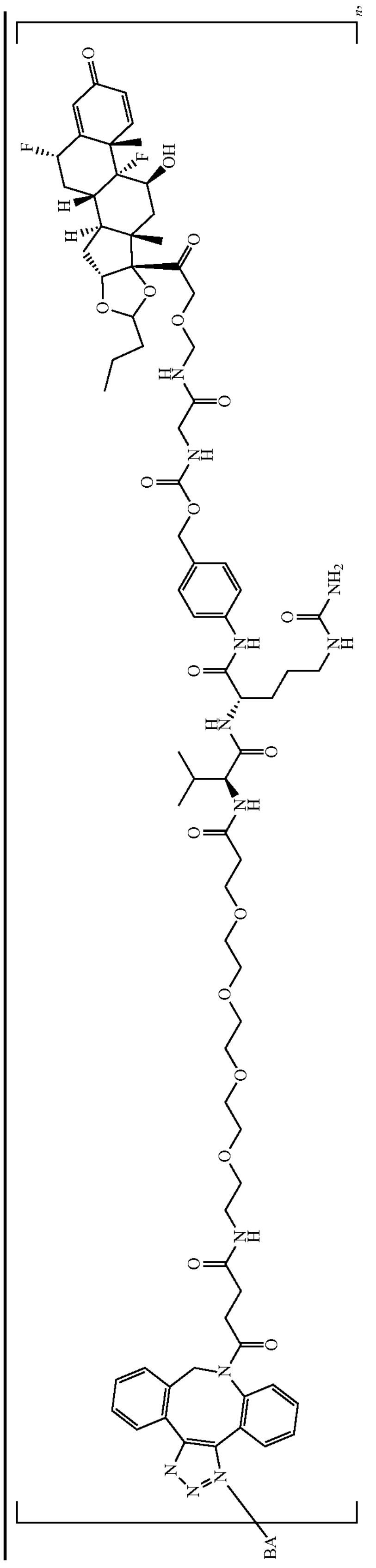
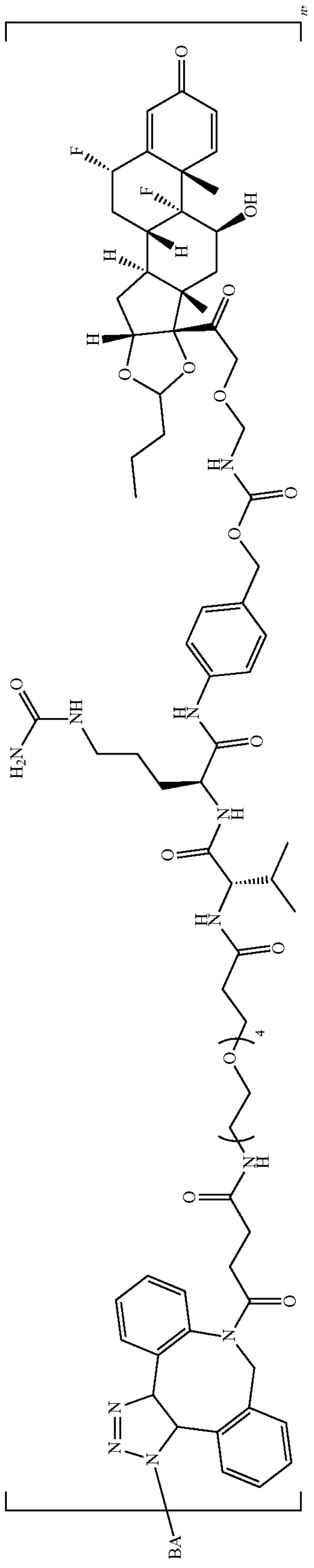
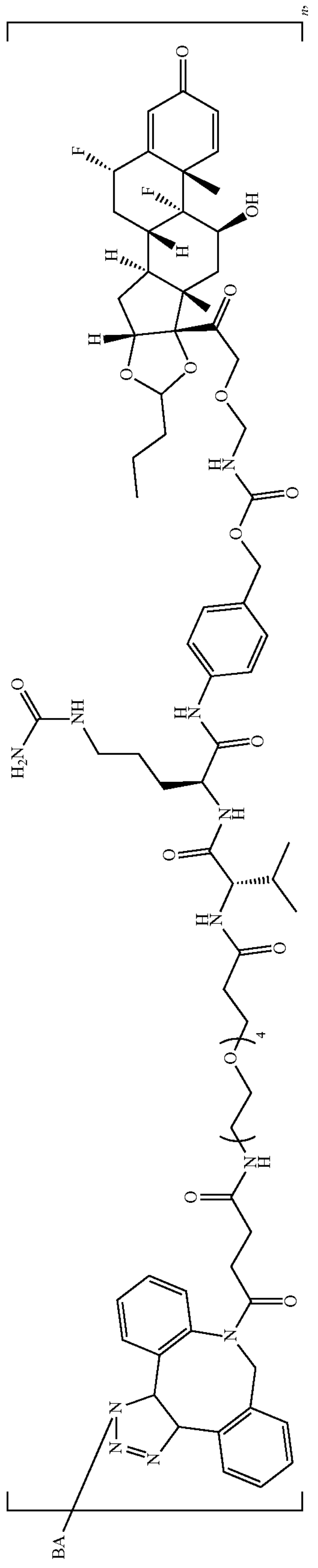

-continued
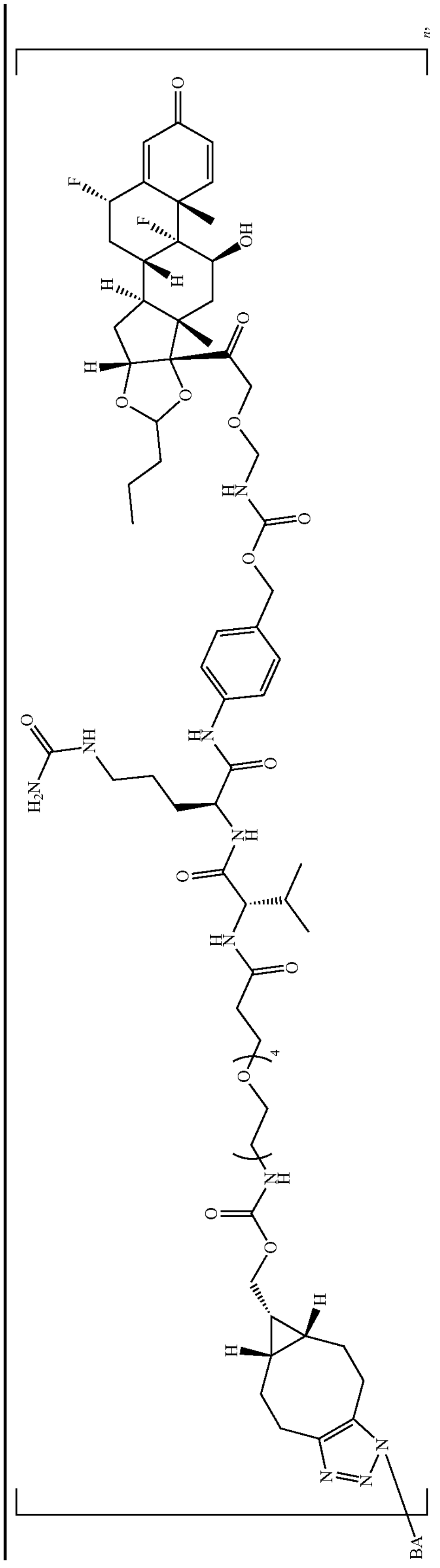
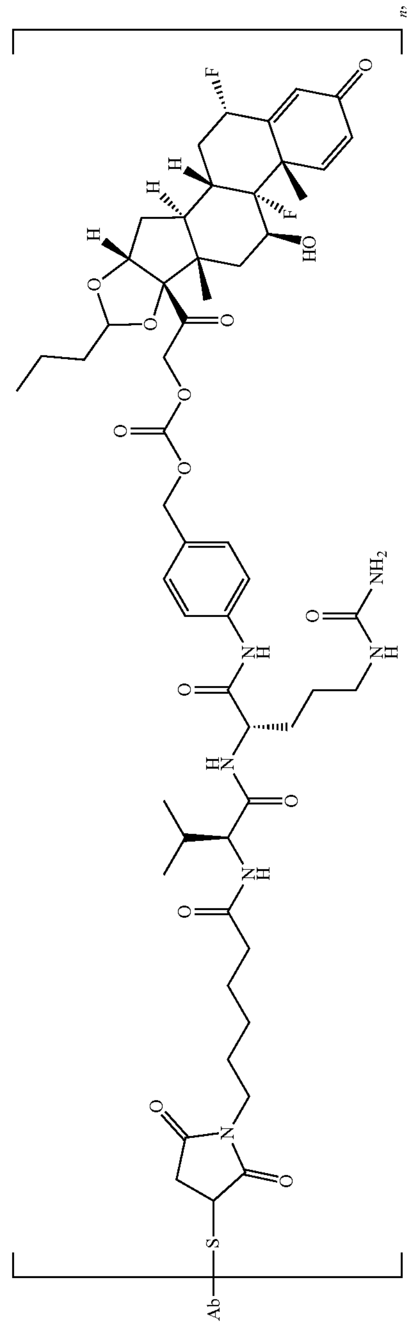

-continued
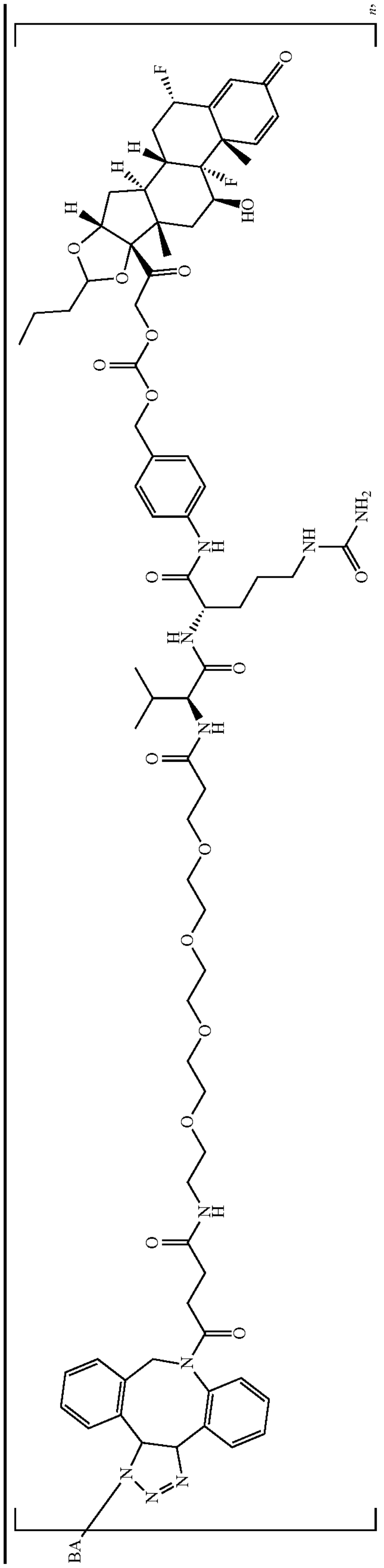
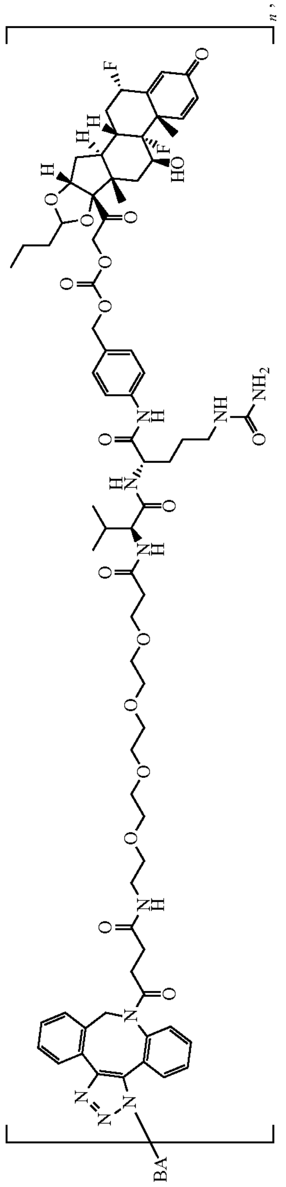

-continued
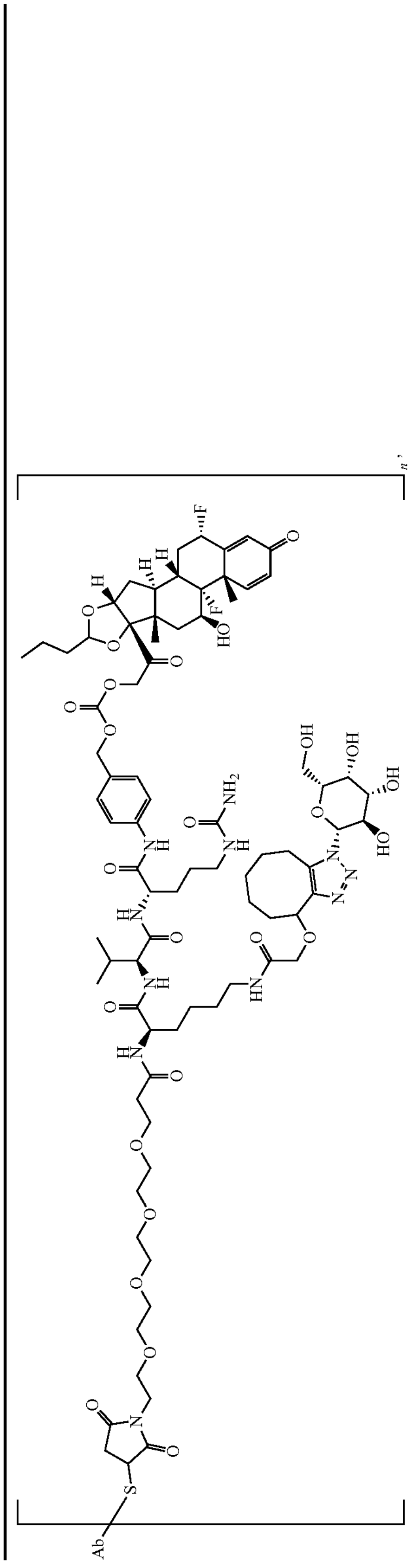
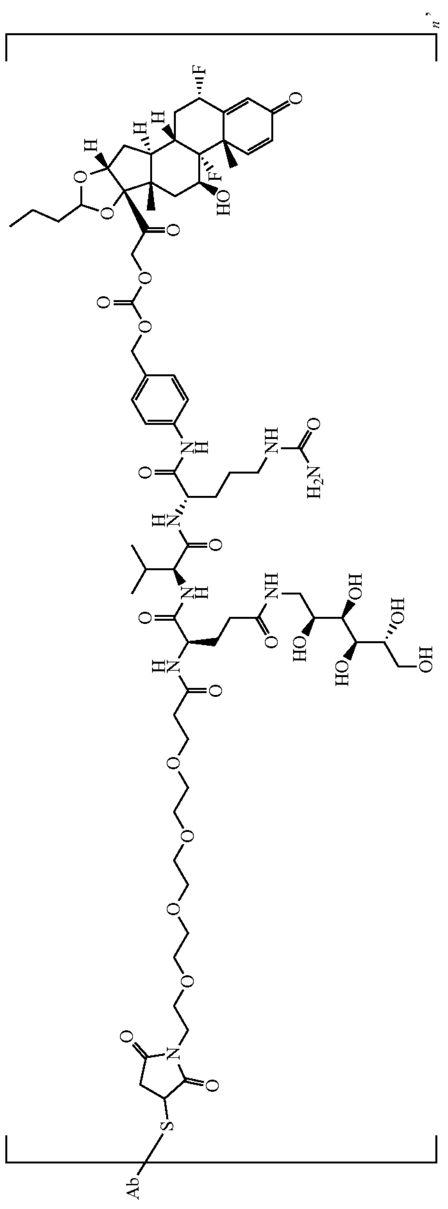

-continued
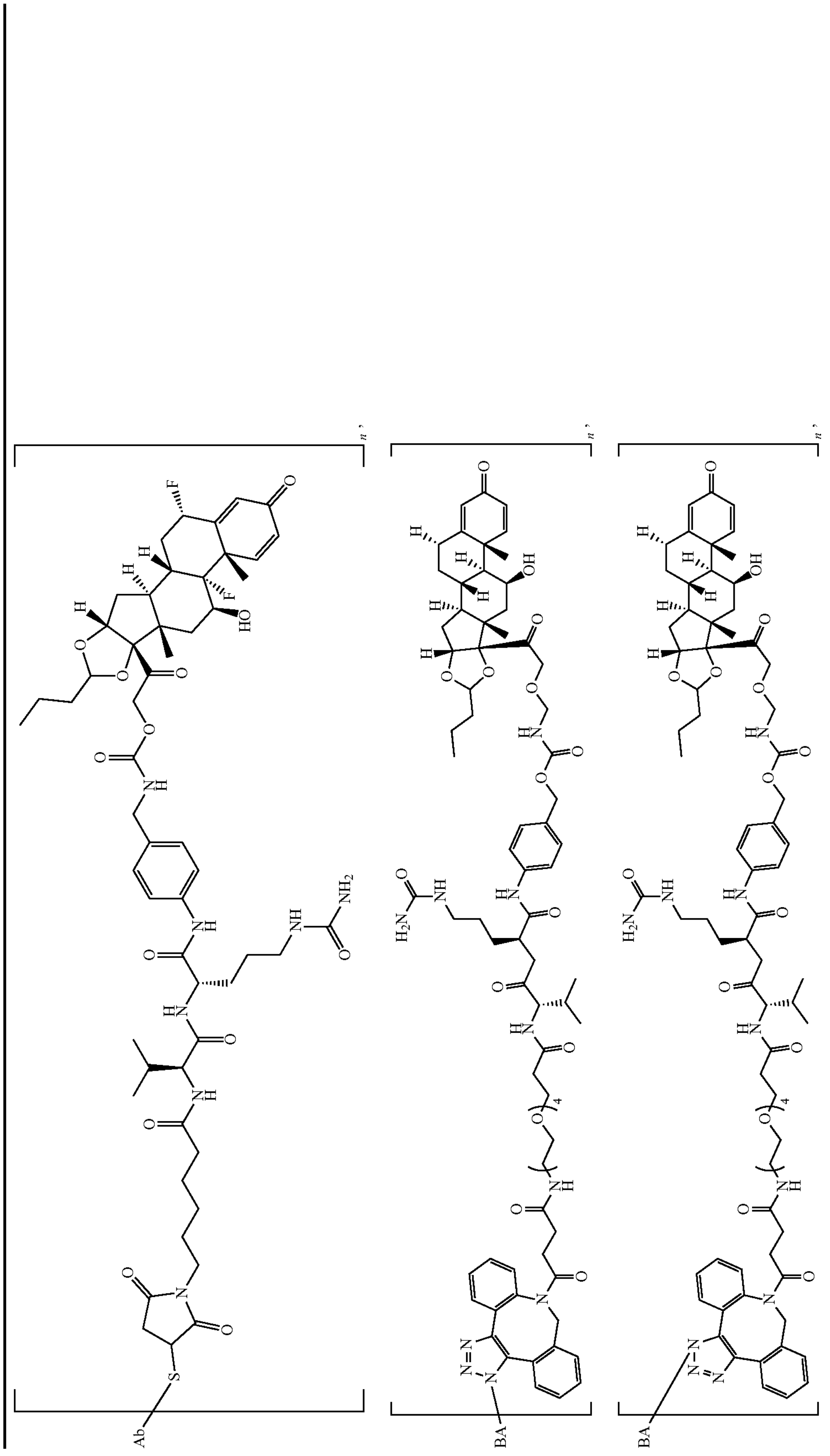

-continued
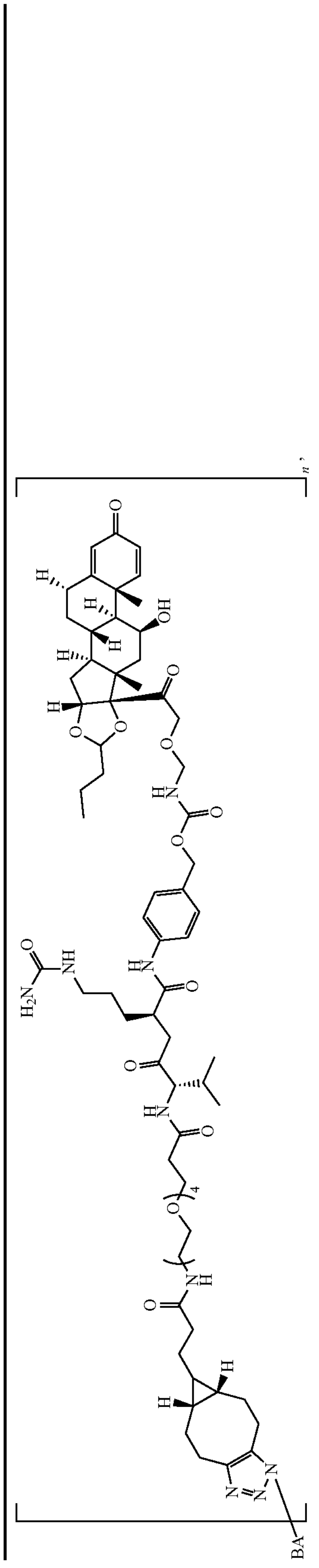
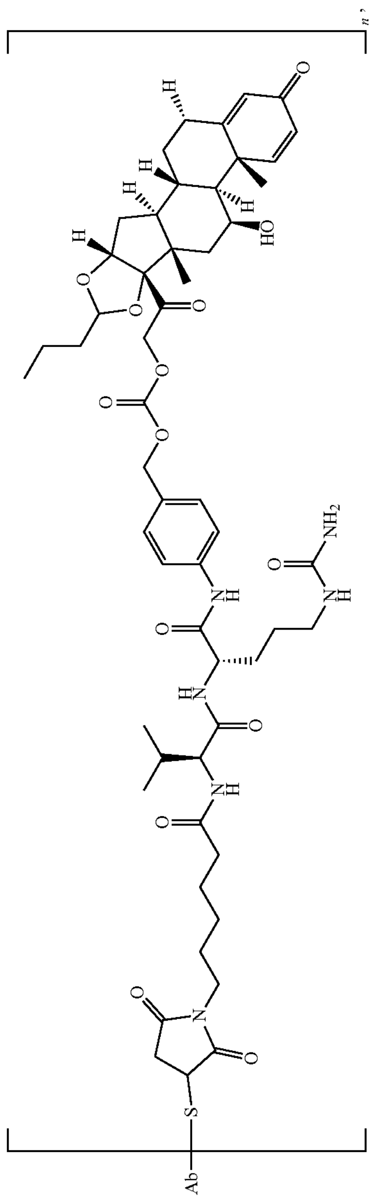
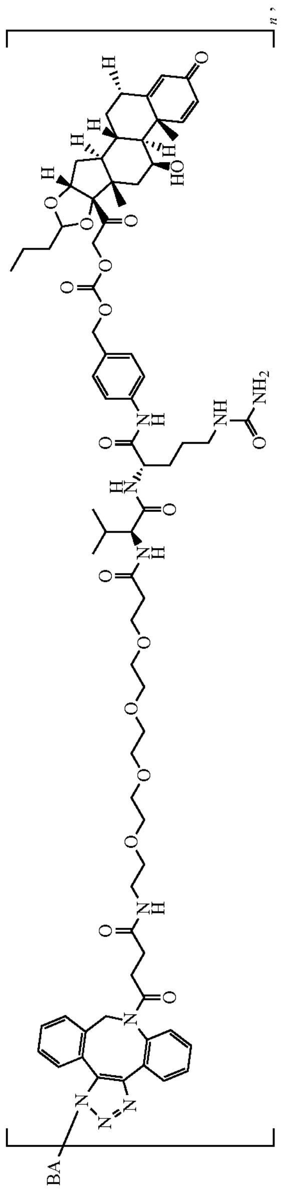

-continued
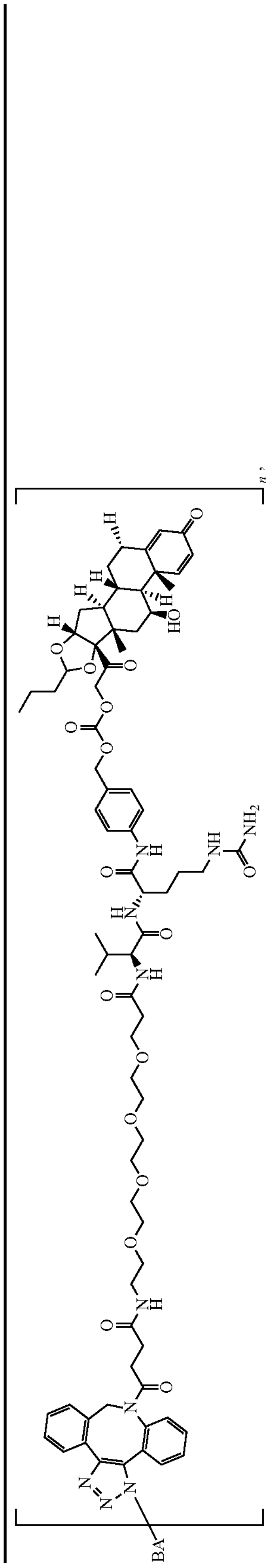
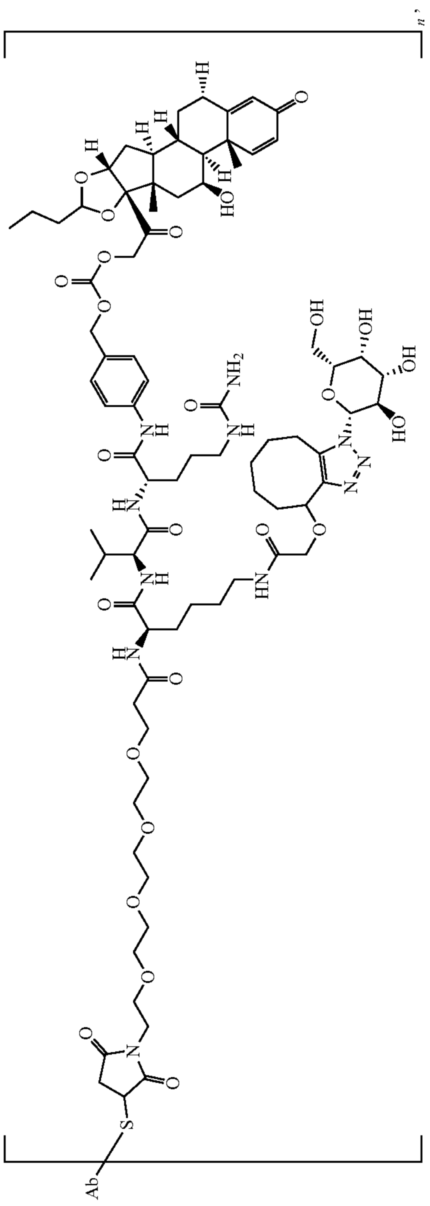

-continued
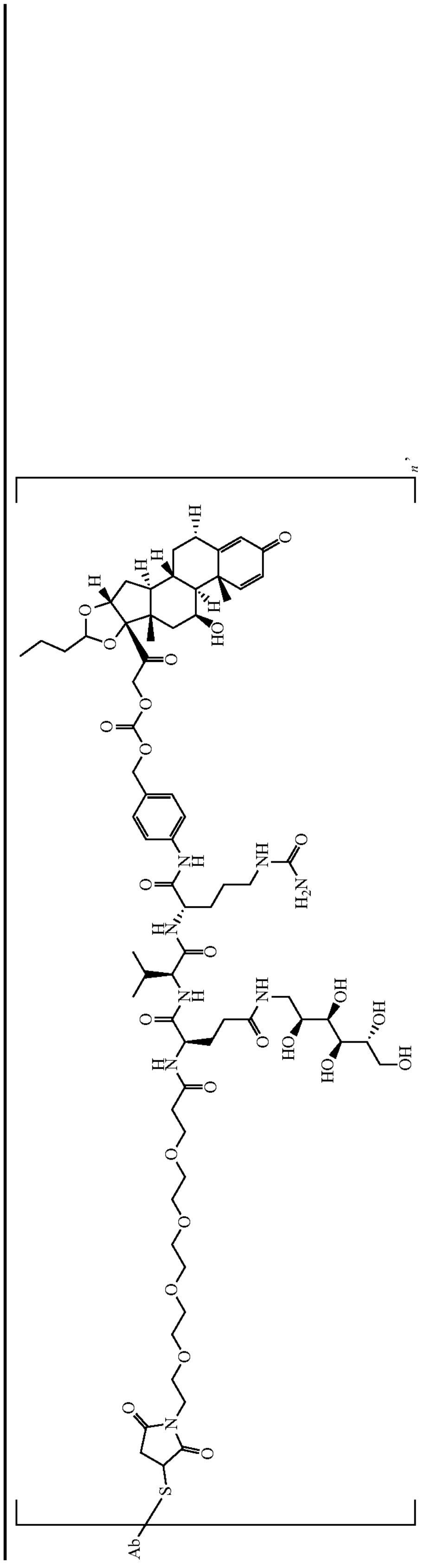
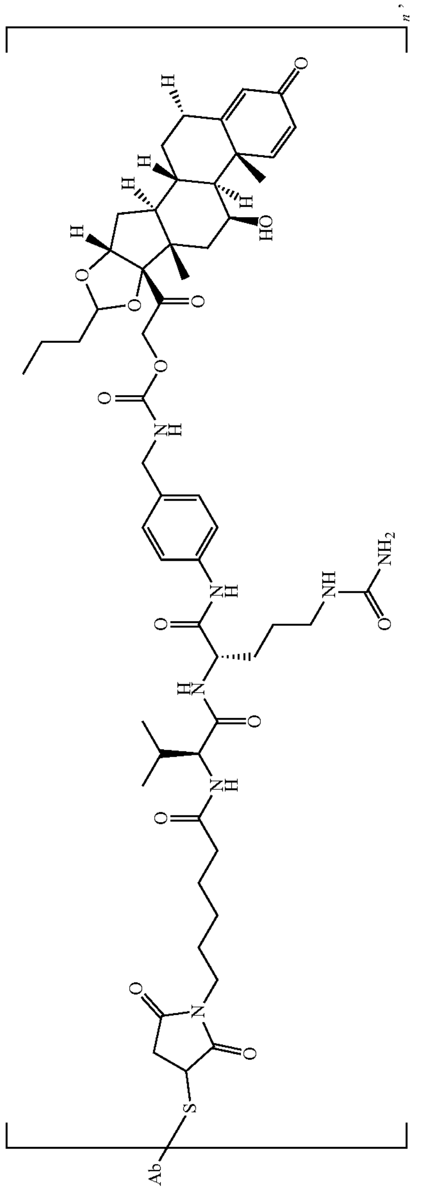

-continued
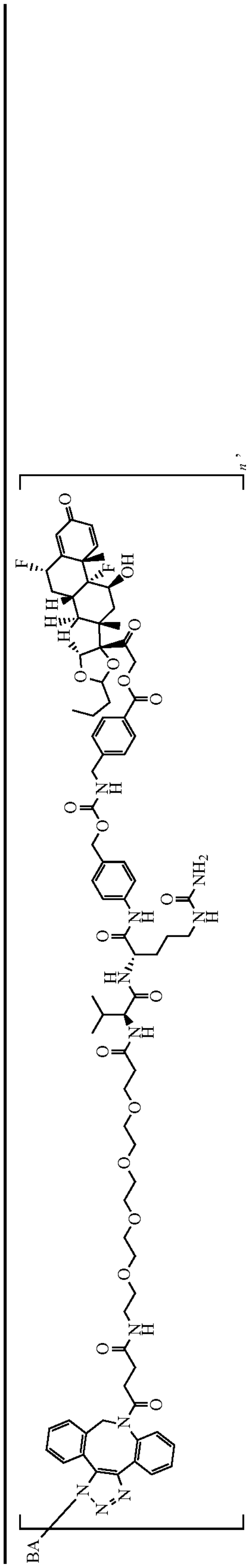
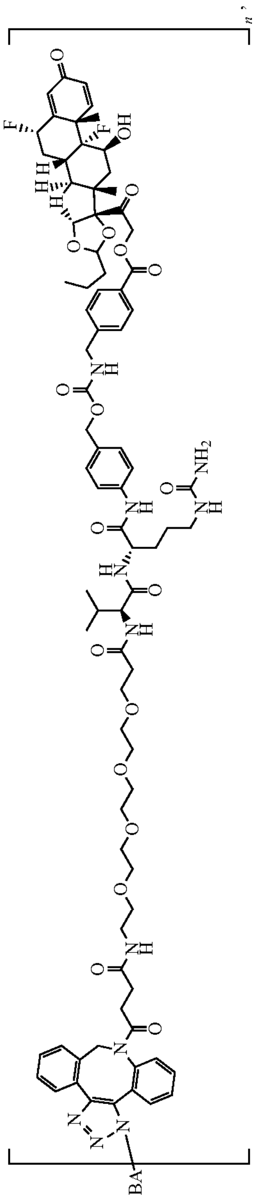
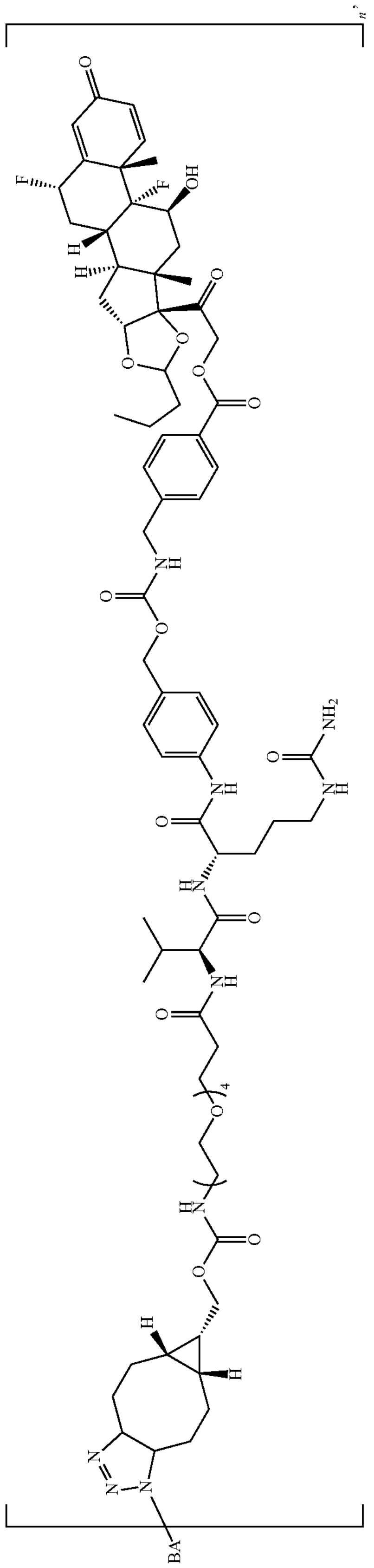

-continued
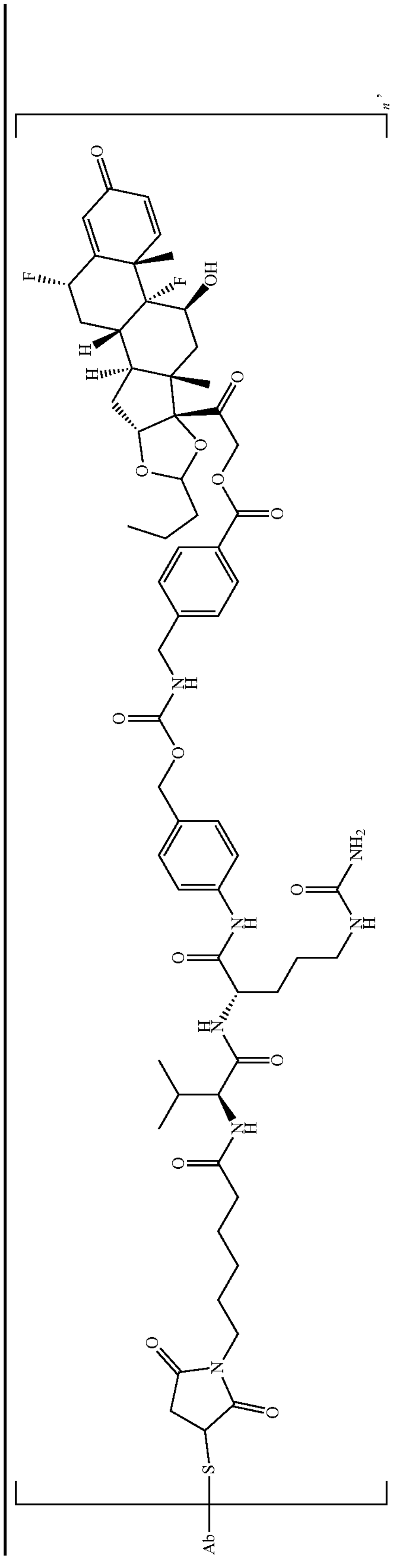
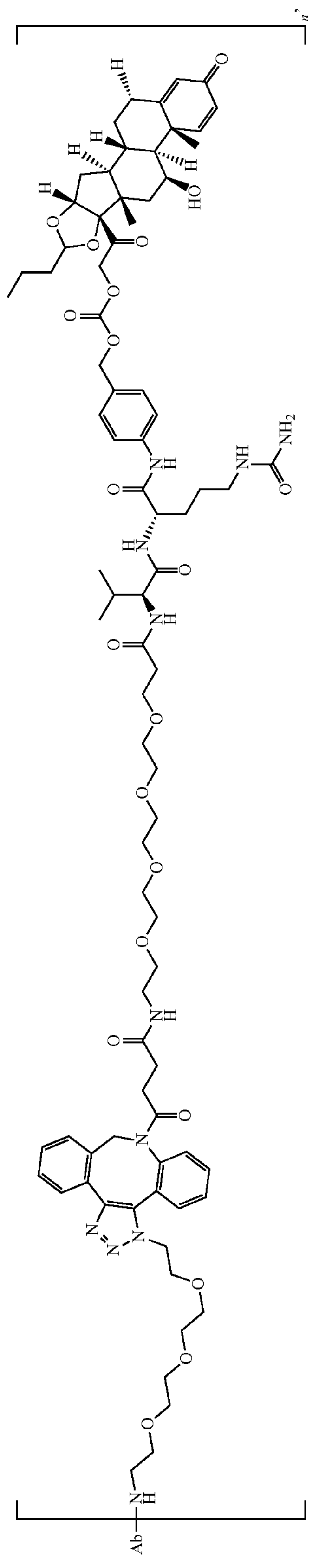
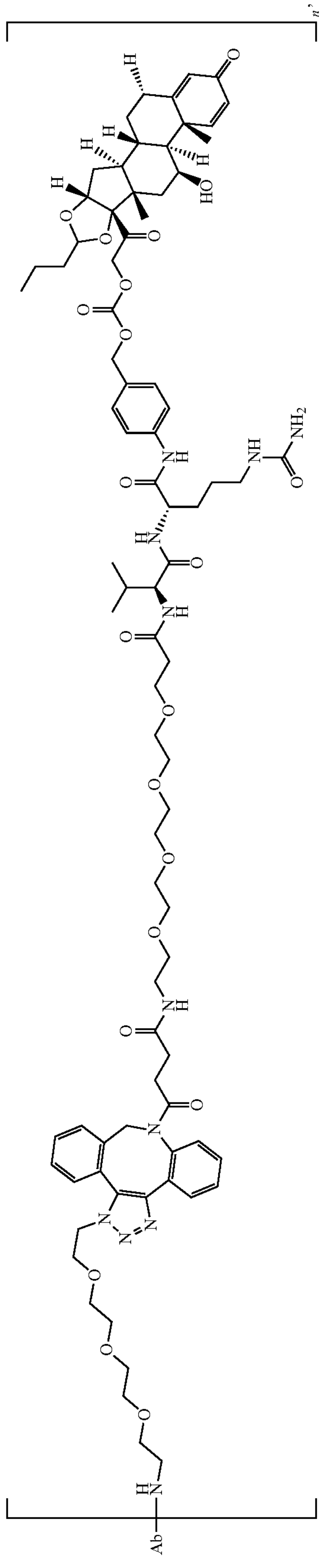

-continued
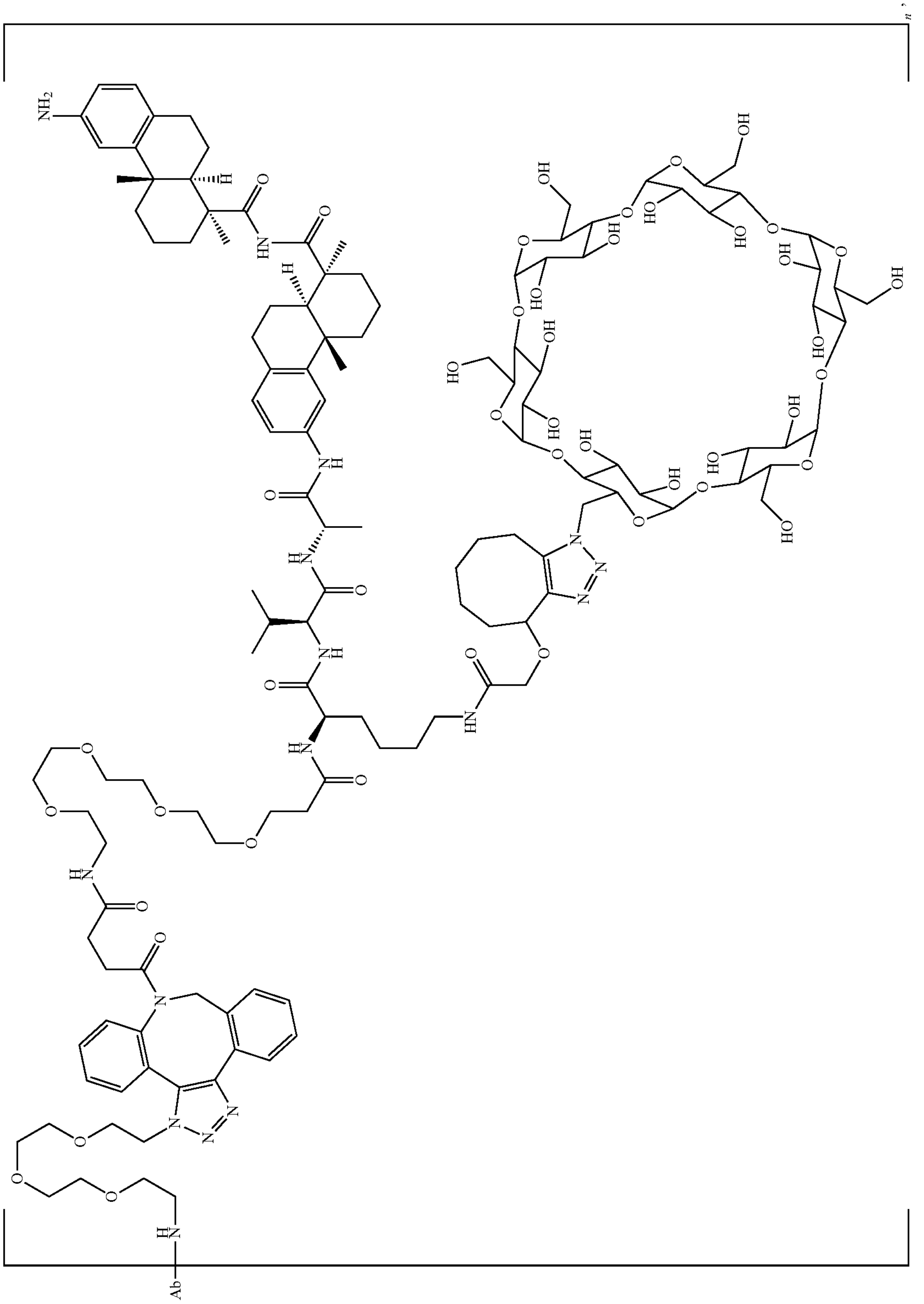

-continued
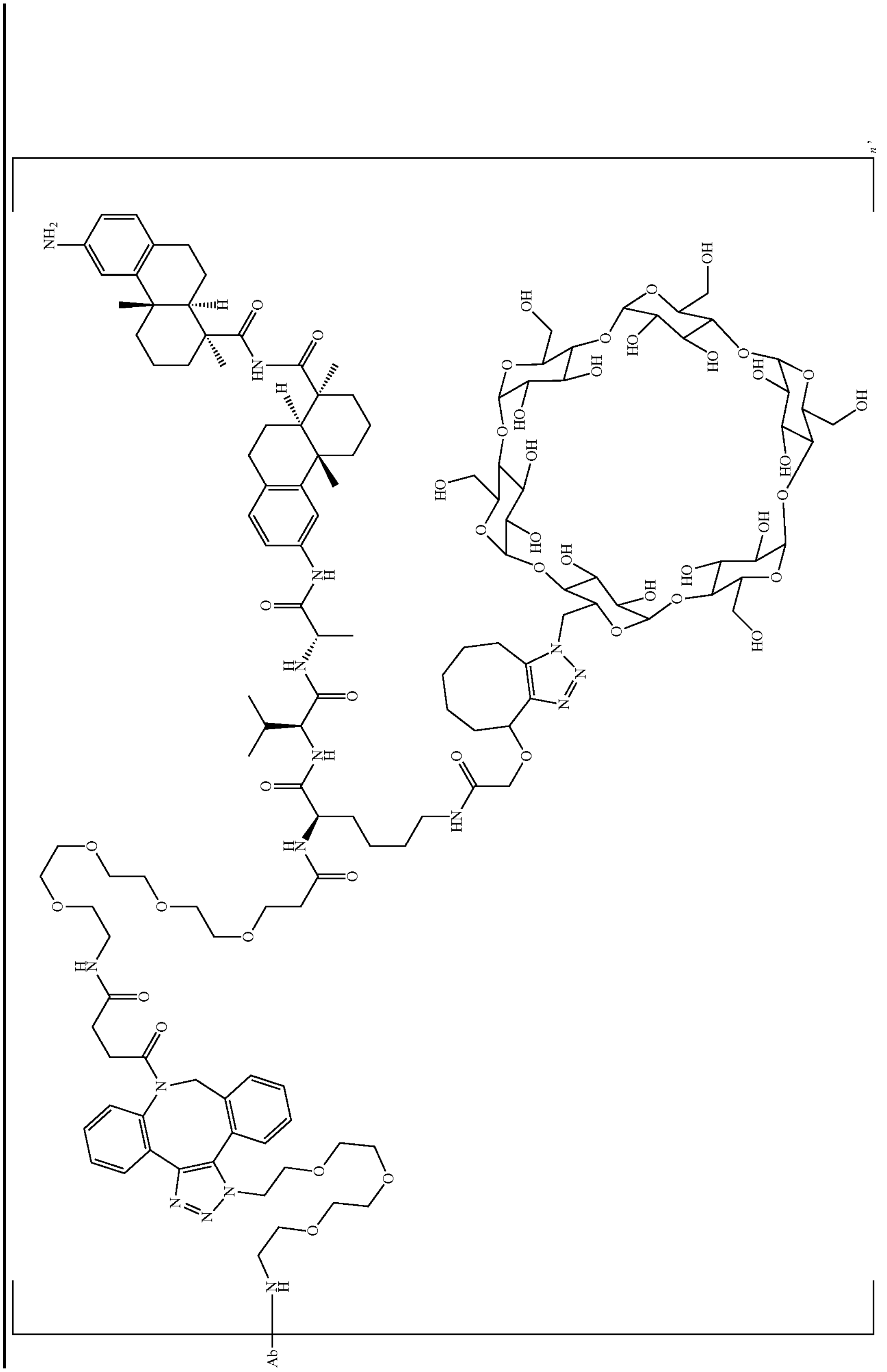

-continued
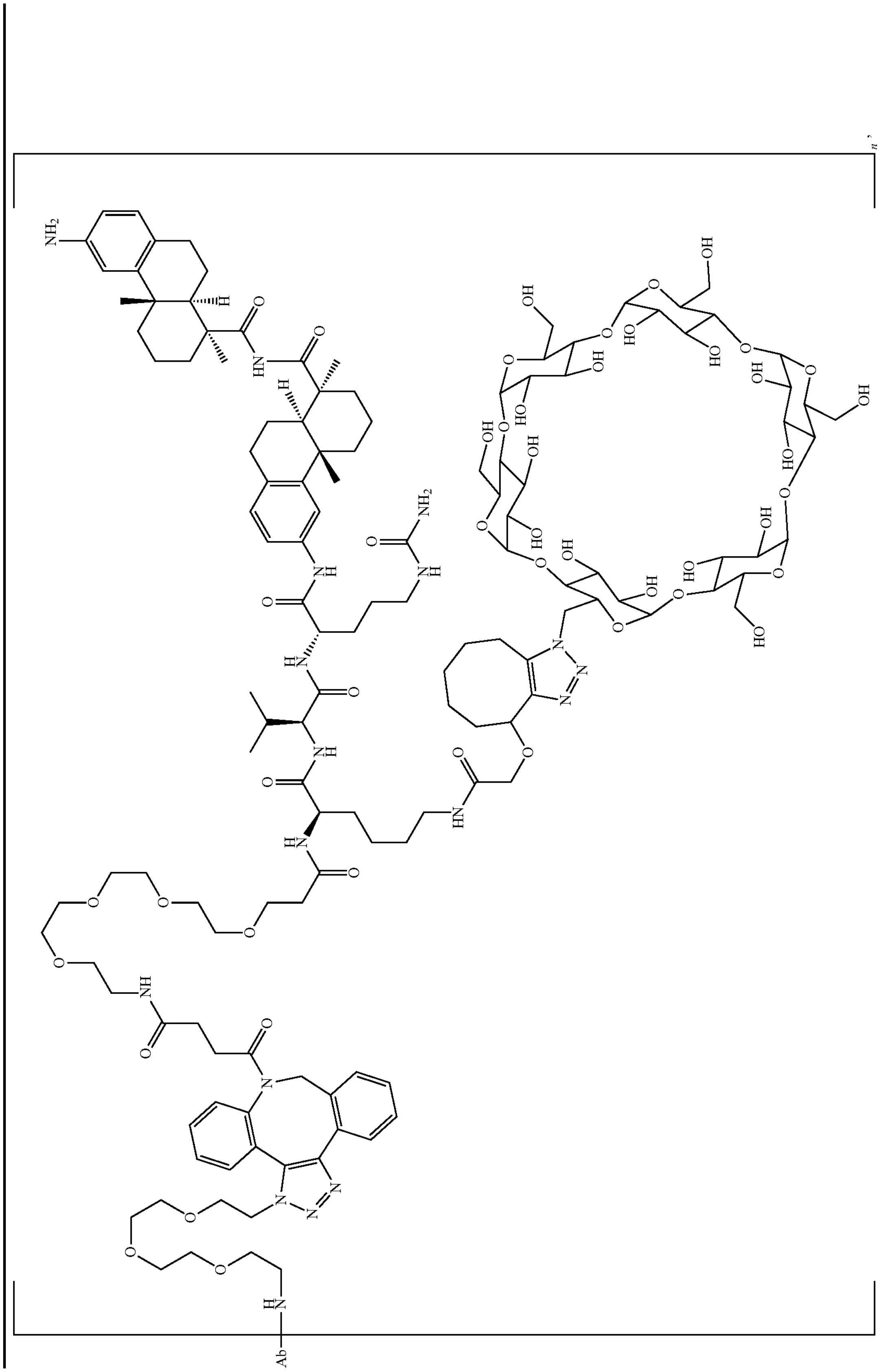

-continued
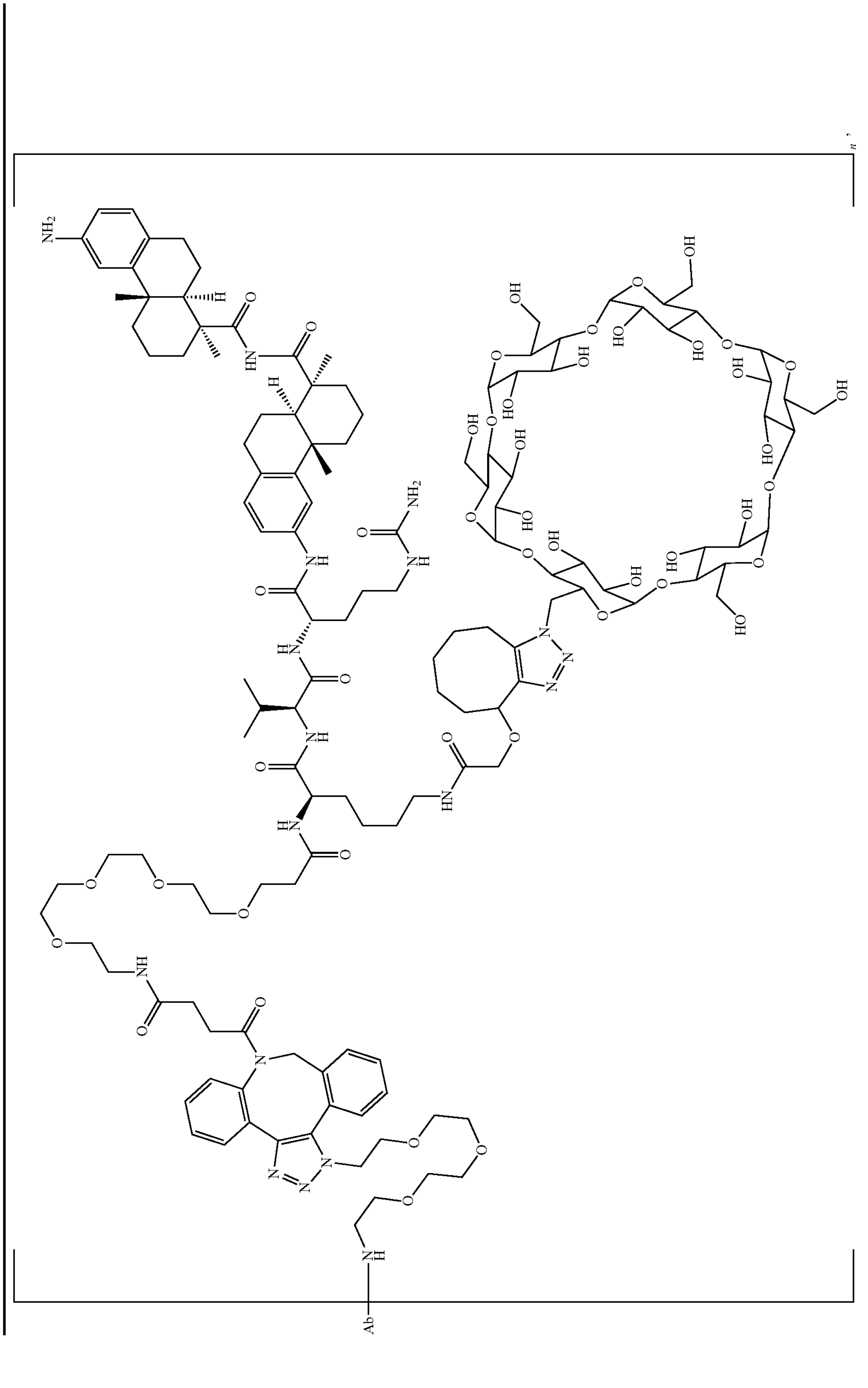

-continued
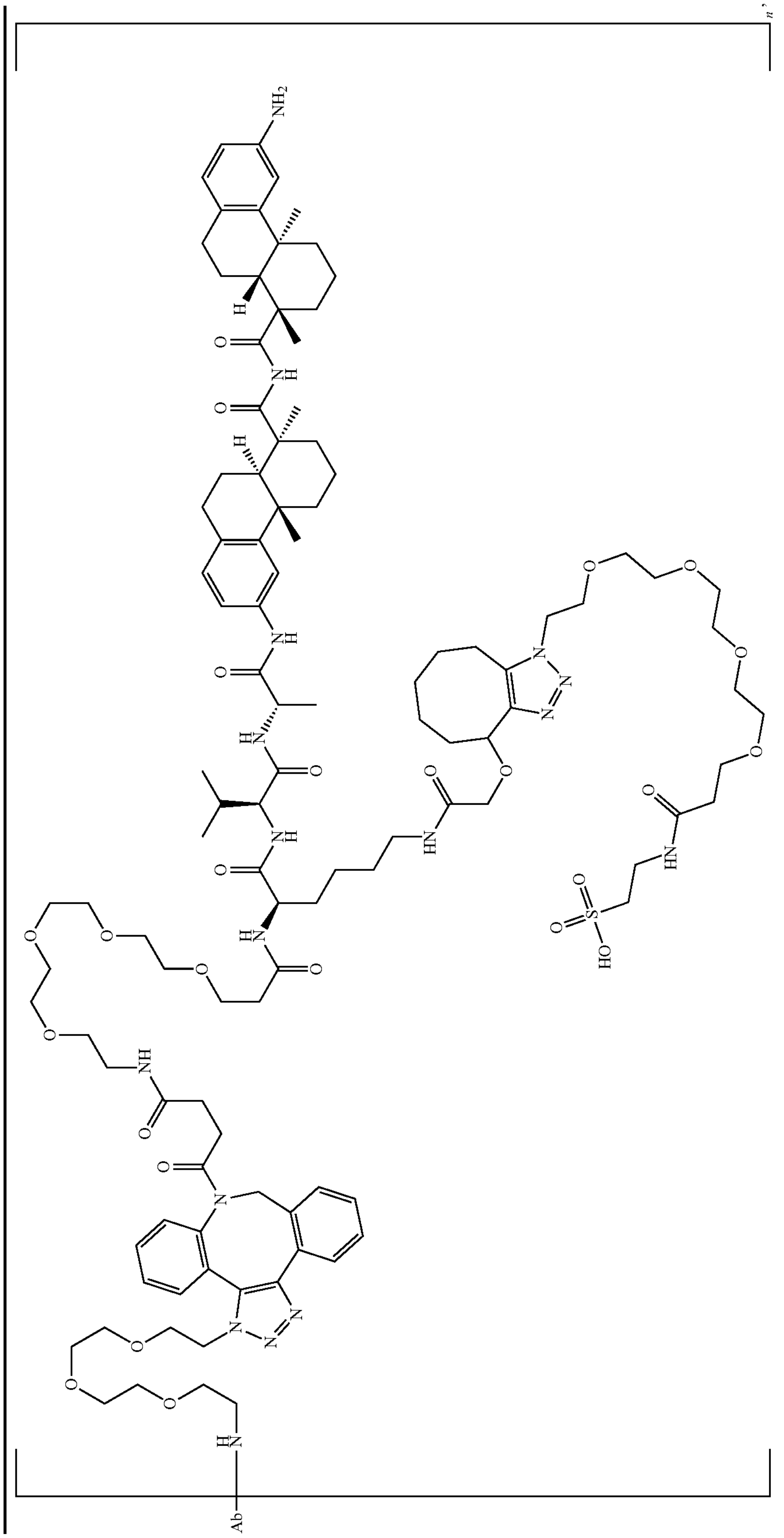

-continued
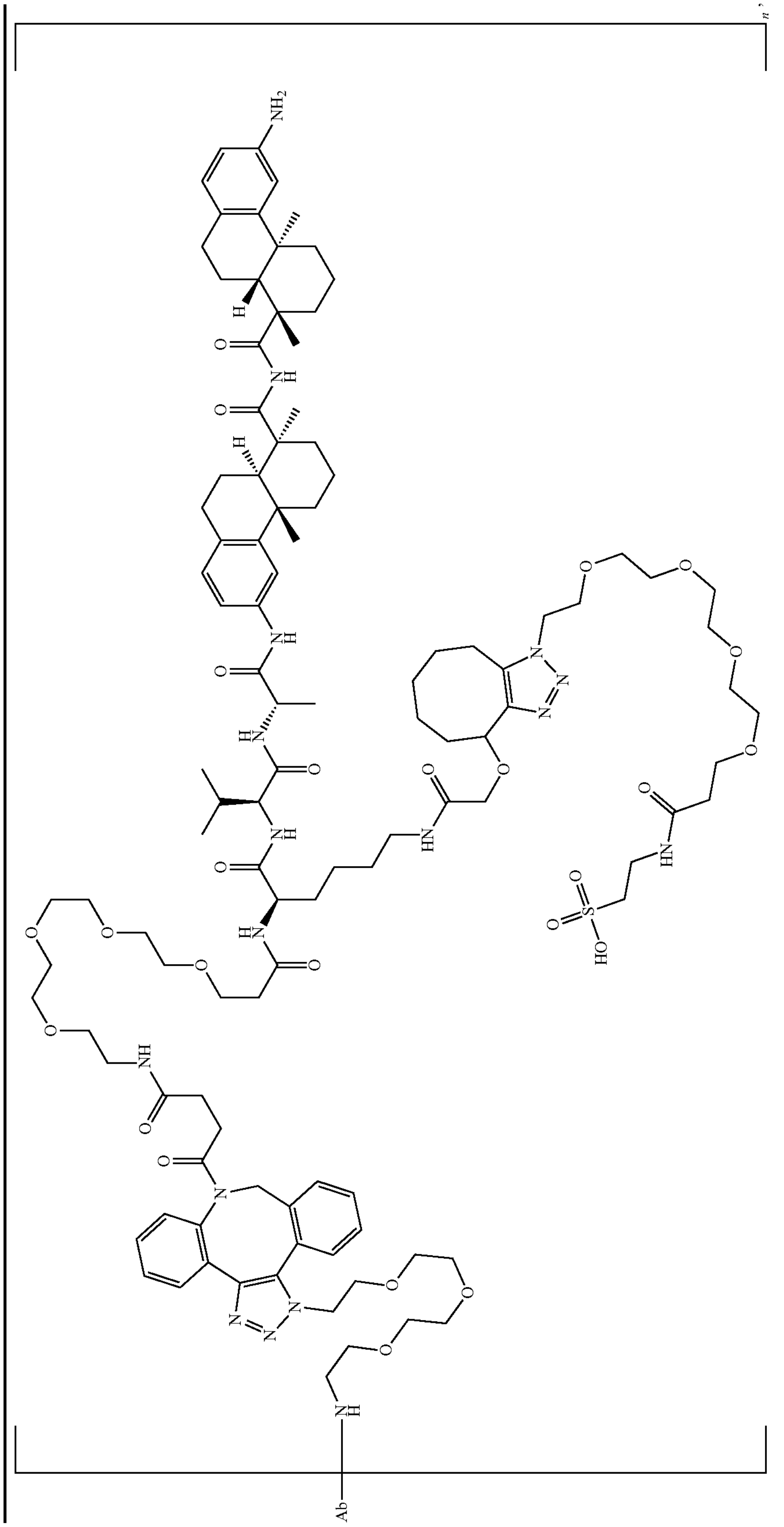

-continued
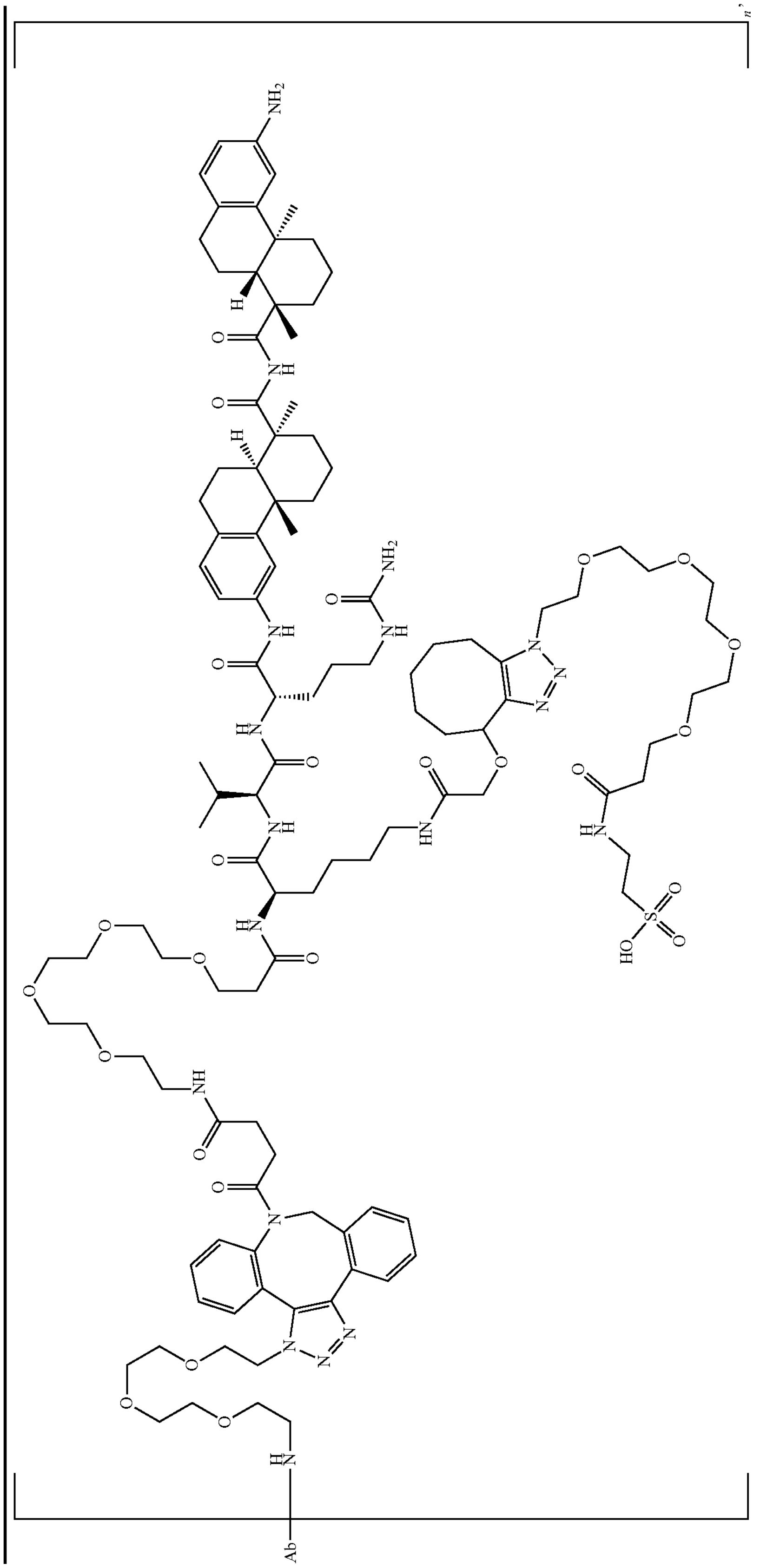

-continued
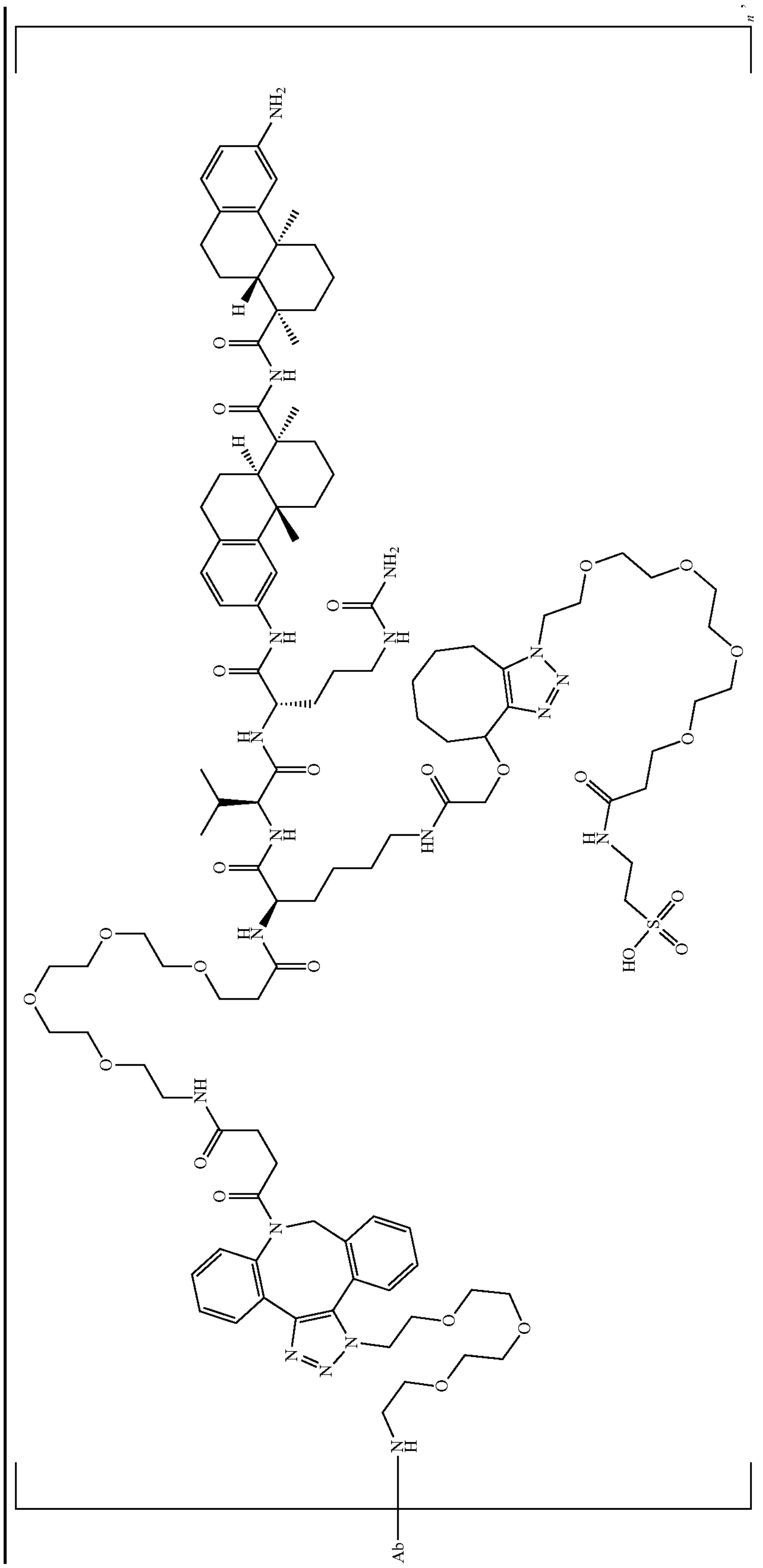

-continued
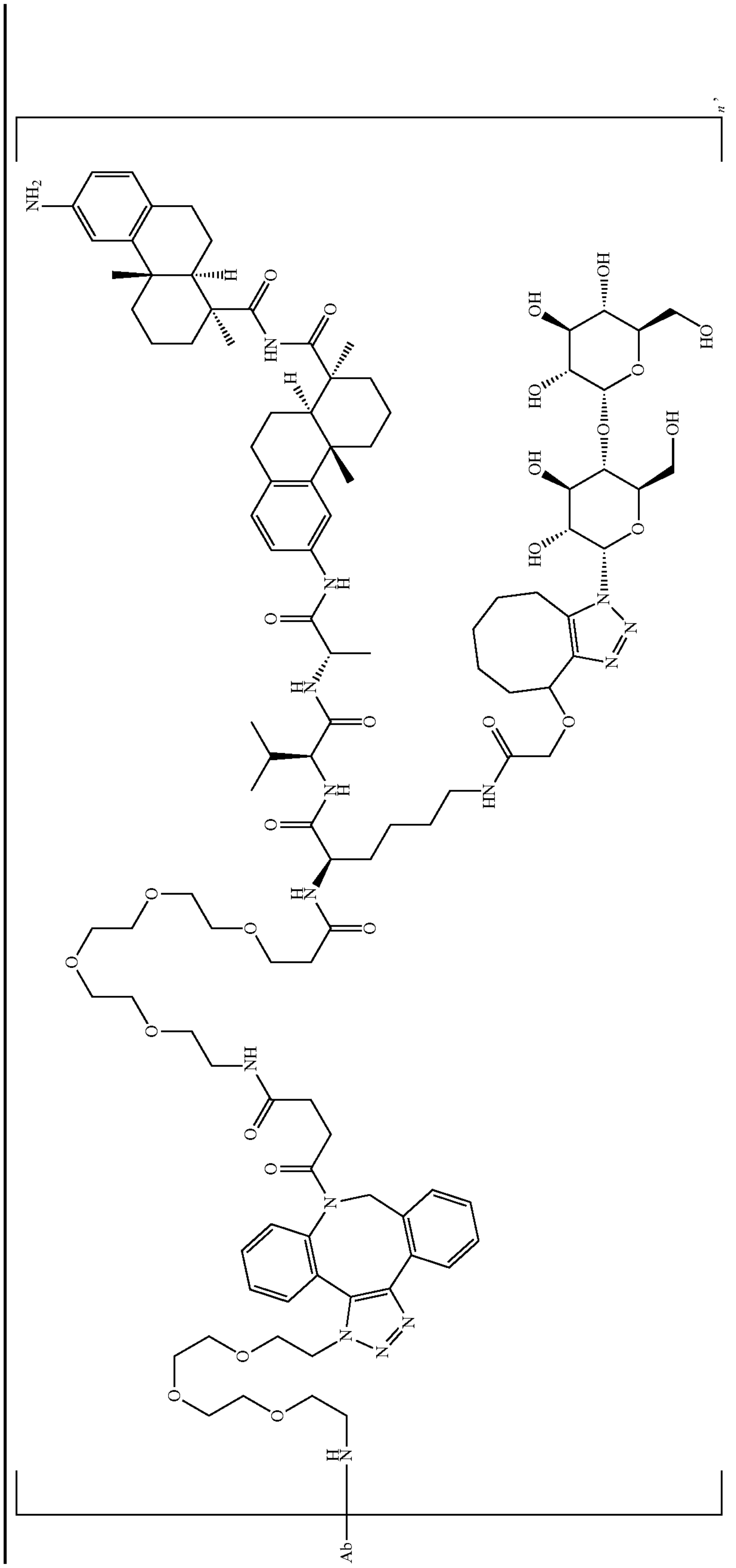

-continued
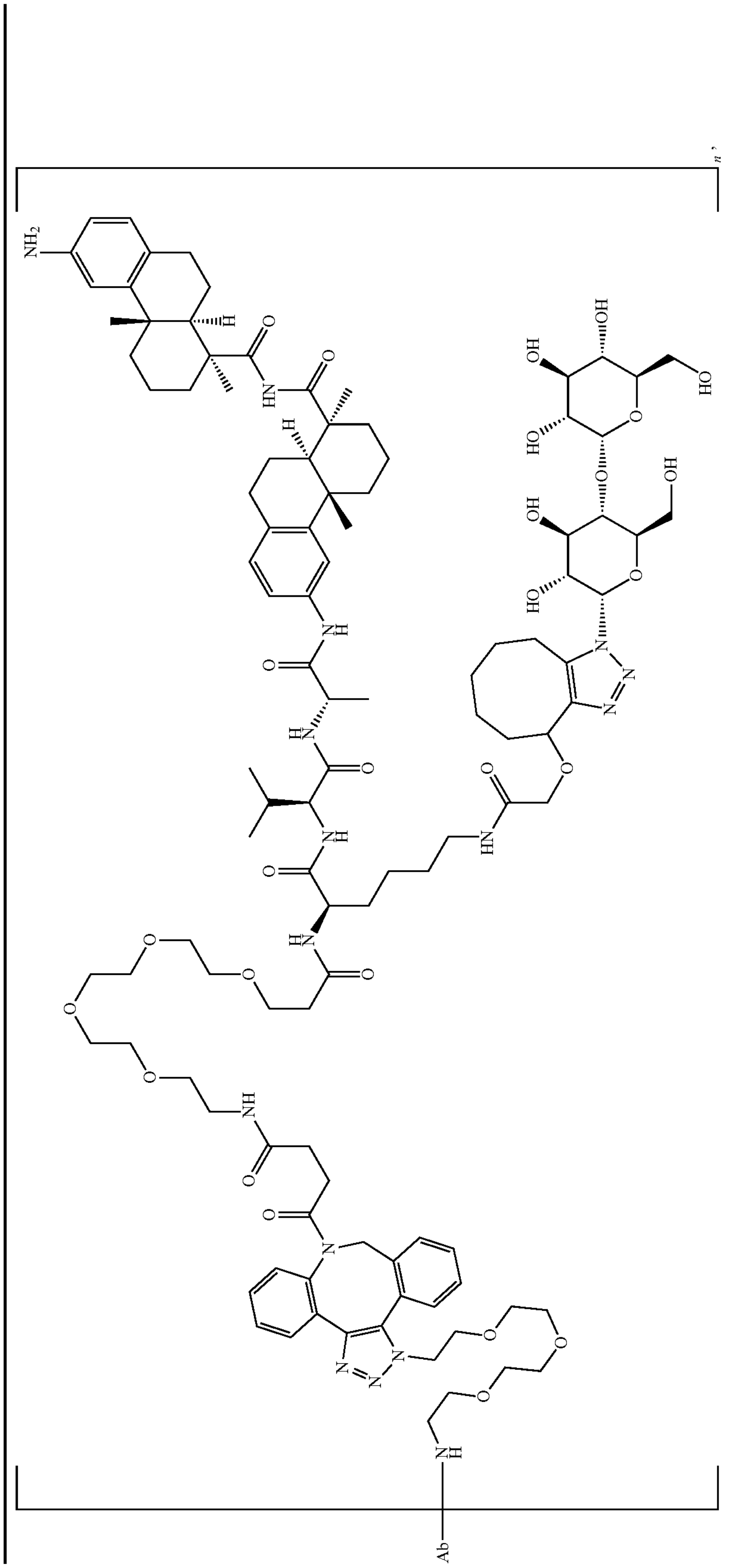

-continued
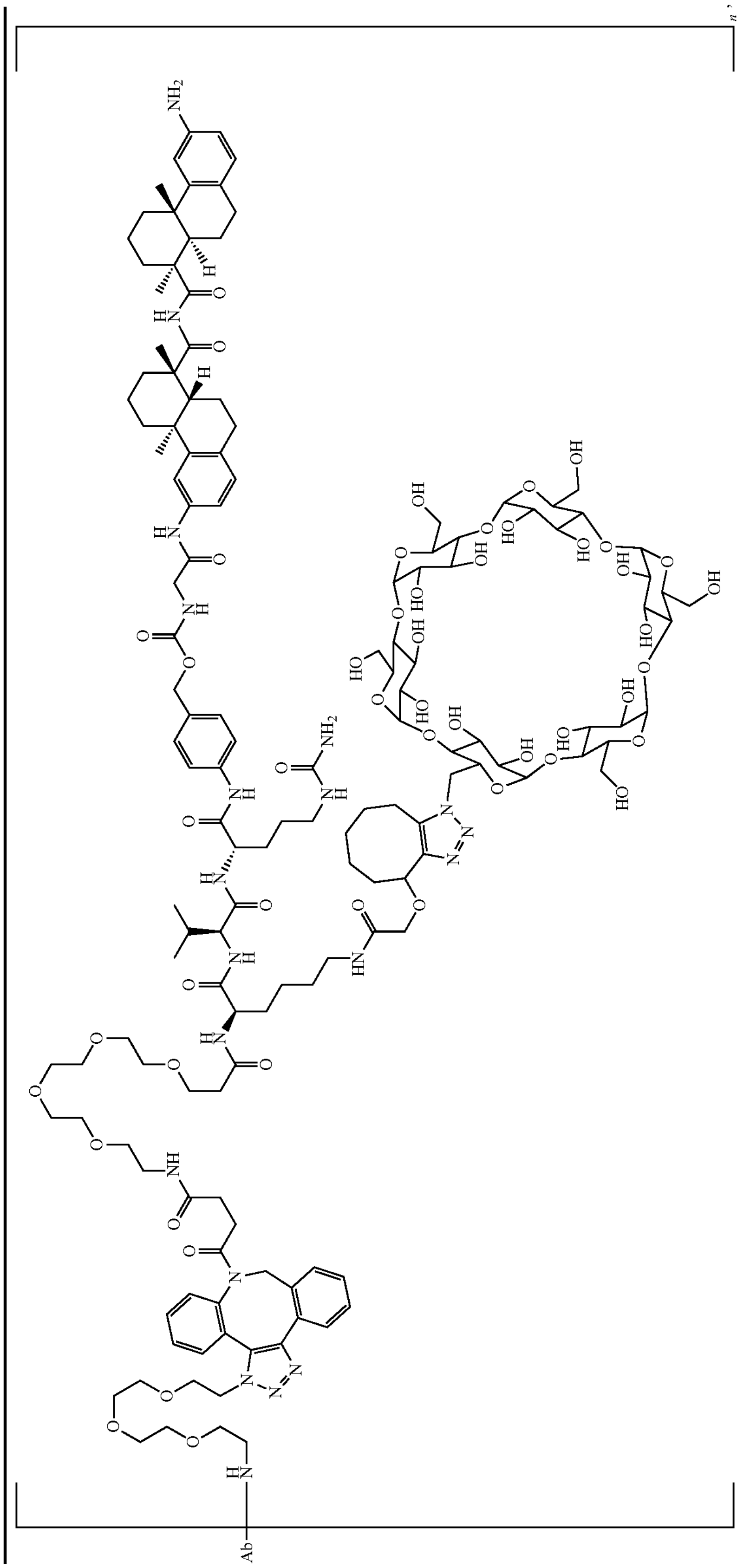

-continued
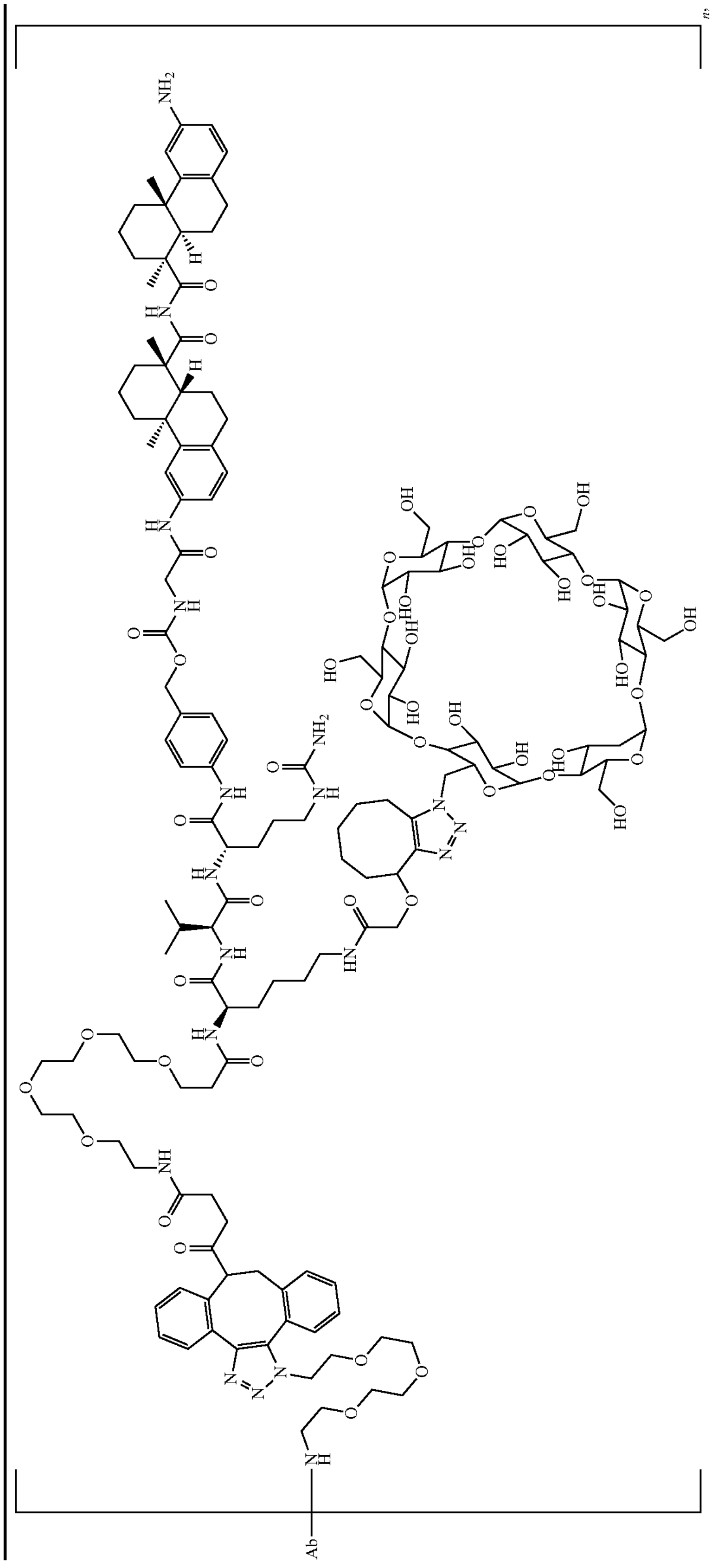

-continued
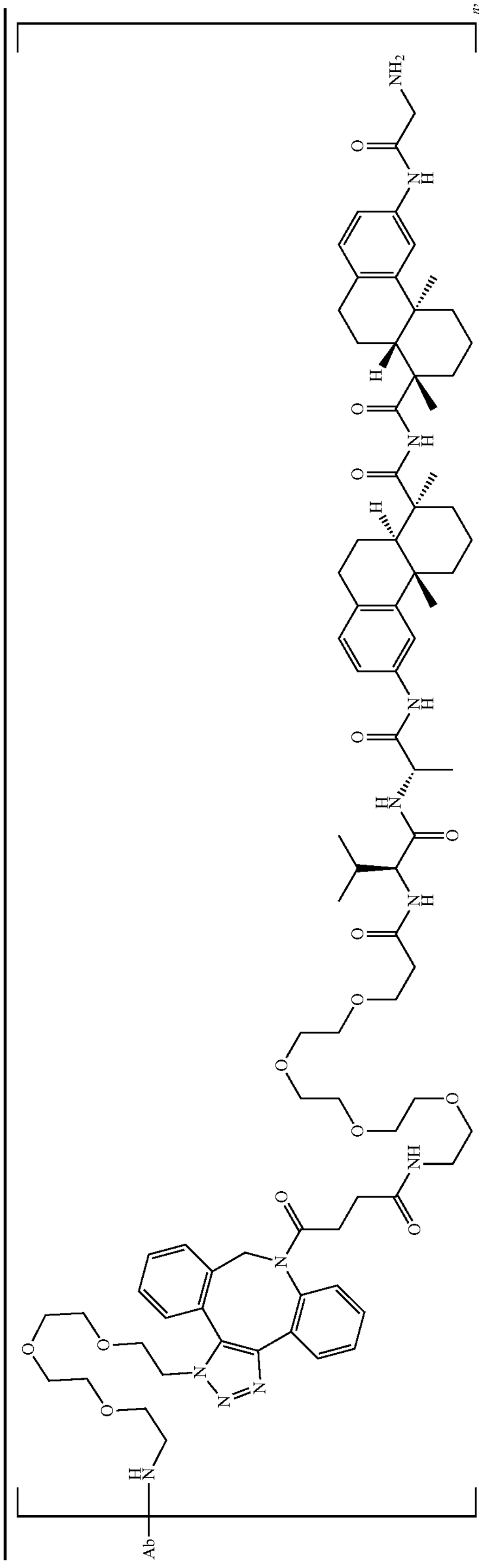
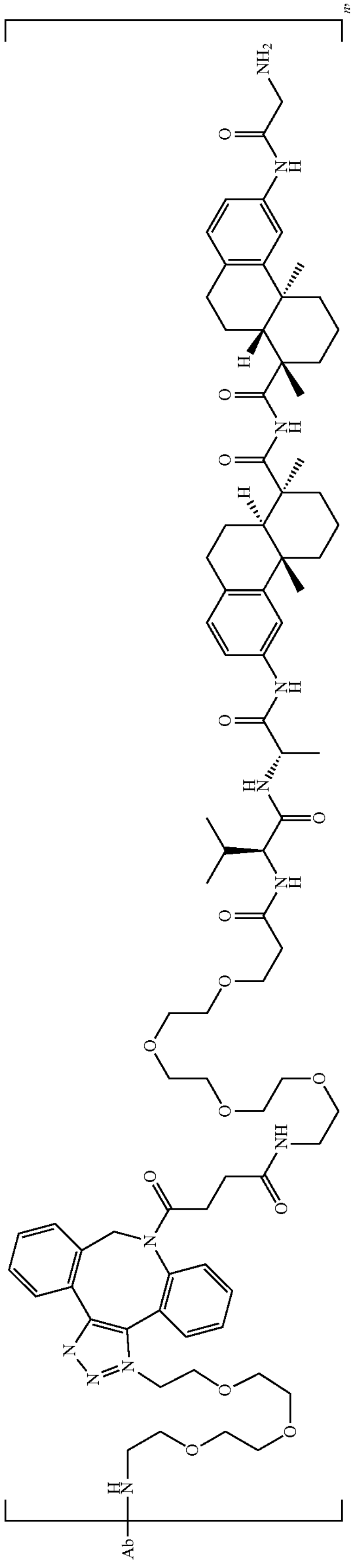

-continued
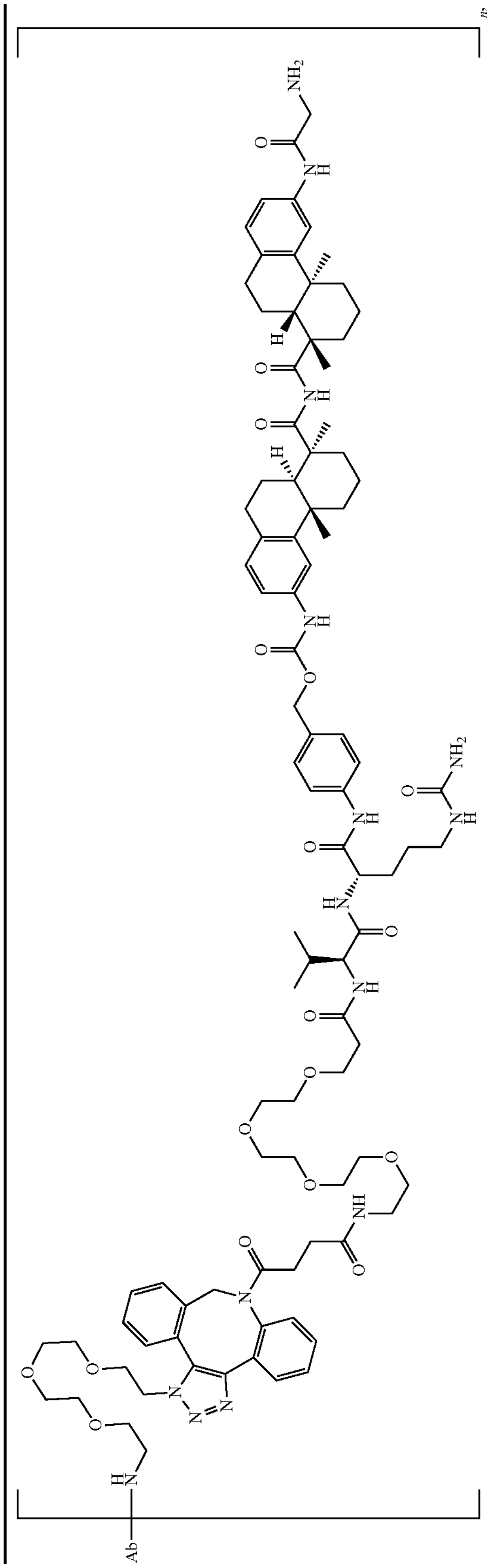
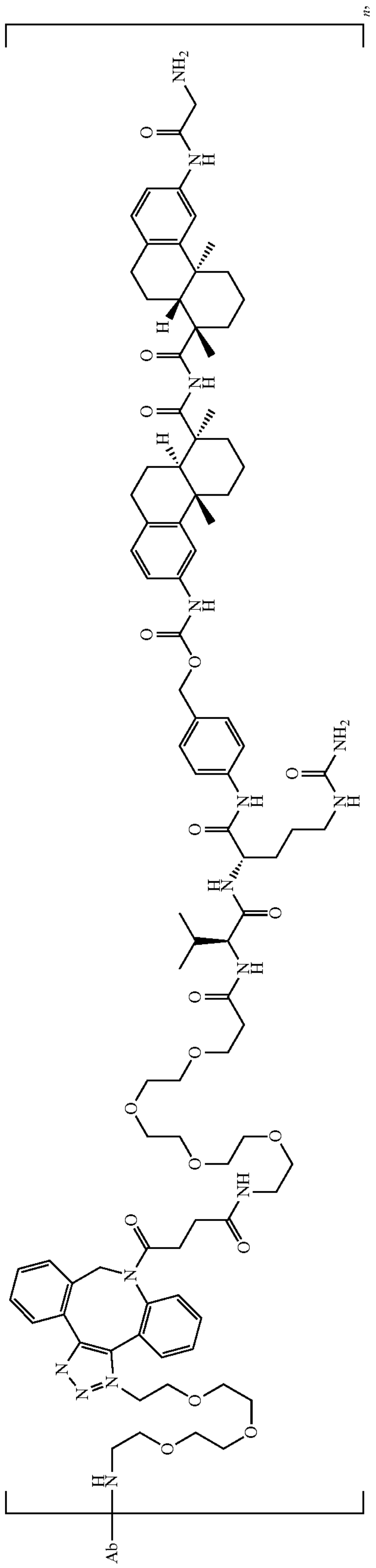

-continued
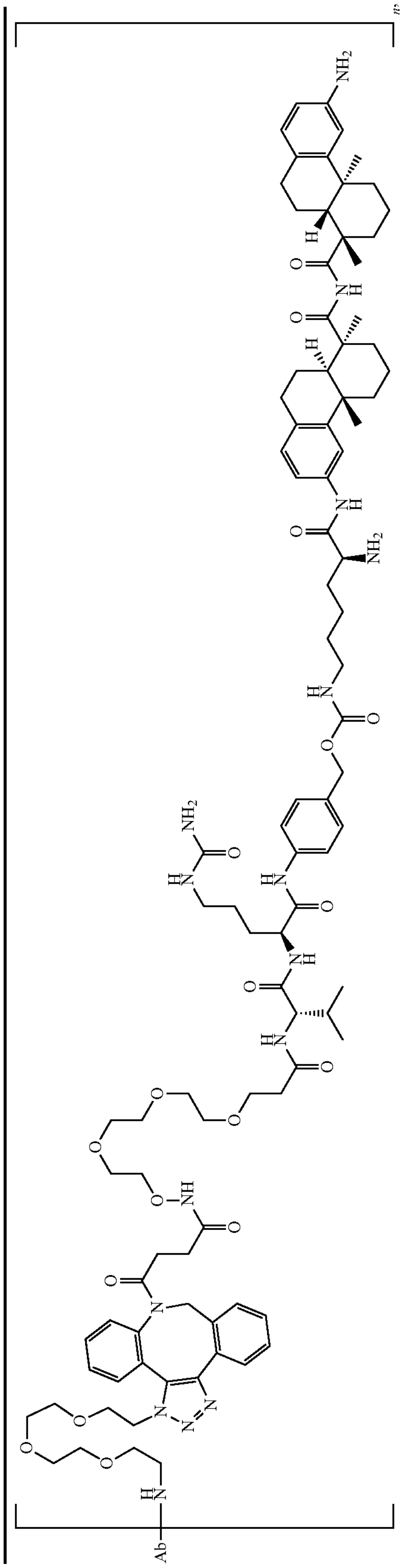
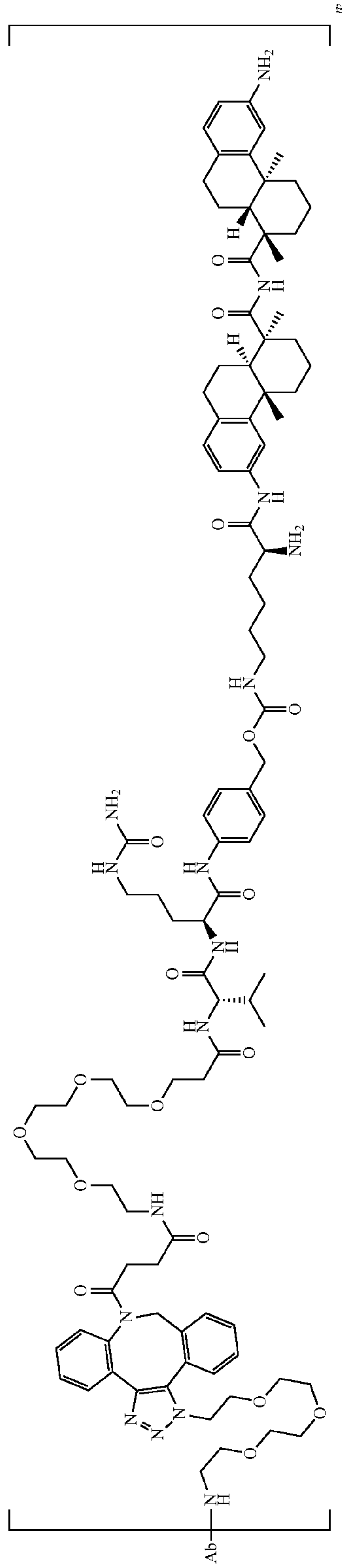

-continued
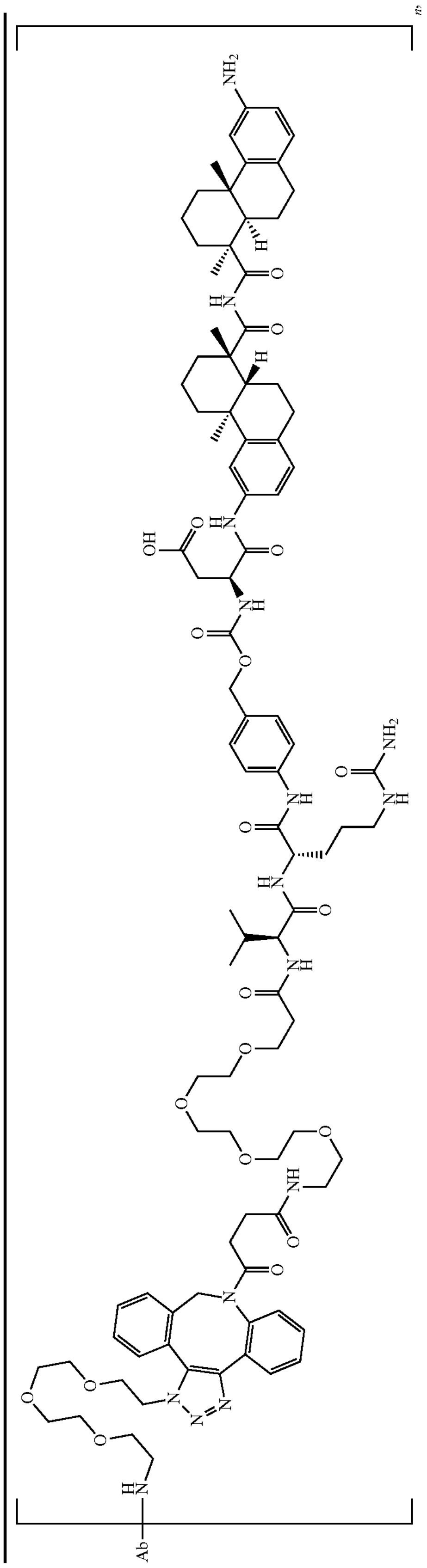
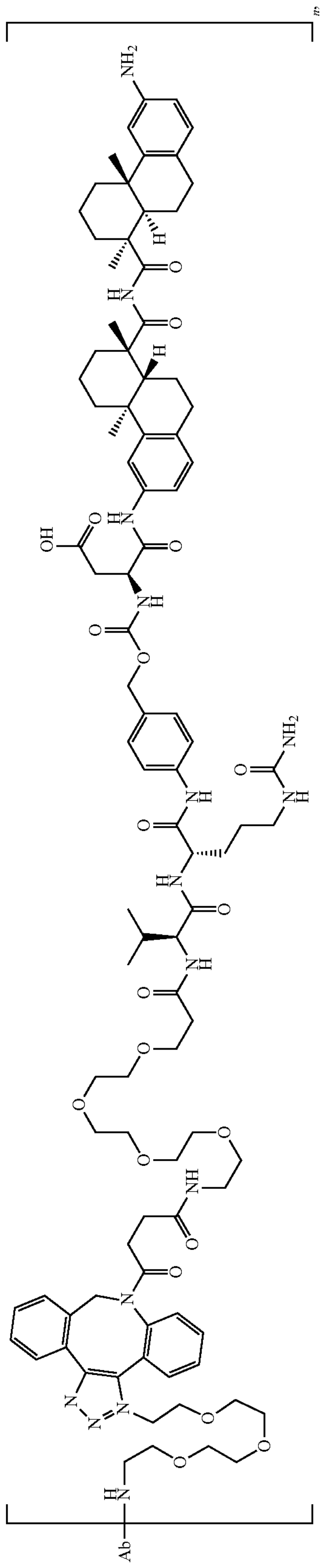

-continued
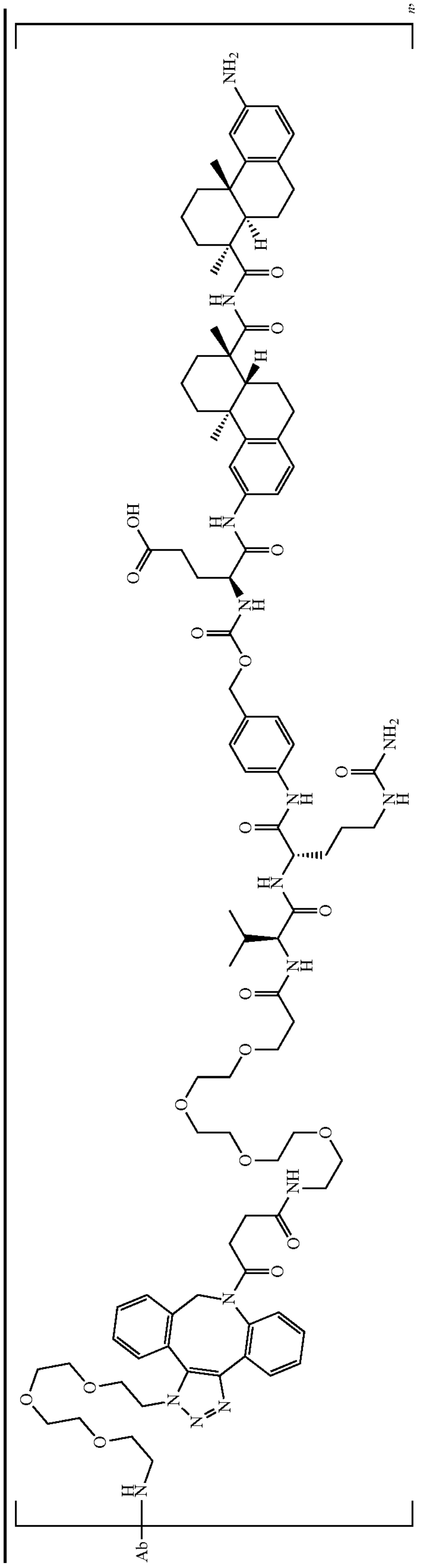
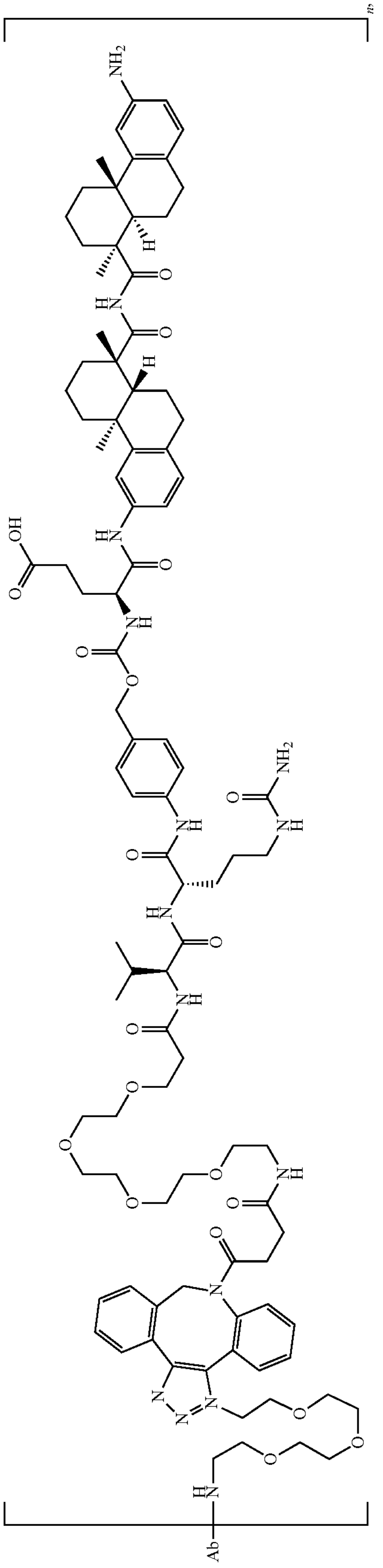

-continued
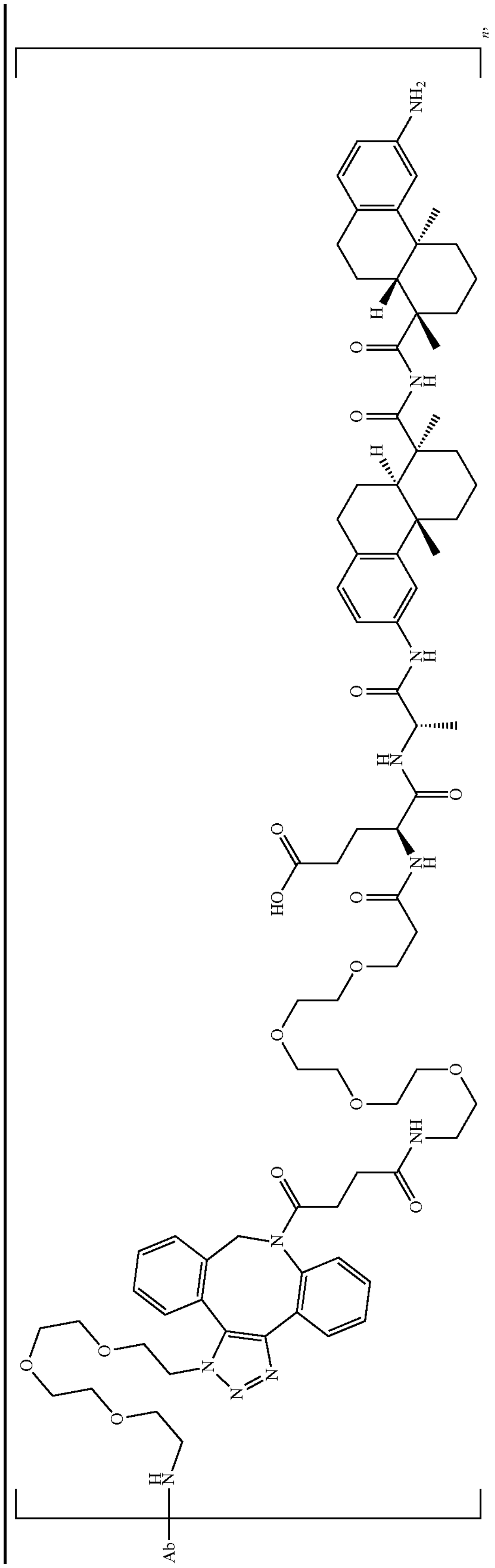
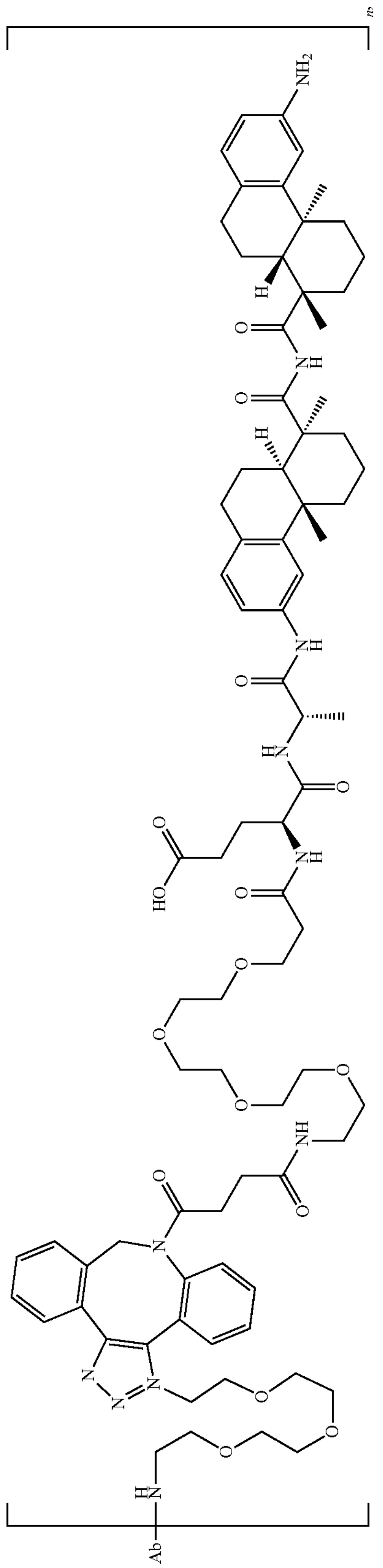

-continued
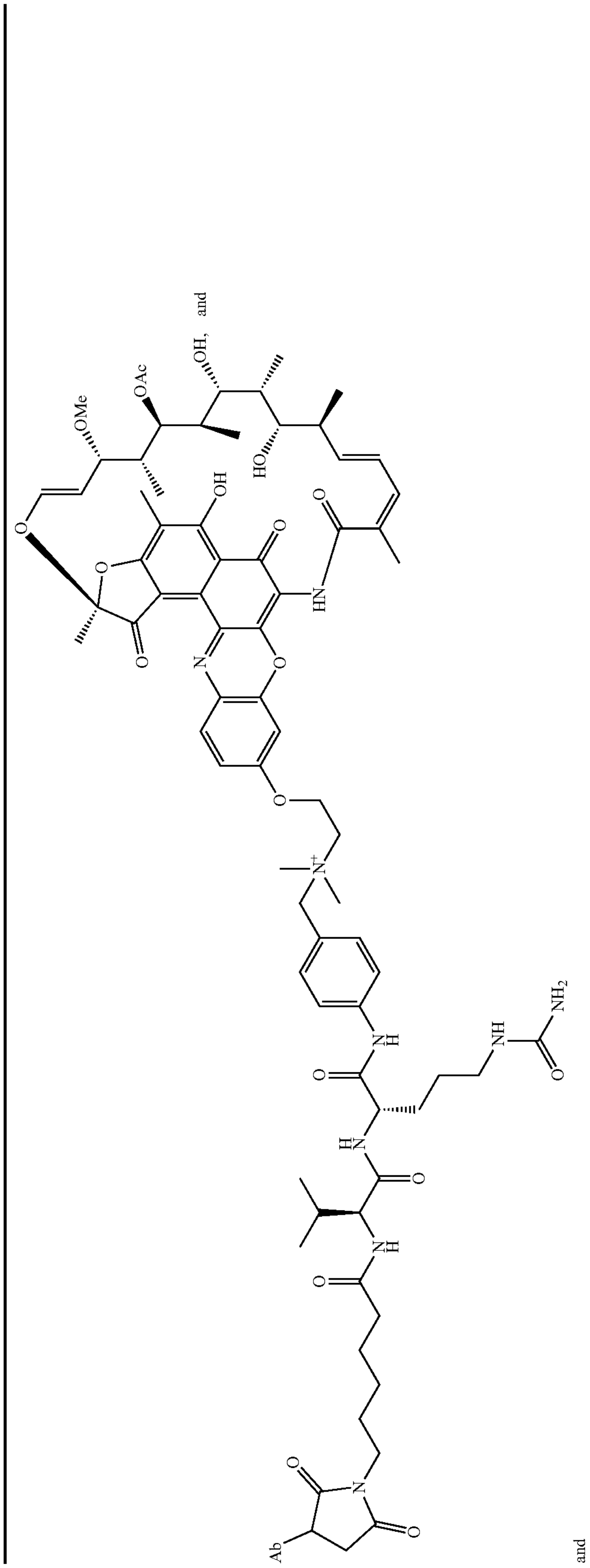
and
and
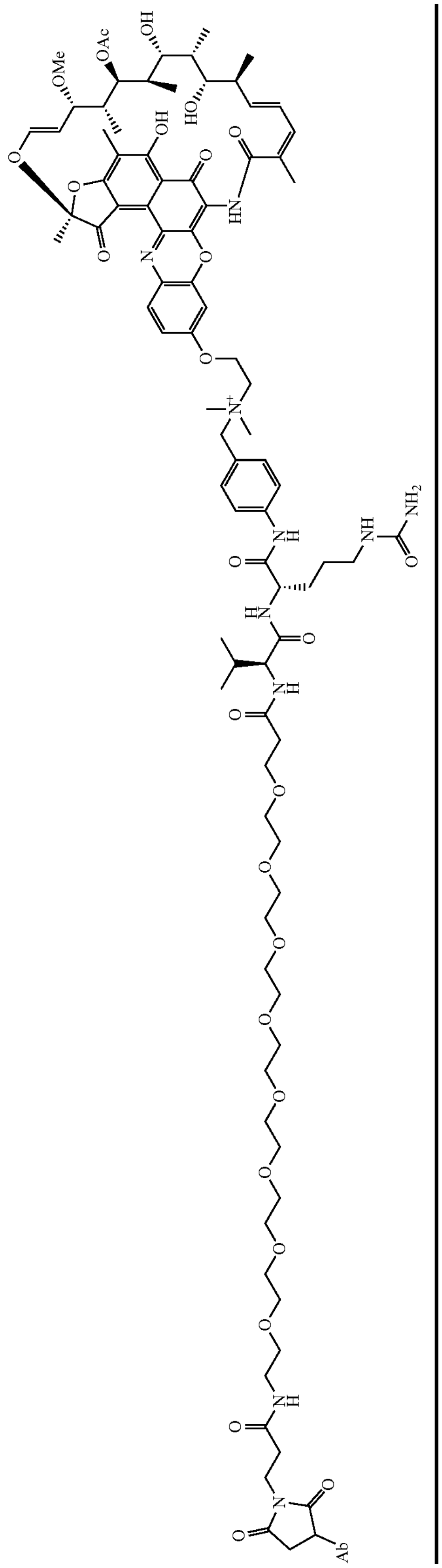

or a stereoisomeric form thereof, or a regioisomer thereof, or a mixture of regioisomers thereof, wherein each Ab is the anti-MSR1 antibody antigen binding fragment thereof;

each BA is

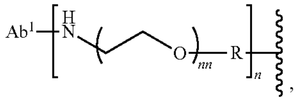

where $Ab^1$ is the anti-MSR1 antibody or antigen-binding fragment thereof;

R is $C_{2-4}$alkylene;

nn is an integer selected from two, three or four; and each n is an integer selected from one to four, inclusive.

5. The antibody-drug conjugate of claim 3, selected from the group consisting of:

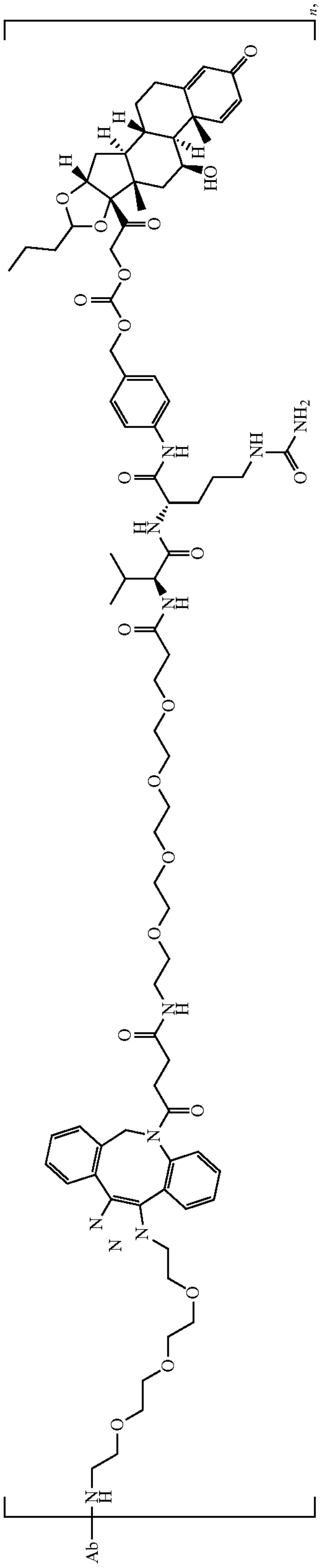
and
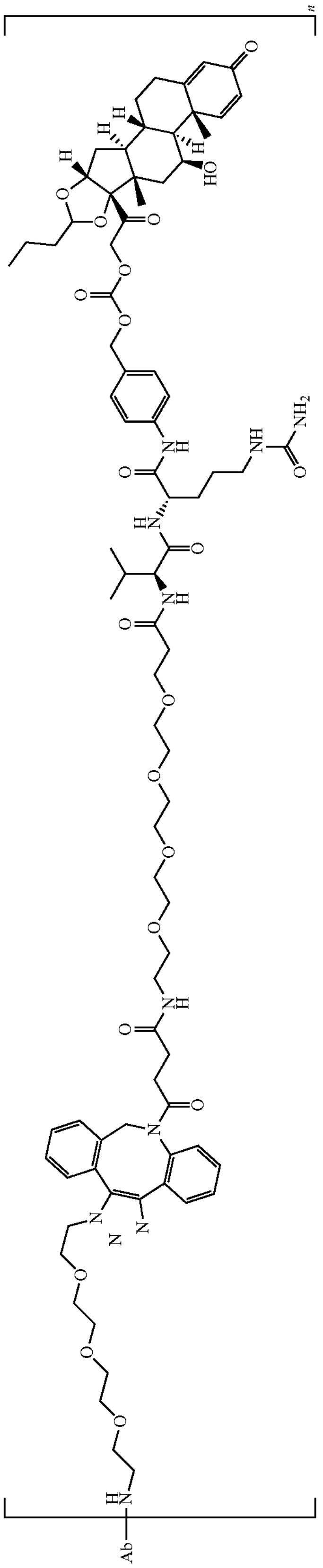

or a stereoisomeric form thereof, or a regioisomer thereof, or a mixture of regioisomers thereof, wherein each Ab is the anti-MSR1 antibody or antigen binding fragment thereof; and each n is an integer from one to four.

6. The antibody-drug conjugate of claim 1, having a structure of Formula (IA):

$$BA{+}RG^1\text{-}SP^1\text{-}AA^1\text{-}AA^2\text{-}(Q)_{0\text{-}1}\text{-}SP\text{-}PA]_n \quad \text{Formula (IA)}$$

wherein

BA is the anti-MSR1 antibody or antigen-binding fragment thereof;

wherein n is one, two, three, or four;

$SP^1$ is absent or a spacer;

$RG^1$ is a reactive group residue;

$AA^1$ is absent or a divalent or trivalent linker comprising an amino acid residue which is bonded directly or indirectly to a HG;

$AA^2$ is absent or a dipeptide, tripeptide, or tetrapeptide residue;

Q, when present, is a connector group residue;

SP is absent or a spacer;

HG, when present, is a hydrophilic group; and

PA is a payload moiety selected from the group consisting of a steroid residue, a LXR modulator residue, and a rifamycin residue.

7. The antibody-drug conjugate of claim 6, wherein

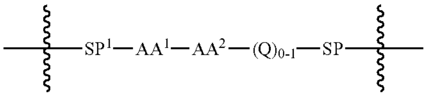 is

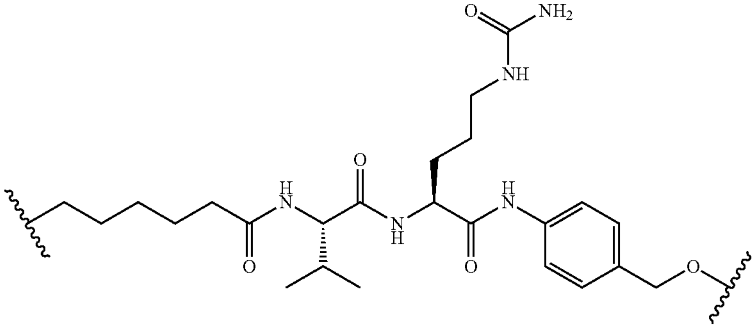

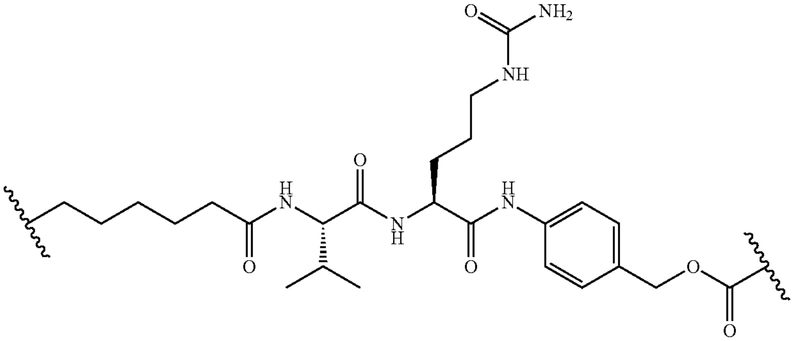

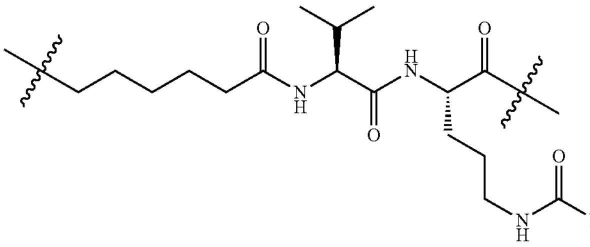

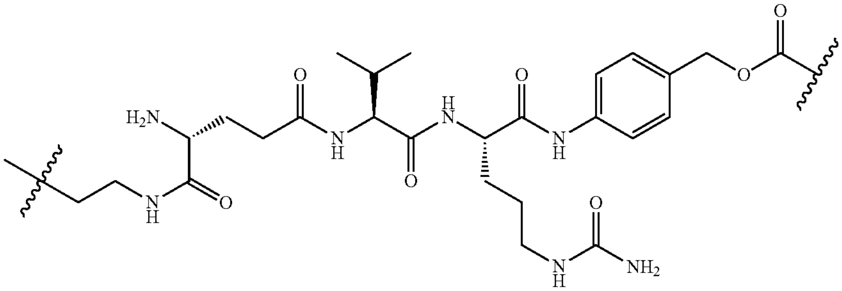

-continued
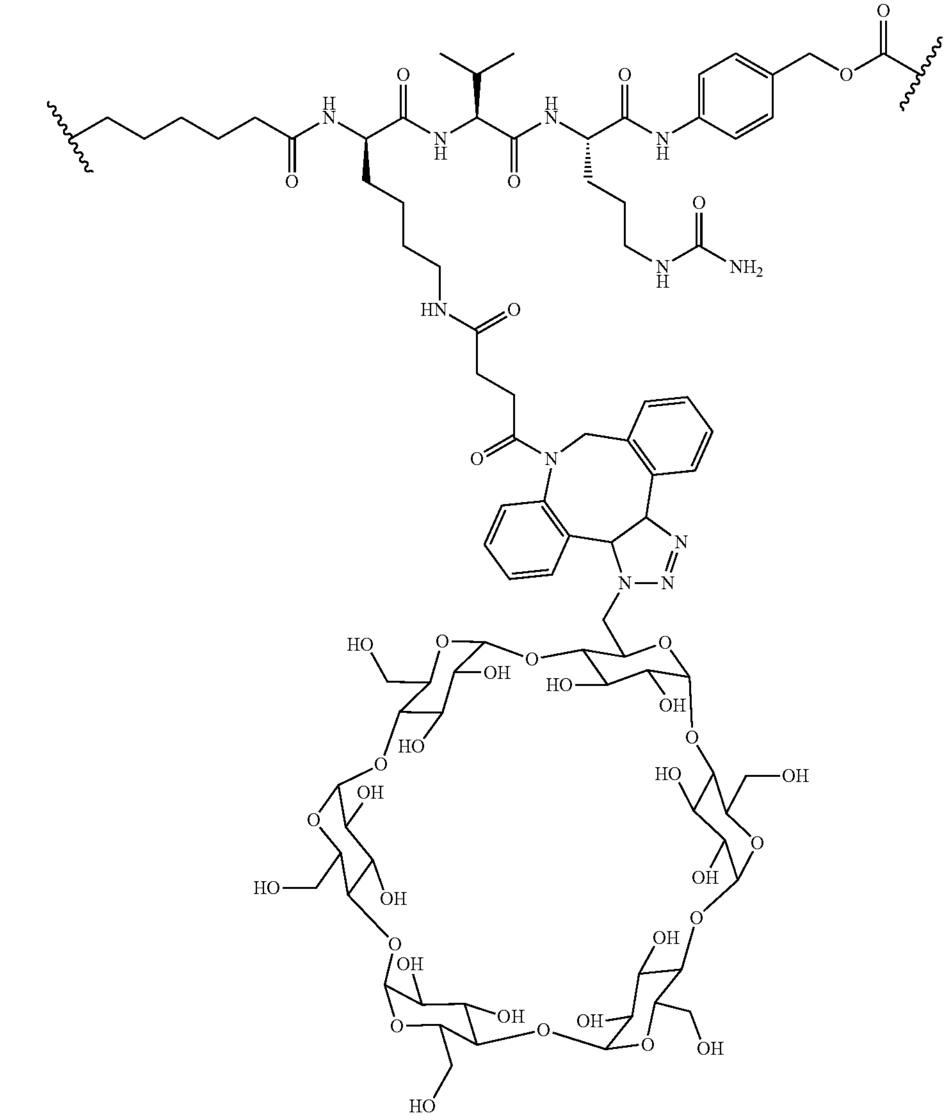
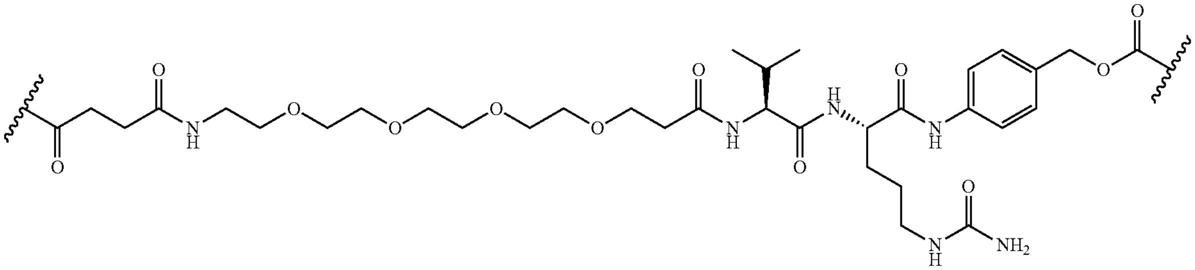
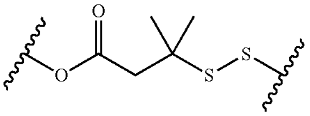 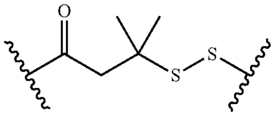 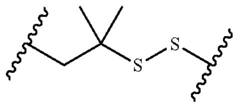
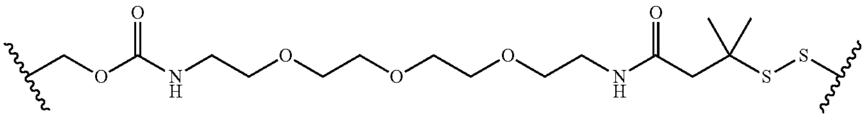

-continued
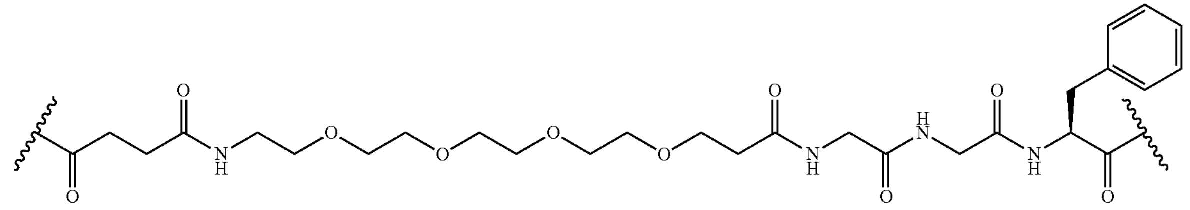
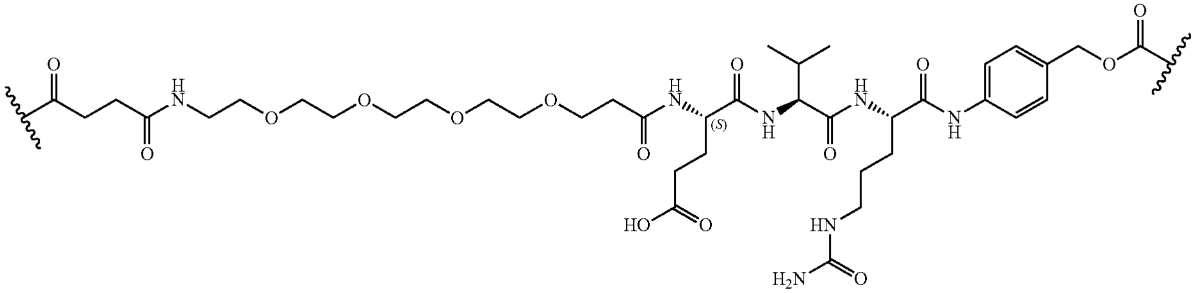
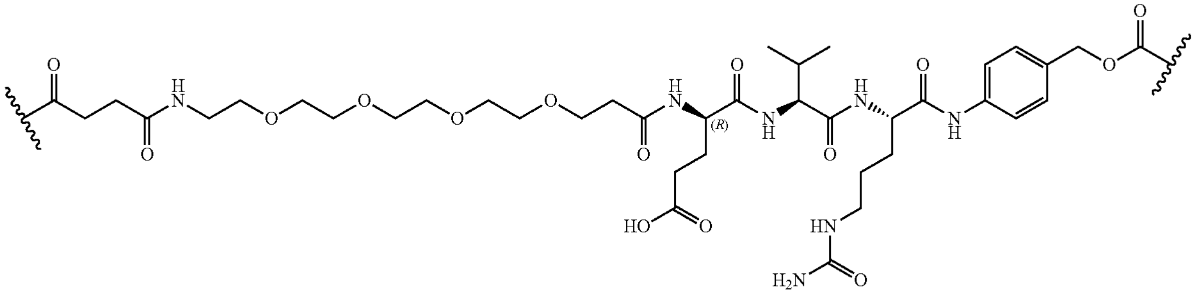
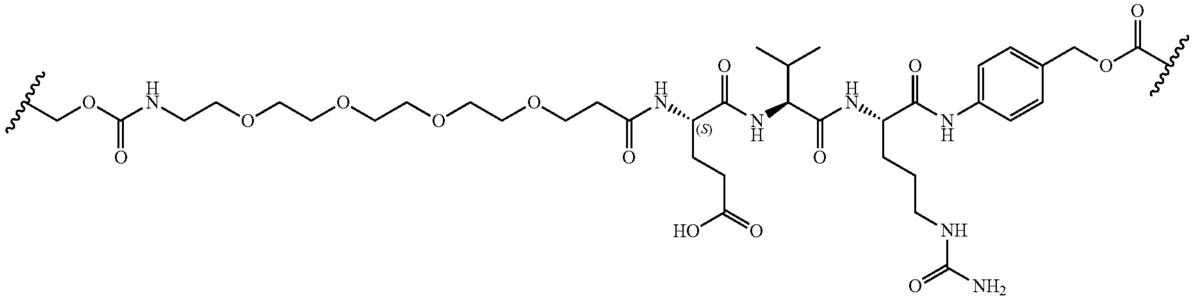
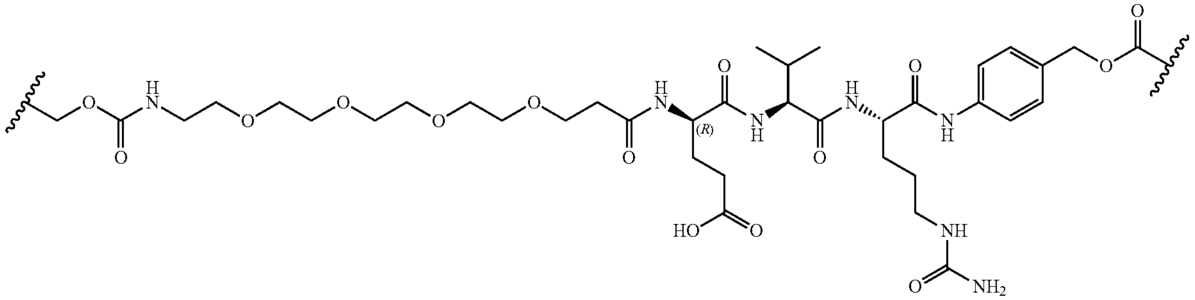
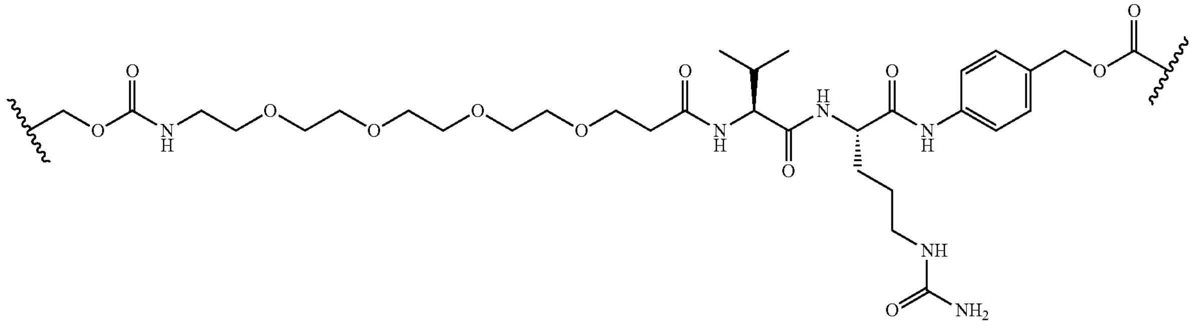

-continued
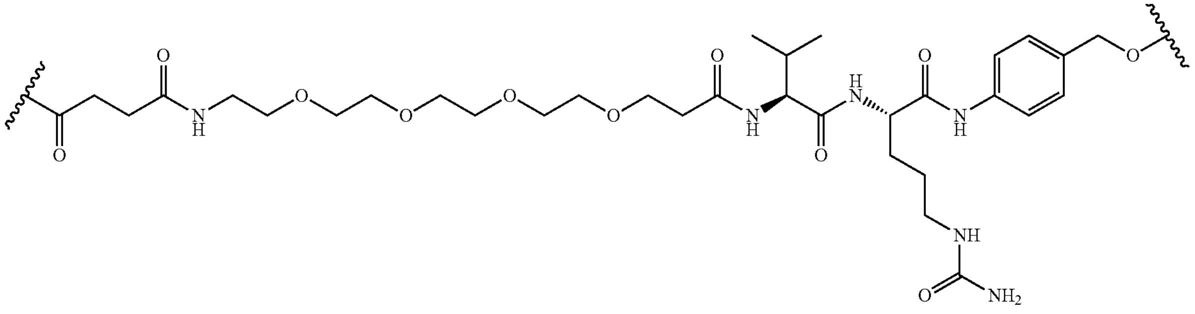
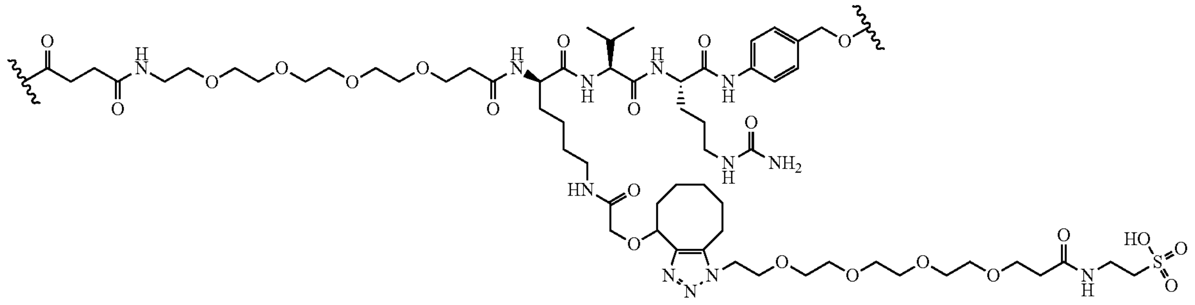
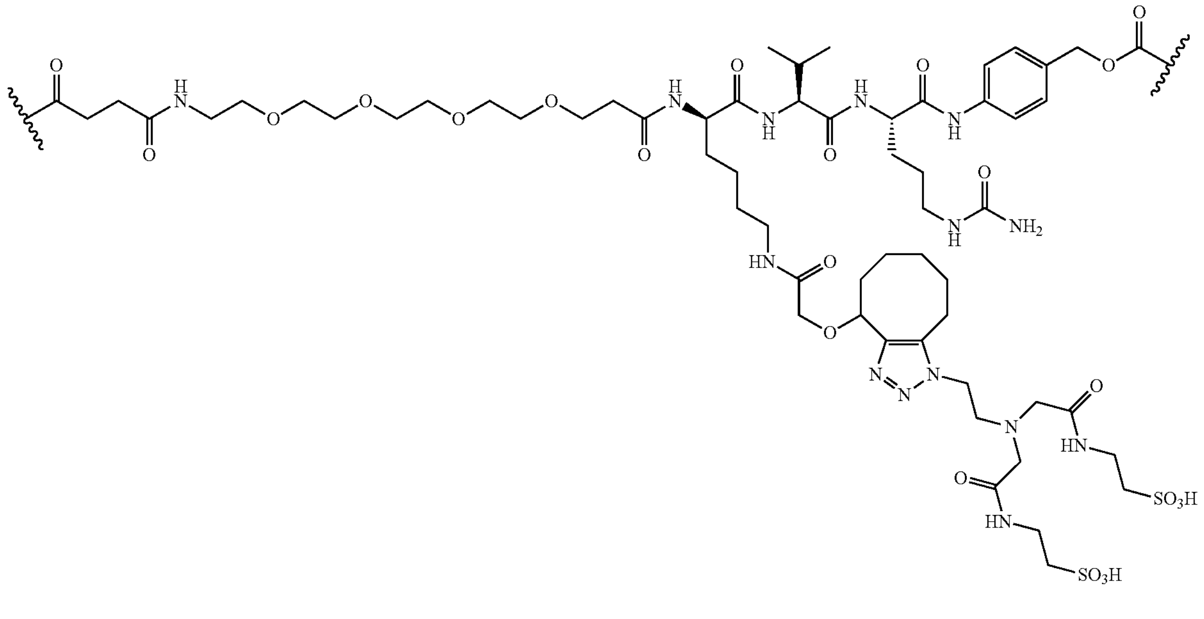
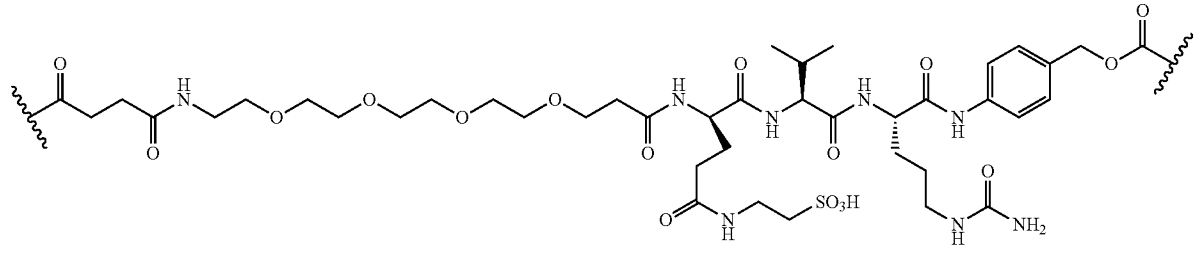

-continued
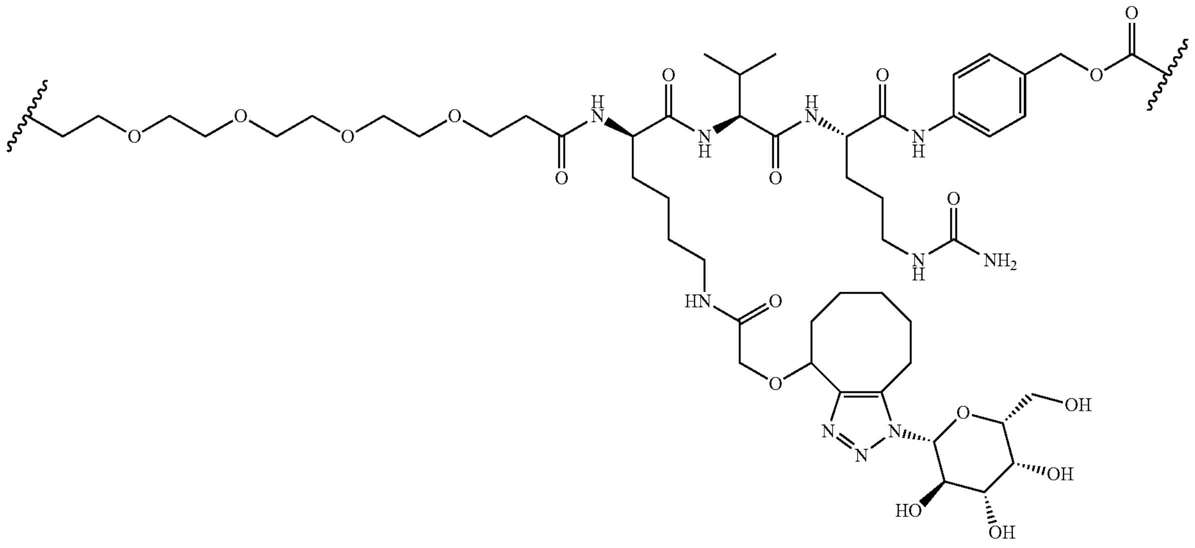
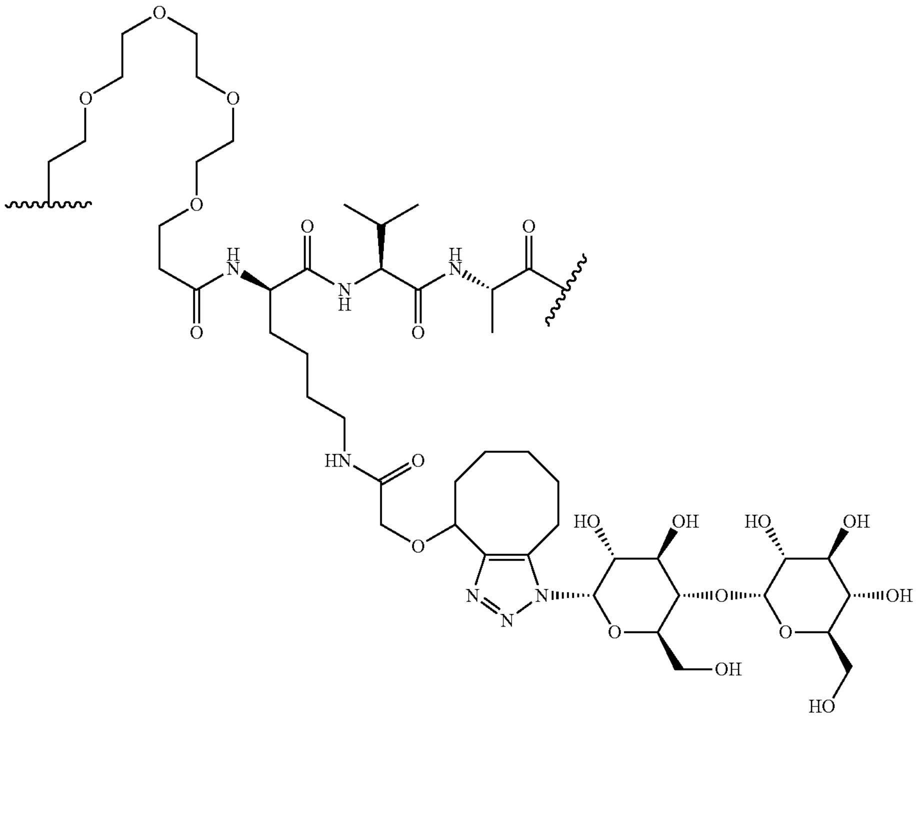
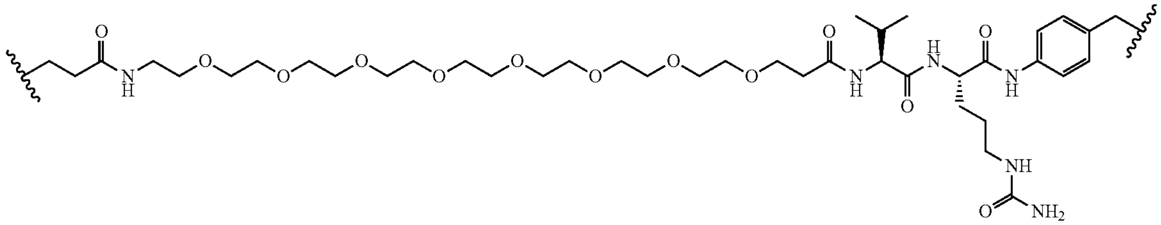
or

-continued

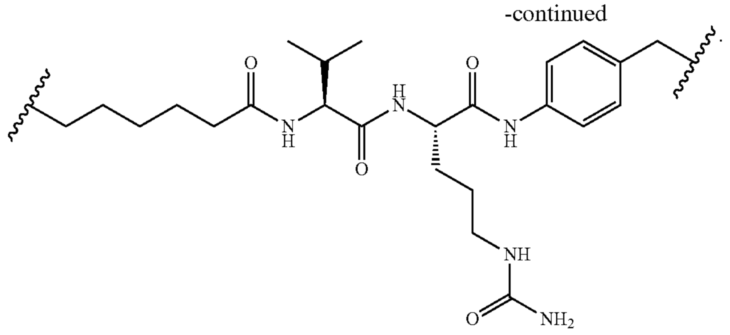

8. The antibody-drug conjugate of claim 1, wherein the anti-MSR1 antibody or antigen-binding fragment thereof is conjugated to a steroid payload through a linker or a linker-spacer.

9. The antibody-drug conjugate of claim 8, wherein the steroid payload conjugated to the anti-MSR1 antibody or antigen-binding fragment thereof through a linker or a linker-spacer is a compound of Formula (A-1)

Formula (A-1)

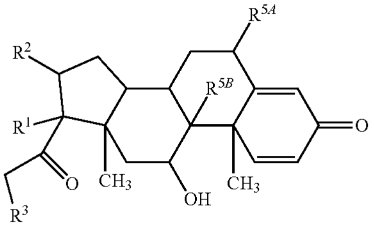

or a pharmaceutically acceptable salt, solvate, or stereoisomeric form thereof;

wherein $R^1$ and $R^2$ are, independently, hydrogen, $C_1$-$C_{20}$alkyl, $C_1$-$C_{20}$alkyl-C(O)—O—, —OH, or halo selected from bromo, chloro, fluoro, and iodo; or $R^1$ and $R^2$ together form

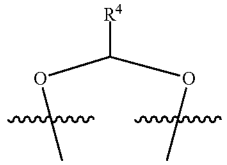

wherein $R^4$ is $C_1$-$C_{20}$alkyl, $C_6$-$C_{20}$aryl, $C_6$-$C_{20}$arylalkyl, 5- or 6-membered N-containing heterocycloalkyl, $C_1$-$C_{20}$alkylene, $C_6$-$C_{20}$arylene, $C_6$-$C_{20}$arylalkylene, or 5- or 6-membered N-containing heterocycloalkylene;

$R^3$ is -O—, $R^z$—C(O)—X—, —$C_1$-$C_{20}$heteroalkylene, piperidinylene, 5- or 6-membered N-containing heterocycloalkylene, —$NR^{Aa}$—, -oxy$C_6$-$C_{20}$aryl-$NR^{Aa}$—, or —Z-A'$(R^P)_t$;

$R^z$ is $C_1$-$C_{20}$ alkylene;

X is —O— or —N($R^{Aa}$)—;

Z is —S—, —S(O)—, —$S(O)_2$—, —$SO_2N(R^{Aa})$—, —O—, —C(O)N($R^{Aa}$)—, —C(O)—, or —N($R^{Aa}$)—;

A' is $C_6$-$C_{20}$ arylene, $C_6$-$C_{20}$ arylalkylene, or a 5- to 20-membered heteroarylene;

$R^P$ is, independently in each instance, halo, selected from bromo, chloro, fluoro, and iodo;

$R^{Aa}$ is hydrogen t is an integer from one to three;

$R^{5A}$ and $R^{5B}$ are each, independently, hydrogen or halo selected from bromo, chloro, fluoro, and iodo; and wherein $R^3$ or $R^4$ is bonded to the linker or the linker-spacer.

10. The antibody-drug conjugate of claim 8, wherein the steroid payload is selected from the group consisting of:

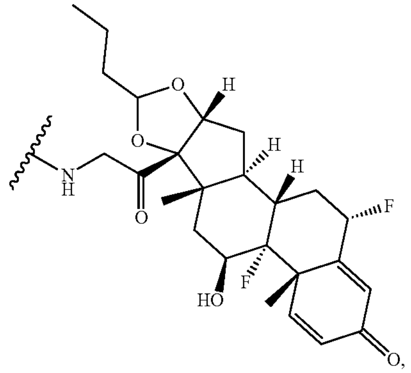

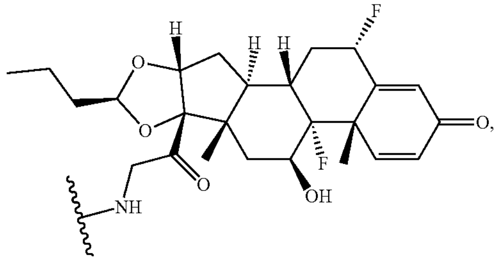

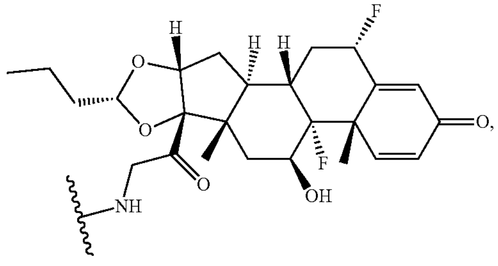

-continued
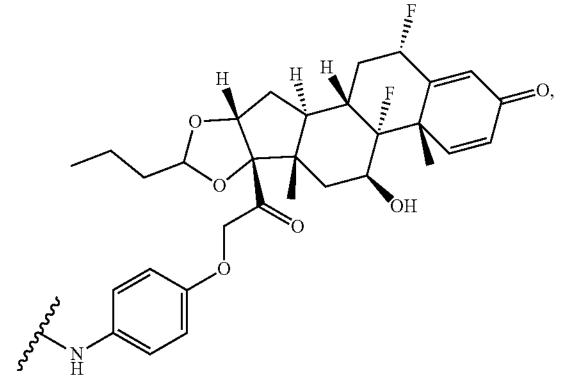
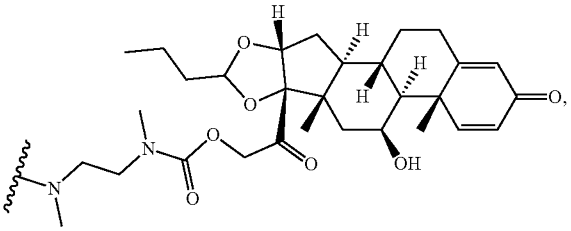
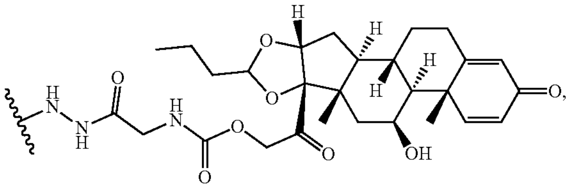
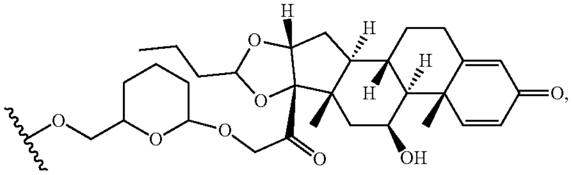
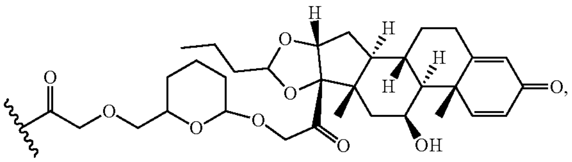
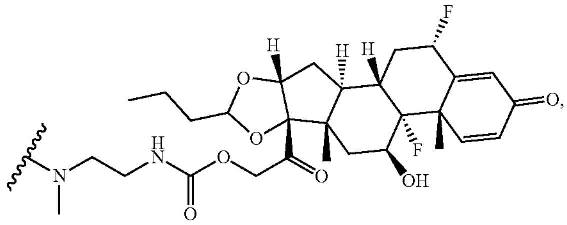
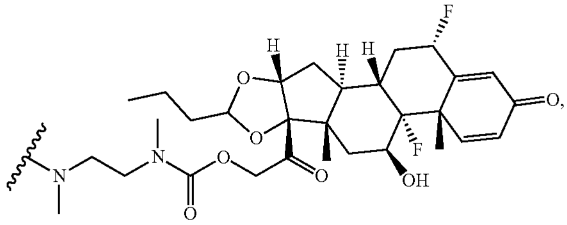
-continued
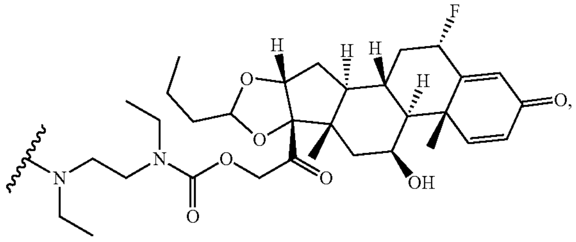
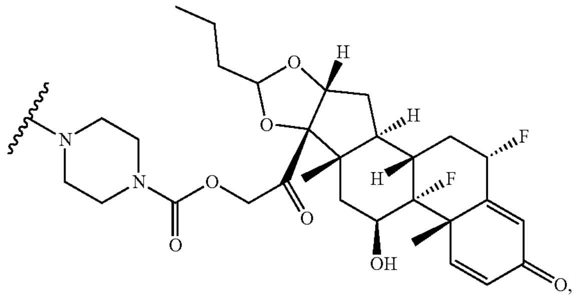
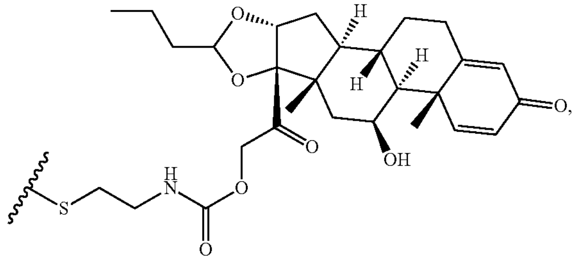
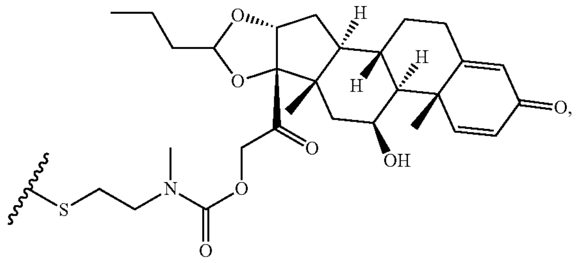
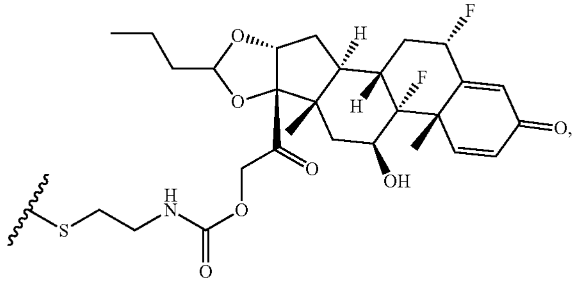
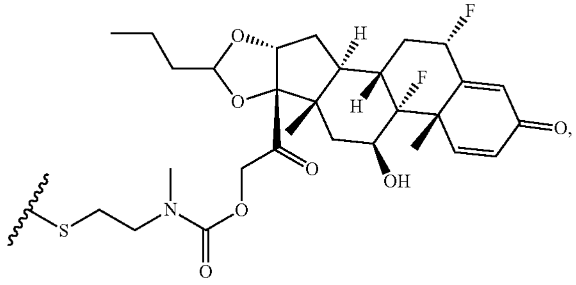

-continued
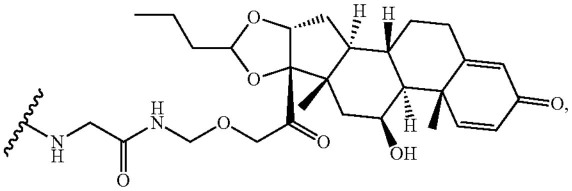
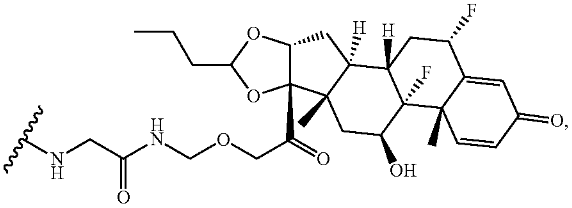
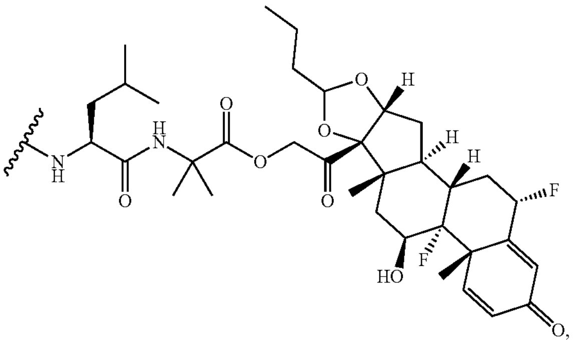
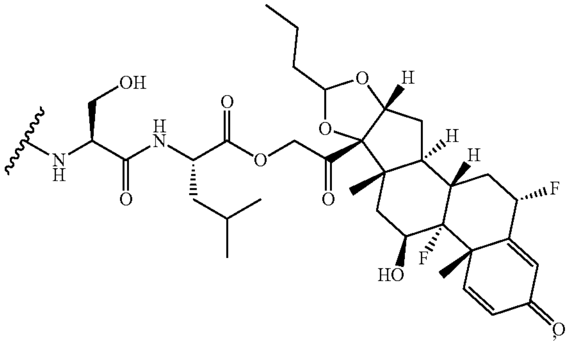
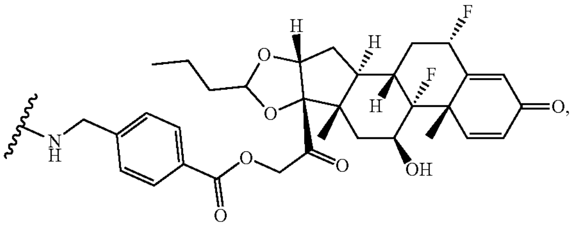
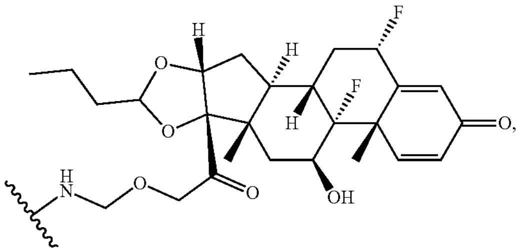
-continued
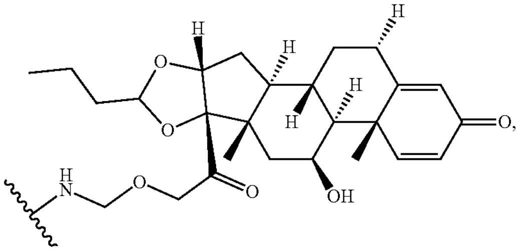
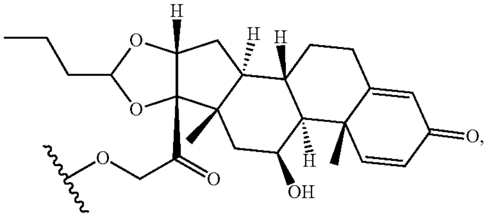
and
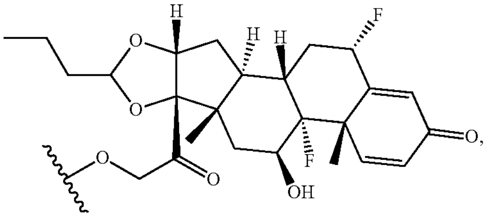
wherein
is the bond to the linker or the linker-spacer.
11. The antibody-drug conjugate of claim 8, wherein the steroid payload is selected from the group consisting of:
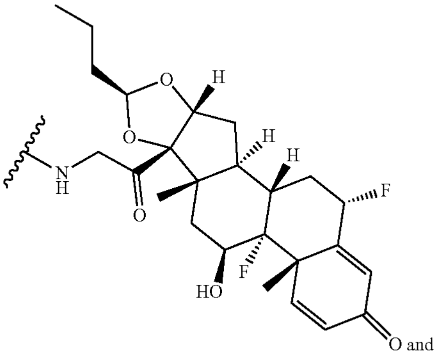
and -continued

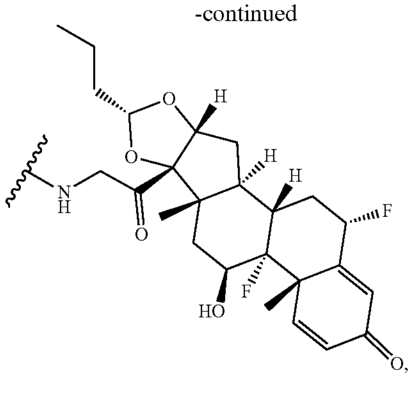

or a mixture thereof.

12. The antibody-drug conjugate of claim 1, wherein the anti-MSR1 antibody or antigen-binding fragment thereof is conjugated to a LXR modulator payload through a linker.

13. The antibody-drug conjugate of claim 12, wherein the LXR modulator payload conjugated to the anti-MSR1 antibody or antigen-binding fragment thereof, through a linker is a compound of Formula (B):

Formula (B)

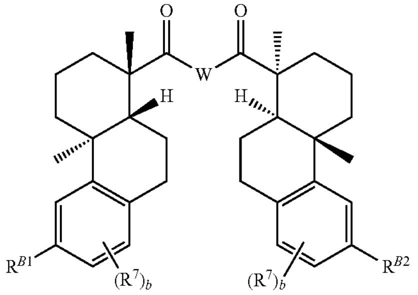

or a pharmaceutically acceptable salt, solvate, or stereoisomeric form, wherein

W is —$CH_2$—, —N(H)—, or —O—;

$R^{B1}$ is hydrogen, —OH, —O—, —$NH_2$, —N(H)—, alkyl, alkylene, —OP(O)($OR^6$) 2 or —OP(O)($OR^6$) $OR^6$—;

$R^{B2}$ is hydrogen, —OH, —O—, —$CH_2NH_2$, —$CH_2$N (H)—, $R^{B3}$, $R^{B4}$, $R^{B5}$, or —O—$R^{B5}$, wherein $R^{B1}$ and $R^{B2}$ are not simultaneously hydrogen;

$R^{B3}$ is —N($R^6$) 2 or —N($R^6$)—$R^6$—;

$R^{B4}$ is —X—Y—Z or —X—Y—Z—;

X is selected from the group consisting of —O— and —N(H)—;

Y is selected from the group consisting of $C_1$-$C_{20}$alkylene, substituted $C_1$-$C_{20}$alkylene, $C_1$-$C_{20}$heteroalkylene, and substituted $C_1$-$C_{20}$heteroalkylene wherein the substituents are selected from the group consisting of halo, cyano, nitro, haloalkyl, azido, epoxy, heteroaryl, heterocycloalkyl,

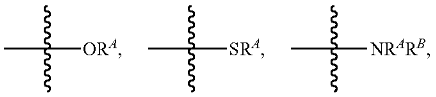

-continued

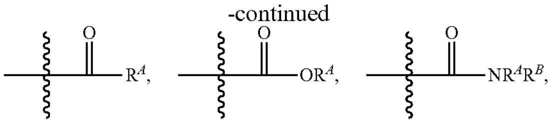

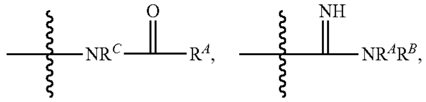

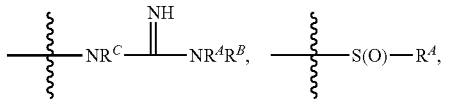

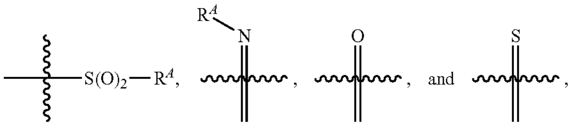

wherein $R^A$, $R^B$, and $R^C$ are, independently at each occurrence, hydrogen, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic or heterocyclic ring;

Z is selected from the group consisting of -OH, -$NH_2$, —O—, and —N(H)—;

$R^{B5}$ is $C_1$-$C_{20}$alkyl, $C_2$-$C_{20}$heterocycloalkyl, substituted $C_2$-$C_{20}$heterocycloalkyl, $C_1$-$C_{20}$alkylene, $C_2$-$C_{20}$heterocycloalkylene, or substituted $C_2$-$C_{20}$heterocycloalkylene wherein each heterocycloalkyl, heterocycloalkylene, or substituted heterocycloalkyl or substituted heterocycloalkylene includes one, two, or three heteroatoms selected from nitrogen and oxygen, and when substituted includes at least one of -OH, and -$CH_2$OH substituent, or at least one a primary or secondary nitrogen, wherein the substituents are selected from the group consisting of halo, cyano, nitro, haloalkyl, azido, epoxy, heteroaryl, heterocycloalkyl,

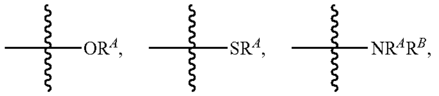

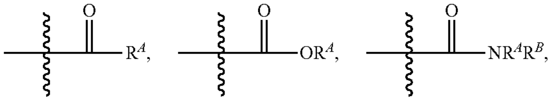

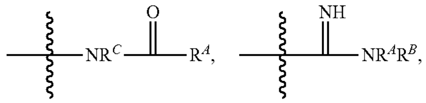

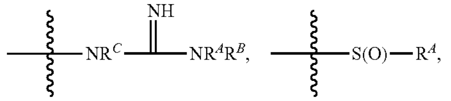

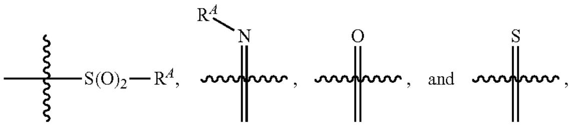

wherein $R^A$, $R^B$, and $R^C$ are, independently at each occurrence, hydrogen, alkyl, alkenyl, alkynyl, aryl, alkylaryl, arylalkyl, heteroalkyl, heteroaryl, or heterocycloalkyl, or $R^A$ and $R^B$ together with the atoms to which they are bonded, form a saturated or unsaturated carbocyclic or heterocyclic ring;

each $R^6$ is, independently, hydrogen, an amino acid residue, an N-alkyl amino acid residue, a peptide comprising two or more amino acid residues, $C_1$-$C_{20}$alkyl, or $C_1$-$C_{20}$alkylene; and each $R^7$ is, independently, halo, $C_{1-6}$ alkyl, $C_{1-6}$ alkoxy, —CN, O-glucose, O-amino acid residue, and O-PEG$_b$, wherein b is an integer from zero to three;

wherein $R^{B1}$ or $R^{B2}$ is bonded to the linker.

14. The antibody-drug conjugate of claim 12, wherein the LXR modulator payload conjugated to the anti-MSR1 antibody or antigen-binding fragment thereof through a linker is a compound of Formula (B-1):

Formula (B-1)

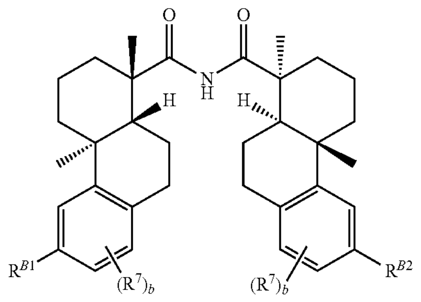

or a pharmaceutically acceptable salt, solvate, or stereoisomeric form thereof; wherein:

$R^{B1}$ is -N(H)$R^8$ or -N($R^9$) $_2$;

$R^{B2}$ is -N(H)$R^8$;

each $R^8$ is, independently in each instance, hydrogen, an amino acid residue, an N-alkyl amino acid residue, a peptide residue comprising two or more amino acid residues, or $C_1$-$C_{20}$alkyl;

$R^3$ is $C_1$-$C_{20}$alkyl, $C_6$-$C_{20}$aryl, $C_6$-$C_{20}$arylalkyl, $C_2$-$C_{20}$heterocycloalkyl, or substituted $C_2$-$C_{20}$heterocycloalkyl, wherein each heterocycloalkyl or substituted heterocycloalkyl comprises one, two, or three heteroatoms selected from nitrogen and oxygen, and when substituted includes at least one-OH, —$CH_2$OH, or primary or secondary nitrogen;

each $R^7$ is independently halo, $C_{1-6}$ alkyl, $C_{1-6}$alkoxy, —CN, O-glucose, O-amino acid residue, or O-PEG$_b$, wherein each subscript b is an integer from zero to three; and wherein $R^{B1}$ or $R^{B2}$ is bonded to the linker.

15. The antibody-drug conjugate of claim 14, having the structure of Formula (6005)

Formula (6005)

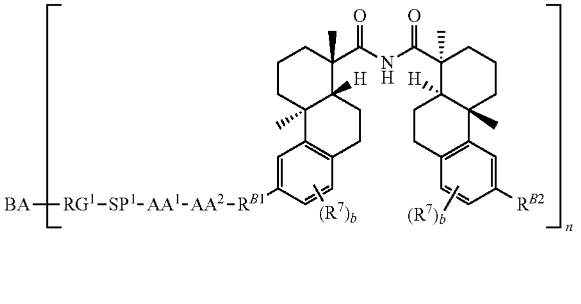

wherein BA is the anti-MSR1 antibody or antigen-binding fragment thereof;

wherein n is one, two, three, or four;

$RG^1$ is a reactive group residue;

$SP^1$ is absent or a spacer;

$AA^1$ is absent or a divalent or trivalent linker comprising an amino acid residue which is bonded directly or indirectly to a HG;

HG, when present, is a hydrophilic group; and $AA^2$ is absent or a dipeptide, tripeptide, or tetrapeptide residue.

16. The antibody-drug conjugate of claim 12, wherein the LXR modulator payload is selected from the group consisting of:

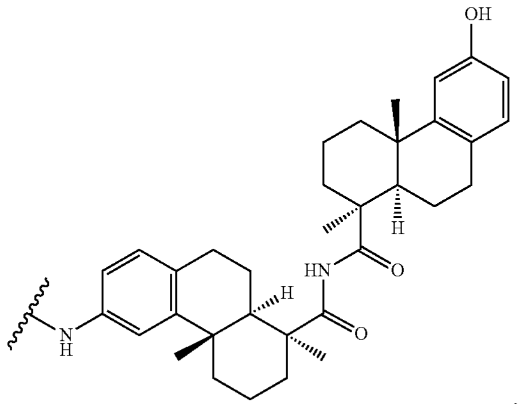

,

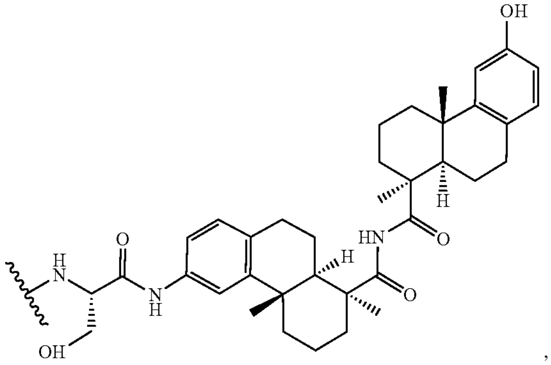

,

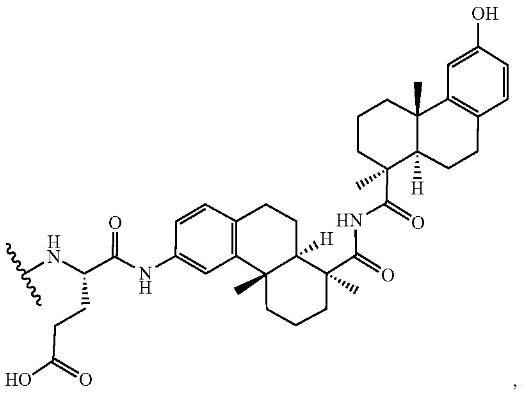

, and

-continued
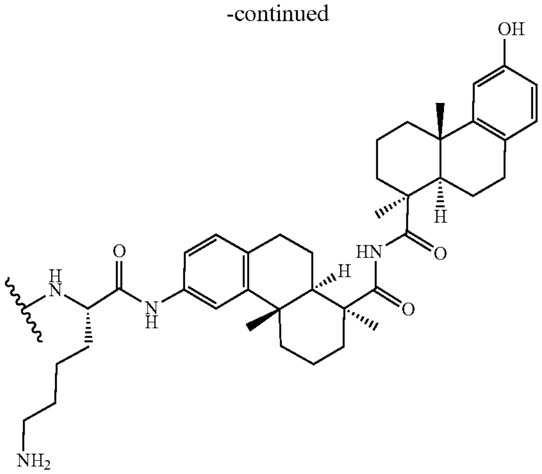
,
wherein
is the bond to the linker.
17. The antibody-drug conjugate of claim 12, wherein the LXR modulator payload is selected from the group consisting of:
P4B
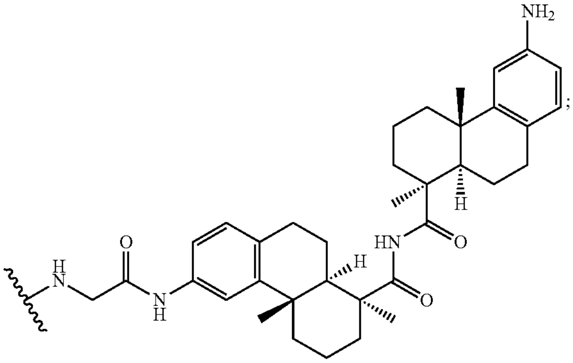
;
P5B
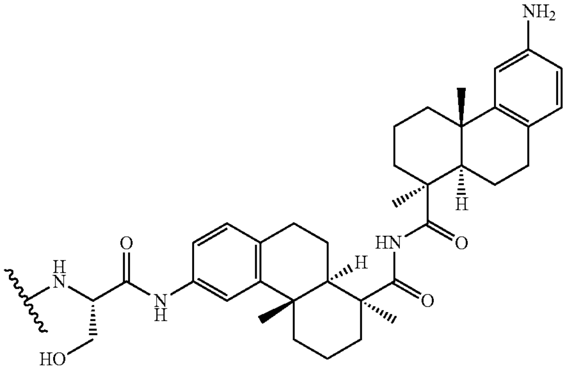
;
P6B
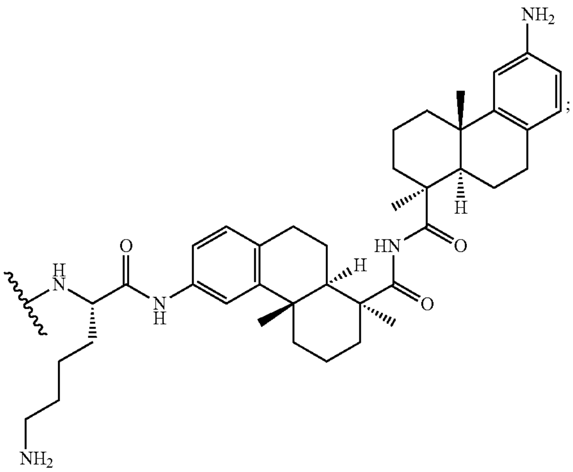
;
P7B
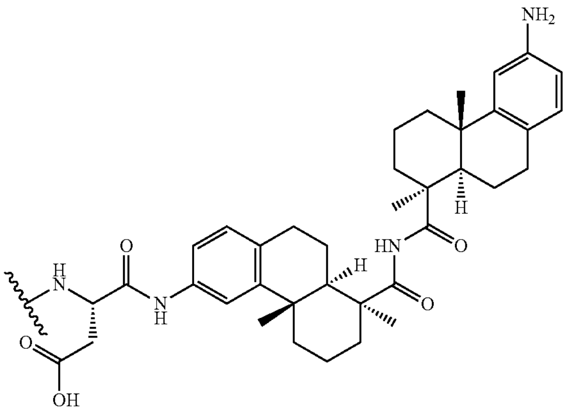
;

-continued
P8B
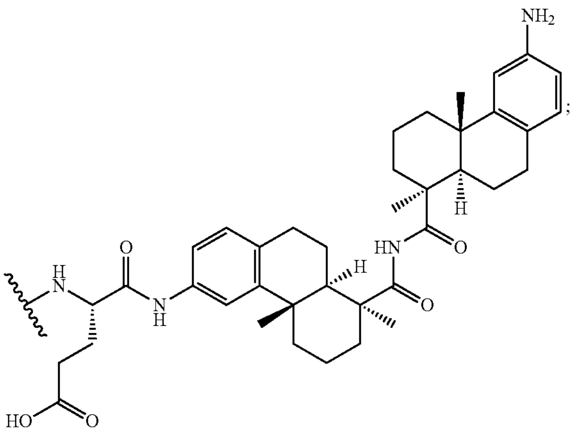
P9B
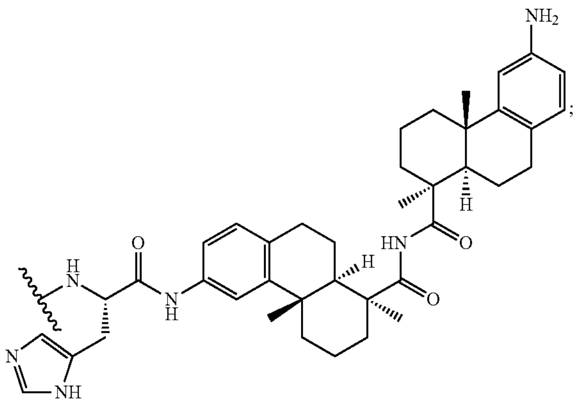
P12B
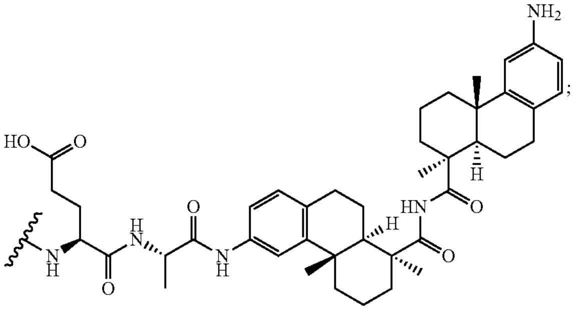
P2B
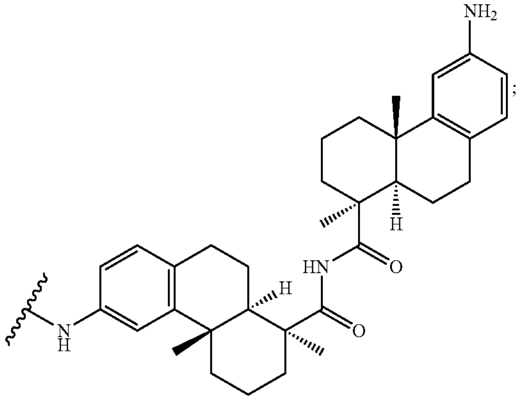
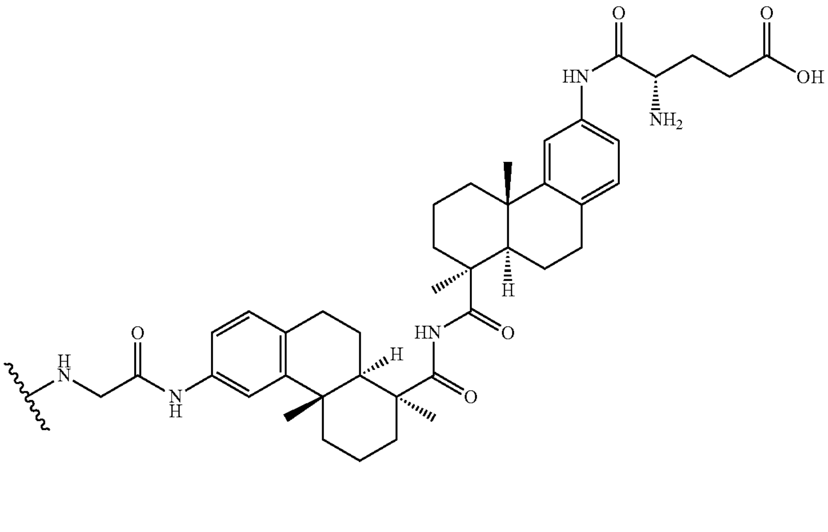
or -continued
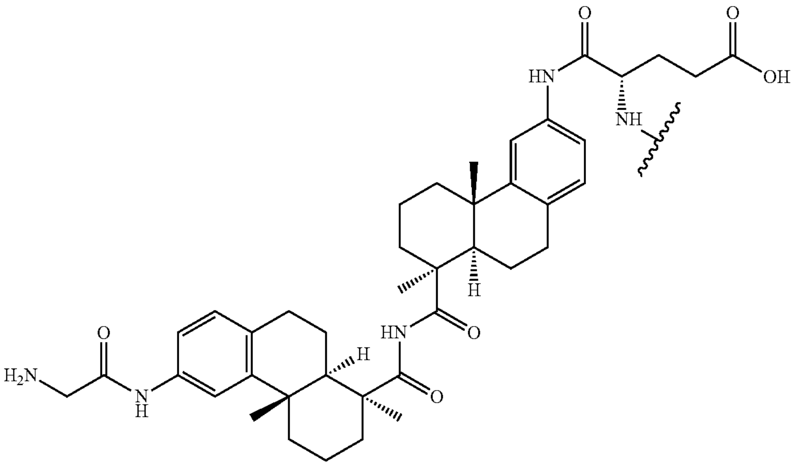
or
P10B
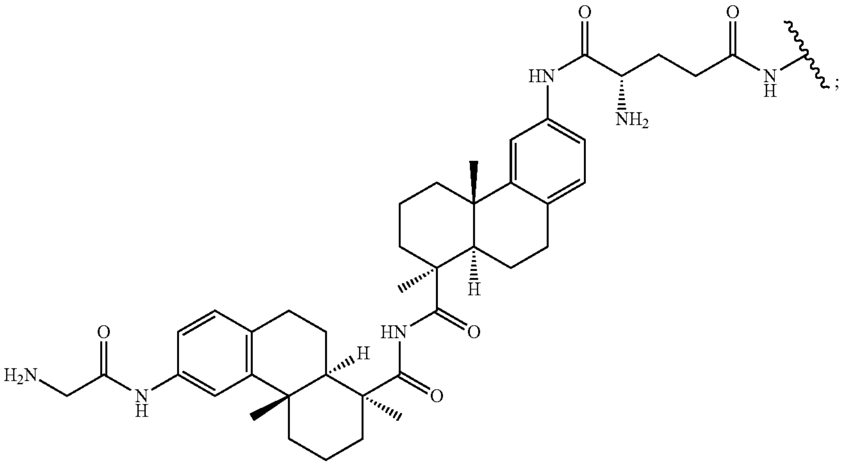
;
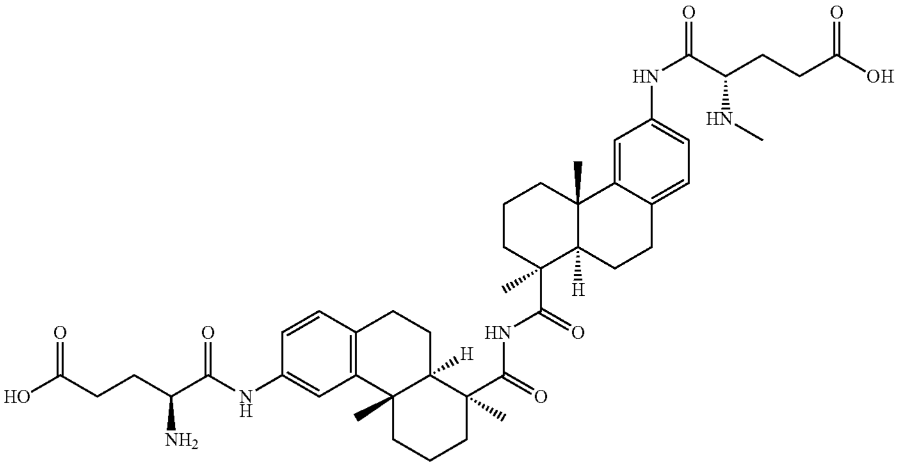

-continued
P11B
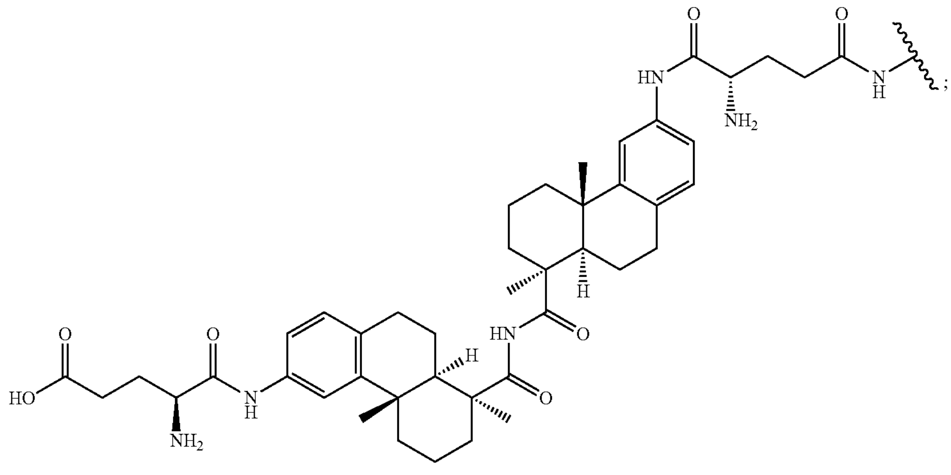
; and
P3B
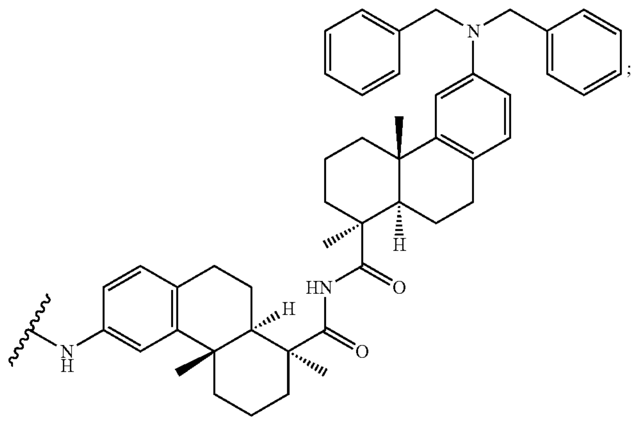
;
and
wherein
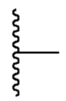
is the bond to the linker.
18. The antibody-drug conjugate of claim 12, wherein the LXR modulator payload is
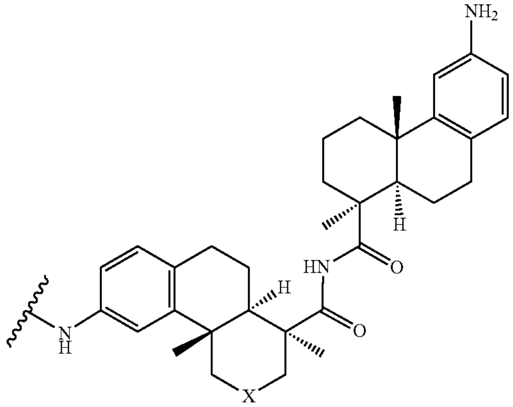
or -continued

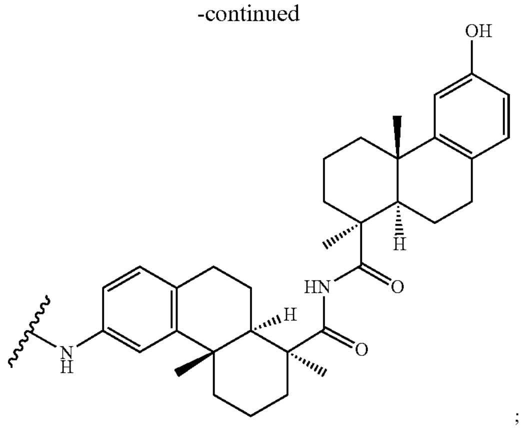

;

wherein

is the bond to the linker.

19. The antibody-drug conjugate of claim 1, wherein the anti-MSR1 antibody or antigen-binding fragment thereof is conjugated to a rifamycin payload through a linker.

20. The antibody-drug conjugate of claim 19, wherein the rifamycin payload is a compound of Formula (C-1):

Formula (C-1)

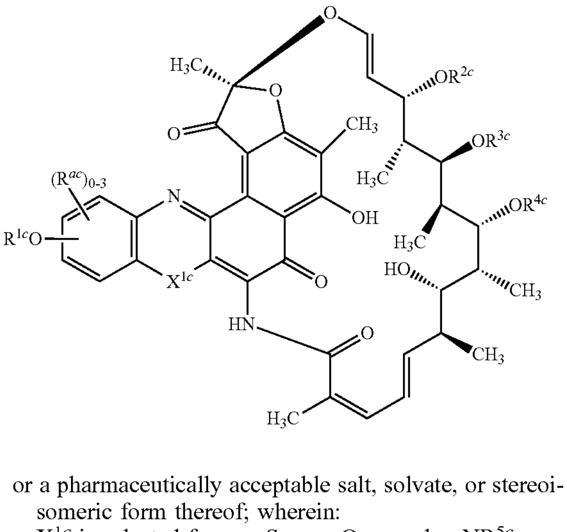

or a pharmaceutically acceptable salt, solvate, or stereoisomeric form thereof; wherein:

$X^{1c}$ is selected from —S—, —O—, and —$NR^{5c}$—;

$R^{1c}$ is amino-$C_{1-6}$ alkyl; $C_{1-6}$ alkylamino; $C_{1-6}$ alkyl; di-$C_{1-6}$ alkylamino; $C_{1-6}$ alkyl; hydroxy-$C_{1-6}$alkyl; HS-$C_{1-6}$ alkyl; $(R^{5c})_2$N-$C_{1-6}$alkylene-N($R^{5c}$)-$C_{1-6}$alkyl; $(R^{5c})_2$N-$C_{1-6}$alkylene-O-$C_{1-6}$alkyl; $(R^{5c})_2$ N-$C_{1-6}$alkylene-S-$C_{1-6}$alkyl; $C_2$-$C_{20}$heterocycloalkyl; or $C_{2-20}$heterocycloalkyl; wherein $C_2$-$C_{20}$heterocycloalkyl includes one, two, or three heteroatoms selected from oxygen, nitrogen, and sulfur;

$R^{2c}$, $R^{3c}$, and $R^{4c}$ are independently selected from hydrogen, $C_{1-6}$alkyl, and -(C═O)-$R^{5c}$;

each $R^{ac}$, when present, is independently selected from fluoro, chloro, bromo, iodo, —OH, —$NH_2$, and $C_{1-6}$ alkoxy;

$R^{5c}$ is independently, at each occurrence, selected from hydrogen and $C_{1-6}$ alkyl; and wherein $R^{1c}$ is bonded to the linker.

21. The antibody-drug conjugate of claim 19, wherein the rifamycin payload is a compound of Formula (C-2):

Formula (C-2)

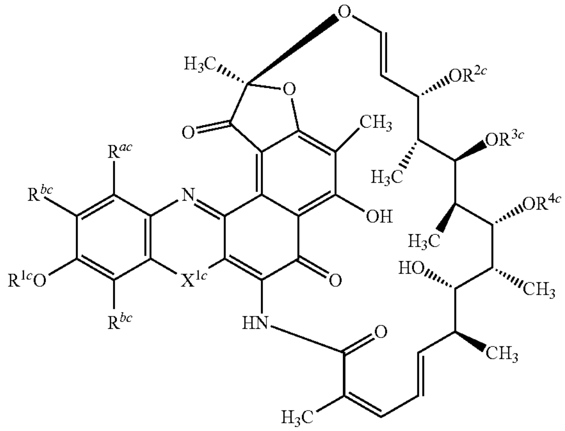

or a pharmaceutically acceptable salt, solvate, or stereoisomeric form thereof; wherein:

$X^{1c}$ is selected from —S—, —O—, and —$NR^{5c}$—;

$R^{1c}$ absent, is -amino-$C_{1-6}$ alkylene; $C_{1-6}$alkylene-amino-; $C_{1-6}$ alkylene; -di-$C_{1-6}$alkylamino$C_{1-6}$alkylene; —O—$C_{1-6}$alkylene; —S—$C_{1-6}$alkylene; —$R^{5c}$-($R^{5c}$)N—$C_{1-6}$alkylene-N($R^{5c}$)—$C_{1-6}$alkylene; —$R^{5c}$-($R^{5c}$)N—$C_{1-6}$ alkylene-O—$C_{1-6}$alkylene; —$R^{5c}$-($R^{5c}$)N—$C_{1-6}$alkylene-S—$C_{1-6}$alkylene; $C_2$-$C_{20}$heterocycloalkyl heterocycloalkylene or $C_2$-$C_{20}$heterocycloalkyl-$C_{1-6}$alkylene; wherein $C_2$-$C_{20}$ heterocycloalkylene includes one, two, or three heteroatoms selected from oxygen, nitrogen, and sulfur;

$R^{2c}$, $R^{3c}$, and $R^{4c}$ are independently selected from hydrogen, $C_{1-6}$alkyl, and —(C═O)—$R^{5c}$;

$R^{ac}$ and $R^{bc}$ are independently selected from fluoro, chloro, bromo, iodo, —OH, —$NH_2$, and $C_{1-6}$alkoxy; and $R^{5c}$ is independently, at each occurrence, selected from hydrogen and $C_{1-6}$alkyl; and wherein $R^{1c}$ is bonded to the linker.

22. The antibody-drug conjugate of claim 19, wherein the rifamycin payload is a compound of Formula (C-3):

Formula (C-3)

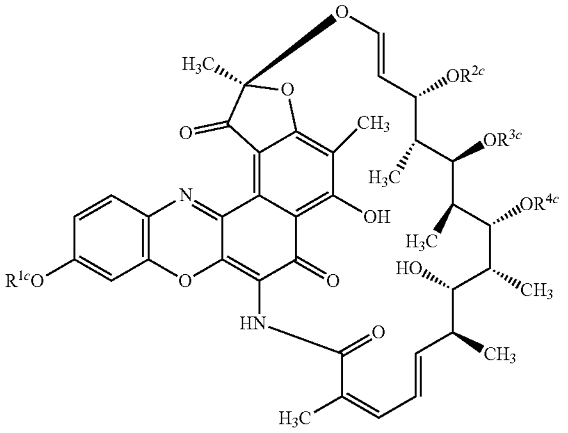

or a pharmaceutically acceptable salt, solvate, or stereoisomeric form thereof;

wherein:

$R^{1c}$ is di-$C_{1-6}$alkylamino$C_{1-6}$alkylene; $(R^{5c})_2$N-$C_{1-6}$alkylene-N($R^{5c}$)-$C_{1-6}$alkylene;

$C_2$-$C_{20}$heterocycloalkylene or $C_2$-$C_{20}$heterocycloalkyl-$C_{1-6}$alkylene; wherein $C_2$-$C_{20}$ heterocycloalkylene includes one, two, or three heteroatoms selected from oxygen, nitrogen, and sulfur;

$R^{2c}$, $R^{3c}$, and $R^{4c}$ are independently selected from hydrogen, $C_{1-6}$alkyl, and -(C═O)-$R^{5c}$;

$R^{5c}$ is selected from hydrogen and $C_{1-6}$alkyl; and wherein $R^{1c}$ is bonded to the linker.

23. The antibody-drug conjugate of claim 19, wherein the rifamycin payload is a compound of Formula (C-4):

Formula (C-4)

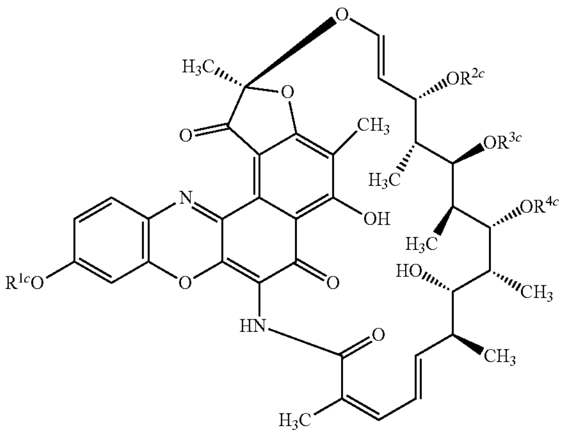

or a pharmaceutically acceptable salt, solvate, or stereoisomeric form thereof; wherein:

$R^{1c}$ is

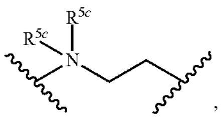

,

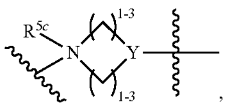

, or

-continued

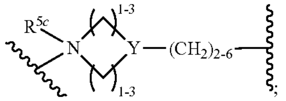

wherein Y is carbon or nitrogen;

$R^{2c}$, $R^{3c}$, and $R^{4c}$ are independently selected from hydrogen, $C_{1-6}$alkyl, and -(C═O)-$R^{5c}$;

$R^{5c}$ is independently, at each occurrence, absent, or selected from hydrogen and $C_{1-6}$alkyl; and wherein $R^{1c}$ is bonded to the linker via a bond to the nitrogen atom as indicated by

.

24. The antibody-drug conjugate of claim 19, wherein the rifamycin payload is selected from the group consisting of:

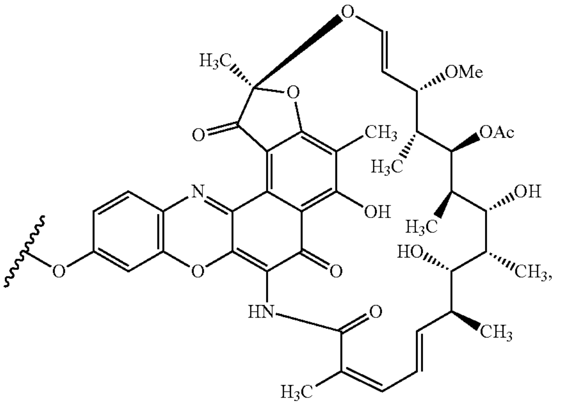

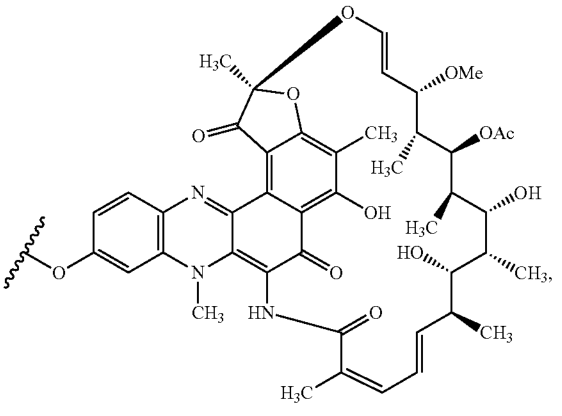

-continued
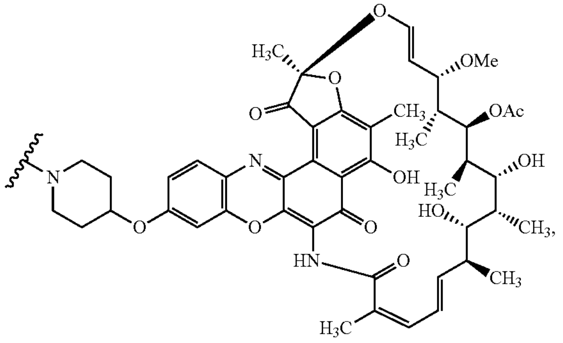
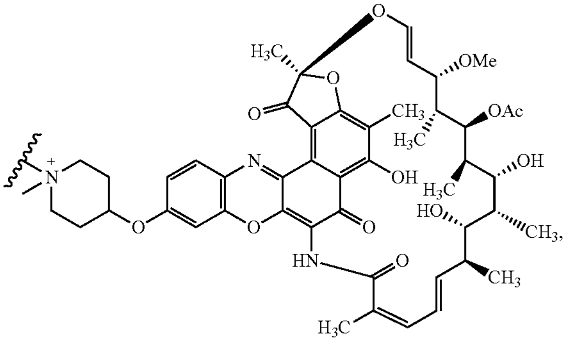
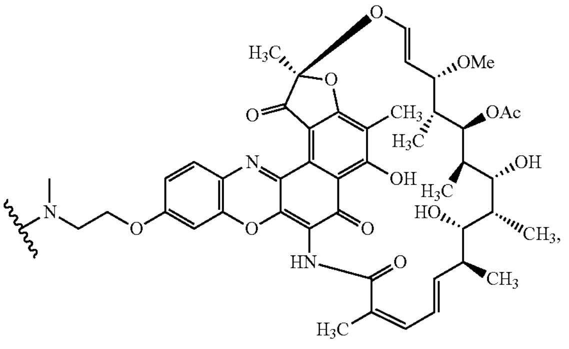
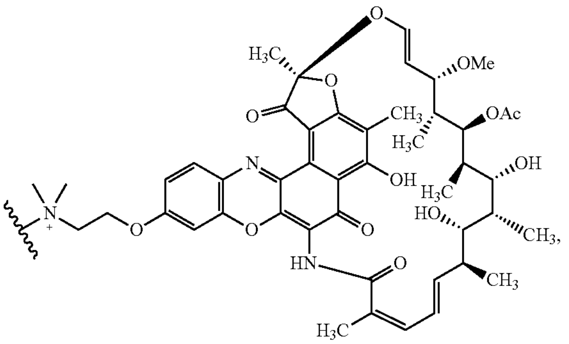
-continued
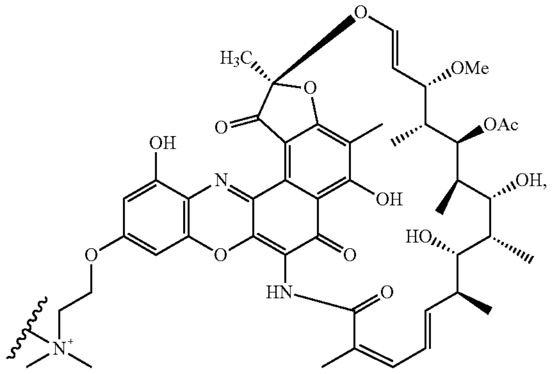
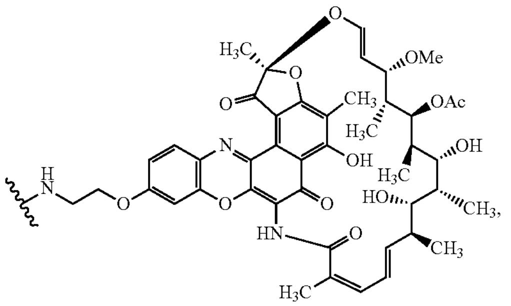
and
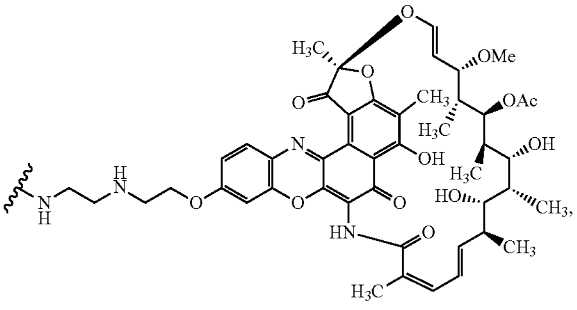
wherein
is the bond to the linker.
25. The antibody-drug conjugate of claim 19 having a structure of Formula (7003):

Formula (7003)

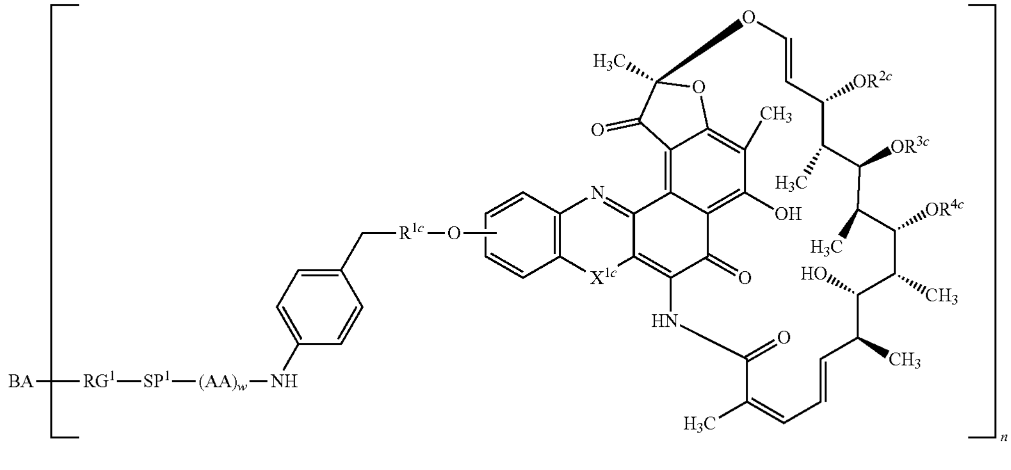

or a pharmaceutically acceptable salt, solvate, or stereoisomeric form thereof; wherein:

$X^{1c}$ is selected from —S—, —O—, and —$NR^{5c}$—;

$R^{1c}$ is

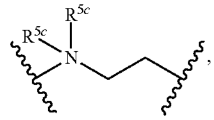,
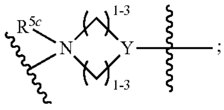;
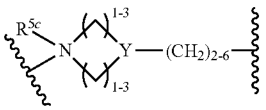
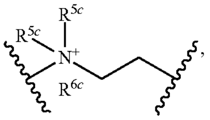,
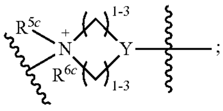; or
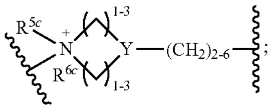;

wherein Y is carbon or nitrogen;

$R^{2c}$, $R^{3c}$, and $R^{4c}$ are independently selected from hydrogen, $C_{1-6}$alkyl, and -(C═O)-$R^{5c}$;

$R^{5c}$ is independently, at each occurrence, absent or selected from hydrogen and $C_{1-6}$alkyl;

each AA is an independently selected amino acid residue;

$SP^1$ is absent or a spacer;

$RG^1$ is a reactive group residue;

BA is the anti-MSR1 antibody or antigen binding fragment thereof;

n is an integer from one to thirty; and w is two, three, or four;

wherein $R^{1c}$ is bonded to the linker via a bond to the nitrogen atom as indicated by the wavy line

.

and $R^{6c}$ is a counter ion.

26. The antibody-drug conjugate of claim 19, wherein the rifamycin payload is:

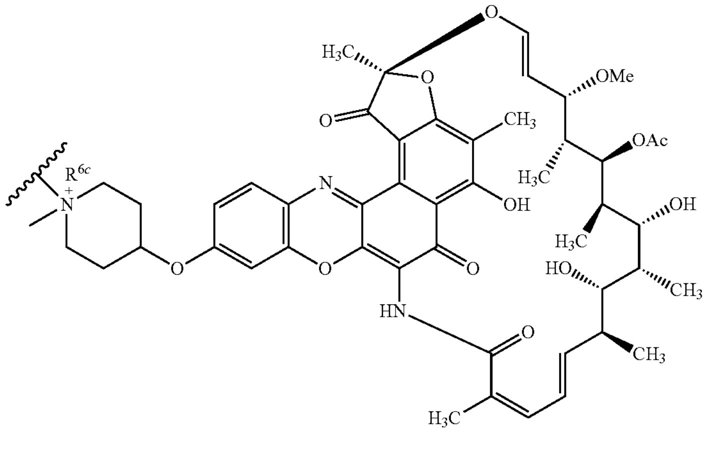

or

-continued

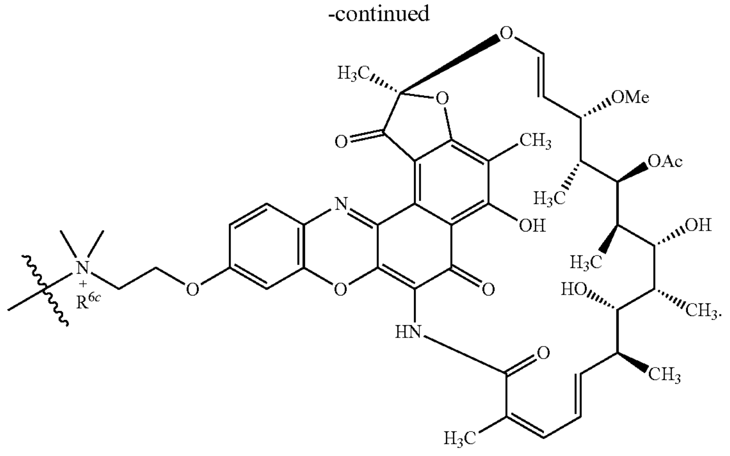

27. The antibody-drug conjugate of claim 1, having a structure of Formula (7002):

Formula (7002)

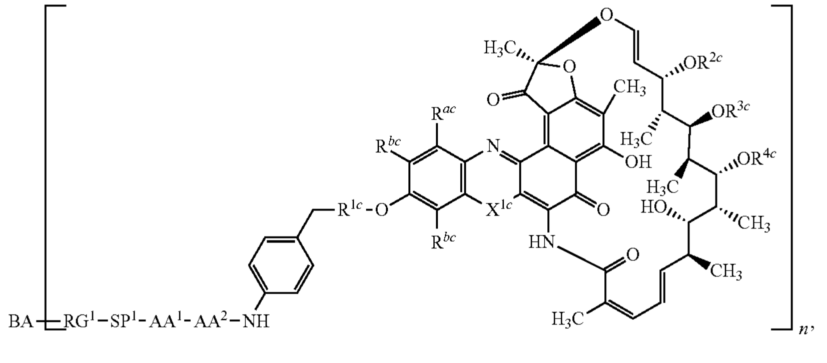

wherein BA is the anti-MSR1 antibody or antigen-binding fragment thereof;

wherein n is one, two, three, or four;

$RG^1$ is a reactive group residue;

$SP^1$ is absent or a spacer;

$AA^1$ is absent or a divalent or trivalent linker comprising an amino acid residue which is bonded directly or indirectly to a HG;

HG, when present, is a hydrophilic group;

$AA^2$ is absent or a dipeptide, tripeptide, or tetrapeptide residue; and

SP is absent or a spacer.

28. The antibody-drug conjugate of claim 1, selected from the group consisting of:

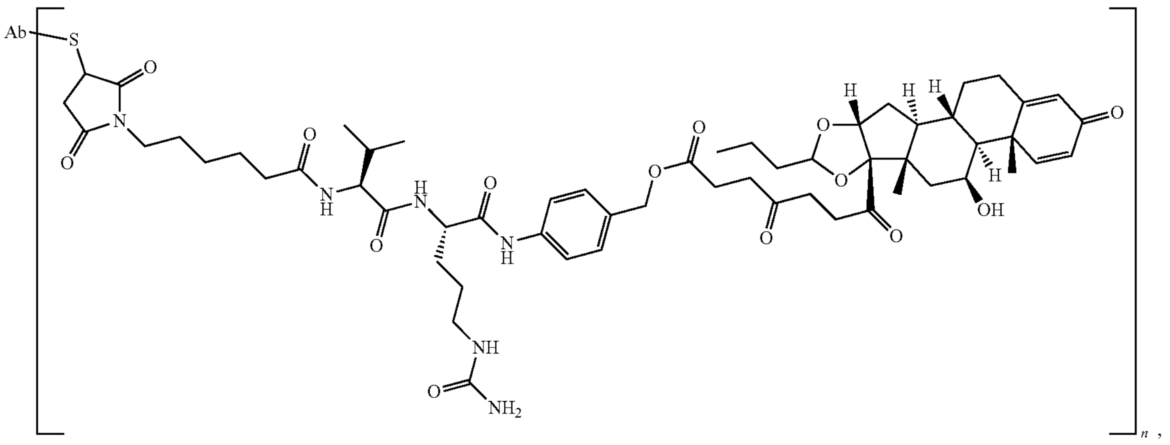

-continued
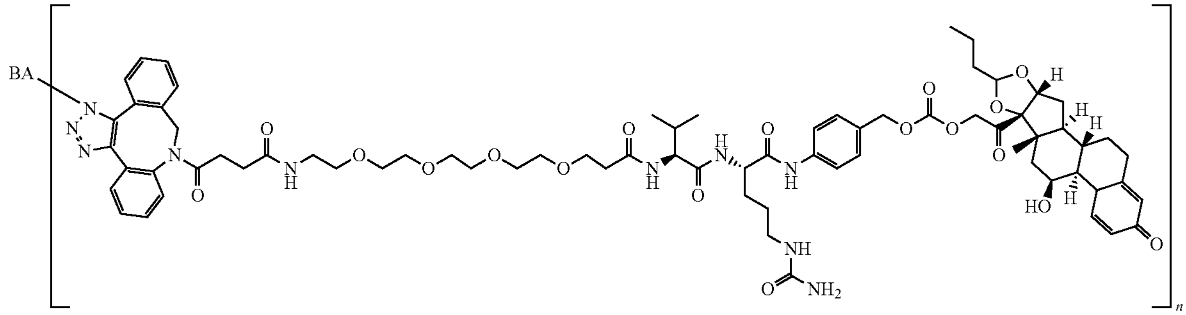
,
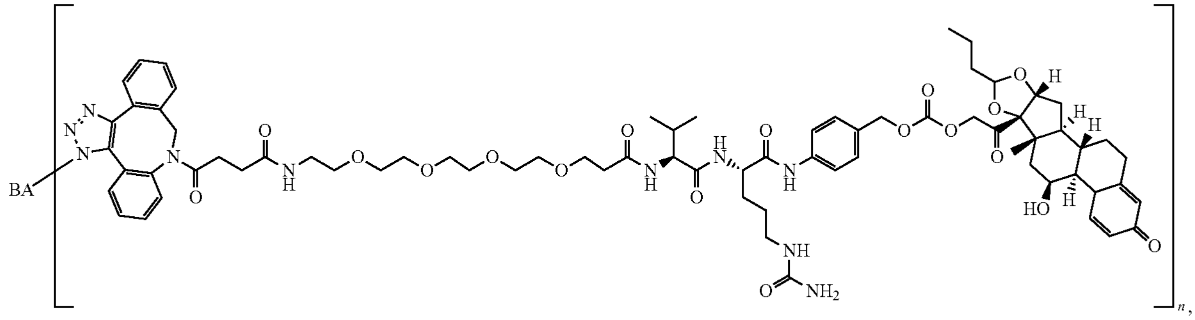
,
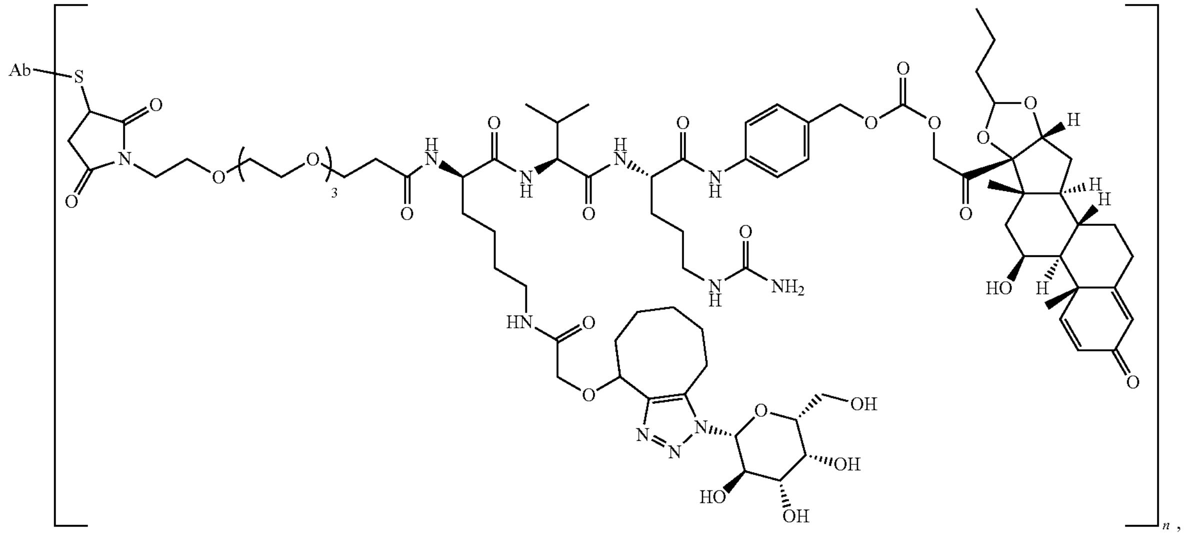
,
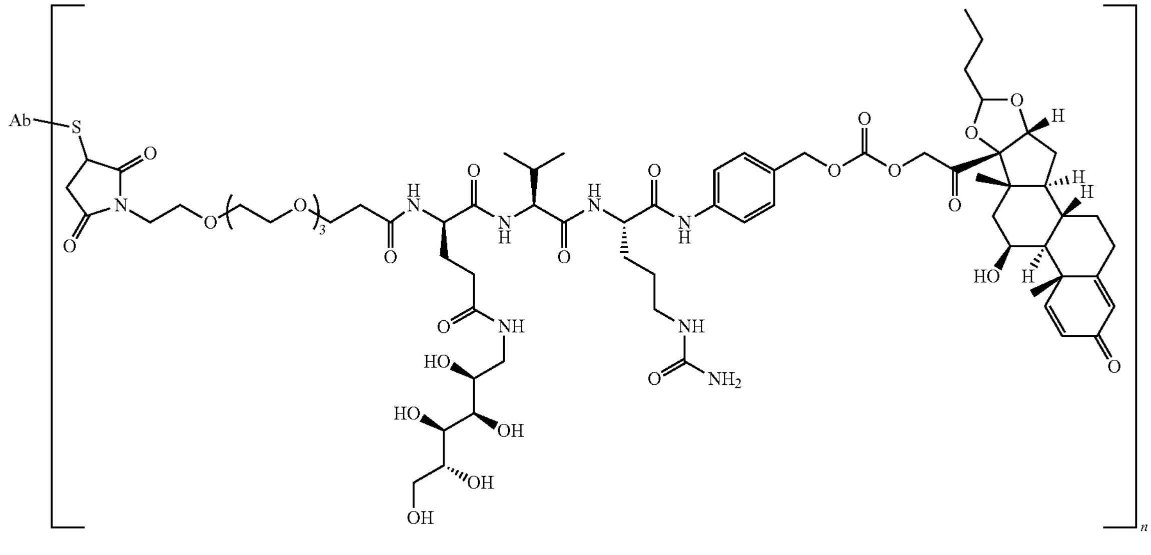
,

-continued
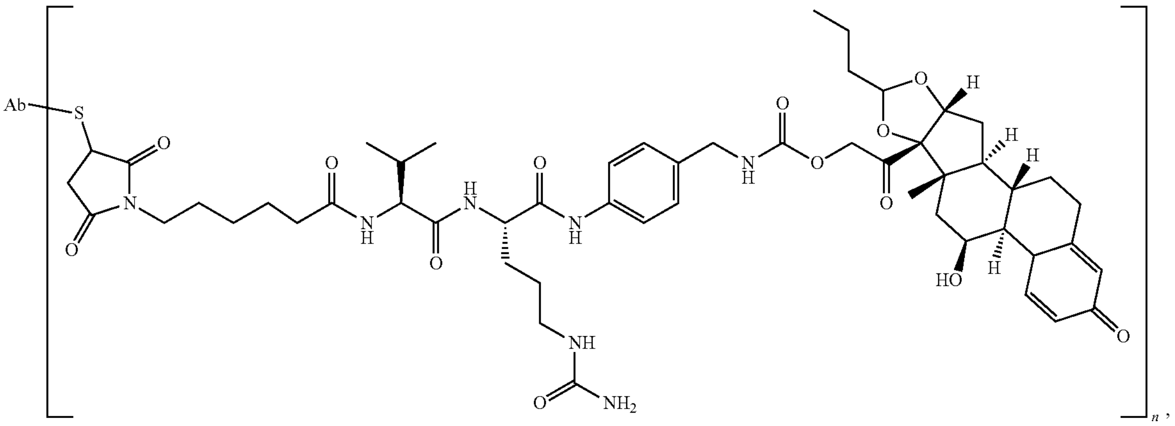
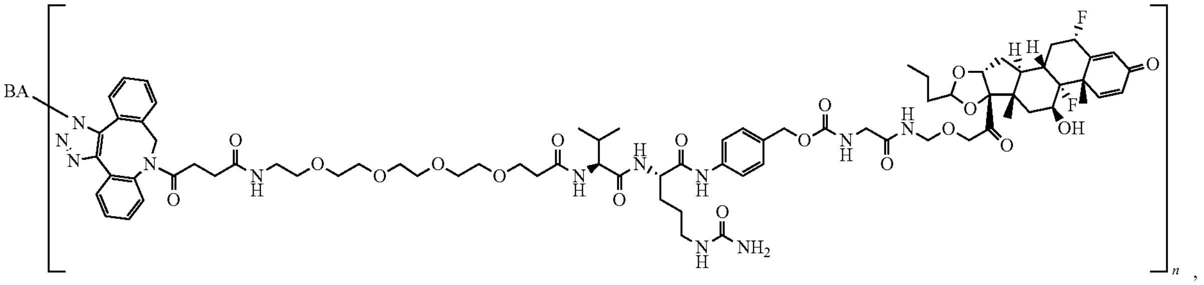
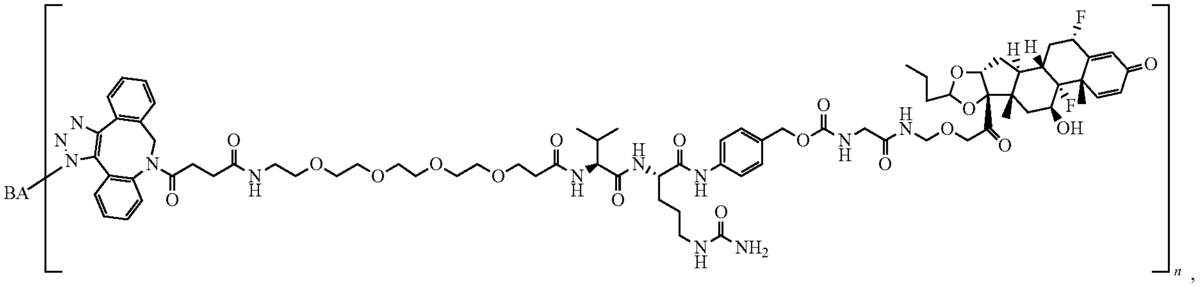
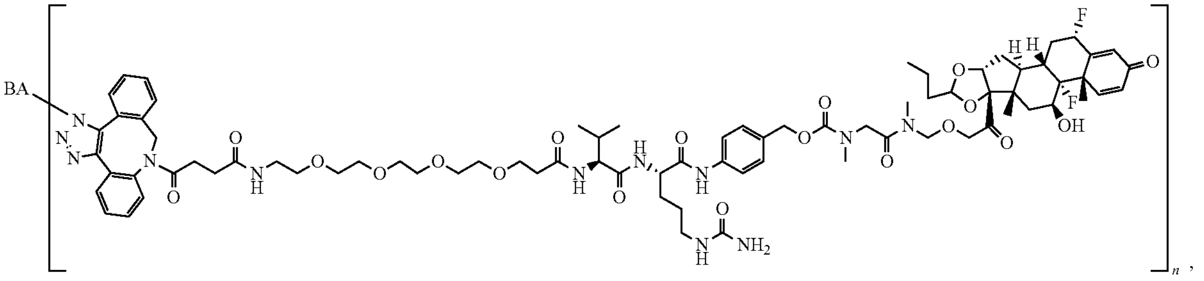
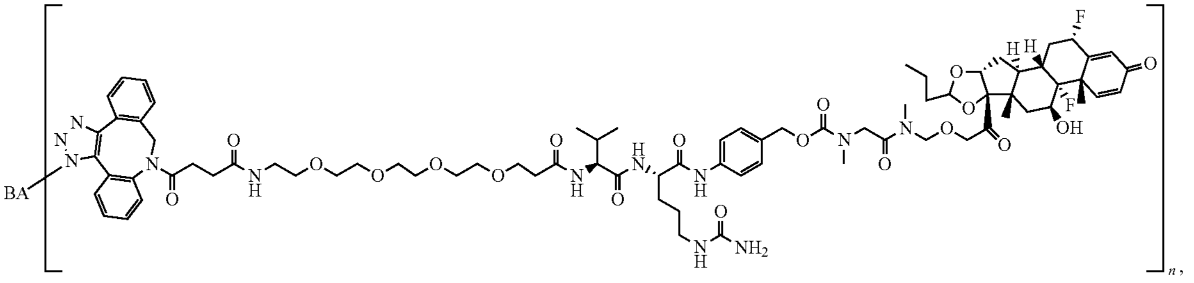

-continued
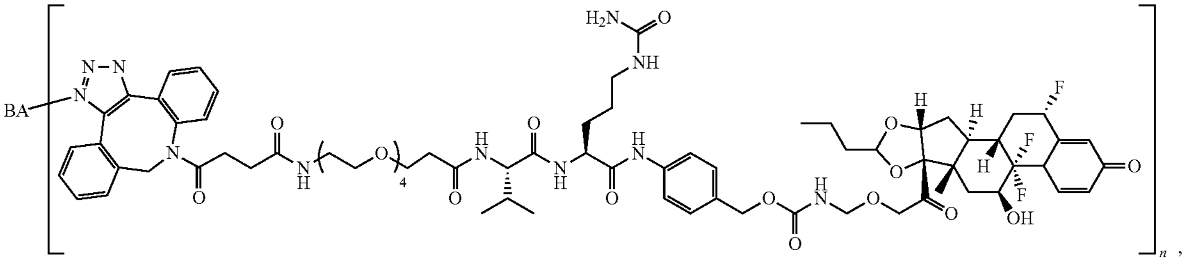
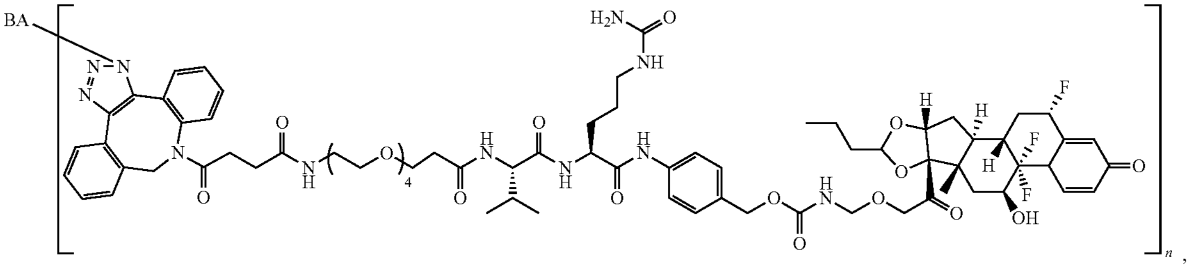
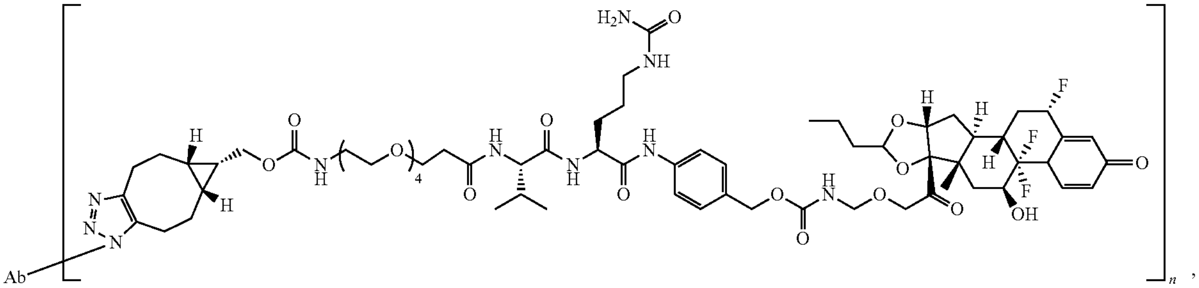
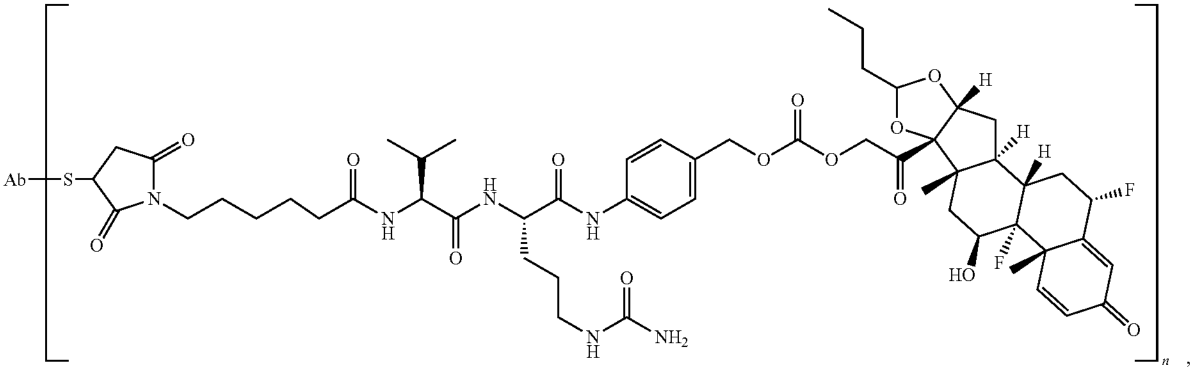
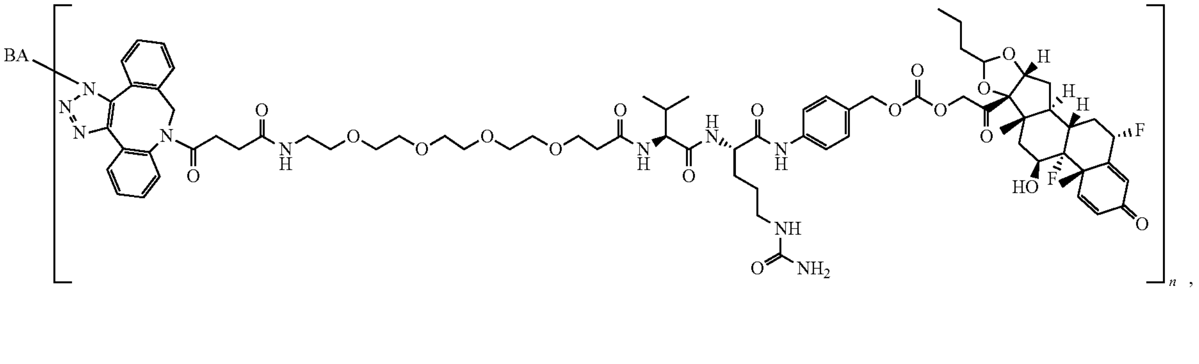

-continued
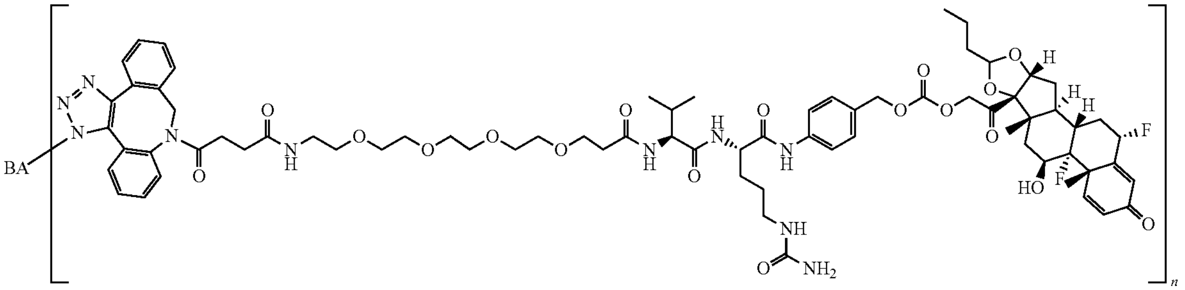
,
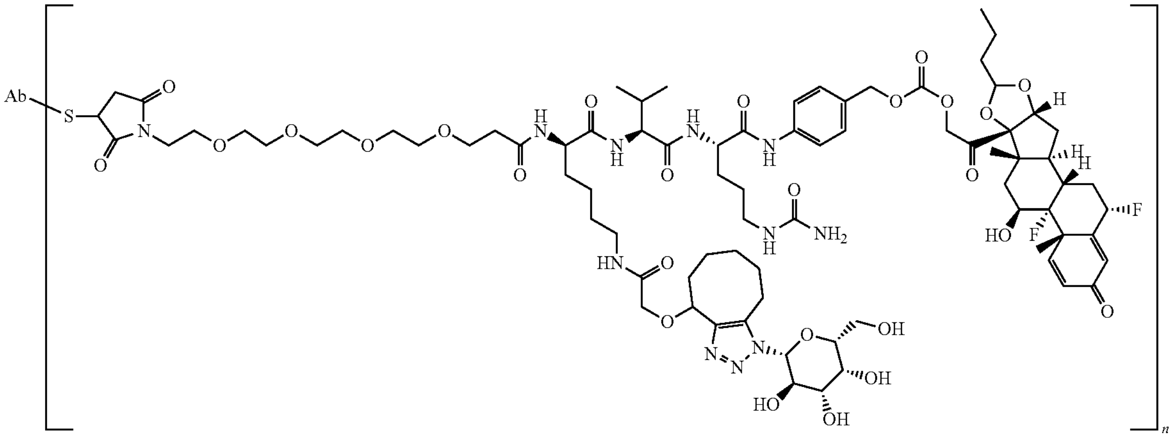
,
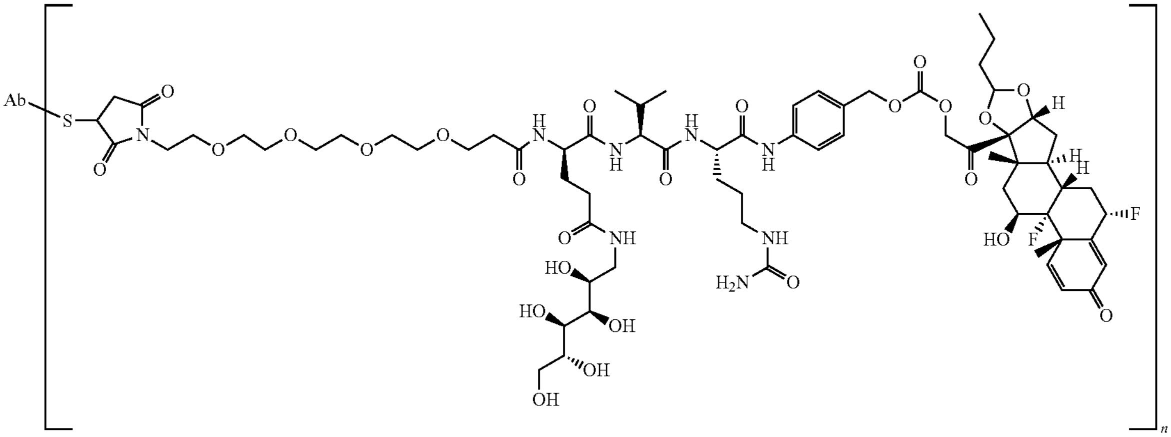
,
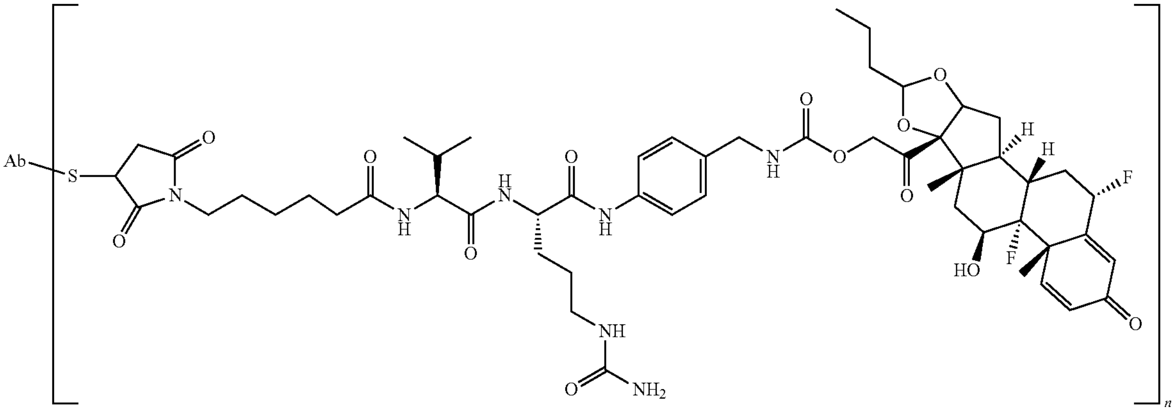
,

-continued

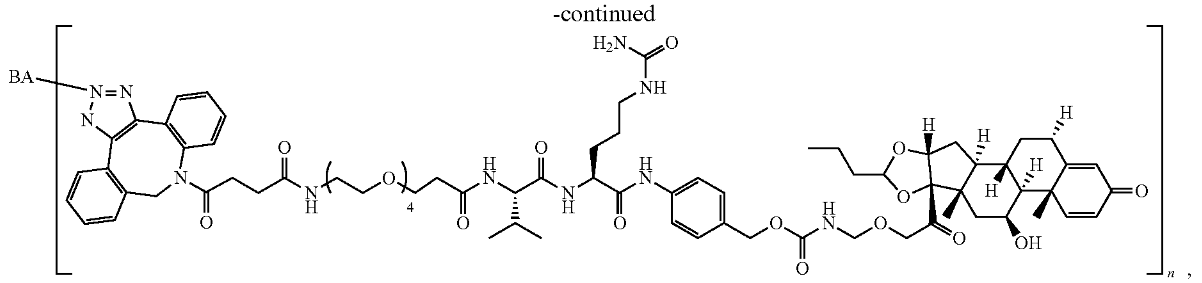

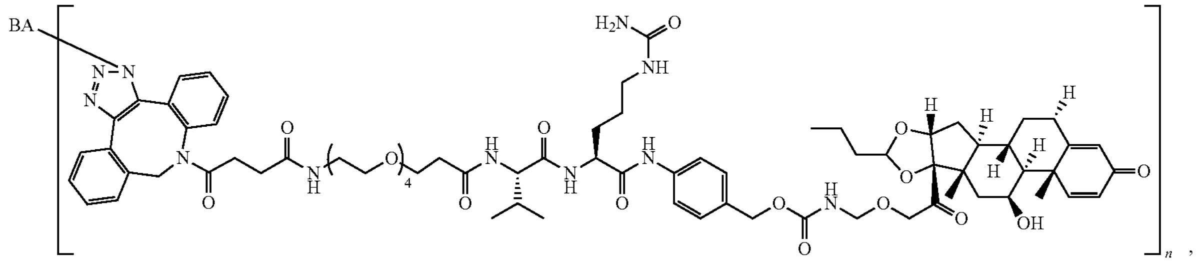

and

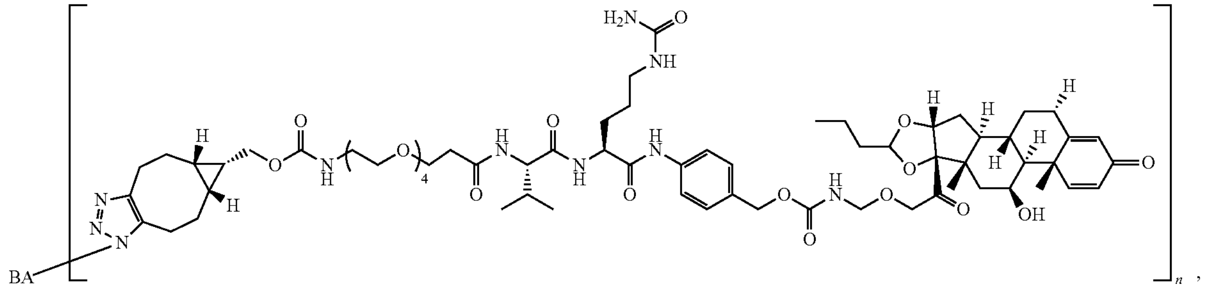

or a stereoisomeric form thereof, or a regioisomer thereof, or a mixture of regioisomers thereof, wherein each Ab is the anti-MSR1 antibody or antigen binding fragment thereof;

each BA is

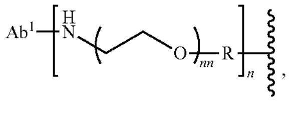

where $Ab^1$ is the anti-MSR1 antibody or antigen-binding fragment thereof;

R is $C_{2-4}$-alkylene;

nn is an integer selected from two to four, inclusive; and each n is an integer from one to four.

29. An antibody-drug conjugate of claim 1, according to Formula (7004):

Formula (7004)

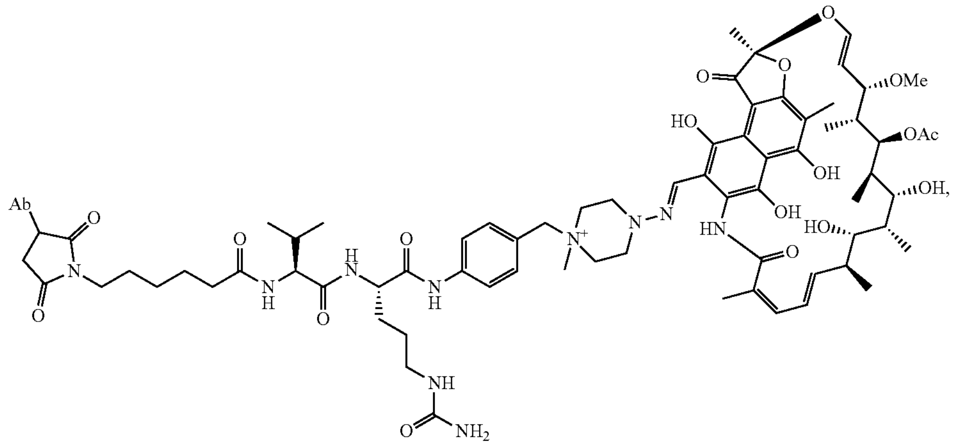

Ab is the anti-MSR1 antibody or antibody fragment thereof.

30. The antibody-drug conjugate of claim 1, prepared by contacting an anti-MSR1 antibody or antigen-binding fragment thereof, or a PEG-modified anti-MSR1 antibody, or antigen-binding fragment thereof, with a linker payload, or a stereoisomeric form thereof, or a regioisomer thereof, according to Formula (D):

Formula (D)

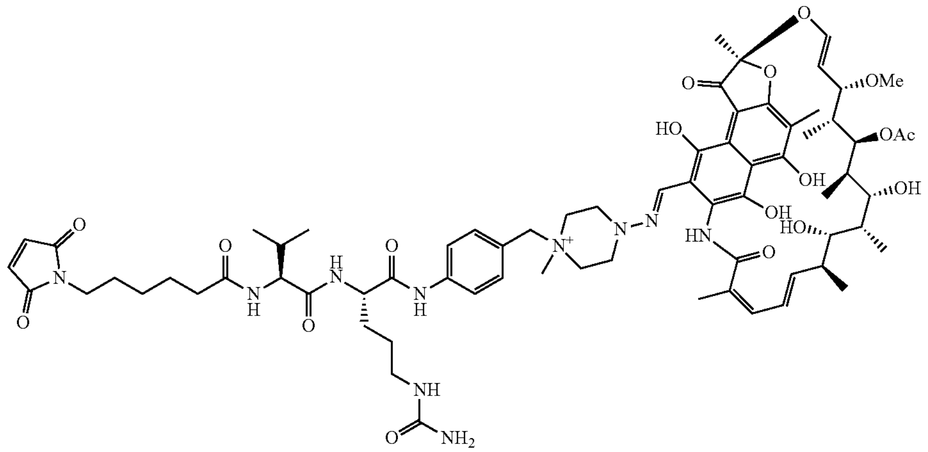

under conditions suitable for forming a bond between the anti-MSR1 antibody or antigen-binding fragment thereof.

* * * * *

SEQUENCE LISTING

<160> NUMBER OF SEQ ID NOS: 466

<210> SEQ ID NO 1
<211> LENGTH: 363
<212> TYPE: DNA
<213> ORGANISM: Artificial Sequence
<220> FEATURE:
<223> OTHER INFORMATION: Synthetic

<400> SEQUENCE: 1
caggtccaat tggtacagtc tggggctgag gtgaagaagc ctggggcctc agtgaaggtg 60
tcctgcaagg tttccggata caccctcact gaattatcca tacactgggt gcgccaggtt 120
cctggaaaag gacttgagtg gatgggaggt tttgatcctg aagagggtga aacaatcttc 180
gcacaggagt tccgggacag agtcaccttg accgaggaca catctccaga cacagcctac 240
atggagttga gcagcctgaa atctgaggac gcggccgtat attactgtac aacccccccga 300 tattgtaata atggtatatg ttatgactac tggggccagg gaaccctggt caccgtctct 360
tca 363

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Val Pro Gly Lys Gly Leu Glu Trp Met
        35                  40                  45

Gly Gly Phe Asp Pro Glu Glu Gly Glu Thr Ile Phe Ala Gln Glu Phe
    50                  55                  60

Arg Asp Arg Val Thr Leu Thr Glu Asp Thr Ser Pro Asp Thr Ala Tyr
65                  70                  75                  80

Met Glu Leu Ser Ser Leu Lys Ser Glu Asp Ala Ala Val Tyr Tyr Cys
                85                  90                  95

Thr Thr Pro Arg Tyr Cys Asn Asn Gly Ile Cys Tyr Asp Tyr Trp Gly
            100                 105                 110

Gln Gly Thr Leu Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggatacaccc tcactgaatt atcc 24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Tyr Thr Leu Thr Glu Leu Ser
1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgatcctg aagagggtga aaca 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asp Pro Glu Glu Gly Glu Thr
1               5

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
acaacccccc gatattgtaa taatggtata tgttatgact ac 42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Thr Thr Pro Arg Tyr Cys Asn Asn Gly Ile Cys Tyr Asp Tyr
1               5                   10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9
gacatccaga tgacccagtc gccttcctcc ctgtctgcat ctgtgggaga cagagtcacc 60
atcacttgcc gggcaagtca gagcattagc aactatttaa attggtatca gcagaaacca 120
gggaaagccc ctaagctcct gatctatact gcatccagtt tgcaaagtgg ggtcccatca 180
aggttcagtg gcagtggatc tgggacagat ttcactctca ccatcagcag tcttcaaact 240
gaagattttg caacttacta ttgtcaacag agttacagta attttccgat caccttcggc 300
caagggacac gactggagat taaacga 327

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Thr
65                  70                  75                  80

Glu Asp Phe Ala Thr Tyr Tyr Cys Gln Gln Ser Tyr Ser Asn Phe Pro
                85                  90                  95

Ile Thr Phe Gly Gln Gly Thr Arg Leu Glu Ile Lys Arg
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcaactat 18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 actgcatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Thr Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
caacagagtt acagtaattt tccgatcacc 30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Ser Asn Phe Pro Ile Thr
1               5                   10

<210> SEQ ID NO 17
<211> LENGTH: 360
<212> TYPE: DNA
<213> ORGANISM: Artificial Sequence
<220> FEATURE:
<223> OTHER INFORMATION: Synthetic

<400> SEQUENCE: 17
gtgcagctgg tggagtctgg gggaggcttg gtccagcctg gagggtccct gagactctcc 60
tgtgcagcct ctggattcac cttcagtgac cactacatgg actgggtccg tcaggctcct 120
gggaaggggc tggagtgggt tggccgaacc agaaacaaag ctaatagtca caccacagaa 180
tacgccgcgt ctgtgagtgg cagattcacc atctcaagag atgattcaaa gaactcattg 240
tatctgcaaa tgaacagcct gaaaaccgag gacacggccg tgtattattg cactagagcc 300
ggtataattg gaaccctctt tgactactgg ggccagggaa ccctggtcac cgtctcctca 360

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

Val Gln Leu Val Glu Ser Gly Gly Gly Leu Val Gln Pro Gly Gly Ser
1 5 10 15

Leu Arg Leu Ser Cys Ala Ala Ser Gly Phe Thr Phe Ser Asp His Tyr
20 25 30

Met Asp Trp Val Arg Gln Ala Pro Gly Lys Gly Leu Glu Trp Val Gly
35 40 45

Arg Thr Arg Asn Lys Ala Asn Ser His Thr Thr Glu Tyr Ala Ala Ser
50 55 60

Val Ser Gly Arg Phe Thr Ile Ser Arg Asp Asp Ser Lys Asn Ser Leu
65 70 75 80

Tyr Leu Gln Met Asn Ser Leu Lys Thr Glu Asp Thr Ala Val Tyr Tyr
85 90 95

Cys Thr Arg Ala Gly Ile Ile Gly Thr Leu Phe Asp Tyr Trp Gly Gln
100 105 110

Gly Thr Leu Val Thr Val Ser Ser
115 120

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtgacca ctac 24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Asp His Tyr 1 5

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
accagaaaca aagctaatag tcacaccaca 30

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Thr Arg Asn Lys Ala Asn Ser His Thr Thr
1 5 10

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
actagagccg gtataattgg aaccctcttt gactac 36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Thr Arg Ala Gly Ile Ile Gly Thr Leu Phe Asp Tyr
1 5 10

<210> SEQ ID NO 25
<211> LENGTH: 327
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaacga 327

<210> SEQ ID NO 26
<211> LENGTH: 109
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagagcatta gcagctat 18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Tyr
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 30

<212> TYPE: DNA
<213> ORGANISM: Artificial Sequence
<220> FEATURE:
<223> OTHER INFORMATION: Synthetic

<400> SEQUENCE: 31
caacagagtt acagtacccc tccgatcacc 30

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gln Gln Ser Tyr Ser Thr Pro Pro Ile Thr
1 5 10

<210> SEQ ID NO 33
<211> LENGTH: 363
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtccagc ctggagggtc cctgagactc 60
tcctgtgcag cctctggatt caccttcagt gaccactata tggactgggt ccgccaggct 120
ccagggaagg ggctggaatg ggttggccgt actcgaaaca aagctaatag tcacaccaca 180
gaatacaccg cgtctgtgac aggcagattc accatctcaa gagatgattc aagaaactca 240
ctatatctgc aaatgaacag cctgaaaacc gaggacacgg ccgtatatta ctgtgttaga 300
gccggtataa ttggaaccct ctttgactat tggggccagg gaaccctggt caccgtctcc 360
tca 363

<210> SEQ ID NO 34
<211> LENGTH: 121
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Asp Trp Val Arg Gln Ala Pro Gly Lys Gly Leu Glu Trp Val
35 40 45

Gly Arg Thr Arg Asn Lys Ala Asn Ser His Thr Thr Glu Tyr Thr Ala
50 55 60

Ser Val Thr Gly Arg Phe Thr Ile Ser Arg Asp Asp Ser Arg Asn Ser
65 70 75 80

Leu Tyr Leu Gln Met Asn Ser Leu Lys Thr Glu Asp Thr Ala Val Tyr
85 90 95

Tyr Cys Val Arg Ala Gly Ile Ile Gly Thr Leu Phe Asp Tyr Trp Gly
100 105 110

Gln Gly Thr Leu Val Thr Val Ser Ser
115 120

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcacct tcagtgacca ctat 24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asp His Tyr
1 5

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
actcgaaaca aagctaatag tcacaccaca 30

<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Thr Arg Asn Lys Ala Asn Ser His Thr Thr
1 5 10

<210> SEQ ID NO 39
<211> LENGTH: 36
<212> TYPE: DNA
<213> ORGANISM: Artificial Sequence
<220> FEATURE:
<223> OTHER INFORMATION: Synthetic

<400> SEQUENCE: 39
gttagagccg gtataattgg aaccctcttt gactat 36

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Val Arg Ala Gly Ile Ile Gly Thr Leu Phe Asp Tyr
1 5 10

<210> SEQ ID NO 41
<211> LENGTH: 327

<212> TYPE: DNA
<213> ORGANISM: Artificial Sequence
<220> FEATURE:
<223> OTHER INFORMATION: Synthetic

<400> SEQUENCE: 41
gacatccaga tgacccagtt tccatcctcc ctgtctgcat ctgtaggaga cagagtcacc 60
atcacttgcc gggcaagtca gagcattagc agctttttaa attggtttca gcagaaacca 120
gggaaagccc ctaagttcct gatctatgct gcatccagtt tgcaaagtgg ggtcccatca 180
aggttcagtg gcagtgggtc tgggacagat ttcactctca ccatcagcag tctacaacct 240
gaagattttg caacttacta ctgtcaacag agttacagtt cccctccgat caccttcggc 300
caagggacac gactggagat taaacga 327

<210> SEQ ID NO 42
<211> LENGTH: 109
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Phe Pro Ser Ser Leu Ser Ala Ser Val Gly
1 5 10 15

Asp Arg Val Thr Ile Thr Cys Arg Ala Ser Gln Ser Ile Ser Ser Phe
20 25 30

Leu Asn Trp Phe Gln Gln Lys Pro Gly Lys Ala Pro Lys Phe Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ser Pro Pro
85 90 95

Ile Thr Phe Gly Gln Gly Thr Arg Leu Glu Ile Lys Arg
100 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagagcatta gcagcttt 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Ile Ser Ser Phe
1 5

<210> SEQ ID NO 45
<211> LENGTH: 9
<212> TYPE: DNA

<213> ORGANISM: Artificial Sequence
<220> FEATURE:
<223> OTHER INFORMATION: Synthetic

<400> SEQUENCE: 45 gctgcatcc 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
caacagagtt acagttcccc tccgatcacc 30

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

Gln Gln Ser Tyr Ser Ser Pro Pro Ile Thr
1 5 10

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tgcaggagtc gggcccagga ctggtgaagc cttcggagac cctgtccctc 60
acctgcactg tcactggtgg ctccatcagt aggaactact ggagttggat ccggcagccc 120
ccagggaagg gactggaatg gattggatat atctattaca gtgggagtat cgactacaat 180
ccctccctca agagtcgagt caccatatca gtagacacgt ccaagaacca gttctccctg 240
aagctgagtt ctatgaccgc tgcggacacg gccgtatact actgtgcgag agatcggtgg 300
aactggaaat acggtatgga cgtctggggc caagggacca cggtcatcgt ctcgtca 357

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

Gln Val Gln Leu Gln Glu Ser Gly Pro Gly Leu Val Lys Pro Ser Glu

```
1               5                   10                  15

Thr Leu Ser Leu Thr Cys Thr Val Thr Gly Gly Ser Ile Ser Arg Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Ile Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Arg Trp Asn Trp Lys Tyr Gly Met Asp Val Trp Gly Gln Gly
            100                 105                 110

Thr Thr Val Ile Val Ser Ser
        115


<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

ggtggctcca tcagtaggaa ctac                                            24


<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Gly Ser Ile Ser Arg Asn Tyr
1               5


<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53

atctattaca gtgggagtat c                                               21


<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Tyr Tyr Ser Gly Ser Ile
1               5


<210> SEQ ID NO 55
<211> LENGTH: 39
<212> TYPE: DNA
<213> ORGANISM: Artificial Sequence
<220> FEATURE:
```

<223> OTHER INFORMATION: Synthetic

<400> SEQUENCE: 55
gcgagagatc ggtggaactg gaaatacggt atggacgtc 39

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ala Arg Asp Arg Trp Asn Trp Lys Tyr Gly Met Asp Val
1 5 10

<210> SEQ ID NO 57
<211> LENGTH: 327
<212> TYPE: DNA
<213> ORGANISM: Artificial Sequence
<220> FEATURE:
<223> OTHER INFORMATION: Synthetic

<400> SEQUENCE: 57
gaaattgtgt tgacgcagtc tccaggcacc ctgtctttgt ctccagggga aagagccacc 60
ctctcctgca gggccagtca gactgttaga aacaactact tagcctggta ccaccagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttacagtgta ttactgtcac cagtatggta actcaccttg gacgttcggc 300
caagggacca aaatggaaat caaacga 327

<210> SEQ ID NO 58
<211> LENGTH: 109
<212> TYPE: PRT
<213> ORGANISM: Artificial Sequence
<220> FEATURE:
<223> OTHER INFORMATION: Synthetic

<400> SEQUENCE: 58

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Thr Val Arg Asn Asn
20 25 30

Tyr Leu Ala Trp Tyr His Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Thr Val Tyr Tyr Cys His Gln Tyr Gly Asn Ser Pro
85 90 95

Trp Thr Phe Gly Gln Gly Thr Lys Met Glu Ile Lys Arg
100 105

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
cagactgtta gaaacaacta c 21

<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Gln Thr Val Arg Asn Asn Tyr
1 5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 ggtgcatcc 9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Gly Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caccagtatg gtaactcacc ttggacg 27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

His Gln Tyr Gly Asn Ser Pro Trp Thr
1 5

<210> SEQ ID NO 65
<211> LENGTH: 363
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtccagc ctggagggtc cctgagactc 60

```
tcctgtgcag cctctggatt caccttcagt gaccactaca tggactgggt ccgccaggct    120

cctgggaagg ggctggagtg ggttggccga actagaaaca aagctaatag ttacaccaca    180

gaatacgccg cgtctgtgag tggcagattc accatctcaa gagatgattc aaagaactca    240

ttatatctgc aaatgaacag cctgaaaacc gaggacacgg ccgtgtatta ttgcactaga    300

gccggtataa ttggaaccct ctttgactac tggggccagg gaaccctggt caccgtctcc    360

tca                                                                  363


<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Ser Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg Ala Gly Ile Ile Gly Thr Leu Phe Asp Tyr Trp Gly
            100                 105                 110

Gln Gly Thr Leu Val Thr Val Ser Ser
        115                 120


<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67

ggattcacct tcagtgacca ctac                                            24


<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Asp His Tyr
1               5


<210> SEQ ID NO 69
<211> LENGTH: 30
<212> TYPE: DNA
<213> ORGANISM: Artificial Sequence
<220> FEATURE:
<223> OTHER INFORMATION: Synthetic
```

<400> SEQUENCE: 69
actagaaaca aagctaatag ttacaccaca 30

<210> SEQ ID NO 70
<211> LENGTH: 10
<212> TYPE: PRT
<213> ORGANISM: Artificial Sequence
<220> FEATURE:
<223> OTHER INFORMATION: Synthetic

<400> SEQUENCE: 70

Thr Arg Asn Lys Ala Asn Ser Tyr Thr Thr
1 5 10

<210> SEQ ID NO 71
<211> LENGTH: 36
<212> TYPE: DNA
<213> ORGANISM: Artificial Sequence
<220> FEATURE:
<223> OTHER INFORMATION: Synthetic

<400> SEQUENCE: 71
actagagccg gtataattgg aaccctcttt gactac 36

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Thr Arg Ala Gly Ile Ile Gly Thr Leu Phe Asp Tyr
1 5 10

<210> SEQ ID NO 73
<211> LENGTH: 327
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcctcc ctgtctgcat ctgtaggaga cagagtcacc 60
atcacttgcc gggcaagtca gatcattggt agatatttaa attggtttca gcagaaacca 120
gggaaagtcc ctaagctcct gatctatgct gcatccagtt tgcaacgtgg ggtcccatca 180
aggttcagtg gcagtggatc tgggacagat ttcactctca ccatcagcag tctgcaacct 240
gaagattttg caacttacta ctgtcaacag agttacaata cccctccgat caccttcggc 300
caagggacac gactggagat taaacga 327

<210> SEQ ID NO 74
<211> LENGTH: 109
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ile Ile Gly Arg Tyr

-continued

```
            20                  25                  30

Leu Asn Trp Phe Gln Gln Lys Pro Gly Lys Val Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Pro
                85                  90                  95

Ile Thr Phe Gly Gln Gly Thr Arg Leu Glu Ile Lys Arg
            100                 105


<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

cagatcattg gtagatat                                                    18


<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Ile Ile Gly Arg Tyr
1               5


<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77

gctgcatcc                                                               9


<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1


<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79

caacagagtt acaatacccc tccgatcacc                                       30
```

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Gln Gln Ser Tyr Asn Thr Pro Pro Ile Thr
1               5                   10

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
caggtccagc tggtgcagtc tggggctgag gtgagggagc ctggggcctc agtgaagctc 60
tcctgcaagg tttccggata caccctcact gaattatcca tccactgggt gcgacaggct 120
cctggaaaag gacttgagtg gatgggaggt tttgatcctg aagagggtga aacagtctac 180
gcacagaagt tccggggcag agtcaccctg accgaggaca taagtccaga cacggcctac 240
atggagctga gcagcctgac ctctgaggac acggccgtat attattgtgc aacccccccgc 300 tattgtaata atggtatatg ttatgactac tggggccagg gaaccctaat caccgtctcc 360
tca 363

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Gln Ser Gly Ala Glu Val Arg Glu Pro Gly Ala
1               5                   10                  15

Ser Val Lys Leu Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Glu Gly Glu Thr Val Tyr Ala Gln Lys Phe
    50                  55                  60

Arg Gly Arg Val Thr Leu Thr Glu Asp Ile Ser Pro Asp Thr Ala Tyr
65                  70                  75                  80

Met Glu Leu Ser Ser Leu Thr Ser Glu Asp Thr Ala Val Tyr Tyr Cys
                85                  90                  95

Ala Thr Pro Arg Tyr Cys Asn Asn Gly Ile Cys Tyr Asp Tyr Trp Gly
            100                 105                 110

Gln Gly Thr Leu Ile Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggatacaccc tcactgaatt atcc 24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Tyr Thr Leu Thr Glu Leu Ser
1 5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
tttgatcctg aagagggtga aaca 24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Phe Asp Pro Glu Glu Gly Glu Thr
1 5

<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87 gcaaccccc gctattgtaa taatggtata tgttatgact ac 42

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Ala Thr Pro Arg Tyr Cys Asn Asn Gly Ile Cys Tyr Asp Tyr
1 5 10

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctcc ctgtctgcat ctgtaggaga cagagtcacc 60

```
atcacttgcc gggcaagtca gagcattagc agctatttaa attggtatca gcagaaacca    120

gggaaagccc ctaagctcct gatctatgct gcatccagtt tgcaaagtgg ggtcccgtca    180

aggttcagtg gcagtggatc tgggacagat ttcactctca ccatcagcag tctgcaacct    240

gaagattttg caacttacta ctgtcaacag agttacagta cccctccgat caccttcggc    300

caagggacac gactggagat taaa                                           324


<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105


<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

cagagcatta gcagctat                                                   18


<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Tyr
1               5


<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93

gctgcatcc                                                              9
```

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
caacagagtt acagtacccc tccgatcacc 30

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Pro Ile Thr
1 5 10

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97
gaggtgcagc tgttggagtc tgggggaggc ttggtacagc ctggggggtc cctgagactc 60
tcctgtgcag cctctggatt cacctttagt aattatgcca tgacctgggt ccgccaggct 120
ccagggacgg ggctggagtg ggtctcagct attagtggtc gtggtagtaa cacatactac 180
acagactccg tgaagggccg gttcaccatc tccagagaca attccaagaa catgctgtat 240
ctgcaaatga acagcctgag agccgaggac acggcctcat attactgtgc gaaagatcgt 300
tttactacag tggggaactg gttcgacccc tggggccagg gaaccctggt caccgtctcc 360
tca 363

<210> SEQ ID NO 98
<211> LENGTH: 121
<212> TYPE: PRT
<213> ORGANISM: Artificial Sequence
<220> FEATURE:
<223> OTHER INFORMATION: Synthetic

<400> SEQUENCE: 98

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met Thr Trp Val Arg Gln Ala Pro Gly Thr Gly Leu Glu Trp Val
35 40 45

```
Ser Ala Ile Ser Gly Arg Gly Ser Asn Thr Tyr Tyr Thr Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Ser Tyr Tyr Cys
                85                  90                  95

Ala Lys Asp Arg Phe Thr Thr Val Gly Asn Trp Phe Asp Pro Trp Gly
            100                 105                 110

Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttagtaatta tgcc 24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Ser Asn Tyr Ala
1               5
```

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggtc gtggtagtaa caca 24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

```
Ile Ser Gly Arg Gly Ser Asn Thr
1               5
```

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gcgaaagatc gttttactac agtggggaac tggttcgacc cc 42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Ala Lys Asp Arg Phe Thr Thr Val Gly Asn Trp Phe Asp Pro
1               5                   10

<210> SEQ ID NO 105
<211> LENGTH: 327
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc 60
atcacttgcc gggcaagtca gagtattagc agctatttaa attggtatca gcagaaacca 120
gggaaagccc ctaagctcct gatctatgct gcgtccagtt tgcaaaatgg ggtcccatca 180
aggttcagtg gcagtggatc tgggacagat ttcactctca ccatcagcag tctgcagcct 240
gaagattttg caacttacta ctgtcaacag agttacagta gtcttccgat caccttcggc 300
caagggacac gactggatat taaacga 327

<210> SEQ ID NO 106
<211> LENGTH: 109
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Leu Pro
                85                  90                  95

Ile Thr Phe Gly Gln Gly Thr Arg Leu Asp Ile Lys Arg
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagagtatta gcagctat 18

<210> SEQ ID NO 108

-continued

<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Tyr
1 5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctgcgtcc 9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1

<210> SEQ ID NO 111
<211> LENGTH: 30
<212> TYPE: DNA
<213> ORGANISM: Artificial Sequence
<220> FEATURE:
<223> OTHER INFORMATION: Synthetic

<400> SEQUENCE: 111
caacagagtt acagtagtct tccgatcacc 30

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Ser Ser Leu Pro Ile Thr
1 5 10

<210> SEQ ID NO 113
<211> LENGTH: 357
<212> TYPE: DNA
<213> ORGANISM: Artificial Sequence
<220> FEATURE:
<223> OTHER INFORMATION: Synthetic

<400> SEQUENCE: 113
caggtgcagc tgcaggagtc gggcccagga ctggtgaagc cttcggagac cctgtccctc 60
acctgcactg tcactggtgg ctccatcagt aggaactact ggagttggat ccggcagccc 120
ccagggaagg gactggaatg gattggatat atctattaca gtgggagtat caactacaat 180
ccctccctca agagtcgagt caccatatca gtggacatgt ctaagaacca gttctcccta 240
aagctgaatt ctgtgaccgc tgcggacacg gccgtgtact actgtgcgag agatcgatgg 300
aactggaaat acggtatgga cgtctggggc caagggacca cggtcatcgt ctcgtca 357

<210> SEQ ID NO 114
<211> LENGTH: 119
<212> TYPE: PRT
<213> ORGANISM: Artificial Sequence
<220> FEATURE:
<223> OTHER INFORMATION: Synthetic

<400> SEQUENCE: 114

Gln Val Gln Leu Gln Glu Ser Gly Pro Gly Leu Val Lys Pro Ser Glu
1 5 10 15

Thr Leu Ser Leu Thr Cys Thr Val Thr Gly Gly Ser Ile Ser Arg Asn
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Ile Asn Tyr Asn Pro Ser Leu Lys
50 55 60

Ser Arg Val Thr Ile Ser Val Asp Met Ser Lys Asn Gln Phe Ser Leu
65 70 75 80

Lys Leu Asn Ser Val Thr Ala Ala Asp Thr Ala Val Tyr Tyr Cys Ala
85 90 95

Arg Asp Arg Trp Asn Trp Lys Tyr Gly Met Asp Val Trp Gly Gln Gly
100 105 110

Thr Thr Val Ile Val Ser Ser
115

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggtggctcca tcagtaggaa ctac 24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Gly Ser Ile Ser Arg Asn Tyr
1 5

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
atctattaca gtgggagtat c 21

<210> SEQ ID NO 118
<211> LENGTH: 7
<212> TYPE: PRT

```
<213> ORGANISM: Artificial Sequence
<220> FEATURE:
<223> OTHER INFORMATION: Synthetic

<400> SEQUENCE: 118

Ile Tyr Tyr Ser Gly Ser Ile
1               5


<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119

gcgagagatc gatggaactg gaaatacggt atggacgtc                            39


<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Arg Asp Arg Trp Asn Trp Lys Tyr Gly Met Asp Val
1               5                   10


<210> SEQ ID NO 121
<211> LENGTH: 327
<212> TYPE: DNA
<213> ORGANISM: Artificial Sequence
<220> FEATURE:
<223> OTHER INFORMATION: Synthetic

<400> SEQUENCE: 121

gaaattgtgt tgacgcagtc tccaggcacc ctgtctttgt ctccagggga aagagccacc     60

ctctcctgca gggccagtca gactgttaga aacagctact tagcctggta ccaccagaaa    120

cctggccagg ctcccaggct cctcatctat ggtgcatcca gcagggccac tggcatccca    180

gacaggttca gtggcagtgg gtctgggaca gacttcactc tcaccatcag cagactggag    240

cctgaagatt ttgcagtgta ttactgtcag cagtatggta gttcatattg gacgttcggc    300

caagggacca aaatggaaat caaacga                                        327


<210> SEQ ID NO 122
<211> LENGTH: 109
<212> TYPE: PRT
<213> ORGANISM: Artificial Sequence
<220> FEATURE:
<223> OTHER INFORMATION: Synthetic

<400> SEQUENCE: 122

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Arg Asn Ser
            20                  25                  30

Tyr Leu Ala Trp Tyr His Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
```

65 70 75 80

Pro Glu Asp Phe Ala Val Tyr Tyr Cys Gln Gln Tyr Gly Ser Ser Tyr
85 90 95

Trp Thr Phe Gly Gln Gly Thr Lys Met Glu Ile Lys Arg
100 105

<210> SEQ ID NO 123
<211> LENGTH: 21
<212> TYPE: DNA
<213> ORGANISM: Artificial Sequence
<220> FEATURE:
<223> OTHER INFORMATION: Synthetic

<400> SEQUENCE: 123
cagactgtta gaaacagcta c 21

<210> SEQ ID NO 124
<211> LENGTH: 7
<212> TYPE: PRT
<213> ORGANISM: Artificial Sequence
<220> FEATURE:
<223> OTHER INFORMATION: Synthetic

<400> SEQUENCE: 124

Gln Thr Val Arg Asn Ser Tyr
1 5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 ggtgcatcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Gly Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
cagcagtatg gtagttcata ttggacg 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Gly Ser Ser Tyr Trp Thr
1               5

<210> SEQ ID NO 129
<211> LENGTH: 363
<212> TYPE: DNA
<213> ORGANISM: Artificial Sequence
<220> FEATURE:
<223> OTHER INFORMATION: Synthetic

<400> SEQUENCE: 129
caggtccagc tggtgcagtc tgggtctgag gtgaagaagc ctggggcctc agtgaaggtc 60
tcctgcaagg tttccggata caccctcact gaattatcca tacactgggt gcgacaggct 120
cctggaaaag gacttgagtg gatgggaggt tttgatcctg aagatggtga aacaatctac 180
gcacagaagt tccggggcag agtcaccatg accgaggaca tatctccaga cacagcctac 240
atggagctga gcagcctgag atctgaagac acggccgtat attactgtgc aaccccccgc 300
tattgtaata atggtatatg ttatgactat tggggccagg gaaccctggt caccgtctcc 360
tca 363

<210> SEQ ID NO 130
<211> LENGTH: 121
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Ser Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Arg Gly Arg Val Thr Met Thr Glu Asp Ile Ser Pro Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Arg Tyr Cys Asn Asn Gly Ile Cys Tyr Asp Tyr Trp Gly
            100                 105                 110

Gln Gly Thr Leu Val Thr Val Ser Ser
        115                 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggatacaccc tcactgaatt atcc 24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Tyr Thr Leu Thr Glu Leu Ser
1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
tttgatcctg aagatggtga aaca 24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Phe Asp Pro Glu Asp Gly Glu Thr
1               5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135 gcaaccccc gctattgtaa taatggtata tgttatgact at 42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Thr Pro Arg Tyr Cys Asn Asn Gly Ile Cys Tyr Asp Tyr
1               5                   10

<210> SEQ ID NO 137
<211> LENGTH: 327
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctataggaga cagagtcacc 60
atcacttgcc gggcaagtca gagcattagc agctatttaa attggtatca gcagaaacca 120
gggaaagccc ctatgctcct gatctatgct gcatccagtt tgcaaagtgg ggtcccatca 180
aggttcagtg gcagtggatc tgggacagat ttcactctca ccatcagcag tctgcaaact 240
gaagattttg caacttacta ctgtcaacag agttacagta cccctccgat caccttcggc 300
caagggacac gactggagat taaacga 327

<210> SEQ ID NO 138
<211> LENGTH: 109
<212> TYPE: PRT
<213> ORGANISM: Artificial Sequence
<220> FEATURE:
<223> OTHER INFORMATION: Synthetic

<400> SEQUENCE: 138

```
Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Met Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Thr
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys Arg
            100                 105
```

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139

```
cagagcatta gcagctat                                                18
```

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

```
Gln Ser Ile Ser Ser Tyr
1               5
```

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141

```
gctgcatcc                                                           9
```

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

```
Ala Ala Ser
1


<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143

caacagagtt acagtacccc tccgatcacc                                      30


<210> SEQ ID NO 144
<211> LENGTH: 10
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ser Thr Pro Pro Ile Thr
1               5                   10


<210> SEQ ID NO 145
<211> LENGTH: 345
<212> TYPE: DNA
<213> ORGANISM: Artificial Sequence
<220> FEATURE:
<223> OTHER INFORMATION: Synthetic

<400> SEQUENCE: 145

caggtgcagc tggtggagtc tgggggaggc ttggtcaagc ctggagggtc cctgagactc     60

tcctgtgcag cctctggatt catttttagt gactactaca tgagctggat ccgccaggct    120

ccagggaagg ggctggagtg ggtttcatac attagtagta gtggtactac catatatgga    180

gactctgtga agggccgatt caccatgtcc agggacaacg ccaagaactc actgtatctg    240

caaatgaaca gcctgagagc cgaggacacg gccgtgtatt actgtgcgag gaactacgct    300

ctctttgact actggggcca gggaaccctg gtcaccgtct cctca                    345


<210> SEQ ID NO 146
<211> LENGTH: 115
<212> TYPE: PRT
<213> ORGANISM: Artificial Sequence
<220> FEATURE:
<223> OTHER INFORMATION: Synthetic

<400> SEQUENCE: 146

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Ile Tyr Gly Asp Ser Val Lys
    50                  55                  60

Gly Arg Phe Thr Met Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Ala Leu Phe Asp Tyr Trp Gly Gln Gly Thr Leu Val Thr
```

100 105 110

Val Ser Ser
115

<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147
ggattcattt ttagtgacta ctac 24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Ile Phe Ser Asp Tyr Tyr
1 5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtagta gtggtactac cata 24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Ser Ser Gly Thr Thr Ile
1 5

<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151
gcgaggaact acgctctctt tgactac 27

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Ala Arg Asn Tyr Ala Leu Phe Asp Tyr
1 5

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctgtaggaga cagagtcacc 60
atcacttgcc aggcgagtca ggacattagc aaatatttaa attggtatca gcagaaacca 120
gggaaagccc ctaagctcct gatctactat acatccaatt tggaaacagg ggtcccatca 180
aggttcagtg gaagtggatc tgggacagat tttactttca ccatcagcag cctgcagcct 240
gaagatattg caacatatta ctgtcaccag tctgattatc tcccattcac tttcggccct 300
gggaccaaag tggatatcaa acga 324

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Lys Tyr
20 25 30

Leu Asn Trp Tyr Gln Gln Lys Pro Gly Lys Ala Pro Lys Leu Leu Ile
35 40 45

Tyr Tyr Thr Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys His Gln Ser Asp Tyr Leu Pro Phe
85 90 95

Thr Phe Gly Pro Gly Thr Lys Val Asp Ile Lys Arg
100 105

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155
caggacatta gcaaatat 18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Ser Lys Tyr
1 5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 tatacatcc 9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Tyr Thr Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caccagtctg attatctccc attcact 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

His Gln Ser Asp Tyr Leu Pro Phe Thr
1 5

<210> SEQ ID NO 161
<211> LENGTH: 363
<212> TYPE: DNA
<213> ORGANISM: Artificial Sequence
<220> FEATURE:
<223> OTHER INFORMATION: Synthetic

<400> SEQUENCE: 161
cagctgcagc tgcaggagtc gggcccagga ctggtgaagc cttcggagac cctgtccctc 60
acctgcactg tctctggtgg ctccatcagc cgtattagtt actactgggg ctggatccgc 120
cagcccccag ggaaggggct ggagtggatt gggagtatct atgatagtgg gagtacctac 180
tacaacccgt ccctcaagag tcgagtcacc atatccatag acacgtccaa gaaccagttc 240
tccctgaagc tgagctctgt gaccgccgca gacacggctg tgtattactg tgtgagatat 300
agcagttcgt ccgccttcgc ttttgactac tggggccagg gaaccctggt caccgtctcc 360
tca 363

<210> SEQ ID NO 162
<211> LENGTH: 121
<212> TYPE: PRT
<213> ORGANISM: Artificial Sequence

```
<220> FEATURE:
<223> OTHER INFORMATION: Synthetic

<400> SEQUENCE: 162

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Ile
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Asp Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Tyr Ser Ser Ser Ser Ala Phe Ala Phe Asp Tyr Trp Gly
            100                 105                 110

Gln Gly Thr Leu Val Thr Val Ser Ser
        115                 120


<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163

ggtggctcca tcagccgtat tagttactac                                        30


<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Gly Gly Ser Ile Ser Arg Ile Ser Tyr Tyr
1               5                   10


<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165

atctatgata gtgggagtac c                                                 21


<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Tyr Asp Ser Gly Ser Thr
1               5
```

<210> SEQ ID NO 167
<211> LENGTH: 39
<212> TYPE: DNA
<213> ORGANISM: Artificial Sequence
<220> FEATURE:
<223> OTHER INFORMATION: Synthetic

<400> SEQUENCE: 167
gtgagatata gcagttcgtc cgccttcgct tttgactac 39

<210> SEQ ID NO 168
<211> LENGTH: 13
<212> TYPE: PRT
<213> ORGANISM: Artificial Sequence
<220> FEATURE:
<223> OTHER INFORMATION: Synthetic

<400> SEQUENCE: 168

Val Arg Tyr Ser Ser Ser Ser Ala Phe Ala Phe Asp Tyr
1 5 10

<210> SEQ ID NO 169
<211> LENGTH: 324
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcttcc gtgtctgcat ctgtaggaga cagagtcacc 60
atcacttgtc gggcgagtca gggtattagc agttggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tcccattcac tttcggccct 300
gggaccaaag tggatatcaa acga 324

<210> SEQ ID NO 170
<211> LENGTH: 108
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Phe
85 90 95

Thr Phe Gly Pro Gly Thr Lys Val Asp Ile Lys Arg
100 105

<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171
cagggtatta gcagttgg 18

<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Ser Ser Trp
1 5

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173 gctgcatcc 9

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175
caacaggcta acagtttccc attcact 27

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

Gln Gln Ala Asn Ser Phe Pro Phe Thr
1 5

<210> SEQ ID NO 177
<211> LENGTH: 360
<212> TYPE: DNA
<213> ORGANISM: Artificial Sequence
<220> FEATURE:
<223> OTHER INFORMATION: Synthetic

<400> SEQUENCE: 177
cagctgcagc tgcaggagtc gggcccagga ctggtgaagc cttcggagac cctgtccctc 60
acctgcactg tctctggtgg ctccatcagc agtagtactt actactgggg ctggatccgc 120
cagcccccag ggaaggggct ggagtggatt gggagtttct attatagtgg gagcacctac 180
tacaacccgt ccctcaagag tcgagtcacc atatccgtag gcacgtccaa gaaccagttc 240
tccctgaagc tgagctctgt gaccgccgca gacacggctg tttatttctg tgcgagaggg 300
gggctcctgg ggagaccttt tgttatctgg ggccaaggga caatggtcac cgtctcttca 360

<210> SEQ ID NO 178
<211> LENGTH: 120
<212> TYPE: PRT
<213> ORGANISM: Artificial Sequence
<220> FEATURE:
<223> OTHER INFORMATION: Synthetic

<400> SEQUENCE: 178

Gln Leu Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Thr Tyr Tyr Trp Gly Trp Ile Arg Gln Pro Pro Gly Lys Gly Leu Glu
35 40 45

Trp Ile Gly Ser Phe Tyr Tyr Ser Gly Ser Thr Tyr Tyr Asn Pro Ser
50 55 60

Leu Lys Ser Arg Val Thr Ile Ser Val Gly Thr Ser Lys Asn Gln Phe
65 70 75 80

Ser Leu Lys Leu Ser Ser Val Thr Ala Ala Asp Thr Ala Val Tyr Phe
85 90 95

Cys Ala Arg Gly Gly Leu Leu Gly Arg Pro Phe Val Ile Trp Gly Gln
100 105 110

Gly Thr Met Val Thr Val Ser Ser
115 120

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179
ggtggctcca tcagcagtag tacttactac 30

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

Gly Gly Ser Ile Ser Ser Ser Thr Tyr Tyr
1 5 10

<210> SEQ ID NO 181
<211> LENGTH: 21

<212> TYPE: DNA
<213> ORGANISM: Artificial Sequence
<220> FEATURE:
<223> OTHER INFORMATION: Synthetic

<400> SEQUENCE: 181
ttctattata gtgggagcac c 21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Phe Tyr Tyr Ser Gly Ser Thr
1 5

<210> SEQ ID NO 183
<211> LENGTH: 36
<212> TYPE: DNA
<213> ORGANISM: Artificial Sequence
<220> FEATURE:
<223> OTHER INFORMATION: Synthetic

<400> SEQUENCE: 183
gcgagagggg ggctcctggg gagacctttt gttatc 36

<210> SEQ ID NO 184
<211> LENGTH: 12
<212> TYPE: PRT
<213> ORGANISM: Artificial Sequence
<220> FEATURE:
<223> OTHER INFORMATION: Synthetic

<400> SEQUENCE: 184

Ala Arg Gly Gly Leu Leu Gly Arg Pro Phe Val Ile
1 5 10

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcctcc ctgtctgcat ctgtaggaga cagagtcacc 60
atcacttgcc gggcaagtca gggcattaga aatgatttag gctggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cataatagtt acccgctcac tttcggcgga 300
gggaccaagg tggagatcaa acga 324

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagggcatta gaaatgat 18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

```
Gln Gly Ile Arg Asn Asp
1               5
```

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 gctgcatcc 9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

```
Ala Ala Ser
1
```

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
ctacagcata atagttaccc gctcact 27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Leu Gln His Asn Ser Tyr Pro Leu Thr
1 5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
gaggtgcagc tggtggagtc taggggaggc ttggtacagc ctgggggtc cctgagactc 60 tcctgtgcag cctctggatt cacttttagc agctatgcca tgagctgggt ccgccaggct 120
ccagggaagg ggctggagtg ggtctcagct attagtggta gtggtggtag cacattctac 180
gcagactccg tgaagggccg gttcaccatc tccagagaca attccaagaa cacggtatat 240
ctgcaaatga acagcctgag agccgaggac acggccgtat attactgtgc gaaagccctc 300
gtattgcgat tttggagtg gttaggggac tactggggcc agggaaccct ggtcaccgtc 360
tcctca 366

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

Glu Val Gln Leu Val Glu Ser Arg Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Phe Tyr Ala Asp Ser Val
50 55 60

Lys Gly Arg Phe Thr Ile Ser Arg Asp Asn Ser Lys Asn Thr Val Tyr
65 70 75 80

Leu Gln Met Asn Ser Leu Arg Ala Glu Asp Thr Ala Val Tyr Tyr Cys
85 90 95

Ala Lys Ala Leu Val Leu Arg Phe Leu Glu Trp Leu Gly Asp Tyr Trp
100 105 110

Gly Gln Gly Thr Leu Val Thr Val Ser Ser
115 120

<210> SEQ ID NO 195
<211> LENGTH: 24
<212> TYPE: DNA

<213> ORGANISM: Artificial Sequence
<220> FEATURE:
<223> OTHER INFORMATION: Synthetic

<400> SEQUENCE: 195
ggattcactt ttagcagcta tgcc 24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Ser Ser Tyr Ala
1 5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attagtggta gtggtggtag caca 24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Gly Ser Gly Gly Ser Thr
1 5

<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199
gcgaaagccc tcgtattgcg atttttggag tggttagggg actac 45

<210> SEQ ID NO 200
<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Lys Ala Leu Val Leu Arg Phe Leu Glu Trp Leu Gly Asp Tyr
1 5 10 15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccttccacc ctgtctgcat ctgtaggaga cagagtcacc 60
atcacttgtc gggccagtca gagtattagt agctggttgg cctggtttca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgtcaacag tataaaagtt attggacgtt cggccaaggg 300
accaaggtgg aaatcaaacg a 321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Thr Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Phe Gln Gln Lys Pro Gly Lys Ala Pro Lys Leu Leu Ile
35 40 45

Tyr Lys Ala Ser Ser Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Lys Ser Tyr Trp Thr
85 90 95

Phe Gly Gln Gly Thr Lys Val Glu Ile Lys Arg
100 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatta gtagctgg 18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Trp
1 5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggcgtct 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ala Ser
1

<210> SEQ ID NO 207
<211> LENGTH: 24
<212> TYPE: DNA
<213> ORGANISM: Artificial Sequence
<220> FEATURE:
<223> OTHER INFORMATION: Synthetic

<400> SEQUENCE: 207
caacagtata aaagttattg gacg 24

<210> SEQ ID NO 208
<211> LENGTH: 8
<212> TYPE: PRT
<213> ORGANISM: Artificial Sequence
<220> FEATURE:
<223> OTHER INFORMATION: Synthetic

<400> SEQUENCE: 208

Gln Gln Tyr Lys Ser Tyr Trp Thr
1 5

<210> SEQ ID NO 209
<211> LENGTH: 372
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ctggtacagc ctggggggtc cctgagactc 60
tcctgtgcag cctctggatt cacctttagc agctatgcca tgagctgggt ccgccaggct 120
ccagggaagg ggctggagtg ggtctcaagt attagtggta gtggtgatag cacattctac 180
acagactccg tgaagggccg gttcaccatc tccagagaca tttccaagaa cacgctgtat 240
ctgcaaatga acagcctgag agccgaggac acggccgtat attactgtgc gaaagatcgt 300
cttctatggt tcggggactt aatatccccc tttcactact ggggccaggg aaccctggtc 360
accgtctcct ca 372

<210> SEQ ID NO 210
<211> LENGTH: 124
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr

```
            20                  25                  30

Ala Met Ser Trp Val Arg Gln Ala Pro Gly Lys Gly Leu Glu Trp Val
        35                  40                  45

Ser Ser Ile Ser Gly Ser Gly Asp Ser Thr Phe Tyr Thr Asp Ser Val
    50                  55                  60

Lys Gly Arg Phe Thr Ile Ser Arg Asp Ile Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Leu Trp Phe Gly Asp Leu Ile Ser Pro Phe His
            100                 105                 110

Tyr Trp Gly Gln Gly Thr Leu Val Thr Val Ser Ser
        115                 120


<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211

ggattcacct ttagcagcta tgcc                                            24


<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ser Tyr Ala
1               5


<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213

attagtggta gtggtgatag caca                                            24


<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Ser Gly Ser Gly Asp Ser Thr
1               5


<210> SEQ ID NO 215
<211> LENGTH: 51
<212> TYPE: DNA
<213> ORGANISM: Artificial Sequence
<220> FEATURE:
<223> OTHER INFORMATION: Synthetic

<400> SEQUENCE: 215
```

gcgaaagatc gtcttctatg gttcggggac ttaatatccc cctttcacta c 51

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Ala Lys Asp Arg Leu Leu Trp Phe Gly Asp Leu Ile Ser Pro Phe His
1 5 10 15

Tyr

<210> SEQ ID NO 217
<211> LENGTH: 327
<212> TYPE: DNA
<213> ORGANISM: Artificial Sequence
<220> FEATURE:
<223> OTHER INFORMATION: Synthetic

<400> SEQUENCE: 217
gaaattgtgt tgacgcagtc tccaggcacc ctgtctttgt ctccagggga aagagccacc 60
ctctcctgca gggccagtca gagtgttagc aacatctact tagcctggta ccagcagaaa 120
cctgcccagg ctcccaggct cctcatctat ggtgcatcca gcagggccac tggcatccca 180
gacaggttta gtgtcagtgg gtctgggaca gacttcactc tcaccatcag cagactggag 240
cctgaagatt ttgcagtgta ttactgtcag cagtatggta gctcacctcg gacgttcggc 300
caagggacca aggtggaaat caaacga 327

<210> SEQ ID NO 218
<211> LENGTH: 109
<212> TYPE: PRT
<213> ORGANISM: Artificial Sequence
<220> FEATURE:
<223> OTHER INFORMATION: Synthetic

<400> SEQUENCE: 218

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Asn Ile
20 25 30

Tyr Leu Ala Trp Tyr Gln Gln Lys Pro Ala Gln Ala Pro Arg Leu Leu
35 40 45

Ile Tyr Gly Ala Ser Ser Arg Ala Thr Gly Ile Pro Asp Arg Phe Ser
50 55 60

Val Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Arg Thr Phe Gly Gln Gly Thr Lys Val Glu Ile Lys Arg
100 105

<210> SEQ ID NO 219
<211> LENGTH: 21
<212> TYPE: DNA
<213> ORGANISM: Artificial Sequence
<220> FEATURE:
<223> OTHER INFORMATION: Synthetic

<400> SEQUENCE: 219
cagagtgtta gcaacatcta c 21

<210> SEQ ID NO 220
<211> LENGTH: 7
<212> TYPE: PRT
<213> ORGANISM: Artificial Sequence
<220> FEATURE:
<223> OTHER INFORMATION: Synthetic

<400> SEQUENCE: 220

Gln Ser Val Ser Asn Ile Tyr
1 5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 ggtgcatcc 9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Gly Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
cagcagtatg gtagctcacc tcggacg 27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Tyr Gly Ser Ser Pro Arg Thr
1 5

<210> SEQ ID NO 225
<211> LENGTH: 366
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagc ctggggggtc cctgagactc 60

-continued

```
tcctgtacag cctctggatt cacctttagc agctatgcca tgagttgggt ccgccaggct    120

ccagggaagg ggctggaatg ggtctcagct attagtggga ctggtagtag tacatacttc    180

acagactccg tgaagggccg gttcgccatc tccagagaca attccaagaa cacgctgtat    240

ctgcaaatga acagcctgag agccgaggac acggccgtat attactgtgc gaaagatgga    300

gagtggctct ctacggtgac ccttttgac tactggggcc agggaaccct ggtcaccgtc    360

tcctca                                                                366
```

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Ser Ser Thr Tyr Phe Thr Asp Ser Val
    50                  55                  60

Lys Gly Arg Phe Ala Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Glu Trp Leu Ser Thr Val Thr Leu Phe Asp Tyr Trp
            100                 105                 110

Gly Gln Gly Thr Leu Val Thr Val Ser Ser
        115                 120
```

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227

```
ggattcacct ttagcagcta tgcc                                             24
```

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

```
Gly Phe Thr Phe Ser Ser Tyr Ala
1               5
```

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggga ctggtagtag taca 24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Thr Gly Ser Ser Thr
1 5

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
gcgaaagatg gagagtggct ctctacggtg accctttttg actac 45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Lys Asp Gly Glu Trp Leu Ser Thr Val Thr Leu Phe Asp Tyr
1 5 10 15

<210> SEQ ID NO 233
<211> LENGTH: 330
<212> TYPE: DNA
<213> ORGANISM: Artificial Sequence
<220> FEATURE:
<223> OTHER INFORMATION: Synthetic

<400> SEQUENCE: 233
gaaattgtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagat ttcactctca ccatcagcag cctgcagtct 240
gaagattttg cactttatta ctgtcagcag tattttatct ggcctccgca tcccactttc 300
ggccctggga ccaaagtgga tatcaaacga 330

<210> SEQ ID NO 234
<211> LENGTH: 110
<212> TYPE: PRT
<213> ORGANISM: Artificial Sequence
<220> FEATURE:
<223> OTHER INFORMATION: Synthetic

<400> SEQUENCE: 234

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

```
Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Leu Tyr Tyr Cys Gln Gln Tyr Phe Ile Trp Pro Pro
                85                  90                  95

His Pro Thr Phe Gly Pro Gly Thr Lys Val Asp Ile Lys Arg
            100                 105                 110


<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

cagagtgtta gcagcaac                                                18


<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Val Ser Ser Asn
1               5


<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237

ggtgcatcc                                                           9


<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Gly Ala Ser
1


<210> SEQ ID NO 239
<211> LENGTH: 33
<212> TYPE: DNA
<213> ORGANISM: Artificial Sequence
<220> FEATURE:
<223> OTHER INFORMATION: Synthetic

<400> SEQUENCE: 239

cagcagtatt ttatctggcc tccgcatccc act                               33
```

<210> SEQ ID NO 240
<211> LENGTH: 11
<212> TYPE: PRT
<213> ORGANISM: Artificial Sequence
<220> FEATURE:
<223> OTHER INFORMATION: Synthetic

<400> SEQUENCE: 240

Gln Gln Tyr Phe Ile Trp Pro Pro His Pro Thr
1 5 10

<210> SEQ ID NO 241
<211> LENGTH: 363
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggagcc gtggtccagc ctgggaggtc cctgagactc 60
tcctgtgcag cctctggatt caccttcagt tactatggca tgcactgggt ccgccaggct 120
ccaggcaagg ggctggagtg ggtggcagtt atatcatatg atggaagtaa aaaatactat 180
gcagactccg tgaagggccg attcaccatc tccagagaca attccaagaa cacgctgtat 240
ctgcaaatga acagcctgag agctgaggac acggctgtgt attactgtgc gaaagatctg 300
acagtagact tctactacgg tatggacgtc tggggccaag ggaccacggt caccgtctcc 360
tca 363

<210> SEQ ID NO 242
<211> LENGTH: 121
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Ala Val Val Gln Pro Gly Arg
1 5 10 15

Ser Leu Arg Leu Ser Cys Ala Ala Ser Gly Phe Thr Phe Ser Tyr Tyr
20 25 30

Gly Met His Trp Val Arg Gln Ala Pro Gly Lys Gly Leu Glu Trp Val
35 40 45

Ala Val Ile Ser Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Leu Thr Val Asp Phe Tyr Tyr Gly Met Asp Val Trp Gly
100 105 110

Gln Gly Thr Thr Val Thr Val Ser Ser
115 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagttacta tggc 24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Tyr Tyr Gly
1 5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaagtaa aaaa 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Ser Lys Lys
1 5

<210> SEQ ID NO 247
<211> LENGTH: 42
<212> TYPE: DNA
<213> ORGANISM: Artificial Sequence
<220> FEATURE:
<223> OTHER INFORMATION: Synthetic

<400> SEQUENCE: 247
gcgaaagatc tgacagtaga cttctactac ggtatggacg tc 42

<210> SEQ ID NO 248
<211> LENGTH: 14
<212> TYPE: PRT
<213> ORGANISM: Artificial Sequence
<220> FEATURE:
<223> OTHER INFORMATION: Synthetic

<400> SEQUENCE: 248

Ala Lys Asp Leu Thr Val Asp Phe Tyr Tyr Gly Met Asp Val
1 5 10

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct acatccagtt tgcaaagtgg ggccccatca 180
aggttcagcg gcagtggatc tgggacagat ttcactctca ccatcagcag cctgcagcct 240
gaagattttg caacttactt ttgtcaacag gctaacagtt tcccatacac ttttggccag 300
gggaccaagc tggagatcaa acga 324

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Thr Ser Ser Leu Gln Ser Gly Ala Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Phe Cys Gln Gln Ala Asn Ser Phe Pro Tyr
85 90 95

Thr Phe Gly Gln Gly Thr Lys Leu Glu Ile Lys Arg
100 105

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cagggtatta gcagctgg 18

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Gly Ile Ser Ser Trp
1 5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gctacatcc 9

<210> SEQ ID NO 254

<211> LENGTH: 3
<212> TYPE: PRT
<213> ORGANISM: Artificial Sequence
<220> FEATURE:
<223> OTHER INFORMATION: Synthetic

<400> SEQUENCE: 254

Ala Thr Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacaggcta acagtttccc atacact 27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Ala Asn Ser Phe Pro Tyr Thr
1 5

<210> SEQ ID NO 257
<211> LENGTH: 342
<212> TYPE: DNA
<213> ORGANISM: Artificial Sequence
<220> FEATURE:
<223> OTHER INFORMATION: Synthetic

<400> SEQUENCE: 257
caggtgcagc tgcaggagtc gggcccagga ctggtgaagc cttcggagac cctgtccctc 60
acctgcactg tctctgatgg ctccatcagt agttactact ggagctggat ccggcagccc 120
ccagggaggg gactggagtg gattgggttt atctattaca gtgggagcac cagctacaac 180
ccctccctca agagtcgagt caccatttca gtagacacgt ccatgagcca gttctccctg 240
aagctgaggt ctgtgaccgc cgcagacacg gccgtgtatt actgtgcgcg tgggagcccc 300
tttgactact ggggcccggg aaccctggtc accgtctcct ca 342

<210> SEQ ID NO 258
<211> LENGTH: 114
<212> TYPE: PRT
<213> ORGANISM: Artificial Sequence
<220> FEATURE:
<223> OTHER INFORMATION: Synthetic

<400> SEQUENCE: 258

Gln Val Gln Leu Gln Glu Ser Gly Pro Gly Leu Val Lys Pro Ser Glu
1 5 10 15

Thr Leu Ser Leu Thr Cys Thr Val Ser Asp Gly Ser Ile Ser Ser Tyr
20 25 30

Tyr Trp Ser Trp Ile Arg Gln Pro Pro Gly Arg Gly Leu Glu Trp Ile
35 40 45

Gly Phe Ile Tyr Tyr Ser Gly Ser Thr Ser Tyr Asn Pro Ser Leu Lys
50 55 60

Ser Arg Val Thr Ile Ser Val Asp Thr Ser Met Ser Gln Phe Ser Leu
65 70 75 80

Lys Leu Arg Ser Val Thr Ala Ala Asp Thr Ala Val Tyr Tyr Cys Ala
85 90 95

Arg Gly Ser Pro Phe Asp Tyr Trp Gly Pro Gly Thr Leu Val Thr Val
100 105 110

Ser Ser

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
gatggctcca tcagtagtta ctac 24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Asp Gly Ser Ile Ser Ser Tyr Tyr
1 5

<210> SEQ ID NO 261
<211> LENGTH: 21
<212> TYPE: DNA
<213> ORGANISM: Artificial Sequence
<220> FEATURE:
<223> OTHER INFORMATION: Synthetic

<400> SEQUENCE: 261
atctattaca gtgggagcac c 21

<210> SEQ ID NO 262
<211> LENGTH: 7
<212> TYPE: PRT
<213> ORGANISM: Artificial Sequence
<220> FEATURE:
<223> OTHER INFORMATION: Synthetic

<400> SEQUENCE: 262

Ile Tyr Tyr Ser Gly Ser Thr
1 5

<210> SEQ ID NO 263
<211> LENGTH: 24
<212> TYPE: DNA
<213> ORGANISM: Artificial Sequence
<220> FEATURE:
<223> OTHER INFORMATION: Synthetic

<400> SEQUENCE: 263
gcgcgtggga gcccctttga ctac 24

<210> SEQ ID NO 264
<211> LENGTH: 8
<212> TYPE: PRT
<213> ORGANISM: Artificial Sequence
<220> FEATURE:
<223> OTHER INFORMATION: Synthetic

<400> SEQUENCE: 264

Ala Arg Gly Ser Pro Phe Asp Tyr
1               5

<210> SEQ ID NO 265
<211> LENGTH: 327
<212> TYPE: DNA
<213> ORGANISM: Artificial Sequence
<220> FEATURE:
<223> OTHER INFORMATION: Synthetic

<400> SEQUENCE: 265
gaaattgtgt tgacgcagtc tccaggcacc ctgtctttgt ctccagggga aagagccacc      60
ctctcctgca gggccagtca gagtgttagc agcagctact tagcctggta ccagcaaaga     120
cctggccagg ctcccagcct cctcatctct ggtgcatcca ggagggccac tggcatccca     180
gacaggttca gtggcagtgg gtctgggaca gacttcactc tcaccatcag aagactggag     240
cctgaagatt ttgcaatgta ttactgtcag cagtatggta gttcacctcc cactttcggc     300
ggagggacca aggtggagat caaacga                                         327

<210> SEQ ID NO 266
<211> LENGTH: 109
<212> TYPE: PRT
<213> ORGANISM: Artificial Sequence
<220> FEATURE:
<223> OTHER INFORMATION: Synthetic

<400> SEQUENCE: 266

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Arg Pro Gly Gln Ala Pro Ser Leu Leu
        35                  40                  45

Ile Ser Gly Ala Ser Arg Arg Ala Thr Gly Ile Pro Asp Arg Phe Ser
    50                  55                  60

Gly Ser Gly Ser Gly Thr Asp Phe Thr Leu Thr Ile Arg Arg Leu Glu
65                  70                  75                  80

Pro Glu Asp Phe Ala Met Tyr Tyr Cys Gln Gln Tyr Gly Ser Ser Pro
                85                  90                  95

Pro Thr Phe Gly Gly Gly Thr Lys Val Glu Ile Lys Arg
            100                 105

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
cagagtgtta gcagcagcta c                                                21

<210> SEQ ID NO 268
<211> LENGTH: 7
<212> TYPE: PRT
<213> ORGANISM: Artificial Sequence
<220> FEATURE:

<223> OTHER INFORMATION: Synthetic

<400> SEQUENCE: 268

Gln Ser Val Ser Ser Ser Tyr
1 5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ggtgcatcc 9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Gly Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
cagcagtatg gtagttcacc tcccact 27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Tyr Gly Ser Ser Pro Pro Thr
1 5

<210> SEQ ID NO 273
<211> LENGTH: 363
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaggc ttggtccagc ctggggggtc cctgagactc 60
tcctgtgcag cctctggatt cacgttcagt aactatgcta tgcactgggt ccgccaggct 120
ccagggaagg gactggaata tgtttcagct attagtagta atgggggtag tacatattat 180
gcagactctg tgaagggcag aatcaccatc tccagagaca attccaagaa cacgctgtat 240
cttcaaatgg gcagcctgag agctgaggat atggctgtgt attactgtgc gagagggcga 300
ccgtactact actacttcgg tatggacgtc tggggccaag ggaccacggt caccgtctcc 360

-continued tca 363

<210> SEQ ID NO 274
<211> LENGTH: 121
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Ile Thr Ile Ser Arg Asp Asn Ser Lys Asn Thr Leu Tyr
65                  70                  75                  80

Leu Gln Met Gly Ser Leu Arg Ala Glu Asp Met Ala Val Tyr Tyr Cys
                85                  90                  95

Ala Arg Gly Arg Pro Tyr Tyr Tyr Tyr Phe Gly Met Asp Val Trp Gly
            100                 105                 110

Gln Gly Thr Thr Val Thr Val Ser Ser
        115                 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacgt tcagtaacta tgct 24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Asn Tyr Ala
1               5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attagtagta atgggggtag taca 24

<210> SEQ ID NO 278
<211> LENGTH: 8
<212> TYPE: PRT
<213> ORGANISM: Artificial Sequence
<220> FEATURE:

<223> OTHER INFORMATION: Synthetic

<400> SEQUENCE: 278

Ile Ser Ser Asn Gly Gly Ser Thr
1               5

<210> SEQ ID NO 279
<211> LENGTH: 42
<212> TYPE: DNA
<213> ORGANISM: Artificial Sequence
<220> FEATURE:
<223> OTHER INFORMATION: Synthetic

<400> SEQUENCE: 279
gcgagagggc gaccgtacta ctactacttc ggtatggacg tc 42

<210> SEQ ID NO 280
<211> LENGTH: 14
<212> TYPE: PRT
<213> ORGANISM: Artificial Sequence
<220> FEATURE:
<223> OTHER INFORMATION: Synthetic

<400> SEQUENCE: 280

Ala Arg Gly Arg Pro Tyr Tyr Tyr Tyr Phe Gly Met Asp Val
1               5                   10

<210> SEQ ID NO 281
<211> LENGTH: 339
<212> TYPE: DNA
<213> ORGANISM: Artificial Sequence
<220> FEATURE:
<223> OTHER INFORMATION: Synthetic

<400> SEQUENCE: 281
gatattgtga tgactcagac tccagtctcc tcacctgtca cccttggaca gccggcctcc 60
atctcctgca ggtctagtca aagcctcgta cacagtgatg gaaacaccta cttgagttgg 120
tttcagcaga ggccgggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
ctcaatttcg gcggagggac caaggtggag atcaaacga 339

<210> SEQ ID NO 282
<211> LENGTH: 113
<212> TYPE: PRT
<213> ORGANISM: Artificial Sequence
<220> FEATURE:
<223> OTHER INFORMATION: Synthetic

<400> SEQUENCE: 282

Asp Ile Val Met Thr Gln Thr Pro Val Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Phe Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

```
Ser Arg Val Glu Ala Glu Asp Val Gly Val Tyr Tyr Cys Met Gln Ala
                85                  90                  95

Thr Gln Phe Pro Leu Asn Phe Gly Gly Gly Thr Lys Val Glu Ile Lys
            100                 105                 110

Arg


<210> SEQ ID NO 283
<211> LENGTH: 33
<212> TYPE: DNA
<213> ORGANISM: Artificial Sequence
<220> FEATURE:
<223> OTHER INFORMATION: Synthetic

<400> SEQUENCE: 283

caaagcctcg tacacagtga tggaaacacc tac                                  33


<210> SEQ ID NO 284
<211> LENGTH: 11
<212> TYPE: PRT
<213> ORGANISM: Artificial Sequence
<220> FEATURE:
<223> OTHER INFORMATION: Synthetic

<400> SEQUENCE: 284

Gln Ser Leu Val His Ser Asp Gly Asn Thr Tyr
1               5                   10


<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285

aagatttct                                                              9


<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Lys Ile Ser
1


<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287

atgcaagcta cacaatttcc tctcaat                                         27


<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288
```

Met Gln Ala Thr Gln Phe Pro Leu Asn
1               5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggggggtc cctgagactc 60
tcctgtgcag cctctggatt cacctttagg acctatgcca tgacctgggt ccgccaggct 120
ccagggaagg ggctagactg ggtctcagct attactggtg atggtggtaa tacatactac 180
gcagactccg tgaagggccg gttcaccatt tccagagaca attccaagaa cacgctgtat 240
ctgcaaatga acagcctgag agccgaggac acggccatct attactgtgc gaaagatcag 300
agattcagct ttgctctata ctactttgac tactggggcc agggaaccct ggtcactgtc 360
tcctca 366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Thr Tyr
            20                  25                  30

Ala Met Thr Trp Val Arg Gln Ala Pro Gly Lys Gly Leu Asp Trp Val
        35                  40                  45

Ser Ala Ile Thr Gly Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Asp Gln Arg Phe Ser Phe Ala Leu Tyr Tyr Phe Asp Tyr Trp
            100                 105                 110

Gly Gln Gly Thr Leu Val Thr Val Ser Ser
        115                 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttaggaccta tgcc 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Arg Thr Tyr Ala
1 5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attactggtg atggtggtaa taca 24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Thr Gly Asp Gly Gly Asn Thr
1 5

<210> SEQ ID NO 295
<211> LENGTH: 45
<212> TYPE: DNA
<213> ORGANISM: Artificial Sequence
<220> FEATURE:
<223> OTHER INFORMATION: Synthetic

<400> SEQUENCE: 295
gcgaaagatc agagattcag ctttgctcta tactactttg actac 45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Ala Lys Asp Gln Arg Phe Ser Phe Ala Leu Tyr Tyr Phe Asp Tyr
1 5 10 15

<210> SEQ ID NO 297
<211> LENGTH: 324
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaacgccc ctaagctcct gatctatgct gcattcagtt tgcaaagtgg ggtcccgtca 180
aggttcagcg gcagtggatc tgggacagat ttcactctca ccatcagcag cctgcagcct 240
gaagattttg caacttacta ttgtcaacag gctaacaatt tcccgtggac gttcggccaa 300
gggaccaagg tggaaatcaa acga 324

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Asn Ala Pro Lys Leu Leu Ile
        35                  40                  45

Tyr Ala Ala Phe Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Trp
                85                  90                  95

Thr Phe Gly Gln Gly Thr Lys Val Glu Ile Lys Arg
            100                 105
```

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggtatta gcagctgg 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

```
Gln Gly Ile Ser Ser Trp
1               5
```

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301 gctgcattc 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Phe
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacaggcta acaatttccc gtggacg 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Ala Asn Asn Phe Pro Trp Thr
1 5

<210> SEQ ID NO 305
<211> LENGTH: 354
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctgggaggtc cctgagactc 60
tcctgtgcag cctctggatt caccttcagt aactatgaca tgcactgggt ccgccaggct 120
ccaggcaagg ggctggagtg gatggcagtt atatcatatg atggaattaa taaatattat 180
gcagactccg tgaagggccg attcaccatc tccagagaca attccaagaa cacgctgtat 240
ctgcaaatga acagcctgag agctgaggac acggctgtgt attactgtgc gaaaggtact 300
tactcctggt acttcgatct ctggggccgt ggcaccctgg tcactgtctc ctca 354

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Asp Met His Trp Val Arg Gln Ala Pro Gly Lys Gly Leu Glu Trp Met
35 40 45

Ala Val Ile Ser Tyr Asp Gly Ile Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Gly Thr Tyr Ser Trp Tyr Phe Asp Leu Trp Gly Arg Gly Thr 100 105 110

Leu Val Thr Val Ser Ser
115

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcacct tcagtaacta tgac 24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Thr Phe Ser Asn Tyr Asp
1 5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atatcatatg atggaattaa taaa 24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Tyr Asp Gly Ile Asn Lys
1 5

<210> SEQ ID NO 311
<211> LENGTH: 33
<212> TYPE: DNA
<213> ORGANISM: Artificial Sequence
<220> FEATURE:
<223> OTHER INFORMATION: Synthetic

<400> SEQUENCE: 311
gcgaaaggta cttactcctg gtacttcgat ctc 33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Gly Thr Tyr Ser Trp Tyr Phe Asp Leu
1 5 10

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccttccacc ctgtctacat ctgtaggaga cagagtcacc 60
atcacttgcc gggccagtca gactattagt agctggttgg cctggtatca gcagaaacca 120
gggaaagccc ctaagctcct gatctataag gcgtctcgtt tagaaagtgg ggtcccatca 180
aggttcagcg gcagtggatc tgggacagaa ttcactctca ccatcagcag cctgcagcct 240
gatgattttg caacttatta ctgccaacag tataatagtt attcgtggac gttcggccaa 300
gggaccaagg tggaaatcaa acga 324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Thr Leu Ser Thr Ser Val Gly
1 5 10 15

Asp Arg Val Thr Ile Thr Cys Arg Ala Ser Gln Thr Ile Ser Ser Trp
20 25 30

Leu Ala Trp Tyr Gln Gln Lys Pro Gly Lys Ala Pro Lys Leu Leu Ile
35 40 45

Tyr Lys Ala Ser Arg Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Ser Trp
85 90 95

Thr Phe Gly Gln Gly Thr Lys Val Glu Ile Lys Arg
100 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagactatta gtagctgg 18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Thr Ile Ser Ser Trp
1 5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 aaggcgtct 9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Lys Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
caacagtata atagttattc gtggacg 27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Gln Tyr Asn Ser Tyr Ser Trp Thr
1 5

<210> SEQ ID NO 321
<211> LENGTH: 366
<212> TYPE: DNA
<213> ORGANISM: Artificial Sequence
<220> FEATURE:
<223> OTHER INFORMATION: Synthetic

<400> SEQUENCE: 321
gaagtgcagc tggtggagtc tgggggaggc ttggtacagc ctggcaggtc cctgagactc 60
tcctgtgcag cctctggatt cacctttgat gcttatgcca tgcactgggt ccggcaagct 120
ccagggaagg gcctggagtg ggtctcaggt attagttgga atagtggtag cataggctat 180
gcggactctg tgaagggccg attcaccatt tccagagaca acgccaagaa ctccctgtat 240
ctgcaaatga acagtctgag agaagaggac acggccttgt attactgtgc aaaagataaa 300
attttggaac tttactacta cggtatggac gtctggggcc aagggaccac ggtcaccgtc 360
tcctca 366

<210> SEQ ID NO 322
<211> LENGTH: 122
<212> TYPE: PRT
<213> ORGANISM: Artificial Sequence
<220> FEATURE:
<223> OTHER INFORMATION: Synthetic

<400> SEQUENCE: 322

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Glu Glu Asp Thr Ala Leu Tyr Tyr Cys
                85                  90                  95

Ala Lys Asp Lys Ile Leu Glu Leu Tyr Tyr Tyr Gly Met Asp Val Trp
            100                 105                 110

Gly Gln Gly Thr Thr Val Thr Val Ser Ser
        115                 120

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttgatgctta tgcc 24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

Gly Phe Thr Phe Asp Ala Tyr Ala
1               5

<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
attagttgga atagtggtag cata 24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Trp Asn Ser Gly Ser Ile
1               5

<210> SEQ ID NO 327
<211> LENGTH: 45
<212> TYPE: DNA
<213> ORGANISM: Artificial Sequence
<220> FEATURE:
<223> OTHER INFORMATION: Synthetic

<400> SEQUENCE: 327
gcaaaagata aaattttgga actttactac tacggtatgg acgtc 45

<210> SEQ ID NO 328
<211> LENGTH: 15
<212> TYPE: PRT
<213> ORGANISM: Artificial Sequence
<220> FEATURE:
<223> OTHER INFORMATION: Synthetic

<400> SEQUENCE: 328

Ala Lys Asp Lys Ile Leu Glu Leu Tyr Tyr Tyr Gly Met Asp Val
1 5 10 15

<210> SEQ ID NO 329
<211> LENGTH: 369
<212> TYPE: DNA
<213> ORGANISM: Artificial Sequence
<220> FEATURE:
<223> OTHER INFORMATION: Synthetic

<400> SEQUENCE: 329
gaggtgcagc tggtggagtc tgggggagac ttggtacagc ctggggggtc cctgagactc 60
tcctgttcag cctctggatt cacctttaac atctatgcca tgagctgggt ccgccaggct 120
ccagggaagg ggctggagtg ggtctcaggt attagtggta gtggtggtag cacatactac 180
gcagactccg tgaagggccg gttcaccatc tccagagaca attcaaagaa cacgctgtat 240
ttccaaatga atagcctgag agtcgaggac acggccgtat attactgtgc gaaaaaaata 300
agcagctcgt cctactacta ctacgctatg gacgtctggg gccaagggac cacggtcacc 360
gtctcctca 369

<210> SEQ ID NO 330
<211> LENGTH: 123
<212> TYPE: PRT
<213> ORGANISM: Artificial Sequence
<220> FEATURE:
<223> OTHER INFORMATION: Synthetic

<400> SEQUENCE: 330

Glu Val Gln Leu Val Glu Ser Gly Gly Asp Leu Val Gln Pro Gly Gly
1 5 10 15

Ser Leu Arg Leu Ser Cys Ser Ala Ser Gly Phe Thr Phe Asn Ile Tyr
20 25 30

Ala Met Ser Trp Val Arg Gln Ala Pro Gly Lys Gly Leu Glu Trp Val
35 40 45

Ser Gly Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Phe Gln Met Asn Ser Leu Arg Val Glu Asp Thr Ala Val Tyr Tyr Cys
85 90 95

Ala Lys Lys Ile Ser Ser Ser Ser Tyr Tyr Tyr Tyr Ala Met Asp Val
100 105 110

Trp Gly Gln Gly Thr Thr Val Thr Val Ser Ser
115 120

<210> SEQ ID NO 331
<211> LENGTH: 24
<212> TYPE: DNA
<213> ORGANISM: Artificial Sequence
<220> FEATURE:
<223> OTHER INFORMATION: Synthetic

<400> SEQUENCE: 331
ggattcacct ttaacatcta tgcc 24

<210> SEQ ID NO 332
<211> LENGTH: 8
<212> TYPE: PRT
<213> ORGANISM: Artificial Sequence
<220> FEATURE:
<223> OTHER INFORMATION: Synthetic

<400> SEQUENCE: 332

Gly Phe Thr Phe Asn Ile Tyr Ala
1 5

<210> SEQ ID NO 333
<211> LENGTH: 24
<212> TYPE: DNA
<213> ORGANISM: Artificial Sequence
<220> FEATURE:
<223> OTHER INFORMATION: Synthetic

<400> SEQUENCE: 333
attagtggta gtggtggtag caca 24

<210> SEQ ID NO 334
<211> LENGTH: 8
<212> TYPE: PRT
<213> ORGANISM: Artificial Sequence
<220> FEATURE:
<223> OTHER INFORMATION: Synthetic

<400> SEQUENCE: 334

Ile Ser Gly Ser Gly Gly Ser Thr
1 5

<210> SEQ ID NO 335
<211> LENGTH: 48
<212> TYPE: DNA
<213> ORGANISM: Artificial Sequence
<220> FEATURE:
<223> OTHER INFORMATION: Synthetic

<400> SEQUENCE: 335
gcgaaaaaaa taagcagctc gtcctactac tactacgcta tggacgtc 48

<210> SEQ ID NO 336
<211> LENGTH: 16
<212> TYPE: PRT
<213> ORGANISM: Artificial Sequence
<220> FEATURE:
<223> OTHER INFORMATION: Synthetic

<400> SEQUENCE: 336

Ala Lys Lys Ile Ser Ser Ser Ser Tyr Tyr Tyr Tyr Ala Met Asp Val
1 5 10 15

<210> SEQ ID NO 337
<211> LENGTH: 355
<212> TYPE: DNA
<213> ORGANISM: Artificial Sequence
<220> FEATURE:
<223> OTHER INFORMATION: Synthetic

<400> SEQUENCE: 337
caggtgcagc tggtgcagtc tggggctgag gtgaagaagc ctgggtcctc ggtgaaggtc 60
tcctgcaagg cttctggagg caccttcagc agatatgata tcagctgggt gcgacaggcc 120
cctggacaag gacttgagtg gatgggaggg atcatcccta tctttggtac atcaaactac 180
gcacagaagt tccagggcag agtcacgatt accacggacg aatccacgag tacagtctac 240
atggagctga gcagtctgag atctgaagac acggccgtgt attattgtgc gagaggaggt 300
cgatatggct ggttcgaccc ctggggccag ggaaccctgg tcaccgtctc ctcag 355

<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Arg Tyr
20 25 30

Asp Ile Ser Trp Val Arg Gln Ala Pro Gly Gln Gly Leu Glu Trp Met
35 40 45

Gly Gly Ile Ile Pro Ile Phe Gly Thr Ser Asn Tyr Ala Gln Lys Phe
50 55 60

Gln Gly Arg Val Thr Ile Thr Thr Asp Glu Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Gly Arg Tyr Gly Trp Phe Asp Pro Trp Gly Gln Gly Thr
100 105 110

Leu Val Thr Val Ser Ser
115

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggaggcacct tcagcagata tgat 24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Gly Thr Phe Ser Arg Tyr Asp 1 5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atcatcccta tctttggtac atca 24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ile Pro Ile Phe Gly Thr Ser
1 5

<210> SEQ ID NO 343
<211> LENGTH: 33
<212> TYPE: DNA
<213> ORGANISM: Artificial Sequence
<220> FEATURE:
<223> OTHER INFORMATION: Synthetic

<400> SEQUENCE: 343
gcgagaggag gtcgatatgg ctggttcgac ccc 33

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Ala Arg Gly Gly Arg Tyr Gly Trp Phe Asp Pro
1 5 10

<210> SEQ ID NO 345
<211> LENGTH: 375
<212> TYPE: DNA
<213> ORGANISM: Artificial Sequence
<220> FEATURE:
<223> OTHER INFORMATION: Synthetic

<400> SEQUENCE: 345
gaggtgcagc tggtggagtc tgggggaggc ttggtacagc ctggggggtc cctgagactc 60
tcctgtgcag cctctggatt cacctttagc agctttgcca tgagctgggt ccgccaggct 120
ccagggaagg aactggagtg ggtctcatct attagtggtc gtggtggtag cacatactac 180
gcagactccg tgaggggccg gttcaccatc tccagagaca attccaagat cacgctgtat 240
ctgcaaatga acagcctgag agccgaggac acggccgtat attactgtgc gaaagatatt 300
gtcttccggt ataccagctc ggcctactgg tacttcgatc tctggggccg tggcaccctg 360
gtcaccgtct cctca 375

<210> SEQ ID NO 346
<211> LENGTH: 125

<212> TYPE: PRT
<213> ORGANISM: Artificial Sequence
<220> FEATURE:
<223> OTHER INFORMATION: Synthetic

<400> SEQUENCE: 346

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Glu Leu Glu Trp Val
        35                  40                  45

Ser Ser Ile Ser Gly Arg Gly Gly Ser Thr Tyr Tyr Ala Asp Ser Val
    50                  55                  60

Arg Gly Arg Phe Thr Ile Ser Arg Asp Asn Ser Lys Ile Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Val Phe Arg Tyr Thr Ser Ser Ala Tyr Trp Tyr Phe
            100                 105                 110

Asp Leu Trp Gly Arg Gly Thr Leu Val Thr Val Ser Ser
        115                 120                 125
```

<210> SEQ ID NO 347
<211> LENGTH: 24
<212> TYPE: DNA
<213> ORGANISM: Artificial Sequence
<220> FEATURE:
<223> OTHER INFORMATION: Synthetic

<400> SEQUENCE: 347
ggattcacct ttagcagctt tgcc 24

<210> SEQ ID NO 348
<211> LENGTH: 8
<212> TYPE: PRT
<213> ORGANISM: Artificial Sequence
<220> FEATURE:
<223> OTHER INFORMATION: Synthetic

<400> SEQUENCE: 348

```
Gly Phe Thr Phe Ser Ser Phe Ala
1               5
```

<210> SEQ ID NO 349
<211> LENGTH: 24
<212> TYPE: DNA
<213> ORGANISM: Artificial Sequence
<220> FEATURE:
<223> OTHER INFORMATION: Synthetic

<400> SEQUENCE: 349
attagtggtc gtggtggtag caca 24

<210> SEQ ID NO 350
<211> LENGTH: 8
<212> TYPE: PRT
<213> ORGANISM: Artificial Sequence
<220> FEATURE:
<223> OTHER INFORMATION: Synthetic

<400> SEQUENCE: 350

Ile Ser Gly Arg Gly Gly Ser Thr 1 5

<210> SEQ ID NO 351
<211> LENGTH: 54
<212> TYPE: DNA
<213> ORGANISM: Artificial Sequence
<220> FEATURE:
<223> OTHER INFORMATION: Synthetic

<400> SEQUENCE: 351
gcgaaagata ttgtcttccg gtataccagc tcggcctact ggtacttcga tctc 54

<210> SEQ ID NO 352
<211> LENGTH: 18
<212> TYPE: PRT
<213> ORGANISM: Artificial Sequence
<220> FEATURE:
<223> OTHER INFORMATION: Synthetic

<400> SEQUENCE: 352

Ala Lys Asp Ile Val Phe Arg Tyr Thr Ser Ser Ala Tyr Trp Tyr Phe
1 5 10 15

Asp Leu

<210> SEQ ID NO 353
<211> LENGTH: 375
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtacagc ctggggggtc cctgagactc 60
tcctgtgcag cctctggatt cacctttagc agctatggca tgaactgggt ccgccaggct 120
ccagggaagg ggctggagtg ggtctcagtt attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagatcgt 300
tggacgtatt actatgatag tagtggttcc ccctttgact actggggcca gggaaccctg 360
gtcaccgtct cctca 375

<210> SEQ ID NO 354
<211> LENGTH: 125
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Asn Trp Val Arg Gln Ala Pro Gly Lys Gly Leu Glu Trp Val
35 40 45

Ser Val Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys

-continued

```
            85                  90                  95

Ala Lys Asp Arg Trp Thr Tyr Tyr Tyr Asp Ser Ser Gly Ser Pro Phe
            100                 105                 110

Asp Tyr Trp Gly Gln Gly Thr Leu Val Thr Val Ser Ser
        115                 120                 125
```

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttagcagcta tggc 24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

```
Gly Phe Thr Phe Ser Ser Tyr Gly
1               5
```

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
attagtggta gtggtggtag caca 24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

```
Ile Ser Gly Ser Gly Gly Ser Thr
1               5
```

<210> SEQ ID NO 359
<211> LENGTH: 54
<212> TYPE: DNA
<213> ORGANISM: Artificial Sequence
<220> FEATURE:
<223> OTHER INFORMATION: Synthetic

<400> SEQUENCE: 359
gcgaaagatc gttggacgta ttactatgat agtagtggtt cccctttga ctac 54

<210> SEQ ID NO 360
<211> LENGTH: 18
<212> TYPE: PRT
<213> ORGANISM: Artificial Sequence
<220> FEATURE:
<223> OTHER INFORMATION: Synthetic

<400> SEQUENCE: 360

Ala Lys Asp Arg Trp Thr Tyr Tyr Tyr Asp Ser Ser Gly Ser Pro Phe
1 5 10 15

Asp Tyr

<210> SEQ ID NO 361
<211> LENGTH: 324
<212> TYPE: DNA
<213> ORGANISM: Artificial Sequence
<220> FEATURE:
<223> OTHER INFORMATION: Synthetic

<400> SEQUENCE: 361
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccttg gacgttcggc 300
caagggacca aggtggaaat caaa 324

<210> SEQ ID NO 362
<211> LENGTH: 108
<212> TYPE: PRT
<213> ORGANISM: Artificial Sequence
<220> FEATURE:
<223> OTHER INFORMATION: Synthetic

<400> SEQUENCE: 362

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 363
<211> LENGTH: 21
<212> TYPE: DNA
<213> ORGANISM: Artificial Sequence
<220> FEATURE:
<223> OTHER INFORMATION: Synthetic

<400> SEQUENCE: 363
cagagtgtta gcagcagcta c 21

<210> SEQ ID NO 364
<211> LENGTH: 7
<212> TYPE: PRT
<213> ORGANISM: Artificial Sequence
<220> FEATURE:
<223> OTHER INFORMATION: Synthetic

<400> SEQUENCE: 364

Gln Ser Val Ser Ser Ser Tyr
1 5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 ggtgcatcc 9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Gly Ala Ser
1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
cagcagtatg gtagctcacc ttggacg 27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Tyr Gly Ser Ser Pro Trp Thr
1 5

<210> SEQ ID NO 369
<211> LENGTH: 363
<212> TYPE: DNA
<213> ORGANISM: Artificial Sequence
<220> FEATURE:
<223> OTHER INFORMATION: Synthetic

<400> SEQUENCE: 369
gaggtgcagc tggtggagtc tgggggaggc tttgtacagc ctgggggggtc cctgagactc 60 tcctgtgcag cctctggatt cacttttagc agttatgcca tgagttgggt ccgccaggct 120
ccaggtaagg ggctggagtg ggtctcagct attagtggta ctggtagtaa cacatactac 180
gcagactccg tgaagggccg gttcaccatc tccagagaca attccaagaa cacgctgtat 240
ctgcaaatga acagcctgag agccgaggac acggccgttt actactgtgc gaaagatcgc 300
gtgactacag taacctacta ctttgactac tggggccagg gaaccctggt caccgtctcc 360
tca 363

<210> SEQ ID NO 370
<211> LENGTH: 121
<212> TYPE: PRT
<213> ORGANISM: Artificial Sequence
<220> FEATURE:
<223> OTHER INFORMATION: Synthetic

<400> SEQUENCE: 370

```
Glu Val Gln Leu Val Glu Ser Gly Gly Gly Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Thr Thr Val Thr Tyr Tyr Phe Asp Tyr Trp Gly
            100                 105                 110

Gln Gly Thr Leu Val Thr Val Ser Ser
        115                 120
```

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcactt ttagcagtta tgcc 24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

```
Gly Phe Thr Phe Ser Ser Tyr Ala
1               5
```

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagtggta ctggtagtaa caca 24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Gly Thr Gly Ser Asn Thr
1               5

<210> SEQ ID NO 375
<211> LENGTH: 42
<212> TYPE: DNA
<213> ORGANISM: Artificial Sequence
<220> FEATURE:
<223> OTHER INFORMATION: Synthetic

<400> SEQUENCE: 375
gcgaaagatc gcgtgactac agtaacctac tactttgact ac 42

<210> SEQ ID NO 376
<211> LENGTH: 14
<212> TYPE: PRT
<213> ORGANISM: Artificial Sequence
<220> FEATURE:
<223> OTHER INFORMATION: Synthetic

<400> SEQUENCE: 376

Ala Lys Asp Arg Val Thr Thr Val Thr Tyr Tyr Phe Asp Tyr
1               5                   10

<210> SEQ ID NO 377
<211> LENGTH: 372
<212> TYPE: DNA
<213> ORGANISM: Artificial Sequence
<220> FEATURE:
<223> OTHER INFORMATION: Synthetic

<400> SEQUENCE: 377
gaggtgcagc tggtggagtc tgggggaggc ttggtacagc ctggggggtc cctgagactc 60
tcctgtgcag cctctggttt cacctttagc agctatgcca tgaactgggt ccgccaggct 120
ccagggaagg gactggagtg ggtctcagct attagtggta gtggtgatag cacatactac 180
gcagactccg tgaagggccg gttcaccatc tccagagaca attccaggac cacgctgtct 240
ctgcaattga acagcctgag agccgaggac acggccgtat attactgtgc gaaagatcga 300
ctactatggt tcggggaatt aggatcccca tttcactact ggggccaggg aaccctggtc 360
accgtctcct ca 372

<210> SEQ ID NO 378
<211> LENGTH: 124
<212> TYPE: PRT
<213> ORGANISM: Artificial Sequence
<220> FEATURE:
<223> OTHER INFORMATION: Synthetic

<400> SEQUENCE: 378

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Arg Thr Thr Leu Ser
65                  70                  75                  80

-continued

Leu Gln Leu Asn Ser Leu Arg Ala Glu Asp Thr Ala Val Tyr Tyr Cys
85 90 95

Ala Lys Asp Arg Leu Leu Trp Phe Gly Glu Leu Gly Ser Pro Phe His
100 105 110

Tyr Trp Gly Gln Gly Thr Leu Val Thr Val Ser Ser
115 120

<210> SEQ ID NO 379
<211> LENGTH: 24
<212> TYPE: DNA
<213> ORGANISM: Artificial Sequence
<220> FEATURE:
<223> OTHER INFORMATION: Synthetic

<400> SEQUENCE: 379
ggtttcacct ttagcagcta tgcc 24

<210> SEQ ID NO 380
<211> LENGTH: 8
<212> TYPE: PRT
<213> ORGANISM: Artificial Sequence
<220> FEATURE:
<223> OTHER INFORMATION: Synthetic

<400> SEQUENCE: 380

Gly Phe Thr Phe Ser Ser Tyr Ala
1 5

<210> SEQ ID NO 381
<211> LENGTH: 24
<212> TYPE: DNA
<213> ORGANISM: Artificial Sequence
<220> FEATURE:
<223> OTHER INFORMATION: Synthetic

<400> SEQUENCE: 381
attagtggta gtggtgatag caca 24

<210> SEQ ID NO 382
<211> LENGTH: 8
<212> TYPE: PRT
<213> ORGANISM: Artificial Sequence
<220> FEATURE:
<223> OTHER INFORMATION: Synthetic

<400> SEQUENCE: 382

Ile Ser Gly Ser Gly Asp Ser Thr
1 5

<210> SEQ ID NO 383
<211> LENGTH: 51
<212> TYPE: DNA
<213> ORGANISM: Artificial Sequence
<220> FEATURE:
<223> OTHER INFORMATION: Synthetic

<400> SEQUENCE: 383
gcgaaagatc gactactatg gttcggggaa ttaggatccc catttcacta c 51

<210> SEQ ID NO 384
<211> LENGTH: 17
<212> TYPE: PRT
<213> ORGANISM: Artificial Sequence
<220> FEATURE:
<223> OTHER INFORMATION: Synthetic

<400> SEQUENCE: 384

Ala Lys Asp Arg Leu Leu Trp Phe Gly Glu Leu Gly Ser Pro Phe His
1 5 10 15

Tyr

<210> SEQ ID NO 385
<211> LENGTH: 363
<212> TYPE: DNA
<213> ORGANISM: Artificial Sequence
<220> FEATURE:
<223> OTHER INFORMATION: Synthetic

<400> SEQUENCE: 385
gaggtgcagc tggtggagtc tgggggaggc ttggaacagc ctgggggtc cctgagactc 60 tcctgtgcag cctctggatt cacctttagc agctatgcca tgagctgggt ccgccaggct 120
ccagggaagg ggctggagtg ggtctcagtc attagtggta gtggtggtta cacaaactac 180
gcagactccg tgaagggccg gttcaccatc tccagagaca attccaagaa cacgctgtat 240
ctgcaaatga accgcctgag agccgaggac tcggccgttt attactgtgc gaggcataat 300
tggaactacg actattacgg tatggacgtc tggggccagg ggaccacggt caccgtctcc 360
tca 363

<210> SEQ ID NO 386
<211> LENGTH: 121
<212> TYPE: PRT
<213> ORGANISM: Artificial Sequence
<220> FEATURE:
<223> OTHER INFORMATION: Synthetic

<400> SEQUENCE: 386

Glu Val Gln Leu Val Glu Ser Gly Gly Gly Leu Glu Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Ser Gly Ser Gly Gly Tyr Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Arg Leu Arg Ala Glu Asp Ser Ala Val Tyr Tyr Cys
85 90 95

Ala Arg His Asn Trp Asn Tyr Asp Tyr Tyr Gly Met Asp Val Trp Gly
100 105 110

Gln Gly Thr Thr Val Thr Val Ser Ser
115 120

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct ttagcagcta tgcc 24

<210> SEQ ID NO 388

<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Ser Tyr Ala
1               5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attagtggta gtggtggtta caca 24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Ser Gly Ser Gly Gly Tyr Thr
1               5

<210> SEQ ID NO 391
<211> LENGTH: 42
<212> TYPE: DNA
<213> ORGANISM: Artificial Sequence
<220> FEATURE:
<223> OTHER INFORMATION: Synthetic

<400> SEQUENCE: 391
gcgaggcata attggaacta cgactattac ggtatggacg tc 42

<210> SEQ ID NO 392
<211> LENGTH: 14
<212> TYPE: PRT
<213> ORGANISM: Artificial Sequence
<220> FEATURE:
<223> OTHER INFORMATION: Synthetic

<400> SEQUENCE: 392

Ala Arg His Asn Trp Asn Tyr Asp Tyr Tyr Gly Met Asp Val
1               5                   10

<210> SEQ ID NO 393
<211> LENGTH: 360
<212> TYPE: DNA
<213> ORGANISM: Artificial Sequence
<220> FEATURE:
<223> OTHER INFORMATION: Synthetic

<400> SEQUENCE: 393
caggtgcagc tggtggagtc tgggggaggc gtggtccagt ctgggaggtc cctgagactc 60
tcctgtgcag ccgctggatt caccttcagt aattatggca tgcactgggt ccgccaggct 120
ccaggcaagg ggctggagtg ggtggcactt atgtcatttg atggaagtga taaatactat 180
gcagactccg tgaagggccg attcaccatc tccagagaca attccaagaa cacgttgtat 240
ctgcaaatga acagcctgag agctgaggac acggctctgt attactgtgc gaaaggatac 300
gatttttgga gtggttattg ggactactgg ggccagggaa ccctggtcac cgtctcctca 360

<210> SEQ ID NO 394
<211> LENGTH: 120
<212> TYPE: PRT
<213> ORGANISM: Artificial Sequence
<220> FEATURE:
<223> OTHER INFORMATION: Synthetic

<400> SEQUENCE: 394

Gln Val Gln Leu Val Glu Ser Gly Gly Gly Val Val Gln Ser Gly Arg
1 5 10 15

Ser Leu Arg Leu Ser Cys Ala Ala Ala Gly Phe Thr Phe Ser Asn Tyr
20 25 30

Gly Met His Trp Val Arg Gln Ala Pro Gly Lys Gly Leu Glu Trp Val
35 40 45

Ala Leu Met Ser Phe Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Leu Tyr Tyr Cys
85 90 95

Ala Lys Gly Tyr Asp Phe Trp Ser Gly Tyr Trp Asp Tyr Trp Gly Gln
100 105 110

Gly Thr Leu Val Thr Val Ser Ser
115 120

<210> SEQ ID NO 395
<211> LENGTH: 24
<212> TYPE: DNA
<213> ORGANISM: Artificial Sequence
<220> FEATURE:
<223> OTHER INFORMATION: Synthetic

<400> SEQUENCE: 395
ggattcacct tcagtaatta tggc 24

<210> SEQ ID NO 396
<211> LENGTH: 8
<212> TYPE: PRT
<213> ORGANISM: Artificial Sequence
<220> FEATURE:
<223> OTHER INFORMATION: Synthetic

<400> SEQUENCE: 396

Gly Phe Thr Phe Ser Asn Tyr Gly
1 5

<210> SEQ ID NO 397
<211> LENGTH: 24
<212> TYPE: DNA
<213> ORGANISM: Artificial Sequence
<220> FEATURE:
<223> OTHER INFORMATION: Synthetic

<400> SEQUENCE: 397
atgtcatttg atggaagtga taaa 24

<210> SEQ ID NO 398
<211> LENGTH: 8
<212> TYPE: PRT

<213> ORGANISM: Artificial Sequence
<220> FEATURE:
<223> OTHER INFORMATION: Synthetic

<400> SEQUENCE: 398

Met Ser Phe Asp Gly Ser Asp Lys
1               5

<210> SEQ ID NO 399
<211> LENGTH: 39
<212> TYPE: DNA
<213> ORGANISM: Artificial Sequence
<220> FEATURE:
<223> OTHER INFORMATION: Synthetic

<400> SEQUENCE: 399
gcgaaaggat acgatttttg gagtggttat tgggactac 39

<210> SEQ ID NO 400
<211> LENGTH: 13
<212> TYPE: PRT
<213> ORGANISM: Artificial Sequence
<220> FEATURE:
<223> OTHER INFORMATION: Synthetic

<400> SEQUENCE: 400

Ala Lys Gly Tyr Asp Phe Trp Ser Gly Tyr Trp Asp Tyr
1               5                   10

<210> SEQ ID NO 401
<211> LENGTH: 351
<212> TYPE: DNA
<213> ORGANISM: Artificial Sequence
<220> FEATURE:
<223> OTHER INFORMATION: Synthetic

<400> SEQUENCE: 401
gaggtgcagc tggtggagtc tgggggaggc ttggtacaac ctggggggtc cctgagactc 60
tcctgtgcag cctctggatt cacctttagc acctatgcca tgagctgggt ccgccaggct 120
ccagggaagg ggcttgagtg ggtctcaact attagtggtc gttctgatat tacatacttc 180
gcagactccg tgaagggccg gtttaccgtc tccagagaca attccaagac cacgctatat 240
ctccaaatga acagtctgag agccgaggac acggccgtat attactgtgc gacagatgac 300
gacctgcccc ttgactactg gggccaggga accctggtca ccgtctcctc a 351

<210> SEQ ID NO 402
<211> LENGTH: 117
<212> TYPE: PRT
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Ser Gly Arg Ser Asp Ile Thr Tyr Phe Ala Asp Ser Val
    50                  55                  60

Lys Gly Arg Phe Thr Val Ser Arg Asp Asn Ser Lys Thr Thr Leu Tyr

-continued

```
65                  70                  75                  80

Leu Gln Met Asn Ser Leu Arg Ala Glu Asp Thr Ala Val Tyr Tyr Cys
                85                  90                  95

Ala Thr Asp Asp Asp Leu Pro Leu Asp Tyr Trp Gly Gln Gly Thr Leu
            100                 105                 110

Val Thr Val Ser Ser
        115


<210> SEQ ID NO 403
<211> LENGTH: 24
<212> TYPE: DNA
<213> ORGANISM: Artificial Sequence
<220> FEATURE:
<223> OTHER INFORMATION: Synthetic

<400> SEQUENCE: 403

ggattcacct ttagcaccta tgcc                                            24


<210> SEQ ID NO 404
<211> LENGTH: 8
<212> TYPE: PRT
<213> ORGANISM: Artificial Sequence
<220> FEATURE:
<223> OTHER INFORMATION: Synthetic

<400> SEQUENCE: 404

Gly Phe Thr Phe Ser Thr Tyr Ala
1               5


<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405

attagtggtc gttctgatat taca                                            24


<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

Ile Ser Gly Arg Ser Asp Ile Thr
1               5


<210> SEQ ID NO 407
<211> LENGTH: 30
<212> TYPE: DNA
<213> ORGANISM: Artificial Sequence
<220> FEATURE:
<223> OTHER INFORMATION: Synthetic

<400> SEQUENCE: 407

gcgacagatg acgacctgcc ccttgactac                                      30


<210> SEQ ID NO 408
<211> LENGTH: 10
<212> TYPE: PRT
<213> ORGANISM: Artificial Sequence
<220> FEATURE:
```

-continued

<223> OTHER INFORMATION: Synthetic

<400> SEQUENCE: 408

Ala Thr Asp Asp Asp Leu Pro Leu Asp Tyr
1 5 10

<210> SEQ ID NO 409
<211> LENGTH: 354
<212> TYPE: DNA
<213> ORGANISM: Artificial Sequence
<220> FEATURE:
<223> OTHER INFORMATION: Synthetic

<400> SEQUENCE: 409
caggtgcagc tggtgcagtc tgggactgag gtgaagaagc ctgggtcctc ggtgaaggtc 60
tcctgcaagg cttctggagg caccttcagc agatatactt tcagctgggt gcgacaggcc 120
cctggacaag ggcttgagtg gatgggaggg atcatcccta tctttggtac aacaaactac 180
gcacagaagt tccagggcag agtcacgatt accacggacg aatccacgag cacagtctac 240
atggagctga gcagcctgag atctgaggac acggccgtgt attattgtac cagaggaggt 300
cgatatggct ggttcgaccc ctggggccag ggaaccctgg tcaccgtctc ctca 354

<210> SEQ ID NO 410
<211> LENGTH: 118
<212> TYPE: PRT
<213> ORGANISM: Artificial Sequence
<220> FEATURE:
<223> OTHER INFORMATION: Synthetic

<400> SEQUENCE: 410

Gln Val Gln Leu Val Gln Ser Gly Thr Glu Val Lys Lys Pro Gly Ser
1 5 10 15

Ser Val Lys Val Ser Cys Lys Ala Ser Gly Gly Thr Phe Ser Arg Tyr
20 25 30

Thr Phe Ser Trp Val Arg Gln Ala Pro Gly Gln Gly Leu Glu Trp Met
35 40 45

Gly Gly Ile Ile Pro Ile Phe Gly Thr Thr Asn Tyr Ala Gln Lys Phe
50 55 60

Gln Gly Arg Val Thr Ile Thr Thr Asp Glu Ser Thr Ser Thr Val Tyr
65 70 75 80

Met Glu Leu Ser Ser Leu Arg Ser Glu Asp Thr Ala Val Tyr Tyr Cys
85 90 95

Thr Arg Gly Gly Arg Tyr Gly Trp Phe Asp Pro Trp Gly Gln Gly Thr
100 105 110

Leu Val Thr Val Ser Ser
115

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411
ggaggcacct tcagcagata tact 24

<210> SEQ ID NO 412
<211> LENGTH: 8
<212> TYPE: PRT

<213> ORGANISM: Artificial Sequence
<220> FEATURE:
<223> OTHER INFORMATION: Synthetic

<400> SEQUENCE: 412

Gly Gly Thr Phe Ser Arg Tyr Thr
1               5

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
atcatcccta tctttggtac aaca 24

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Ile Pro Ile Phe Gly Thr Thr
1               5

<210> SEQ ID NO 415
<211> LENGTH: 33
<212> TYPE: DNA
<213> ORGANISM: Artificial Sequence
<220> FEATURE:
<223> OTHER INFORMATION: Synthetic

<400> SEQUENCE: 415
accagaggag gtcgatatgg ctggttcgac ccc 33

<210> SEQ ID NO 416
<211> LENGTH: 11
<212> TYPE: PRT
<213> ORGANISM: Artificial Sequence
<220> FEATURE:
<223> OTHER INFORMATION: Synthetic

<400> SEQUENCE: 416

Thr Arg Gly Gly Arg Tyr Gly Trp Phe Asp Pro
1               5                   10

<210> SEQ ID NO 417
<211> LENGTH: 403
<212> TYPE: PRT
<213> ORGANISM: Homo sapiens
<220> FEATURE:
<221> NAME/KEY: misc_feature
<223> OTHER INFORMATION: His-myc tagged human MSR1 antibody
(extracellular domain)

<400> SEQUENCE: 417

His His His His His His Glu Gln Lys Leu Ile Ser Glu Glu Asp Leu
1               5                   10                  15

Gly Gly Glu Gln Lys Leu Ile Ser Glu Glu Asp Leu Lys Trp Glu Thr
            20                  25                  30

Lys Asn Cys Ser Val Ser Ser Thr Asn Ala Asn Asp Ile Thr Gln Ser
        35                  40                  45

```
Leu Thr Gly Lys Gly Asn Asp Ser Glu Glu Glu Met Arg Phe Gln Glu
    50                  55                  60

Val Phe Met Glu His Met Ser Asn Met Glu Lys Arg Ile Gln His Ile
65                  70                  75                  80

Leu Asp Met Glu Ala Asn Leu Met Asp Thr Glu His Phe Gln Asn Phe
                85                  90                  95

Ser Met Thr Thr Asp Gln Arg Phe Asn Asp Ile Leu Leu Gln Leu Ser
            100                 105                 110

Thr Leu Phe Ser Ser Val Gln Gly His Gly Asn Ala Ile Asp Glu Ile
        115                 120                 125

Ser Lys Ser Leu Ile Ser Leu Asn Thr Thr Leu Leu Asp Leu Gln Leu
    130                 135                 140

Asn Ile Glu Asn Leu Asn Gly Lys Ile Gln Glu Asn Thr Phe Lys Gln
145                 150                 155                 160

Gln Glu Glu Ile Ser Lys Leu Glu Glu Arg Val Tyr Asn Val Ser Ala
                165                 170                 175

Glu Ile Met Ala Met Lys Glu Glu Gln Val His Leu Glu Gln Glu Ile
            180                 185                 190

Lys Gly Glu Val Lys Val Leu Asn Asn Ile Thr Asn Asp Leu Arg Leu
        195                 200                 205

Lys Asp Trp Glu His Ser Gln Thr Leu Arg Asn Ile Thr Leu Ile Gln
    210                 215                 220

Gly Pro Pro Gly Pro Pro Gly Glu Lys Gly Asp Arg Gly Pro Thr Gly
225                 230                 235                 240

Glu Ser Gly Pro Arg Gly Phe Pro Gly Pro Ile Gly Pro Pro Gly Leu
                245                 250                 255

Lys Gly Asp Arg Gly Ala Ile Gly Phe Pro Gly Ser Arg Gly Leu Pro
            260                 265                 270

Gly Tyr Ala Gly Arg Pro Gly Asn Ser Gly Pro Lys Gly Gln Lys Gly
        275                 280                 285

Glu Lys Gly Ser Gly Asn Thr Leu Thr Pro Phe Thr Lys Val Arg Leu
    290                 295                 300

Val Gly Gly Ser Gly Pro His Glu Gly Arg Val Glu Ile Leu His Ser
305                 310                 315                 320

Gly Gln Trp Gly Thr Ile Cys Asp Asp Arg Trp Glu Val Arg Val Gly
                325                 330                 335

Gln Val Val Cys Arg Ser Leu Gly Tyr Pro Gly Val Gln Ala Val His
            340                 345                 350

Lys Ala Ala His Phe Gly Gln Gly Thr Gly Pro Ile Trp Leu Asn Glu
        355                 360                 365

Val Phe Cys Phe Gly Arg Glu Ser Ser Ile Glu Glu Cys Lys Ile Arg
    370                 375                 380

Gln Trp Gly Thr Arg Ala Cys Ser His Ser Glu Asp Ala Gly Val Thr
385                 390                 395                 400

Cys Thr Leu
```

<210> SEQ ID NO 418
<211> LENGTH: 403
<212> TYPE: PRT
<213> ORGANISM: Macaca fascicularis
<220> FEATURE:
<221> NAME/KEY: misc_feature
<223> OTHER INFORMATION: His-myc tagged monkey MSR1 antibody
(extracellular domain)

-continued

<400> SEQUENCE: 418

```
His His His His His His Glu Gln Lys Leu Ile Ser Glu Glu Asp Leu
1               5                   10                  15

Gly Gly Glu Gln Lys Leu Ile Ser Glu Glu Asp Leu Lys Trp Glu Thr
            20                  25                  30

Lys Asn Cys Ser Ile Gly Ser Thr Asn Ala Asp Asp Ile Thr Gln Ser
        35                  40                  45

Leu Thr Gly Lys Gly Asn Asp Ser Glu Ala Glu Thr Arg Phe Gln Glu
    50                  55                  60

Val Phe Met Glu His Met Ser Asn Met Glu Lys Arg Ile Gln His Ile
65                  70                  75                  80

Ser Asp Met Glu Ala Asn Leu Ile Asp Ala Glu His Phe Gln Asn Phe
                85                  90                  95

Ser Met Thr Thr Asp Gln Arg Phe Asn Asp Ile Leu Leu Gln Leu Ser
            100                 105                 110

Thr Leu Phe Ser Ser Val Gln Gly His Gly Asn Thr Ile Asp Glu Ile
        115                 120                 125

Ser Lys Ser Leu Ile Ser Leu Asn Thr Thr Leu Leu Asp Leu Gln Leu
    130                 135                 140

Asn Ile Glu Lys Leu Asn Gly Lys Ile Gln Glu Lys Thr Phe Lys Gln
145                 150                 155                 160

Gln Glu Glu Ile Ser Lys Leu Glu Glu His Val Tyr Asn Val Ser Ala
                165                 170                 175

Glu Ile Met Ala Met Lys Glu Glu Gln Val His Leu Glu Gln Glu Ile
            180                 185                 190

Lys Gly Glu Val Lys Val Leu Asn Asn Ile Thr Asn Asp Leu Arg Leu
        195                 200                 205

Lys Asp Trp Glu His Ser Gln Thr Leu Arg Asn Ile Thr Leu Ile Gln
    210                 215                 220

Gly Pro Pro Gly Pro Pro Gly Glu Lys Gly Asp Arg Gly Pro Thr Gly
225                 230                 235                 240

Glu Ser Gly Pro Arg Gly Phe Pro Gly Pro Val Gly Pro Pro Gly Leu
                245                 250                 255

Lys Gly Asp Arg Gly Ala Ile Gly Phe Pro Gly Ser Arg Gly Leu Pro
            260                 265                 270

Gly Tyr Ala Gly Arg Pro Gly Asn Ser Gly Pro Lys Gly Gln Lys Gly
        275                 280                 285

Glu Lys Gly Ser Gly Asn Thr Leu Thr Ser Phe Lys Lys Val Arg Leu
    290                 295                 300

Val Gly Gly Ser Gly Pro His Glu Gly Arg Val Glu Ile Leu His Ser
305                 310                 315                 320

Gly Gln Trp Gly Thr Ile Cys Asp Asp Arg Trp Glu Val Arg Val Gly
                325                 330                 335

Gln Val Ile Cys Arg Ser Leu Gly Tyr Pro Gly Val Gln Ala Val His
            340                 345                 350

Lys Ala Ala His Phe Gly Gln Gly Thr Gly Pro Ile Trp Leu Asn Glu
        355                 360                 365

Val Tyr Cys Phe Gly Arg Glu Ser Ser Ile Glu Glu Cys Lys Ile Arg
    370                 375                 380

Gln Trp Gly Thr Arg Thr Cys Ser His Ser Glu Asp Ala Gly Val Thr
385                 390                 395                 400

Cys Thr Leu
```

-continued

<210> SEQ ID NO 419
<211> LENGTH: 360
<212> TYPE: DNA
<213> ORGANISM: Artificial Sequence
<220> FEATURE:
<223> OTHER INFORMATION: Synthetic

<400> SEQUENCE: 419
gaggtgcagc tggtggagtc tgggggaggc ctggtcaagc cggggggggtc cctgagactc 60 tcctgtgcag cctctggatt cactttcagt agatatagta tgaactgggt ccgccaggct 120
ccagggaagg ggctggagtg ggtctcatcc attagcagta gcagtagtta catatactac 180
ggagacacag tgaagggccg attcaccatc tccagagaca acgccaagaa gtcactgtat 240
ctgcaaatga acagcctgag agccgaggac acggctgtct attactgtgt gagagatcga 300
ggacagctcg tcctctactt tgactactgg ggccagggaa ccctggtcac cgtctcctca 360

<210> SEQ ID NO 420
<211> LENGTH: 120
<212> TYPE: PRT
<213> ORGANISM: Artificial Sequence
<220> FEATURE:
<223> OTHER INFORMATION: Synthetic

<400> SEQUENCE: 420

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Arg Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Gly Asp Thr Val
50 55 60

Lys Gly Arg Phe Thr Ile Ser Arg Asp Asn Ala Lys Lys Ser Leu Tyr
65 70 75 80

Leu Gln Met Asn Ser Leu Arg Ala Glu Asp Thr Ala Val Tyr Tyr Cys
85 90 95

Val Arg Asp Arg Gly Gln Leu Val Leu Tyr Phe Asp Tyr Trp Gly Gln
100 105 110

Gly Thr Leu Val Thr Val Ser Ser
115 120

<210> SEQ ID NO 421
<211> LENGTH: 24
<212> TYPE: DNA
<213> ORGANISM: Artificial Sequence
<220> FEATURE:
<223> OTHER INFORMATION: Synthetic

<400> SEQUENCE: 421
ggattcactt tcagtagata tagt 24

<210> SEQ ID NO 422
<211> LENGTH: 8
<212> TYPE: PRT
<213> ORGANISM: Artificial Sequence
<220> FEATURE:
<223> OTHER INFORMATION: Synthetic

<400> SEQUENCE: 422

Gly Phe Thr Phe Ser Arg Tyr Ser 1 5

<210> SEQ ID NO 423
<211> LENGTH: 24
<212> TYPE: DNA
<213> ORGANISM: Artificial Sequence
<220> FEATURE:
<223> OTHER INFORMATION: Synthetic

<400> SEQUENCE: 423
attagcagta gcagtagtta cata 24

<210> SEQ ID NO 424
<211> LENGTH: 8
<212> TYPE: PRT
<213> ORGANISM: Artificial Sequence
<220> FEATURE:
<223> OTHER INFORMATION: Synthetic

<400> SEQUENCE: 424

Ile Ser Ser Ser Ser Ser Tyr Ile
1 5

<210> SEQ ID NO 425
<211> LENGTH: 39
<212> TYPE: DNA
<213> ORGANISM: Artificial Sequence
<220> FEATURE:
<223> OTHER INFORMATION: Synthetic

<400> SEQUENCE: 425
gtgagagatc gaggacagct cgtcctctac tttgactac 39

<210> SEQ ID NO 426
<211> LENGTH: 13
<212> TYPE: PRT
<213> ORGANISM: Artificial Sequence
<220> FEATURE:
<223> OTHER INFORMATION: Synthetic

<400> SEQUENCE: 426

Val Arg Asp Arg Gly Gln Leu Val Leu Tyr Phe Asp Tyr
1 5 10

<210> SEQ ID NO 427
<211> LENGTH: 324
<212> TYPE: DNA
<213> ORGANISM: Artificial Sequence
<220> FEATURE:
<223> OTHER INFORMATION: Synthetic

<400> SEQUENCE: 427
gacatccaga tgacccagtc tccagcctcc ctgtctacat ctataagaga cagagtcacc 60
atcacttgcc gggcaagtct gagcattagc agctttttaa attggtttca gcagagacca 120
gggaaagccc ctaaactcct gatctatgtt gcatccaatt tgcaaagtgg ggtcccatca 180
agattcagtg acagtggatc tgggacagat ttcactctca ccatcagcag tctgcaacct 240
gaagattttg caacttacta ctgtcaacag aattacagta cccctccgat caccttcggc 300
caagggacac gactggagat taaa 324

<210> SEQ ID NO 428
<211> LENGTH: 108
<212> TYPE: PRT
<213> ORGANISM: Artificial Sequence
<220> FEATURE:
<223> OTHER INFORMATION: Synthetic

<400> SEQUENCE: 428

Asp Ile Gln Met Thr Gln Ser Pro Ala Ser Leu Ser Thr Ser Ile Arg
1 5 10 15

Asp Arg Val Thr Ile Thr Cys Arg Ala Ser Leu Ser Ile Ser Ser Phe
20 25 30

Leu Asn Trp Phe Gln Gln Arg Pro Gly Lys Ala Pro Lys Leu Leu Ile
35 40 45

Tyr Val Ala Ser Asn Leu Gln Ser Gly Val Pro Ser Arg Phe Ser Asp
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Asn Tyr Ser Thr Pro Pro
85 90 95

Ile Thr Phe Gly Gln Gly Thr Arg Leu Glu Ile Lys
100 105

<210> SEQ ID NO 429
<211> LENGTH: 18
<212> TYPE: DNA
<213> ORGANISM: Artificial Sequence
<220> FEATURE:
<223> OTHER INFORMATION: Synthetic

<400> SEQUENCE: 429
ctgagcatta gcagcttt 18

<210> SEQ ID NO 430
<211> LENGTH: 6
<212> TYPE: PRT
<213> ORGANISM: Artificial Sequence
<220> FEATURE:
<223> OTHER INFORMATION: Synthetic

<400> SEQUENCE: 430

Leu Ser Ile Ser Ser Phe
1 5

<210> SEQ ID NO 431
<211> LENGTH: 9
<212> TYPE: DNA
<213> ORGANISM: Artificial Sequence
<220> FEATURE:
<223> OTHER INFORMATION: Synthetic

<400> SEQUENCE: 431 gttgcatcc 9

<210> SEQ ID NO 432
<211> LENGTH: 3
<212> TYPE: PRT
<213> ORGANISM: Artificial Sequence
<220> FEATURE:
<223> OTHER INFORMATION: Synthetic

<400> SEQUENCE: 432

Val Ala Ser
1

<210> SEQ ID NO 433
<211> LENGTH: 30

<212> TYPE: DNA
<213> ORGANISM: Artificial Sequence
<220> FEATURE:
<223> OTHER INFORMATION: Synthetic

<400> SEQUENCE: 433
caacagaatt acagtacccc tccgatcacc 30

<210> SEQ ID NO 434
<211> LENGTH: 10
<212> TYPE: PRT
<213> ORGANISM: Artificial Sequence
<220> FEATURE:
<223> OTHER INFORMATION: Synthetic

<400> SEQUENCE: 434

Gln Gln Asn Tyr Ser Thr Pro Pro Ile Thr
1 5 10

<210> SEQ ID NO 435
<211> LENGTH: 369
<212> TYPE: DNA
<213> ORGANISM: Artificial Sequence
<220> FEATURE:
<223> OTHER INFORMATION: Synthetic

<400> SEQUENCE: 435
caggtgcagc tggtggagtc tgggggaggc gtggtccagc ctgggaggtc cctgagactc 60
tcctgtgcgg gctctggatt caccttcagt agctatggct tgcactgggt ccgccaggct 120
ccaggcaagg ggctggagtg ggtggcagtt atatcatatg atggaagtaa taaatattat 180
gcagactccg tgaagggccg attcaccatc tccagagaca attccaagaa cacgctgtat 240
ctgcaaatga gcagcctgag agctgaggac acggctgtgt attactgtgc gaaagatcga 300
cttgtacgat attctgactg gccattcttt gactattggg gccagggaac cctggtcacc 360
gtctcctca 369

<210> SEQ ID NO 436
<211> LENGTH: 123
<212> TYPE: PRT
<213> ORGANISM: Artificial Sequence
<220> FEATURE:
<223> OTHER INFORMATION: Synthetic

<400> SEQUENCE: 436

Gln Val Gln Leu Val Glu Ser Gly Gly Gly Val Val Gln Pro Gly Arg
1 5 10 15

Ser Leu Arg Leu Ser Cys Ala Gly Ser Gly Phe Thr Phe Ser Ser Tyr
20 25 30

Gly Leu His Trp Val Arg Gln Ala Pro Gly Lys Gly Leu Glu Trp Val
35 40 45

Ala Val Ile Ser Tyr Asp Gly Ser Asn Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Ser Ser Leu Arg Ala Glu Asp Thr Ala Val Tyr Tyr Cys
85 90 95

Ala Lys Asp Arg Leu Val Arg Tyr Ser Asp Trp Pro Phe Phe Asp Tyr
100 105 110

Trp Gly Gln Gly Thr Leu Val Thr Val Ser Ser
115 120

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
ggattcacct tcagtagcta tggc 24

<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Gly Phe Thr Phe Ser Ser Tyr Gly
1 5

<210> SEQ ID NO 439
<211> LENGTH: 24
<212> TYPE: DNA
<213> ORGANISM: Artificial Sequence
<220> FEATURE:
<223> OTHER INFORMATION: Synthetic

<400> SEQUENCE: 439
atatcatatg atggaagtaa taaa 24

<210> SEQ ID NO 440
<211> LENGTH: 8
<212> TYPE: PRT
<213> ORGANISM: Artificial Sequence
<220> FEATURE:
<223> OTHER INFORMATION: Synthetic

<400> SEQUENCE: 440

Ile Ser Tyr Asp Gly Ser Asn Lys
1 5

<210> SEQ ID NO 441
<211> LENGTH: 48
<212> TYPE: DNA
<213> ORGANISM: Artificial Sequence
<220> FEATURE:
<223> OTHER INFORMATION: Synthetic

<400> SEQUENCE: 441
gcgaaagatc gacttgtacg atattctgac tggccattct ttgactat 48

<210> SEQ ID NO 442
<211> LENGTH: 16
<212> TYPE: PRT
<213> ORGANISM: Artificial Sequence
<220> FEATURE:
<223> OTHER INFORMATION: Synthetic

<400> SEQUENCE: 442

Ala Lys Asp Arg Leu Val Arg Tyr Ser Asp Trp Pro Phe Phe Asp Tyr
1 5 10 15

<210> SEQ ID NO 443
<211> LENGTH: 324

<212> TYPE: DNA
<213> ORGANISM: Artificial Sequence
<220> FEATURE:
<223> OTHER INFORMATION: Synthetic

<400> SEQUENCE: 443
gacatccaga tgacccagtc tccatcctcc ctgtctgcat ctgtaggaga cagagtcacc 60
atcacttgcc gggcaagtca aaacattacc agctatttga attgctatca gcagaaacca 120
gggaaagccc ctaaactcct gatctatgct gcatccagtt tgyaaagtgg ggtcccatca 180
aggttcagtg gcagtggatc tgggacagat ttcactctca ccatcagcag tctgcaacct 240
gaagattttg caacttacta ctgtcaacag agtttcagta gtcctccgat caccttcggc 300
caagggacac gactggagat taca 324

<210> SEQ ID NO 444
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (55)..(55)
<223> OTHER INFORMATION: Xaa can be any naturally occurring amino acid

<400> SEQUENCE: 444

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Thr Ser Tyr
            20                  25                  30

Leu Asn Cys Tyr Gln Gln Lys Pro Gly Lys Ala Pro Lys Leu Leu Ile
        35                  40                  45

Tyr Ala Ala Ser Ser Leu Xaa Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Ser Pro Pro
                85                  90                  95

Ile Thr Phe Gly Gln Gly Thr Arg Leu Glu Ile Thr
            100                 105

<210> SEQ ID NO 445
<211> LENGTH: 18
<212> TYPE: DNA
<213> ORGANISM: Artificial Sequence
<220> FEATURE:
<223> OTHER INFORMATION: Synthetic

<400> SEQUENCE: 445
caaaacatta ccagctat 18

<210> SEQ ID NO 446
<211> LENGTH: 6
<212> TYPE: PRT
<213> ORGANISM: Artificial Sequence
<220> FEATURE:
<223> OTHER INFORMATION: Synthetic

<400> SEQUENCE: 446

Gln Asn Ile Thr Ser Tyr
1               5

<210> SEQ ID NO 447
<211> LENGTH: 9
<212> TYPE: DNA
<213> ORGANISM: Artificial Sequence
<220> FEATURE:
<223> OTHER INFORMATION: Synthetic

<400> SEQUENCE: 447 gctgcatcc 9

<210> SEQ ID NO 448
<211> LENGTH: 3
<212> TYPE: PRT
<213> ORGANISM: Artificial Sequence
<220> FEATURE:
<223> OTHER INFORMATION: Synthetic

<400> SEQUENCE: 448

Ala Ala Ser
1

<210> SEQ ID NO 449
<211> LENGTH: 30
<212> TYPE: DNA
<213> ORGANISM: Artificial Sequence
<220> FEATURE:
<223> OTHER INFORMATION: Synthetic

<400> SEQUENCE: 449
caacagagtt tcagtagtcc tccgatcacc 30

<210> SEQ ID NO 450
<211> LENGTH: 10
<212> TYPE: PRT
<213> ORGANISM: Artificial Sequence
<220> FEATURE:
<223> OTHER INFORMATION: Synthetic

<400> SEQUENCE: 450

Gln Gln Ser Phe Ser Ser Pro Pro Ile Thr
1 5 10

<210> SEQ ID NO 451
<211> LENGTH: 348
<212> TYPE: DNA
<213> ORGANISM: Artificial Sequence
<220> FEATURE:
<223> OTHER INFORMATION: Synthetic

<400> SEQUENCE: 451
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggaatg gattgggtac atctattaca gtgggagcgc caactacaac 180
ccctccctca agagtcgagt caccatatca gtagacacgt ccaagaacca gttctccctg 240
aagctaagct ctgtgaccgc tgcggacacg gccgtgtatt actgtgtgag agaccgggac 300
ctactccttg accactgggg ccagggaacc ctggtcaccg tctcctca 348

<210> SEQ ID NO 452
<211> LENGTH: 116
<212> TYPE: PRT
<213> ORGANISM: Artificial Sequence
<220> FEATURE:
<223> OTHER INFORMATION: Synthetic

<400> SEQUENCE: 452

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Ala Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Val
85 90 95

Arg Asp Arg Asp Leu Leu Leu Asp His Trp Gly Gln Gly Thr Leu Val
100 105 110

Thr Val Ser Ser
115

<210> SEQ ID NO 453
<211> LENGTH: 24
<212> TYPE: DNA
<213> ORGANISM: Artificial Sequence
<220> FEATURE:
<223> OTHER INFORMATION: Synthetic

<400> SEQUENCE: 453
ggtggctcca tcagtagtta ctac 24

<210> SEQ ID NO 454
<211> LENGTH: 8
<212> TYPE: PRT
<213> ORGANISM: Artificial Sequence
<220> FEATURE:
<223> OTHER INFORMATION: Synthetic

<400> SEQUENCE: 454

Gly Gly Ser Ile Ser Ser Tyr Tyr
1 5

<210> SEQ ID NO 455
<211> LENGTH: 21
<212> TYPE: DNA
<213> ORGANISM: Artificial Sequence
<220> FEATURE:
<223> OTHER INFORMATION: Synthetic

<400> SEQUENCE: 455
atctattaca gtgggagcgc c 21

<210> SEQ ID NO 456
<211> LENGTH: 7
<212> TYPE: PRT
<213> ORGANISM: Artificial Sequence
<220> FEATURE:
<223> OTHER INFORMATION: Synthetic

<400> SEQUENCE: 456

Ile Tyr Tyr Ser Gly Ser Ala
1 5

<210> SEQ ID NO 457

<211> LENGTH: 30
<212> TYPE: DNA
<213> ORGANISM: Artificial Sequence
<220> FEATURE:
<223> OTHER INFORMATION: Synthetic

<400> SEQUENCE: 457
gtgagagacc gggacctact ccttgaccac 30

<210> SEQ ID NO 458
<211> LENGTH: 10
<212> TYPE: PRT
<213> ORGANISM: Artificial Sequence
<220> FEATURE:
<223> OTHER INFORMATION: Synthetic

<400> SEQUENCE: 458

Val Arg Asp Arg Asp Leu Leu Leu Asp His
1 5 10

<210> SEQ ID NO 459
<211> LENGTH: 324
<212> TYPE: DNA
<213> ORGANISM: Artificial Sequence
<220> FEATURE:
<223> OTHER INFORMATION: Synthetic

<400> SEQUENCE: 459
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 460
<211> LENGTH: 108
<212> TYPE: PRT
<213> ORGANISM: Artificial Sequence
<220> FEATURE:
<223> OTHER INFORMATION: Synthetic

<400> SEQUENCE: 460

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 461
<211> LENGTH: 18

<212> TYPE: DNA
<213> ORGANISM: Artificial Sequence
<220> FEATURE:
<223> OTHER INFORMATION: Synthetic

<400> SEQUENCE: 461
cagagcatta gcagctat 18

<210> SEQ ID NO 462
<211> LENGTH: 6
<212> TYPE: PRT
<213> ORGANISM: Artificial Sequence
<220> FEATURE:
<223> OTHER INFORMATION: Synthetic

<400> SEQUENCE: 462

Gln Ser Ile Ser Ser Tyr
1 5

<210> SEQ ID NO 463
<211> LENGTH: 9
<212> TYPE: DNA
<213> ORGANISM: Artificial Sequence
<220> FEATURE:
<223> OTHER INFORMATION: Synthetic

<400> SEQUENCE: 463 gctgcatcc 9

<210> SEQ ID NO 464
<211> LENGTH: 3
<212> TYPE: PRT
<213> ORGANISM: Artificial Sequence
<220> FEATURE:
<223> OTHER INFORMATION: Synthetic

<400> SEQUENCE: 464

Ala Ala Ser
1

<210> SEQ ID NO 465
<211> LENGTH: 30
<212> TYPE: DNA
<213> ORGANISM: Artificial Sequence
<220> FEATURE:
<223> OTHER INFORMATION: Synthetic

<400> SEQUENCE: 465
caacagagtt acagtacccc tccgatcacc 30

<210> SEQ ID NO 466
<211> LENGTH: 10
<212> TYPE: PRT
<213> ORGANISM: Artificial Sequence
<220> FEATURE:
<223> OTHER INFORMATION: Synthetic

<400> SEQUENCE: 466

Gln Gln Ser Tyr Ser Thr Pro Pro Ile Thr
1 5 10